United States Patent
Yeager et al.

(10) Patent No.: US 11,040,954 B1
(45) Date of Patent: Jun. 22, 2021

(54) CXCR3 RECEPTOR AGONISTS

(71) Applicant: RECEPTOS LLC, New York, NY (US)

(72) Inventors: Adam Yeager, San Diego, CA (US); Philip Turnbull, San Diego, CA (US); Lin Zhang, San Diego, CA (US); Junhua Fan, San Diego, CA (US); Junko Tamiya, San Diego, CA (US); Marcos Steinberg, San Diego, CA (US); Tom Fowler, Nottinghamshire (GB); Hanae Benelkebir, Nottinghamshire (GB); Raffaele Pasceri, Nottinghamshire (GB); Maria Ieva, Nottinghamshire (GB); Kevan Grant, Nottinghamshire (GB); Yang Tran, San Diego, CA (US)

(73) Assignee: RECEPTOS LLC, New York, NY (US)

(*) Notice: Subject to any disclaimer, the term of this patent is extended or adjusted under 35 U.S.C. 154(b) by 0 days.

(21) Appl. No.: 16/872,161

(22) Filed: May 11, 2020

Related U.S. Application Data

(63) Continuation of application No. 16/335,641, filed as application No. PCT/US2017/049768 on Aug. 31, 2017.

(60) Provisional application No. 62/478,496, filed on Mar. 29, 2017, provisional application No. 62/383,202, filed on Sep. 2, 2016.

(51) Int. Cl.
| | |
|---|---|
| *C07D 217/04* | (2006.01) |
| *A61K 31/472* | (2006.01) |
| *C07D 401/06* | (2006.01) |
| *C07D 217/26* | (2006.01) |
| *C07D 405/12* | (2006.01) |
| *C07D 401/14* | (2006.01) |
| *C07D 401/12* | (2006.01) |

(52) U.S. Cl.
CPC ........ *C07D 401/06* (2013.01); *C07D 217/26* (2013.01); *C07D 401/12* (2013.01); *C07D 401/14* (2013.01); *C07D 405/12* (2013.01)

(58) Field of Classification Search
CPC ............. C07D 217/26; C07D 217/04; A61K 31/4725; A61K 31/472
USPC ......................................... 546/146; 514/307
See application file for complete search history.

(56) References Cited

PUBLICATIONS

Scholten et al., "Pharmacological characterization of a small-molecule agonist for the chemokine receptor CXCR3", *British Journal of Pharmacology 166*, pp. 898-911, 2012.
Stroke et al., "Identification of CXCR3 receptor agonists in combinatorial small-molecule libraries", *Biochemical and Biophysical Research Communications 349*, pp. 221-228, 2006.
Wijtmans et al., "Chemical Subtleties in Small-Molecule Modulation of Peptide Receptor Function: The Case of CXCR3 Biaryl-Type Ligands", *Journal of Medicinal Chemistry 55*, pp. 10572-10583, 2012.

*Primary Examiner* — Charanjit Aulakh
(74) *Attorney, Agent, or Firm* — Seed IP Law Group LLP

(57) ABSTRACT

Compounds are provided having the structure of the following Formula I:

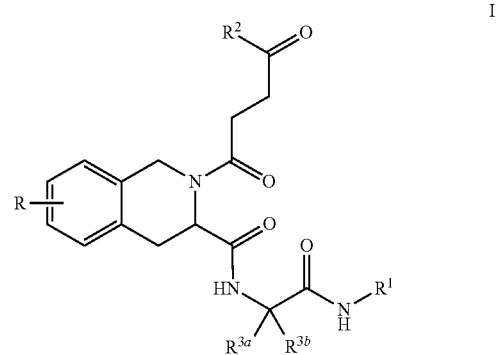

where R, $R^1$, $R^2$, $R^{3a}$ and $R^{3b}$ are as defined herein. Pharmaceutical compositions comprising such compounds, as well as methods related to their manufacture and use, are also provided.

36 Claims, No Drawings

CXCR3 RECEPTOR AGONISTS

FIELD OF THE INVENTION

This disclosure is directed to small molecule agonists of the chemokine receptor CXCR3, and product containing the same, as well as to methods related to the use of such small molecule agonists.

BACKGROUND

The chemokine receptor CXCR3 is a member of the seven transmembrane-spanning G protein-coupled receptor (GPCR) superfamily. CXCR3 is primarily expressed on activated T lymphocytes and NK cells. CXCL9/Mig, CXCL10/IP-10 and CXCL11/I-TAC, the natural chemokine ligands for CXCR3, are involved in directing activated T cells and other cells, such as NK cells, to sites of inflammation. CXCR3 has been implicated in Th1 cell-mediated inflammation, and upregulation of CXCR3 has been shown in a number of diseases involving T cells, such as inflammatory bowel disease '(IBD), multiple sclerosis (MS), rheumatoid arthritis (RA) and diabetes, to name a few.

CXCR3 receptor agonists inhibit migration of activated T lymphocytes and NK cells. As described by O'Boyle et al ("Chemokine receptor CXCR3 agonist prevents human T-cell migration in a humanized model of arthritic inflammation," PNAS, 109(12):4598-4603, 2012), generalized chemokine receptor desensitization can be induced by specific stimulation of a CXCR3 receptor on the surface of activated T cells, resulting in the inhibition of the inflammatory response that is normally produced. In effect, CXCR3 receptor agonists may act as functional antagonists through chemokine receptor desensitization.

Prior efforts directed to the identification of small molecule agonists of CXCR3 have been undertaken, resulting in the identification of several compounds. As described by Stroke et al ("Identification of CXCR3 receptor agonists in combinatorial small-molecule libraries," Biochemical and Biophysical Research Communication, 349:221-228, 2006), high-throughput screening of encoded combinatorial libraries have identified two classes of receptor agonists. In one class, compounds A and B have been identified, while the other class includes compound C:

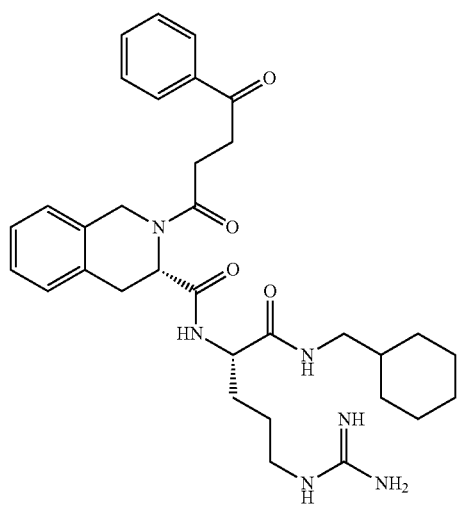

A

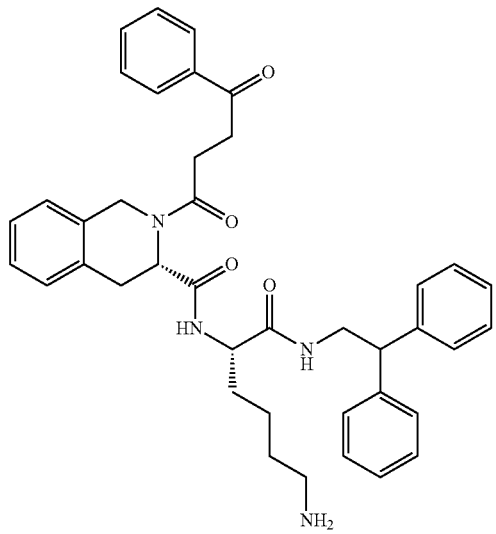

B

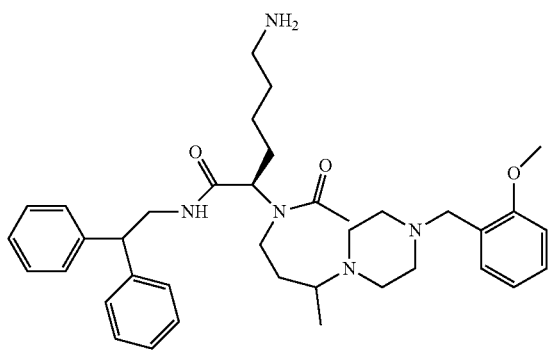

C

While advances have been made in this field, there remains a significant need for small molecule agonists of CXCR3, as well as for products and methods related to the same. The present disclosure fulfills these and other needs, as described in more detail in the following detailed description.

SUMMARY OF THE INVENTION

The present disclosure is generally directed to compounds which serve as agonists of the chemokine receptor CXCR3, as well as to composition containing the same, and to methods of their preparation and use.

In one embodiment, compounds are provided having the structure of the following Formula I, including stereoisomers hydrates, solvates, isotopes, or pharmaceutically acceptable salts thereof:


wherein R, $R^1$, $R^2$, $R^{3a}$ and $R^{3b}$ are as defined below.

In one embodiment, a pharmaceutical composition comprising a compound of Formula I together with at least one pharmaceutically acceptable carrier, diluent or excipient is provided.

In one embodiment, a method of use of a compound of Formula I comprising preparation of a medicament is provided.

In one embodiment, a method of agonism of the CXCR3 receptor is provided comprising contacting the receptor with a compound of Formula I, or a pharmaceutical composition comprising the same.

In one embodiment, a method is provided for treatment of a disease or condition in a subject for which agonism of the CXCR3 receptor is medically indicated, comprising administering to the subject a compound of Formula I, or a pharmaceutical composition comprising the same.

In one embodiment, a method is provided for treating rheumatoid arthritis, multiple sclerosis, or inflammatory bowel disease in a subject in need thereof, comprising administering to the subject a compound of Formula I, or a pharmaceutical composition comprising the same.

DETAILED DESCRIPTION OF THE INVENTION

As used in the specification and the appended claims, the singular forms "a," "an" and "the" include plural referents unless the context clearly dictates otherwise.

In one embodiment, compounds are provided having the following Formula I, including stereoisomers, hydrates, solvates, isotopes or pharmaceutically acceptable salts thereof:

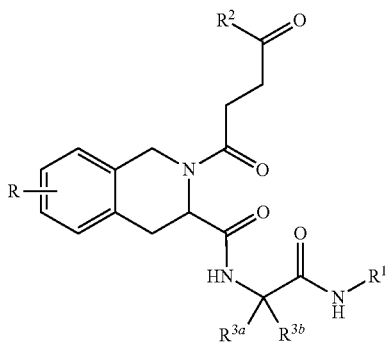

wherein:
R is hydrogen, hydroxy, cyano, halo or $-OS(=O)_2R^6$;
$R^1$ is aryl or heteroaryl and substituted with 0-4 $R^4$ groups;
$R^2$ is aryl or heteroaryl and substituted with 0-3 $R^5$ groups, or $R^2$ is $-NR^8R^9$;
$R^{3a}$ is hydrogen or alkyl and $R^{3b}$ is a nitrogen- or amine-containing moiety of carbon, at least one nitrogen atom and hydrogen,
or $R^{3a}$ and $R^{3b}$ taken together with the carbon to which they are attached form a cyclic nitrogen- or amine-containing moiety of carbon, at least one nitrogen atom and hydrogen;
$R^4$ and $R^5$ are, at each occurrence, cyano, halo, alkyl, haloalkyl, aminoalkyl, hydroxyalkyl, hydroxy, alkoxy, phenyl, heterocyclyl, $-S(=O)_2R^6$, $-C(=O)R^6$, $-C(=O)OR^6$, $-C(=O)NR^6N^7$ or $-NR^6R^7$;
$R^6$ and $R^7$ are, at each occurrence, hydrogen or alkyl; and
$R^8$ is hydrogen or alkyl and $R^9$ is alkyl or aryl substituted with 0-4 $R^4$ groups,
or $R^8$ and $R^9$ taken together with the nitrogen atom to which they are attached form a heterocyclyl substituted with 0-4 $R^4$ groups and optionally substituted with oxo (=O) or thioxo (=S).

As used herein, "alkyl" groups include straight chain and branched alkyl groups and cycloalkyl groups having from 1 to about 20 carbon atoms, and typically from 1 to 12 carbons ($C_1$-$C_{12}$ alkyl), or, in some embodiments, from 1 to 8 carbon atoms ($C_1$-$C_8$ alkyl), or, in some embodiments, from 1 to 4 carbon atoms ($C_1$-$C_4$ alkyl). In the case of cycloalkyl groups, such groups have from 3-20 carbon atoms as more specifically defined below. Examples of straight chain alkyl groups include, but are not limited to, methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups.

"Alkenyl" groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to $-CH=CH_2$, $-CH=CH(CH_3)$, $-CH=C(CH_3)_2$, $-C(CH_3)=CH_2$, $-C(CH_3)=CH(CH_3)$, $-C(CH_2CH_3)=CH_2$, $-CH=CHCH_2CH_3$, $-CH=CH(CH_2)_2CH_3$, $-CH=CH(CH_2)_3CH_3$, $-CH=CH(CH_2)_4CH_3$, vinyl, cyclohexenyl, cyclopentenyl, cyclohexadienyl, butadienyl, pentadienyl, and hexadienyl among others.

"Alkynyl" groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to $-C\equiv C(CH_3)$, $-C\equiv C(CH_2CH_3)$, $-CH_2C\equiv CH$, $-CH_2C\equiv C(CH_3)$, and $-CH_2C\equiv C(CH_2CH_3)$, among others.

"Cycloalkyl" groups are alkyl groups forming a ring structure, which can be substituted or unsubstituted, wherein the ring is either completely saturated, partially unsaturated, or fully unsaturated, wherein if there is unsaturation, the conjugation of the pi-electrons in the ring do not give rise to aromaticity. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

"(Cycloalkyl)alkyl" groups, also referred to as "cycloalkylalkyl", are alkyl groups as defined above in which a hydrogen or carbon bond of the alkyl group is replaced with a bond to a cycloalkyl group as defined above.

The term "cycloalkenyl" alone or in combination denotes a cyclic alkenyl group wherein at least one double bond is present in the ring structure. Cycloalkenyl groups include cycloalkyl groups having at least one double bond between two adjacent carbon atoms. Thus for example, cycloalkenyl groups include but are not limited to cyclohexenyl, cyclopentenyl, and cyclohexadienyl groups, as well as polycyclic and/or bridging ring systems such as adamantine.

"(Cycloalkenyl)alkyl" groups, also referred to as "cycloalkylalkyl", are alkyl groups as defined above in which a hydrogen or carbon bond of the alkyl group is replaced with a bond to a cycloalkenyl group as defined above.

The terms "carbocyclic" and "carbocyclyl" denote a ring structure wherein the atoms of the ring are carbon. In some embodiments, the carbocyclyl has 3 to 8 ring members, whereas in other embodiments the number of ring carbon atoms is 4, 5, 6, or 7. Carbocyclyl includes, for example, cycloalkyl and cycloalkenyl.

"(Carbocyclyl)alkyl" groups, also referred to as "carbocyclylalkyls", are alkyl groups as defined above in which a hydrogen or carbon bond of the alkyl group is replaced with a bond to a carbocyclyl as defined above.

A "nonaromatic carbocyclyl" or a "nonaromatic carbocyclylalkyl" is a group in which the carbocyclic ring of the carbocyclyl or carbocyclylalkyl is a completely saturated, a partially unsaturated, or a fully unsaturated carbocyclyl, wherein if there is unsaturation, the conjugation of the pi-electrons of the carbocyclic ring do not give rise to aromaticity.

"Aryl" groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The phrase "aryl groups" includes groups containing fused rings, such as fused aromatic-aliphatic ring systems (e.g., indanyl, tetrahydronaphthyl, and the like).

"Aralkyl" groups are alkyl, alkenyl or alkynyl groups as defined above in which a hydrogen atom of an alkyl, alkenyl or alkynyl group is replaced with an aryl group as defined above. Representative aralkyl groups include benzyl (—CH$_2$phenyl), phenylethyl (—CH$_2$CH$_2$phenyl) and phenylethylene (—CH=CHphenyl) groups and fused (cycloalkylaryl)alkyl groups such as 4-ethyl-indanyl. Aralky groups can be substituted on the aryl moiety, the alkyl, alkenyl or alkynyl moiety, or both.

"Heterocyclyl" or "heterocyclic" groups include aromatic and non-aromatic ring moieties containing 3 or more ring members, of which one or more is a heteroatom such as, but not limited to, N, O, S, or P. In some embodiments, heterocyclyl groups include 3 to 20 ring members, whereas other such groups have 3 to 15 ring members, including for example single ring systems containing 5, 6 or 7 ring members. At least one ring contains a heteroatom, but every ring in a polycyclic system need not contain a heteroatom.

For example, a dioxolanyl ring and a benzdioxolanyl ring system (methylenedioxyphenyl ring system) are both heterocyclyl groups within the meaning herein. A heterocyclyl group designated as a $C_2$-heterocyclyl can be a 5-ring with two carbon atoms and three heteroatoms, a 6-ring with two carbon atoms and four heteroatoms, and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms.

The term "heterocyclyl" includes fused ring species including those having fused aromatic and non-aromatic groups. The phrase also includes polycyclic and/or bridging ring systems containing a heteroatom such as, but not limited to, quinuclidyl and 7-azabicyclo[2.2.1]heptane. A heterocyclyl group as defined herein can be a heteroaryl group or a partially or completely saturated cyclic group including at least one ring heteroatom. Heterocyclyl groups include, but are not limited to, pyrazinyl, pyrimidinyl, pyridazinyl, thiadiazolyl, oxadiazolyl, imidazolinyl, hexahydropyrimidinyl, diazepanyl, triazinyl, imidazolyl, pyrrolidinyl, furanyl, tetrahydrofuranyl, tetrahydro-2H-pyranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups.

"Heteroaryl" groups are aromatic ring moieties containing 5 or more ring members, of which, one or more is a heteroatom such as, but not limited to, N, O, and S. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, pyridinyl, pyridazinyl, pyrimidyl, pyrazyl, pyrazinyl, pyrimidinyl, thiadiazolyl, imidazolyl, oxadiazolyl, thienyl, triazolyl, tetrazolyl, triazinyl, thiazolyl, thiophenyl, oxazolyl, isoxazolyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl and 2,3-dihydro indolyl.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl (1,2,4-oxadiazolyl, 1,3,4-oxadiazolyl), thiadiazolyl (1,2,4-thiadiazolyl, 1,3,4-thiadiazolyl), isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl, 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl, pyrimidinyl (2-pyrimidinyl, 4-pyrimidinyl, 5-pyrimidinyl, 6pyrimidinyl), pyrazinyl, pyridazinyl (3-pyridazinyl, 4-pyridazinyl, 5-pyridazinyl), prazolo[1,5-ϵ]pyridinyl, quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), isobenzofuranyl, 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo [b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), benzo[d]isoxazolyl, carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f] azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

"Heterocyclylalkyl" groups are alkyl, alkenyl or alkynyl groups as defined above in which a hydrogen or carbon bond of an alkyl, alkenyl or alkynyl group is replaced with a bond to a heterocyclyl group as defined above. Representative heterocyclyl alkyl groups include, but are not limited to, furan-2-yl methyl, furan-3-yl methyl, pyridine-2-yl methyl (α-picolyl), pyridine-3-yl methyl (β-picolyl), pyridine-4-yl methyl (γ-picolyl), tetrahydrofuran-2-yl ethyl, and indol-2-yl propyl. Heterocyclylalkyl groups can be substituted on the heterocyclyl moiety, the alkyl, alkenyl or alkynyl moiety, or both.

"Heteroarylalkyl" groups are alkyl, alkenyl or alkynyl groups as defined above in which a hydrogen or carbon bond of an alkyl, alkenyl or alkynyl group is replaced with a bond to a heteroaryl group as defined above. Heteroarylalkyl groups can be substituted on the heteroaryl moiety, the alkyl, alkenyl or alkynyl moiety, or both.

An "optionally substituted" heterocyclyl, heteroaryl, heterocyclylalkyl or heteroarylalkyl refers to a heterocyclyl, heteroaryl, heterocyclylalkyl or heteroarylalkyl as defined above having no additional substituents (i.e., unsubstituted) or have one or more substituents (i.e., substituted), wherein such substituents independently one or more $R^4$ groups as defined above, and in the case of a single carbon atom bearing two substituents includes oxo (=O) and thioxo (=S).

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

A "monocyclic, bicyclic or polycyclic, aromatic or partially aromatic ring" as the term is used herein refers to a ring system including an unsaturated ring possessing 4n+2 pi electrons, or a partially reduced (hydrogenated) form thereof. The aromatic or partially aromatic ring can include additional fused, bridged, or spiro rings that are not themselves aromatic or partially aromatic. For example, naphthalene and tetrahydronaphthalene are both a "monocyclic, bicyclic or polycyclic, aromatic or partially aromatic ring" within the meaning herein. Also, for example, a benzo-[2.2.2]-bicyclooctane is also a "monocyclic, bicyclic or polycyclic, aromatic or partially aromatic ring" within the meaning herein, containing a phenyl ring fused to a bridged bicyclic system. A fully saturated ring has no double bonds therein, and is carbocyclic or heterocyclic depending on the presence of heteroatoms within the meaning herein.

When two "R" groups are said to be joined together or taken together to form a ring, it is meant that together with the carbon atom or a non-carbon atom (e.g., nitrogen atom), to which they are bonded, they may form a ring system. In general, they are bonded to one another to form a 3- to 7-membered ring, or a 5- to 7-membered ring. Non-limiting specific examples are the cyclopentyl, cyclohexyl, cycloheptyl, piperidinyl, piperazinyl, pyrolidinyl, pyrrolyl, pyridinyl.

The term "alkoxy" refers to an oxygen atom connected to an alkyl group, including a cycloalkyl group, as are defined above. Examples of linear alkoxy groups include but are not limited to methoxy, ethoxy, n-propoxy, n-butoxy, n-pentyloxy, n-hexyloxy, n-heptyloxy, n-octyloxy n-nonyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula $N(group)_3$ wherein each group can independently be H or non-H, such as alkyl, aryl, and the like. Amines include but are not limited to $R-NH_2$, for example, alkylamines, arylamines, alkylarylamines; $R_2NH$ wherein each R is independently selected, such as dialkylamines, diarylamines, aralkyl amines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

An "amino" group is a substituent of the form $-NH_2$, $-NHR$, $-NR_2$, $-NR_3^+$, wherein each R is independently selected, and protonated forms of each. Accordingly, any compound substituted with an amino group can be viewed as an amine.

An "ammonium" ion includes the unsubstituted ammonium ion $NH_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., $-C(O)NR_2$, and $-NRC(O)R$ groups, respectively. Amide groups therefore include but are not limited to carbamoyl groups ($-C(O)NH_2$) and formamide groups ($-NHC(O)H$). A "carboxamido" group is a group of the formula $C(O)NR_2$, wherein R can be H, alkyl, aryl, etc.

The term "hydroxyl" refers to an $-OH$ group.

The term "hydroxyalkyl" refers to an -alkyl-OH group.

The term "cyano" refers to a $-CN$ group.

The term "carbonyl," refers to a $-C(=O)-$ group.

"Halo," "halogen," and "halide" include fluorine, chlorine, bromine and iodine.

The term "perhaloalkyl" refers to an alkyl group where all of the hydrogen atoms are replaced by halogen atoms. Perhaloalkyl groups include, but are not limited to, $-CF_3$ and $-C(CF_3)_3$. The term "haloalkyl" refers to an alkyl group where some but not necessarily all of the hydrogen atoms are replaced by halogen atoms. Haloalkyl groups include but are not limited to $-CHF_2$ and $-CH_2F$.

The term "perhaloalkoxy" refers to an alkoxy group where all of the hydrogen atoms are replaced by halogen atoms. Perhaloalkoxy groups include, but are not limited to, $-OCF_3$ and $-OC(CF_3)_3$. The term "haloalkoxy" refers to an alkoxy group where some but not necessarily all of the hydrogen atoms are replaced by halogen atoms. Haloalkoxy groups include but are not limited to $-OCHF_2$ and $-OCH_2F$.

The compounds disclosed herein may be in the form of a neutral compound, or in the form of the free acid or free base. Alternatively, the compounds disclosed herein may be associated with a counter ion, and be in the form a salt. In one embodiment, the compound is in the form of a "pharmaceutically acceptable" salt, which refers to a salt possessing toxicity profiles within a range that affords utility in pharmaceutical applications.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form (i.e., a compound in water solution, while it may be hydrated, is not a hydrate as the term is used herein).

A "solvate" is a similar composition except that a solvent other that water replaces the water. For example, methanol or ethanol can form an "alcoholate", which can again be stoichiometric or non-stoichiometric. As the term is used herein a "solvate" refers to a solid form (i.e., a compound in solution in a solvent, while it may be solvated, is not a solvate as the term is used herein).

A prodrug is a substance that can be administered to a patient where the substance is converted in vivo by the action of biochemicals within the patient's body, such as enzymes, to the active pharmaceutical ingredient. Examples of prodrugs include esters of carboxylic acid groups, which can be hydrolyzed by endogenous esterases as are found in the bloodstream of humans and other mammals. In one embodiment of the present invention, substances are provided that can be administered to a patient where the substance is converted in vivo by the action of biochemical within the patient's body, such as enzymes, to a compound having the structure of any one of Formulas (I)-(IV).

The term "isotope" refers to atoms with the same number of protons but a different number of neutrons, and an isotope of a compound of Formula (I) includes any such compound wherein one or more atoms are replaced by an isotope of that atom. For example, carbon 12, the most common form of carbon, has six protons and six neutrons, whereas carbon 13 has six protons and seven neutrons, and carbon 14 has six protons and eight neutrons. Hydrogen has two stable isotopes, deuterium (one proton and one neutron) and tritium (one proton and two neutrons). While fluorine has a number of isotopes, fluorine 19 is longest-lived. Thus, an isotope of a compound having the structure of Formula (I) includes, but not limited to, compounds of Formula (I) wherein one or more carbon 12 atoms are replaced by carbon 13 and/or 14 atoms, wherein one or more hydrogen atoms are replaced with deuterium and/or tritium, and/or wherein one or more fluorine atoms are replaced by fluorine 19.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

All chiral, diastereomeric, racemic forms of a structure are intended, unless a particular stereochemistry or isomeric form is specifically indicated. Compounds of the present invention include enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the invention.

"Isolated optical isomer" means a compound which has been substantially purified from the corresponding optical isomer(s) of the same formula. In an embodiment, the isolated isomer is at least about 80% pure by weight, or at least 80% pure by weight, or at least 85% pure by weight. In other embodiments, the isolated isomer is at least 90% pure by weight, or at least 98% pure by weight, or at least 99% pure by weight.

"Substantially enantiomerically or diastereomerically" pure means a level of enantiomeric or diastereomeric enrichment of one enantiomer with respect to the other enantiomer or diastereomer of at least 80%, and in other embodiments means in excess of 80%, 85%, 90%, 95%, 98%, 99%, 99.5% or 99.9%.

Enantiomers are sometimes called optical isomers because a pure enantiomer rotates plane-polarized light in a particular direction. If the light rotates clockwise, then that enantiomer is labeled "(+)" or "d" for dextrorotatory, its counterpart will rotate the light counterclockwise and is labeled "(−)" or "l" for levorotatory.

The terms "racemate" and "racemic mixture" are frequently used interchangeably. A racemate is an equal mixture of two enantiomers. A racemate is labeled "(±)" because it is not optically active (i.e., will not rotate plane-polarized light in either direction since its constituent enantiomers cancel each other out).

All structures encompassed within a claim are "chemically feasible," by which is meant that the structure depicted by any combination or subcombination of optional substituents meant to be recited by the claim is physically capable of existence with at least some stability as can be determined by the laws of structural chemistry and by experimentation. Structures that are not chemically feasible are not within a claimed set of compounds. Further, isotopes of the atoms depicted (such as deuterium and tritium in the case of hydrogen) are encompassed within the scope of this invention.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

The term "heteroatoms" as used herein refers to non-carbon and non-hydrogen atoms, capable of forming covalent bonds with carbon, and is not otherwise limited. Typical heteroatoms are N, O, and S. When sulfur (S) is referred to, it is understood that the sulfur can be in any of the oxidation states in which it is found, thus including sulfoxides (R—S(O)—R') and sulfones (R—S(O)$_2$—R'), unless the oxidation state is specified; thus, the term "sulfone" encompasses only the sulfone form of sulfur; the term "sulfide" encompasses only the sulfide (R—S—R') form of sulfur.

In one embodiment, compounds are provided having the structure of the following Formula II, including stereoisomers, hydrates, solvates, isotopes or pharmaceutically acceptable salts thereof:

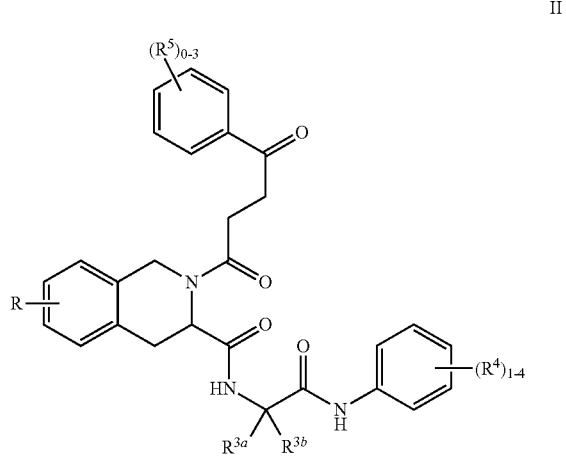

II wherein R, $R^{3a}$, $R^{3b}$, $R^4$, and $R^5$ are as defined above.

In one embodiment, compounds are provided having the structure of the following Formula III, including stereoisomers, hydrates, solvates, or pharmaceutically acceptable salts thereof:

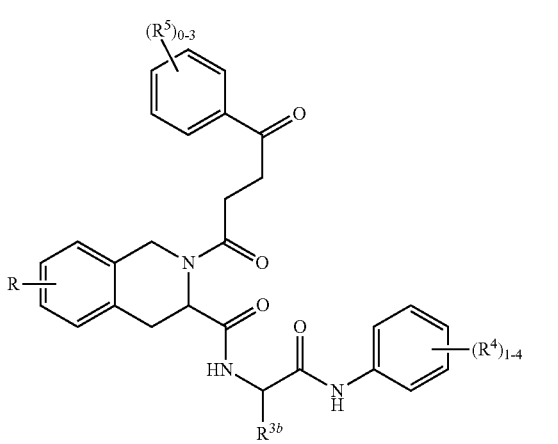

III wherein R, $R^{3b}$, $R^4$ and $R^5$ are as defined above.

In one embodiment, compounds are provided having the structure of the following Formula IV, including stereoisomers, hydrates, solvates, isotopes or pharmaceutically acceptable salts thereof:

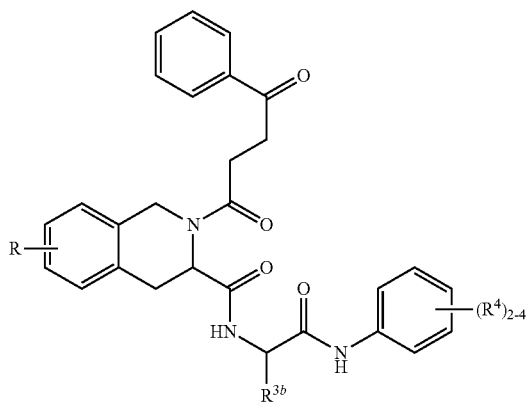

IV wherein R, R³ᵇ and R⁴ are as defined above.

In one embodiment, compounds are provided having the structure of the following Formula V, including stereoisomers, hydrates, solvates, isotopes or pharmaceutically acceptable salts thereof:

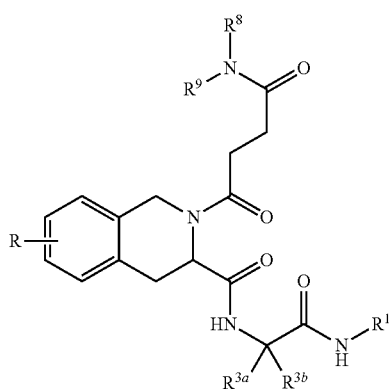

V wherein R, R¹, R³ᵃ, R³ᵇ, R⁸ and R⁹ are as defined above.

In one embodiment, compounds are provided having the structure of the following Formula VI, including stereoisomers, hydrates, solvates, isotopes or pharmaceutically acceptable salts thereof:

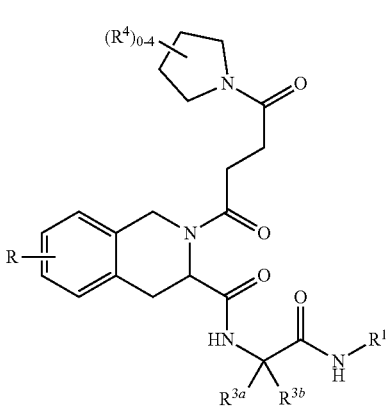

VI wherein R, R¹, R³ᵃ, R³ᵇ and R⁴ are as defined above.

In one embodiment, compounds are provided having the structure of the following Formula VII, including stereoisomers, hydrates, solvates, isotopes or pharmaceutically acceptable salts thereof:

VII wherein R, R¹, R³ᵃ, R³ᵇ and R⁴ are as defined above.

In one embodiment, compounds are provided having the structure of the following Formula VIII, including stereoisomers, hydrates, solvates, isotopes or pharmaceutically acceptable salts thereof:

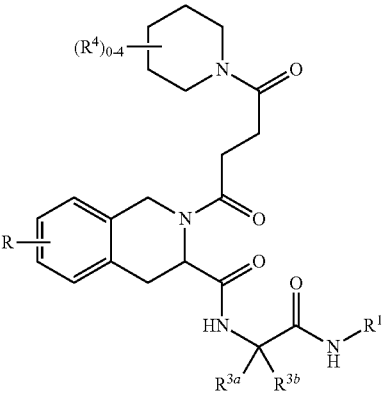

VIII wherein R, R¹, R³ᵃ, R³ᵇ and R⁴ are as defined above.

In one embodiment, compounds are provided having the structure of the following Formula IX, including stereoisomers, hydrates, solvates, isotopes or pharmaceutically acceptable salts thereof:

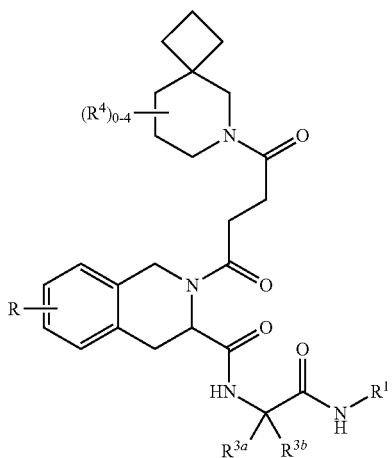

wherein R, $R^1$, $R^{3a}$, $R^{3b}$ and $R^4$ are as defined above.

In one embodiment, compounds are provided having the structure of the following Formula X, including stereoisomers, hydrates, solvates, isotopes or pharmaceutically acceptable salts thereof:

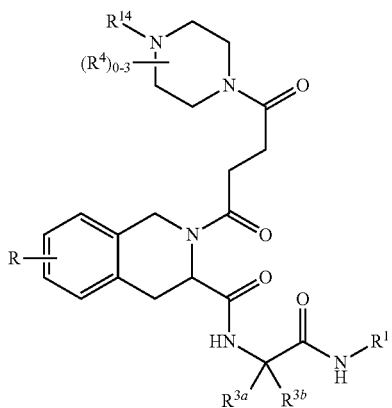

wherein $R^{14}$ is H or $R^4$ and R, $R^1$, $R^{3a}$, $R^{3b}$ and $R^4$ are as defined above.

In the following more specific embodiments, the various "R" groups are set forth in more detail with respect to the compounds of each of Formulas I through V, as applicable to the R group being further defined. For example, reference to $R^1$ below is intended to further limit the compounds of Formulas I, V and VI, but not Formulas II, III and IV (since $R^1$ has already been further limited in those structures). Similarly, reference to $R^{3b}$ below would be applicable to each of Formulas I through VI since such structures list $R^{3a}$ as a variable group.

In one embodiment, $R^1$ is aryl.

In one embodiment, $R^1$ is aryl substituted with 1-4 $R^4$ groups.

In one embodiment, $R^1$ is aryl substituted with 0 $R^4$ groups.

In one embodiment, $R^1$ is heteroaryl.

In one embodiment, $R^1$ is heteroaryl substituted with 1-4 $R^4$ groups.

In one embodiment, $R^1$ is heteroaryl substituted with 0 $R^4$ groups.

In one embodiment, $R^1$ is substituted with at least one $R^4$ group. In another embodiment, $R^1$ is substituted with at least two $R^4$ groups. In another embodiment, $R^1$ is substituted with at least three $R^4$ groups.

In one embodiment, $R^4$ is selected from halo and alkyl. In one embodiment, $R^4$ is halo. In another embodiment, $R^4$ is alkyl.

In one embodiment, $R^1$ is substituted with at least three $R^4$ groups selected from halo and alkyl.

In one embodiment, $R^2$ is aryl.

In one embodiment, $R^2$ is heteroaryl.

In one embodiment, $R^2$ is substituted with zero $R^5$ groups. In another embodiment, $R^2$ is substituted with at least one $R^5$ groups. In another embodiment, $R^2$ is substituted with at least two $R^5$ groups. In another embodiment, $R^2$ is substituted with three $R^5$ groups.

In one embodiment, $R^{3a}$ is hydrogen.

In another embodiment, $R^{3a}$ is alkyl.

In one embodiment, $R^{3a}$ is hydrogen and $R^{3b}$ is a nitrogen or amine-containing moiety of carbon with at least one nitrogen atom and hydrogen.

In one embodiment, $R^{3a}$ is hydrogen and $R^{3b}$ is alkyl substituted with —$NR^{10}R^{11}$, —$N^+R^{10}R^{11}R^{12}$, —$NR^{12}C(=O)NR^{10}R^{11}$, —$C(=O)NR^{10}R^{11}$, —$NR^{12}C(=O)CH_2NR^{10}R^{11}$, —$NR^{12}N(=NR^{13})NR^{10}R^{11}$, —$NR^{10}SO_2R^{11}$, wherein $R^{10}$, $R^{11}$, $R^{12}$ and $R^{13}$ are independently hydrogen or $R^4$. In another embodiment, $R^{10}$, $R^{11}$, $R^{12}$ and $R^{13}$ are independently hydrogen, alkyl or haloalkyl.

In another embodiment, $R^{3a}$ is hydrogen and $R^{3b}$ is alkyl substituted with —$NR^{10}R^{11}$ or —$N^+R^{10}R^{11}R^{12}$.

In another embodiment, $R^{3a}$ is hydrogen and $R^{3b}$ is —$(CH_2)_{2-4}NH_2$.

In one embodiment, $R^{3a}$ is hydrogen and $R^{3b}$ is:

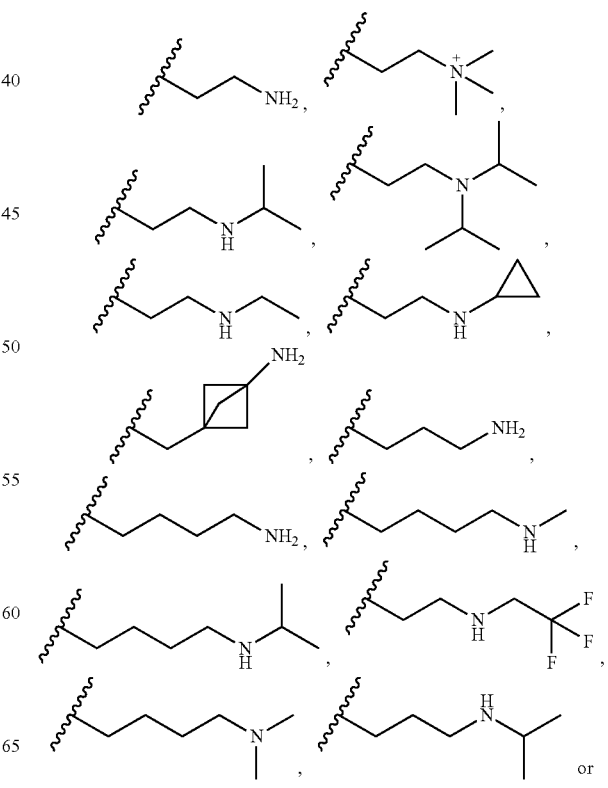

-continued

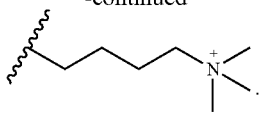

In another embodiment, $R^{3a}$ is hydrogen and $R^{3b}$ is alkyl substituted with $-NR^{12}N(=NR^{13})NR^{10}R^{11}$.

In one embodiment, $R^{3a}$ is hydrogen and $R^{3b}$ is:

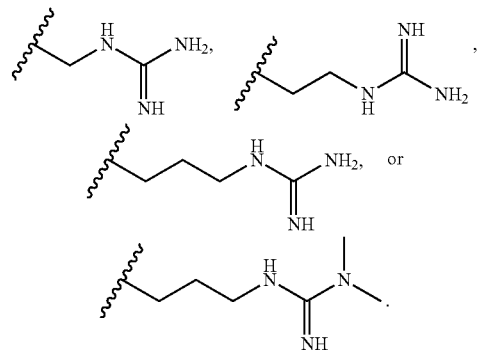

In another embodiment, $R^{3a}$ is hydrogen and $R^{3b}$ is alkyl substituted with $-C(=O)NR^{10}R^{11}$, $-NR^{12}C(=O)NR^{10}R^{11}$ or $-NR^{12}C(=O)CH_2NR^{10}R^{11}$.

In one embodiment, $R^{3a}$ is hydrogen and $R^{3b}$ is:

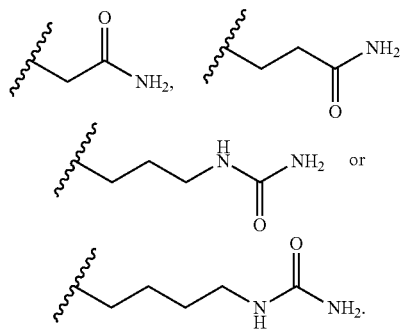

In one embodiment, $R^{3a}$ is hydrogen and $R^{3b}$ is a nitrogen-containing heterocyclyl substituted with 0-4 $R^4$ groups.

In one embodiment, $R^{3a}$ is hydrogen and $R^{3b}$ is:

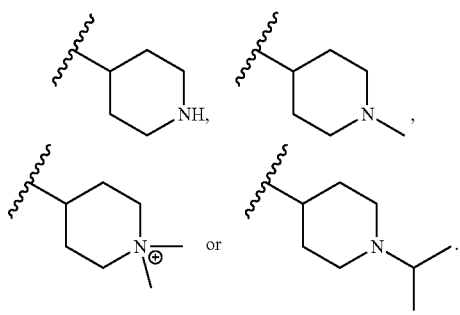

In one embodiment, $R^{3a}$ is hydrogen and $R^{3b}$ is alkyl substituted with a nitrogen-containing heterocyclyl substituted with 0-4 $R^4$ groups.

In one embodiment, $R^{3a}$ is hydrogen and $R^{3b}$ is:

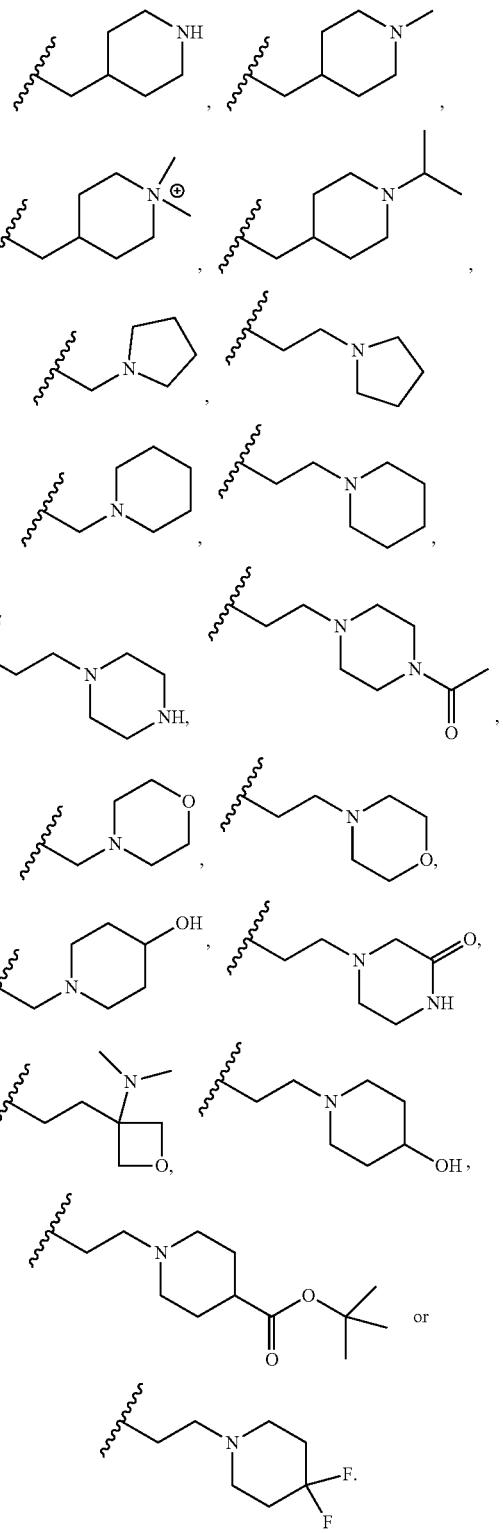

In one embodiment, $R^{3a}$ is hydrogen and $R^{3b}$ is heteroaryl substituted with 0-4 $R^4$ groups.

In one embodiment, $R^{3a}$ is hydrogen and $R^{3b}$ is alkyl substituted with heteroaryl substituted with 0-4 $R^4$ groups.

In one embodiment, $R^{3a}$ is hydrogen and $R^{3b}$ is:

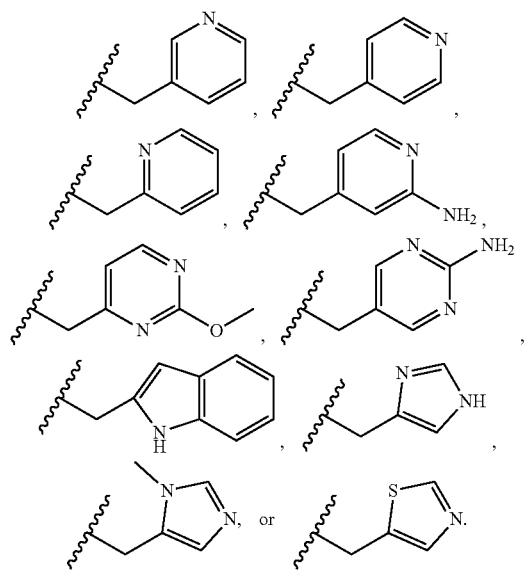

In one embodiment, $R^{3a}$ and $R^{3b}$ are taken together with the carbon atom to which they are attached to form a cyclic nitrogen- or amine-containing moiety of carbon, at least one nitrogen atom and hydrogen.

In one embodiment, $R^{3a}$ and $R^{3b}$ are taken together with the carbon atom to which they are attached to form a nitrogen-containing heterocyclyl substituted with 0-4 $R^4$ groups.

In one embodiment, $R^{3a}$ and $R^{3b}$ are taken together with the carbon atom to which they are attached to form:

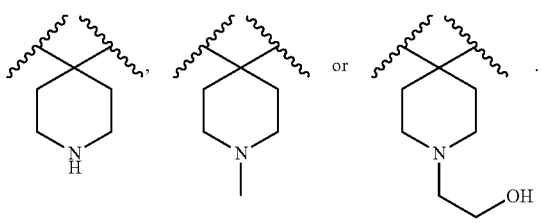

In one embodiment, $R^2$ is $-NR^8R^9$, wherein $R^8$ is hydrogen or alkyl and $R^9$ is alkyl or aryl substituted with 0-4 $R^4$ groups.

In one embodiment, $-NR^8R^9$ is:

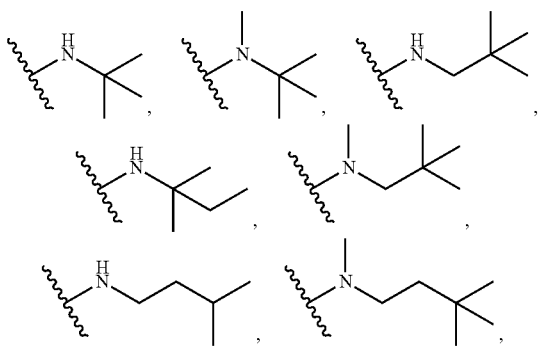

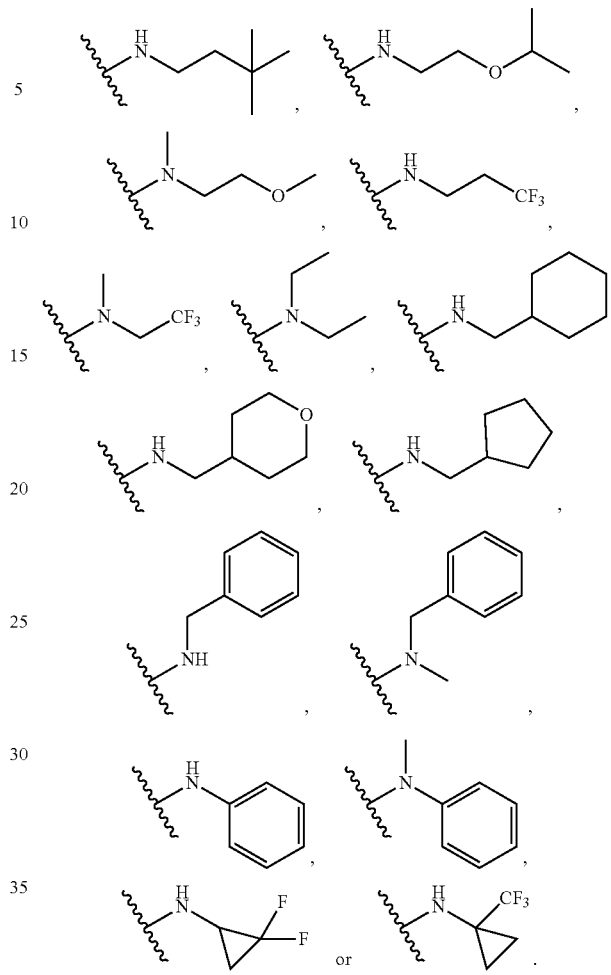

In one embodiment, $R^1$ is $-NR^8R^9$ and $R^8$ and $R^9$ taken together with the nitrogen atom to which they are attached form a heterocyclyl substituted with 0-4 $R^4$ groups and optionally substituted with oxo (=O) or thioxo (=S).

In one embodiment, $-NR^8R^9$ is:

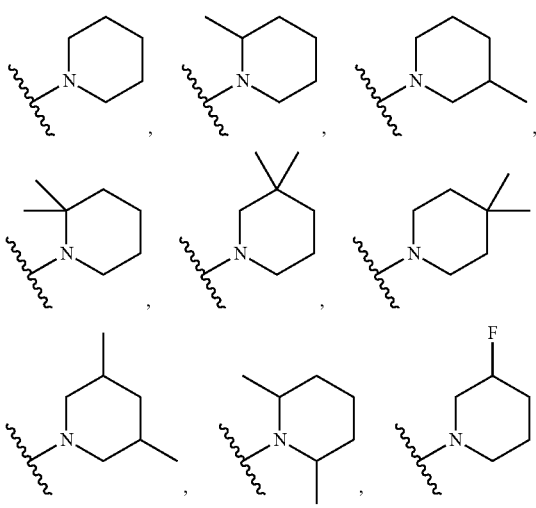

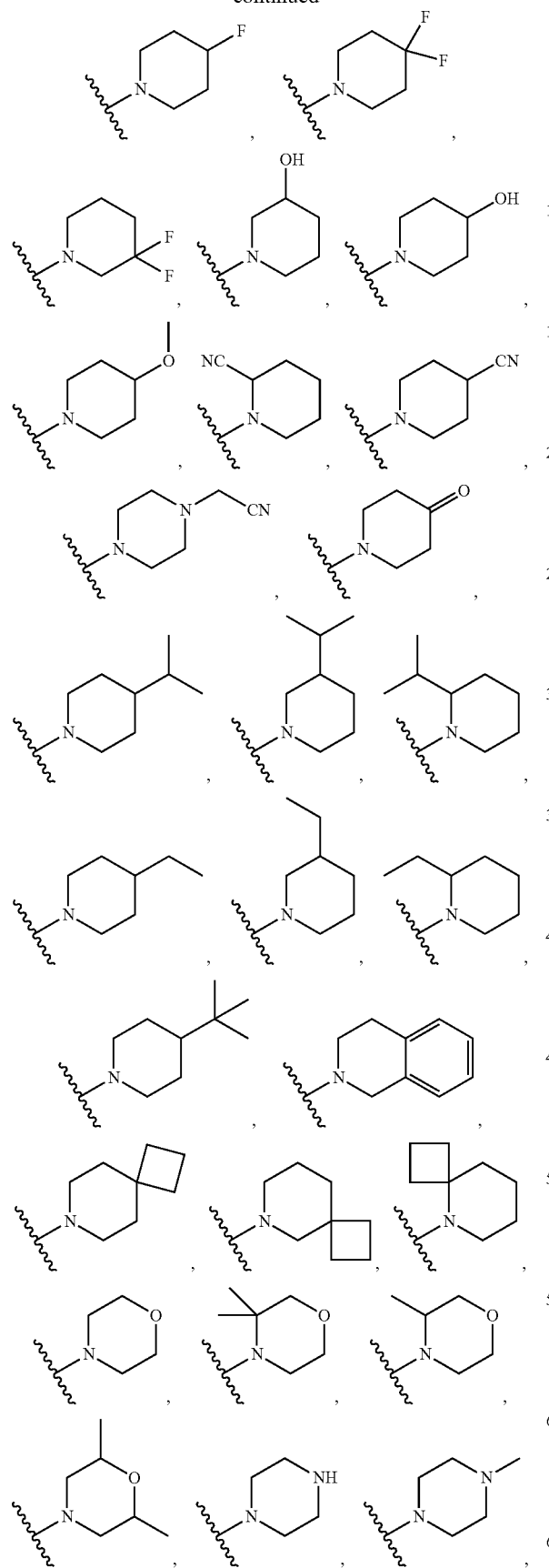
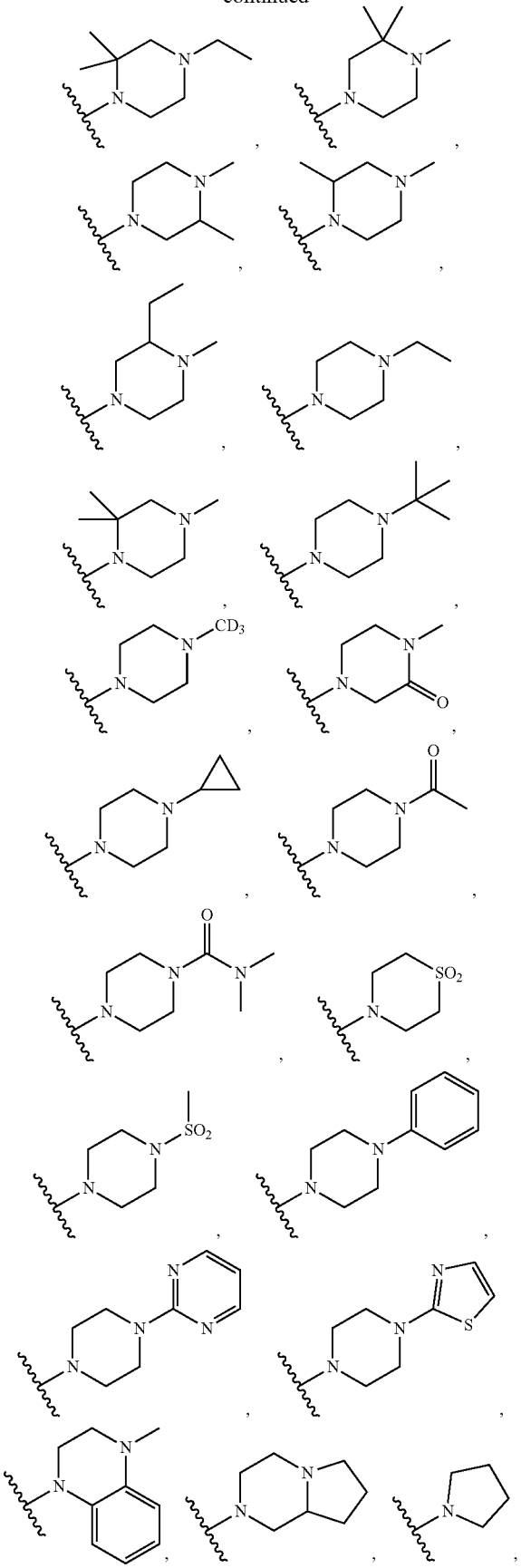

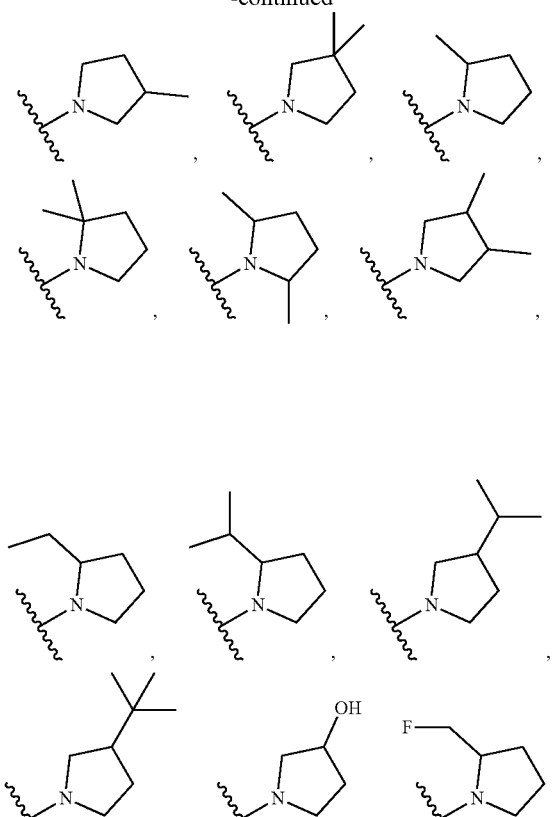
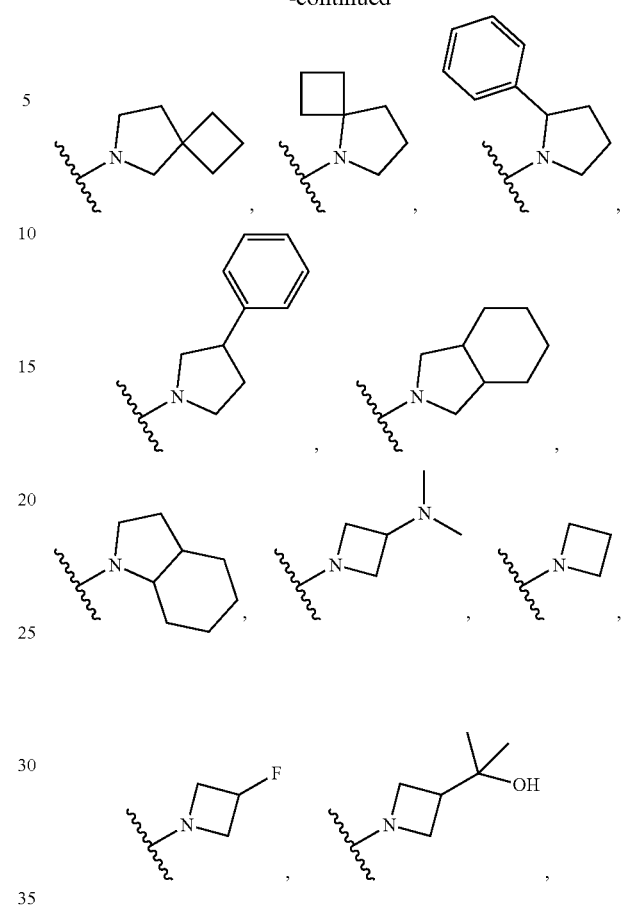
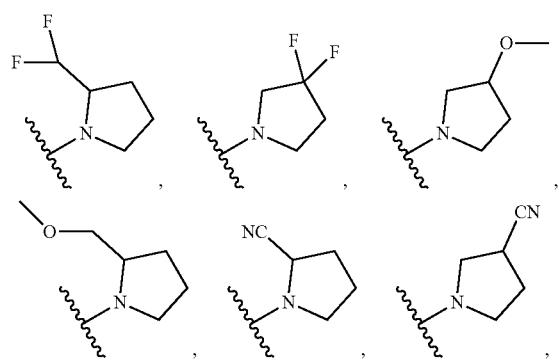
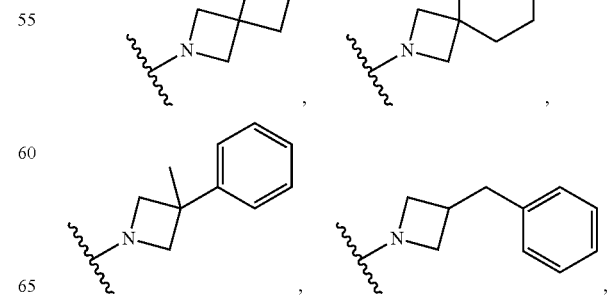

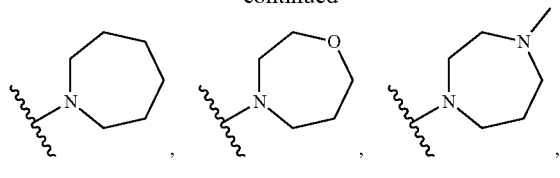

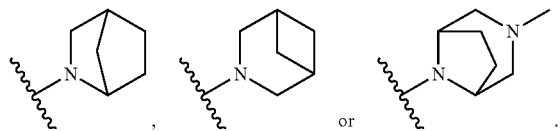

or

In one embodiment, compounds are provided having the structure of the following Formula XI, including hydrates, solvates, isotopes or pharmaceutically acceptable salts thereof:

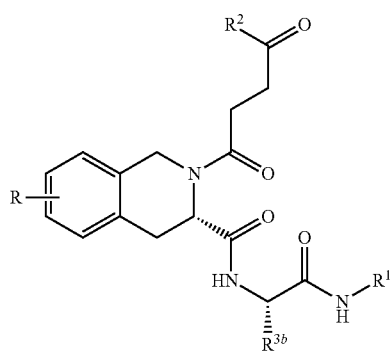

XI wherein R, $R^1$, $R^2$ and $R^{3b}$ are as defined above.

In one embodiment, compounds are provided having the structure of the following Formula XII, including hydrates, solvates, isotopes or pharmaceutically acceptable salts thereof:

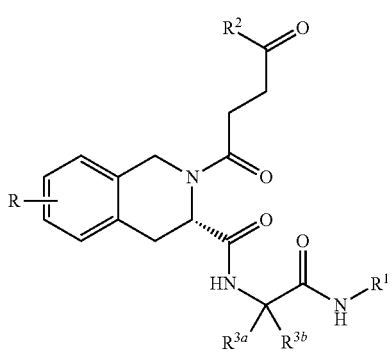

XII wherein

R, $R^1$ and $R^2$ are as defined above; and $R^{3a}$ and $R^{3b}$ taken together with the carbon to which they are attached form a cyclic nitrogen- or amine-containing moiety of carbon.

In another embodiment, a compound is provided having the structure as shown in the following Table A.

TABLE A

REPRESENTATIVE COMPOUNDS

| Structure | Cpd. No. |
|---|---|
| 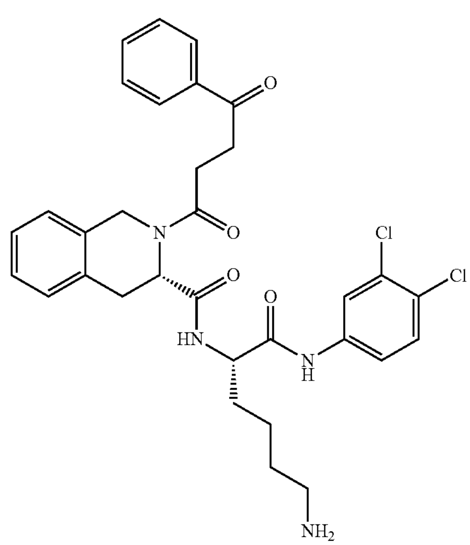 [SMILES: NCCCC[C@H](NC(=O)[C@@H]1Cc2ccccc2CN1C(=O)CCC(=O)c1ccccc1)C(=O)Nc1ccc(Cl)c(Cl)c1] | 1-1 |

TABLE A-continued
REPRESENTATIVE COMPOUNDS
| Structure | Cpd. No. |
|---|---|
| 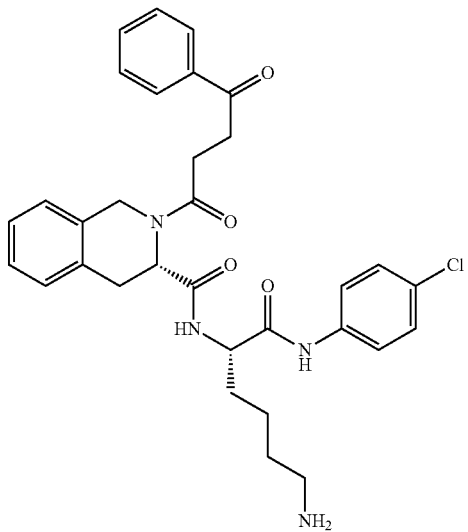 [SMILES: NCCCC[C@H](NC(=O)[C@@H]1Cc2ccccc2CN1C(=O)CCC(=O)c1ccccc1)C(=O)Nc1ccc(Cl)cc1] | 1-2 |
| 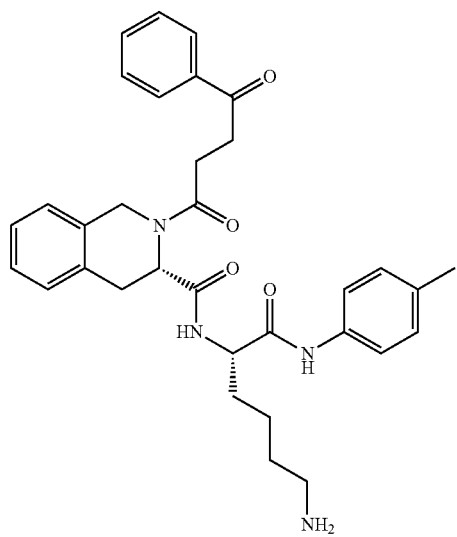 [SMILES: Cc1ccc(NC(=O)[C@H](CCCCN)NC(=O)[C@@H]2Cc3ccccc3CN2C(=O)CCC(=O)c2ccccc2)cc1] | 1-3 |

TABLE A-continued
REPRESENTATIVE COMPOUNDS
| Structure | Cpd. No. |
|---|---|
| 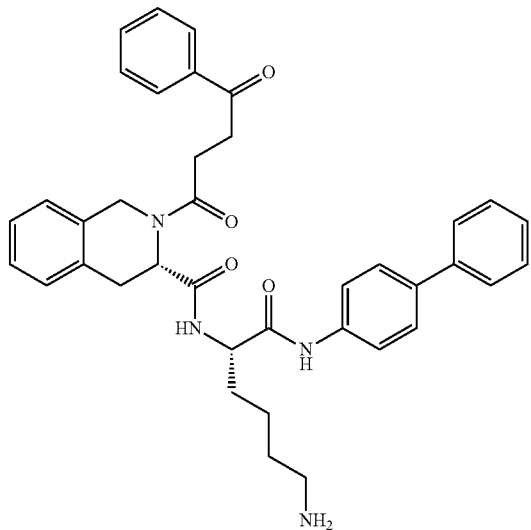 [SMILES: NCCCC[C@H](NC(=O)[C@@H]1Cc2ccccc2CN1C(=O)CCC(=O)c1ccccc1)C(=O)Nc1ccc(-c2ccccc2)cc1] | 1-5 |
| 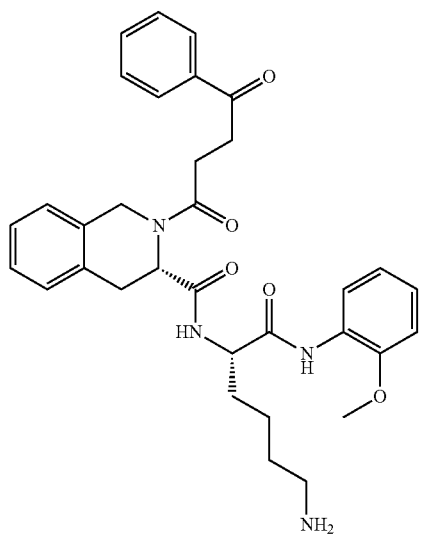 [SMILES: COc1ccccc1NC(=O)[C@H](CCCCN)NC(=O)[C@@H]1Cc2ccccc2CN1C(=O)CCC(=O)c1ccccc1] | 1-6 |

TABLE A-continued
REPRESENTATIVE COMPOUNDS
| Structure | Cpd. No. |
|---|---|
| 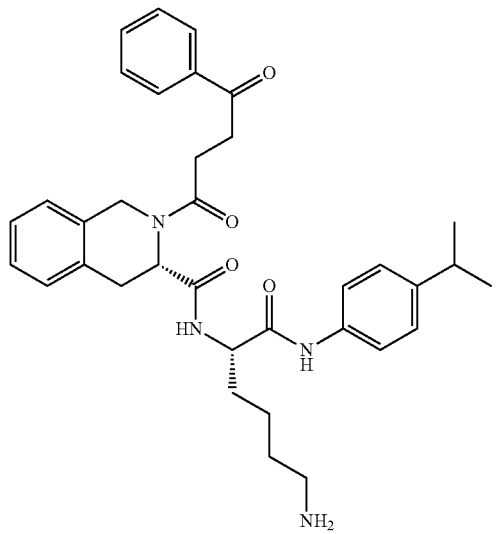 | 1-7 |
| 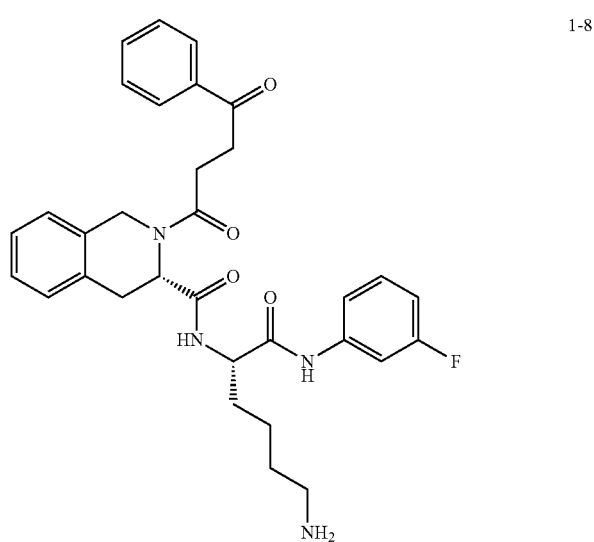 | 1-8 |

TABLE A-continued
REPRESENTATIVE COMPOUNDS
| Structure | Cpd. No. |
|---|---|
| 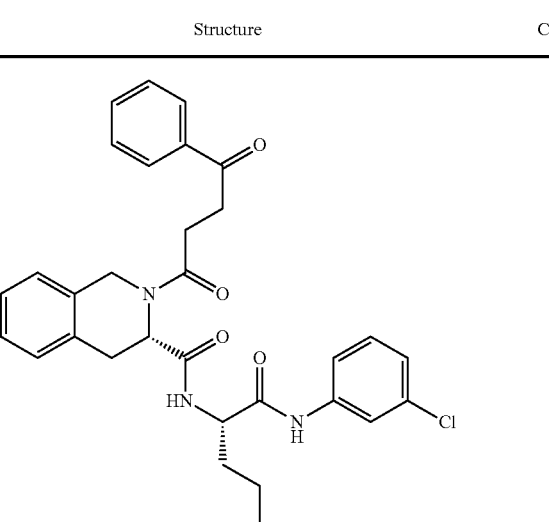 | 1-9 |
| 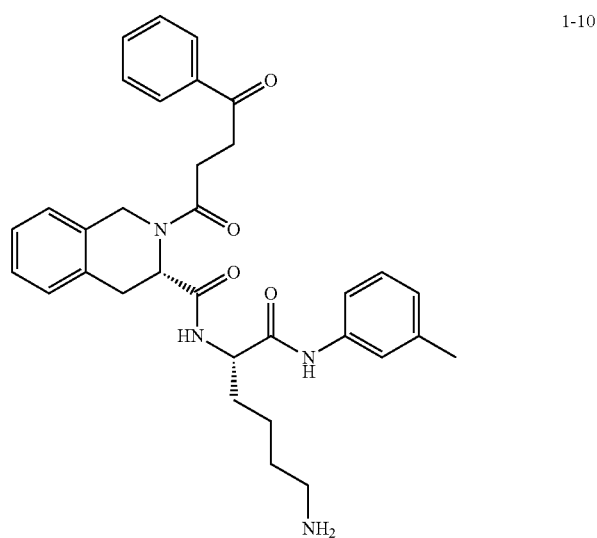 | 1-10 |

TABLE A-continued
REPRESENTATIVE COMPOUNDS
| Structure | Cpd. No. |
|---|---|
| 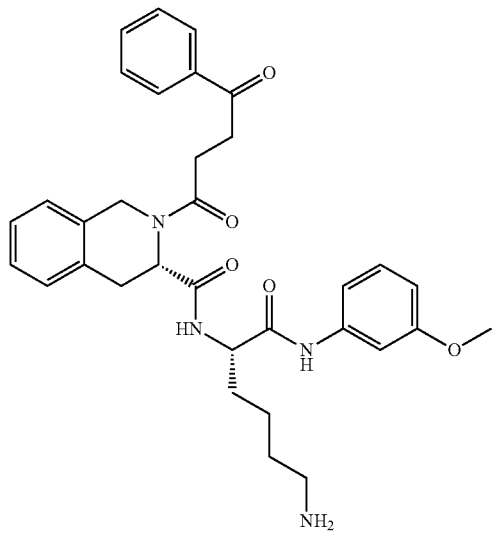 [SMILES: COc1cccc(NC(=O)[C@H](CCCCN)NC(=O)[C@@H]2Cc3ccccc3CN2C(=O)CCC(=O)c2ccccc2)c1] | 1-11 |
| 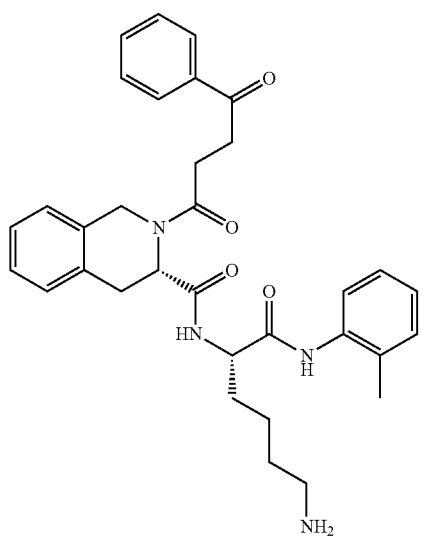 [SMILES: Cc1ccccc1NC(=O)[C@H](CCCCN)NC(=O)[C@@H]1Cc2ccccc2CN1C(=O)CCC(=O)c1ccccc1] | 1-12 |

TABLE A-continued
REPRESENTATIVE COMPOUNDS
| Structure | Cpd. No. |
|---|---|
| 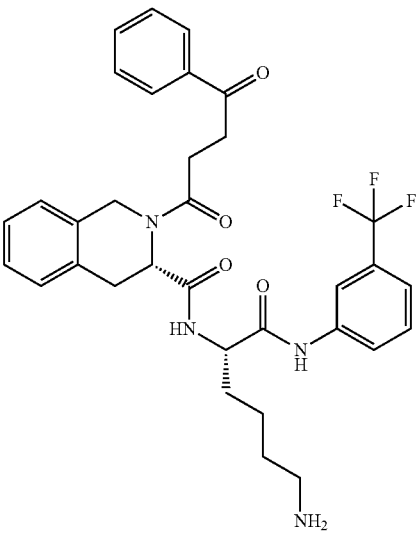 [SMILES: NCCCC[C@H](NC(=O)[C@@H]1Cc2ccccc2CN1C(=O)CCC(=O)c1ccccc1)C(=O)Nc1cccc(C(F)(F)F)c1] | 1-13 |
| 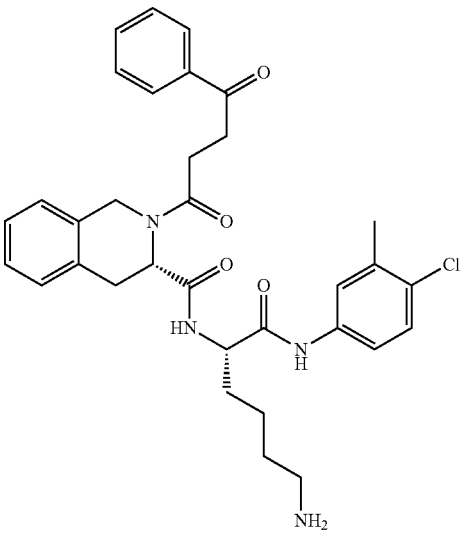 [SMILES: Cc1cc(NC(=O)[C@H](CCCCN)NC(=O)[C@@H]2Cc3ccccc3CN2C(=O)CCC(=O)c2ccccc2)ccc1Cl] | 1-14 |

TABLE A-continued
REPRESENTATIVE COMPOUNDS
| Structure | Cpd. No. |
|---|---|
| 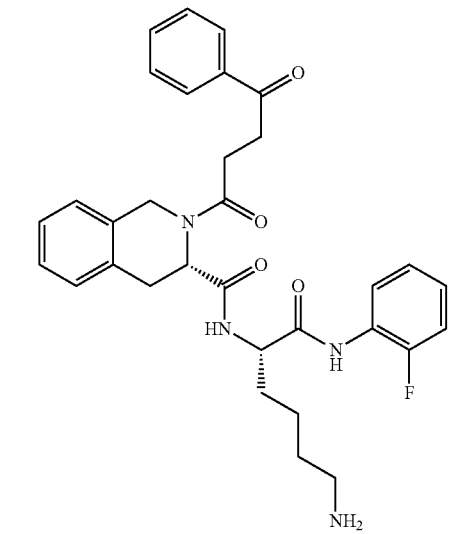 [SMILES: NCCCC[C@H](NC(=O)[C@@H]1Cc2ccccc2CN1C(=O)CCC(=O)c1ccccc1)C(=O)Nc1ccccc1F] | 1-15 |
| 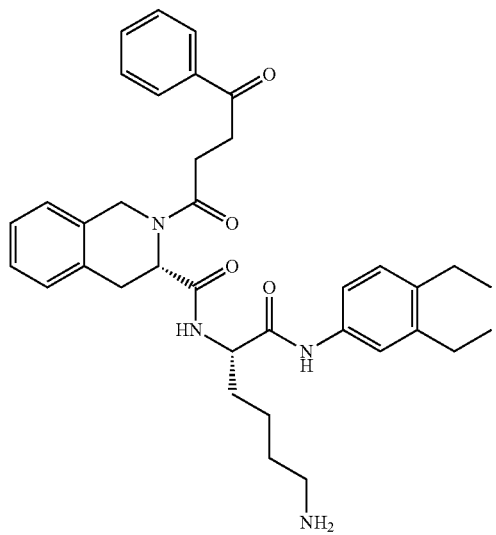 [SMILES: CCc1ccc(NC(=O)[C@H](CCCCN)NC(=O)[C@@H]2Cc3ccccc3CN2C(=O)CCC(=O)c2ccccc2)cc1CC] | 1-16 |

TABLE A-continued
| REPRESENTATIVE COMPOUNDS | |
|---|---|
| Structure | Cpd. No. |
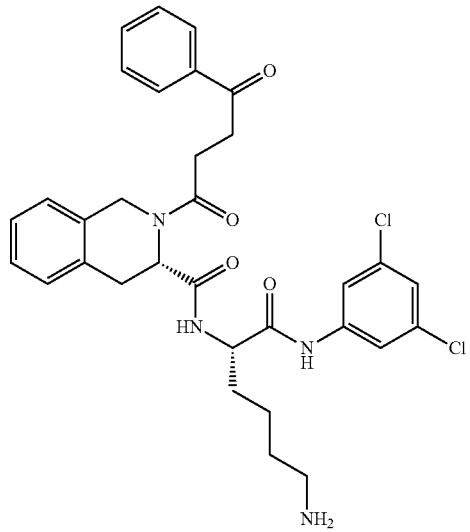 [SMILES: NCCCC[C@H](NC(=O)[C@@H]1Cc2ccccc2CN1C(=O)CCC(=O)c1ccccc1)C(=O)Nc1cc(Cl)cc(Cl)c1]
1-17
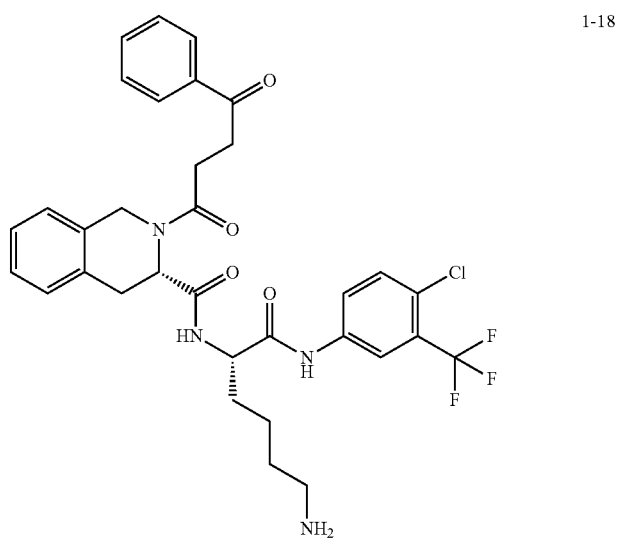
1-18

TABLE A-continued
REPRESENTATIVE COMPOUNDS
| Structure | Cpd. No. |
|---|---|
| 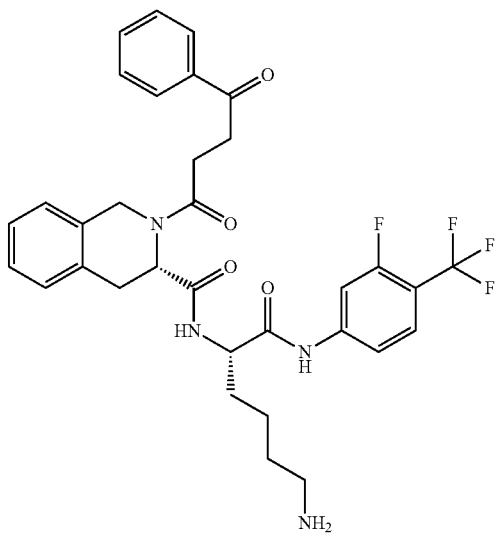 [SMILES: NCCCC[C@H](NC(=O)[C@@H]1Cc2ccccc2CN1C(=O)CCC(=O)c1ccccc1)C(=O)Nc1ccc(C(F)(F)F)c(F)c1] | 1-19 |
| 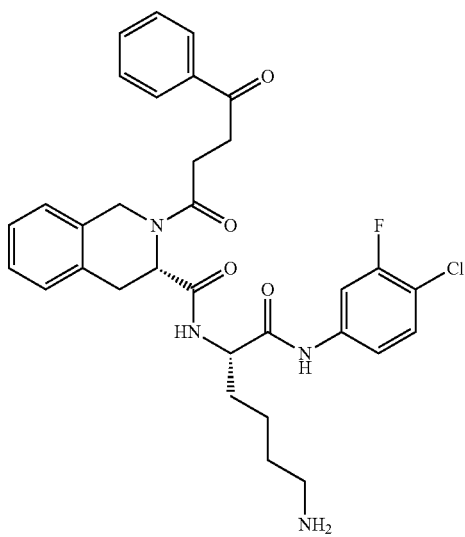 [SMILES: NCCCC[C@H](NC(=O)[C@@H]1Cc2ccccc2CN1C(=O)CCC(=O)c1ccccc1)C(=O)Nc1ccc(Cl)c(F)c1] | 1-20 |

TABLE A-continued

REPRESENTATIVE COMPOUNDS

| Structure | Cpd. No. |
|---|---|
| 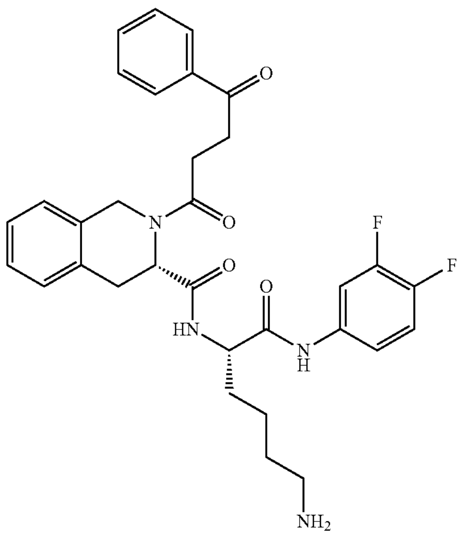 [SMILES: NCCCC[C@H](NC(=O)[C@@H]1Cc2ccccc2CN1C(=O)CCC(=O)c1ccccc1)C(=O)Nc1ccc(F)c(F)c1] | 1-21 |
| 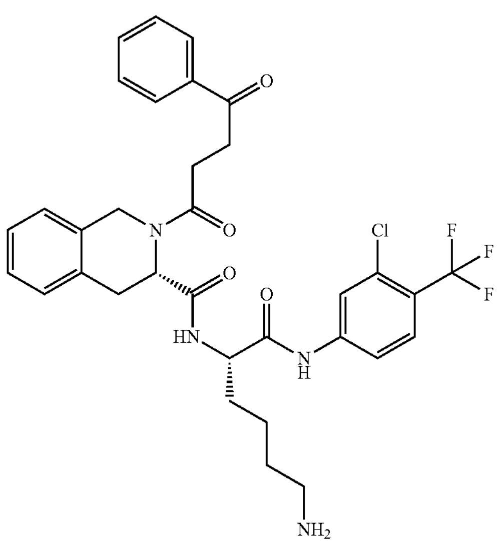 [SMILES: NCCCC[C@H](NC(=O)[C@@H]1Cc2ccccc2CN1C(=O)CCC(=O)c1ccccc1)C(=O)Nc1ccc(C(F)(F)F)c(Cl)c1] | 1-22 |

TABLE A-continued
REPRESENTATIVE COMPOUNDS
| Structure | Cpd. No. |
|---|---|
| 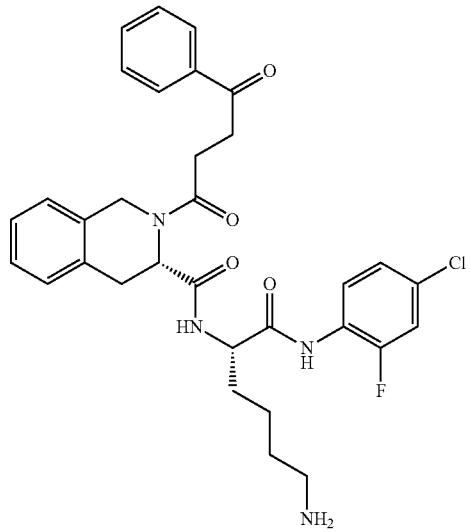 [SMILES: NCCCC[C@H](NC(=O)[C@@H]1Cc2ccccc2CN1C(=O)CCC(=O)c1ccccc1)C(=O)Nc1ccc(Cl)cc1F] | 1-23 |
| 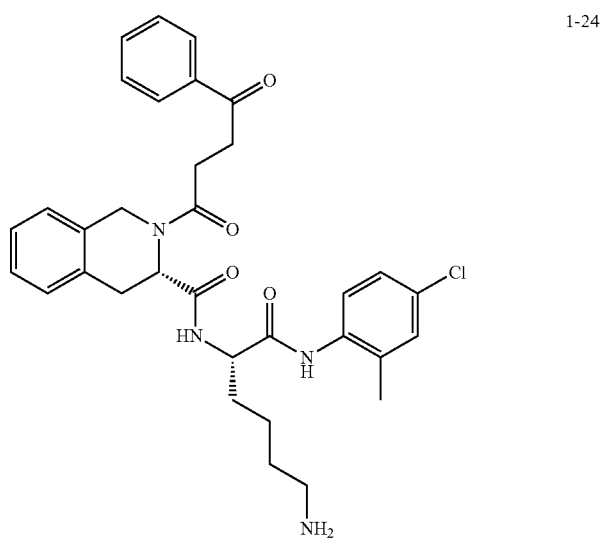 | 1-24 |

TABLE A-continued
REPRESENTATIVE COMPOUNDS
| Structure | Cpd. No. |
|---|---|
| 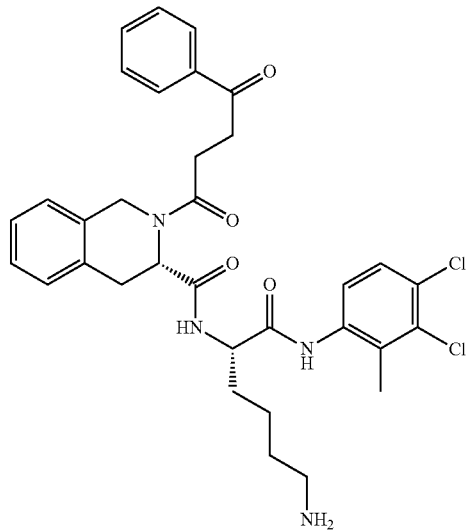 [SMILES: Cc1c(NC(=O)[C@H](CCCCN)NC(=O)[C@@H]2Cc3ccccc3CN2C(=O)CCC(=O)c2ccccc2)ccc(Cl)c1Cl] | 1-25 |
| 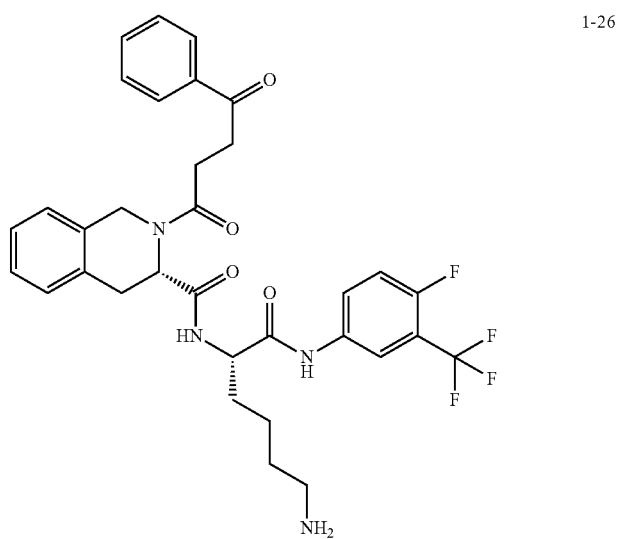 | 1-26 |

TABLE A-continued
REPRESENTATIVE COMPOUNDS
| Structure | Cpd. No. |
|---|---|
| 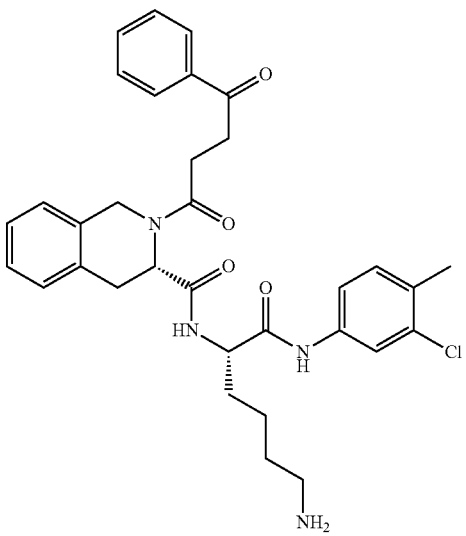 [SMILES: Cc1ccc(NC(=O)[C@H](CCCCN)NC(=O)[C@@H]2Cc3ccccc3CN2C(=O)CCC(=O)c2ccccc2)cc1Cl] | 1-27 |
| 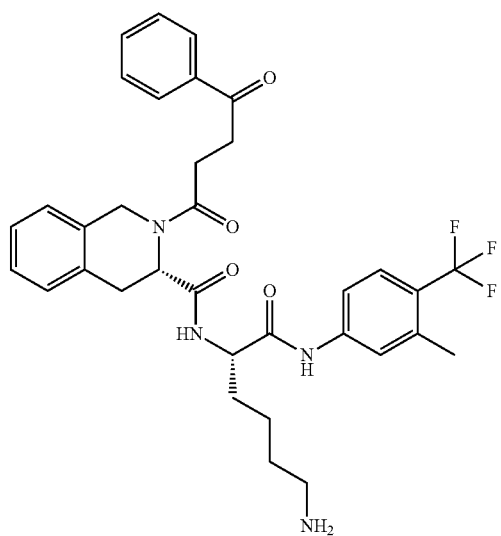 [SMILES: Cc1cc(NC(=O)[C@H](CCCCN)NC(=O)[C@@H]2Cc3ccccc3CN2C(=O)CCC(=O)c2ccccc2)ccc1C(F)(F)F] | 1-28 |

TABLE A-continued
REPRESENTATIVE COMPOUNDS
| Structure | Cpd. No. |
|---|---|
| 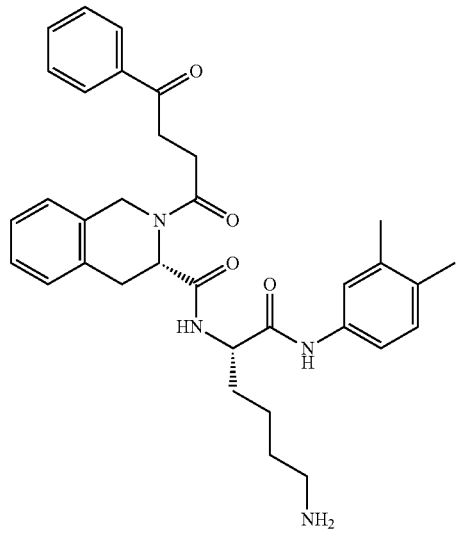 [SMILES: Cc1ccc(NC(=O)[C@H](CCCCN)NC(=O)[C@@H]2Cc3ccccc3CN2C(=O)CCC(=O)c2ccccc2)cc1C] | 1-29 |
| 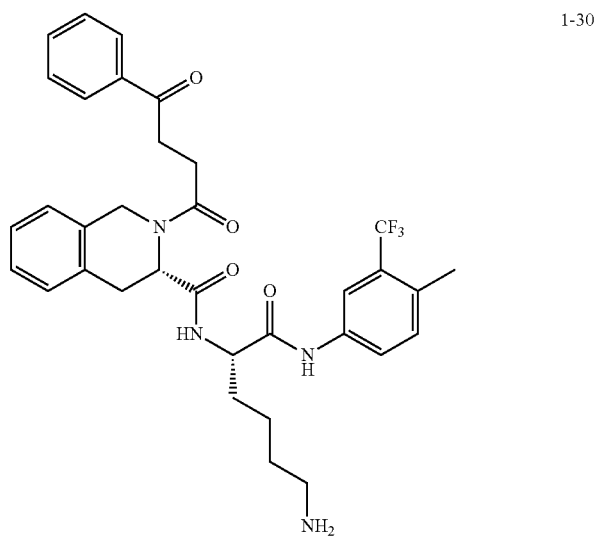 | 1-30 |

TABLE A-continued
REPRESENTATIVE COMPOUNDS
| Structure | Cpd. No. |
|---|---|
| 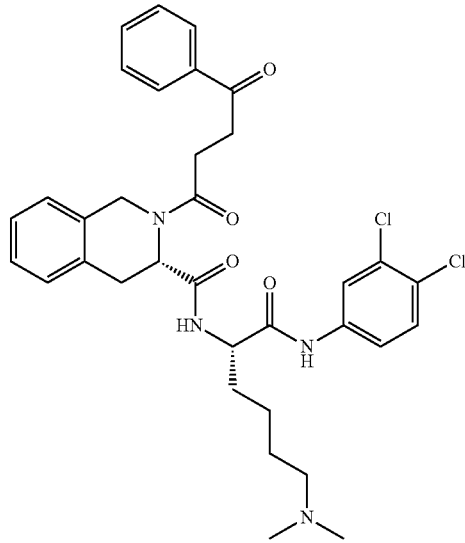 [SMILES: CN(C)CCCC[C@H](NC(=O)[C@@H]1Cc2ccccc2CN1C(=O)CCC(=O)c1ccccc1)C(=O)Nc1ccc(Cl)c(Cl)c1] | 1-31 |
| 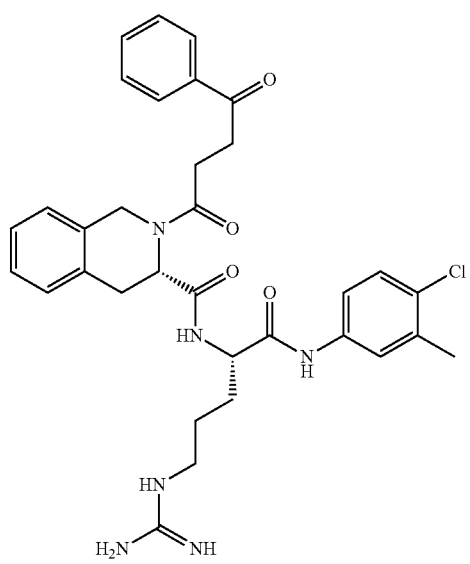 [SMILES: Cc1cc(NC(=O)[C@H](CCCNC(=N)N)NC(=O)[C@@H]2Cc3ccccc3CN2C(=O)CCC(=O)c2ccccc2)ccc1Cl] | 1-32 |

TABLE A-continued

REPRESENTATIVE COMPOUNDS

| Structure | Cpd. No. |
|---|---|
| 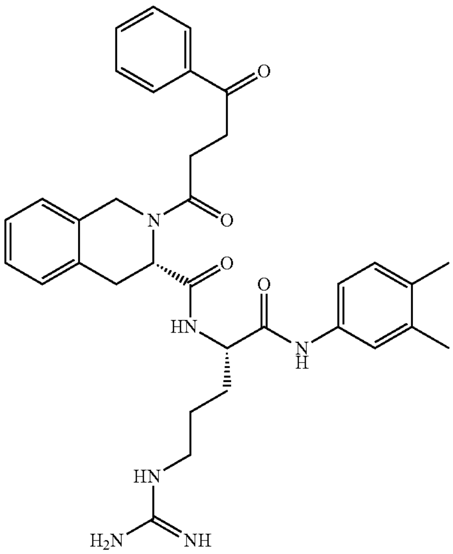 [SMILES: Cc1ccc(NC(=O)[C@H](CCCNC(=N)N)NC(=O)[C@@H]2Cc3ccccc3CN2C(=O)CCC(=O)c2ccccc2)cc1C] | 1-33 |
| 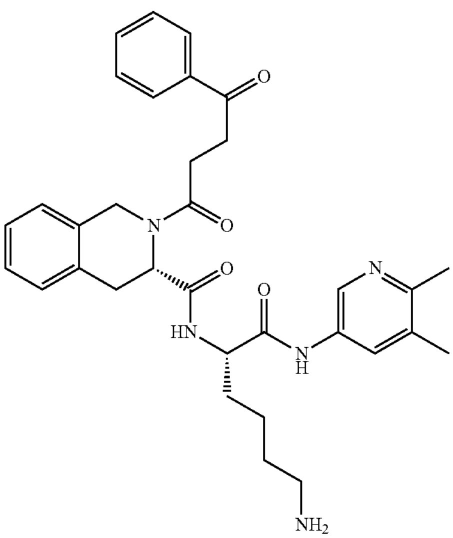 [SMILES: Cc1cc(NC(=O)[C@H](CCCCN)NC(=O)[C@@H]2Cc3ccccc3CN2C(=O)CCC(=O)c2ccccc2)cnc1C] | 1-34 |
| 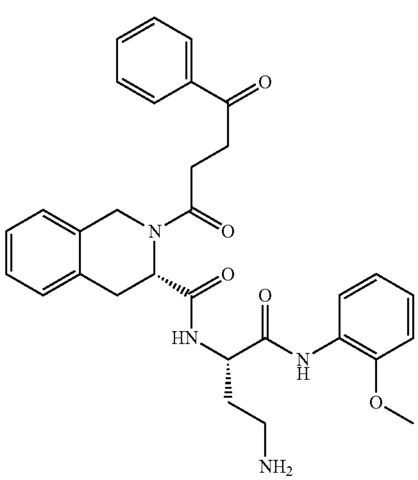 [SMILES: COc1ccccc1NC(=O)[C@H](CCN)NC(=O)[C@@H]1Cc2ccccc2CN1C(=O)CCC(=O)c1ccccc1] | 1-35 |

TABLE A-continued
REPRESENTATIVE COMPOUNDS
| Structure | Cpd. No. |
|---|---|
| 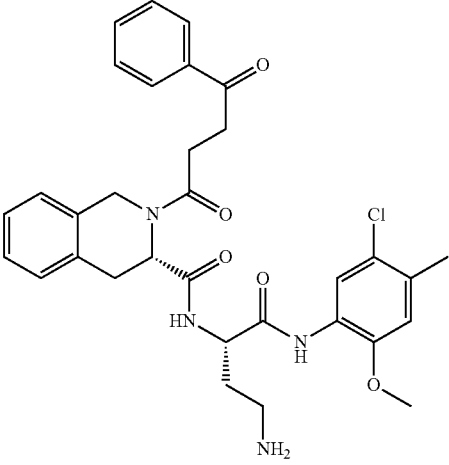 [SMILES: COc1cc(C)c(Cl)cc1NC(=O)[C@H](CCN)NC(=O)[C@@H]1Cc2ccccc2CN1C(=O)CCC(=O)c1ccccc1] | 1-36 |
| 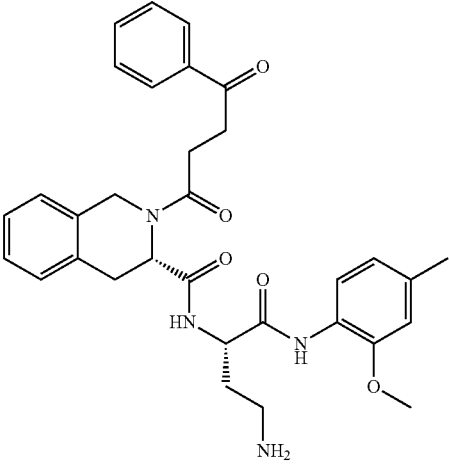 [SMILES: COc1cc(C)ccc1NC(=O)[C@H](CCN)NC(=O)[C@@H]1Cc2ccccc2CN1C(=O)CCC(=O)c1ccccc1] | 1-37 |
| 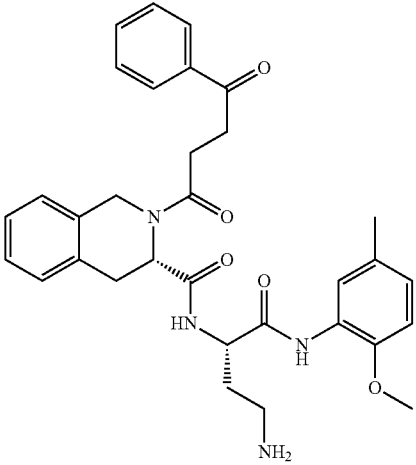 [SMILES: COc1ccc(C)cc1NC(=O)[C@H](CCN)NC(=O)[C@@H]1Cc2ccccc2CN1C(=O)CCC(=O)c1ccccc1] | 1-38 |

TABLE A-continued
REPRESENTATIVE COMPOUNDS
| Structure | Cpd. No. |
|---|---|
| 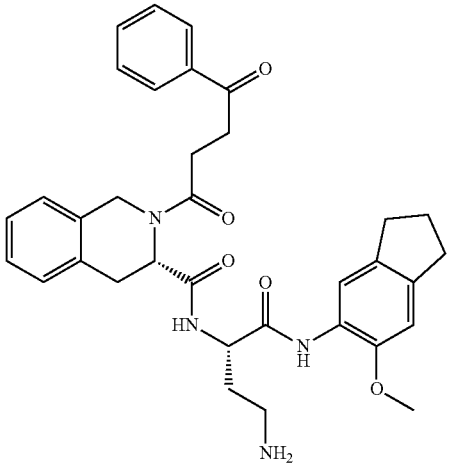 [SMILES: COc1cc2c(cc1NC(=O)[C@H](CCN)NC(=O)[C@@H]1Cc3ccccc3CN1C(=O)CCC(=O)c1ccccc1)CCC2] | 1-39 |
| 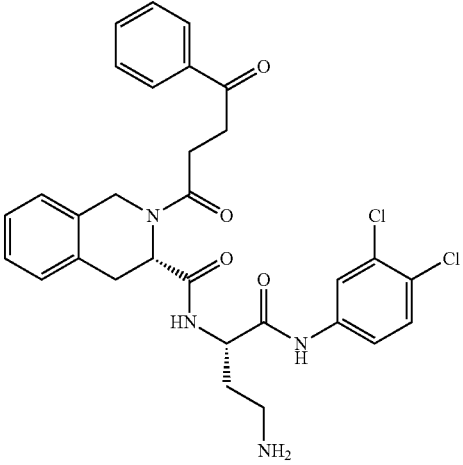 | 2-1 |
| 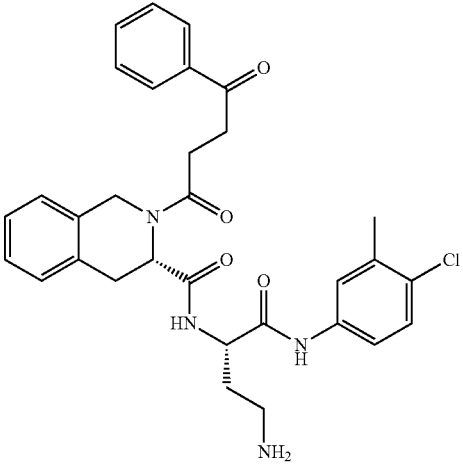 | 2-2 |

TABLE A-continued

REPRESENTATIVE COMPOUNDS

| Structure | Cpd. No. |
|---|---|
| 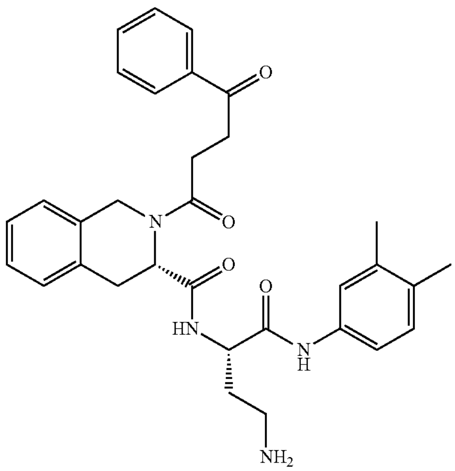 [SMILES: Cc1ccc(NC(=O)[C@H](CCN)NC(=O)[C@@H]2Cc3ccccc3CN2C(=O)CCC(=O)c2ccccc2)cc1C] | 2-3 |
| 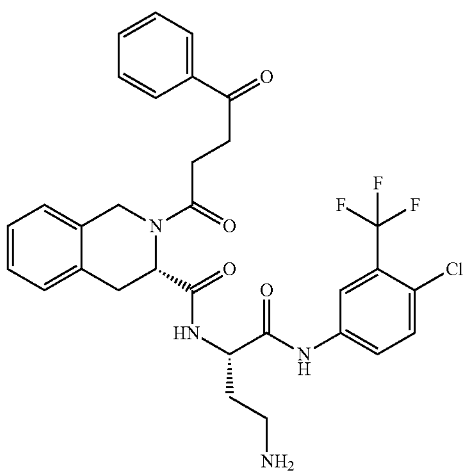 [SMILES: NCC[C@H](NC(=O)[C@@H]1Cc2ccccc2CN1C(=O)CCC(=O)c1ccccc1)C(=O)Nc1ccc(Cl)c(C(F)(F)F)c1] | 2-4 |
| 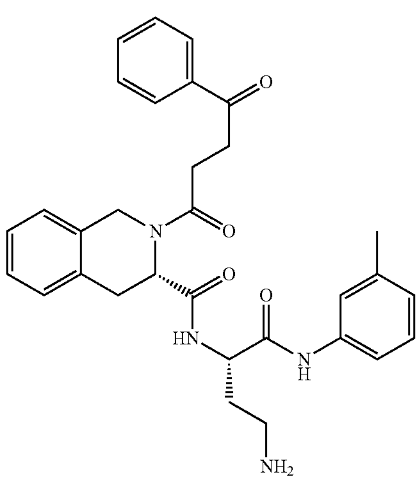 [SMILES: Cc1cccc(NC(=O)[C@H](CCN)NC(=O)[C@@H]2Cc3ccccc3CN2C(=O)CCC(=O)c2ccccc2)c1] | 2-5 |

TABLE A-continued
REPRESENTATIVE COMPOUNDS
| Structure | Cpd. No. |
|---|---|
| 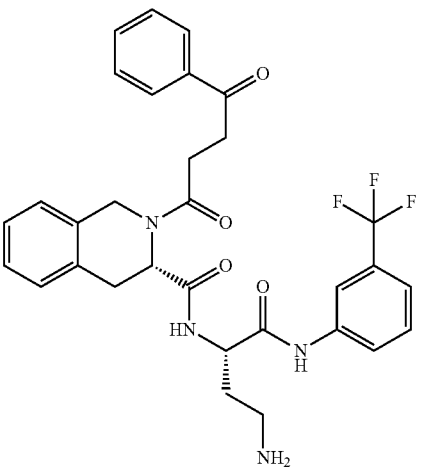 [SMILES: NCC[C@H](NC(=O)[C@@H]1Cc2ccccc2CN1C(=O)CCC(=O)c1ccccc1)C(=O)Nc1cccc(C(F)(F)F)c1] | 2-6 |
| 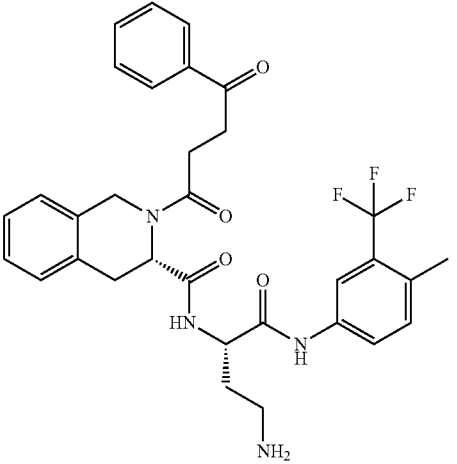 [SMILES: Cc1ccc(NC(=O)[C@H](CCN)NC(=O)[C@@H]2Cc3ccccc3CN2C(=O)CCC(=O)c2ccccc2)cc1C(F)(F)F] | 2-7 |
| 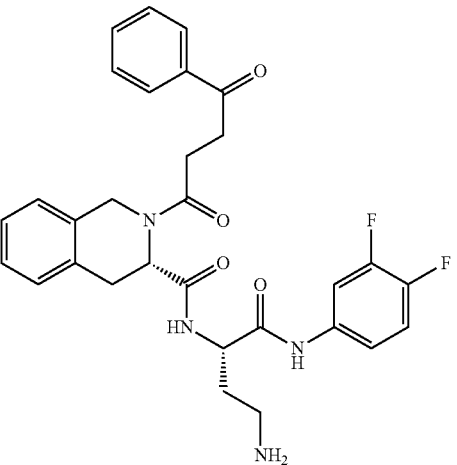 [SMILES: NCC[C@H](NC(=O)[C@@H]1Cc2ccccc2CN1C(=O)CCC(=O)c1ccccc1)C(=O)Nc1ccc(F)c(F)c1] | 2-8 |

TABLE A-continued
REPRESENTATIVE COMPOUNDS
| Structure | Cpd. No. |
|---|---|
| 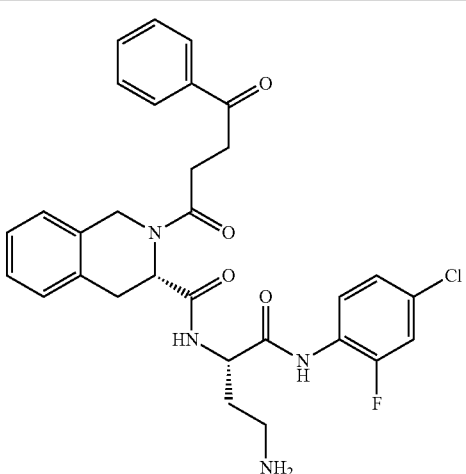 | 2-9 |
| 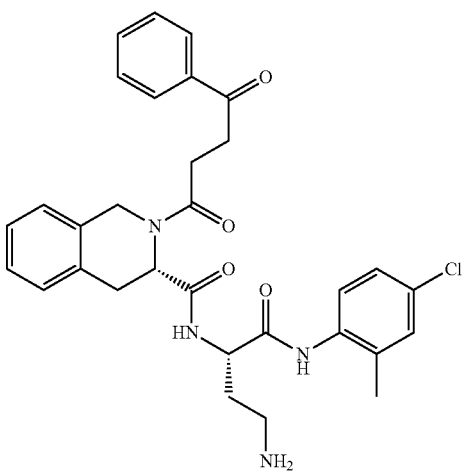 | 2-10 |
| 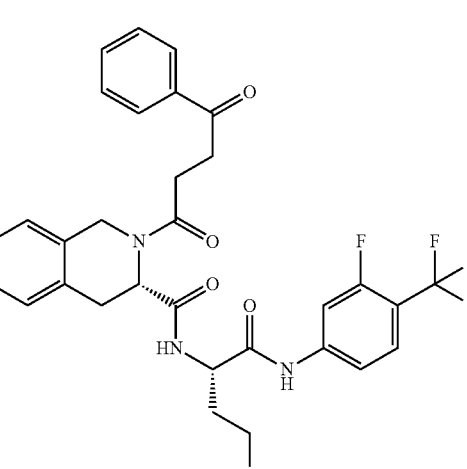 | 2-11 |

TABLE A-continued
REPRESENTATIVE COMPOUNDS
| Structure | Cpd. No. |
|---|---|
| 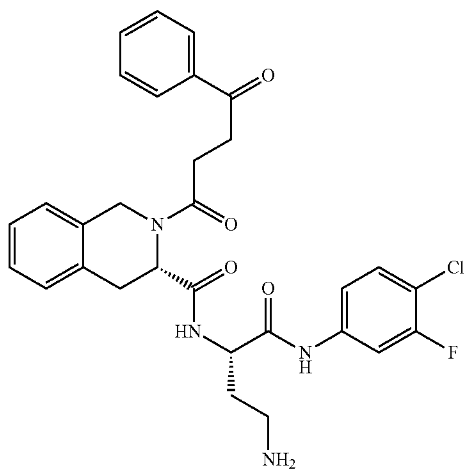 [SMILES: NCC[C@H](NC(=O)[C@@H]1Cc2ccccc2CN1C(=O)CCC(=O)c1ccccc1)C(=O)Nc1ccc(Cl)c(F)c1] | 2-12 |
| 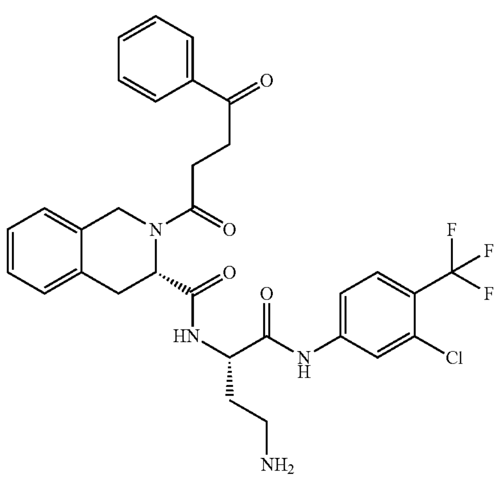 [SMILES: NCC[C@H](NC(=O)[C@@H]1Cc2ccccc2CN1C(=O)CCC(=O)c1ccccc1)C(=O)Nc1ccc(C(F)(F)F)c(Cl)c1] | 2-13 |
| 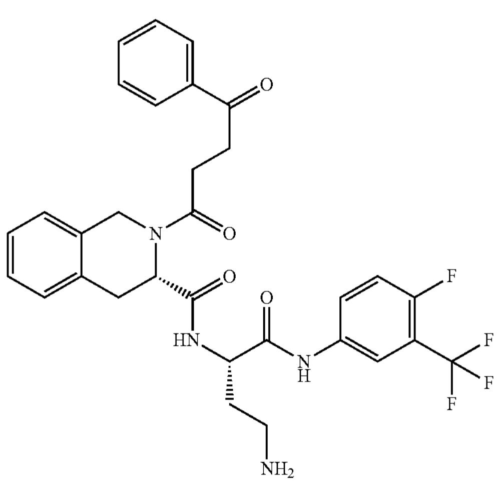 [SMILES: NCC[C@H](NC(=O)[C@@H]1Cc2ccccc2CN1C(=O)CCC(=O)c1ccccc1)C(=O)Nc1ccc(F)c(C(F)(F)F)c1] | 2-14 |

TABLE A-continued

| REPRESENTATIVE COMPOUNDS | |
|---|---|
| Structure | Cpd. No. |
| | 2-15 |
| | 2-16 |
| | 2-17 |

TABLE A-continued

REPRESENTATIVE COMPOUNDS

| Structure | Cpd. No. |
|---|---|
| 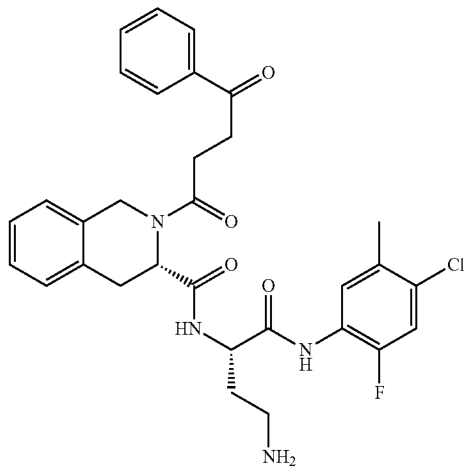 | 2-18 |
| 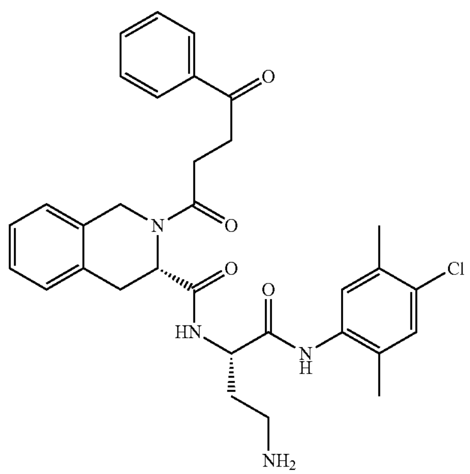 | 2-19 |
| 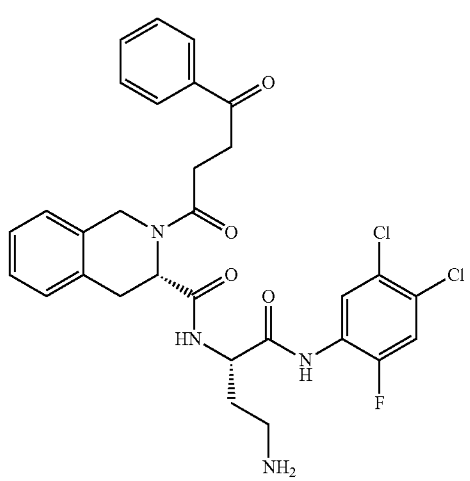 | 2-20 |

TABLE A-continued

| REPRESENTATIVE COMPOUNDS | |
|---|---|
| Structure | Cpd. No. |
| | 2-21 |
| | 2-22 |
| | 2-23 |

TABLE A-continued

REPRESENTATIVE COMPOUNDS

| Structure | Cpd. No. |
|---|---|
| 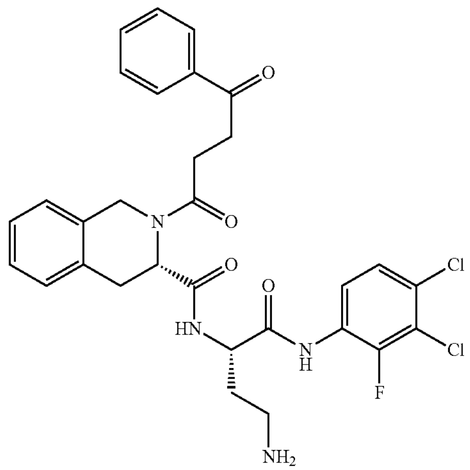 [SMILES: NCC[C@H](NC(=O)[C@@H]1Cc2ccccc2CN1C(=O)CCC(=O)c1ccccc1)C(=O)Nc1ccc(Cl)c(Cl)c1F] | 2-24 |
| 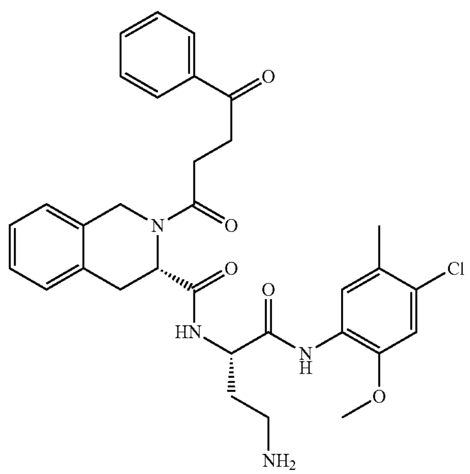 | 2-25 |
| 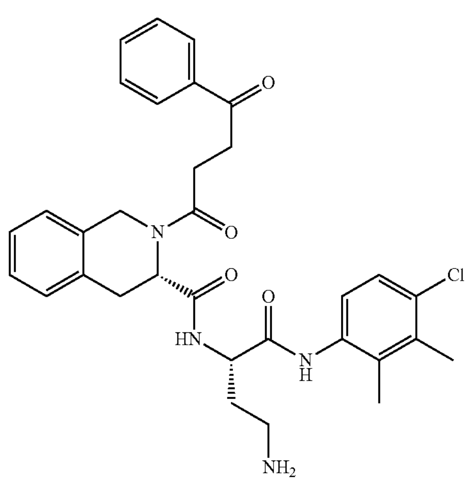 [SMILES: Cc1c(Cl)ccc(NC(=O)[C@H](CCN)NC(=O)[C@@H]2Cc3ccccc3CN2C(=O)CCC(=O)c2ccccc2)c1C] | 2-26 |

TABLE A-continued
REPRESENTATIVE COMPOUNDS
| Structure | Cpd. No. |
|---|---|
| 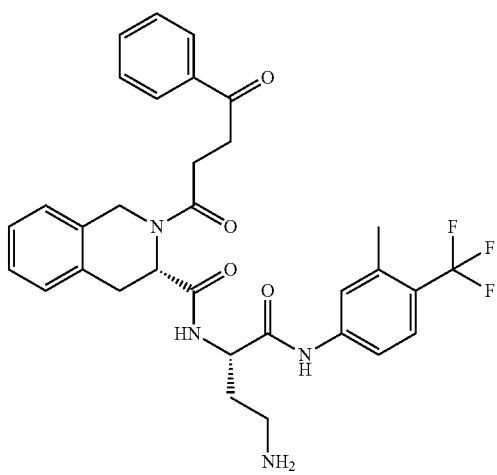 | 2-27 |
| 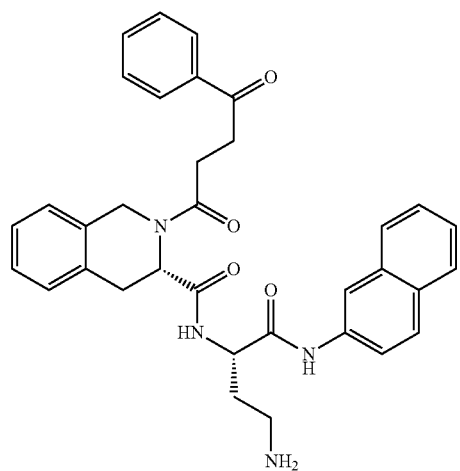 | 2-28 |
| 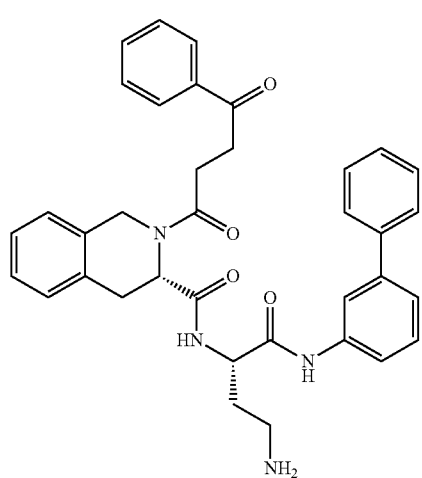 [SMILES: NCC[C@H](NC(=O)[C@@H]1Cc2ccccc2CN1C(=O)CCC(=O)c1ccccc1)C(=O)Nc1cccc(-c2ccccc2)c1] | 2-29 |

TABLE A-continued
REPRESENTATIVE COMPOUNDS
| Structure | Cpd. No. |
|---|---|
| 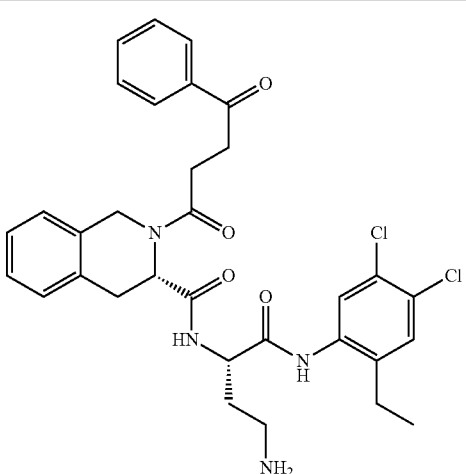 | 2-30 |
| 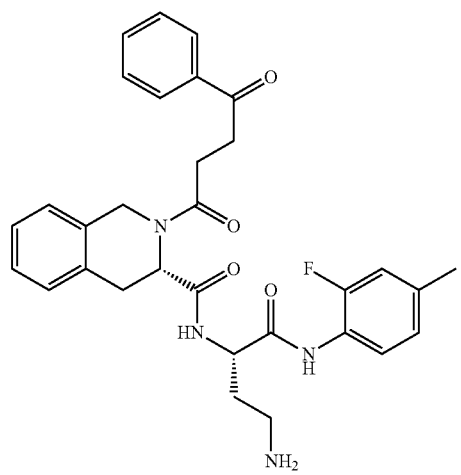 [SMILES: Cc1ccc(NC(=O)[C@H](CCN)NC(=O)[C@@H]2Cc3ccccc3CN2C(=O)CCC(=O)c2ccccc2)c(F)c1] | 2-31 |
| 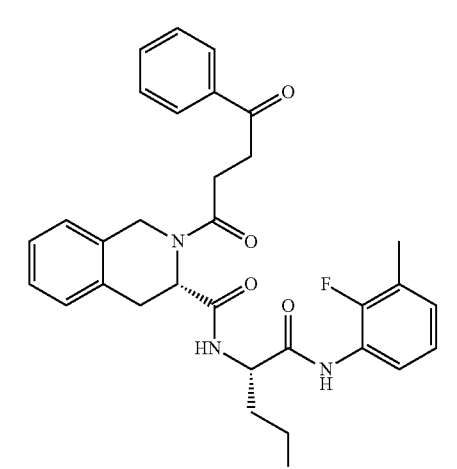 | 2-32 |

TABLE A-continued

REPRESENTATIVE COMPOUNDS

| Structure | Cpd. No. |
|---|---|
| 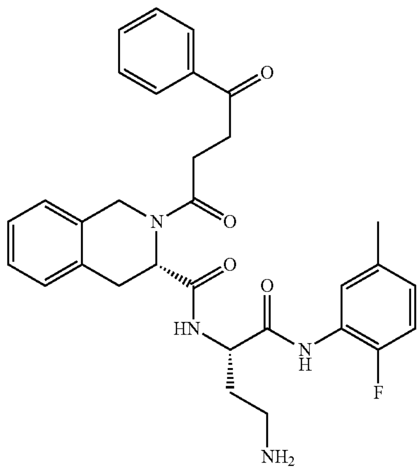 | 2-33 |
| 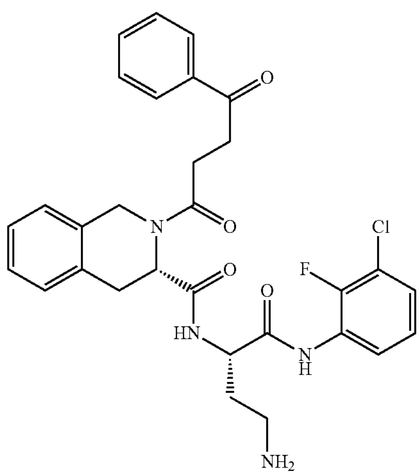 | 2-34 |
| 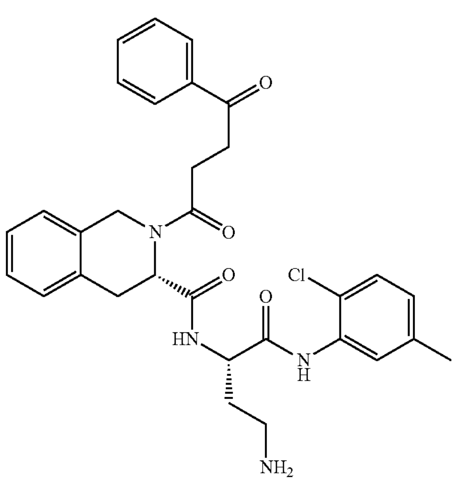 [SMILES: Cc1ccc(Cl)c(NC(=O)[C@H](CCN)NC(=O)[C@@H]2Cc3ccccc3CN2C(=O)CCC(=O)c2ccccc2)c1] | 2-35 |

TABLE A-continued
REPRESENTATIVE COMPOUNDS
| Structure | Cpd. No. |
|---|---|
| 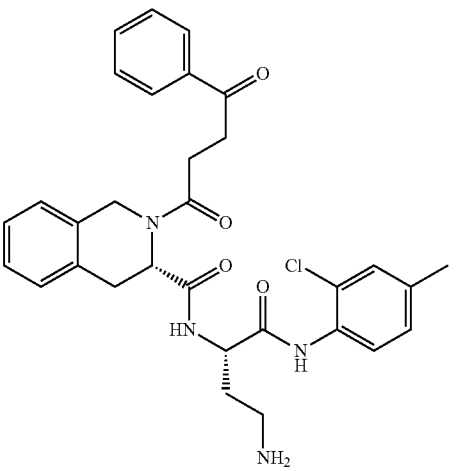 | 2-36 |
| 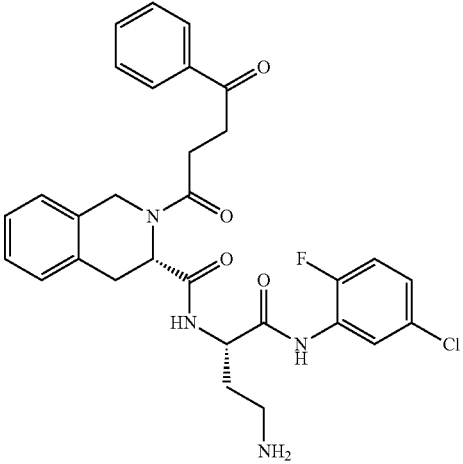 [SMILES: NCC[C@H](NC(=O)[C@@H]1Cc2ccccc2CN1C(=O)CCC(=O)c1ccccc1)C(=O)Nc1cc(Cl)ccc1F] | 2-37 |
| 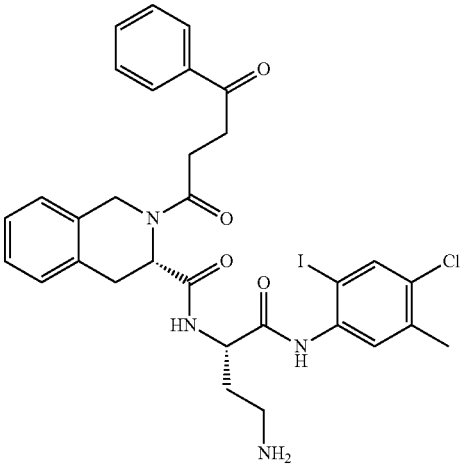 [SMILES: Cc1cc(NC(=O)[C@H](CCN)NC(=O)[C@@H]2Cc3ccccc3CN2C(=O)CCC(=O)c2ccccc2)c(I)cc1Cl] | 2-38 |

TABLE A-continued

REPRESENTATIVE COMPOUNDS

| Structure | Cpd. No. |
|---|---|
| 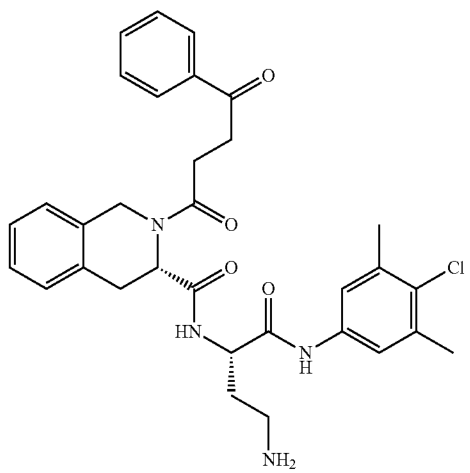 | 2-39 |
| 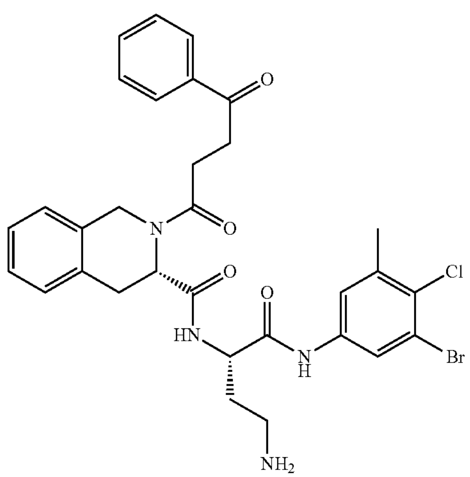 [SMILES: Cc1cc(NC(=O)[C@H](CCN)NC(=O)[C@@H]2Cc3ccccc3CN2C(=O)CCC(=O)c2ccccc2)cc(Br)c1Cl] | 2-40 |
| 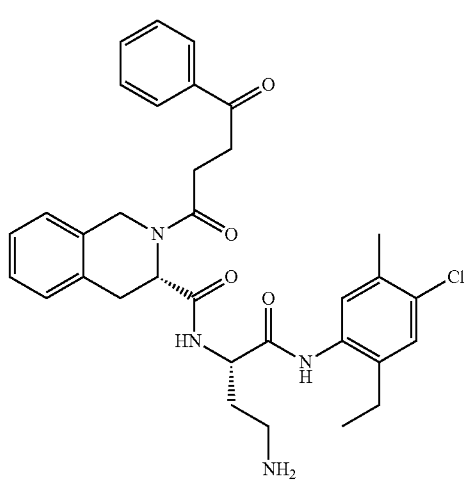 | 2-41 |

TABLE A-continued

REPRESENTATIVE COMPOUNDS

| Structure | Cpd. No. |
|---|---|
| 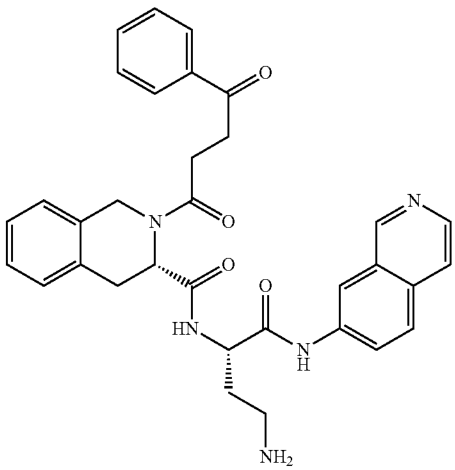 | 2-42 |
| 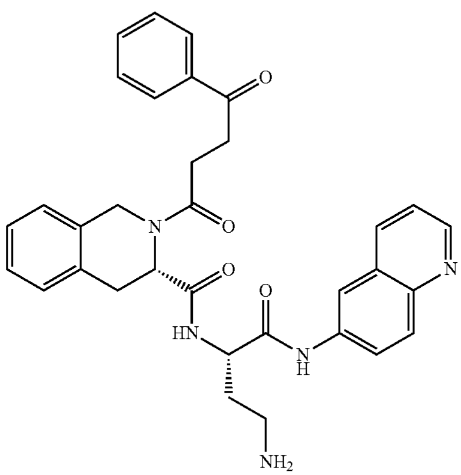 [SMILES: NCC[C@H](NC(=O)[C@@H]1Cc2ccccc2CN1C(=O)CCC(=O)c1ccccc1)C(=O)Nc1ccc2ncccc2c1] | 2-43 |
| 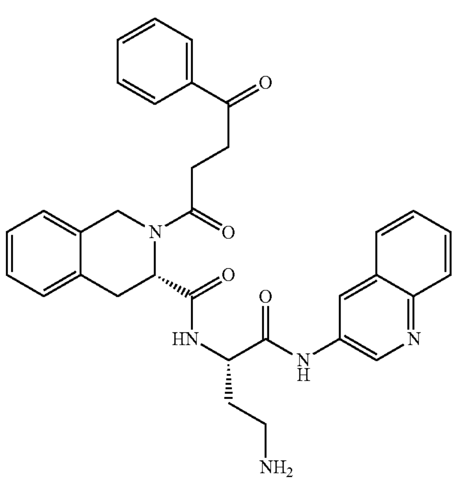 [SMILES: NCC[C@H](NC(=O)[C@@H]1Cc2ccccc2CN1C(=O)CCC(=O)c1ccccc1)C(=O)Nc1cnc2ccccc2c1] | 2-44 |

TABLE A-continued
REPRESENTATIVE COMPOUNDS
| Structure | Cpd. No. |
|---|---|
| 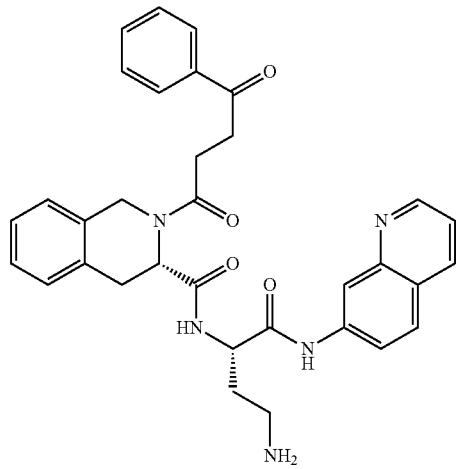 | 2-45 |
| 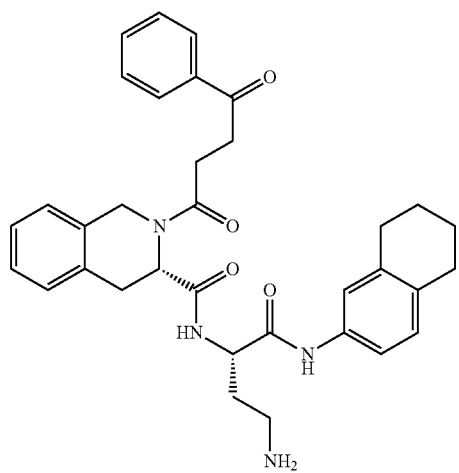 [SMILES: NCC[C@H](NC(=O)[C@@H]1Cc2ccccc2CN1C(=O)CCC(=O)c1ccccc1)C(=O)Nc1ccc2c(c1)CCCC2] | 2-46 |
| 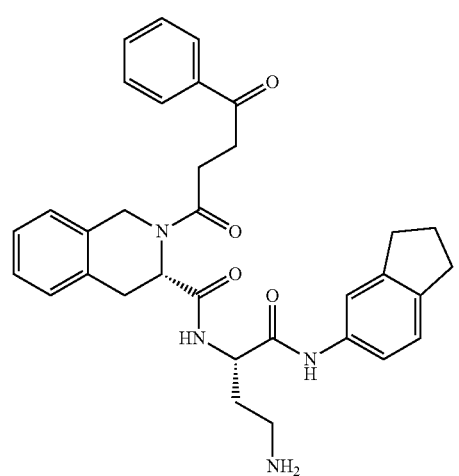 [SMILES: NCC[C@H](NC(=O)[C@@H]1Cc2ccccc2CN1C(=O)CCC(=O)c1ccccc1)C(=O)Nc1ccc2c(c1)CCC2] | 2-47 |

TABLE A-continued

REPRESENTATIVE COMPOUNDS

| Structure | Cpd. No. |
|---|---|
| 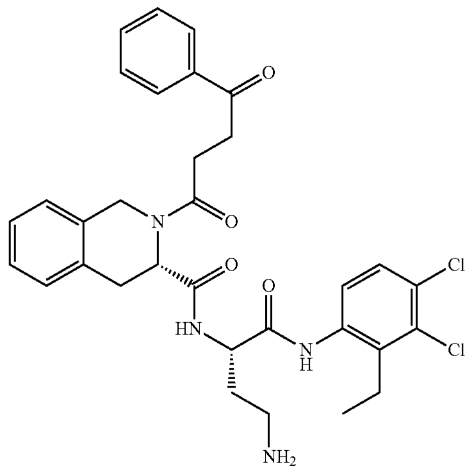 [SMILES: CCc1c(NC(=O)[C@H](CCN)NC(=O)[C@@H]2Cc3ccccc3CN2C(=O)CCC(=O)c2ccccc2)ccc(Cl)c1Cl] | 2-48 |
| 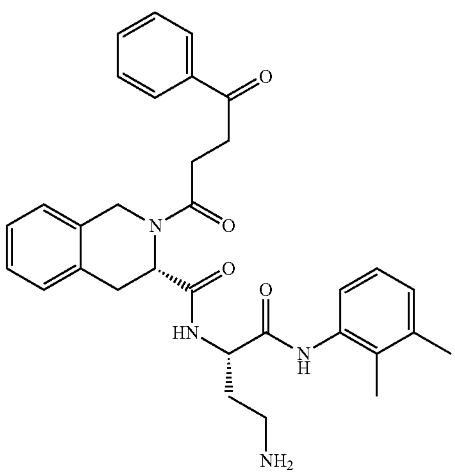 [SMILES: Cc1cccc(NC(=O)[C@H](CCN)NC(=O)[C@@H]2Cc3ccccc3CN2C(=O)CCC(=O)c2ccccc2)c1C] | 2-49 |
| 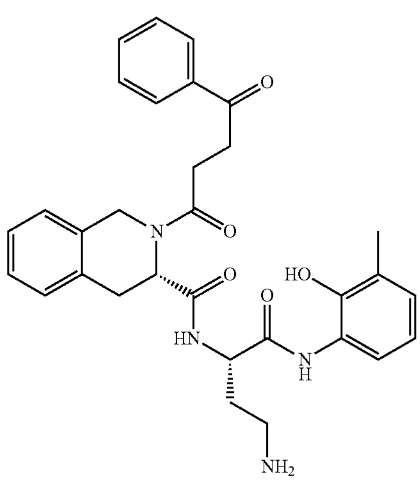 | 2-50 |

TABLE A-continued
REPRESENTATIVE COMPOUNDS
| Structure | Cpd. No. |
|---|---|
| 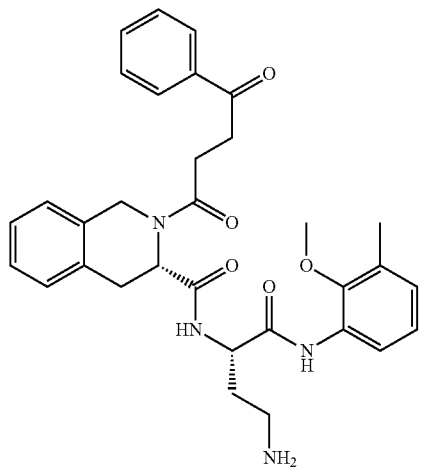 | 2-51 |
| 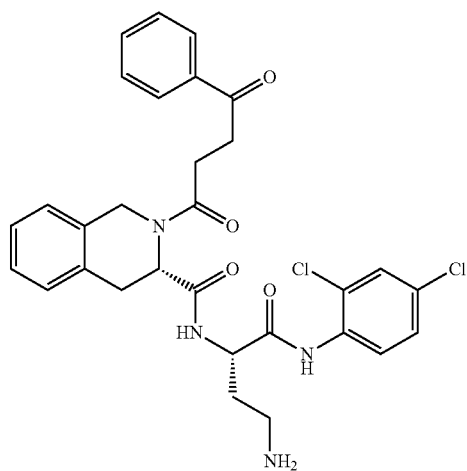 [SMILES: NCC[C@H](NC(=O)[C@@H]1Cc2ccccc2CN1C(=O)CCC(=O)c1ccccc1)C(=O)Nc1ccc(Cl)cc1Cl] | 2-52 |
| 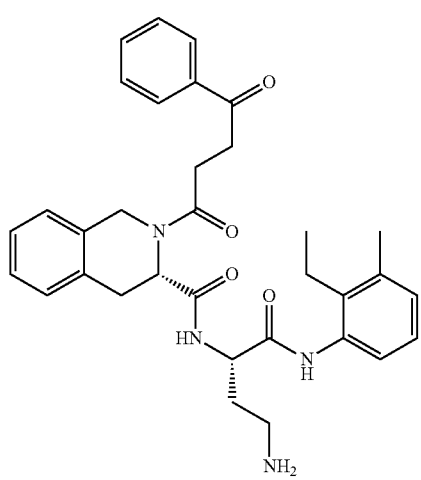 | 2-53 |

TABLE A-continued

REPRESENTATIVE COMPOUNDS

| Structure | Cpd. No. |
|---|---|
| 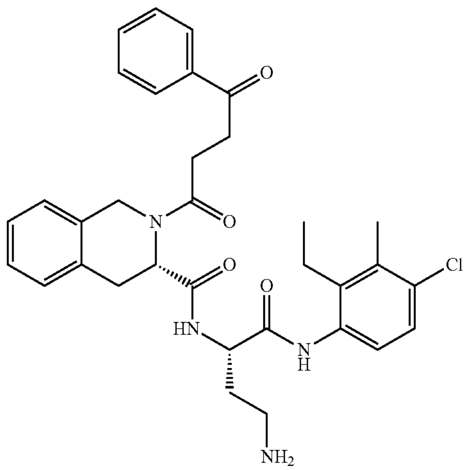 | 2-54 |
| 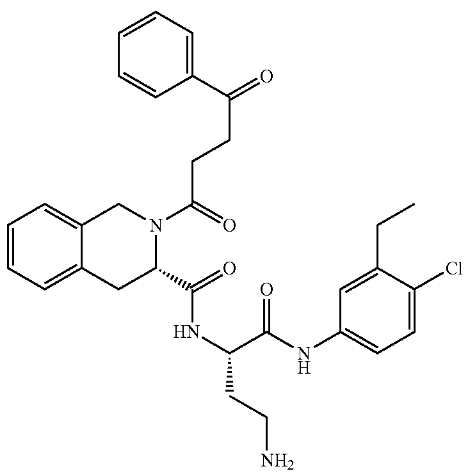 [SMILES: CCc1cc(NC(=O)[C@H](CCN)NC(=O)[C@@H]2Cc3ccccc3CN2C(=O)CCC(=O)c2ccccc2)ccc1Cl] | 2-55 |
| 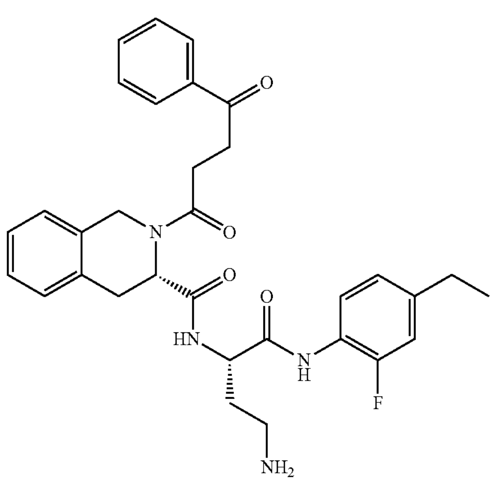 [SMILES: CCc1ccc(NC(=O)[C@H](CCN)NC(=O)[C@@H]2Cc3ccccc3CN2C(=O)CCC(=O)c2ccccc2)c(F)c1] | 2-56 |

TABLE A-continued

REPRESENTATIVE COMPOUNDS

| Structure | Cpd. No. |
|---|---|
| 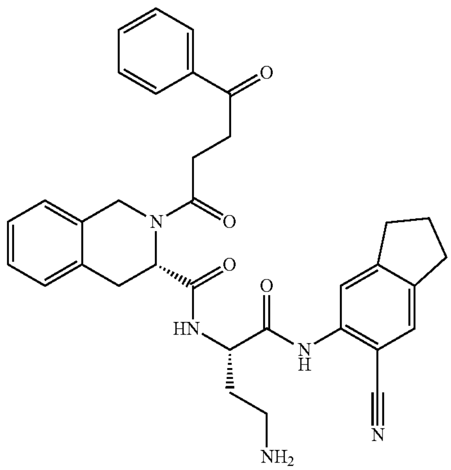 [SMILES: N#Cc1cc2c(cc1NC(=O)[C@H](CCN)NC(=O)[C@@H]1Cc3ccccc3CN1C(=O)CCC(=O)c1ccccc1)CCC2] | 2-57 |
| 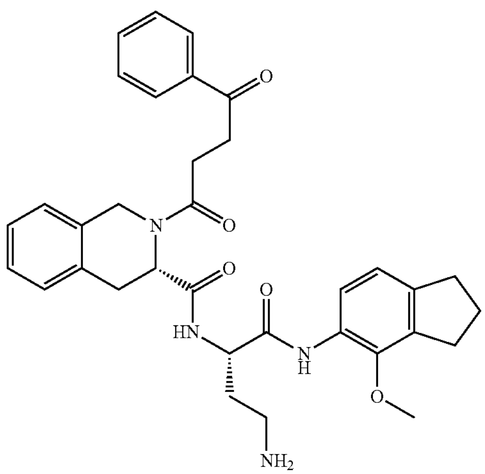 | 2-58 |
| 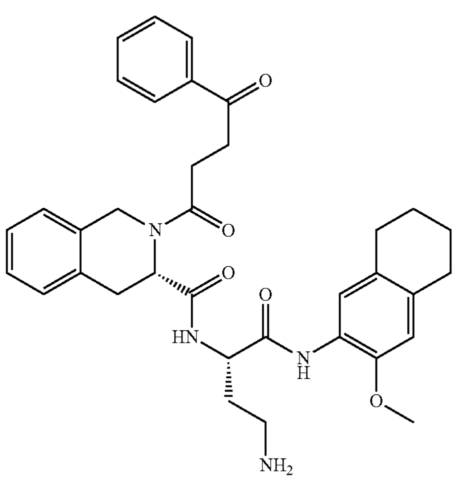 [SMILES: COc1cc2c(cc1NC(=O)[C@H](CCN)NC(=O)[C@@H]1Cc3ccccc3CN1C(=O)CCC(=O)c1ccccc1)CCCC2] | 2-59 |

TABLE A-continued
REPRESENTATIVE COMPOUNDS
| Structure | Cpd. No. |
|---|---|
| 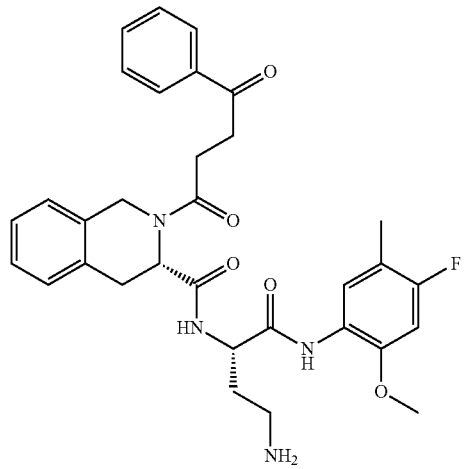 | 2-60 |
| 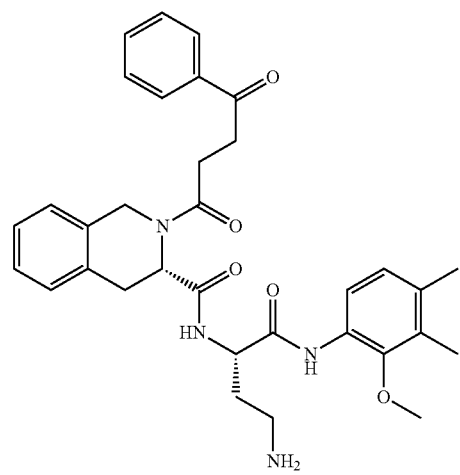 | 2-61 |
| 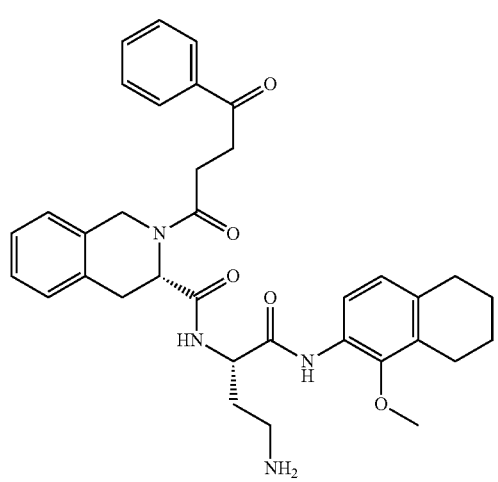 [SMILES: COc1c(NC(=O)[C@H](CCN)NC(=O)[C@@H]2Cc3ccccc3CN2C(=O)CCC(=O)c2ccccc2)ccc2c1CCCC2] | 2-62 |

TABLE A-continued

REPRESENTATIVE COMPOUNDS

| Structure | Cpd. No. |
|---|---|
| 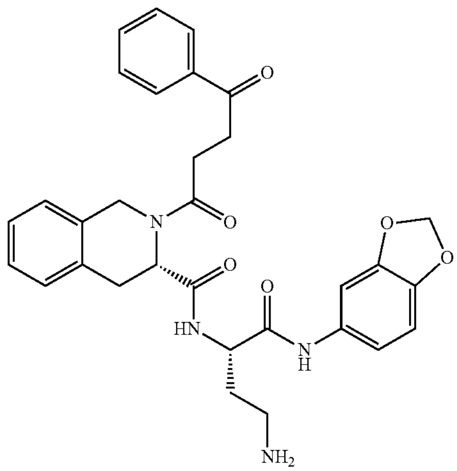 | 2-63 |
| 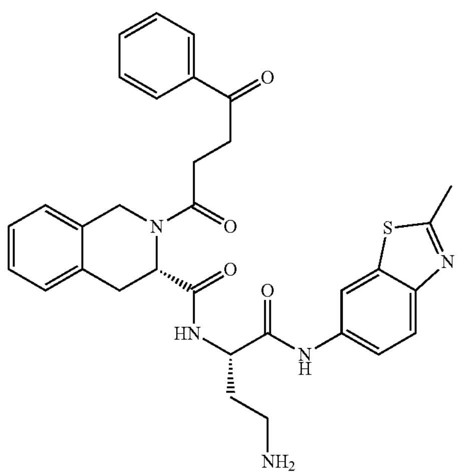 [SMILES: Cc1nc2ccc(NC(=O)[C@H](CCN)NC(=O)[C@@H]3Cc4ccccc4CN3C(=O)CCC(=O)c3ccccc3)cc2s1] | 2-64 |
| 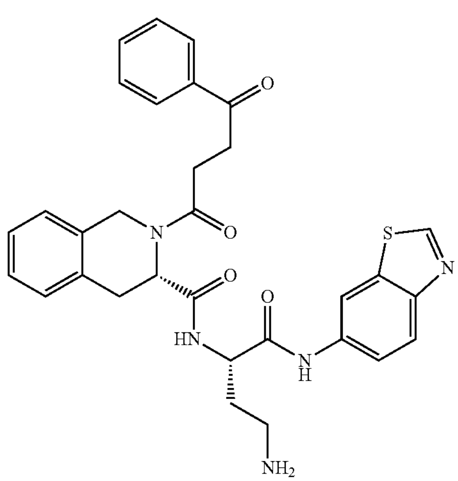 | 2-65 |

105
106
TABLE A-continued
REPRESENTATIVE COMPOUNDS
| Structure | Cpd. No. |
|---|---|
| 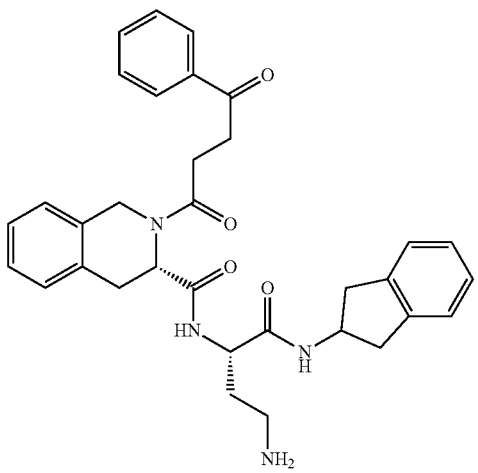 [SMILES: NCC[C@H](NC(=O)[C@@H]1Cc2ccccc2CN1C(=O)CCC(=O)c1ccccc1)C(=O)NC1Cc2ccccc2C1] | 2-66 |
| 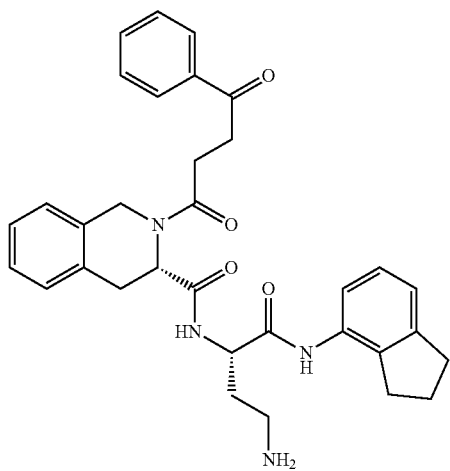 [SMILES: NCC[C@H](NC(=O)[C@@H]1Cc2ccccc2CN1C(=O)CCC(=O)c1ccccc1)C(=O)Nc1cccc2c1CCC2] | 2-67 |
| 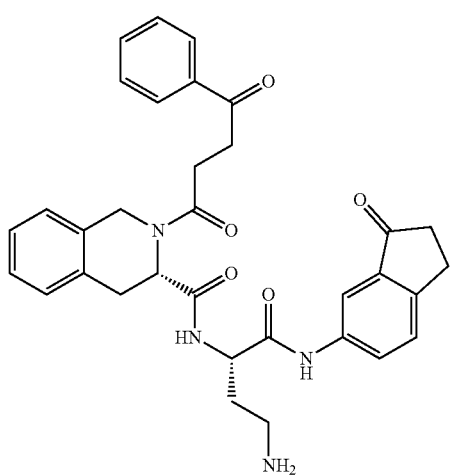 [SMILES: NCC[C@H](NC(=O)[C@@H]1Cc2ccccc2CN1C(=O)CCC(=O)c1ccccc1)C(=O)Nc1ccc2c(c1)C(=O)CC2] | 2-68 |

TABLE A-continued
REPRESENTATIVE COMPOUNDS
| Structure | Cpd. No. |
|---|---|
| 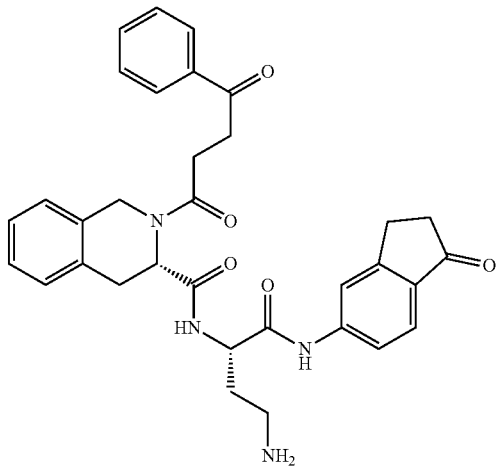 [SMILES: NCC[C@H](NC(=O)[C@@H]1Cc2ccccc2CN1C(=O)CCC(=O)c1ccccc1)C(=O)Nc1ccc2c(c1)CCC2=O] | 2-69 |
| 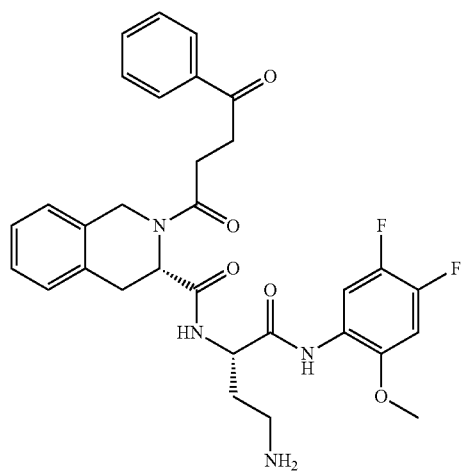 [SMILES: COc1cc(F)c(F)cc1NC(=O)[C@H](CCN)NC(=O)[C@@H]1Cc2ccccc2CN1C(=O)CCC(=O)c1ccccc1] | 2-70 |
| 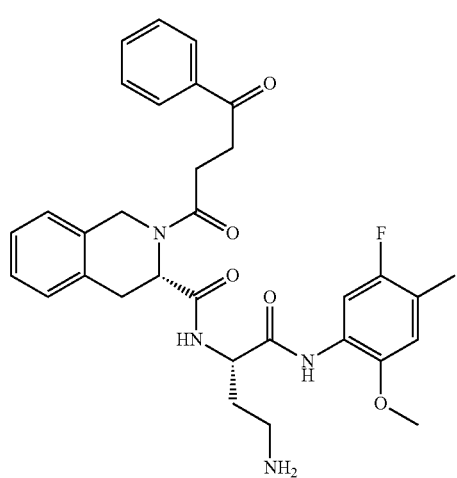 | 2-71 |

TABLE A-continued

REPRESENTATIVE COMPOUNDS

| Structure | Cpd. No. |
|---|---|
| 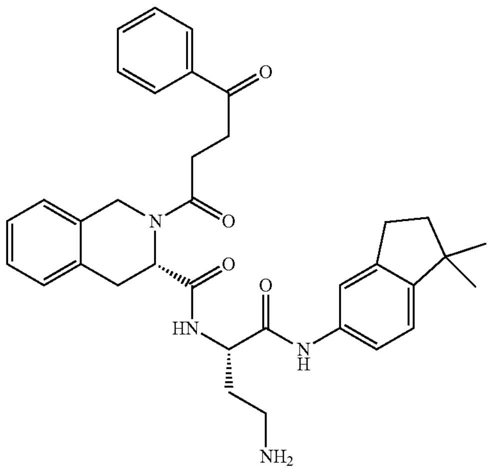 [SMILES: CC1(C)CCc2cc(NC(=O)[C@H](CCN)NC(=O)[C@@H]3Cc4ccccc4CN3C(=O)CCC(=O)c3ccccc3)ccc21] | 2-72 |
| 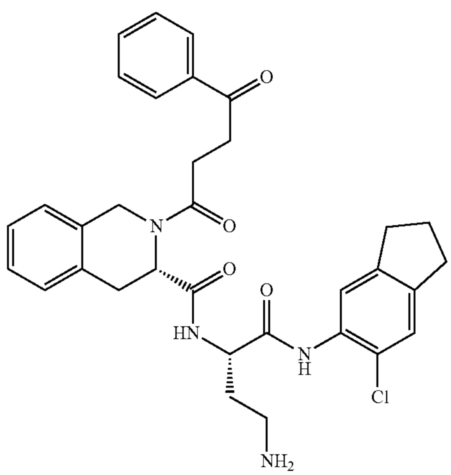 | 2-73 |
| 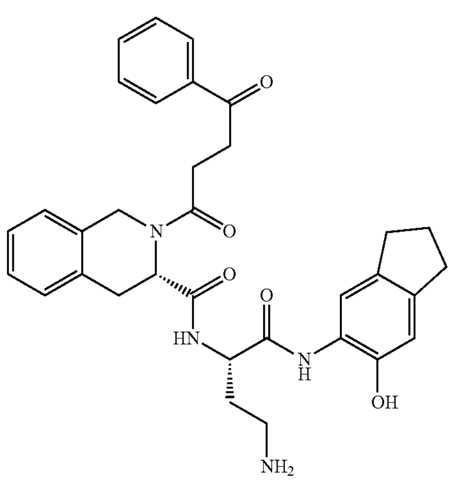 [SMILES: NCC[C@H](NC(=O)[C@@H]1Cc2ccccc2CN1C(=O)CCC(=O)c1ccccc1)C(=O)Nc1cc2c(cc1O)CCC2] | 2-74 |

TABLE A-continued

REPRESENTATIVE COMPOUNDS

| Structure | Cpd. No. |
|---|---|
| 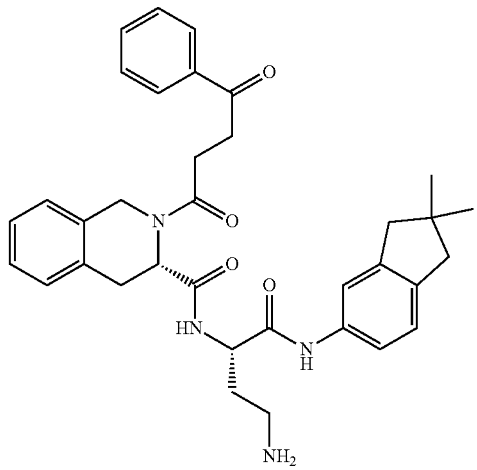 [SMILES: CC1(C)Cc2ccc(NC(=O)[C@H](CCN)NC(=O)[C@@H]3Cc4ccccc4CN3C(=O)CCC(=O)c3ccccc3)cc2C1] | 2-75 |
| 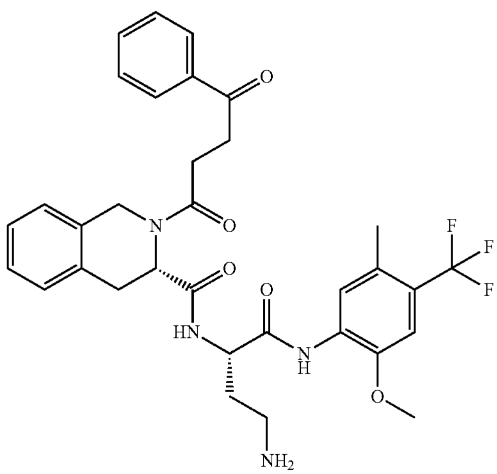 [SMILES: COc1cc(C(F)(F)F)c(C)cc1NC(=O)[C@H](CCN)NC(=O)[C@@H]1Cc2ccccc2CN1C(=O)CCC(=O)c1ccccc1] | 2-76 |
| 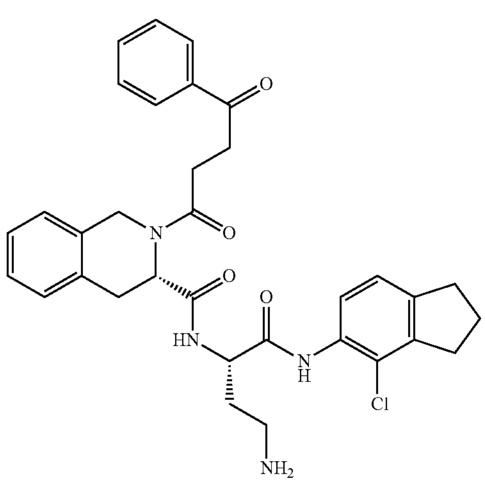 [SMILES: NCC[C@H](NC(=O)[C@@H]1Cc2ccccc2CN1C(=O)CCC(=O)c1ccccc1)C(=O)Nc1ccc2c(c1Cl)CCC2] | 2-77 |

TABLE A-continued

REPRESENTATIVE COMPOUNDS

| Structure | Cpd. No. |
|---|---|
| 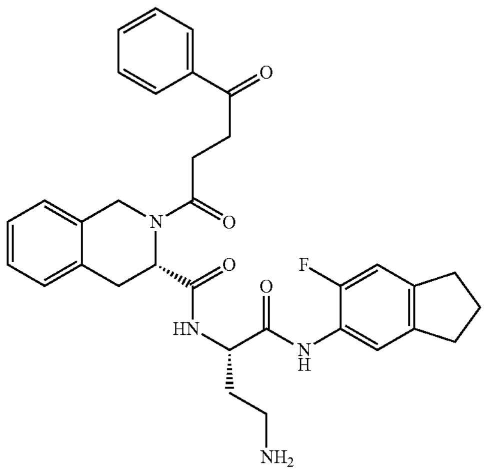 [SMILES: NCC[C@H](NC(=O)[C@@H]1Cc2ccccc2CN1C(=O)CCC(=O)c1ccccc1)C(=O)Nc1cc2c(cc1F)CCC2] | 2-78 |
| 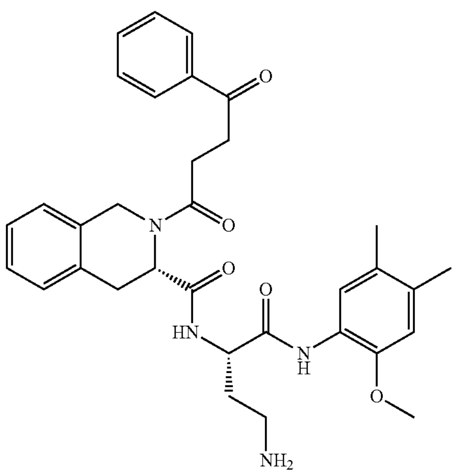 | 2-79 |
| 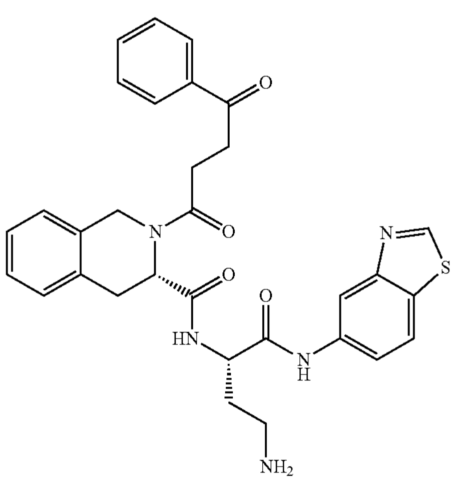 [SMILES: NCC[C@H](NC(=O)[C@@H]1Cc2ccccc2CN1C(=O)CCC(=O)c1ccccc1)C(=O)Nc1ccc2scnc2c1] | 2-80 |

TABLE A-continued
REPRESENTATIVE COMPOUNDS
| Structure | Cpd. No. |
|---|---|
| 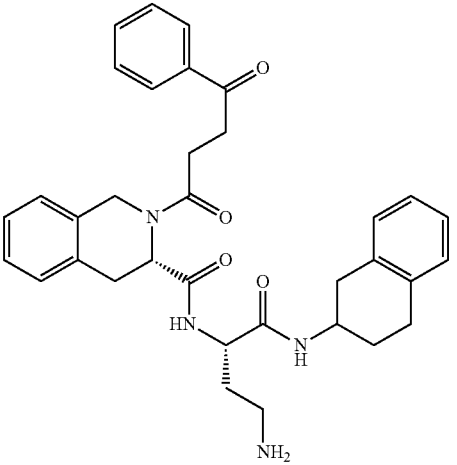 [SMILES: NCC[C@H](NC(=O)[C@@H]1Cc2ccccc2CN1C(=O)CCC(=O)c1ccccc1)C(=O)NC1CCc2ccccc2C1] | 2-81 |
| 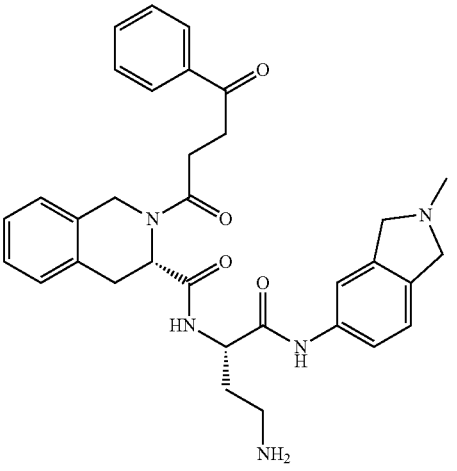 | 2-82 |
| 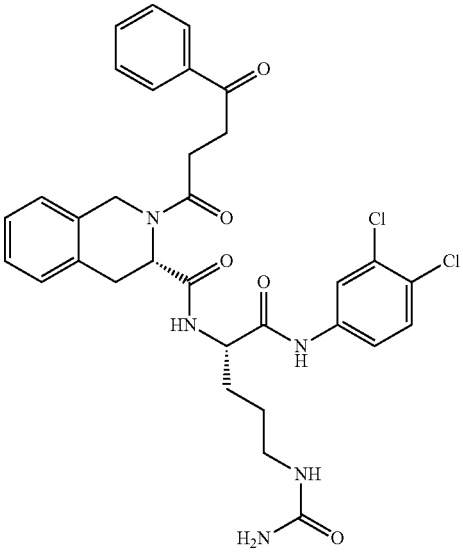 [SMILES: NC(=O)NCCC[C@H](NC(=O)[C@@H]1Cc2ccccc2CN1C(=O)CCC(=O)c1ccccc1)C(=O)Nc1ccc(Cl)c(Cl)c1] | 3-1 |

TABLE A-continued

REPRESENTATIVE COMPOUNDS

| Structure | Cpd. No. |
|-----------|----------|
| 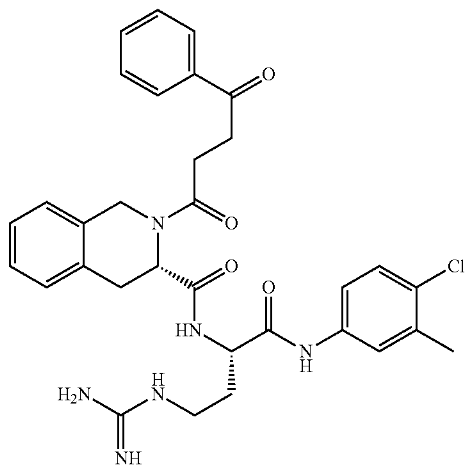 [SMILES: Cc1cc(NC(=O)[C@H](CCNC(=N)N)NC(=O)[C@@H]2Cc3ccccc3CN2C(=O)CCC(=O)c2ccccc2)ccc1Cl] | 3-2 |
| 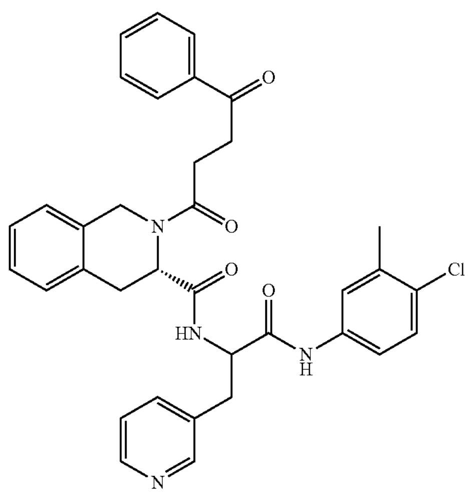 [SMILES: Cc1cc(NC(=O)C(Cc2cccnc2)NC(=O)[C@@H]2Cc3ccccc3CN2C(=O)CCC(=O)c2ccccc2)ccc1Cl] | 3-3 |
| 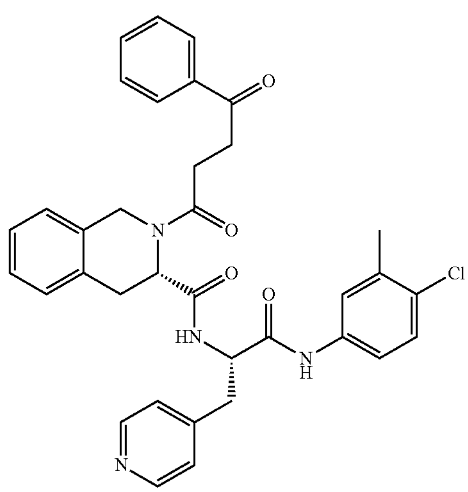 [SMILES: Cc1cc(NC(=O)[C@H](Cc2ccncc2)NC(=O)[C@@H]2Cc3ccccc3CN2C(=O)CCC(=O)c2ccccc2)ccc1Cl] | 3-4 |

119
120

TABLE A-continued

REPRESENTATIVE COMPOUNDS

| Structure | Cpd. No. |
|---|---|
| 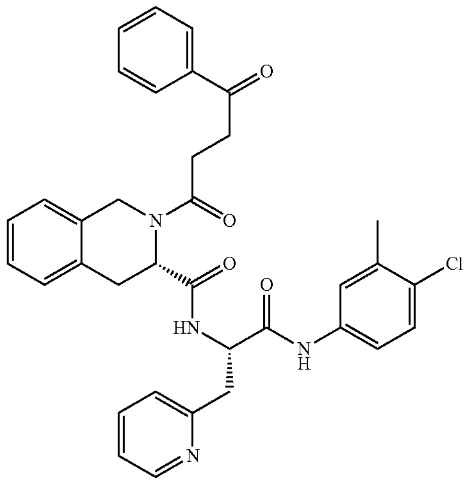 [SMILES: Cc1cc(NC(=O)[C@H](Cc2ccccn2)NC(=O)[C@@H]2Cc3ccccc3CN2C(=O)CCC(=O)c2ccccc2)ccc1Cl] | 3-5 |
| 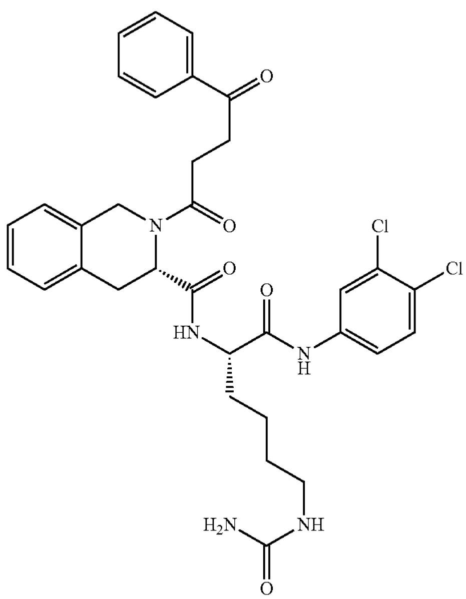 [SMILES: NC(=O)NCCCC[C@H](NC(=O)[C@@H]1Cc2ccccc2CN1C(=O)CCC(=O)c1ccccc1)C(=O)Nc1ccc(Cl)c(Cl)c1] | 3-6 |
| 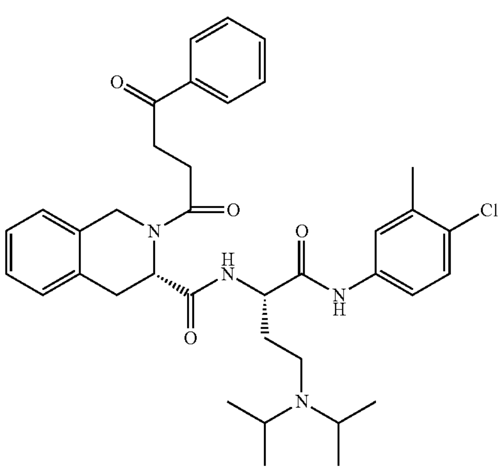 [SMILES: Cc1cc(NC(=O)[C@H](CCN(C(C)C)C(C)C)NC(=O)[C@@H]2Cc3ccccc3CN2C(=O)CCC(=O)c2ccccc2)ccc1Cl] | 3-7 |

TABLE A-continued

REPRESENTATIVE COMPOUNDS

| Structure | Cpd. No. |
|---|---|
| 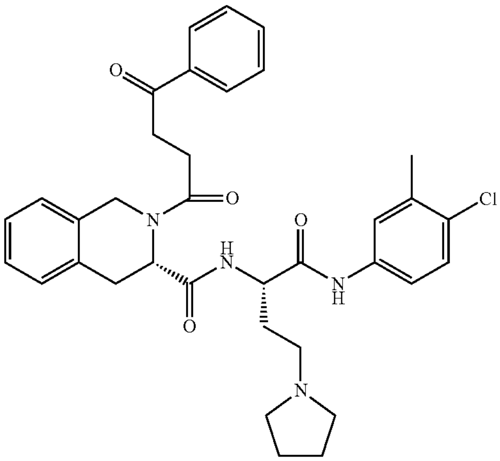 [SMILES: Cc1cc(NC(=O)[C@H](CCN2CCCC2)NC(=O)[C@@H]2Cc3ccccc3CN2C(=O)CCC(=O)c2ccccc2)ccc1Cl] | 3-8 |
| 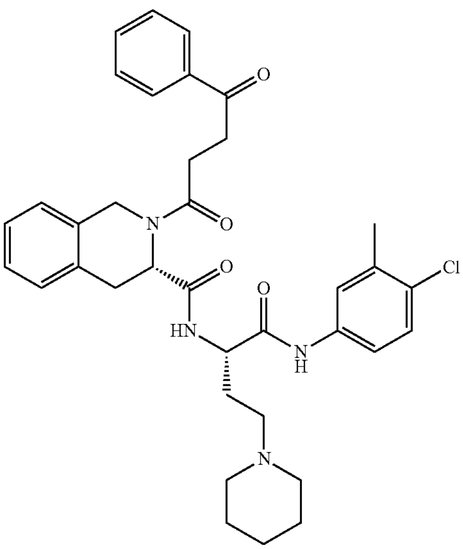 [SMILES: Cc1cc(NC(=O)[C@H](CCN2CCCCC2)NC(=O)[C@@H]2Cc3ccccc3CN2C(=O)CCC(=O)c2ccccc2)ccc1Cl] | 3-9 |
| 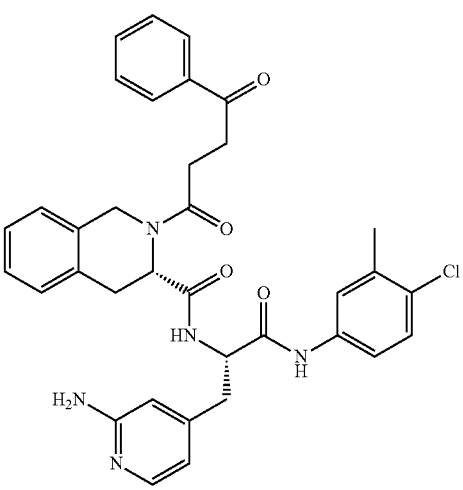 [SMILES: Cc1cc(NC(=O)[C@H](Cc2ccnc(N)c2)NC(=O)[C@@H]2Cc3ccccc3CN2C(=O)CCC(=O)c2ccccc2)ccc1Cl] | 3-10 |

TABLE A-continued
REPRESENTATIVE COMPOUNDS
| Structure | Cpd. No. |
|---|---|
| 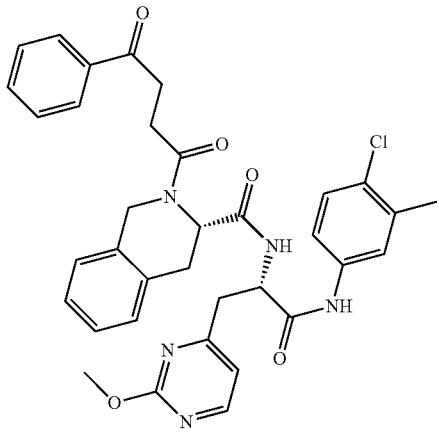 [SMILES: COc1nccc(C[C@H](NC(=O)[C@@H]2Cc3ccccc3CN2C(=O)CCC(=O)c2ccccc2)C(=O)Nc2ccc(Cl)c(C)c2)n1] | 3-11 |
| 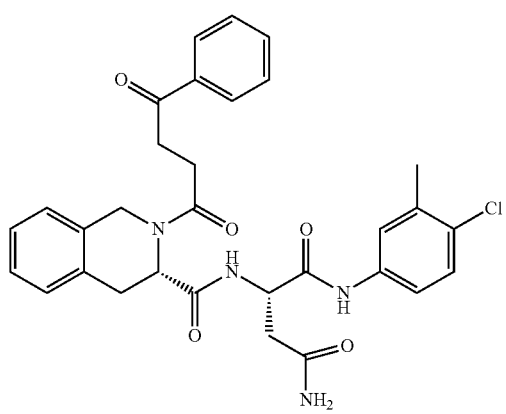 [SMILES: Cc1cc(NC(=O)[C@H](CC(N)=O)NC(=O)[C@@H]2Cc3ccccc3CN2C(=O)CCC(=O)c2ccccc2)ccc1Cl] | 3-12 |
| 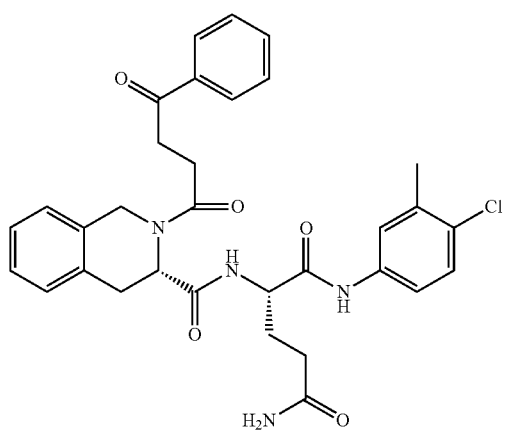 [SMILES: Cc1cc(NC(=O)[C@H](CCC(N)=O)NC(=O)[C@@H]2Cc3ccccc3CN2C(=O)CCC(=O)c2ccccc2)ccc1Cl] | 3-13 |

TABLE A-continued
REPRESENTATIVE COMPOUNDS
| Structure | Cpd. No. |
|---|---|
| 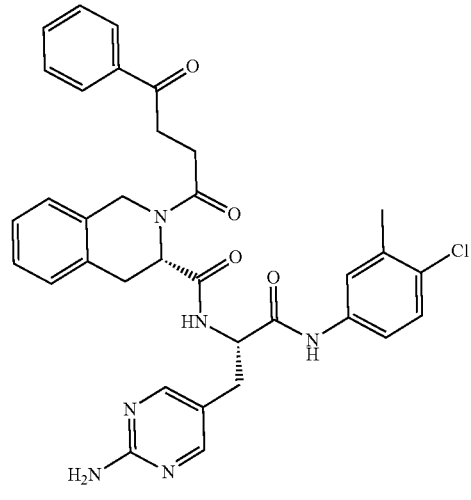 [SMILES: Cc1cc(NC(=O)[C@H](Cc2cnc(N)nc2)NC(=O)[C@@H]2Cc3ccccc3CN2C(=O)CCC(=O)c2ccccc2)ccc1Cl] | 3-14 |
| 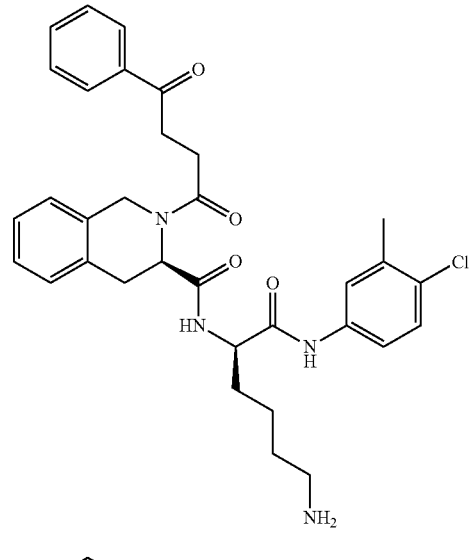 | 4-2 |
| 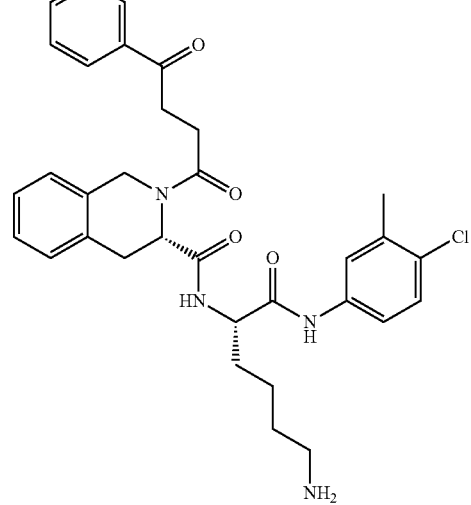 | 4-3 |

TABLE A-continued
REPRESENTATIVE COMPOUNDS
| Structure | Cpd. No. |
|---|---|
| 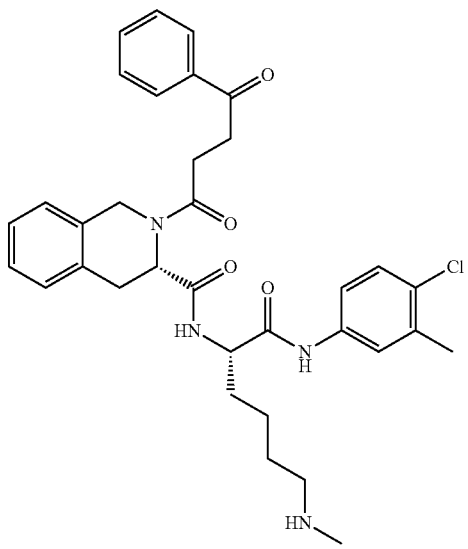 [SMILES: CNCCCC[C@H](NC(=O)[C@@H]1Cc2ccccc2CN1C(=O)CCC(=O)c1ccccc1)C(=O)Nc1ccc(Cl)c(C)c1] | 4-4 |
| 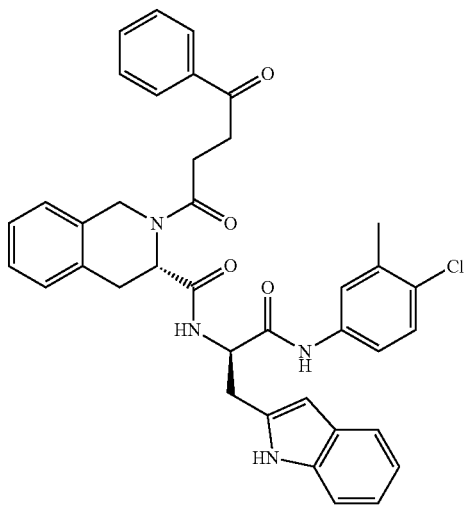 [SMILES: Cc1cc(NC(=O)[C@@H](Cc2cc3ccccc3[nH]2)NC(=O)[C@@H]2Cc3ccccc3CN2C(=O)CCC(=O)c2ccccc2)ccc1Cl] | 4-5 |

129 130
TABLE A-continued
REPRESENTATIVE COMPOUNDS
| Structure | Cpd. No. |
|---|---|
| 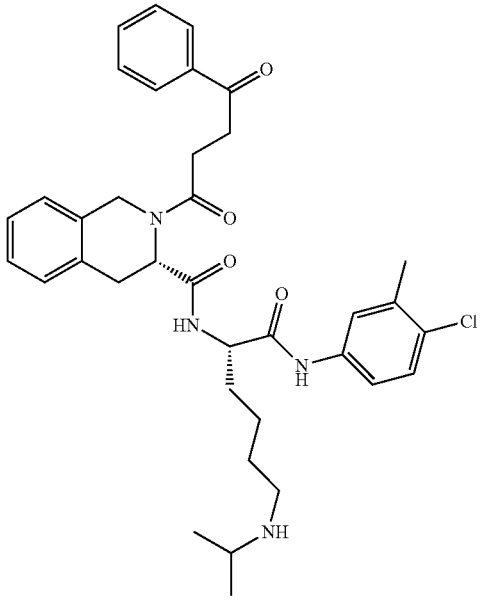 [SMILES: Cc1cc(NC(=O)[C@H](CCCCNC(C)C)NC(=O)[C@@H]2Cc3ccccc3CN2C(=O)CCC(=O)c2ccccc2)ccc1Cl] | 4-6 |
| 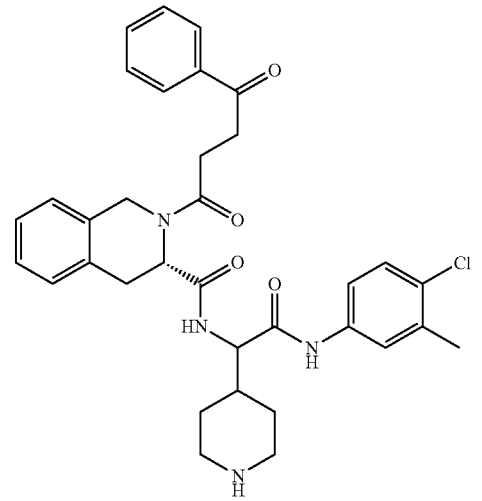 [SMILES: Cc1cc(NC(=O)C(NC(=O)[C@@H]2Cc3ccccc3CN2C(=O)CCC(=O)c2ccccc2)C2CCNCC2)ccc1Cl] | 4-7 |
| 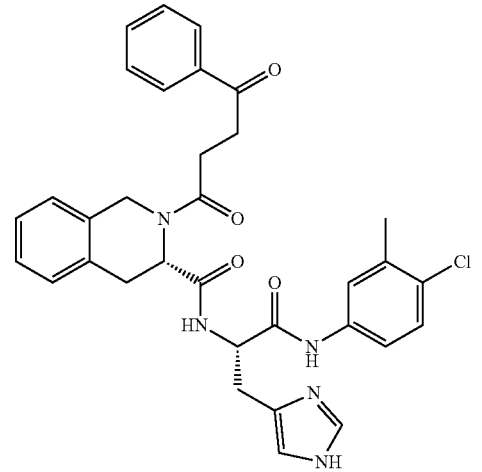 [SMILES: Cc1cc(NC(=O)[C@H](Cc2c[nH]cn2)NC(=O)[C@@H]2Cc3ccccc3CN2C(=O)CCC(=O)c2ccccc2)ccc1Cl] | 4-8 |

TABLE A-continued

REPRESENTATIVE COMPOUNDS

| Structure | Cpd. No. |
|---|---|
| 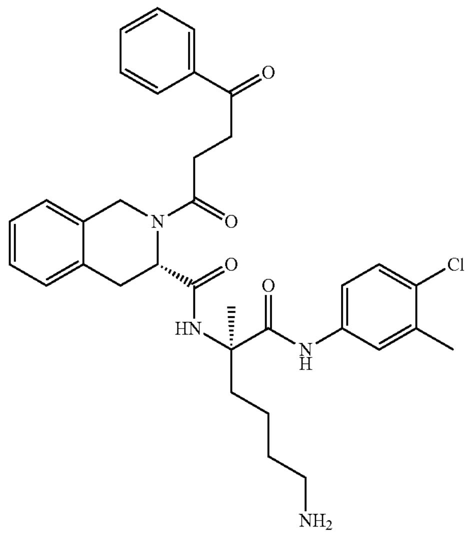 [SMILES: Cc1cc(NC(=O)[C@@](C)(CCCCN)NC(=O)[C@@H]2Cc3ccccc3CN2C(=O)CCC(=O)c2ccccc2)ccc1Cl] | 4-9 |
| 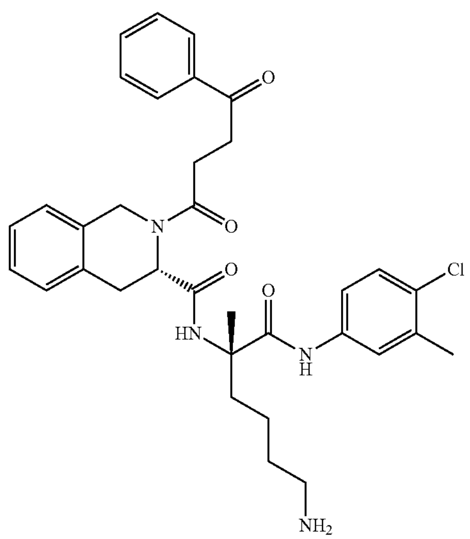 [SMILES: Cc1cc(NC(=O)[C@](C)(CCCCN)NC(=O)[C@@H]2Cc3ccccc3CN2C(=O)CCC(=O)c2ccccc2)ccc1Cl] | 4-10 |
| 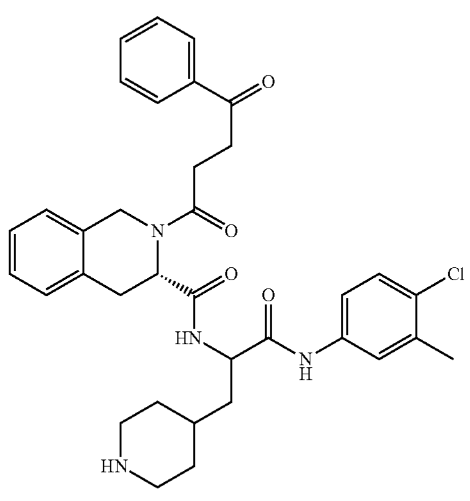 [SMILES: Cc1cc(NC(=O)C(CC2CCNCC2)NC(=O)[C@@H]2Cc3ccccc3CN2C(=O)CCC(=O)c2ccccc2)ccc1Cl] | 4-11 |

TABLE A-continued
REPRESENTATIVE COMPOUNDS
| Structure | Cpd. No. |
|---|---|
| 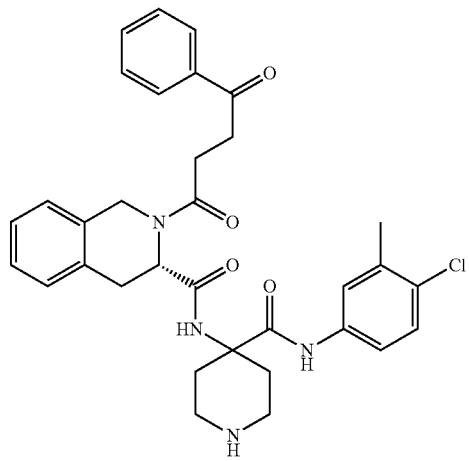 [SMILES: Cc1cc(NC(=O)C2(NC(=O)[C@@H]3Cc4ccccc4CN3C(=O)CCC(=O)c3ccccc3)CCNCC2)ccc1Cl] | 4-12 |
| 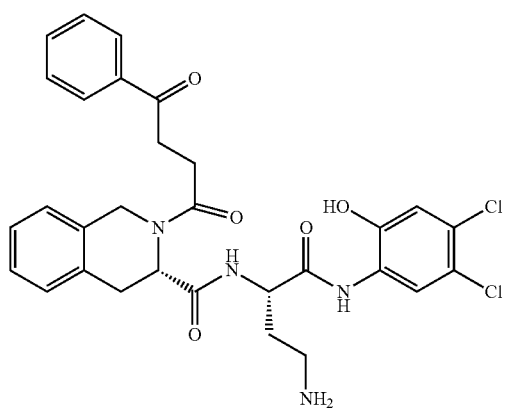 | 4-13 |
| 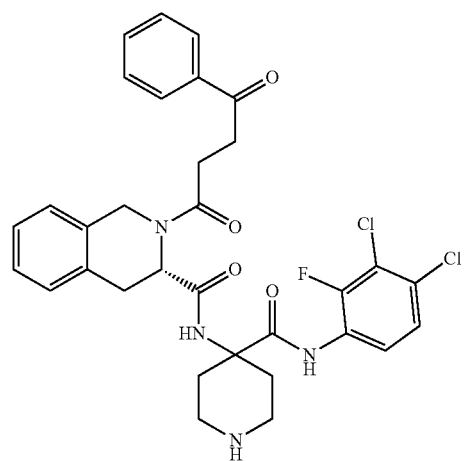 [SMILES: O=C(CCC(=O)N1Cc2ccccc2C[C@H]1C(=O)NC1(C(=O)Nc2ccc(Cl)c(Cl)c2F)CCNCC1)c1ccccc1] | 4-14 |

TABLE A-continued
REPRESENTATIVE COMPOUNDS
| Structure | Cpd. No. |
|---|---|
| 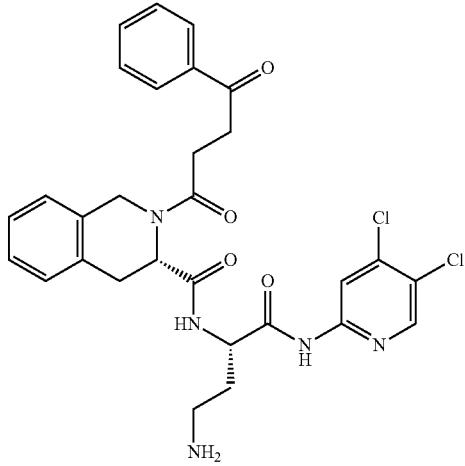 | 4-15 |
| 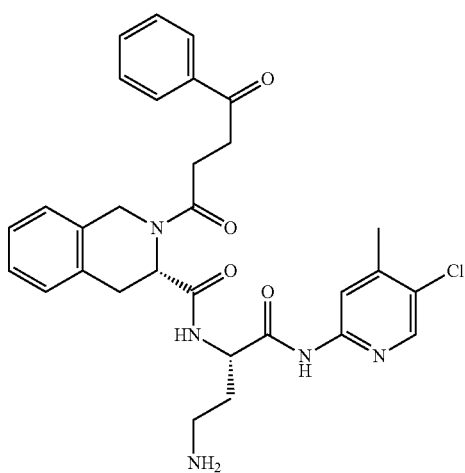 [SMILES: Cc1cc(NC(=O)[C@H](CCN)NC(=O)[C@@H]2Cc3ccccc3CN2C(=O)CCC(=O)c2ccccc2)ncc1Cl] | 4-16 |
| 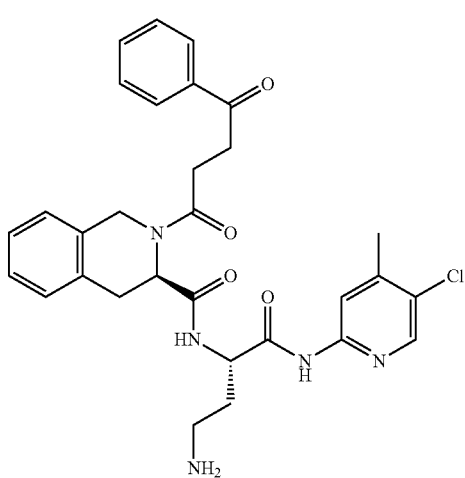 [SMILES: Cc1cc(NC(=O)[C@H](CCN)NC(=O)[C@H]2Cc3ccccc3CN2C(=O)CCC(=O)c2ccccc2)ncc1Cl] | 4-17 |

TABLE A-continued
REPRESENTATIVE COMPOUNDS
| Structure | Cpd. No. |
|---|---|
| 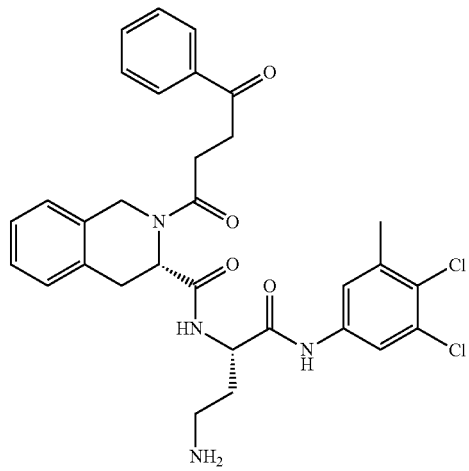 [SMILES: Cc1cc(NC(=O)[C@H](CCN)NC(=O)[C@@H]2Cc3ccccc3CN2C(=O)CCC(=O)c2ccccc2)cc(Cl)c1Cl] | 4-18 |
| 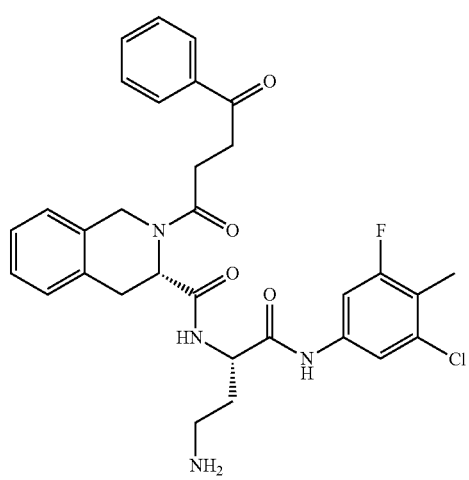 [SMILES: Cc1c(F)cc(NC(=O)[C@H](CCN)NC(=O)[C@@H]2Cc3ccccc3CN2C(=O)CCC(=O)c2ccccc2)cc1Cl] | 4-19 |
| 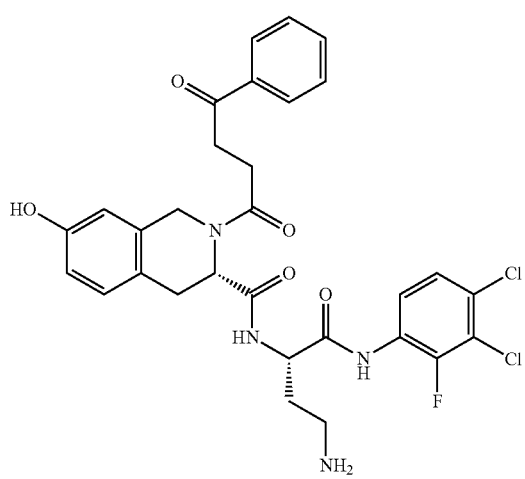 [SMILES: NCC[C@H](NC(=O)[C@@H]1Cc2ccc(O)cc2CN1C(=O)CCC(=O)c1ccccc1)C(=O)Nc1ccc(Cl)c(Cl)c1F] | 4-20 |

TABLE A-continued
REPRESENTATIVE COMPOUNDS
| Structure | Cpd. No. |
|---|---|
| 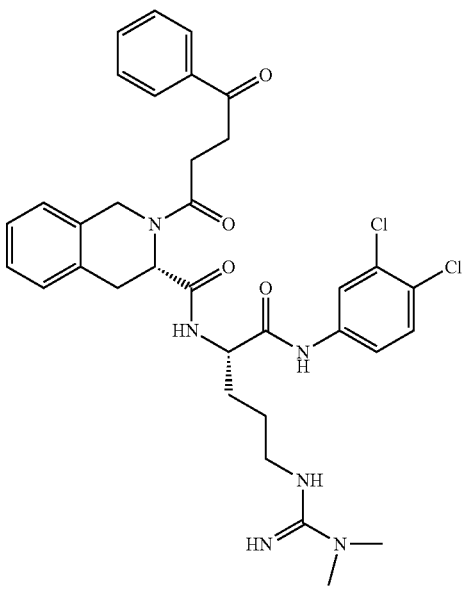 [SMILES: CN(C)C(=N)NCCC[C@H](NC(=O)[C@@H]1Cc2ccccc2CN1C(=O)CCC(=O)c1ccccc1)C(=O)Nc1ccc(Cl)c(Cl)c1] | 5-1 |
| 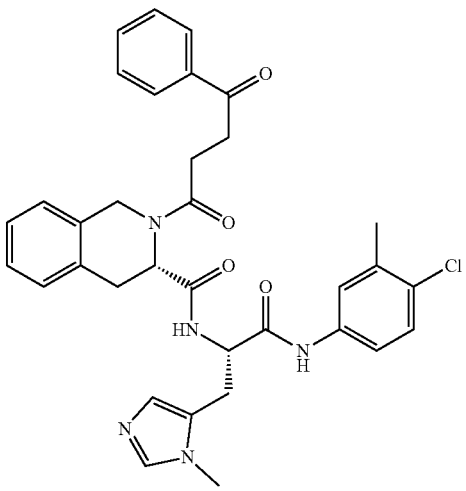 [SMILES: Cc1cc(NC(=O)[C@H](Cc2cncn2C)NC(=O)[C@@H]2Cc3ccccc3CN2C(=O)CCC(=O)c2ccccc2)ccc1Cl] | 5-2 |
| 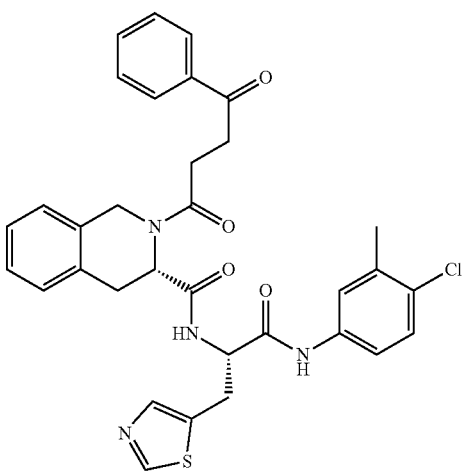 [SMILES: Cc1cc(NC(=O)[C@H](Cc2cncs2)NC(=O)[C@@H]2Cc3ccccc3CN2C(=O)CCC(=O)c2ccccc2)ccc1Cl] | 5-3 |

TABLE A-continued
REPRESENTATIVE COMPOUNDS
| Structure | Cpd. No. |
|---|---|
| 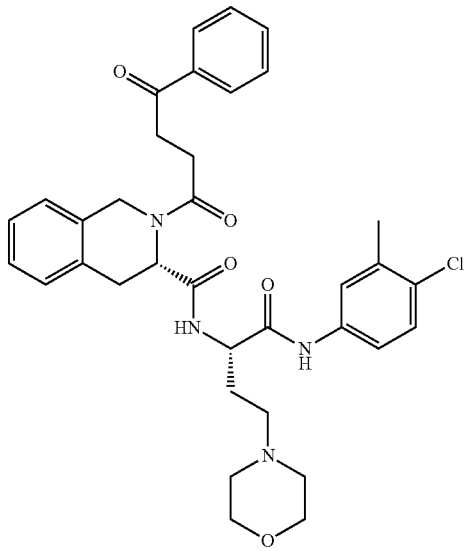 [SMILES: Cc1cc(NC(=O)[C@H](CCN2CCOCC2)NC(=O)[C@@H]2Cc3ccccc3CN2C(=O)CCC(=O)c2ccccc2)ccc1Cl] | 5-4 |
| 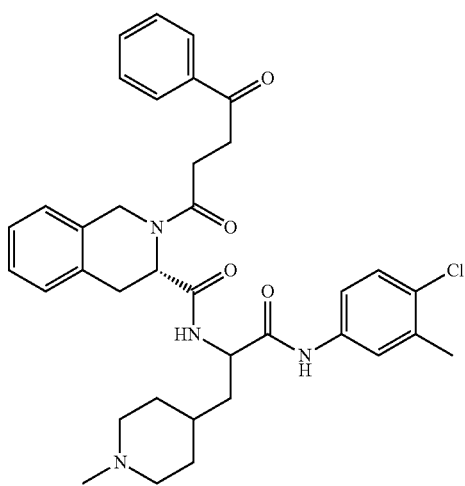 [SMILES: Cc1cc(NC(=O)C(CC2CCN(C)CC2)NC(=O)[C@@H]2Cc3ccccc3CN2C(=O)CCC(=O)c2ccccc2)ccc1Cl] | 6-1 |
| 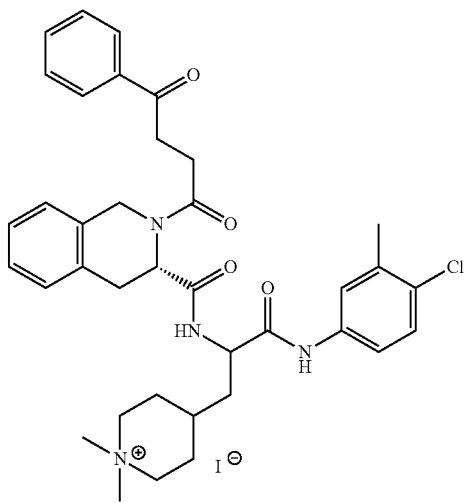 [SMILES: Cc1cc(NC(=O)C(CC2CC[N+](C)(C)CC2)NC(=O)[C@@H]2Cc3ccccc3CN2C(=O)CCC(=O)c2ccccc2)ccc1Cl ; [I-]] | 6-2 |

TABLE A-continued
REPRESENTATIVE COMPOUNDS
| Structure | Cpd. No. |
|---|---|
| 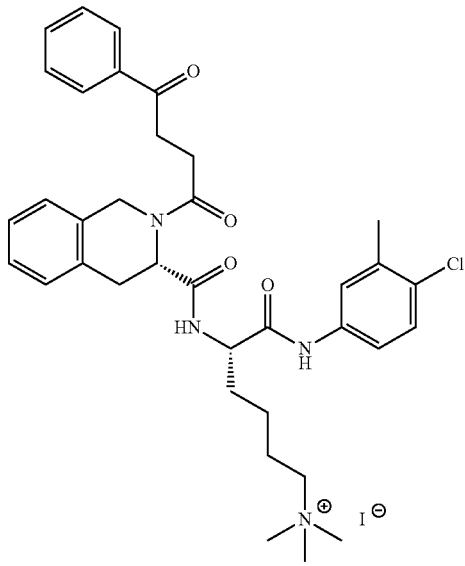 [SMILES: Cc1cc(NC(=O)[C@H](CCCC[N+](C)(C)C)NC(=O)[C@@H]2Cc3ccccc3CN2C(=O)CCC(=O)c2ccccc2)ccc1Cl ; [I-]] | 6-3 |
| 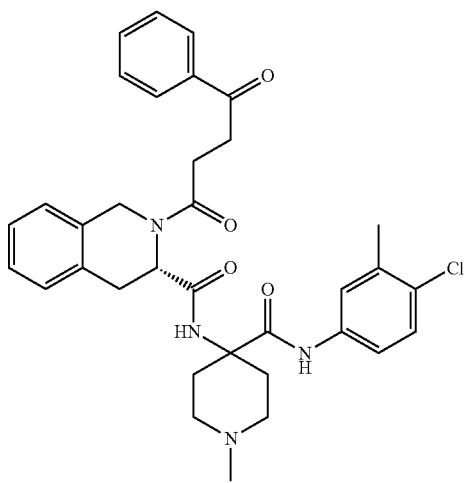 [SMILES: Cc1cc(NC(=O)C2(NC(=O)[C@@H]3Cc4ccccc4CN3C(=O)CCC(=O)c3ccccc3)CCN(C)CC2)ccc1Cl] | 6-4 |
| 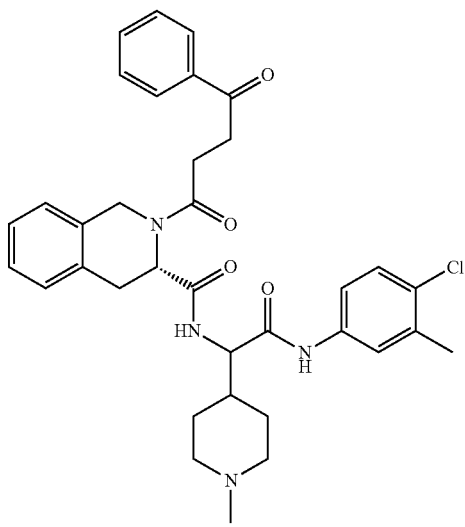 [SMILES: Cc1cc(NC(=O)C(NC(=O)[C@@H]2Cc3ccccc3CN2C(=O)CCC(=O)c2ccccc2)C2CCN(C)CC2)ccc1Cl] | 6-5 |

TABLE A-continued
REPRESENTATIVE COMPOUNDS
| Structure | Cpd. No. |
|---|---|
| 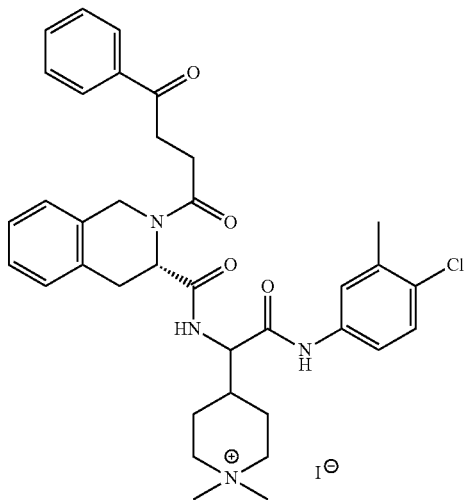 [SMILES: Cc1cc(NC(=O)C(NC(=O)[C@@H]2Cc3ccccc3CN2C(=O)CCC(=O)c2ccccc2)C2CC[N+](C)(C)CC2)ccc1Cl ; [I-]] | 6-6 |
| 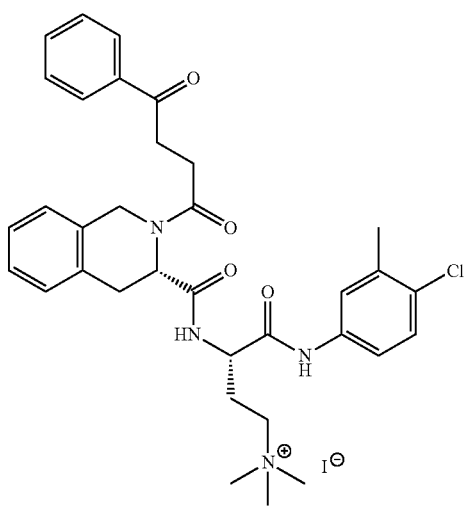 [SMILES: Cc1cc(NC(=O)[C@H](CC[N+](C)(C)C)NC(=O)[C@@H]2Cc3ccccc3CN2C(=O)CCC(=O)c2ccccc2)ccc1Cl ; [I-]] | 6-7 |
| 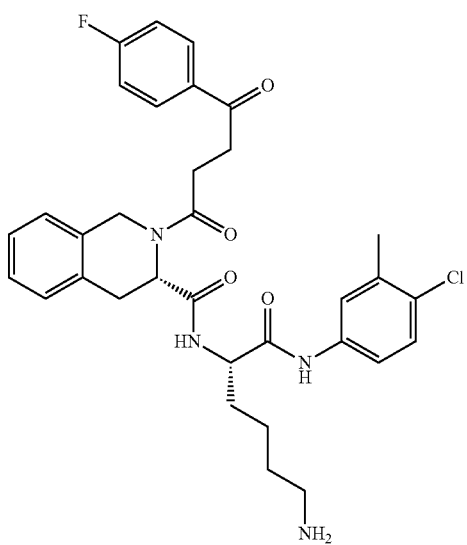 [SMILES: Cc1cc(NC(=O)[C@H](CCCCN)NC(=O)[C@@H]2Cc3ccccc3CN2C(=O)CCC(=O)c2ccc(F)cc2)ccc1Cl] | 7-1 |

TABLE A-continued
REPRESENTATIVE COMPOUNDS
| Structure | Cpd. No. |
|---|---|
| 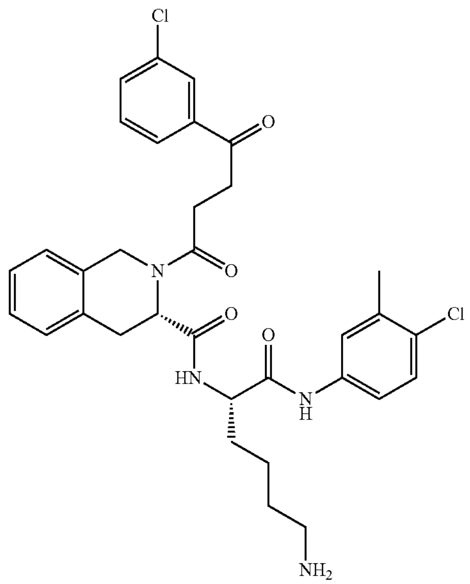 [SMILES: Cc1cc(NC(=O)[C@H](CCCCN)NC(=O)[C@@H]2Cc3ccccc3CN2C(=O)CCC(=O)c2cccc(Cl)c2)ccc1Cl] | 7-2 |
| 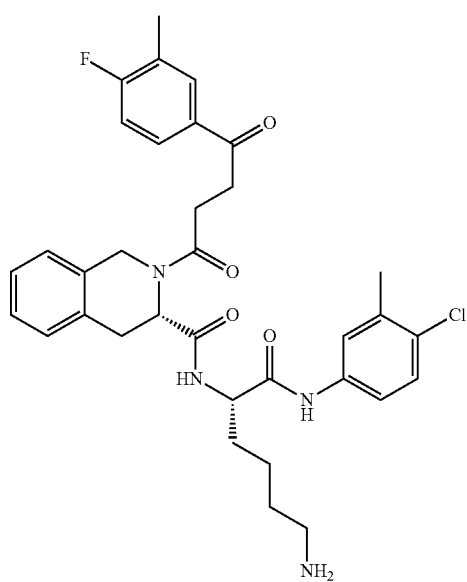 [SMILES: Cc1cc(C(=O)CCC(=O)N2Cc3ccccc3C[C@H]2C(=O)N[C@@H](CCCCN)C(=O)Nc2ccc(Cl)c(C)c2)ccc1F] | 7-3 |

TABLE A-continued
REPRESENTATIVE COMPOUNDS
| Structure | Cpd. No. |
|---|---|
| 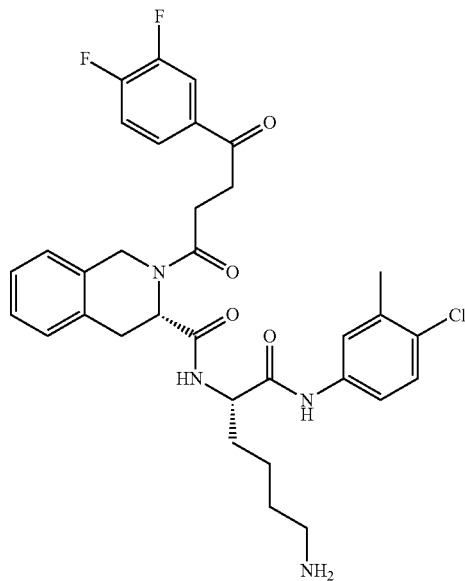 [SMILES: Cc1cc(NC(=O)[C@H](CCCCN)NC(=O)[C@@H]2Cc3ccccc3CN2C(=O)CCC(=O)c2ccc(F)c(F)c2)ccc1Cl] | 7-4 |
| 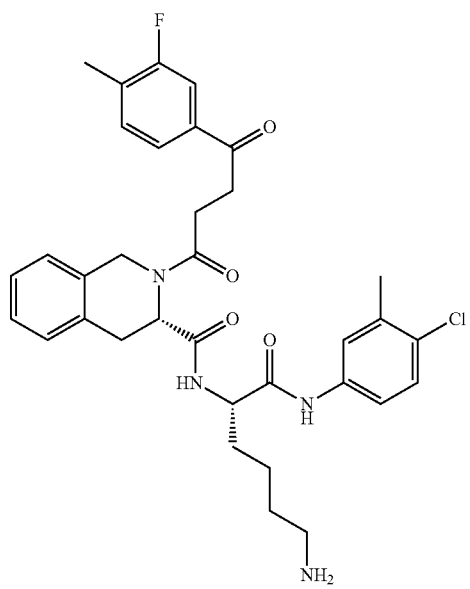 [SMILES: Cc1ccc(C(=O)CCC(=O)N2Cc3ccccc3C[C@H]2C(=O)N[C@@H](CCCCN)C(=O)Nc2ccc(Cl)c(C)c2)cc1F] | 7-5 |

TABLE A-continued
REPRESENTATIVE COMPOUNDS
| Structure | Cpd. No. |
|---|---|
| 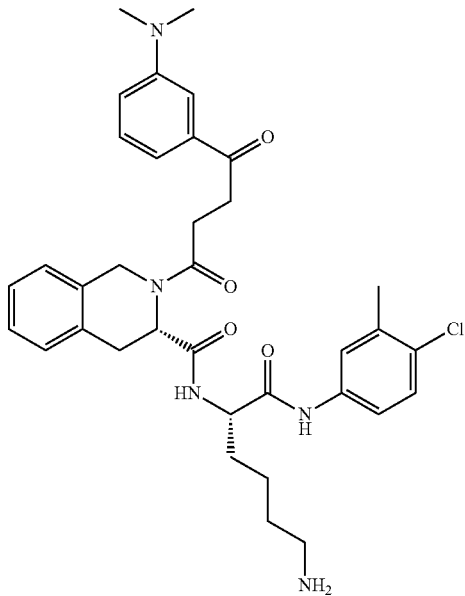 [SMILES: Cc1cc(NC(=O)[C@H](CCCCN)NC(=O)[C@@H]2Cc3ccccc3CN2C(=O)CCC(=O)c2cccc(N(C)C)c2)ccc1Cl] | 7-6 |
| 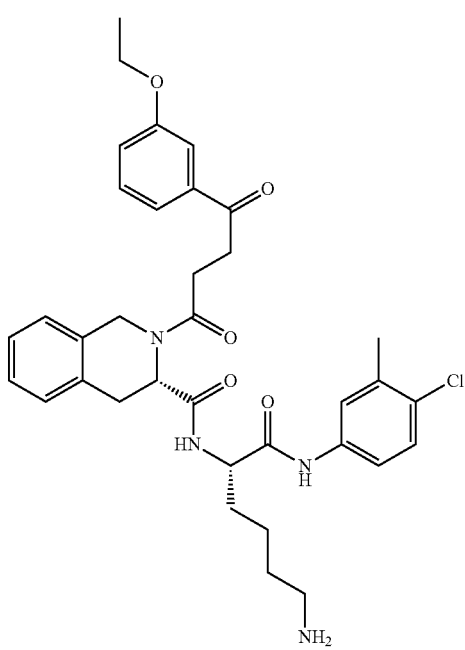 [SMILES: CCOc1cccc(C(=O)CCC(=O)N2Cc3ccccc3C[C@H]2C(=O)N[C@@H](CCCCN)C(=O)Nc2ccc(Cl)c(C)c2)c1] | 7-7 |

TABLE A-continued
REPRESENTATIVE COMPOUNDS
| Structure | Cpd. No. |
|---|---|
| 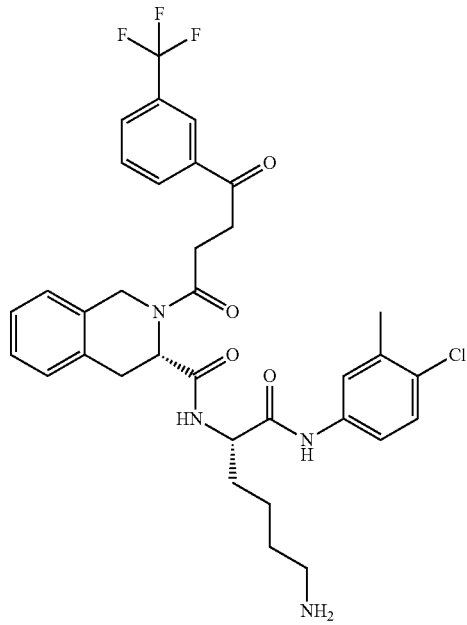 [SMILES: Cc1cc(NC(=O)[C@H](CCCCN)NC(=O)[C@@H]2Cc3ccccc3CN2C(=O)CCC(=O)c2cccc(C(F)(F)F)c2)ccc1Cl] | 7-8 |
| 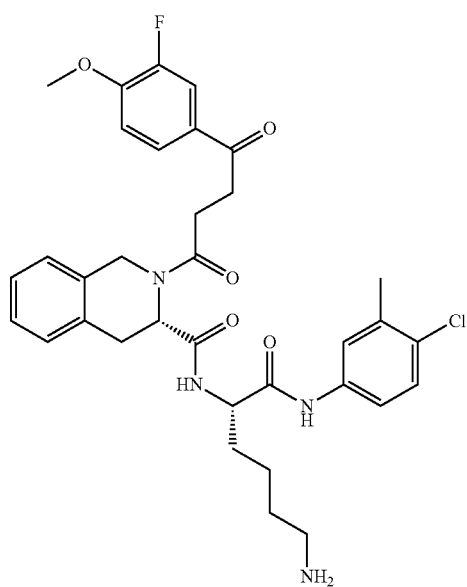 [SMILES: COc1ccc(C(=O)CCC(=O)N2Cc3ccccc3C[C@H]2C(=O)N[C@@H](CCCCN)C(=O)Nc2ccc(Cl)c(C)c2)cc1F] | 7-9 |

TABLE A-continued
REPRESENTATIVE COMPOUNDS
| Structure | Cpd. No. |
|---|---|
| 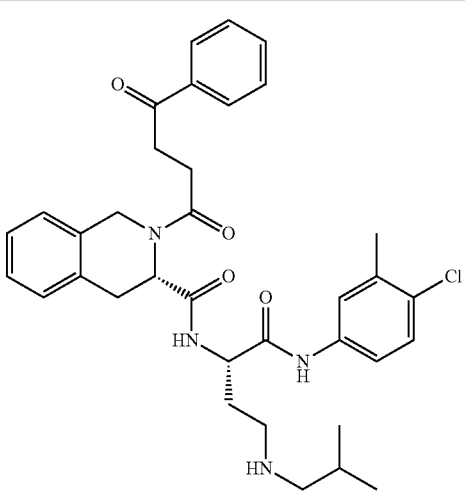 [SMILES: Cc1cc(NC(=O)[C@H](CCNCC(C)C)NC(=O)[C@@H]2Cc3ccccc3CN2C(=O)CCC(=O)c2ccccc2)ccc1Cl] | 8-1 |
| 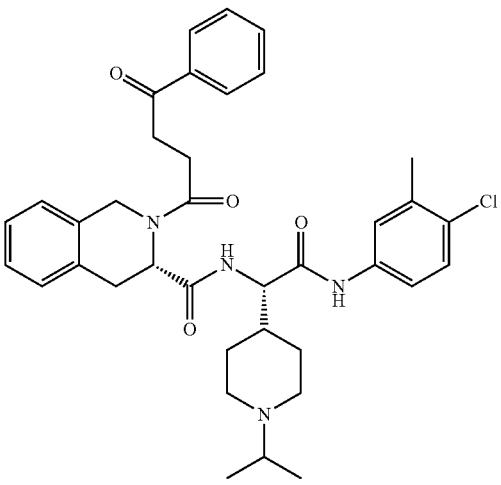 [SMILES: Cc1cc(NC(=O)[C@@H](NC(=O)[C@@H]2Cc3ccccc3CN2C(=O)CCC(=O)c2ccccc2)C2CCN(C(C)C)CC2)ccc1Cl] | 8-2 |
| 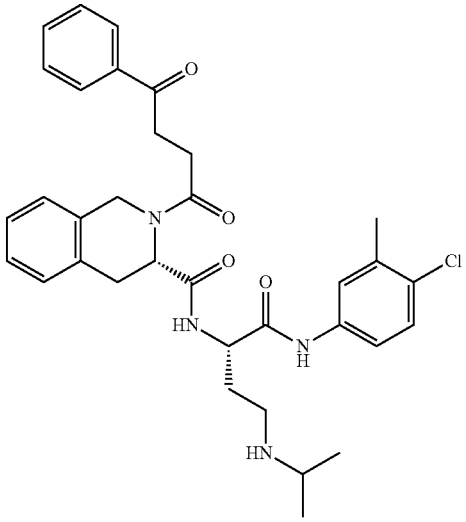 [SMILES: Cc1cc(NC(=O)[C@H](CCNC(C)C)NC(=O)[C@@H]2Cc3ccccc3CN2C(=O)CCC(=O)c2ccccc2)ccc1Cl] | 8-3 |

TABLE A-continued
REPRESENTATIVE COMPOUNDS
| Structure | Cpd. No. |
|---|---|
| 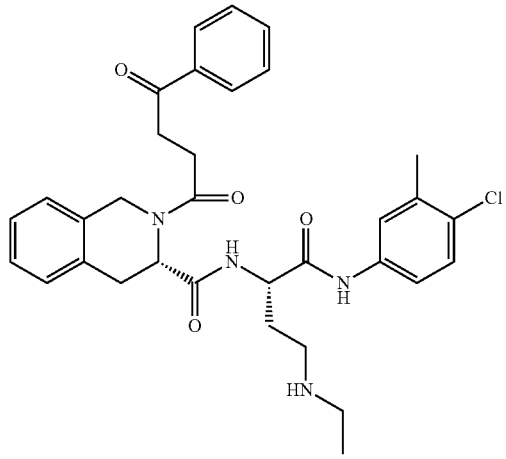 [SMILES: CCNCC[C@H](NC(=O)[C@@H]1Cc2ccccc2CN1C(=O)CCC(=O)c1ccccc1)C(=O)Nc1ccc(Cl)c(C)c1] | 8-4 |
| 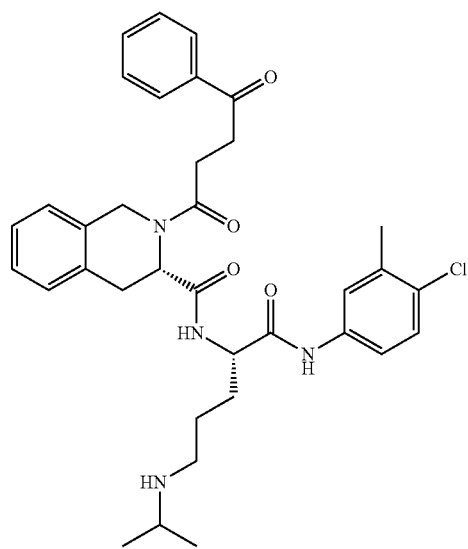 [SMILES: Cc1cc(NC(=O)[C@H](CCCNC(C)C)NC(=O)[C@@H]2Cc3ccccc3CN2C(=O)CCC(=O)c2ccccc2)ccc1Cl] | 8-5 |
| 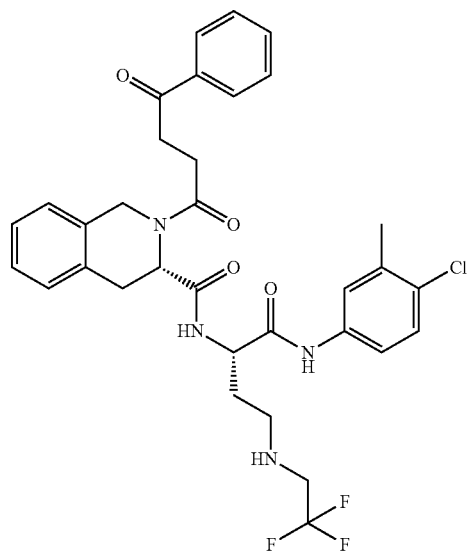 [SMILES: Cc1cc(NC(=O)[C@H](CCNCC(F)(F)F)NC(=O)[C@@H]2Cc3ccccc3CN2C(=O)CCC(=O)c2ccccc2)ccc1Cl] | 8-6 |

TABLE A-continued

REPRESENTATIVE COMPOUNDS

| Structure | Cpd. No. |
|---|---|
| 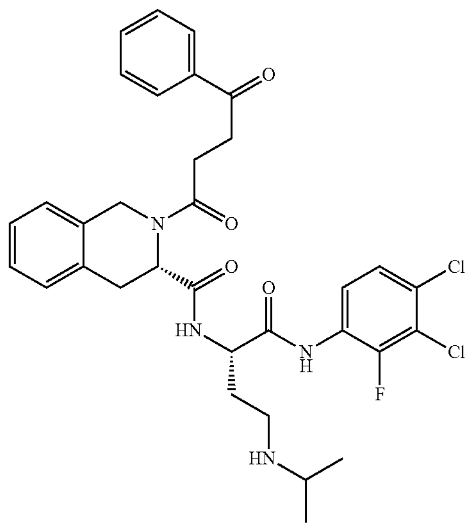 [SMILES: CC(C)NCC[C@H](NC(=O)[C@@H]1Cc2ccccc2CN1C(=O)CCC(=O)c1ccccc1)C(=O)Nc1ccc(Cl)c(Cl)c1F] | 8-7 |
| 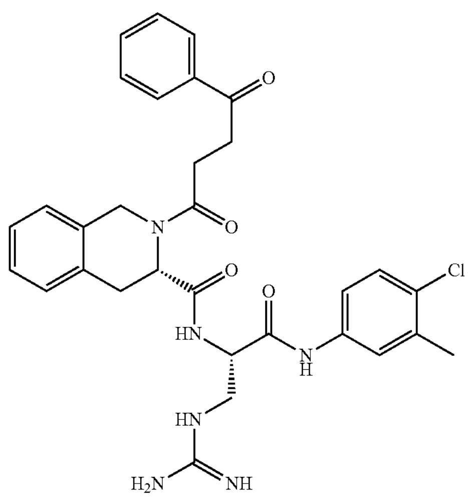 [SMILES: Cc1cc(NC(=O)[C@H](CNC(=N)N)NC(=O)[C@@H]2Cc3ccccc3CN2C(=O)CCC(=O)c2ccccc2)ccc1Cl] | 9-1 |
| 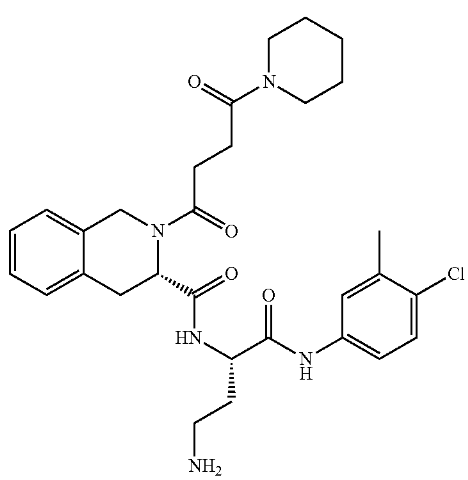 | 10-1 |

TABLE A-continued

REPRESENTATIVE COMPOUNDS

| Structure | Cpd. No. |
|---|---|
| 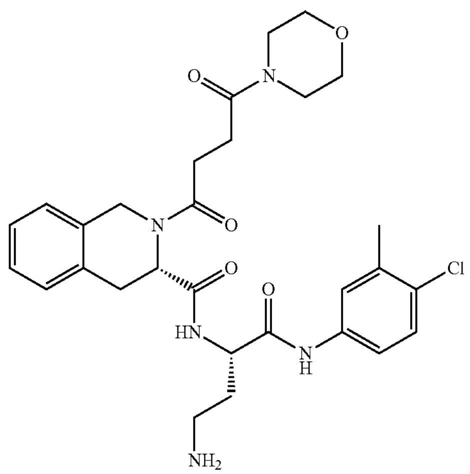 | 10-2 |
| 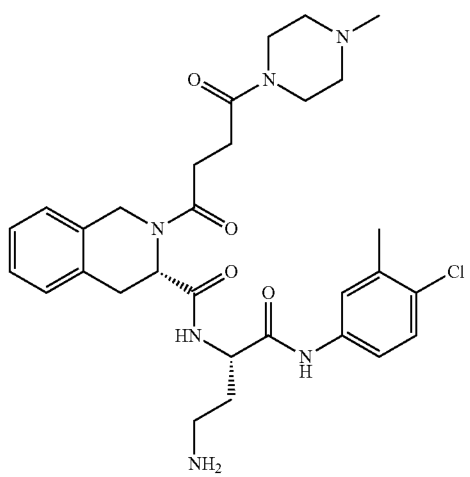 [SMILES: Cc1cc(NC(=O)[C@H](CCN)NC(=O)[C@@H]2Cc3ccccc3CN2C(=O)CCC(=O)N2CCN(C)CC2)ccc1Cl] | 10-3 |
| 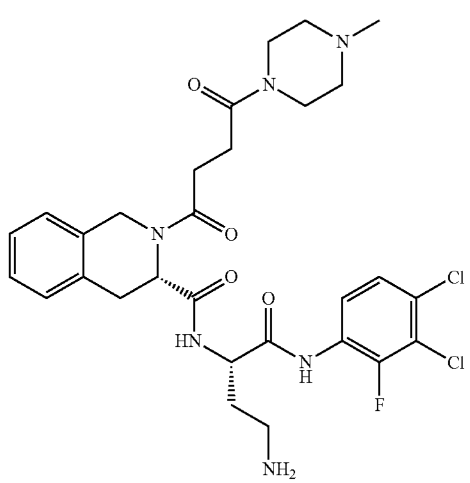 [SMILES: CN1CCN(C(=O)CCC(=O)N2Cc3ccccc3C[C@H]2C(=O)N[C@@H](CCN)C(=O)Nc2ccc(Cl)c(Cl)c2F)CC1] | 10-4 |

TABLE A-continued
REPRESENTATIVE COMPOUNDS
| Structure | Cpd. No. |
|---|---|
| 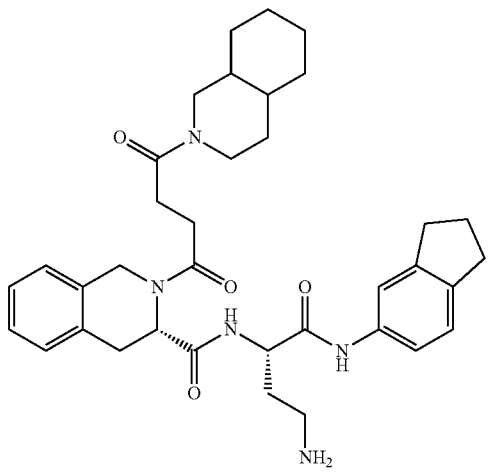 [SMILES: NCC[C@H](NC(=O)[C@@H]1Cc2ccccc2CN1C(=O)CCC(=O)N1CCC2CCCCC2C1)C(=O)Nc1ccc2c(c1)CCC2] | 10-5 |
| 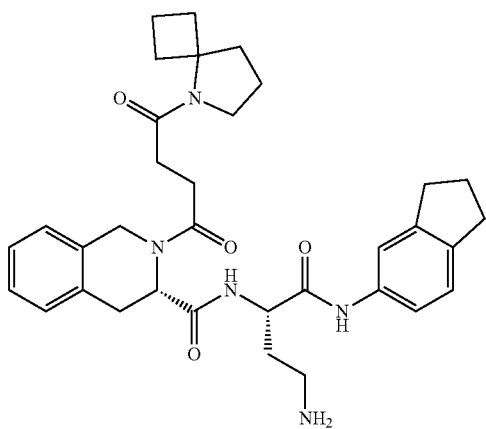 [SMILES: NCC[C@H](NC(=O)[C@@H]1Cc2ccccc2CN1C(=O)CCC(=O)N1CCCC12CCC2)C(=O)Nc1ccc2c(c1)CCC2] | 10-6 |
| 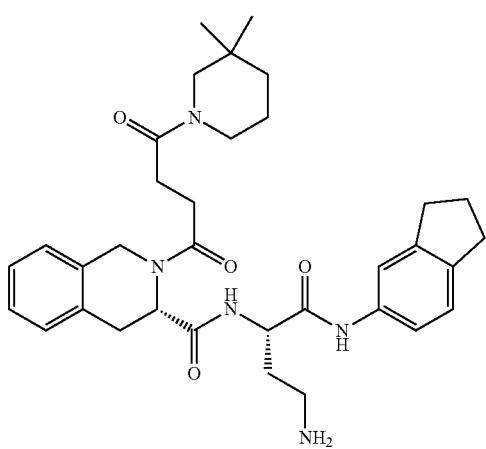 [SMILES: CC1(C)CCCN(C(=O)CCC(=O)N2Cc3ccccc3C[C@H]2C(=O)N[C@@H](CCN)C(=O)Nc2ccc3c(c2)CCC3)C1] | 10-7 |

TABLE A-continued

REPRESENTATIVE COMPOUNDS

| Structure | Cpd. No. |
|---|---|
| 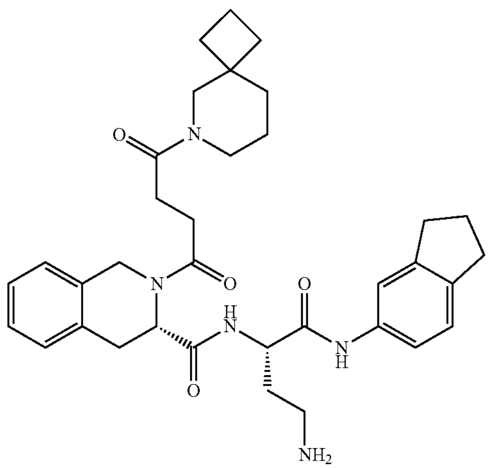 [SMILES: NCC[C@H](NC(=O)[C@@H]1Cc2ccccc2CN1C(=O)CCC(=O)N1CCCC2(CCC2)C1)C(=O)Nc1ccc2c(c1)CCC2] | 10-8 |
| 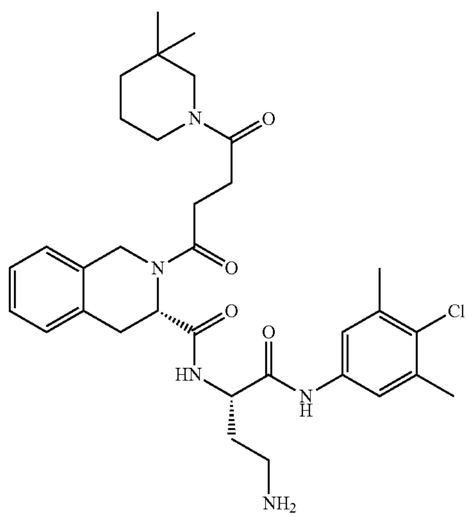 [SMILES: Cc1cc(NC(=O)[C@H](CCN)NC(=O)[C@@H]2Cc3ccccc3CN2C(=O)CCC(=O)N2CCCC(C)(C)C2)cc(C)c1Cl] | 10-9 |
| 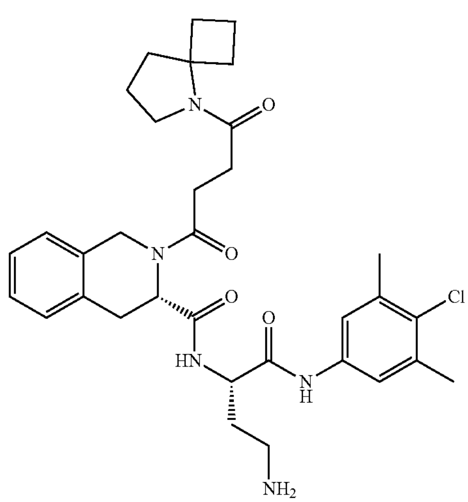 [SMILES: Cc1cc(NC(=O)[C@H](CCN)NC(=O)[C@@H]2Cc3ccccc3CN2C(=O)CCC(=O)N2CCCC23CCC3)cc(C)c1Cl] | 10-10 |

TABLE A-continued

REPRESENTATIVE COMPOUNDS

| Structure | Cpd. No. |
|---|---|
| 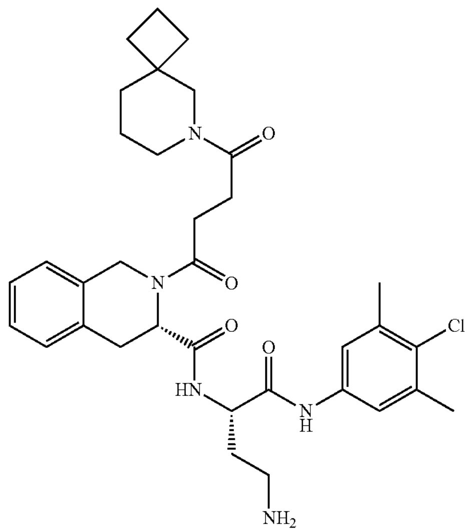 [SMILES: Cc1cc(NC(=O)[C@H](CCN)NC(=O)[C@@H]2Cc3ccccc3CN2C(=O)CCC(=O)N2CCCC3(CCC3)C2)cc(C)c1Cl] | 10-11 |
| 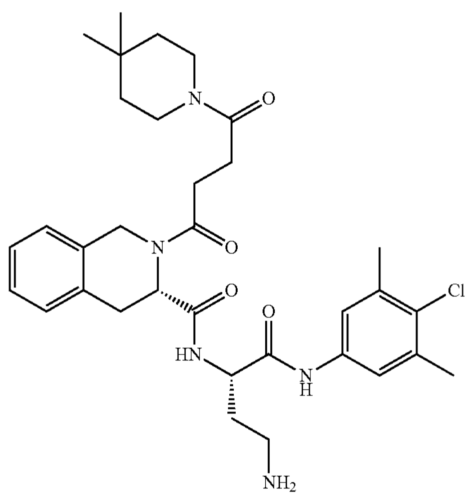 [SMILES: Cc1cc(NC(=O)[C@H](CCN)NC(=O)[C@@H]2Cc3ccccc3CN2C(=O)CCC(=O)N2CCC(C)(C)CC2)cc(C)c1Cl] | 10-12 |
| 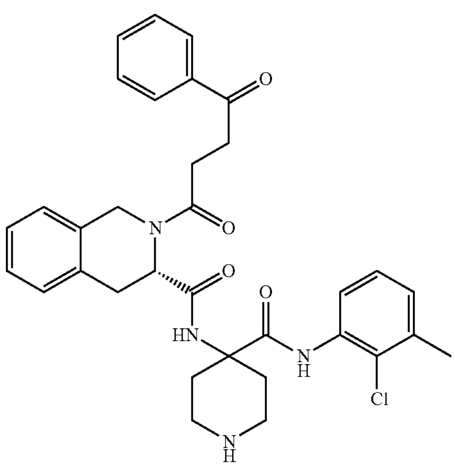 [SMILES: Cc1cccc(NC(=O)C2(NC(=O)[C@@H]3Cc4ccccc4CN3C(=O)CCC(=O)c3ccccc3)CCNCC2)c1Cl] | 11-1 |

TABLE A-continued

REPRESENTATIVE COMPOUNDS

| Structure | Cpd. No. |
|---|---|
| 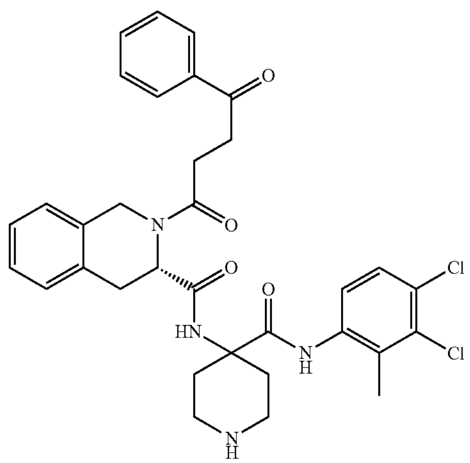 [SMILES: Cc1c(NC(=O)C2(NC(=O)[C@@H]3Cc4ccccc4CN3C(=O)CCC(=O)c3ccccc3)CCNCC2)ccc(Cl)c1Cl] | 11-2 |
| 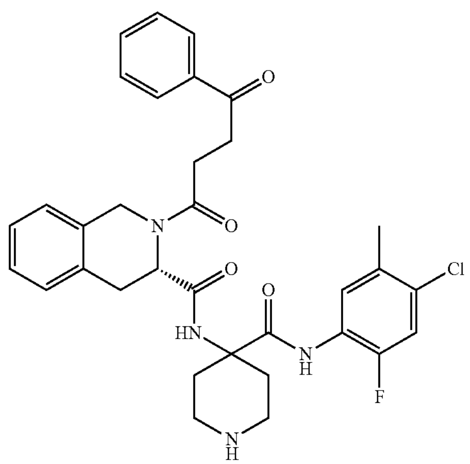 [SMILES: Cc1cc(NC(=O)C2(NC(=O)[C@@H]3Cc4ccccc4CN3C(=O)CCC(=O)c3ccccc3)CCNCC2)c(F)cc1Cl] | 11-3 |
| 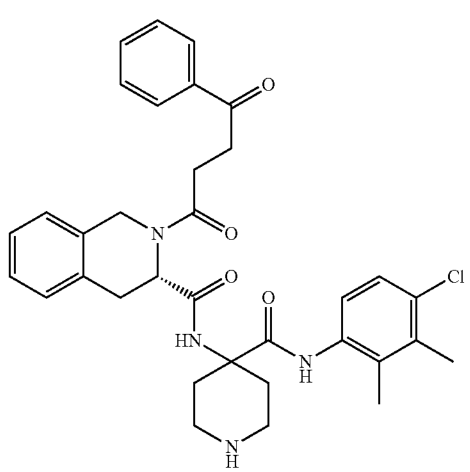 [SMILES: Cc1c(Cl)ccc(NC(=O)C2(NC(=O)[C@@H]3Cc4ccccc4CN3C(=O)CCC(=O)c3ccccc3)CCNCC2)c1C] | 11-4 |

TABLE A-continued

REPRESENTATIVE COMPOUNDS

| Structure | Cpd. No. |
|---|---|
| 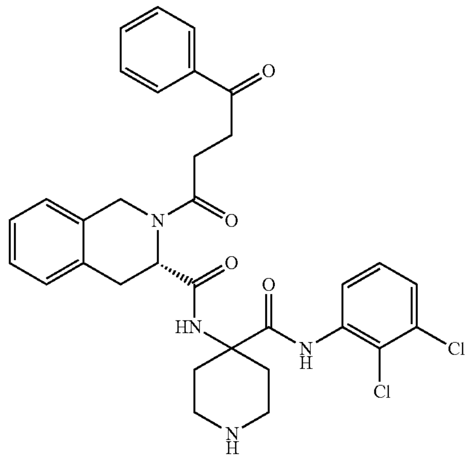 [SMILES: O=C(CCC(=O)N1Cc2ccccc2C[C@H]1C(=O)NC1(C(=O)Nc2cccc(Cl)c2Cl)CCNCC1)c1ccccc1] | 11-5 |
| 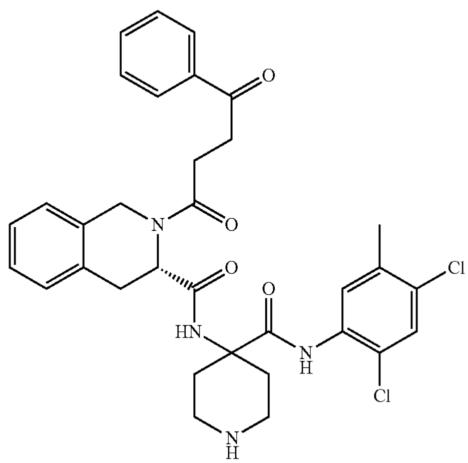 [SMILES: Cc1cc(NC(=O)C2(NC(=O)[C@@H]3Cc4ccccc4CN3C(=O)CCC(=O)c3ccccc3)CCNCC2)c(Cl)cc1Cl] | 11-6 |
| 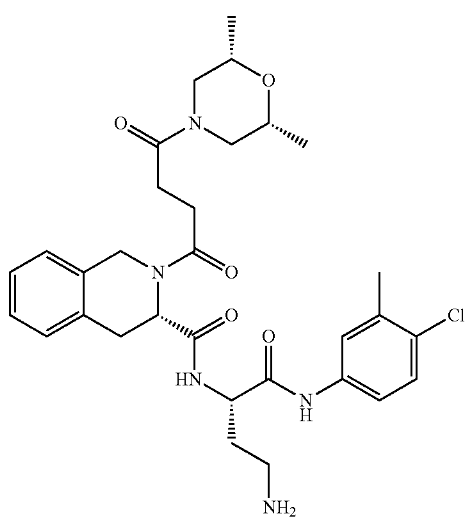 [SMILES: Cc1cc(NC(=O)[C@H](CCN)NC(=O)[C@@H]2Cc3ccccc3CN2C(=O)CCC(=O)N2C[C@@H](C)O[C@@H](C)C2)ccc1Cl] | 12-1 |

TABLE A-continued

REPRESENTATIVE COMPOUNDS

| Structure | Cpd. No. |
|---|---|
| 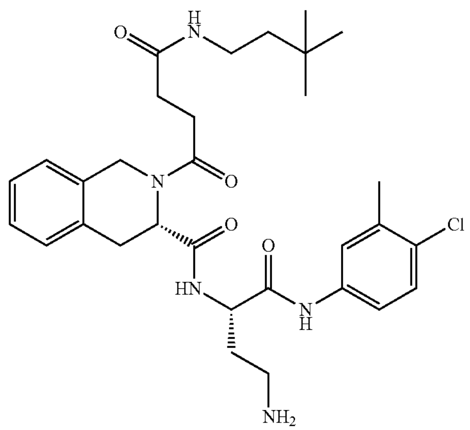 [SMILES: Cc1cc(NC(=O)[C@H](CCN)NC(=O)[C@@H]2Cc3ccccc3CN2C(=O)CCC(=O)NCCC(C)(C)C)ccc1Cl] | 12-2 |
| 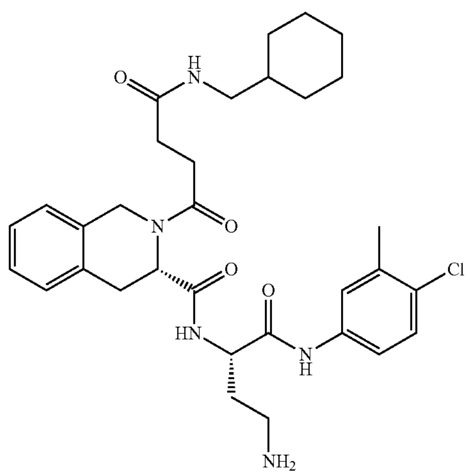 | 12-3 |
| 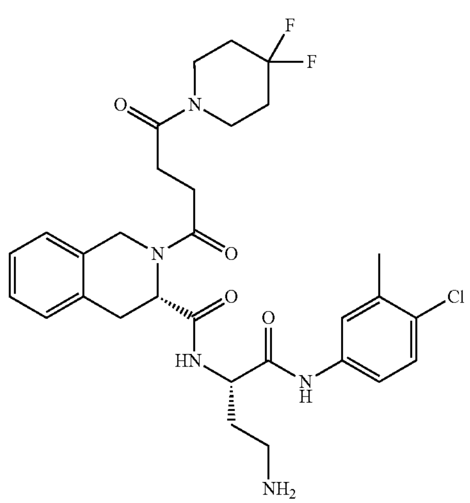 [SMILES: Cc1cc(NC(=O)[C@H](CCN)NC(=O)[C@@H]2Cc3ccccc3CN2C(=O)CCC(=O)N2CCC(F)(F)CC2)ccc1Cl] | 12-4 |

TABLE A-continued

REPRESENTATIVE COMPOUNDS

| Structure | Cpd. No. |
|---|---|
| 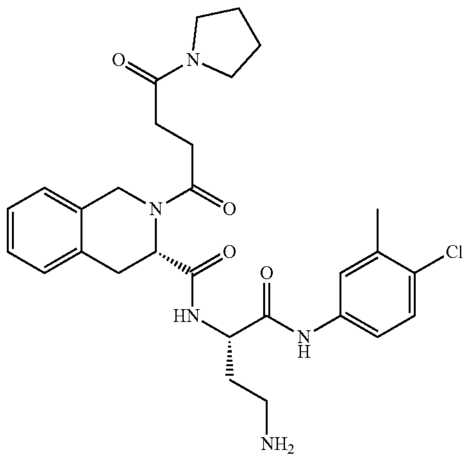 [SMILES: Cc1cc(NC(=O)[C@H](CCN)NC(=O)[C@@H]2Cc3ccccc3CN2C(=O)CCC(=O)N2CCCC2)ccc1Cl] | 12-5 |
| 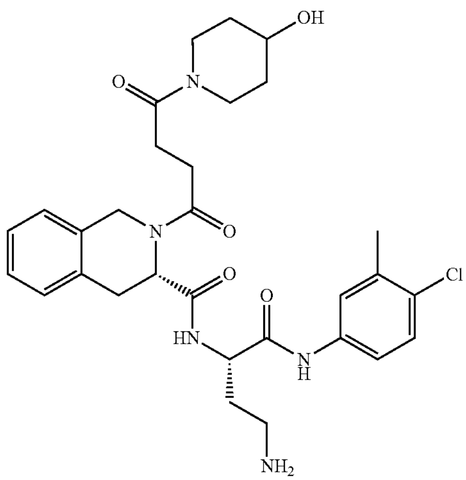 [SMILES: Cc1cc(NC(=O)[C@H](CCN)NC(=O)[C@@H]2Cc3ccccc3CN2C(=O)CCC(=O)N2CCC(O)CC2)ccc1Cl] | 12-6 |
| 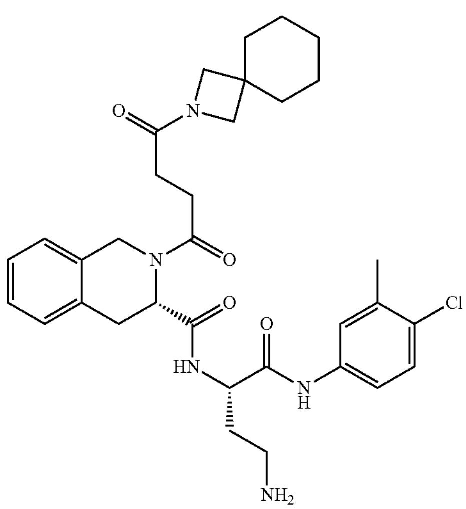 [SMILES: Cc1cc(NC(=O)[C@H](CCN)NC(=O)[C@@H]2Cc3ccccc3CN2C(=O)CCC(=O)N2CC3(CCCCC3)C2)ccc1Cl] | 12-7 |

TABLE A-continued

REPRESENTATIVE COMPOUNDS

| Structure | Cpd. No. |
|---|---|
| 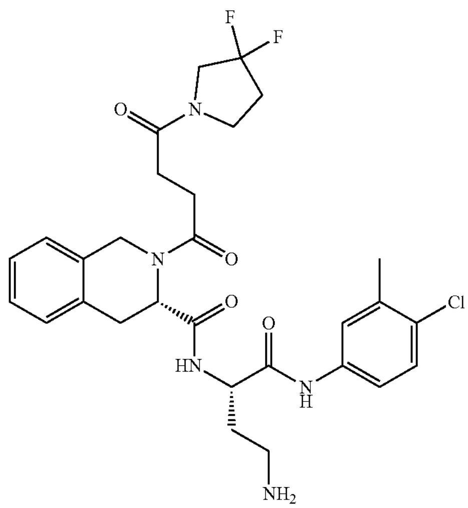 [SMILES: Cc1cc(NC(=O)[C@H](CCN)NC(=O)[C@@H]2Cc3ccccc3CN2C(=O)CCC(=O)N2CCC(F)(F)C2)ccc1Cl] | 12-8 |
| 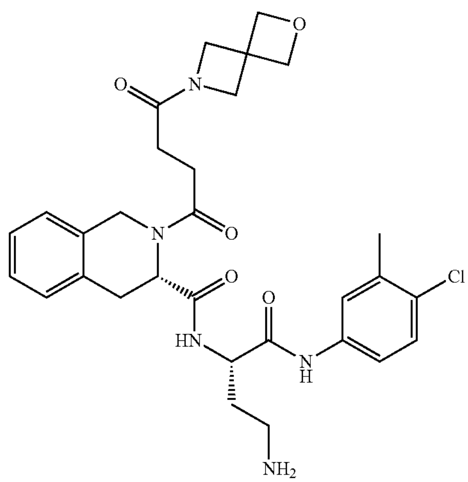 [SMILES: Cc1cc(NC(=O)[C@H](CCN)NC(=O)[C@@H]2Cc3ccccc3CN2C(=O)CCC(=O)N2CC3(COC3)C2)ccc1Cl] | 12-9 |
| 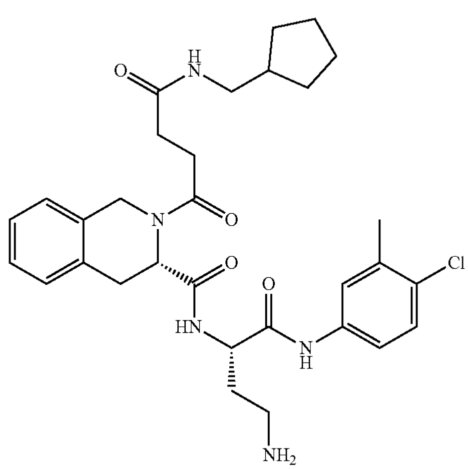 [SMILES: Cc1cc(NC(=O)[C@H](CCN)NC(=O)[C@@H]2Cc3ccccc3CN2C(=O)CCC(=O)NCC2CCCC2)ccc1Cl] | 12-10 |

TABLE A-continued

REPRESENTATIVE COMPOUNDS

| Structure | Cpd. No. |
|---|---|
| 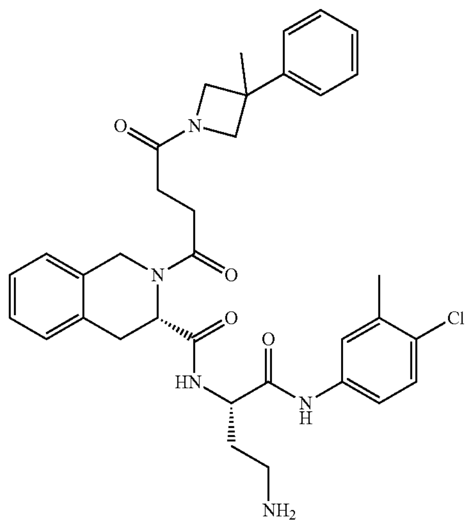 [SMILES: Cc1cc(NC(=O)[C@H](CCN)NC(=O)[C@@H]2Cc3ccccc3CN2C(=O)CCC(=O)N2CC(C)(c3ccccc3)C2)ccc1Cl] | 12-11 |
| 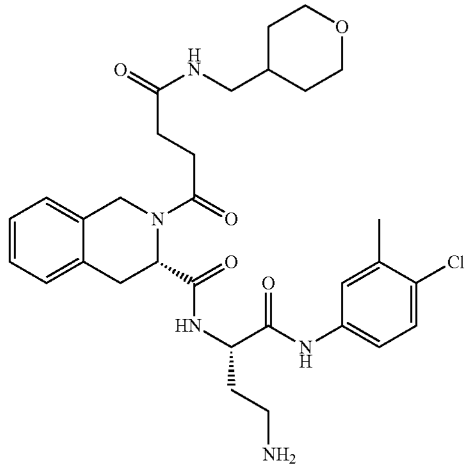 [SMILES: Cc1cc(NC(=O)[C@H](CCN)NC(=O)[C@@H]2Cc3ccccc3CN2C(=O)CCC(=O)NCC2CCOCC2)ccc1Cl] | 12-12 |
| 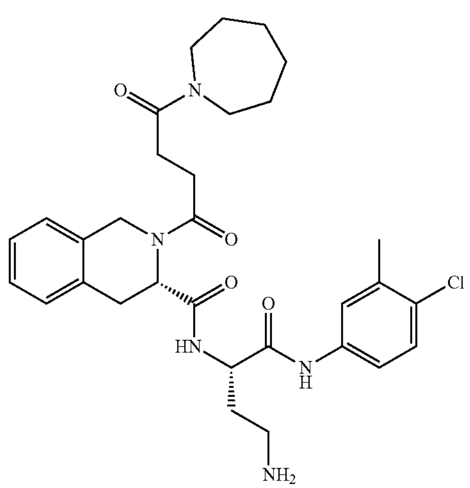 [SMILES: Cc1cc(NC(=O)[C@H](CCN)NC(=O)[C@@H]2Cc3ccccc3CN2C(=O)CCC(=O)N2CCCCCC2)ccc1Cl] | 12-13 |

TABLE A-continued

REPRESENTATIVE COMPOUNDS

| Structure | Cpd. No. |
|---|---|
| 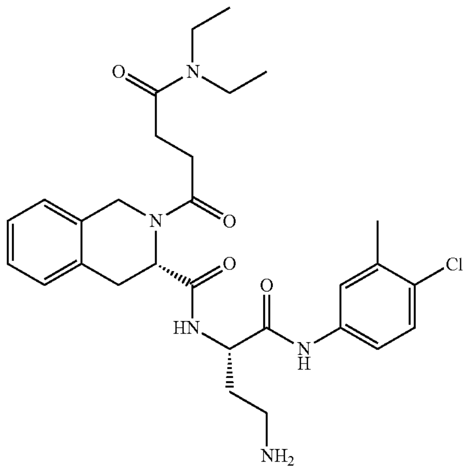 [SMILES: CCN(CC)C(=O)CCC(=O)N1Cc2ccccc2C[C@H]1C(=O)N[C@@H](CCN)C(=O)Nc1ccc(Cl)c(C)c1] | 12-14 |
| 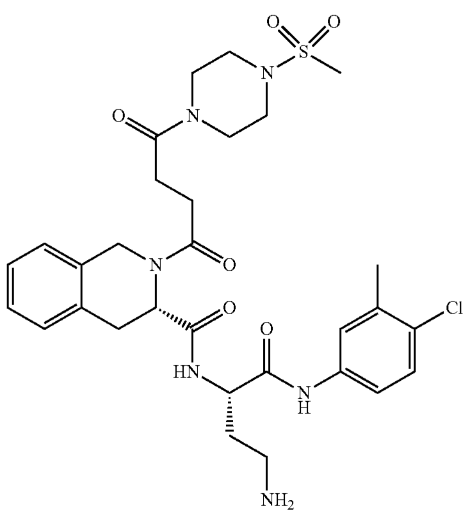 [SMILES: Cc1cc(NC(=O)[C@H](CCN)NC(=O)[C@@H]2Cc3ccccc3CN2C(=O)CCC(=O)N2CCN(S(C)(=O)=O)CC2)ccc1Cl] | 12-15 |
| 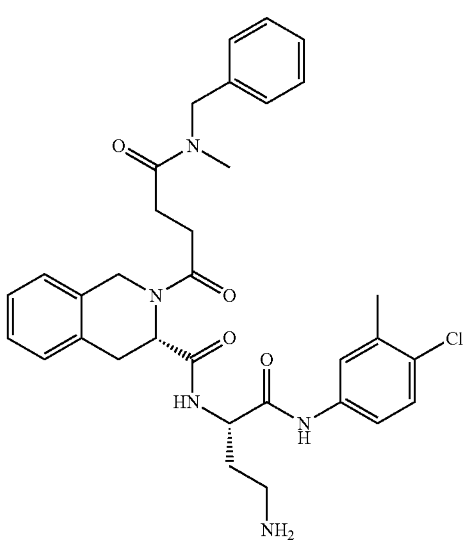 [SMILES: Cc1cc(NC(=O)[C@H](CCN)NC(=O)[C@@H]2Cc3ccccc3CN2C(=O)CCC(=O)N(C)Cc2ccccc2)ccc1Cl] | 12-16 |

TABLE A-continued

REPRESENTATIVE COMPOUNDS

| Structure | Cpd. No. |
|---|---|
| 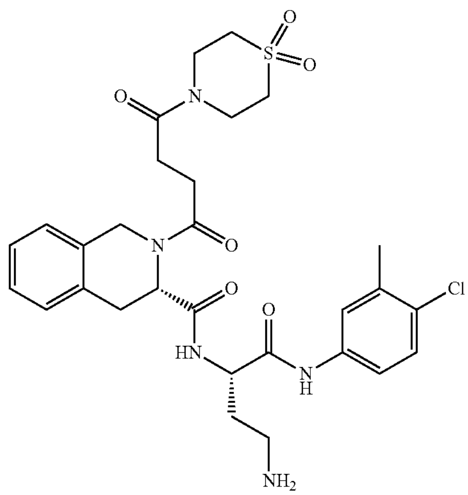 [SMILES: Cc1cc(NC(=O)[C@H](CCN)NC(=O)[C@@H]2Cc3ccccc3CN2C(=O)CCC(=O)N2CCS(=O)(=O)CC2)ccc1Cl] | 12-17 |
| 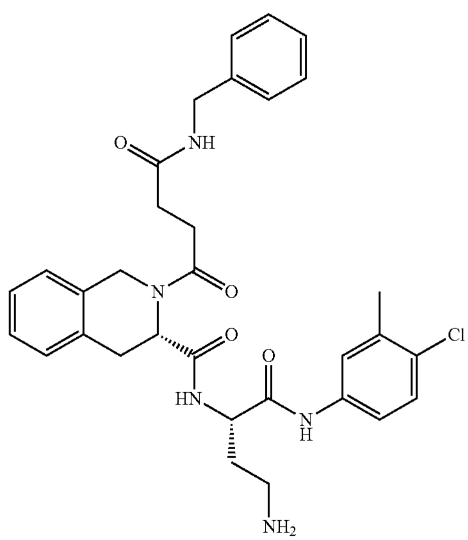 [SMILES: Cc1cc(NC(=O)[C@H](CCN)NC(=O)[C@@H]2Cc3ccccc3CN2C(=O)CCC(=O)NCc2ccccc2)ccc1Cl] | 12-18 |
| 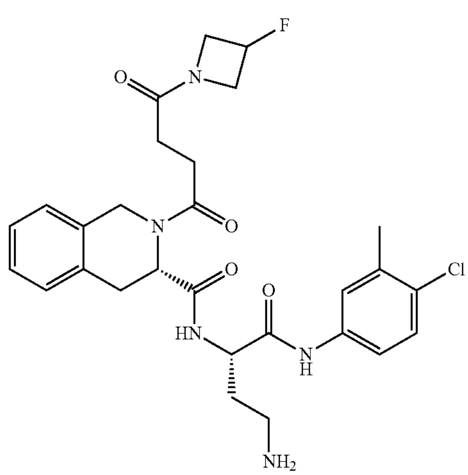 [SMILES: Cc1cc(NC(=O)[C@H](CCN)NC(=O)[C@@H]2Cc3ccccc3CN2C(=O)CCC(=O)N2CC(F)C2)ccc1Cl] | 12-19 |

TABLE A-continued
REPRESENTATIVE COMPOUNDS
| Structure | Cpd. No. |
|---|---|
| 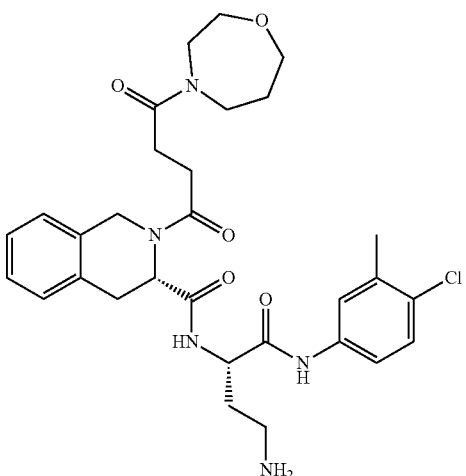 | 12-20 |
| 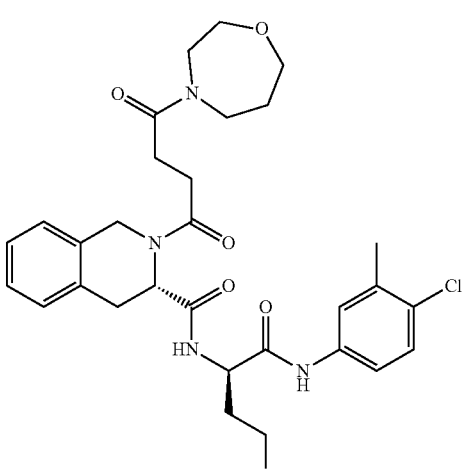 | 12-21 |
| 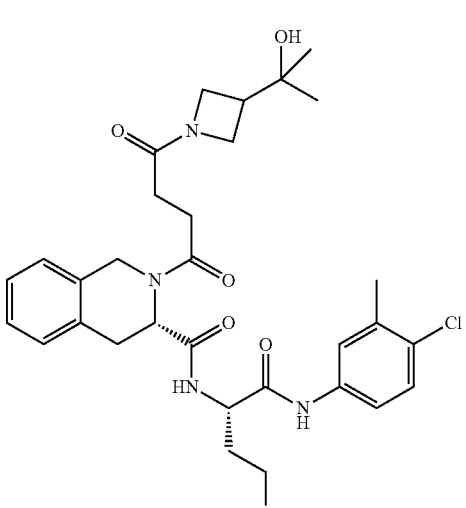 | 12-22 |

TABLE A-continued

REPRESENTATIVE COMPOUNDS

| Structure | Cpd. No. |
|---|---|
| 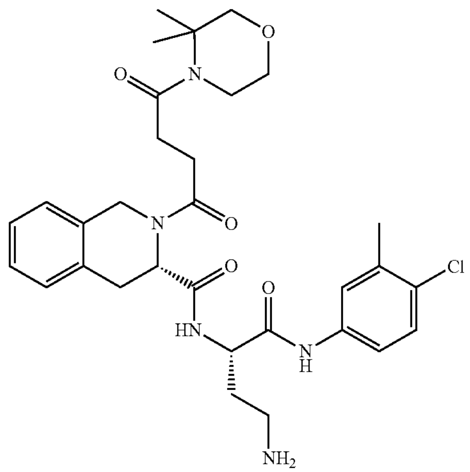 [SMILES: Cc1cc(NC(=O)[C@H](CCN)NC(=O)[C@@H]2Cc3ccccc3CN2C(=O)CCC(=O)N2CCOCC2(C)C)ccc1Cl] | 12-23 |
| 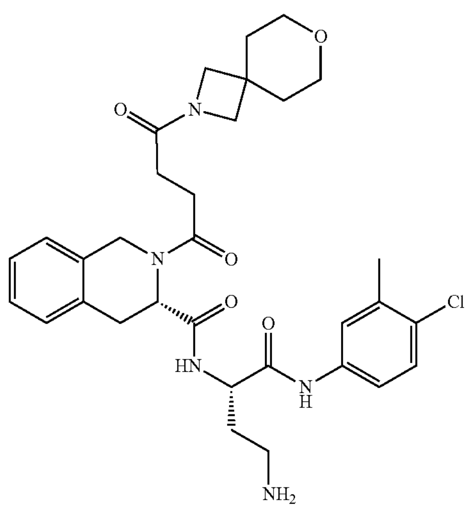 | 12-24 |
| 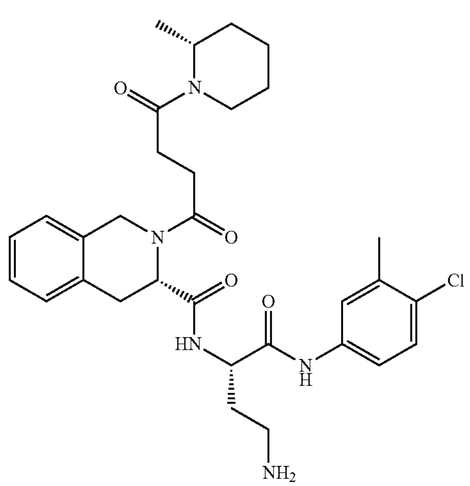 [SMILES: Cc1cc(NC(=O)[C@H](CCN)NC(=O)[C@@H]2Cc3ccccc3CN2C(=O)CCC(=O)N2CCCC[C@H]2C)ccc1Cl] | 12-25 |

TABLE A-continued
REPRESENTATIVE COMPOUNDS
| Structure | Cpd. No. |
|---|---|
| 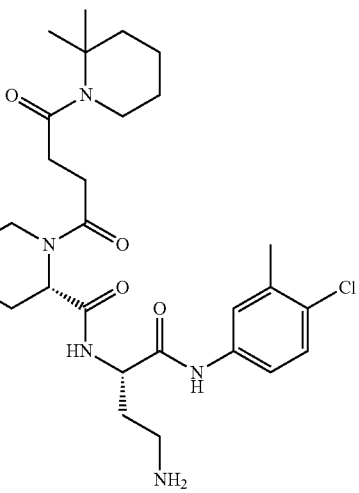 | 12-26 |
| 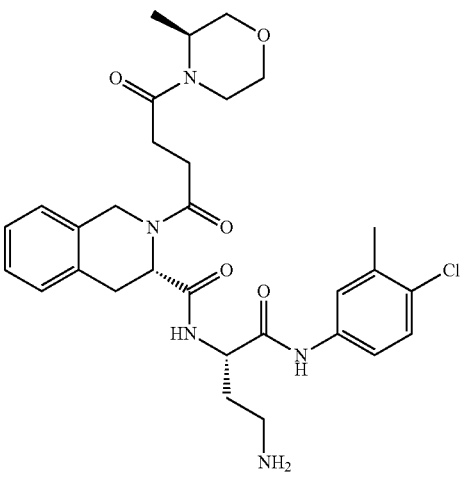 | 12-27 |
| 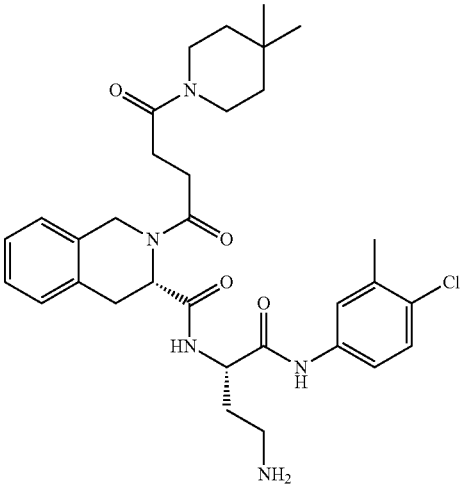 [SMILES: Cc1cc(NC(=O)[C@H](CCN)NC(=O)[C@@H]2Cc3ccccc3CN2C(=O)CCC(=O)N2CCC(C)(C)CC2)ccc1Cl] | 12-28 |

TABLE A-continued

REPRESENTATIVE COMPOUNDS

| Structure | Cpd. No. |
|---|---|
| 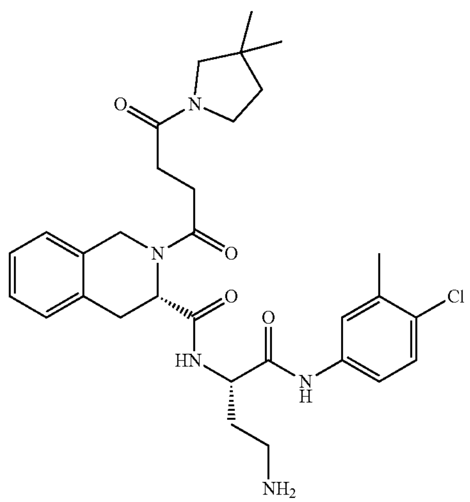 [SMILES: Cc1cc(NC(=O)[C@H](CCN)NC(=O)[C@@H]2Cc3ccccc3CN2C(=O)CCC(=O)N2CCC(C)(C)C2)ccc1Cl] | 12-29 |
| 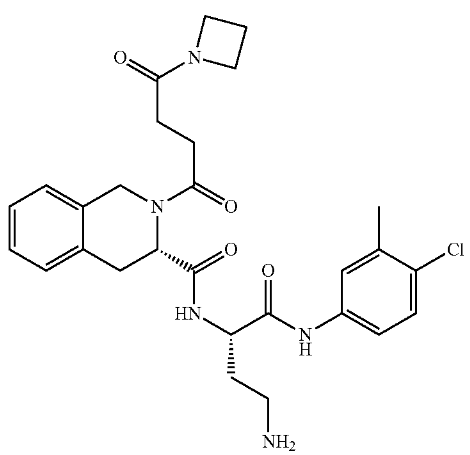 [SMILES: Cc1cc(NC(=O)[C@H](CCN)NC(=O)[C@@H]2Cc3ccccc3CN2C(=O)CCC(=O)N2CCC2)ccc1Cl] | 12-30 |
| 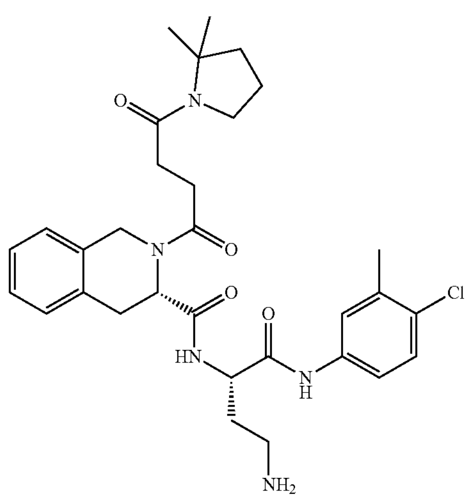 [SMILES: Cc1cc(NC(=O)[C@H](CCN)NC(=O)[C@@H]2Cc3ccccc3CN2C(=O)CCC(=O)N2CCCC2(C)C)ccc1Cl] | 12-31 |

TABLE A-continued

REPRESENTATIVE COMPOUNDS

| Structure | Cpd. No. |
|---|---|
| 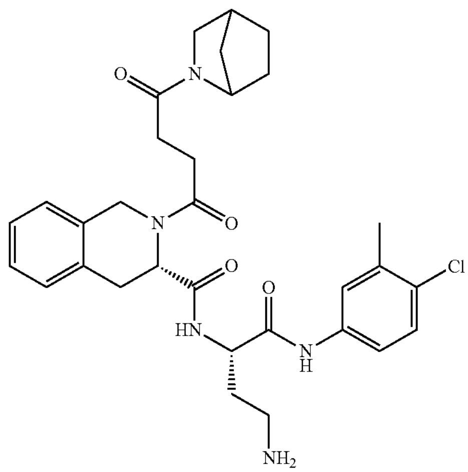 [SMILES: Cc1cc(NC(=O)[C@H](CCN)NC(=O)[C@@H]2Cc3ccccc3CN2C(=O)CCC(=O)N2CC3CCC2C3)ccc1Cl] | 12-32 |
| 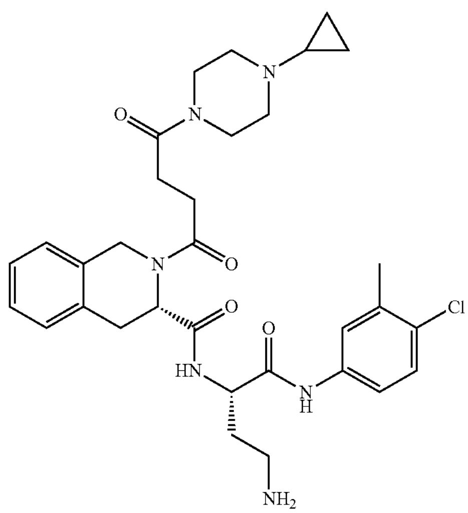 [SMILES: Cc1cc(NC(=O)[C@H](CCN)NC(=O)[C@@H]2Cc3ccccc3CN2C(=O)CCC(=O)N2CCN(C3CC3)CC2)ccc1Cl] | 12-33 |
| 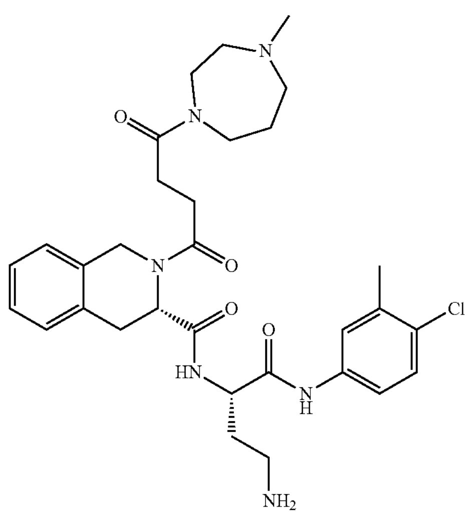 [SMILES: Cc1cc(NC(=O)[C@H](CCN)NC(=O)[C@@H]2Cc3ccccc3CN2C(=O)CCC(=O)N2CCCN(C)CC2)ccc1Cl] | 12-34 |

TABLE A-continued

REPRESENTATIVE COMPOUNDS

| Structure | Cpd. No. |
|---|---|
| 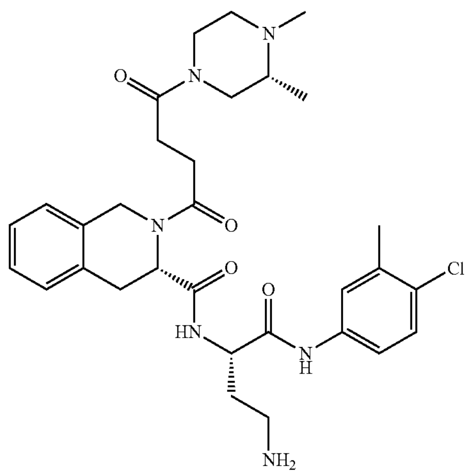 | 12-35 |
| 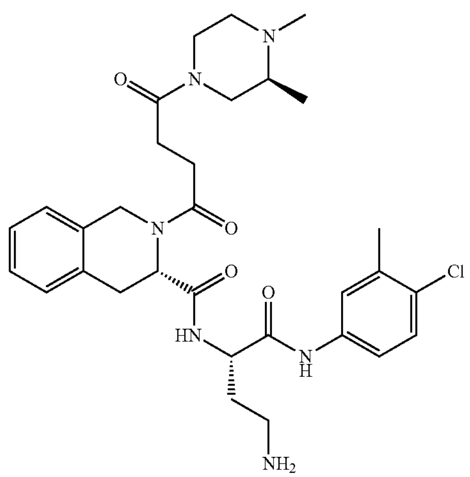 [SMILES: Cc1cc(NC(=O)[C@H](CCN)NC(=O)[C@@H]2Cc3ccccc3CN2C(=O)CCC(=O)N2CCN(C)[C@@H](C)C2)ccc1Cl] | 12-36 |
| 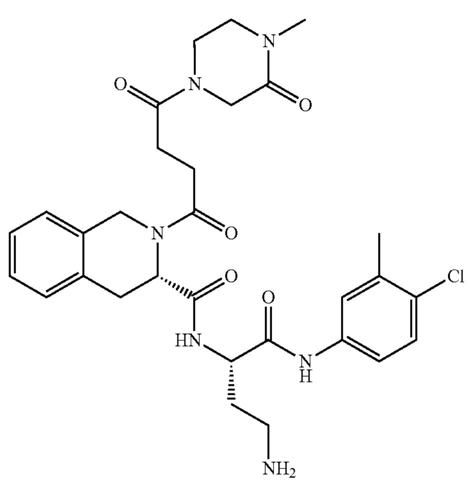 [SMILES: Cc1cc(NC(=O)[C@H](CCN)NC(=O)[C@@H]2Cc3ccccc3CN2C(=O)CCC(=O)N2CCN(C)C(=O)C2)ccc1Cl] | 12-37 |

TABLE A-continued

REPRESENTATIVE COMPOUNDS

| Structure | Cpd. No. |
|---|---|
| 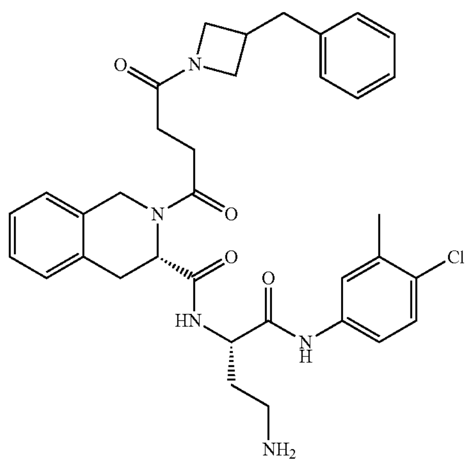 [SMILES: Cc1cc(NC(=O)[C@H](CCN)NC(=O)[C@@H]2Cc3ccccc3CN2C(=O)CCC(=O)N2CC(Cc3ccccc3)C2)ccc1Cl] | 12-38 |
| 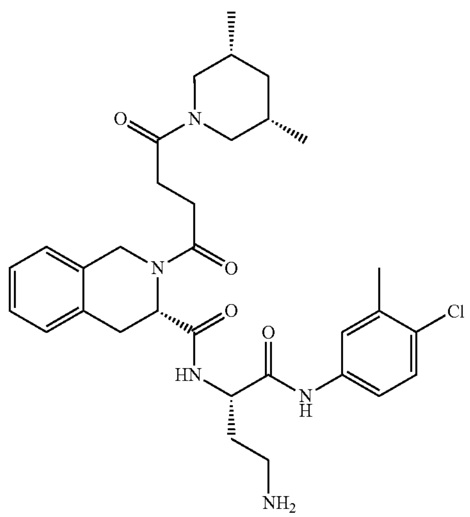 | 12-39 |
| 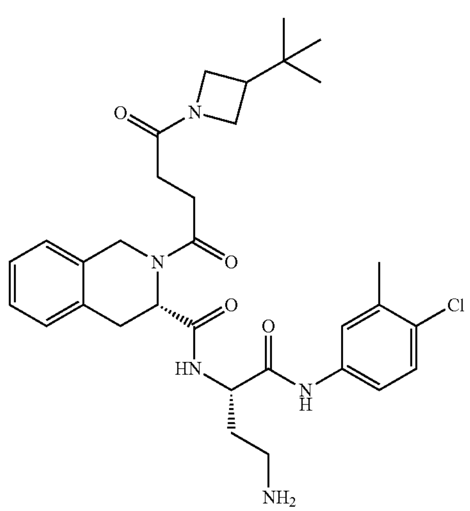 [SMILES: Cc1cc(NC(=O)[C@H](CCN)NC(=O)[C@@H]2Cc3ccccc3CN2C(=O)CCC(=O)N2CC(C(C)(C)C)C2)ccc1Cl] | 12-40 |

TABLE A-continued

REPRESENTATIVE COMPOUNDS

| Structure | Cpd. No. |
|---|---|
| 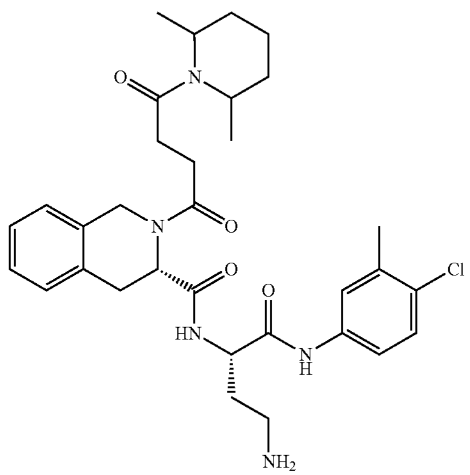 | 12-41 |
| 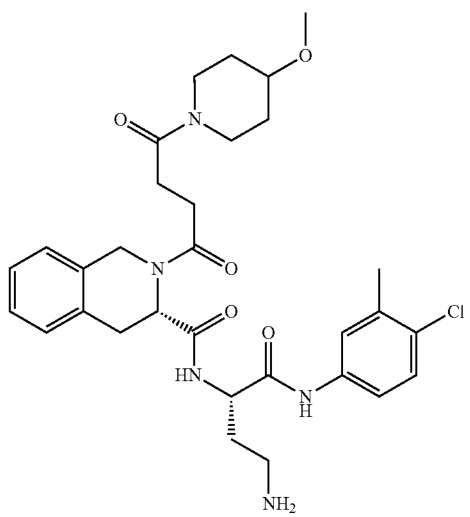 [SMILES: COC1CCN(C(=O)CCC(=O)N2Cc3ccccc3C[C@H]2C(=O)N[C@@H](CCN)C(=O)Nc2ccc(Cl)c(C)c2)CC1] | 12-42 |
| 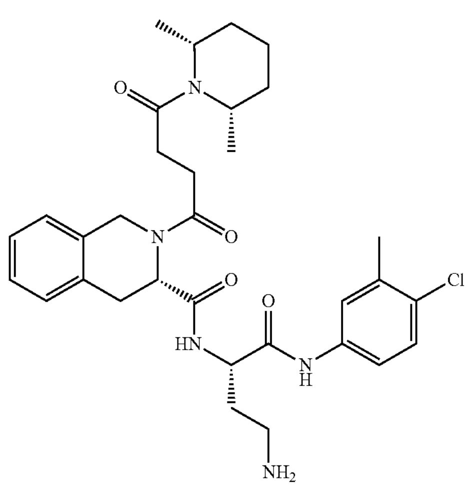 [SMILES: Cc1cc(NC(=O)[C@H](CCN)NC(=O)[C@@H]2Cc3ccccc3CN2C(=O)CCC(=O)N2[C@H](C)CCC[C@@H]2C)ccc1Cl] | 12-43 |

TABLE A-continued
REPRESENTATIVE COMPOUNDS
| Structure | Cpd. No. |
|---|---|
| 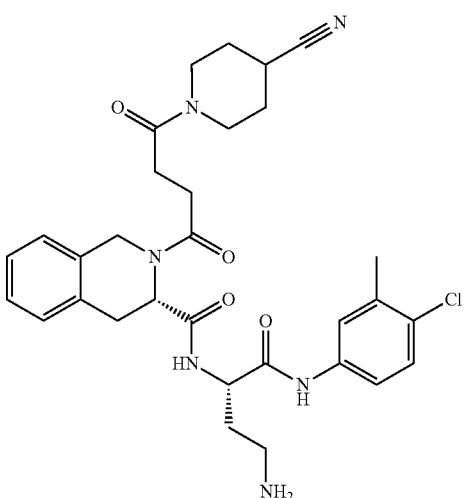 | 12-44 |
| 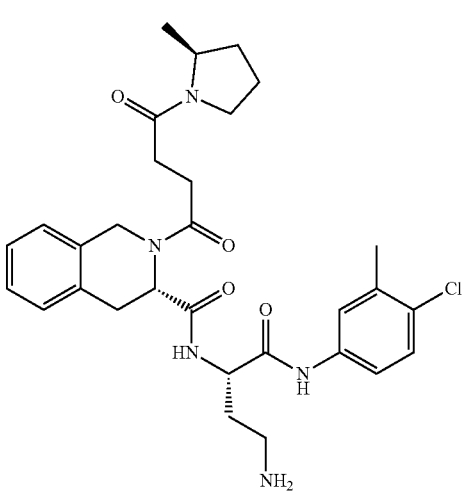 [SMILES: Cc1cc(NC(=O)[C@H](CCN)NC(=O)[C@@H]2Cc3ccccc3CN2C(=O)CCC(=O)N2CCC[C@@H]2C)ccc1Cl] | 12-45 |
| 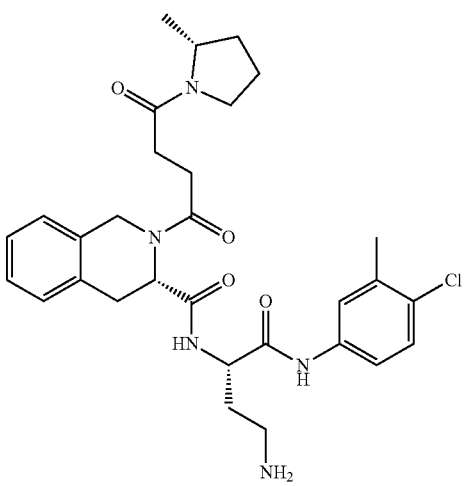 [SMILES: Cc1cc(NC(=O)[C@H](CCN)NC(=O)[C@@H]2Cc3ccccc3CN2C(=O)CCC(=O)N2CCC[C@H]2C)ccc1Cl] | 12-46 |

TABLE A-continued

REPRESENTATIVE COMPOUNDS

| Structure | Cpd. No. |
|---|---|
| 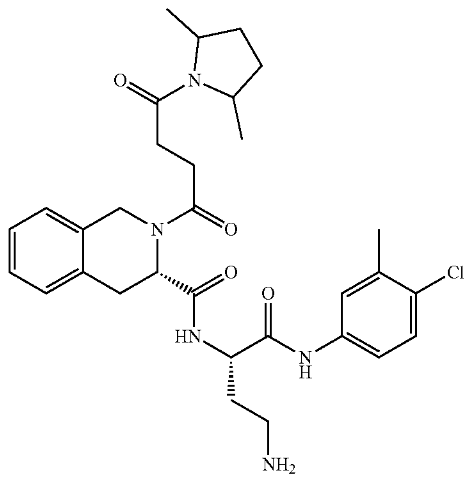 [SMILES: Cc1cc(NC(=O)[C@H](CCN)NC(=O)[C@@H]2Cc3ccccc3CN2C(=O)CCC(=O)N2C(C)CCC2C)ccc1Cl] | 12-47 |
| 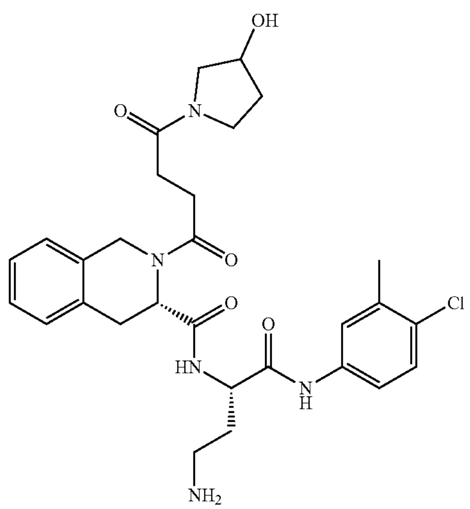 [SMILES: Cc1cc(NC(=O)[C@H](CCN)NC(=O)[C@@H]2Cc3ccccc3CN2C(=O)CCC(=O)N2CCC(O)C2)ccc1Cl] | 12-48 |
| 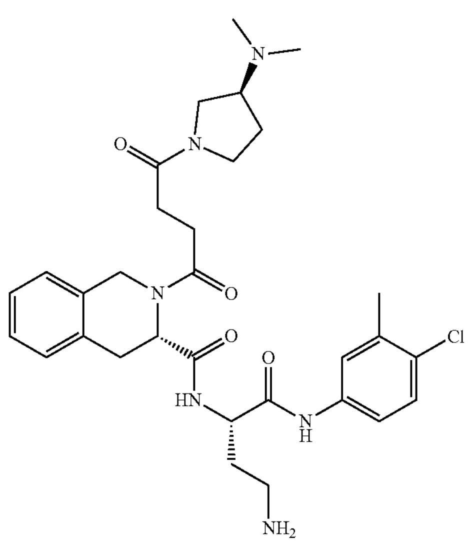 [SMILES: Cc1cc(NC(=O)[C@H](CCN)NC(=O)[C@@H]2Cc3ccccc3CN2C(=O)CCC(=O)N2CC[C@H](N(C)C)C2)ccc1Cl] | 12-49 |

TABLE A-continued
REPRESENTATIVE COMPOUNDS
| Structure | Cpd. No. |
|---|---|
| 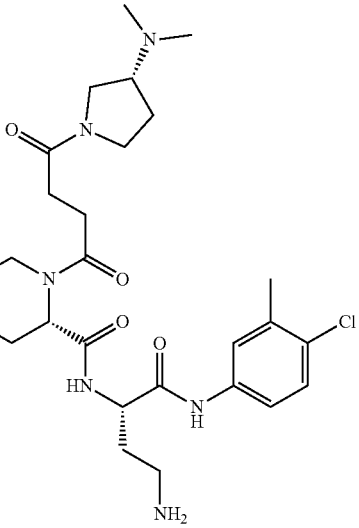 | 12-50 |
| 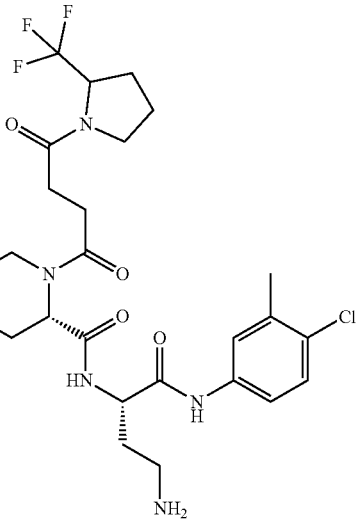 | 12-51 |
| 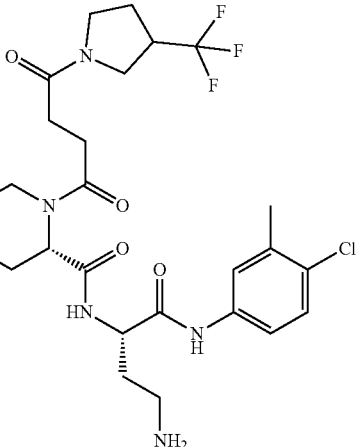 | 12-52 |

TABLE A-continued
REPRESENTATIVE COMPOUNDS
| Structure | Cpd. No. |
|---|---|
| 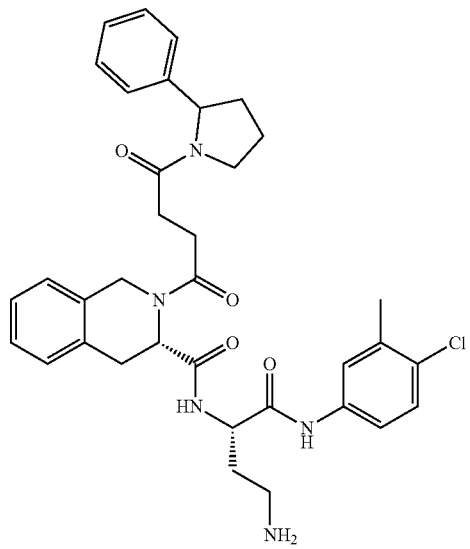 [SMILES: Cc1cc(NC(=O)[C@H](CCN)NC(=O)[C@@H]2Cc3ccccc3CN2C(=O)CCC(=O)N2CCCC2c2ccccc2)ccc1Cl] | 12-53 |
| 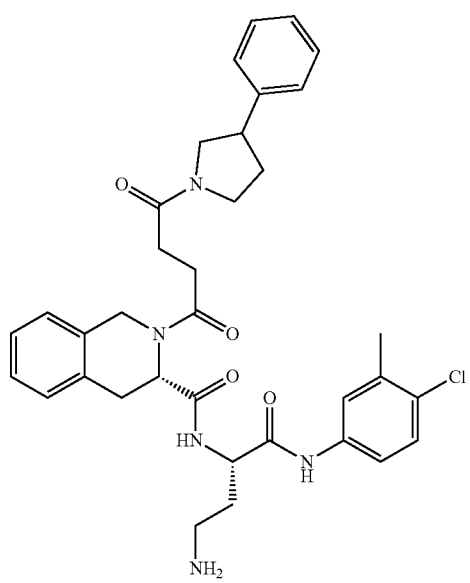 [SMILES: Cc1cc(NC(=O)[C@H](CCN)NC(=O)[C@@H]2Cc3ccccc3CN2C(=O)CCC(=O)N2CCC(c3ccccc3)C2)ccc1Cl] | 12-54 |

TABLE A-continued
REPRESENTATIVE COMPOUNDS
| Structure | Cpd. No. |
|---|---|
| 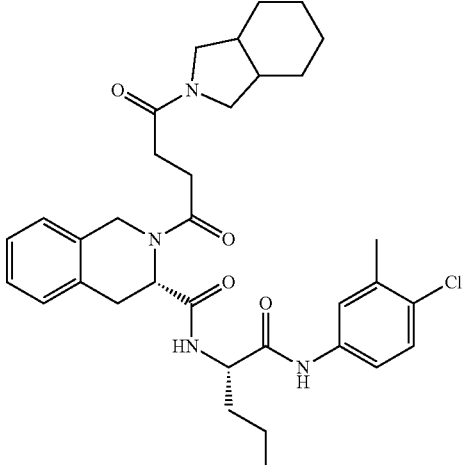 | 12-55 |
| 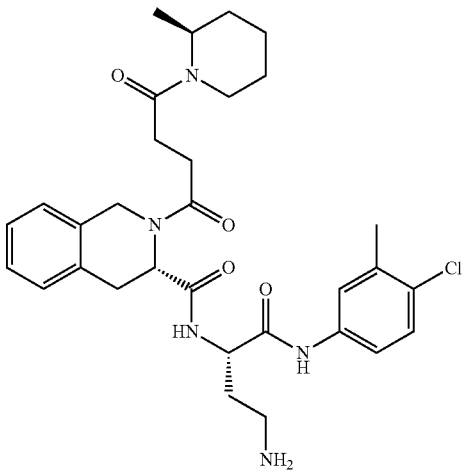 [SMILES: Cc1cc(NC(=O)[C@H](CCN)NC(=O)[C@@H]2Cc3ccccc3CN2C(=O)CCC(=O)N2CCCC[C@@H]2C)ccc1Cl] | 12-56 |
| 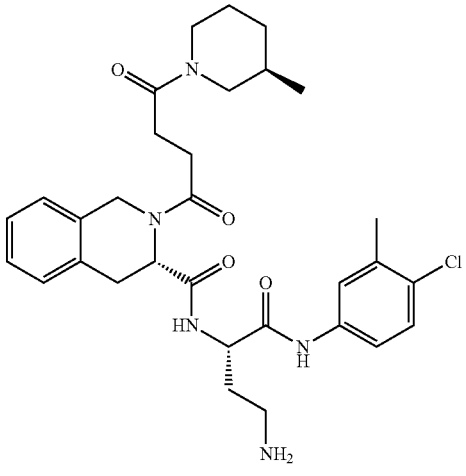 [SMILES: Cc1cc(NC(=O)[C@H](CCN)NC(=O)[C@@H]2Cc3ccccc3CN2C(=O)CCC(=O)N2CCC[C@@H](C)C2)ccc1Cl] | 12-57 |

TABLE A-continued

REPRESENTATIVE COMPOUNDS

| Structure | Cpd. No. |
|---|---|
| 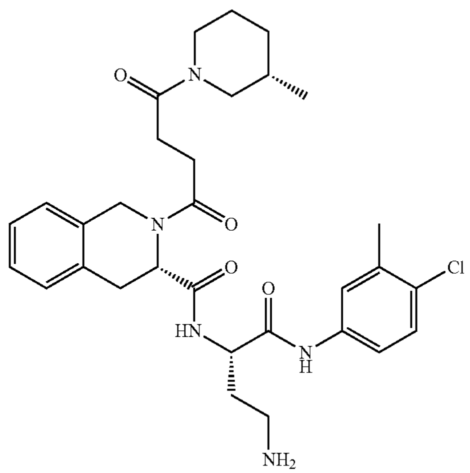 [SMILES: Cc1cc(NC(=O)[C@H](CCN)NC(=O)[C@@H]2Cc3ccccc3CN2C(=O)CCC(=O)N2CCC[C@H](C)C2)ccc1Cl] | 12-58 |
| 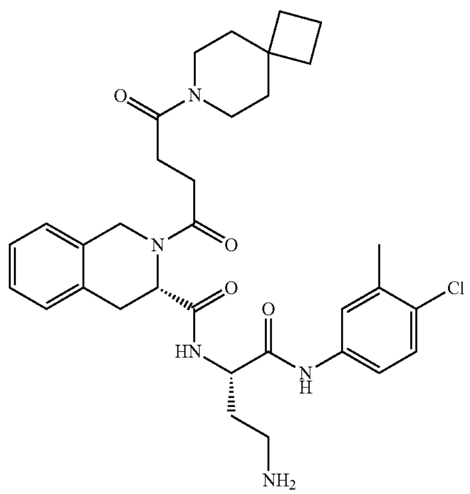 [SMILES: Cc1cc(NC(=O)[C@H](CCN)NC(=O)[C@@H]2Cc3ccccc3CN2C(=O)CCC(=O)N2CCC3(CCC3)CC2)ccc1Cl] | 12-59 |
| 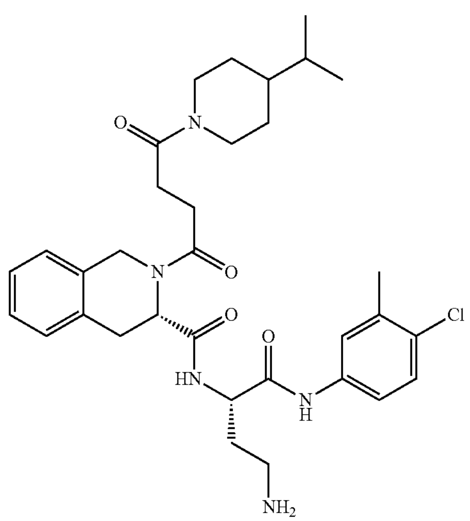 [SMILES: Cc1cc(NC(=O)[C@H](CCN)NC(=O)[C@@H]2Cc3ccccc3CN2C(=O)CCC(=O)N2CCC(C(C)C)CC2)ccc1Cl] | 12-60 |

TABLE A-continued
REPRESENTATIVE COMPOUNDS
| Structure | Cpd. No. |
|---|---|
| 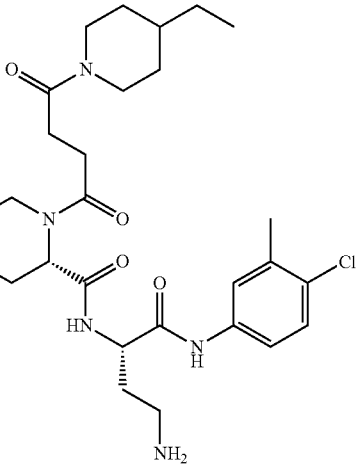 | 12-61 |
| 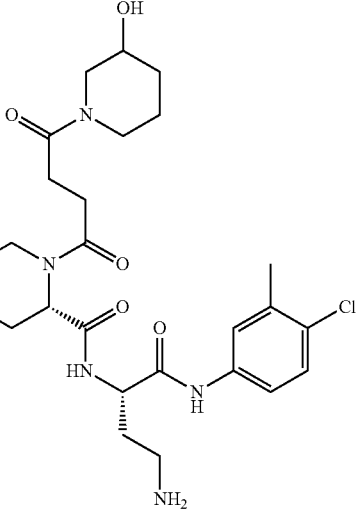 | 12-62 |
| 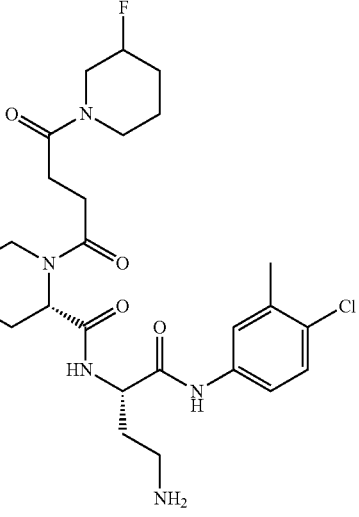 | 12-63 |

TABLE A-continued

REPRESENTATIVE COMPOUNDS

| Structure | Cpd. No. |
|---|---|
| 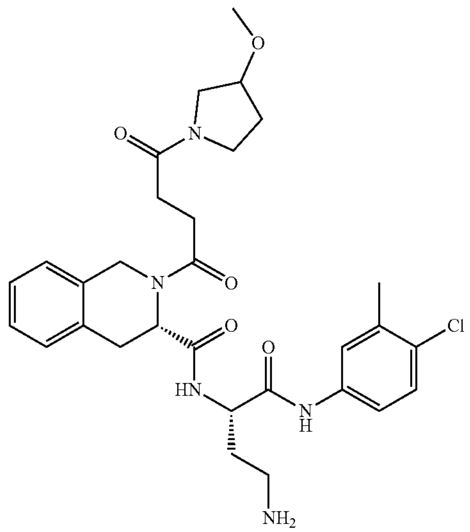 [SMILES: COC1CCN(C(=O)CCC(=O)N2Cc3ccccc3C[C@H]2C(=O)N[C@@H](CCN)C(=O)Nc2ccc(Cl)c(C)c2)C1] | 12-64 |
| 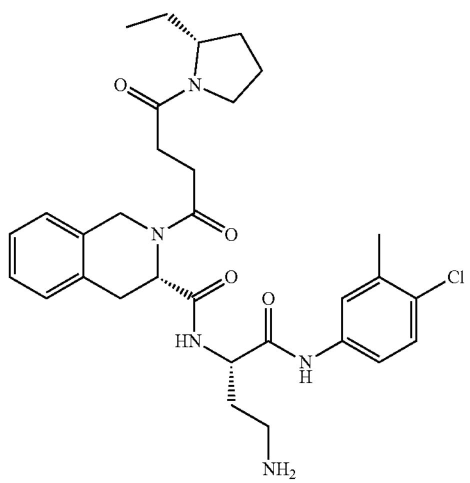 [SMILES: CC[C@@H]1CCCN1C(=O)CCC(=O)N1Cc2ccccc2C[C@H]1C(=O)N[C@@H](CCN)C(=O)Nc1ccc(Cl)c(C)c1] | 12-65 |
| 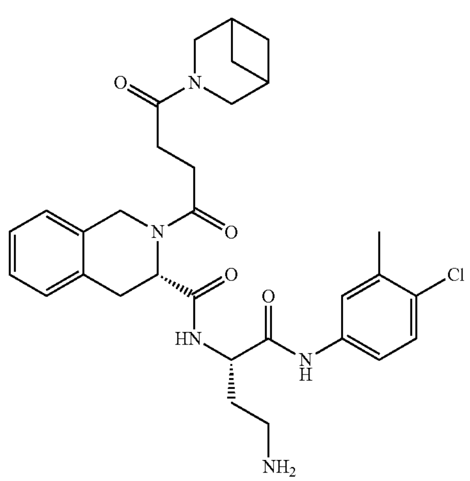 [SMILES: Cc1cc(NC(=O)[C@H](CCN)NC(=O)[C@@H]2Cc3ccccc3CN2C(=O)CCC(=O)N2CC3CC(C3)C2)ccc1Cl] | 12-66 |

TABLE A-continued

REPRESENTATIVE COMPOUNDS

| Structure | Cpd. No. |
|---|---|
| 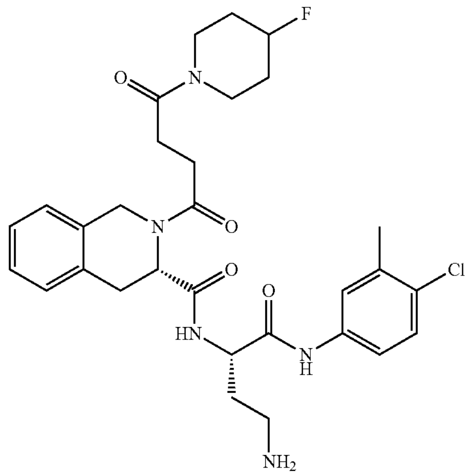 [SMILES: Cc1cc(NC(=O)[C@H](CCN)NC(=O)[C@@H]2Cc3ccccc3CN2C(=O)CCC(=O)N2CCC(F)CC2)ccc1Cl] | 12-67 |
| 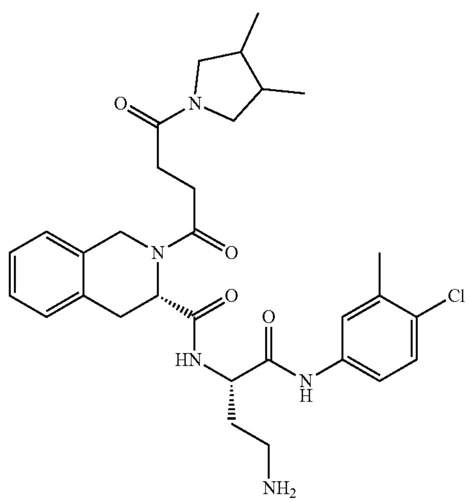 [SMILES: Cc1cc(NC(=O)[C@H](CCN)NC(=O)[C@@H]2Cc3ccccc3CN2C(=O)CCC(=O)N2CC(C)C(C)C2)ccc1Cl] | 12-68 |
| 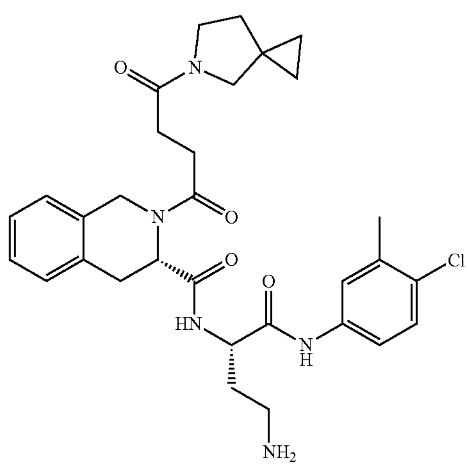 [SMILES: Cc1cc(NC(=O)[C@H](CCN)NC(=O)[C@@H]2Cc3ccccc3CN2C(=O)CCC(=O)N2CCC3(CC3)C2)ccc1Cl] | 12-69 |

TABLE A-continued

REPRESENTATIVE COMPOUNDS

| Structure | Cpd. No. |
| --- | --- |
| 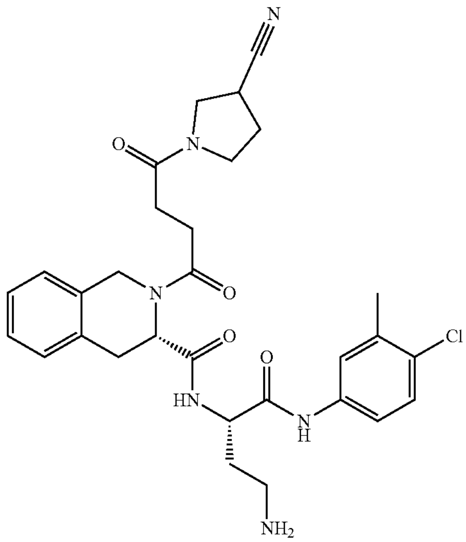 [SMILES: Cc1cc(NC(=O)[C@H](CCN)NC(=O)[C@@H]2Cc3ccccc3CN2C(=O)CCC(=O)N2CCC(C#N)C2)ccc1Cl] | 12-70 |
| 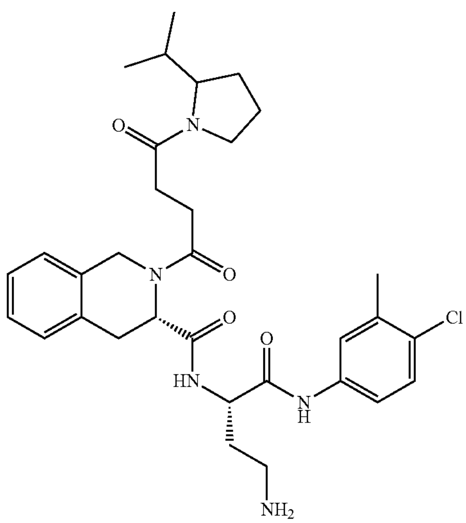 [SMILES: Cc1cc(NC(=O)[C@H](CCN)NC(=O)[C@@H]2Cc3ccccc3CN2C(=O)CCC(=O)N2CCCC2C(C)C)ccc1Cl] | 12-71 |
| 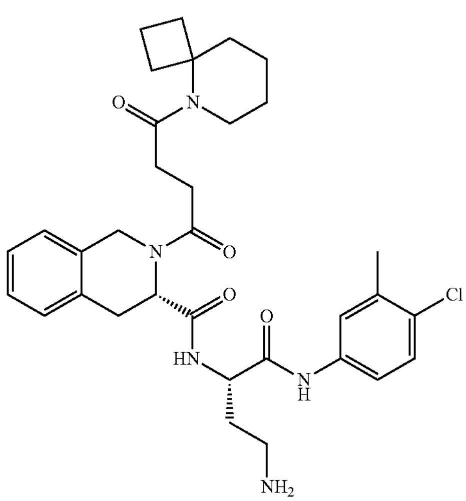 [SMILES: Cc1cc(NC(=O)[C@H](CCN)NC(=O)[C@@H]2Cc3ccccc3CN2C(=O)CCC(=O)N2CCCCC23CCC3)ccc1Cl] | 12-72 |

TABLE A-continued

REPRESENTATIVE COMPOUNDS

| Structure | Cpd. No. |
|---|---|
| 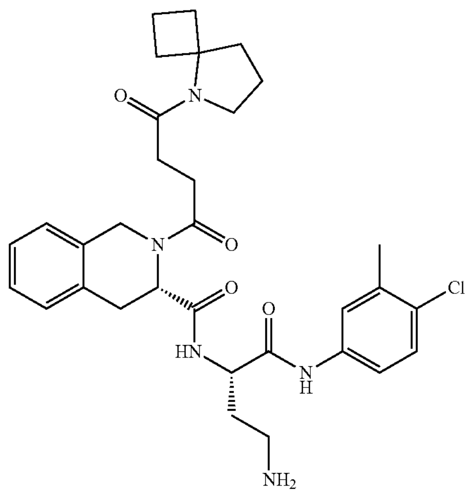 [SMILES: Cc1cc(NC(=O)[C@H](CCN)NC(=O)[C@@H]2Cc3ccccc3CN2C(=O)CCC(=O)N2CCCC23CCC3)ccc1Cl] | 12-73 |
| 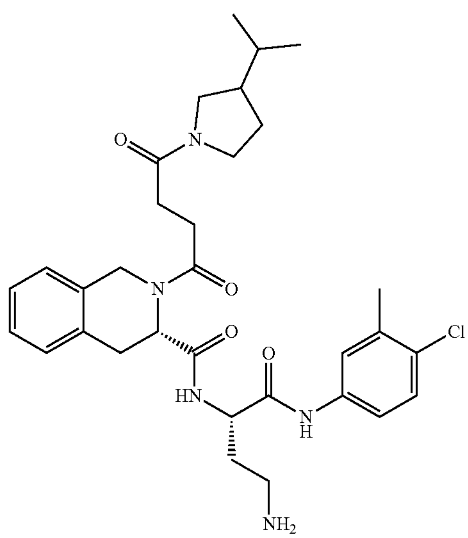 [SMILES: Cc1cc(NC(=O)[C@H](CCN)NC(=O)[C@@H]2Cc3ccccc3CN2C(=O)CCC(=O)N2CCC(C(C)C)C2)ccc1Cl] | 12-74 |
| 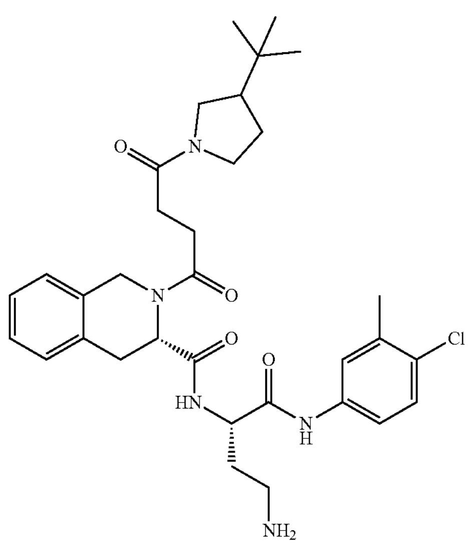 [SMILES: Cc1cc(NC(=O)[C@H](CCN)NC(=O)[C@@H]2Cc3ccccc3CN2C(=O)CCC(=O)N2CCC(C(C)(C)C)C2)ccc1Cl] | 12-75 |

TABLE A-continued

REPRESENTATIVE COMPOUNDS

| Structure | Cpd. No. |
|---|---|
| 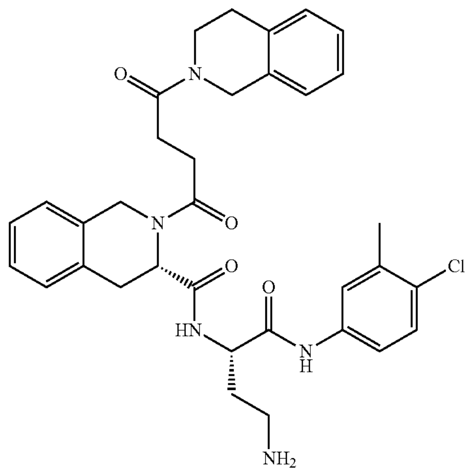 [SMILES: Cc1cc(NC(=O)[C@H](CCN)NC(=O)[C@@H]2Cc3ccccc3CN2C(=O)CCC(=O)N2CCc3ccccc3C2)ccc1Cl] | 12-76 |
| 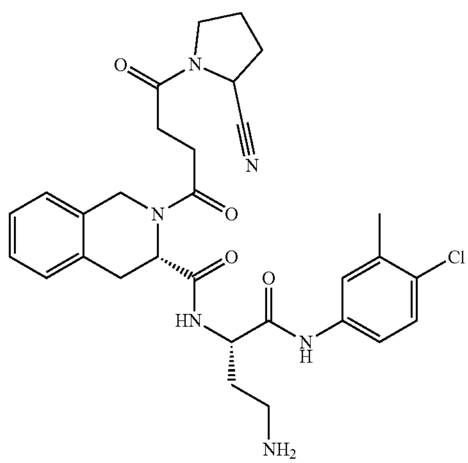 [SMILES: Cc1cc(NC(=O)[C@H](CCN)NC(=O)[C@@H]2Cc3ccccc3CN2C(=O)CCC(=O)N2CCCC2C#N)ccc1Cl] | 12-77 |
| 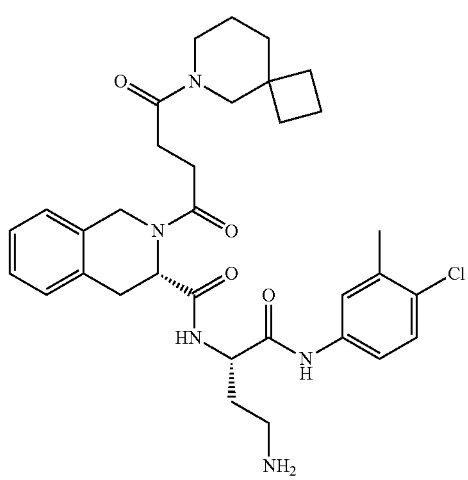 [SMILES: Cc1cc(NC(=O)[C@H](CCN)NC(=O)[C@@H]2Cc3ccccc3CN2C(=O)CCC(=O)N2CCCC3(CCC3)C2)ccc1Cl] | 12-78 |

TABLE A-continued

REPRESENTATIVE COMPOUNDS

| Structure | Cpd. No. |
|---|---|
| 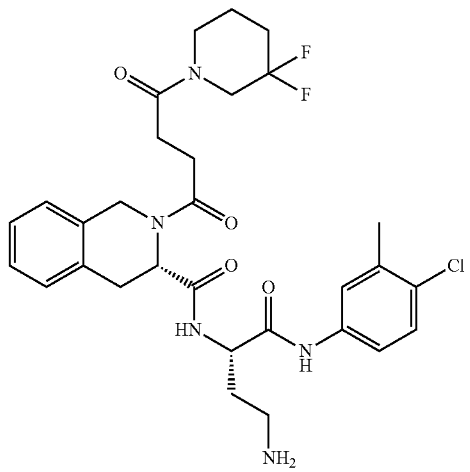 [SMILES: Cc1cc(NC(=O)[C@H](CCN)NC(=O)[C@@H]2Cc3ccccc3CN2C(=O)CCC(=O)N2CCCC(F)(F)C2)ccc1Cl] | 12-79 |
| 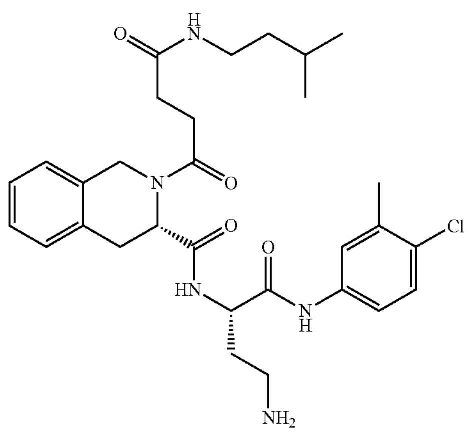 [SMILES: Cc1cc(NC(=O)[C@H](CCN)NC(=O)[C@@H]2Cc3ccccc3CN2C(=O)CCC(=O)NCCC(C)C)ccc1Cl] | 12-80 |
| 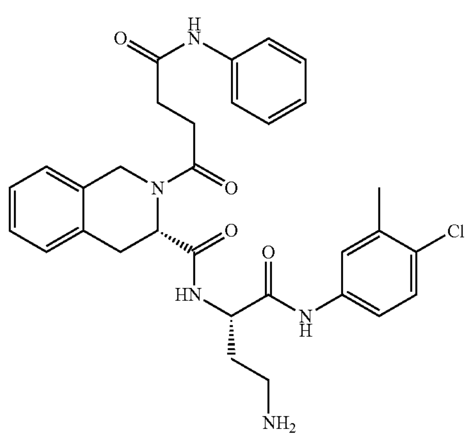 [SMILES: Cc1cc(NC(=O)[C@H](CCN)NC(=O)[C@@H]2Cc3ccccc3CN2C(=O)CCC(=O)Nc2ccccc2)ccc1Cl] | 12-81 |

TABLE A-continued
REPRESENTATIVE COMPOUNDS
| Structure | Cpd. No. |
|---|---|
| 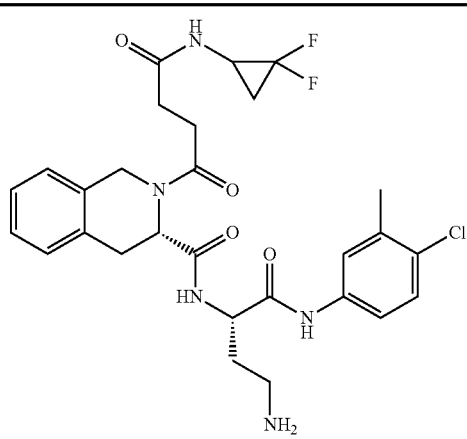 | 12-82 |
| 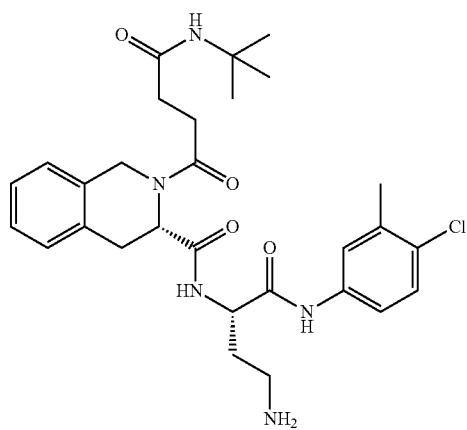 [SMILES: Cc1cc(NC(=O)[C@H](CCN)NC(=O)[C@@H]2Cc3ccccc3CN2C(=O)CCC(=O)NC(C)(C)C)ccc1Cl] | 12-83 |
| 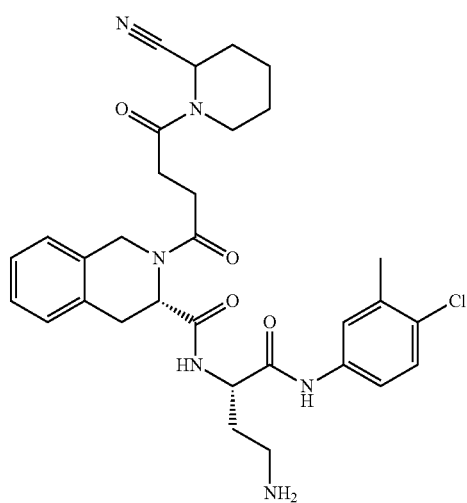 [SMILES: Cc1cc(NC(=O)[C@H](CCN)NC(=O)[C@@H]2Cc3ccccc3CN2C(=O)CCC(=O)N2CCCCC2C#N)ccc1Cl] | 12-84 |

TABLE A-continued

REPRESENTATIVE COMPOUNDS

| Structure | Cpd. No. |
|---|---|
| 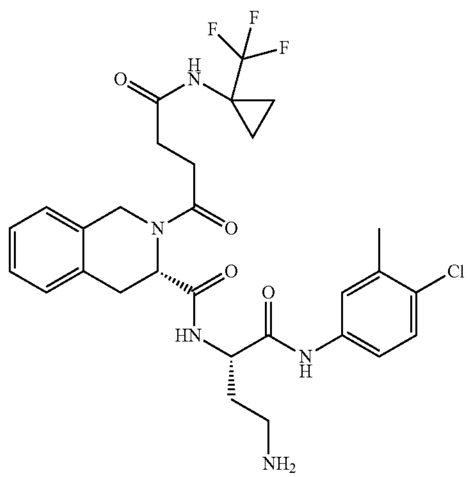 [SMILES: Cc1cc(NC(=O)[C@H](CCN)NC(=O)[C@@H]2Cc3ccccc3CN2C(=O)CCC(=O)NC2(C(F)(F)F)CC2)ccc1Cl] | 12-85 |
| 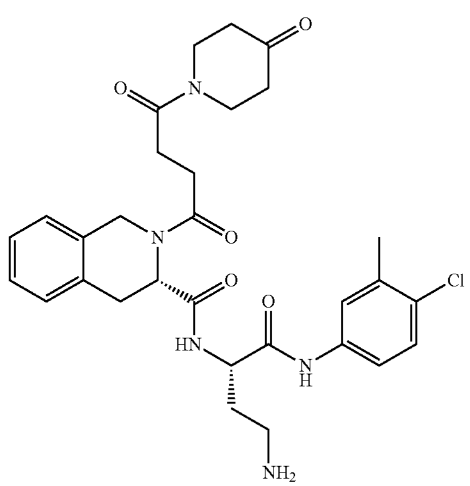 [SMILES: Cc1cc(NC(=O)[C@H](CCN)NC(=O)[C@@H]2Cc3ccccc3CN2C(=O)CCC(=O)N2CCC(=O)CC2)ccc1Cl] | 12-86 |
| 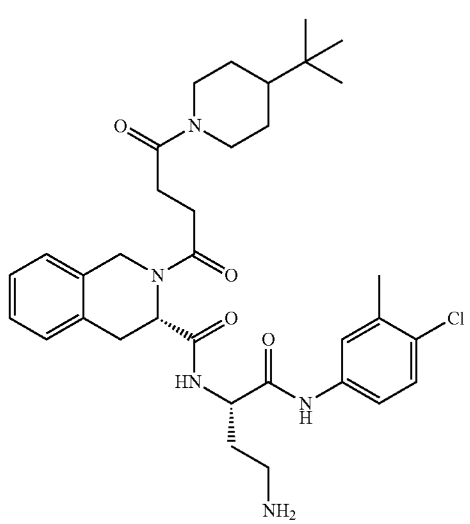 [SMILES: Cc1cc(NC(=O)[C@H](CCN)NC(=O)[C@@H]2Cc3ccccc3CN2C(=O)CCC(=O)N2CCC(C(C)(C)C)CC2)ccc1Cl] | 12-87 |

TABLE A-continued
REPRESENTATIVE COMPOUNDS
| Structure | Cpd. No. |
|---|---|
| 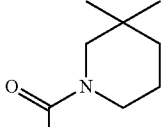 | 12-88 |
| 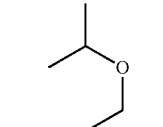 | 12-89 |

TABLE A-continued

REPRESENTATIVE COMPOUNDS

| Structure | Cpd. No. |
|---|---|
| 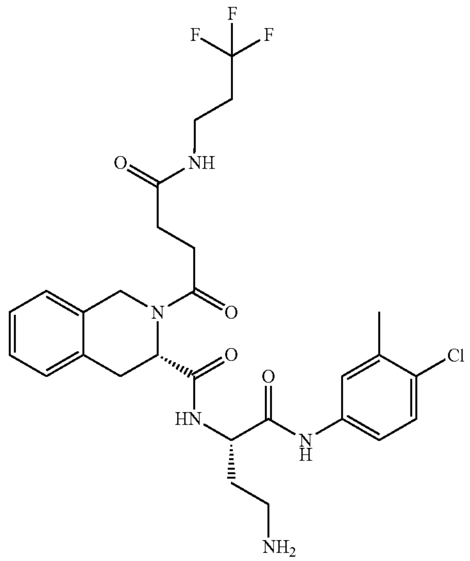 [SMILES: Cc1cc(NC(=O)[C@H](CCN)NC(=O)[C@@H]2Cc3ccccc3CN2C(=O)CCC(=O)NCCC(F)(F)F)ccc1Cl] | 12-90 |
| 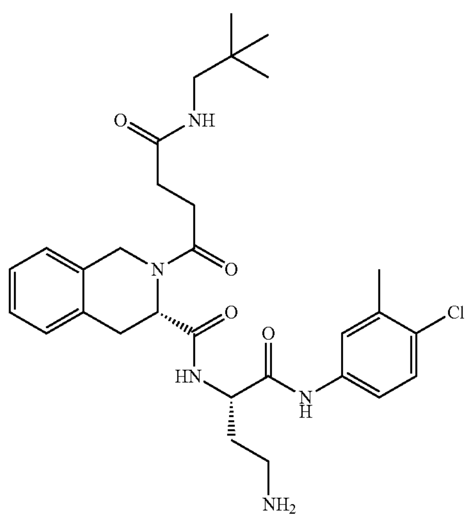 [SMILES: Cc1cc(NC(=O)[C@H](CCN)NC(=O)[C@@H]2Cc3ccccc3CN2C(=O)CCC(=O)NCC(C)(C)C)ccc1Cl] | 12-91 |
| 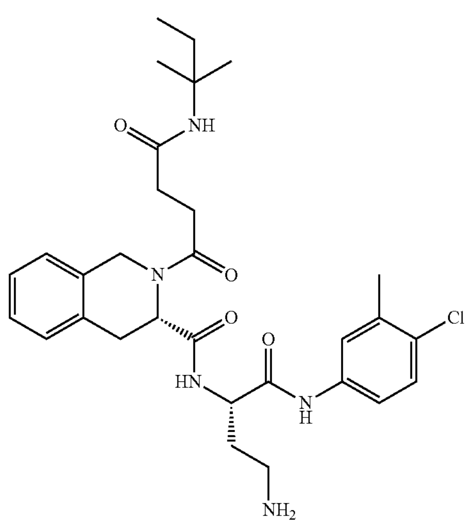 [SMILES: CCC(C)(C)NC(=O)CCC(=O)N1Cc2ccccc2C[C@H]1C(=O)N[C@@H](CCN)C(=O)Nc1ccc(Cl)c(C)c1] | 12-92 |

TABLE A-continued
REPRESENTATIVE COMPOUNDS
| Structure | Cpd. No. |
|---|---|
| 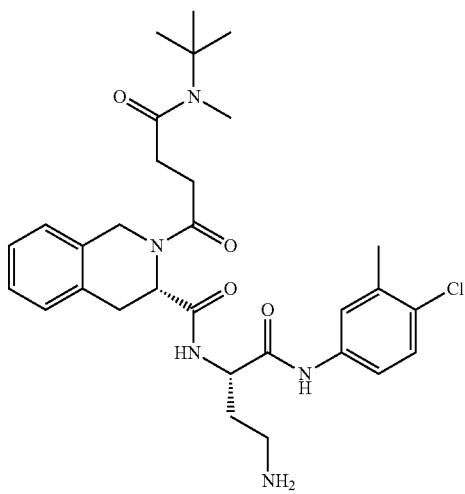 [SMILES: Cc1cc(NC(=O)[C@H](CCN)NC(=O)[C@@H]2Cc3ccccc3CN2C(=O)CCC(=O)N(C)C(C)(C)C)ccc1Cl] | 12-93 |
| 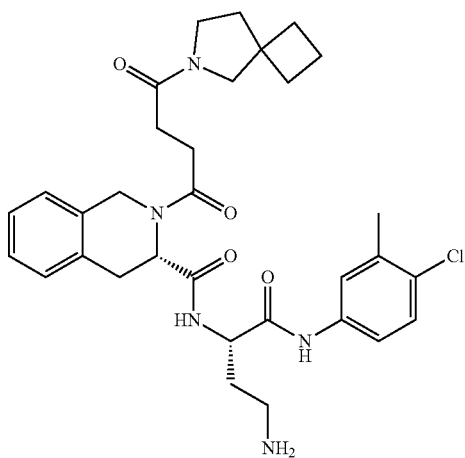 [SMILES: Cc1cc(NC(=O)[C@H](CCN)NC(=O)[C@@H]2Cc3ccccc3CN2C(=O)CCC(=O)N2CCC3(CCC3)C2)ccc1Cl] | 12-94 |
| 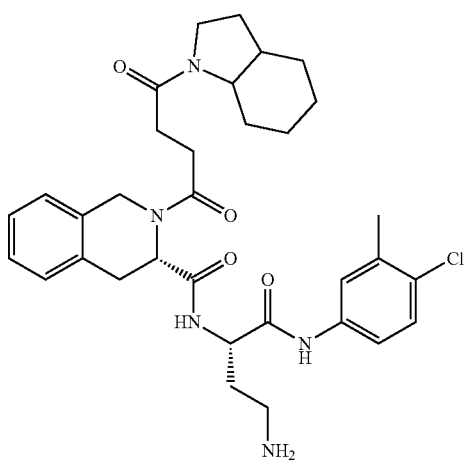 [SMILES: Cc1cc(NC(=O)[C@H](CCN)NC(=O)[C@@H]2Cc3ccccc3CN2C(=O)CCC(=O)N2CCC3CCCCC32)ccc1Cl] | 12-95 |

TABLE A-continued

REPRESENTATIVE COMPOUNDS

| Structure | Cpd. No. |
|---|---|
| 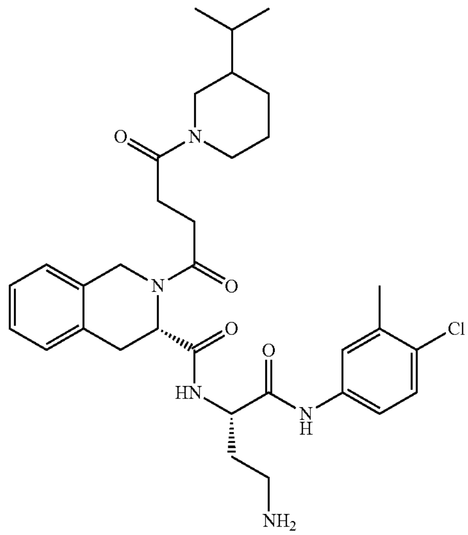 [SMILES: Cc1cc(NC(=O)[C@H](CCN)NC(=O)[C@@H]2Cc3ccccc3CN2C(=O)CCC(=O)N2CCCC(C(C)C)C2)ccc1Cl] | 12-96 |
| 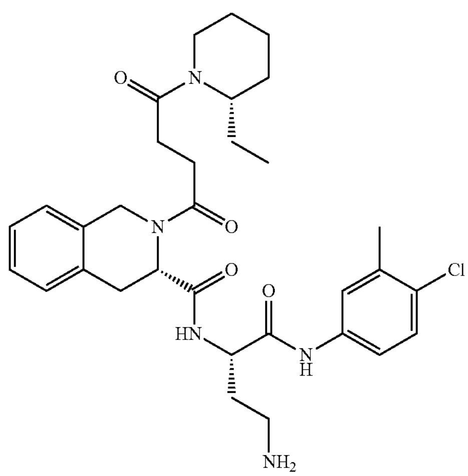 [SMILES: CC[C@H]1CCCCN1C(=O)CCC(=O)N1Cc2ccccc2C[C@H]1C(=O)N[C@@H](CCN)C(=O)Nc1ccc(Cl)c(C)c1] | 12-97 |
| 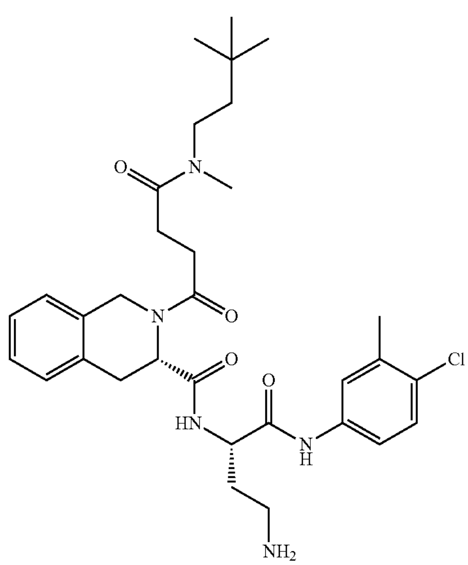 [SMILES: Cc1cc(NC(=O)[C@H](CCN)NC(=O)[C@@H]2Cc3ccccc3CN2C(=O)CCC(=O)N(C)CCC(C)(C)C)ccc1Cl] | 12-98 |

TABLE A-continued
REPRESENTATIVE COMPOUNDS
| Structure | Cpd. No. |
|---|---|
| 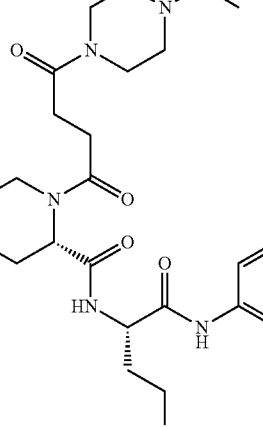 | 12-99 |
| 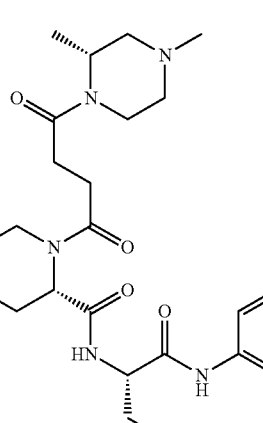 | 12-100 |
| 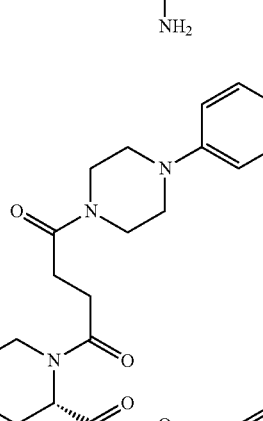 | 12-101 |

TABLE A-continued
REPRESENTATIVE COMPOUNDS
| Structure | Cpd. No. |
|---|---|
| 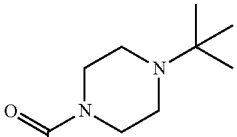 | 12-102 |
| 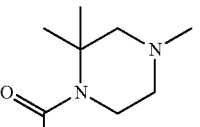 | 12-103 |
| 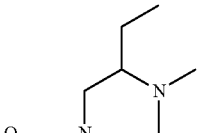 | 12-104 |

TABLE A-continued
REPRESENTATIVE COMPOUNDS
| Structure | Cpd. No. |
|---|---|
| 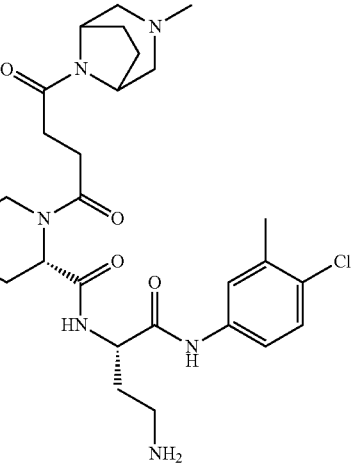 | 12-105 |
| 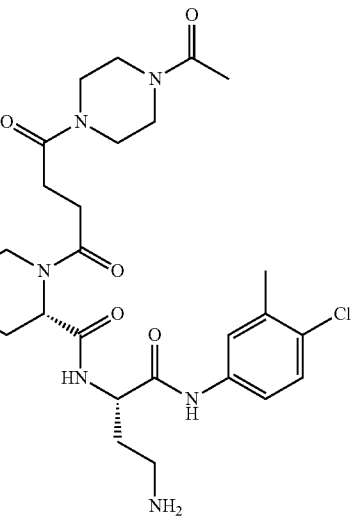 | 12-106 |
| 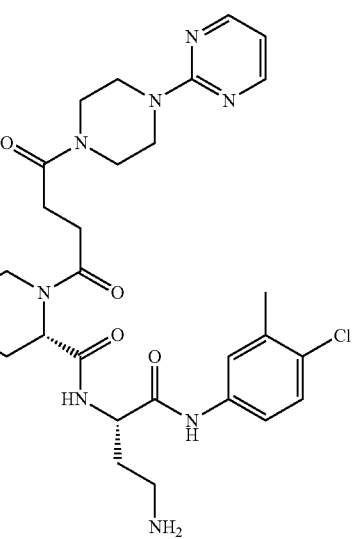 | 12-107 |

TABLE A-continued

REPRESENTATIVE COMPOUNDS

| Structure | Cpd. No. |
|---|---|
| 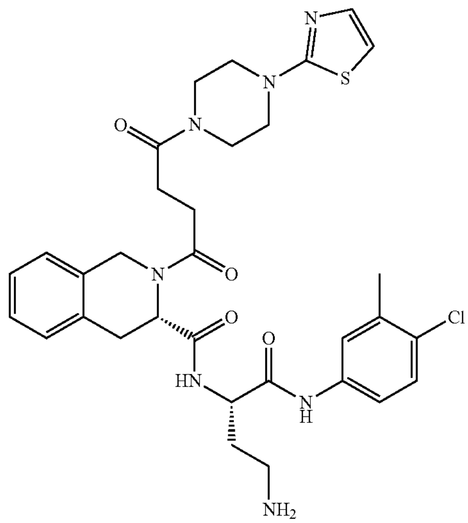 [SMILES: Cc1cc(NC(=O)[C@H](CCN)NC(=O)[C@@H]2Cc3ccccc3CN2C(=O)CCC(=O)N2CCN(c3nccs3)CC2)ccc1Cl] | 12-108 |
| 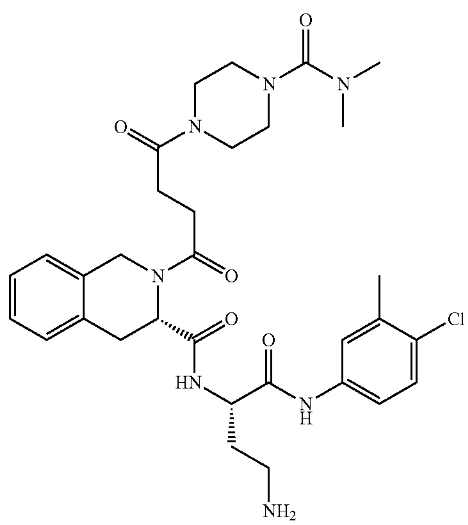 [SMILES: Cc1cc(NC(=O)[C@H](CCN)NC(=O)[C@@H]2Cc3ccccc3CN2C(=O)CCC(=O)N2CCN(C(=O)N(C)C)CC2)ccc1Cl] | 12-109 |
| 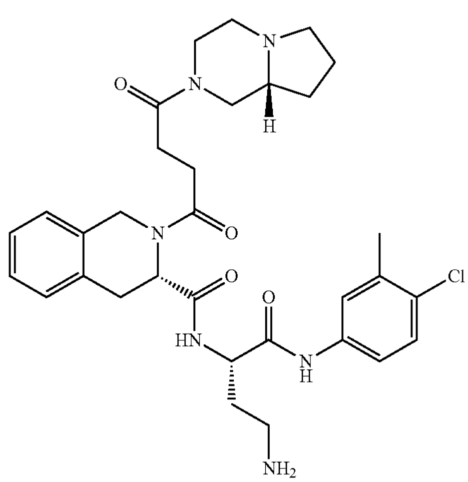 [SMILES: Cc1cc(NC(=O)[C@H](CCN)NC(=O)[C@@H]2Cc3ccccc3CN2C(=O)CCC(=O)N2CCN3CCC[C@@H]3C2)ccc1Cl] | 12-110 |

TABLE A-continued

REPRESENTATIVE COMPOUNDS

| Structure | Cpd. No. |
|---|---|
| 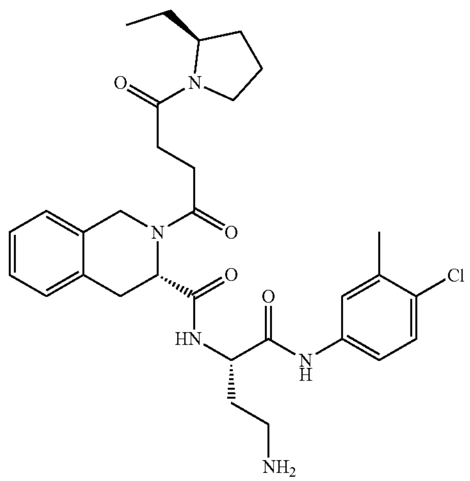 [SMILES: CC[C@H]1CCCN1C(=O)CCC(=O)N1Cc2ccccc2C[C@H]1C(=O)N[C@@H](CCN)C(=O)Nc1ccc(Cl)c(C)c1] | 12-111 |
| 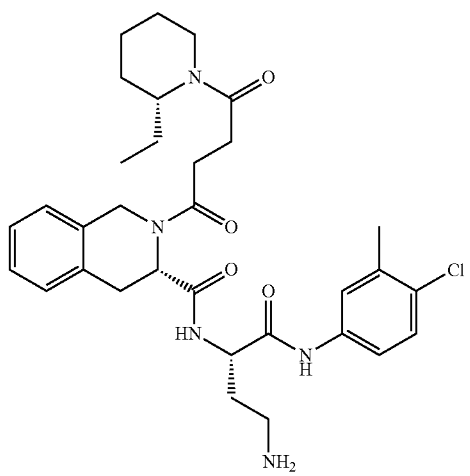 [SMILES: CC[C@@H]1CCCCN1C(=O)CCC(=O)N1Cc2ccccc2C[C@H]1C(=O)N[C@@H](CCN)C(=O)Nc1ccc(Cl)c(C)c1] | 12-112 |
| 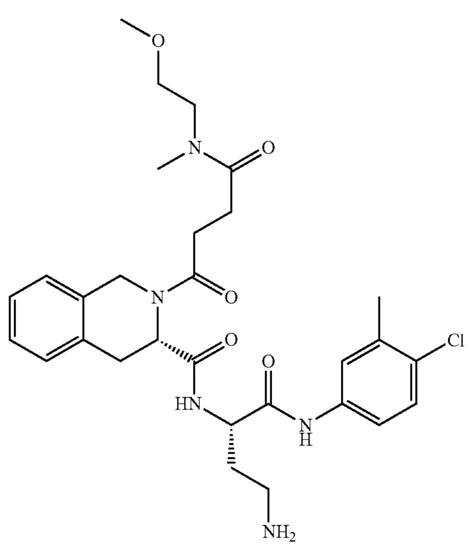 [SMILES: COCCN(C)C(=O)CCC(=O)N1Cc2ccccc2C[C@H]1C(=O)N[C@@H](CCN)C(=O)Nc1ccc(Cl)c(C)c1] | 12-113 |

TABLE A-continued

REPRESENTATIVE COMPOUNDS

| Structure | Cpd. No. |
|-----------|----------|
| 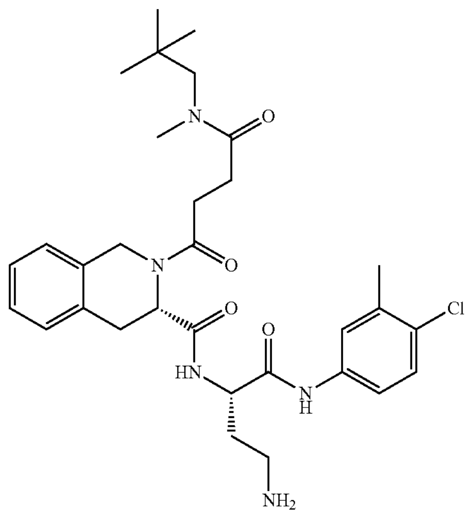 [SMILES: Cc1cc(NC(=O)[C@H](CCN)NC(=O)[C@@H]2Cc3ccccc3CN2C(=O)CCC(=O)N(C)CC(C)(C)C)ccc1Cl] | 12-114 |
| 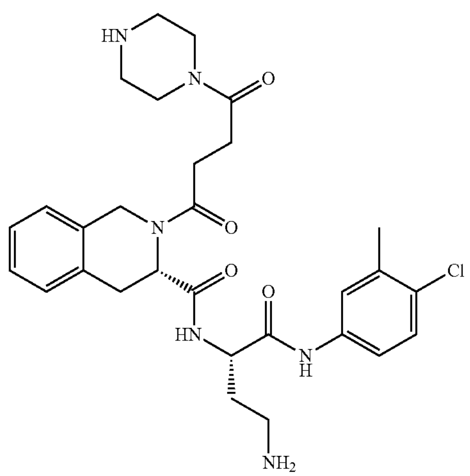 [SMILES: Cc1cc(NC(=O)[C@H](CCN)NC(=O)[C@@H]2Cc3ccccc3CN2C(=O)CCC(=O)N2CCNCC2)ccc1Cl] | 12-115 |
| 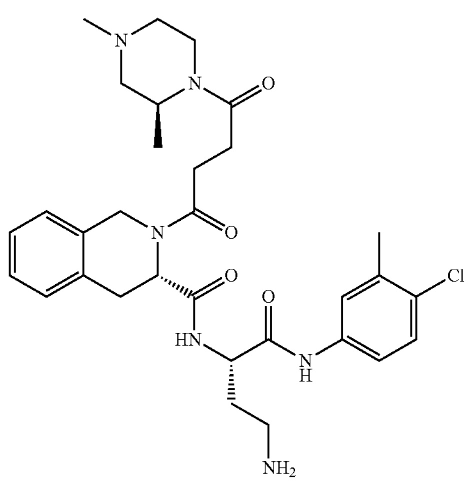 [SMILES: Cc1cc(NC(=O)[C@H](CCN)NC(=O)[C@@H]2Cc3ccccc3CN2C(=O)CCC(=O)N2CCN(C)C[C@@H]2C)ccc1Cl] | 12-116 |

TABLE A-continued

REPRESENTATIVE COMPOUNDS

| Structure | Cpd. No. |
|---|---|
| 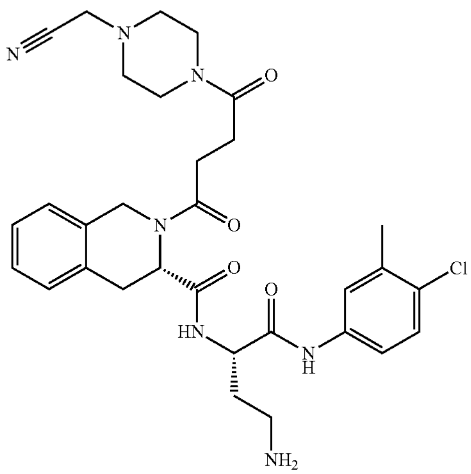 [SMILES: Cc1cc(NC(=O)[C@H](CCN)NC(=O)[C@@H]2Cc3ccccc3CN2C(=O)CCC(=O)N2CCN(CC#N)CC2)ccc1Cl] | 12-117 |
| 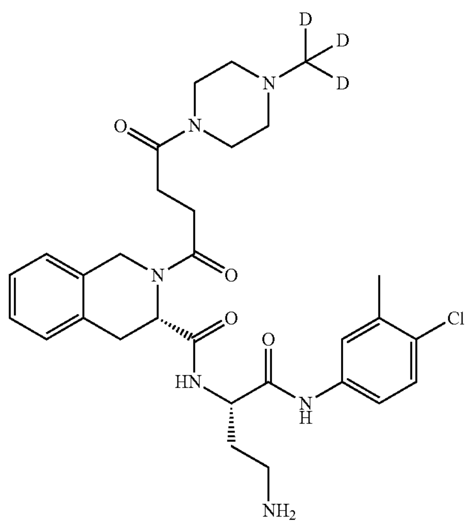 [SMILES: [2H]C([2H])([2H])N1CCN(C(=O)CCC(=O)N2Cc3ccccc3C[C@H]2C(=O)N[C@@H](CCN)C(=O)Nc2ccc(Cl)c(C)c2)CC1] | 12-118 |
| 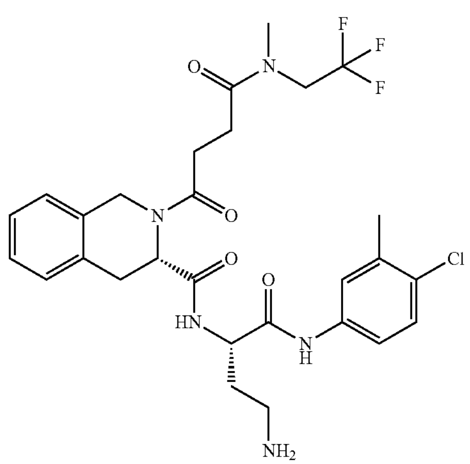 [SMILES: Cc1cc(NC(=O)[C@H](CCN)NC(=O)[C@@H]2Cc3ccccc3CN2C(=O)CCC(=O)N(C)CC(F)(F)F)ccc1Cl] | 12-119 |

TABLE A-continued

REPRESENTATIVE COMPOUNDS

| Structure | Cpd. No. |
|---|---|
| 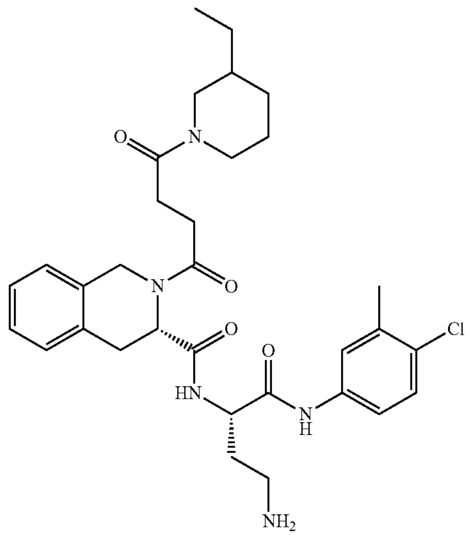 [SMILES: CCC1CCCN(C(=O)CCC(=O)N2Cc3ccccc3C[C@H]2C(=O)N[C@@H](CCN)C(=O)Nc2ccc(Cl)c(C)c2)C1] | 12-120 |
| 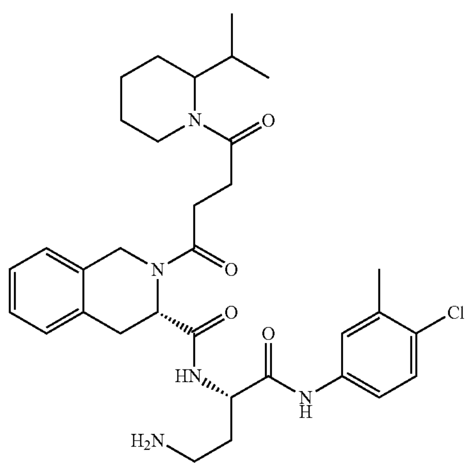 [SMILES: Cc1cc(NC(=O)[C@H](CCN)NC(=O)[C@@H]2Cc3ccccc3CN2C(=O)CCC(=O)N2CCCCC2C(C)C)ccc1Cl] | 12-121 |
| 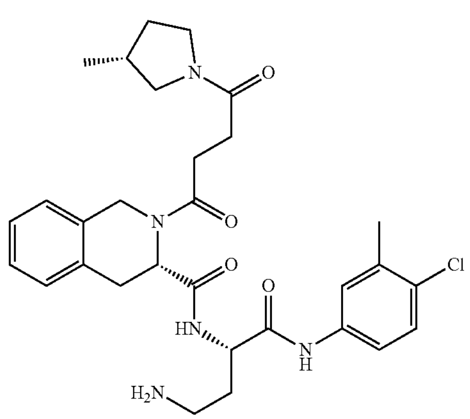 [SMILES: Cc1cc(NC(=O)[C@H](CCN)NC(=O)[C@@H]2Cc3ccccc3CN2C(=O)CCC(=O)N2CC[C@@H](C)C2)ccc1Cl] | 12-122 |

TABLE A-continued

REPRESENTATIVE COMPOUNDS

| Structure | Cpd. No. |
|---|---|
| 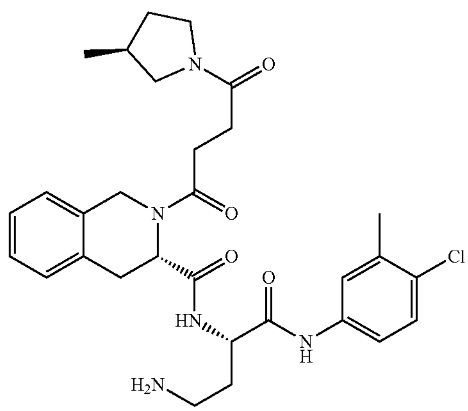 [SMILES: Cc1cc(NC(=O)[C@H](CCN)NC(=O)[C@@H]2Cc3ccccc3CN2C(=O)CCC(=O)N2CC[C@H](C)C2)ccc1Cl] | 12-123 |
| 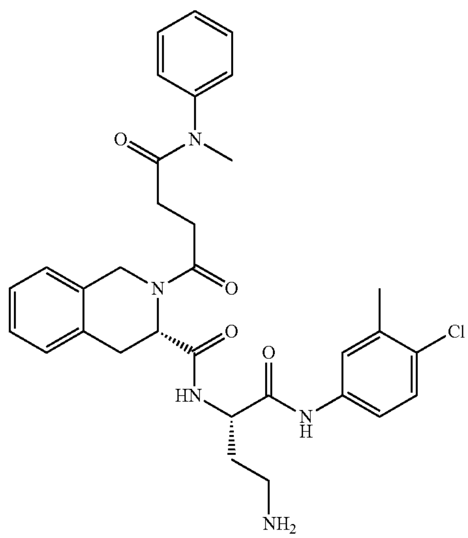 [SMILES: Cc1cc(NC(=O)[C@H](CCN)NC(=O)[C@@H]2Cc3ccccc3CN2C(=O)CCC(=O)N(C)c2ccccc2)ccc1Cl] | 12-124 |
| 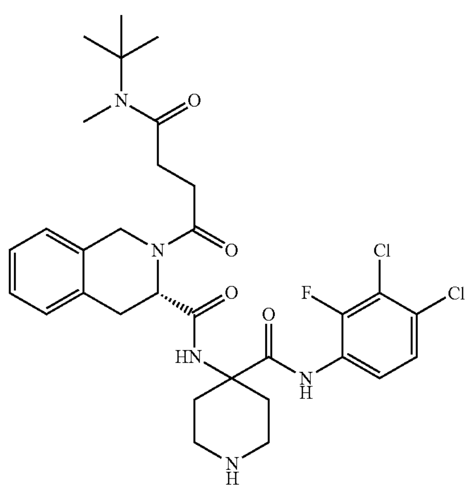 [SMILES: CN(C(=O)CCC(=O)N1Cc2ccccc2C[C@H]1C(=O)NC1(C(=O)Nc2ccc(Cl)c(Cl)c2F)CCNCC1)C(C)(C)C] | 12-125 |

TABLE A-continued
REPRESENTATIVE COMPOUNDS
| Structure | Cpd. No. |
|---|---|
| 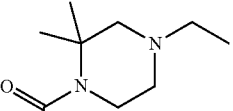 | 12-126 |
| 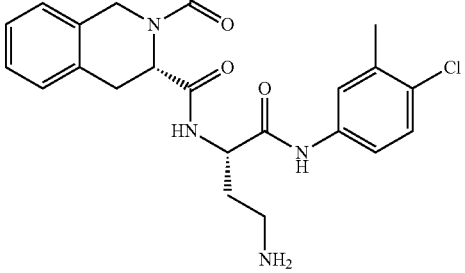 | 12-127 |
| 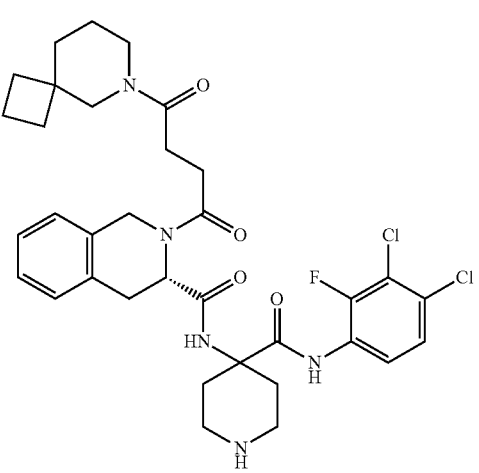 [SMILES: O=C(NC1(C(=O)Nc2ccc(Cl)c(Cl)c2F)CCNCC1)[C@@H]1Cc2ccccc2CN1C(=O)CCC(=O)N1CCCC2(CCC2)C1] | 12-128 |

TABLE A-continued
REPRESENTATIVE COMPOUNDS
| Structure | Cpd. No. |
|---|---|
| 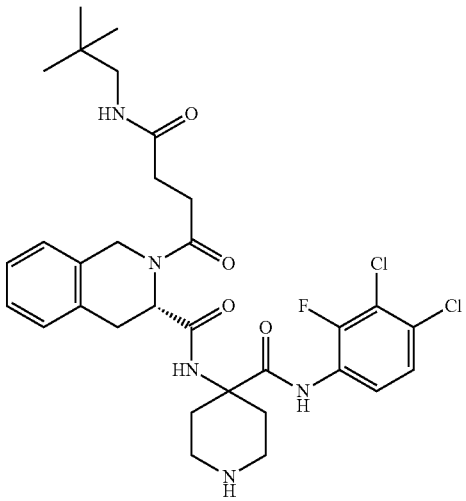 [SMILES: CC(C)(C)CNC(=O)CCC(=O)N1Cc2ccccc2C[C@H]1C(=O)NC1(C(=O)Nc2ccc(Cl)c(Cl)c2F)CCNCC1] | 12-129 |
| 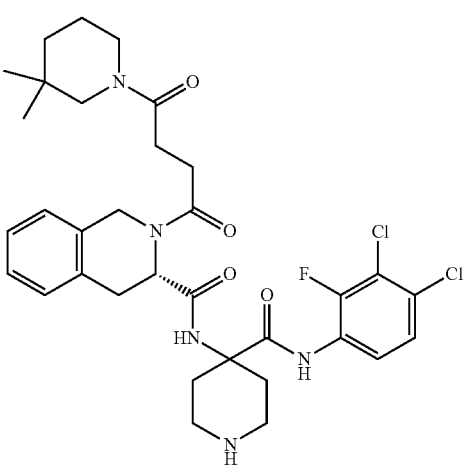 [SMILES: CC1(C)CCCN(C(=O)CCC(=O)N2Cc3ccccc3C[C@H]2C(=O)NC2(C(=O)Nc3ccc(Cl)c(Cl)c3F)CCNCC2)C1] | 12-130 |
| 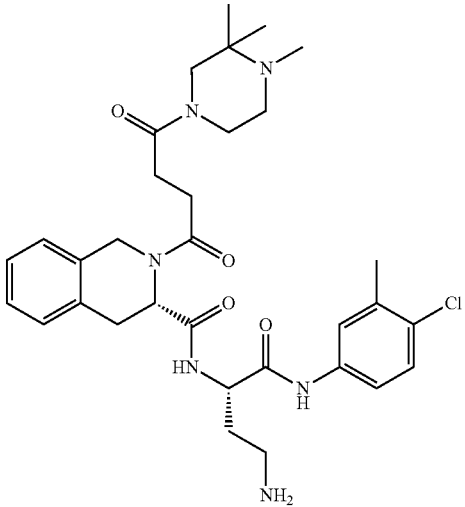 [SMILES: Cc1cc(NC(=O)[C@H](CCN)NC(=O)[C@@H]2Cc3ccccc3CN2C(=O)CCC(=O)N2CCN(C)C(C)(C)C2)ccc1Cl] | 12-131 |

TABLE A-continued
REPRESENTATIVE COMPOUNDS
| Structure | Cpd. No. |
|---|---|
| 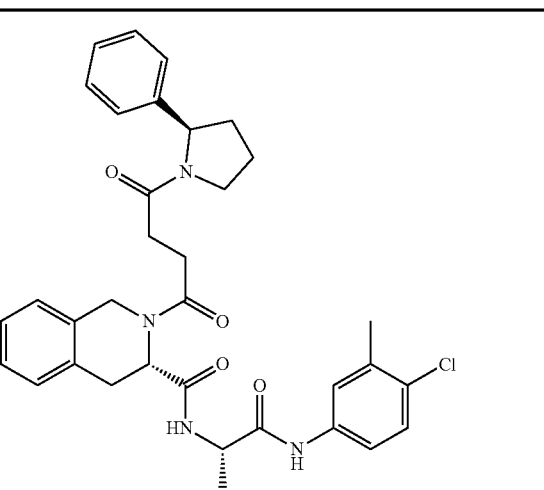 | 12-132 |
| 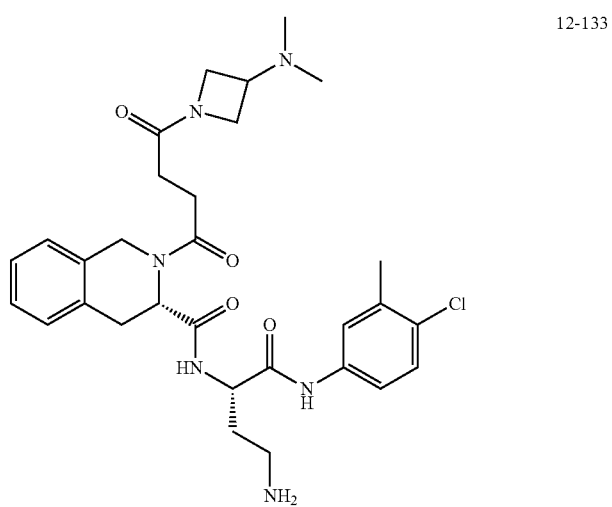 | 12-133 |

TABLE A-continued
REPRESENTATIVE COMPOUNDS
| Structure | Cpd. No. |
| --- | --- |
| 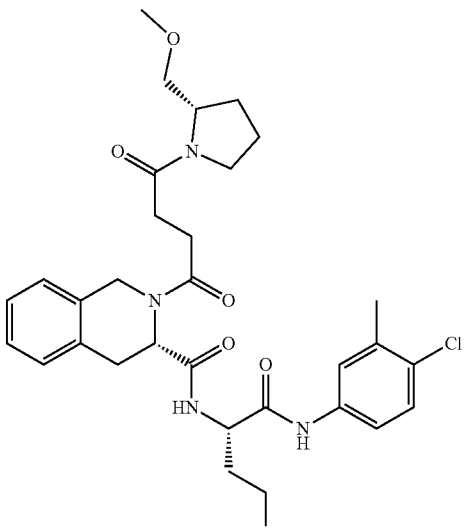 | 12-134 |
| 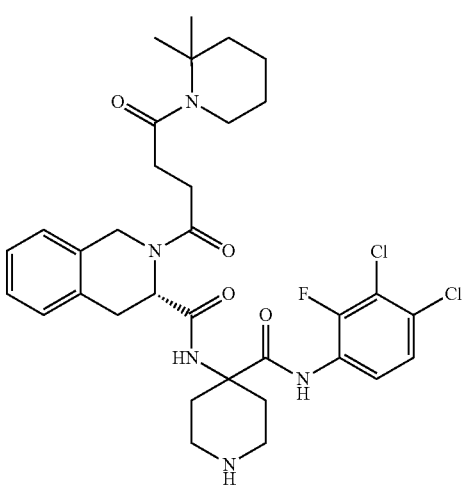 [SMILES: CC1(C)CCCCN1C(=O)CCC(=O)N1Cc2ccccc2C[C@H]1C(=O)NC1(C(=O)Nc2ccc(Cl)c(Cl)c2F)CCNCC1] | 12-135 |
| 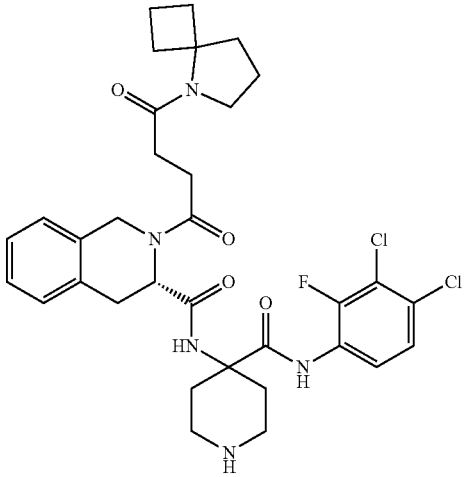 [SMILES: O=C(NC1(C(=O)Nc2ccc(Cl)c(Cl)c2F)CCNCC1)[C@@H]1Cc2ccccc2CN1C(=O)CCC(=O)N1CCCC12CCC2] | 12-136 |

TABLE A-continued

REPRESENTATIVE COMPOUNDS

| Structure | Cpd. No. |
|---|---|
| 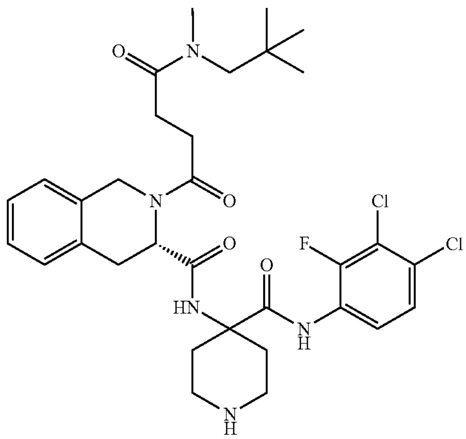 [SMILES: CN(CC(C)(C)C)C(=O)CCC(=O)N1Cc2ccccc2C[C@H]1C(=O)NC1(C(=O)Nc2ccc(Cl)c(Cl)c2F)CCNCC1] | 12-137 |
| 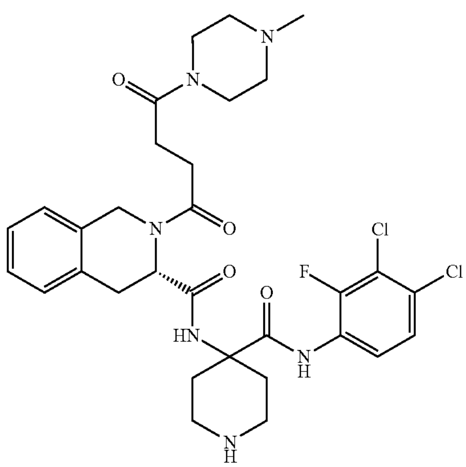 [SMILES: CN1CCN(C(=O)CCC(=O)N2Cc3ccccc3C[C@H]2C(=O)NC2(C(=O)Nc3ccc(Cl)c(Cl)c3F)CCNCC2)CC1] | 12-138 |
| 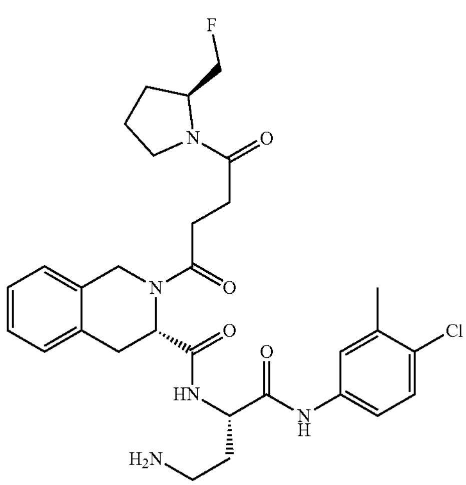 [SMILES: Cc1cc(NC(=O)[C@H](CCN)NC(=O)[C@@H]2Cc3ccccc3CN2C(=O)CCC(=O)N2CCC[C@H]2CF)ccc1Cl] | 12-139 |

TABLE A-continued
REPRESENTATIVE COMPOUNDS
| Structure | Cpd. No. |
|---|---|
| 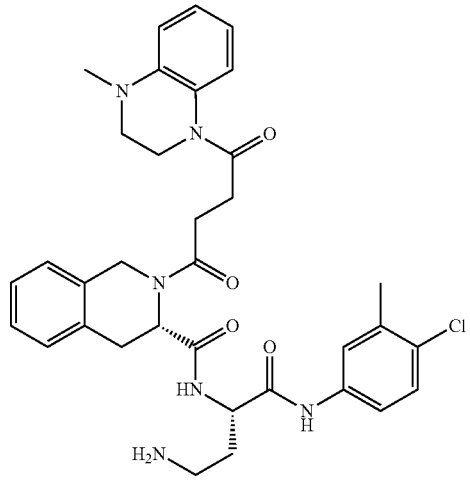 [SMILES: Cc1cc(NC(=O)[C@H](CCN)NC(=O)[C@@H]2Cc3ccccc3CN2C(=O)CCC(=O)N2CCN(C)c3ccccc32)ccc1Cl] | 12-140 |
| 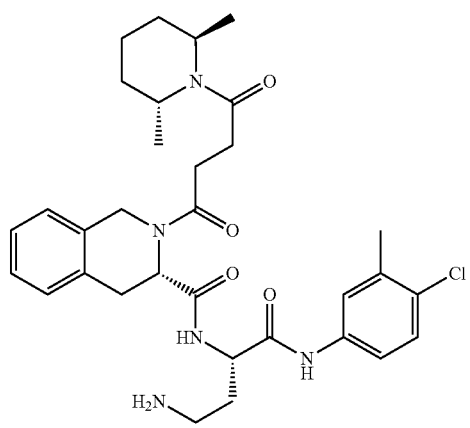 [SMILES: Cc1cc(NC(=O)[C@H](CCN)NC(=O)[C@@H]2Cc3ccccc3CN2C(=O)CCC(=O)N2[C@H](C)CCC[C@H]2C)ccc1Cl] | 12-141 |
| 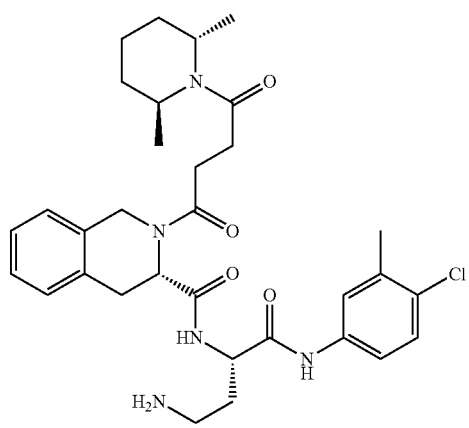 [SMILES: Cc1cc(NC(=O)[C@H](CCN)NC(=O)[C@@H]2Cc3ccccc3CN2C(=O)CCC(=O)N2[C@@H](C)CCC[C@@H]2C)ccc1Cl] | 12-142 |

TABLE A-continued

REPRESENTATIVE COMPOUNDS

| Structure | Cpd. No. |
|---|---|
| 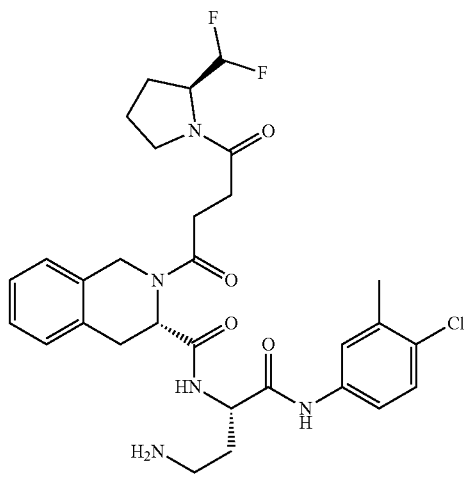 [SMILES: Cc1cc(NC(=O)[C@H](CCN)NC(=O)[C@@H]2Cc3ccccc3CN2C(=O)CCC(=O)N2CCC[C@H]2C(F)F)ccc1Cl] | 12-143 |
| 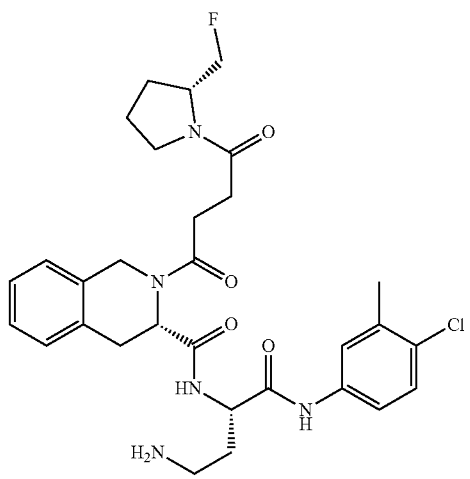 [SMILES: Cc1cc(NC(=O)[C@H](CCN)NC(=O)[C@@H]2Cc3ccccc3CN2C(=O)CCC(=O)N2CCC[C@@H]2CF)ccc1Cl] | 12-144 |
| 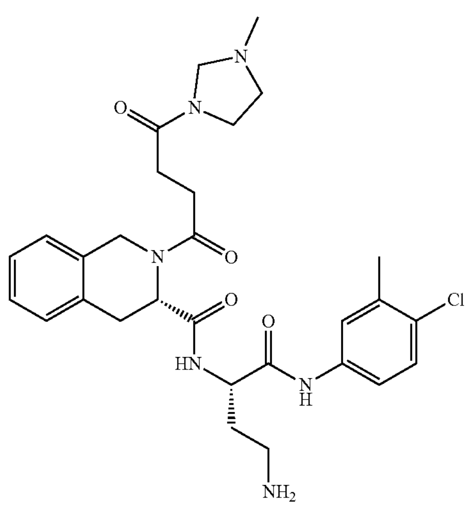 [SMILES: Cc1cc(NC(=O)[C@H](CCN)NC(=O)[C@@H]2Cc3ccccc3CN2C(=O)CCC(=O)N2CCN(C)C2)ccc1Cl] | 12-145 |

TABLE A-continued
REPRESENTATIVE COMPOUNDS
| Structure | Cpd. No. |
|---|---|
| 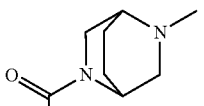 | 12-146 |
| 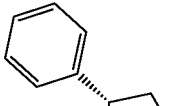 | 12-147 |
| 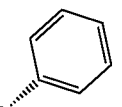 | 12-148 |

TABLE A-continued
REPRESENTATIVE COMPOUNDS
| Structure | Cpd. No. |
|---|---|
| 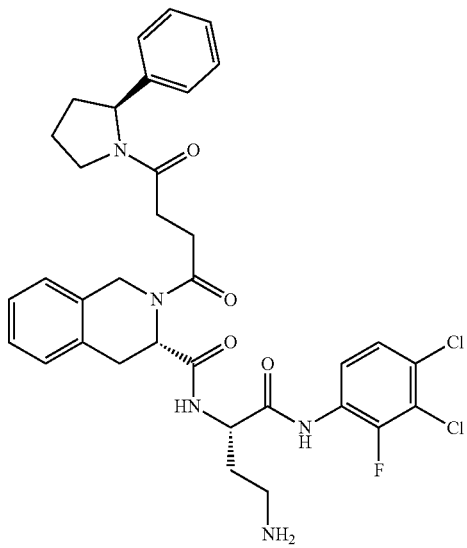 [SMILES: NCC[C@H](NC(=O)[C@@H]1Cc2ccccc2CN1C(=O)CCC(=O)N1CCC[C@H]1c1ccccc1)C(=O)Nc1ccc(Cl)c(Cl)c1F] | 12-149 |
| 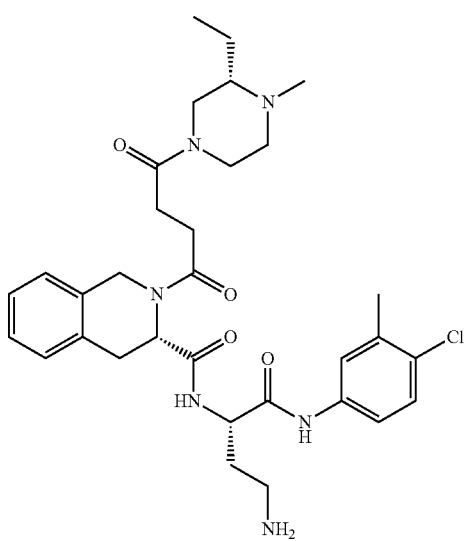 [SMILES: CC[C@H]1CN(C(=O)CCC(=O)N2Cc3ccccc3C[C@H]2C(=O)N[C@@H](CCN)C(=O)Nc2ccc(Cl)c(C)c2)CCN1C] | 12-150 |

TABLE A-continued
REPRESENTATIVE COMPOUNDS
| Structure | Cpd. No. |
|---|---|
| 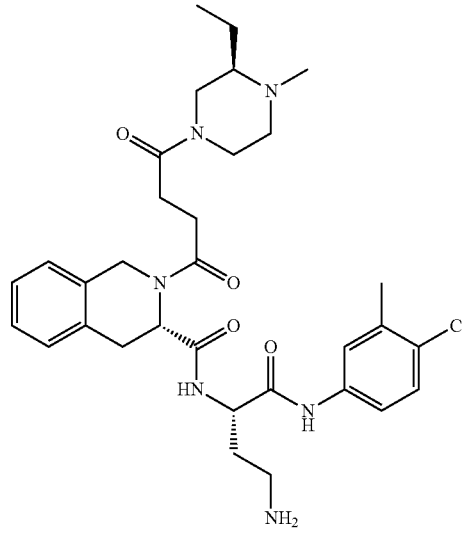 | 12-151 |
| 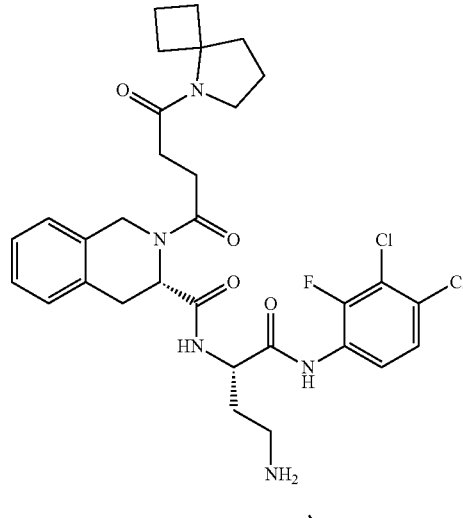 | 12-152 |
| 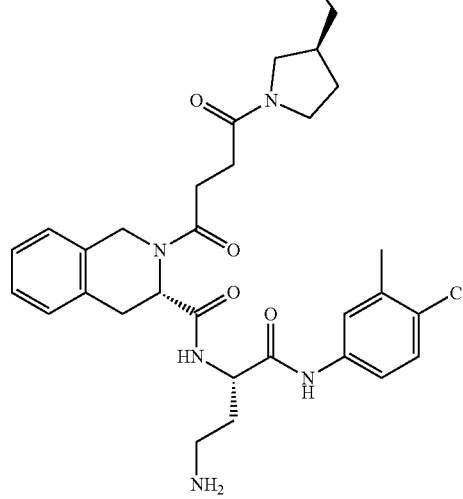 | 12-153 |

TABLE A-continued
REPRESENTATIVE COMPOUNDS
| Structure | Cpd. No. |
|---|---|
| 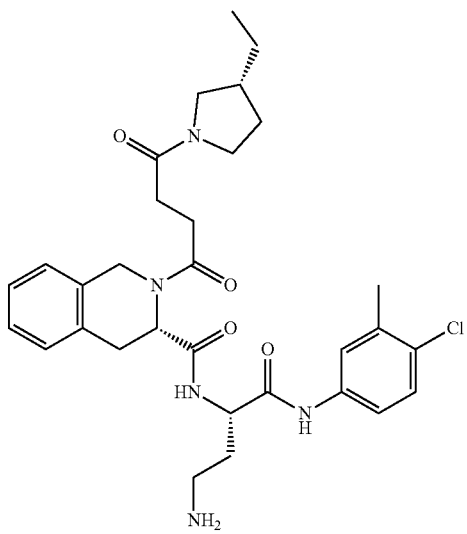 [SMILES: CC[C@@H]1CCN(C(=O)CCC(=O)N2Cc3ccccc3C[C@H]2C(=O)N[C@@H](CCN)C(=O)Nc2ccc(Cl)c(C)c2)C1] | 12-154 |
| 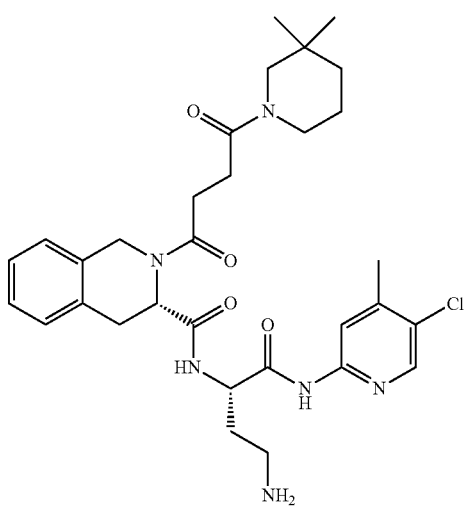 [SMILES: Cc1cc(NC(=O)[C@H](CCN)NC(=O)[C@@H]2Cc3ccccc3CN2C(=O)CCC(=O)N2CCCC(C)(C)C2)ncc1Cl] | 12-155 |
| 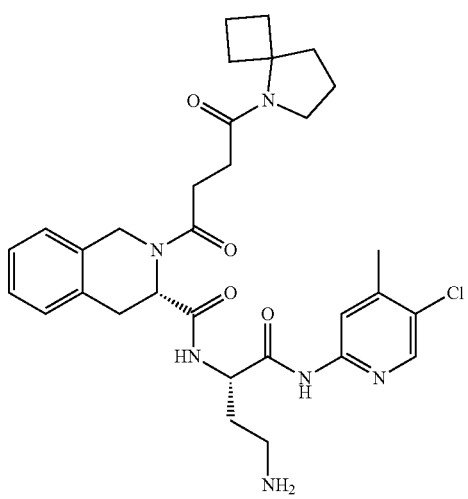 [SMILES: Cc1cc(NC(=O)[C@H](CCN)NC(=O)[C@@H]2Cc3ccccc3CN2C(=O)CCC(=O)N2CCCC23CCC3)ncc1Cl] | 12-156 |

TABLE A-continued
REPRESENTATIVE COMPOUNDS
| Structure | Cpd. No. |
|---|---|
| 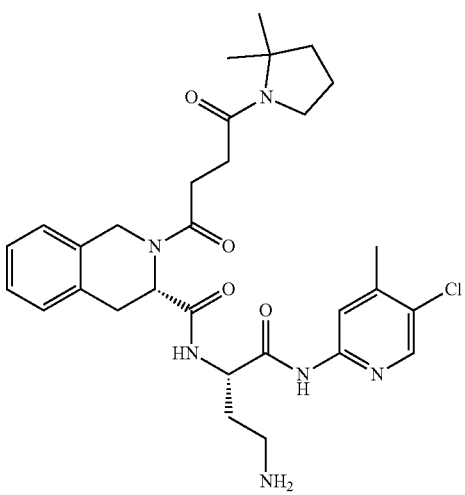 [SMILES: Cc1cc(NC(=O)[C@H](CCN)NC(=O)[C@@H]2Cc3ccccc3CN2C(=O)CCC(=O)N2CCCC2(C)C)ncc1Cl] | 12-157 |
| 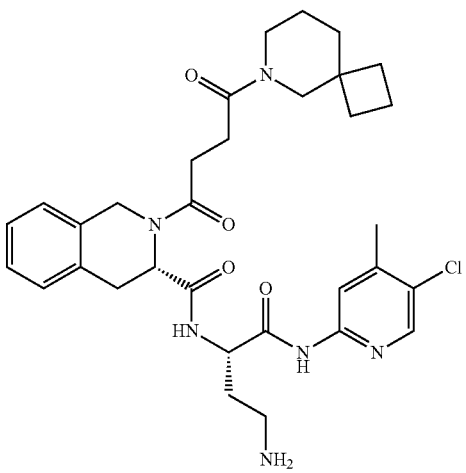 [SMILES: Cc1cc(NC(=O)[C@H](CCN)NC(=O)[C@@H]2Cc3ccccc3CN2C(=O)CCC(=O)N2CCCC3(CCC3)C2)ncc1Cl] | 12-158 |
| 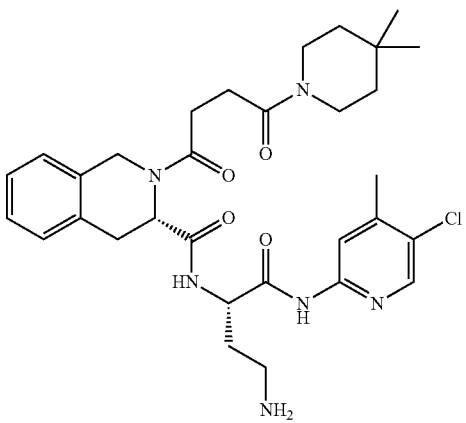 [SMILES: Cc1cc(NC(=O)[C@H](CCN)NC(=O)[C@@H]2Cc3ccccc3CN2C(=O)CCC(=O)N2CCC(C)(C)CC2)ncc1Cl] | 12-159 |

TABLE A-continued

REPRESENTATIVE COMPOUNDS

| Structure | Cpd. No. |
|---|---|
| 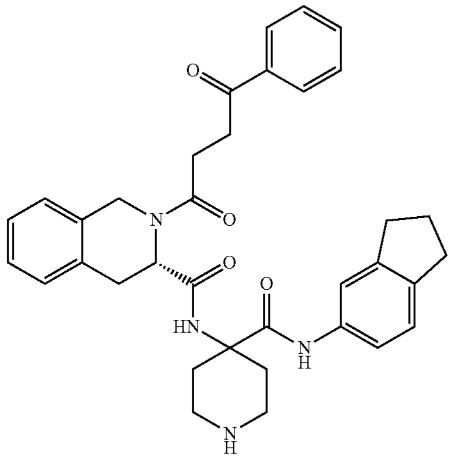 [SMILES: O=C(CCC(=O)N1Cc2ccccc2C[C@H]1C(=O)NC1(C(=O)Nc2ccc3c(c2)CCC3)CCNCC1)c1ccccc1] | 13-1 |
| 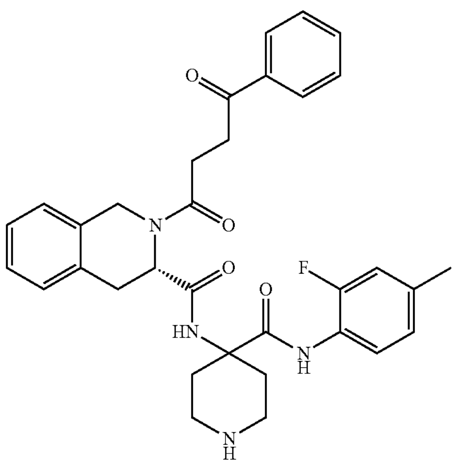 [SMILES: Cc1ccc(NC(=O)C2(NC(=O)[C@@H]3Cc4ccccc4CN3C(=O)CCC(=O)c3ccccc3)CCNCC2)c(F)c1] | 13-2 |
| 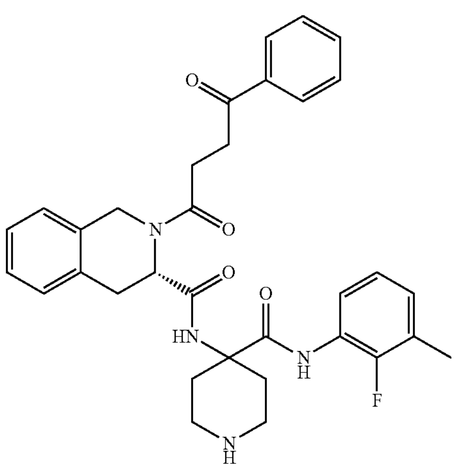 [SMILES: Cc1cccc(NC(=O)C2(NC(=O)[C@@H]3Cc4ccccc4CN3C(=O)CCC(=O)c3ccccc3)CCNCC2)c1F] | 13-3 |

TABLE A-continued

REPRESENTATIVE COMPOUNDS

| Structure | Cpd. No. |
|---|---|
| 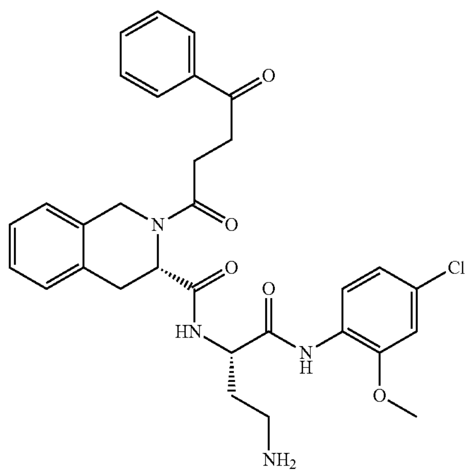 [SMILES: COc1cc(Cl)ccc1NC(=O)[C@H](CCN)NC(=O)[C@@H]1Cc2ccccc2CN1C(=O)CCC(=O)c1ccccc1] | 13-4 |
| 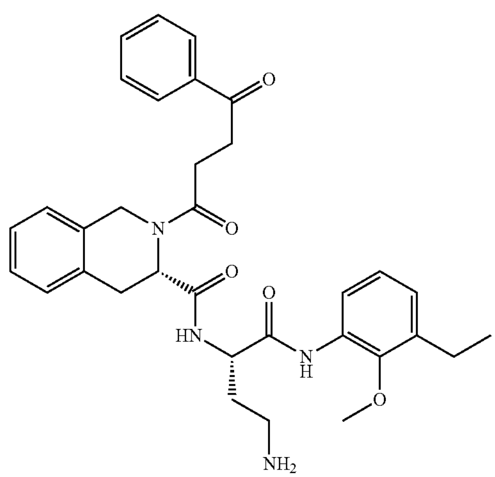 [SMILES: CCc1cccc(NC(=O)[C@H](CCN)NC(=O)[C@@H]2Cc3ccccc3CN2C(=O)CCC(=O)c2ccccc2)c1OC] | 13-5 |
| 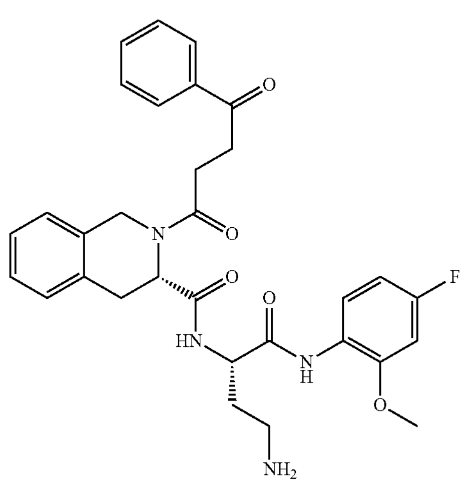 [SMILES: COc1cc(F)ccc1NC(=O)[C@H](CCN)NC(=O)[C@@H]1Cc2ccccc2CN1C(=O)CCC(=O)c1ccccc1] | 13-6 |

TABLE A-continued

REPRESENTATIVE COMPOUNDS

| Structure | Cpd. No. |
|---|---|
| 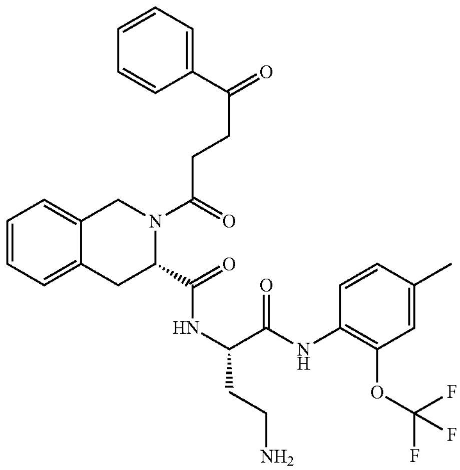 [SMILES: Cc1ccc(NC(=O)[C@H](CCN)NC(=O)[C@@H]2Cc3ccccc3CN2C(=O)CCC(=O)c2ccccc2)c(OC(F)(F)F)c1] | 13-7 |
| 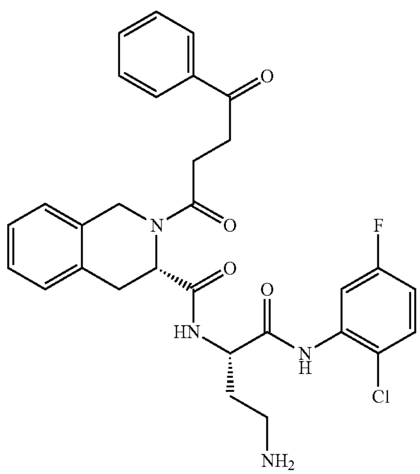 [SMILES: NCC[C@H](NC(=O)[C@@H]1Cc2ccccc2CN1C(=O)CCC(=O)c1ccccc1)C(=O)Nc1cc(F)ccc1Cl] | 14-1 |
| 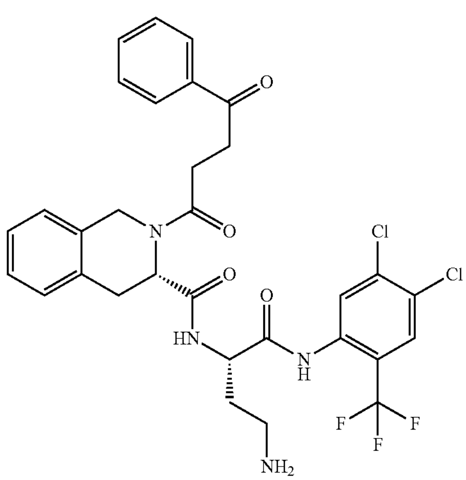 [SMILES: NCC[C@H](NC(=O)[C@@H]1Cc2ccccc2CN1C(=O)CCC(=O)c1ccccc1)C(=O)Nc1cc(Cl)c(Cl)cc1C(F)(F)F] | 14-2 |

TABLE A-continued
REPRESENTATIVE COMPOUNDS
| Structure | Cpd. No. |
|---|---|
| 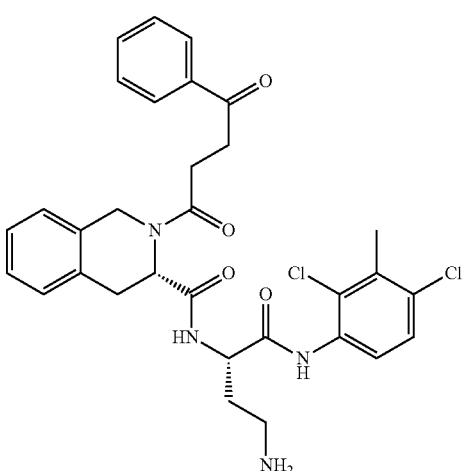 | 14-3 |
| 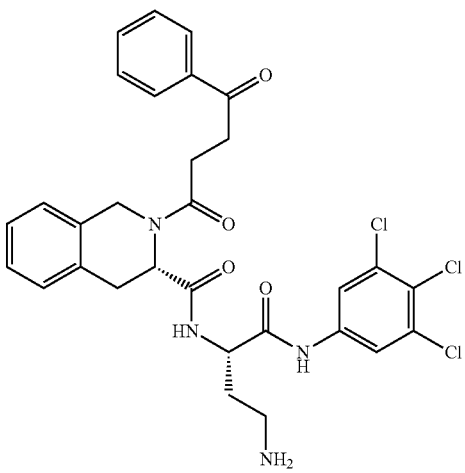 | 14-4 |
| 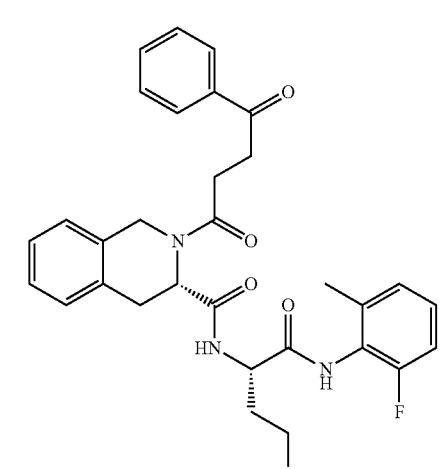 | 14-5 |

TABLE A-continued
REPRESENTATIVE COMPOUNDS
| Structure | Cpd. No. |
|---|---|
| 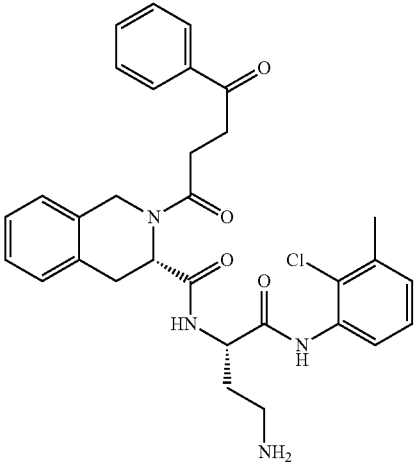 | 14-6 |
| 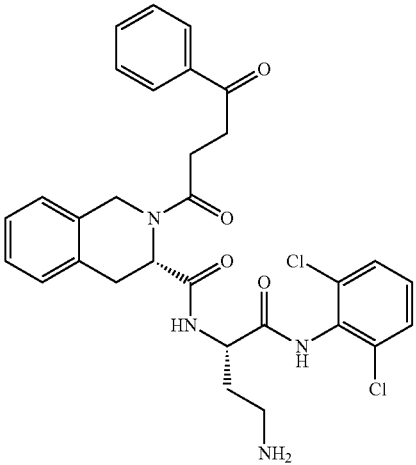 [SMILES: NCC[C@H](NC(=O)[C@@H]1Cc2ccccc2CN1C(=O)CCC(=O)c1ccccc1)C(=O)Nc1c(Cl)cccc1Cl] | 14-7 |
| 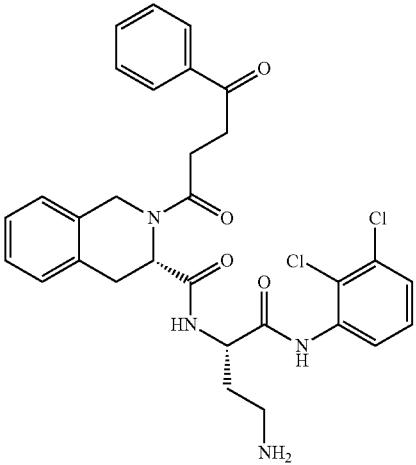 | 14-8 |

TABLE A-continued

REPRESENTATIVE COMPOUNDS

| Structure | Cpd. No. |
|---|---|
| 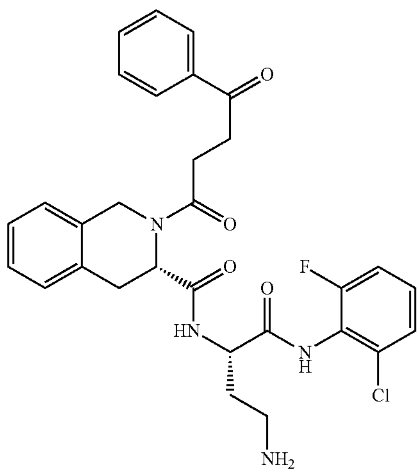 [SMILES: NCC[C@H](NC(=O)[C@@H]1Cc2ccccc2CN1C(=O)CCC(=O)c1ccccc1)C(=O)Nc1c(F)cccc1Cl] | 14-9 |
| 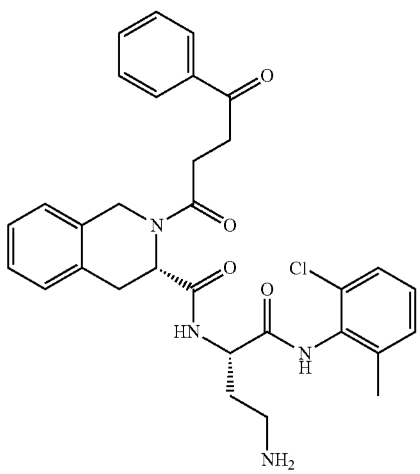 | 14-10 |
| 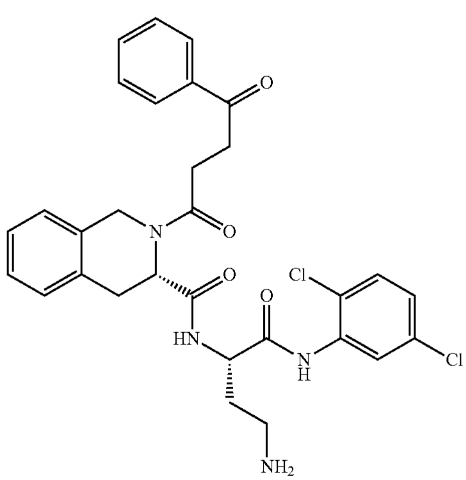 | 14-11 |

TABLE A-continued

REPRESENTATIVE COMPOUNDS

| Structure | Cpd. No. |
|---|---|
| 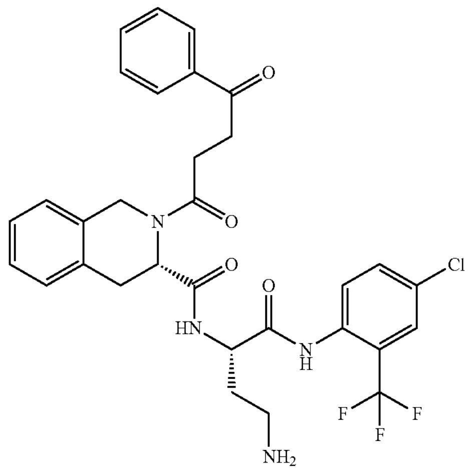 [SMILES: NCC[C@H](NC(=O)[C@@H]1Cc2ccccc2CN1C(=O)CCC(=O)c1ccccc1)C(=O)Nc1ccc(Cl)cc1C(F)(F)F] | 14-12 |
| 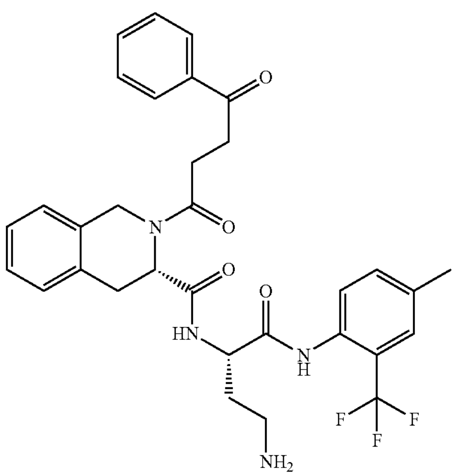 [SMILES: Cc1ccc(NC(=O)[C@H](CCN)NC(=O)[C@@H]2Cc3ccccc3CN2C(=O)CCC(=O)c2ccccc2)c(C(F)(F)F)c1] | 14-13 |
| 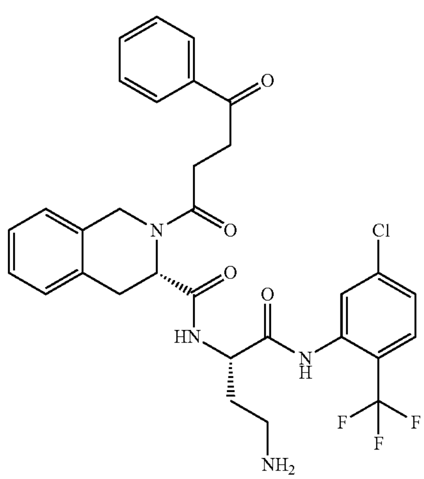 | 14-14 |

TABLE A-continued

REPRESENTATIVE COMPOUNDS

| Structure | Cpd. No. |
|---|---|
| 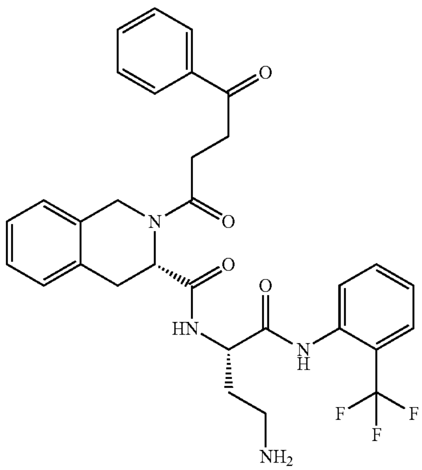 [SMILES: NCC[C@H](NC(=O)[C@@H]1Cc2ccccc2CN1C(=O)CCC(=O)c1ccccc1)C(=O)Nc1ccccc1C(F)(F)F] | 14-15 |
| 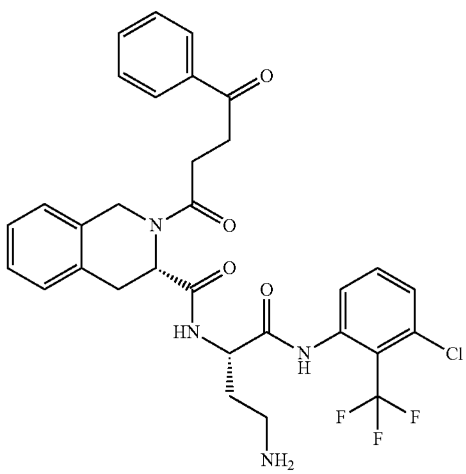 [SMILES: NCC[C@H](NC(=O)[C@@H]1Cc2ccccc2CN1C(=O)CCC(=O)c1ccccc1)C(=O)Nc1cccc(Cl)c1C(F)(F)F] | 14-16 |
| 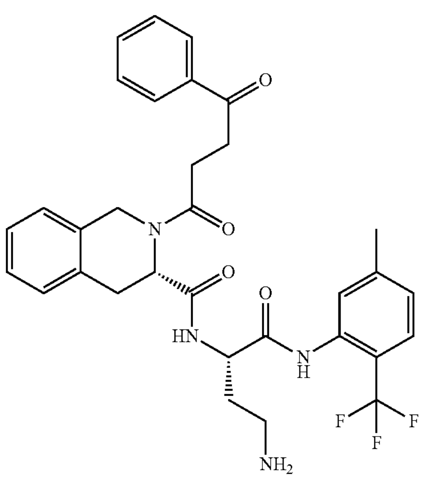 [SMILES: Cc1ccc(C(F)(F)F)c(NC(=O)[C@H](CCN)NC(=O)[C@@H]2Cc3ccccc3CN2C(=O)CCC(=O)c2ccccc2)c1] | 14-17 |

TABLE A-continued
REPRESENTATIVE COMPOUNDS
| Structure | Cpd. No. |
|---|---|
| 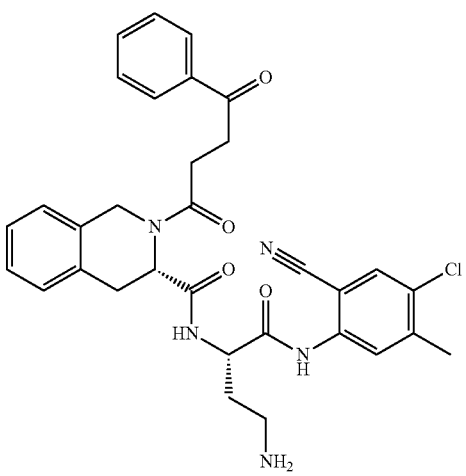 [SMILES: Cc1cc(NC(=O)[C@H](CCN)NC(=O)[C@@H]2Cc3ccccc3CN2C(=O)CCC(=O)c2ccccc2)c(C#N)cc1Cl] | 14-18 |
| 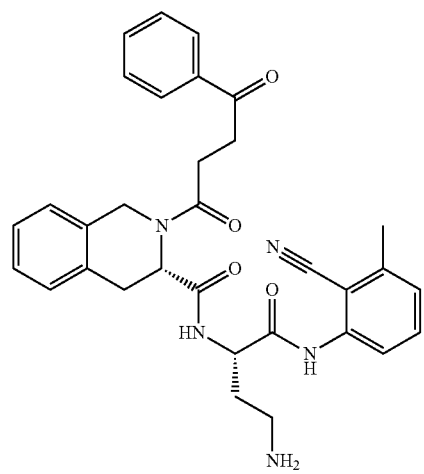 [SMILES: Cc1cccc(NC(=O)[C@H](CCN)NC(=O)[C@@H]2Cc3ccccc3CN2C(=O)CCC(=O)c2ccccc2)c1C#N] | 14-19 |
| 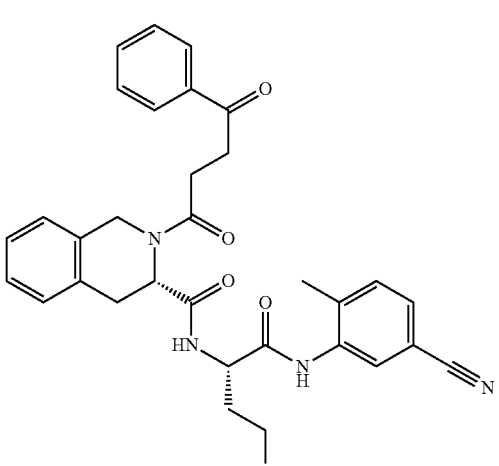 | 14-20 |

TABLE A-continued
REPRESENTATIVE COMPOUNDS
| Structure | Cpd. No. |
|---|---|
| 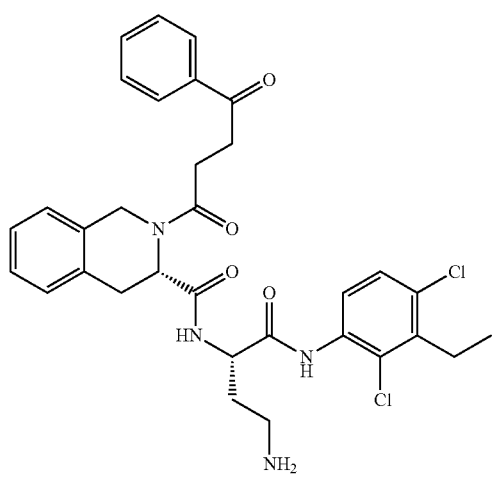 [SMILES: CCc1c(Cl)ccc(NC(=O)[C@H](CCN)NC(=O)[C@@H]2Cc3ccccc3CN2C(=O)CCC(=O)c2ccccc2)c1Cl] | 14-21 |
| 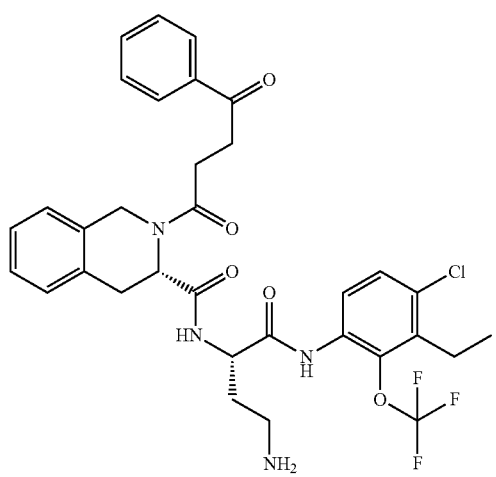 [SMILES: CCc1c(Cl)ccc(NC(=O)[C@H](CCN)NC(=O)[C@@H]2Cc3ccccc3CN2C(=O)CCC(=O)c2ccccc2)c1OC(F)(F)F] | 14-23 |
| 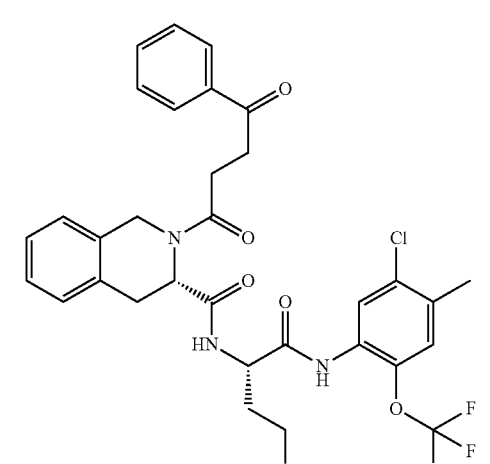 | 14-24 |

TABLE A-continued
REPRESENTATIVE COMPOUNDS
| Structure | Cpd. No. |
|---|---|
| 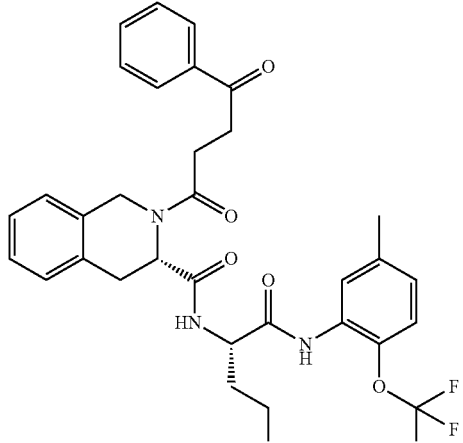 | 14-25 |
| 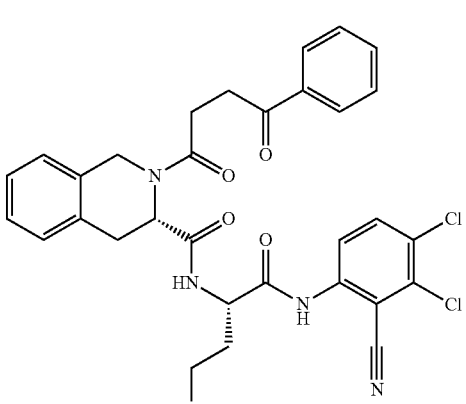 | 14-26 |
| 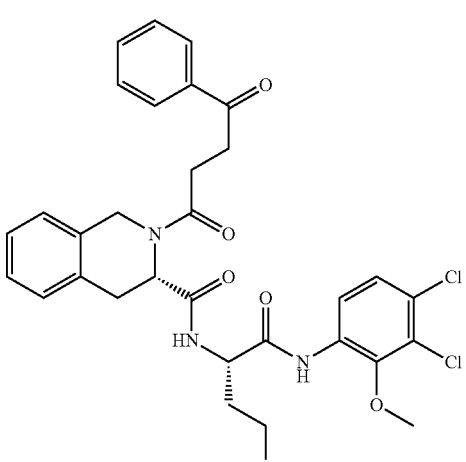 | 14-27 |

TABLE A-continued

REPRESENTATIVE COMPOUNDS

| Structure | Cpd. No. |
|---|---|
| 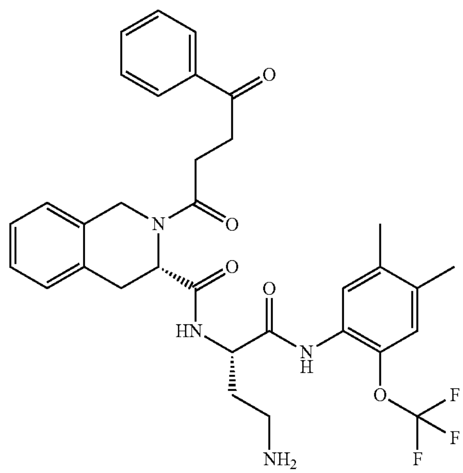 [SMILES: Cc1cc(NC(=O)[C@H](CCN)NC(=O)[C@@H]2Cc3ccccc3CN2C(=O)CCC(=O)c2ccccc2)c(OC(F)(F)F)cc1C] | 14-28 |
| 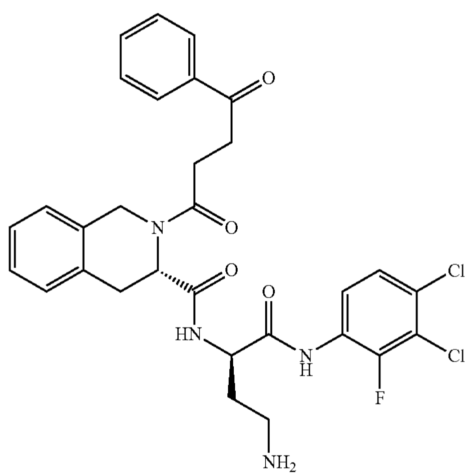 [SMILES: NCC[C@@H](NC(=O)[C@@H]1Cc2ccccc2CN1C(=O)CCC(=O)c1ccccc1)C(=O)Nc1ccc(Cl)c(Cl)c1F] | 14-29 |
| 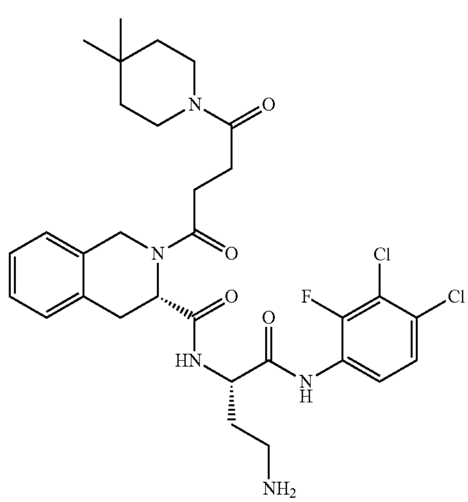 [SMILES: CC1(C)CCN(C(=O)CCC(=O)N2Cc3ccccc3C[C@H]2C(=O)N[C@@H](CCN)C(=O)Nc2ccc(Cl)c(Cl)c2F)CC1] | 15-1 |

TABLE A-continued
REPRESENTATIVE COMPOUNDS
| Structure | Cpd. No. |
|---|---|
| 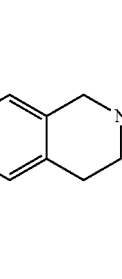 | 15-2 |
| 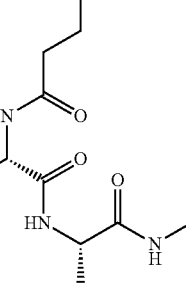 | 15-3 |
| 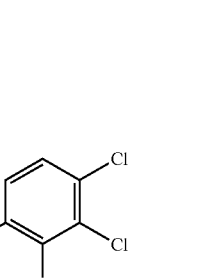 | 15-4 |

TABLE A-continued
REPRESENTATIVE COMPOUNDS
| Structure | Cpd. No. |
|---|---|
| 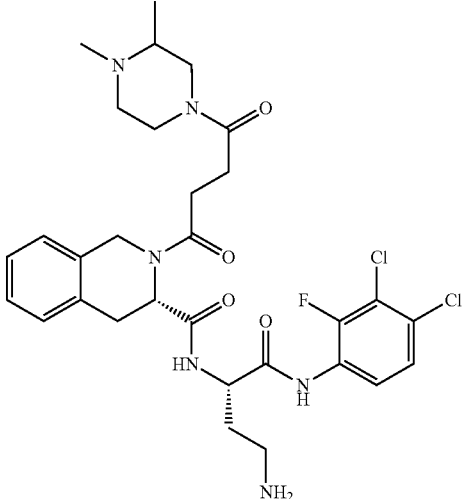 | 15-5 |
| 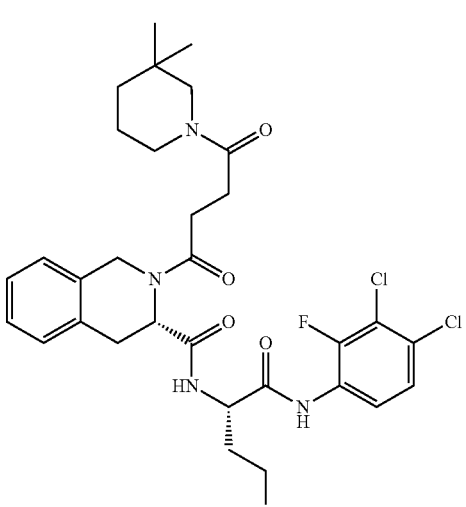 | 15-6 |
| 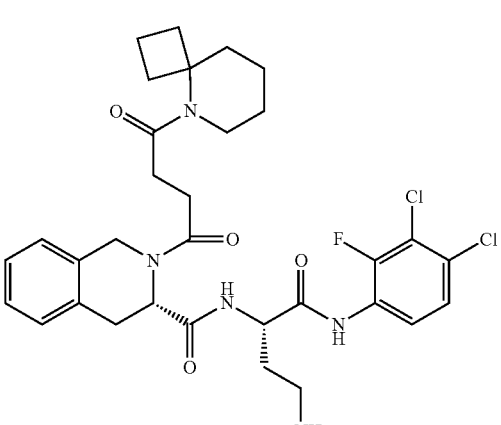 | 15-7 |

TABLE A-continued

REPRESENTATIVE COMPOUNDS

| Structure | Cpd. No. |
|---|---|
| 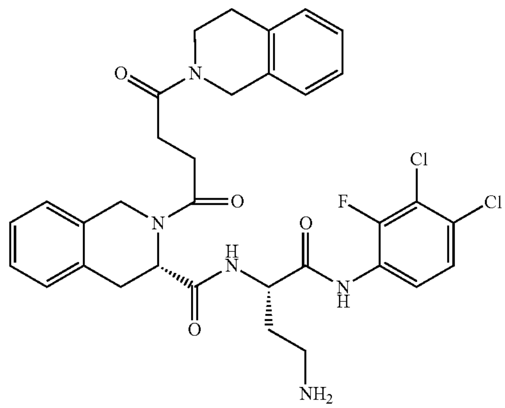 [SMILES: NCC[C@H](NC(=O)[C@@H]1Cc2ccccc2CN1C(=O)CCC(=O)N1CCc2ccccc2C1)C(=O)Nc1ccc(Cl)c(Cl)c1F] | 15-8 |
| 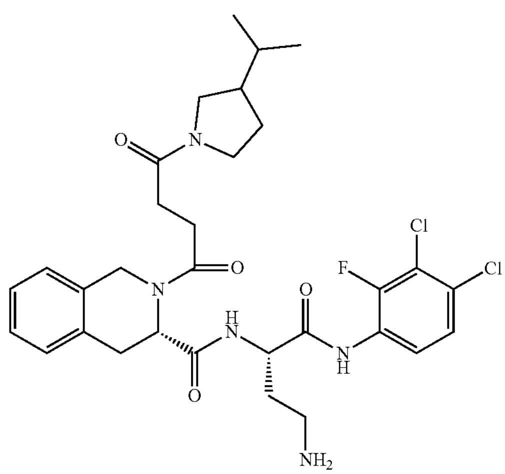 [SMILES: CC(C)C1CCN(C(=O)CCC(=O)N2Cc3ccccc3C[C@H]2C(=O)N[C@@H](CCN)C(=O)Nc2ccc(Cl)c(Cl)c2F)C1] | 15-9 |
| 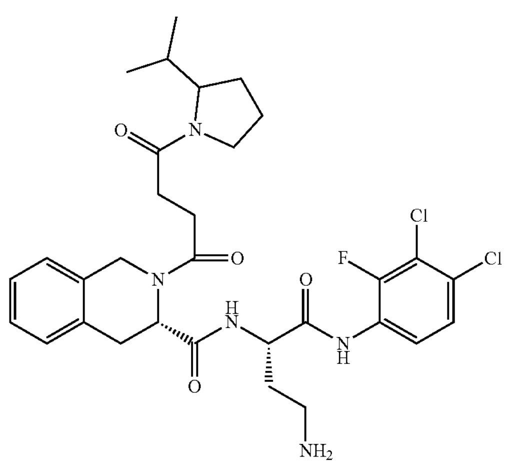 [SMILES: CC(C)C1CCCN1C(=O)CCC(=O)N1Cc2ccccc2C[C@H]1C(=O)N[C@@H](CCN)C(=O)Nc1ccc(Cl)c(Cl)c1F] | 15-10 |

TABLE A-continued
REPRESENTATIVE COMPOUNDS
| Structure | Cpd. No. |
|---|---|
| 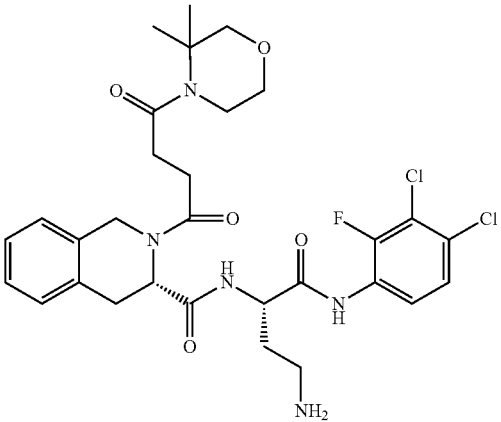 [SMILES: CC1(C)COCCN1C(=O)CCC(=O)N1Cc2ccccc2C[C@H]1C(=O)N[C@@H](CCN)C(=O)Nc1ccc(Cl)c(Cl)c1F] | 15-11 |
| 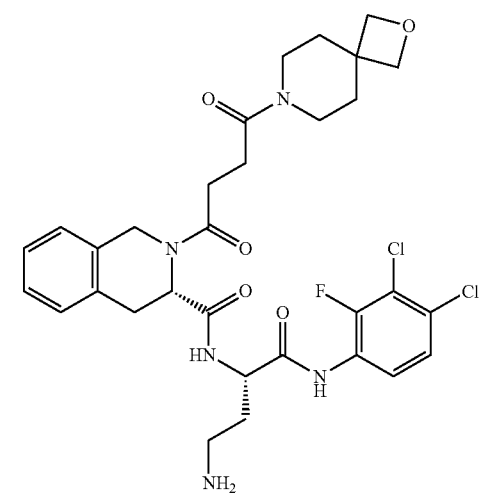 [SMILES: NCC[C@H](NC(=O)[C@@H]1Cc2ccccc2CN1C(=O)CCC(=O)N1CCC2(CC1)COC2)C(=O)Nc1ccc(Cl)c(Cl)c1F] | 15-12 |
| 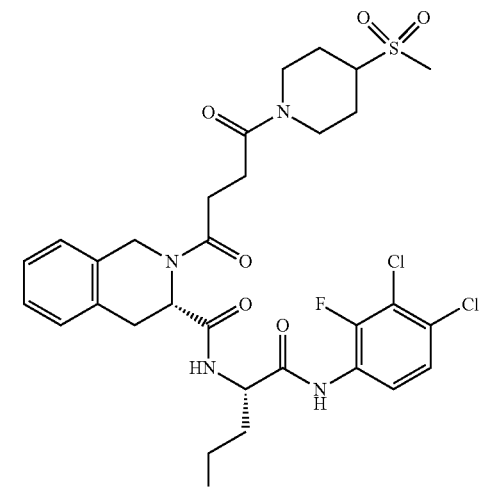 | 15-13 |

TABLE A-continued

REPRESENTATIVE COMPOUNDS

| Structure | Cpd. No. |
|---|---|
| 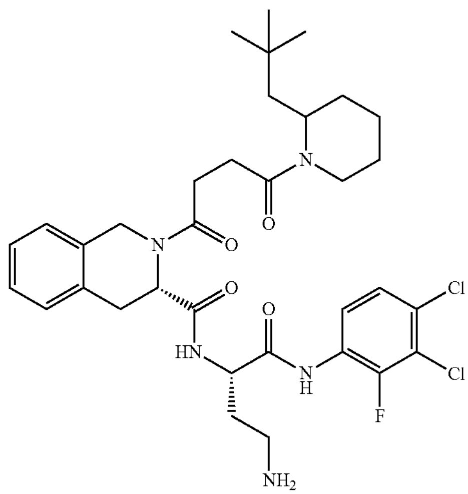 [SMILES: CC(C)(C)CC1CCCCN1C(=O)CCC(=O)N1Cc2ccccc2C[C@H]1C(=O)N[C@@H](CCN)C(=O)Nc1ccc(Cl)c(Cl)c1F] | 15-14 |
| 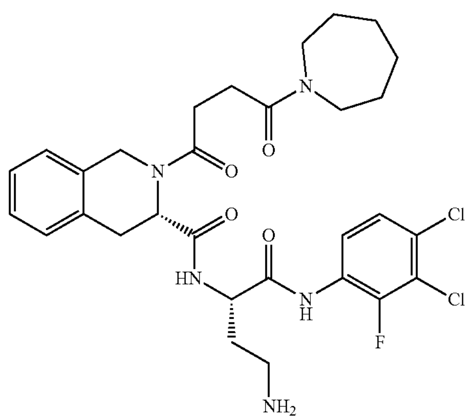 [SMILES: NCC[C@H](NC(=O)[C@@H]1Cc2ccccc2CN1C(=O)CCC(=O)N1CCCCCC1)C(=O)Nc1ccc(Cl)c(Cl)c1F] | 15-15 |
| 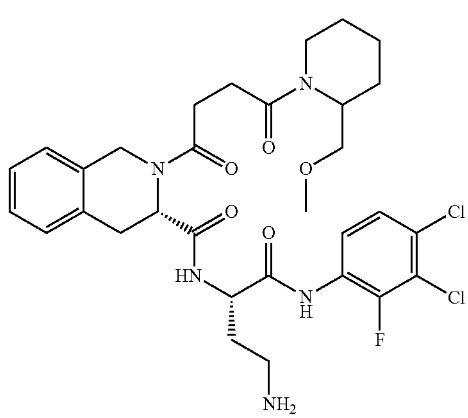 [SMILES: COCC1CCCCN1C(=O)CCC(=O)N1Cc2ccccc2C[C@H]1C(=O)N[C@@H](CCN)C(=O)Nc1ccc(Cl)c(Cl)c1F] | 15-16 |

TABLE A-continued

REPRESENTATIVE COMPOUNDS

| Structure | Cpd. No. |
|---|---|
| 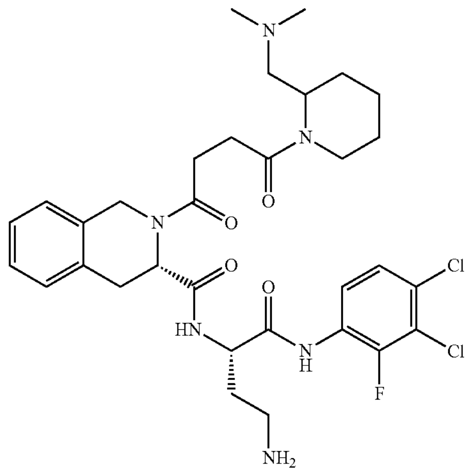 [SMILES: CN(C)CC1CCCCN1C(=O)CCC(=O)N1Cc2ccccc2C[C@H]1C(=O)N[C@@H](CCN)C(=O)Nc1ccc(Cl)c(Cl)c1F] | 15-17 |
| 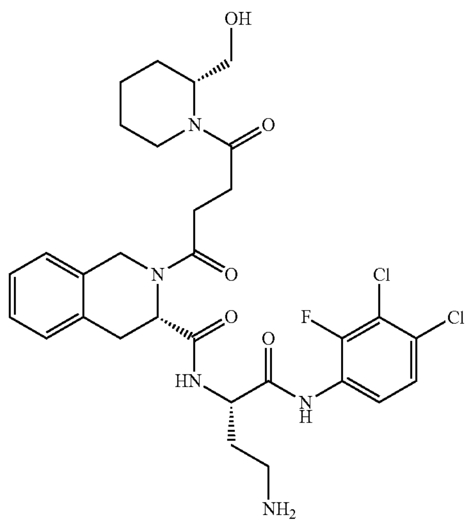 [SMILES: NCC[C@H](NC(=O)[C@@H]1Cc2ccccc2CN1C(=O)CCC(=O)N1CCCC[C@@H]1CO)C(=O)Nc1ccc(Cl)c(Cl)c1F] | 15-18 |
| 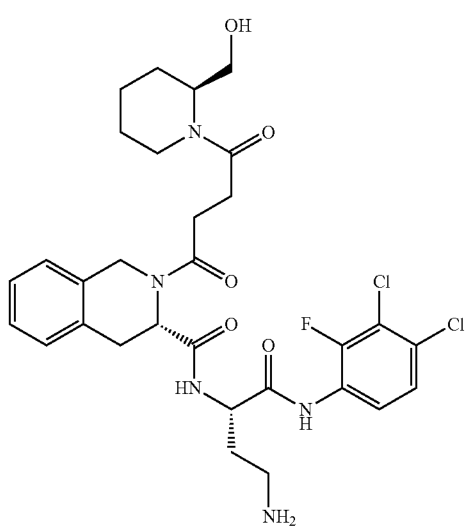 [SMILES: NCC[C@H](NC(=O)[C@@H]1Cc2ccccc2CN1C(=O)CCC(=O)N1CCCC[C@H]1CO)C(=O)Nc1ccc(Cl)c(Cl)c1F] | 15-19 |

TABLE A-continued
REPRESENTATIVE COMPOUNDS
| Structure | Cpd. No. |
|---|---|
| 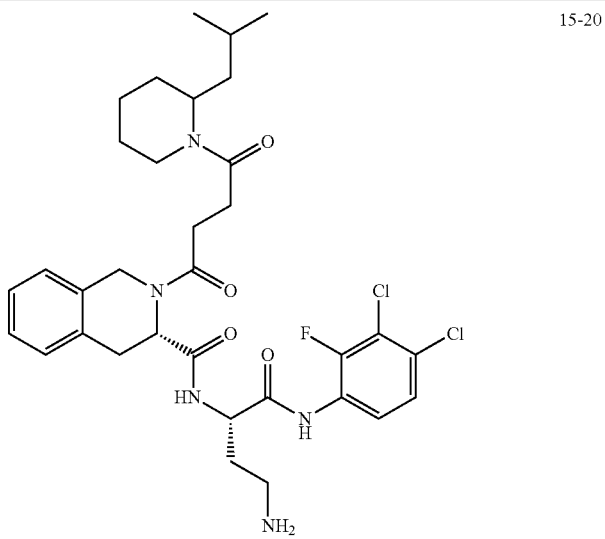 | 15-20 |
| 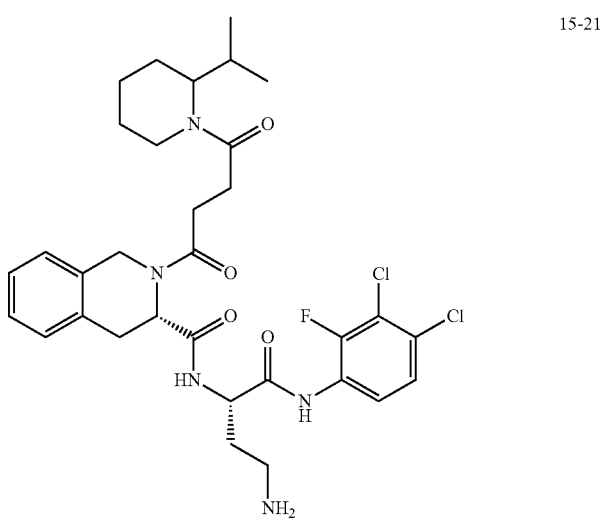 | 15-21 |
| 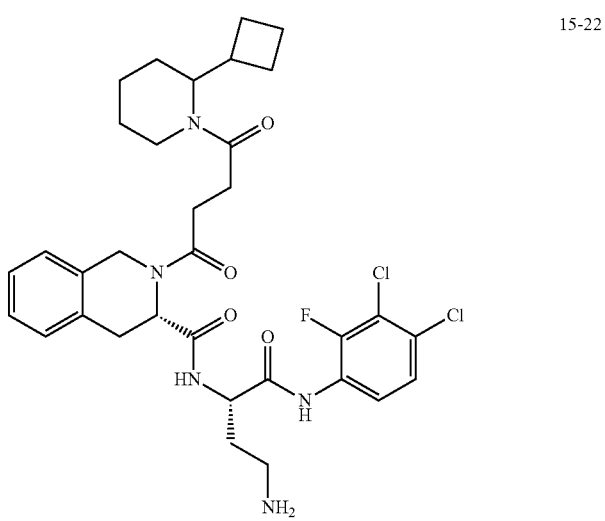 | 15-22 |

TABLE A-continued
REPRESENTATIVE COMPOUNDS
| Structure | Cpd. No. |
|---|---|
| 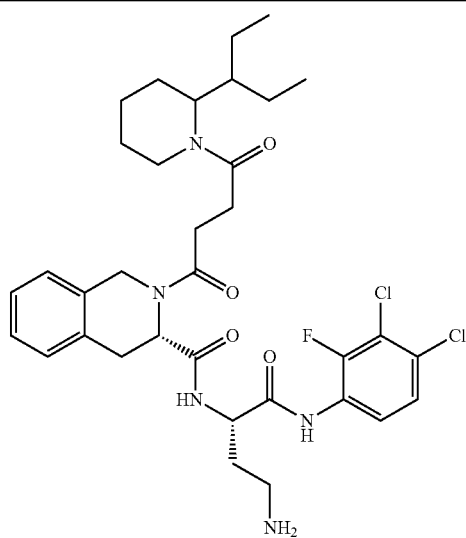 | 15-23 |
| 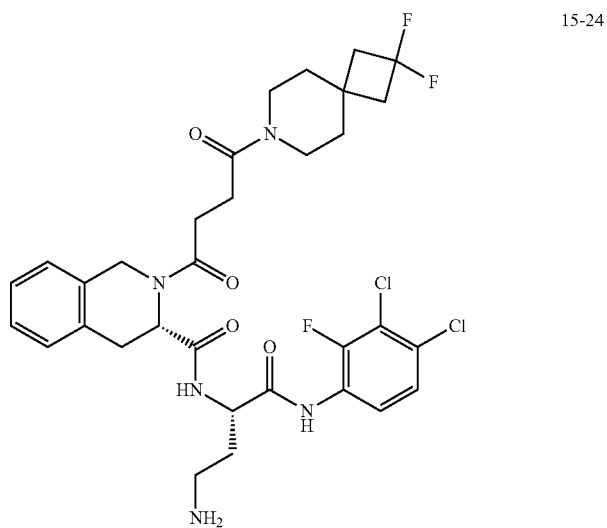 | 15-24 |

TABLE A-continued
REPRESENTATIVE COMPOUNDS
| Structure | Cpd. No. |
|---|---|
| 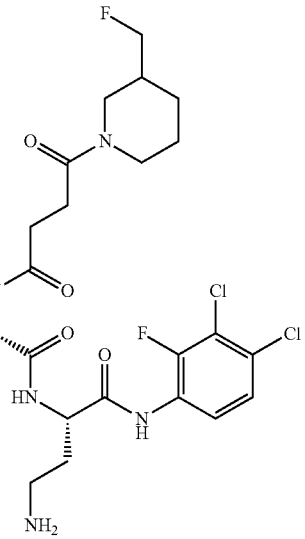 | 15-25 |
| 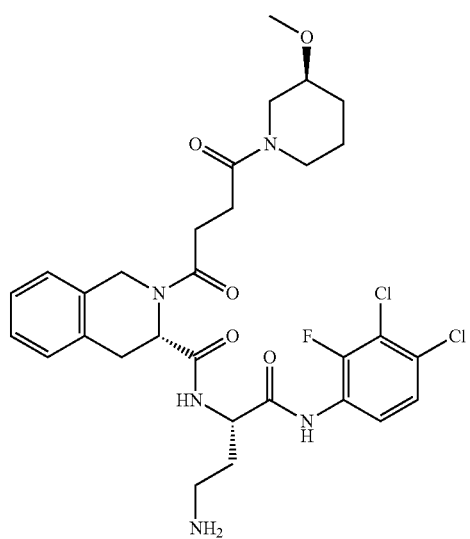 [SMILES: CO[C@H]1CCCN(C(=O)CCC(=O)N2Cc3ccccc3C[C@H]2C(=O)N[C@@H](CCN)C(=O)Nc2ccc(Cl)c(Cl)c2F)C1] | 15-26 |

TABLE A-continued
REPRESENTATIVE COMPOUNDS
| Structure | Cpd. No. |
|---|---|
| 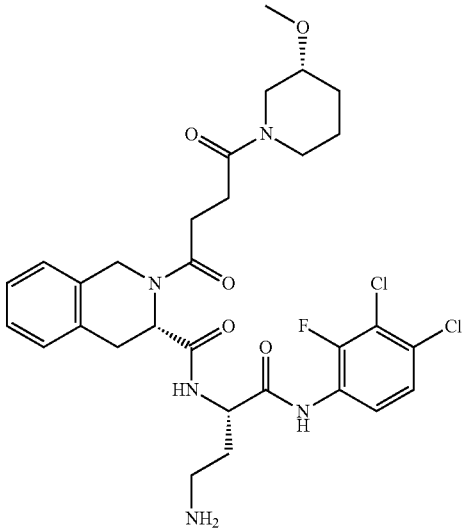 [SMILES: CO[C@@H]1CCCN(C(=O)CCC(=O)N2Cc3ccccc3C[C@H]2C(=O)N[C@@H](CCN)C(=O)Nc2ccc(Cl)c(Cl)c2F)C1] | 15-27 |
| 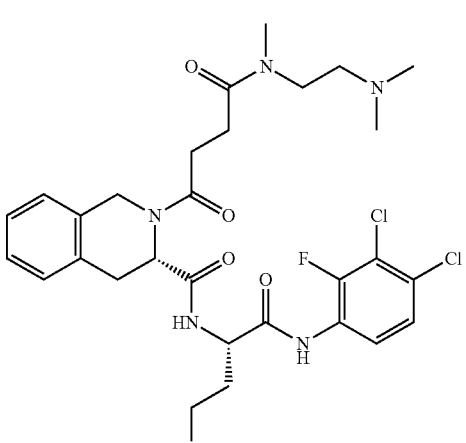 | 15-28 |
| 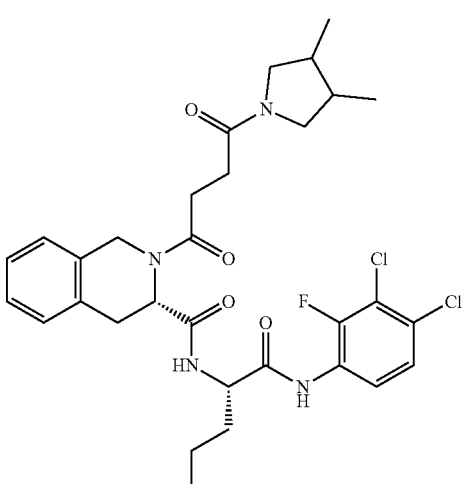 | 15-29 |

TABLE A-continued

REPRESENTATIVE COMPOUNDS

| Structure | Cpd. No. |
|---|---|
| 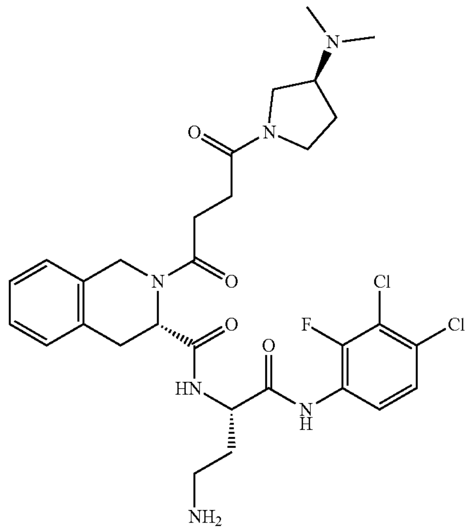 [SMILES: CN(C)[C@H]1CCN(C(=O)CCC(=O)N2Cc3ccccc3C[C@H]2C(=O)N[C@@H](CCN)C(=O)Nc2ccc(Cl)c(Cl)c2F)C1] | 15-30 |
| 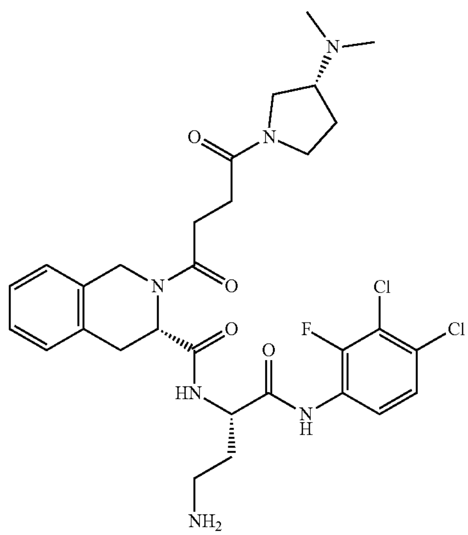 [SMILES: CN(C)[C@@H]1CCN(C(=O)CCC(=O)N2Cc3ccccc3C[C@H]2C(=O)N[C@@H](CCN)C(=O)Nc2ccc(Cl)c(Cl)c2F)C1] | 15-31 |
| 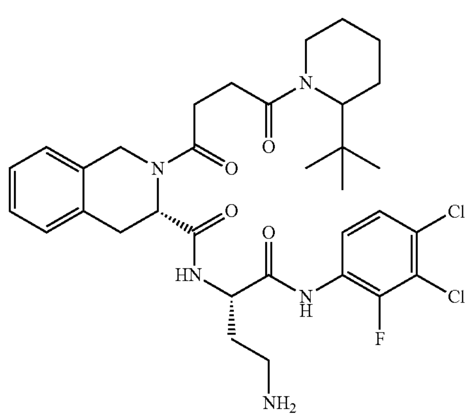 [SMILES: CC(C)(C)C1CCCCN1C(=O)CCC(=O)N1Cc2ccccc2C[C@H]1C(=O)N[C@@H](CCN)C(=O)Nc1ccc(Cl)c(Cl)c1F] | 15-32 |

TABLE A-continued

REPRESENTATIVE COMPOUNDS

| Structure | Cpd. No. |
|---|---|
| 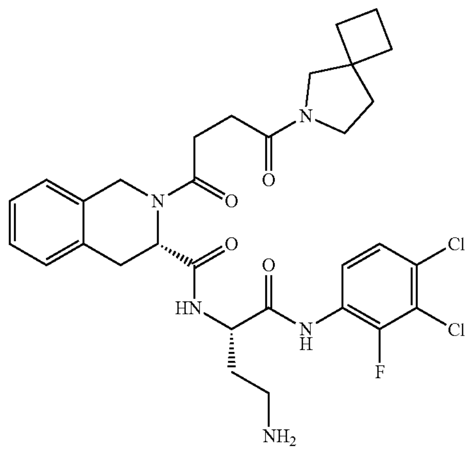 [SMILES: NCC[C@H](NC(=O)[C@@H]1Cc2ccccc2CN1C(=O)CCC(=O)N1CCC2(CCC2)C1)C(=O)Nc1ccc(Cl)c(Cl)c1F] | 15-33 |
| 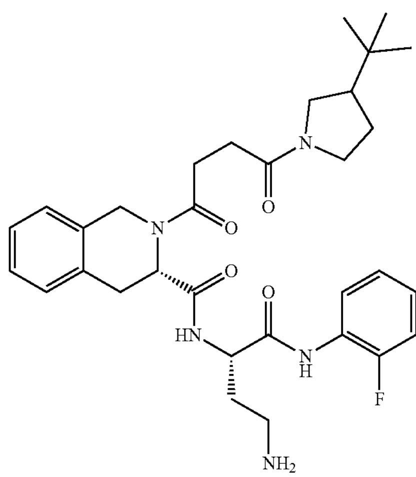 | 15-34 |
| 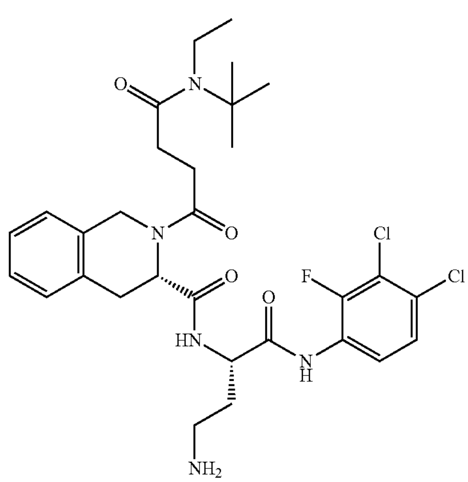 [SMILES: CCN(C(=O)CCC(=O)N1Cc2ccccc2C[C@H]1C(=O)N[C@@H](CCN)C(=O)Nc1ccc(Cl)c(Cl)c1F)C(C)(C)C] | 15-35 |

TABLE A-continued

REPRESENTATIVE COMPOUNDS

| Structure | Cpd. No. |
|---|---|
| 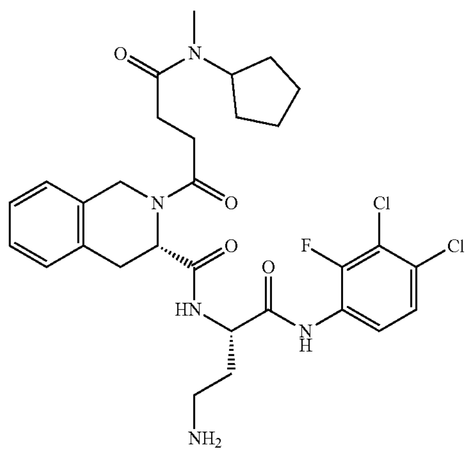 [SMILES: CN(C(=O)CCC(=O)N1Cc2ccccc2C[C@H]1C(=O)N[C@@H](CCN)C(=O)Nc1ccc(Cl)c(Cl)c1F)C1CCCC1] | 15-36 |
| 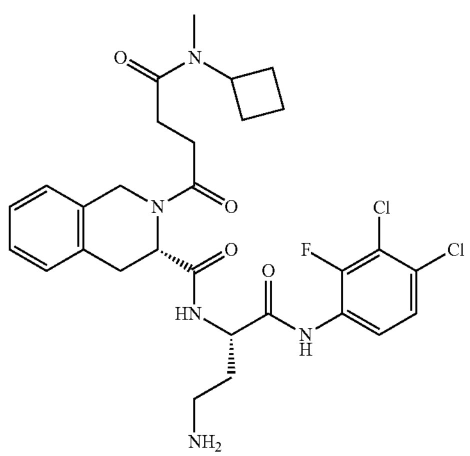 [SMILES: CN(C(=O)CCC(=O)N1Cc2ccccc2C[C@H]1C(=O)N[C@@H](CCN)C(=O)Nc1ccc(Cl)c(Cl)c1F)C1CCC1] | 15-37 |
| 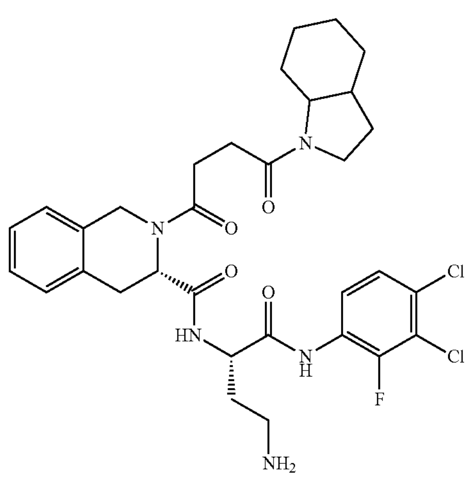 [SMILES: NCC[C@H](NC(=O)[C@@H]1Cc2ccccc2CN1C(=O)CCC(=O)N1CCC2CCCCC21)C(=O)Nc1ccc(Cl)c(Cl)c1F] | 15-38 |

TABLE A-continued
REPRESENTATIVE COMPOUNDS
| Structure | Cpd. No. |
|---|---|
| 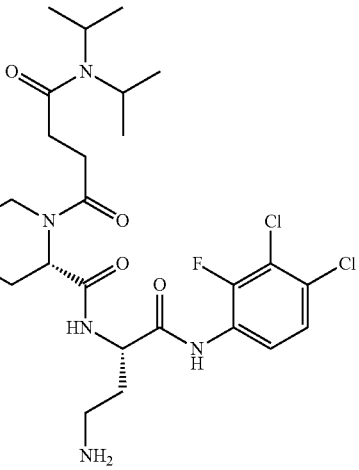 | 15-39 |
| 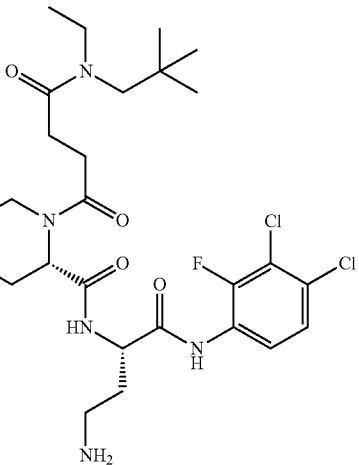 | 15-40 |
| 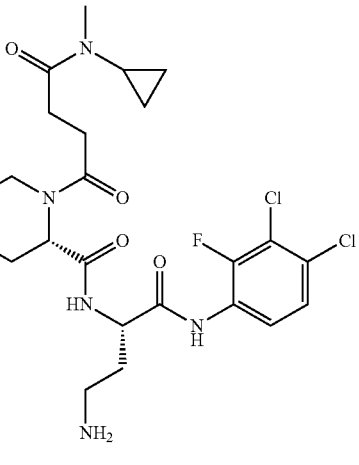 | 15-41 |

TABLE A-continued

REPRESENTATIVE COMPOUNDS

| Structure | Cpd. No. |
|---|---|
| 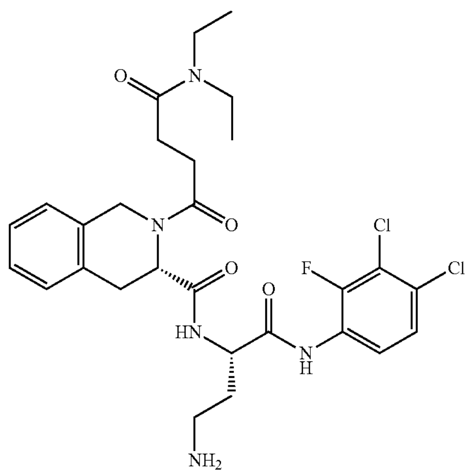 [SMILES: CCN(CC)C(=O)CCC(=O)N1Cc2ccccc2C[C@H]1C(=O)N[C@@H](CCN)C(=O)Nc1ccc(Cl)c(Cl)c1F] | 15-42 |
| 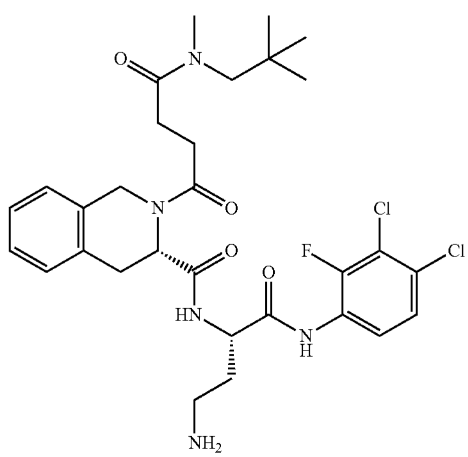 [SMILES: CN(CC(C)(C)C)C(=O)CCC(=O)N1Cc2ccccc2C[C@H]1C(=O)N[C@@H](CCN)C(=O)Nc1ccc(Cl)c(Cl)c1F] | 15-43 |
| 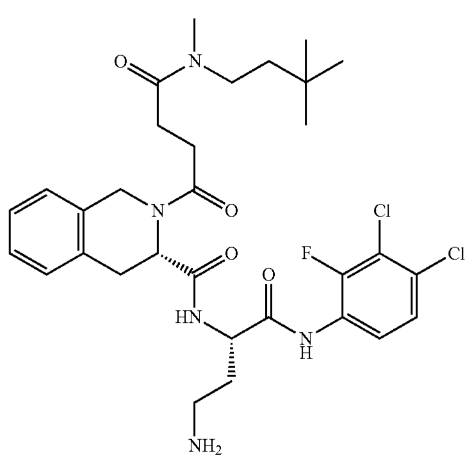 [SMILES: CN(CCC(C)(C)C)C(=O)CCC(=O)N1Cc2ccccc2C[C@H]1C(=O)N[C@@H](CCN)C(=O)Nc1ccc(Cl)c(Cl)c1F] | 15-44 |

TABLE A-continued

REPRESENTATIVE COMPOUNDS

| Structure | Cpd. No. |
|---|---|
| 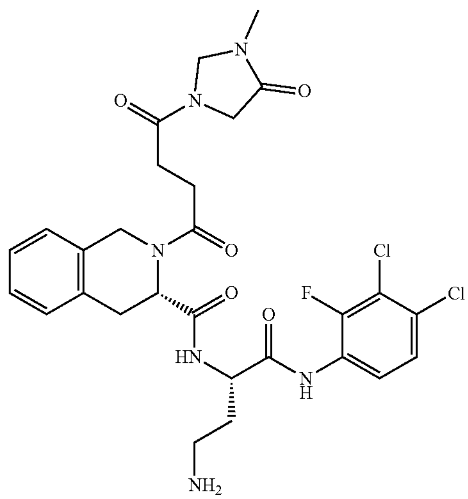 [SMILES: CN1CN(C(=O)CCC(=O)N2Cc3ccccc3C[C@H]2C(=O)N[C@@H](CCN)C(=O)Nc2ccc(Cl)c(Cl)c2F)CC1=O] | 15-45 |
| 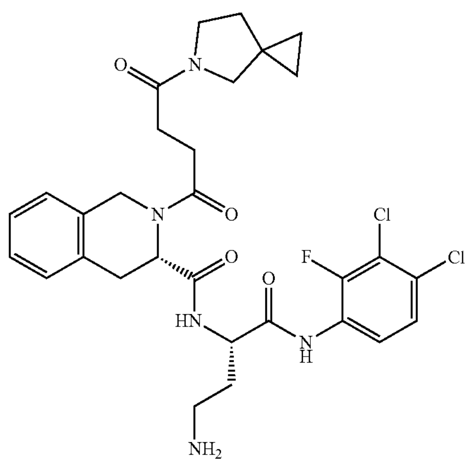 [SMILES: NCC[C@H](NC(=O)[C@@H]1Cc2ccccc2CN1C(=O)CCC(=O)N1CCC2(CC2)C1)C(=O)Nc1ccc(Cl)c(Cl)c1F] | 15-46 |
| 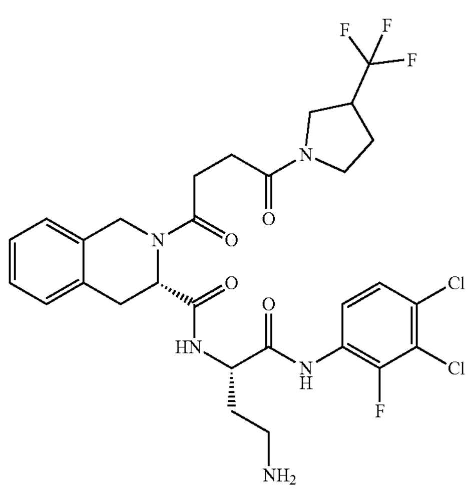 [SMILES: NCC[C@H](NC(=O)[C@@H]1Cc2ccccc2CN1C(=O)CCC(=O)N1CCC(C(F)(F)F)C1)C(=O)Nc1ccc(Cl)c(Cl)c1F] | 15-47 |

TABLE A-continued

REPRESENTATIVE COMPOUNDS

| Structure | Cpd. No. |
|---|---|
| 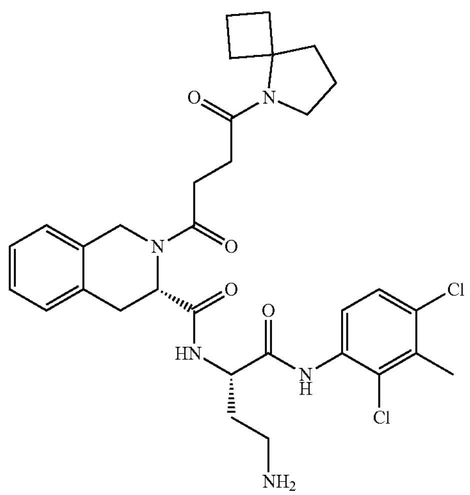 [SMILES: Cc1c(Cl)ccc(NC(=O)[C@H](CCN)NC(=O)[C@@H]2Cc3ccccc3CN2C(=O)CCC(=O)N2CCCC23CCC3)c1Cl] | 15-48 |
| 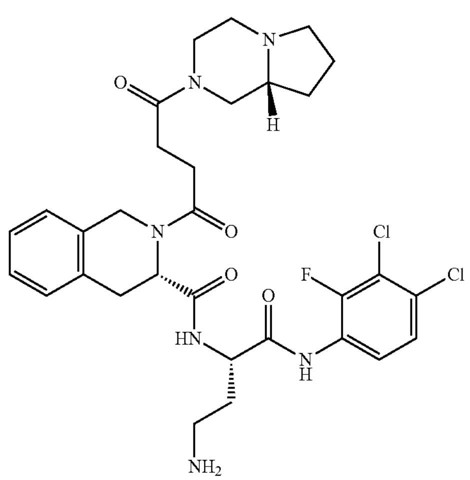 [SMILES: NCC[C@H](NC(=O)[C@@H]1Cc2ccccc2CN1C(=O)CCC(=O)N1CCN2CCC[C@@H]2C1)C(=O)Nc1ccc(Cl)c(Cl)c1F] | 15-49 |
| 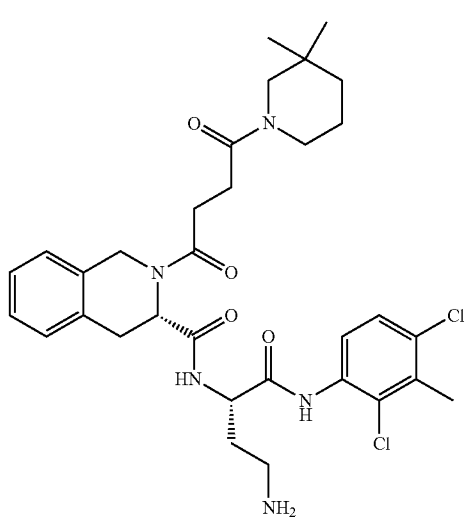 [SMILES: Cc1c(Cl)ccc(NC(=O)[C@H](CCN)NC(=O)[C@@H]2Cc3ccccc3CN2C(=O)CCC(=O)N2CCCC(C)(C)C2)c1Cl] | 15-50 |

TABLE A-continued

REPRESENTATIVE COMPOUNDS

| Structure | Cpd. No. |
|---|---|
| 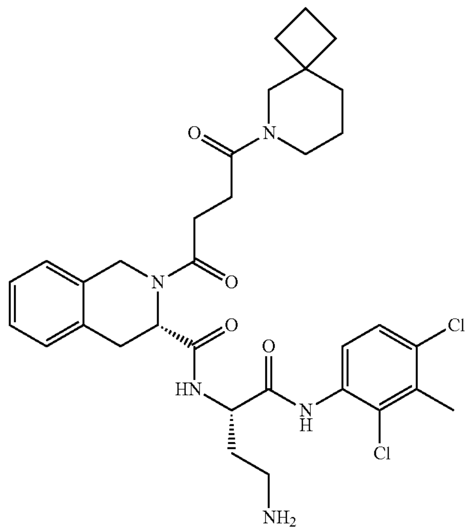 [SMILES: Cc1c(Cl)ccc(NC(=O)[C@H](CCN)NC(=O)[C@@H]2Cc3ccccc3CN2C(=O)CCC(=O)N2CCCC3(CCC3)C2)c1Cl] | 15-51 |
| 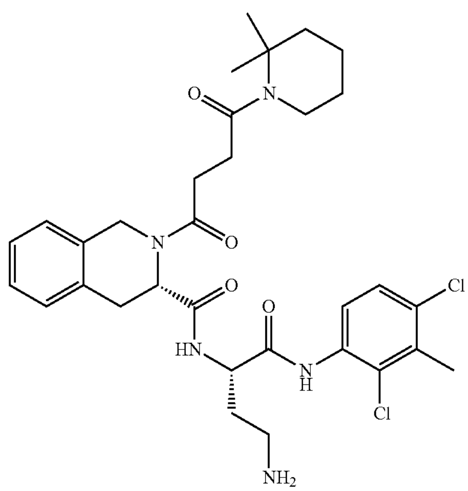 [SMILES: Cc1c(Cl)ccc(NC(=O)[C@H](CCN)NC(=O)[C@@H]2Cc3ccccc3CN2C(=O)CCC(=O)N2CCCCC2(C)C)c1Cl] | 15-52 |
| 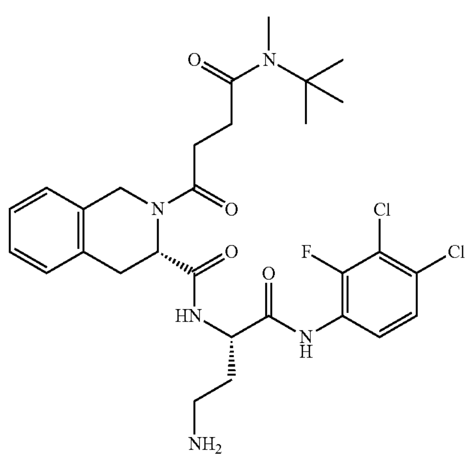 [SMILES: CN(C(=O)CCC(=O)N1Cc2ccccc2C[C@H]1C(=O)N[C@@H](CCN)C(=O)Nc1ccc(Cl)c(Cl)c1F)C(C)(C)C] | 15-53 |

TABLE A-continued

REPRESENTATIVE COMPOUNDS

| Structure | Cpd. No. |
|---|---|
| 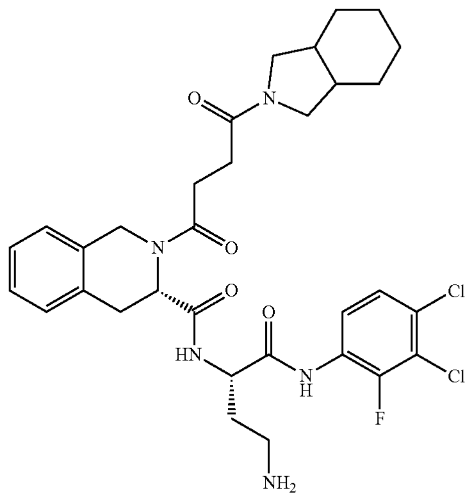 [SMILES: NCC[C@H](NC(=O)[C@@H]1Cc2ccccc2CN1C(=O)CCC(=O)N1CC2CCCCC2C1)C(=O)Nc1ccc(Cl)c(Cl)c1F] | 15-54 |
| 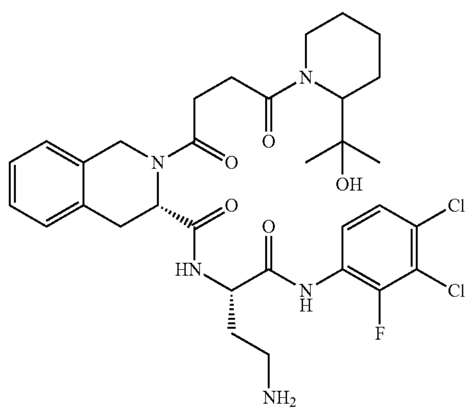 [SMILES: CC(C)(O)C1CCCCN1C(=O)CCC(=O)N1Cc2ccccc2C[C@H]1C(=O)N[C@@H](CCN)C(=O)Nc1ccc(Cl)c(Cl)c1F] | 15-55 |
| 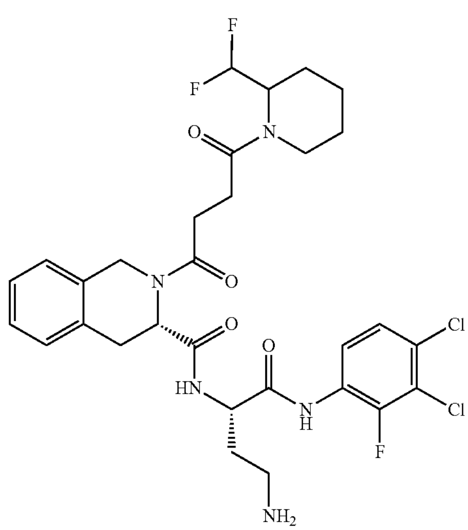 [SMILES: NCC[C@H](NC(=O)[C@@H]1Cc2ccccc2CN1C(=O)CCC(=O)N1CCCCC1C(F)F)C(=O)Nc1ccc(Cl)c(Cl)c1F] | 15-56 |

TABLE A-continued
REPRESENTATIVE COMPOUNDS
| Structure | Cpd. No. |
|---|---|
| 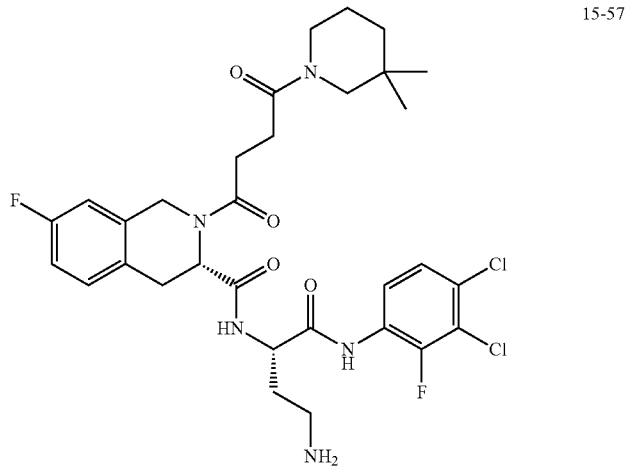 | 15-57 |
| 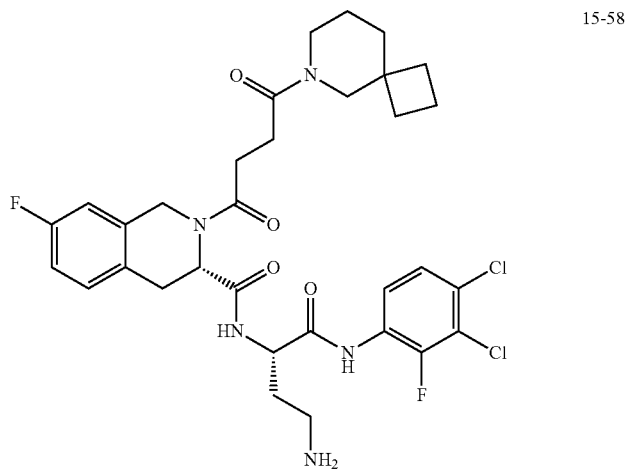 | 15-58 |
| 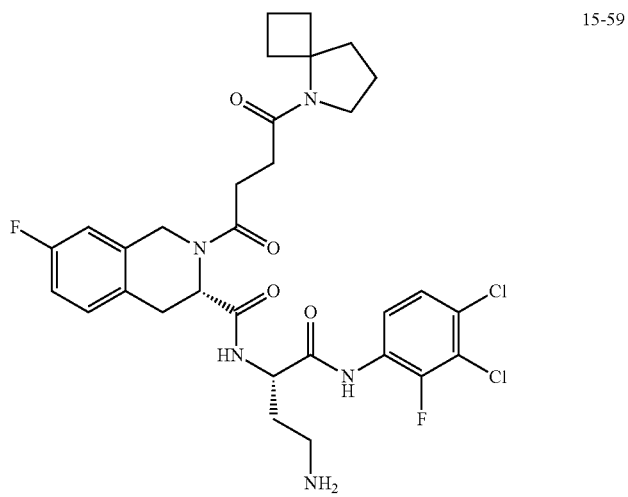 | 15-59 |

TABLE A-continued

REPRESENTATIVE COMPOUNDS

| Structure | Cpd. No. |
|---|---|
| 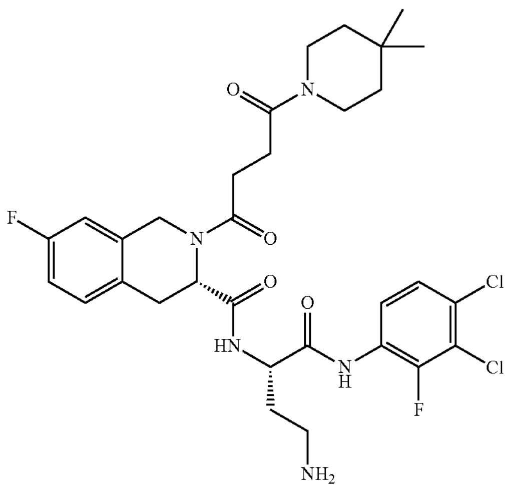 [SMILES: CC1(C)CCN(C(=O)CCC(=O)N2Cc3cc(F)ccc3C[C@H]2C(=O)N[C@@H](CCN)C(=O)Nc2ccc(Cl)c(Cl)c2F)CC1] | 15-60 |
| 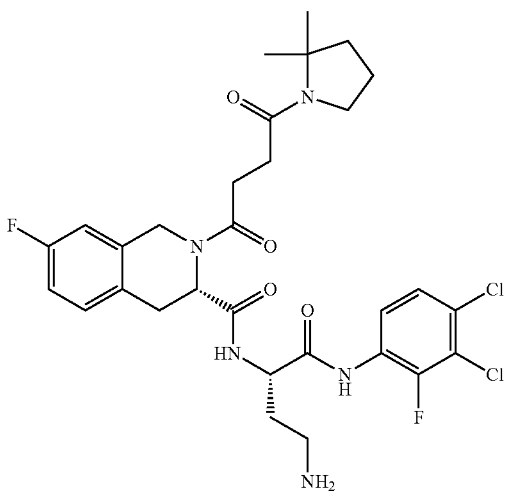 [SMILES: CC1(C)CCCN1C(=O)CCC(=O)N1Cc2cc(F)ccc2C[C@H]1C(=O)N[C@@H](CCN)C(=O)Nc1ccc(Cl)c(Cl)c1F] | 15-61 |
| 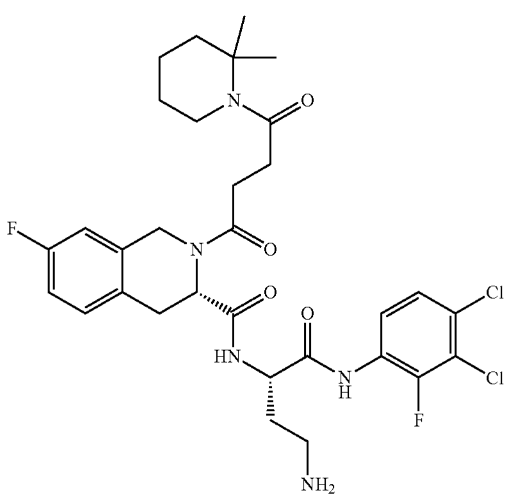 [SMILES: CC1(C)CCCCN1C(=O)CCC(=O)N1Cc2cc(F)ccc2C[C@H]1C(=O)N[C@@H](CCN)C(=O)Nc1ccc(Cl)c(Cl)c1F] | 15-62 |

TABLE A-continued

REPRESENTATIVE COMPOUNDS

| Structure | Cpd. No. |
|---|---|
| 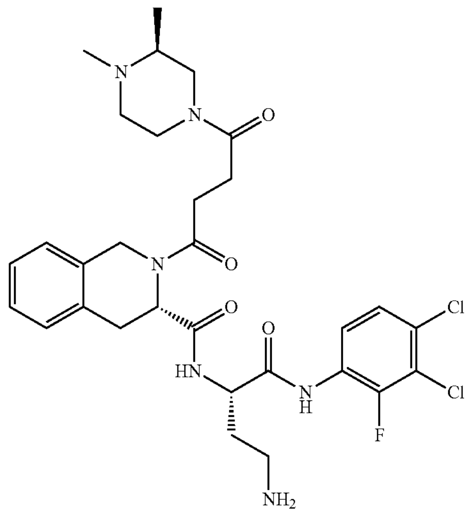 [SMILES: C[C@H]1CN(C(=O)CCC(=O)N2Cc3ccccc3C[C@H]2C(=O)N[C@@H](CCN)C(=O)Nc2ccc(Cl)c(Cl)c2F)CCN1C] | 15-63 |
| 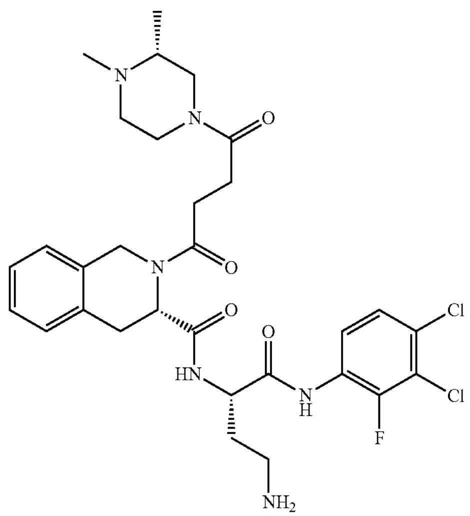 [SMILES: C[C@@H]1CN(C(=O)CCC(=O)N2Cc3ccccc3C[C@H]2C(=O)N[C@@H](CCN)C(=O)Nc2ccc(Cl)c(Cl)c2F)CCN1C] | 15-64 |
| 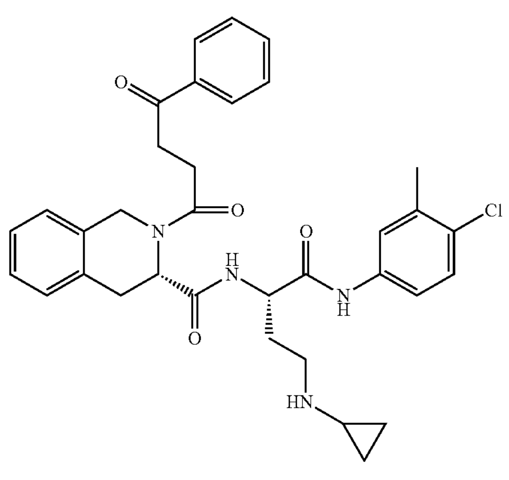 [SMILES: Cc1cc(NC(=O)[C@H](CCNC2CC2)NC(=O)[C@@H]2Cc3ccccc3CN2C(=O)CCC(=O)c2ccccc2)ccc1Cl] | 16-1 |

TABLE A-continued
REPRESENTATIVE COMPOUNDS
| Structure | Cpd. No. |
|---|---|
| 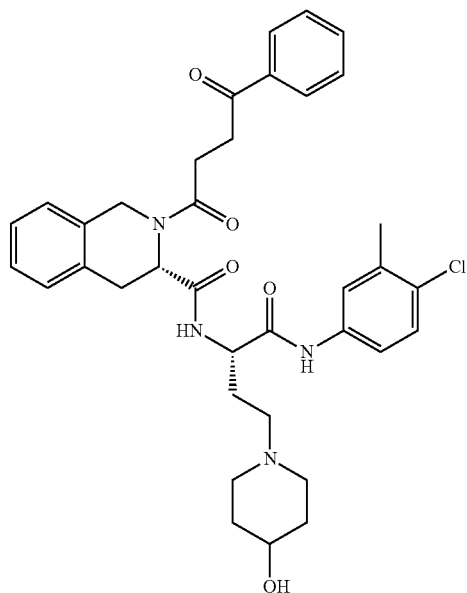 [SMILES: Cc1cc(NC(=O)[C@H](CCN2CCC(O)CC2)NC(=O)[C@@H]2Cc3ccccc3CN2C(=O)CCC(=O)c2ccccc2)ccc1Cl] | 17-1 |
| 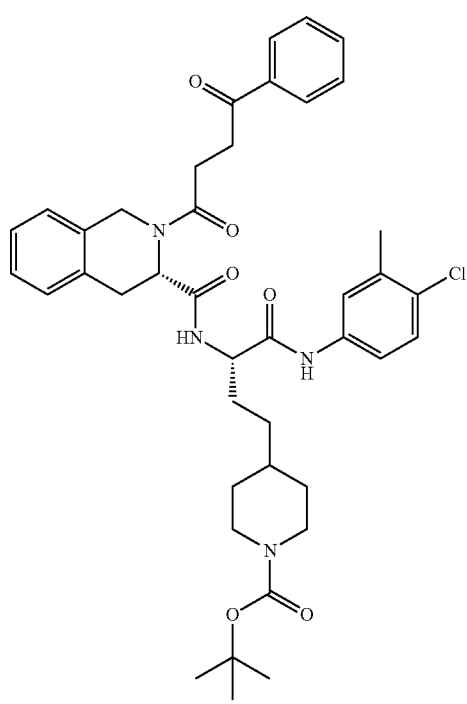 [SMILES: Cc1cc(NC(=O)[C@H](CCC2CCN(C(=O)OC(C)(C)C)CC2)NC(=O)[C@@H]2Cc3ccccc3CN2C(=O)CCC(=O)c2ccccc2)ccc1Cl] | 17-2 |

TABLE A-continued
REPRESENTATIVE COMPOUNDS
| Structure | Cpd. No. |
|---|---|
| 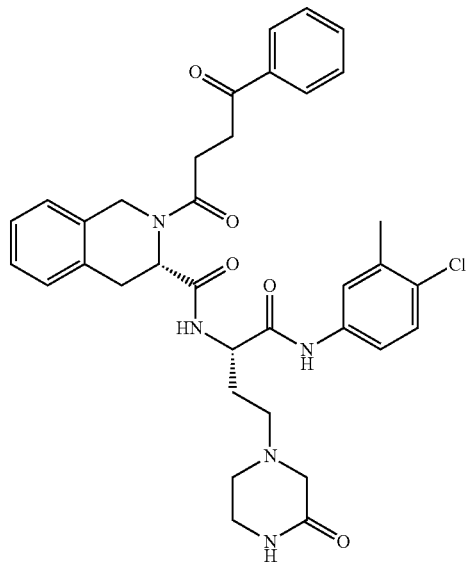 [SMILES: Cc1cc(NC(=O)[C@H](CCN2CCNC(=O)C2)NC(=O)[C@@H]2Cc3ccccc3CN2C(=O)CCC(=O)c2ccccc2)ccc1Cl] | 17-3 |
| 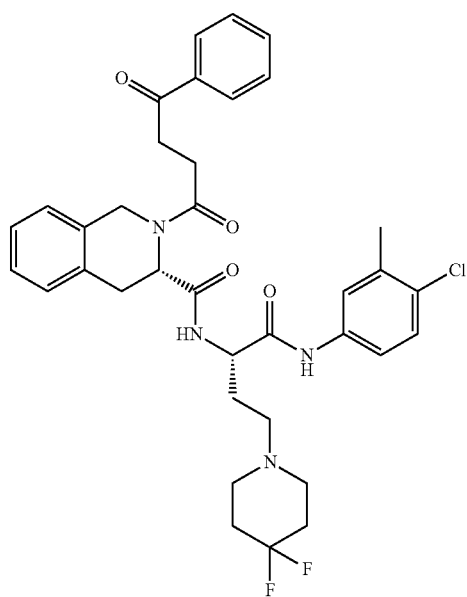 [SMILES: Cc1cc(NC(=O)[C@H](CCN2CCC(F)(F)CC2)NC(=O)[C@@H]2Cc3ccccc3CN2C(=O)CCC(=O)c2ccccc2)ccc1Cl] | 17-4 |

TABLE A-continued
REPRESENTATIVE COMPOUNDS
| Structure | Cpd. No. |
|---|---|
| 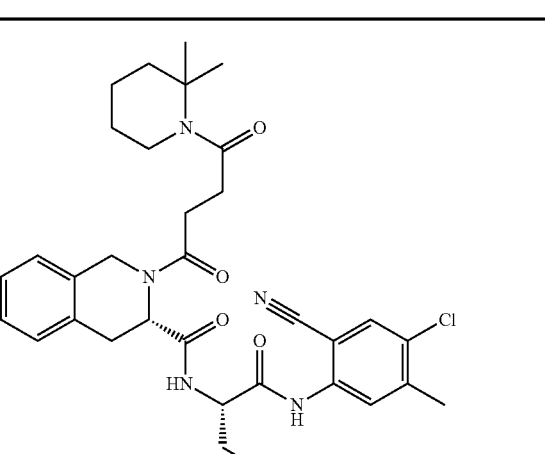 | 18-1 |
| 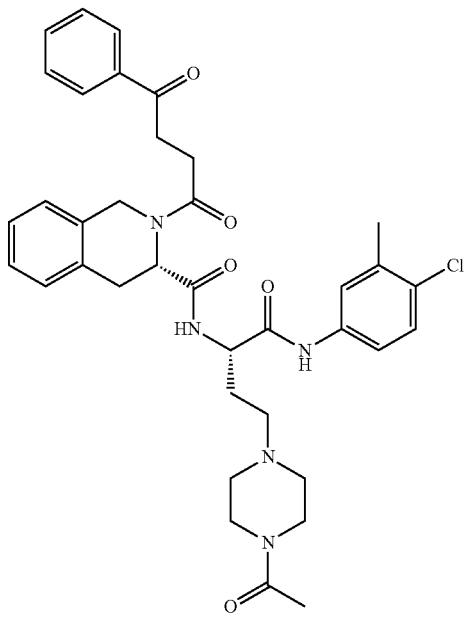 [SMILES: CC(=O)N1CCN(CC[C@H](NC(=O)[C@@H]2Cc3ccccc3CN2C(=O)CCC(=O)c2ccccc2)C(=O)Nc2ccc(Cl)c(C)c2)CC1] | 19-1 |

TABLE A-continued
REPRESENTATIVE COMPOUNDS
| Structure | Cpd. No. |
|---|---|
| 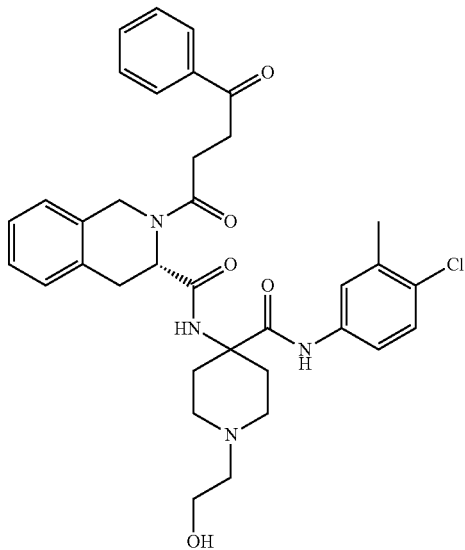 [SMILES: Cc1cc(NC(=O)C2(NC(=O)[C@@H]3Cc4ccccc4CN3C(=O)CCC(=O)c3ccccc3)CCN(CCO)CC2)ccc1Cl] | 20-1 |
| 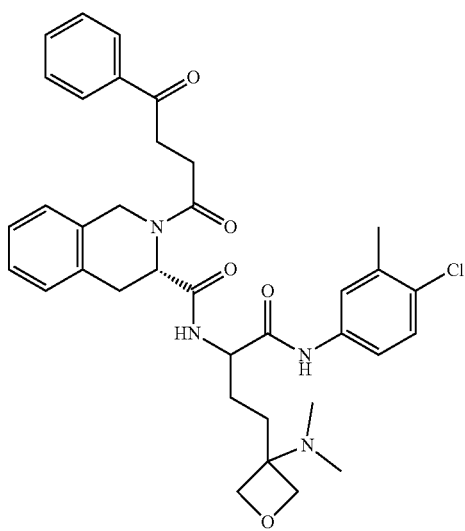 [SMILES: Cc1cc(NC(=O)C(CCC2(N(C)C)COC2)NC(=O)[C@@H]2Cc3ccccc3CN2C(=O)CCC(=O)c2ccccc2)ccc1Cl] | 21-1 |
| 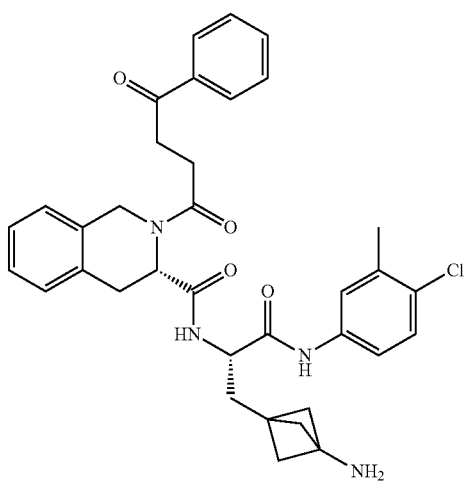 [SMILES: Cc1cc(NC(=O)[C@H](CC23CC(N)(C2)C3)NC(=O)[C@@H]2Cc3ccccc3CN2C(=O)CCC(=O)c2ccccc2)ccc1Cl] | 22-1 |

TABLE A-continued
REPRESENTATIVE COMPOUNDS
| Structure | Cpd. No. |
|---|---|
| 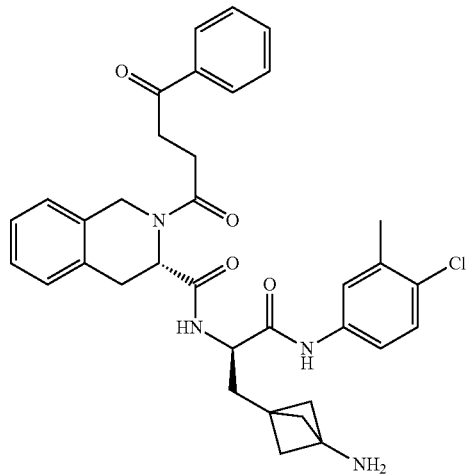 [SMILES: Cc1cc(NC(=O)[C@@H](CC23CC(N)(C2)C3)NC(=O)[C@@H]2Cc3ccccc3CN2C(=O)CCC(=O)c2ccccc2)ccc1Cl] | 22-2 |
| 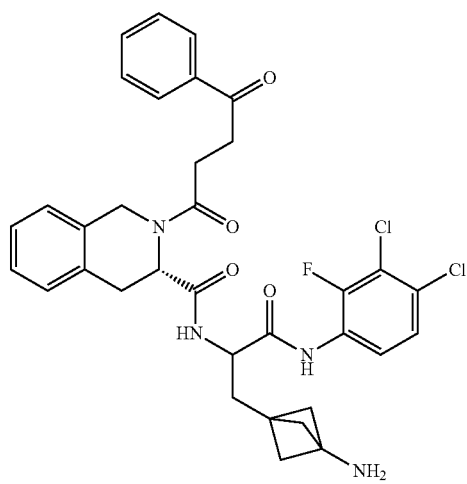 [SMILES: NC12CC(CC(NC(=O)[C@@H]3Cc4ccccc4CN3C(=O)CCC(=O)c3ccccc3)C(=O)Nc3ccc(Cl)c(Cl)c3F)(C1)C2] | 22-3 |
| 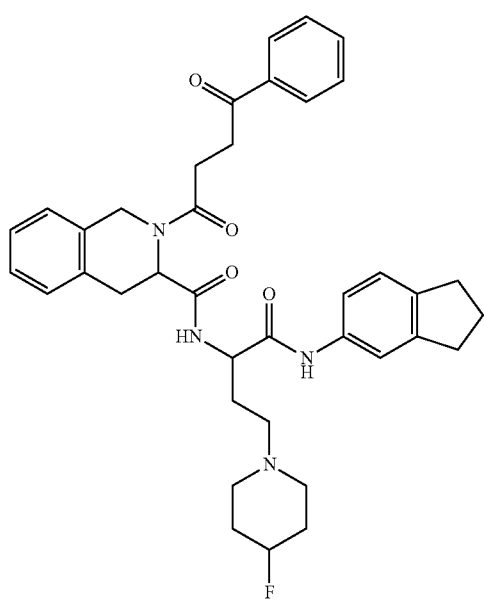 [SMILES: O=C(CCC(=O)N1Cc2ccccc2CC1C(=O)NC(CCN1CCC(F)CC1)C(=O)Nc1ccc2c(c1)CCC2)c1ccccc1] | 23-1 |

TABLE A-continued
REPRESENTATIVE COMPOUNDS
| Structure | Cpd. No. |
|---|---|
| 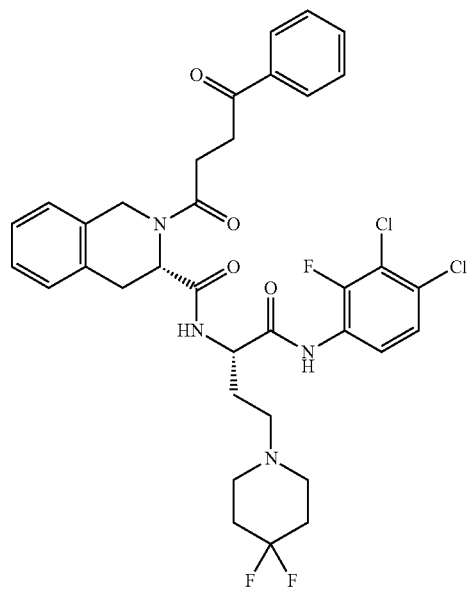 [SMILES: O=C(CCC(=O)N1Cc2ccccc2C[C@H]1C(=O)N[C@@H](CCN1CCC(F)(F)CC1)C(=O)Nc1ccc(Cl)c(Cl)c1F)c1ccccc1] | 23-2 |
| 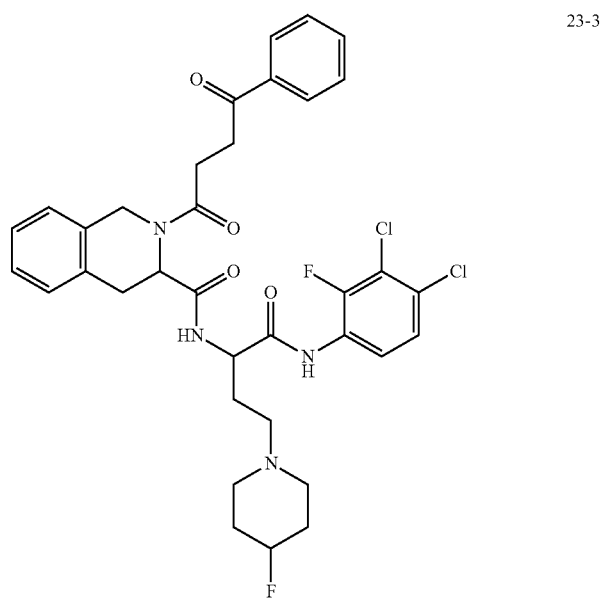 | 23-3 |

TABLE A-continued
REPRESENTATIVE COMPOUNDS
| Structure | Cpd. No. |
|---|---|
| 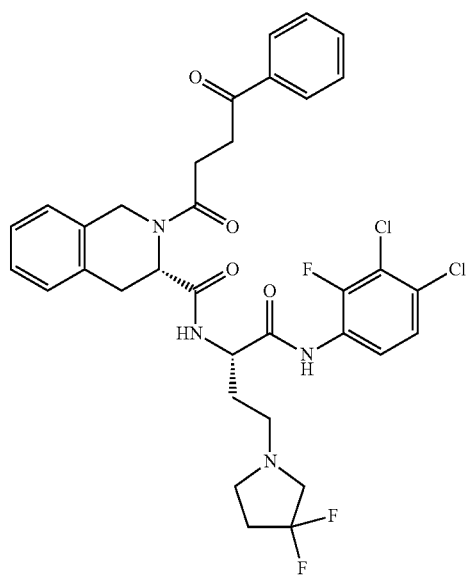 [SMILES: O=C(CCC(=O)N1Cc2ccccc2C[C@H]1C(=O)N[C@@H](CCN1CCC(F)(F)C1)C(=O)Nc1ccc(Cl)c(Cl)c1F)c1ccccc1] | 23-4 |
| 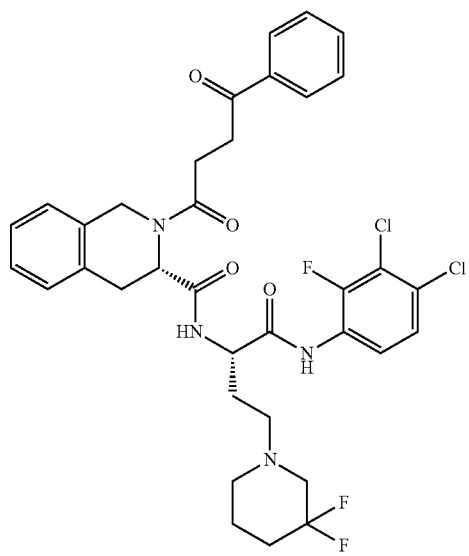 [SMILES: O=C(CCC(=O)N1Cc2ccccc2C[C@H]1C(=O)N[C@@H](CCN1CCCC(F)(F)C1)C(=O)Nc1ccc(Cl)c(Cl)c1F)c1ccccc1] | 23-5 |

TABLE A-continued

REPRESENTATIVE COMPOUNDS

| Structure | Cpd. No. |
|---|---|
| 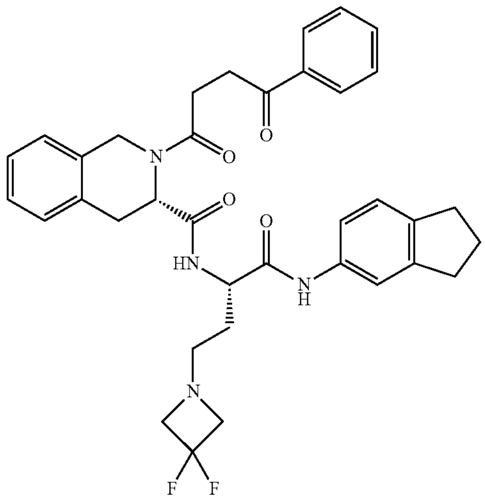 [SMILES: O=C(CCC(=O)N1Cc2ccccc2C[C@H]1C(=O)N[C@@H](CCN1CC(F)(F)C1)C(=O)Nc1ccc2c(c1)CCC2)c1ccccc1] | 23-6 |
| 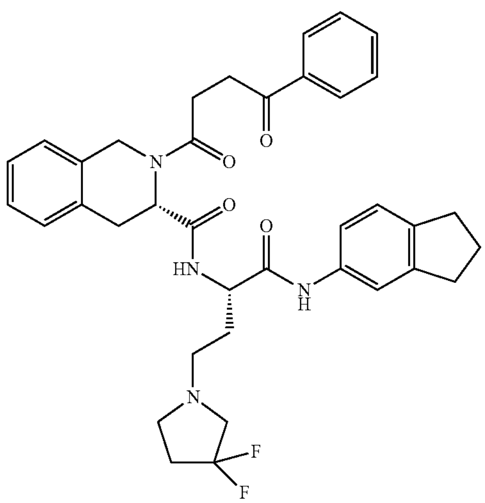 [SMILES: O=C(CCC(=O)N1Cc2ccccc2C[C@H]1C(=O)N[C@@H](CCN1CCC(F)(F)C1)C(=O)Nc1ccc2c(c1)CCC2)c1ccccc1] | 23-7 |
| 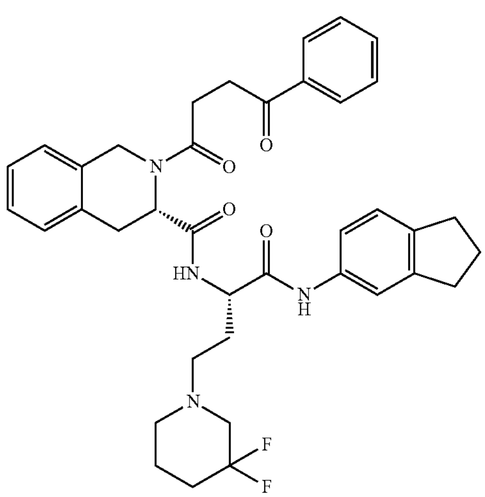 [SMILES: O=C(CCC(=O)N1Cc2ccccc2C[C@H]1C(=O)N[C@@H](CCN1CCCC(F)(F)C1)C(=O)Nc1ccc2c(c1)CCC2)c1ccccc1] | 23-8 |

TABLE A-continued
REPRESENTATIVE COMPOUNDS
| Structure | Cpd. No. |
|---|---|
| 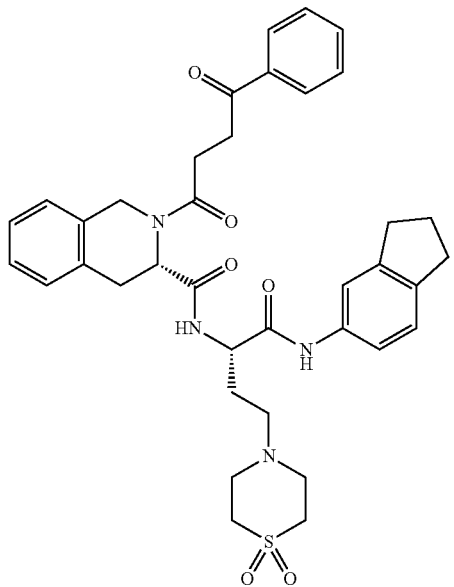 [SMILES: O=C(CCC(=O)N1Cc2ccccc2C[C@H]1C(=O)N[C@@H](CCN1CCS(=O)(=O)CC1)C(=O)Nc1ccc2c(c1)CCC2)c1ccccc1] | 23-9 |
| 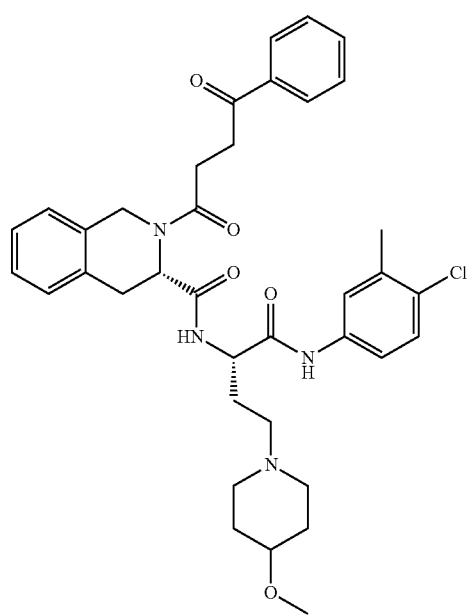 [SMILES: COC1CCN(CC[C@H](NC(=O)[C@@H]2Cc3ccccc3CN2C(=O)CCC(=O)c2ccccc2)C(=O)Nc2ccc(Cl)c(C)c2)CC1] | 24-1 |

TABLE A-continued
REPRESENTATIVE COMPOUNDS
| Structure | Cpd. No. |
|---|---|
| 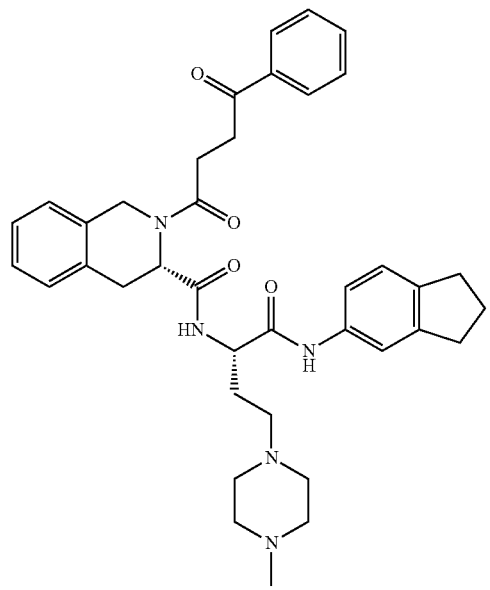 [SMILES: CN1CCN(CC[C@H](NC(=O)[C@@H]2Cc3ccccc3CN2C(=O)CCC(=O)c2ccccc2)C(=O)Nc2ccc3c(c2)CCC3)CC1] | 24-2 |
| 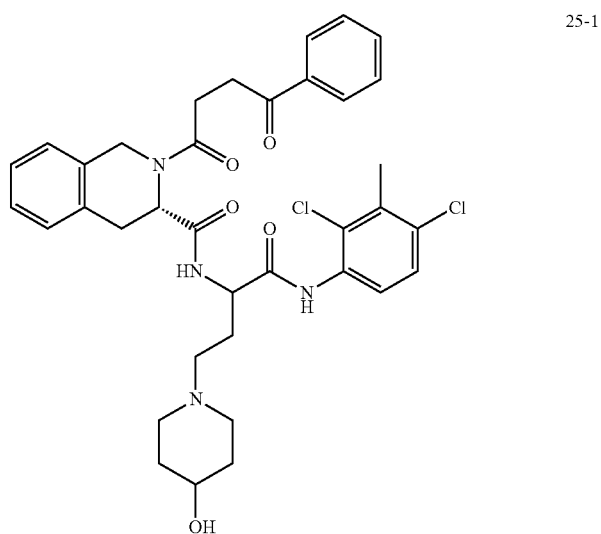 | 25-1 |

TABLE A-continued
REPRESENTATIVE COMPOUNDS
| Structure | Cpd. No. |
|---|---|
| 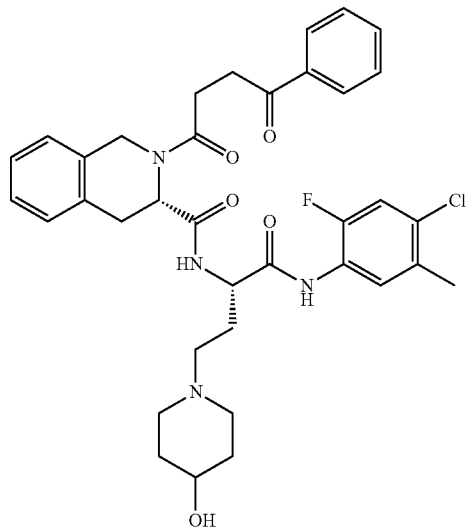 [SMILES: Cc1cc(NC(=O)[C@H](CCN2CCC(O)CC2)NC(=O)[C@@H]2Cc3ccccc3CN2C(=O)CCC(=O)c2ccccc2)c(F)cc1Cl] | 25-2 |
| 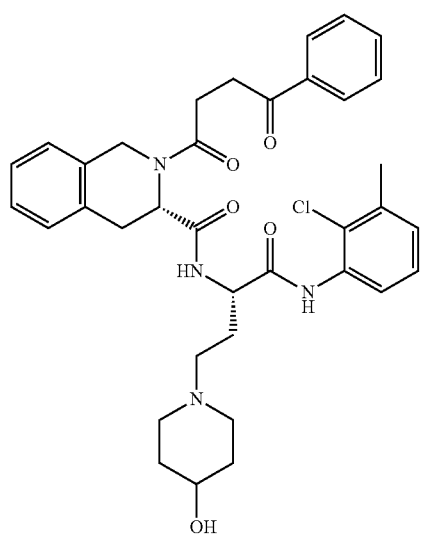 [SMILES: Cc1cccc(NC(=O)[C@H](CCN2CCC(O)CC2)NC(=O)[C@@H]2Cc3ccccc3CN2C(=O)CCC(=O)c2ccccc2)c1Cl] | 25-3 |

TABLE A-continued
REPRESENTATIVE COMPOUNDS
| Structure | Cpd. No. |
|---|---|
| 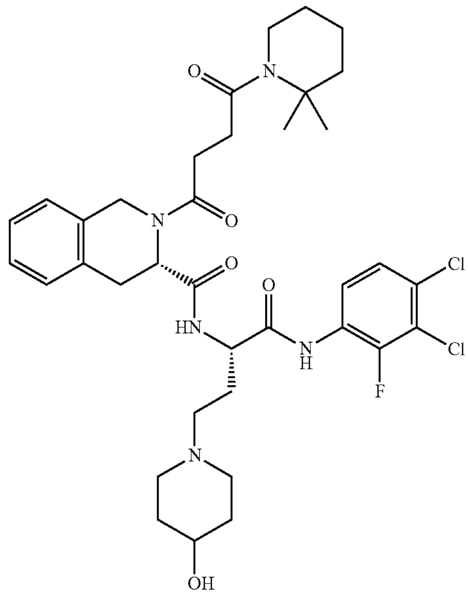 [SMILES: CC1(C)CCCCN1C(=O)CCC(=O)N1Cc2ccccc2C[C@H]1C(=O)N[C@@H](CCN1CCC(O)CC1)C(=O)Nc1ccc(Cl)c(Cl)c1F] | 26-1 |
| 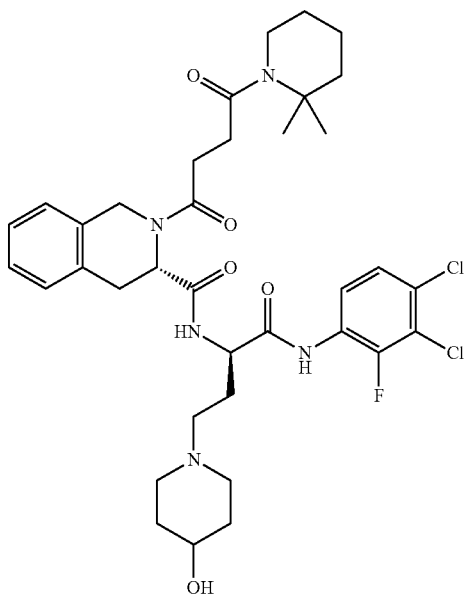 [SMILES: CC1(C)CCCCN1C(=O)CCC(=O)N1Cc2ccccc2C[C@H]1C(=O)N[C@H](CCN1CCC(O)CC1)C(=O)Nc1ccc(Cl)c(Cl)c1F] | 26-2 |

TABLE A-continued
REPRESENTATIVE COMPOUNDS
| Structure | Cpd. No. |
|---|---|
| 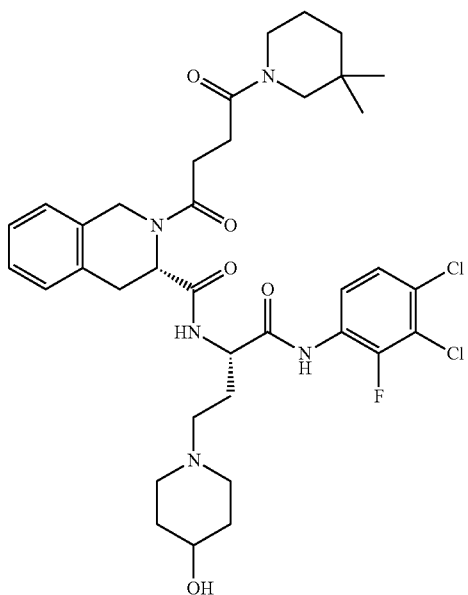 [SMILES: CC1(C)CCCN(C(=O)CCC(=O)N2Cc3ccccc3C[C@H]2C(=O)N[C@@H](CCN2CCC(O)CC2)C(=O)Nc2ccc(Cl)c(Cl)c2F)C1] | 26-3 |
| 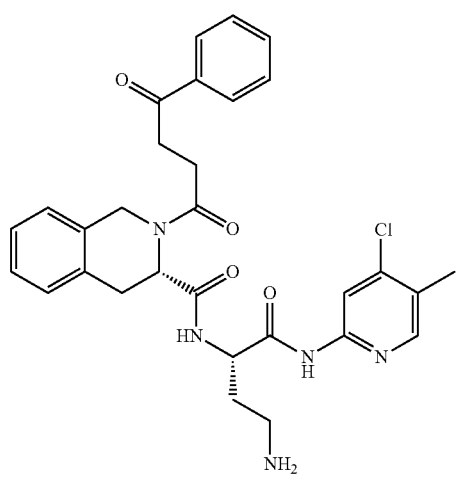 [SMILES: Cc1cnc(NC(=O)[C@H](CCN)NC(=O)[C@@H]2Cc3ccccc3CN2C(=O)CCC(=O)c2ccccc2)cc1Cl] | 27-1 |
| 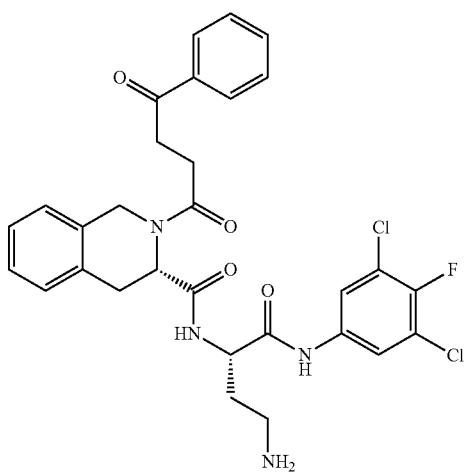 [SMILES: NCC[C@H](NC(=O)[C@@H]1Cc2ccccc2CN1C(=O)CCC(=O)c1ccccc1)C(=O)Nc1cc(Cl)c(F)c(Cl)c1] | 27-2 |

TABLE A-continued

REPRESENTATIVE COMPOUNDS

| Structure | Cpd. No. |
|---|---|
| 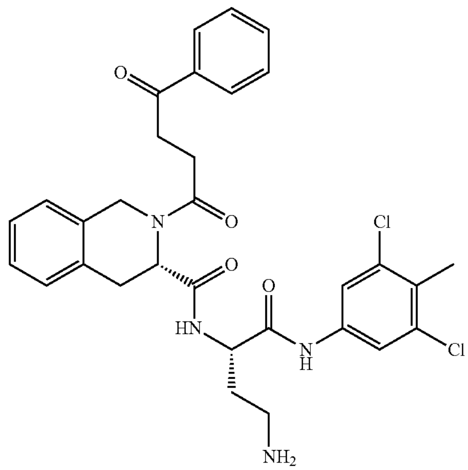 [SMILES: Cc1c(Cl)cc(NC(=O)[C@H](CCN)NC(=O)[C@@H]2Cc3ccccc3CN2C(=O)CCC(=O)c2ccccc2)cc1Cl] | 27-3 |
| 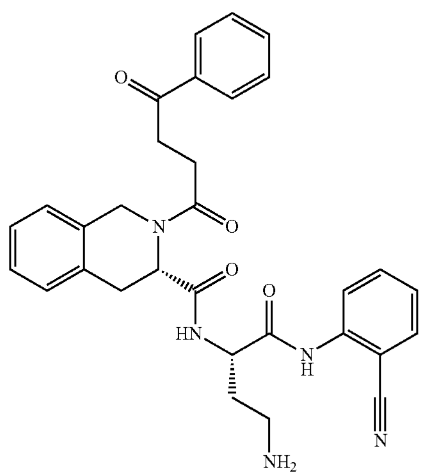 [SMILES: N#Cc1ccccc1NC(=O)[C@H](CCN)NC(=O)[C@@H]1Cc2ccccc2CN1C(=O)CCC(=O)c1ccccc1] | 27-4 |
| 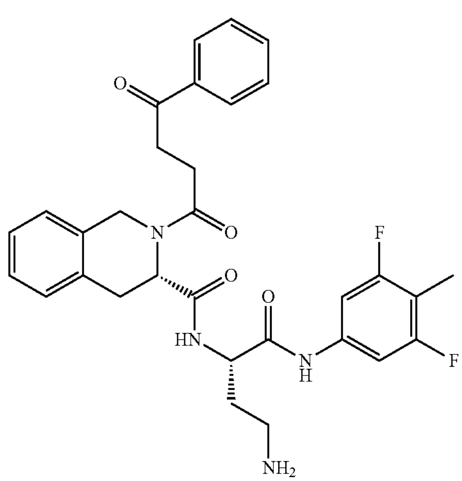 [SMILES: Cc1c(F)cc(NC(=O)[C@H](CCN)NC(=O)[C@@H]2Cc3ccccc3CN2C(=O)CCC(=O)c2ccccc2)cc1F] | 27-5 |

TABLE A-continued
REPRESENTATIVE COMPOUNDS
| Structure | Cpd. No. |
|---|---|
| 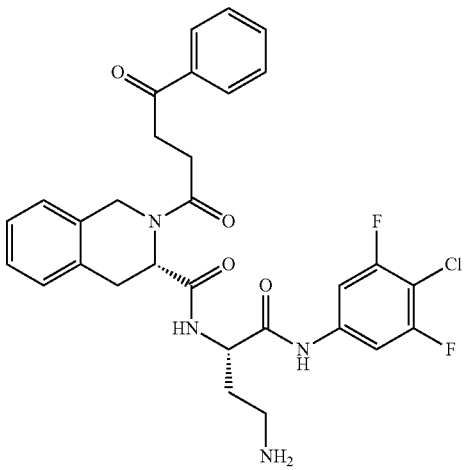 [SMILES: NCC[C@H](NC(=O)[C@@H]1Cc2ccccc2CN1C(=O)CCC(=O)c1ccccc1)C(=O)Nc1cc(F)c(Cl)c(F)c1] | 27-6 |
| 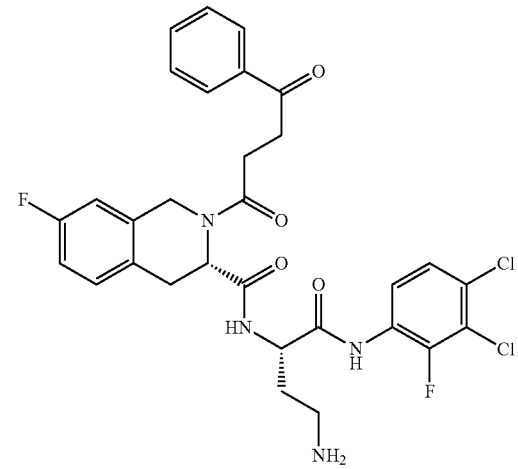 [SMILES: NCC[C@H](NC(=O)[C@@H]1Cc2ccc(F)cc2CN1C(=O)CCC(=O)c1ccccc1)C(=O)Nc1ccc(Cl)c(Cl)c1F] | 27-7 |
| 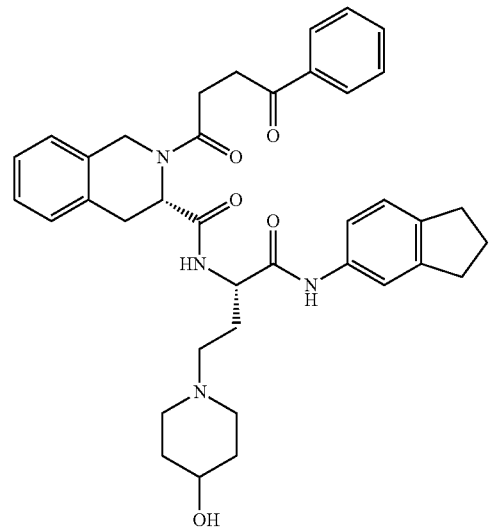 [SMILES: O=C(CCC(=O)N1Cc2ccccc2C[C@H]1C(=O)N[C@@H](CCN1CCC(O)CC1)C(=O)Nc1ccc2c(c1)CCC2)c1ccccc1] | 28-1 |

TABLE A-continued

REPRESENTATIVE COMPOUNDS

| Structure | Cpd. No. |
|---|---|
| 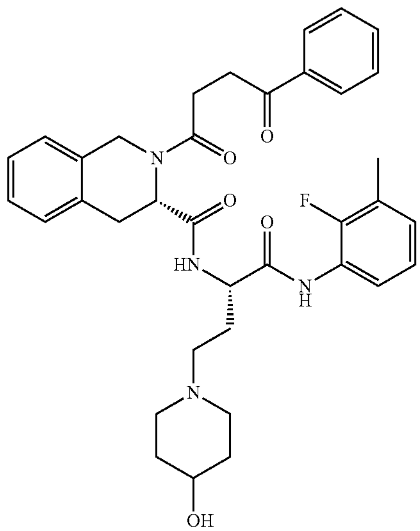 [SMILES: Cc1cccc(NC(=O)[C@H](CCN2CCC(O)CC2)NC(=O)[C@@H]2Cc3ccccc3CN2C(=O)CCC(=O)c2ccccc2)c1F] | 28-2 |
| 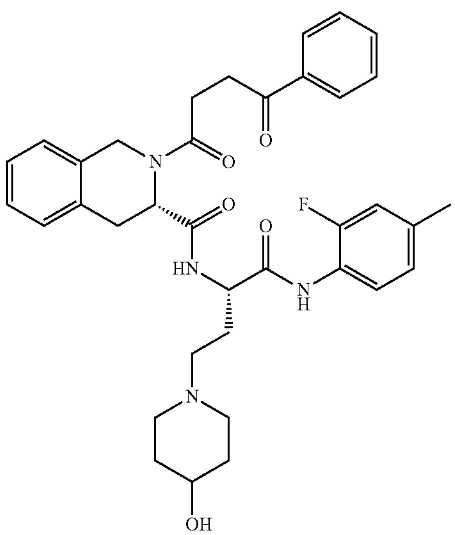 [SMILES: Cc1ccc(NC(=O)[C@H](CCN2CCC(O)CC2)NC(=O)[C@@H]2Cc3ccccc3CN2C(=O)CCC(=O)c2ccccc2)c(F)c1] | 28-3 |
| 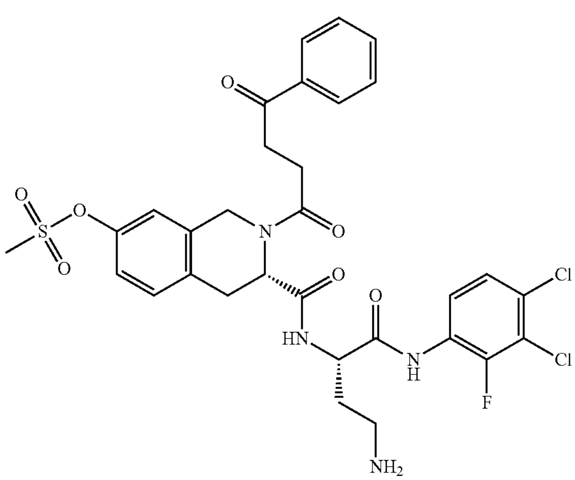 [SMILES: CS(=O)(=O)Oc1ccc2c(c1)CN(C(=O)CCC(=O)c1ccccc1)[C@H](C(=O)N[C@@H](CCN)C(=O)Nc1ccc(Cl)c(Cl)c1F)C2] | 29-1 |

TABLE A-continued

REPRESENTATIVE COMPOUNDS

| Structure | Cpd. No. |
|---|---|
| 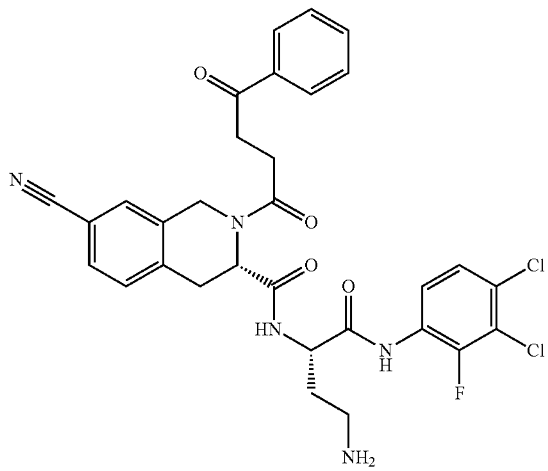 [SMILES: N#Cc1ccc2c(c1)CN(C(=O)CCC(=O)c1ccccc1)[C@H](C(=O)N[C@@H](CCN)C(=O)Nc1ccc(Cl)c(Cl)c1F)C2] | 30-1 |
| 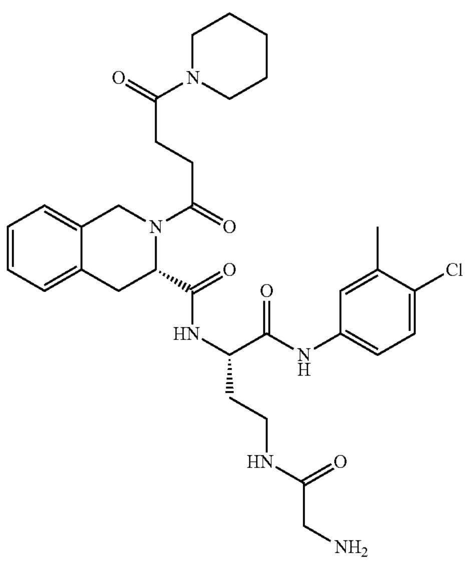 [SMILES: Cc1cc(NC(=O)[C@H](CCNC(=O)CN)NC(=O)[C@@H]2Cc3ccccc3CN2C(=O)CCC(=O)N2CCCCC2)ccc1Cl] | 31-1 |
| 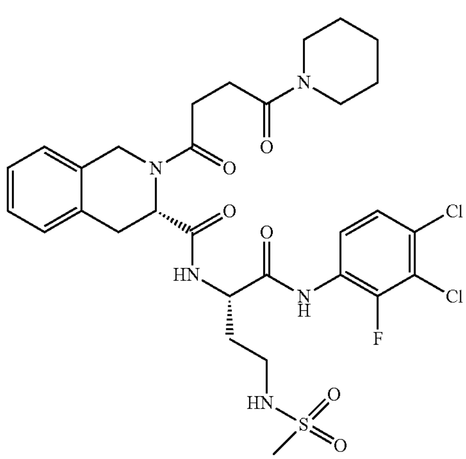 [SMILES: CS(=O)(=O)NCC[C@H](NC(=O)[C@@H]1Cc2ccccc2CN1C(=O)CCC(=O)N1CCCCC1)C(=O)Nc1ccc(Cl)c(Cl)c1F] | 32-1 |

TABLE A-continued

REPRESENTATIVE COMPOUNDS

| Structure | Cpd. No. |
|---|---|
| 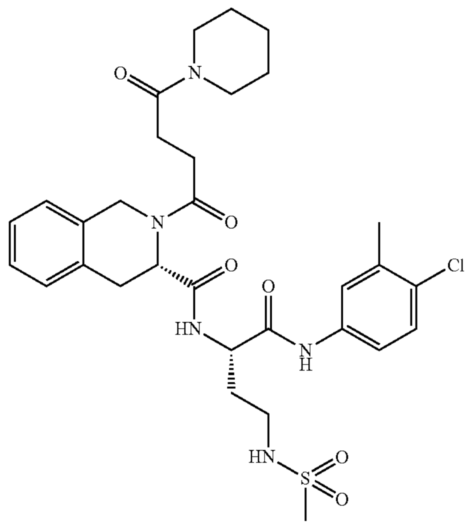 [SMILES: Cc1cc(NC(=O)[C@H](CCNS(C)(=O)=O)NC(=O)[C@@H]2Cc3ccccc3CN2C(=O)CCC(=O)N2CCCCC2)ccc1Cl] | 32-2 |
| 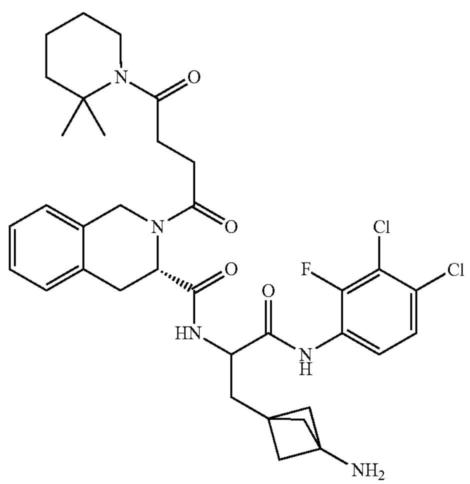 [SMILES: CC1(C)CCCCN1C(=O)CCC(=O)N1Cc2ccccc2C[C@H]1C(=O)NC(CC12CC(N)(C1)C2)C(=O)Nc1ccc(Cl)c(Cl)c1F] | 33-1 |
| 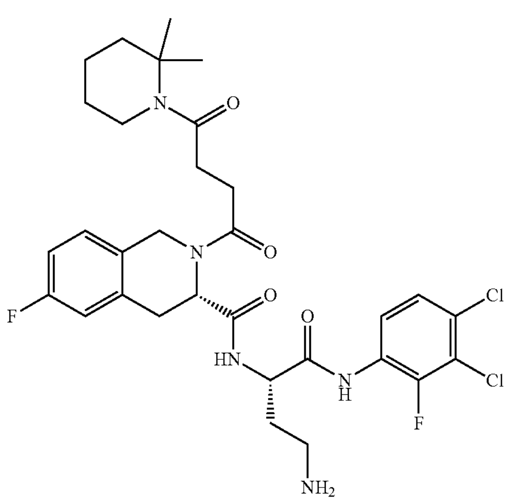 [SMILES: CC1(C)CCCCN1C(=O)CCC(=O)N1Cc2ccc(F)cc2C[C@H]1C(=O)N[C@@H](CCN)C(=O)Nc1ccc(Cl)c(Cl)c1F] | 34-1 |

TABLE A-continued
REPRESENTATIVE COMPOUNDS
| Structure | Cpd. No. |
|---|---|
| 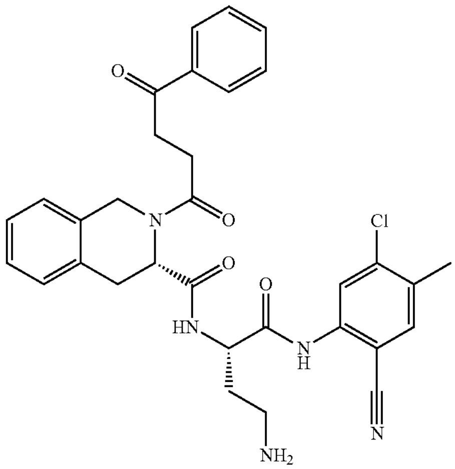 [SMILES: Cc1cc(C#N)c(NC(=O)[C@H](CCN)NC(=O)[C@@H]2Cc3ccccc3CN2C(=O)CCC(=O)c2ccccc2)cc1Cl] | 35-2 |
| 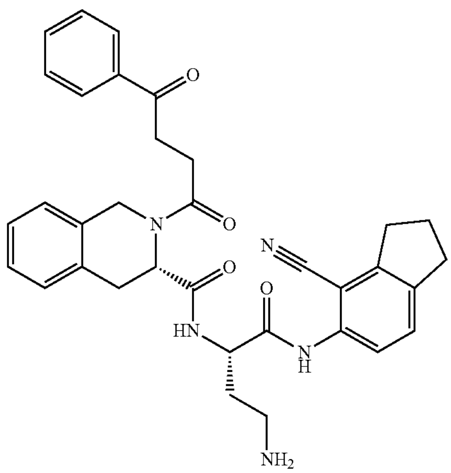 [SMILES: N#Cc1c(NC(=O)[C@H](CCN)NC(=O)[C@@H]2Cc3ccccc3CN2C(=O)CCC(=O)c2ccccc2)ccc2c1CCC2] | 35-1 |
In one embodiment, compounds are provided having the structure of the following Formula I, including stereoisomers, hydrates, solvates, isotopes or pharmaceutically acceptable salts thereof:
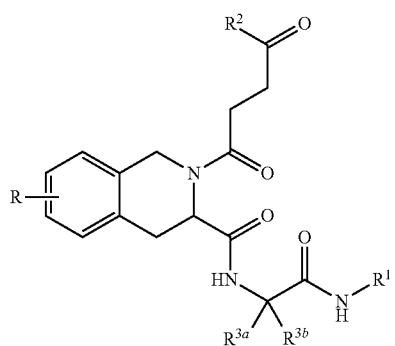 I
wherein:
R is H;
$R^1$ is
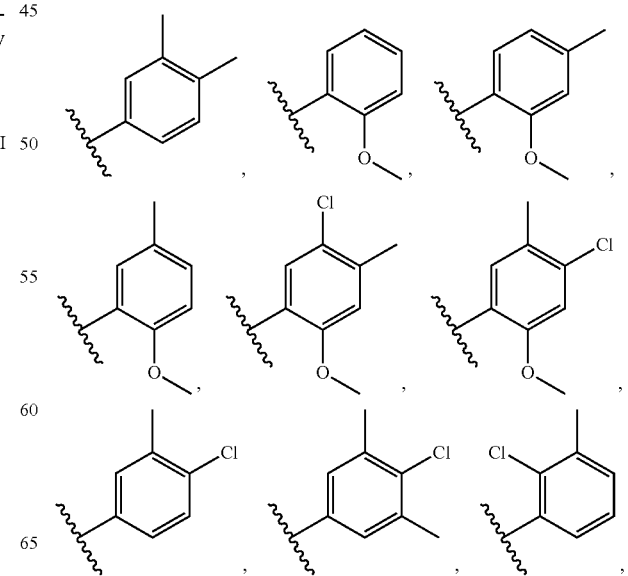

-continued

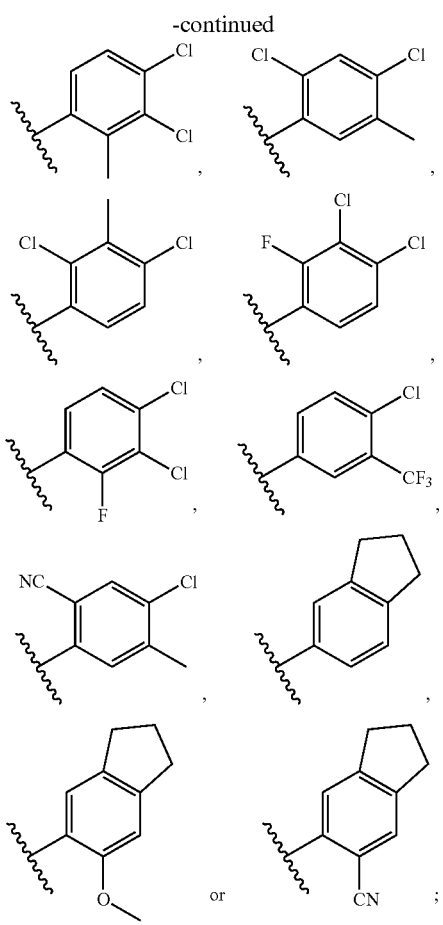

R² is

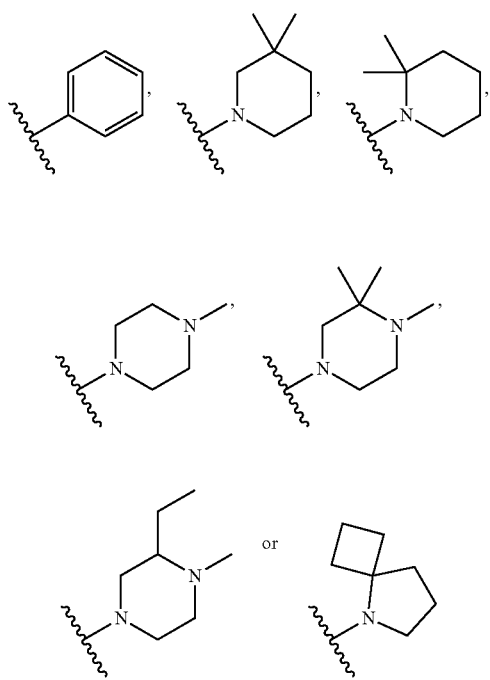

and
R³ᵃ is hydrogen and R³ᵇ is

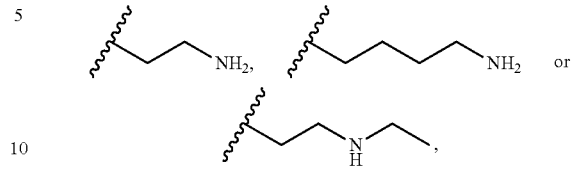

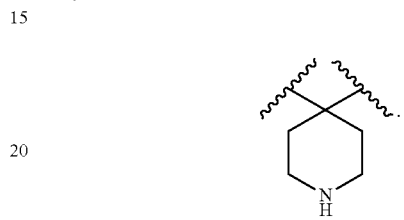

or R³ᵃ and R³ᵇ taken together with the carbon to which they are attached is

In another embodiment, a compound is provided as listed in the following Table B.

TABLE B

REPRESENTATIVE COMPOUNDS

| | | | | |
|---|---|---|---|---|
| 1-14 | 1-18 | 1-29 | 1-35 | 1-36 |
| 1-37 | 1-38 | 1-39 | 2-2 | 2-15 |
| 2-22 | 2-24 | 2-25 | 2-39 | 2-57 |
| 4-12 | 4-14 | 8-4 | 10-3 | 12-73 |
| 12-88 | 12-104 | 12-131 | 12-136 | 13-1 |
| 14-3 | 14-6 | 14-18 | 15-3 | 15-6 |
| 18-1 | | | | |

As used herein, "individual" (as in the subject or patient of the treatment) means both mammals and non-mammals. Mammals include, for example, humans; non-human primates, e.g., apes and monkeys; cattle; horses; sheep; and goats. Non-mammals include, for example, fish and birds.

A "receptor", as is well known in the art, is a biomolecular entity usually comprising a protein that specifically binds a structural class of ligands or a single native ligand in a living organism, the binding of which causes the receptor to transduce the binding signal into another kind of biological action, such as signaling a cell that a binding event has occurred, which causes the cell to alter its function in some manner. Any molecule, naturally occurring or not, that binds to a receptor and activates it for signal transduction, is referred to as an "agonist" or "activator." Any molecule, naturally occurring or not, that binds to a receptor, but does not cause signal transduction to occur, and which can block the binding of an agonist and its consequent signal transduction, is referred to as an "antagonist." Certain molecules bind to receptors at locations other than the binding sites of their natural ligands and such allosteric binding molecules may potentiate, activate or agonize the receptor and may enhance the effect of a natural ligand or a co-administered ligand.

A "CXCR3 compound" or "CXCR3 agonist" or "CXCR3 activator" or "CXCR3 modulator" or "CXCR3 antagonist" or "CXCR3 potentiator" or "CXCR3 modulator" as the terms are used herein refer to compounds that interact in some way with the CXCR3 receptor. They can be agonists, potentiators, or activators, or they can be antagonists or inhibitors, and can be selective for action of the CXCR3 receptor family.

The term "disease" or "disorder" or "malcondition" are used interchangeably, and are used to refer to diseases or conditions wherein a CXCR3 receptor plays a role in the biochemical mechanisms involved in the disease or malcondition or symptom(s) thereof such that a therapeutically beneficial effect can be achieved by acting on a CXCR3 receptor.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder.

The expression "effective amount", when used to describe use of a compound of the invention in providing therapy to a patient suffering from a disorder or malcondition mediated by a CXCR3 receptor refers to the amount of a compound of the invention that is effective to bind to as an agonist or as an antagonist a CXCR3 receptor in the individual's tissues, wherein the CXCR3 is implicated in the disorder, wherein such binding occurs to an extent sufficient to produce a beneficial therapeutic effect on the patient. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result by acting as an agonist of CXCR3 activity. A therapeutically effective amount is also one in which any toxic or detrimental effects of compounds of the invention are outweighed by the therapeutically beneficial effects. For example, in the context of treating a malcondition mediated by activation of a CXCR3 receptor, a therapeutically effective amount of a CXCR3 receptor antagonist of the invention is an amount sufficient to control the malcondition, to mitigate the progress of the malcondition, or to relieve the symptoms of the malcondition.

In the following disclosure, reference to "a compound of Formula I" is intended to include the more specific embodiment of Formulas II-XII, as well as the compounds listed in the above Tables A and B.

In certain embodiments, a pharmaceutical composition is provided comprising a compound of Formula I together with at least one pharmaceutically acceptable carrier, diluent or excipient.

In certain embodiments, a method is provided for activating, potentiating, or agonizing (i.e., to have an agonic effect, to act as an agonist) a CXCR3 receptor, with a compound of Formula I. The method involves contacting the receptor with a suitable concentration of a compound of Formula I to bring about activation of the receptor. The contacting can take place in vitro, for example in carrying out an assay to determine the CXCR3 receptor activation activity of a compound undergoing experimentation related to a submission for regulatory approval.

In certain embodiments, the method for activating a CXCR3 receptor can be carried out in vivo; that is, within the living body of a mammal, such as a human patient or a test animal. The compound of Formula I can be supplied to the living organism via a suitable route (e.g., orally), or can be provided locally within the body tissues.

In one embodiment, a method is provided for treatment of a disease or condition in a subject or patient for which activation of a CXCR3 receptor is medically indicated, wherein the subject or patient is administered a therapeutically effective amount of a compound of Formula I.

In one embodiment, a method is provided for treating or preventing a disease or condition comprising administering a pharmaceutical composition comprising a compound of Formula I together with at least one pharmaceutically acceptable carrier, diluent or excipient to a subject or patient in need thereof.

In more specific embodiments, the subject or patient is afflicted with, or at risk of developing, rheumatoid arthritis, multiple sclerosis, or inflammatory bowel disease.

In certain embodiments, use of a compound of Formula I is provided for preparation of a medicament.

In certain embodiments, methods are provided for synthesis of compounds of Formula I, including compounds of the invention as more fully illustrated herein. In certain other embodiments, the invention provides certain intermediate compounds associated with such methods of synthesis as illustrated herein.

EXAMPLES

The invention is further illustrated by the following examples. The examples below are non-limiting and are merely representative of various aspects of the invention. Solid and dotted wedges within the structures herein disclosed illustrate relative stereochemistry, with absolute stereochemistry depicted only when specifically stated or delineated.

General Methods
  NMR Spectra
  $^1$H NMR (400 MHz) and $^{13}$C NMR (100 MHz) were obtained in solution of deuterochloroform (CDCl$_3$) or dimethyl sulfoxide (d$_6$-DMSO). NMR spectra were processed using MestReNova 6.0.3-5604.
  LCMS Data
  Mass spectra (LCMS) were obtained using one of 2 systems. System 1: Agilent 1100 HPLC system equipped with a Agilent Eclipse XDB-C18, 3.5µ (4.6×150 mm) column using water with 0.05% TFA as the mobile phase A, and acetonitrile with 0.05% TFA as the mobile phase B with a flow rate of 1 mL/min. Method 1: 5% B (95% A) to 95% B over 12 min then held at 95% B for 3 min and to 5% B over 1 min. Method 2: 50% B (50% A) to 95% B over 4 min then held at 95% B for 4 min and to 50% B over 0.1 min. System 2: Agilent 1100/6110 HPLC system equipped with a Agilent Poroshell 120 EC-C8, 2.7μ (50×3 mm) column using water with 5 mM ammonium acetate as the mobile phase C, and acetonitrile with 5 mM ammonium acetate as the mobile phase D with a flow rate of 1 mL/min. Method 3: 5% D (95% C) to 95% D over 12 min then held at 95% D for 2.8 min and then to 5% D over 0.2 min. Agilent 1260 LCMS equipped with a Waters Sect CSH C18 3.5 μm (4.6×50 mm) column using water with 0.1% formic acid as mobile phase A and acetonitrile with 0.1% formic acid as mobile phase B. Method 4: The gradient was 5-95% mobile phase B over 3.0 min with a flow rate of 2.5 mL/min, then held at 95% for 0.6 min with an flow rate of 4.5 mL/min. Method 5: The gradient was 5-95% mobile phase B over 13.0 min with a flow rate of 2.5 mL/min, then held at 95% for 1.0 min with a flow rate of 4.5 mL/min.

Reaction Conditions and Abbreviations

Pyridine, dichloromethane (DCM), tetrahydrofuran (THF), and toluene used in the procedures were from Aldrich Sure-Seal bottles or Acros AcroSeal dry solvent and kept under nitrogen ($N_2$). All reactions were stirred magnetically and temperatures are external reaction temperatures. The following abbreviations are used: ammonia ($NH_3$), tetrahydrofuran (THF), hydrochloric acid (HCl), sodium bicarbonate ($NaHCO_3$), dichloroethane (DCE), trifluoroacetic acid (TFA), magnesium sulfate ($MgSO_4$), hydrogen ($H_2$), tetrabutylammonium fluoride (TBAF), diazabicycloundecene (DBU), methyl tert-butyl ether (MTBE), nitric acid ($HNO_3$), ethyl acetate (EA), 1-methy-2-pyrrolidinone (NMP), triethylamine (TEA), 1-[Bis(dimethylamino)methylene]-1H-1,2,3-triazolo[4,5-b]pyridinium 3-oxid hexafluorophosphate (HATU), N-hydroxybenzotriazole (HOBt), 1-ethyl-3-(3-dimethylaminopropyl) carbodiimide hydrochloride (EDC), N,N-dimethylformamide (DMF), dimethyl acetamide (DMA), di-tert-butyl dicarbonate ($Boc_2O$), N,N-diisopropylethylamine (DIEA), acetic acid (AcOH), hydrochloric acid (HCl), O-(7-azabenzotriazol-1-yl)-N,N,N',N'-tetramethyluronium hexafluorophosphate (HATU), 4-dimethylaminopyridine (DMAP), tert-butanol (t-BuOH), sodium hydride (NaH), sodium triacetoxyborohydride ($Na(OAc)_3BH$), ethanol (EtOH), methanol (MeOH), sodium sulfate ($Na_2SO_4$), dichloromethane (DCM), acetonitrile (ACN), water ($H_2O$), room temperature (rt), hour (h), minute (min) and silica gel ($SiO_2$).

Purifications

Chromatographies were carried out using a Combiflash Rf flash purification system (Teledyne Isco) equipped with Redisep (Teledyne Isco), Telos (Kinesis) or GraceResolv (Grace Davison Discovery Sciences) silica gel ($SiO_2$) or RediSep Rf Gold C18 column. Preparative HPLC purifications were performed using one of two systems. System 1: Dionex Ultimate 3000 system equipped with an Waters-Sunfire Prep-C18, OBD, 5 μm (30×150 mm) column using water containing 0.1% formic acid as mobile phase A and methanol with 0.1% formic acid as mobile phase B. The gradient was 10% mobile phase B held for 2 min, then, 10-95% mobile phase B over 13 min, held at 95% for 7 min, and then returned to 10% over 0.1 min with a flow rate of 10 mL/min. Fractions were collected by UV detection at 254 nm. System 2: Waters X-Select CSH C18, 5 μm, 19×50 mm or Waters X-Bridge BEH C18, 5 μm, 19×50 mm column using either a gradient of 0.1% formic acid in MeCN and 0.1% aqueous formic acid, or a gradient of MeCN and 10 mM ammonium bicarbonate (aq). Fractions were collected following detection by either UV at a single wavelength measured by a variable wavelength detector on a Gilson 215 or by mass ion and UV detection at a single wavelength measured by a ZQ single quadropole mass spectrometer, with positive and negative ion electrospray, and dual wavelength detection on a Waters FractionLynx LCMS. System 3: Waters Fractionlynx system equipped with an Agilent Prep-C18, 5 μm (21.2×50 mm) column using water containing 0.1% formic acid as mobile phase A, and acetonitrile with 0.1% formic acid as mobile phase B. The gradient was 20-95% mobile phase B over 12 min, held at 95% for 4 min, and then returned to 20% over 1.5 min with a flow rate of 28 mL/min. Fractions were collected by UV detection at 254 nm or by mass and concentrated using a Genevac EZ-2.

Synthetic Methods for Preparing Compounds

Molecular embodiments of the present invention can be synthesized using standard synthetic techniques known to those of skill in the art. Compounds of the present invention can be synthesized using the general synthetic procedures set forth in Schemes 1-22.

Scheme 1

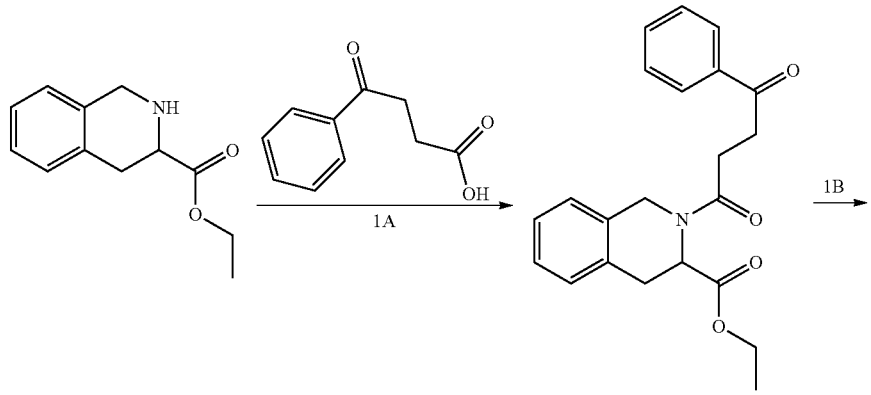

393    394
-continued
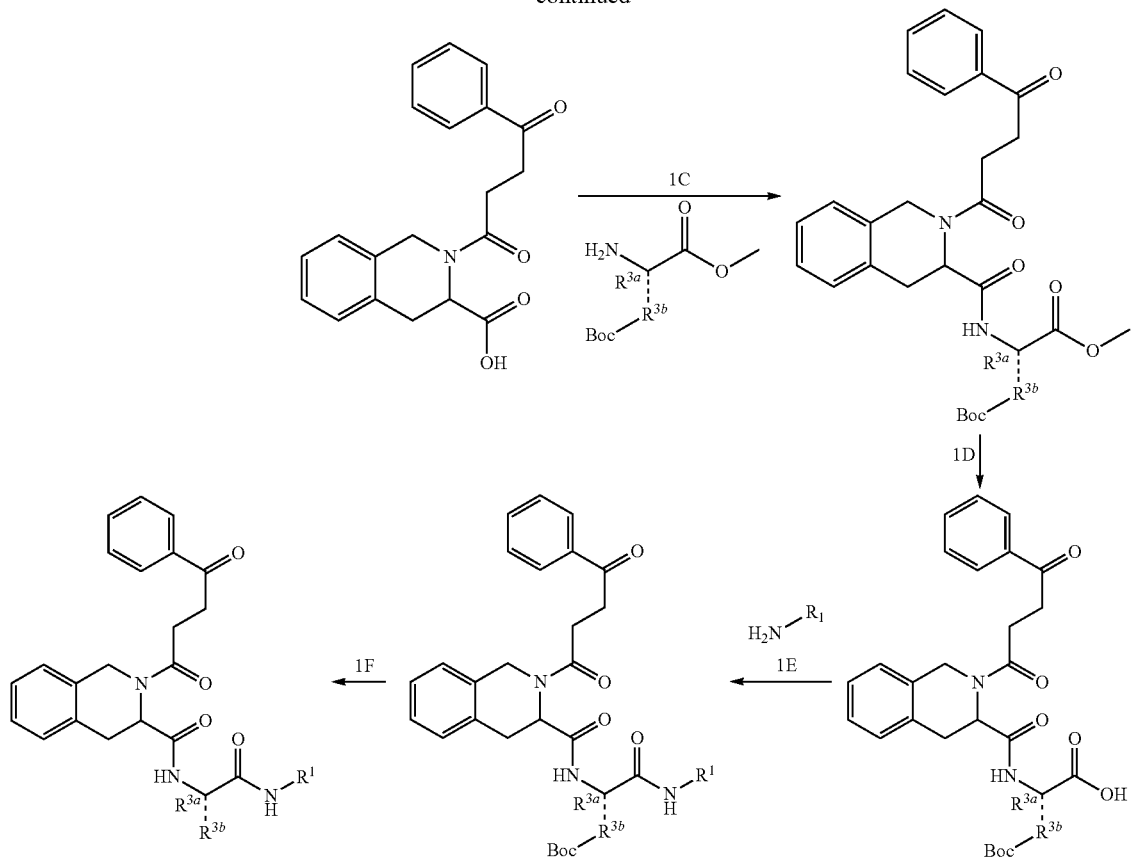
Example 1
Synthesis of (S)—S—((S)-6-amino-1-((3,4-dichlorophenyl)amino)-1-oxohexan-2-yl)-2-(4-oxo-4-phenylbutanoyl)-1,2,3,4-tetrahydroisoquinoline-3-carboxamide (Compound 1-1)
1-1
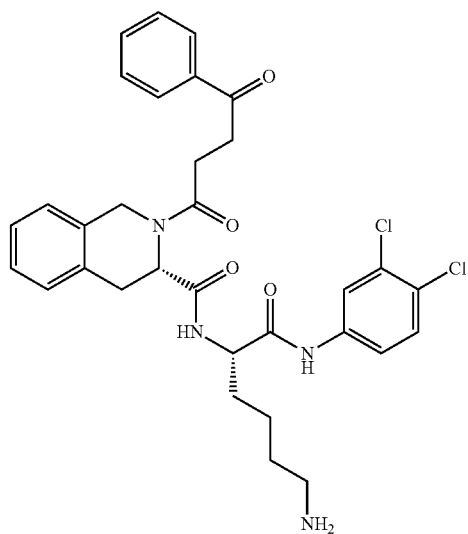

Step 1A: Ethyl (S)-2-(4-oxo-4-phenylbutanoyl)-1,2,3,4-tetrahydroisoquinoline-3-carboxylate (Intermediate 1A)

Step 1B: (S)-2-(4-oxo-4-phenylbutanoyl)-1,2,3,4-tetrahydroisoquinoline-3-carboxylic Acid (Intermediate 1B)

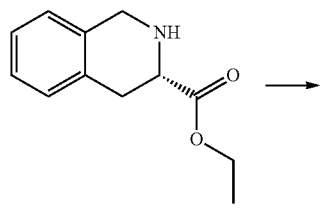 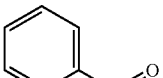

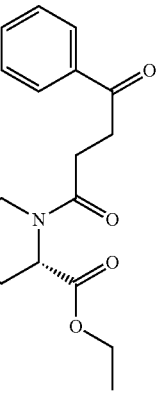

1A

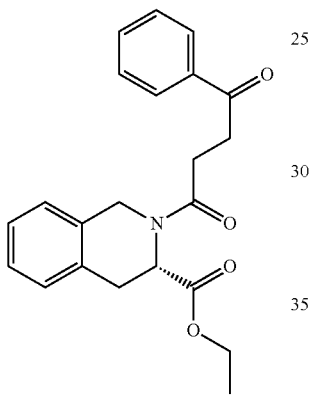

1A

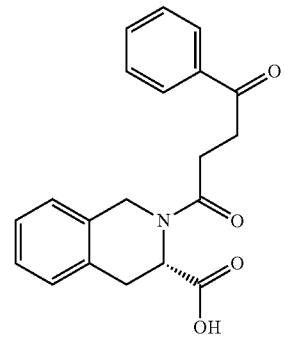

1B

A stirring solution of THF (100 mL) and DMF (20 mL) containing ethyl (S)-1,2,3,4-tetrahydroisoquinoline-3-carboxylate HCl (4.5 g, 18.5 mmol), 4-oxo-4-phenylbutanoic acid (3.0 g, 16.8 mmol) and DIEA (20.3 mmol, 58.9 mmol) in THF (100 mL) and DMF (20 mL) was cooled to 0° C. HATU (6.7 g, 17.7 mmol) was added over 5 min and the reaction mixture was warmed to rt and stirred for 2 h. The mixture was diluted with EA and washed with NaHCO$_3$ (sat. aqueous). The aqueous fraction was back-extracted with EA and the combined organic fractions were dried over Na$_2$SO$_4$ and purified by column chromatography (EA/Hexane) to provide Intermediate 1A. Yield 4.9 g (81%). LCMS (m/z) calculated for C$_{22}$H$_{23}$NO$_4$: 365.2; found 366 [M+H]$^+$, t$_R$=6.43 min (Method 1).

Into a mixture of Intermediate 1A (7.7 g, 20.5 mmol) in THF (40 mL) and water (10 mL) was added 1.0M LiOH (24.6 mL, 24.6 mmol). The reaction mixture was stirred overnight at rt, then diluted with water. The THF was removed in vacuo. The aqueous layer was washed with ether, acidified with 1N HCl and extracted with EA. The EA layers were dried (Na$_2$SO$_4$) and concentrated to provide Intermediate 1B (5.8 g, 82%). LCMS (m/z) calculated for C$_{20}$H$_{19}$NO$_4$: 337.1; found 338.0 [M+H]$^+$, t$_R$=10.78 min (Method 1).

Step 1C: Methyl N⁶-(tert-butoxycarbonyl)-N²—((S)-2-(4-oxo-4-phenylbutanoyl)-1,2,3,4-tetrahydroisoquinoline-3-carbonyl)-L-lysinate (Intermediate 1C)

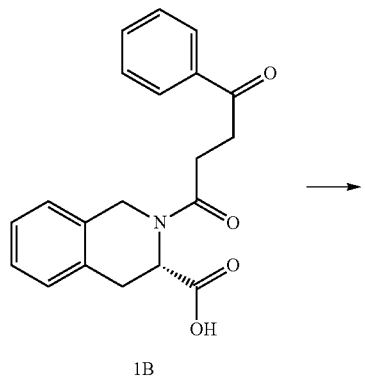

1B

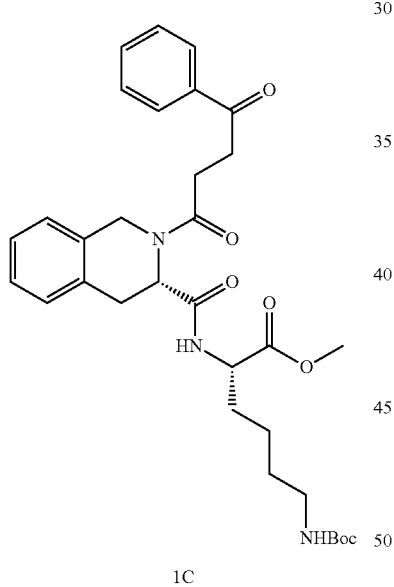

1C

Step 1D: N⁶-(tert-butoxycarbonyl)-N²—((S)-2-(4-oxo-4-phenylbutanoyl)-1,2,3,4-tetrahydroisoquinoline-3-carbonyl)-L-lysine (Intermediate 1D)

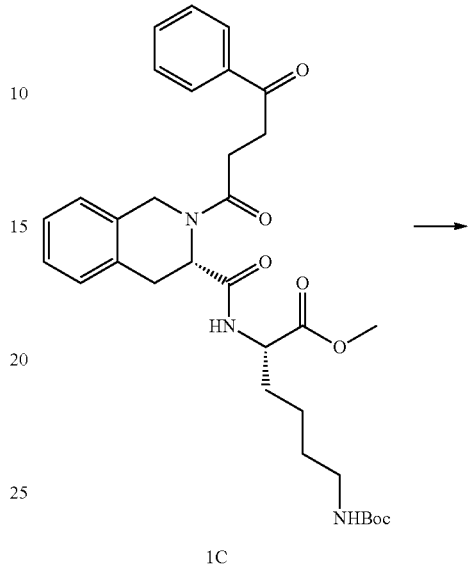

1C

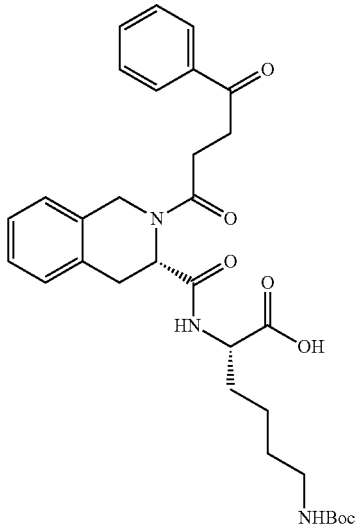

1D

A stirring solution of Intermediate 1B (1.2 g, 3.6 mmol), H-lys(Boc)OMe HCl (1.0 g, 3.4 mmol) and DIEA (2.05 mL, 11.8 mmol) in THF (30 mL) was cooled to 0° C. A solution of HATU (1.3 g, 3.5 mmol) in THF (8 mL) was added dropwise over 5 min. The reaction mixture was warmed to rt and stirred for 2 h then diluted with EA and washed with NaHCO₃ (sat. aqueous) The aqueous fraction was back-extracted with EA. The combined organic fractions were dried (Na₂SO₄) then concentrated and purified by column chromatography (EA/hexane then MeOH/DCM) to provide Intermediate 1C (1.5 g, 76%). LCMS (m/z) calculated for $C_{32}H_{41}N_3O_7$: 579.3; found 580.0 [M+H]⁺, $t_R$=17 min (Method 1).

Into a mixture of Intermediate 1C (1.5 g, 2.6 mmol) in THF (25 mL) and H₂O (5 mL) was added 1.0M LiOH (3.1 mL, 3.1 mmol). The reaction mixture was stirred overnight at rt, then diluted with H₂O. The THF was removed in vacuo. The aqueous layer was washed with ether, acidified with 1N HCl and extracted with EA. The EA layers were dried (Na₂SO₄) and concentrated to provide Intermediate 1D (1.2 g, 79%). LCMS (m/z) calculated for $C_{31}H_{39}N_3O_7$: 565.3; found 566.0 [M+H]⁺, $t_R$=11.72 min (Method 1).

Step 1E: Tert-butyl ((S)-6-((3,4-dichlorophenyl)amino)-6-oxo-5-((S)-2-(4-oxo-4-phenylbutanoyl)-1,2,3,4-tetrahydroisoquinoline-3-carboxamido)hexyl) carbamate (Intermediate 1E)

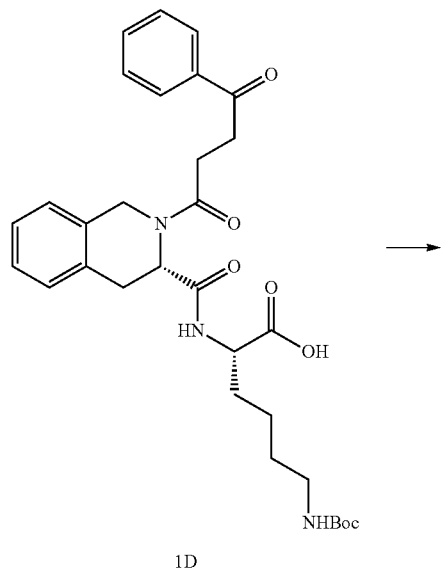

1D

Step 1F: (S)—N—((S)-6-amino-1-((3,4-dichlorophenyl)amino)-1-oxohexan-2-yl)-2-(4-oxo-4-phenylbutanoyl)-1,2,3,4-tetrahydroisoquinoline-3-carboxamide (Compound 1-1)

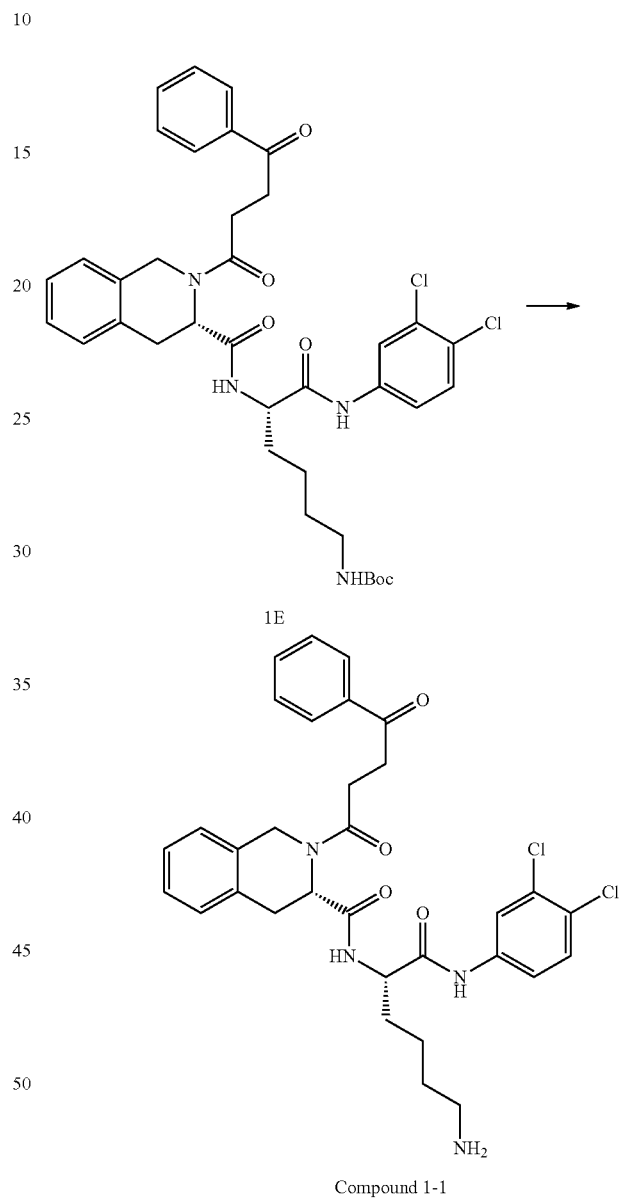

A stirring solution of Intermediate 1D (30 mg, 0.053 mmol), 3,4-dichloroaniline (8.2 mg, 0.05 mmol) and DIEA (0.023 mL, 0.13 mmol) in THF (5 mL) was cooled to 0° C. A solution of HATU (20 mg, 0.05 mmol) in THF (1 mL) was added dropwise over 5 min. The reaction mixture was warmed to rt, stirred for 2 h, then diluted with EA and washed with NaHCO₃ (sat.) The aqueous fraction was back-extracted with EA. The combined organic fractions were dried (Na₂SO₄) then purified by column chromatography (EA/hexane then MeOH/DCM) to provide Intermediate 1E (28 mg, 78%). LCMS (m/z) calculated for $C_{37}H_{42}Cl_2N_4O_6$: 708.3; found 609.0 [M-Boc]⁺, $t_R$=13.25 min (Method 1).

A solution of 4N HCl in dioxane (0.03 mL, 0.1 mmol) was added to Intermediate 1E (28 mg, 0.04 mmol) in DCM (0.5 mL). The reaction mixture was allowed to stir for 2 h at rt, then concentrated in vacuo and suspended in diethyl ether. The resulting precipitate was filtered, washed with diethyl ether, and dried to give Compound 1-1. LCMS (m/z) calculated for $C_{32}H_{34}Cl_2N_4O_4$: 608.2; found 609.2 [M+H]⁺, $t_R$=11.31 min (Method 1).

Following the procedures as set forth in Scheme 1 above, the compounds of the following Table 1 were prepared using the appropriate $R^1$, $R^{3a}$ and $R^{3b}$ reagents.

TABLE 1

| Cpd. No. | R¹ | R³ᵃ | R³ᵇ | R³ᵃ, R³ᵇ Stereo-chem. | MS Calc | MS Obs (MH)⁺ | LCMS Ret. (min) | Purity Method |
|---|---|---|---|---|---|---|---|---|
| 1-1 | 3,4-dichlorophenyl | H | (CH₂)₄NH₂ | S | 608.2 | 609.2 | 11.31 | 1 |
| 1-2 | 4-chlorophenyl | H | (CH₂)₄NH₂ | S | 574.2 | 575.0 | 10.70 | 1 |
| 1-3 | 4-methylphenyl | H | (CH₂)₄NH₂ | S | 554.3 | 555.5 | 10.42 | 1 |
| 1-5 | biphenyl | H | (CH₂)₄NH₂ | S | 616.3 | 617.3 | 11.28 | 1 |
| 1-6 | 2-methoxyphenyl | H | (CH₂)₄NH₂ | S | 570.3 | 571.9 | 10.15 | 1 |

TABLE 1-continued

| Cpd. No. | R¹ | R³ᵃ | R³ᵇ | R³ᵃ, R³ᵇ Stereo- chem. | MS Calc | MS Obs (MH)⁺ | LCMS Ret. (min) | Purity Method |
|---|---|---|---|---|---|---|---|---|
| 1-7 | 4-isopropylphenyl | H | (CH₂)₄NH₂ | S | 582.3 | 583.3 | 11.38 | 1 |
| 1-8 | 3-fluorophenyl | H | (CH₂)₄NH₂ | S | 558.3 | 559.3 | 10.29 | 1 |
| 1-9 | 3-chlorophenyl | H | (CH₂)₄NH₂ | S | 574.2 | 576.0 | 10.73 | 1 |
| 1-10 | 3-methylphenyl | H | (CH₂)₄NH₂ | S | 554.3 | 555.2 | 10.41 | 1 |
| 1-11 | 3-methoxyphenyl | H | (CH₂)₄NH₂ | S | 570.3 | 571.3 | 10.27 | 1 |

TABLE 1-continued
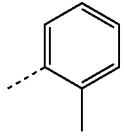
| Cpd. No. | R¹ | R³ᵃ | R³ᵇ | R³ᵃ, R³ᵇ Stereo- chem. | MS Calc | MS Obs (MH)⁺ | LCMS Ret. (min) | Purity Method |
|---|---|---|---|---|---|---|---|---|
| 1-12 | 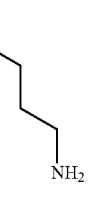 | H | 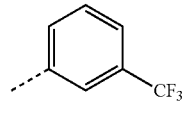 NH₂ | S | 554.3 | 555.1 | 10.14 | 1 |
| 1-13 | 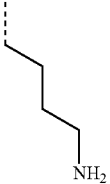 CF₃ | H | 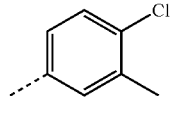 NH₂ | S | 608.3 | 609.2 | 10.83 | 1 |
| 1-14 | 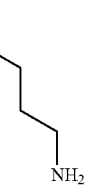 Cl | H | 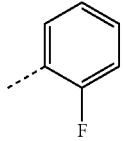 NH₂ | S | 588.3 | 589.2 | 10.95 | 1 |
| 1-15 | 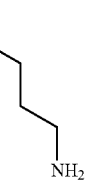 F | H | 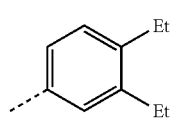 NH₂ | S | 558.3 | 559.1 | 9.78 | 1 |
| 1-16 | 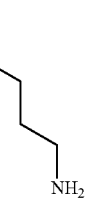 Et Et | H | NH₂ | S | 596.3 | 597.3 | 11.65 | 1 |

TABLE 1-continued
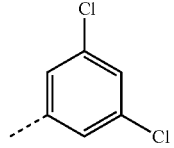
| Cpd. No. | R[1] | R[3a] | R[3b] | R[3a], R[3b] Stereochem. | MS Calc | MS Obs (MH)+ | LCMS Ret. (min) | Purity Method |
|---|---|---|---|---|---|---|---|---|
| 1-17 | 3,5-dichlorophenyl | H | (CH2)4NH2 | S | 608.2 | 609.2 | 10.36 | 1 |
| 1-18 | 4-Cl-3-CF3-phenyl | H | (CH2)4NH2 | S | 642.2 | 643.3 | 12.42 | 1 |
| 1-19 | 4-CF3-3-F-phenyl | H | (CH2)4NH2 | S | 626.3 | 627.0 | 11.03 | 1 |
| 1-20 | 3-F-4-Cl-phenyl | H | (CH2)4NH2 | S | 592.2 | 593.0 | 11.88 | 1 |
| 1-21 | 3,4-difluorophenyl | H | (CH2)4NH2 | S | 576.3 | 577.5 | 10.22 | 1 |

TABLE 1-continued
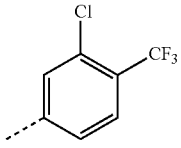
| Cpd. No. | R¹ | R³ᵃ | R³ᵇ | R³ᵃ, R³ᵇ Stereo- chem. | MS Calc | MS Obs (MH)⁺ | LCMS Ret. (min) | Purity Method |
|---|---|---|---|---|---|---|---|---|
| 1-22 | 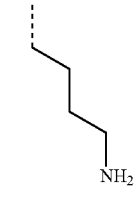 | 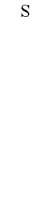 | 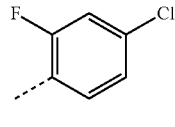 | S | 642.2 | 643.2 | 11.39 | 1 |
| 1-23 | 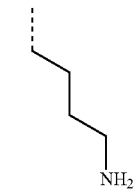 |  | 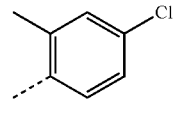 | S | 592.2 | 593.2 | 11.86 | 1 |
| 1-24 | 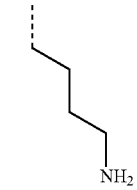 |  | 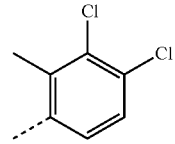 | S | 588.3 | 588.9 | 12.03 | 1 |
| 1-25 | 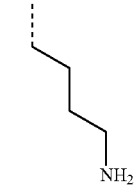 |  | 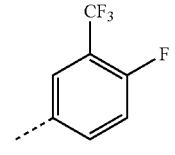 | S | 622.2 | 623.2 | 12.43 | 1 |
| 1-26 | 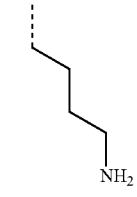 |  | | S | 626.3 | 627.4 | 10.82 | 1 |

TABLE 1-continued

| Cpd. No. | R¹ | R³ᵃ | R³ᵇ | R³ᵃ, R³ᵇ Stereo-chem. | MS Calc | MS Obs (MH)⁺ | LCMS Ret. (min) | Purity Method |
|---|---|---|---|---|---|---|---|---|
| 1-27 | 4-methyl-3-chlorophenyl | H | -(CH₂)₄-NH₂ | S | 588.3 | 589.3 | 12.21 | 1 |
| 1-28 | 3-methyl-4-trifluoromethylphenyl | H | -(CH₂)₄-NH₂ | S | 622.2 | 623.0 | 11.12 | 1 |
| 1-29 | 3,4-dimethylphenyl | H | -(CH₂)₄-NH₂ | S | 568.3 | 569.3 | 10.51 | 1 |
| 1-30 | 4-methyl-3-trifluoromethylphenyl | H | -(CH₂)₄-NH₂ | S | 622.3 | 623.3 | 11.10 | 1 |
| 1-31 | 3,4-dichlorophenyl | H | -(CH₂)₄-N(CH₃)₂ | S | 636.2 | 637.3 | 10.42 | 1 |

TABLE 1-continued

| Cpd. No. | R¹ | R³ᵃ | R³ᵇ | R³ᵃ, R³ᵇ Stereo-chem. | MS Calc | MS Obs (MH)⁺ | LCMS Ret. (min) | Purity Method |
|---|---|---|---|---|---|---|---|---|
| 1-32 | 4-Cl-3-Me-phenyl | H | -(CH₂)₄-NH-C(=NH)-NH₂ | S | 616.3 | 617.0 | 12.27 | 1 |
| 1-33 | 3,4-diMe-phenyl | H | -(CH₂)₄-NH-C(=NH)-NH₂ | S | 596.3 | 596.0 | 11.95 | 1 |
| 1-34 | 5,6-dimethylpyridin-3-yl | H | -(CH₂)₅-N(Me)₂ | S | 569.3 | 570.3 | 9.02 | 1 |
| 1-35 | 2-OMe-phenyl | H | -(CH₂)₂-NH₂ | S | 542.3 | 543.1 | 11.23 | 1 |
| 1-36 | 4-Cl-2-OMe-phenyl | H | -(CH₂)₂-NH₂ | S | 590.2 | 592.0 | 11.9 | 1 |

TABLE 1-continued
| Cpd. No. | R¹ | R³ᵃ | R³ᵇ | R³ᵃ, R³ᵇ Stereo-chem. | MS Calc | MS Obs (MH)⁺ | LCMS Ret. (min) | Purity Method |
|---|---|---|---|---|---|---|---|---|
| 1-37 | 4-methyl-2-methoxyphenyl | H | CH₂CH₂NH₂ | S | 556.3 | 557.0 | 11.67 | 1 |
| 1-38 | 3-methyl-4-methoxyphenyl | H | CH₂CH₂NH₂ | S | 556.3 | 557.2 | 11.78 | 1 |
| 1-39 | 5-methoxyindanyl | H | CH₂CH₂NH₂ | S | 582.3 | 583.4 | 12.26 | 1 |
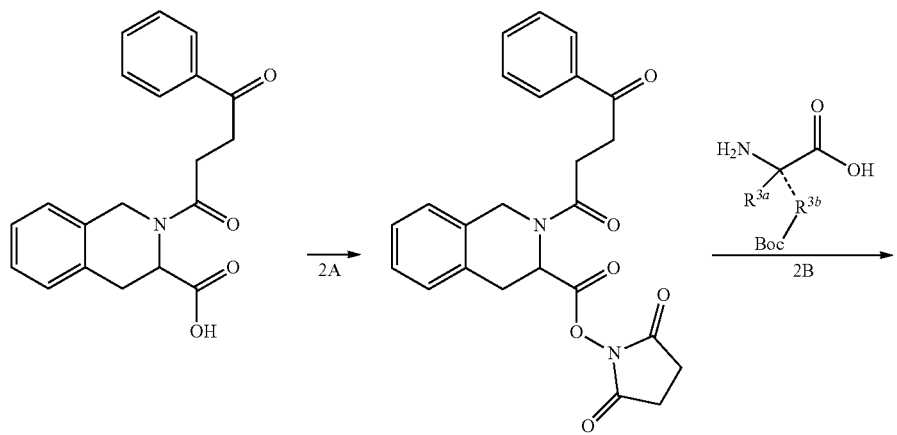
Scheme 2

-continued
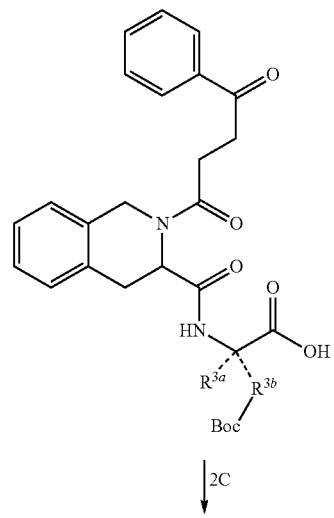
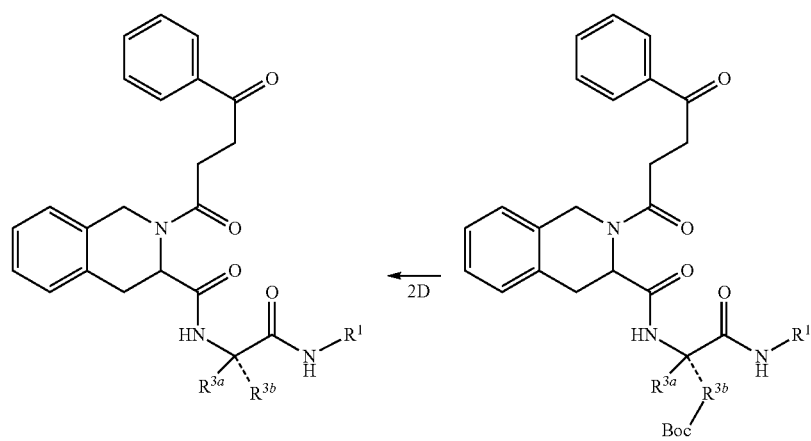

Example 2

Synthesis of (S)—N—((S)-4-amino-1-((3,4-dichlorophenyl)amino)-1-oxobutan-2-yl)-2-(4-oxo-4-phenylbutanoyl)-1,2,3,4-tetrahydroisoquinoline-3-carboxamide (Compound 2-1)

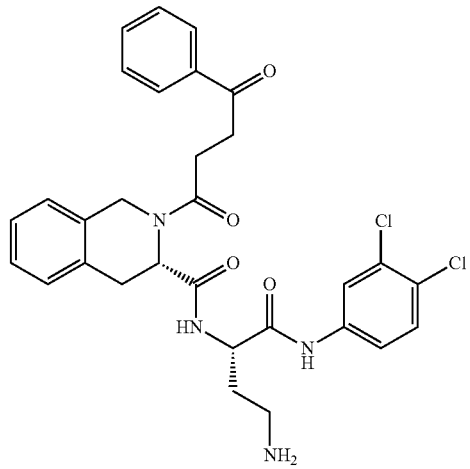

Step 2A: 2,5-dioxopyrrolidin-1-yl (S)-2-(4-oxo-4-phenylbutanoyl)-1,2,3,4-tetra hydroisoquinoline-3-carboxylate (Intermediate 2A)

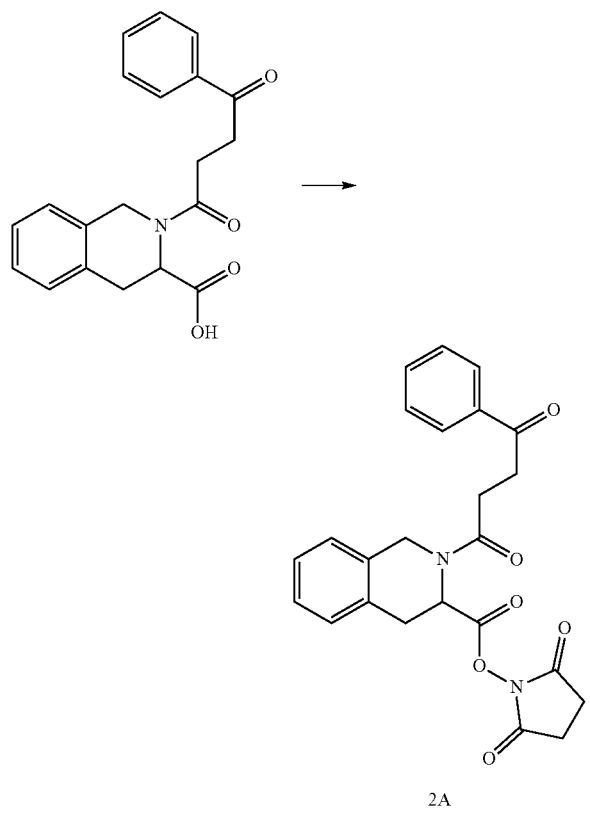

EDCI (4.9 g, 26 mmol) was added to a solution of N-hydroxysuccinimide (2.96 g, 26 mmol) and (S)-2-(4-oxo-4-phenylbutanoyl)-1,2,3,4-tetrahydroisoquinoline-3-carboxylic acid (Intermediate 1B) (6.2 g, 18 mmol) in DCM (25 mL). After stirring overnight, the reaction mixture was concentrated and purified over $SiO_2$ (EA/Hexane) to provide Intermediate 2A (5.6 g, 70%). LCMS (m/z) calculated for $C_{24}H_{22}N_2O_6$: 434.2; found 434.9 $[M+H]^+$, $t_R$=3.99 min (Method 2).

Step 2B: (S)-4-((tert-butoxycarbonyl)amino)-2-((S)-2-(4-oxo-4-phenylbutanoyl)-1,2,3,4-tetrahydroisoquinoline-3-carboxamido)butanoic Acid (Intermediate 2B)

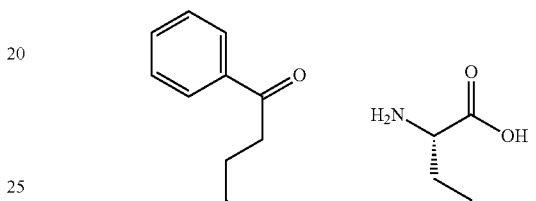

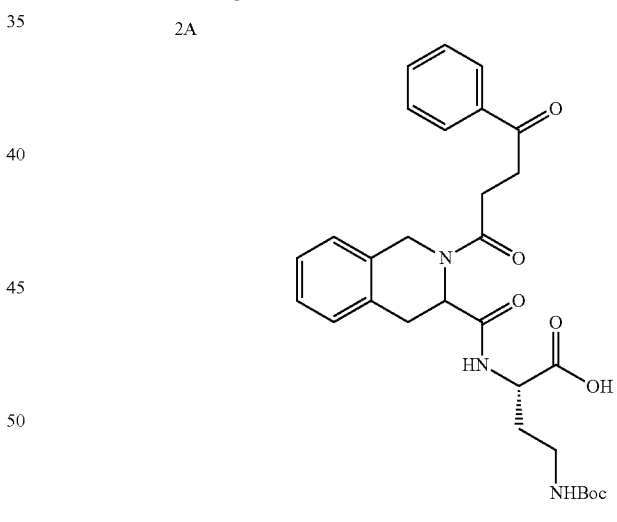

DIEA (0.5 mL, 2.8 mmol) was added to a solution of (S)-2-amino-4-((tert-butoxycarbonyl)amino)butanoic acid (0.27 g, 1.23 mmol) and Intermediate 2A (0.5 g, 1.15 mmol) in DCM (2.5 mL) and stirred overnight. The reaction mixture was diluted with EA and washed with 1N HCl and water. The organic layer was dried ($Na_2SO_4$), concentrated and purified over $SiO_2$ (MeOH/DCM). The resulting material was recrystallized from THF/$Et_2O$ to provide Intermediate 2B (0.3 g, 49%). LCMS (m/z) calculated for $C_{29}H_{35}N_3O_7$: 537.3; found 537.9 $[M+H]^+$, $t_R$=4.67 min (Method 2).

421

Step 2C: tert-butyl ((S)-4-((3,4-dichlorophenyl)amino)-4-oxo-3-((S)-2-(4-oxo-4-phenylbutanoyl)-1,2,3,4-tetrahydroisoquinoline-3-carboxamido)butyl)carbamate (Intermediate 2C)

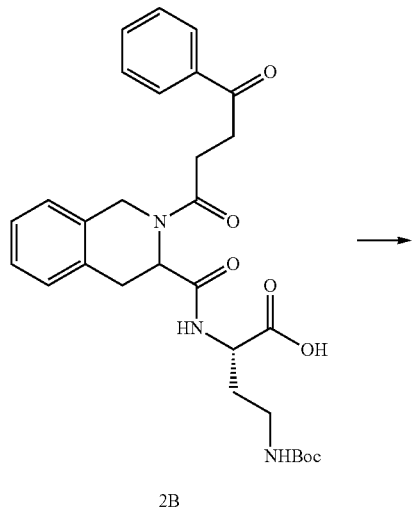

2B

422

Step 2D: (S)—N—((S)-4-amino-1-((3,4-dichlorophenyl)amino)-1-oxobutan-2-yl)-2-(4-oxo-4-phenylbutanoyl)-1,2,3,4-tetrahydroisoquinoline-3-carboxamide (Compound 2-1)

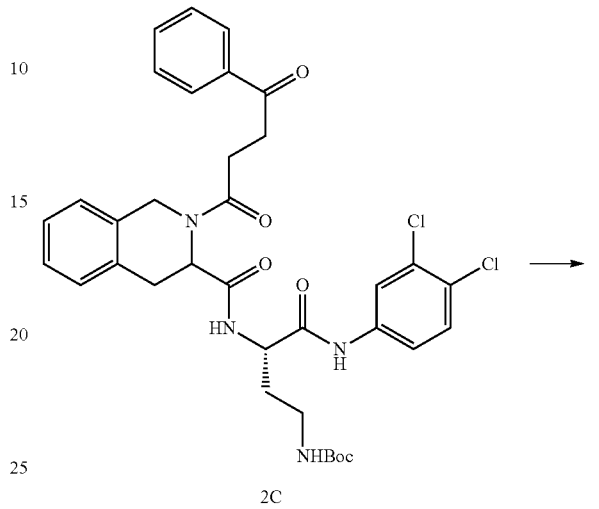

2C

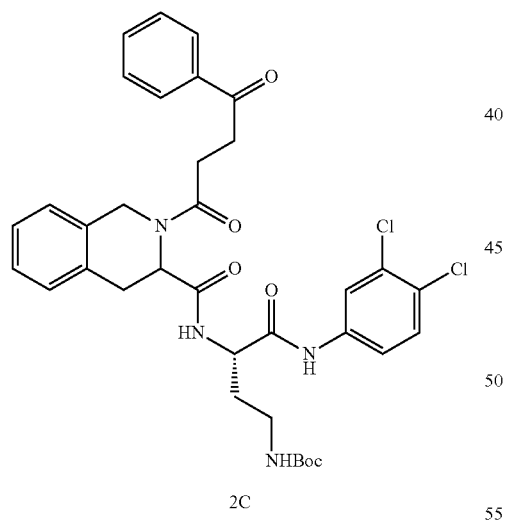

2C

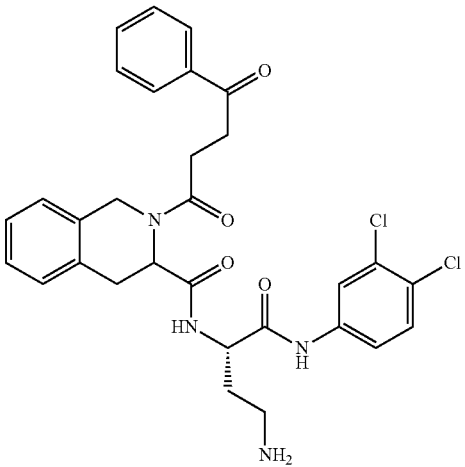

2-1

HATU (233 mg, 0.61 mmol) and DIEA (0.25 mL, 1.4 mmol) were added to a solution of Intermediate 2B (0.3 g, 0.6 mmol) and 3,4-dichloroaniline (99 mg, 0.61 mmol) in THF (15 mL). After stirring overnight, the reaction mixture was concentrated, diluted with EA and washed with 0.1 M HCl, 0.1 M NaOH, saturated NaHCO$_3$, water and brine. The resulting material (Intermediate 2C) was used without further purification. LCMS (m/z) calculated for $C_{35}H_{38}Cl_2N_4O_6$: 680.2; found 681.1 [M+H]$^+$, $t_R$=13.28 min (Method 1).

A solution of 4M HCl (4.4 mL, 17.6 mmol) in dioxane was added to a solution of Intermediate 2C (0.3 g, 0.44 mmol) in THF (5 mL) at 0° C. DCM (5 mL) was added to dissolve the resulting precipitate. After 4 h, the reaction mixture was concentrated and purified by RP-Prep HPLC to provide Compound 2-1 (31 mg, 12%). LCMS (m/z) calculated for $C_{30}H_{30}Cl_2N_4O_4$: 580.2; found 582.0 [M+H]$^+$, $t_R$=12.42 min (Method 1).

Following the procedures as set forth in Example 2 above, the compounds of the following Table 2 were prepared using the appropriate R$^1$ reagents:

TABLE 2

| Compound Number | R¹ | MS Calc | MS Obs (MH)⁺ | LCMS Retention (min) | Purity Method |
|---|---|---|---|---|---|
| 2-1 | 3,4-dichlorophenyl | 580.2 | 582.0 | 12.42 | 1 |
| 2-2 | 3-chloro-4-methylphenyl | 560.2 | 561.2 | 12.23 | 1 |
| 2-3 | 3,4-dimethylphenyl | 540.3 | 541.0 | 10.43 | 1 |
| 2-4 | 3-chloro-4-(trifluoromethyl)phenyl | 614.2 | 615.0 | 10.09 | 1 |
| 2-5 | 3-methylphenyl | 526.3 | 527.1 | 11.50 | 1 |
| 2-6 | 3-(trifluoromethyl)phenyl | 580.2 | 581.0 | 11.48 | 1 |
| 2-7 | 3-methyl-4-(trifluoromethyl)phenyl | 594.3 | 595.0 | 12.19 | 1 |
| 2-8 | 3,4-difluorophenyl | 548.2 | 549.0 | 11.6 | 1 |
| 2-9 | 3-fluoro-4-chlorophenyl | 564.2 | 565.3 | 11.81 | 1 |

TABLE 2-continued
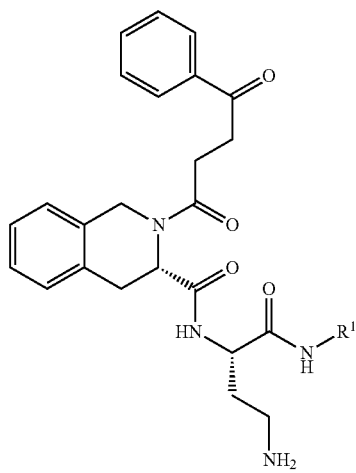
| Compound Number | R¹ | MS Calc | MS Obs (MH)⁺ | LCMS Retention (min) | Purity Method |
|---|---|---|---|---|---|
| 2-10 | 2-methyl-4-chlorophenyl | 560.2 | 561.3 | 12.03 | 1 |
| 2-11 | 2-fluoro-4-(from para)-CF₃... (2-F, 4-CF₃ phenyl) | 598.2 | 599.0 | 12.06 | 1 |
| 2-12 | 4-chloro-3-fluorophenyl | 564.2 | 565.0 | 11.96 | 1 |
| 2-13 | 3-chloro-4-trifluoromethylphenyl | 614.2 | 615.0 | 12.4 | 1 |
| 2-14 | 2-CF₃-4-fluorophenyl | 598.2 | 599.0 | 12.67 | 1 |
| 2-15 | 2,3-dichloro-4-methylphenyl | 594.2 | 595.0 | 12.38 | 1 |
| 2-16 | 3-methyl-4-chlorophenyl | 560.2 | 561.0 | 12.16 | 1 |

TABLE 2-continued
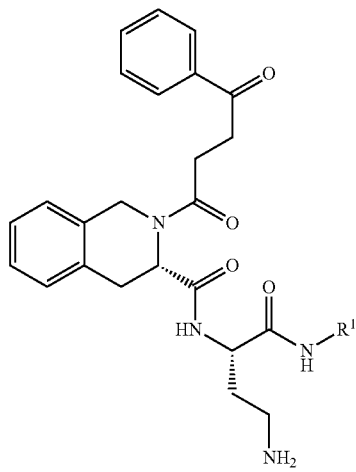
| Compound Number | R[1] | MS Calc | MS Obs (MH)+ | LCMS Retention (min) | Purity Method |
|---|---|---|---|---|---|
| 2-17 | 3,5-diCl-phenyl | 580.2 | 581.0 | 12.59 | 1 |
| 2-18 | 3-Cl-4-F-phenyl (with Me) | 578.2 | 579.0 | 12.07 | 1 |
| 2-19 | 3-Cl-phenyl (with 2 Me) | 574.2 | 575.1 | 12.28 | 1 |
| 2-20 | 3,4-diCl-5-F-phenyl | 598.2 | 598.9 | 12.22 | 1 |
| 2-21 | 3,4-diCl-phenyl (with Me) | 594.2 | 595.0 | 12.3 | 1 |
| 2-22 | 2,5-diCl-phenyl (with Me) | 594.2 | 595.2 | 12.49 | 1 |

TABLE 2-continued

| Compound Number | R¹ | MS Calc | MS Obs (MH)⁺ | LCMS Retention (min) | Purity Method |
|---|---|---|---|---|---|
| 2-23 | 3,5-dichloro-4-methoxyphenyl | 610.2 | 611.0 | 12.22 | 1 |
| 2-24 | 2,3-dichloro-4-fluorophenyl (Cl, Cl, F substituents) | 598.2 | 599.0 | 12.35 | 1 |
| 2-25 | 3-chloro-4-methoxy-6-methylphenyl | 590.2 | 591.3 | 12.22 | 1 |
| 2-26 | 2-chloro-3,4-dimethylphenyl | 574.2 | 575.0 | 12.14 | 1 |
| 2-27 | 3-methyl-4-trifluoromethylphenyl | 594.2 | 595 | 12.32 | 1 |
| 2-28 | naphthalen-2-yl | 562.3 | 563.4 | 11.98 | 1 |

TABLE 2-continued
| Compound Number | R[1] | MS Calc | MS Obs (MH)+ | LCMS Retention (min) | Purity Method |
|---|---|---|---|---|---|
| 2-29 | 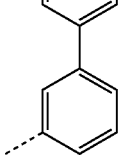 | 588.3 | 589.2 | 12.38 | 1 |
| 2-30 | 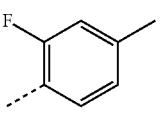 | 608.2 | 609.5 | 12.74 | 1 |
| 2-31 | 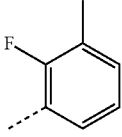 | 544.3 | 545.4 | 11.5 | 1 |
| 2-32 | 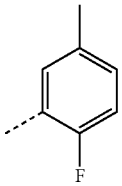 | 544.3 | 544.6 | 11.54 | 1 |
| 2-33 | 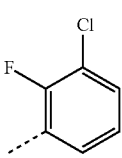 | 544.3 | 545.0 | 11.5 | 1 |
| 2-34 | | 564.2 | 565.0 | 11.69 | 1 |

TABLE 2-continued
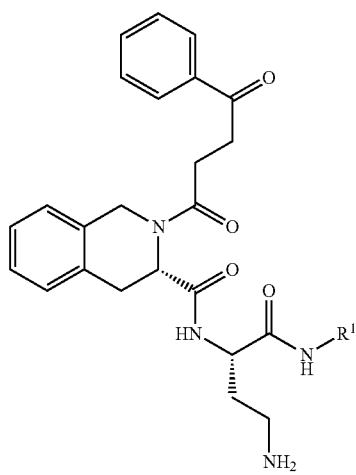
| Compound Number | R¹ | MS Calc | MS Obs (MH)⁺ | LCMS Retention (min) | Purity Method |
|---|---|---|---|---|---|
| 2-35 | Cl, Me phenyl | 560.2 | 561.0 | 11.79 | 1 |
| 2-36 | Cl, Me phenyl | 560.2 | 561.0 | 11.83 | 1 |
| 2-37 | F, Cl phenyl | 564.2 | 565.0 | 11.72 | 1 |
| 2-38 | I, Cl, Me phenyl | 686.1 | 687.0 | 12.6 | 1 |
| 2-39 | Me, Cl, Me phenyl | 574.2 | 575.0 | 11.55 | 1 |
| 2-40 | Me, Cl, Br phenyl | 638.1 | 640.0 | 12.77 | 1 |
| 2-41 | Me, Cl, Et phenyl | 588.3 | 589.0 | 12.51 | 1 |

TABLE 2-continued
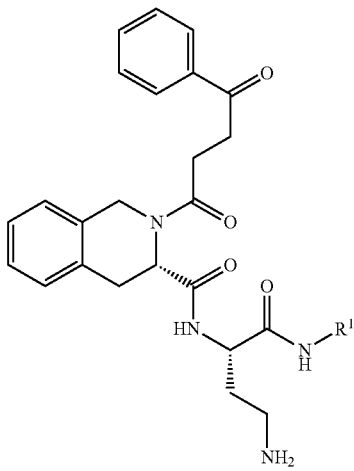
| Compound Number | R¹ | MS Calc | MS Obs (MH)⁺ | LCMS Retention (min) | Purity Method |
|---|---|---|---|---|---|
| 2-42 | isoquinolin-7-yl | 563.3 | 564.0 | 8.89 | 1 |
| 2-43 | quinolin-6-yl | 563.3 | 564.0 | 8.69 | 1 |
| 2-44 | quinolin-3-yl | 563.3 | 564.0 | 8.75 | 1 |
| 2-45 | quinolin-7-yl | 563.3 | 564.0 | 8.75 | 1 |
| 2-46 | 1,2,3,4-tetrahydronaphthalen-6-yl | 566.3 | 566.7 | 12.3 | 1 |
| 2-47 | 2,3-dihydro-1H-inden-5-yl | 552.3 | 553.0 | 12.07 | 1 |

TABLE 2-continued
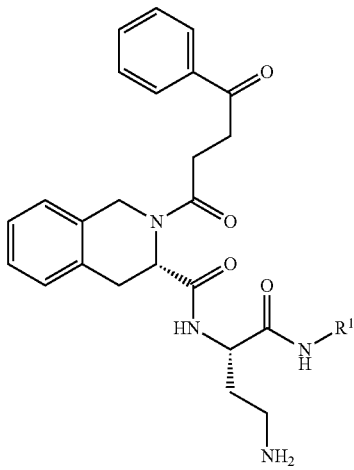
| Compound Number | R¹ | MS Calc | MS Obs (MH)⁺ | LCMS Retention (min) | Purity Method |
|---|---|---|---|---|---|
| 2-48 | 2,3-dichloro-6-ethylphenyl | 608.2 | 609.0 | 12.52 | 1 |
| 2-49 | 2,3-dimethylphenyl | 540.3 | 541.0 | 11.42 | 1 |
| 2-50 | 2-hydroxy-6-methylphenyl | 542.3 | 543.0 | 11.42 | 1 |
| 2-51 | 2-methoxy-6-methylphenyl | 556.3 | 557.0 | 11.64 | 1 |
| 2-52 | 2,4-dichlorophenyl | 580.2 | 581.2 | 12.23 | 1 |
| 2-53 | 2-ethyl-6-methylphenyl | 554.3 | 555.4 | 11.72 | 1 |
| 2-54 | 2-ethyl-3-chloro-6-methylphenyl | 588.3 | 589.0 | 12.42 | 1 |

TABLE 2-continued
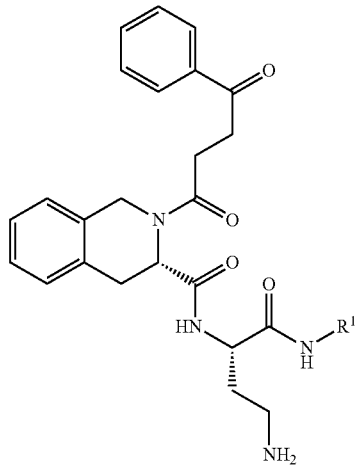
| Compound Number | R¹ | MS Calc | MS Obs (MH)⁺ | LCMS Retention (min) | Purity Method |
|---|---|---|---|---|---|
| 2-55 | 2-Cl, 4-ethylphenyl | 574.2 | 575.0 | 12.38 | 1 |
| 2-56 | 3-F, 5-ethylphenyl | 558.3 | 559.0 | 11.77 | 1 |
| 2-57 | 5-CN-indanyl | 577.3 | 578.0 | 11.52 | 1 |
| 2-58 | 4-OMe-indanyl | 582.3 | 583.2 | 12.12 | 1 |
| 2-59 | 6-OMe-tetrahydronaphthyl | 596.3 | 597.3 | 12.57 | 1 |

TABLE 2-continued
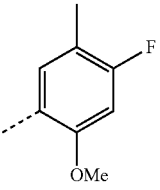
| Compound Number | R[1] | MS Calc | MS Obs (MH)+ | LCMS Retention (min) | Purity Method |
|---|---|---|---|---|---|
| 2-60 | 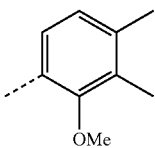 | 574.3 | 575.5 | 11.86 | 1 |
| 2-61 | 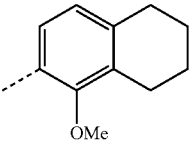 | 570.3 | 571.2 | 11.92 | 1 |
| 2-62 | 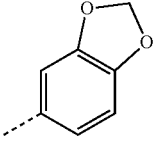 | 596.3 | 597.3 | 12.48 | 1 |
| 2-63 | 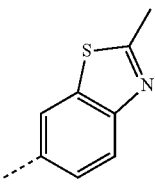 | 556.2 | 557.2 | 10.76 | 1 |
| 2-64 | 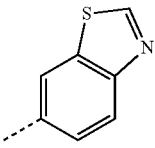 | 583.2 | 584.2 | 12.43 | 1 |
| 2-65 | | 569.2 | 570.4 | 10.48 | 1 |

TABLE 2-continued
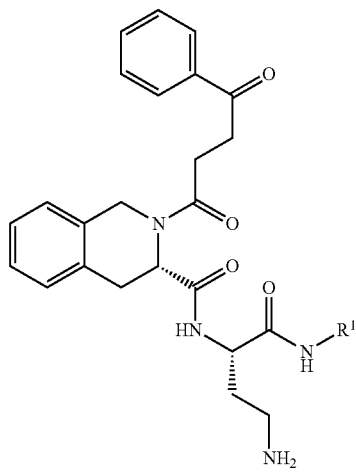
| Compound Number | R¹ | MS Calc | MS Obs (MH)⁺ | LCMS Retention (min) | Purity Method |
|---|---|---|---|---|---|
| 2-66 | 2,3-dihydro-1H-inden-2-yl | 552.3 | 553.3 | 11.85 | 1 |
| 2-67 | 2,3-dihydro-1H-inden-4-yl | 552.3 | 553.3 | 11.97 | 1 |
| 2-68 | 1-oxo-2,3-dihydro-1H-inden-6-yl | 566.3 | 567.5 | 10.42 | 1 |
| 2-69 | 1-oxo-2,3-dihydro-1H-inden-5-yl | 566.3 | 567.3 | 10.34 | 1 |
| 2-70 | 2,3-difluoro-4-methoxyphenyl | 578.2 | 579.3 | 11.53 | 1 |
| 2-71 | 2-fluoro-4-methoxy-3-methylphenyl | 574.3 | 575.3 | 11.61 | 1 |

TABLE 2-continued
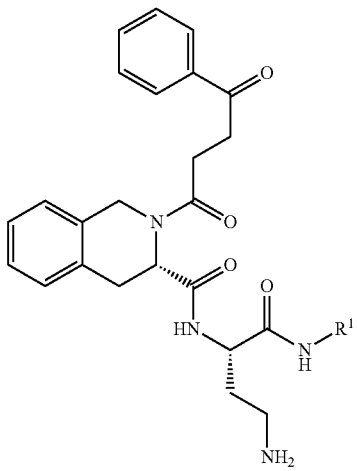
| Compound Number | R¹ | MS Calc | MS Obs (MH)⁺ | LCMS Retention (min) | Purity Method |
|---|---|---|---|---|---|
| 2-72 | 1,1-dimethyl-indanyl | 580.3 | 581.2 | 12.71 | 1 |
| 2-73 | 6-chloro-indanyl | 586.2 | 587.2 | 12.03 | 1 |
| 2-74 | 6-hydroxy-indanyl | 568.3 | 569.1 | 11.61 | 1 |
| 2-75 | 2,2-dimethyl-indanyl | 580.3 | 581.2 | 12.77 | 1 |
| 2-76 | 2-methyl-5-methoxy-4-trifluoromethylphenyl | 624.3 | 625.5 | 12.09 | 1 |
| 2-77 | 4-chloro-indanyl | 586.2 | 587.2 | 12.09 | 1 |

TABLE 2-continued
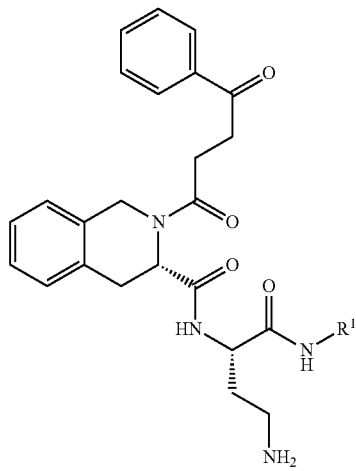
| Compound Number | R[1] | MS Calc | MS Obs (MH)+ | LCMS Retention (min) | Purity Method |
|---|---|---|---|---|---|
| 2-78 | 5-fluoro-2,3-dihydro-1H-inden-5-yl | 570.3 | 571.2 | 11.84 | 1 |
| 2-79 | 2,5-dimethyl-4-methoxyphenyl | 570.3 | 571.2 | 12.00 | 1 |
| 2-80 | benzothiazol-6-yl | 569.2 | 570.2 | 10.67 | 1 |
| 2-81 | 1,2,3,4-tetrahydronaphthalen-2-yl | 566.3 | 567.5 | 12.06 | 1 |
| 2-82 | 2-methyl-2,3-dihydro-1H-isoindol-5-yl | 567.3 | 568.1 | 8.89 | 1 |
Scheme 3
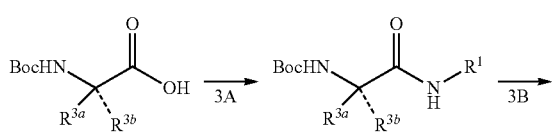

449

-continued

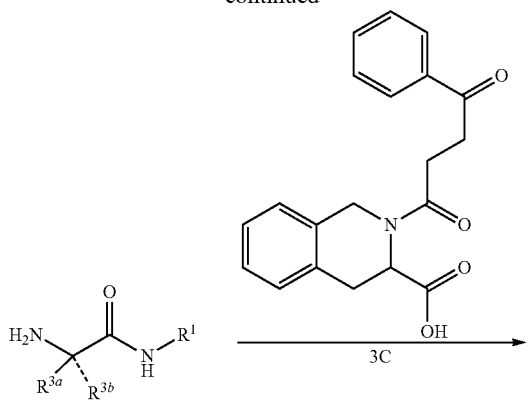

Example 3

Synthesis of (S)—N—((S)-1-((3,4-dichlorophenyl)amino)-1-oxo-5-ureidopentan-2-yl)-2-(4-oxo-4-phenylbutanoyl)-1,2,3,4-tetrahydroisoquinoline-3-carboxamide (Compound 3-1)

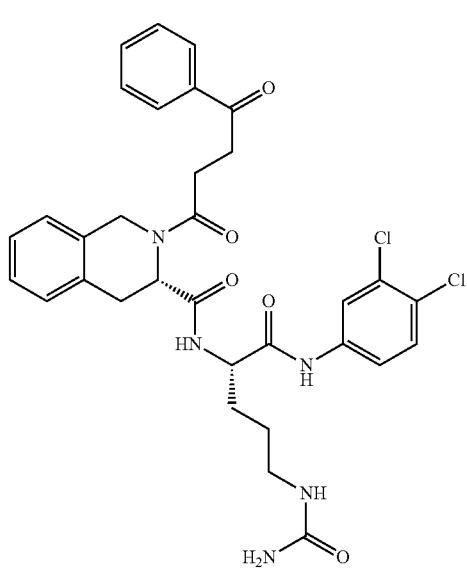

3-1

450

Step 3A: Synthesis of tert-butyl (S)-(1-((3,4-dichlorophenyl)amino)-1-oxo-5-ureidopentan-2-yl)carbamate (Intermediate 3A)

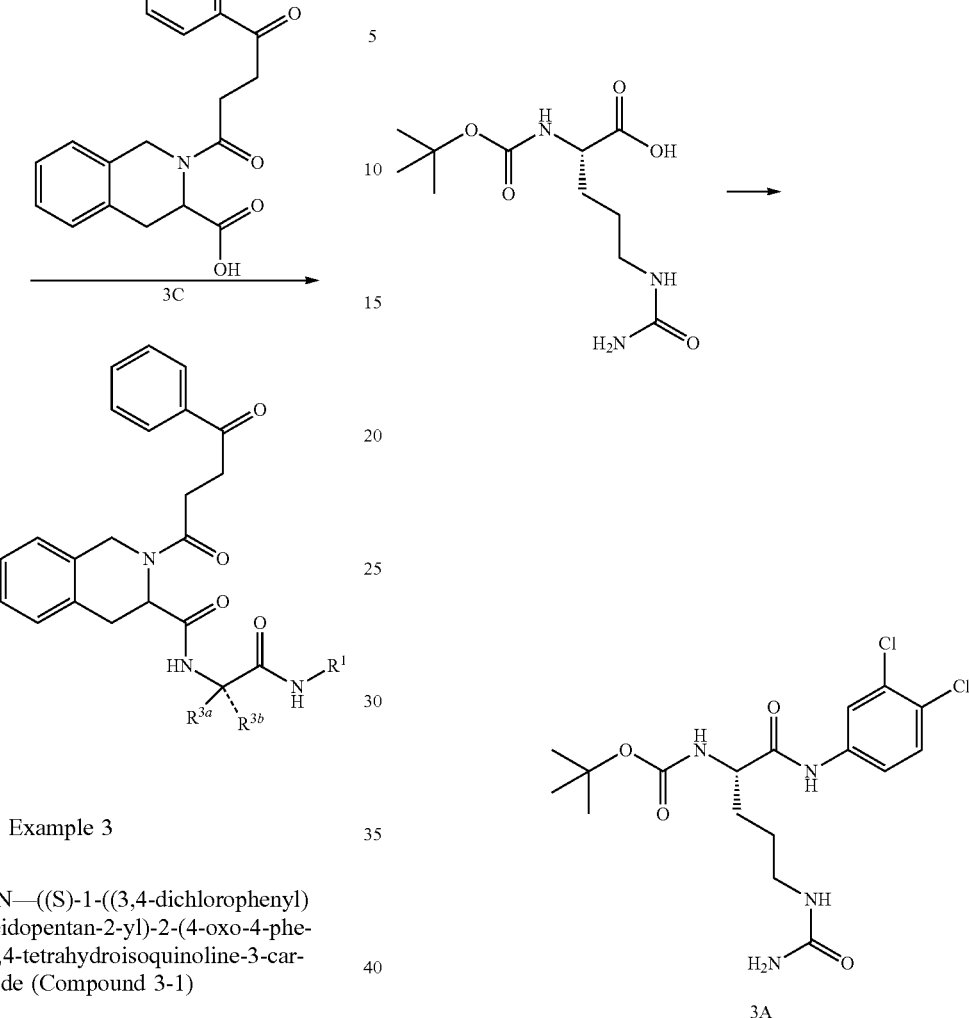

3A

A stirring solution of (S)-2-((tert-butoxycarbonyl)amino)-5-ureidopentanoic acid (1.0 g, 3.6 mmol), 3,4-dichloroaniline (0.56 g, 3.5 mmol) and DIEA (1.5 mL, 8.7 mmol) in 10 mL of THF was cooled to 0° C. A solution of HATU (1.4 g, 3.6 mmol) in 1 mL of THF was added dropwise over 5 min. The reaction mixture was allowed to warm to rt and stirred for 2 h. The mixture was diluted with EA and washed with NaHCO$_3$ (sat. aqueous). The organic solvent was concentrated water was added. The resulting solid was filtered and dried to provide Intermediate 3A. LCMS (m/z) calculated for $C_{17}H_{24}Cl_2N_4O_4$: 418.1; found 419 [M+H]$^+$, $t_R$=4.73 min (Method 2).

451

Step 3B: Synthesis of (S)-2-amino-N-(3,4-dichlorophenyl)-5-ureidopentanamide. (Intermediate 3B)

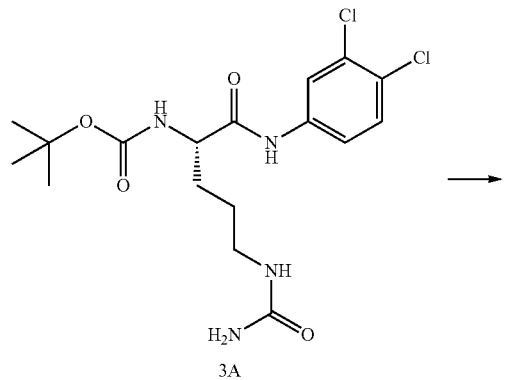

A solution of 4N HCl in dioxane (3.3 mL, 13.1 mmol) was added to Intermediate 3A (1.1 g, 2.6 mmol) in DCM (10 mL). The mixture was stirred overnight and then concentrated. Diethyl ether was added and the resulting solid was collected by filtration to provide Intermediate 3B. LCMS (m/z) calculated for $C_{12}H_{16}Cl_2N_4O_2$: 318.1; found 319 [M+H]$^+$, $t_R$=3.08 min (Method 2).

452

Step 3C: Synthesis of (S)—N—((S)-1-((3,4-dichlorophenyl)amino)-1-oxo-5-ureidopentan-2-yl)-2-(4-oxo-4-phenylbutanoyl)-1,2,3,4-tetrahydroisoquinoline-3-carboxamide (Compound 3-1)

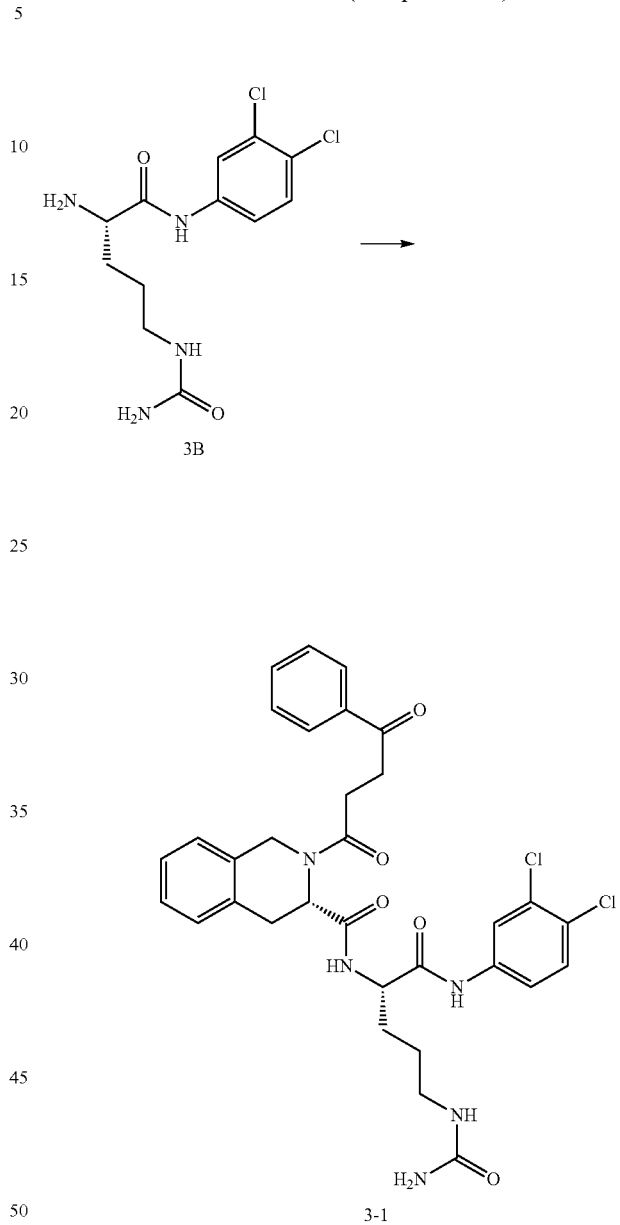

A stirring solution of Intermediate 1B (50 mg, 0.15 mmol), Intermediate 3B (50 mg, 0.14 mmol) and DIEA (0.09 mL, 0.5 mmol) in THF (3 mL) was cooled to 0° C. A solution of HATU (56 mg, 0.15 mmol) in THF (2 mL) was added dropwise over 5 min. The reaction mixture was allowed to warm to rt, stirred for 2 h, then diluted with EA and washed with NaHCO$_3$ (sat.). The aqueous fraction was back-extracted with EA. The combined organic fractions were dried (Na$_2$SO$_4$) then concentrated and purified by prep-HPLC to provide Compound 3-1. LCMS (m/z) calculated for $C_{32}H_{33}Cl_2N_5O_5$: 637.2; found 638.0 [M+H]$^+$, $t_R$=11.94 min (Method 1).

Following the procedures as set forth in Example 3 above, the compounds of the following Table 3 were prepared using the appropriate $R^1$, $R^{3a}$ and $R^{3b}$ reagents:

TABLE 3
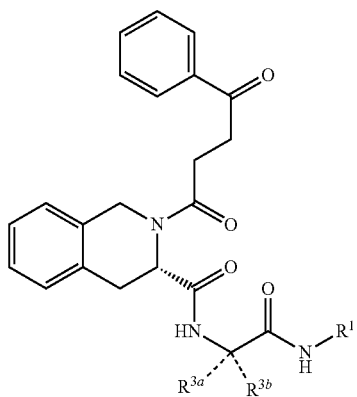
| Cmpd Number | R¹ | R³ᵃ | R³ᵇ | R³ᵃ, R³ᵇ Stereo-chem. | MS Calc | MS Obs (MH)⁺ | LCMS Ret. (min) | Purity Method |
|---|---|---|---|---|---|---|---|---|
| 3-1 | 3,4-dichlorophenyl | H | propyl-NH-C(O)-NH₂ | S | 637.2 | 638.0 | 11.94 | 1 |
| 3-2 | 4-chloro-3-methylphenyl-NH | H | ethyl-NH-C(=NH)-NH₂ | S | 602.2 | 603.3 | 12.24 | 1 |
| 3-3 | 4-chloro-3-methylphenyl-NH | H | 3-pyridylmethyl | Racemic | 608.2 | 609.0 | 12.37 | 1 |
| 3-4 | 4-chloro-3-methylphenyl-NH | H | 4-pyridylmethyl | S | 608.2 | 609.0 | 12.22 | 1 |
| 3-5 | 4-chloro-3-methylphenyl-NH | H | 2-pyridylmethyl | S | 608.2 | 609.0 | 12.58 | 1 |
| 3-6 | 3,4-dichlorophenyl | H | butyl-NH-C(O)-NH₂ | S | 651.2 | 652.5 | 12.01 | 1 |

TABLE 3-continued

| Cmpd Number | R¹ | R³ᵃ | R³ᵇ | R³ᵃ, R³ᵇ Stereo-chem. | MS Calc | MS Obs (MH)⁺ | LCMS Ret. (min) | Purity Method |
|---|---|---|---|---|---|---|---|---|
| 3-7 | 4-(2-chloro-methylphenyl) | H | CH₂CH₂N(iPr)₂ | S | 644.3 | 645.4 | 4.88 | 5 |
| 3-8 | 4-(2-chloro-methylphenyl) | H | CH₂CH₂-pyrrolidinyl | S | 614.3 | 615.3 | 4.55 | 5 |
| 3-9 | 4-(2-chloro-methylphenyl) | H | CH₂CH₂-piperidinyl | S | 628.3 | 629.3 | 4.71 | 5 |
| 3-10 | 4-(2-chloro-methylphenyl) | H | CH₂-(2-aminopyridin-4-yl) | S | 623.2 | 624.2 | 4.61 | 5 |
| 3-11 | 4-(2-chloro-methylphenyl) | H | CH₂-(2-methoxypyrimidin-4-yl) | S | 639.2 | 640.3 | 7.03 | 5 |
| 3-12 | 4-(2-chloro-methylphenyl) | H | CH₂C(O)NH₂ | S | 574.2 | 575.2 | 6.24 | 5 |

TABLE 3-continued
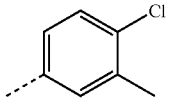
| Cmpd Number | R¹ | R³ᵃ | R³ᵇ | R³ᵃ, R³ᵇ Stereo-chem. | MS Calc | MS Obs (MH)⁺ | LCMS Ret. (min) | Purity Method |
|---|---|---|---|---|---|---|---|---|
| 3-13 |  | 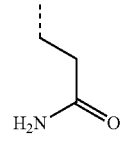 | 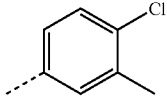 | S | 588.2 | 589.2 | 6.36 | 5 |
| 3-14 |  | 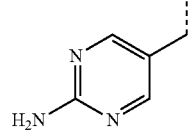 | 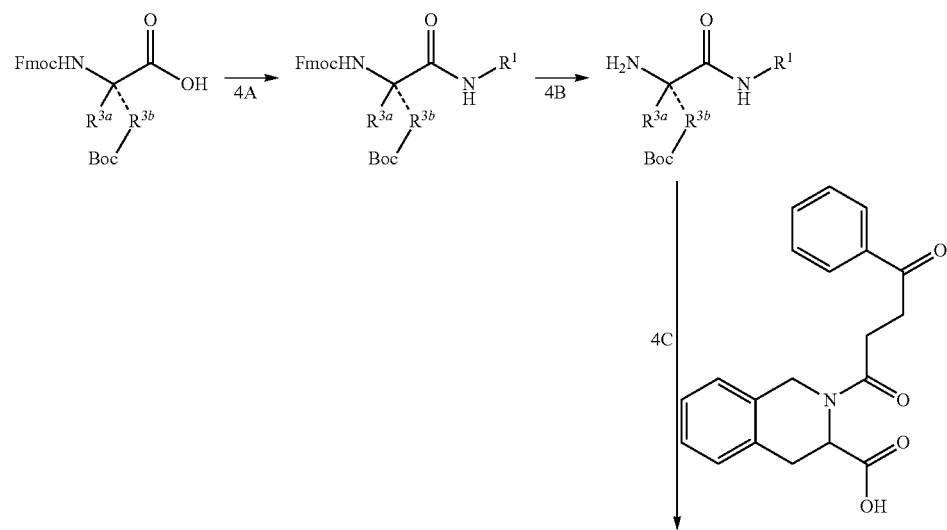 | S | 624.2 | 625.0 | 5.35 | 5 |
Scheme 4

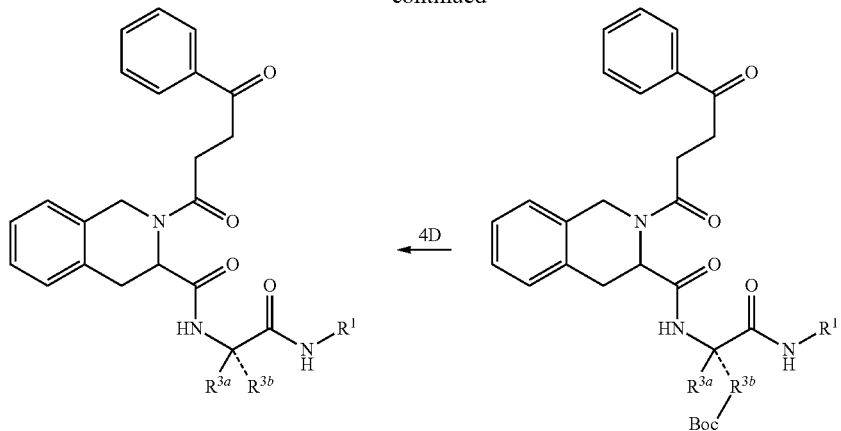

Example 4

Synthesis of (S)—N—((S)-6-amino-1-((4-chloro-3-methylphenyl)amino)-1-oxohexan-2-yl)-2-(4-oxo-4-phenylbutanoyl)-1,2,3,4-tetrahydroisoquinoline-3-carboxamide (Compound 4-2)

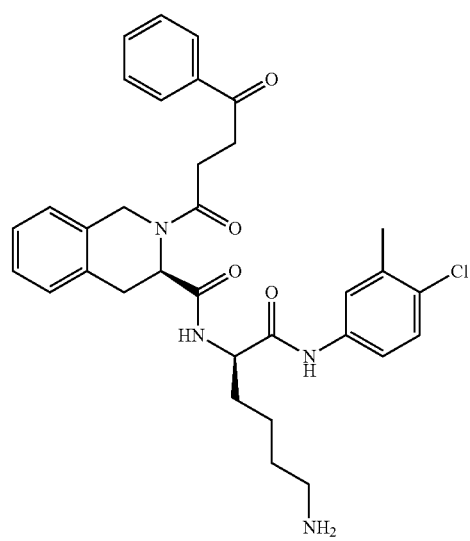

Step 4A: Synthesis of (9H-fluoren-9-yl)methyl tert-butyl (6-((4-chloro-3-methylphenyl)amino)-6-oxo-hexane-1,5-diyl)(S)-dicarbamate (Intermediate 4A)

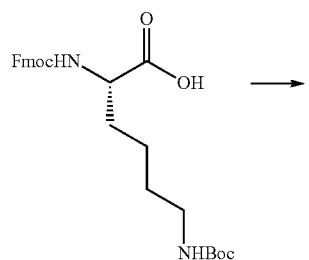

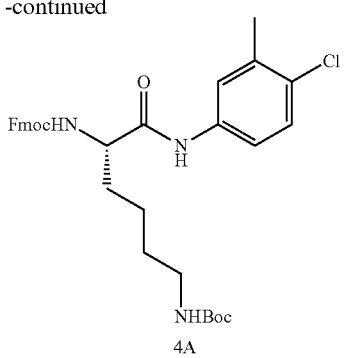

A stirring solution of $N^2$-(((9H-fluoren-9-yl)methoxy)carbonyl)-$N^6$-(tert-butoxycarbonyl)-L-lysine (2.0 g, 4.3 mmol), 4-chloro-3-methylaniline (0.58 g, 4.1 mmol) and DIEA (1.77 mL, 10.2 mmol) in THF (15 mL) was cooled to 0° C. A solution of HATU (1.62 g, 4.3 mmol) in THF (1 mL) was added dropwise over 5 min. The reaction mixture was allowed to warm to rt and stirred for 2 h, then diluted with EA and washed with $NaHCO_3$ (sat. aqueous) The aqueous fraction was back-extracted with EA. The combined organic fractions were dried ($Na_2SO_4$) then concentrated to provide 2 g (83%) of crude Intermediate 4A. LCMS (m/z) calculated for $C_{33}H_{38}ClN_3O_5$: 591.3; found 592.0 [M+H]$^+$, $t_R$=6.4 min (Method 2).

Step 4B: Synthesis of tert-butyl (S)-(5-amino-6-((4-chloro-3-methylphenyl)amino)-6-oxohexyl)carbamate (Intermediate 4B)

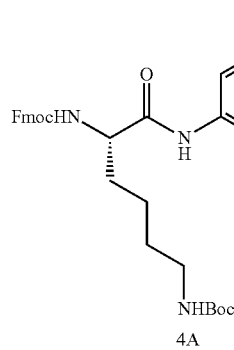

4A

A solution of 50% piperidine in DMF (1 mL) was added to a solution of Intermediate 4A (2.0 g, 3.4 mmol) DCM (25 mL) and the mixture was stirred for 30 min at rt. The reaction mixture was concentrated in vacuo and the residue (Intermediate 4B) was directly used for the next step without purification. LCMS (m/z) calculated for $C_{18}H_{27}ClN_3O_3$: 369.2; found 370.0 [M+H]$^+$, $t_R$=4.5 min (Method 2).

Step 4C: Synthesis of tert-butyl ((S)-6-((4-chloro-3-methylphenyl)amino)-6-oxo-5-((S)-2-(4-oxo-4-phenylbutanoyl)-1,2,3,4-tetrahydroisoquinoline-3-carboxamido) hexyl) carbamate. (Intermediate 4C)

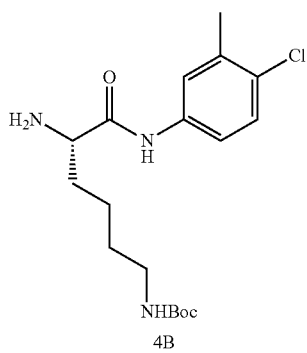

4B

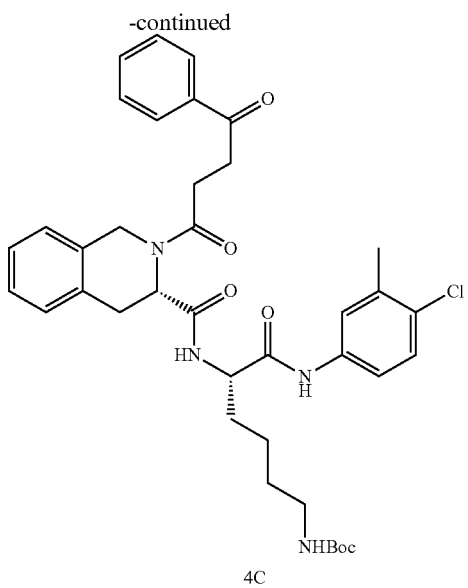

4C

A stirring solution of Intermediate 1B (80 mg, 0.24 mmol), Intermediate 4B (88 mg, 0.24 mmol) and DIEA (0.87 mL, 0.6 mmol) in THF (5 mL) was cooled to 0° C. A solution of HATU (90 mg, 0.24 mmol) in THF (1 mL) was added dropwise over 5 min. The reaction mixture was allowed to warm to rt and stirred for 2 h, then diluted with EA and washed with NaHCO$_3$ (sat. aqueous). The aqueous fraction was back-extracted with EA. The combined organic fractions were dried (Na$_2$SO$_4$) then concentrated to provide crude Intermediate 4C. LCMS (m/z) calculated for $C_{38}H_{45}ClN_4O_6$: 688.3; found 689.0 [M+H]$^+$, $t_R$=4.5 min (Method 2).

Step 4D: Synthesis of (S)—N—((S)-6-amino-1-((4-chloro-3-methylphenyl)amino)-1-oxohexan-2-yl)-2-(4-oxo-4-phenylbutanoyl)-1,2,3,4-tetrahydroisoquinoline-3-carboxamide (Compound 4-2)

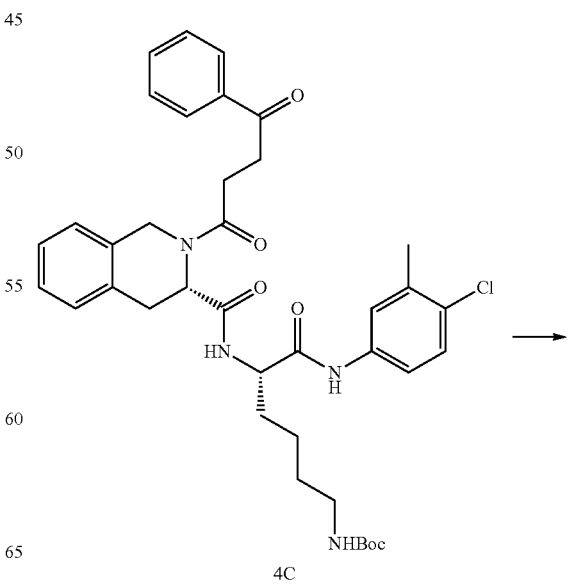

4C

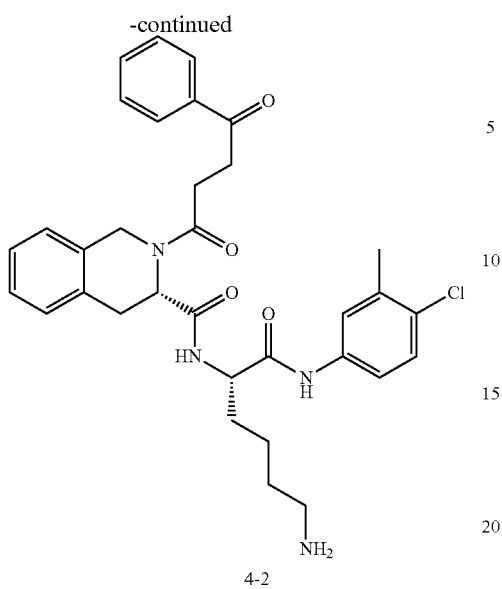

4-2

A solution of 4N HCl in dioxane (0.5 mL, 2 mmol) was added to a solution of Intermediate 4C (100 mg, 0.15 mmol) in DCM (2 mL). After stirring overnight at rt, the reaction mixture was concentrated in vacuo and purified by RP-prep HPLC to provide Compound 4-2. LCMS [m/z] calculated for $C_{33}H_{37}ClN_4O_4$: 588.3; found: 589.0 [M+H]$^+$, $t_R$=11.05 min (Method 1).

Following the procedures as set forth in Example 4 above, the compounds of the following Table 4 were prepared using the appropriate $R^1$, $R^{3a}$ and $R^{3b}$ reagents.

TABLE 4

| Cmpd No. | $R^1$ | $R^{3a}$ | $R^{3b}$ | *1 Core Stereo-chem. | *2 $R^{3a}/R^{3b}$ Stereo-chem. | MS Calc | MS Obs (MH)$^+$ | LCMS Ret. (min) | Purity Method |
|---|---|---|---|---|---|---|---|---|---|
| 4-2 | ⌬-Cl (4-Cl-3-Me-phenyl) | -(CH$_2$)$_4$NH$_2$ | H | R | R | 588.3 | 589.0 | 11.05 | 1 |

TABLE 4-continued

| Cmpd No. | R¹ | R³ᵃ | R³ᵇ | *¹ Core Stereo-chem. | *² R³ᵃ/R³ᵇ Stereo-chem. | MS Calc | MS Obs (MH)⁺ | LCMS Ret. (min) | Purity Method |
|---|---|---|---|---|---|---|---|---|---|
| 4-3 | 4-Cl, 3-Me-phenyl | H | propyl-NH₂ | S | S | 574.2 | 575.0 | 10.97 | 1 |
| 4-4 | 4-Cl, 3-Me-phenyl | H | butyl-NHMe | S | S | 602.3 | 603.0 | 12.28 | 1 |
| 4-5 | 4-Cl, 3-Me-phenyl | indol-2-ylmethyl | H | S | R | 646.2 | 647.0 | 11.13 | 1 |
| 4-6 | 4-Cl, 3-Me-phenyl | H | pentyl-NH-iPr | S | S | 630.3 | 631.0 | 12.43 | 1 |
| 4-7 | 4-Cl, 3-Me-phenyl | H | piperidin-4-yl | S | Racemic | 600.3 | 601.3 | 12.66 | 1 |
| 4-8 | 4-Cl, 3-Me-phenyl | H | (1H-imidazol-4-yl)methyl | S | S | 597.2 | 598.0 | 12.3 | 1 |

TABLE 4-continued

| Cmpd No. | R¹ | R³ᵃ | R³ᵇ | *¹ Core Stereo-chem. | *² R³ᵃ/R³ᵇ Stereo-chem. | MS Calc | MS Obs (MH)⁺ | LCMS Ret. (min) | Purity Method |
|---|---|---|---|---|---|---|---|---|---|
| 4-9 | 4-Cl, 3-Me-phenyl | -(CH₂)₄-NH₂ | Me | S | R | 602.3 | 604.0 | 12.52 | 1 |
| 4-10 | 4-Cl, 3-Me-phenyl | Me | -(CH₂)₄-NH₂ | S | S | 602.3 | 604.0 | 12.32 | 1 |
| 4-11 | 4-Cl, 3-Me-phenyl | H | piperidin-4-ylmethyl | S | Racemic | 614.3 | 615.0 | 12.22 | 1 |
| 4-12 | 4-Cl, 3-Me-phenyl | piperidinyl | piperidinyl | S | NA | 586.2 | 587.2 | 12.21 | 1 |
| 4-13 | 3-HO, 4-Cl, 5-Cl-phenyl | H | -(CH₂)₂-NH₂ | S | Racemic | 596.2 | 599 | 6.04 | 4 |
| 4-14 | 2-F, 3-Cl, 4-Cl-phenyl | piperidinyl | piperidinyl | S | NA | 624.2 | 626.9 | 6.59 | 4 |
| 4-15 | 4-Cl, 5-Cl-pyridin-2-yl | H | -(CH₂)₂-NH₂ | S | S | 581.2 | 582 | 3.98 | 5 |

TABLE 4-continued
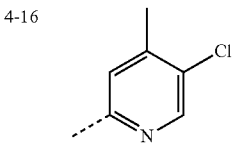
| Cmpd No. | R[1] | R[3a] | R[3b] | *[1] Core Stereo-chem. | *[2] R[3a]/R[3b] Stereo-chem. | MS Calc | MS Obs (MH)+ | LCMS Ret. (min) | Purity Method |
|---|---|---|---|---|---|---|---|---|---|
| 4-16 |  |  | 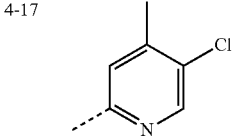 | S | S | 561.2 | 562 | 3.78 | 5 |
| 4-17 |  | 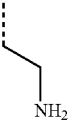 | 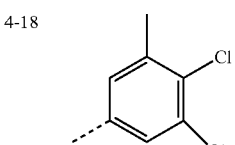 | R | S | 561.2 | 562.1 | 4.12 | 5 |
| 4-18 |  | 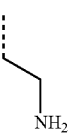 | 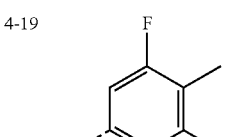 | S | S | 594.2 | 595.3 | 4.76 | 5 |
| 4-19 |  | 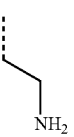 | 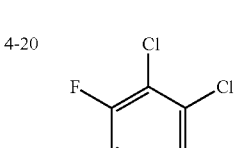 | S | S | 578.2 | 579.3 | 4.61 | 5 |
| 4-20 |  |  | | S | S | 614.2 | 615.2 | 3.99 | 5 |

471
Scheme 5
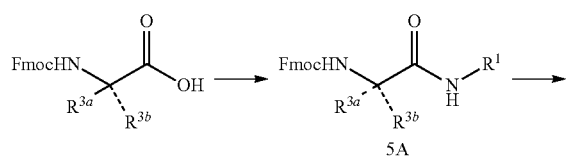
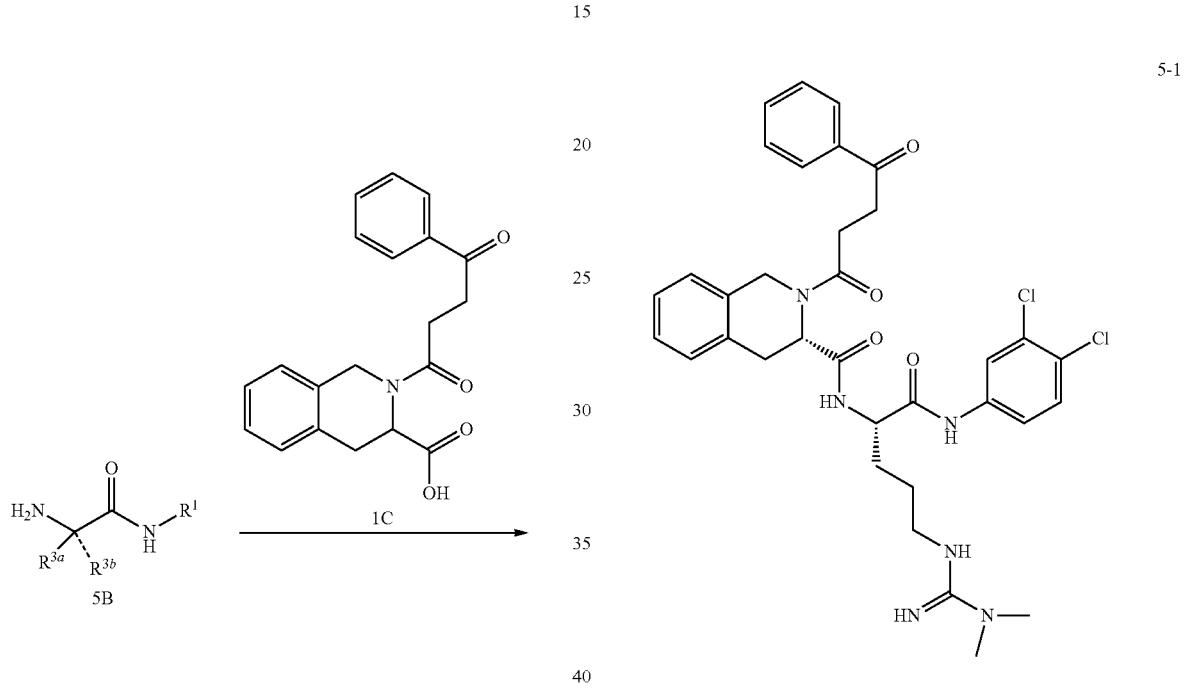
472
Example 5
Synthesis of (S)—N—((S)-1-((3,4-dichlorophenyl)amino)-5-(3,3-dimethylguanidino)-1-oxopentan-2-yl)-2-(4-oxo-4-phenylbutanoyl)-1,2,3,4-tetrahydroisoquinoline-3-carboxamide (Compound 5-1)
Step 5A. Synthesis of (9H-fluoren-9-yl)methyl (S)-(1-(3,4-dichlorophenyl)amino)-5-(3,3-dimethylguanidino)-1-oxopentan-2-yl)carbamate (Intermediate 5A)
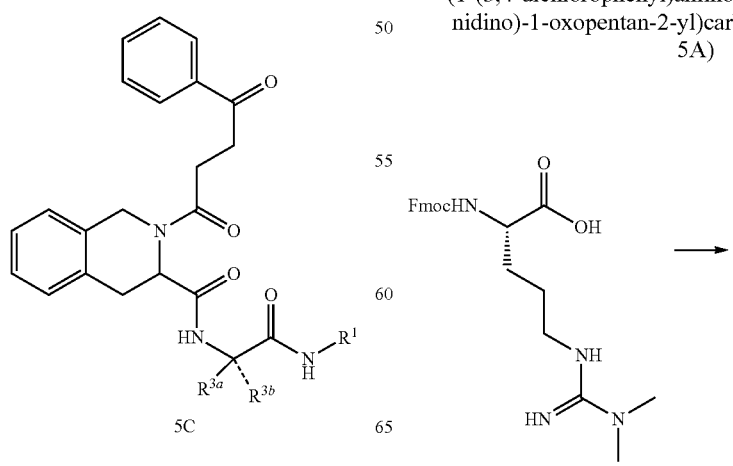

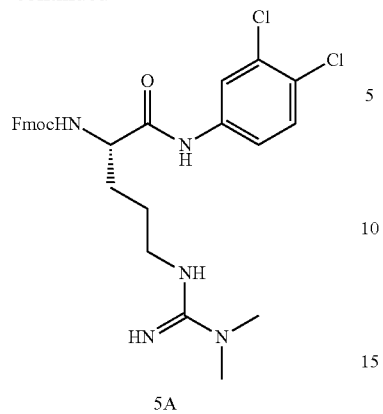

5A

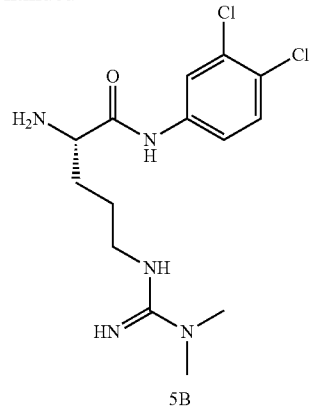

5B

A stirring solution of N²-(((9H-fluoren-9-yl)methoxy)carbonyl)-Nω,Nω-dimethyl-L-arginine (0.20 g, 0.47 mmol), 3,4-dichloroaniline (0.076 g, 0.47 mmol) and DIEA (0.2 mL, 1.2 mmol) in THF (8 mL) was cooled to 0° C. A solution of HATU (0.18 g, 0.47 mmol) in THF (1 mL) was added dropwise over 5 min. The reaction mixture was allowed to warm to rt and stirred for 2 h, then diluted with EA and washed with NaHCO₃ (sat. aqueous) The aqueous fraction was back-extracted with EA. The combined organic fractions were dried (Na₂SO₄) then concentrated to provide crude Intermediate 5A. LCMS (m/z) calculated for $C_{29}H_{31}Cl_2N_5O_3$: 567.2; found 568.0 [M+H]⁺, $t_R$=5.2 (Method 2).

A solution of 50% piperidine in DMF (10 mL) was added to a solution of Intermediate 5A (70 mg, 0.12 mmol) in DCM (5 mL) and the mixture was stirred for 30 min at rt. The reaction mixture was concentrated in vacuo and the residue (Intermediate 5B) was directly used for next step without purification. LCMS (m/z) calculated for $C_{14}H_{21}Cl_2N_5O$: 345.1; found 346.0 [M+H]⁺, $t_R$=2.7 min (Method 2).

Step 5B. Synthesis of (S)-2-amino-N-(3,4-dichlorophenyl)-5-(3,3-dimethylguanidino) pentanamide (Intermediate 5B)

Step 5C. Synthesis of (S)—N—((S)-1-((3,4-dichlorophenyl) amino)-5-(3,3-dimethylguanidino)-1-oxopentan-2-yl)-2-(4-oxo-4-phenylbutanoyl)-1,2,3,4-tetrahydroisoquinoline-3-carboxamide. (Compound 5-1)

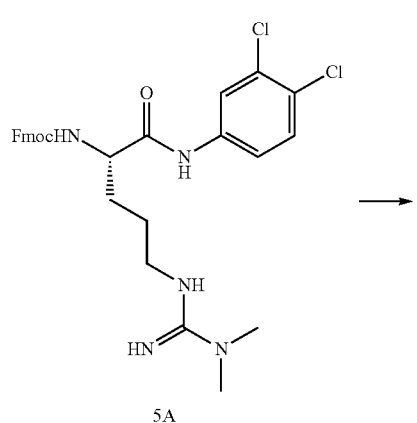

5A

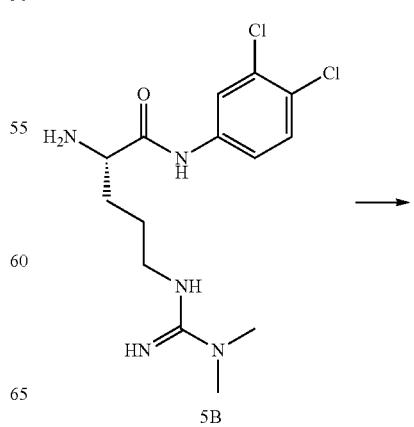

5B

-continued

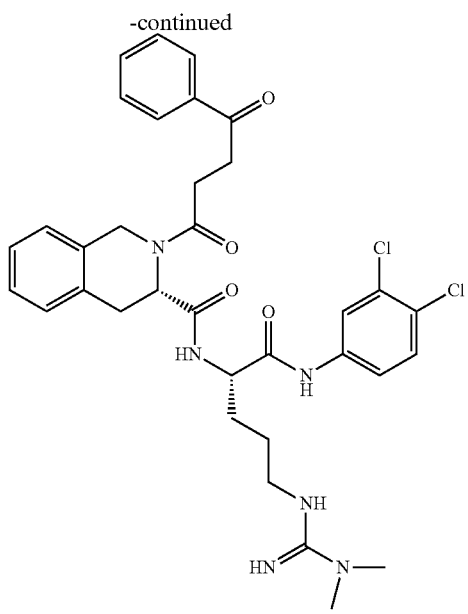

5-1

A stirring solution of Intermediate 1D (30 mg, 0.09 mmol), Intermediate 5B (31 mg, 0.09 mmol) and DIEA (0.054 mL, 0.31 mmol) in THF (10 mL) was cooled to 0° C. A solution of HATU (36 mg, 0.09 mmol) in THF (8 mL) was added dropwise over 5 min. The reaction mixture was allowed to warm to rt and stirred for 2 h, then diluted with EA and washed with NaHCO$_3$ (sat. aqueous) The aqueous fraction was back-extracted with EA. The combined organic fractions were dried (Na$_2$SO$_4$) then concentrated to provide crude material which was purified by RP-Prep HPLC to provide product Compound 5-1. LCMS [m/z] calculated for C$_{34}$H$_{38}$Cl$_2$N$_6$O$_4$: 665.6; found 666.9[M+H]$^+$, t$_R$=11.56 min (Method 1).

Following the procedures as set forth in Example 5 above, the compounds of the following Table 5 were prepared using the appropriate R$^1$, R$^{3a}$ and R$^{3b}$ reagents.

TABLE 5

| Cmpd # | R$^1$ | R$^{3a}$ | R$^{3b}$ | *1 Core Stereochem. | *2 R$^{3a}$/R$^{3b}$ Stereochem. | MS Calc | MS Obs (MH)$^+$ | LCMS Ret. (min) | Purity Method |
|---|---|---|---|---|---|---|---|---|---|
| 5-1 | 3,4-diCl-phenyl | H | propyl-NH-C(=NH)-N(CH$_3$)$_2$ | S | S | 664.2 | 666.9 | 11.56 | 1 |
| 5-2 | 4-Cl-3-Me-phenyl | H | (1-methyl-1H-imidazol-5-yl)methyl | S | S | 611.2 | 612 | 12.45 | 1 |

TABLE 5-continued
| Cmpd # | R¹ | R³ᵃ | R³ᵇ | *¹ Core Stereo-chem. | *² R³ᵃ/R³ᵇ Stereo-chem. | MS Calc | MS Obs (MH)⁺ | LCMS Ret. (min) | Purity Method |
|---|---|---|---|---|---|---|---|---|---|
| 5-3 | 4-Cl-3-methylphenyl | H | thiazol-5-ylmethyl | S | S | 614.2 | 615 | 13.6 | 1 |
| 5-4 | 4-Cl-3-methylphenyl | H | 2-morpholinoethyl | S | S | 630.3 | 631 | 4.5 | 5 |
Scheme 6
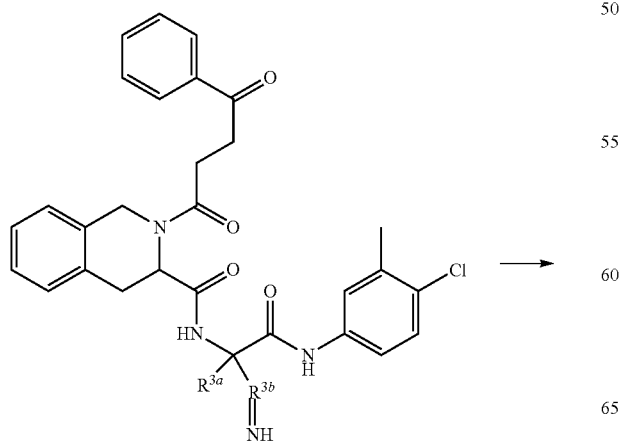

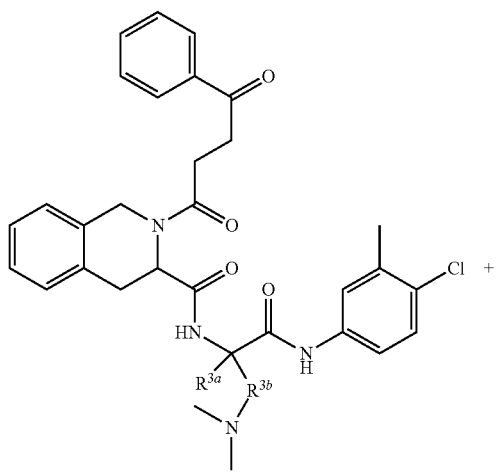

Example 6

Synthesis of (S)—N—((S)-1-((4-chloro-3-methylphenyl)amino)-3-(1-methylpiperidin-4-yl)-1-oxo-propan-2-yl)-2-(4-oxo-4-phenylbutanoyl)-1,2,3,4-tetrahydroisoquinoline-3-carboxamide (Compound 6-1) and 4-((S)-3-((4-chloro-3-methylphenyl)amino)-3-oxo-2-((S)-2-(4-oxo-4-phenylbutanoyl)-1,2,3,4-tetrahydroisoquinoline-3-carboxamido)propyl)-1,1-dimethylpiperidin-1-ium iodide (Compound 6-2)

Compound 4-11 (15 mg, 0.024 mmol) was dissolved in DMF (1 mL). $Cs_2CO_3$ (20 mg, 0.06 mmol) was added and the mixture was degassed ($N_2$ bubbling). MeI (3.5 mg, 0.024 mmol) was added and the reaction mixture was stirred for 1 h, protected from light. The reaction mixture was concentrated and purified by RP-HPLC to provide both Compound 6-1, LCMS [m/z] calculated for $C_{36}H_{41}ClN_4O_4$: 628.3; found 629.0 [M+H]$^+$, $t_R$=12.33 min (Method 1) and Compound 6-2 LCMS [m/z] calculated for $C_{37}H_{44}ClN_4O_4$: 643.3; found 643.0 [M+H]$^+$, $t_R$=12.34 min (Method 1).

Following the procedures as set forth in Example 6 above, the compounds of the following Table 6 were prepared from the appropriate amine starting material.

TABLE 6

| Compound Number | R³ᵃ | R³ᵇ | R³ᵃ/R³ᵇ Stereo-chemistry | MS Calc | MS Obs (MH)⁺ | LCMS Ret. (min) | Purity Method |
|---|---|---|---|---|---|---|---|
| 6-1 | ⋯H | (1-methylpiperidin-4-yl)methyl | Racemic | 628.3 | 629.0 | 12.33 | 1 |
| 6-2 | ⋯H | (1,1-dimethylpiperidin-4-yl)methyl iodide | Racemic | 643.3 | 643.0 | 12.34 | 1 |
| 6-3 | ⋯H | 4-(trimethylammonio)butyl iodide | S | 631.3 | 631.0 | 12.17 | 1 |
| 6-4 | 1-methylpiperidin-4-yl | 1-methylpiperidin-4-yl | No stereo-center | 600.3 | 600.8 | 12.14 | 1 |
| 6-5 | ⋯H | 1-methylpiperidin-4-yl | Racemic | 614.3 | 615.0 | 12.63 | 1 |
| 6-6 | ⋯H | 1,1-dimethylpiperidin-4-yl iodide | Racemic | 629.3 | 629.0 | 12.38 | 1 |

TABLE 6-continued
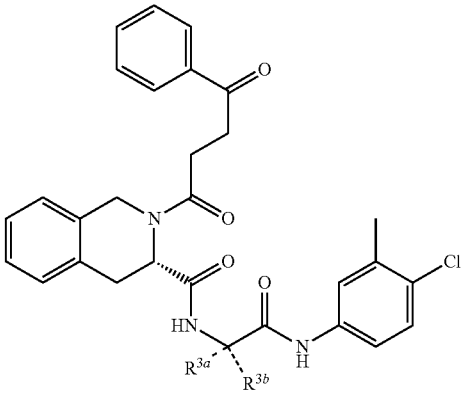
| Compound Number | $R^{3a}$ | $R^{3b}$ | $R^{3a}/R^{3b}$ Stereo-chemistry | MS Calc | MS Obs $(MH)^+$ | LCMS Ret. (min) | Purity Method |
|---|---|---|---|---|---|---|---|
| 6-7 | H | (trimethylammonium ethyl, I⁻) | S | 603.3 | 603.3 | 12.11 | 1 |
Scheme 7
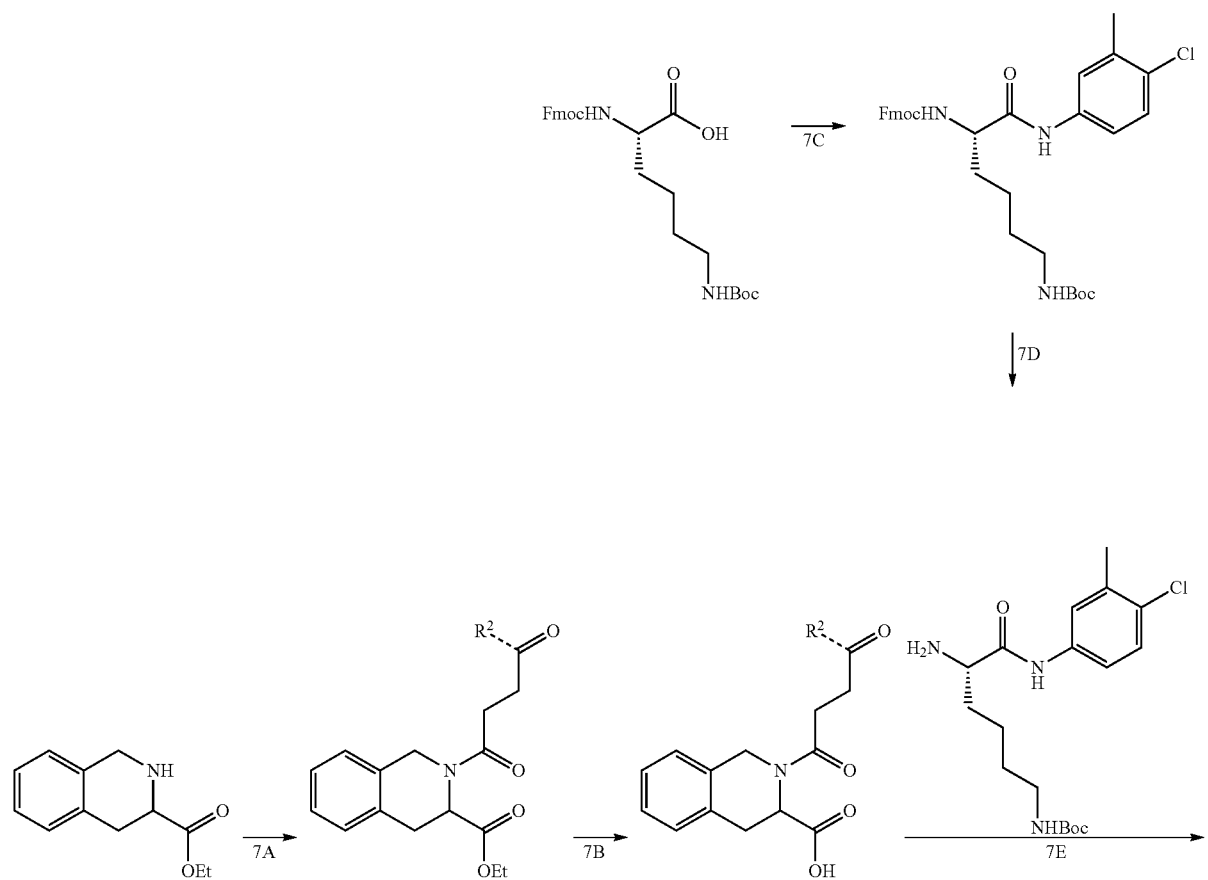

-continued
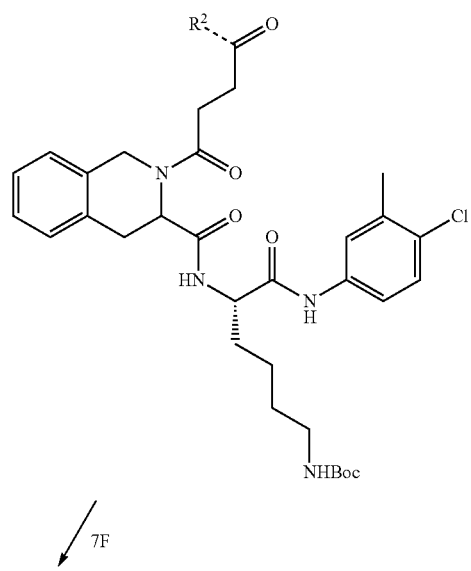
↙ 7F
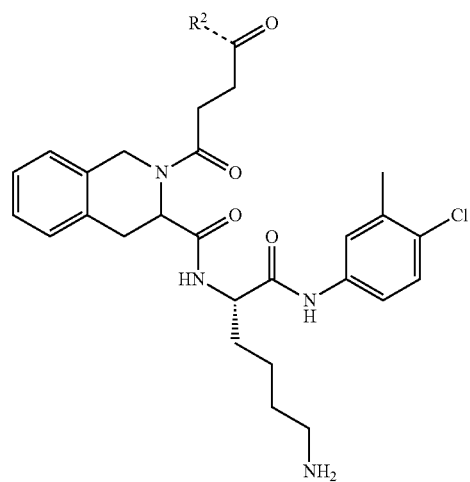

Example 7

Synthesis of N—((S)-6-amino-1-((4-chloro-3-methylphenyl)amino)-1-oxohexan-2-yl)-2-(4-(4-fluorophenyl)-4-oxobutanoyl)-1,2,3,4-tetrahydroisoquinoline-3-carboxamide (Compound 7-1)

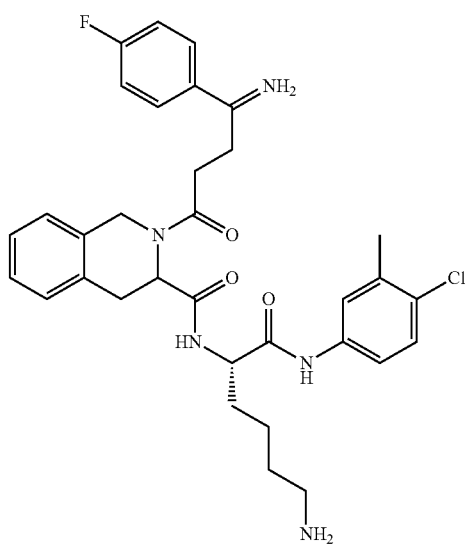

Step 7A. Synthesis of 2-(4-(4-fluorophenyl)-4-oxobutanoyl)-1,2,3,4-tetrahydroisoquinoline-3-carboxylic Acid (Intermediate 7A)

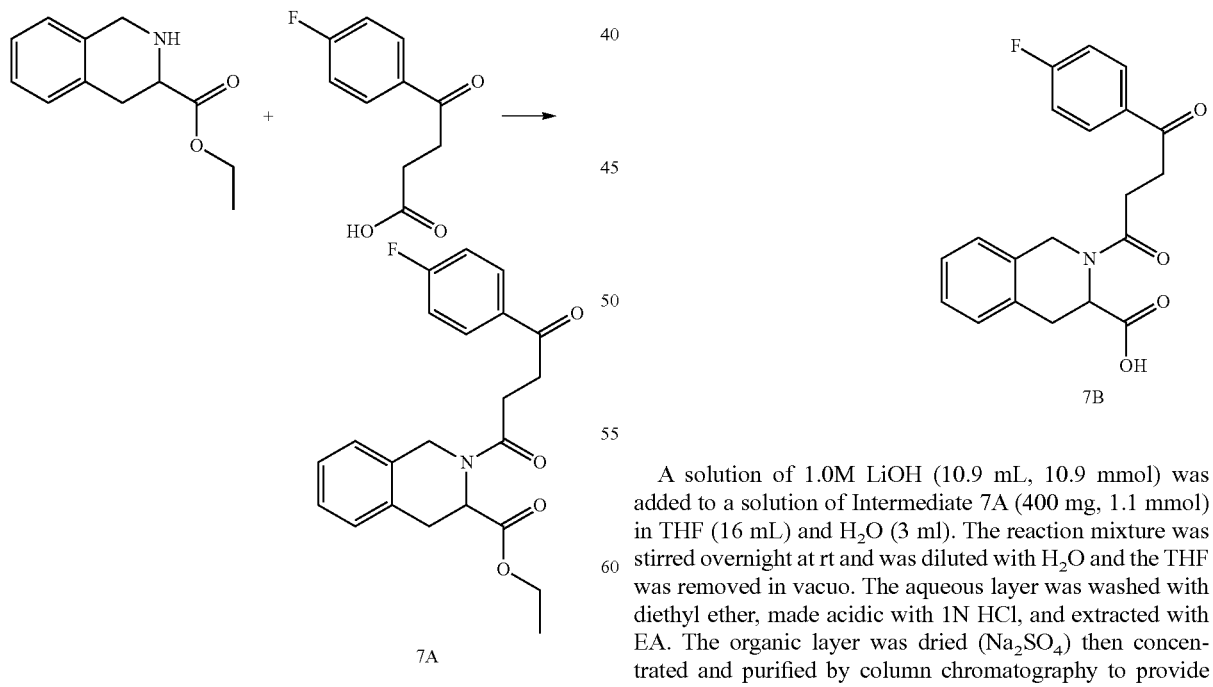

A stirring solution of ethyl 1,2,3,4-tetrahydroisoquinoline-3-carboxylate HCl (680 mg, 2.8 mmol), 4-(4-fluorophenyl)-4-oxobutanoic acid (500 mg, 2.55 mmol) and DIEA (1.6 ml, 8.9 mmol) in THF (8 mL) and DMF (2 mL) was cooled to 0° C. HATU (1.0 g, 2.7 mmol) was added over 5 min and the reaction mixture was allowed to warm to rt and stirred for 2 h. The reaction mixture was diluted with EA and washed with NaHCO$_3$ (sat. aqueous). The aqueous fraction was back-extracted with EA and the combined organic fractions were dried (Na$_2$SO$_4$), then concentrated onto celite and purified by column chromatography (EA/Hexane) to provide Intermediate 7A (980 mg, 46%). LCMS [m/z] calculated for C$_{22}$H$_{22}$FNO$_4$: 383.2; found 384.0 [M+H]$^+$, t$_R$=4.96 min (Method 2).

Step 7B. Synthesis of 2-(4-(4-fluorophenyl)-4-oxobutanoyl)-1,2,3,4-tetrahydroisoquinoline-3-carboxylic Acid (Intermediate 7B)

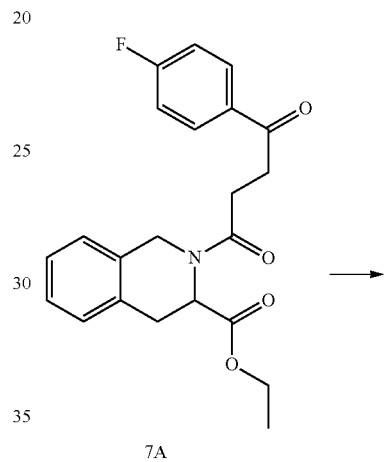

A solution of 1.0M LiOH (10.9 mL, 10.9 mmol) was added to a solution of Intermediate 7A (400 mg, 1.1 mmol) in THF (16 mL) and H$_2$O (3 ml). The reaction mixture was stirred overnight at rt and was diluted with H$_2$O and the THF was removed in vacuo. The aqueous layer was washed with diethyl ether, made acidic with 1N HCl, and extracted with EA. The organic layer was dried (Na$_2$SO$_4$) then concentrated and purified by column chromatography to provide Intermediate 7B (250 mg, 66%). LCMS [m/z] calculated for C$_{20}$H$_{18}$FNO$_4$: 355.1; found 338.0 [M+H]$^+$, t$_R$=4.4 min (Method 2).

Step 7C. Synthesis of (9H-fluoren-9-yl)methyl tert-butyl (6-((4-chloro-3-methylphenyl)amino)-6-oxo-hexane-1,5-diyl)(S)-dicarbamate (Intermediate 7C)

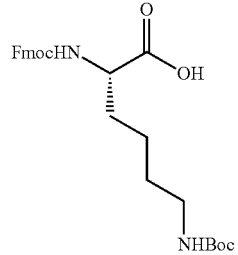

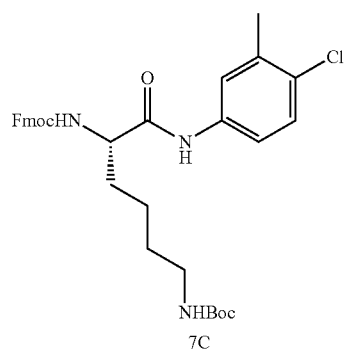

A stirring solution of $N^2$-(((9H-fluoren-9-yl)methoxy)carbonyl)-$N^6$-(tert-butoxycarbonyl)-L-lysine (4.0 g, 8.52 mmol), 4-chloro-3-methylaniline (1.2 g, 8.2 mmol) and DIEA (3.5 mL, 20.3 mmol) THF (20 mL) was cooled to 0° C. A solution of HATU (3.2 g, 8.5 mmol) in THF (2 mL) was added dropwise over 5 min and the mixture was allowed to warm to rt, stirred for 2 h, then diluted with EA and washed with NaHCO$_3$ (sat. aqueous). The aqueous fraction was back-extracted with EA and the combined organic fractions were dried (Na$_2$SO$_4$), concentrated and purified by column chromatography to provide 5 g of Intermediate 7C. LCMS (m/z) calculated for $C_{33}H_{38}ClN_3O_5$: 591.3; found 492.0 [M-Boc]$^+$, $t_R$=6.5 min (Method 2).

Step 7D. Synthesis of tert-butyl (S)-(5-amino-6-((4-chloro-3-methylphenyl)amino)-6-oxohexyl)carbamate (Intermediate 7D)

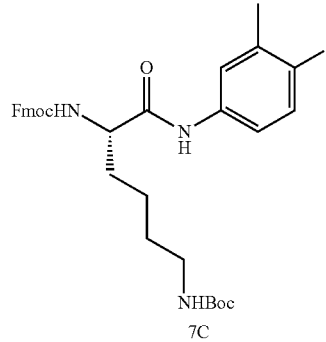

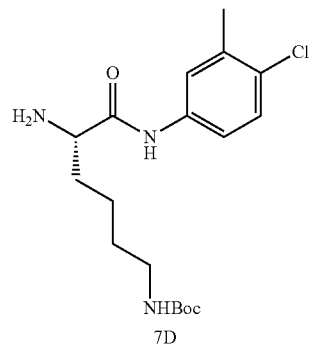

A solution of piperidine (1.8 g, 84.4 mmol) in DMF (1 mL) was added to a solution of Intermediate 7C (5 g, 8.44 mmol) in DCM (50 mL). The mixture is stirred for 30 min at rt then was concentrated in vacuo. The residue, Intermediate 7D, was directly used for next step without purification. LCMS (m/z) calculated for $C_{18}H_{28}ClN_3O_3$: 369.2; found 370.0 [M+H]$^+$, $t_R$=11.23 min (Method 1).

Step 7E. Synthesis of tert-butyl ((5S)-6-((4-chloro-3-methylphenyl)amino)-5-(2-(4-(4-fluorophenyl)-4-oxobutanoyl)-1,2,3,4-tetrahydroisoquinoline-3-carboxamido)-6-oxohexyl) carbamate (Intermediate 7E)

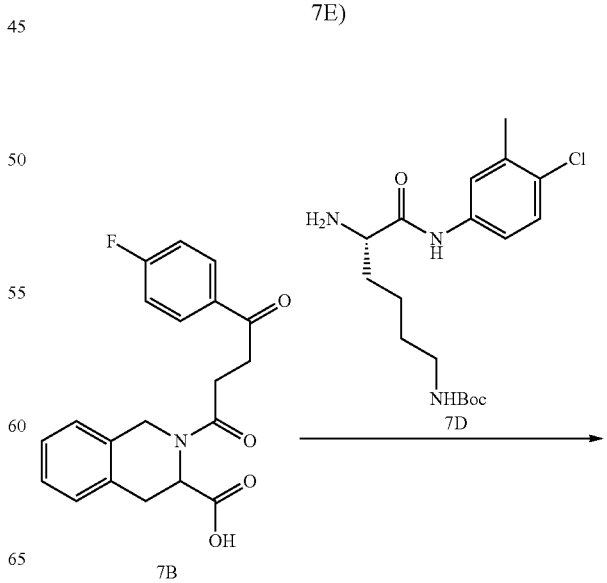

491

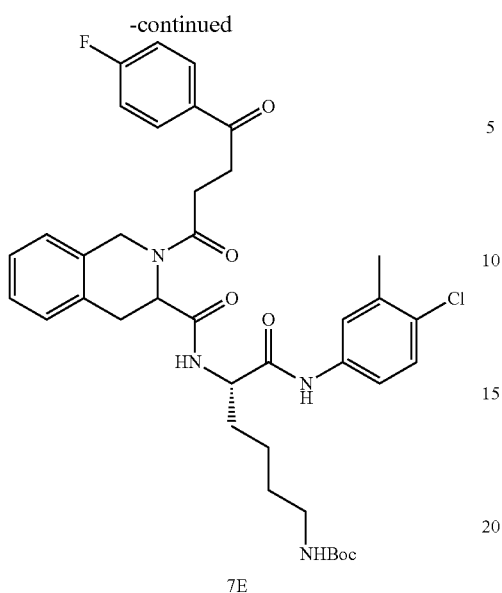

7E

492

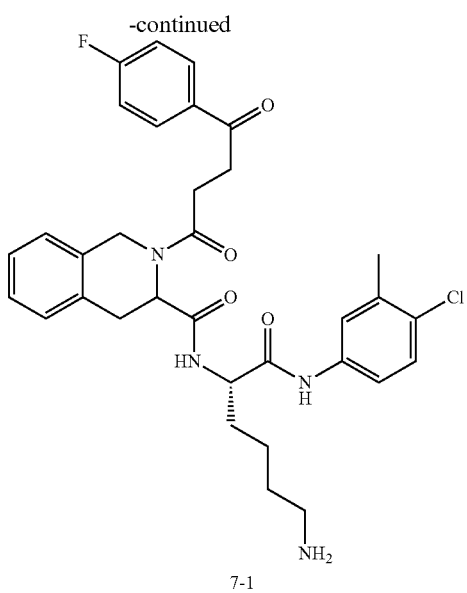

7-1

A stirring solution of Intermediate 7B (70 mg, 0.2 mmol), Intermediate 7D (70 mg, 0.2 mmol) and DIEA (0.083 mL, 0.47 mmol) in THF (2.5 mL) was cooled to 0° C. A solution of HATU (75 mg, 0.2 mmol) in THF (1 mL) was added dropwise over 5 min. The reaction mixture was allowed to warm to rt, stirred for 2 h, then diluted with EA and washed with NaHCO$_3$ (sat.). The aqueous fraction was back-extracted with EA. The combined organic fractions were dried (Na$_2$SO$_4$), concentrated and purified by column chromatography to provide Intermediate 7E (20 mg, 15%). LCMS [m/z] calculated for C$_{38}$H$_{44}$ClFN$_4$O$_4$: 706.3; found 707 [M+H]$^+$, t$_R$=12.3 min (Method 2).

Step 7F. Synthesis of N—((S)-6-amino-1-((4-chloro-3-methylphenyl)amino)-1-oxohexan-2-yl)-2-(4-(4-fluorophenyl)-4-oxobutanoyl)-1,2,3,4-tetrahydroisoquinoline-3-carboxamide (Compound 7-1)

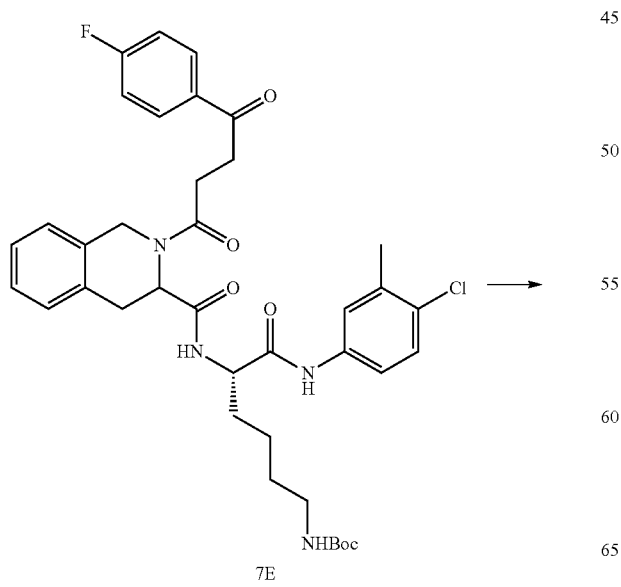

7E

A solution of 4N HCl in dioxane (0.5 ml, 2 mmol) was added to a solution of Intermediate 7E (20 mg, 0.03 mmol) in DCM (0.5 mL). The reaction mixture was allowed stirred for 2 h at rt then concentrated and purified by prep-HPLC to give Compound 7-1 (6 mg, 30%). LCMS [m/z] calculated for C$_{33}$H$_{36}$ClFN$_4$O$_4$: 606.2; found 607.0 [M+H]+, t$_R$=11.20 min. (Method 1).

Following the procedures as set forth in Example 7 above, the compounds of the following Table 7 were prepared using the appropriate R$^2$ reagents.

TABLE 7
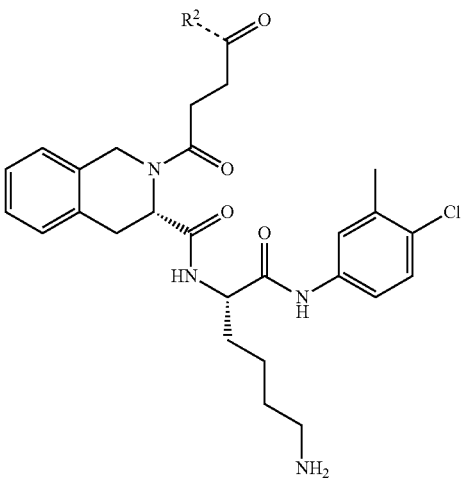
| Compound Number | R² | MS Calc | MS Obs (MH)⁺ | LCMS Retention (min) | Purity | Method |
|---|---|---|---|---|---|---|
| 7-1 | 4-F-phenyl | 606.2 | 607.0 | 11.20 | | 1 |
| 7-2 | 3-Cl-phenyl | 622.2 | 623.0 | 11.47 | | 1 |
| 7-3 | 4-F-3-methyl-phenyl | 620.3 | 621.0 | 11.49 | | 1 |
| 7-4 | 3,4-diF-phenyl | 624.2 | 625.0 | 11.2 | | 1 |
| 7-5 | 3-F-4-methyl-phenyl | 620.3 | 621.0 | 11.55 | | 1 |
| 7-6 | 3-(N,N-dimethylamino)-phenyl | 631.3 | 632.0 | 10.73 | | 1 |

TABLE 7-continued
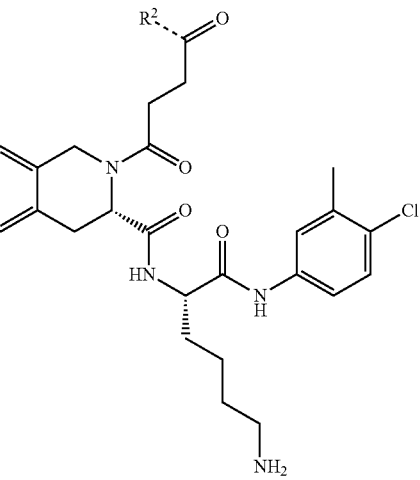
| Compound Number | R² | MS Calc | MS Obs (MH)⁺ | LCMS Retention (min) | Purity | Method |
|---|---|---|---|---|---|---|
| 7-7 | | 632.3 | 633.1 | Not recorded | | 1 |
| 7-8 | | 656.2 | 657.0 | 11.29 | | 1 |
| 7-9 | | 636.3 | 638.3 | 10.81 | | 1 |
Scheme 8
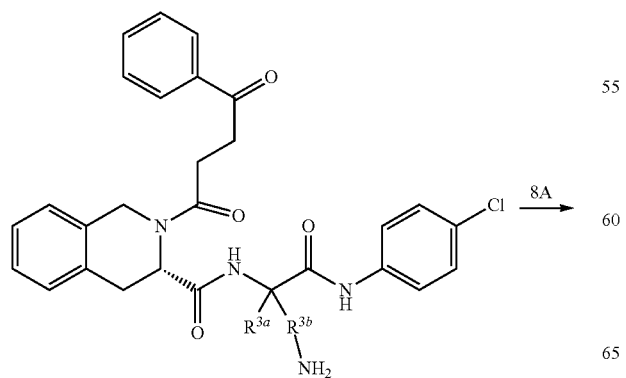

497
-continued

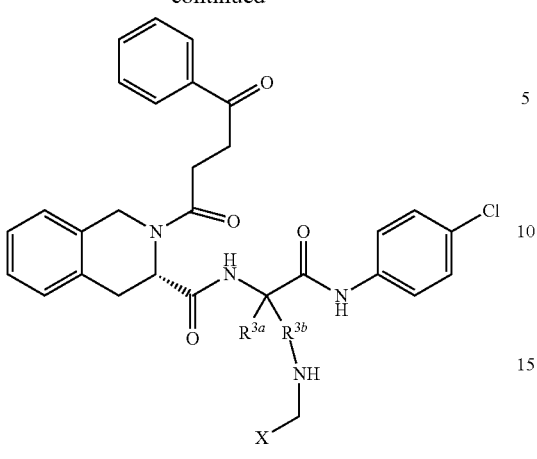

Example 8

Synthesis of (S)—N—((S)-1-((4-chloro-3-methylphenyl)amino)-4-(isobutylamino)-1-oxobutan-2-yl)-2-(4-oxo-4-phenylbutanoyl)-1,2,3,4-tetrahydroisoquinoline-3-carboxamide (Compound 8-1)

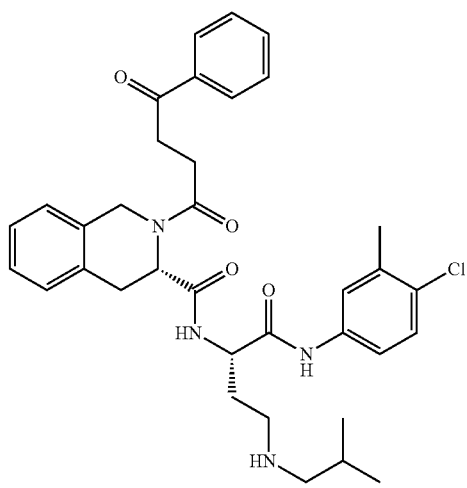

8-1

498

Step 8A. Synthesis of (S)—N—((S)-1-((4-chloro-3-methylphenyl)amino)-4-(isobutylamino)-1-oxobutan-2-yl)-2-(4-oxo-4-phenylbutanoyl)-1,2,3,4-tetrahydroisoquinoline-3-carboxamide (Compound 8-1)

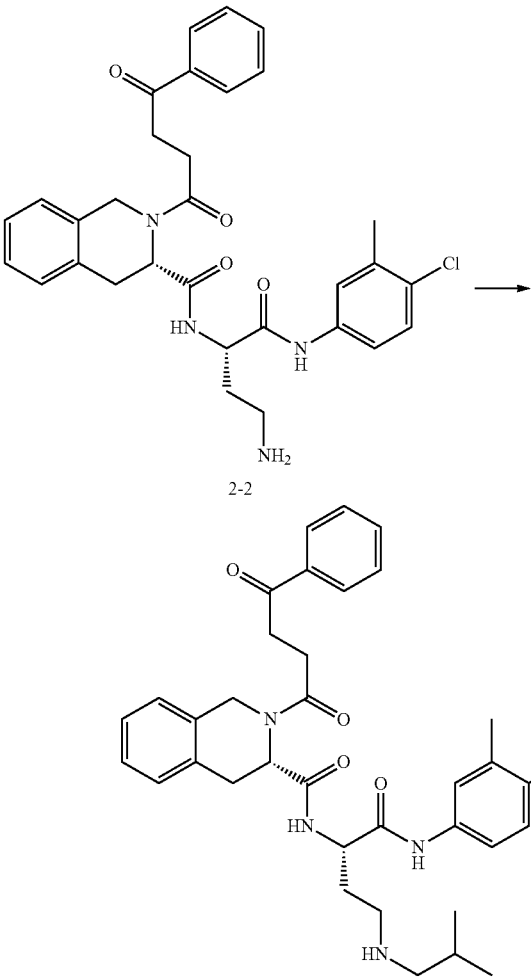

To a solution of Compound 2-2 (180 mg, 0.32 mmol) in DCE (5 mL) were added isobutyraldehyde (38.5 µL, 0.422 mmol) and AcOH (46.4 µL, 0.811 mmol). The reaction mixture was stirred at rt for 1 h. Sodium triacetoxyborohydride (172 mg, 0.811 mmol) was added and the reaction mixture was stirred at rt overnight. The reaction mixture was quenched with a saturated aqueous solution of NaHCO$_3$ (5 mL) and stirred for 20 min. DCM (10 mL) was added and the layers were separated using a phase sep-cartridge. The aqueous layer was re-extracted with DCM (10 mL). The combined organic phases were concentrated in vacuo. The crude product was purified by chromatography (MeOH/DCM with NH$_3$) to afford Compound 8-1 (25 mg, 0.04 mmol, 12% yield) as a white foam. LCMS [m/z] calculated for C$_{35}$H$_{41}$ClN$_4$O$_4$: 616.3; found 617.3 [M+H]$^+$, t$_R$=4.94 min (Method 3).

Following the procedures as set forth in Example 8 above, the following compounds of the following Table 8 were made using the appropriate amine and aldehyde building blocks.

TABLE 8
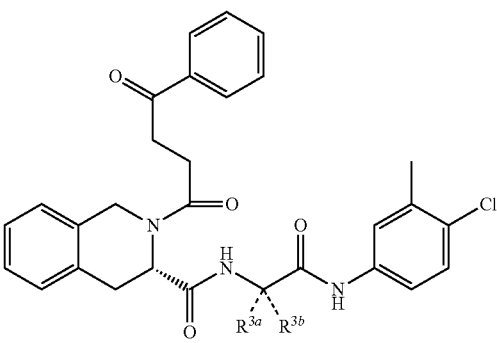
| Compound Number | R³ᵃ | R³ᵇ | R³ᵃ/R³ᵇ Stereo-chemistry | MS Calc | MS Obs (MH)⁺ | LCMS Retention (min) | Purity Method |
|---|---|---|---|---|---|---|---|
| 8-1 | H | CH₂CH₂NH-iBu | S | 616.3 | 617.3 | 4.94 | 3 |
| 8-2 | H | 1-isopropylpiperidin-4-yl | S | 642.3 | 643.4 | 4.63 | 3 |
| 8-3 | H | CH₂CH₂NH-iPr | S | 602.3 | 604.3 | 7.5 | 4 |
| 8-4 | H | CH₂CH₂NHEt | S | 588.3 | 589.3 | 4.49 | 5 |
| 8-5 | H | CH₂CH₂CH₂NH-iPr | S | 616.3 | 617.4 | 4.53 | 5 |
| 8-6 | H | CH₂CH₂NHCH₂CF₃ | S | 642.2 | 643.0 | 6.3 | 5 |

TABLE 8-continued
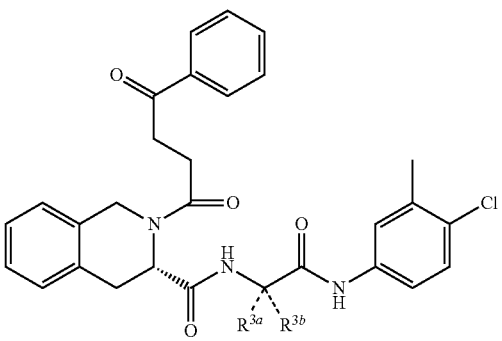
| Compound Number | $R^{3a}$ | $R^{3b}$ | $R^{3a}/R^{3b}$ Stereo-chemistry | MS Calc | MS Obs $(MH)^+$ | LCMS Retention (min) | Purity Method |
|---|---|---|---|---|---|---|---|
| 8-7 | H | | S | 640.2 | 642 | 7.3 | 3 |
Scheme 9
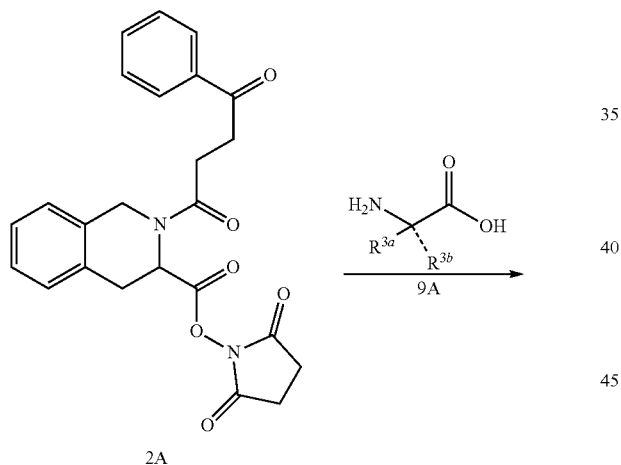
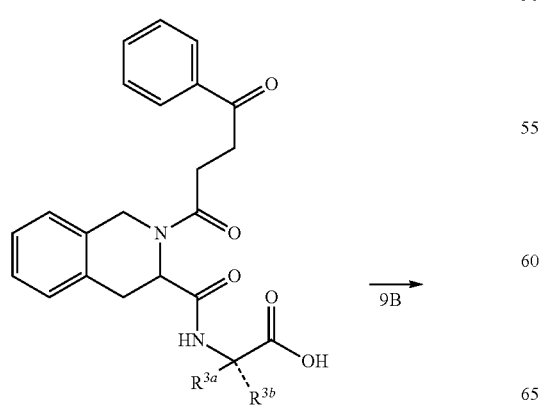

503
-continued

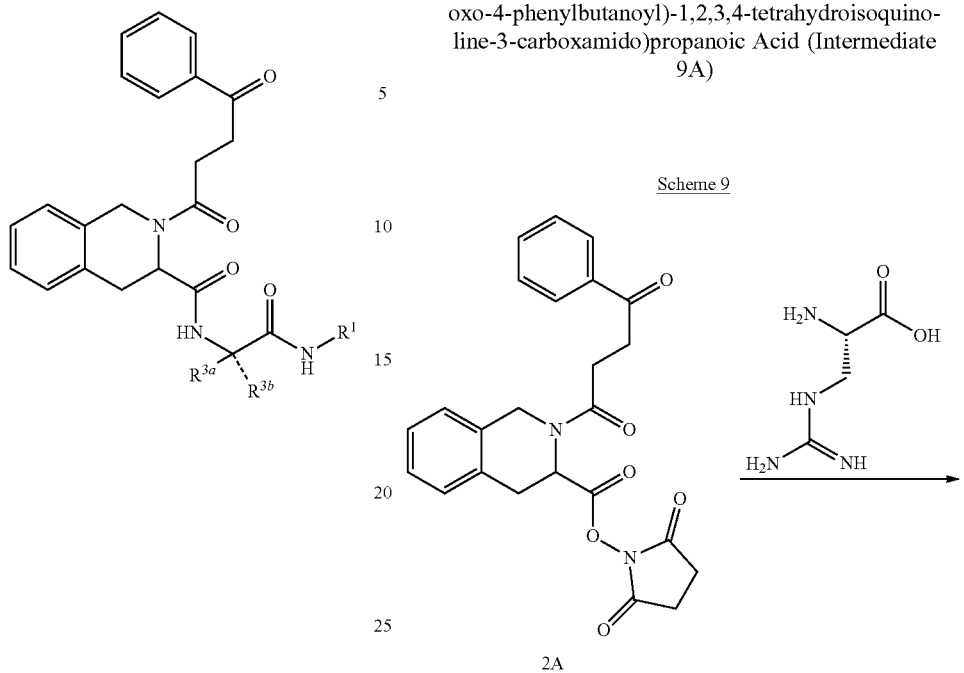

Example 9

Synthesis of (S)—N—((S)-1-((4-chloro-3-methylphenyl)amino)-3-guanidino-1-oxopropan-2-yl)-2-(4-oxo-4-phenylbutanoyl)-1,2,3,4-tetrahydroisoquinoline-3-carboxamide (Compound 9-1)

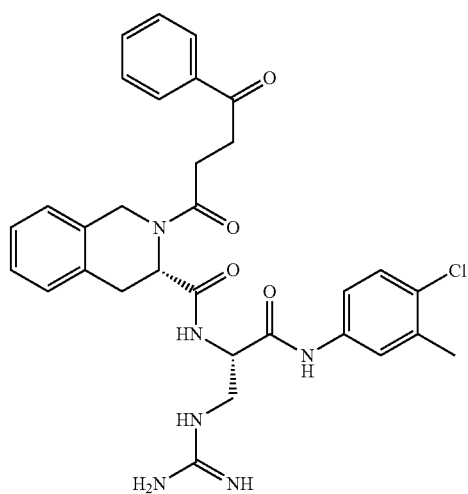

9-1

Step 9A. Synthesis of (2S)-3-guanidino-2-(2-(4-oxo-4-phenylbutanoyl)-1,2,3,4-tetrahydroisoquinoline-3-carboxamido)propanoic Acid (Intermediate 9A)

Scheme 9

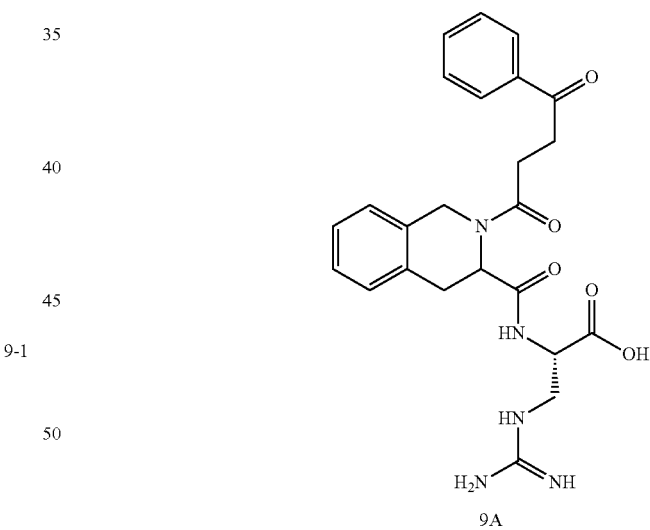

9A

A solution of Intermediate 2A (400 mg, 1.19 mmol), N-hydroxysuccinimide (191 mg, 1.66 mmol) and HATU (450 mg, 1.19 mmol) were stirred at rt for 2 h. H-guanidine (DAP)-OH (238 mg, 1.3 mmol) and DIEA (460 μL, 3.6 mmol) were added. After 2 h, the reaction mixture was quenched with 0.5 M HCl (aq), and extracted with DCM. The organic layer was washed with H$_2$O and brine, then dried (Na$_2$SO$_4$), filtered and concentrated to provide Intermediate 9A which was used without further purification.

Step 9B. Synthesis of (S)—N—((S)-1-((4-chloro-3-methylphenyl)amino)-3-guanidino-1-oxopropan-2-yl)-2-(4-oxo-4-phenylbutanoyl)-1,2,3,4-tetrahydroisoquinoline-3-carboxamide (Compound 9-1)

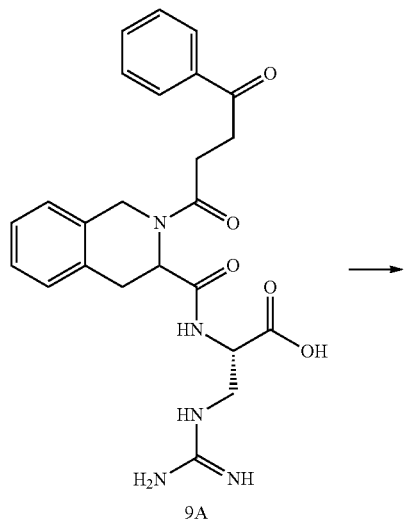

9A

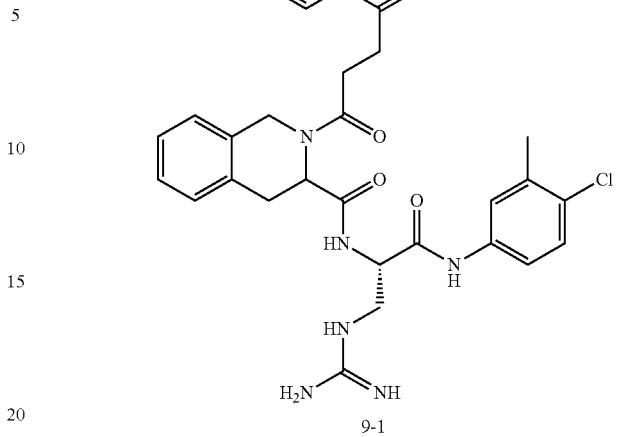

9-1

Intermediate 9A (250 mg, 0.54 mmol), 4-chloro-3-methylaniline (106 mg, 0.75 mmol) and DIEA (277 μL, 0.21 mmol) were stirred in DMF (1.25 mL). HATU (265 mg, 0.7 mmol) was added and the mixture was stirred overnight. The mixture was diluted with EA, washed with $H_2O$, $NaHCO_3$ and brine, then dried ($Na_2SO_4$), filtered, and concentrated. The resulting material was purified by RP-chromatography to provide 4.8 mg (1.5%) of Compound 9-1. LCMS [m/z] calculated for $C_{35}H_{41}ClN_4O_4$: 589.1; found 589.3 $[M+H]^+$, $t_R$=12.43 min (Method 2).

Scheme 10

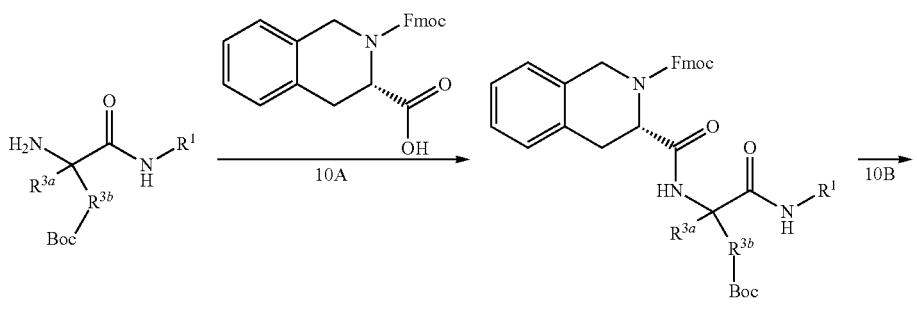

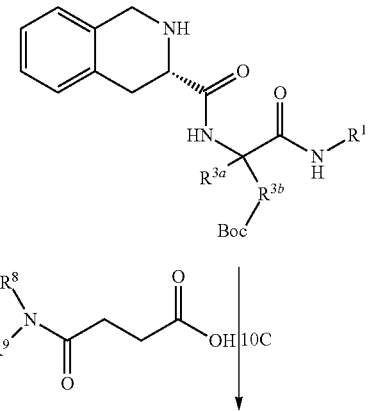

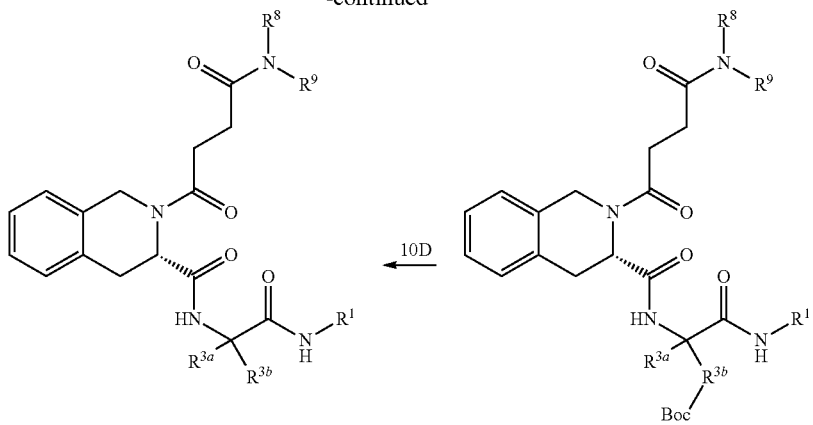

Example 10

Synthesis of (S)—N—((S)-4-amino-1-((4-chloro-3-methylphenyl)amino)-1-oxobutan-2-yl)-2-(4-oxo-4-(piperidin-1-yl)butanoyl)-1,2,3,4-tetrahydroisoquinoline-3-carboxamide (Compound 10-1)

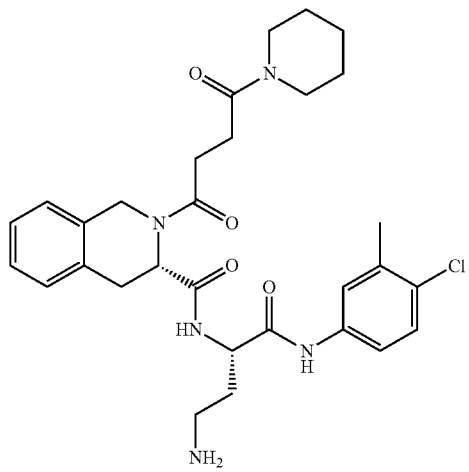

10-1

Step 10A. Synthesis of (9H-fluoren-9-yl)methyl (S)-3-(((S)-4-((tert-butoxycarbonyl)amino)-1-((4-chloro-3-methylphenyl)amino)-1-oxobutan-2-yl)carbamoyl)-3,4-dihydroisoquinoline-2(1H)-carboxylate (Intermediate 10A)

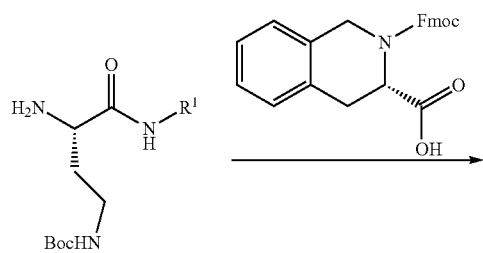

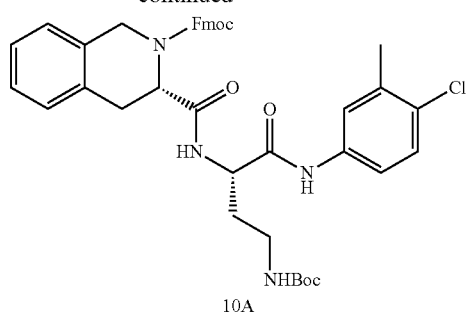

10A

Into a solution of (S)-tert-butyl (3-amino-4-((4-chloro-3-methylphenyl)amino)-4-oxobutyl)carbamate (2.06 g, 6.03 mmol) in DMF (20 mL) at 0° C. were added (S)-2-((((9H-fluoren-9-yl)methoxy)carbonyl)-1,2,3,4-tetrahydroisoquinoline-3-carboxylic acid (2.19 g, 5.48 mmol) and N-ethyl-N-isopropylpropan-2-amine (2.86 mL, 16.44 mmol). After 5 min, HATU (3.12 g, 8.22 mmol) was added portionwise and the mixture was stirred at 0° C. for 2 h. Water (20 mL) was added and the resulting white precipitate was collected by filtration. The solid was dissolved in DCM, dried (MgSO$_4$), filtered and concentrated to afford an orange oil. The crude product was purified by chromatography (EA/isohexane) to afford 3.2 g (77%) of Intermediate 10A as a white solid. $^1$H NMR (400 MHz, DMSO-d$_6$, 363 K) δ 9.49 (s, 1H), 7.92-7.81 (m, 2H), 7.75 (d, J=8.0 Hz, 1H), 7.68-7.56 (m, 2H), 7.47-7.37 (m, 3H), 7.37-7.28 (m, 3H), 7.26 (d, J=8.6 Hz, 1H), 7.23-7.09 (m, 4H), 6.15 (s, 1H), 4.75 (t, J=5.6 Hz, 1H), 4.64 (d, J=15.7 Hz, 1H), 4.53 (d, J=15.7 Hz, 1H), 4.48-4.20 (m, 4H), 3.22-3.09 (m, 2H), 2.95-2.77 (m, 2H), 2.27 (s, 3H), 1.93-1.78 (m, 1H), 1.71 (dtd, J=13.9, 8.0, 6.1 Hz, 1H), 1.36 (s, 9H).

Step 10B. Synthesis of tert-butyl ((S)-4-((4-chloro-3-methylphenyl)amino)-4-oxo-3-((S)-1,2,3,4-tetrahydroisoquinoline-3-carboxamido)butyl)carbamate (Intermediate 10B)

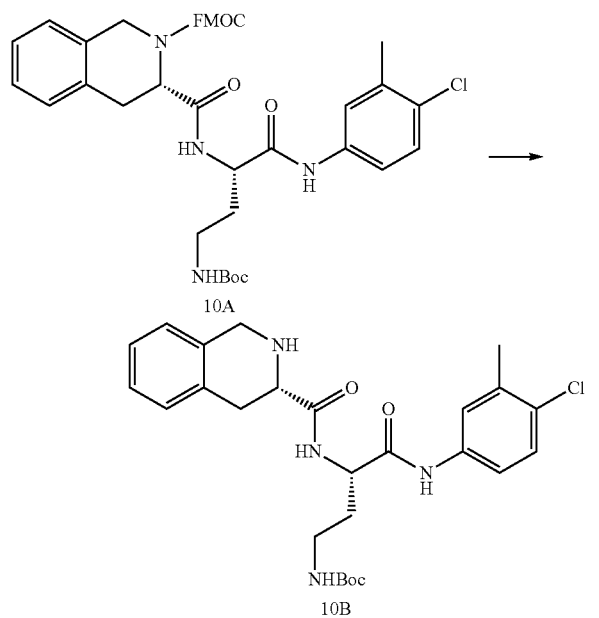

A solution of Intermediate 10A (3.2 g, 4.4 mmol) in DCM (15 mL) was treated with diethylamine (15 mL). After 1 h, the reaction mixture was concentrated, resuspended in toluene and concentrated (2×). The resulting crude product was purified by chromatography (MeOH, 0.3% NH$_3$/DCM) to afford 1.66 g (75%) of Intermediate 10B as a white solid. LCMS [m/z] calculated for C$_{26}$H$_{33}$ClN$_4$O$_4$: 500.2; found 501.3 [M+H]$^+$, t$_R$=1.72 min (Method 4). $^1$H NMR (400 MHz, DMSO-d$_6$) δ 10.15 (s, 1H), 8.14 (d, J=8.0 Hz, 1H), 7.63-7.54 (m, 1H), 7.45 (dd, J=8.6, 2.6 Hz, 1H), 7.35 (d, J=8.7 Hz, 1H), 7.11 (d, J=2.8 Hz, 3H), 7.08-7.01 (m, 1H), 6.75 (t, J=5.5 Hz, 1H), 4.45 (q, J=7.6 Hz, 1H), 3.99-3.81 (m, 2H), 3.49 (dd, J=10.0, 4.7 Hz, 1H), 3.06-2.86 (m, 3H), 2.82-2.58 (m, 2H), 2.30 (s, 3H), 1.96-1.66 (m, 2H), 1.36 (s, 9H).

Step 10C. Synthesis of tert-butyl ((S)-4-((4-chloro-3-methylphenyl)amino)-4-oxo-3-((S)-2-(4-oxo-4-(piperidin-1-yl)butanoyl)-1,2,3,4-tetrahydroisoquinoline-3-carboxamido) butyl) carbamate (Intermediate 10C)

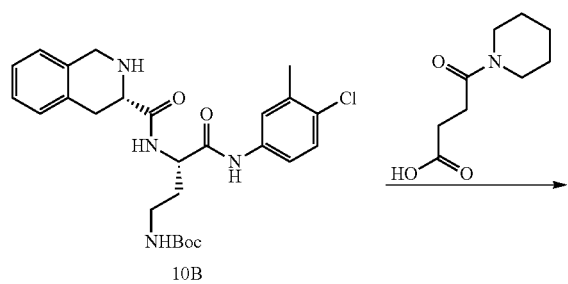

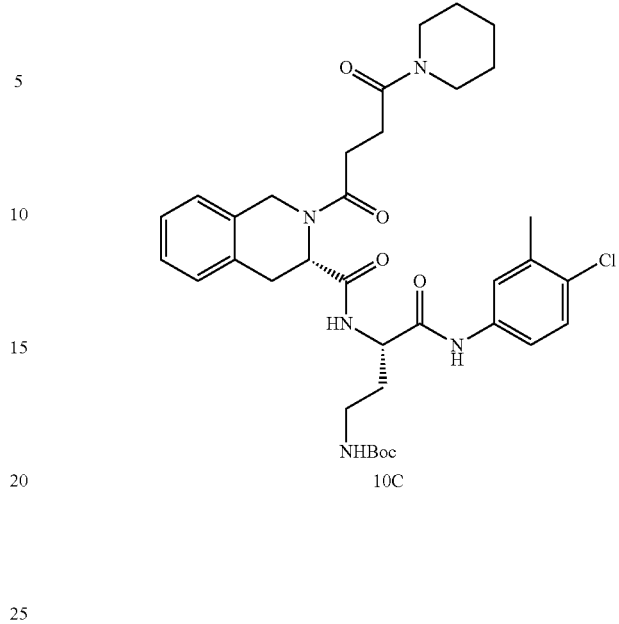

A solution of Intermediate 10B (60 mg, 0.12 mmol) and 4-oxo-4-(piperidin-1-yl)butanoic acid (33 mg, 0.18 mmol) in DCM (4 mL) was treated with DIEA (83 µL, 0.48 mmol) and HATU (91 mg, 0.24 mmol). After 12 h, the reaction mixture was partitioned between DCM (5 mL) and 1 M aqueous HCl solution (5 mL). The layers were separated using a phase sep-cartridge then re-extracted with DCM (5 mL). The combined organic layers were concentrated in vacuo to afford the Boc protected intermediate 10C. LCMS [m/z] calculated for C$_{35}$H$_{46}$ClN$_5$O$_6$: 667.3; found 668.1[M+H]$^+$, t$_R$=2.65 min (Method 4).

Step 10D. Synthesis of (S)—N—((S)-4-amino-1-((4-chloro-3-methylphenyl)amino)-1-oxobutan-2-yl)-2-(4-oxo-4-(piperidin-1-yl) butanoyl)-1,2,3,4-tetrahydro isoquino line-3-carboxamide (Compound 10-1)

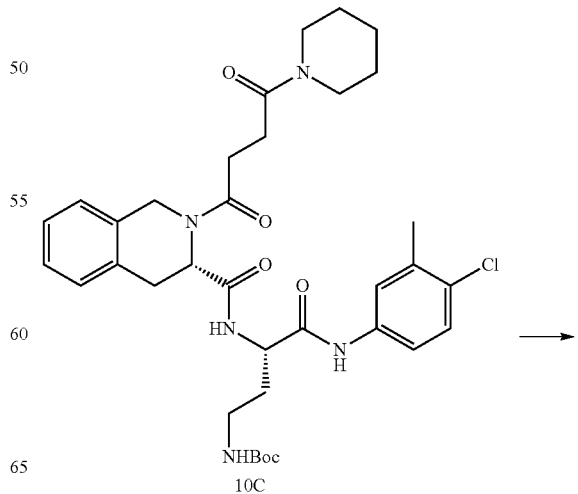

-continued

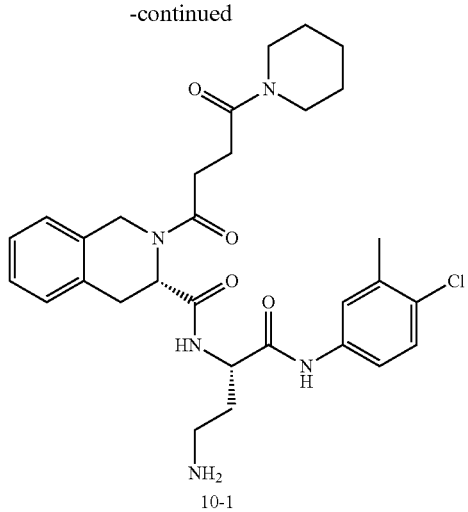

10-1

Crude intermediate 10C was dissolved in DCM (5 mL) and TFA (1 mL). After 4 h, the solvents were removed under vacuum and the resulting crude products were purified by chromatography (0.7 M $NH_3$/MeOH/DCM) to provide 43 mg (63%) of Compound 10-1. LCMS [m/z] calculated for $C_{30}H_{38}ClN_5O_4$: 567.3; found 568.3 [M+H]$^+$, $t_R$=4.11 min (Method 4). $^1$H NMR (400 MHz, DMSO-$d_6$, 363 K) δ 7.61 (br s, 1H), 7.48 (br s, 1H), 7.37-6.79 (m, 6H), 5.21-4.50 (m, 3H), 4.43-4.23 (m, 1H), 3.28-3.11 (m, 4H), 2.96 (br s, 2H), 2.75-2.63 (m, 2H), 2.58 (dt, J=15.4, 5.6 Hz, 1H), 2.51-2.39 (m, 3H), 2.32 (s, 3H), 2.08-2.00 (m, 1H), 1.81-1.72 (d, J=5.7 Hz, 1H), 1.51 (br s, 2H), 1.37 (br s, 4H), NH$_2$, NHAr not observed.

The procedures as set forth in Example 10 above, the compounds of the following Table 10 were prepared using the appropriate $R^1$, $R^8$ and $R^9$ reagents.

TABLE 10

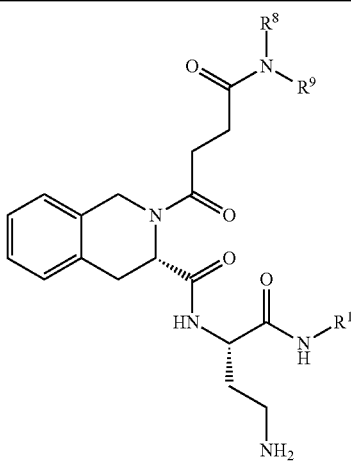

| Compound Number | $R^8$ \ N \ $R^9$ | $R^1$ | MS Calc | MS Obs (MH)$^+$ | LCMS Retention (min) | Purity Method |
|---|---|---|---|---|---|---|
| 10-1 | piperidinyl | 4-chloro-3-methylphenyl | 567.3 | 568.3 | 4.11 | 5 |
| 10-2 | morpholinyl | 4-chloro-3-methylphenyl | 569.2 | 570.3 | 3.29 | 5 |
| 10-3 | 4-methylpiperazinyl | 4-chloro-3-methylphenyl | 582.3 | 583.4 | 1.92 | 5 |
| 10-4 | 4-methylpiperazinyl | 2,3-dichloro-4-fluorophenyl | 620.2 | 621 | 1.95 | 5 |

TABLE 10-continued

| Compound Number | R8,R9 N group | R1 | MS Calc | MS Obs (MH)+ | LCMS Retention (min) | Purity Method |
|---|---|---|---|---|---|---|
| 10-5 | decahydroisoquinoline | indane | 613.4 | 614.1 | 7.49 | 5 |
| 10-6 | 5-azaspiro[3.4] | indane | 585.3 | 586.1 | 5.94 | 5 |
| 10-7 | 3,3-dimethylpiperidine | indane | 587.4 | 588.1 | 6.18 | 5 |
| 10-8 | 2-azaspiro[3.5] | indane | 599.4 | 600.1 | 6.49 | 5 |
| 10-9 | 3,3-dimethylpiperidine | 2-Cl-4,6-diMe-phenyl | 609.3 | 611 | 7.19 | 5 |
| 10-10 | 5-azaspiro[3.4] | 2-Cl-4,6-diMe-phenyl | 607.3 | 609 | 7.15 | 5 |

TABLE 10-continued
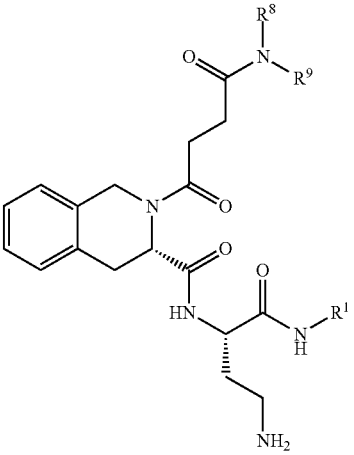
| Compound Number | R⁸\N\R⁹ | R¹ | MS Calc | MS Obs (MH)⁺ | LCMS Retention (min) | Purity Method |
|---|---|---|---|---|---|---|
| 10-11 |  | 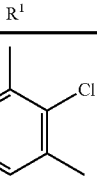 | 621.3 | 623 | 7.51 | 5 |
| 10-12 |  | 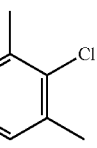 | 609.3 | 611 | 7.57 | 5 |
Scheme 11
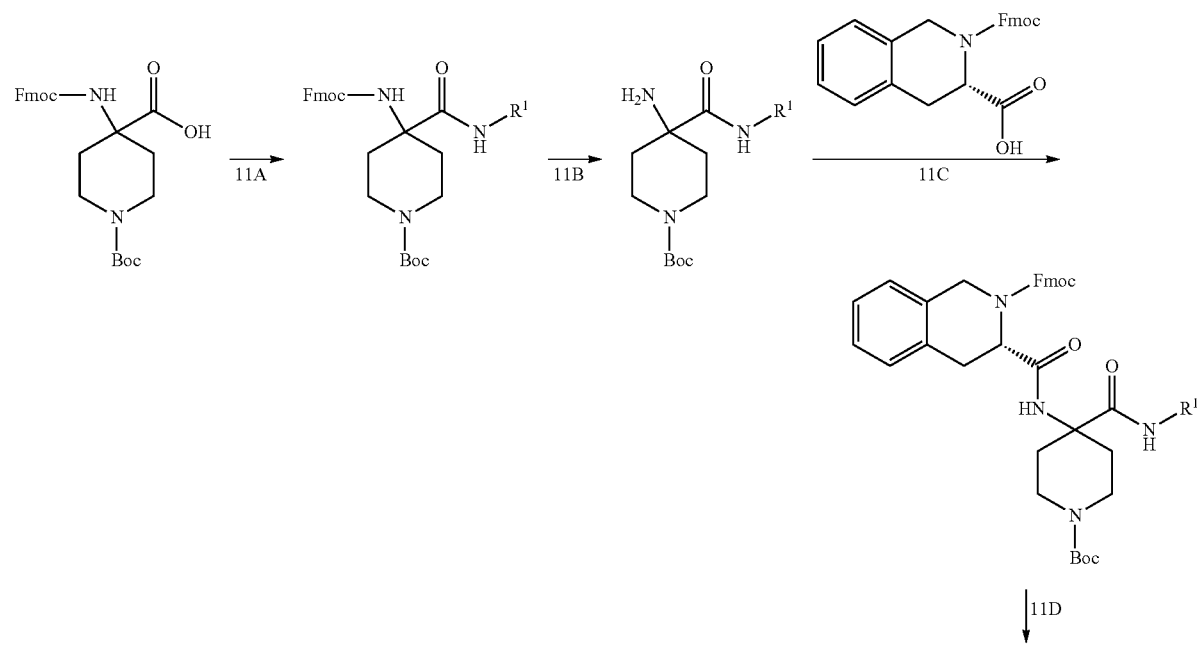

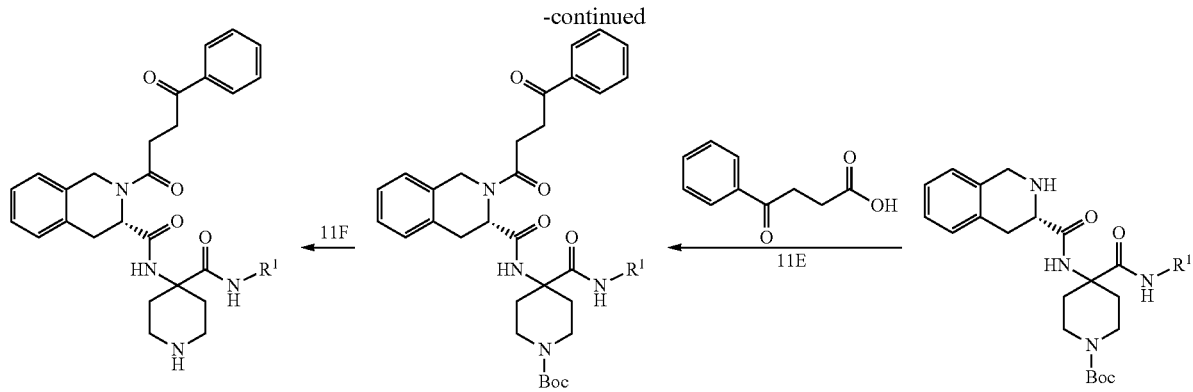

Example 11

Synthesis of (S)—N-(4-((2-chloro-3-methylphenyl)carbamoyl)piperidin-4-yl)-2-(4-oxo-4-phenylbutanoyl)-1,2,3,4-tetrahydroisoquinoline-3-carboxamide (Compound 11-1)

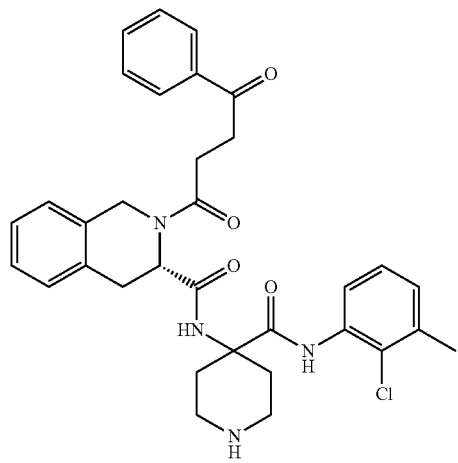

11-1

Step 11A. Synthesis of tert-butyl 4-((((9H-fluoren-9-yl)methoxy)carbonyl)amino)-4-((2-chloro-3-methylphenyl)carbamoyl)piperidine-1-carboxylate (Intermediate 11A)

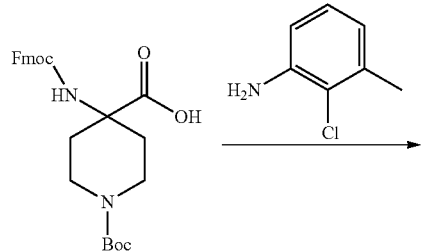

-continued

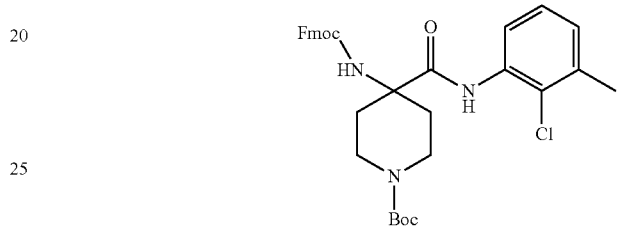

11A

A solution of 4-((((9H-fluoren-9-yl)methoxy)carbonyl)amino)-1-(tert-butoxycarbonyl)piperidine-4-carboxylic acid (130 mg, 0.28 mmol) in DCM (3 mL) was treated with 1-chloro-N,N,2-trimethylprop-1-en-1-amine (74 μL, 0.56 mmol). After 1 h, 2-chloro-3-methylaniline (79 mg, 0.56 mmol) in pyridine (1 mL) was added. After stirring overnight, the reaction mixture was partitioned between DCM and 1 M aqueous solution of HCl (5 mL each). The phases were passed through phase sep cartridge and the solvent was removed under vacuum. The crude products were purified by chromatography (EA/isohexane) to afford 144 mg (87%) of Intermediate 11A. LCMS [m/z] calculated for $C_{33}H_{36}ClN_3O_5$: 589.2; found 612.0 [M+Na]$^+$, $t_R$=3.04 min (Method 4).

Step 11B. Synthesis of tert-butyl 4-amino-4-((2-chloro-3-methylphenyl) carbamoyl) piperidine-1-carboxylate (Intermediate 11B)

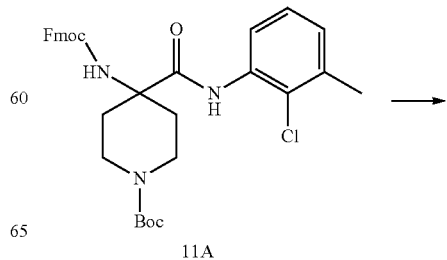

11A

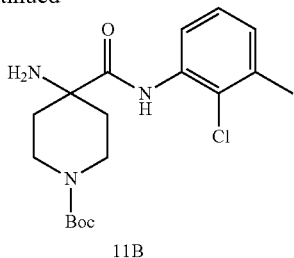

11B

A solution of Intermediate 11A (144 mg, 0.24 mmol) in DCM (4 mL) was treated with diethylamine (1 mL). After 6 h the reaction mixture was concentrated and the crude product co-evaporated with DCM/toluene and purified by chromatography (MeOH (0.7N $NH_3$)/DCM) to afford 96 mg (50%) of Intermediate 11B. LCMS [m/z] calculated for $C_{18}H_{26}ClN_3O_3$: 367.2; found 268.1 [M+H-Boc]$^+$, $t_R$=1.51 min (Method 4).

Step 11C. Synthesis of tert-butyl (S)-4-((2-chloro-3-methylphenyl)carbamoyl)-4-(1,2,3,4-tetrahydroisoquinoline-3-carboxamido)piperidine-1-carboxylate (Intermediate 11C)

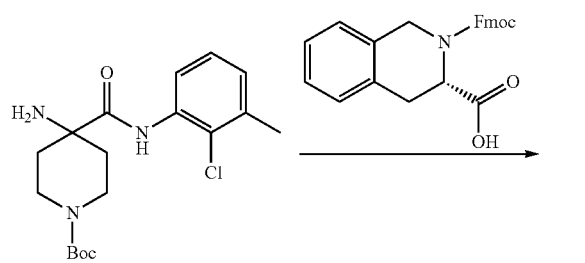

11B

A solution of Intermediate 11B (95 mg, 0.26 mmol) and (S)-2-(((9H-fluoren-9-yl)methoxy)carbonyl)-1,2,3,4-tetrahydroisoquinoline-3-carboxylic acid (155 mg, 0.39 mmol) in DCM (4 mL) was treated with DIEA (225 μL, 0.26 mmol) and HATU (295 mg, 0.8 mmol). After stirring overnight, the reaction mixture was partitioned between DCM and 1 M aqueous solution of HCl (5 mL each). The aqueous layer was re-extracted with DCM (5 mL). The combined organic layers were dried (MgSO$_4$), filtered and concentrated and the crude product was purified by chromatography (EA/hexane) to afford 208 mg (38%) of Intermediate 11C. LCMS [m/z] calculated for $C_{43}H_{45}ClN_4O_6$: 748.3; found 771.0 [M+Na]$^+$, $t_R$=2.85 min (Method 4).

Step 11D. Synthesis of tert-butyl (S)-4-((2-chloro-3-methylphenyl)carbamoyl)-4-(1,2,3,4-tetrahydroisoquinoline-3-carboxamido)piperidine-1-carboxylate (Intermediate 11D)

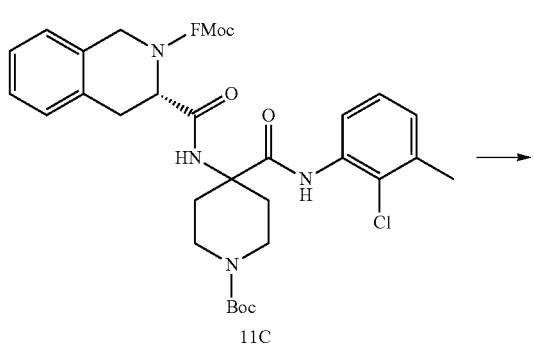

11C

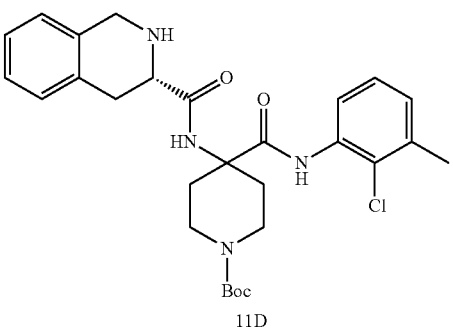

11D

A solution of Intermediate 11C (206 mg, 0.28 mmol) in DCM (3 mL) was treated with diethylamine (1 mL). After 6 h the reaction mixture was concentrated and the crude product was purified by chromatography (MeOH (0.7 N $NH_3$)/DCM) to afford 75 mg (35%) of Intermediate 11D. LCMS [m/z] calculated for $C_{28}H_{35}ClN_4O_4$: 526.2; found 527.1 [M+H]$^+$, $t_R$=1.63 min (Method 4).

Step 11E. Synthesis of tert-butyl (S)-4-((2-chloro-3-methylphenyl)carbamoyl)-4-(2-(4-oxo-4-phenylbutanoyl)-1,2,3,4-tetrahydroisoquinoline-3-carboxamido)piperidine-1-carboxylate (Intermediate 11E)

Step 11F. Synthesis of (S)—N-(4-((2-chloro-3-methylphenyl)carbamoyl)piperidin-4-yl)-2-(4-oxo-4-phenylbutanoyl)-1,2,3,4-tetrahydroisoquinoline-3-carboxamide (Compound 11-1)

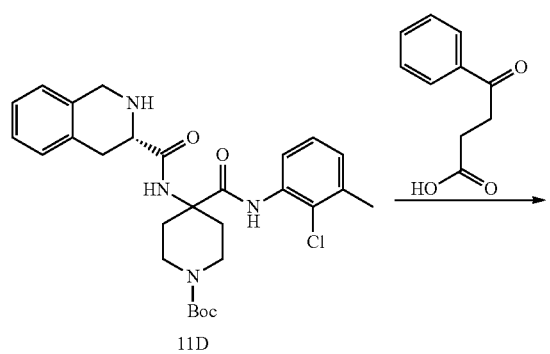

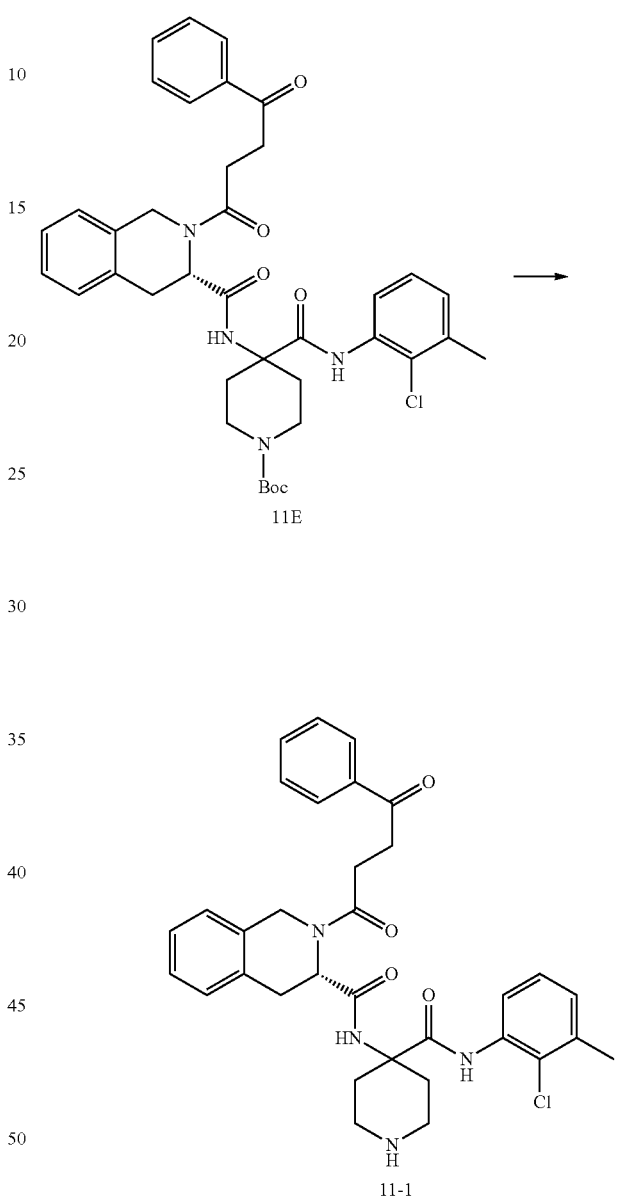

A solution of Intermediate 11D (75 mg, 0.14 mmol) and 4-oxo-4-phenylbutanoic acid (51 mg, 0.29 mmol) in DCM (4 mL) was treated with N-ethyl-N-isopropylpropan-2-amine (120 μl, 0.71 mmol) and HATU (162 mg, 0.43 mmol). The reaction mixture was stirred at rt for 4 h. The reaction mixture was partitioned between DCM (5 mL) and 1 M aq HCl solution. The layers were separated using a phase sep-cartridge then re-extracted with DCM (5 mL). The combined organic layers were concentrated and the crude product was purified by chromatography (EA/isohexane) to afford 56 mg (57%) of Intermediate 11E. LCMS [m/z] calculated for $C_{38}H_{43}ClN_4O_6$: 686.3; found 709 [M+Na]$^+$, $t_R$=2.72 min (Method 4).

Into a solution of Intermediate 11E (56 mg, 0.08 mmol) in DCM (4 mL) was added TFA (1 mL) and the reaction mixture was stirred at rt. The solvent was removed and the crude products were purified by chromatography (0.7 M NH$_3$/MeOH)/DCM) to afford 34 mg (39%) of Compound 11-1. LCMS [m/z] calculated for $C_{33}H_{35}ClN_4O_4$: 586.2; found 587.1 [M+H]$^+$, $t_R$=3.99 min (Method 4).

Following the procedures as set forth in Example 11 above, the compounds of the following Table 11 were prepared using the appropriate R$^1$ reagents.

TABLE 11
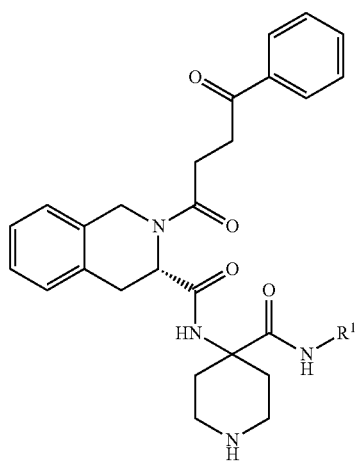
| Cmpd Number | R¹ | MS Calc | MS Obs (MH)⁺ | LCMS Ret. (min) | Purity Method |
|---|---|---|---|---|---|
| 11-1 | 2-Cl, 3-Me phenyl | 586.2 | 587.1 | 3.99 | 5 |
| 11-2 | 2,3-diCl phenyl | 620.2 | 621 | 4.58 | 5 |
| 11-3 | 3-Cl, 4-F, 6-Me phenyl | 604.2 | 605.1 | 4.33 | 5 |
| 11-4 | 2-Cl, 3,4-diMe phenyl | 600.3 | 601.1 | 4.44 | 5 |
| 11-5 | 2,3-diCl phenyl | 606.2 | 607 | 4.12 | 5 |
| 11-6 | 2,5-diCl, 6-Me phenyl | 620.2 | 621 | 4.51 | 5 |

Scheme 12
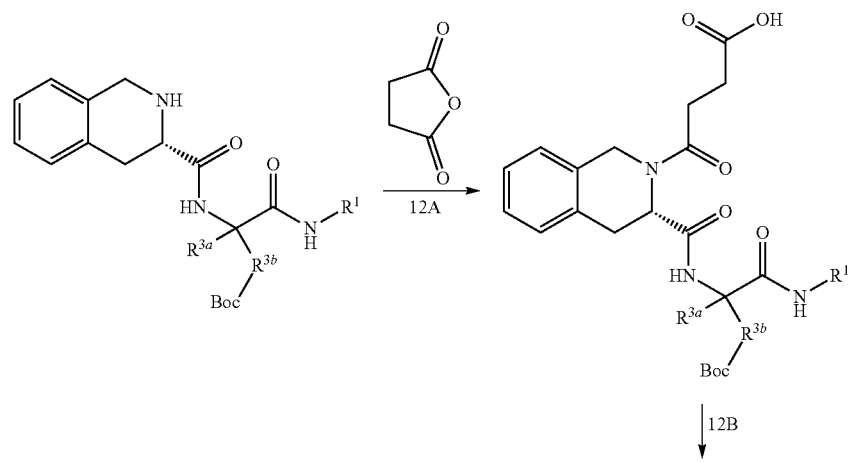
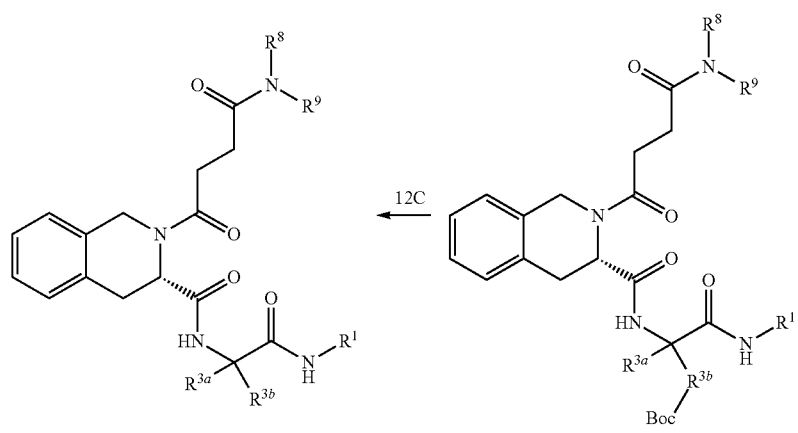

Example 12

Synthesis of (S)—N—((S)-4-amino-1-((4-chloro-3-methylphenyl)amino)-1-oxobutan-2-yl)-2-(4-((2R,6S)-2,6-dimethylmorpholino)-4-oxobutanoyl)-1,2,3,4-tetrahydroisoquinoline-3-carboxamide (Compound 12-1)

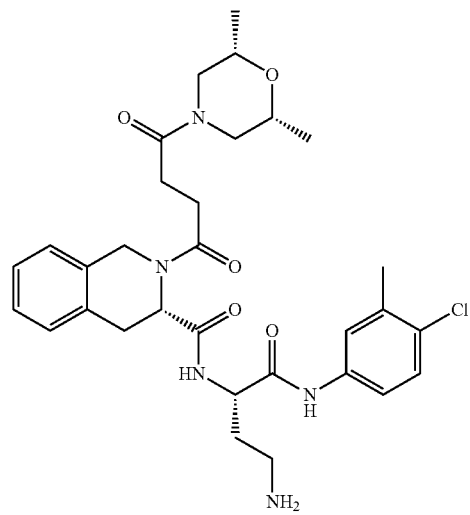

12-1

Step 12A. Synthesis of 4-((S)-3-4(S)-4-((tert-butoxycarbonyl)amino)-1-((4-chloro-3-methylphenyl)amino)-1-oxobutan-2-yl)carbamoyl)-3,4-dihydroisoquinolin-2(1H)-yl)-4-oxobutanoic Acid (Intermediate 12A)

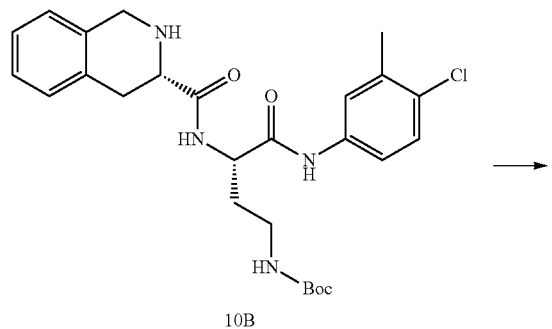

10B

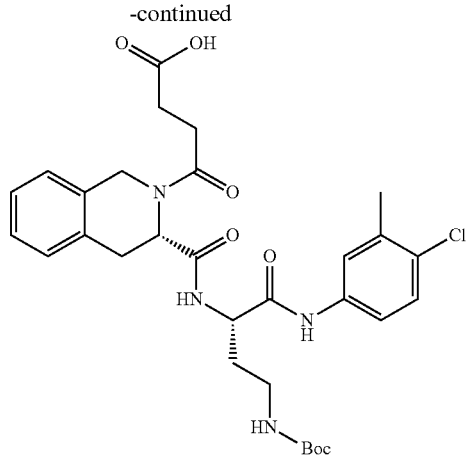

12A

Succinic anhydride (0.23 g, 2.26 mmol) in DCM (10 mL) was added dropwise to a solution of Intermediate 10B (1.13 g, 2.3 mmol) in DCM (40 mL) under $N_2$. After 36 h, the solvent was removed in vacuo and the crude product purified by chromatography (MeOH (+0.1% AcOH)/DCM) to provide 1.22 g (85%) of Intermediate 12A as a white solid. LCMS [m/z] calculated for $C_{30}H_{37}ClN_4O_7$: 600.2; found 501.1 [M-Boc]$^+$, $t_R$=2.35 min (Method 4). $^1$H NMR (400 MHz, DMSO-d$_6$, 363K) δ 11.68 (br s, 1H), 9.30 (br s, 1H), 7.52 (br s, 1H), 7.46-7.36 (m, 1H), 7.29 (d, J=8.7 Hz, 1H), 7.26-7.15 (m, 4H), 6.16 (br s, 1H), 4.92 (t, J=5.4 Hz, 1H), 4.83-4.74 (m, 1H), 4.66 (br s, 1H), 4.35-4.25 (m, 1H), 3.23-3.07 (m, 2H), 2.90-2.66 (m, 4H), 2.55 (t, J=6.3 Hz, 2H), 2.32 (s, 3H), 1.86 (dq, J=13.5, 6.9 Hz, 1H), 1.68 (dq, J=14.9, 8.1 Hz, 1H), 1.39 (s, 9H), NH not observed.

Step 12B. Synthesis of tert-butyl ((S)-4-((4-chloro-3-methylphenyl)amino)-3-((S)-2-(4-((2R,6S)-2,6-dimethylmorpholino)-4-oxobutanoyl)-1,2,3,4-tetrahydroisoquinoline-3-carboxamido)-4-oxobutyl)carbamate (Intermediate 12B)

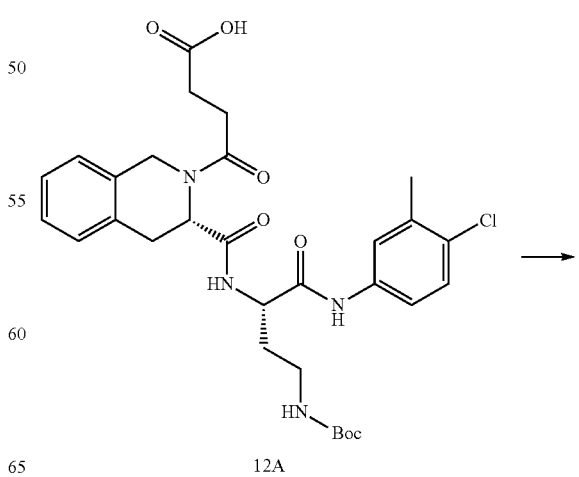

12A

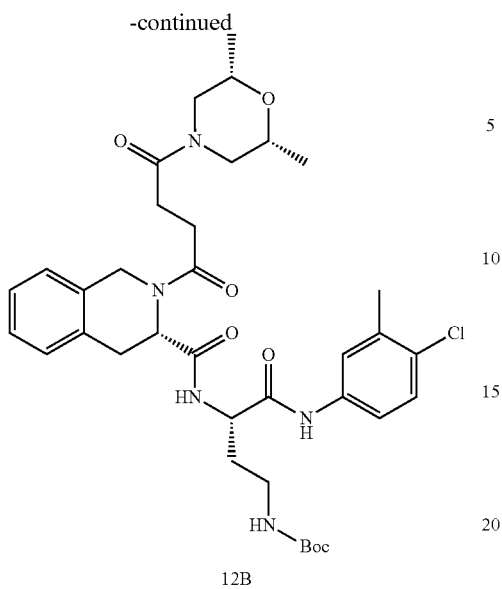

12B

Intermediate 12A (50 mg, 0.083 mmol) and (2S, 6R)-2,6-dimethylmorpholine (0.03 mL, 0.21 mmol), were dissolved in DCM (3 mL). DIEA (0.07 mL, 0.42 mmol) was added, followed after 10 min by HATU (95 mg, 0.25 mmol). After 2 h, the reaction mixture was partitioned between DCM (5 mL) and 1 M aqueous solution of HCl (5 mL). The layers were separated using a phase sep-cartridge and the aqueous layer was re-extracted with DCM (5 mL). The combined organic phases were concentrated in vacuo to afford Intermediate 12B, which was used directly without further purification.

Synthesis of (S)—N—((S)-4-amino-1-((4-chloro-3-methylphenyl)amino)-1-oxobutan-2-yl)-2-(4-((2R,6S)-2,6-dimethylmorpholino)-4-oxobutanoyl)-1,2,3,4-tetrahydroisoquinoline-3-carboxamide (Compound 12-1)

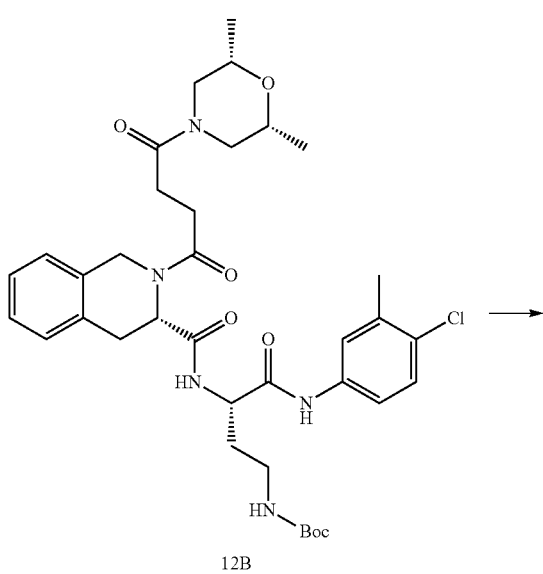

12B

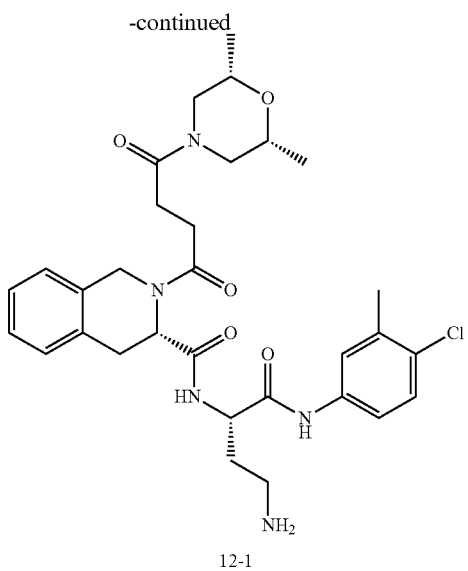

12-1

Intermediate 12B was stirred in a solution of DCM (4 mL) and TFA (1 mL) for 2 h. The solvents were evaporated and the resulting crude material was purified by chromatography (0.7 M Ammonia/MeOH)/DCM) to afford 46 mg (88%) of Compound 12-1 as a white solid. LCMS [m/z] calculated for $C_{31}H_{40}ClN_5O_5$: 597.3; found 598.1 [M+H]$^+$, $t_R$=3.79 min (Method 4). $^1$H NMR (400 MHz, DMSO-d$_6$, 363 K) δ 7.61 (br s, 1H), 7.47 (br s, 1H), 7.38-7.06 (m, 6H), 5.10-4.65 (m, 3H), 4.39 (t, J=7.1 Hz, 1H), 3.91 (br s, 1H), 3.39-3.13 (m, 3H), 2.99 (br s, 4H), 2.78-2.70 (m, 2H), 2.60 (dt, J=15.4, 5.7 Hz, 1H), 2.50-2.40 (m, 2H), 2.33 (s, 3H), 2.30-2.15 (br s, 1H), 2.09-2.00 (m, 1H), 1.78 (br s, 1H), 1.06 (s, 3H), 1.04 (s, 3H), NH$_2$, NHAr not observed.

Following the procedures as set forth in Example 12 above, the compounds of the following Table 12 were prepared using the appropriate R$^1$, R$^{3a}$, R$^{3b}$, R$^8$ and R$^9$ reagents.

TABLE 12
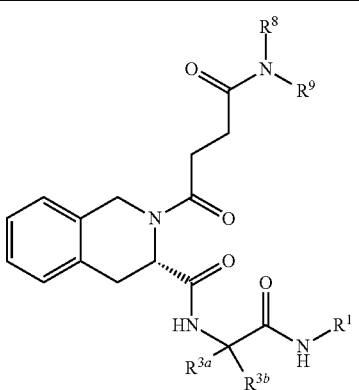
| Cmpd # | R¹ | R³ᵃ | R³ᵇ | *1 R³ᵃ/R³ᵇ Stereo-chem | 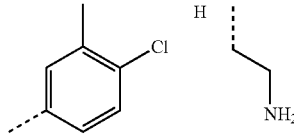 | MS Calc | MS (MH)⁺ | Purity RT | Purity Method |
|---|---|---|---|---|---|---|---|---|---|
| 12-1 | 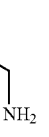 | H | 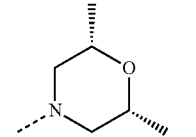 | S | 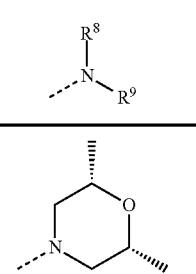 | 597.3 | 598.1 | 3.79 | 5 |
| 12-2 | 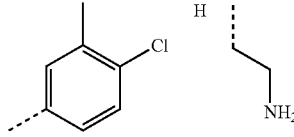 | H | 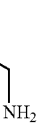 | S | 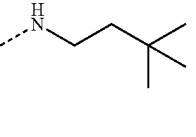 | 583.3 | 584.1 | 4.56 | 5 |
| 12-3 | 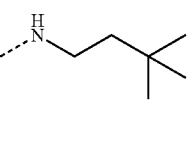 | H | 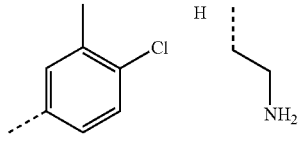 | S |  | 595.3 | 596.1 | 4.68 | 5 |
| 12-4 | 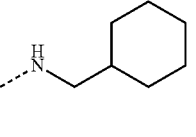 | H | 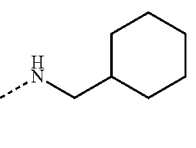 | S | 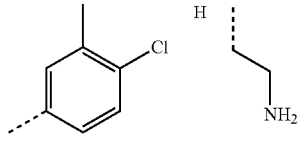 | 603.2 | 604.1 | 4.08 | 5 |
| 12-5 |  | H | 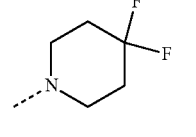 | S | 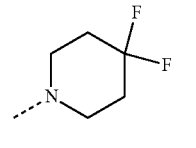 | 553.3 | 554.1 | 3.77 | 5 |
| 12-6 | 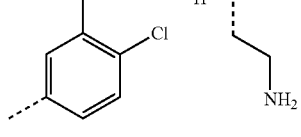 | H |  | S | 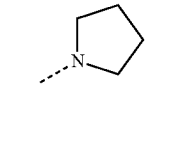 | 583.3 | 584.1 | 3.15 | 5 |
| 12-7 | 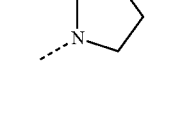 | H | 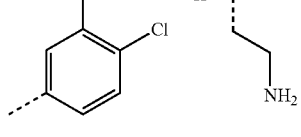 | S |  | 607.3 | 608.1 | 4.94 | 5 |

TABLE 12-continued
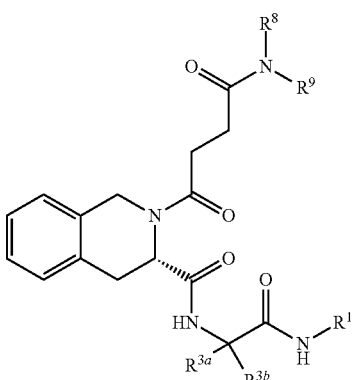
| Cmpd # | R¹ | R³ᵃ | R³ᵇ | *1 R³ᵃ/R³ᵇ Stereo-chem | $\underset{R^9}{\overset{R^8}{N}}$ | MS Calc | MS (MH)⁺ | Purity RT | Purity Method |
|---|---|---|---|---|---|---|---|---|---|
| 12-8 | 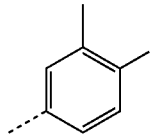 | H |  | S | 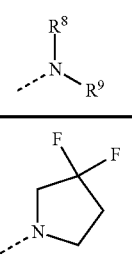 | 589.2 | 590.1 | 3.86 | 5 |
| 12-9 | 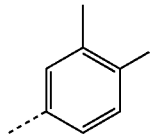 | H |  | S | 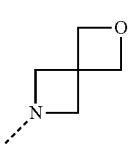 | 581.2 | 582.1 | 3.24 | 5 |
| 12-10 | 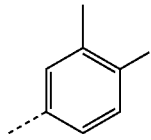 | H |  | S | 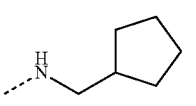 | 581.3 | 582.1 | 4.4 | 5 |
| 12-11 | 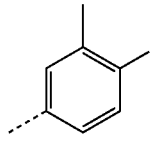 | H |  | S | 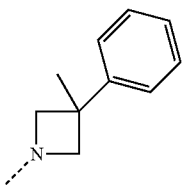 | 629.3 | 630.1 | 4.87 | 5 |
| 12-12 | 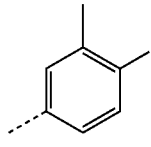 | H |  | S | 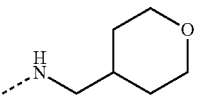 | 597.3 | 598.1 | 3.4 | 5 |
| 12-13 | 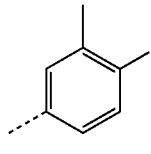 | H |  | S | 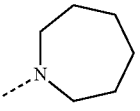 | 581.3 | 582.1 | 4.41 | 5 |
| 12-14 | 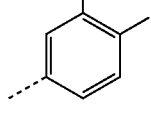 | H |  | S | 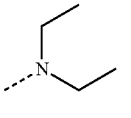 | 555.3 | 556.1 | 4.04 | 5 |

TABLE 12-continued
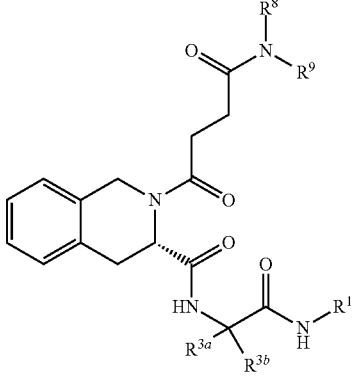
| Cmpd # | R¹ | R³ᵃ | R³ᵇ | *1 R³ᵃ/R³ᵇ Stereo-chem | 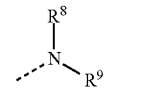 | MS Calc | MS (MH)⁺ | Purity RT | Purity Method |
|---|---|---|---|---|---|---|---|---|---|
| 12-15 | 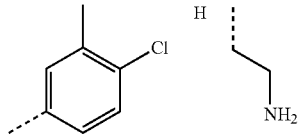 | H |  | S | 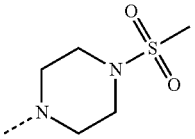 | 646.2 | 647 | 3.41 | 5 |
| 12-16 | 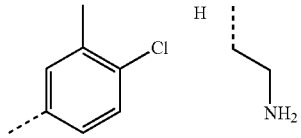 | H |  | S | 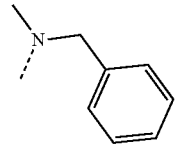 | 603.3 | 604.1 | 4.58 | 5 |
| 12-17 | 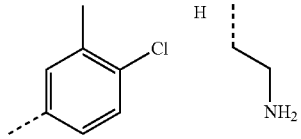 | H |  | S | 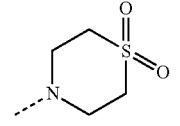 | 617.2 | 618 | 3.17 | 5 |
| 12-18 | 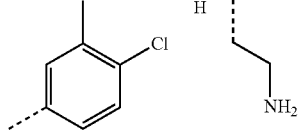 | H |  | S | 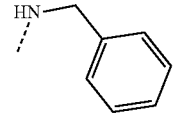 | 589.2 | 590 | 4.15 | 5 |
| 12-19 | 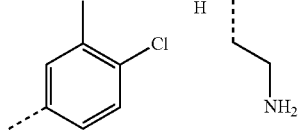 | H |  | S | 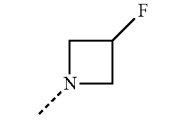 | 557.2 | 558 | 3.44 | 5 |
| 12-20 | 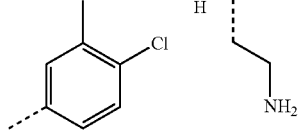 | H |  | S | 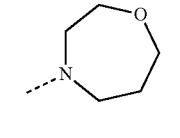 | 583.3 | 584.1 | 3.39 | 5 |
| 12-21 | 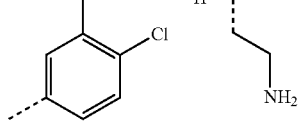 | H |  | R | 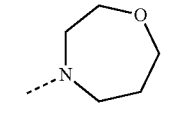 | 583.3 | 584.1 | 3.39 | 5 |

TABLE 12-continued

| Cmpd # | R¹ | R³ᵃ | R³ᵇ | *1 R³ᵃ/R³ᵇ Stereo-chem | R⁸\N\R⁹ | MS Calc | MS (MH)⁺ | Purity RT | Purity Method |
|---|---|---|---|---|---|---|---|---|---|
| 12-22 | 2-Cl-4-methylphenyl | H | CH₂CH₂NH₂ | S | 3-(2-hydroxypropan-2-yl)azetidinyl | 597.3 | 598.1 | 3.47 | 5 |
| 12-23 | 2-Cl-4-methylphenyl | H | CH₂CH₂NH₂ | S | 3-methylmorpholinyl | 597.3 | 598.1 | 3.79 | 5 |
| 12-24 | 2-Cl-4-methylphenyl | H | CH₂CH₂NH₂ | S | 7-oxa-2-azaspiro[3.5]nonanyl | 609.3 | 610.1 | 3.51 | 5 |
| 12-25 | 2-Cl-4-methylphenyl | H | CH₂CH₂NH₂ | S | (2S)-2-methylpiperidinyl | 581.3 | 582.1 | 4.27 | 5 |
| 12-26 | 2-Cl-4-methylphenyl | H | CH₂CH₂NH₂ | S | 2,2-dimethylpiperidinyl | 595.3 | 596.1 | 4.69 | 5 |
| 12-27 | 2-Cl-4-methylphenyl | H | CH₂CH₂NH₂ | S | (3S)-3-methylmorpholinyl | 583.3 | 584.1 | 3.4 | 5 |
| 12-28 | 2-Cl-4-methylphenyl | H | CH₂CH₂NH₂ | S | 4,4-dimethylpiperidinyl | 595.3 | 596.1 | 4.65 | 5 |

TABLE 12-continued
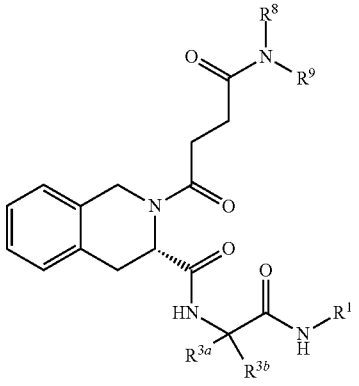
| Cmpd # | R¹ | R³ᵃ | R³ᵇ | *1 R³ᵃ/R³ᵇ Stereo-chem | $\overset{R^8}{\underset{R^9}{N}}$ | MS Calc | MS (MH)⁺ | Purity RT | Purity Method |
|---|---|---|---|---|---|---|---|---|---|
| 12-29 | 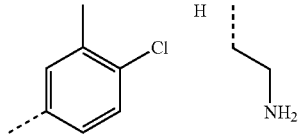 | H | 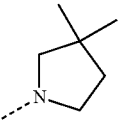 | S | 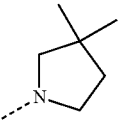 | 581.3 | 582.1 | 4.34 | 5 |
| 12-30 | 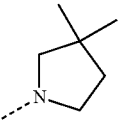 | H | 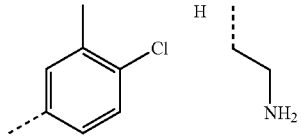 | S | 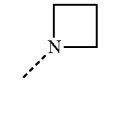 | 539.2 | 540 | 3.36 | 5 |
| 12-31 | 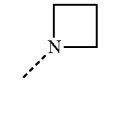 | H | 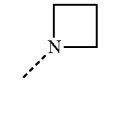 | S | 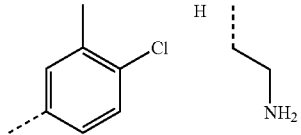 | 581.3 | 582.1 | 4.26 | 5 |
| 12-32 | 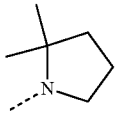 | H | 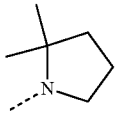 | S | 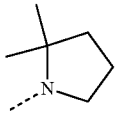 | 579.3 | 580.1 | 4.1 | 5 |
| 12-33 | 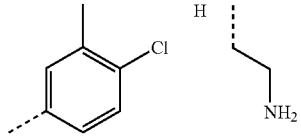 | H | 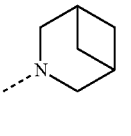 | S | 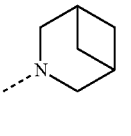 | 608.3 | 609.1 | 1.97 | 5 |
| 12-34 | 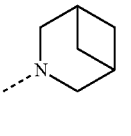 | H | 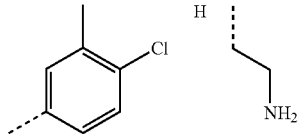 | S | 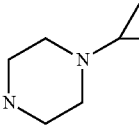 | 596.3 | 597.1 | 1.71 | 5 |
| 12-35 | 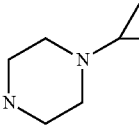 | H | 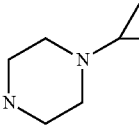 | S | 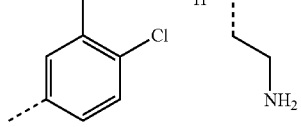 | 596.3 | 597.1 | 1.68 | 5 |

TABLE 12-continued

| Cmpd # | R¹ | R³ᵃ | R³ᵇ | *1 R³ᵃ/R³ᵇ Stereo- chem | R⁸\N/R⁹ | MS Calc | MS (MH)⁺ | Purity RT | Purity Method |
|---|---|---|---|---|---|---|---|---|---|
| 12-36 | 2-chloro-4-methylphenyl | H | CH₂CH₂NH₂ | S | (S)-3-methyl-4-methylpiperazin-1-yl | 596.3 | 597.1 | 1.93 | 5 |
| 12-37 | 2-chloro-4-methylphenyl | H | CH₂CH₂NH₂ | S | 4-methyl-3-oxopiperazin-1-yl | 596.3 | 597.1 | 2.9 | 5 |
| 12-38 | 2-chloro-4-methylphenyl | H | CH₂CH₂NH₂ | S | 3-benzylazetidin-1-yl | 629.3 | 630.1 | 4.74 | 5 |
| 12-39 | 2-chloro-4-methylphenyl | H | CH₂CH₂NH₂ | S | (3R,5S)-3,5-dimethylpiperidin-1-yl | 595.3 | 596.1 | 4.67 | 5 |
| 12-40 | 2-chloro-4-methylphenyl | H | CH₂CH₂NH₂ | S | 3-tert-butylazetidin-1-yl | 595.3 | 596.1 | 4.6 | 5 |
| 12-41 | 2-chloro-4-methylphenyl | H | CH₂CH₂NH₂ | S | 2,6-dimethylpiperidin-1-yl | 595.3 | 596.1 | 4.61 | 5 |
| 12-42 | 2-chloro-4-methylphenyl | H | CH₂CH₂NH₂ | S | 4-methoxypiperidin-1-yl | 597.3 | 598.1 | 3.66 | 5 |

TABLE 12-continued
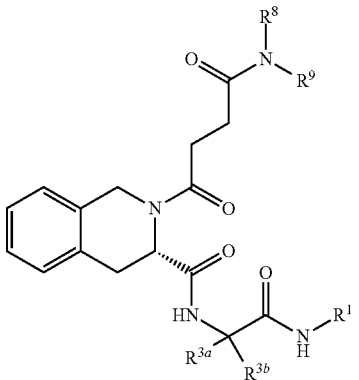
| Cmpd # | R¹ | R³ᵃ | R³ᵇ | *1 R³ᵃ/R³ᵇ Stereo-chem | 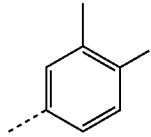 | MS Calc | MS (MH)⁺ | Purity RT | Purity Method |
|---|---|---|---|---|---|---|---|---|---|
| 12-43 | 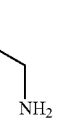 | H | 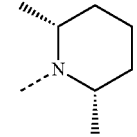 | S | 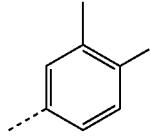 | 595.3 | 596.1 | 4.62 | 5 |
| 12-44 |  | H | 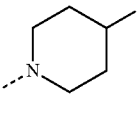 | S | 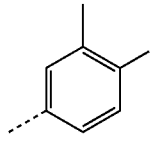 | 592.3 | 593.1 | 3.51 | 5 |
| 12-45 |  | H | 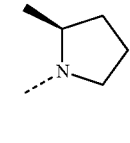 | S | 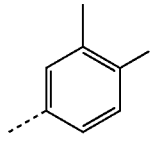 | 567.3 | 568.1 | 3.89 | 5 |
| 12-46 | 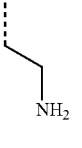 | H | 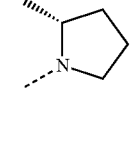 | S | 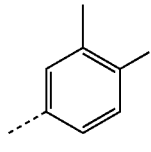 | 567.3 | 568.1 | 3.94 | 5 |
| 12-47 |  | H | 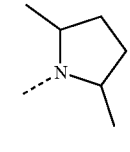 | S | 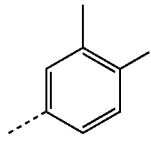 | 581.3 | 582.1 | 4.01 | 5 |
| 12-48 | 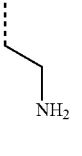 | H | 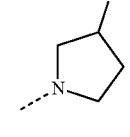 | S | 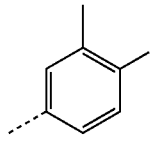 | 569.2 | 570.1 | 3.07 | 5 |
| 12-49 | 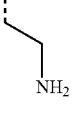 | H | 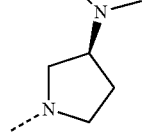 | S |  | 596.3 | 597.1 | 2 | 5 |

TABLE 12-continued

| Cmpd # | R¹ | R³ᵃ | R³ᵇ | *1 R³ᵃ/R³ᵇ Stereo-chem | R⁸\N\R⁹ | MS Calc | MS (MH)⁺ | Purity RT | Purity Method |
|---|---|---|---|---|---|---|---|---|---|
| 12-50 | 2-Cl,4-methylphenyl | H | CH₂CH₂NH₂ | S | (3)-1-methyl-3-dimethylaminopyrrolidine | 596.3 | 597.1 | 1.91 | 5 |
| 12-51 | 2-Cl,4-methylphenyl | H | CH₂CH₂NH₂ | S | 2-(trifluoromethyl)pyrrolidine | 621.2 | 622.1 | 4.26 | 5 |
| 12-52 | 2-Cl,4-methylphenyl | H | CH₂CH₂NH₂ | S | 3-(trifluoromethyl)pyrrolidine | 621.2 | 622.1 | 4.18 | 5 |
| 12-53 | 2-Cl,4-methylphenyl | H | CH₂CH₂NH₂ | S | 2-phenylpyrrolidine | 629.3 | 630.1 | 1.77 | 5 |
| 12-54 | 2-Cl,4-methylphenyl | H | CH₂CH₂NH₂ | S | 3-phenylpyrrolidine | 629.3 | 630.1 | 4.84 | 5 |
| 12-55 | 2-Cl,4-methylphenyl | H | CH₂CH₂NH₂ | S | octahydroisoindole | 607.3 | 608.1 | 4.67 | 5 |

TABLE 12-continued
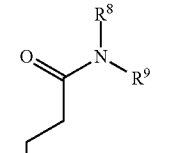
| Cmpd # | R¹ | R³ᵃ | R³ᵇ | *1 R³ᵃ/R³ᵇ Stereo-chem | 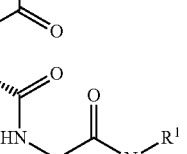 | MS Calc | MS (MH)⁺ | Purity RT | Purity Method |
|---|---|---|---|---|---|---|---|---|---|
| 12-56 | 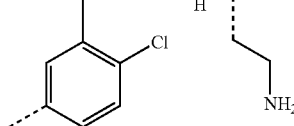 | H | 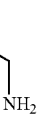 | S | 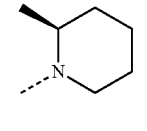 | 581.3 | 582.1 | 4.22 | 5 |
| 12-57 | 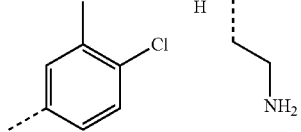 | H |  | S | 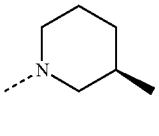 | 581.3 | 582.1 | 4.31 | 5 |
| 12-58 | 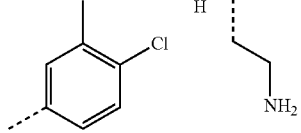 | H |  | S | 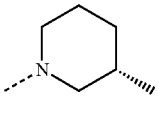 | 581.3 | 582.1 | 4.29 | 5 |
| 12-59 | 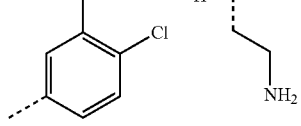 | H |  | S | 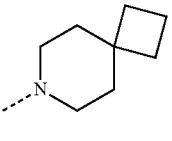 | 607.3 | 608.1 | 4.74 | 5 |
| 12-60 | 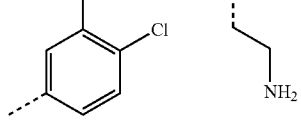 | H |  | S | 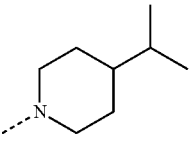 | 609.3 | 610.1 | 4.92 | 5 |
| 12-61 | 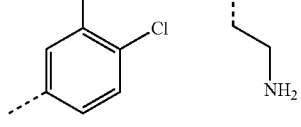 | H |  | S | 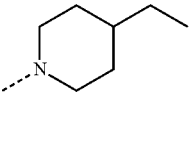 | 595.3 | 596.1 | 4.67 | 5 |
| 12-62 | 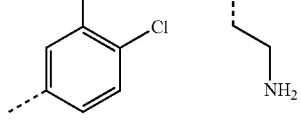 | H |  | S | 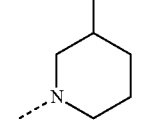 | 583.3 | 584.1 | 3.21 | 5 |

TABLE 12-continued

| Cmpd # | R¹ | R³ᵃ | R³ᵇ | *1 R³ᵃ/R³ᵇ Stereo- chem | R⁸\N-R⁹ | MS Calc | MS (MH)⁺ | Purity RT | Purity Method |
|---|---|---|---|---|---|---|---|---|---|
| 12-63 | 2-Cl-4-Me-phenyl | H | -CH₂CH₂NH₂ | S | 3-fluoropiperidinyl | 585.3 | 586.1 | 3.64 | 5 |
| 12-64 | 2-Cl-4-Me-phenyl | H | -CH₂CH₂NH₂ | S | 3-methoxypyrrolidinyl | 583.3 | 584.1 | 3.41 | 5 |
| 12-65 | 2-Cl-4-Me-phenyl | H | -CH₂CH₂NH₂ | S | 2-ethylpyrrolidinyl | 581.3 | 582.1 | 4.15 | 5 |
| 12-66 | 2-Cl-4-Me-phenyl | H | -CH₂CH₂NH₂ | S | 3-azabicyclo[2.2.1] | 579.3 | 580 | 4.08 | 5 |
| 12-67 | 2-Cl-4-Me-phenyl | H | -CH₂CH₂NH₂ | S | 4-fluoropiperidinyl | 585.3 | 586.1 | 3.62 | 5 |
| 12-68 | 2-Cl-4-Me-phenyl | H | -CH₂CH₂NH₂ | S | 3,4-dimethylpyrrolidinyl | 581.3 | 582.1 | 3.97 | 5 |
| 12-69 | 2-Cl-4-Me-phenyl | H | -CH₂CH₂NH₂ | S | 5-azaspiro[2.4]heptanyl | 579.3 | 580.1 | 4.11 | 5 |

TABLE 12-continued

| Cmpd # | R¹ | R³ᵃ | R³ᵇ | *1 R³ᵃ/R³ᵇ Stereo-chem | N-R⁸/R⁹ | MS Calc | MS (MH)⁺ | Purity RT | Purity Method |
|---|---|---|---|---|---|---|---|---|---|
| 12-70 | 2-Cl,5-Me-phenyl | H | CH₂CH₂NH₂ | S | 3-cyanopyrrolidin-1-yl | 578.2 | 579 | 3.27 | 5 |
| 12-71 | 2-Cl,5-Me-phenyl | H | CH₂CH₂NH₂ | S | 2-isopropylpyrrolidin-1-yl | 595.3 | 596.1 | 4.2 | 5 |
| 12-72 | 2-Cl,5-Me-phenyl | H | CH₂CH₂NH₂ | S | spiro[3.5] | 607.3 | 608.1 | 4.7 | 5 |
| 12-73 | 2-Cl,5-Me-phenyl | H | CH₂CH₂NH₂ | S | spiro[3.4] | 593.3 | 594.1 | 4.44 | 5 |
| 12-74 | 2-Cl,5-Me-phenyl | H | CH₂CH₂NH₂ | S | 3-isopropylpyrrolidin-1-yl | 595.3 | 596.1 | 4.7 | 5 |
| 12-75 | 2-Cl,5-Me-phenyl | H | CH₂CH₂NH₂ | S | 3-tert-butylpyrrolidin-1-yl | 609.3 | 610.1 | 4.88 | 5 |
| 12-76 | 2-Cl,5-Me-phenyl | H | CH₂CH₂NH₂ | S | 1,2,3,4-tetrahydroisoquinolin-2-yl | 615.3 | 616.3 | 4.17 | 5 |

TABLE 12-continued
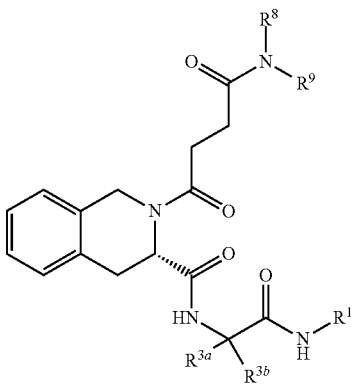
| Cmpd # | R¹ | R³ᵃ | R³ᵇ | *1 R³ᵃ/R³ᵇ Stereo-chem | 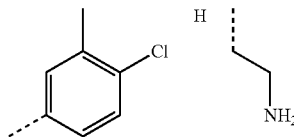 | MS Calc | MS (MH)⁺ | Purity RT | Purity Method |
|---|---|---|---|---|---|---|---|---|---|
| 12-77 | 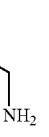 | H | 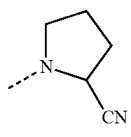 | S | 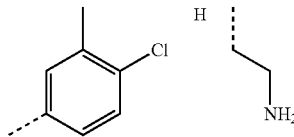 | 578.2 | 579.1 | 3.31 | 5 |
| 12-78 | 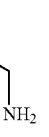 | H | 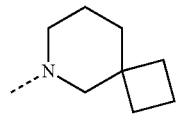 | S | 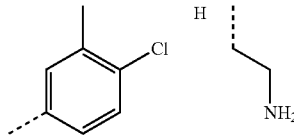 | 607.3 | 608.1 | 4.39 | 5 |
| 12-79 | 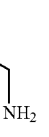 | H | 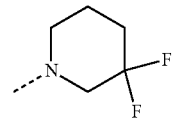 | S | 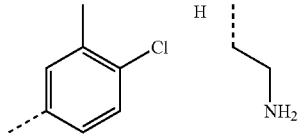 | 603.2 | 604.1 | 3.87 | 5 |
| 12-80 |  | H | 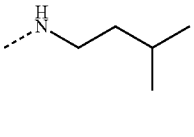 | S | 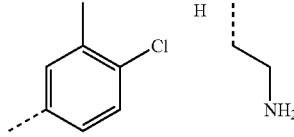 | 569.3 | 570.1 | 5.02 | 5 |
| 12-81 | 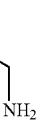 | H | 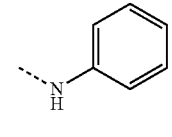 | S | 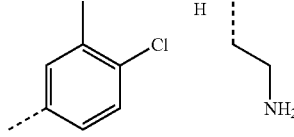 | 575.2 | 576.1 | 4.76 | 5 |
| 12-82 | 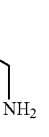 | H | 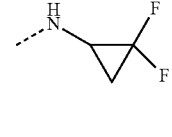 | S | 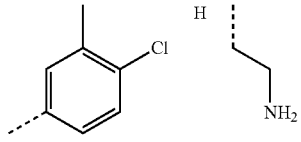 | 575.2 | 576 | 4.33 | 5 |
| 12-83 |  | H | 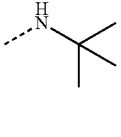 | S | (t-Bu-NH-) | 555.3 | 556.1 | 4.7 | 5 |

TABLE 12-continued
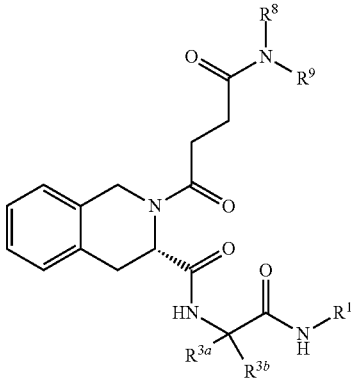
| Cmpd # | R¹ | R³ᵃ | R³ᵇ | *1 R³ᵃ/R³ᵇ Stereo-chem | R⁸\N\R⁹ | MS Calc | MS (MH)⁺ | Purity RT | Purity Method |
|---|---|---|---|---|---|---|---|---|---|
| 12-84 |  | H | 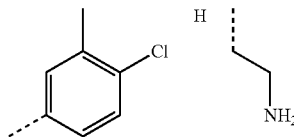 | S | 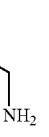 | 592.3 | 593.1 | 3.6 | 5 |
| 12-85 | 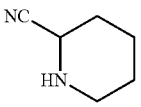 | H | 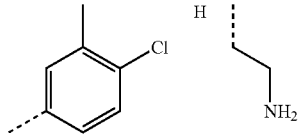 | S |  | 607.2 | 608 | 3.61 | 5 |
| 12-86 | 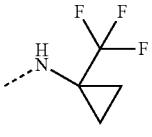 | H | 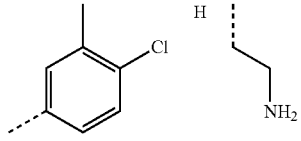 | S |  | 581.2 | 582.1 | 2.89 | 5 |
| 12-87 | 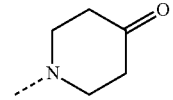 | H | 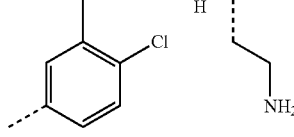 | S | 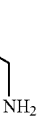 | 623.3 | 624.1 | 5.22 | 5 |
| 12-88 | 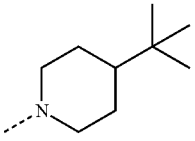 | H | 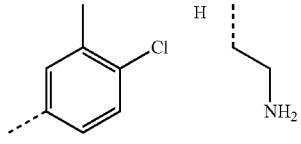 | S |  | 595.3 | 596.1 | 4.61 | 5 |
| 12-89 | 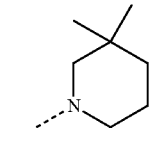 | H | 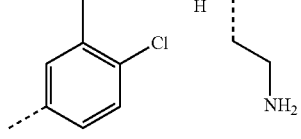 | S |  | 585.3 | 586.1 | 3.64 | 5 |
| 12-90 | 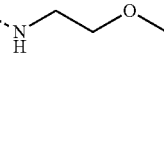 | H | 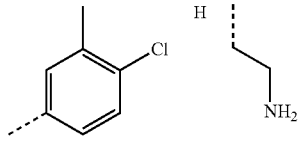 | S |  | 595.2 | 596 | 3.74 | 5 |

TABLE 12-continued
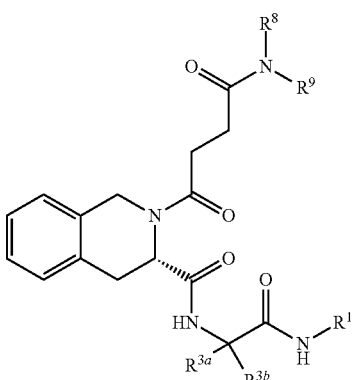
| Cmpd # | R¹ | R³ᵃ | R³ᵇ | *1 R³ᵃ/R³ᵇ Stereo-chem | 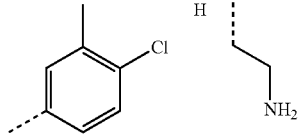 | MS Calc | MS (MH)⁺ | Purity RT | Purity Method |
|---|---|---|---|---|---|---|---|---|---|
| 12-91 | 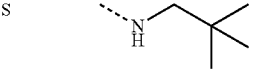 | H | 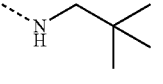 | S | 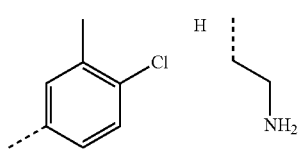 | 569.3 | 570.1 | 4.09 | 5 |
| 12-92 | 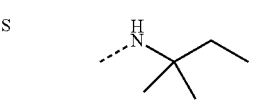 | H | 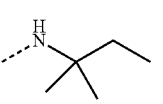 | S | 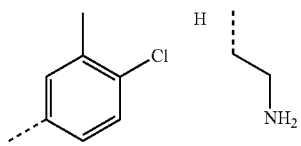 | 569.3 | 570.1 | 4.11 | 5 |
| 12-93 | 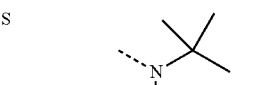 | H | 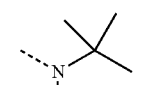 | S | 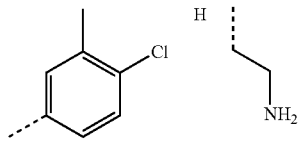 | 569.3 | 570.1 | 4.23 | 5 |
| 12-94 | 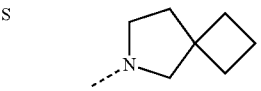 | H | 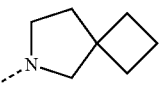 | S | 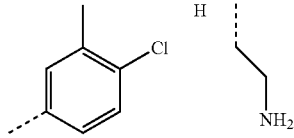 | 593.3 | 594.1 | 4.45 | 5 |
| 12-95 | 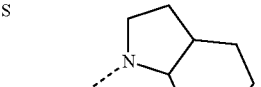 | H | 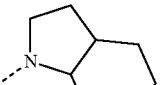 | S | 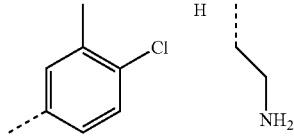 | 607.3 | 608.1 | 4.61 | 5 |
| 12-96 |  | H | 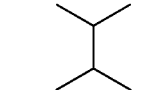 | S | 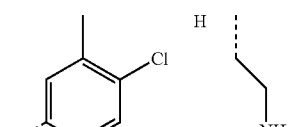 | 609.3 | 610.1 | 4.93 | 5 |
| 12-97 | 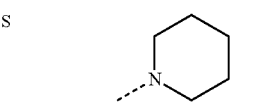 | H | 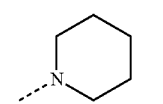 | S | | 595.3 | 596.1 | 4.53 | 5 |

TABLE 12-continued
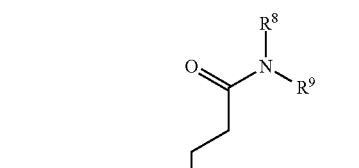
| Cmpd # | R¹ | R³ᵃ | R³ᵇ | *1 R³ᵃ/R³ᵇ Stereo-chem | 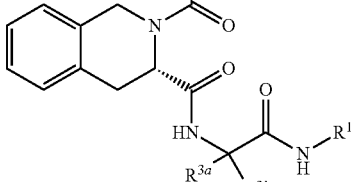 | MS Calc | MS (MH)⁺ | Purity RT | Purity Method |
|---|---|---|---|---|---|---|---|---|---|
| 12-98 | 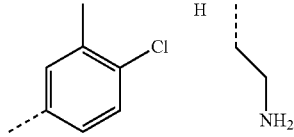 | H | 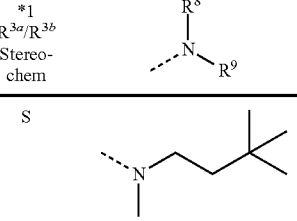 | S | 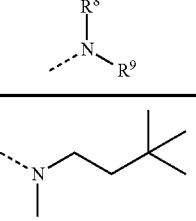 | 597.3 | 598.1 | 4.98 | 5 |
| 12-99 | 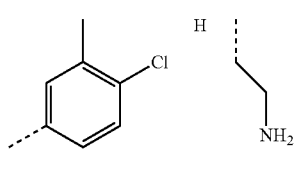 | H | 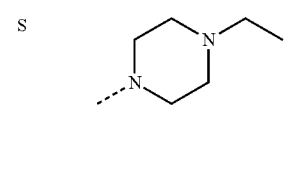 | S | 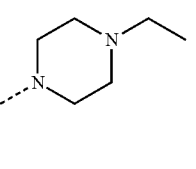 | 596.3 | 597.1 | 1.85 | 5 |
| 12-100 | 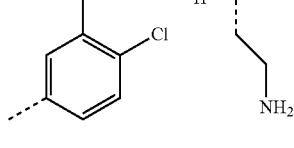 | H | 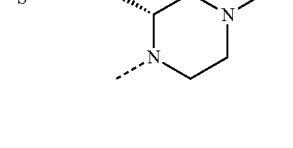 | S | 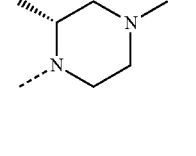 | 596.3 | 597.1 | 1.9 | 5 |
| 12-101 | 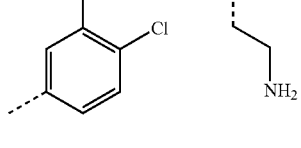 | H | 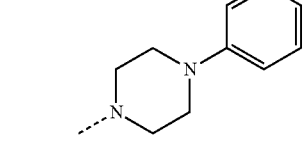 | S | 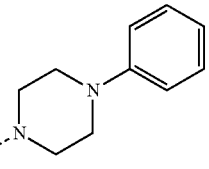 | 644.3 | 645.1 | 4.46 | 5 |
| 12-102 | 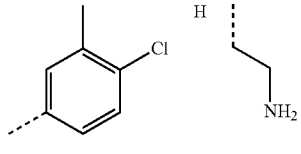 | H | 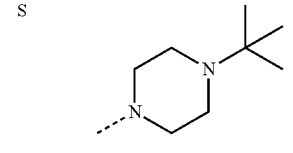 | S | 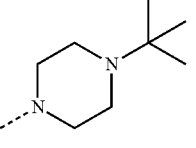 | 624.3 | 625.1 | 2.05 | 5 |
| 12-103 | 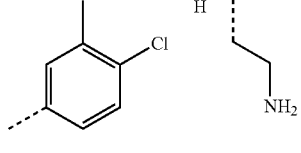 | H | 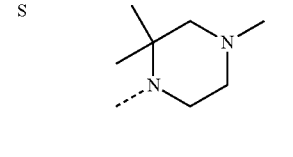 | S | 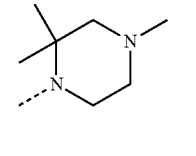 | 610.3 | 611.1 | 2.18 | 5 |
| 12-104 | 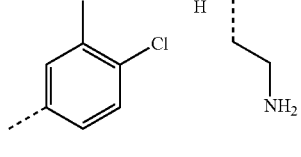 | H | 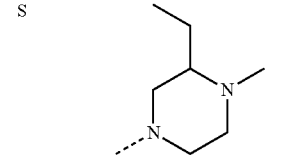 | S | 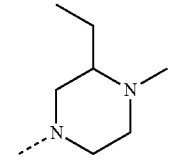 | 610.3 | 611.1 | 2.02 | 5 |

TABLE 12-continued
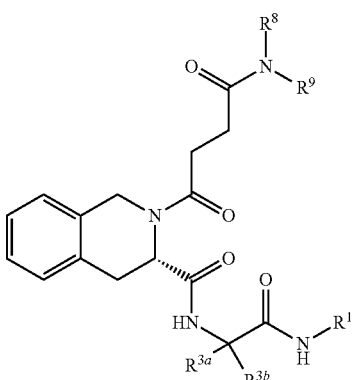
| Cmpd # | R¹ | R³ᵃ | R³ᵇ | *1 R³ᵃ/R³ᵇ Stereo-chem | 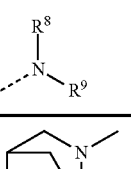 | MS Calc | MS (MH)⁺ | Purity RT | Purity Method |
|---|---|---|---|---|---|---|---|---|---|
| 12-105 | 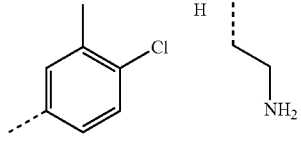 | H | 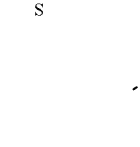 | S | 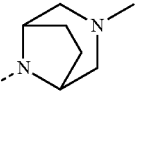 | 608.3 | 609.1 | 2.01 | 5 |
| 12-106 | 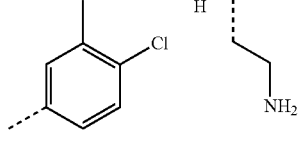 | H | 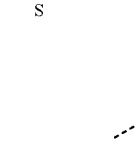 | S | 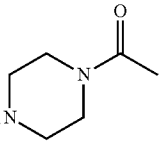 | 610.3 | 611.1 | 3.02 | 5 |
| 12-107 | 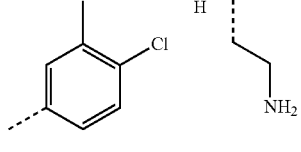 | H | 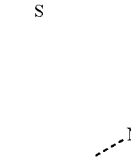 | S | 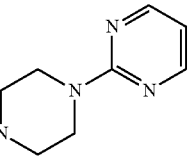 | 646.3 | 647.1 | 3.72 | 5 |
| 12-108 | 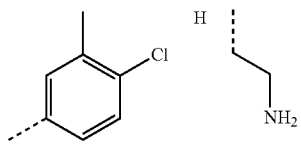 | H | 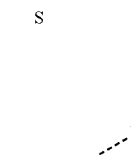 | S | 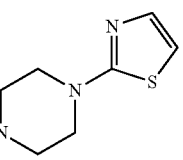 | 651.2 | 652 | 3.31 | 5 |
| 12-109 | 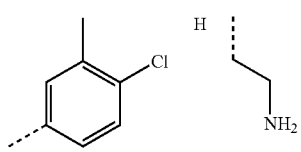 | H | 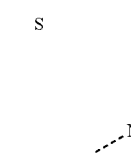 | S | 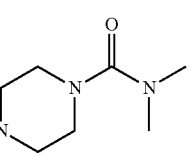 | 639.3 | 640.1 | 3.39 | 5 |
| 12-110 | 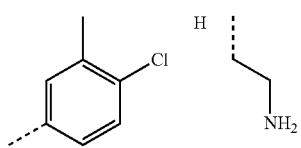 | H | 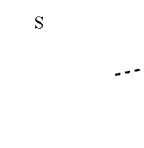 | S | 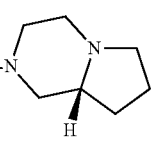 | 608.3 | 609.1 | 2 | 5 |
| 12-111 | 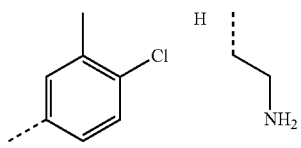 | H | 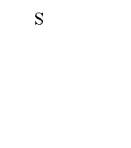 | S | 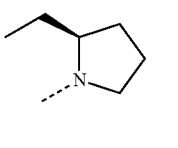 | 581.3 | 582.1 | 4.2 | 5 |

TABLE 12-continued
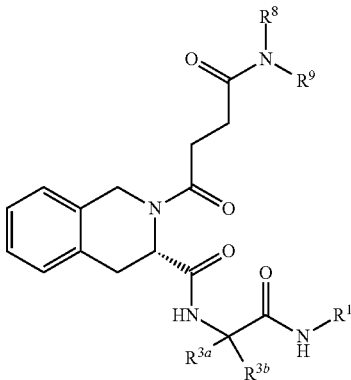
| Cmpd # | R¹ | R³ᵃ | R³ᵇ | *1 R³ᵃ/R³ᵇ Stereo-chem | NR⁸R⁹ | MS Calc | MS (MH)⁺ | Purity RT | Purity Method |
|---|---|---|---|---|---|---|---|---|---|
| 12-112 | 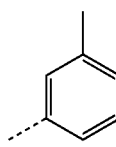 | H | 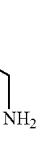 | S | 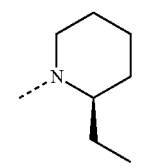 | 595.3 | 596.1 | 4.51 | 5 |
| 12-113 | 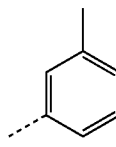 | H | 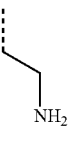 | S | 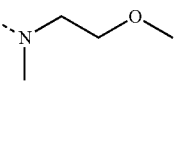 | 571.3 | 572.1 | 3.45 | 5 |
| 12-114 | 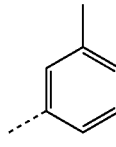 | H |  | S | 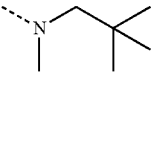 | 583.3 | 584.1 | 4.5 | 5 |
| 12-115 | 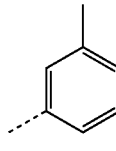 | H |  | S | 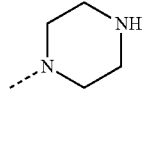 | 568.3 | 569.1 | 1.78 | 5 |
| 12-116 | 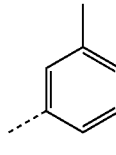 | H |  | S | 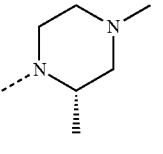 | 596.3 | 597.1 | 1.86 | 5 |
| 12-117 | 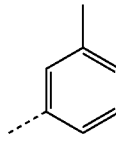 | H |  | S | 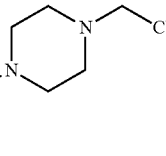 | 607.3 | 608.1 | 3.33 | 5 |
| 12-118 | 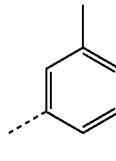 | H |  | S | 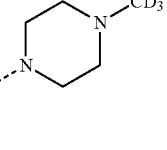 | 585.3 | 586.1 | 1.83 | 5 |

TABLE 12-continued
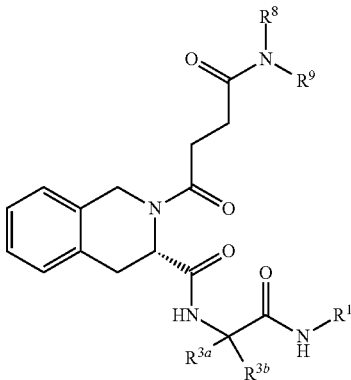
| Cmpd # | R¹ | R³ᵃ | R³ᵇ | *1 R³ᵃ/R³ᵇ Stereo-chem | 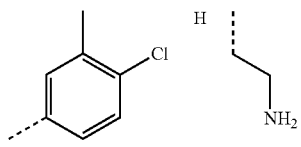 | MS Calc | MS (MH)⁺ | Purity RT | Purity Method |
|---|---|---|---|---|---|---|---|---|---|
| 12-119 | 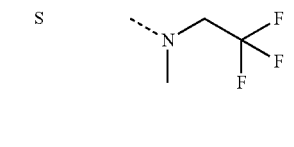 | H | 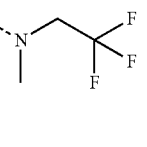 | S | 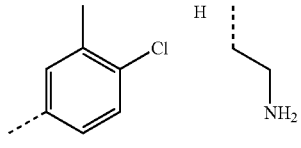 | 595.2 | 596 | 3.96 | 5 |
| 12-120 | 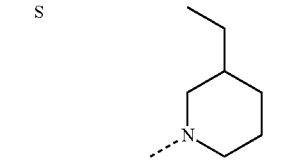 | H | 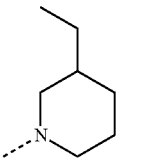 | S | 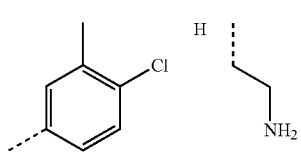 | 595.3 | 596.1 | 4.31 | 5 |
| 12-121 | 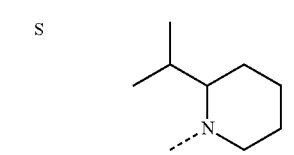 | H | 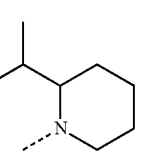 | S | 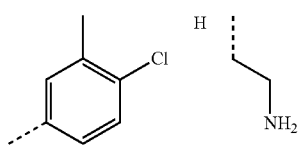 | 609.3 | 610.1 | 4.87 | 5 |
| 12-122 | 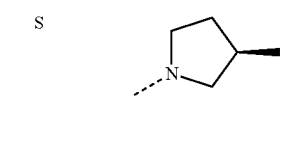 | H | 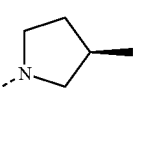 | S | 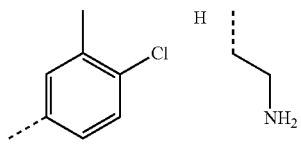 | 567.3 | 568.1 | 4.04 | 5 |
| 12-123 | 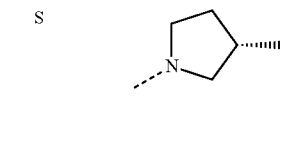 | H | 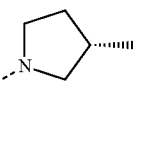 | S | 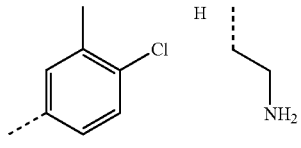 | 567.3 | 568.1 | 4.05 | 5 |
| 12-124 | 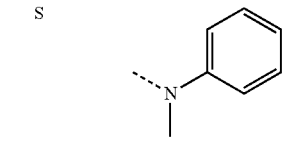 | H | 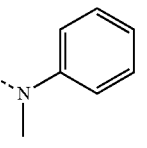 | S | 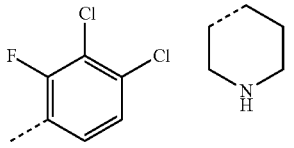 | 589.3 | 590 | 4.43 | 5 |
| 12-125 | 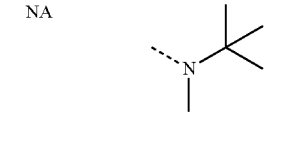 | \multicolumn{2}{c}{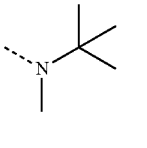} | NA | | 633.2 | 636 | 4.41 | 5 |

TABLE 12-continued

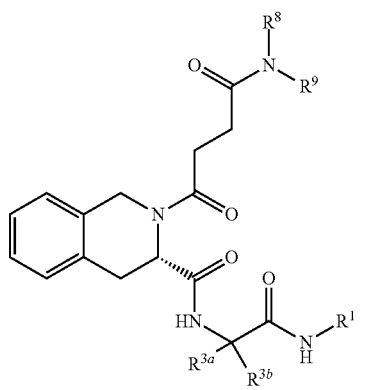

| Cmpd # | R¹ | R³ᵃ | R³ᵇ | *1 R³ᵃ/R³ᵇ Stereo- chem | $\underset{R^9}{\overset{R^8}{N}}$ | MS Calc | MS (MH)⁺ | Purity RT | Purity Method |
|---|---|---|---|---|---|---|---|---|---|
| 12-126 | 3-methyl-4-chlorophenyl | H | CH₂CH₂NH₂ | S | 4-ethyl-2,2-dimethylpiperazinyl | 624.3 | 625.1 | 2.34 | 5 |
| 12-127 | 2-fluoro-3,4-dichlorophenyl | piperidinyl | | NA | 3,3-dimethylmorpholinyl | 661.2 | 664 | 3.89 | 5 |
| 12-128 | 2-fluoro-3,4-dichlorophenyl | piperidinyl | | NA | 6-azaspiro[3.5]nonyl | 671.2 | 674 | 4.51 | 5 |
| 12-129 | 2-fluoro-3,4-dichlorophenyl | piperidinyl | | NA | neopentylamino | 633.2 | 636 | 4.34 | 5 |
| 12-130 | 2-fluoro-3,4-dichlorophenyl | piperidinyl | | NA | 3,3-dimethylpiperidinyl | 659.2 | 662.1 | 4.74 | 5 |
| 12-131 | 3-methyl-4-chlorophenyl | H | CH₂CH₂NH₂ | S | 1,3,3-trimethylpiperazinyl | 610.3 | 611.1 | 1.52 | 5 |
| 12-132 | 3-methyl-4-chlorophenyl | H | CH₂CH₂NH₂ | S | (2S)-1-methyl-2-phenylpyrrolidinyl | 629.3 | 630.1 | 4.6 | 5 |

TABLE 12-continued
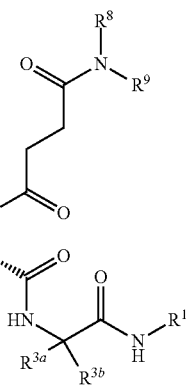
| Cmpd # | R¹ | R³ᵃ | R³ᵇ | *1 R³ᵃ/R³ᵇ Stereo-chem | 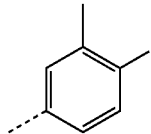 | MS Calc | MS (MH)⁺ | Purity RT | Purity Method |
|---|---|---|---|---|---|---|---|---|---|
| 12-133 |  | H | 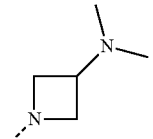 | S | 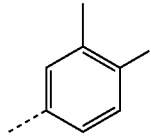 | 582.3 | 583.1 | 1.86 | 5 |
| 12-134 |  | H | 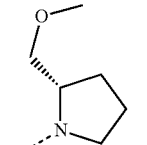 | S | 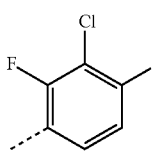 | 597.3 | 598.1 | 3.77 | 5 |
| 12-135 | 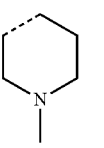 | 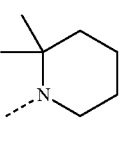 | | NA | 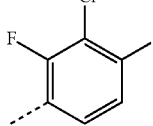 | 659.2 | 662.1 | 4.42 | 5 |
| 12-136 | 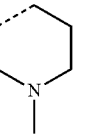 | 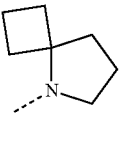 | | NA | 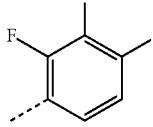 | 657.2 | 660 | 4.32 | 5 |
| 12-137 | 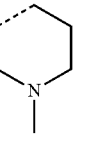 | 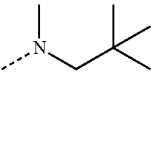 | | NA | 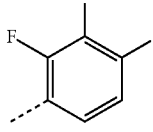 | 647.2 | 650 | 4.29 | 5 |
| 12-138 | 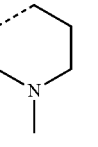 | 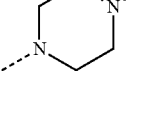 | | NA | 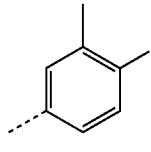 | 646.2 | 649 | 2.15 | 5 |
| 12-139 |  | H | 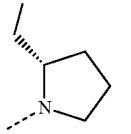 | S | | 585.3 | 586.1 | 3.88 | 5 |

TABLE 12-continued
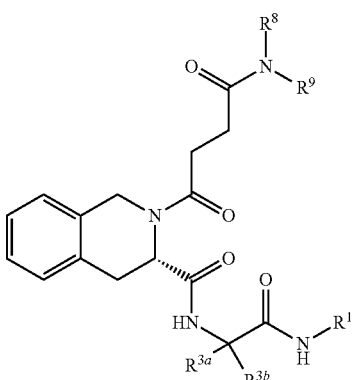
| Cmpd # | R¹ | R³ᵃ | R³ᵇ | *1 R³ᵃ/R³ᵇ Stereo-chem | 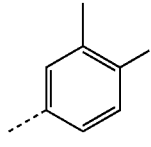 | MS Calc | MS (MH)⁺ | Purity RT | Purity Method |
|---|---|---|---|---|---|---|---|---|---|
| 12-140 | 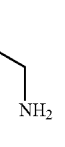 | H | 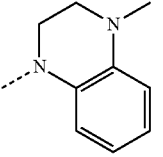 | S | 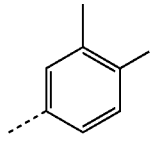 | 630.3 | 631.1 | 4.7 | 5 |
| 12-141 | 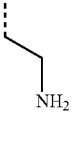 | H | 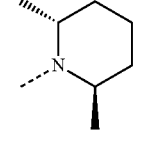 | S | 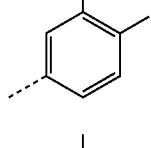 | 595.3 | 596.1 | 4.53 | 5 |
| 12-142 | 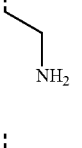 | H | 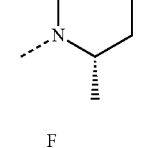 | S | 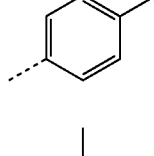 | 595.3 | 596.1 | 4.59 | 5 |
| 12-143 |  | H | 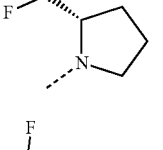 | S | 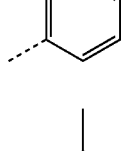 | 603.2 | 604.1 | 4.04 | 5 |
| 12-144 |  | H | 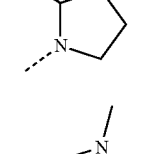 | S | 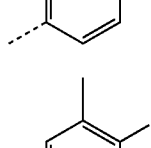 | 585.3 | 586.1 | 3.94 | 5 |
| 12-145 |  | H | 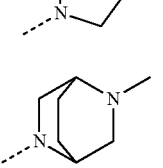 | S | 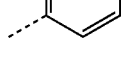 | 568.3 | 569.1 | 1.91 | 5 |
| 12-146 |  | H |  | S | | 608.3 | 609.1 | 2.00 | 5 |

TABLE 12-continued
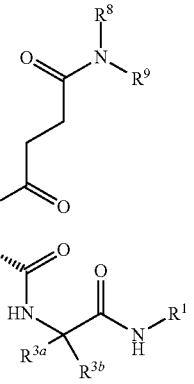
| Cmpd # | R¹ | R³ᵃ | R³ᵇ | *1 R³ᵃ/R³ᵇ Stereo-chem | NR⁸R⁹ | MS Calc | MS (MH)⁺ | Purity RT | Purity Method |
|---|---|---|---|---|---|---|---|---|---|
| 12-147 | 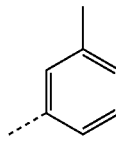 | H |  | S | 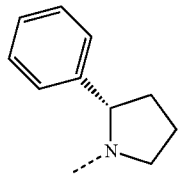 | 629.3 | 631.1 | 4.87 | 5 |
| 12-148 | 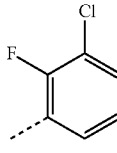 | H | 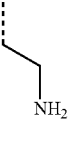 | S | 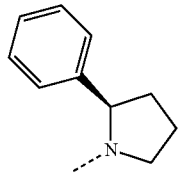 | 667.2 | 668 | 4.65 | 5 |
| 12-149 | 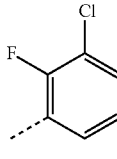 | H |  | S | 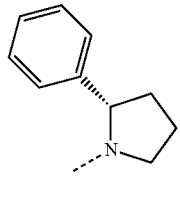 | 667.2 | 668 | 4.75 | 5 |
| 12-150 | 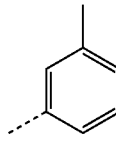 | H | 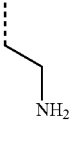 | S | 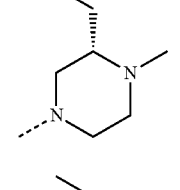 | 610.3 | 611.1 | 4.49 | 5 |
| 12-151 | 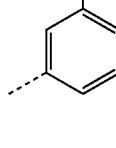 | H | 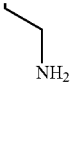 | S | 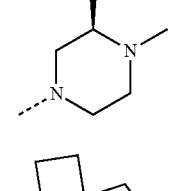 | 610.3 | 611.1 | 4.32 | 5 |
| 12-152 | 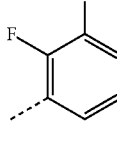 | H | 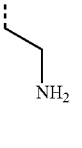 | S | 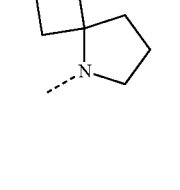 | 631.2 | 632 | 4.5 | 5 |

TABLE 12-continued

| Cmpd # | R¹ | R³ᵃ | R³ᵇ | *1 R³ᵃ/R³ᵇ Stereo-chem | R⁸\N\R⁹ | MS Calc | MS (MH)⁺ | Purity RT | Purity Method |
|---|---|---|---|---|---|---|---|---|---|
| 12-153 | 2-Cl-4-Me-phenyl | H | CH₂CH₂NH₂ | S | (3S)-3-ethylpyrrolidin-1-yl | 581.3 | 582.1 | 4.45 | 5 |
| 12-154 | 2-Cl-4-Me-phenyl | H | CH₂CH₂NH₂ | S | (3R)-3-ethylpyrrolidin-1-yl | 581.3 | 582.1 | 4.38 | 5 |
| 12-155 | 5-Cl-4-Me-pyridin-2-yl | H | CH₂CH₂NH₂ | S | 3,3-dimethylpiperidin-1-yl | 596.3 | 597.3 | 3.94 | 5 |
| 12-156 | 5-Cl-4-Me-pyridin-2-yl | H | CH₂CH₂NH₂ | S | 5-azaspiro[3.4]octan-5-yl | 594.3 | 595.3 | 3.82 | 5 |
| 12-157 | 5-Cl-4-Me-pyridin-2-yl | H | CH₂CH₂NH₂ | S | 2,2-dimethylpyrrolidin-1-yl | 582.3 | 583.4 | 3.79 | 5 |
| 12-158 | 5-Cl-4-Me-pyridin-2-yl | H | CH₂CH₂NH₂ | S | 6-azaspiro[3.5]nonan-6-yl | 608.3 | 609.4 | 4.24 | 5 |

Scheme 13
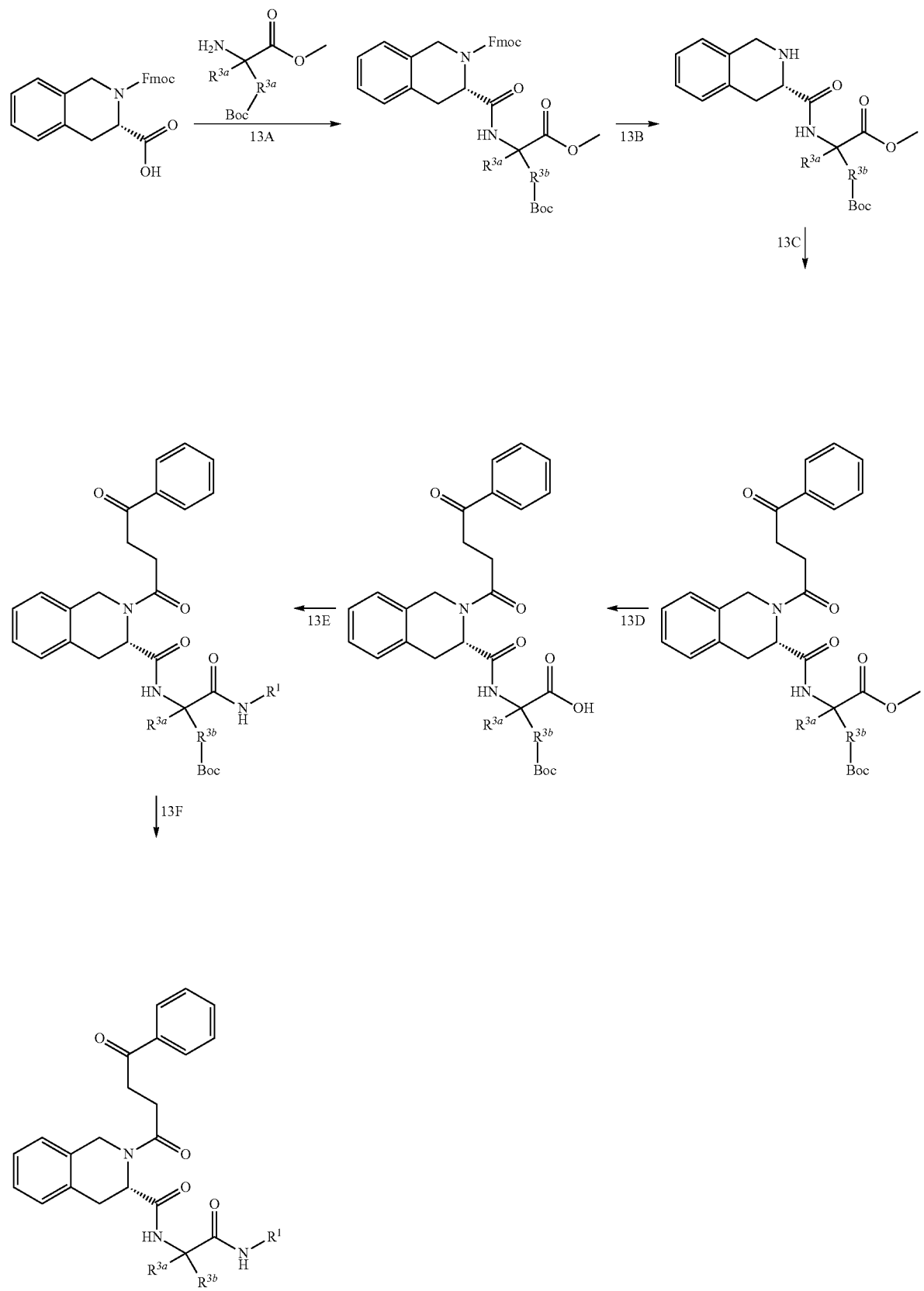

Example 13

Synthesis of ((S)—N-(4-((2,3-dihydro-1H-inden-5-yl)carbamoyl)piperidin-4-yl)-2-(4-oxo-4-phenylbutanoyl)-1,2,3,4-tetrahydroisoquinoline-3-carboxamide (Compound 13-1)

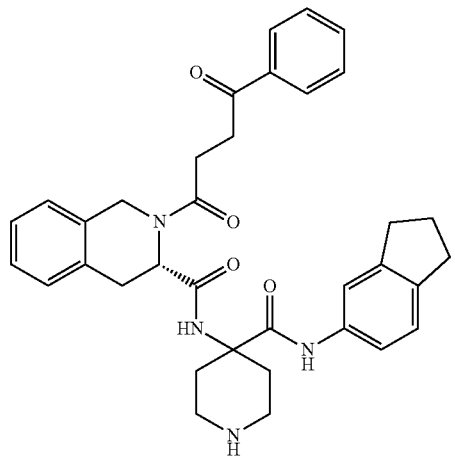

13-1

Step 13A. Synthesis of 1-(tert-butyl) 4-methyl (S)-4-(2-(((9H-fluoren-9-yl)methoxy)carbonyl)-1,2,3,4-tetrahydroisoquinoline-3-carboxamido) piperidine-1,4-dicarboxylate (Intermediate 13A)

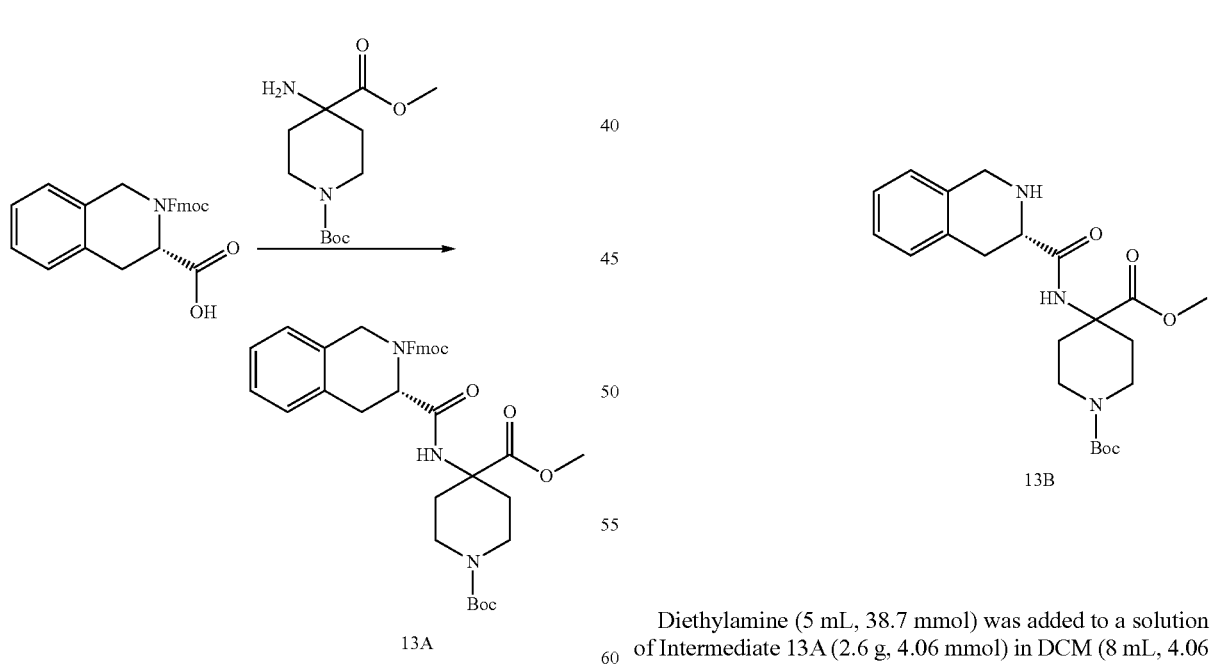

13A

Into a solution of (S)-2-(((9H-fluoren-9-yl)methoxy)carbonyl)-1,2,3,4-tetrahydroisoquinoline-3-carboxylic acid (1.7 g, 4.3 mmol) and 1-tert-butyl 4-methyl 4-aminopiperidine-1,4-dicarboxylate (1.0 g, 3.9 mmol) in DCM (100 mL) were added DIEA (3.0 mL, 19.4 mmol) and, after 20 min, HATU (4.4 g, 11.6 mmol). After 2 h, the reaction mixture was partitioned between DCM (5 mL) and a 1 M aqueous solution of HCl (100 mL). The layers were separated using a phase sep-cartridge and the aqueous layer was re-extracted with DCM (100 mL). The combined organic phases were concentrated. The crude product was purified by chromatography (EA/isohexane) to afford 2.6 g (93%) of Intermediate 13 as a white foaming solid. LCMS [m/z] calculated for $C_{37}H_{41}N_3O_7$: 639.3; found 662.1 [M+Na]$^+$, $t_R$=2.85 min (Method 4).

Step 13B. Synthesis of 1-(tert-butyl) 4-methyl (S)-4-(1,2,3,4-tetrahydroisoquinoline-3-carboxamido) piperidine-1,4-dicarboxylate (Intermediate 13B)

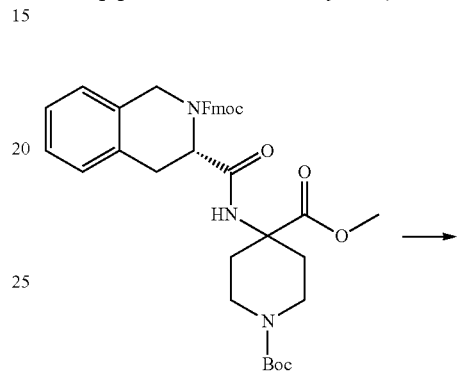

13A

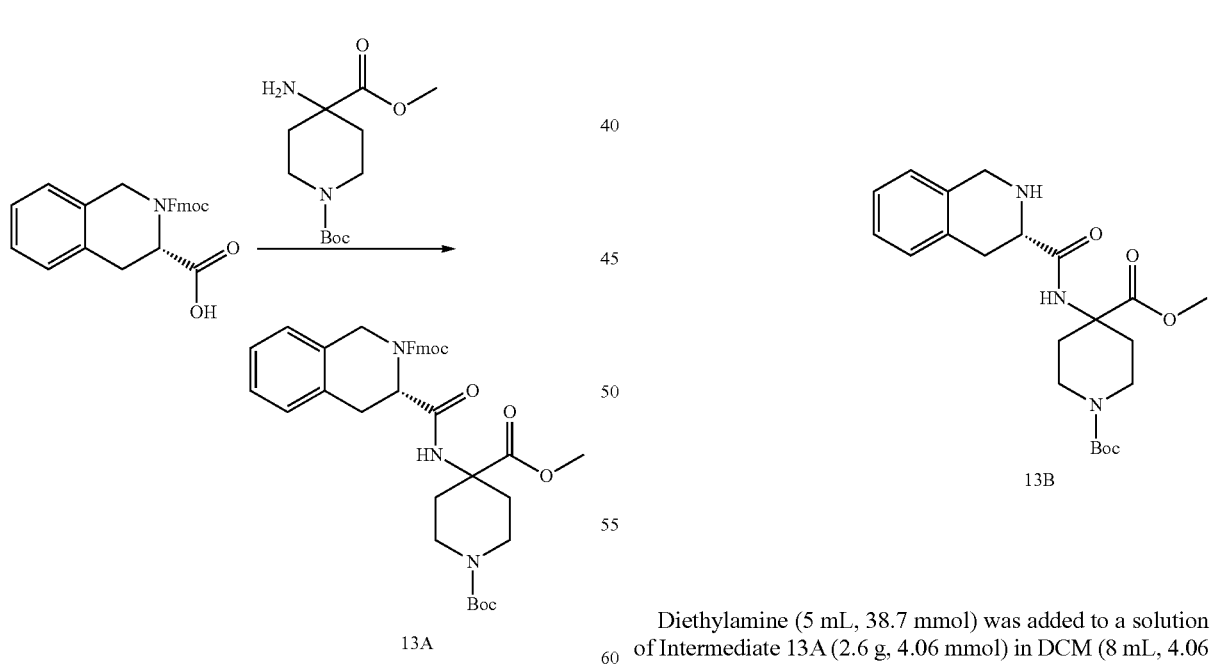

13B

Diethylamine (5 mL, 38.7 mmol) was added to a solution of Intermediate 13A (2.6 g, 4.06 mmol) in DCM (8 mL, 4.06 mmol). After 30 min, the reaction mixture was concentrated in vacuo and dissolved in toluene/DCM and re-concentrated (2×). The crude product was purified by chromatography (MeOH (+1% NH$_3$)/DCM) to afford 1.6 g (94%) of Intermediate 13 as a white sticky solid. LCMS [m/z] calculated for $C_{22}H_{31}N_3O_5$: 417.2; found 418.2 [M+H]$^+$, $t_R$=1.36 min (Method 4).

Step 13C. Synthesis of (S)-1-tert-butyl 4-methyl 4-(2-(4-oxo-4-phenylbutanoyl)-1,2,3,4-tetrahydroisoquinoline-3-carboxamido)piperidine-1,4-dicarboxylate (Intermediate 13C)

Step 13D. Synthesis of (S)-1-(tert-butoxycarbonyl)-4-(2-(4-oxo-4-phenylbutanoyl)-1,2,3,4-tetrahydroisoquinoline-3-carboxamido) piperidine-4-carboxylic acid (Intermediate 13D)

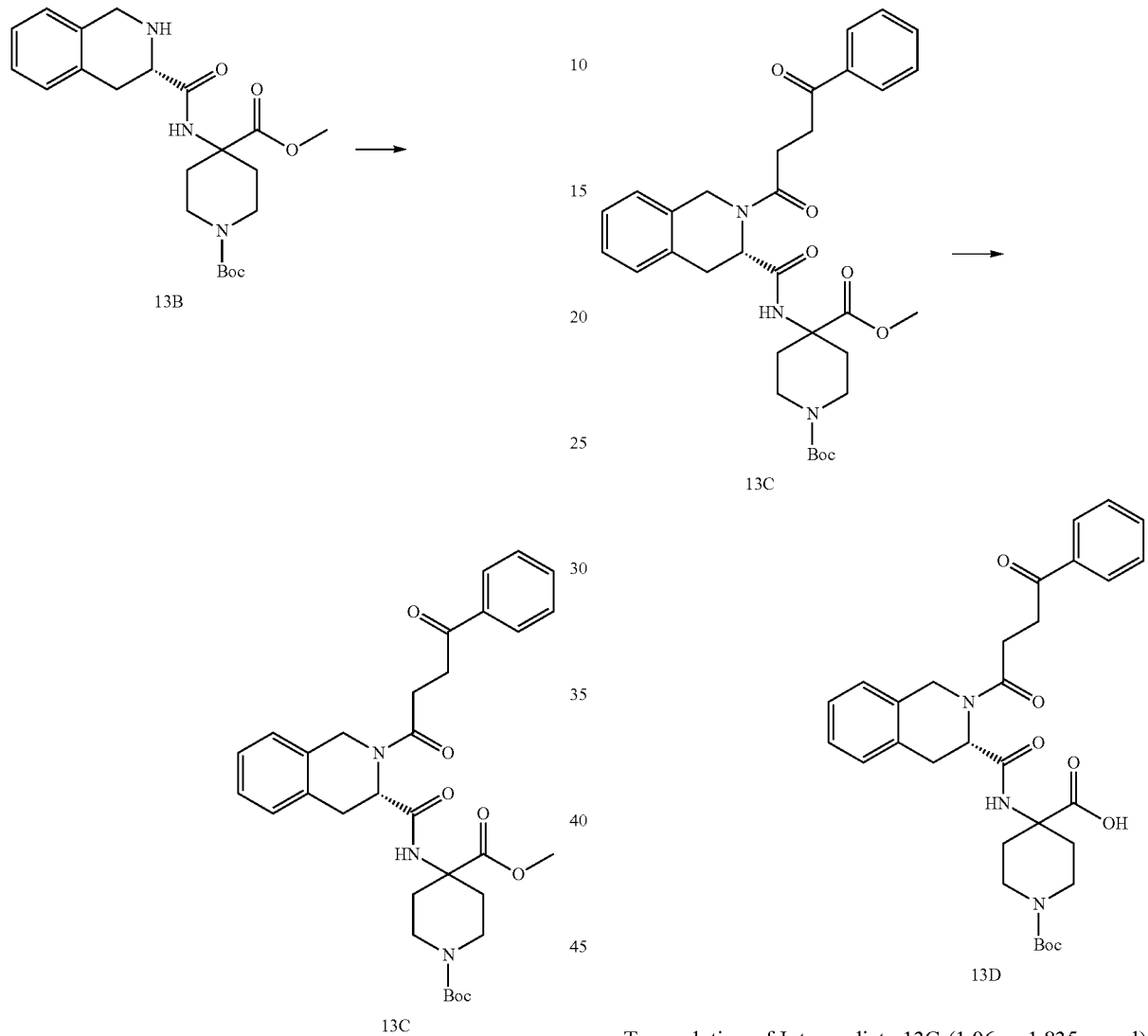

Into a solution of Intermediate 13B (1.5 g, 3.6 mmol) and 4-oxo-4-phenylbutanoic acid (1.3 g, 7.2 mmol) in DCM (15 mL) was added N-ethyl-N-isopropylpropan-2-amine (3.13 mL, 17.96 mmol). After 10 min, HATU (4.10 g, 10.78 mmol) was added. After 2 h, the reaction mixture was partitioned between DCM (20 mL) and 1 M aqueous solution of HCl (20 mL). The layers were separated using a phase sep-cartridge and the aqueous layer was re-extracted with DCM (20 mL). The combined organic phases were concentrated and the crude product was purified by chromatography (EA/isohexane) to afford 1 g (43%) of Intermediate 13C as a sticky yellow gum. LCMS [m/z] calculated for $C_{32}H_{39}N_3O_7$: 577.7; found 600.1 [M+Na]$^+$, $t_R$=2.34 min (Method 4).

To a solution of Intermediate 13C (1.06 g, 1.835 mmol) in a mixture of H$_2$O/THF (3/1, 12 mL) was added LiOH (0.439 g, 18.35 mmol). The reaction mixture was stirred for 36 h then diluted with DCM (20 mL). The aqueous layer was acidified with aq. 1 M HCl (15 mL). The layers were separated and the aqueous layer was re-extracted with DCM (20 mL). The combined organic layers were dried (MgSO$_4$), filtered, and concentrated. The resulting crude product was purified by chromatography (EA(+1% AcOH)/isohexane) to afford 1.1 g (97%) of Intermediate 13D as a white solid. LCMS [m/z] calculated for $C_{31}H_{37}N_3O_7$: 563.3; found 586.1 [M+Na]$^+$, $t_R$=2.21 min (Method 4). $^1$H NMR (400 MHz, DMSO-d6) δ 12.36 (br s, 1H), 8.14 (br s, 0.5H), 8.03-7.95 (m, 2H), 7.78 (br s, 0.5H), 7.69-7.60 (m, 1H), 7.59-7.48 (m, 2H), 7.31-7.11 (m, 4H), 5.06 (app t, J=5.2 Hz, 0.5H), 4.99-4.83 (m, 1H), 4.79-4.65 (m, 1H), 4.43 (d, J=16.3 Hz, 0.5H), 3.60 (br s, 2H), 3.48-2.99 (m, 5H), 2.97-2.66 (m, 3H), 2.05-1.77 (m, 2H), 1.76-1.49 (m, 2H), 1.39 (d, J=4.6 Hz, 9H).

Step 13E. Synthesis of tert-butyl (S)-4-((2,3-di-hydro-1H-inden-5-yl)carbamoyl)-4-(2-(4-oxo-4-phenylbutanoyl)-1,2,3,4-tetrahydroisoquinoline-3-carboxamido)piperidine-1-carboxylate (Intermediate 13E)

Step 13F. Synthesis of ((S)—N-(4-((2,3-dihydro-1H-inden-5-yl)carbamoyl) piperidin-4-yl)-2-(4-oxo-4-phenylbutanoyl)-1,2,3,4-tetrahydroisoquinoline-3-carboxamide (Compound 13-1)

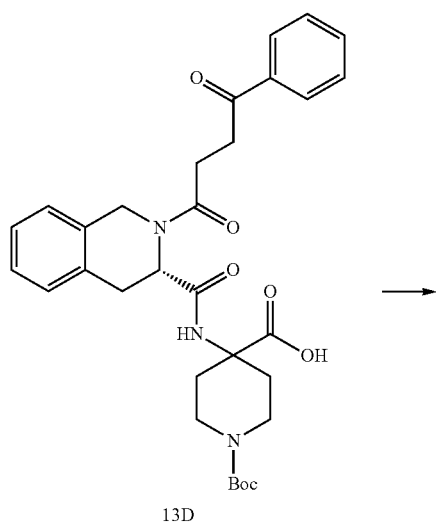

13D

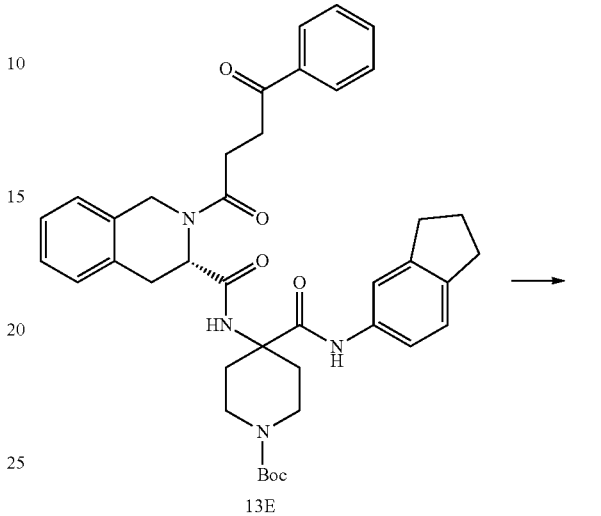

13E

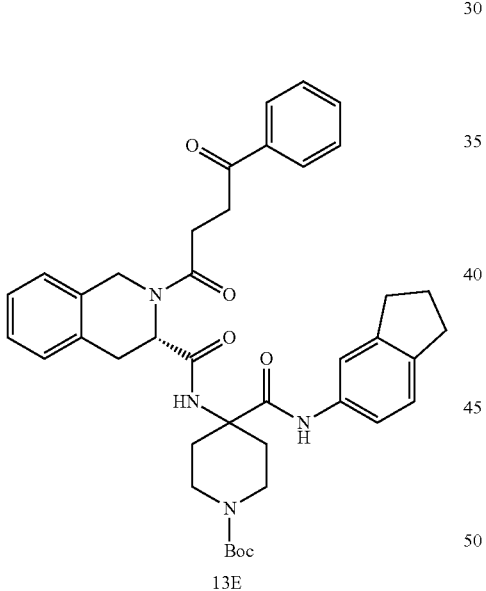

13E

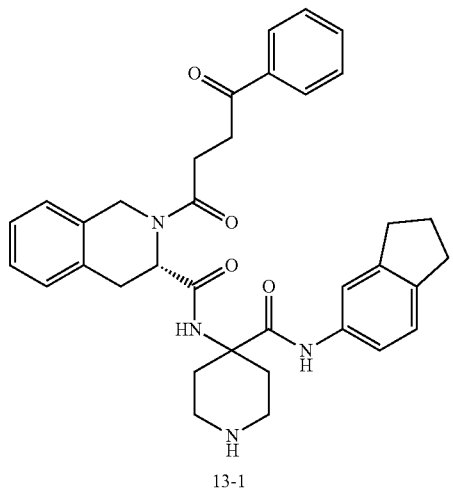

13-1

Into a solution of Intermediate 13D (50 mg, 0.09 mmol) and 2,3-dihydro-1H-inden-5-amine (35.4 mg, 0.27 mmol) in DMF (3 mL) was added DIEA (0.08 mL, 0.44 mmol). The reaction mixture was heated at 50° C. for 10 min and HATU (101 mg, 0.266 mmol) was added. The reaction mixture was stirred at 50° C. overnight then partitioned between DCM (5 mL) and 1 M aqueous solution of HCl (5 mL). The layers were separated using a phase sep-cartridge and the aqueous layer was re-extracted with DCM (5 mL). The combined organic phases were concentrated in vacuo and the resulting crude material was purified by chromatography (MeOH/DCM) to afford unclean Intermediate 13E, which was used without further purification.

Intermediate 13E was dissolved in DCM (5 mL) and TFA (1 mL). After 4 h, the solvents were removed and the crude product was purified by chromatography (0.7 M $NH_3$/MeOH)/DCM) to afford 16 mg (30%) of Compound 13-1 as a white solid. LCMS [m/z] calculated for $C_{35}H_{38}N_4O_4$: 578.3; found 579.1 [M+H]$^+$, $t_R$=4.31 min (Method 5). $^1$H NMR (400 MHz, DMSO-$d_6$, 363 K) δ 8.68 (br s, 1H), 8.00-7.83 (m, 2H), 7.62 (t, J=7.4 Hz, 1H), 7.49 (t, J=7.6 Hz, 2H), 7.35 (br s, 2H), 7.25-7.18 (m, 4H), 6.97 (d, J=8.2 Hz, 1H), 4.85-4.74 (m, 3H), 3.34 (br s, 2H), 3.21 (br s, 2H), 2.97-2.82 (m, 4H), 2.79-2.73 (m, 4H), 2.68-2.64 (m, 1H), 2.62-2.55 (m, 1H), 2.18-1.74 (m, 6H), CH$_2$NH, NHAr not observed.

Following the procedures as set forth in Example 13 above, the compounds of the following Table 13 were prepared using the appropriate R$^1$ reagents.

TABLE 13

| Compound Number | R¹ | MS Calc | MS (MH)⁺ | LCMS Retention (min) | Purity Method |
|---|---|---|---|---|---|
| 13-1 | indanyl | 578.7 | 579.1 | 4.31 | 5 |
| 13-2 | 3-F-phenyl (F meta) | 570.6 | 571.1 | 3.87 | 5 |
| 13-3 | 2-F-phenyl | 570.6 | 571.1 | 3.79 | 5 |
| 13-4 | 5-Cl-2-OMe-phenyl | 576.2 | 577.3 | 12.01 | 2 |
| 13-5 | 2-OMe-6-ethyl-phenyl | 570.3 | 571.1 | 12.19 | 2 |
| 13-6 | 4-F-2-OMe-phenyl | 560.2 | 561.1 | 11.22 | 2 |
| 13-7 | 2-OCF₃-phenyl | 610.2 | 611.1 | 11.89 | 2 |

Scheme 14
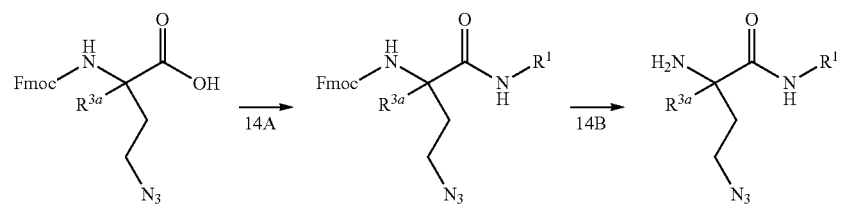
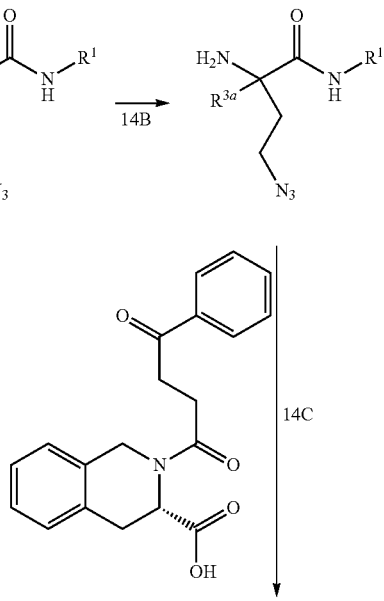
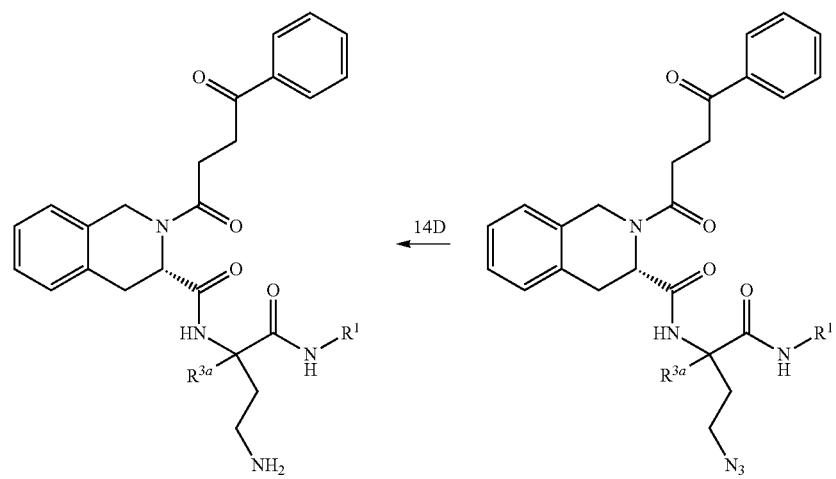

Example 14

Synthesis of (S)—N—((S)-4-amino-1-((2-chloro-5-fluorophenyl)amino)-1-oxobutan-2-yl)-2-(4-oxo-4-phenylbutanoyl)-1,2,3,4-tetrahydroisoquinoline-3-carboxamide (Compound 14-1)

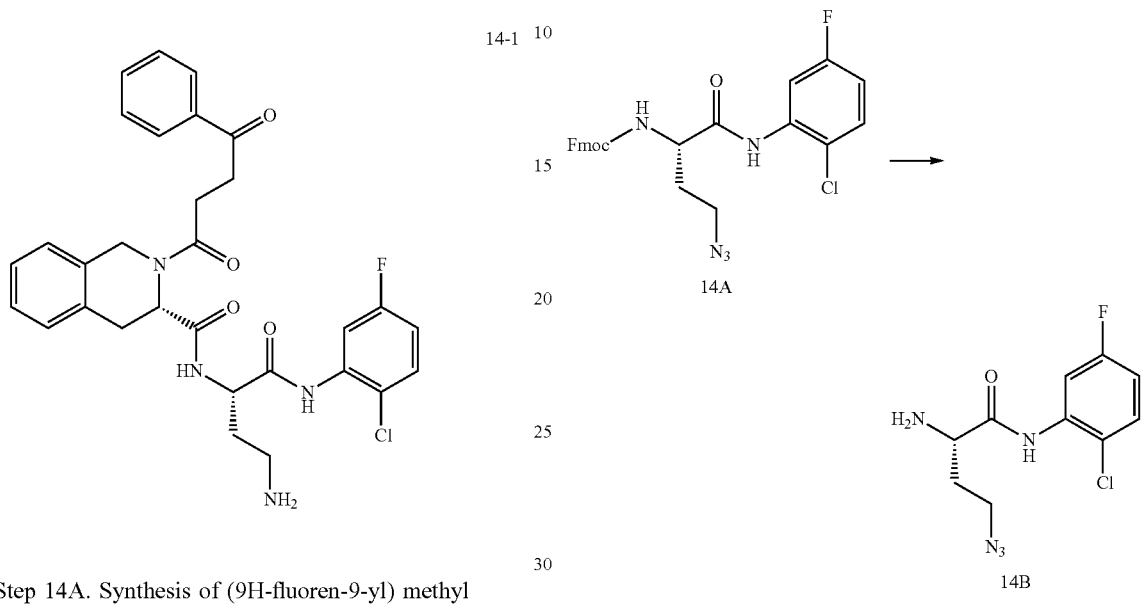

Step 14A. Synthesis of (9H-fluoren-9-yl) methyl (S)-(4-azido-1-((2-chloro-5-fluoro phenyl) amino)-1-oxo butan-2-yl)carbamate (Intermediate 14A)

A solution of (S)-2-((((9H-fluoren-9-yl)methoxy)carbonyl)amino)-4-azidobutanoic acid (300 mg, 0.81 mmol) in anhydrous DCM (15 mL) in a flame-dried round-bottom flask under $N_2$ was cooled to 0° C. 1-Chloro-N, N-2-trimethylprop-1-en-1-amine (0.18 mL, 1.5 mmol) was added. After 10 min, a solution of 2-chloro-5-fluoroaniline (108 mg, 0.75 mmol) in 2 mL of 1:1 DCM: pyridine was added. After 10 min, the reaction was diluted with DCM and washed with brine (2×). The organic layer was dried ($Na_2SO_4$) and concentrated to provide crude Intermediate 14A, which was used without further purification. LCMS [m/z] calculated for $C_{25}H_{21}ClFN_5O_3$: 493.1; found 494.3 [M+H]$^+$, $t_R$=5.9 min (Method 1).

Step 14B. Synthesis of (S)-2-amino-4-azido-N-(2-chloro-5-fluorophenyl)butanamide (Intermediate 14B)

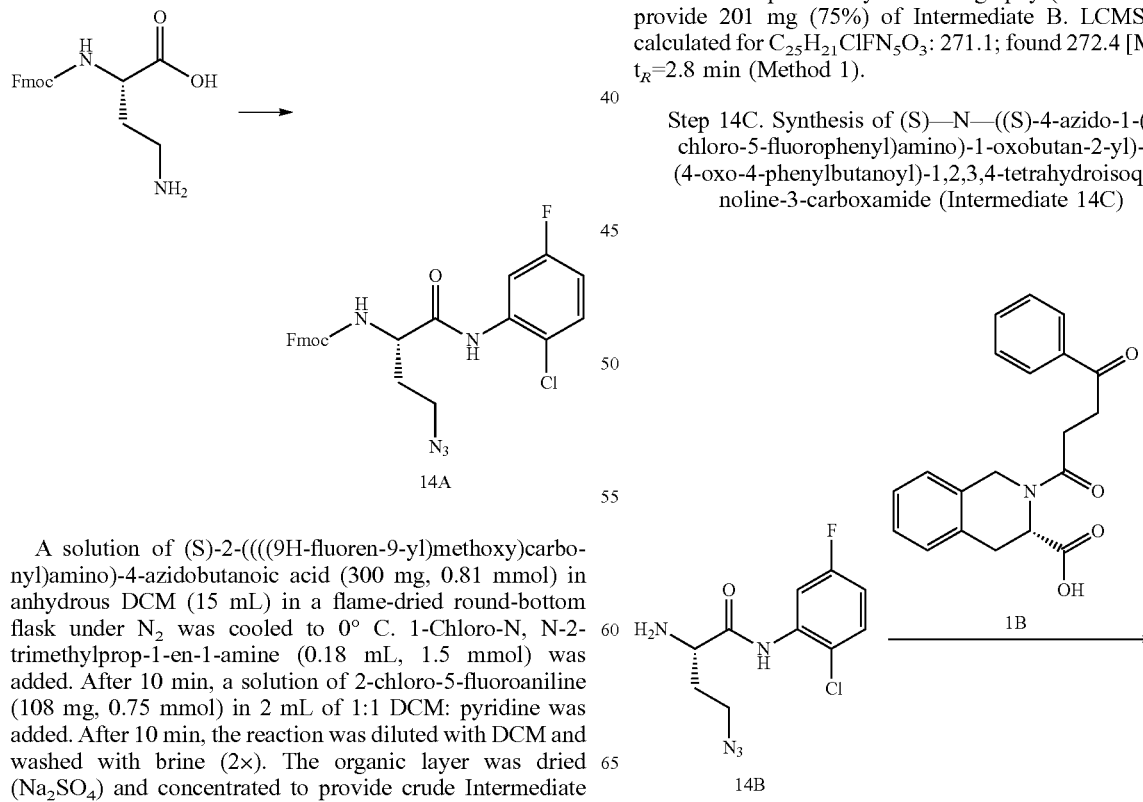

Pyrrolidine (1 mL) was added to a solution of Intermediate 14A in DCM (2 mL). After 30 min, the reaction mixture was concentrated in vacuo. The resulting crude material was purified by chromatography (EA/hexanes) to provide 201 mg (75%) of Intermediate B. LCMS [m/z] calculated for $C_{25}H_{21}ClFN_5O_3$: 271.1; found 272.4 [M+H]$^+$, $t_R$=2.8 min (Method 1).

Step 14C. Synthesis of (S)—N—((S)-4-azido-1-((2-chloro-5-fluorophenyl)amino)-1-oxobutan-2-yl)-2-(4-oxo-4-phenylbutanoyl)-1,2,3,4-tetrahydroisoquinoline-3-carboxamide (Intermediate 14C)

579
-continued

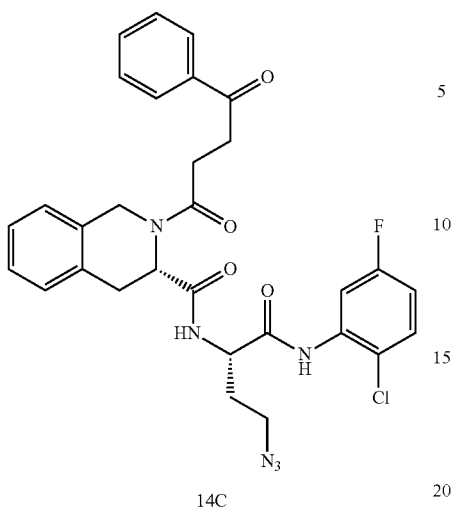

14C

580
-continued

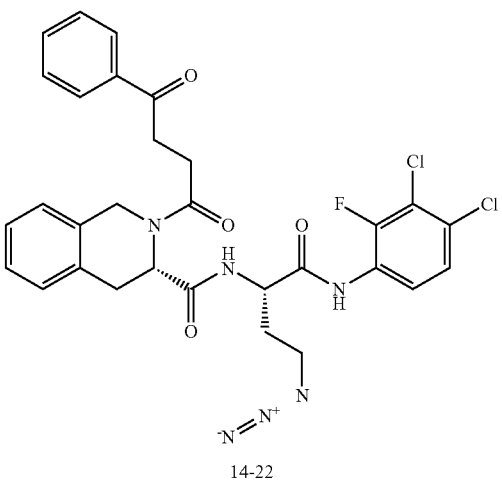

14-22

Into a solution of Intermediate 14B (150 mg, 0.55 mmol) and Intermediate 1B (170 mg, 0.5 mmol) in DMF (2 mL) and THF (2 mL) was added DIEA (0.22 mL, 1.26 mmol). The reaction mixture was cooled to 0° C. and HATU (191 mg, 0.5 mmol) was added. The reaction mixture was stirred for 6 h then diluted with EA and washed with water (3×), NaHCO$_3$, and dried (MgSO$_4$). The resulting crude material was purified by chromatography (MeOH/DCM) to afford 150 mg (51%) Intermediate 14C. LCMS [m/z] calculated for $C_{30}H_{28}ClFN_6O_4$: 590.2; found 591.3 [M+H]$^+$, $t_R$=5.41 min (Method 1).

Synthesis of (S)—N—((S)-4-azido-1-((3,4-dichloro-2-fluorophenyl)amino)-1-oxobutan-2-yl)-2-(4-oxo-4-phenylbutanoyl)-1,2,3,4-tetrahydroisoquinoline-3-carboxamide (Compound 14-22)

Compound 14-22 was synthesized from (S)-2-amino-4-azido-N-(3,4-dichloro-2-fluorophenyl)butanamide according to Step 14C. LCMS [m/z] calculated for $C_{30}H_{27}Cl2FN_6O_4$: 625.5; found 627.9 [M+H]$^+$, $t_R$=8.33 min (Method 3).

Step 14D. Synthesis of (S)—N—((S)-4-amino-1-((2-chloro-5-fluorophenyl) amino)-1-oxobutan-2-yl)-2-(4-oxo-4-phenylbutanoyl)-1,2,3,4-tetrahydroisoquinoline-3-carboxamide (Compound 14-1)

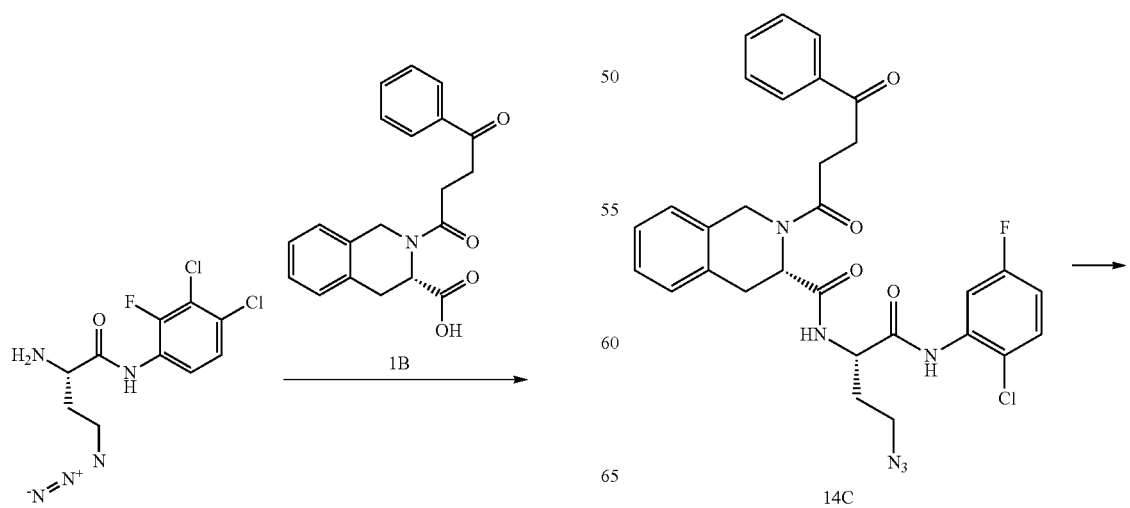

14C

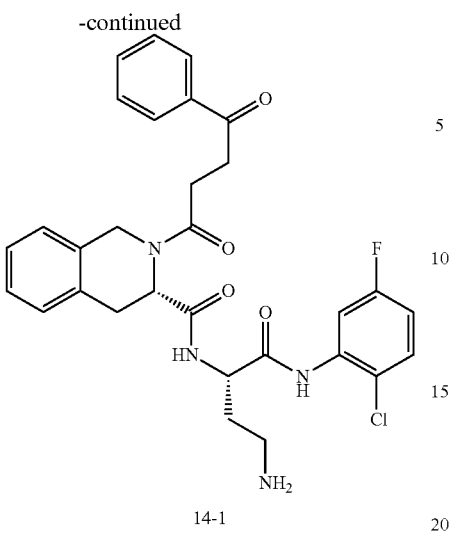

14-1

Into a solution of Intermediate 14C (150 mg, 0.25 mmol) in THF (5 mL) were added H$_2$O (0.2 mL) and PS—PPh$_3$ resin (250 mg, 0.5 mmol equiv). After shaking for 24 h, the resin was removed via filtration through celite. The resulting solution was concentrated and purified by RP-HPLC (MeOH/H$_2$O) to afford 22.4 mg (16%) Compound 14-1. LCMS [m/z] calculated for C$_{30}$H$_{30}$ClFN$_4$O$_4$: 564.2; found 565.2 [M+H]$^+$, t$_R$=11.33 min (Method 1).

Following the procedures as set forth in Example 14 above, the compounds of the following Table 14 were prepared using the appropriate R$^1$ reagents.

TABLE 14

| Compound Number | R$^1$ | *2 R$^{3a}$/R$^{3b}$ Stereochemistry | MS Calc | LCMS MS (MH)$^+$ | Retention (min) | Purity Method |
|---|---|---|---|---|---|---|
| 14-1 | ![F,Cl phenyl] | S | 564.2 | 565 | 11.33 | 1 |
| 14-2 | ![Cl,Cl,CF3 phenyl] | S | 648.2 | 649.5 | 12.56 | 1 |

TABLE 14-continued

| Compound Number | R¹ | *² R³ᵃ/R³ᵇ Stereochemistry | MS Calc | MS (MH)⁺ | LCMS Retention (min) | Purity Method |
|---|---|---|---|---|---|---|
| 14-3 | 2,6-dichloro-3-methylphenyl | S | 594.2 | 596.9 | 12.38 | 1 |
| 14-4 | 3,4,5-trichlorophenyl | S | 614.1 | 615 | 11.68 | 1 |
| 14-5 | 3-fluoro-2-methylphenyl | S | 544.3 | 545 | 10.3 | 1 |
| 14-6 | 2-chloro-6-methylphenyl | S | 560.2 | 561.3 | 11.76 | 1 |
| 14-7 | 2,6-dichlorophenyl | S | 580.2 | 581.3 | 11.24 | 1 |
| 14-8 | 2,3-dichlorophenyl | S | 580.2 | 581 | 11.91 | 1 |
| 14-9 | 2-fluoro-6-chlorophenyl | S | 564.2 | 565.4 | 10.92 | 1 |

TABLE 14-continued
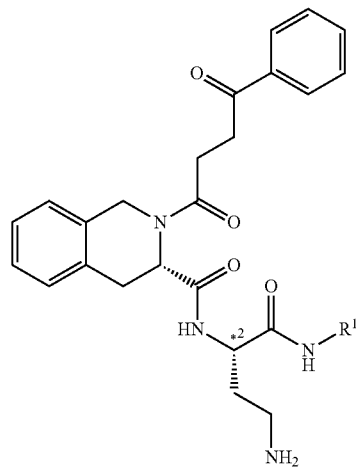
| Compound Number | R¹ | *² R$^{3a}$/R$^{3b}$ Stereochemistry | MS Calc | MS (MH)⁺ | LCMS Retention (min) | Purity Method |
|---|---|---|---|---|---|---|
| 14-10 | 2-Cl, 6-Me-phenyl | S | 560.2 | 561.1 | 11.3 | 1 |
| 14-11 | 2,5-diCl-phenyl | S | 580.2 | 581 | 11.8 | 1 |
| 14-12 | 4-Cl, 2-CF₃-phenyl | S | 614.2 | 615 | 12.14 | 1 |
| 14-13 | 3-CF₃, 5-Me-phenyl | S | 594.3 | 595 | 11.69 | 1 |
| 14-14 | 5-Cl, 2-CF₃-phenyl | S | 614.2 | 615 | 11.93 | 1 |
| 14-15 | 2-CF₃-phenyl | S | 580.2 | 581 | 11.34 | 1 |

TABLE 14-continued
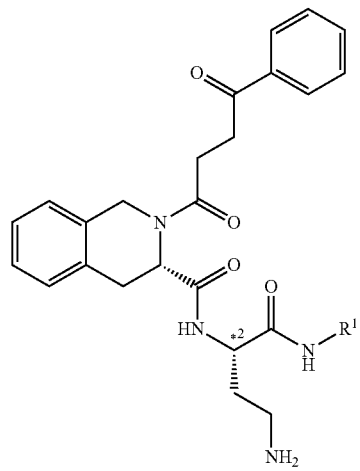
| Compound Number | R¹ | *² R³ᵃ/R³ᵇ Stereochemistry | MS Calc | MS (MH)⁺ | LCMS Retention (min) | Purity Method |
|---|---|---|---|---|---|---|
| 14-16 | 3-Cl, 2-CF₃-phenyl | S | 614.2 | 615 | 11.73 | 1 |
| 14-17 | 4-CF₃, 3-Me-phenyl | S | 594.3 | 595 | 11.7 | 1 |
| 14-18 | 5-CN, 2-Cl, 4-Me-phenyl | S | 585.2 | 586 | 11.64 | 1 |
| 14-19 | 2-CN, 3-Me-phenyl | S | 551.3 | 552.4 | 10.88 | 1 |
| 14-20 | 3-CN, 4-Me-phenyl | S | 551.3 | 552 | 10.83 | 1 |
| 14-21 | 2,6-diCl, 3-Et-phenyl | S | 608.2 | 609 | 12.82 | 1 |
| 14-23 | 4-Cl, 2-OCF₃-phenyl | S | 630.2 | 631.3 | 12.49 | 1 |

TABLE 14-continued
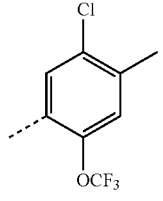
| Compound Number | R¹ | *² R³ᵃ/R³ᵇ Stereochemistry | MS Calc | MS (MH)⁺ | LCMS Retention (min) | Purity Method |
|---|---|---|---|---|---|---|
| 14-24 | 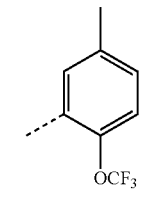 (4-Cl, 3-Me, 5-OCF₃ phenyl) | S | 644.2 | 645.2 | 12.5 | 1 |
| 14-25 | 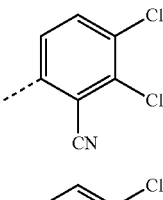 (4-OCF₃, 3-Me phenyl) | S | 610.2 | 611.3 | 11.94 | 1 |
| 14-26 | 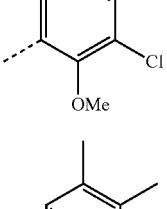 (2,3-diCl, CN phenyl) | S | 605.2 | 606 | 4.27 | 5 |
| 14-27 | (2,3-diCl, OMe phenyl) | S | 610.2 | 613.1 | 12.36 | 1 |
| 14-28 | 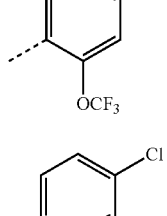 (3,5-diMe, 4-OCF₃ phenyl) | S | 624.3 | 625.1 | 12.13 | 1 |
| 14-29 | 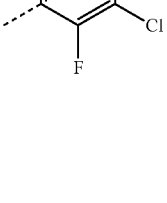 (2,3-diCl, F phenyl) | R | 598.2 | 600.9 | 6.66 | 3 |

TABLE 14-continued
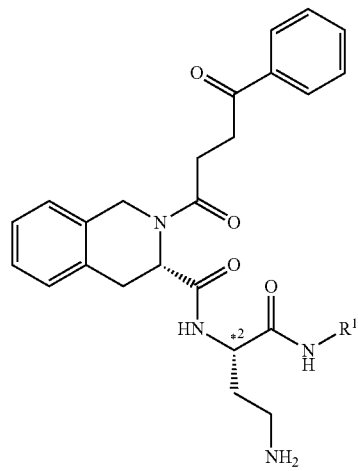
| Compound Number | R[1] | *[2] R[3a]/R[3b] Stereochemistry | MS Calc | MS (MH)+ | LCMS Retention (min) | Purity Method |
|---|---|---|---|---|---|---|
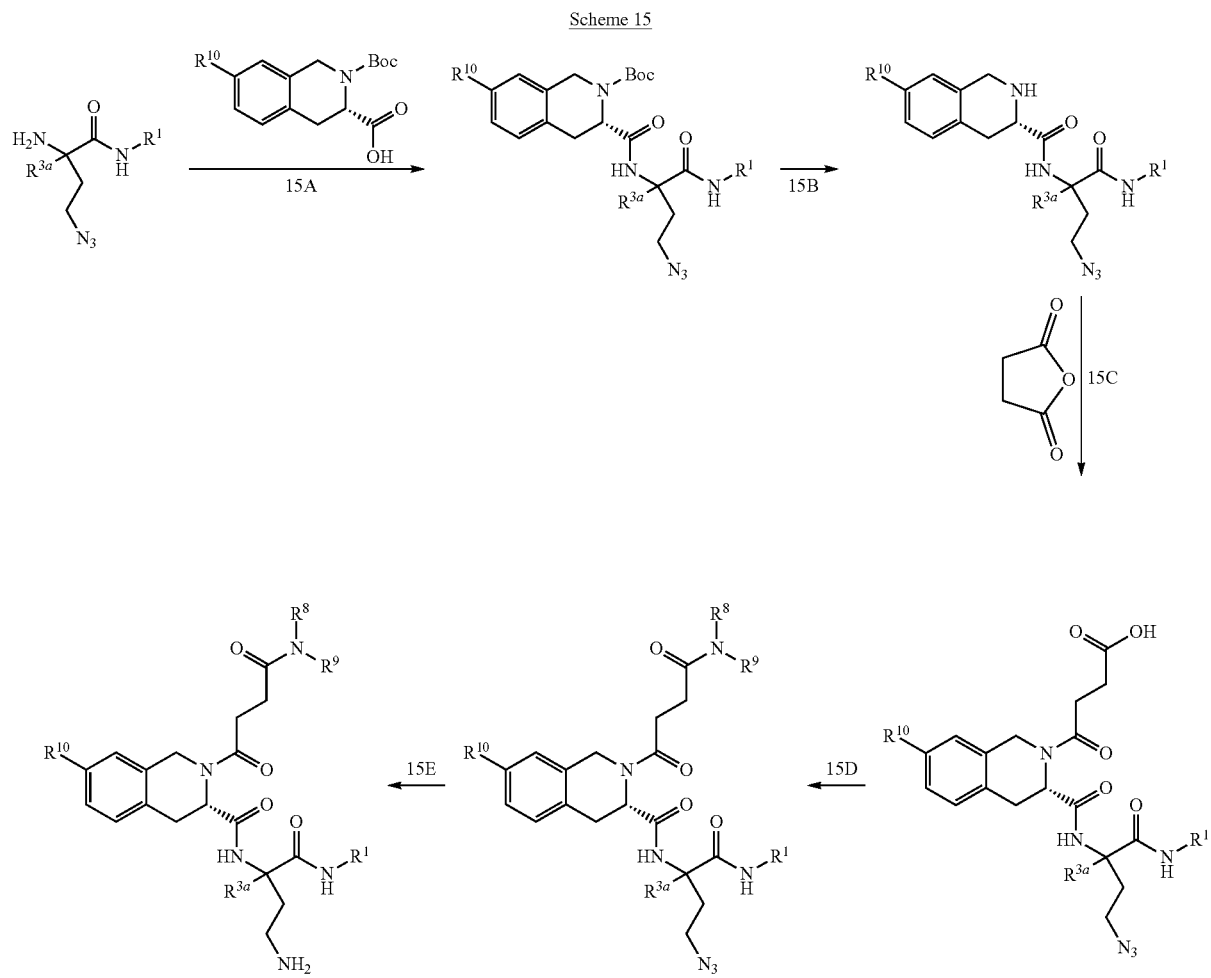
Scheme 15

Example 15

Synthesis of (S)—N—((S)-4-amino-1-((3,4-dichloro-2-fluorophenyl)amino)-1-oxobutan-2-yl)-2-(4-(4,4-dimethylpiperidin-1-yl)-4-oxobutanoyl)-1,2,3,4-tetrahydroisoquinoline-3-carboxamide (Compound 15-1)

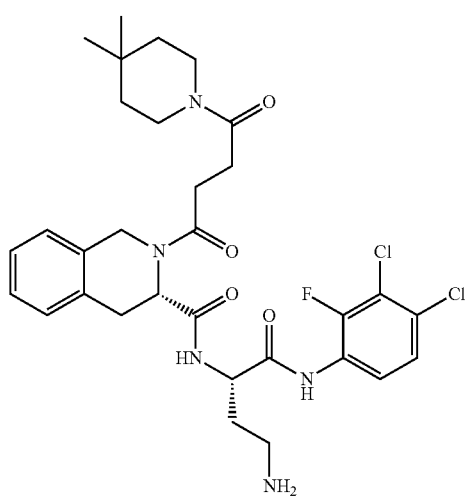

15-1

Step 15A. Synthesis of tert-butyl (S)-3-(((S)-4-azido-1-((3,4-dichloro-2-fluorophenyl)amino)-1-oxobutan-2-yl)carbamoyl)-3,4-dihydroisoquinoline-2(1H)-carboxylate (Intermediate 15A)

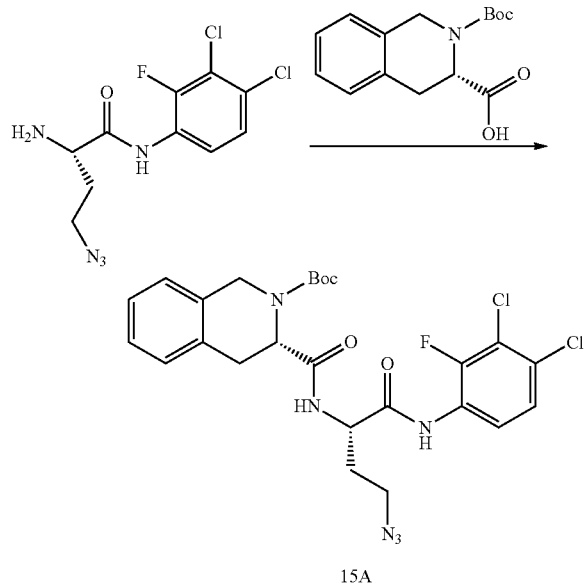

15A

Into a solution of (S)-2-(tert-butoxycarbonyl)-1,2,3,4-tetrahydroisoquinoline-3-carboxylic acid (500 mg, 1.8 mmol) and (S)-2-amino-4-azido-N-(3,4-dichloro-2-fluorophenyl)butanamide (600 mg, 1.98 mmol) in DMF (3 mL) and THF (8 mL) at to 0° C. was added DIEA (0.79 mL, 4.5 mmol), followed by HATU (0.69 g, 1.8 mmol). After 5 h, the reaction was diluted with EA and washed with H$_2$O (3×), and NaHCO$_3$, then dried (MgSO$_4$), concentrated and purified by column chromatography to provide 660 mg (65%) of Intermediate 15A. LCMS [m/z] calculated for C$_{25}$H$_{27}$Cl$_2$FN$_6$O$_4$: 564.2; found 564.4 [M+H]$^+$, t$_R$=6.1 min (Method 1).

Step 15B. Synthesis of (S)—N—((S)-4-azido-1-((3,4-dichloro-2-fluorophenyl)amino)-1-oxobutan-2-yl)-1,2,3,4-tetrahydroisoquinoline-3-carboxamide (Intermediate 15B)

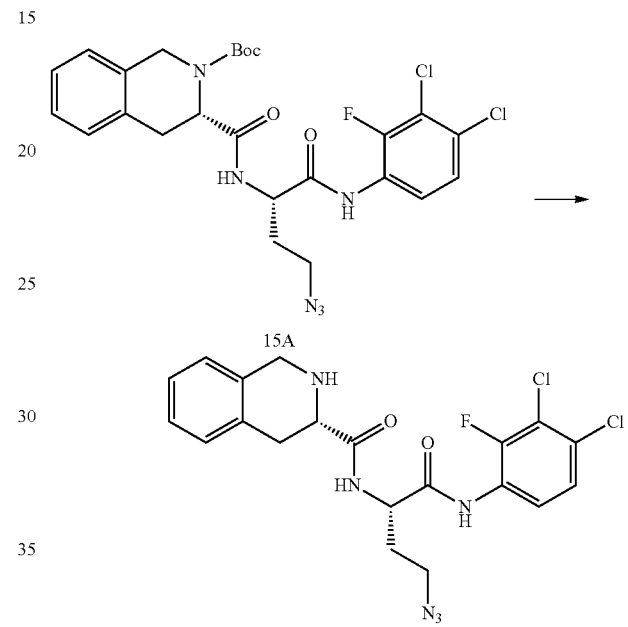

Into a solution of Intermediate 15A (2.1 g, 3.7 mmol) in DCM (8 mL) was added 4N HCl in dioxane (2.79 mL, 11.17 mmol). After 5 h, the reaction was concentrated and purified by prep-HPLC to provide 1.5 g (87%) of Intermediate 15B. LCMS [m/z] calculated for C$_{20}$H$_{19}$Cl$_2$FN$_6$O$_2$: 464.1; found 465.1 [M+H]$^+$, t$_R$=4.3 min (Method 1).

Step 15C. Synthesis of 4-((S)-3-(((S)-4-azido-1-((3,4-dichloro-2-fluorophenyl)amino)-1-oxobutan-2-yl)carbamoyl)-3,4-dihydroisoquinolin-2 (1H)-yl)-4-oxobutanoic Acid (Intermediate 15C)

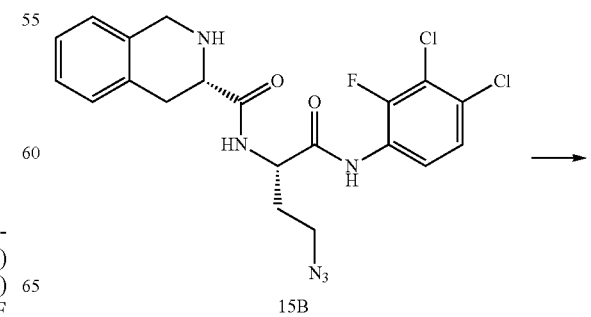

15B

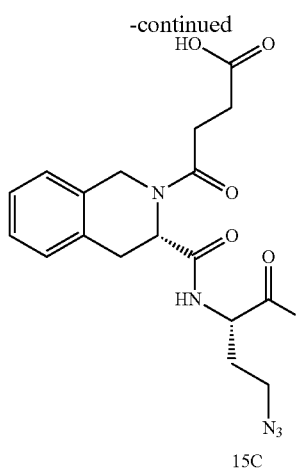

15C

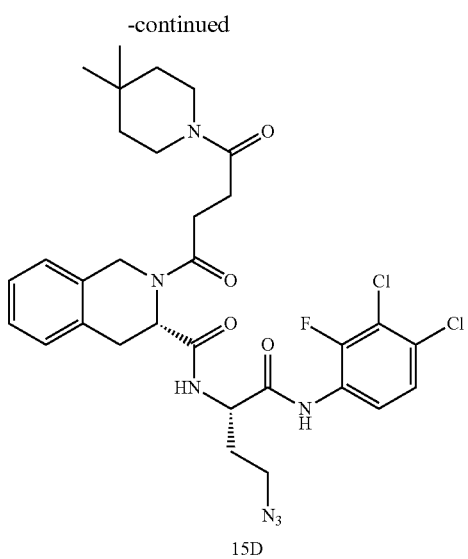

15D

Into a solution of Intermediate 15B (1.5 g, 3.2 mmol) in DCM (10 mL) were added NEt₃ (0.45 mL, 3.2 mmol) and succinic anhydride (0.32 g, 3.2 mmol) After 18 h, the reaction was concentrated and purified by column chromatography (MeOH/DCM) to provide 1.5 g (83%) of Intermediate 15C. LCMS [m/z] calculated for $C_{24}H_{23}Cl_2FN_6O_5$: 564.1; found 565.2 [M+H]$^+$, $t_R$=6.08 min (Method 1).

Step 15D. Synthesis of (S)—N—((S)-4-azido-1-((3,4-dichloro-2-fluorophenyl)amino)-1-oxobutan-2-yl)-2-(4-(4,4-dimethylpiperidin-1-yl)-4-oxobutanoyl)-1,2,3,4-tetrahydroisoquinoline-3-carboxamide (Intermediate 15D)

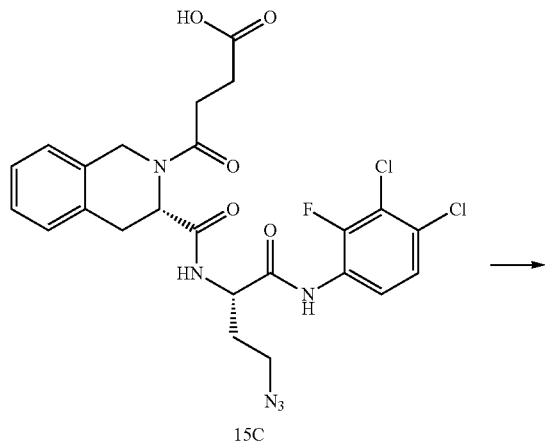

15C

Into a solution of Intermediate 15C (0.2 g, 0.35 mmol) in DMF (2 mL) at 0° C. were added DIEA (0.22 mL, 1.2 mmol), 4,4-dimethylpiperidine (52 mg, 0.35 mmol) and HATU (0.14 g, 0.37 mmol) After 2 h, the reaction was diluted with EA and washed with NaHCO₃. The organic layer was dried (Na₂SO₄), concentrated and purified by column chromatography (EA/hexane) to provide 0.2 g (86%) of Intermediate 15D. LCMS [m/z] calculated for $C_{31}H_{36}Cl_2FN_7O_4$: 659.2; found 660.1 [M+H]$^+$, $t_R$=6.04 min (Method 1).

Step 15E. Synthesis of (S)—N—((S)-4-amino-1-((3,4-dichloro-2-fluorophenyl)amino)-1-oxobutan-2-yl)-2-(4-(4,4-dimethylpiperidin-1-yl)-4-oxobutanoyl)-1,2,3,4-tetrahydro isoquinoline-3-carboxamide (Compound 15-1)

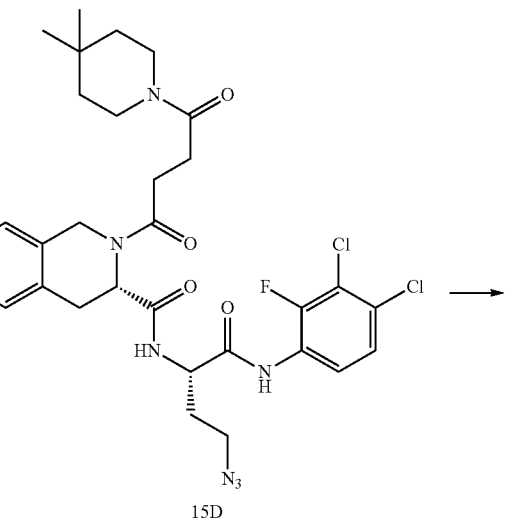

15D

-continued

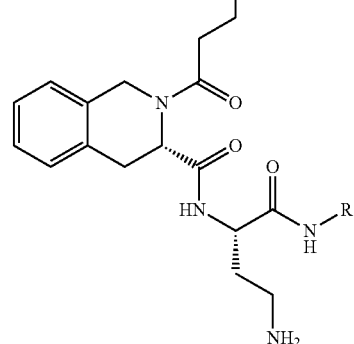

15-1

Into a solution of Intermediate 15D (92 mg, 0.14 mmol) in THF (5 mL) were added H₂O (0.1 mL) and PS—PPH₃ resin (210 mg, 0.42 mmol equivalents). After shaking for 24 h, the resin was removed via filtration through celite. The resulting solution was concentrated and purified by RP-Column Chromatography (MeOH/H₂O) to afford 10.4 mg (12%) Compound 15-1. LCMS [m/z] calculated for $C_{31}H_{38}Cl_2FN_5O_4$: 633.2; found 634.2 [M+H]⁺, $t_R$=4.75 min (Method 1).

Following the procedures as set forth in Example 15 above, the compounds of the following Table 15 were prepared using the appropriate NR⁸ and NR⁹ reagents.

TABLE 15

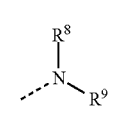

| Compound Number | R¹⁰ | R¹ | $\overset{R^8}{\underset{R^9}{-N}}$ | MS Calc | MS (MH)⁺ | LCMS Retention (min) | Purity Method |
|---|---|---|---|---|---|---|---|
| 15-1 | H | 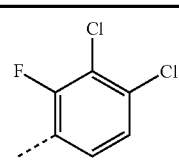 | 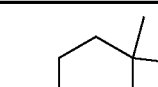 | 633.2 | 634 | 12.63 | 1 |
| 15-2 | H | 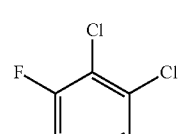 |  | 619.2 | 620 | 12.19 | 1 |
| 15-3 | H | 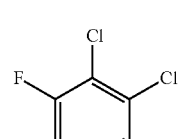 | 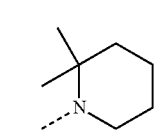 | 633.2 | 634.3 | 12.69 | 1 |

TABLE 15-continued
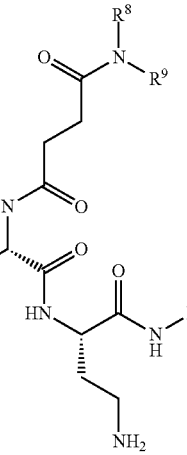
| Compound Number | R[10] | R[1] | 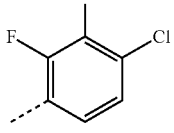 | MS Calc | MS (MH)+ | LCMS Retention (min) | Purity Method |
|---|---|---|---|---|---|---|---|
| 15-4 | H | 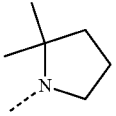 | 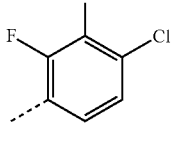 | 619.2 | 620.5 | 12.43 | 1 |
| 15-5 | H | 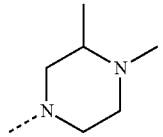 | 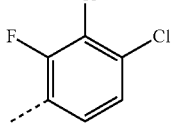 | 634.2 | 635 | 10.25 | 1 |
| 15-6 | H | 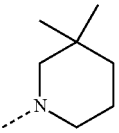 | 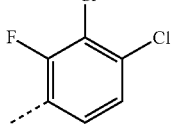 | 633.2 | 634 | 12.65 | 1 |
| 15-7 | H | 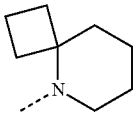 | 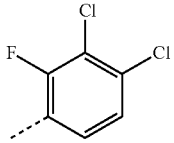 | 645.2 | 647 | 7.14 | 3 |
| 15-8 | H | 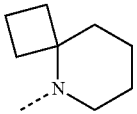 | 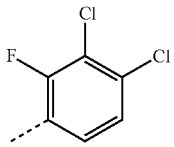 | 653.2 | 655.8 | 6.56 | 3 |
| 15-9 | H | 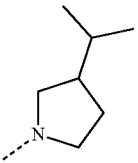 |  | 633.2 | 635 | 6.93 | 3 |

TABLE 15-continued

| Compound Number | R[10] | R[1] | $\overset{R^8}{\underset{R^9}{N}}$ | MS Calc | MS (MH)+ | LCMS Retention (min) | Purity Method |
|---|---|---|---|---|---|---|---|
| 15-10 | H | 3,4-dichloro-2-fluorophenyl | 2-isopropylpyrrolidin-1-yl | 633.2 | 635 | 6.83 | 3 |
| 15-11 | H | 3,4-dichloro-2-fluorophenyl | 3,3-dimethylmorpholin-4-yl | 635.2 | 637.9 | 5.49 | 3 |
| 15-12 | H | 3,4-dichloro-2-fluorophenyl | 2-oxa-7-azaspiro[3.5]nonan-7-yl | 647.2 | 648 | 3.61 | 5 |
| 15-13 | H | 3,4-dichloro-2-fluorophenyl | 4-(methylsulfonyl)piperidin-1-yl | 683.2 | 683.9 | 3.42 | 5 |
| 15-14 | H | 3,4-dichloro-2-fluorophenyl | 2-neopentylpiperidin-1-yl | 675.3 | 676 | 5.8 | 5 |
| 15-15 | H | 3,4-dichloro-2-fluorophenyl | azepan-1-yl | 619.2 | 620 | 4.47 | 5 |

TABLE 15-continued

| Compound Number | R[10] | R[1] | ![N(R8)(R9)] | MS Calc | MS (MH)+ | LCMS Retention (min) | Purity Method |
|---|---|---|---|---|---|---|---|
| 15-16 | H | 2,3-diCl-F-phenyl | OMe-CH2-piperidin-2-yl | 649.2 | 650 | 4.37 | 5 |
| 15-17 | H | 2,3-diCl-F-phenyl | Me2N-CH2-piperidin-2-yl | 662.3 | 663 | 2.75 | 5 |
| 15-18 | H | 2,3-diCl-F-phenyl | HO-CH2-piperidin-2-yl | 635.2 | 636 | 3.76 | 5 |
| 15-19 | H | 2,3-diCl-F-phenyl | HO-CH2-piperidin-2-yl | 635.2 | 636 | 3.8 | 5 |
| 15-20 | H | 2,3-diCl-F-phenyl | iBu-piperidin-2-yl | 661.3 | 662 | 5.57 | 5 |
| 15-21 | H | 2,3-diCl-F-phenyl | iPr-piperidin-2-yl | 647.2 | 648 | 5.05 | 5 |

TABLE 15-continued
| Compound Number | R10 | R1 | N(R8)(R9) | MS Calc | MS (MH)+ | LCMS Retention (min) | Purity Method |
|---|---|---|---|---|---|---|---|
| 15-22 | H | (F, Cl, Cl-phenyl) | cyclobutyl-piperidinyl | 659.2 | 660 | 5.12 | 5 |
| 15-23 | H | (F, Cl, Cl-phenyl) | 3-pentyl-piperidinyl | 675.3 | 676 | 5.54 | 5 |
| 15-24 | H | (F, Cl, Cl-phenyl) | 2,2-difluoro-6-azaspiro[3.5]... | 681.2 | 682 | 4.38 | 5 |
| 15-25 | H | (F, Cl, Cl-phenyl) | 3-(fluoromethyl)piperidinyl | 637.2 | 638 | 3.91 | 5 |
| 15-26 | H | (F, Cl, Cl-phenyl) | (3R)-3-methoxypiperidinyl | 635.2 | 636 | 3.67 | 5 |
| 15-27 | H | (F, Cl, Cl-phenyl) | (3S)-3-methoxypiperidinyl | 635.2 | 636 | 3.56 | 5 |

TABLE 15-continued

| Compound Number | R10 | R1 | ⟋N(R8)(R9) | MS Calc | MS (MH)+ | LCMS Retention (min) | Purity Method |
|---|---|---|---|---|---|---|---|
| 15-28 | H | 3,4-dichloro-2-fluorophenyl | -N(Me)CH2CH2N(Me)2 | 622.2 | 623 | 2.08 | 5 |
| 15-29 | H | 3,4-dichloro-2-fluorophenyl | 3,4-dimethylpyrrolidin-1-yl | 619.2 | 620 | 4.04 | 5 |
| 15-30 | H | 3,4-dichloro-2-fluorophenyl | (3R)-3-(dimethylamino)pyrrolidin-1-yl | 634.2 | 635.3 | 4.32 | 5 |
| 15-31 | H | 3,4-dichloro-2-fluorophenyl | (3S)-3-(dimethylamino)pyrrolidin-1-yl | 634.2 | 635.2 | 4.51 | 5 |
| 15-32 | H | 3,4-dichloro-2-fluorophenyl | 2-tert-butylpiperidin-1-yl | 661.3 | 683 | 5.64 | 5 |
| 15-33 | H | 3,4-dichloro-2-fluorophenyl | 2-azaspiro[3.4]octan-2-yl | 631.2 | 632 | 4.92 | 5 |

TABLE 15-continued

| Compound Number | R[10] | R[1] | -N(R8)(R9) | MS Calc | MS (MH)+ | LCMS Retention (min) | Purity Method |
|---|---|---|---|---|---|---|---|
| 15-34 | H | 2,3-dichloro-4-fluorophenyl | 3-tert-butylpyrrolidin-1-yl | 647.2 | 648 | 5.37 | 5 |
| 15-35 | H | 2,3-dichloro-4-fluorophenyl | N-ethyl-N-tert-butyl | 621.2 | 622.3 | 4.78 | 5 |
| 15-36 | H | 2,3-dichloro-4-fluorophenyl | N-methyl-N-cyclopentyl | 619.2 | 620.3 | 4.61 | 5 |
| 15-37 | H | 2,3-dichloro-4-fluorophenyl | N-methyl-N-cyclobutyl | 605.2 | 606.3 | 4.33 | 5 |
| 15-38 | H | 2,3-dichloro-4-fluorophenyl | octahydroindol-1-yl | 645.2 | 646.3 | 4.79 | 5 |
| 15-39 | H | 2,3-dichloro-4-fluorophenyl | N,N-diisopropyl | 621.2 | 622.3 | 4.67 | 5 |

TABLE 15-continued
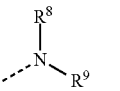
| Compound Number | R[10] | R[1] | 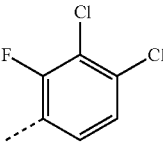 | MS Calc | MS (MH)+ | LCMS Retention (min) | Purity Method |
|---|---|---|---|---|---|---|---|
| 15-40 | H | 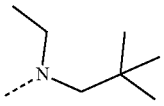 | 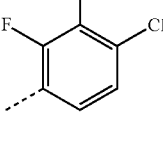 | 635.2 | 636.3 | 4.92 | 5 |
| 15-41 | H | 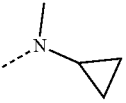 | 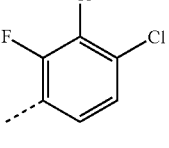 | 591.2 | 592.2 | 3.85 | 5 |
| 15-42 | H | 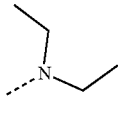 | 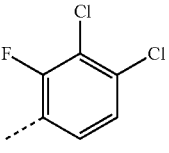 | 593.2 | 594.3 | 3.97 | 5 |
| 15-43 | H | 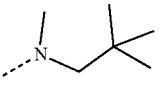 | 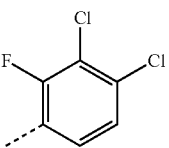 | 621.2 | 622.3 | 4.61 | 5 |
| 15-44 | H | 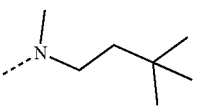 | 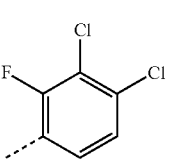 | 635.2 | 636.3 | 4.98 | 5 |
| 15-45 | H | | 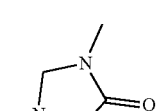 | 620.2 | 621.2 | 3.09 | 5 |

TABLE 15-continued
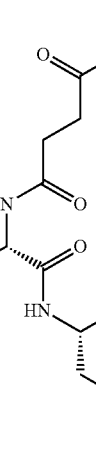
| Compound Number | R[10] | R[1] | 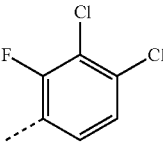 | MS Calc | MS (MH)+ | LCMS Retention (min) | Purity Method |
|---|---|---|---|---|---|---|---|
| 15-46 | H | 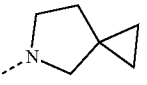 | 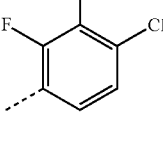 | 617.2 | 618.3 | 4.16 | 5 |
| 15-47 | H | 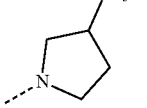 | 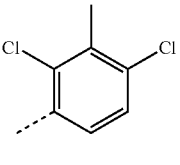 | 659.2 | 660.2 | 4.29 | 5 |
| 15-48 | H | 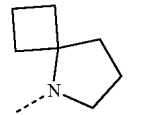 | 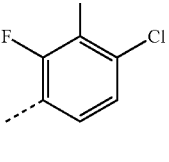 | 627.2 | 629 | 5.25 | 3 |
| 15-49 | H | 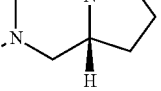 | 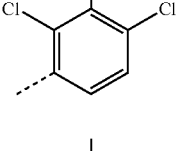 | 646.2 | 647.3 | 2.27 | 5 |
| 15-50 | H | 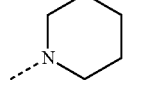 | 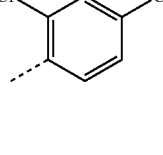 | 629.3 | 632 | 5.98 | 3 |
| 15-51 | H | 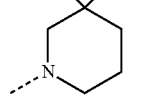 | | 641.3 | 643 | 6.43 | 3 |

TABLE 15-continued

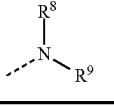

| Compound Number | R[10] | R[1] | (N with R[8], R[9]) | MS Calc | MS (MH)+ | LCMS Retention (min) | Purity Method |
|---|---|---|---|---|---|---|---|
| 15-52 | H | 2,6-dichloro-3-methylphenyl | 2,2-dimethylpiperidinyl | 629.3 | 632 | 6.22 | 3 |
| 15-53 | H | 2,3-dichloro-4-fluorophenyl | N-methyl-tert-butylamino | 607.2 | 608.3 | 3.8 | 5 |
| 15-54 | H | 2,3-dichloro-4-fluorophenyl | octahydroisoindolyl | 645.2 | 646.3 | 4.52 | 5 |
| 15-55 | H | 2,3-dichloro-4-fluorophenyl | 2-(2-hydroxypropan-2-yl)piperidinyl | 663.2 | 664.3 | 4.31 | 5 |
| 15-56 | H | 2,3-dichloro-4-fluorophenyl | 2-(difluoromethyl)piperidinyl | 655.2 | 656.3 | 4.49 | 5 |
| 15-57 | F | 2,3-dichloro-4-fluorophenyl | 3,3-dimethylpiperidinyl | 651.2 | 652.3 | 4.7 | 5 |

TABLE 15-continued

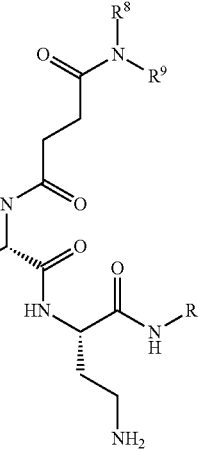

| Compound Number | R[10] | R[1] | ⋯N(R[8])(R[9]) | MS Calc | MS (MH)+ | LCMS Retention (min) | Purity Method |
|---|---|---|---|---|---|---|---|
| 15-58 | F | 2,3-dichloro-4-fluorophenyl | 2-azaspiro[3.5]nonane | 663.2 | 664.3 | 5.06 | 5 |
| 15-59 | F | 2,3-dichloro-4-fluorophenyl | 1-azaspiro[3.4]octane | 649.2 | 650.3 | 4.71 | 5 |
| 15-60 | F | 2,3-dichloro-4-fluorophenyl | 4,4-dimethylpiperidine | 651.2 | 652.3 | 4.77 | 5 |
| 15-61 | F | 2,3-dichloro-4-fluorophenyl | 2,2-dimethylpyrrolidine | 637.2 | 638.3 | 4.39 | 5 |
| 15-62 | F | 2,3-dichloro-4-fluorophenyl | 2,2-dimethylpiperidine | 651.2 | 652 | 4.89 | 5 |
| 15-63 | H | 2,3-dichloro-4-fluorophenyl | (3S)-3,4-dimethylpiperazine | 634.2 | 653.3 | 10.46 | 1 |

Scheme 16

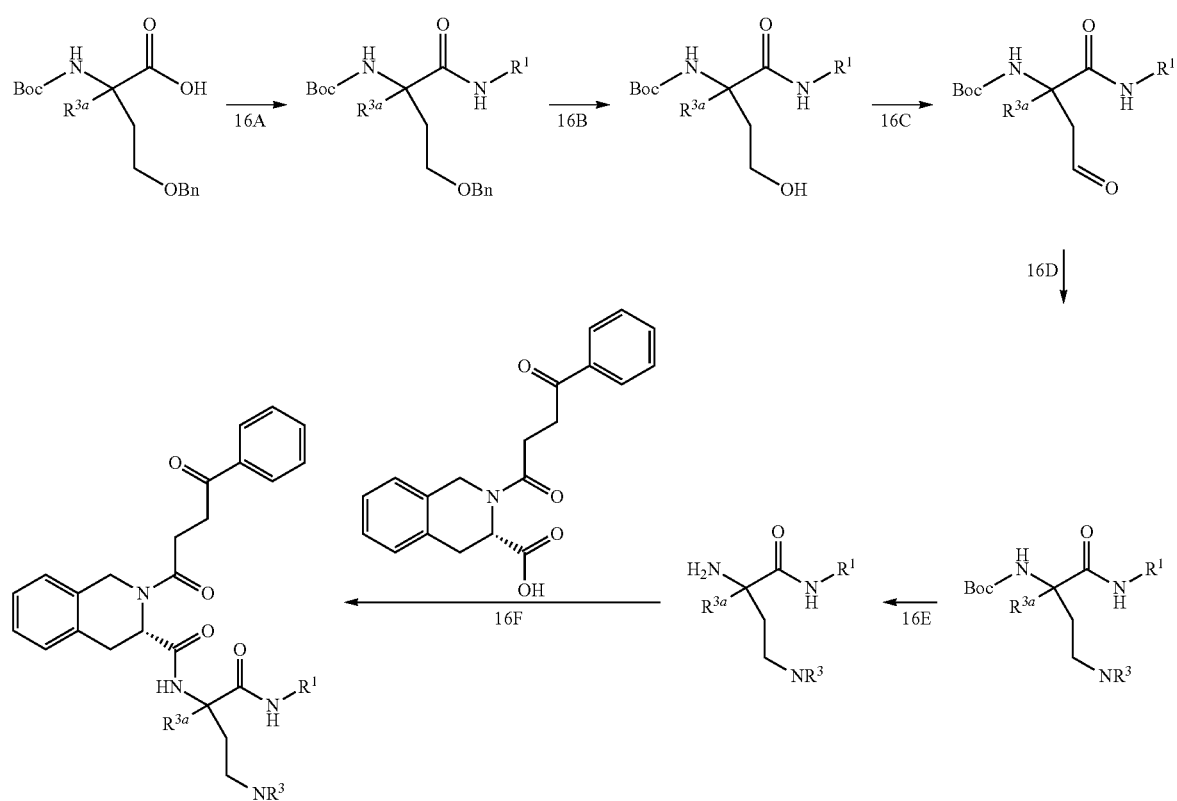

Example 16

Synthesis of (S)—N—((S)-1-((4-chloro-3-methylphenyl)amino)-4-(cyclopropylamino)-1-oxobutan-2-yl)-2-(4-oxo-4-phenylbutanoyl)-1,2,3,4-tetrahydroisoquinoline-3-carboxamide (Compound 16-1)

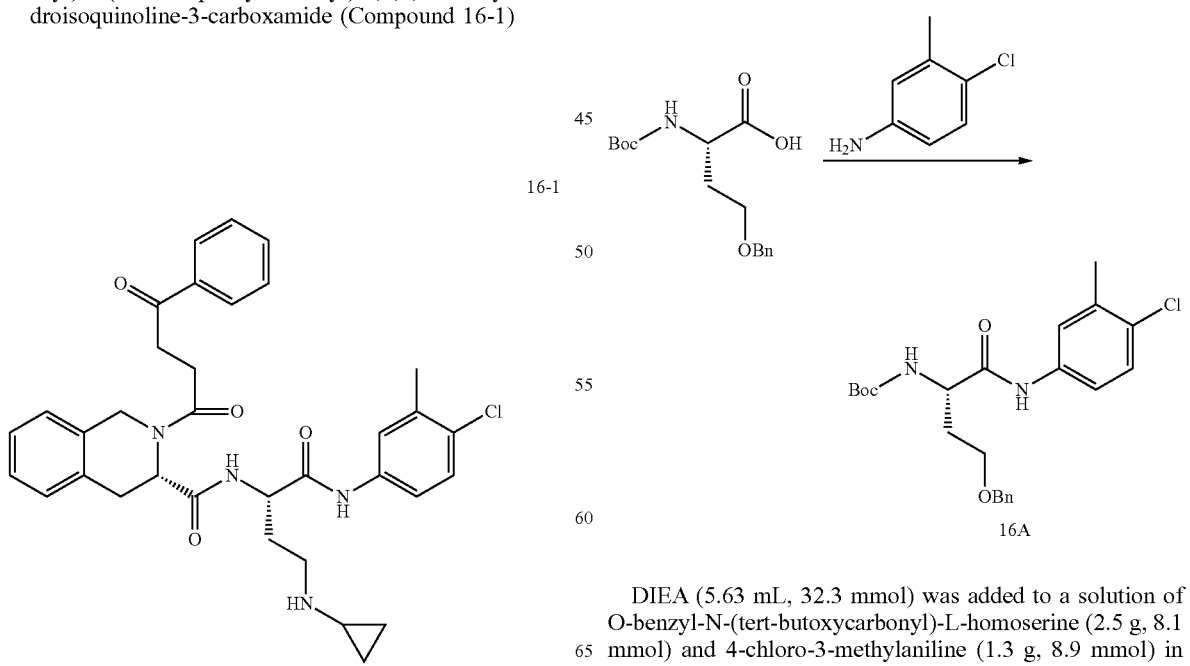

Step 16A. Synthesis of tert-butyl (S)-(4-(benzyloxy)-1-((4-chloro-3-methylphenyl) amino)-1-oxobutan-2-yl) carbamate (Intermediate 16A)

DIEA (5.63 mL, 32.3 mmol) was added to a solution of O-benzyl-N-(tert-butoxycarbonyl)-L-homoserine (2.5 g, 8.1 mmol) and 4-chloro-3-methylaniline (1.3 g, 8.9 mmol) in DCM (15 mL) at 0° C., followed by HATU (6.2 g, 16.6 mmol). After 2 h, the reaction was partitioned between DCM (50 mL) and H$_2$O (40 mL). The layers were separated using a phase separator and the aqueous layer was re-extracted with DCM (50 mL). The combined organic layers were concentrated and purified by column chromatography (EA/isohexane) to provide 3.2 g (87%) of Intermediate 16A as a foaming white solid. LCMS [m/z] calculated for C$_{23}$H$_{29}$ClN$_2$O$_4$: 432.2; found 455.2 [M+Na]$^+$, t$_R$=2.79 min (Method 4). $^1$H NMR (400 MHz, DMSO-d$_6$) δ 10.05 (br s, 1H), 7.60 (d, J=2.5 Hz, 1H), 7.46 (dd, J=8.6, 2.5 Hz, 1H), 7.37-7.20 (m, 6H), 7.09 (d, J=7.8 Hz, 1H), 4.45 (q, J=12.0 Hz, 2H), 4.28-4.15 (m, 1H), 3.59-3.44 (m, 2H), 2.29 (s, 3H), 2.04-1.90 (m, 1H), 1.90-1.75 (m, 1H), 1.39 (s, 9H).

Step 16B. Synthesis of tert-butyl (S)-(1-((4-chloro-3-methylphenyl)amino)-4-hydroxy-1-oxobutan-2-yl) carbamate (Intermediate 16B)

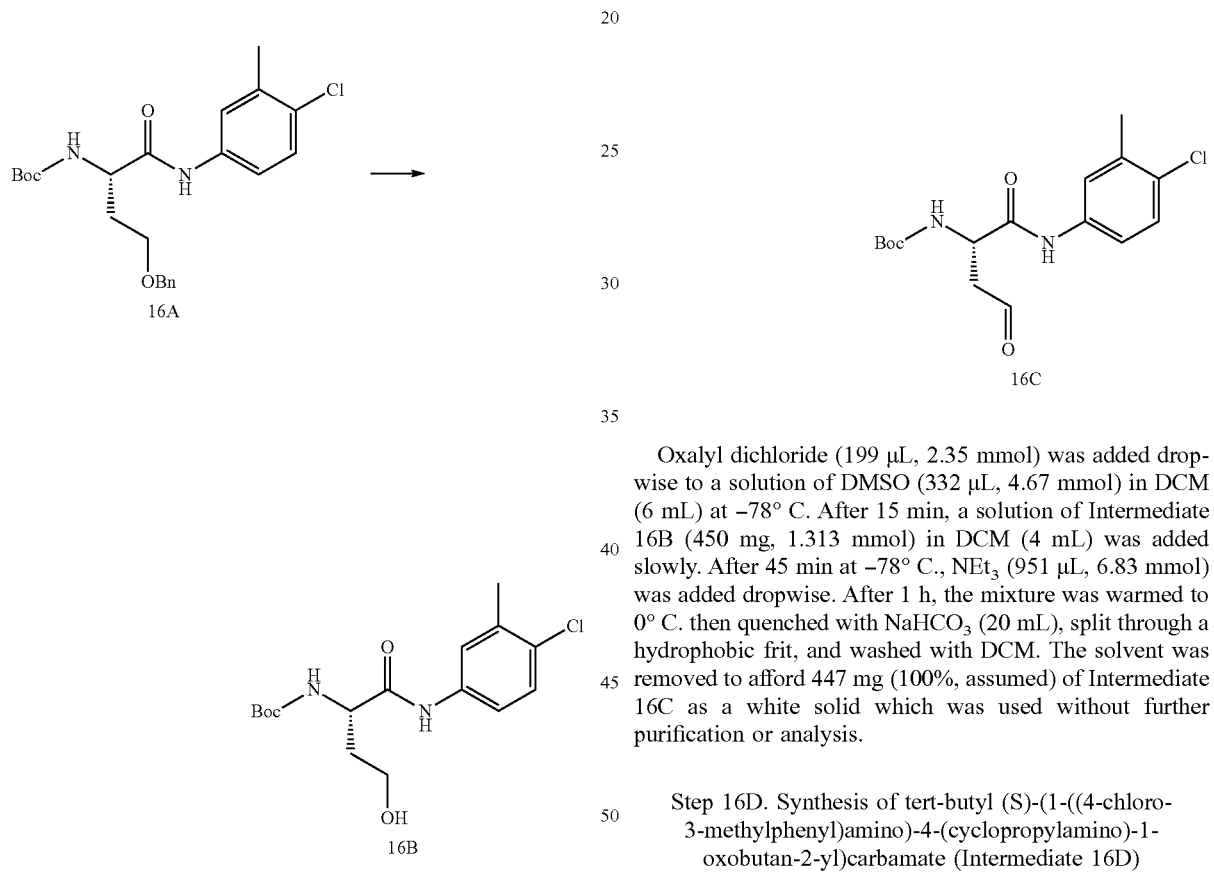

Palladium (10%) on carbon (280 mg, 2.6 mmol) was added to a solution of Intermediate 16A (2.8 g, 6.4 mmol) in EtOH (105 mL). The solution was purged with N$_2$ (3×) and H$_2$ (3×), then was stirred under hydrogen (1 bar) for 40 min. The reaction mixture was filtered through a glass microfiber filter, rinsing with EtOH. The solution was concentrated in vacuo to afford an yellow oil (1.8 g) which was purified by RP-C18 flash chromatography (MeCN/H$_2$O with 0.1% formic acid) to provide 1.4 g (64%) of Intermediate 16B as a white solid. LCMS [m/z] calculated for C$_{16}$H$_{23}$ClN$_2$O$_4$: 342.1; found 365.1 [M+Na]$^+$, t$_R$=2.08 min (Method 4).

Step 16C. Synthesis of tert-butyl (S)-(1-((4-chloro-3-methylphenyl)amino)-1,4-dioxobutan-2-yl) carbamate (Intermediate 16C)

Oxalyl dichloride (199 μL, 2.35 mmol) was added dropwise to a solution of DMSO (332 μL, 4.67 mmol) in DCM (6 mL) at −78° C. After 15 min, a solution of Intermediate 16B (450 mg, 1.313 mmol) in DCM (4 mL) was added slowly. After 45 min at −78° C., NEt$_3$ (951 μL, 6.83 mmol) was added dropwise. After 1 h, the mixture was warmed to 0° C. then quenched with NaHCO$_3$ (20 mL), split through a hydrophobic frit, and washed with DCM. The solvent was removed to afford 447 mg (100%, assumed) of Intermediate 16C as a white solid which was used without further purification or analysis.

Step 16D. Synthesis of tert-butyl (S)-(1-((4-chloro-3-methylphenyl)amino)-4-(cyclopropylamino)-1-oxobutan-2-yl)carbamate (Intermediate 16D)

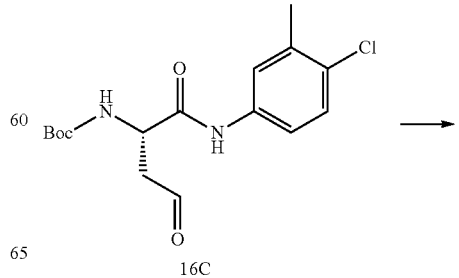

-continued

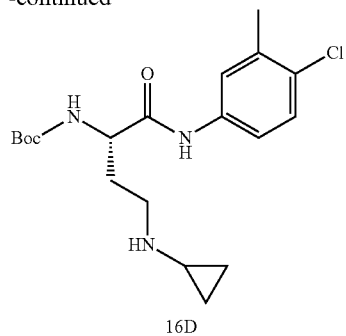

16D

To a solution of Intermediate 16C (220 mg, 0.65 mmol) in DCE (5 mL) was added AcOH (94 µl, 1.64 mmol) and cyclopropanamine (136 mL, 1.96 mmol). The reaction mixture was stirred for 30 min before sodium triacetoxyborohydride (350 mg, 1.64 mmol) was added. After stirring overnight, additional cyclopropanamine (140 µl, 1.96 mmol), AcOH (94 µl, 1.64 mmol) and sodium triacetoxyborohydride (347 mg, 1.636 mmol) were added. After 2 h, further cyclopropanamine (136 µl, 1.96 mmol) was added and the reaction mixture was stirred for 3 h. The reaction mixture was quenched with NaHCO$_3$ (10 mL) and stirred for 5 min. DCM (20 mL) was added and the layers were separated using a phase sep-cartridge. The aqueous layer was re-extracted with DCM (15 mL). The combined organic phases were concentrated. The crude product was purified by chromatography ((MeOH+NH$_3$)/DCM) to afford 76 mg (30%) of Intermediate 16D as a colourless oil. LCMS [m/z] calculated for C$_{19}$H$_{28}$ClN$_3$O$_3$: 381.2; found 382.1 [M+H]$^+$, t$_R$=1.57 min (Method 4).

Step 16E. Synthesis (S)-2-amino-N-(4-chloro-3-methylphenyl)-4-(cyclopropylamino) butanamide (Intermediate 16E)

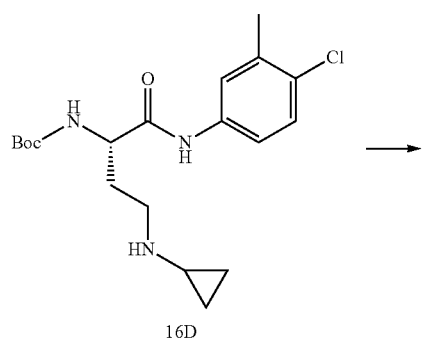

A solution of Intermediate 16D (77 mg, 0.2 mmol) in DCM (6 mL) was treated with TFA (1 ml, 12.9 mmol), stirred for 1 h, then concentrated and coevaporated with toluene. The crude product was partitioned between DCM (5 mL) and NaHCO$_3$ (5 mL). The layers were separated using a phase sep-cartridge and the aqueous layer was re-extracted with DCM (2×5 mL). The solvent was removed to afford 28 mg (68%) of Intermediate 16E as a colourless oil, which was used without further purification. LCMS [m/z] calculated for C$_{14}$H$_{20}$ClN$_3$O: 281.1; found 282.1 [M+H]$^+$, t$_R$=0.33 min (Method 4).

Step 16F: Synthesis of (S)—N—((S)-1-((4-chloro-3-methylphenyl)amino)-4-(cyclopropylamino)-1-oxobutan-2-yl)-2-(4-oxo-4-phenylbutanoyl)-1,2,3,4-tetrahydroisoquinoline-3-carboxamide (Compound 16-1)

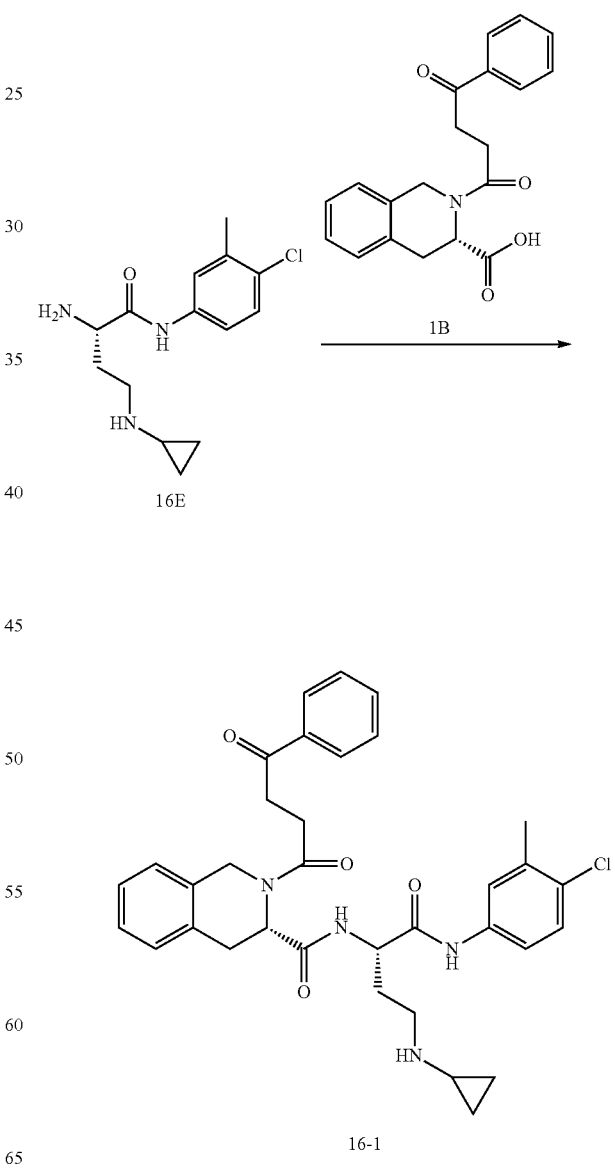

A solution of Intermediate 1B (40.2 mg, 0.12 mmol) and Intermediate 16E (28 mg, 0.1 mmol) in DMF (4 mL) was treated with DIEA (52 μl, 0.3 mmol) and HATU (76 mg, 0.2 mmol) at 0° C. The reaction mixture was stirred at 0° C. for 2 h, then partitioned between DCM (5 mL) and a NaHCO$_3$ (5 mL). The layers were separated and re-extracted with DCM (5 mL). The combined organic layers were concentrated. The crude product was purified by chromatography (MeOH (with 1% NH$_3$)/DCM)) to afford 13 mg (21%) of Compound 16 as a white solid. LCMS [m/z] calculated for C$_{34}$H$_{37}$ClN$_4$O$_4$: 600.2; found 601.3 [M+H]$^+$, t$_R$=4.83 min (Method 5). $^1$H NMR (400 MHz, DMSO-d$_6$, 363 K) δ 7.76-7.63 (m, 2H), 7.43-7.35 (m, 1H), 7.30-7.22 (m, 3H), 7.14 (dd, J=8.6, 2.6 Hz, 1H), 7.07-6.97 (m, 5H), 4.82-4.42 (m, 3H), 3.11 (br s, 2H), 2.96 (br s, 2H), 2.71-2.54 (m, 2H), 2.23-2.14 (m, 1H), 2.02 (s, 3H), 1.87-1.75 (m, 1H), 1.61 (dd, J=13.9, 7.5 Hz, 1H), 1.51-1.42 (m, 1H), 0.97-0.84 (m, 2H), 0.13 (d, J=6.5 Hz, 2H), 0.03-0.02 (m, 2H), 3× NH not observed.

Scheme 17

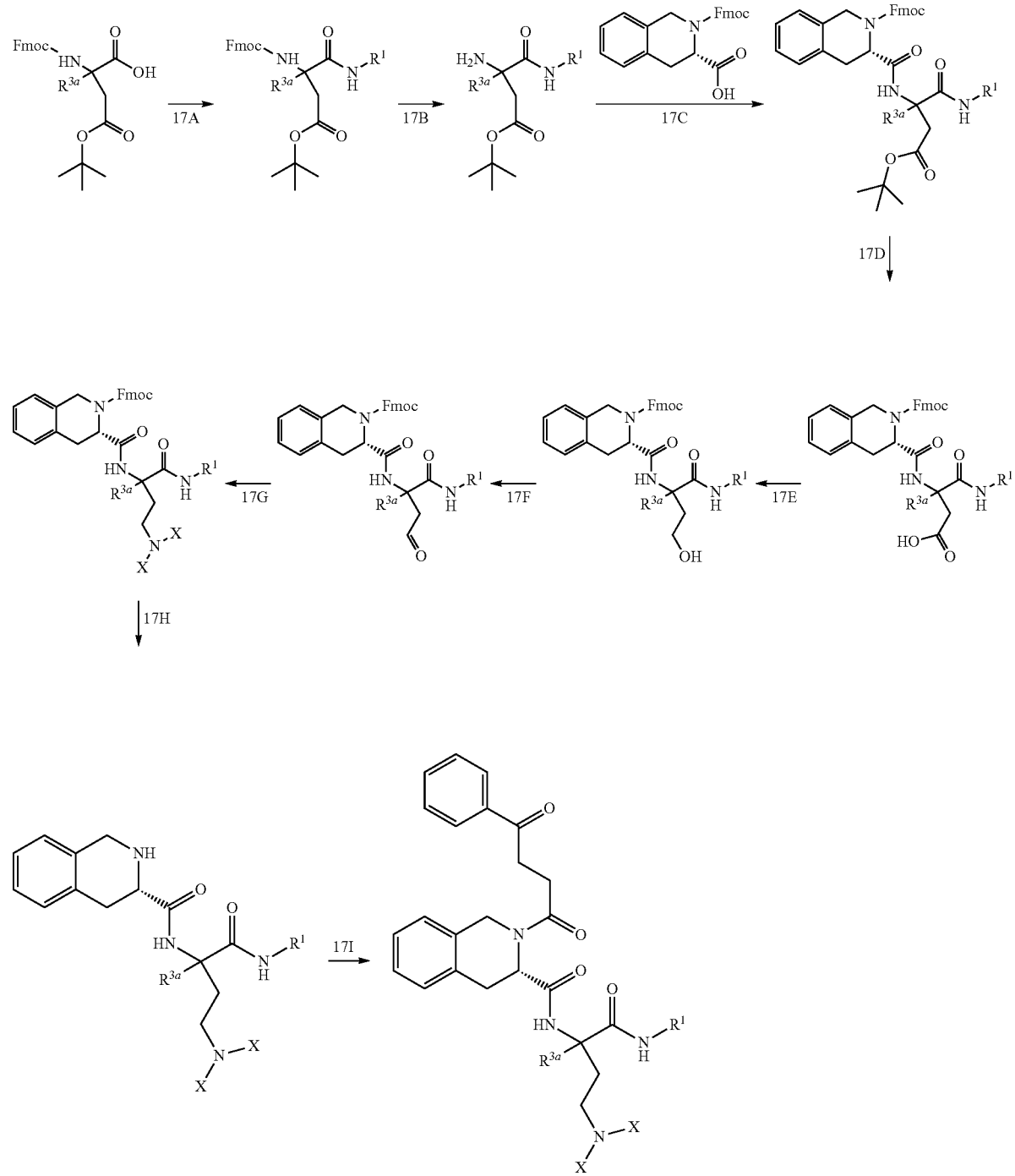

Example 17

Synthesis of (S)—N—((S)-1-((4-chloro-3-methylphenyl)amino)-4-(4-hydroxypiperidin-1-yl)-1-oxobutan-2-yl)-2-(4-oxo-4-phenylbutanoyl)-1,2,3,4-tetrahydroisoquinoline-3-carboxamide (Compound 17-1)

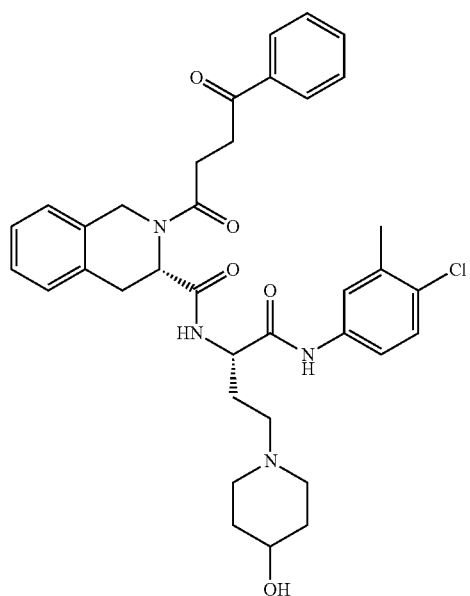

17-1

Step 17A: Synthesis of tert-butyl (S)-3-((((9H-fluoren-9-yl)methoxy) carbonyl)amino)-4-((4-chloro-3-methylphenyl)amino)-4-oxobutanoate (Compound 17A)

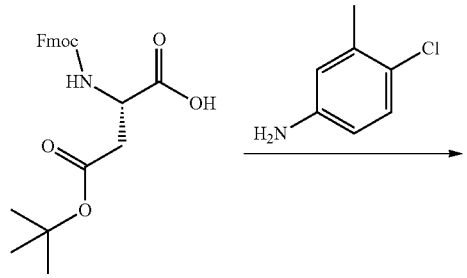

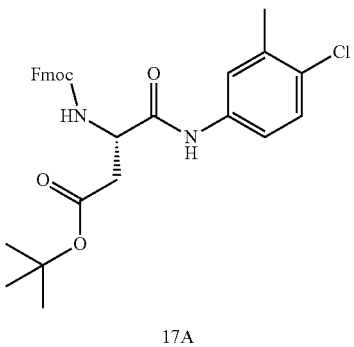

17A

A solution of (S)-2-(((((9H-fluoren-9-yl)methoxy)carbonyl)amino)-4-(tert-butoxy)-4-oxobutanoic acid (10 g, 24.30 mmol) and 4-chloro-3-methylaniline (5.16 g, 36.5 mmol) in DCM (150 mL) at 0° C. was treated with DIEA (16.93 ml, 97 mmol) and cooled to ° C. After 10 min, HATU (18.48 g, 48.6 mmol) was added portionwise. The reaction mixture was stirred at 0° C. for 1 h and the reaction mixture was partitioned between EA (50 mL) and an aqueous 1 M HCl solution (200 mL). The layers were separated and the organic layer was re-washed with an aqueous 1 M HCl solution (2×200 mL) and brine (200 mL). The combined organic layers were dried (MgSO$_4$), filtered, and concentrated to 18.7 g (101%) of Intermediate 17A as a beige solid. LCMS [m/z] calculated for $C_{30}H_{31}ClN_2O_5$: 534.2; found 557.2 [M+Na]$^+$, $t_R$=3.01 min (Method 4). $^1$H NMR (400 MHz, DMSO-d$_6$) δ 10.17 (s, 1H), 7.98-7.78 (m, 3H), 7.78-7.57 (m, 3H), 7.57-7.29 (m, 6H), 4.50 (td, J=8.4, 5.9 Hz, 1H), 4.43-4.15 (m, 3H), 2.71 (dd, J=15.9, 5.9 Hz, 1H), 2.55 (dd, J=16.0, 8.7 Hz, 1H), 2.29 (s, 3H), 1.37 (s, 9H).

Step 17B: Synthesis of tert-butyl (S)-3-amino-4-((4-chloro-3-methylphenyl) amino)-4-oxobutanoate (Compound 17B)

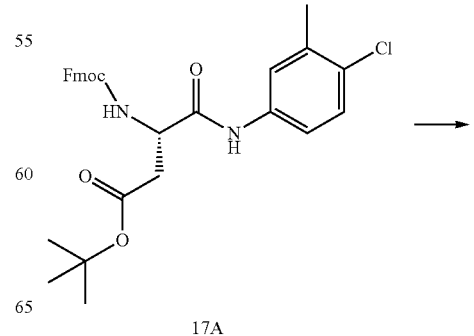

17A

-continued

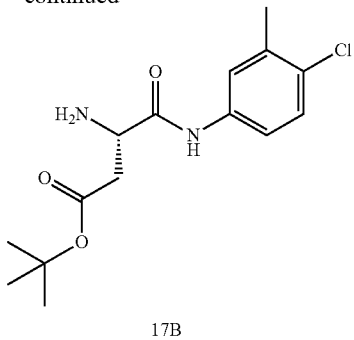

17B

Diethylamine (25.1 mL, 243 mmol) was added to a solution of Intermediate 17A (13 g, 24.3 mmol) in DCM (25 mL, 24.3 mmol) and the reaction mixture was stirred at rt for 1 h. The reaction mixture was concentrated, redissolved in toluene/DCM and concentrated (2×). The crude product was dissolved in DCM and washed with H₂O (100 mL) then redissolved in EA (100 mL) and washed with water (2×50 mL). The organic phase was dried (MgSO₄), filtered, and concentrated to afford 13 g (103%) of Intermediate 17B as a brown oil which crystallized upon standing. LCMS [m/z] calculated for $C_{15}H_{21}ClN_2O_3$: 312.1; found 257 [M+H−$^t$Bu]$^+$, $t_R$=1.46 min (Method 4), 60% purity, used without further purification.

Step 17C: Synthesis of (9H-fluoren-9-yl)methyl (S)-3-(((S)-4-(tert-butoxy)-1-((4-chloro-3-methylphenyl) amino)-1,4-dioxobutan-2-yl) carbamoyl)-3,4-dihydroisoquinoline-2(1H)-carboxylate (Compound 17C)

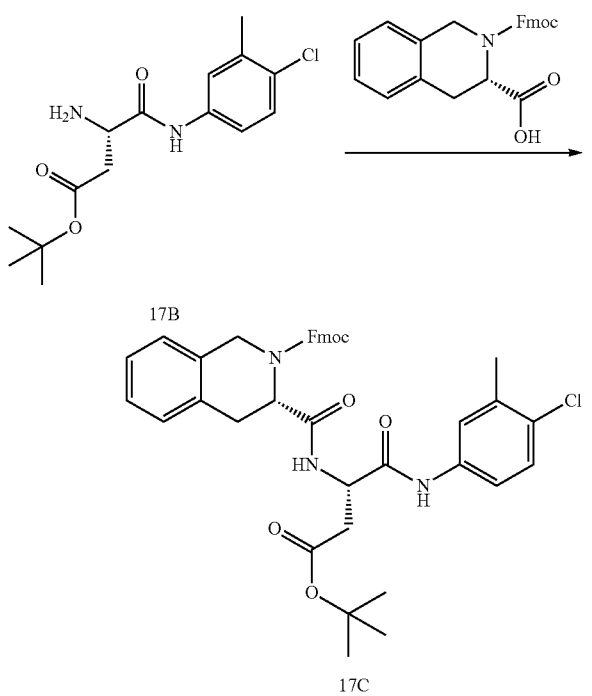

A solution of (S)-2-(((9H-fluoren-9-yl)methoxy)carbonyl)-1,2,3,4-tetrahydroisoquinoline-3-carboxylic acid (10.5 g, 26.2 mmol) and Intermediate 17B (13 g, 24.9 mmol) in DCM (100 mL) at 0° C. was treated with DIEA (17.4 ml, 100 mmol) and, after 10 min, HATU (18.96 g, 49.9 mmol) was added portionwise at 0° C. The reaction mixture was stirred at 0° C. for 3 h. The reaction mixture was partitioned between DCM (200 mL) and an aqueous 1 M HCl solution (200 mL). The layers were separated and the organic layer was washed an aqueous 1 M HCl solution (2×200 mL) and brine (200 mL). The combined organic layers were dried (MgSO₄), filtered, and concentrated. The resulting crude material was purified by chromatography (EA/isohexane) to afford 13.6 g (65%) of Intermediate 17C as a white foam. LCMS [m/z] calculated for $C_{40}H_{40}ClN_3O_6$: 693.3; found 716 [M+Na]$^+$, $t_R$=3.13 min (Method 4).

Step 17D: Synthesis of (S)-3-((S)-2-(((9H-fluoren-9-yl)methoxy)carbonyl)-1,2,3,4-tetrahydroisoquinoline-3-carboxamido)-4-((4-chloro-3-methylphenyl) amino)-4-oxobutanoic Acid (Compound 17D)

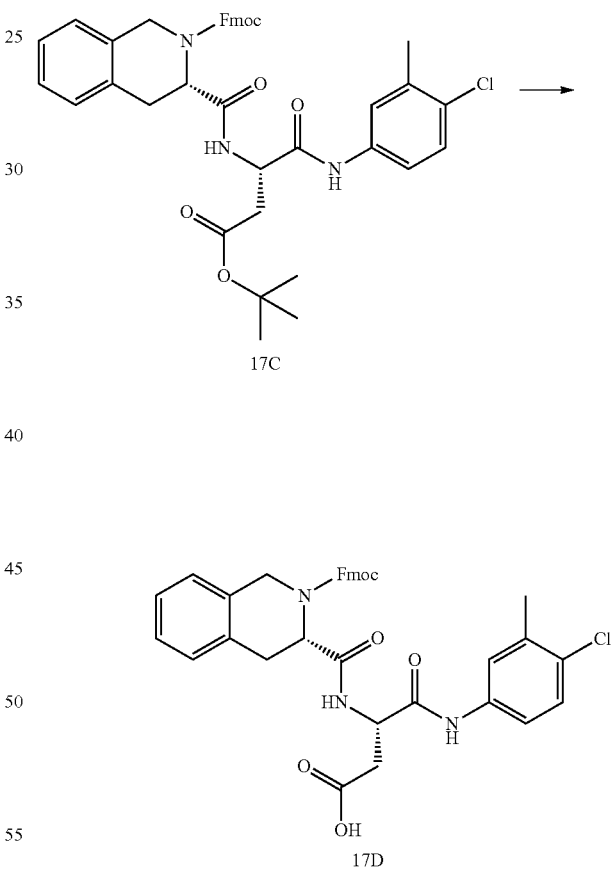

A solution of Intermediate 17C (13.6 g, 19.6 mmol) in DCM (30 mL) was treated with TFA (20 mL, 260 mmol) and stirred for 3.5 h. The reaction mixture was concentrated, redissolved in toluene and re-concentrated (2×). The crude product was purified by chromatography (EA(+1% AcOH)/isohexane) to afford 9.6 g (73%) of Intermediate 17D as a white solid. LCMS [m/z] calculated for $C_{36}H_{32}ClN_3O_6$: 637.2; found 638 [M+H]$^+$, $t_R$=2.78 min (Method 4).

Step 17E: Synthesis of (9H-fluoren-9-yl)methyl (S)-3-(((S)-1-((4-chloro-3-methylphenyl)amino)-4-hydroxy-1-oxobutan-2-yl)carbamoyl)-3,4-dihydroisoquinoline-2(1H)-carboxylate (Compound 17E)

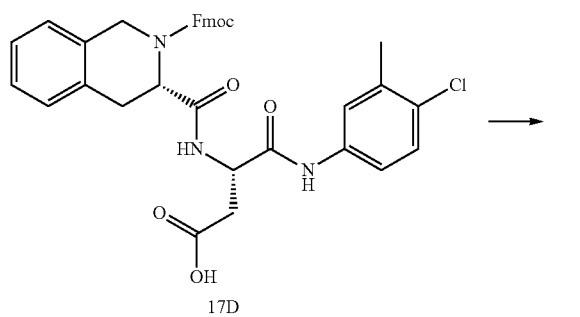

17D

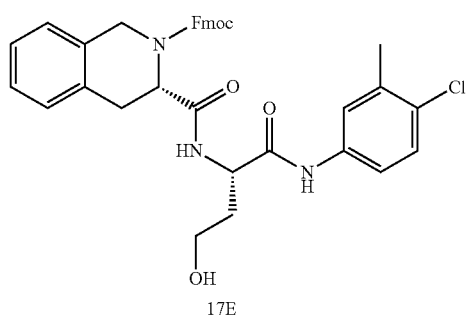

17E

Intermediate 17D (9.5 g, 14.9 mmol) was dissolved in THF (200 mL). N-Methylmorpholine (1.64 mL, 14.9 mmol) was added and the resulting mixture was cooled to −5° C. using an ice/salt bath. Ethyl chloroformate (1.43 mL, 14.9 mmol) was added and, after 1 h, the formed precipitate was filtered off using a phase sep cartridge. The filtrate was cooled (−5° C.) and a solution of sodium borohydride (0.73 g, 19.4 mmol) in 30 mL of H$_2$O/THF (1/1) was added. The resulting mixture was stirred at −5° C. and then allowed to warm to rt overnight. The solvent was evaporated and the residue dissolved in EA (100 mL) and washed with 1 M HCl solution (100 mL), NaHCO$_3$ (100 mL), H$_2$O (30 mL) and brine (30 mL). The organic phase was dried (MgSO$_4$). Filtration and evaporation gave a crude product that was purified by chromatography (EA/isohexane) to provide 5 g (51.1%) of Intermediate 17E as a white solid. LCMS [m/z] calculated for C$_{36}$H$_{34}$ClN$_3$O$_5$: 623.2; found 624 [M+H]$^+$, t$_R$=2.76 min (Method 4).

Step 17F: Synthesis of (9H-fluoren-9-yl)methyl (S)-3-(((S)-1-((4-chloro-3-methylphenyl)amino)-4-hydroxy-1-oxobutan-2-yl)carbamoyl)-3,4-dihydroisoquinoline-2(1H)-carboxylate (Compound 17F)

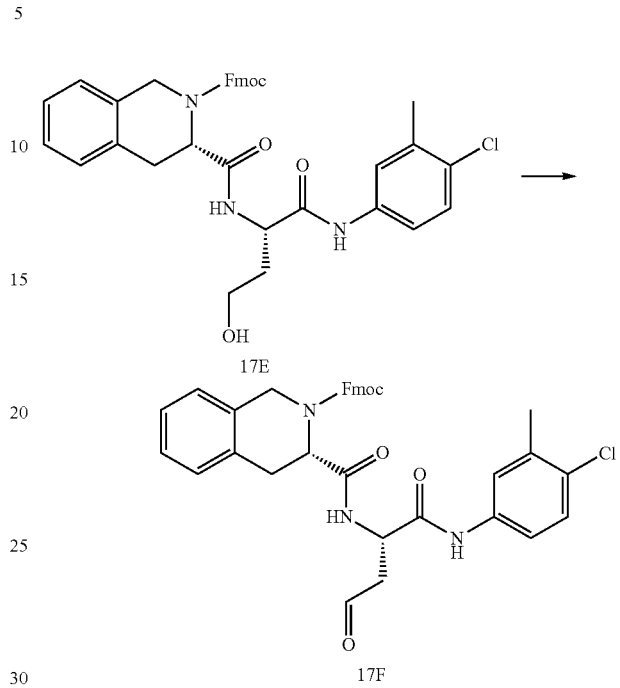

A stirred solution of DMSO (0.73 mL, 10.3 mmol) in DCM (12 mL) at −78° C. was treated dropwise with oxalyl dichloride (0.44 mL, 5.2 mmol). After 15 min at −78° C., a solution of Intermediate 17E (2.0 g, 3.2 mmol) in DCM (20 mL) was added slowly. After 45 min at −78° C., Hunig's base (2.96 mL, 16.0 mmol) was added slowly. The reaction mixture was stirred at −70° C. overnight. The mixture was quenched with NaHCO$_3$ (20 mL), then passed through a hydrophobic frit, and washed with DCM. The solution was concentrated and the resulting crude product was purified by chromatography (EA/isohexane) to provide 1.6 g (84%) of Intermediate 17F as a white solid. LCMS [m/z] calculated for C$_{36}$H$_{32}$ClN$_3$O$_5$: 621.2; found 622 [M+H]$^+$, t$_R$=2.7 min (Method 4).

Step 17G: Synthesis of (9H-fluoren-9-yl)methyl (S)-3-(((S)-1-((4-chloro-3-methylphenyl)amino)-4-(4-hydroxypiperidin-1-yl)-1-oxobutan-2-yl)carbamoyl)-3,4-dihydroisoquinoline-2(1H)-carboxylate (Compound 17G)

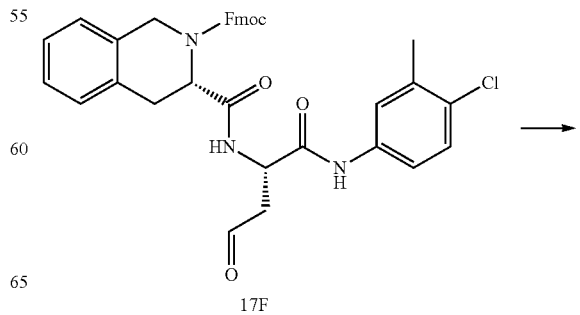

17F

-continued

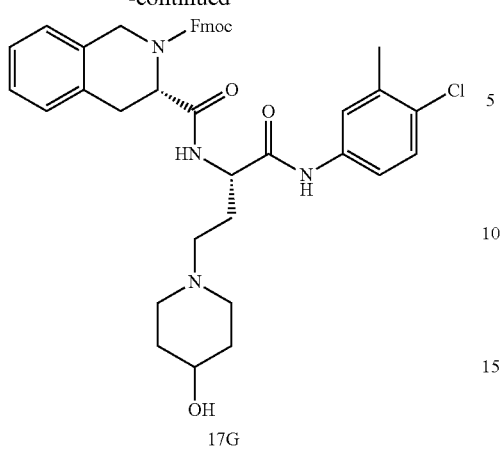

17G

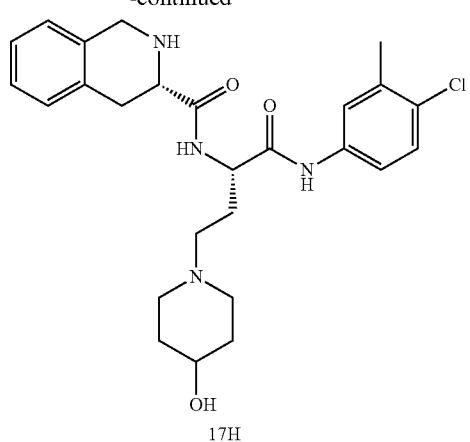

17H

To a solution of Intermediate 17F (320 mg, 0.51 mmol) in DCM (6 mL) was added piperidin-4-ol (175 mg, 1.73 mmol) and acetic acid (138 μl, 2.41 mmol). The reaction mixtures were stirred at rt for 15 min. Sodium triacetoxyborohydride (382 mg, 1.8 mmol) was added and the reaction mixture was stirred at overnight. Additional piperidin-4-ol (2 equiv), AcOH (138 μl, 2.4 mmol), sodium triacetoxyborohydride (382 mg, 1.8 mmol), and THF (2 mL) were added. The reaction mixture was heated to 45° C. over 4 h and overnight at 45° C. The reaction mixture was partitioned between DCM (10 mL) and 1 M aqueous HCl (10 mL) using a phase sep-cartridge and the aqueous layer was re-extracted with DCM (10 mL). The combined organic phases were concentrated. The crude product was purified by chromatography (0.7 M $NH_3$/MeOH)/DCM) to afford 220 mg (61%) of Intermediate 17G as a white solid. LCMS [m/z] calculated for $C_{41}H_{43}ClN_4O_5$: 706.3; found 707.0 $[M+H]^+$, $t_R$=2.12 min (Method 4).

Diethylamine (0.32 mL, 3.1 mmol) was added to a solution of Intermediate 17G in DCM (5 ml) and the mixture was stirred at rt for 1 h. The reaction mixture was concentrated, dissolved in toluene and re-concentrated. The resulting crude product was purified by chromatography (MeOH (+1% $NH_3$)/DCM) to afford 130 mg (72%) of Intermediate 17H. LCMS [m/z] calculated for $C_{26}H_{33}ClN_4O_3$: 484.2; found 485.3 $[M+H]^+$, $t_R$=1.7 min (Method 4).

Step 17H: Synthesis of (9H-fluoren-9-yl)methyl (S)-3-4(S)-1-((4-chloro-3-methylphenyl)amino)-4-(4-hydroxypiperidin-1-yl)-1-oxobutan-2-yl)carbamoyl)-3,4-dihydroisoquinoline-2(1H)-carboxylate (Compound 17H)

Step 17I: Synthesis of (S)—N—((S)-1-((4-chloro-3-methyl phenyl)amino)-4-(4-hydroxypiperidin-1-yl)-1-oxobutan-2-yl)-2-(4-oxo-4-phenylbutanoyl)-1,2,3,4-tetrahydroisoquinoline-3-carboxamide (Compound 17-1)

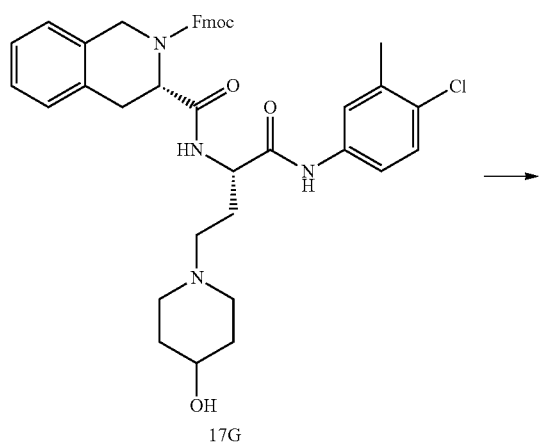

17G

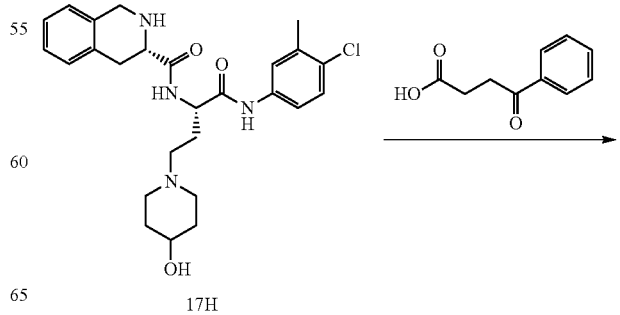

17H

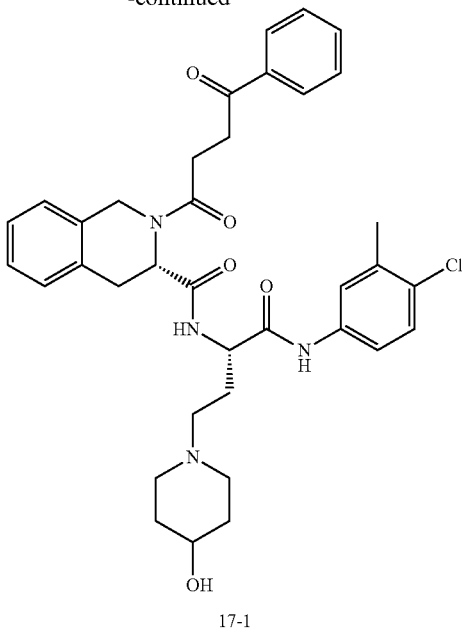

17-1

A solution of Intermediate 17H (130 mg, 0.27 mmol) and 4-oxo-4-phenylbutanoic acid (71.6 mg, 0.40 mmol) in DCM (10 mL) was treated with DIEA (280 μl, 1.61 mmol). After 10 min, HATU (153 mg, 0.40 mmol) was added. The reaction mixture was stirred for 5 h and additional 4-oxo-4-phenylbutanoic acid (71.6 mg, 0.40 mmol), DIEA (280 μl, 1.61 mmol) and HATU (153 mg, 0.40 mmol) were added. The reaction mixture was stirred for 3 h, then partitioned between DCM (10 mL) and 1 M aqueous solution of HCl (10 mL). The layers were separated using a phase separating-cartridge and the aqueous layer was re-extracted with DCM (10 mL). The combined organic phases were concentrated. The crude product was purified by chromatography (MeOH/DCM) to afford 25 mg (14%) of Compound 17-1. LCMS [m/z] calculated for $C_{36}H_{41}ClN_4O_5$: 644.3; found 645.2[M+H]$^+$, $t_R$=2.5 min (Method 4). $^1$H NMR (400 MHz, DMSO-$d_6$, 363 K) δ 9.87 (br s, 1H), 9.45 (br s, 1H), 8.03-7.76 (m, 3H), 7.66-7.59 (m, 1H), 7.56-7.47 (m, 3H), 7.42 (dd, J=8.7, 2.6 Hz, 1H), 7.35-7.14 (m, 5H), 4.91 (br s, 1H), 4.82-4.79 (m, 2H), 4.59 (br s, 1H), 4.44 (br s, 1H), 3.67 (br s, 1H), 3.38-3.28 (m, 2H), 3.20 (br s, 3H), 3.05-2.87 (m, 3H), 2.77-2.54 (m, 2H), 2.46 (s, 1H), 2.27 (s, 3H), 2.17 (br s, 1H), 1.90 (br s, 3H), 1.63 (br s, 2H).

Following the procedures as set forth in Scheme 17 above, the compounds of the following Table 17 were prepared using the appropriate $R^{3a}$ and $R^{3b}$ reagents.

TABLE 17

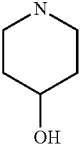

| Compound Number | $R^{3a}$ | $R^{3b}$ | *2 $R^{3a}/R^{3b}$ Stereo-chem. | MS Calc | MS Obs (MH)$^+$ | LCMS Retention (min) | Purity Method |
|---|---|---|---|---|---|---|---|
| 17-1 | H | ethyl-(4-hydroxypiperidin-1-yl) | S | 644.3 | 645 | 4.59 | 5 |

TABLE 17-continued

| Compound Number | R³ᵃ | R³ᵇ | *2 R³ᵃ/R³ᵇ Stereo-chem. | MS Calc | MS Obs (MH)⁺ | LCMS Retention (min) | Purity Method |
|---|---|---|---|---|---|---|---|
| 17-2 | H | (2-(1-Boc-piperidin-4-yl)ethyl) | S | 728.3 | 730.1 | 5.65 | 5 |
| 17-3 | H | (2-(3-oxopiperazin-1-yl)ethyl) | S | 643.3 | 644.1 | 4.76 | 5 |
| 17-4 | H | (2-(4,4-difluoropiperidin-1-yl)ethyl) | S | 664.3 | 665.1 | 4.84 | 5 |

Scheme 18
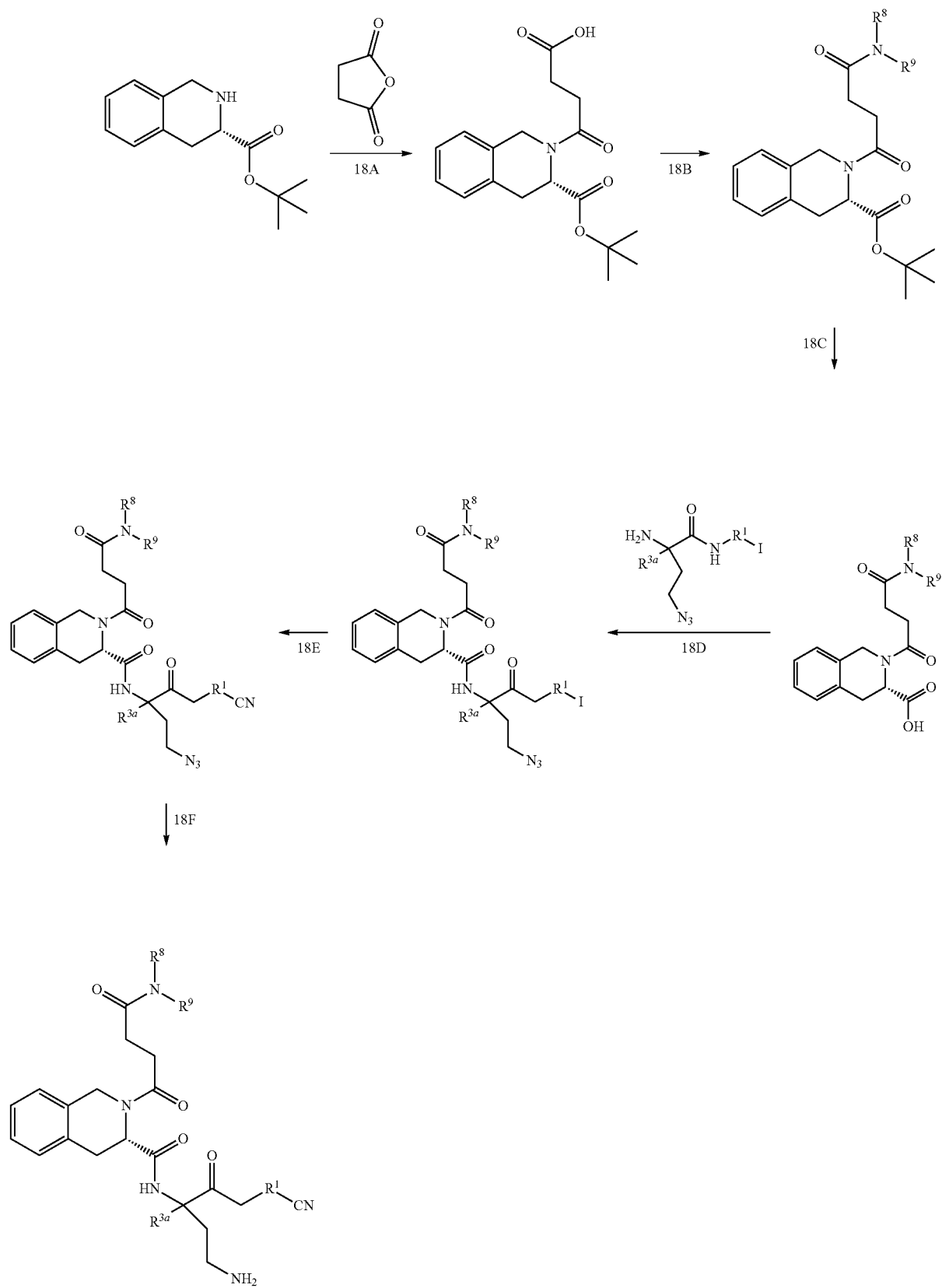

Example 18

Synthesis of (S)—N—((S)-4-amino-1-((4-chloro-2-cyano-5-methylphenyl)amino)-1-oxobutan-2-yl)-2-(4-(2,2-dimethylpiperidin-1-yl)-4-oxobutanoyl)-1,2,3,4-tetrahydroisoquinoline-3-carboxamide (Compound 18-1)

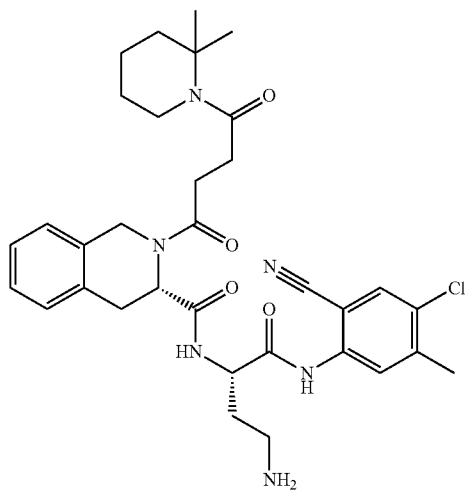

18-1

Step 18A: Synthesis of (S)-4-(3-(tert-butoxycarbonyl)-3,4-dihydroisoquinolin-2(1H)-yl)-4-oxobutanoic Acid (Compound 18A)

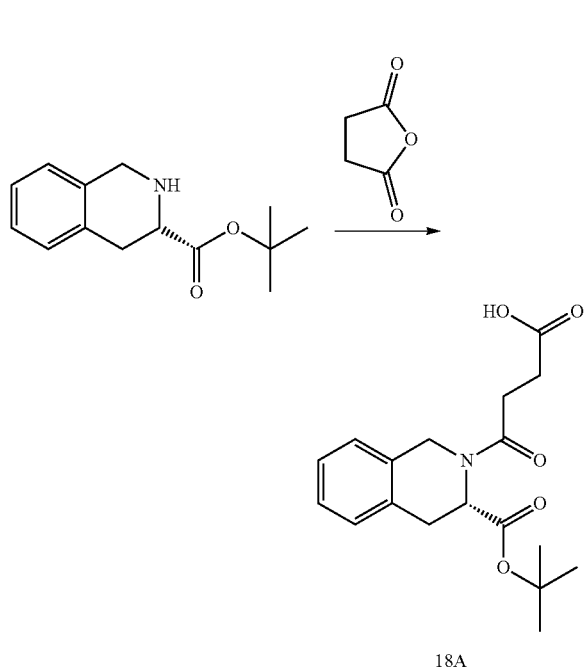

18A

NEt$_3$ (3 mL, 21.4 mmol) was added to a solution of tert-butyl (S)-1,2,3,4-tetrahydroisoquinoline-3-carboxylate (5.0 g, 21.4 mmol) in DCM (10 mL). After 5 min, a solution of succinic anhydride (3.21 g, 32.2 mmol) in DCM (2 mL) was added dropwise. After 2 days, additional succinic anhydride (1.1 g, 10.7 mmol) was added. After 2 h, the reaction mixture was concentrated and purified by chromatography (MeOH/DCM) to afford 5 g (70%) of Intermediate 18A. LCMS [m/z] calculated for $C_{18}H_{23}NO_5$: 333.2; found 334.3 [M+H]$^+$, $t_R$=4.41 (Method 2).

Step 18B: Synthesis of tert-butyl (S)-2-(4-(2,2-dimethylpiperidin-1-yl)-4-oxobutanoyl)-1,2,3,4-tetrahydroisoquinoline-3-carboxylate (Compound 18B)

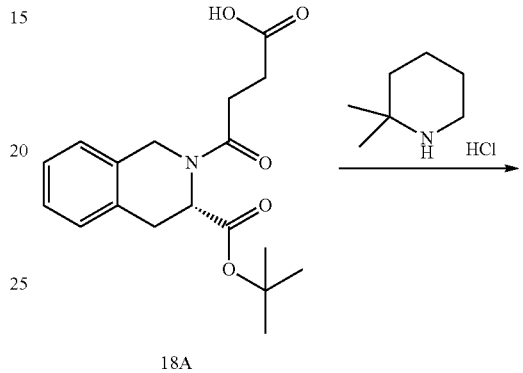

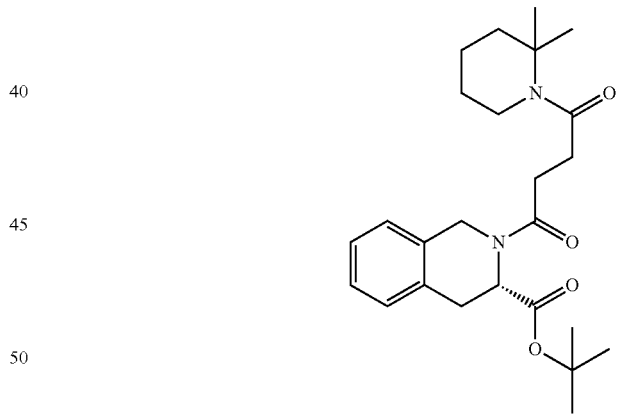

18B

HATU (855 mg, 2.25 mmol) was added to a solution of Intermediate 18A (500 mg, 1.5 mmol), 2,2-dimethylpiperidine, HCl (224 mg, 1.5 mmol), and DIEA (0.92 mL, 5.25 mmol) in DMF (3 mL) at 0° C. After 3 h, the mixture was concentrated and diluted with EA and washed with NaHCO$_3$ (sat). The organic layer was dried (Na$_2$SO$_4$) and purified by chromatography (EA/hex) to afford 620 mg (96%) of Intermediate 18B. LCMS [m/z] calculated for $C_{25}H_{36}N_2O_4$: 428.3; found 429.7[M+H]$^+$, $t_R$=5.75 (Method 2).

Step 18C: Synthesis of (S)-2-(4-(2,2-dimethylpiperidin-1-yl)-4-oxobutanoyl)-1,2,3,4-tetrahydroisoquinoline-3-carboxylic Acid (Compound 18C)

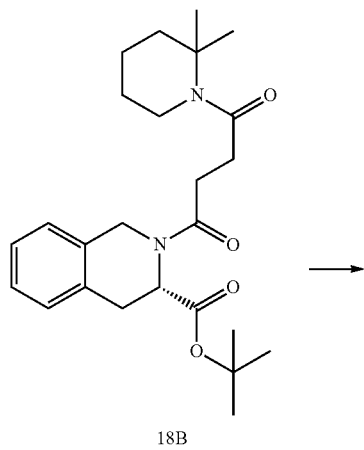

Step 18D: Synthesis of (S)—N—((S)-4-azido-1-((4-chloro-2-iodo-5-methylphenyl) amino)-1-oxobutan-2-yl)-2-(4-(2,2-dimethylpiperidin-1-yl)-4-oxobutanoyl)-1,2,3,4-tetrahydroisoquinoline-3-carboxamide (Compound 18D)

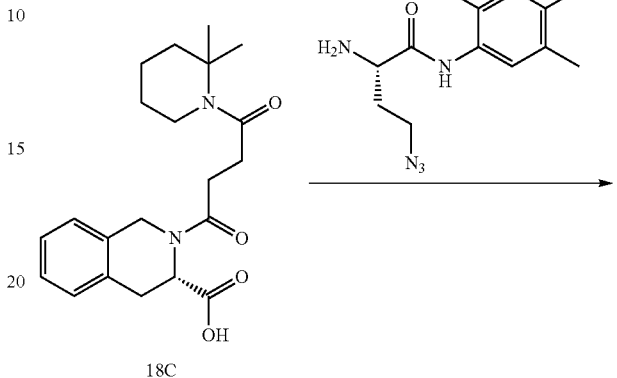

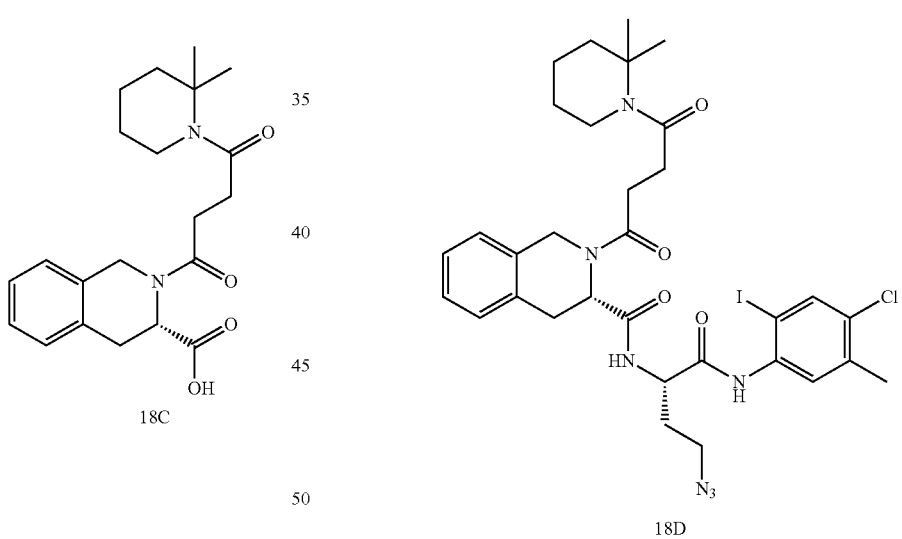

TFA (1 mL) was added to a solution of Intermediate 18B (620 mg, 1.45 mmol), in DCM (4 mL). After 16 h, the mixture was diluted with EA and washed with NaHCO$_3$ (sat). The organic layer was dried (Na$_2$SO$_4$) and concentrated to afford 232 mg (43%) of Intermediate 18C. LCMS [m/z] calculated for C$_{21}$H$_{28}$N$_2$O$_4$: 372.2; found 373.4[M+H]$^+$, t$_R$=4.79 (Method 2).

HATU (356 mg, 0.93 mmol) was added to a solution of Intermediate 18C (232 mg, 0.62 mmol), (S)-2-amino-4-azido-N-(4-chloro-2-iodo-5-methyl phenyl) butanamide (245 mg, 0.62 mmol, prepared as shown in Scheme 14, step B), and DIEA (0.22 mL, 1.3 mmol) in DMF (5 mL). After 3 h, the mixture was concentrated and diluted with EA and washed with NaHCO$_3$ (sat). The organic layer was dried (Na$_2$SO$_4$) and purified by chromatography (EA/hex) to afford 466 mg (43%) of Intermediate 18D. LCMS [m/z] calculated for C$_{32}$H$_{39}$ClIN$_7$O$_4$: 747.2; found 748 [M+H]$^+$, t$_R$=6.31 (Method 2).

Step 18E: Synthesis of (S)—N—((S) ((4-chloro-2-cyano-5-methyl phenyl) amino)-1-oxobutan-2-yl)-2-(4-(2,2-dimethylpiperidin-1-yl)-4-oxobutanoyl)-1,2,3,4-tetrahydroisoquinoline-3-carboxamide (Compound 18E)

Step 18F: Synthesis of (S)—N—((S)-4-amino-1-((4-chloro-2-cyano-5-methyl phenyl) amino)-1-oxobutan-2-yl)-2-(4-(2,2-dimethyl piperidin-1-yl)-4-oxobutanoyl)-1,2,3,4-tetrahydroisoquinoline-3-carboxamide (Compound 18-1)

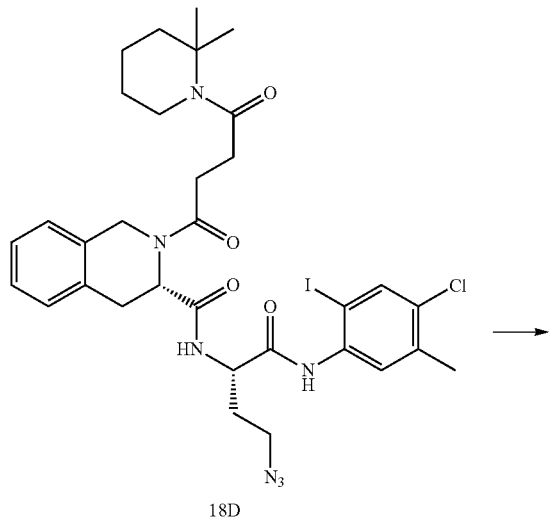

18D

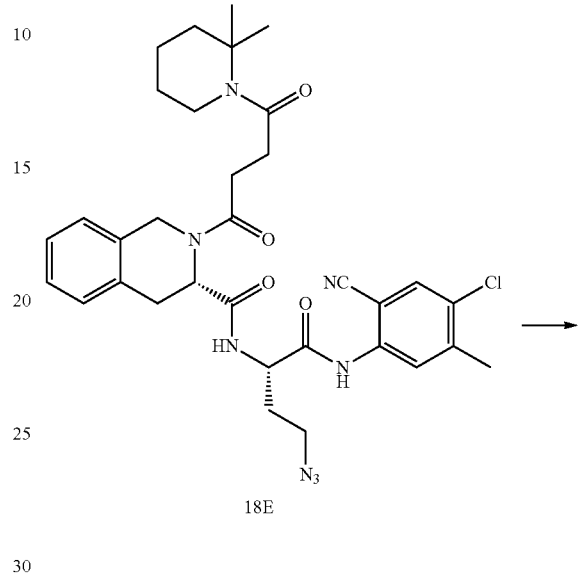

18E

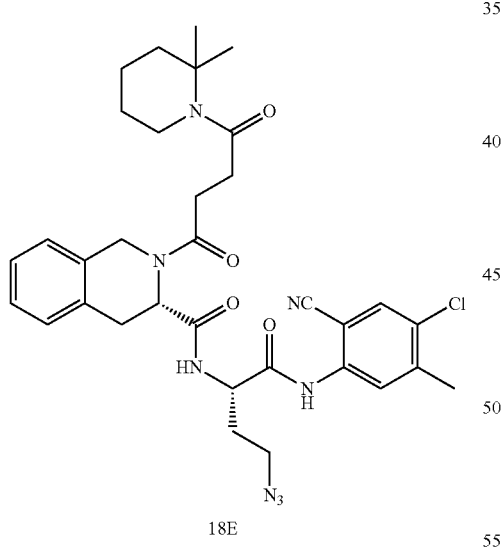

18E

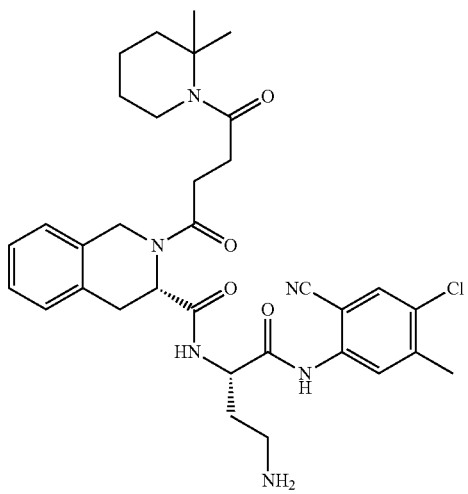

18-1

A flask containing 18D (201 mg, 0.27 mmol) and Zn(CN)$_2$ (33 mg, 0.28 mmol) in DMF (8 mL) was degassed by N$_2$ purging for 2 min, after which Pd(PPh$_3$)$_4$ was added. After further degassing (1 min), the reaction mixture was heated at 90° C. for 2 h, then diluted with EA and washed with 50% NH$_4$OH/H$_2$O. The organic layer was concentrated and purified by chromatography (EA/hexane) to afford 46.2 mg (27%) of Compound 18E. LCMS [m/z] calculated for C$_{33}$H$_{39}$ClN$_8$O$_4$: 646.3; found 647.2[M+H]$^+$, t$_R$=5.81 (Method 2).

Into a solution of Intermediate 18E (46.2 mg, 0.07 mmol) in THF (3 mL) were added water (0.5 mL) and PS—PPH$_3$ resin (135 mg, 0.3 mmol equiv). After shaking for 24 h, the resin was removed via filtration through celite. The resulting solution was concentrated and purified by RP-HPLC (MeOH/H$_2$O) to afford 3.6 mg (8%) of Compound 18-1. LCMS [m/z] calculated for C$_{33}$H$_{41}$ClN$_6$O$_4$: 620.3; found 621.6 [M+H]$^+$, t$_R$=12.47 min (Method 1).

Scheme 19
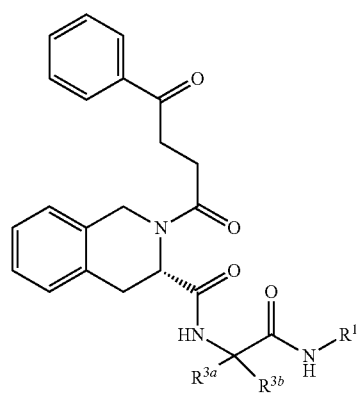
Example 19
Synthesis of (S)—N—((S)-4-(4-acetylpiperazin-1-yl)-1-((4-chloro-3-methylphenyl) amino)-1-oxobutan-2-yl)-2-(4-oxo-4-phenylbutanoyl)-1,2,3,4-tetrahydroisoquinoline-3-carboxamide (Compound 19-1)
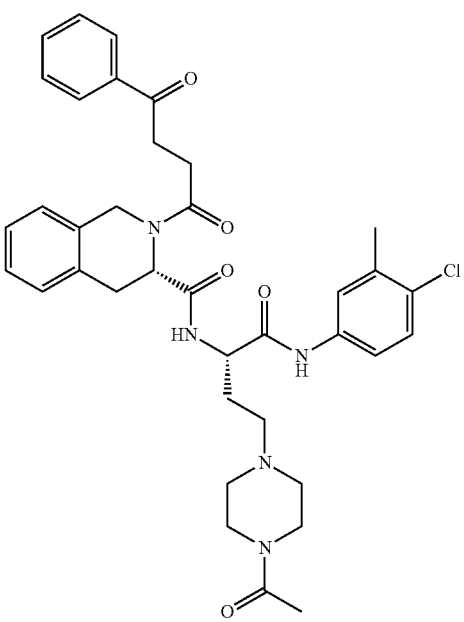
19-1
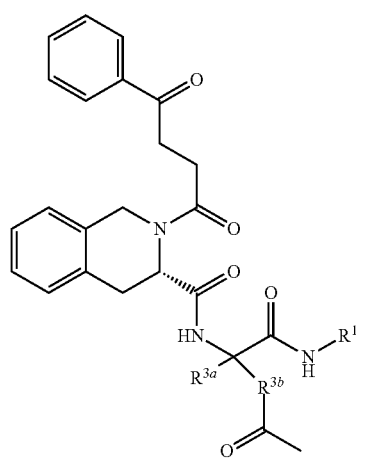
Scheme 19
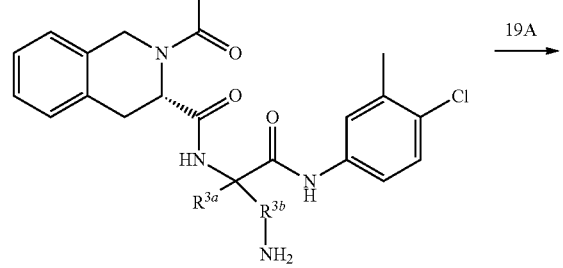

649
-continued

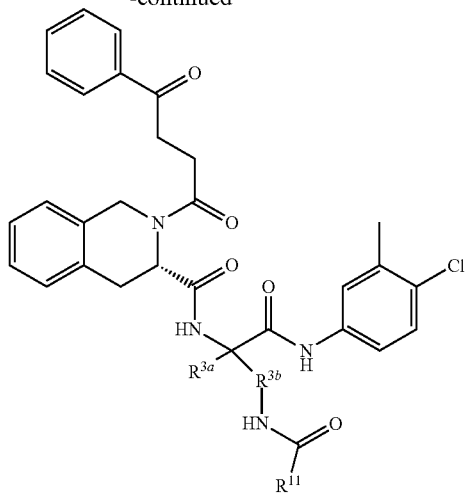

650
-continued

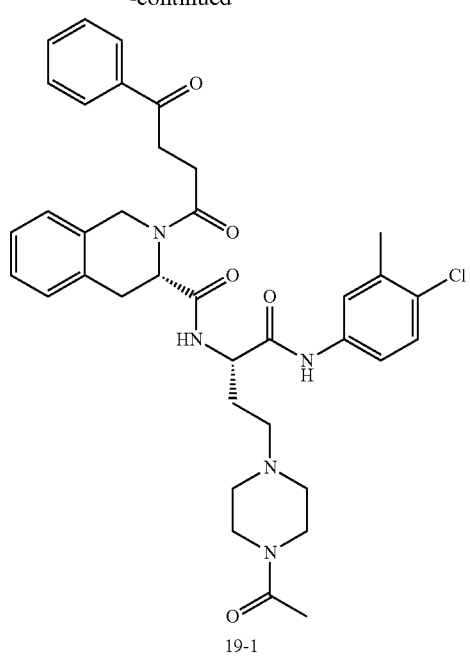

19-1

To (S)—N—((S)-1-((4-chloro-3-methyl phenyl) amino)-1-oxo-4-(piperazin-1-yl) butan-2-yl)-2-(4-oxo-4-phenylbutanoyl)-1,2,3,4-tetrahydroisoquinoline-3-carboxamide, HCl (57 mg, 0.09 mmol, made via Scheme 17) in CH$_3$CN (2 mL) was added DIEA (0.07 mL, 0.43 mmol) followed by acetic anhydride (0.03 mL, 0.34 mmol). After 1 h, reaction mixture was concentrated and the residue was partitioned between DCM (5 mL) and NaHCO$_3$ (sat) (5 mL). The layers were separated using a phase sep-cartridge and the aqueous layer was re-extracted with DCM (5 mL). The combined organic phases were concentrated and the crude product was purified by chromatography (MeOH/DCM) to afford 20 mg (33%) of Compound 19-1 as a white solid. LCMS [m/z] calculated for C$_{37}$H$_{42}$ClN$_5$O$_5$: 671.3; found 672.1[M+H]$^+$, t$_R$=4.48 min (Method 2).

Step 19A: Synthesis of (S)-4-(3-(tert-butoxycarbonyl)-3,4-dihydroisoquinolin-2(1H)-yl)-4-oxobutanoic Acid (Compound 19-1)

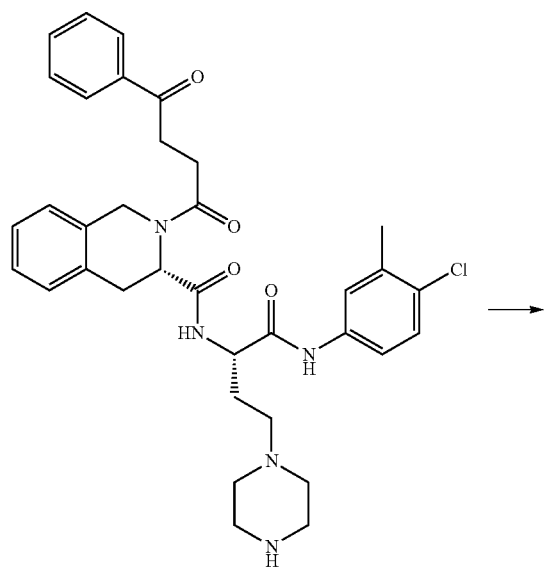

Scheme 20

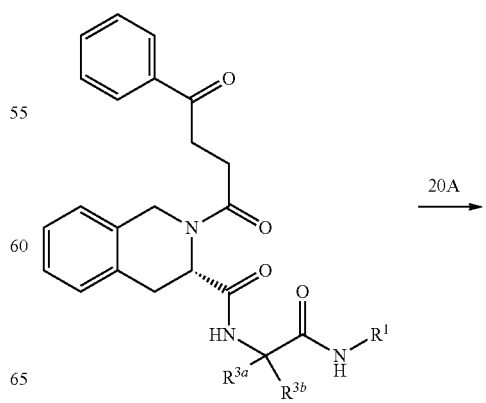

20A

651
-continued
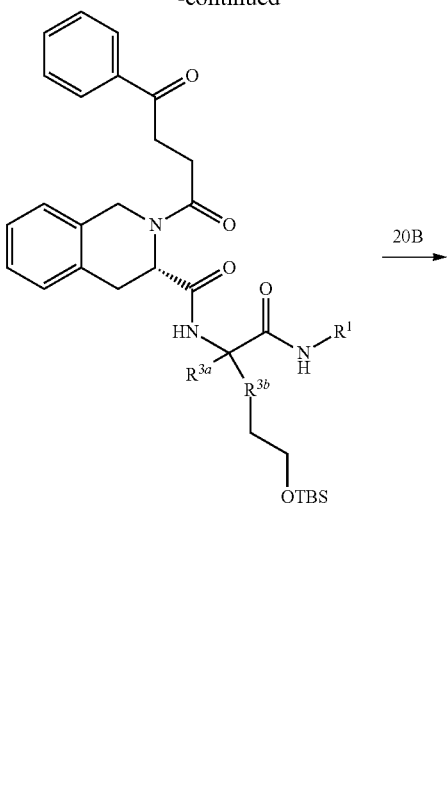
20B →
652
Example 20
Synthesis of (S)—N-(4-((4-chloro-3-methylphenyl) carbamoyl)-1-(2-hydroxyethyl) piperidin-4-yl)-2-(4-oxo-4-phenylbutanoyl)-1,2,3,4-tetrahydroisoquinoline-3-carboxamide (Compound 20-1)
Step 20A: Synthesis of (S)—N-(1-(2-((tert-butyldimethylsilyl)oxy)ethyl)-4-((4-chloro-3-methyl phenyl) carbamoyl)piperidin-4-yl)-2-(4-oxo-4-phenylbutanoyl)-1,2,3,4-tetrahydro isoquinoline-3-carboxamide (Compound 20A)
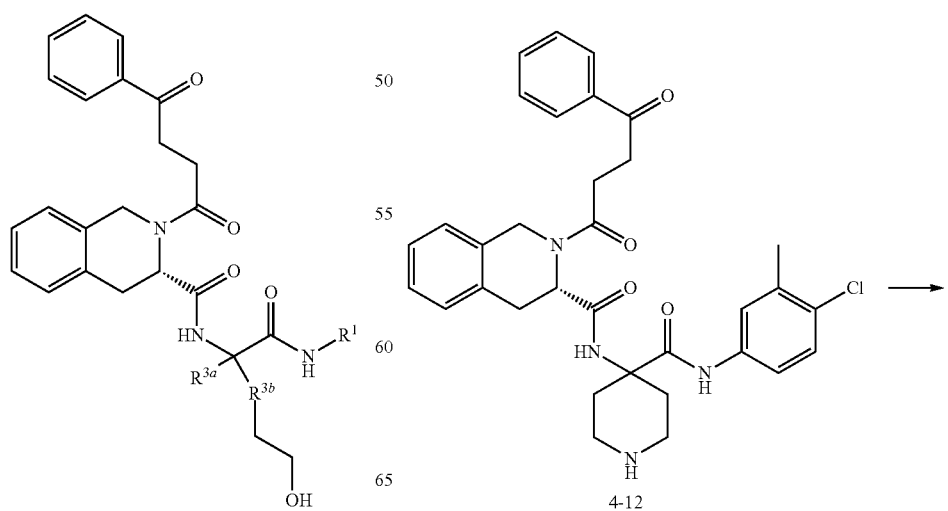

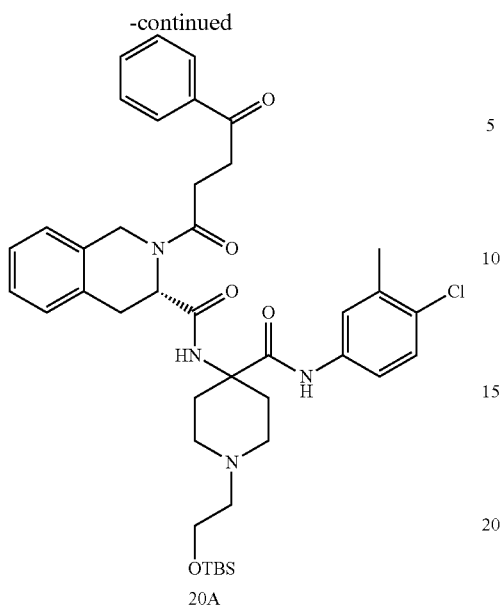

20A

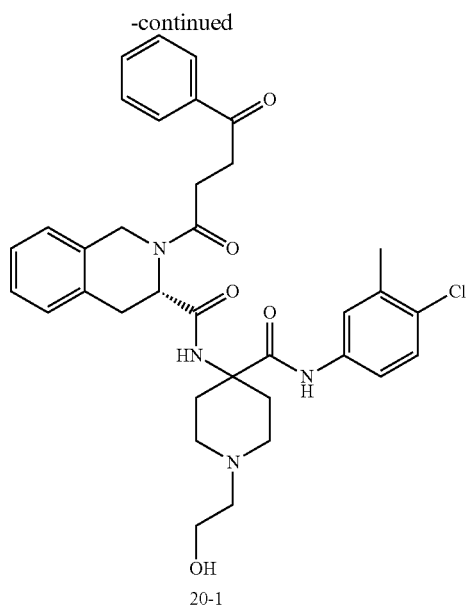

20-1

To Compound 4-12 (50 mg, 0.09 mmol) in CH₃CN (2.5 mL) were added K₂CO₃ (23.5 mg, 0.17 mmol) and 2-bromoethoxy-tert-butyldimethylsilane (54 mg, 0.26 mmol). The mixture was heated to 40° C. After 18 h, the reaction mixture was diluted with EA (100 mL) and washed with NaHCO₃ (sat) (100 mL). The organic layer was dried (Na₂SO₄), concentrated and purified by chromatography (EA/hexane) to afford 30.3 mg (48%) of Intermediate 20A as a white solid. LCMS [m/z] calculated for $C_{41}H_{53}ClN_4O_5Si$: 744.4; found 746.1[M+H]⁺, $t_R$=4.61 min (Method 4).

Step 20B: Synthesis of (S)—N-(4-((4-chloro-3-methyl phenyl) carbamoyl)-1-(2-hydroxyethyl) piperidin-4-yl)-2-(4-oxo-4-phenylbutanoyl)-1,2,3,4-tetrahydro isoquinoline-3-carboxamide (Compound 20-1)

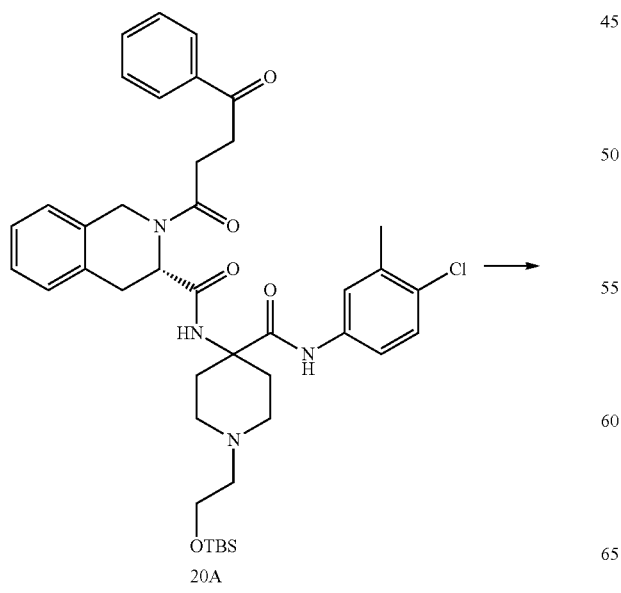

20A

A solution of 1M TBAF in THF (51 μL) was added to a solution of Intermediate 20A (30 mg, 0.05 mmol) in THF (2.5 mL). After 2 h, the reaction mixture was concentrated and purified by RP-HPLC to afford 13.6 mg (43%) of Compound 20-1. LCMS [m/z] calculated for $C_{35}H_{39}ClN_4O_5$: 630.3; found 632 [M+H]⁺, $t_R$=7.04 min (Method 3).

Scheme 21
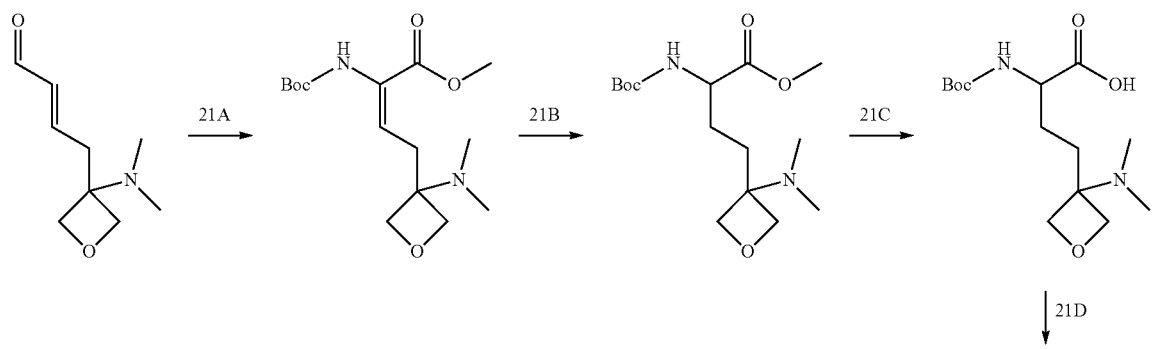
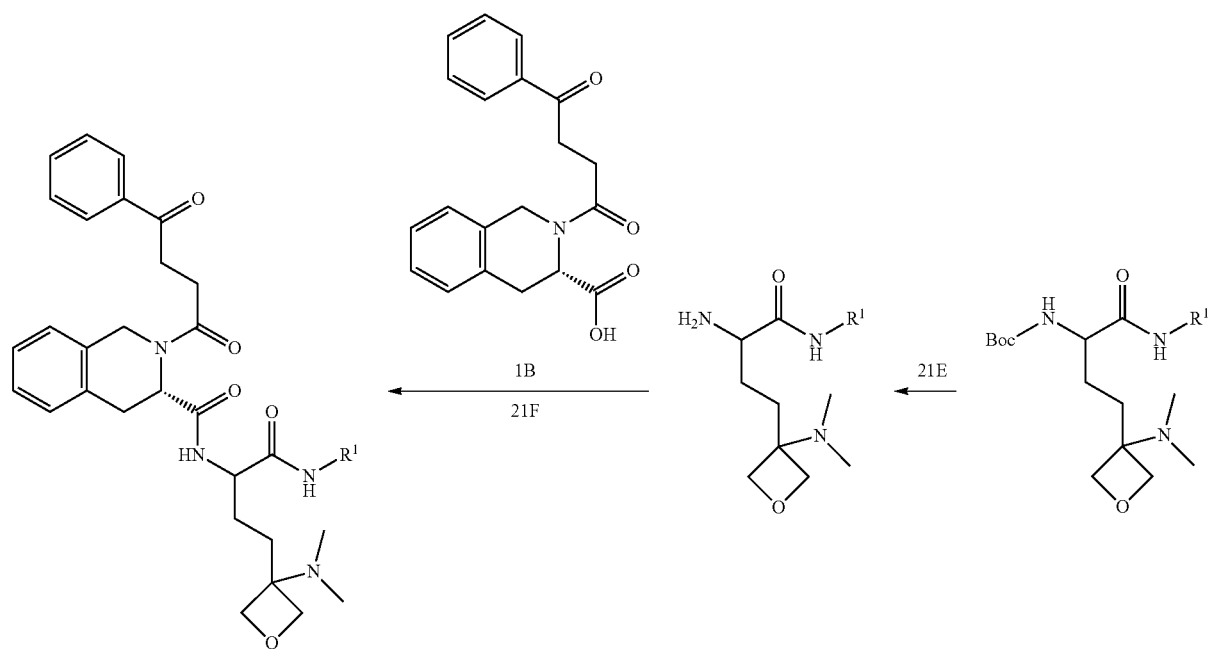
21-1

Example 21

Synthesis of (3S)—N-(1-((4-chloro-3-methylphenyl)amino)-4-(3-(dimethylamino)oxetan-3-yl)-1-oxobutan-2-yl)-2-(4-oxo-4-phenylbutanoyl)-1,2,3,4-tetrahydroisoquinoline-3-carboxamide (Compound 21-1)

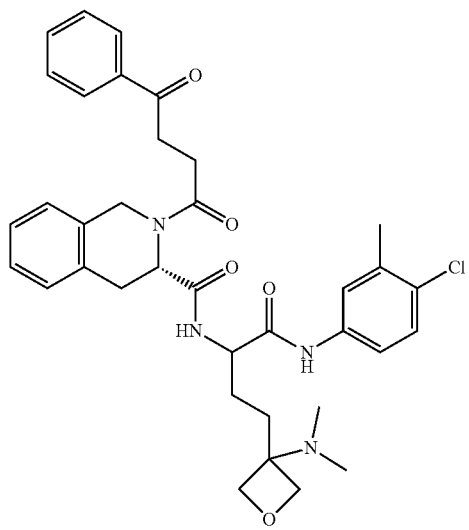

21-1

Step 21A: Synthesis of methyl (E)-2-((tert-butoxycarbonyl)amino)-4-(3-(dimethylamino)oxetan-3-yl)but-2-enoate (Intermediate 21A)

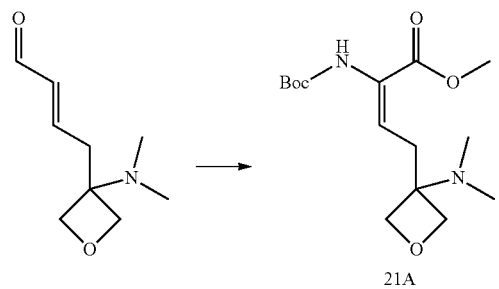 [SMILES: CN(C)C1(C/C=C/C=O)COC1 ; COC(=O)/C(=C\CC1(N(C)C)COC1)NC(=O)OC(C)(C)C]

21A

To a solution of a catalytic amount of DBU (0.046 mL, 0.31 mmol) in dry THF (5 mL, 3.1 mmol) dimethylamine (1.84 mL, 3.7 mmol) was added dimethylamine (1.84 mL, 3.7 mmol) followed by a solution of 2-(oxetan-3-ylidene)acetaldehyde (500 mg, 3.1 mmol) in dry THF (3 mL) at −15° C. After 50 min at −15° C., the solution was added to another solution of methyl 2-((tert-butoxy carbonyl) amino)-2-(dimethoxyphosphoryl) acetate (1091 mg, 3.7 mmol) in dry THF (50 mL) and DBU (0.46 ml, 3.1 mmol) at 0° C. After 30 min, the mixture was warmed to 60° C. for 30 min, then was then left stirring at rt overnight. The mixture was quenched with 1 M HCl (10 mL) and the volatiles removed by concentration. Toluene was added and the mixture was extracted with DCM (3×50 mL). The organic phases were washed with 1 M HCl (50 mL), brine (50 mL) and the organics were dried (MgSO$_4$), concentrated, and the resulting material was loaded onto a column of SCX (5 g) in MeOH. The column was washed (3×10 ml MeOH) and then the product was eluted with MeOH (0.7 M NH$_3$). The resultant mixture was concentrated to afford 400 mg (35%) of Intermediate 21A as a colourless oil. LCMS [m/z] calculated for $C_{15}H_{26}N_2O_5$: 314.2; found 315.1 [M+H]$^+$, $t_R$=0.7 min (Method 4).

Step 21B: Synthesis of methyl 2-((tert-butoxycarbonyl)amino)-4-(3-(dimethylamino) oxetan-3-yl)butanoate (Intermediate 21B)

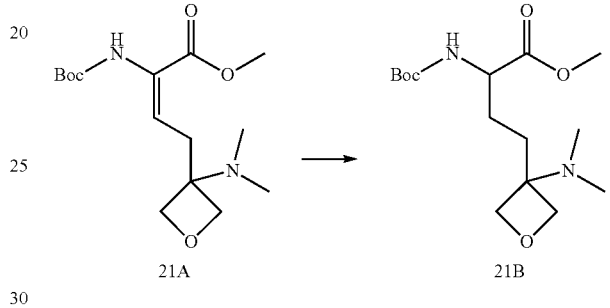

Intermediate 21A (400 mg, 1.3 mmol) was dissolved in MeOH (20 mL) and AcOH (1 mL) was added. The reaction mixture was hydrogenated in an H-Cube (10% Pd/C, 30×4 mm, Full hydrogen, 60° C., 1 mL/min). The solvent was evaporated to afford 176 mg (44%) of Intermediate 21B as a colourless oil. LCMS [m/z] calculated for $C_{15}H_{28}N_2O_5$: 316.2; found 317.1 [M+H]$^+$, $t_R$=1.54 min (Method 4).

Step 21C: Synthesis of 2-((tert-butoxycarbonyl)amino)-4-(3-(dimethylamino) oxetan-3-yl) butanoic Acid (Intermediate 21C)

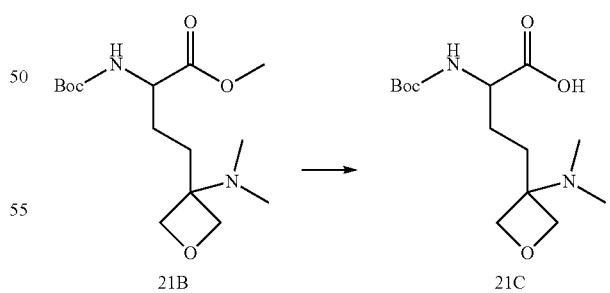

Lithium hydroxide (8.48 mg, 0.35 mmol) was added to a solution of Intermediate 21B (56 mg, 0.18 mmol) in MeOH (2 mL, 49.4 mmol) and the reaction stirred at rt for 1.5 h. The solvent was removed to provide 54 mg (99%) of Intermediate 21C, which was used without further purification. LCMS [m/z] calculated for $C_{14}H_{25}N_2O_5$: 302.2; found 303.1 [M+H]$^+$, $t_R$=0.84 min (Method 4).

659

Step 21D: Synthesis of tert-butyl (1-((4-chloro-3-methylphenyl)amino)-4-(3-(dimethylamino)oxetan-3-yl)-1-oxobutan-2-yl)carbamate (Intermediate 21D)

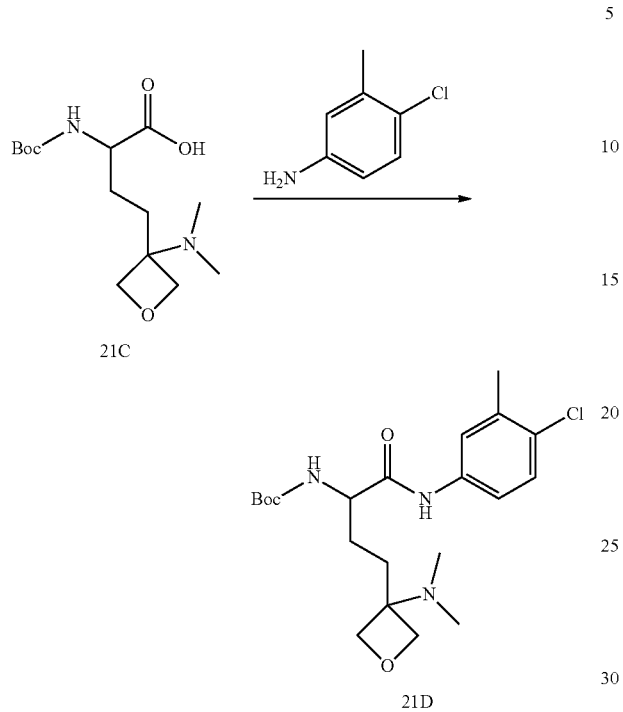

Intermediate 21C (54 mg, 0.18 mmol) was dissolved in DCM (3 mL, 0.18 mmol). 4-chloro-3-methylaniline (27.2 mg, 0.19 mmol) and DIEA (0.091 mL, 0.52 mmol) were added, followed by HATU (100 mg, 0.26 mmol) and DMF (1 mL) to help solubility of the reagents. After stirring overnight, the mixture was diluted DCM (20 mL) and the reaction quenched with 10% citric acid (20 mL). The phases were separated and the organic phase washed with NaHCO$_3$ and brine and the volatiles were evaporated. The crude product was purified by chromatography [MeOH (0.7 N NH$_3$/DCM to afford 38.9 mg (47%) of Intermediate 21D as an orange oily solid. LCMS [m/z] calculated for C$_{21}$H$_{32}$ClN$_3$O$_4$: 425.2; found 426.1 [M+H]$^+$, t$_R$=1.49 min (Method 4).

Step 21E: Synthesis of 2-amino-N-(4-chloro-3-methyl phenyl)-4-(3-(dimethyl amino) oxetan-3-yl) butanamide (Intermediate 21E)

660

-continued

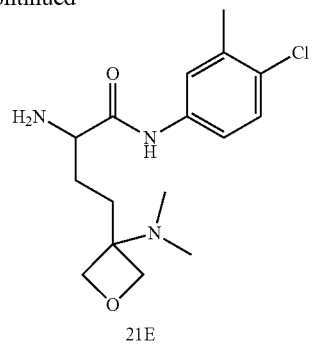

TFA (0.2 mL, 2.6 mmol) was added to a solution of Intermediate 21E (37 mg, 0.09 mmol) in DCM (1 mL). After 4 h, additional TFA (0.2 mL, 2.6 mmol) was added. After stirring overnight, the volatile solvents were removed to afford Intermediate 21E (assuming 100%), which was used without further purification. LCMS [m/z] calculated for C$_{16}$H$_{24}$ClN$_3$O$_4$: 325.2; found 326.1 [M+H]$^+$, t$_R$=1.59 min (Method 4).

Step 21F: Synthesis of (3 S)—N-(1-((4-chloro-3-methylphenyl)amino)-4-(3-(dimethylamino)oxetan-3-yl)-1-oxobutan-2-yl)-2-(4-oxo-4-phenylbutanoyl)-1,2,3,4-tetrahydroisoquinoline-3-carboxamide (Compound 21-1)

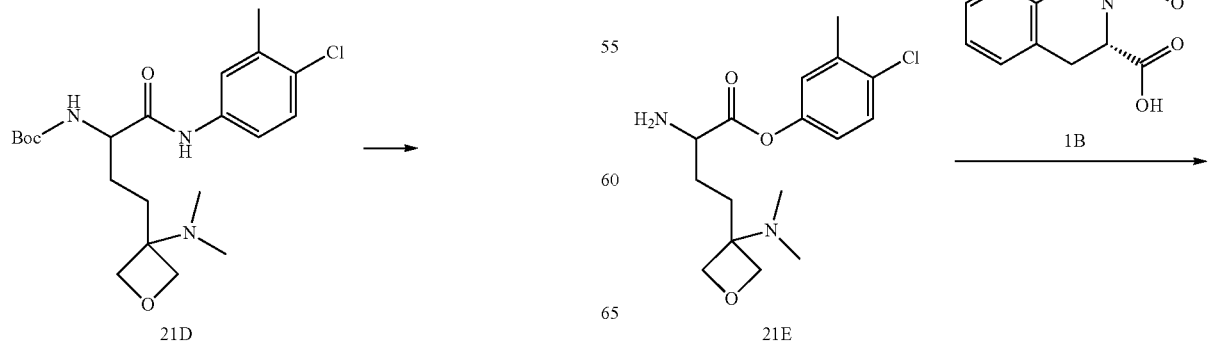

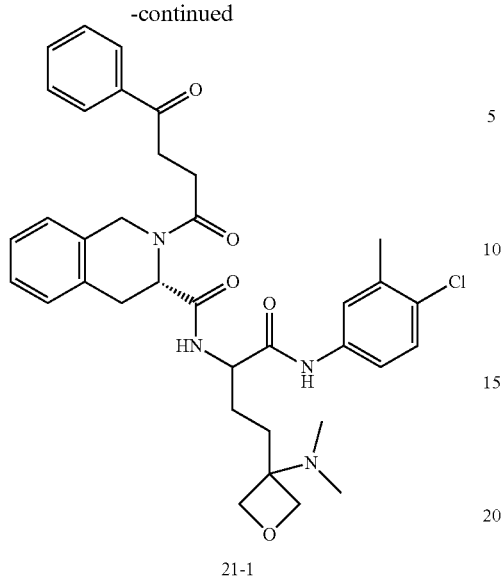

21-1

DIEA (75 µL, 0.43 mmol) was added to a solution of Intermediate 21E (28.3 mg, 0.09 mmol) and Intermediate 1B (32.2 mg, 0.1 mmol) in DCM (3 mL). HATU (50 mg, 0.13 mmol) was added. After 1 h, the solution was diluted with DCM (10 mL) and washed with NaHCO$_3$ (10 mL). The organics were dried (MgSO$_4$), filtered, concentrated, and purified by chromatography (MeOH (0.7 N NH$_3$)/DCM) to afford 25 mg (42%) of Compound 21-1 as a white solid. LCMS [m/z] calculated for C$_{36}$H$_{41}$ClN$_4$O$_5$: 644.3; found 645.1 [M+H]$^+$, t$_R$=4.85 min (Method 4).

Scheme 22

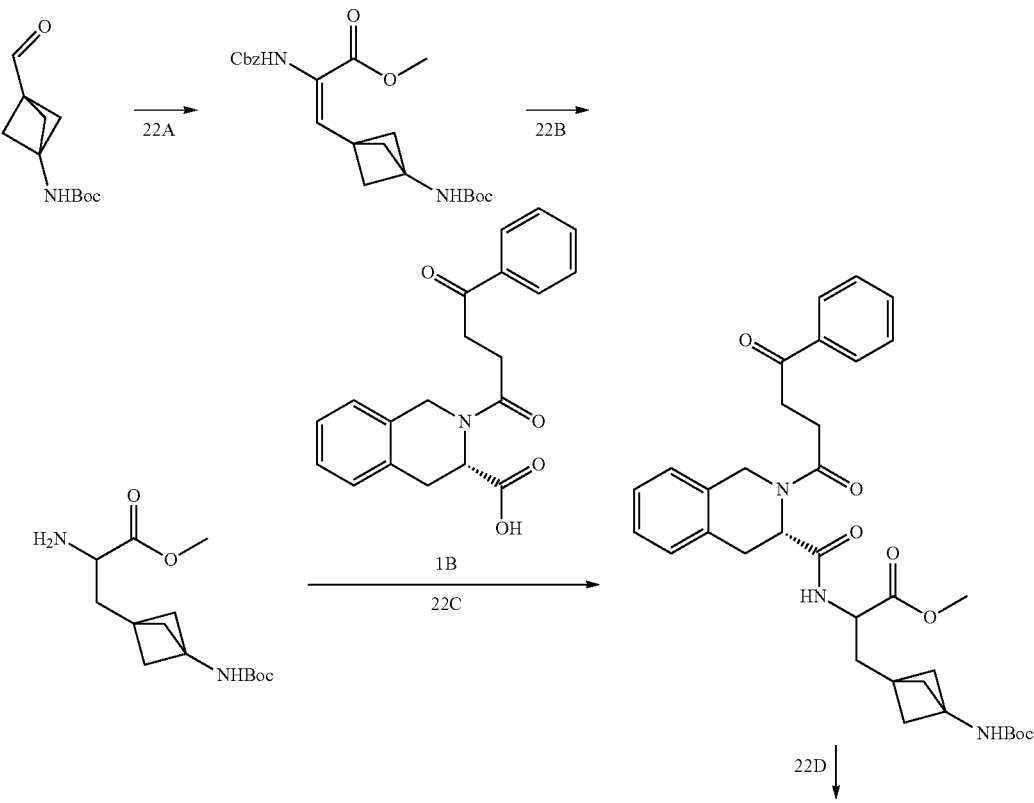

663

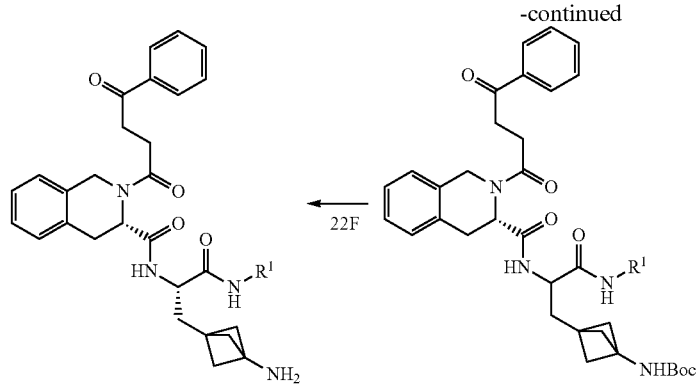

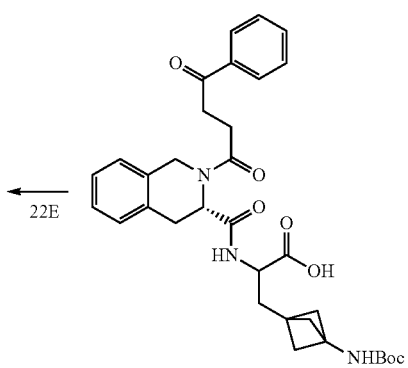

Example 22

Synthesis of ((S)—N—((S)-3-(3-aminobicyclo [1.1.1]pentan-1-yl)-1-((4-chloro-3-methyl phenyl) amino)-1-oxopropan-2-yl)-2-(4-oxo-4-phenylbutanoyl)-1,2,3,4-tetrahydro isoquinoline-3-carboxamide (Compound 22-1) and (S)—N—((R)-3-(3-amino bicycle [1.1.1] pentan-1-yl)-1-((4-chloro-3-methylphenyl)amino)-1-oxopropan-2-yl)-2-(4-oxo-4-phenyl butanoyl)-1,2,3,4-tetrahydroisoquinoline-3-carboxamide (Compound 22-2)

22-1

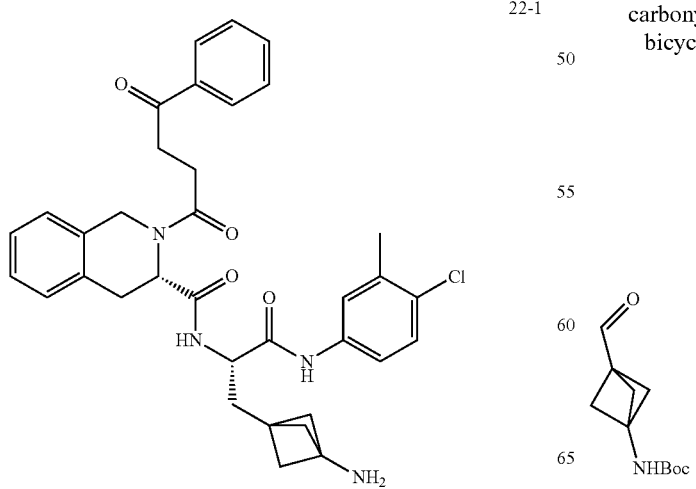

22-2

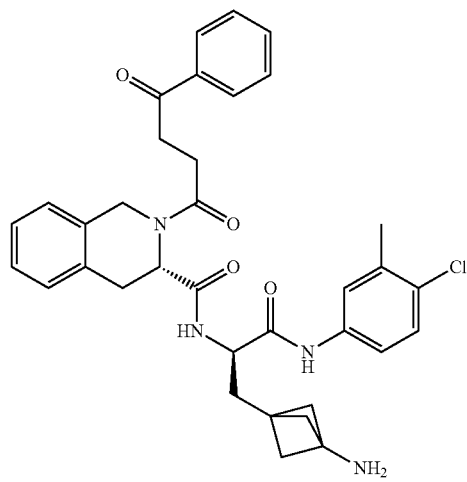

Step 22A: Synthesis of (E)-methyl 2-(((benzyloxy) carbonyl)amino)-3-(3-((tert-butoxycarbonyl)amino) bicyclo[1.1.1]pentan-1-yl)acrylate (Intermediate 22A)

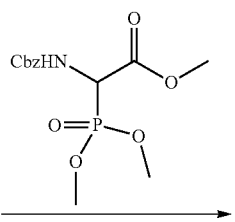

-continued

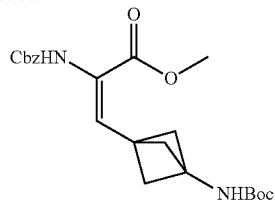

22A

DBU (102 μL, 0.68 mmol) was added to a solution of tert-butyl (3-formyl bicycle [1.1.1] pentan-1-yl)carbamate (110 mg, 0.52 mmol) and methyl 2-(((benzyloxy) carbonyl) amino)-2-(dimethoxyphosphoryl)acetate (224 mg, 0.68 mmol) in DCM (3 mL) at 0° C. After stirring at rt overnight, the reaction mixture was quenched with 1 M HCl, and the two phases separated by sept cartridge. The organic layer was concentrated and the resulting crude material was purified by chromatography (EA/isohexane) to provide 144 mg (60%) Intermediate 22A. LCMS [m/z] calculated for $C_{22}H_{28}N_2O_6$: 416.2; found 417.3 $[M+H]^+$, $t_R$=2.31 min (Method 4).

Step 22B: Synthesis of methyl 2-amino-3-(3-((tert-butoxycarbonyl) amino) bicyclo[1.1.1]pentan-1-yl) propanoate (Intermediate 22B)

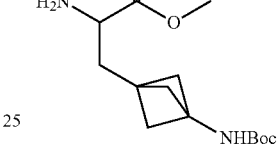

22A

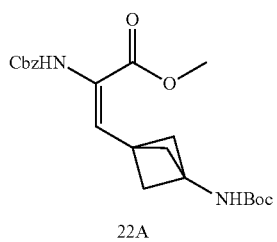

22B

Intermediate 22A (144 mg, 0.35 mmol) was dissolved in MeOH (1 mL) and the solution was degassed with $N_2$. Pd—C (36.8 mg, 0.35 mmol) was added and the mixture was shaken under 5 atm of H2 overnight. The mixture was filtered through celite and concentrated to provide 85 mg (74%) of Intermediate 22B, which was used without further purification. LCMS [m/z] calculated for $C_{14}H_{42}N_2O_4$: 284.2; found 197.3 $[M+H-^tBu]^+$, $t_R$=0.19 min (Method 4).

Step 22C: Synthesis of (3-(3-((tert-butoxycarbonyl) amino)bicyclo[1.1.1]pentan-1-yl)-2-((S)-2-(4-oxo-4-phenylbutanoyl)-1,2,3,4-tetrahydroisoquinoline-3-carboxamido)propanoic Acid (Intermediate 22C)

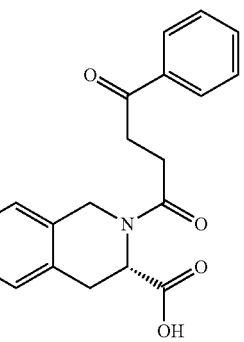

1B

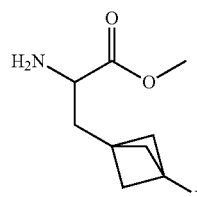

22B

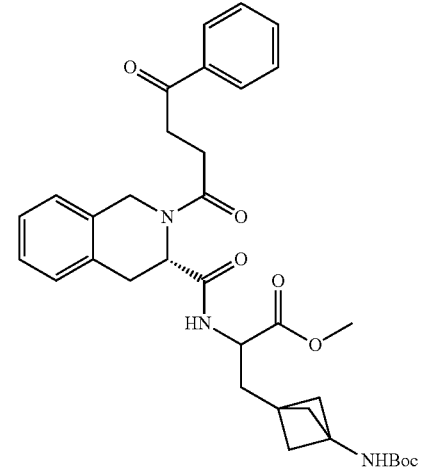

22C

DIEA (300 μL, 1.7 mmol) was added to a solution of Intermediate 22B (98 mg, 0.35 mmol) and Intermediate 1B (128 mg, 0.38 mmol) in DCM (5 mL). HATU (157 mg, 0.41 mmol) was added. After 2 h, the reaction was diluted with 1M HCl (3 mL) and the two phases were separated with a sep-cartridge. The organic layer was concentrated and the resulting crude material was purified by chromatography (EA/isohexane) to provide 60 mg (27%) of Intermediate 22C. LCMS [m/z] calculated for $C_{34}H_{41}N_3O_7$: 603.3; found 604.3 $[M+H]^+$, $t_R$=2.65 min (Method 4).

Step 22D: Synthesis of 3-(3-((tert-butoxycarbonyl)amino)bicyclo[1.1.1]pentan-1-yl)-2-((S)-2-(4-oxo-4-phenylbutanoyl)-1,2,3,4-tetrahydroisoquinoline-3-carboxamido) propanoic Acid (Intermediate 22D)

Step 22E: Synthesis of tert-butyl (3-(3-((4-chloro-3-methylphenyl)amino)-3-oxo-2-((S)-2-(4-oxo-4-phenylbutanoyl)-1,2,3,4-tetrahydroisoquinoline-3-carboxamido)propyl)bicyclo[1.1.1]pentan-1-yl) carbamate (Intermediate 22E)

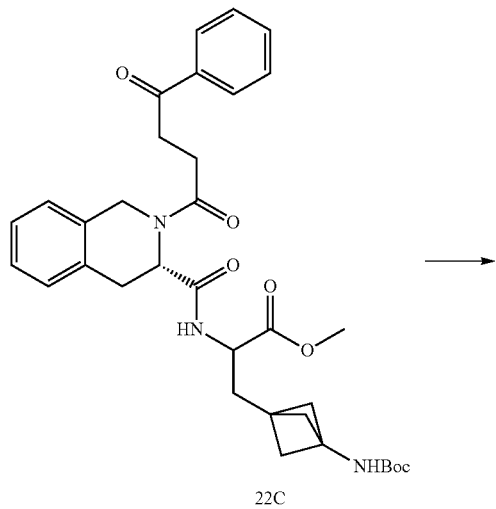

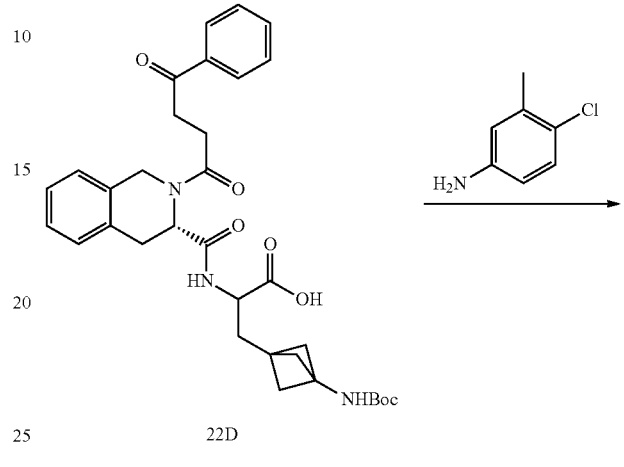

LiOH (39.7 mg, 1.7 mmol) was added to a solution of Intermediate 22C (100 mg, 0.17 mmol) in THF (2.5 mL) and MeOH (2.5 mL). After 3 h, the solvent was removed and the resulting crude material was partitioned between aq. 1 M HCl (10 mL) and DCM (20 mL). The organic phase was dried (MgSO$_4$), filtered and concentrated to give 102 mg (99%) of Intermediate 22D that was used in the next step without further purification LCMS [m/z] calculated for C$_{33}$H$_{39}$N$_3$O$_7$: 589.3; found 590.3 [M+H]$^+$, t$_R$=1.69 min (Method 4).

DIEA (0.12 mL, 0.67 mmol) and HATU (82 mg, 0.22 mmol) were added to a solution of Intermediate 22D (98 mg, 0.17 mmol) in DCM (30 ml). The reaction mixture was cooled to 0° C. and 4-chloro-3-methylaniline (28.2 mg, 0.2 mmol) was added. After 2 h, the reaction was diluted with THF and washed with H$_2$O. The organic layers were dried (MgSO$_4$), filtered, concentrated, and purified by chromatography (EA/isohexane) to give 110 mg (85%) of Intermediate 22E. LCMS [m/z] calculated for C$_{40}$H$_{45}$ClN$_4$O$_6$: 712.3; found 713 [M+H]$^+$, t$_R$=1.97 min (Method 4).

Step 22F: Synthesis of (S)—N—((S)-3-(3-aminobicyclo[1.1.1]pentan-1-yl)-1-((4-chloro-3-methylphenyl)amino)-1-oxopropan-2-yl)-2-(4-oxo-4-phenylbutanoyl)-1,2,3,4-tetrahydroisoquinoline-3-carboxamide (Compound 22-1) and (S)—N—((R)-3-(3-aminobicyclo[1.1.1]pentan-1-yl)-1-((4-chloro-3-methylphenyl)amino)-1-oxopropan-2-yl)-2-(4-oxo-4-phenylbutanoyl)-1,2,3,4-tetrahydroisoquinoline-3-carboxamide (Compound 22-2)

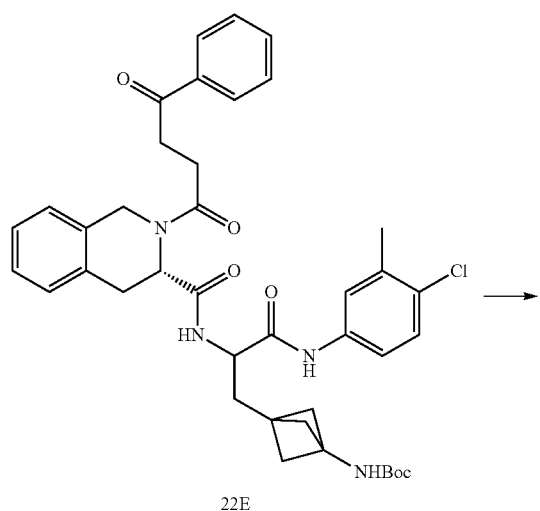

22E

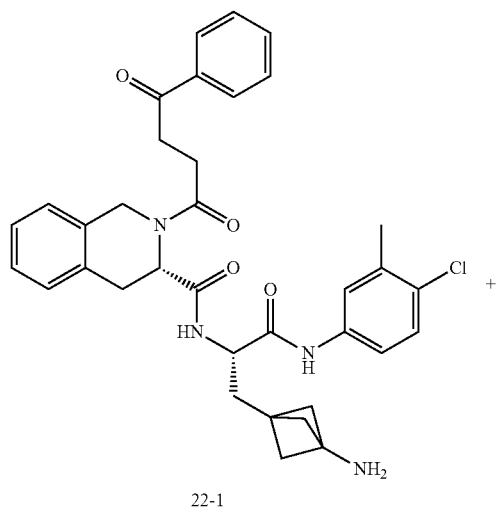

22-1

-continued

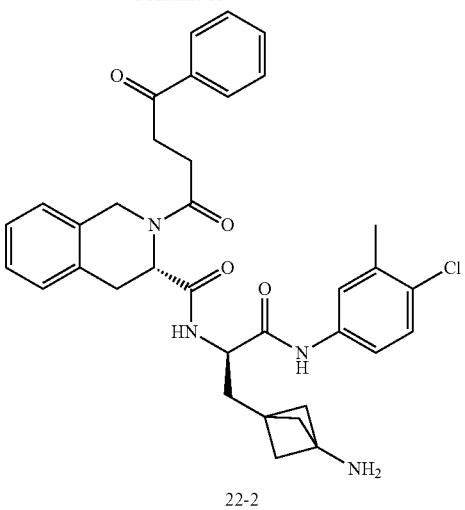

22-2

A solution of Intermediate 22E (100 mg, 0.14 mmol) in DCM (2 ml) was treated with TFA (0.1 mL). After 3 h, the reaction mixture was concentrated and the resulting crude material was partitioned between DCM (10 mL) and 1 M HCl (10 mL). The organic layer was dried (MgSO$_4$), filtered, concentrated and purified by chromatography (MeOH (0.7 M NH$_3$)/DCM) to give 15 mg (17%) of Compound 22-1 and 12 mg (13%) of Compound 22-2. Compound 22-1: LCMS [m/z] calculated for C$_{35}$H$_{37}$ClN$_4$O$_4$: 612.3; found 613.1 [M+H]$^+$, t$_R$=4.51 min (Method 5). Compound 22-2: LCMS [m/z] calculated for C$_{35}$H$_{37}$ClN$_4$O$_4$: 612.3; found 613.1 [M+H]$^+$, t$_R$=4.67 min (Method 5).

Following the procedures as set forth in Scheme 22 above, the compounds of the following Table 2 were prepared using the appropriate R$^1$, R$^{3a}$ and R$^{3b}$ reagents.

TABLE 22

| Cmpd. # | R¹ | R³ᵃ | R³ᵇ | R³ᵃ/R³ᵇ Stereo-chemistry | MS Calc | MS (MH)⁺ | LCMS Retention Time(min) | Purity Method |
|---|---|---|---|---|---|---|---|---|
| 22-1 | 2-chloro-4-methylphenyl | H | bicyclo[1.1.1]pentyl-CH₂-NH₂ | S | 612.3 | 613.1 | 4.51 | 5 |
| 22-2 | 2-chloro-4-methylphenyl | H | bicyclo[1.1.1]pentyl-CH₂-NH₂ | R | 612.3 | 613.1 | 4.67 | 5 |
| 22-3 | bicyclo[1.1.1]pentyl-CH₂-NH₂ | H | 2-fluoro-3,4-dichlorophenyl | racemic | 650.2 | 651 | 6.08 | 5 |

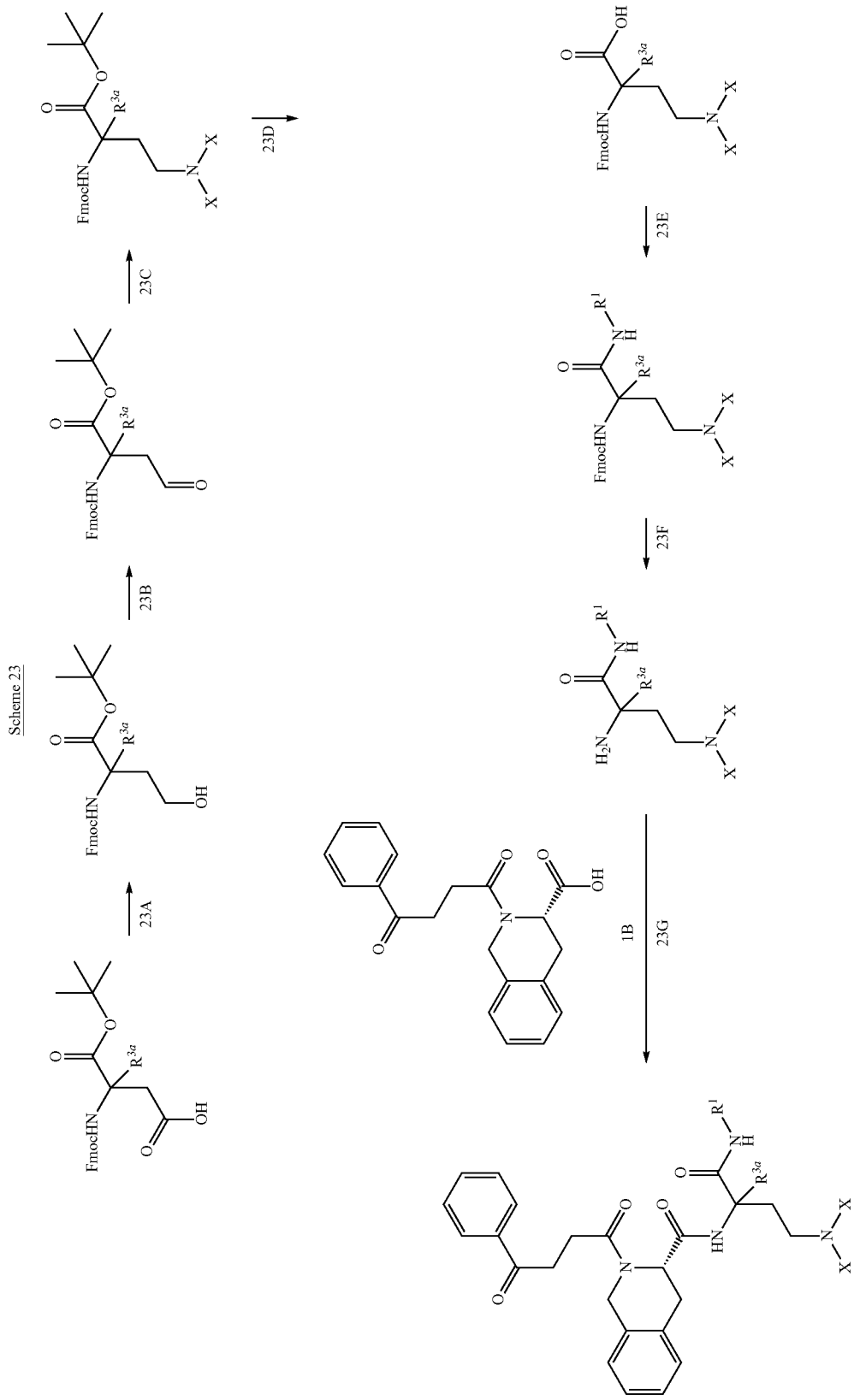
Scheme 23

Example 23

Synthesis of N-(1-((2,3-dihydro-1H-inden-5-yl)amino)-4-(4-fluoropiperidin-1-yl)-1-oxobutan-2-yl)-2-(4-oxo-4-phenylbutanoyl)-1,2,3,4-tetrahydroisoquinoline-3-carboxamide (Compound 23-1)

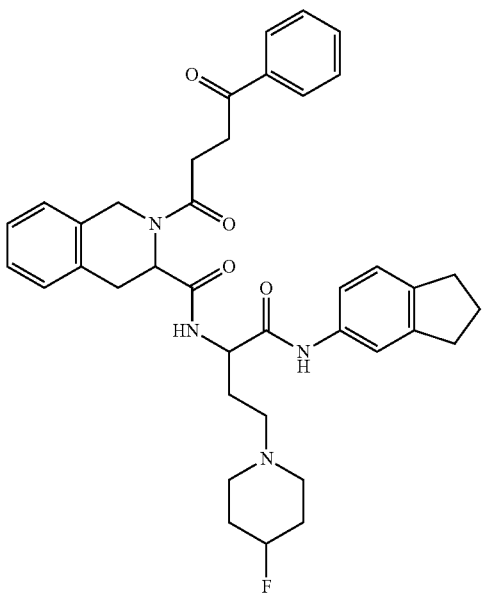

23-1

Step 23A: Synthesis of tert-butyl (((9H-fluoren-9-yl)methoxy)carbonyl)-L-homoserinate (Intermediate 23A)

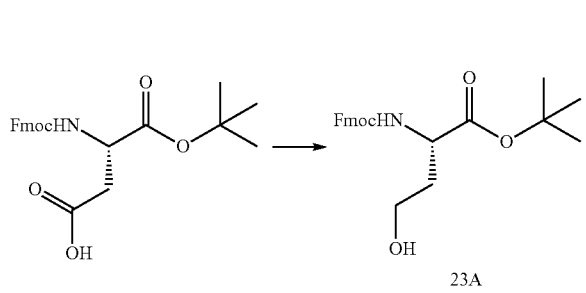

23A

To a stirred solution of (S)-3-((((9H-fluoren-9-yl)methoxy)carbonyl)amino)-4-(tert-butoxy)-4-oxobutanoic acid (6.7 g, 16.3 mmol) in THF (65.1 mL, 16.3 mmol) was added N-methylmorpholine (1.8 mL, 16.3 mmol). The reaction was cooled to 0° C. followed by the slow addition of ethyl chloroformate (1.6 mL, 16.3 mmol). A colourless precipitate began to form immediately. The reaction was warmed to rt and stirred for 1 h. The formed precipitate was filtered off using a phase sep cartridge, rinsing with THF (10 mL). The filtrate was cooled again to 0° C. and a solution of sodium borohydride (0.8 g, 21.2 mmol) in 21 mL of H$_2$O/THF (1:1) was added. The resulting mixture was stirred at 0° C., followed by slow warming to rt over 1 h. The reaction mixture was then concentrated under reduced pressure and the residue was dissolved in EA (120 mL), washed with 1 M HCl (2×50 mL) and dried (MgSO$_4$). The solvent was removed in vacuo to afford 7.3 g (104%) of Intermediate 22A as a colorless oil. LCMS [m/z] calculated for C$_{23}$H$_{27}$NO$_5$: 397.2; found 420.0 [M+Na]$^+$, t$_R$=2.55 min (Method 4).

Step 23B: Synthesis of tert-butyl (S)-2-((((9H-fluoren-9-yl)methoxy)carbonyl)amino)-4-oxobutanoate (Intermediate 23B)

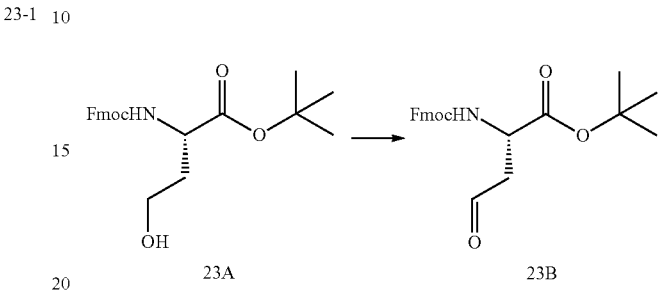

23A                              23B

To a round bottom flask containing Intermediate 23A (7.3 g, 16.9 mmol) in DCM (70 mL, 17.5 mmol) at 0° C. was added DMP (7.8 g, 18.4 mmol). The reaction was warmed to rt. The solution was washed with NaHCO$_3$ (3×75 mL). The organic phase was dried (MgSO$_4$) and the solvent was removed in vacuo. The residue was purified by column chromatography (EA/isohexane) to afford Intermediate 23B (4.4 g, 9.9 mmol, 57% yield) as a thick colourless oil. LCMS [m/z] calculated for C$_{23}$H$_{25}$NO$_5$: 395.2; found 418.1 [M+Na]$^+$, t$_R$=2.54 min (Method 4).

Step 23C: Synthesis of tert-butyl (S)-2-((((9H-fluoren-9-yl)methoxy)carbonyl)amino)-4-(4-fluoropiperidin-1-yl)butanoate (Intermediate 23C)

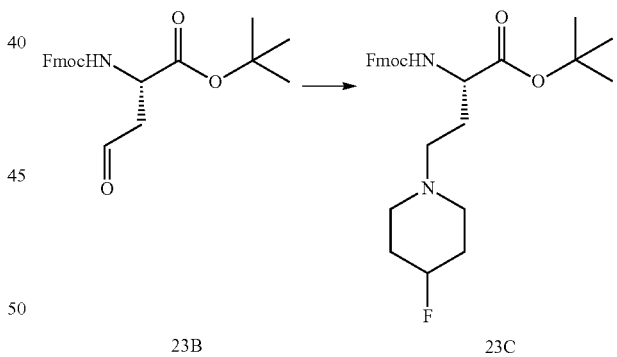

23B                              23C

To a round bottom flask containing Intermediate 23B (500 mg, 1.3 mmol) in DCM (1.8 mL) and THF (6.3 mL) was added 4-fluoropiperidine, HCl (194 mg, 1.4 mmol) followed by acetic acid (80 μl, 1.4 mmol). The reaction was stirred at rt under N$_2$ for 15 min, then cooled to 0° C. and sodium triacetoxyborohydride (670 mg, 3.2 mmol) was added to the reaction mixture portionwise. The reaction was then allowed to warm to rt overnight. The reaction mixture was diluted with DCM (30 mL) and washed with a NaHCO$_3$ (2×30 mL) before being passed through a hydrophobic frit. The solvent was removed in vacuo to afford Intermediate 23C (695 mg, 1.3 mmol, 100% yield) as a colourless oil. LCMS [m/z] calculated for C$_{28}$H$_{35}$FN$_2$O$_4$: 482.3; found 483.1 [M+H]$^+$, t$_R$=1.8 min (Method 4).

Step 23D: Synthesis of (S)-2-((((9H-fluoren-9-yl)methoxy)carbonyl)amino)-4-(4-fluoropiperidin-1-yl)butanoic acid (Intermediate 23D)

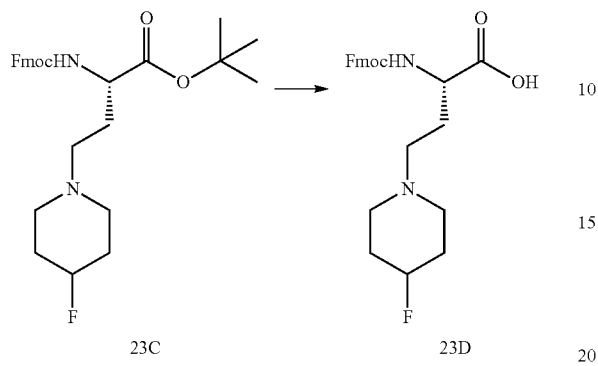

Intermediate 23C (675 mg, 1.4 mmol) was dissolved in DCM (3 mL). TFA (1 ml, 12.9 mmol) was added and the reaction mixture was stirred at rt for 2 h. Additional TFA (1 mL) was added. After 1.5 h, the solvent was removed in vacuo and chased with toluene (2×5 mL) before DCM (3 mL) was added and the mixtures were stood at rt overnight. Isohexane (10 mL) was added to the resultant oil and the mixture was sonicated before the solvent was removed in vacuo to afford Intermediate 23D (662 mg, 1.4 mmol, 100% yield) as a white solid. LCMS [m/z] calculated for $C_{24}H_{27}FN_2O_4$: 426.2; found 427.0 [M+H]$^+$, $t_R$=1.54 min (Method 4).

Step 23E: Synthesis of (9H-fluoren-9-yl)methyl (S)-(1-((2,3-dihydro-1H-inden-5-yl)amino)-4-(4-fluoropiperidin-1-yl)-1-oxobutan-2-yl)carbamate (Intermediate 23E)

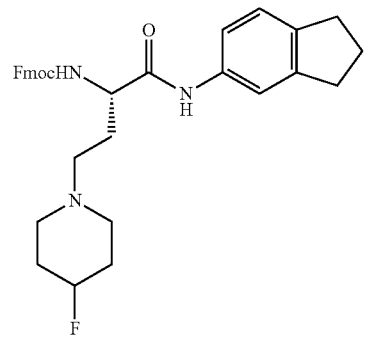

To a vial containing 2,3-dihydro-1H-inden-5-amine (68.3 mg, 0.51 mmol) was added Intermediate 23D (182 mg, 0.43 mmol) in DCM (2 mL). The reaction mixture was cooled to 0° C., followed by the addition of DIEA (0.22 mL, 1.28 mmol) and HATU (244 mg, 0.64 mmol). The reaction mixture was stirred at 0° C. for 10 min and then warmed to rt. Additional DCM (3 mL) was added. After 1.5 h, the reaction mixture was diluted with DCM (10 mL) and sat. aq. NH$_4$Cl (10 mL) and the mixture was transferred to a separating funnel. The layers were partitioned and the aqueous layer was further extracted with DCM (2×10 mL). The combined organics were dried (MgSO$_4$), filtered, and the solvent was removed in vacuo. The material was purified by chromatography (MeOH (0.7 M NH$_3$)/DCM), to provide 191 mg (74%) of Intermediate 23E as a clear colourless oil. LCMS [m/z] calculated for $C_{33}H_{36}FN_3O_3$: 541.3; found 542.1 [M+H]$^+$, $t_R$=1.95 min (Method 4).

Step 23F: Synthesis of (S)-2-amino-N-(2,3-dihydro-1H-inden-5-yl)-4-(4-fluoropiperidin-1-yl)butanamide (Intermediate 23F)

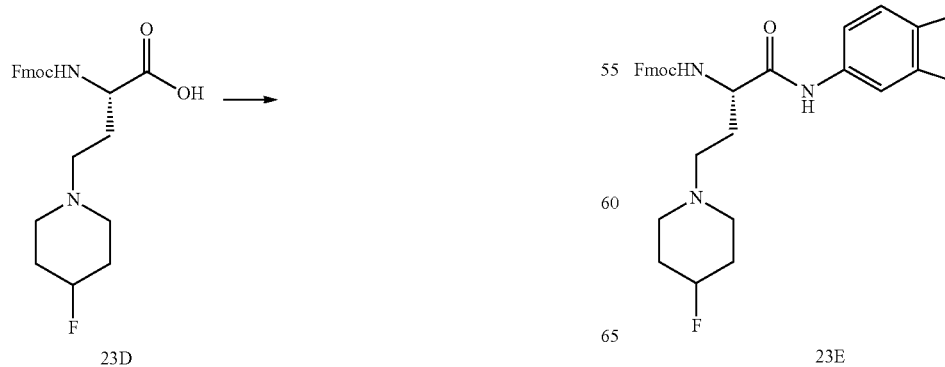

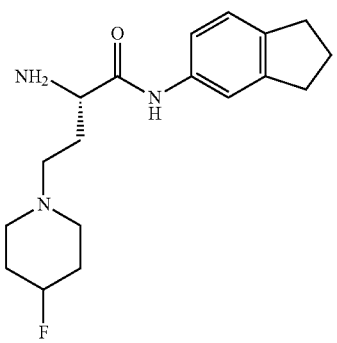

23F

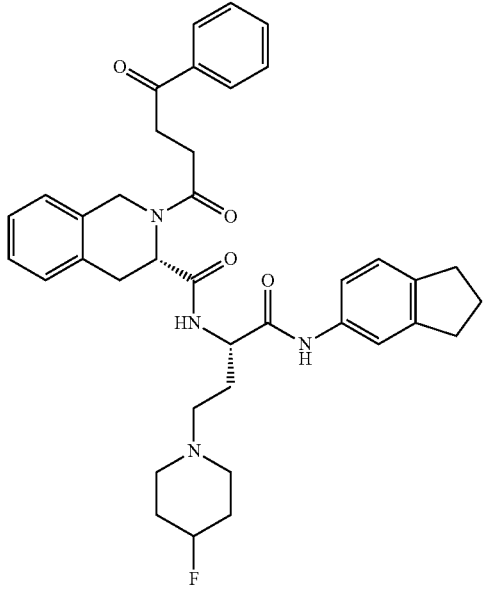

23-1

Intermediate 23E (191 mg, 0.32 mmol) was dissolved in DCM (4 mL). Diethylamine (1 mL) was added and the mixture was stirred for 2.5 h, then concentrated under vacuum, co-evaporating with DCM/PhMe (X2) to afford 29 mg (28%) of the crude Intermediate 23F as a clear, orange oil. LCMS [m/z] calculated for $C_{18}H_{26}FN_3O$: 319.2; found 320.1 [M+H]$^+$, $t_R$=0.45 min (Method 4).

Step 23G: Synthesis of N-(1-((2,3-dihydro-1H-inden-5-yl)amino)-4-(4-fluoropiperidin-1-yl)-1-oxobutan-2-yl)-2-(4-oxo-4-phenylbutanoyl)-1,2,3,4-tetrahydroisoquinoline-3-carboxamide (Compound 23-1)

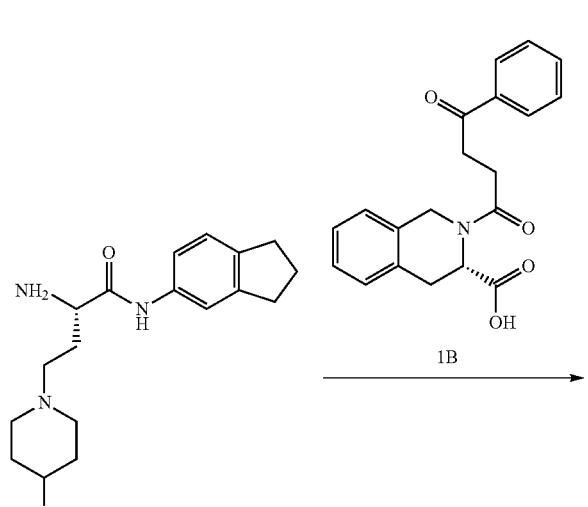

23F    1B

To a vial were combined Intermediate 1B (35.7 mg, 0.11 mmol) and Intermediate 23F (29 mg, 0.09 mmol) in DCM (0.9 mL). The mixture was cooled to 0° C., followed by the addition of DIEA (0.08 mL, 0.44 mmol). After stirring at 0° C. for 10 min, HATU (67.1 mg, 0.18 mmol) was added and the reaction was stirred at 0° C. under an atmosphere of $N_2$. After stirring for 1.5 h, the reaction mixture was diluted with DCM (10 mL) and sat. aq. $NH_4Cl$ (10 mL). The layers were partitioned and the aqueous phase was further extracted with DCM (5 mL). The combined organic extracts were filtered through a phase sep cartridge and the solvent was removed in vacuo. The crude material was purified by column chromatography (MeOH (0.7 M $NH_3$) in DCM) to afford 5 mg (9%) of Compound 23-1 as a mixture of diastereomers. LCMS [m/z] calculated for $C_{38}H_{43}FN_4O_4$: 638.3; found 639.1 [M+H]$^+$, $t_R$=4.79 min (Method 4).

Following the procedures as set forth in Scheme 23 above, the compounds of the following Table 23 were prepared using the appropriate R$^1$, R$^{3a}$ and R$^{3b}$ reagents.

TABLE 23

| Cmpd. # | R[1] | R[3a] | R[3b] | R[3a]/R[3b] Stereo-chemistry | MS Calc | MS (MH)+ | LCMS Retention Time (min) | Purity Method |
|---|---|---|---|---|---|---|---|---|
| 23-1 | indanyl | H | 4-fluoropiperidinyl-ethyl | racemic | 638.3 | 639.1 | 4.79 | 5 |
| 23-2 | 2-fluoro-3,4-dichlorophenyl | H | 4,4-difluoropiperidinyl-ethyl | S | 702.2 | 702.9 | 5.16 | 5 |
| 23-3 | 2-fluoro-3,4-dichlorophenyl | H | 4-fluoropiperidinyl-ethyl | racemic | 684.2 | 685 | 4.92 | 5 |
| 23-4 | 2-fluoro-3,4-dichlorophenyl | H | 3,3-difluoropyrrolidinyl-ethyl | S | 688.2 | 690.9 | 5.43 | 5 |

TABLE 23-continued
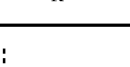
| Cmpd. # | R[1] | R[3a] | R[3b] | R[3a]/R[3b] Stereo-chemistry | MS Calc | MS (MH)+ | LCMS Retention Time (min) | Purity Method |
|---|---|---|---|---|---|---|---|---|
| 23-5 | 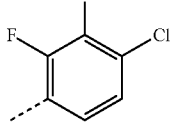 | H | 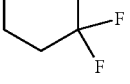 | S | 702.2 | 704.9 | 5.43 | 5 |
| 23-6 |  | H | 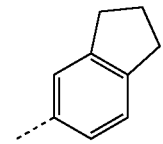 | S | 628.3 | 629.1 | 5.26 | 5 |
| 23-7 | 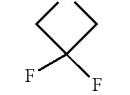 | H |  | S | 642.3 | 643.1 | 5.11 | 5 |

TABLE 23-continued
| Cmpd. # | R¹ | R³ᵃ | R³ᵇ | R³ᵃ/R³ᵇ Stereo-chemistry | MS Calc | MS (MH)⁺ | LCMS Retention Time (min) | Purity Method |
|---|---|---|---|---|---|---|---|---|
| 23-8 | | H | | S | 656.3 | 657.1 | 5.13 | 5 |
| 23-9 | | H | | S | 670.3 | 671.1 | 6.01 | 5 |
Scheme 24
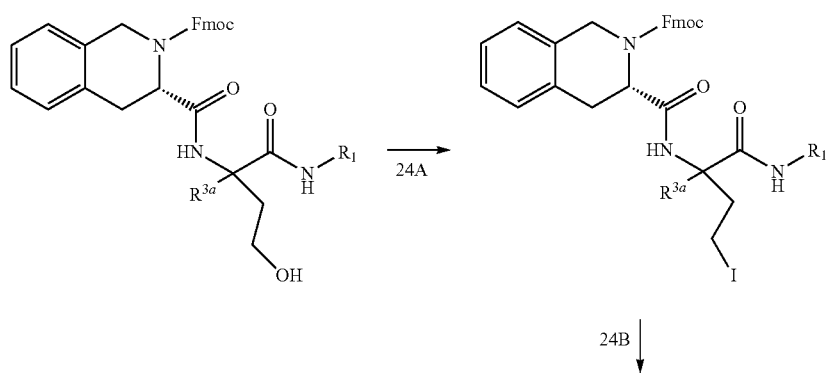

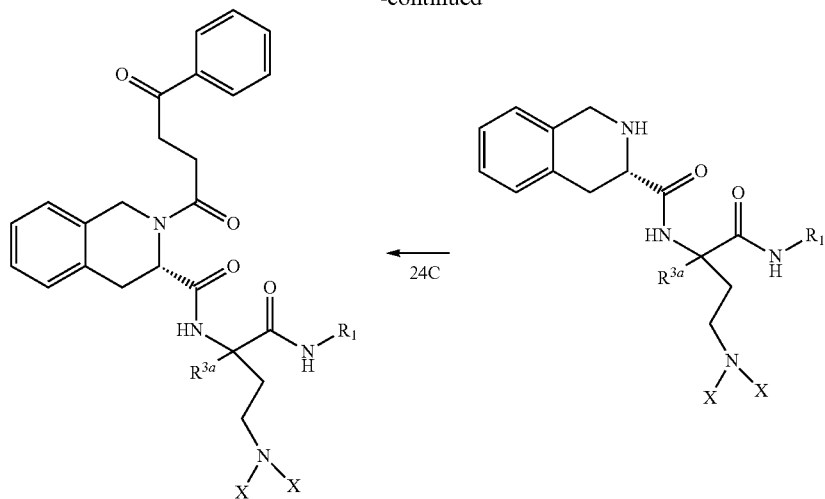

Example 24

(S)—N—((S)-1-(((4-chloro-3-methylphenyl)amino)-4-methoxypiperidin-1-yl)-1-oxobutan-2-yl)-2-(4-oxo-4-phenylbutanoyl)-1,2,3-tetrahydroisoquinoline-3-carboxamide (Compound 24-1)

Step 24A: Synthesis of (9H-fluoren-9-yl)methyl (S)-3-(((S)-1-((4-chloro-3-methylphenyl)amino)-4-iodo-1-oxobutan-2-yl)carbamoyl)-3,4-dihydroisoquinoline-2(1H)-carboxylate (Intermediate 24A)

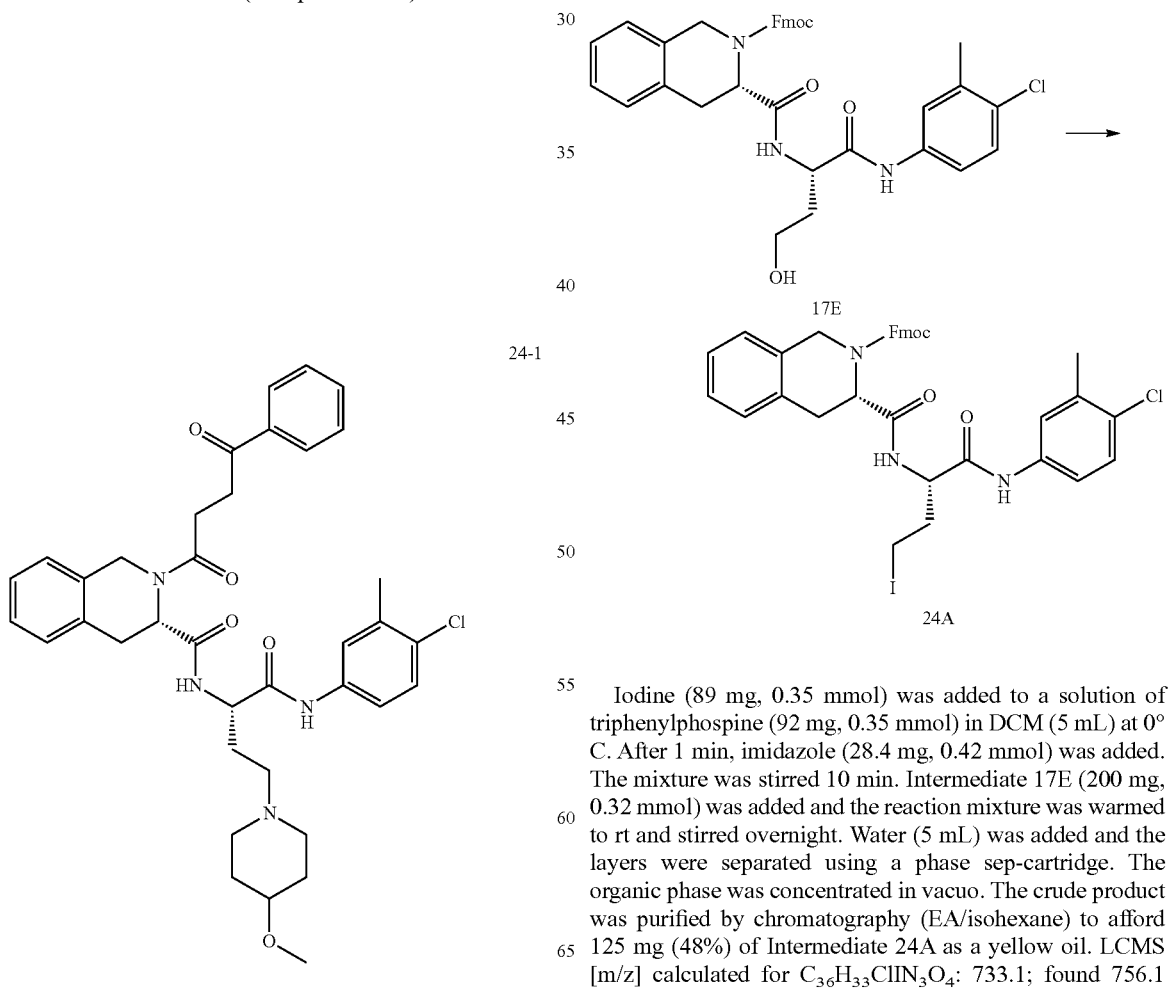

Iodine (89 mg, 0.35 mmol) was added to a solution of triphenylphospine (92 mg, 0.35 mmol) in DCM (5 mL) at 0° C. After 1 min, imidazole (28.4 mg, 0.42 mmol) was added. The mixture was stirred 10 min. Intermediate 17E (200 mg, 0.32 mmol) was added and the reaction mixture was warmed to rt and stirred overnight. Water (5 mL) was added and the layers were separated using a phase sep-cartridge. The organic phase was concentrated in vacuo. The crude product was purified by chromatography (EA/isohexane) to afford 125 mg (48%) of Intermediate 24A as a yellow oil. LCMS [m/z] calculated for $C_{36}H_{33}ClIN_3O_4$: 733.1; found 756.1 [M+Na]$^+$, $t_R$=3.14 min (Method 4).

Step 24B: Synthesis of (S)—N—((S)-1-((4-chloro-3-methylphenyl)amino)-4-(4-methoxypiperidin-1-yl)-1-oxobutan-2-yl)-1,2,3,4-tetrahydroisoquinoline-3-carboxamide (Intermediate 24B)

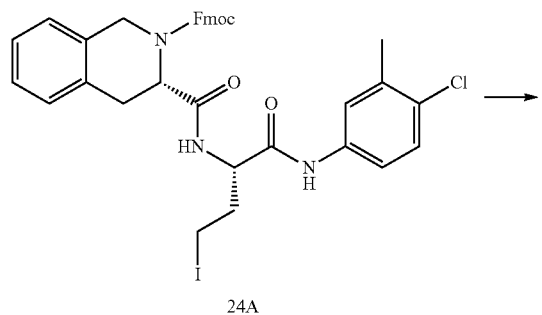

24A

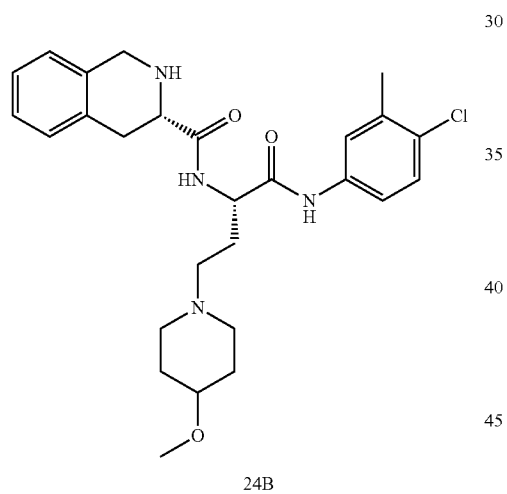

24B

To a solution of Intermediate 24A (98 mg, 0.13 mmol) in dioxane (2 mL) was added 4-methoxypiperidine (76.0 mg, 0.67 mmol). The reaction was stirred at 50° C. overnight. The reaction was diluted with NaHCO$_3$ (5 mL) and extracted with EA (2×5 mL). The combined organic extracts were dried (MgSO$_4$), filtered and concentrated in vacuo to afford 67 mg (99%) of Intermediate 24B. LCMS [m/z] calculated for C$_{27}$H$_{35}$ClN$_4$O$_3$: 498.2; found 499.3 [M+H]$^+$, t$_R$=1.17 min (Method 4).

Step 24C: Synthesis of (S)—N—((S)-1-((4-chloro-3-methyl phenyl)amino)-4-(4-methoxypiperidin-1-yl)-1-oxobutan-2-yl)-2-(4-oxo-4-phenylbutanoyl)-1,2,3,4-tetrahydroisoquinoline-3-carboxamide (Intermediate 24-1)

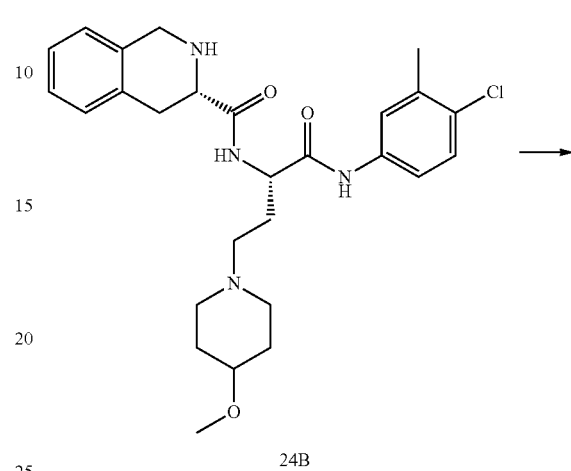

24B

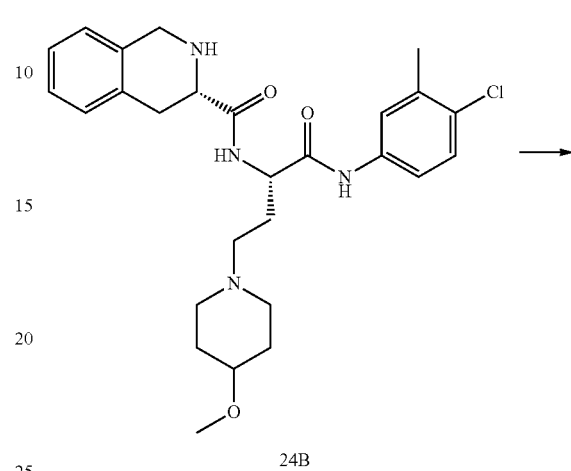

24-1

A solution of Intermediate 24B (67 mg, 0.13 mmol) and 4-oxo-4-phenylbutanoic acid (59.8 mg, 0.34 mmol) in DCM (2 mL) was treated with N-ethyl-N-isopropylpropan-2-amine (117 µl, 0.67 mmol) and HATU (153 mg, 0.40 mmol). The reaction mixture was stirred at rt for 2 h. The reaction mixture was partitioned between DCM (5 mL) and aq NH$_4$Cl solution (5 mL). The layers were separated using a phase sep-cartridge then re-extracted with DCM (5 mL). The combined organic layers were concentrated in vacuo. The crude product was purified by chromatography (0.7 M Ammonia/MeOH)/DCM) to afford 26 mg (28%) of Compound 24-1 as a white solid. LCMS [m/z] calculated for C$_{37}$H$_{43}$ClN$_4$O$_5$: 658.3; found 659.1 [M+H]$^+$, t$_R$=4.81 min (Method 5).

Following the procedures as set forth in Scheme 24 above, the compounds of the following Table 24 were prepared using the appropriate R$^1$, R$^{3a}$ and R$^{3b}$ reagents.

TABLE 24
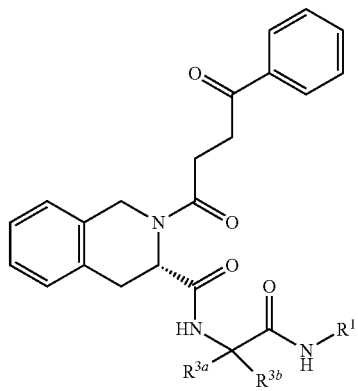
| Cmpd. # | R[1] | R[3a] | R[3b] | R[3a]/R[3b] Stereo-chemistry | MS Calc | MS (MH)+ | LCMS Retention Time (min) | Purity Method |
|---|---|---|---|---|---|---|---|---|
| 24-1 | 2-chloro-5-methylphenyl | H | 2-(4-methoxypiperidin-1-yl)ethyl | S | 658.3 | 659.1 | 4.81 | 5 |
| 24-2 | 2,3-dihydro-1H-inden-5-yl | H | 2-(4-methylpiperazin-1-yl)ethyl | S | 635.3 | 636.1 | 4.28 | 5 |

693 694
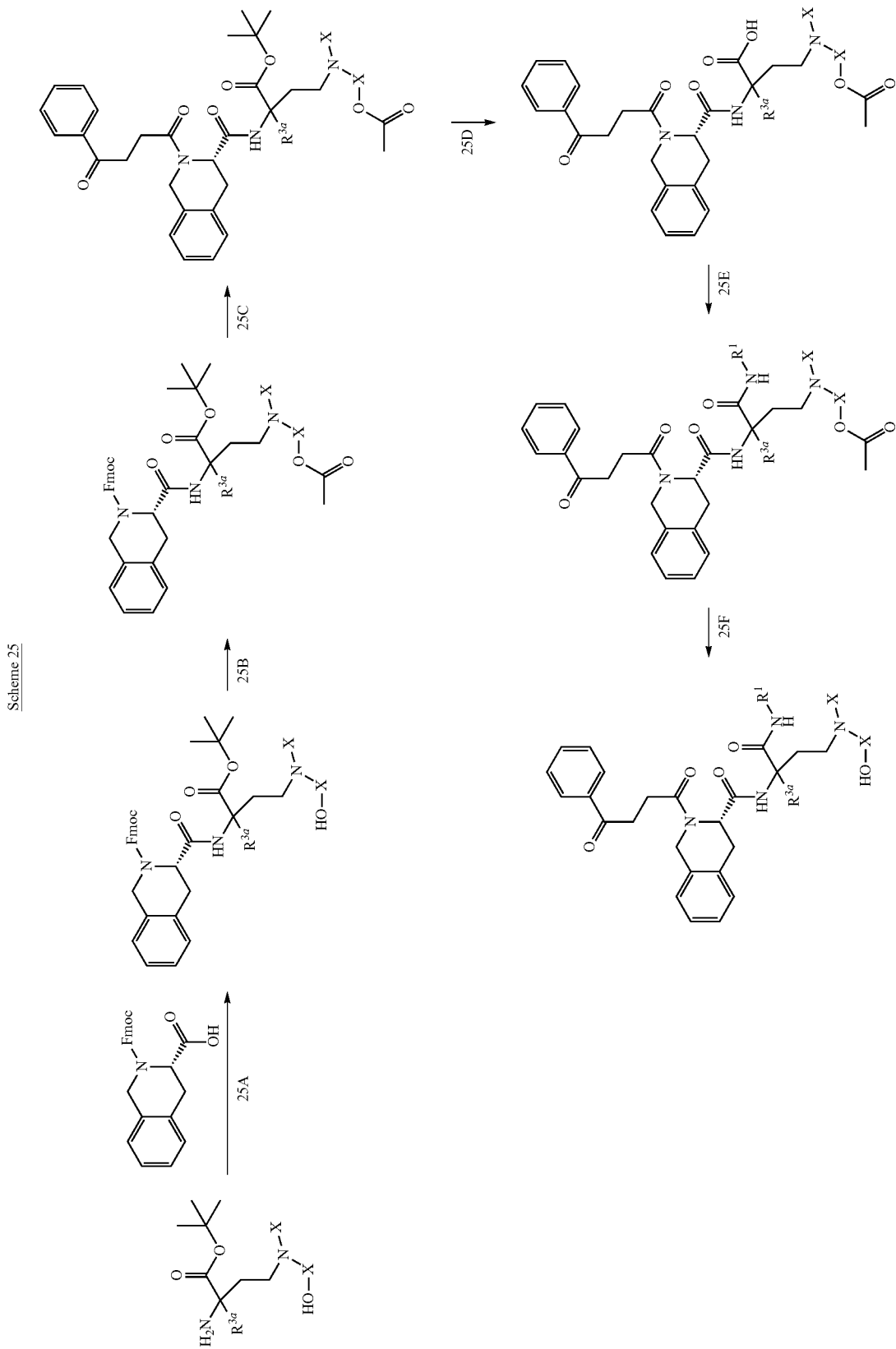
Scheme 25

Example 25

(3S)—N-(1-((2,4-dichloro-3-methylphenyl)amino)-4-(4-hydroxypiperidin-1-yl)-1-oxobutan-2-yl)-2-(4-oxo-4-phenylbutanoyl)-1,2,3,4-tetrahydroisoquinoline-3-carboxamide (Compound 25-1)

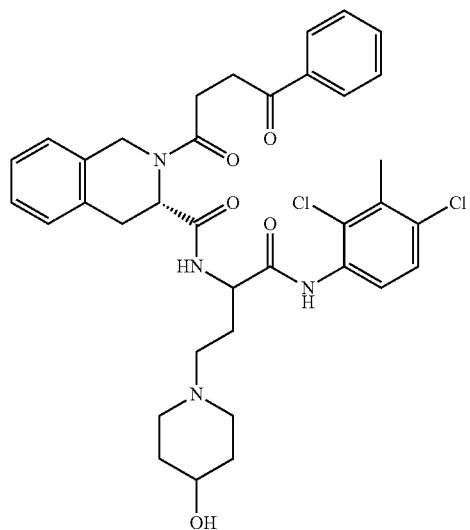

25-1

Step 25A: Synthesis of (9H-fluoren-9-yl)methyl (3S)-3-((1-(tert-butoxy)-4-(4-hydroxypiperidin-1-yl)-1-oxobutan-2-yl)carbamoyl)-3,4-dihydroisoquinoline-2(1H)-carboxylate (Intermediate 25A)

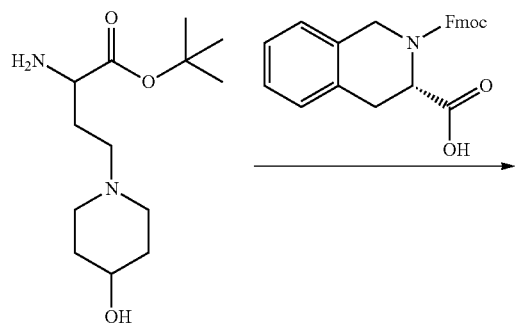

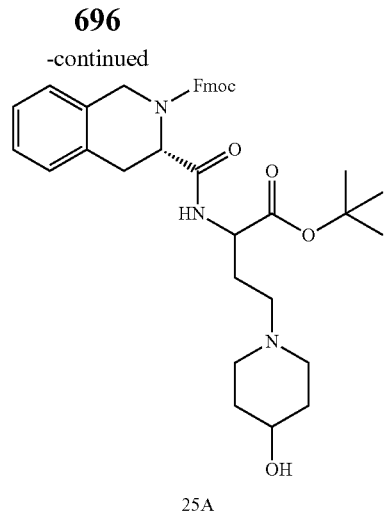

25A

Crude tert-butyl 2-amino-4-(4-hydroxypiperidin-1-yl)butanoate (1.3 g, 5.2 mmol) (per scheme 23) was dissolved in DCM (52.2 mL). Into that flask were added N-ethyl-N-isopropylpropan-2-amine (3.64 mL, 20.9 mmol) and (S)-2-(((9H-fluoren-9-yl)methoxy)carbonyl)-1,2,3,4-tetrahydroisoquinoline-3-carboxylic acid (2.5 g, 6.3 mmol) and the mixture was cooled to 0° C. HATU was added (3.97 g, 10.4 mmol) portionwise. After 3 h, additional DCM (50 mL) was added and the organic layer was washed with 2M HCl (2×100 mL), dried (MgSO$_4$) and concentrated under reduced pressure. The residue was purified by flash column chromatography (MeOH/DCM) to provide 1.45 g (40%) of Intermediate 25A as a white solid. LCMS [m/z] calculated for C$_{38}$H$_{45}$N$_3$O$_6$: 639.3; found 640.6 [M+H]$^+$, t$_R$=1.65 min (Method 4).

Step 25B: Synthesis of (9H-fluoren-9-yl)methyl (3S)-3-((4-(4-acetoxypiperidin-1-yl)-1-(tert-butoxy)-1-oxobutan-2-yl)carbamoyl)-3,4-dihydroisoquinoline-2(1H)-carboxylate (Intermediate 25B)

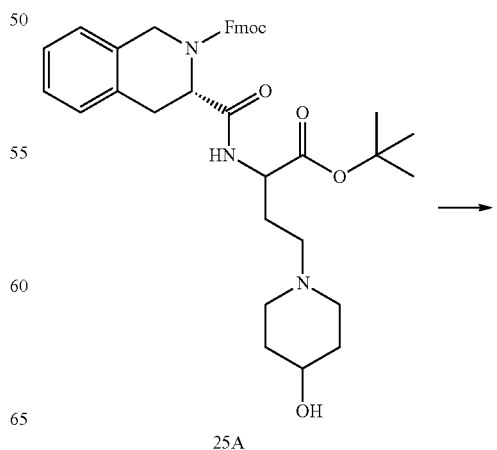

25A

697
-continued

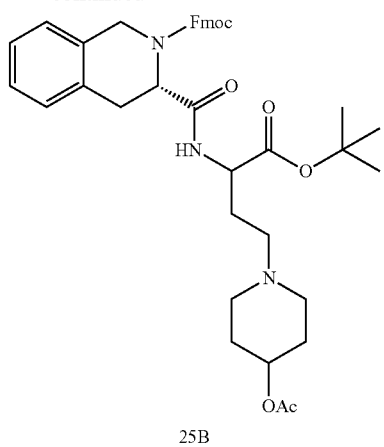
25B

698
-continued

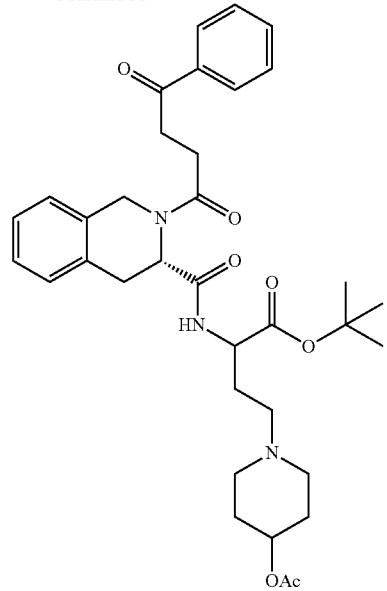
25C

Acetic anhydride (0.56 mL, 5.9 mmol) was added dropwise to a solution of Intermediate 25A (3.16 g, 4.9 mmol) and pyridine (0.64 mL, 7.9 mmol) in DCM (24.7 mL, 4.9 mmol). After 1 h, the reaction mixture was diluted with DCM (100 mL), then washed with 1M HCl (2×50 mL), dried (MgSO$_4$) then concentrated under reduced pressure. Crude intermediate 25B (3.42 g, 96% yield) was used without further purification. LCMS [m/z] calculated for $C_{40}H_{47}N_3O_7$: 681.3; found 682.6 [M+H]$^+$, $t_R$=1.89 min (Method 4).

Step 25C: Synthesis of tert-butyl 4-(4-acetoxypiperidin-1-yl)-2-((S)-2-(4-oxo-4-phenylbutanoyl)-1,2,3,4-tetrahydroisoquinoline-3-carboxamido)butanoate (Intermediate 25C)

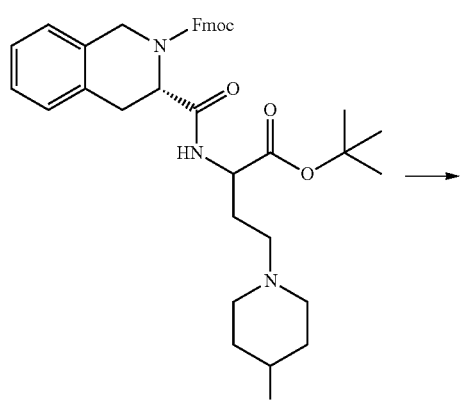
25B →

Diethylamine (15.49 mL, 148 mmol) was added to a solution of Intermediate 25B (3.37 g, 4.9 mmol) in DCM (10 mL). After 1 h, toluene (100 mL) was added and the mixture was concentrated under reduced pressure to remove excess diethylamine. The crude material was redissolved in DCM (25 mL) and DIEA (3.45 mL, 19.8 mmol) was added. The mixture was cooled to 0° C. and 4-oxo-4-phenylbutanoic acid (1.06 g, 5.9 mmol) was added, followed by HATU (3.76 g, 9.9 mmol). After stirring for 2 h at rt, additional 4-oxo-4-phenylbutanoic acid (0.5 g, 2.9 mmol) and HATU (1 g, 2.6 mmol) were added. After 6 h, the mixture was diluted with DCM (70 mL) and washed with 1M HCl (2×50 mL), dried (MgSO$_4$), then concentrated under reduced pressure.

The crude material was purified chromatography (MeOH/DCM/Hexanes) to provide 813 mg, (19%) of Intermediate 25C as a yellow oil. LCMS [m/z] calculated for $C_{35}H_{45}N_3O_7$: 619.3; found 620.1 [M+H]$^+$, $t_R$=1.6 min (Method 4).

Step 25D: Synthesis of 4-(4-acetoxypiperidin-1-yl)-2-((S)-2-(4-oxo-4-phenylbutanoyl)-1,2,3,4-tetrahydroisoquinoline-3-carboxamido)butanoic Acid (Intermediate 25D)

Step 25E: Synthesis of 1-(4-((2,4-dichloro-3-methylphenyl)amino)-4-oxo-3-((S)-2-(4-oxo-4-phenylbutanoyl)-1,2,3,4-tetrahydroisoquinoline-3-carboxamido)butyl)piperidin-4-yl acetate (Compound 25-E)

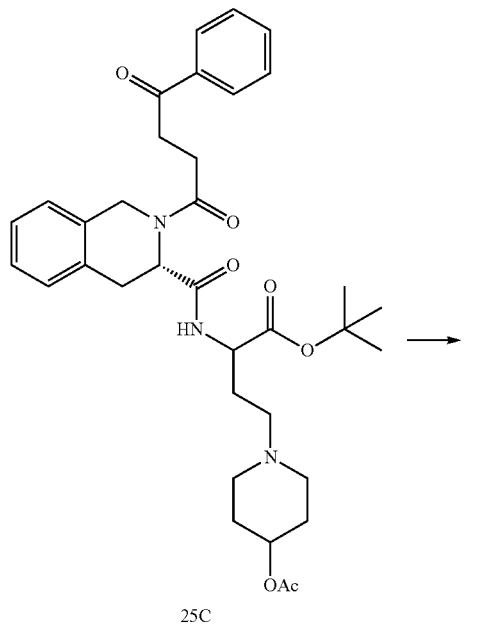

25C

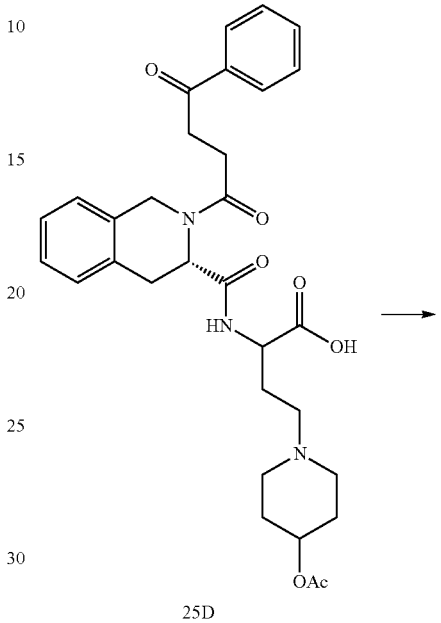

25D

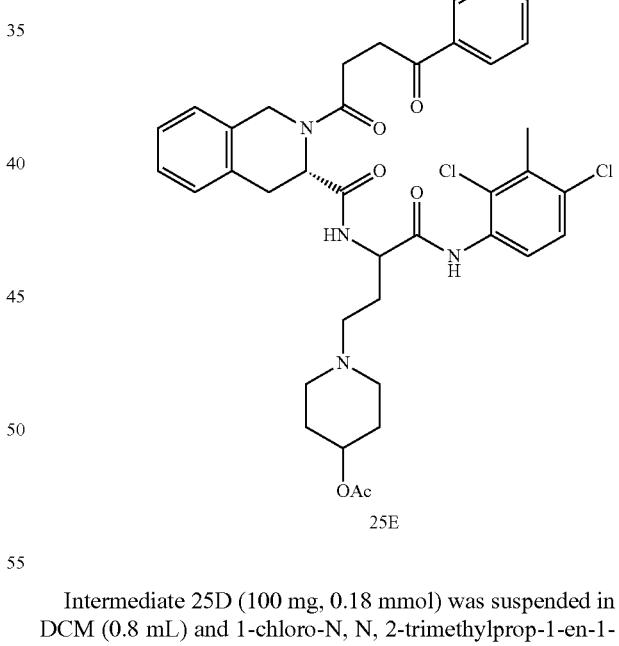

25E

25D

Intermediate 25C (800 mg, 1.291 mmol) was suspended in DCM (3 mL) and TFA (1.3 mL). After 6 h, the mixture was diluted with toluene (20 mL) and concentrated under reduced pressure to obtain 770 mg (85%) of Intermediate 25D as a pale yellow solid. LCMS [m/z] calculated for $C_{31}H_{37}N_3O_7$: 563.3; found 564.4 [M+H]$^+$, $t_R$=0.98 min (Method 4).

Intermediate 25D (100 mg, 0.18 mmol) was suspended in DCM (0.8 mL) and 1-chloro-N, N, 2-trimethylprop-1-en-1-amine (47.4 mg, 0.355 mmol) in DCM (0.7 mL) was added dropwise After 20 min, 2,4-dichloro-3-methylaniline (46.8 mg, 0.27 mmol) in pyridine (0.5 mL, 0.177 mmol) was added dropwise. After 2 days, the mixture was diluted with DCM (4 mL), washed with 1 M HCl (3×3 mL), dried (MgSO$_4$) and concentrated under reduced pressure to provide 153 mg (36%) of Intermediate 25E. LCMS [m/z] calculated for $C_{38}H_{42}Cl_2N_4O_6$: 720.3; found 720.3 [M]$^+$, $t_R$=1.7 min (Method 4).

Step 25F: Synthesis of (3S)—N-(1-((2,4-dichloro-3-methylphenyl)amino)-4-(4-hydroxypiperidin-1-yl)-1-oxobutan-2-yl)-2-(4-oxo-4-phenylbutanoyl)-1,2,3,4-tetrahydroisoquinoline-3-carboxamide (Compound 25-1)

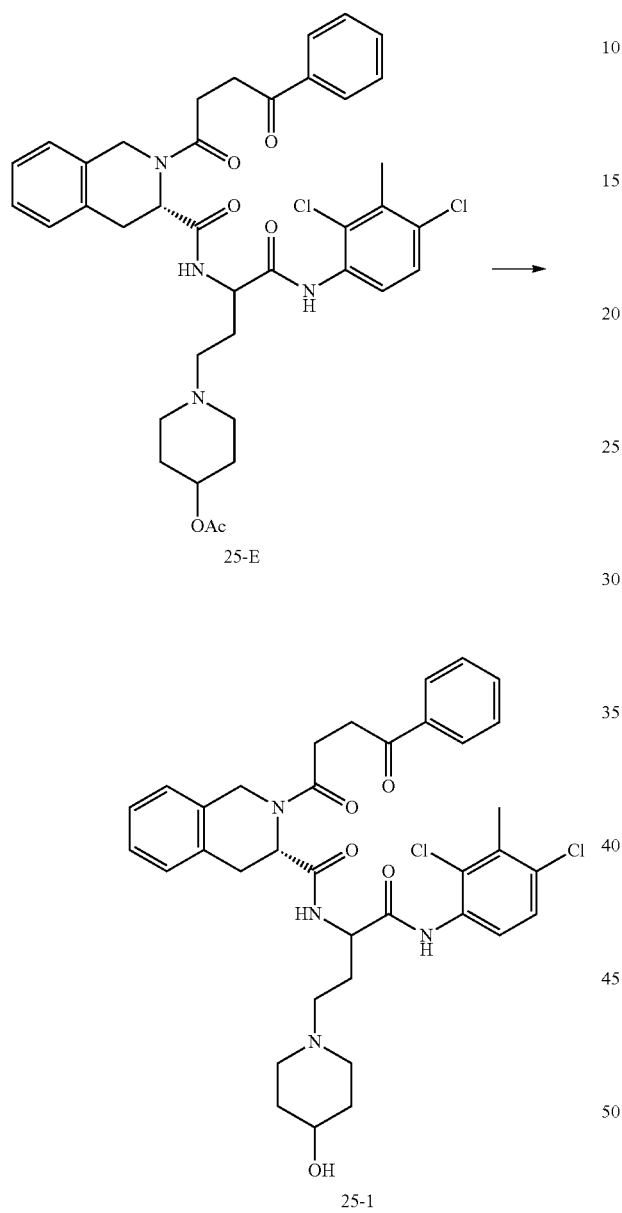

Intermediate 25E (153.3 mg, 0.212 mmol) was dissolved in MeOH (8 mL). Potassium carbonate (117 mg, 0.85 mmol) was added. After 3 h, the mixture was diluted with DCM (4 mL), washed with brine (3×4 mL), dried (MgSO$_4$) then concentrated under reduced pressure. The crude material was purified by chromatography (MeOH/DCM/0.7M NH$_3$) to obtain 18 mg (12%) of Compound 25-1. LCMS [m/z] calculated for C$_{36}$H$_{40}$Cl$_2$N$_4$O$_5$: 678.2; found 679.0 [M+H]$^+$, t$_R$=4.49 min (Method 5).

Following the procedures as set forth in Scheme 25 above, the compounds of the following Table 25 were prepared using the appropriate R$^1$, R$^{3a}$ and R$^{3b}$ reagents.

TABLE 25

| Cmpd. # | R¹ | R³ᵃ | R³ᵇ | R³ᵃ/R³ᵇ Stereo-chemistry | MS Calc | MS (MH)⁺ | LCMS Retention Time (min) | Purity Method |
|---|---|---|---|---|---|---|---|---|
| 25-1 | 2,6-dichloro-3-methylphenyl | H | 4-hydroxypiperidin-1-yl-ethyl | racemic | 678.2 | 679 | 4.49 | 5 |
| 25-2 | 4-fluoro-2-chloro-5-methylphenyl | H | 4-hydroxypiperidin-1-yl-ethyl | racemic | 662.3 | 663 | 4.18 | 5 |
| 25-3 | 2-chloro-3-methylphenyl | H | 4-hydroxypiperidin-1-yl-ethyl | racemic | 644.3 | 645.1 | 3.88 | 5 |

705 706
Scheme 26
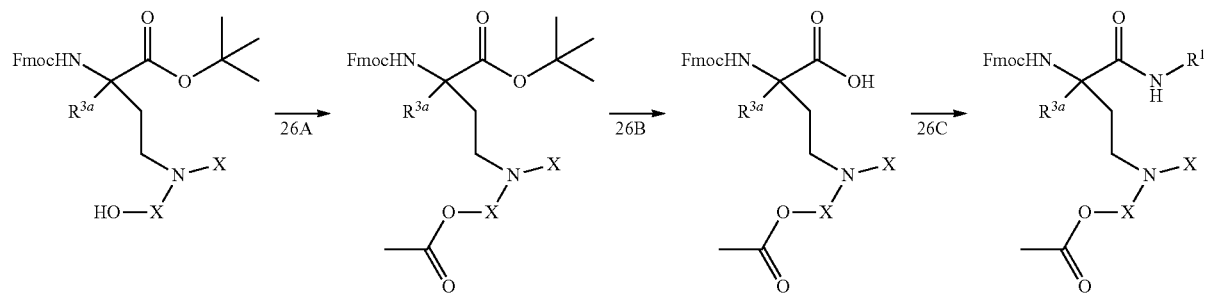
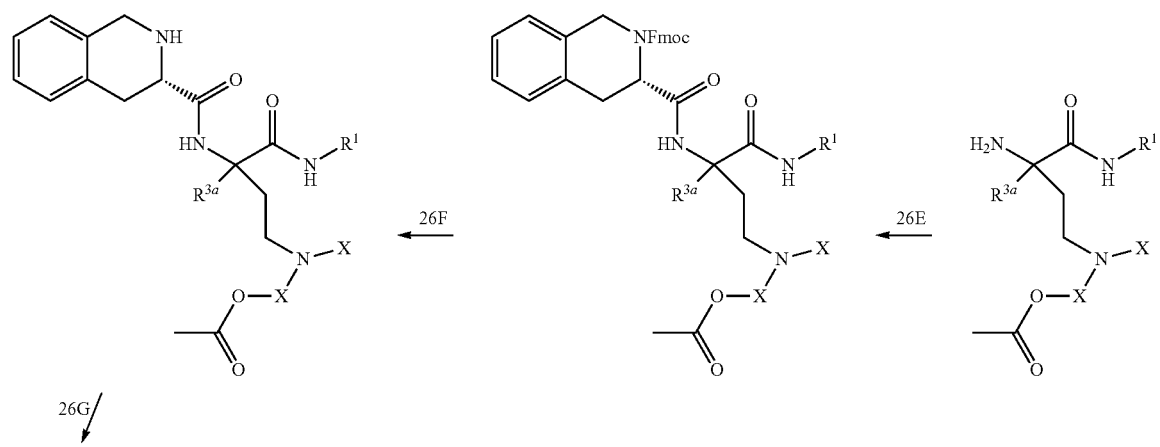
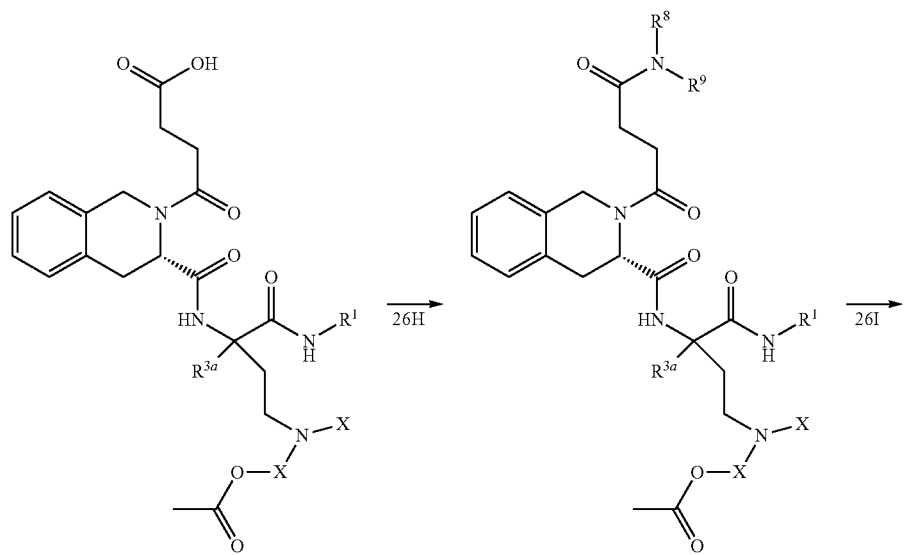

-continued

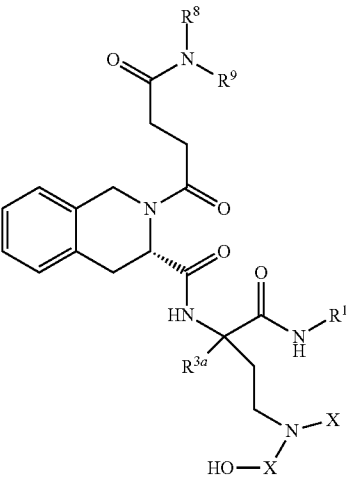

Example 26

(S)—N—((S)-1-((3,4-dichloro-2-fluorophenyl)amino)-4-(4-hydroxypiperidin-1-yl)-1-oxobutan-2-yl)-2-(4-(2,2-dimethylpiperidin-1-yl)-4-oxobutanoyl)-1,2,3,4-tetrahydroisoquinoline-3-carboxamide (Compound 26-1)

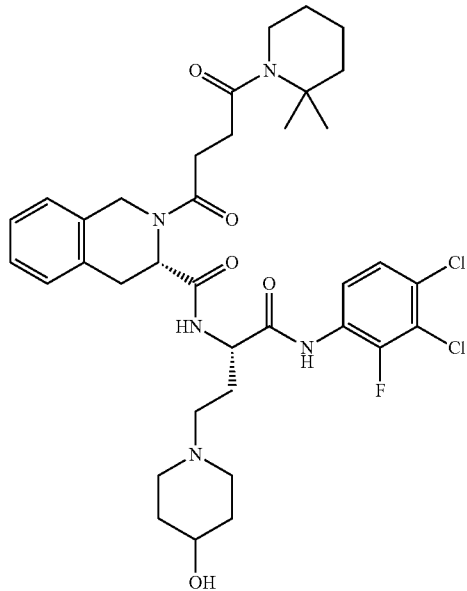

26-1

Step 26A: Synthesis of tert-butyl (S)-2-((((9H-fluoren-9-yl)methoxy)carbonyl)amino)-4-(4-acetoxypiperidin-1-yl)butanoate (Intermediate 26A)

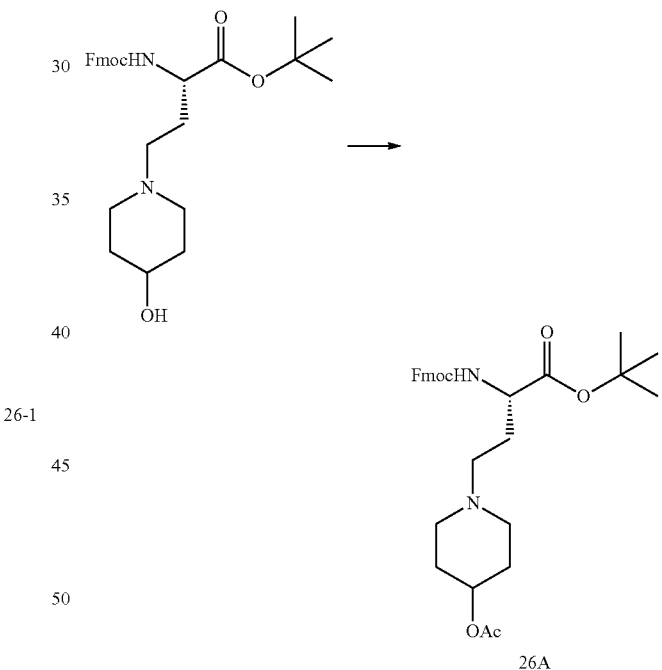

26A

To a round bottom flask containing tert-butyl (S)-2-((((9H-fluoren-9-yl)methoxy)carbonyl)amino)-4-(4-hydroxypiperidin-1-yl)butanoate (prepared via Scheme 23, 4.95 g, 10.3 mmol) was added DCM (51.5 mL)) and pyridine (1.3 mL, 16.5 mmol). Acetic anhydride (1.17 mL, 12.4 mmol) was then added to the reaction mixture dropwise and the reaction was allowed to stir at rt overnight, under an atmosphere of $N_2$. Additional portions of pyridine (1.3 mL, 16.5 mmol) and acetic anhydride (1.17 mL, 12.4 mmol) were added. After 3 h, DMAP (0.13 g, 1.03 mmol) was added and, after stirring for 2 h, the reaction mixture was then diluted with DCM (70 mL) and transferred to a separating funnel and washed with 1 M aqueous HCl (2×70 mL).

The organic phase was then dried (Mg$_2$SO$_4$) and the solvent was removed in vacuo to afford 5.64 g, (94%) of Intermediate 26A as a thick yellow oil. LCMS [m/z] calculated for C$_{30}$H$_{38}$N$_2$O$_6$: 522.3; found 523.2 [M+H]$^+$, t$_R$=1.81 min (Method 4).

Step 26B: Synthesis of (S)-2-((((9H-fluoren-9-yl)methoxy)carbonyl)amino)-4-(4-acetoxypiperidin-1-yl)butanoic Acid (Intermediate 26B)

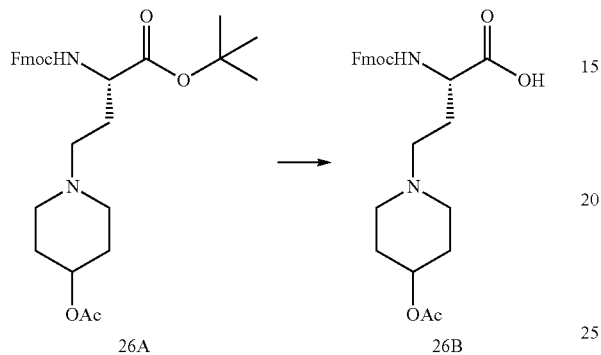

To a round bottom flask containing Intermediate 26B (5.64 g, 10.8 mmol) in DCM (32.2 mL) was added TFA (21.5 mL, 280 mmol). The reaction was stirred under an atmosphere of N$_2$. After stirring for 3.5 h, the solvent was removed under vacuum and the resulting material was coevaporated with toluene/DCM (×3) and EA (×1). The crude material was then slurried with iso-hexane to afford a pale yellow solid which was collected by filtration, and dried in the vacuum oven at 40° C. for 2 h. The material was re-suspended in DCM/toluene and concentrated under vacuum to afford a thick yellow oil. The material was then dissolved in minimum DCM and iso-hexane (approx. 100 mL) was added to aid precipitation and the pale yellow solid was collected by filtration and dried in a vacuum oven at 40° C. to afford 1.91 g (32%) of Intermediate 26B. LCMS [m/z] calculated for C$_{26}$H$_{30}$N$_2$O$_6$: 466.2; found 467.2 [M+H]$^+$, t$_R$=1.60 min (Method 4).

Step 26C: Synthesis of (S)-1-(3-((((9H-fluoren-9-yl)methoxy)carbonyl)amino)-4-((3,4-dichloro-2-fluorophenyl)amino)-4-oxobutyl)piperidin-4-yl acetate (Intermediate 26C)

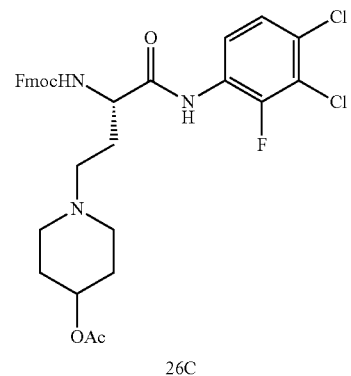

To an oven dried round bottom flask was combined Intermediate 26B (16.4 mL, 4.1 mmol). 1-chloro-N,N,2-trimethylprop-1-en-1-amine (1.083 mL, 8.19 mmol) was added to the reaction mixture, which was stirred for 10 min under an atmosphere of N$_2$. 3,4-dichloro-2-fluoroaniline (1.47 g, 8.2 mmol) was then added to the reaction mixture as a solution in pyridine (1.61 ml, 20 mmol). Upon complete addition the reaction mixture was stirred under an atmosphere of N$_2$ for 2 h, then was diluted with DCM (70 mL) and transferred to a separating funnel where it was washed with 1 M HCl (aq.). The organic phase was dried (Mg$_2$SO$_4$) and the solvent was removed in vacuo to afford the crude product as a yellow oil. The material was purified by column chromatography (MeOH (w/0.7 M NH$_3$)/DCM), to afford 1.36 g (51%) of Intermediate 26C. LCMS t$_R$=1.59 min (Method 4).

Step 26D: Synthesis of (S)-1-(3-amino-4-((3,4-dichloro-2-fluorophenyl)amino)-4-oxobutyl)piperidin-4-yl acetate (Intermediate 26D)

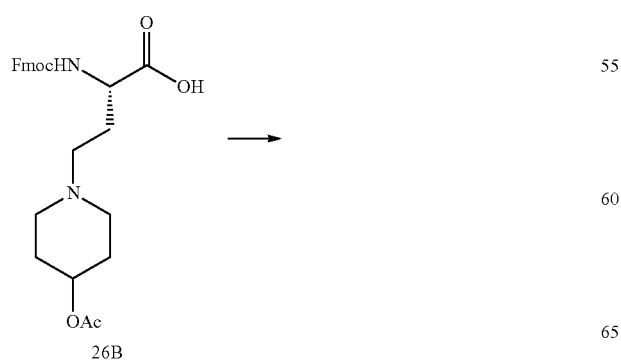

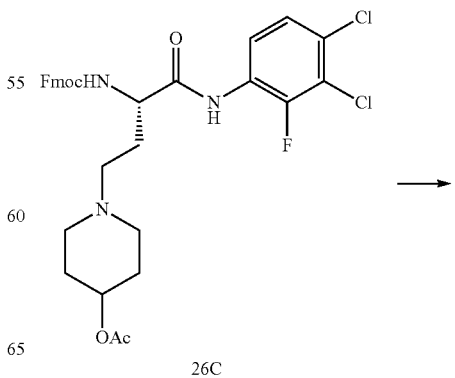

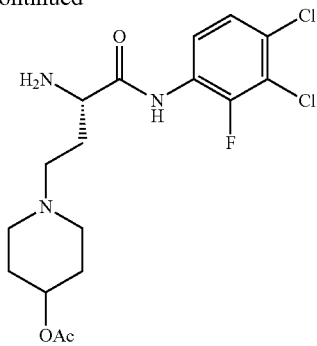

26D

Into a flask was added Intermediate 26C (1.36 g, 2.16 mmol) and DCM (10 mL). Diethylamine (2 mL, 19.1 mmol) was added and the reaction mixture was stirred for 4 h, concentrated in vacuo (co-evaporating with DCM/toluene) to afford the crude product. The material was used directly in the next step without further purification nor analysis, assuming 100% yield and 100% purity. LCMS $t_R$=1.59 min (Method 4).

Step 26E: Synthesis of (9H-fluoren-9-yl)methyl (S)-3-(((S)-4-(4-acetoxypiperidin-1-yl)-1-(3,4-dichloro-2-fluorophenyl)amino)-1-oxobutan-2-yl)carbamoyl)-3,4-dihydroisoquinoline-2(1H)-carboxylate (Intermediate 26E)

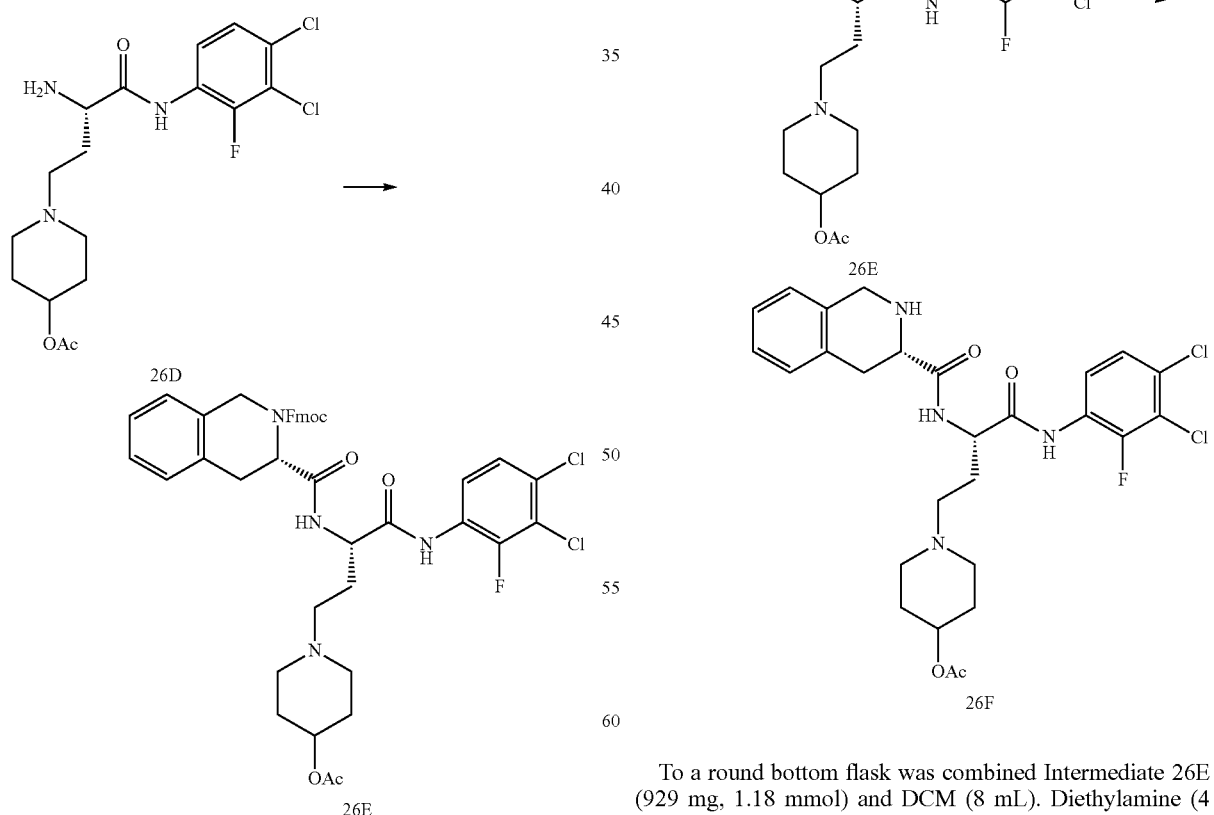

To a round bottom flask was combined Intermediate 26D (879 mg, 2.16 mmol) and DCM (21.6 mL). DIEA (1.13 mL, 6.5 mmol) was added to the mixture and the reaction was cooled to 0° C. using an ice/water bath. HATU (1232 mg, 3.24 mmol) was added portionwise. Upon complete addition, the reaction was stirred at 0° C. for 5 minutes before warming to rt and stirring under an atmosphere of $N_2$. After 1 h of stirring at rt, the reaction mixture was diluted with DCM (50 mL) and 1M HCl (aq.) (50 mL) and the mixture was transferred to a separating funnel. The layers were partitioned and the aqueous layer was further extracted with DCM (50 mL). The combined organics were then washed with a saturated aqueous solutions of $NaHCO_3$ (50 mL) and brine (50 mL) and dried ($MgSO_4$) and the solvent was removed in vacuo to afford the crude product as a thick clear yellow oil. The crude material was purified by column chromatography (MeOH (0.7M $NH_3$)/DCM), to provide 929 mg (48%) of Intermediate 26E. LCMS [m/z] calculated for $C_{42}H_{41}Cl_2FN_4O_6$: 786.2; found 787.2 [M+H]$^+$, $t_R$=2.24 min (Method 4).

Step 26F: Synthesis of 1-((S)-4-(3,4-dichloro-2-fluorophenyl)amino)-4-oxo-3-((S)-1,2,3,4-tetrahydroisoquinoline-3-carboxamido)butyl)piperidin-4-yl acetate (Intermediate 26F)

To a round bottom flask was combined Intermediate 26E (929 mg, 1.18 mmol) and DCM (8 mL). Diethylamine (4 mL, 38.3 mmol) was added and the reaction mixture was stirred at rt under an atmosphere of $N_2$ overnight. The reaction mixture was concentrated under reduced pressure (co-evaporating with DCM/toluene) to afford the crude product as a thick orange oil. The crude material was purified by column chromatography (MeOH (0.7 M NH₃)/DCM) to afford 417 mg (62%) Intermediate 26F as a sticky off-white solid. LCMS [m/z] calculated for $C_{27}H_{31}Cl_2FN_4O_4$: 564.2; found 565.2 [M+H]⁺, $t_R$=2.5 min (Method 4).

Step 26G: Synthesis of 4-((S)-3-(((S)-4-(4-acetoxypiperidin-1-yl)-1-((3,4-dichloro-2-fluorophenyl)amino)-1-oxobutan-2-yl)carbamoyl)-3,4-dihydroisoquinolin-2(1H)-yl)-4-oxobutanoic Acid (Intermediate 26G)

Step 26H: Synthesis of 1-((S)-4-((3,4-dichloro-2-fluorophenyl)amino)-3-((S)-2-(4-(2,2-dimethylpiperidin-1-yl)-4-oxobutanoyl)-1,2,3,4-tetrahydroisoquinoline-3-carboxamido)-4-oxobutyl)piperidin-4-yl acetate (Intermediate 26H)

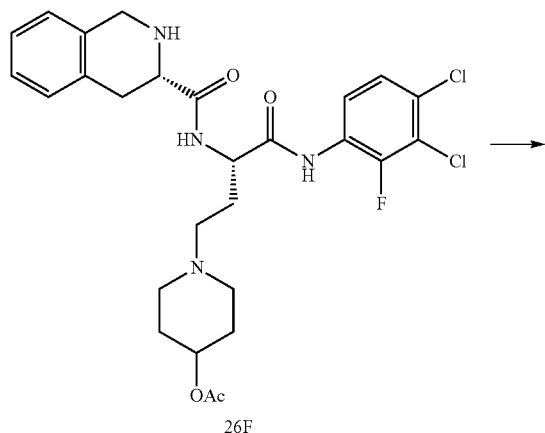

26F

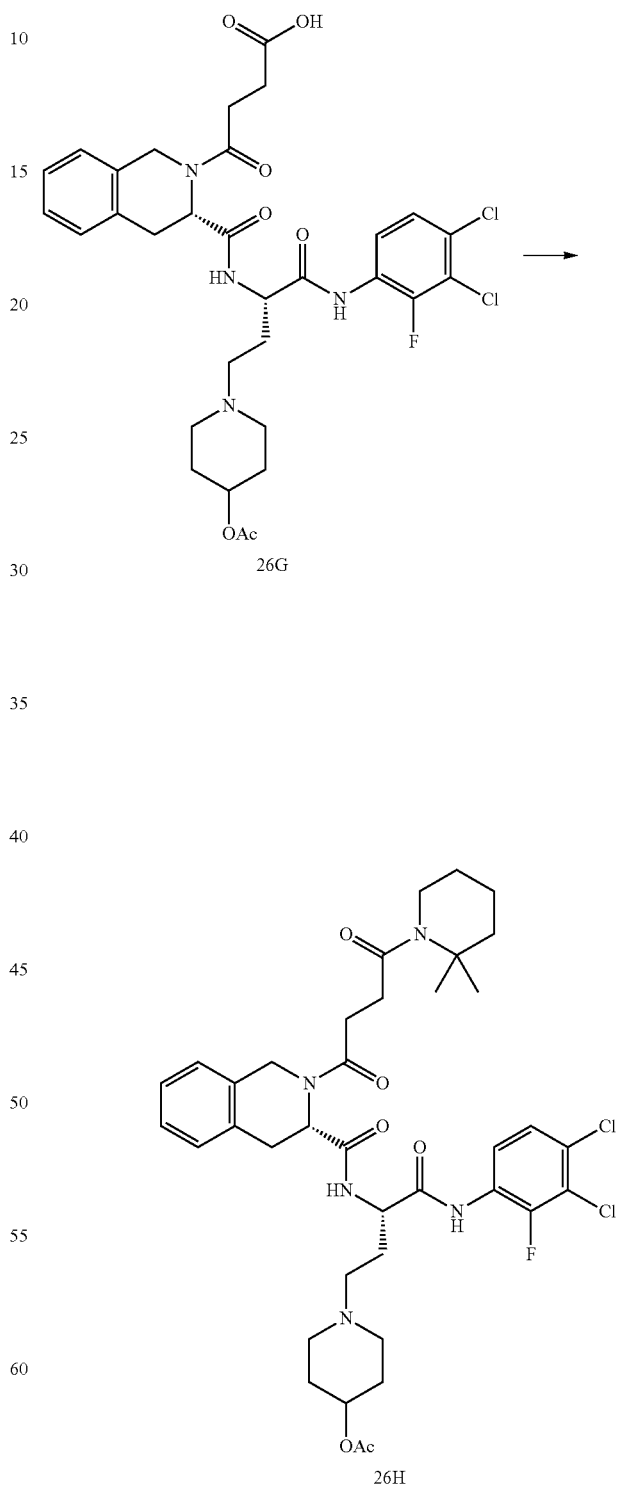

Into a round bottom flask were combined Intermediate 26F (417 mg, 0.74 mmol), DCM (9.8 mL) and THF (1 mL). Dihydrofuran-2,5-dione (77 mg, 0.77 mmol) was added. After stirring at rt overnight, under N₂, the reaction was concentrated in vacuo, and used directly without further purification. LCMS [m/z] calculated for $C_{31}H_{35}Cl_2FN_4O_7$: 664.2; found 665.2 [M+H]⁺, $t_R$=1.59 min (Method 4).

Into a vial were combined 2,2-dimethylpiperidine (22.12 mg, 0.195 mmol) and Intermediate 26A (100 mg, 0.15 mmol) in DCM (1.5 mL). DIPEA (0.079 mL, 0.45 mmol) was added and the mixture was cooled to 0° C. HATU (86 mg, 0.23 mmol) was then added and the reaction mixture was stirred at 0° C. for 10 min, then warmed to rt. After stirring at rt for 1.5 h, the mixture was diluted with DCM (10 mL) and 1 M HCl (aq.) (10 mL) and the mixture was transferred to a separating funnel. The layers were partitioned and the aqueous layer was further extracted with DCM (10 mL). The combined organics were then washed with a saturated aqueous solution of NaHCO$_3$ (10 mL), brine (10 mL) and dried (MgSO$_4$) and the solvent was removed in vacuo to afford 114 mg (100%) of Intermediate 26H as an orange oil.

Step 26I: Synthesis of (S)—N—((S)-1-((3,4-dichloro-2-fluorophenyl)amino)-4-(4-hydroxypiperidin-1-yl)-1-oxobutan-2-yl)-2-(4-(2,2-dimethylpiperidin-1-yl)-4-oxobutanoyl)-1,2,3,4-tetrahydroisoquinoline-3-carboxamide (Compound 26-1)

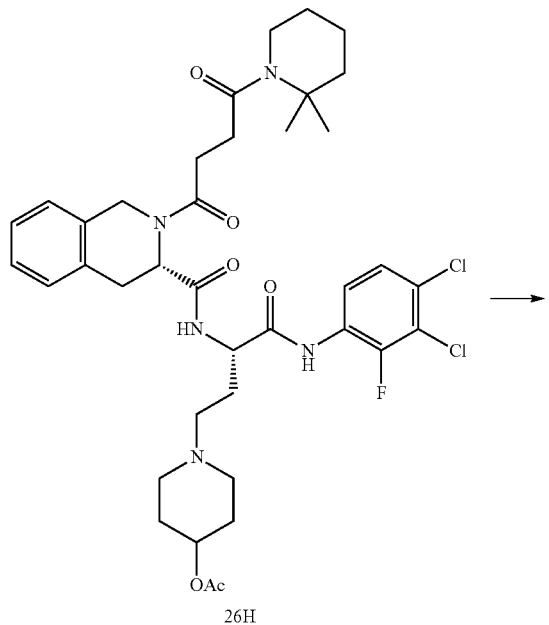

26H

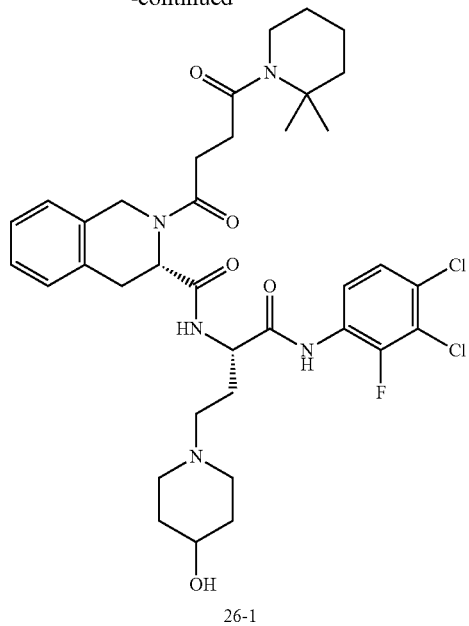

26-1

Into a round bottom flask were added Intermediate 26H (114 mg, 0.15 mmol) and MeOH (1.5 mL) and K$_2$CO$_3$ (83 mg, 0.6 mmol) under an atmosphere of N$_2$. After stirring at rt for 2 h, the mixture was concentrated, followed by dissolving in DCM (20 mL) and brine (10 mL). The mixture was transferred to a separating funnel and the layers were partitioned. The organic phase was further washed with brine (10 mL), dried (MgSO$_4$) and the solvent was removed in vacuo to afford the crude material as a clear orange oil. The crude material was purified by chromatography (MeOH (0.7 M NH$_3$) in DCM), to afford 21.5 mg (19%) of Compound 26-1. (LCMS [m/z] calculated for C$_{36}$H$_{46}$Cl$_2$FN$_5$O$_5$: 717.3; found 718.1 [M+H]$^+$, t$_R$=4.72 min (Method 5).

Following the procedures as set forth in Scheme 26 above, the compounds of the following Table 26 were prepared using the appropriate R$^1$, R$^{3a}$ and R$^{3b}$ reagents.

TABLE 26
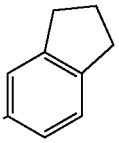
| Cmpd. # | R³ᵃ | R³ᵇ | R³ᵃ/R³ᵇ Stereo-chemistry | 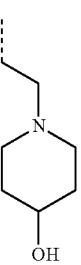 | MS Calc | MS (MH)⁺ | LCMS Retention Time (min) | Purity Method |
|---|---|---|---|---|---|---|---|---|
| 26-1 | H | 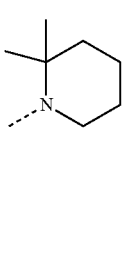 | S | 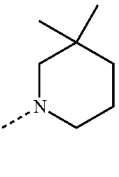 | 717.3 | 718.1 | 4.72 | 5 |
| 26-2 | H | 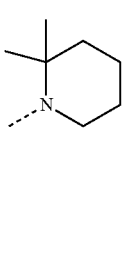 | R | 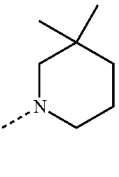 | 717.3 | 718.1 | 4.98 | 5 |
| 26-3 | H | 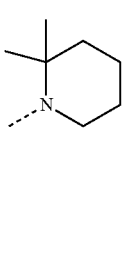 | S | 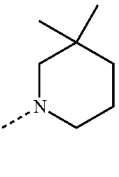 | 717.3 | 718.1 | 4.69 | 5 |

719
Scheme 27
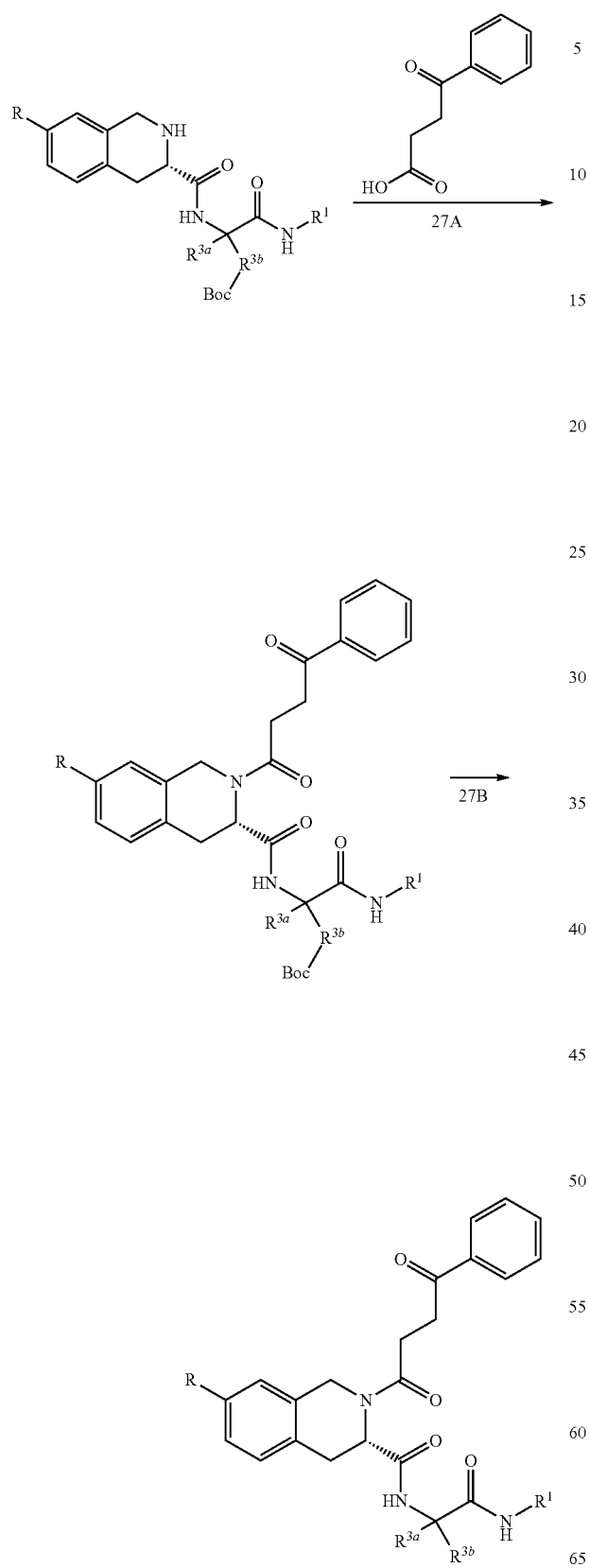
720
Example 27
(S)—N—((S)-4-amino-1-((4-chloro-5-methylpyridin-2-yl)amino)-1-oxobutan-2-yl)-2-(4-oxo-4-phenylbutanoyl)-1,2,3,4-tetrahydroisoquinoline-3-carboxamide (Compound 27-1)
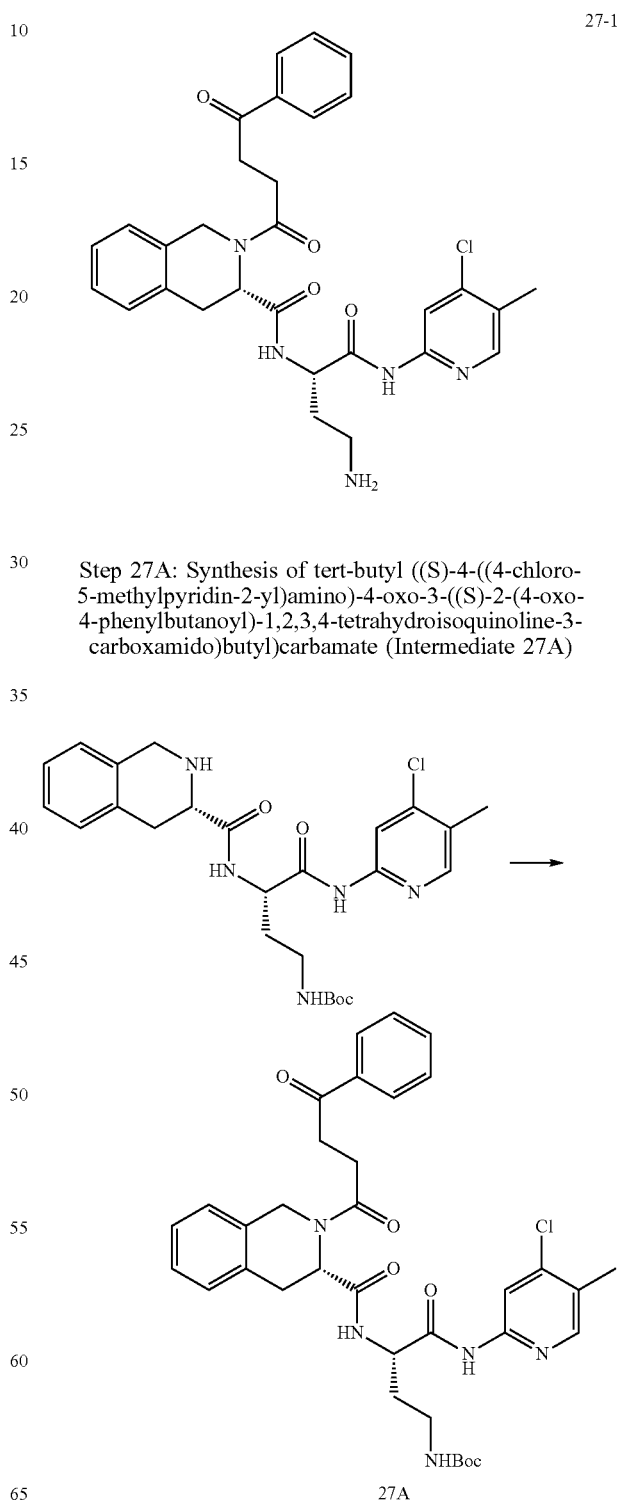
Step 27A: Synthesis of tert-butyl ((S)-4-((4-chloro-5-methylpyridin-2-yl)amino)-4-oxo-3-((S)-2-(4-oxo-4-phenylbutanoyl)-1,2,3,4-tetrahydroisoquinoline-3-carboxamido)butyl)carbamate (Intermediate 27A)

tert-butyl ((S)-4-((4-chloro-5-methylpyridin-2-yl)amino)-4-oxo-3 tetrahydroisoquinoline-3-carboxamido)butyl)carbamate (made per Scheme 10, 60 mg, 0.12 mmol) and 4-oxo-4-phenylbutanoic acid (42.6 mg, 0.24 mmol) were dissolved in DCM (3 mL). DIEA (0.1 mL, 0.6 mmol) was added. After 10 min, HATU (136 mg, 0.36 mmol) was added. After 1 h, the reaction mixture was partitioned between DCM (5 mL) and sat aqueous solution of NaHCO$_3$ (5 mL). The layers were separated using a phase sep-cartridge and the aqueous layer was re-extracted with DCM (5 mL). The combined organic phases were concentrated in vacuo. The crude material was purified by chromatography (MeOH/DCM) 80 mg, (99%) of Intermediate 27A as a white solid. LCMS [m/z] calculated for $C_{35}H_{40}ClN_5O_6$: 661.3; found 662.1 [M+H]$^+$, $t_R$=2.57 min (Method 4).

Step 27B: Synthesis of (S)—N—((S)-4-amino-1-((4-chloro-5-methylpyridin-2-yl)amino)-1-oxobutan-2-yl)-2-(4-oxo-4-phenylbutanoyl)-1,2,3,4-tetrahydroisoquinoline-3-carboxamide (Compound 27-1)

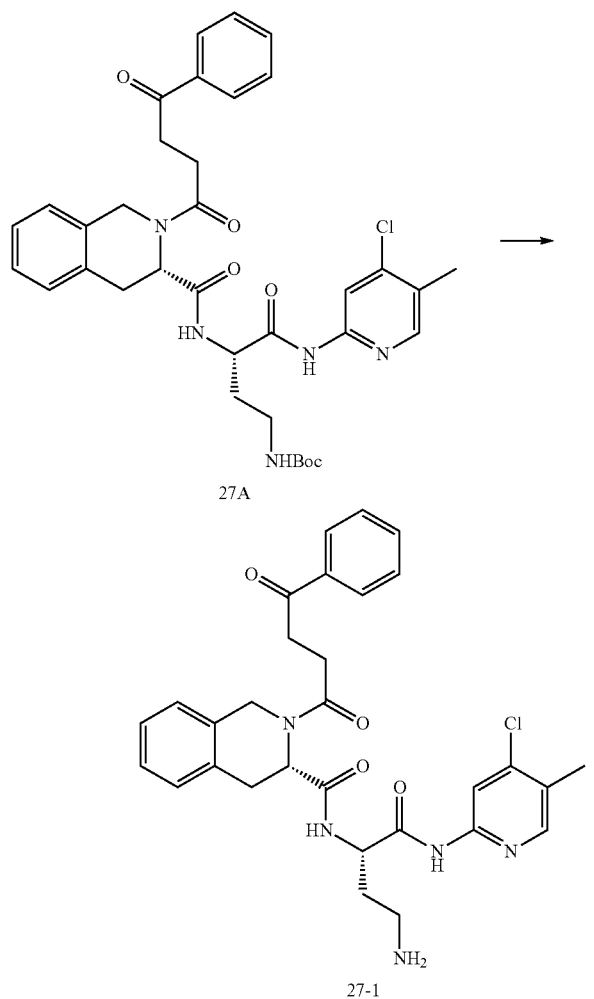

27A 27-1

Into a solution of Intermediate 27A (80 mg, 0.12 mmol) in DCM (5 mL) was added TFA (1 mL). After 30 min, the solvent was evaporated and the crude product was purified by chromatography ((0.7 M Ammonia/MeOH)/DCM) to afford an off-white solid. The product was partitioned between DCM (5 mL) and sat aq NaHCO$_3$ solution (5 mL). The layers were separated using a phase sep-cartridge and the aqueous layer was re-extracted with DCM (5 mL). The combined organic phases were concentrated in vacuo to provide 47 mg, (66.5%) of Compound 27-1 as a white solid. LCMS [m/z] calculated for $C_{30}H_{32}ClN_5O_4$: 561.2; found 562.0 [M+H]$^+$, $t_R$=3.74 min (Method 5).

Following the procedures as set forth in Scheme 27 above, the compounds of the following Table 27 were prepared using the appropriate $R^1$ and $R^{10}$ reagents.

TABLE 27

| Compound Number | $R^1$ | $R^{10}$ | MS Calc | MS (MH)$^+$ | LCMS Retention Time (min) | Purity Method |
|---|---|---|---|---|---|---|
| 27-1 | (4-chloro-5-methylpyridin-2-yl) | H | 561.2 | 562 | 7.74 | 5 |
| 27-2 | (2,6-dichloro-3-fluorophenyl) | H | 598.2 | 599 | 4.69 | 5 |
| 27-3 | (2,6-dichloro-3-methylphenyl) | H | 594.2 | 595 | 4.89 | 5 |
| 27-4 | (2-cyanophenyl) | H | 537.2 | 538.1 | 3.2 | 5 |
| 27-5 | (2,6-difluoro-3-methylphenyl) | F | 562.2 | 563.1 | 4.44 | 5 |

TABLE 27-continued
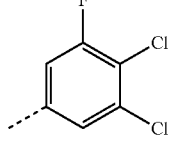
| Compound Number | R¹ | R¹⁰ | MS Calc | MS (MH)⁺ | LCMS Retention Time (min) | Purity Method |
|---|---|---|---|---|---|---|
| 27-6 | ![F, 2,3-diCl-phenyl] | H | 598.2 | 599 | 5.11 | 5 |
| 27-7 | ![F, 2,3-diCl-phenyl] | F | 616.1 | 617.2 | 4.59 | 5 |
Scheme 28
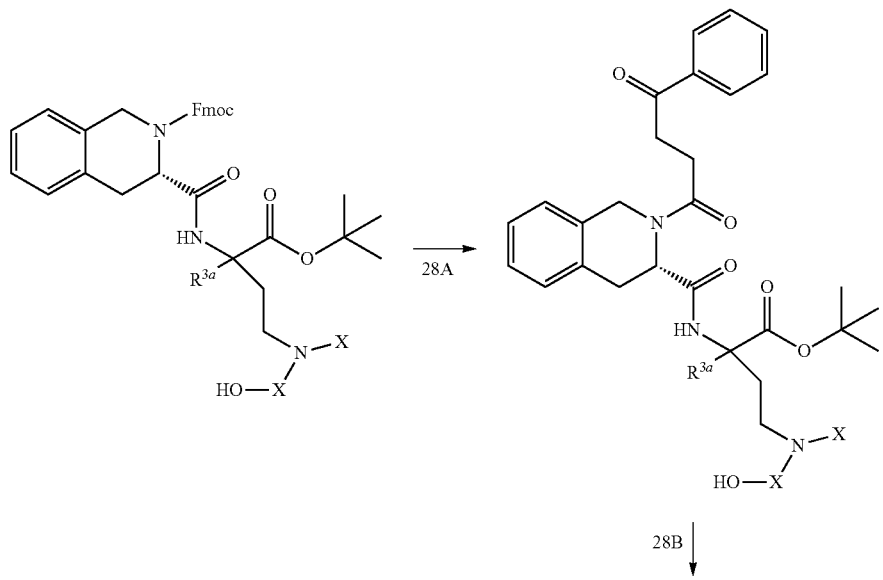
28B ↓

-continued
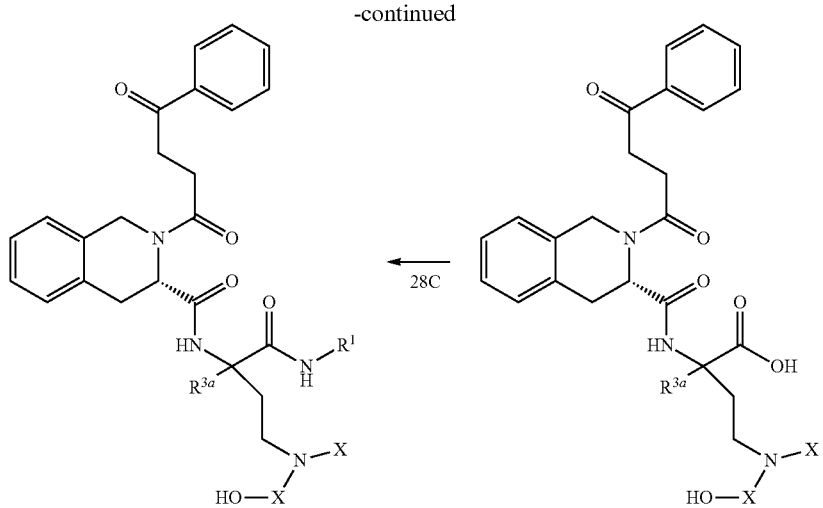
Example 28
(S)—N—((S)-1-((2,3-dihydro-1H-inden-5-yl)amino)-4-(4-hydroxypiperidin-1-yl)-1-oxobutan-2-yl)-2-(4-oxo-4-phenylbutanoyl)-1,2,3,4-tetrahydroisoquinoline-3-carboxamide (Compound 28-1)
Step 28A: Synthesis of tert-butyl (S)-4-(4-hydroxypiperidin-1-yl)-2-((S)-2-(4-oxo-4-phenylbutanoyl)-1,2,3,4-tetrahydroisoquinoline-3-carboxamido)butanoate (Intermediate 28A)
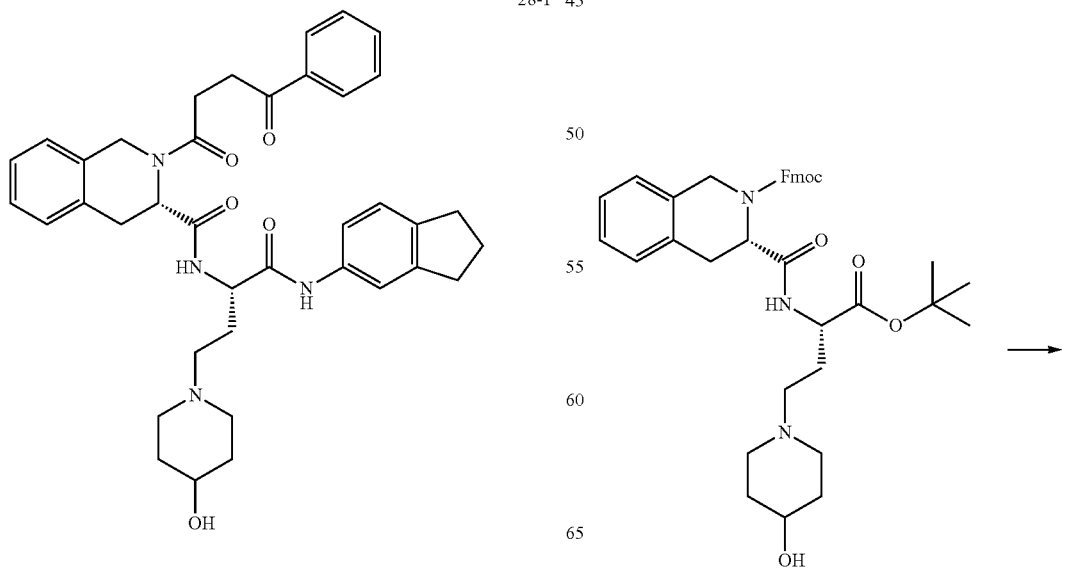

728

Step 28B: Synthesis of (S)-4-(4-hydroxypiperidin-1-yl)-2-((S)-2-(4-oxo-4-phenylbutanoyl)-1,2,3,4-tetrahydroisoquinoline-3-carboxamido)butanoic Acid (Intermediate 28B)

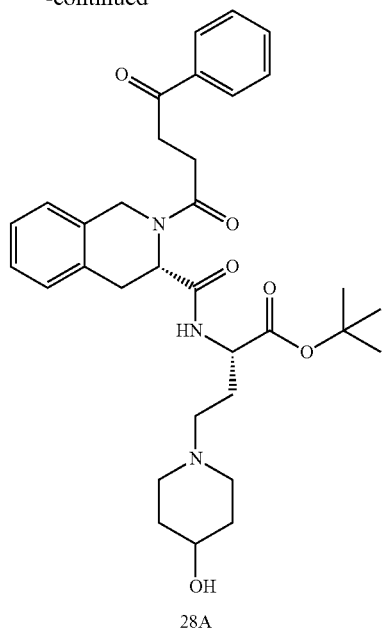

28A

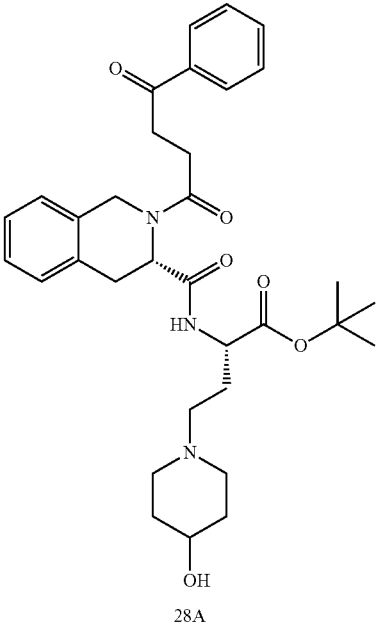

28A

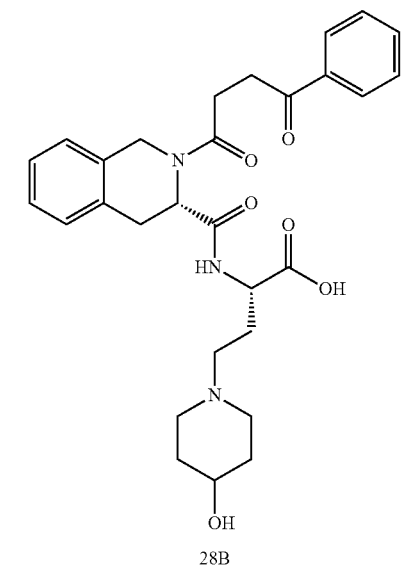

28B

Diethylamine (4.85 mL, 46.9 mmol) was added to a solution of (S)-(9H-fluoren-9-yl)methyl 3-(((S)-1-(tert-butoxy)-4-(4-hydroxypiperidin-1-yl)-1-oxobutan-2-yl)carbamoyl)-3,4-dihydroisoquinoline-2(1H)-carboxylate (made per scheme 25) (1 g, 1.56 mmol) in DCM (5 mL). After 16 h, toluene (2×50 mL) was added and the mixture concentrated under reduced pressure to remove any excess diethylamine. The resulting residue was dissolved in DCM (40 mL). DIEA (1.09 mL, 6.3 mmol) and 4-oxo-4-phenylbutanoic acid (0.33 g, 1.88 mmol) were added. The mixture was cooled to 0° C. and HATU (1.19 g, 3.1 mmol) was added. After 4 h, the reaction mixture was washed with 1M HCl (2×50 mL) then dried (MgSO$_4$) and concentrated under reduced pressure. Purification by chromatography (EA/hexanes) provided 431 mg (46%) of Intermediate 28A as a colorless solid. LCMS [m/z] calculated for $C_{33}H_{43}N_3O_6$: 577.3; found 578.5 [M+H]$^+$, t$_R$=1.28 min (Method 4).

Into a solution of Intermediate 28A (331 mg, 0.57 mmol) in DCM (1 mL) was added 2,2,2-trifluoroacetic acid (570 μl, 7.5 mmol). After 3 h the mixture was diluted with toluene and concentrated under reduced pressure to obtain 348 mg (99%) of Intermediate 28B. LCMS [m/z] calculated for $C_{29}H_{35}N_3O_6$: 521.3; found 522.3 [M+H]$^+$, t$_R$=1.29 min (Method 4).

Step 28C: Synthesis of (S)—N—((S)-1-((2,3-di-hydro-1H-inden-5-yl)amino)-4-(4-hydroxypiperidin-1-yl)-1-oxobutan-2-yl)-2-(4-oxo-4-phenylbutanoyl)-1,2,3,4-tetrahydroisoquinoline-3-carboxamide (Compound 28-1)

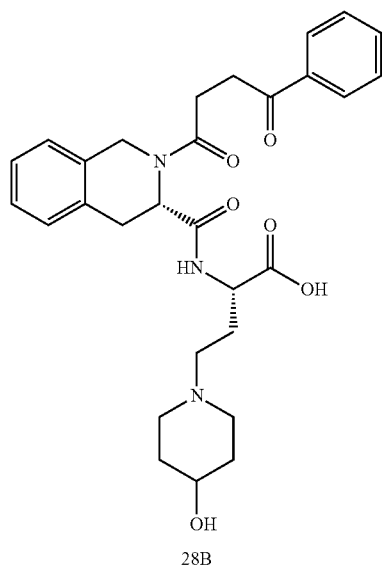

28B

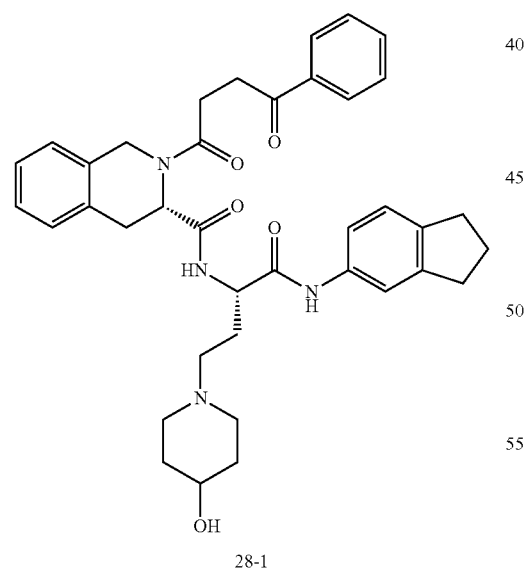

28-1

To a solution of Intermediate 28B (100 mg, 0.19 mmol), 2,3-dihydro-1H-inden-5-amine (30.6 mg, 0.23 mmol) and DIEA (167 µl, 0.96 mmol) in DCM (2 mL) was added HATU (87 mg, 0.23 mmol). After 3 h, 1 M aq solution HCl (2 mL) was added and the layers were separated using a sep. cartridge. The aqueous layer was re-extracted with DCM (3 mL). The combined organic layers were concentrated in vacuo and the crude product was purified by chromatography (MeOH/DCM). Further purification by preparative HPLC provided 13 mg, (10%) of Compound 28-1. LCMS [m/z] calculated for $C_{38}H_{44}N_4O_5$: 636.3; found 637.1 [M+H]$^+$, $t_R$=4.24 min (Method 5).

Following the procedures as set forth in Scheme 28 above, the compounds of the following Table 28 were prepared using the appropriate $R^1$ reagents.

TABLE 28

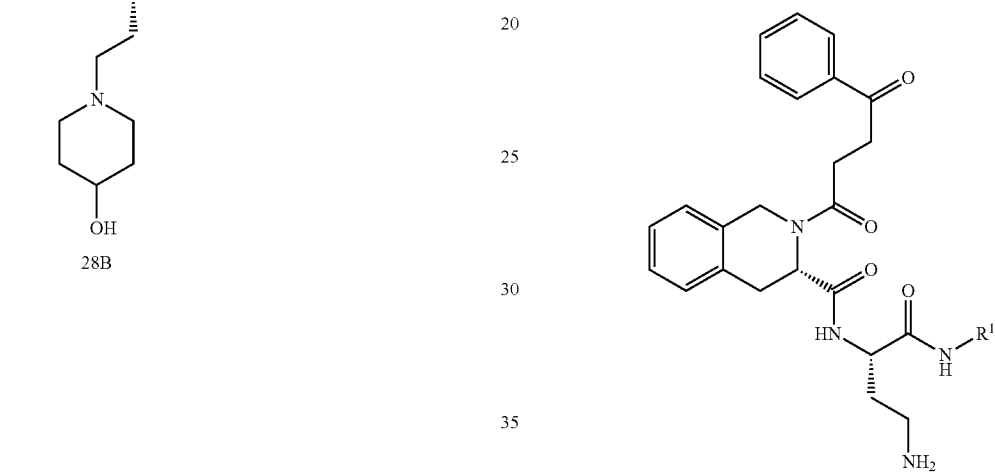

| Compound Number | $R^1$ | MS Calc | MS (MH)$^+$ | LCMS Retention Time | Purity Method |
|---|---|---|---|---|---|
| 28-1 | indanyl | 636.3 | 637.1 | 4.24 | 5 |
| 28-2 | 2-F,3-Me-phenyl | 628.3 | 629.1 | 3.79 | 5 |
| 28-3 | 3-F,4-Me-phenyl | 628.3 | 629.1 | 3.78 | 5 |

Example 29

(S)-3-(((S)-4-amino-1-((3,4-dichloro-2-fluorophenyl)amino)-1-oxobutan-2-yl)carbamoyl)-2-(4-oxo-4-phenylbutanoyl)-1,2,3,4-tetrahydroisoquinolin-7-yl methanesulfonate (Compound 29-1)

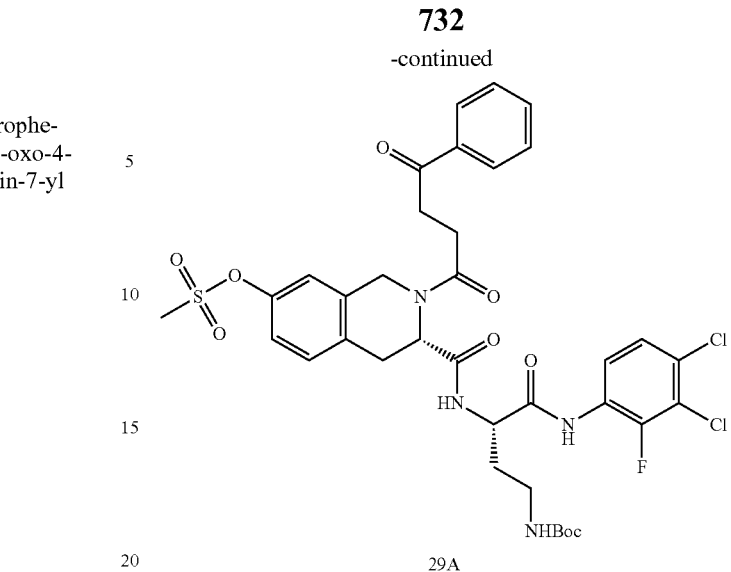

29A

A solution of methane sulfonyl-Cl (2 M in DCM) (0.038 ml, 0.077 mmol) was added to a solution of tert-butyl ((S)-4-((3,4-dichloro-2-fluorophenyl)amino)-3-((S)-7-hydroxy-2-(4-oxo-4-phenylbutanoyl)-1,2,3,4-tetrahydroisoquinoline-3-carboxamido)-4-oxobutyl)carbamate (prepared via Scheme 4, 0.05 g, 0.07 mmol) and DIEA (0.018 mL, 0.105 mmol) in DCM (0.7 mL) at rt. The mixture was stirred overnight, diluted with DCM (10 mL) and quenched with $H_2O$ (10 mL). The layers were separated and the organic layer was concentrated in vacuo. Purification by chromatography (MeOH/DCM) afforded 0.041 g (73%) of Intermediate as a white solid. LCMS [m/z] calculated for $C_{36}H_{39}ClFN_4O_9S$: 792.2; found 793.3 $[M+H]^+$, $t_R$=2.63 min (Method 4).

Step 29A: Synthesis of (S)-3-(((S)-4-((tert-butoxycarbonyl)amino)-1-((3,4-dichloro-2-fluorophenyl)amino)-1-oxobutan-2-yl)carbamoyl)-2-(4-oxo-4-phenylbutanoyl)-1,2,3,4-tetrahydroisoquinolin-7-yl methanesulfonate (Intermediate 29A)

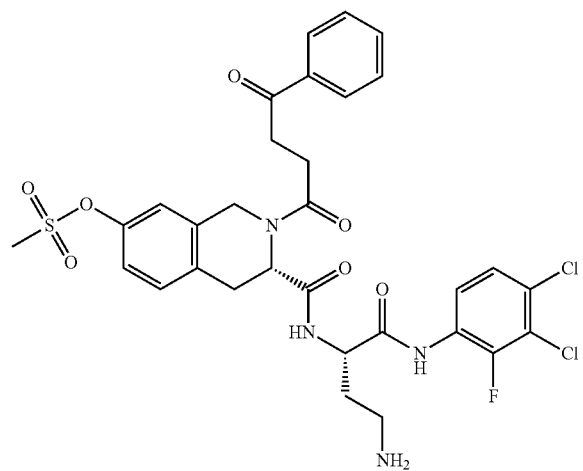 [SMILES: CS(=O)(=O)Oc1ccc2c(c1)CN(C(=O)CCC(=O)c1ccccc1)[C@H](C(=O)N[C@@H](CCN)C(=O)Nc1ccc(Cl)c(Cl)c1F)C2]

Step 29B: Synthesis of (S)-3-(((S)-4-amino-1-((3,4-dichloro-2-fluorophenyl)amino)-1-oxobutan-2-yl)carbamoyl)-2-(4-oxo-4-phenylbutanoyl)-1,2,3,4-tetrahydroisoquinolin-7-yl methanesulfonate (Compound 29-1)

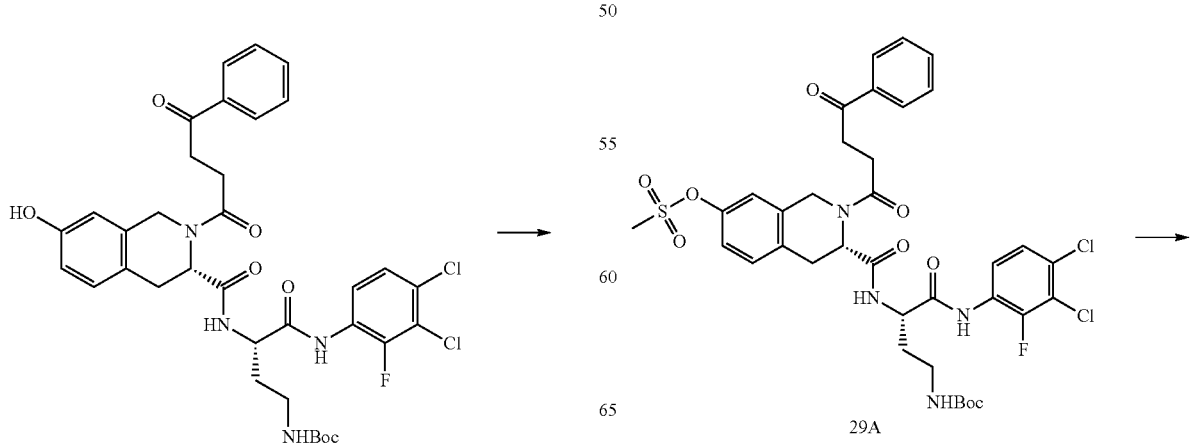

29A

-continued

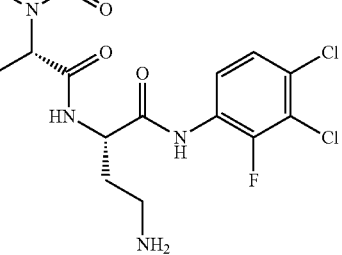

29-1

Intermediate 29A (0.041 g, 0.052 mmol) was stirred in DCM (1 mL) and TFA (0.5 mL) for 1.5 h. The volatiles were removed in vacuo and the residue was dissolved in MeOH and transferred onto an SCX column. The column was washed with MeOH (12 mL). The product was eluted with 0.7 M $NH_3$ in MeOH (12 mL) to afford 0.030 g, (80%) of Compound 29-1 as a white solid. LCMS [m/z] calculated for $C_{31}H_{31}Cl_2FN_4O_7S$: 692.1; found 693.2 [M+H]$^+$, $t_R$=4.42 min (Method 5).

Example 30

(S)—N—((S)-4-amino-1-((3,4-dichloro-2-fluorophenyl)amino)-1-oxobutan-2-yl)-7-cyano-2-(4-oxo-4-phenylbutanoyl)-1,2,3,4-tetrahydroisoquinoline-3-carboxamide (Compound 30-1)

30-1

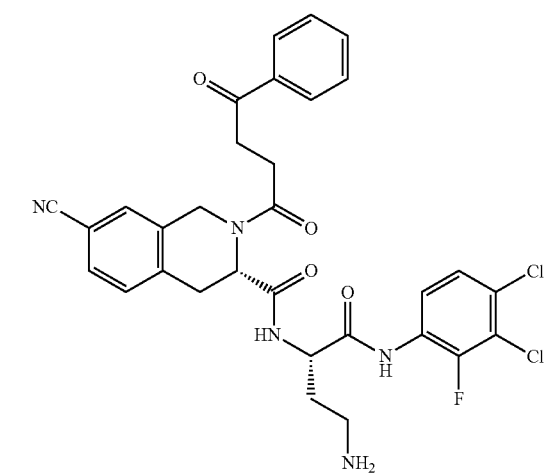

Step 30A: Synthesis of tert-butyl ((S)-4-((3,4-dichloro-2-fluorophenyl)amino)-4-oxo-3-((S)-2-(4-oxo-4-phenylbutanoyl)-7-((trifluoromethyl)sulfonyl)-1,2,3,4-tetra hydroisoquinoline-3-carboxamido) butyl)carbamate (Intermediate 30A)

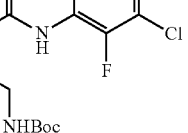

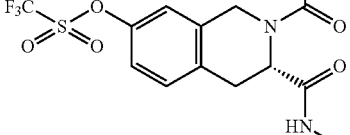

30A tert-butyl ((S)-4-((3,4-dichloro-2-fluorophenyl)amino)-3-((S)-7-hydroxy-2-(4-oxo-4-phenylbutanoyl)-1,2,3,4-tetrahydroisoquinoline-3-carboxamido)-4-oxobutyl)carbamate (prepared via Scheme 4, 0.13 g, 0.18 mmol), DIEA (0.041 mL, 0.24 mmol) and 1,1,1-trifluoro-N-phenyl-N-((trifluoromethyl) sulfonyl) methanesulfonamide (0.078 g, 0.22 mmol) were stirred in DCM (1.5 mL) at rt overnight. The reaction mixture was diluted with DCM (10 mL) and washed with 10% citric acid solution (5 mL), sat. $NaHCO_3$ solution (5 mL) and brine (5 mL). After drying ($MgSO_4$) the solvent was removed in vacuo. Purification via chromatography (MeOH/DCM) afforded 0.133 g (86%) of Intermediate 30A as a white solid. LCMS [m/z] calculated for $C_{36}H_{36}Cl_2F_4N_4O_9S$: 846.2; found 847.2 [M+H]$^+$, $t_R$=2.97 min (Method 4).

Step 30B: Synthesis of tert-butyl ((S)-3-((S)-7-cyano-2-(4-oxo-4-phenylbutanoyl)-1,2,3,4-tetrahydroisoquinoline-3-carboxamido)-4-((3,4-dichloro-2-fluorophenyl) amino)-4-oxobutyl)carbamate (Intermediate 30B)

Step 30C: Synthesis of (S)—N—((S)-4-amino-1-((3,4-dichloro-2-fluorophenyl)amino)-1-oxobutan-2-yl)-7-cyano-2-(4-oxo-4-phenylbutanoyl)-1,2,3,4-tetrahydroisoquinoline-3-carboxamide (Compound 30-1)

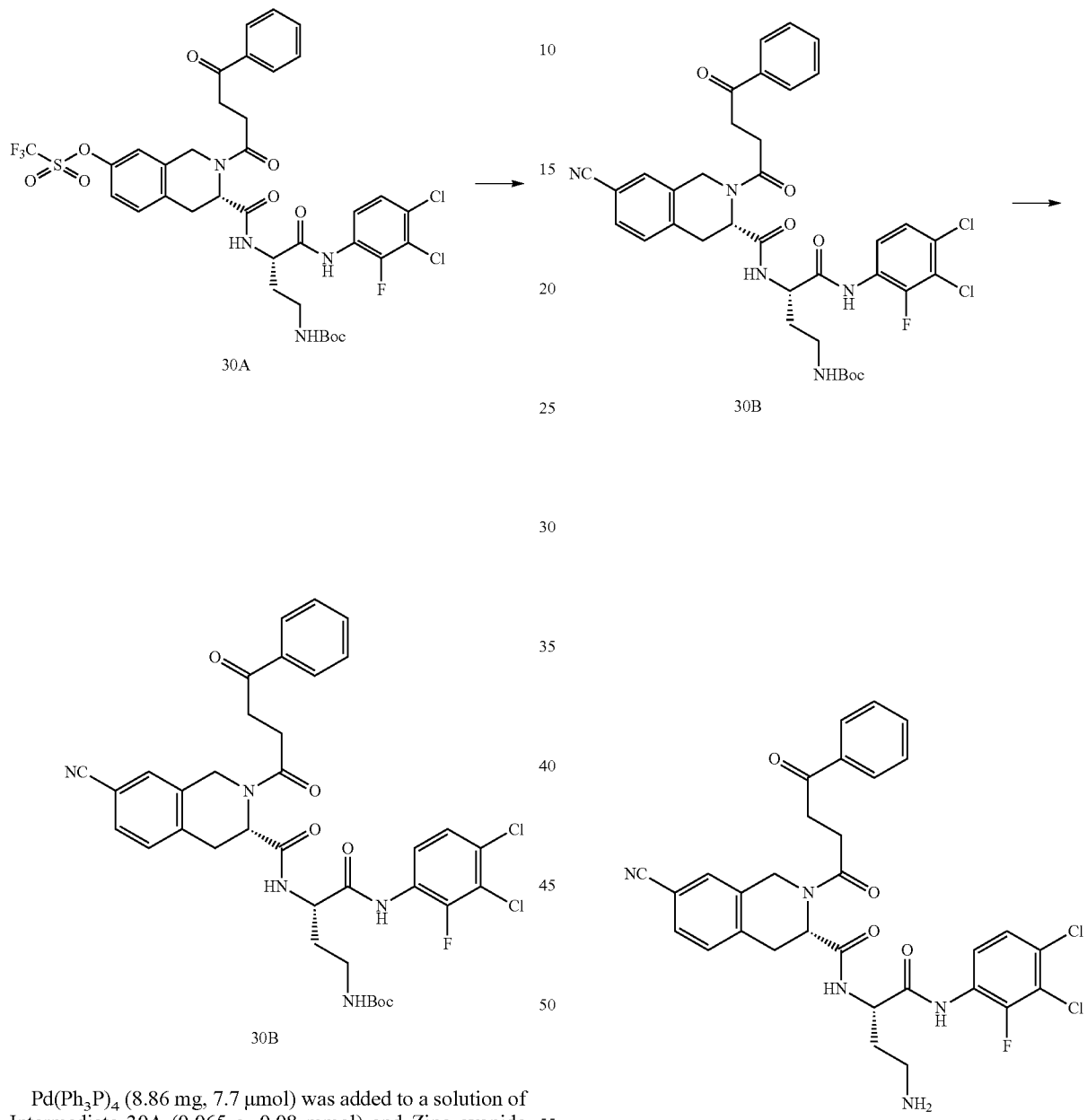

Pd(Ph₃P)₄ (8.86 mg, 7.7 μmol) was added to a solution of Intermediate 30A (0.065 g, 0.08 mmol) and Zinc cyanide (0.012 g, 0.1 mmol) in degassed DMF (0.7 mL). The reaction mixture was degassed for another 10 min and heated to 80° C. for 2.5 h under $N_2$. Additional Pd(Ph₃P)₄ (8.86 mg, 7.7 μmol) was added and the temperature increased to 120° C. and stirred for 6 h. The reaction mixture was cooled to rt, diluted with EA (5 mL), washed with NaHCO₃ solution (2×3 mL) and brine (3 mL). The organic layer was dried (MgSO₄), filtered and concentrated in vacuo. Chromatography (EA/iHex) afforded 0.013 g, (23.2%) of Intermediate 30B as a colourless oil. LCMS [m/z] calculated for $C_{36}H_{36}Cl_2FN_5O_6$: 723.2; found 746.2 [M+Na]⁺, $t_R$=2.67 min (Method 4).

Intermediate 30B (0.013 g, 0.018 mmol) was stirred in DCM (1 mL) and TFA (0.5 mL) for 1 h. The volatiles were removed in vacuo and the residue was dissolved in MeOH and transferred onto an SCX column. The resin was washed with MeOH (15 mL) and the product was eluted with 0.7 M NH₃ in MeOH (13 mL) to afford 0.009 g, (76%) of Compound 30-1 as a beige solid. LCMS [m/z] calculated for $C_{31}H_{28}Cl_2FN_5O_4$: 623.2; found 624.2 [M+Na]⁺, $t_R$=4.55 min (Method 5).

Example 31

(S)—N—((S)-4-(2-aminoacetamido)-1-((4-chloro-3-methylphenyl)amino)-1-oxobutan-2-yl)-2-(4-oxo-4-(piperidin-1-yl)butanoyl)-1,2,3,4-tetrahydroisoquinoline-3-carboxamide (Compound 31-1)

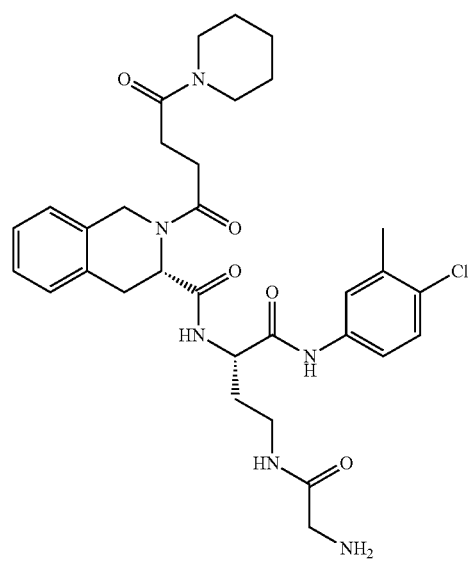

31-1

Step 31A: Synthesis of tert-butyl (2-(((S)-4-((4-chloro-3-methylphenyl)amino)-4-oxo-3-((S)-2-(4-oxo-4-(piperidin-1-yl) butanoyl)-1,2,3,4 tetrahydroisoquinoline-3-carboxamido) butyl)amino)-2-oxoethyl)carbamate (Intermediate 31A)

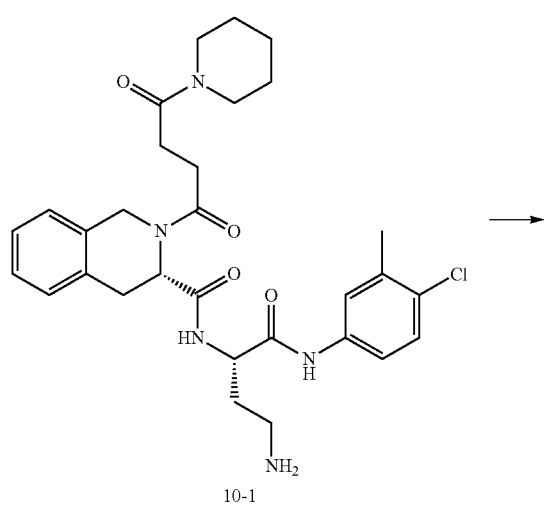

10-1

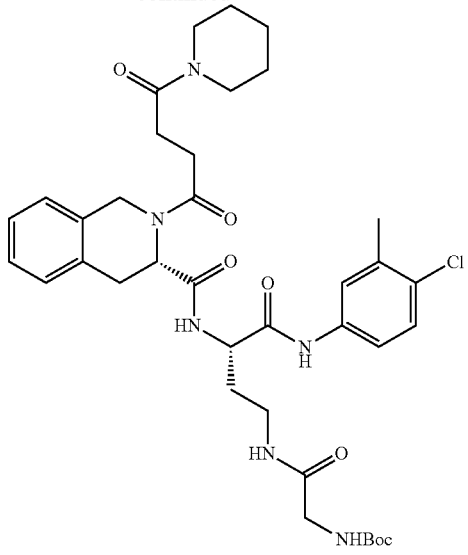

31A

A solution of Compound 10-1 (120 mg, 0.21 mmol) and 2-((tert-butoxycarbonyl)amino)acetic acid (55.5 mg, 0.32 mmol) in DCM (4 mL) was treated with DIPEA (184 μl, 1.06 mmol) and HATU (161 mg, 0.42 mmol). The reaction mixture was stirred at rt for 2 h. The reaction mixture was partitioned between DCM (5 mL) and 1 M aq HCl solution (5 mL). The organic layer was washed with sat. aq. NaHCO$_3$ (10 mL) and brine (10 mL) before the pooled aqueous layers were extracted with DCM (20 mL). The pooled organics were passed through a phase separator. The product was purified by chromatography (MeOH/DCM) to afford the product as a sticky, yellow oil. The solvent was removed in vacuo and the sticky yellow oil was dried in the dessicator at 40° C. overnight. To the product was added MTBE (2 mL) and this was sonicated for 30 sec. The filtrate was decanted and the process repeated 4 times. The residual solvent was removed in vacuo to afford 36 mg (22%) of Intermediate 31A as white, fluffy solid. LCMS [m/z] calculated for $C_{37}H_{49}ClN_6O_7$: 724.3; found 725.1 [M+H]$^+$, $t_R$=6.83 min (Method 5).

Step 31B: Synthesis of (S)—N—((S)-4-(2-aminoac-etamido)-1-((4-chloro-3-methylphenyl) amino)-1-oxobutan-2-yl)-2-(4-oxo-4-(piperidin-1-yl) butanoyl)-1,2,3,4-tetra hydroisoquinoline-3-carbox-amide (Compound 31-1)

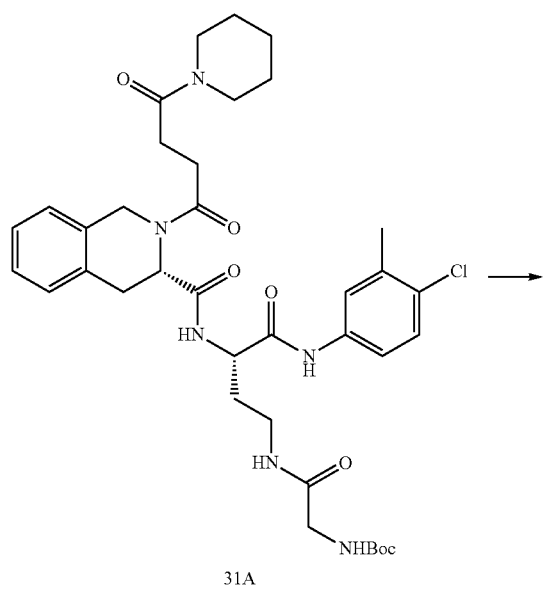

31A

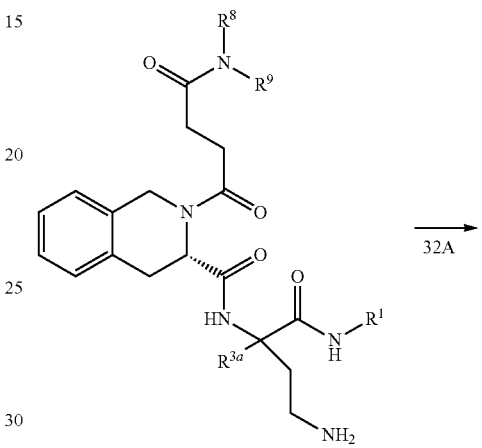

Scheme 32

32A

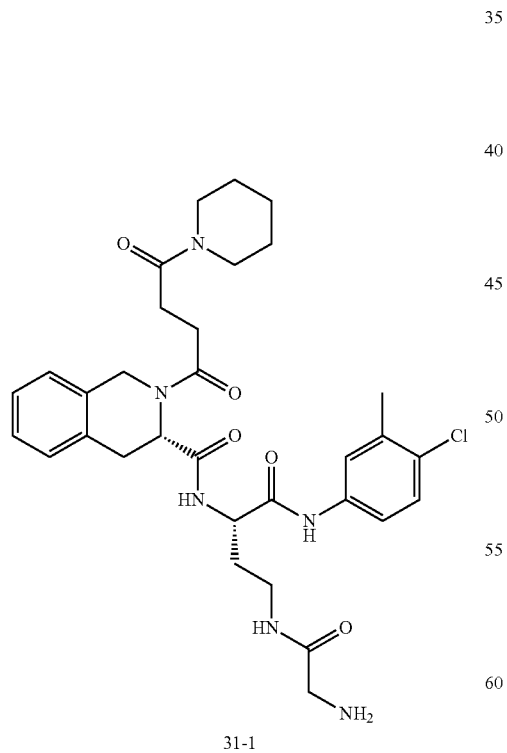

31-1

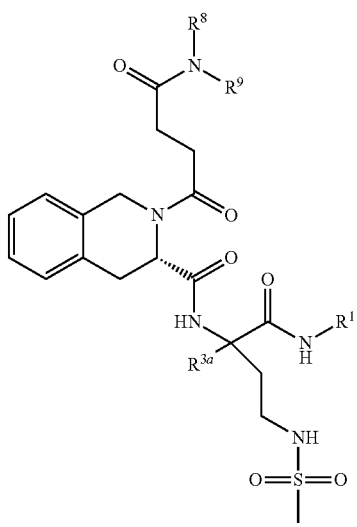

Intermediate 31A (30 mg, 0.04 mmol) was dissolved in DCM (3 mL) and TFA (0.3 mL). After stirring at rt for 2 h, the solvent was removed in vacuo and dissolved in toluene and re-concentrated (2×10 mL). The residue was taken up in DCM (10 mL) and sat. aq. NaHCO$_3$ (10 mL) was added before the layers were separated. The organic layer was washed with sat. aq. NaHCO$_3$ (10 mL). The pooled aqueous layers were extracted with DCM (10 mL) and the organics were passed through a phase separator and the solvent was removed in vacuo. The crude product was purified by chromatography (0.7 M NH$_3$/MeOH/DCM) to afford 4 mg, (15%) of Compound 31-1 as a white solid. LCMS [m/z] calculated for C$_{32}$H$_{41}$ClN$_6$O$_5$: 624.3; found 625.1 [M+H]$^+$, $t_R$=4.12 min (Method 5).

Example 32

(S)—N—((S)-1-((3,4-dichloro-2-fluorophenyl)amino)-4-(methylsulfonamido)-1-oxobutan-2-yl)-2-(4-oxo-4-(piperidin-1-yl)butanoyl)-1,2,3,4-tetrahydroisoquinoline-3-carboxamide (Compound 32-1)

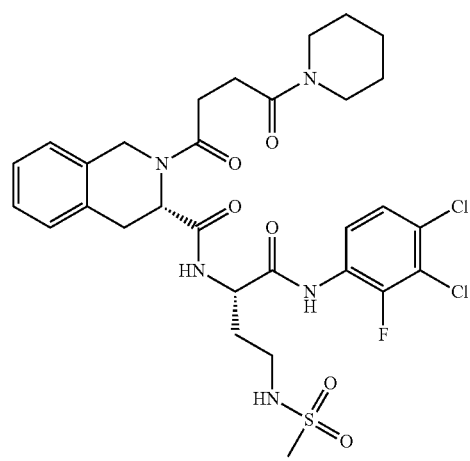

32-1

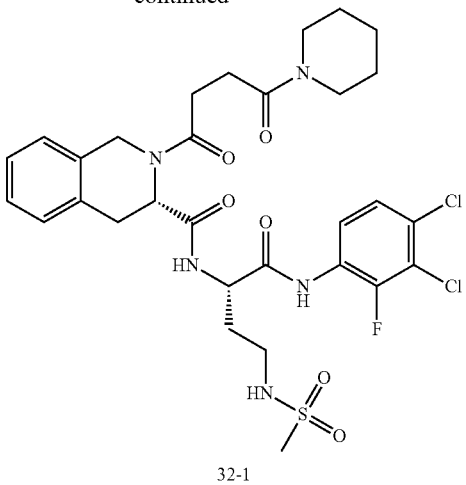

32-1

Step 32A: Synthesis of (S)—N—((S)-1-((3,4-dichloro-2-fluorophenyl)amino)-4-(methylsulfonamido)-1-oxobutan-2-yl)-2-(4-oxo-4-(piperidin-1-yl)butanoyl)-1,2,3,4-tetrahydroisoquinoline-3-carboxamide (Compound 32-1)

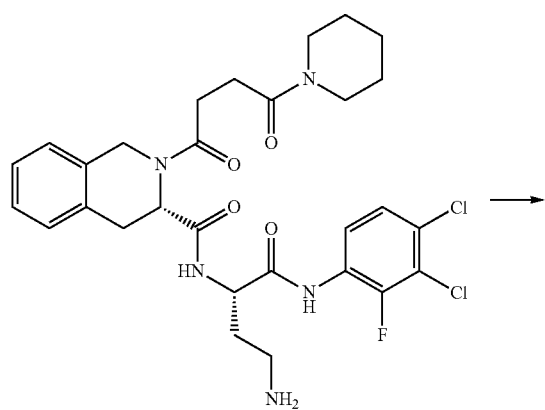

Methane sulfonyl chloride (14.04 µl, 0.18 mmol) was added dropwise to a solution of (S)—N—((S)-4-amino-1-((3,4-dichloro-2-fluorophenyl)amino)-1-oxobutan-2-yl)-2-(4-oxo-4-(piperidin-1-yl)butanoyl)-1,2,3,4-tetrahydroisoquinoline-3-carboxamide (prepared via Scheme 15, 110 mg, 0.18 mmol) and DIEA (63.2 µl, 0.36 mmol) in DCM (1.8 mL). After 2 h, added DCM (4 mL), washed with 1M hydrochloric acid (2×5 mL), dried (MgSO$_4$) and concentrated under reduced pressure. Purification by flash column chromatography (MeOH/DCM) afforded a colourless solid that was further purified by reverse phase flash column chromatography using (ammonium carbonate/acetonitrile) to afford 29 mg, (23%) of Compound 32-1 as a colourless solid. LCMS [m/z] calculated for C$_{34}$H$_{36}$Cl$_2$FN$_5$O$_6$S: 683.2; found 683.9 [M+H]$^+$, t$_R$=6.47 min (Method 5).

Following the procedures as set forth in Scheme 32 above, the compounds of the following Table 32 were prepared using the appropriate R$^1$ reagents.

TABLE 32

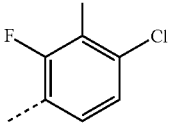

| Compound Number | R¹ | MS Calc | MS (MH)⁺ | LCMS Retention Time | Purity Method |
|---|---|---|---|---|---|
| 32-1 | 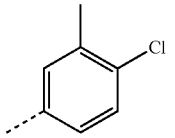 | 683.2 | 683.9 | 6.47 | 5 |
| 32-2 | | 645.2 | 646 | 6.27 | 5 |

Example 33

(3S)—N-(3-(3-aminobicyclo[1.1.1]pentan-1-yl)-1-((3,4-dichloro-2-fluorophenyl)amino)-1-oxopropan-2-yl)-2-(4-(2,2-dimethylpiperidin-1-yl)-4-oxobutanoyl)-1,2,3,4-tetrahydroisoquinoline-3-carboxamide (Compound 33-1)

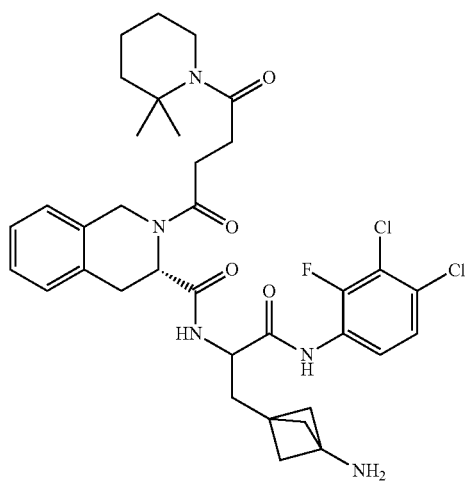

33-1

Step 33A: Synthesis of methyl 3-(3-((tert-butoxy-carbonyl)amino)bicyclo[1.1.1] pentan-1-yl)-2-((S)-2-(4-(2,2-dimethylpiperidin-1-yl)-4-oxobutanoyl)-1,2,3,4-tetra hydroisoquinoline-3-carboxamido) propanoate (Intermediate 33A)

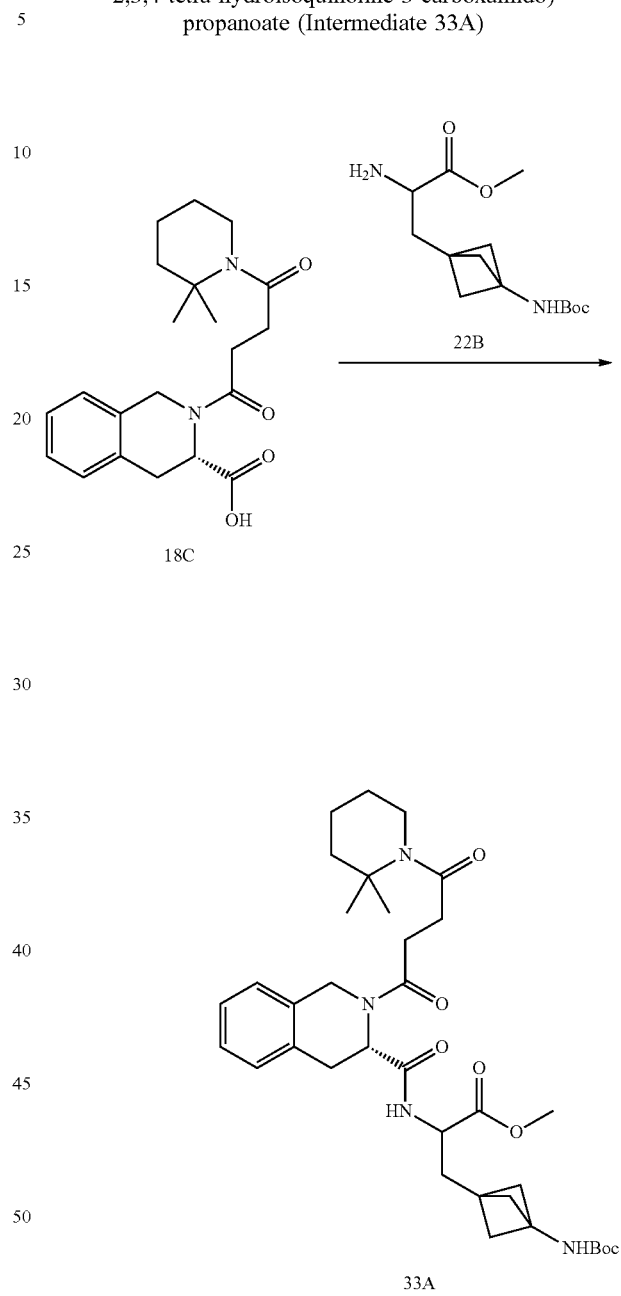

Into a flask containing Intermediate 18C (0.24 g, 0.56 mmol), Intermediate 22B (0.18 g, 0.63 mmol) and DIPEA (0.30 mL, 1.73 mmol) in DCM (11.5 mL, 0.56 mmol) at 0° C. was added HATU (0.656 g, 1.73 mmol). After 1.5 h at 0° C., 1M HCl (50 mL) was added and the mixture stirred for 30 min, then passed through a phase separator. The aqueous layer was further washed with DCM (20 mL), the organics were combined, concentrated and purified by chromatography (EA/hexanes) to provide 0.362 g (94%) of Intermediate 33A as an off-white solid. LCMS [m/z] calculated for $C_{35}H_{50}N_4O_7$: 638.4; found 639.4 [M+H]⁺, $t_R$=2.56 min (Method 4).

Step 33B: Synthesis of 3-(3-((tert-butoxycarbonyl)amino)bicyclo[1.1.1]pentan-1-yl)-2-((S)-2-(4-(2,2-dimethylpiperidin-1-yl)-4-oxobutanoyl)-1,2,3,4-tetrahydroisoquinoline-3-carboxamido)propanoic Acid (Intermediate 33-B)

Step 33C: Synthesis of tert-butyl (3-(3-((3,4-dichloro-2-fluorophenyl)amino)-2-((S)-2-(4-(2,2-dimethylpiperidin-1-yl)-4-oxobutanoyl)-1,2,3,4-tetrahydroisoquinoline-3-carboxamido)-3-oxopropyl)bicyclo[1.1.1]pentan-1-yl)carbamate (Intermediate 33-C)

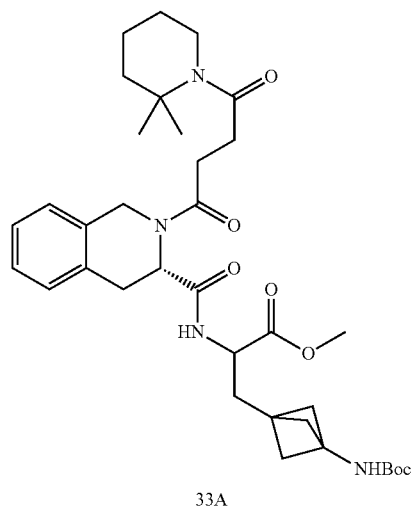

33A

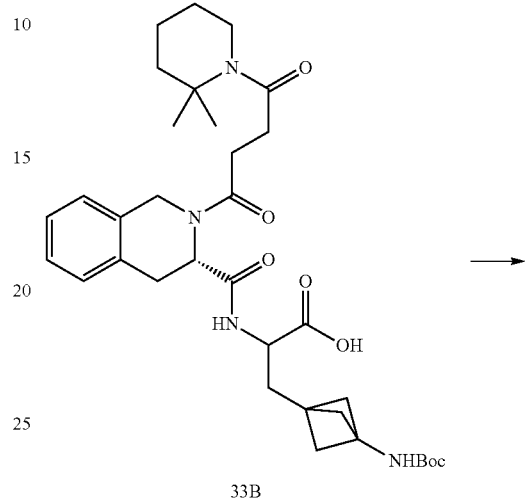

33B

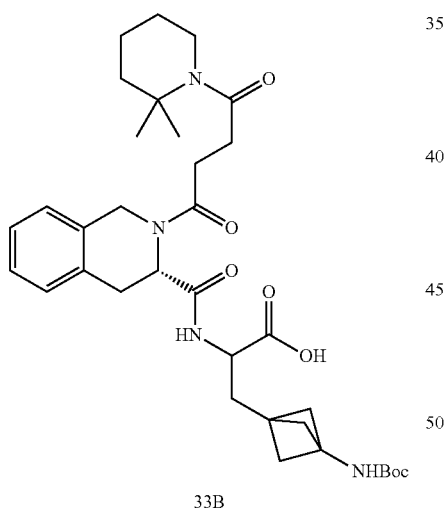

33B

To a solution of Intermediate 33A (0.362 g, 0.57 mmol) in a mixture of THF (3.8 mL) and water (1.4 mL) was added LiOH (0.02 g, 0.85 mmol). After stirring for 2 h at 0° C., the solvent was removed in vacuo and the crude material was partitioned between aq. 1 M HCl (5 mL) and DCM (5 mL). The layers were separated using a phase sep-cartridge and the aqueous layer was re-extracted with DCM (10 mL). The combined organic layers were concentrated in vacuo to give the desired compound which was used for the next step without further purification. LCMS [m/z] calculated for $C_{34}H_{48}N_4O_7$: 624.4; found 625.6 [M+H]$^+$, $t_R$=1.54 min (Method 4).

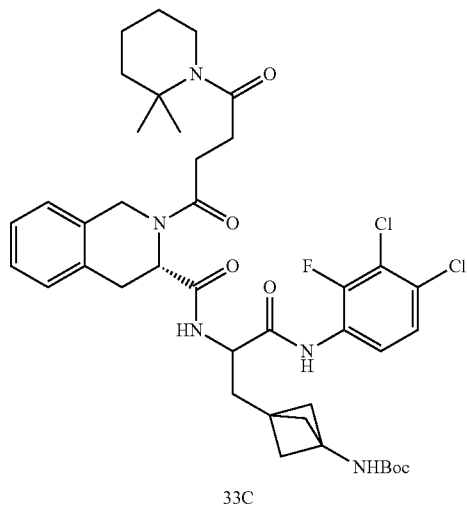

33C

Into vial containing Intermediate 33B (0.354 g, 0.57 mmol), 3,4-dichloro-2-fluoroaniline (0.122 g, 0.68 mmol) and DIEA (0.297 mL, 1.7 mmol) in DCM (11.33 mL) at 0° C. was added HATU (0.646 g, 1.7 mmol). After 1.5 h at 0° C., 1M HCl (10 mL) was added and the mixture was passed through a phase separator. The organics were collected, concentrated and purified by chromatography (EA/hexanes) to provide 0.315 g, (68.5%) of Intermediate 33C as an off-white solid. LCMS [m/z] calculated for $C_{44}H_{50}Cl_2FN_5O_6$: 785.3; found 786.3 [M+H]$^+$, $t_R$=3.03 min (Method 4).

Step 33D: Synthesis of (3S)—N-(3-(3-aminobicyclo [1.1.1]pentan-1-yl)-1-((3,4-dichloro-2-fluorophenyl) amino)-1-oxopropan-2-yl)-2-(4-(2,2-dimethylpiperidin-1-yl)-4-oxobutanoyl)-1,2,3,4-tetrahydroisoquinoline-3-carboxamide (Compound 33-1)

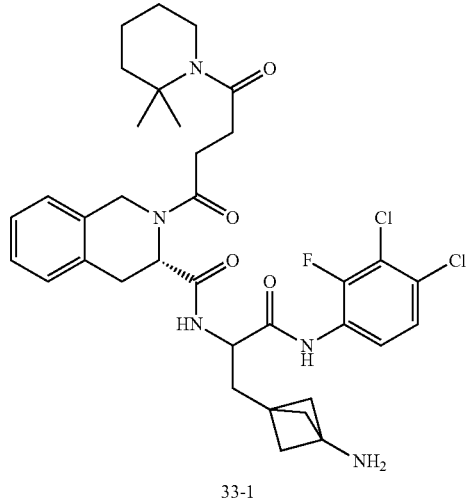

33-1

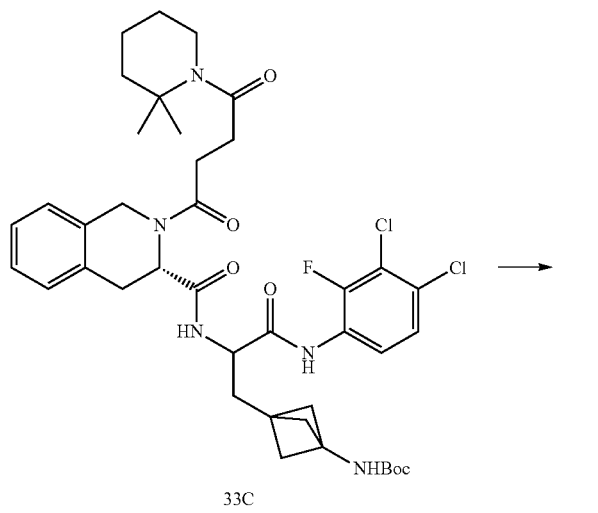

33C

A solution of Intermediate 33C (0.315, 0.40 mmol) in DCM (2 mL, 31.1 mmol) was treated with TFA (0.308 mL, 4.0 mmol). After 2 h, the reaction mixture was concentrated in vacuo and the crude was partitioned between DCM (10 mL) and NaHCO$_3$ (10 mL). The mixture was passed through a phase separator and the organics were concentrated and purified by chromatography (MeOH (1% NH$_3$)/DCM) to provide 0.09 g (31%) of Compound 33-1 as an off-white solid. LCMS [m/z] calculated for $C_{35}H_{42}Cl_2FN_5O_4$: 685.3; found 686 [M+H]$^+$, $t_R$=6.76 min (Method 5).

Scheme 34

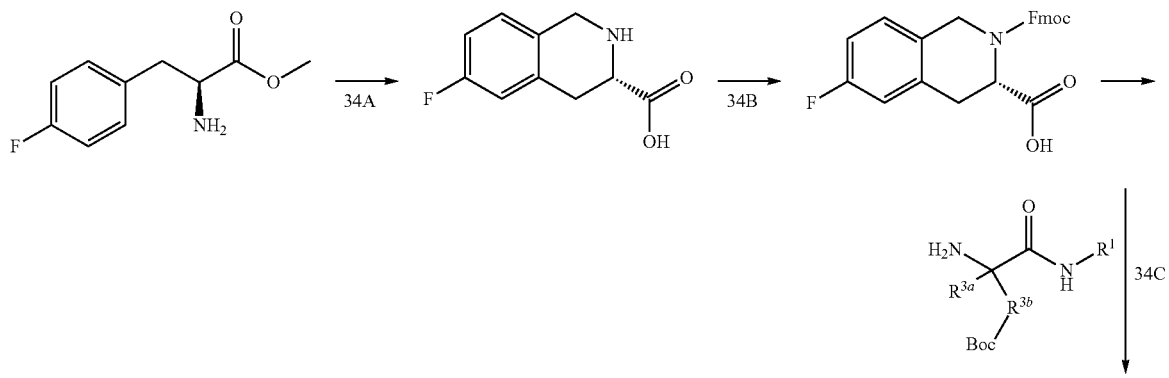

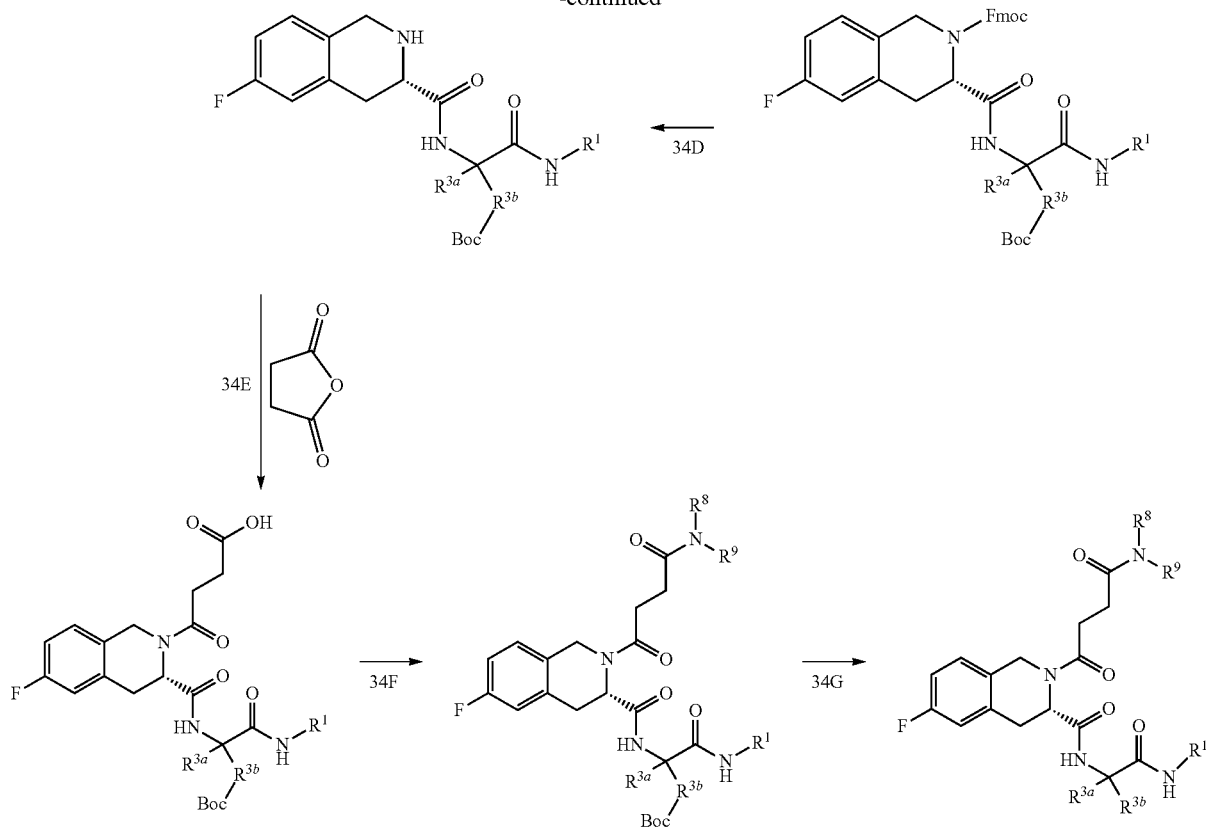

Example 34

(S)—N—((S)-4-amino-1-((3,4-dichloro-2-fluorophenyl)amino)-1-oxobutan-2-yl)-2-(4-(2,2-dimethylpiperidin-1-yl)-4-oxobutanoyl)-6-fluoro-1,2,3,4-tetrahydroisoquinoline-3-carboxamide (Compound 34-1)

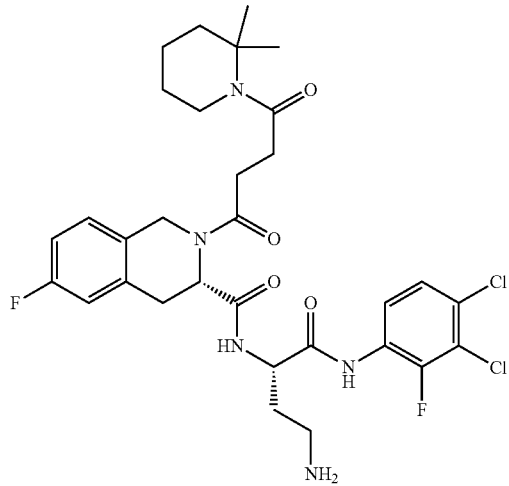

34-1

Step 34A: Synthesis of (S)-6-fluoro-1,2,3,4-tetrahydroisoquinoline-3-carboxylic Acid (Intermediate 34A)

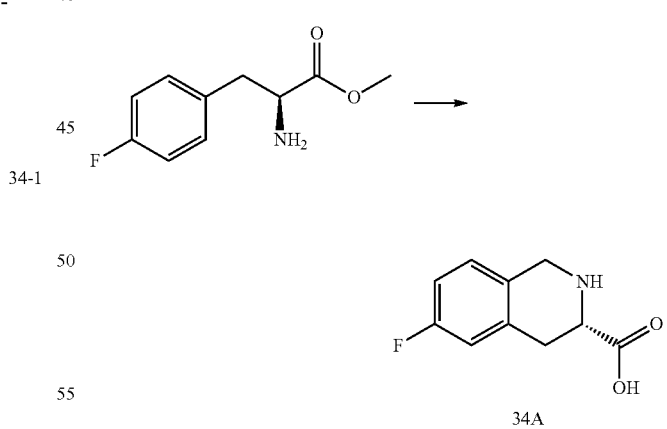

34A

Into a suspension of (S)-2-amino-3-(3-fluorophenyl)propanoic acid, HCl (250 mg, 1.14 mmol) in conc HCl (2500 µl, 82 mmol) was added formaldehyde in water (1000 µl, 13.4 mmol). The mixture was heated at 90° C. for 1 h, then was left to stand at rt for 2 d. The solvent was removed under vacuum and the solid was triturated with MTBE and filtered to afford 261 mg, (94% yield) of Intermediate 34A as a yellow solid. LCMS [m/z] calculated for $C_{10}H_{10}FNO_2$: 195.1; found 196.1 [M+H]$^+$, $t_R$=0.41 min (Method 4).

Step 34B: Synthesis of (S)-2-(((9H-fluoren-9-yl)methoxy)carbonyl)-6-fluoro-1,2,3,4-tetrahydroisoquinoline-3-carboxylic Acid (Intermediate 34B)

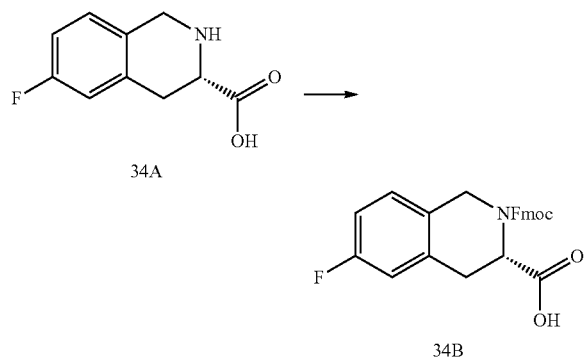

Into a solution of Intermediate 34A (261 mg, 1.13 mmol) and NaHCO₃ (2250 µl, 4.51 mmol) in THF (3 mL) and water (2 mL) was added (9H-fluoren-9-yl)methyl carbonochloridate (350 mg, 1.35 mmol). After 2 h, the reaction was diluted with a 1 M aqueous solution of HCl (20 mL) and extracted with EA (2×20 mL). The combined organic extracts were washed with brine (10 mL), dried (MgSO₄), filtered and concentrated in vacuo to afford a 501 mg of crude material that was purified by chromatography (EA/isohexane) to afford 260 mg (48%) of Intermediate 34B as a colourless oil. LCMS [m/z] calculated for $C_{25}H_{20}FNO_4$: 417.1; found 418.1 [M+H]⁺, $t_R$=2.59 min (Method 4).

Step 34C: Synthesis of (9H-fluoren-9-yl)methyl (S)-3-(((S)-4-((tert-butoxycarbonyl)amino)-1-((3,4-dichloro-2-fluorophenyl)amino)-1-oxobutan-2-yl)carbamoyl)-6-fluoro-3,4-dihydroisoquinoline-2(1H)-carboxylate (Intermediate 34C)

Intermediate 34B (0.135 g, 0.32 mmol) was dissolved in DCM (3 mL). Into this solution were added (S)-tert-butyl (3-amino-4-((3,4-dichloro-2-fluorophenyl)amino)-4-oxobutyl)carbamate (prepared via Scheme 4, 0.123 g, 0.32 mmol), DIEA (0.169 mL, 0.97 mmol) and HATU (0.135 g, 0.36 mmol) at 0° C. The mixture was stirred at 0° C. for 2 h and at rt overnight. The mixture was then diluted with DCM (3 mL) and quenched with water (3 mL). The layers were separated and the organics concentrated in vacuo and purified by chromatography (EA/hexanes) to provide 0.17 g, (64%) of Intermediate 34C as a white solid. LCMS [m/z] calculated for $C_{40}H_{38}Cl_2F_2N_4O_4$: 778.2; found 800.9 [M+Na]⁺, $t_R$=3.10 min (Method 4).

Step 34D: Synthesis of tert-butyl ((S)-4-((3,4-dichloro-2-fluorophenyl)amino)-3-((S)-6-fluoro-1,2,3,4-tetrahydroisoquinoline-3-carboxamido)-4-oxobutyl)carbamate (Intermediate 34D)

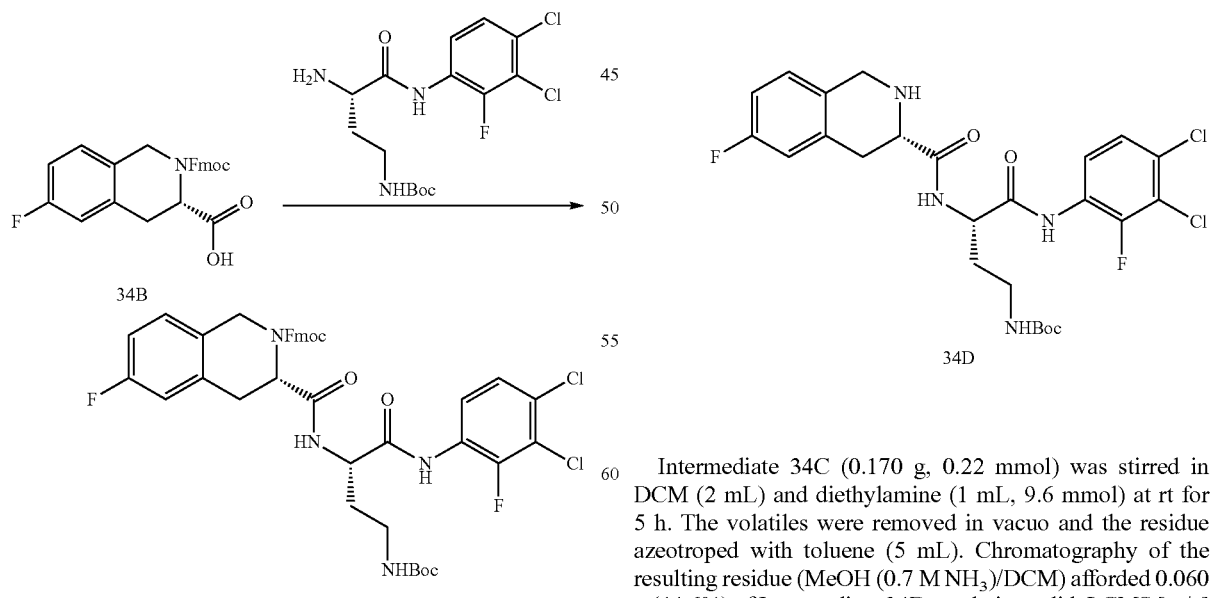

Intermediate 34C (0.170 g, 0.22 mmol) was stirred in DCM (2 mL) and diethylamine (1 mL, 9.6 mmol) at rt for 5 h. The volatiles were removed in vacuo and the residue azeotroped with toluene (5 mL). Chromatography of the resulting residue (MeOH (0.7 M NH₃)/DCM) afforded 0.060 g (44.6%) of Intermediate 34D as a beige solid. LCMS [m/z] calculated for $C_{25}H_{28}Cl_2F_2N_4O_4$: 556.2; found 557.1 [M+Na]⁺, $t_R$=1.87 min (Method 4).

Step 34E: Synthesis of 4-((S)-3-(((S)-4-((tert-butoxycarbonyl)amino)-1-((3,4-dichloro-2-fluorophenyl)amino)-1-oxobutan-2-yl)carbamoyl)-6-fluoro-3,4-dihydroisoquinolin-2(1H)-yl)-4-oxobutanoic Acid (Intermediate 34E)

Step 34F: Synthesis of tert-butyl ((S)-4-(3,4-dichloro-2-fluorophenyl)amino)-3-((S)-2-(4-(2,2-dimethylpiperidin-1-yl)-4-oxobutanoyl)-6-fluoro-1,2,3,4-tetrahydroisoquinoline-3-carboxamido)-4-oxobutyl)carbamate (Intermediate 34F)

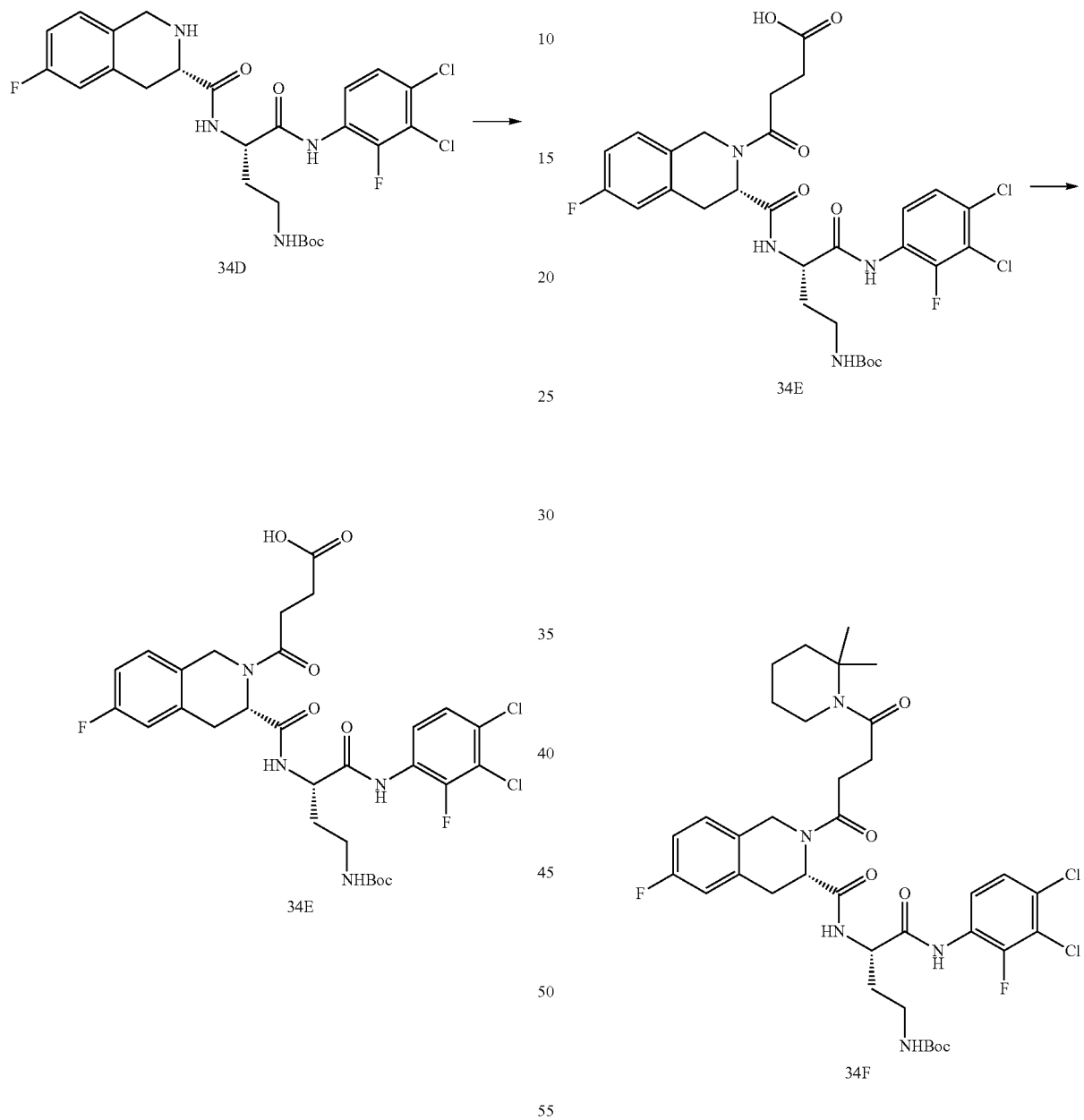

Succinic anhydride (11 mg, 0.11 mmol) was added to a solution of Intermediate 34D (60 mg, 0.11 mmol) and DIEA (0.056 mL, 0.32 mmol) in DCM (2 mL) at rt. After stirring overnight, the mixture was diluted with DCM (2 mL) and washed with 1 M aq. HCl (3 mL). The organic phase was concentrated in vacuo and purified by chromatography (EA/isohexane) to provide 56 mg (76%) of Intermediate 34E as a white solid. LCMS [m/z] calculated for $C_{29}H_{32}Cl_2F_2N_4O_7$: 656.2; found 678.9 [M+Na]$^+$, $t_R$=2.35 min (Method 4).

HATU (42 mg, 0.11 mmol) was added to a solution of 2,2-dimethylpiperidine (15 µl, 0.11 mmol), Intermediate 34E (56 mg, 0.09 mmol) and DIEA (45 µl, 0.26 mmol) in DCM (1.5 mL) at rt. The mixture was stirred for 2 h, diluted with DCM (3 mL) and washed with 1 M aq. HCl (3 mL). The organic phase was concentrated in vacuo to afford 64 mg (100%) of Intermediate 34F as a yellow oil that was carried forward without further purification or analysis. LCMS [m/z] calculated for $C_{36}H_{45}Cl_2F_2N_5O_6$: 751.3; found 752 [M+H]$^+$, $t_R$=2.35 min (Method 4).

Step 34G: Synthesis of (S)—N—((S)-4-amino-1-(3,4-dichloro-2-fluorophenyl)amino)-1-oxobutan-2-yl)-2-(4-(2,2-dimethylpiperidin-1-yl)-4-oxobutanoyl)-6-fluoro-1,2,3,4-tetrahydroisoquinoline-3-carboxamide (Compound 34-1)

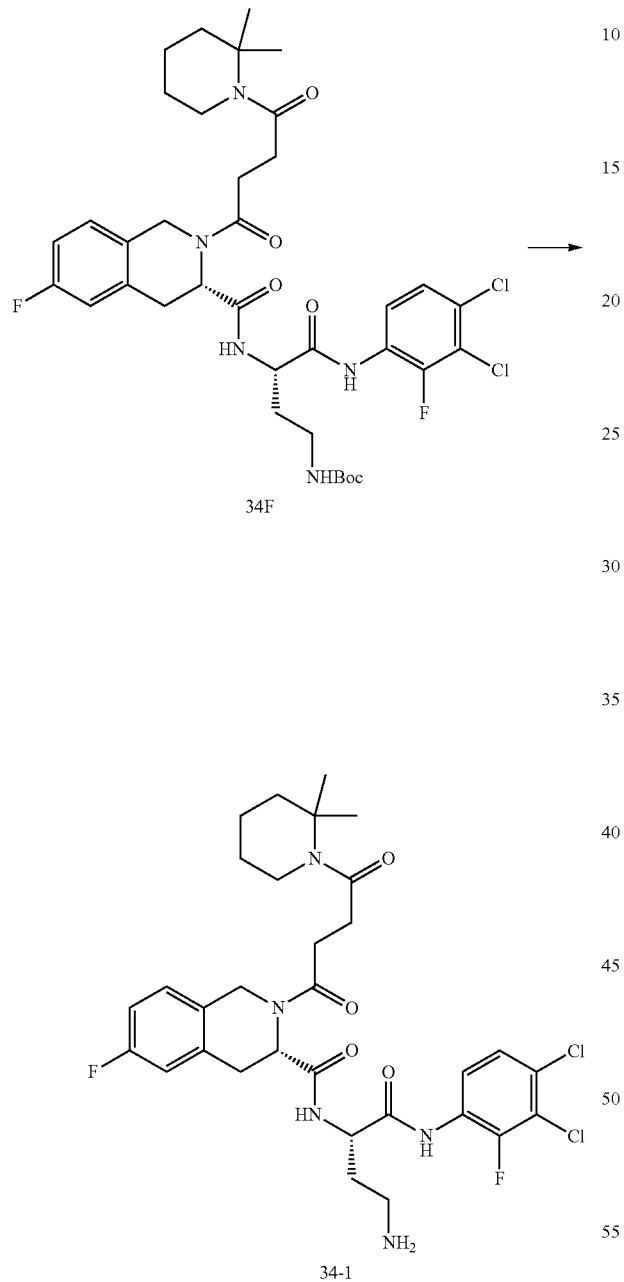

Intermediate 34F (61 mg, 0.09 mmol) was stirred in DCM (2 mL) and TFA (1 mL) at rt for 2 h. Volatiles were removed in vacuo and the residue azeotroped with toluene (4 mL). Chromatography of the resulting residue (MeOH (0.7 M NH$_3$)/DCM) afforded 7 mg (13%) of Compound 34-1 as a white solid. LCMS [m/z] calculated for C$_{31}$H$_{37}$Cl$_2$F$_2$N$_5$O$_4$: 651.2; found 652.0 [M+H]$^+$, t$_R$=4.79 min (Method 5).

Scheme 35

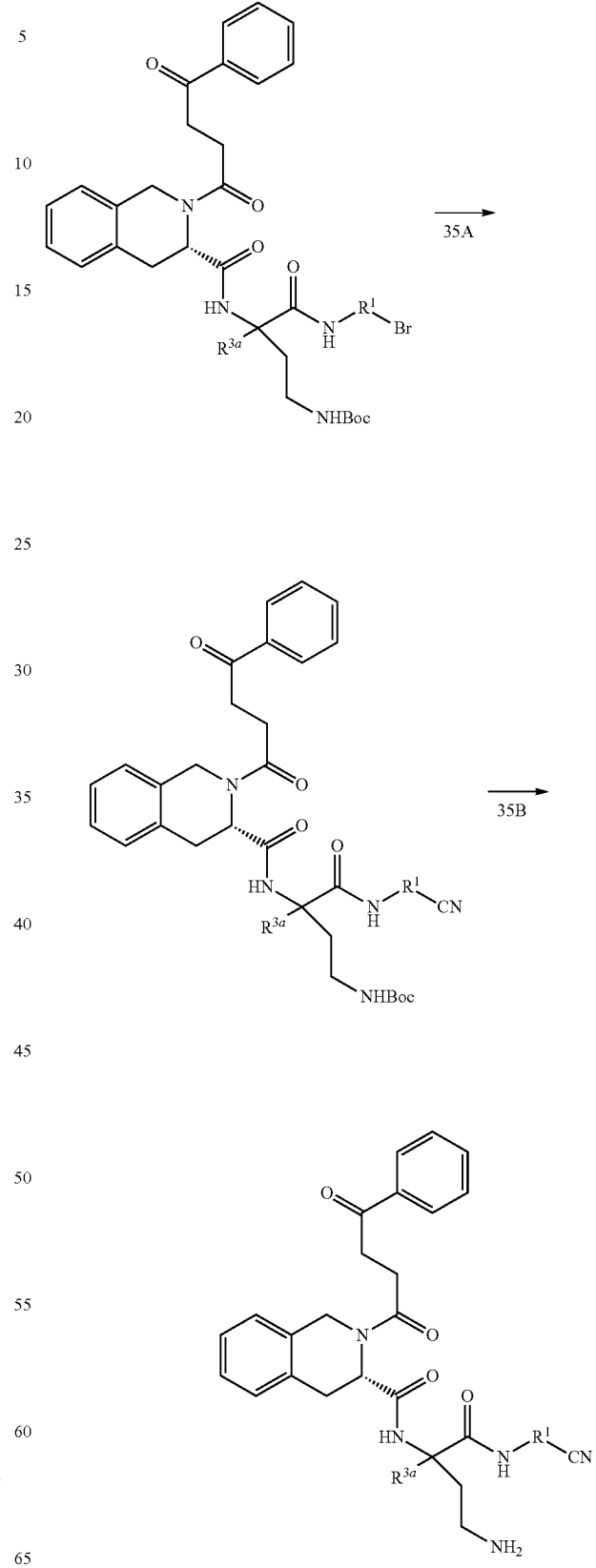

Example 35

(S)—N—((S)-4-amino-1-((4-cyano-2,3-dihydro-1h-inden-5-yl)amino)-1-oxobutan-2-yl)-2-(4-oxo-4-phenylbutanoyl)-1,2,3,4-tetrahydroisoquinoline-3-carboxamide (Compound 35-1)

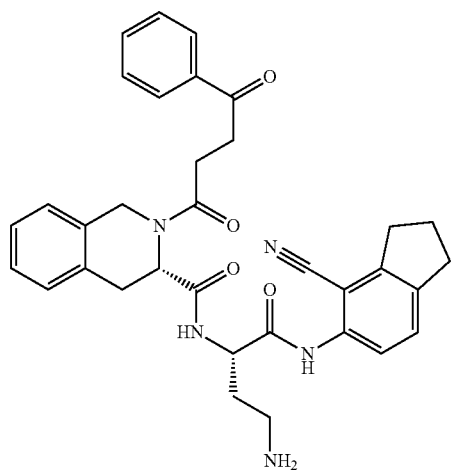

35-1

Step 35A: Synthesis of tert-butyl ((S)-4-((4-cyano-2,3-dihydro-1H-inden-5-yl)amino)-4-oxo-3-((S)-2-(4-oxo-4-phenylbutanoyl)-1,2,3,4-tetrahydroisoquinoline-3-carboxamido) butyl)carbamate (Intermediate 35A)

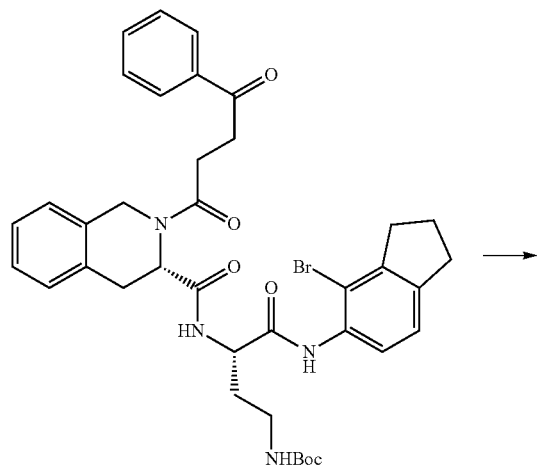

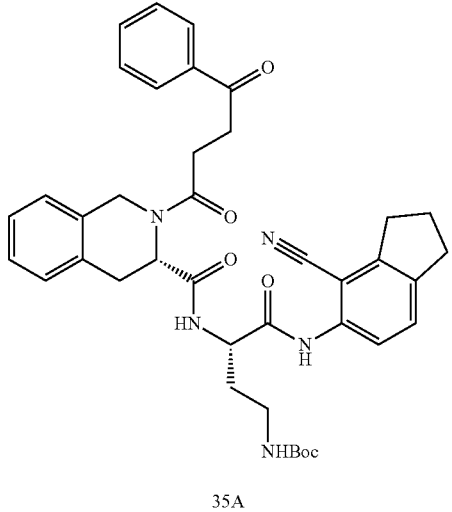

35A

To a stirred solution of tert-butyl ((S)-4-((4-bromo-2,3-dihydro-1H-inden-5-yl)amino)-4-oxo-3-((S)-2-(4-oxo-4-phenylbutanoyl)-1,2,3,4-tetrahydroisoquinoline-3-carboxamido)butyl)carbamate (prepared via Scheme 4 using 4-bromo-2,3-dihydro-1H-inden-5-amine, 200 mg, 0.27 mmol) in DMF, was added CuCN (29 mg, 0.33 mmol) under $N_2$. The reaction was heated to 140° C., stirred overnight, allowed to cool to rt, diluted with $H_2O$ and extracted with DCM. The organic phase was washed with $H_2O$, separated, and then dried ($NaSO_4$), filtered, and the solvent was removed. The resulting residue was purified by chromatography (EA/hexanes) to provide 123 mg (66%) of Intermediate 35A. LCMS [m/z] calculated for $C_{39}H_{43}N_5O_6$: 677.3; found 678.3 [M+H]$^+$, $t_R$=5.35 min (Method 4).

Step 35B: Synthesis of (S)—N—((S)-4-amino-1-((4-cyano-2,3-dihydro-1H-inden-5-yl)amino)-1-oxobutan-2-yl)-2-(4-oxo-4-phenylbutanoyl)-1,2,3,4-tetrahydroisoquinoline-3-carboxamide (Compound 35-1)

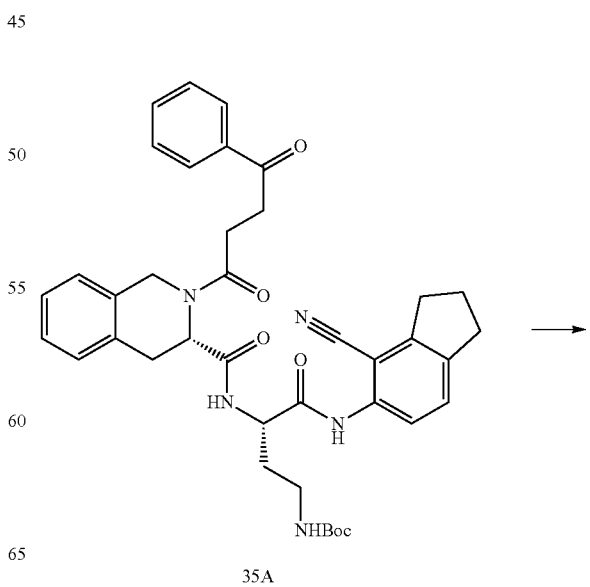

35A

759
-continued

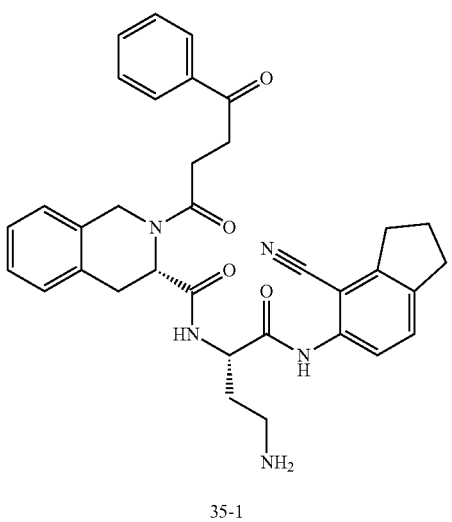

35-1

Into a solution of Intermediate 35 A (100 mg (0.15 mmol) in DCM (2 mL) was added TFA (2 mL). After 20 min, the solvents were removed and the residue was purified by prep-HPLC. Fractions were combined, concentrated, and lyophilized from MeOH/H$_2$O to provide 34 mg (44%) of Compound 35-1. LCMS [m/z] calculated for $C_{34}H_{35}N_5O_4$: 577.3; found 578.3 [M+H]$^+$, $t_R$=5.31 min (Method 4).

Following the procedures as set forth in Scheme 35 above, the compounds of the following Table 35 were prepared using the appropriate R$^1$ reagents.

TABLE 35

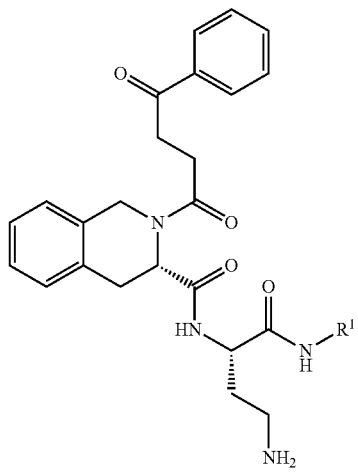

| Compound Number | R$^1$ | MS Calc | MS (MH)$^+$ | LCMS Retention Time | Purity Method |
|---|---|---|---|---|---|
| 35-1 | 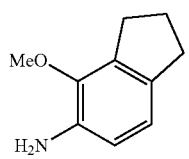 | 577.3 | 578.3 | 11.35 | 1 |

TABLE 35-continued

| Compound Number | R$^1$ | MS Calc | MS (MH)$^+$ | LCMS Retention Time | Purity Method |
|---|---|---|---|---|---|
| 35-2 | 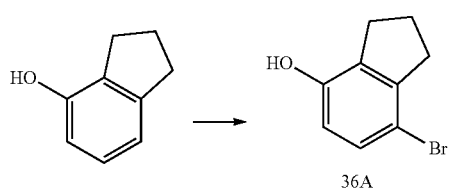 | 585.2 | 586.3 | 4.18 | 5 |

Example 36

4-methoxy-2,3-dihydro-1H-inden-5-amine (Intermediate 36-1)

36-1

Step 36A: Synthesis of 7-bromo-2,3-dihydro-1H-inden-4-ol (Intermediate 36A)

36A

A 2M solution of Br$_2$ (519 mg, 3.3 mmol) in CCl$_4$ (1.5 mL) was added to a solution of 2,3-dihydro-1H-inden-4-ol (400 mg, 3.0 mmol) in DCM (11 mL). After 1 hr, the reaction mixture was concentrated and purified by chromatography to provide 200 mg (31%) of Intermediate 36A. LCMS [m/z] calculated for C₉H₉BrO: 212.0; found 213.3 [M+H]⁺, t$_R$=5.14 min (Method 4).

Step 36B: Synthesis of 7-bromo-5-nitro-2,3-dihydro-1H-inden-4-ol (Intermediate 36B)

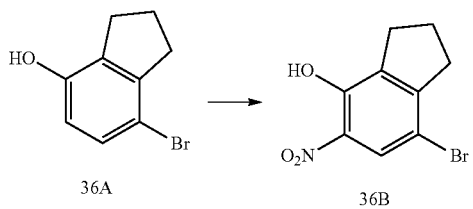 [SMILES: Oc1ccc(Br)c2c1CCC2 ; O=[N+]([O-])c1cc(Br)c2c(c1O)CCC2]

Intermediate 36A (1.64 g, 7.7 mmol) was dissolved in AcOH (2.3 mL) and H₂O (0.46 mL). After cooling at 5° C., fuming HNO₃ (0.13 mL) in AcOH (0.9 mL) of was added dropwise. The mixture was stirred 15 min at 5° C., diluted with H₂O, extracted with DCM, washed with water, dried (Na₂SO₄), concentrated and purified by chromatography (EA/hexane) to provide 400 mg (20%) of Intermediate 36B. LCMS [m/z] calculated for C₉H₈BrNO₃: 257.0; found 258.3 [M+H]⁺, t$_R$=5.13 min (Method 4).

Step 36C: Synthesis of 7-bromo-4-methoxy-5-nitro-2,3-dihydro-1H-indenene (Intermediate 36C)

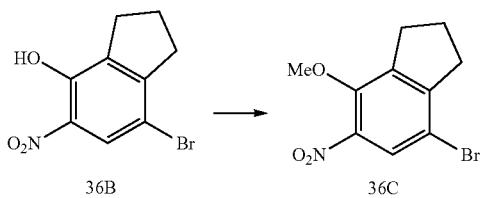 [SMILES: O=[N+]([O-])c1cc(Br)c2c(c1O)CCC2 ; COc1c([N+](=O)[O-])cc(Br)c2c1CCC2]

To Intermediate 36B (350 mg, 1.4 mmol) in DMF (5 mL) was added K₂CO₃ (375 mg, 2.7 mmol) and CH₃I (290 mg, 2 mmol). After stirring overnight, the solvent was removed in vacuo and the residue was dissolved in DCM, washed with H₂O, dried (Na₂SO₄), concentrated and purified by chromatography (EA/hexanes) to provide 200 mg (54%) of Intermediate 36C. LCMS [m/z] calculated for C₁₀H₁₀BrNO₃: 271; found 272.2 [M+H]⁺, t$_R$=5.73 min (Method 4).

Step 36D: Synthesis of 4-methoxy-2,3-dihydro-1H-inden-5-amine (Intermediate 36-1)

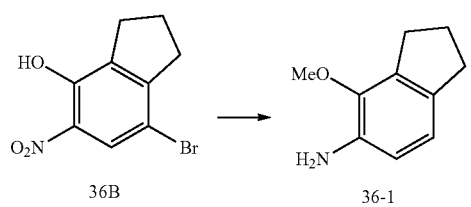 [SMILES: O=[N+]([O-])c1cc(Br)c2c(c1O)CCC2 ; COc1c(N)ccc2c1CCC2]

Intermediate 36B (200 mg, 0.74 mmol) was dissolved in a mixture of MeOH (2 mL) and THF (2 mL) and 10% Pd/C (200 mg) was added. The reaction mixture was purged with H2 and stirred under H2 for 24 h. After filtration and evaporation in vacuo, a solid was obtained which was recrystallized in ether to afford 70 mg (58%) of Intermediate 36-1 as a gray solid. LCMS [m/z] calculated for C₁₀H₁₃NO: 163.1; found 164 [M+H]⁺, t$_R$=2.45 min (Method 4).

Example 37

2-methoxy-3,4-dimethylaniline (Intermediate 37-1)

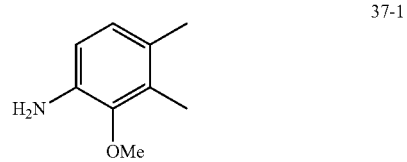

Step 37A: Synthesis of 2,3-dimethylphenol (Intermediate 37A)

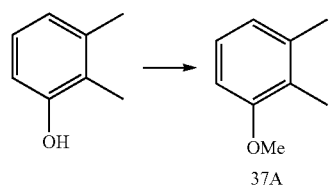

K₂CO₃ (11 g 79.7 mmol) and CH₃I (8.7 g, 61.4 mmol) were added to a solution of 2,3-dimethylphenol (5 g, 41 mmol) in DMF (20 mL) After stirring overnight, the reaction mixture was diluted with DCM, washed with H₂O, dried (Na₂SO₄), concentrated and purified by chromatography (EA/hexanes) to provide 4.1 g (74%) of Intermediate 37A. No analytical data were obtained.

Step 37B: Synthesis of 1-bromo-4-methoxy-2,3-dimethylbenzene (Intermediate 37B)

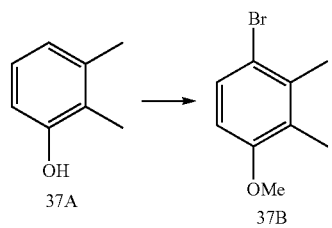

A solution of Br₂ (5.3 g, 33.2 mmol) in CCl₄ (15 mL) was added to a solution of Intermediate 37B (4.1 g, 30.2 mmol) in DCM (100 mL) and the resulting solution was stirred for 1 h. The reaction mixture was concentrated and purified by chromatography to provide 1.7 g (26%) of Intermediate 37B. ¹HNMR (DMSO-d6): 7.33 (d, J=8 Hz, 1H), 6.58 (d, J=8 Hz, 1H), 3.78 (s, 3H), 2.36 (s, 3H), 2.19 (s, 3H).

Step 37C: Synthesis of 1-bromo-4-methoxy-2,3-dimethylbenzene (Intermediate 37C)

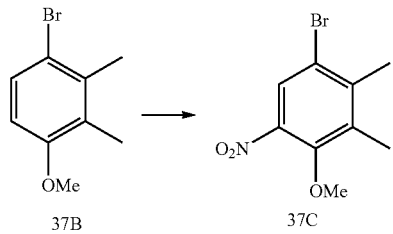

Intermediate 37B (1.5 g, 7 mmol) was dissolved in AcOH (9.2 mL) and $H_2O$ (1.6 mL). After cooling at 5° C., fuming $HNO_3$ (0.49 mL) in AcOH (3.6 mL) was added dropwise. The mixture was stirred 15 min at 5° C., $H_2O$ was added, and the mixture was extracted with DCM. The organic layer was washed with $H_2O$, dried ($Na_2SO_4$), concentrated, and purified by chromatography (EA/hexanes) to provide 1.2 g (66%) of Intermediate 37C. LCMS [m/z] calculated for $C_9H_{10}BrNO_3$: 259.0; found 261.1 [M+H]⁺, $t_R$=5.60 min (Method 4).

Step 37D: Synthesis of 2-methoxy-3,4-dimethylaniline (Intermediate 37-1)

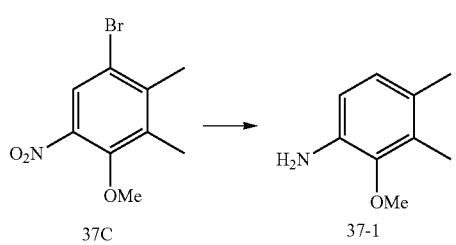

Intermediate 37C (1.0 g, 3.9 mmol) was dissolved in a mixture of MeOH (2 mL) and THF (2 mL). 10% Pd/C (0.2 g) was added and the mixture was flushed with H2 and stirred for 24 h under an atmosphere of H2. The mixture was filtered and concentrated in vacuo, to provide a solid that was crystallized from diethyl ether to afford 0.2 g (34%) of Intermediate 37-1 as a gray solid. LCMS [m/z] calculated for $C_9H_{13}NO$: 151.0; found 152 [M+H]⁺, $t_R$=2.31 min (Method 4).

Example 38

1-methoxy-5,6,7,8-tetrahydronaphthalen-2-amine (Intermediate 38-1)

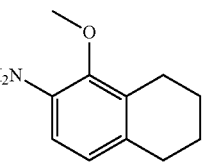

Step 38A: Synthesis of 5-methoxy-1,2,3,4-tetrahydronaphthalene (Intermediate 38A)

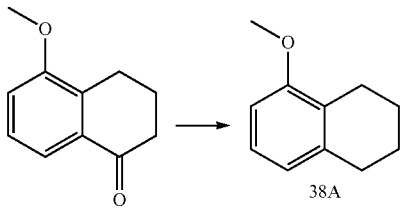

Into a solution of 5-methoxy-3,4-dihydronaphthalen-1 (2H)-one (3 g, 1.7 mmol) in MeOH (60 mL) and THF (16 mL) was added 20% $Pd(OH)_2/C$ (0.5 g). The solution was degassed with $N_2$, then stirred under H2 (1 atm) for 24 h. The mixture was filtered through celite and the filtrate was concentrated to give crude product which was purified by chromatography to provide 1.5 g (54%) of Intermediate 38A. LCMS [m/z] calculated for $C_{11}H_{14}NO$: 162.1; no m/z observed; $t_R$=6.14 min (Method 4).

Step 38B: Synthesis of 5-bromo-8-methoxy-1,2,3,4-tetrahydronaphthalene (Intermediate 38B)

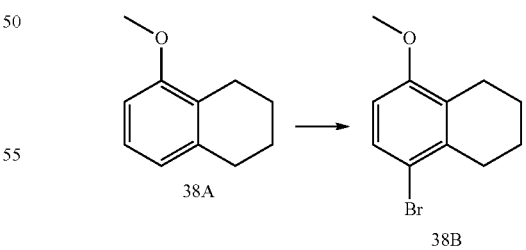

A solution of $Br_2$ (1.6 g, 10.2 mmol) in $CCl_4$ (3 mL) was added to a solution of Intermediate 38A (1.5 g, 9.3 mmol) in DCM (20 mL) and the resulting solution was stirred for 1 h. The reaction mixture was concentrated and purified by chromatography to provide 1.2 g (54%) of Intermediate 38B. LCMS [m/z] calculated for $C_{11}H_{13}BrO$: 240.1; found 241.3 [M+H]⁺, $t_R$=6.5 min (Method 4).

Step 38C: Synthesis of 8-bromo-5-methoxy-6-nitro-1,2,3,4-tetrahydronaphthalene (Intermediate 38C)

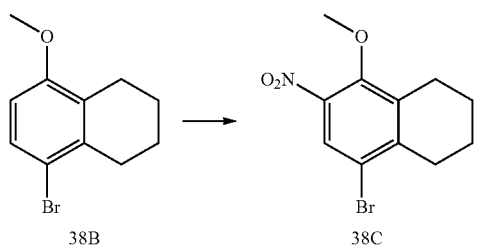 [SMILES: COc1ccc(Br)c2c1CCCC2 ; COc1c([N+](=O)[O-])cc(Br)c2c1CCCC2]

Intermediate 38B (1.2 g, 5.0 mmol) was dissolved in AcOH (5 mL) and cooled to 5° C. Fuming $HNO_3$ (0.41 mL) in AcOH (1 mL) was added. The mixture was stirred for 15 min at 5° C., and then $H_2O$ was added. The solution was extracted with DCM, washed with $H_2O$, dried ($Na_2SO_4$), concentrated, and purified by chromatography (EA/hexane) to provide 0.85 g (60%) of Intermediate 38C. LCMS [m/z] calculated for $C_{11}H_{12}BrNO_3$: 285.0; found 286.0 $[M+H]^+$, $t_R$=5.42 min (Method 4).

Step 38D: Synthesis of 1-methoxy-5,6,7,8-tetrahydronaphthalen-2-amine (Intermediate 38-1)

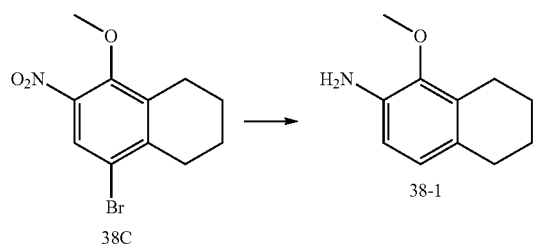 [SMILES: COc1c([N+](=O)[O-])cc(Br)c2c1CCCC2 ; COc1c(N)ccc2c1CCCC2]

Intermediate 38C (0.85 g, 2.97 mmol) was dissolved in a mixture of MeOH (2 mL) and THF (2 mL). 10% Pd/C (200 mg) was added and the mixture was flushed with $H_2$ and stirred for 24 h under an atmosphere of $H_2$. After filtration and evaporation in vacuo, a solid was obtained that was crystallized from diethyl ether to afford 200 mg (38%) of Intermediate 38-1 as gray solid. LCMS [m/z] calculated for $C_{11}H_{15}NO$: 177.1; found 178.4 $[M+H]^+$, $t_R$=2.8 min (Method 4).

Example 39

5-fluoro-2-methoxy-4-methylaniline (Intermediate 39-1)

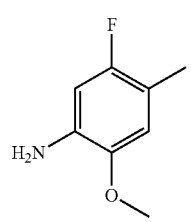

Step 39A: Synthesis of 1-fluoro-4-methoxy-2-methyl-5-nitrobenzene (Intermediate 39A)

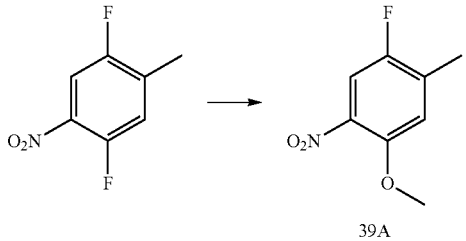

To a suspension of NaH (200 mg, 5 mmol) in THF (10 mL) was added MeOH (203 µL, 5 mmol) dropwise and the mixture was stirred for 30 min. 1,4-Difluoro-2-methyl-5-nitrobenzene (865 mg, 5 mmol) was added and the mixture was heated to 60° C. for 12 h. The contents were poured into $H_2O$ and extracted with EA. The organic phase was washed with diluted NaOH, then $H_2O$, and brine. The organic phase was dried ($Na_2SO_4$), filtered, and the solvent was removed in vacuo. The resulting residue was purified by chromatography (EA/hexanes) to provide 640 mg (68%) of Intermediate 39A. LCMS [m/z] calculated for $C_8H_8FNO$: 185.1; found 186.4 $[M+H]^+$, $t_R$=4.2 min (Method 4).

Step 39B: Synthesis of 1-fluoro-4-methoxy-2-methyl-5-nitrobenzene (Intermediate 39-1)

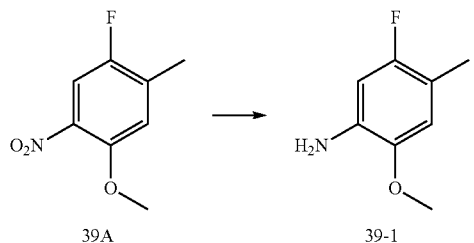

Into a solution of Fe (1290 mg, 23 mmol), AcOH (0.4 mL), THF (2.4 mL) and $H_2O$ was added Intermediate 39A (425 mg, 2.3 mmol). The mixture was heated to 100° C. for 6 h and then was cooled to rt. The solid was collected and diluted with EA. The mixture was filtered through a pad of celite. The organic phase was washed with $H_2O$, dried, filtered, and the solvent removed in vacuo to provide 294 mg (83%) of Intermediate 39-1. LCMS [m/z] calculated for $C_8H_{10}FNO$: 155.1; found 156.2 $[M+H]^+$, $t_R$=2.26 min (Method 4).

Example 40

1,1-dimethyl-2,3-dihydro-1H-inden-5-amine (Intermediate 40a)

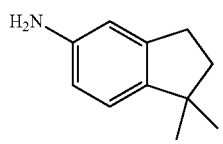

Step 40A: Synthesis of 1,1-dimethyl-2,3-dihydro-1H-inden-5-amine (Intermediate 40-1)

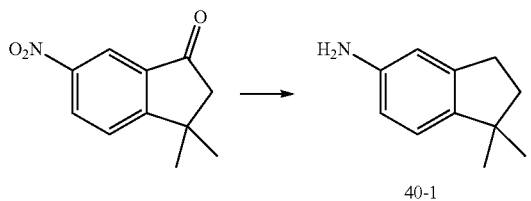

3,3-dimethyl-6-nitro-2,3-dihydro-1H-inden-1-one (600 mg, 2.93 mmol) was dissolved in MeOH (5 mL), and Pd/C (20% weight, 0.2 eq) and CH$_3$SO$_3$H (0.37 mL, 3.8 mmol) were added. The reaction mixture was purged with H$_2$, and the mixture was stirred for 24 h under an atmosphere of H$_2$. The mixture was filtered, concentrated in vacuo, and purified by chromatography to provide 200 mg (42%) of Intermediate 40-1. LCMS [m/z] calculated for C$_{11}$H$_{15}$N: 161.1; found 162.4 [M+H]$^+$, t$_R$=3.11 min (Method 4).

Example 41

2,2-dimethyl-2,3-dihydro-1H-inden-5-amine (Intermediate 41-1)

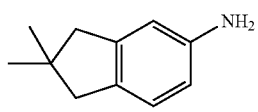

Step 41A: Synthesis of 2,2-dimethyl-2,3-dihydro-1H-inden-5-amine (Intermediate 41A)

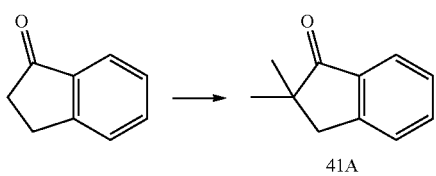

To a cooled (0° C.) solution of NaH (1.9 g, 47 mmol) in DMF (15 mL) was added 2,3-dihydro-1H-inden-1-one (2.5 g, 19 mmol). The mixture was stirred for 20 min before MeI (3.5 mL, 57 mmol) was added dropwise. The mixture was stirred for 2 h, then was quenched with MeOH and H$_2$O and extracted with EA. The organic layer was collected, dried over (Na$_2$SO$_4$), filtered and the solvent was removed in vacuo. The resulting residue was purified by chromatography (EA/hexanes) to provide 2.8 g (90%) of Intermediate 41A. LCMS [m/z] calculated for C$_{11}$H$_{12}$O: 160.1; found 161.4 [M+H]$^+$, t$_R$=4.3 min (Method 4).

Step 41B: Synthesis of 2,2-dimethyl-6-nitro-2,3-dihydro-1H-inden-1-one (Intermediate 41B)

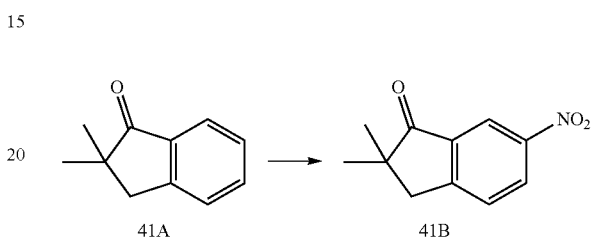

Into a solution of Intermediate 41A (600 mg, 3.8 mmol) in H2504 (5 mL) at 0° C. was added KNO$_3$ in H$_2$SO$_4$ (2 mL). The mixture was stirred for 1 h at 0° C. then warmed to rt and stirred overnight. The reaction was quenched with ice, extracted with EA, then washed with H$_2$O, dried (Na$_2$SO$_4$), and concentrated in vacuo. The crude product was purified by chromatography (EA/hexane) to provide 680 mg (88%) of Intermediate 41B. LCMS [m/z] calculated for C$_{11}$H$_{11}$NO$_3$: 205.1; found 206.5 [M+H]$^+$, t$_R$=4.2 min (Method 4).

Step 41C: Synthesis of 2,2-dimethyl-2,3-dihydro-1H-inden-5-amine (Intermediate 41-1)

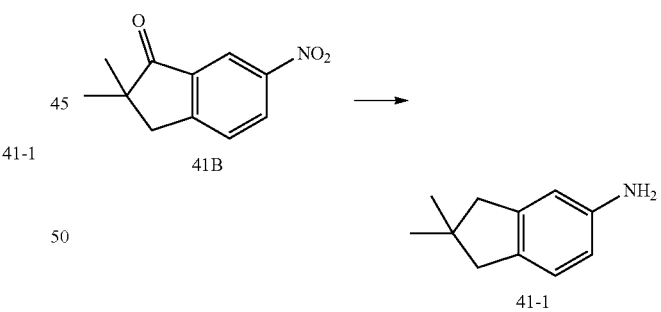

Intermediate 41B (680 mg, 3.3 mmol) was dissolved in a mixture of MeOH (6 mL) and THF (1 mL). 10% Pd/C (800 mg, 3.32 mmol) and methanesulfonic acid (280 μL, 4.3 mmol) were added. The mixture was flushed with N$_2$ and purged, then was stirred at rt for 24 h under an atmosphere of H$_2$. The mixture was filtered, concentrated in vacuo, and purified by chromatography (EA/Hexanes). The resulting material was dissolved in EA, washed with H$_2$O, dried (Na$_2$SO$_4$), and concentrated in vacuo. The resulting material was re-chromatographed (MeOH/DCM) to provide 400 mg (75%) of Intermediate 41-1. LCMS [m/z] calculated for C$_{11}$H$_{15}$N: 161.1 found 162.4 [M+H]$^+$, t$_R$=3.61 min (Method 4).

Example 42

3-ethyl-2-methoxyaniline (Intermediate 42-1)

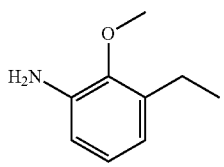

42-1

Step 42A: Synthesis of 2-methoxy-1-nitro-3-vinylbenzene (Intermediate 42A)

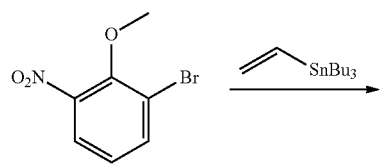

42-A

To a 50 mL flask were added 1-bromo-2-methoxy-3-nitrobenzene (1 g, 4.31 mmol), tributyl(vinyl)stannane (1.26 mL, 4.31 mmol), and toluene (8 mL). The mixture was degassed for 1 min by $N_2$ bubbling. $Pd(PPh_3)_4$ (104 mg, 0.22 mmol) was added to the mixture, which was again purged by $N_2$ bubbling for 1 min. The reaction mixture was stirred at 110° C. under $N_2$ for 18 h. The mixture was allowed to cool to rt and quenched with 1M KF (aq), then extracted with EA. The organic layer was washed with brine, dried ($MgSO_4$), filtered and concentrated. The crude product was purified by chromatography (EA/Hexane) to give 500 mg (65%) of Intermediate 42A, which was used without further analytical evaluation.

Step 42B: Synthesis of 3-ethyl-2-methoxyaniline (Intermediate 42-1)

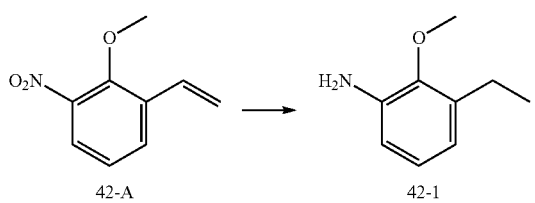

To a flask containing Intermediate 42A (500 mg, 2.8 mmol) was added Pd/C (10%, 500 mg, 0.28 mmol), and MeOH (8 mL). The flask was placed under vacuum for 1 min, then a $H_2$ balloon was attached and the reaction was stirred at rt overnight.

The reaction was filtered and concentrated to provide 420 mg (99%) of Intermediate 42-1 which was used without further purification. LCMS [m/z] calculated for $C_9H_{13}NO$: 151.1 found 152.2 $[M+H]^+$, $t_R$=2.9 min (Method 4).

Example 43

3,4-dichloro-2-methoxyaniline (Intermediate 43-1)

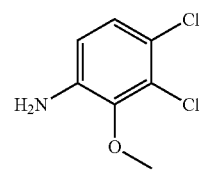

43-1

Step 43A: Synthesis of tert-butyl (3,4-dichloro-2-hydroxyphenyl)carbamate (Intermediate 43A)

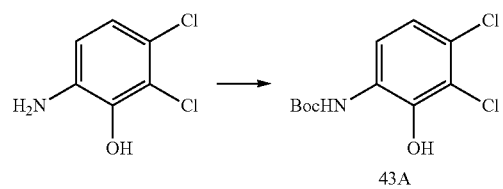 [SMILES: Nc1ccc(Cl)c(Cl)c1O ; CC(C)(C)OC(=O)Nc1ccc(Cl)c(Cl)c1O]

43A

To a solution of 6-amino-2,3-dichlorophenol (100 mg, 0.57 mmol) in DCM (5 mL) were added $Boc_2O$ (370 mg (1.7 mmol) and $ZnCl_2$ (77 mg, 0.57 mmol). The reaction mixture was stirred overnight, diluted with EA and washed with $H_2O$ and brine. The organic layer was collected, dried ($Na_2SO_4$), filtered and concentrated. The residue was purified by chromatography (EA/Hexanes) to provide 116 mg (74%) of Intermediate 43A. LCMS [m/z] calculated for $C_{11}H_{13}Cl_2NO_3$: 277.0 found 278.2 $[M+H]^+$, $t_R$=5.33 min (Method 4).

Step 43B: Synthesis of tert-butyl (3,4-dichloro-2-methoxyphenyl)carbamate (Intermediate 43B)

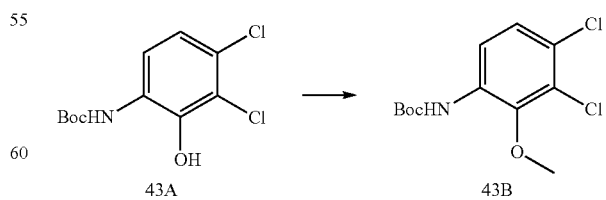

43A          43B

To a stirring solution of Intermediate 43A (173 mg, 0.62 mmol) in DMF (5 mL) was added $K_2CO_3$ (129 mg, 0.93 mmol). MeI (58 μL, 0.93 mmol) was added after 5 min. The reaction mixture was stirred at rt for 16 h under an atmosphere of N₂. The mixture was diluted with EA and washed with H₂O. The organic layer was collected, dried (Na₂SO₄) and concentrated. The residue was purified by chromatography (EA/hexanes) to provide 95 mg (52%) of Intermediate 43B. LCMS [m/z] calculated for $C_{12}H_{15}Cl_2NO_3$: 291.0, found 294.2 [M+H]⁺, $t_R$=5.81 min (Method 4).

Step 43C: Synthesis of
3,4-dichloro-2-methoxyaniline (Intermediate 43-1)

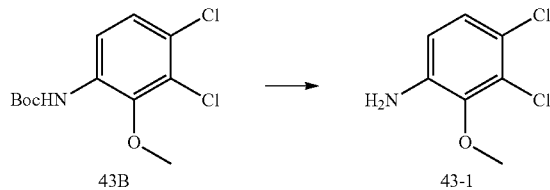 [SMILES: COc1c(NC(=O)OC(C)(C)C)ccc(Cl)c1Cl ; COc1c(N)ccc(Cl)c1Cl]

To a solution of Intermediate 43B (95 mg, 0.32 mmol) in DCM (4 mL) was added TFA (1 mL). The reaction mixture was stirred for 20 min then was diluted with DCM and concentrated multiple times to remove residual TFA to provide 51 mg (62%) of Intermediate 43-1. LCMS [m/z] calculated for $C_7H_7Cl_2NO$: 191.0, found 192.3 [M+H]⁺, $t_R$=4.18 min (Method 4).

Example 44

4,5-dimethyl-2-(trifluoromethoxy)aniline
(Intermediate 43-1)

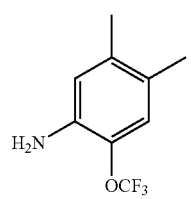

Step 44A: Synthesis of
5-methyl-2-(trifluoromethoxy)aniline (Intermediate 44A)

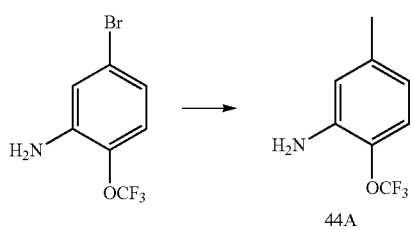

A mixture of 5-bromo-2-(trifluoromethoxy)aniline (2 g, 7.8 mmol), K₂CO₃ (2.7 g, 19.5 mmol), and 2,4,6-trimethyl-1,3,5,2,4,6-trioxatriborinane (50% in THF, 4.4 mL, 15.6 mmol) in dioxane (60 mL) was degassed for 20 min with N₂. PdCl₂(dppf)-CH₂Cl₂ (319 mg, 0.39 mmol) was added and the mixture was further degassed for 10 min then heated to 100° C. for 1 h. The reaction mixture was cooled to rt, filtered through a pad of celite, concentrated, and purified by chromatography (EA/hexane) to provide 1.49 g (74%) of Intermediate 44A. LCMS [m/z] calculated for $C_8H_8F_3NO$: 191.1 found 192.2[M+H]⁺, $t_R$=4.22 min (Method 4).

Step 44B: Synthesis of
4-bromo-5-methyl-2-(trifluoromethoxy)aniline
(Intermediate 44B)

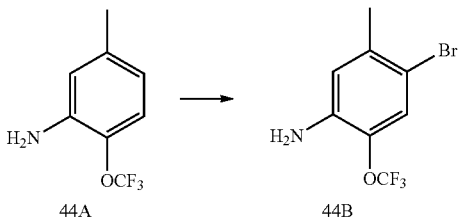

Intermediate 44A (1.11 g, 5.8 mmol) was dissolved in DCM (20 mL). A solution of Br₂ (330 μL, 6.4 mmol) in CCl₄ (6 mL) was added. The reaction was stirred at rt for 1 h then was concentrated and the residual solid was filtered and washed with hexane. The washed solid was then dissolved in DCM and washed with NaHCO₃ (aq) to provide 1.31 g (83.8%) of Intermediate 44B. LCMS [m/z] calculated for $C_8H_7BrF_3NO$: 269.0 found 270.4 [M+H]⁺, $t_R$=5.18 min (Method 4).

Step 44C: Synthesis of
4,5-dimethyl-2-(trifluoromethoxy)aniline
(Intermediate 44-1)

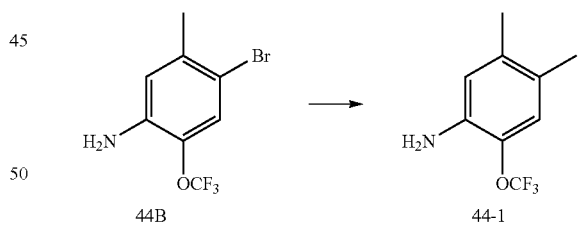

A mixture of Intermediate 44B (1.3 g, 4.9 mmol), K₂CO₃ (1.7 g, 12.2 mmol), and 2,4,6-trimethyl-1,3,5,2,4,6-trioxatriborinane (50% in THF, 2.7 mL, 9.7 mmol) in dioxane (60 mL) was degassed for 20 min with N₂ bubbling. PdCl₂(dppf)-CH₂Cl₂ (197 mg, 0.24 mmol) was added and the mixture was further degassed for 10 min. The reaction mixture was heated to at 100° C. for 1 h, then was cooled to rt, filtered through a pad of celite and concentrated. The resulting residue was purified by chromatography (EA/Hexane) to provide 602 mg (60%) of Intermediate 44-1. LCMS [m/z] calculated for $C_9H_{10}F_3NO$: 205.1 found 206.3 [M+H]⁺, $t_R$=4.16 min (Method 4).

Example 45

6-fluoro-2,3-dihydro-1h-inden-5-amine (Intermediate 45-1)

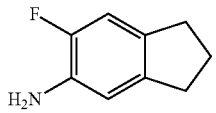

45-1

Step 45A: Synthesis of 5-fluoro-6-nitro-2,3-dihydro-1H-inden-1-one (Intermediate 45A)

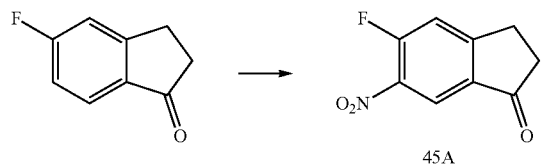 [SMILES: O=C1CCc2cc(F)ccc21 ; O=C1CCc2cc(F)c([N+](=O)[O-])cc21]

45A

Fuming $HNO_3$ (31.3 mmol) was added dropwise to 5-fluoro-2,3-dihydro-1H-inden-1-one (4.7 g, 31.3 mmol) at 0° C. The reaction mixture was stirred for 1.5 h. The reaction mixture was quenched with the addition of $H_2O$ (50 mL). The precipitated solid was collected by filtration and washed with $H_2O$. The resulting crude residue (2 g, 33%) was dried under high vac and used without further purification. LCMS [m/z] calculated for $C_9H_6FNO_3$: 195.0 found 196.2 $[M+H]^+$, $t_R$=3.15 min (Method 4).

Step 45B: Synthesis of 6-fluoro-2,3-dihydro-1H-inden-5-amine (Intermediate 45-1)

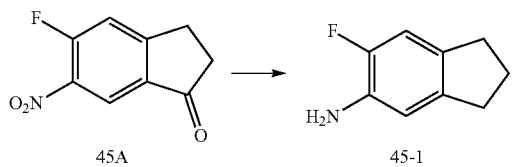 [SMILES: O=C1CCc2cc(F)c([N+](=O)[O-])cc21 ; Nc1cc2c(cc1F)CCC2]

To a solution of Intermediate 45A (1.3 g, 6.7 mmol) in MeOH (20 mL) and THF (10 mL) was added $MeSO_3H$ (0.83 g, 8.66 mmol) followed by Pd/C (10%, 650 mg). The reaction mixture was evacuated and filled with $H_2$. The mixture was stirred overnight under an atmosphere of $H_2$. The reaction mixture was filtered through a pad of Celite and washed with MeOH. The solvents were removed in vacuo and the resulting crude residue was purified by chromatography (EA/hexanes) to provide 614 mg (61%) of Intermediate 45-1. LCMS [m/z] calculated for $C_9H_{10}FN$: 151.1 found 152.3 $[M+H]^+$, $t_R$=7.83 min (Method 5).

Example 46

4-chloro-2,3-dihydro-1h-inden-5-amine (Intermediate 46-1)

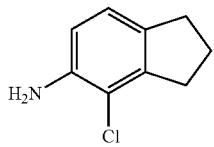

46-1

Step 46A: Synthesis of 4,6-dibromo-2,3-dihydro-1H-inden-5-amine (Intermediate 46A)

46A

To a solution of 2,3-dihydro-1H-inden-5-amine (2.5 g, 18.8 mmol) in AcOH (100 mL) was added $Br_2$ (3.0 g, 18.8 mmol). After 1 h, the reaction mixture was concentrated to ~20 mL. DCM and $H_2O$ were added. The mixture was neutralized to pH-5 with $NaHCO_3$ (sat). The DCM was separated and concentrated. The resulting crude material was purified by chromatography to provide 5.5 g (55%) of Intermediate 46A. LCMS [m/z] calculated for $C_9H_9Br_2N$: 288.9 found 289.9 $[M+H]^+$, $t_R$=6.08 min (Method 4).

Step 46B: Synthesis of 4-bromo-2,3-dihydro-1H-inden-5-amine (Intermediate 46B)

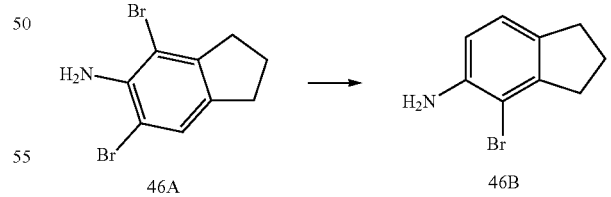

46A    46B

To a solution of Intermediate 46A (6.4 g, 22.2 mmol) in AcOH (30 mL) and HCl (conc) (24 mL) was added tin chloride (6 g, 26.6 mmol). The reaction mixture was stirred at 120° C. for 30 min then cooled to rt. The solvents were removed en vacuo, diluted with DCM and neutralized with NaOH. The organic layer was collected, dried ($Na_2SO_4$), filtered, and concentrated in vacuo to provide 3.76 g (81%) of Intermediate 46B. LCMS [m/z] calculated for $C_9H_{10}BrN$: 211.0 found 212.1 $[M+H]^+$, $t_R$=3.81 min (Method 4).

Step 46C: Synthesis of 4-chloro-2,3-dihydro-1H-inden-5-amine (Intermediate 46-1)

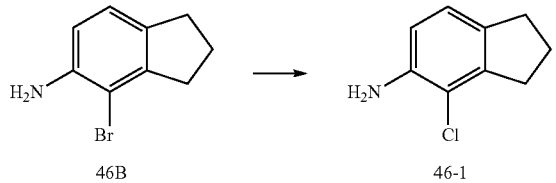 [SMILES: Nc1ccc2c(c1Br)CCC2 ; Nc1ccc2c(c1Cl)CCC2]

To a sealed tube, was added Cu$_2$O (70 mg, 0.5 mmol), Bu$_4$NCl (2.62 g, 9.4 mmol) Intermediate 46B (1.0 g, 4.7 mmol), proline (100 mg, 0.94 mmol) and EtOH (3 mL). The mixture was heated at 110° C. for 24 h. The reaction mixture was diluted with EA and washed consecutively with sat. NaHCO$_3$, H$_2$O, and brine then concentrated. The resulting crude residue was purified by chromatography (EA/hexanes) to provide 103 mg (13%) of Intermediate 46-1. LCMS [m/z] calculated for C$_9$H$_{10}$ClN: 167.1 found 167.4 [M+H]$^+$, t$_R$=3.42 min (Method 4).

Example 47

2-methoxy-5-methyl-4-(trifluoromethyl)aniline (Intermediate 47-1)

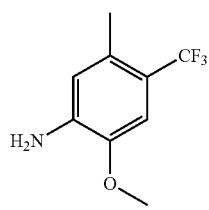

Step 47A: Synthesis of 1-bromo-4-methoxy-5-nitro-2-(trifluoromethyl)benzene (Intermediate 47A)

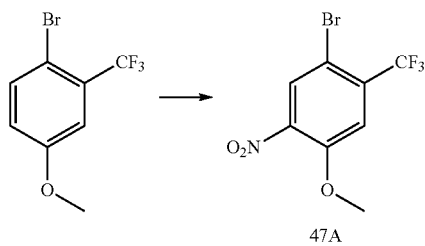 [SMILES: COc1ccc(Br)c(C(F)(F)F)c1 ; COc1cc(C(F)(F)F)c(Br)cc1[N+](=O)[O-]]

To 1-bromo-4-methoxy-2-(trifluoromethyl)benzene (2.0 g, 7.88 mmol) in H$_2$SO$_4$ (6 mL) at 0° C. was added KNO$_3$ (0.53 mL, 7.88 mmol) in H2SO4 (2 mL). The mixture was stirred or 1 h at 0° C. then warmed to rt and stirred overnight. The reaction was quenched with ice and extracted with EA. The organic layer was washed with H$_2$O, dried, and concentrated in vacuo. The crude product was purified by chromatography (EA/hexane) to provide 500 mg (22%) of Intermediate 47A. LCMS [m/z] calculated for C$_8$H$_5$BrF$_3$NO$_3$: 298.9 found 300.2 [M+H]$^+$, t$_R$=5.01 min (Method 4).

Step 47B: Synthesis of 1-methoxy-4-methyl-2-nitro-5-(trifluoromethyl)benzene (Intermediate 47B)

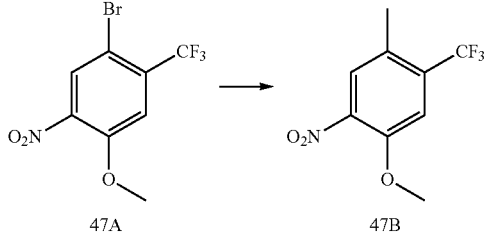 [SMILES: COc1cc(C(F)(F)F)c(Br)cc1[N+](=O)[O-] ; COc1cc(C(F)(F)F)c(C)cc1[N+](=O)[O-]]

A mixture of Intermediate 47A (500 mg, 1.67 mmol), K$_2$CO$_3$ (691 mg, 5 mmol) and 2,4,6-trimethyl-1,3,5,2,4,6-trioxatriborinane (420 mg, 3.34 mmol) in dioxane (30 mL) was degassed for 20 min with N$_2$. PdCl$_2$(pddf)-CH$_2$Cl$_2$ (70 mg, 0.08 mmol) was added and the mixture was further degassed for 10 min. The mixture was heated at 80° C. for 2 h under N$_2$. The mixture was filtered through a pad of celite, concentrated, and the resulting crude material was purified by chromatography (EA/hexane) to provide 250 mg (63%) of Intermediate 47B. LCMS [m/z] calculated for C$_9$H$_8$F$_3$NO$_3$: 235.1 found 236.3 [M+H]$^+$, t$_R$=4.81 min (Method 4).

Step 47C: Synthesis of 2-methoxy-5-methyl-4-(trifluoromethyl)aniline (Intermediate 47-1)

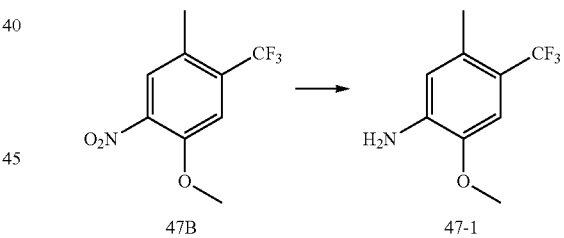

To a solution of Fe (596 mg, 10.6 mmol), AcOH (0.092 mL), THF (1.5 mL) and H$_2$O (1.5 mL) was added Intermediate 47B (250 mg, 1.1 mmol). The mixture was heated to 100° C. for 2 h then cooled to rt. The solid was collected, diluted with EA, and then filtered through a pad of celite. The organic phase was washed with H$_2$O, dried, filtered, and the solvent was removed in vacuo to provide 148 mg (68%) of Intermediate 47-1. LCMS [m/z] calculated for C$_9$H$_{10}$F$_3$NO: 205.1 found 206.3 [M+H]$^+$, t$_R$=4.06 min (Method 4).

Example 48

Biological Assays

CXCR3 cAMP Assay

The cAMP Hunter™ CHOK1 CXCR3 Gi cell line was purchased from DiscoveRx. Cells were seeded into a 96-well white assay plate at 50,000 cells/well/94 µl assay buffer (Hank's Buffered Saline Solution, 10 mM HEPES, 0.1% fatty acid-free BSA, pH 7.4) and immediately assayed in suspension. Forskolin was added to 20 µM (5 µl of 400 µM stock) simultaneously with a 12-point dose response curve of compound at 0-10 µM (1 µl of 100× stock in 100% DMSO), and cells were incubated for 30 minutes. A cAMP standard curve is run as an assay control. A CXCL11 dose response was included to determine maximum efficacy. Direct detection of cAMP was carried out using the DiscoveRx HitHunter cAMP kit according to manufacturer's instructions, and luminescence was read using a SpectraMax M5 plate reader.

CXCR3 Activity

Activity data for representative CXCR3 agonists are displayed in Table 36. The CXCR3 cAMP agonist assay compound EC50 is denoted as follows: + denotes activity <0.050++ denotes activity between 0.050 and 0.25+++ denotes activity between 0.25 and 0.5 µM, and ++++ denotes activity >0.5 µM.

TABLE 36

CXCR3 ACTIVITY

| Compound Number | Activity |
|---|---|
| 1-1 | ++ |
| 1-2 | +++ |
| 1-3 | ++ |
| 1-5 | ++++ |
| 1-6 | +++ |
| 1-7 | ++++ |
| 1-8 | ++++ |
| 1-9 | ++ |
| 1-10 | ++ |
| 1-11 | +++ |
| 1-12 | +++ |
| 1-13 | ++ |
| 1-14 | + |
| 1-15 | +++ |
| 1-16 | ++ |
| 1-17 | ++ |
| 1-18 | + |
| 1-19 | +++ |
| 1-20 | ++ |
| 1-21 | ++++ |
| 1-22 | +++ |
| 1-23 | ++ |
| 1-24 | ++ |
| 1-25 | + |
| 1-26 | + |
| 1-27 | + |
| 1-28 | ++ |
| 1-29 | + |
| 1-30 | + |
| 1-31 | +++ |
| 1-32 | + |
| 1-33 | + |
| 1-34 | + |
| 1-35 | +++ |
| 1-36 | + |
| 1-37 | ++ |
| 1-38 | + |
| 1-39 | + |
| 2-1 | ++ |
| 2-2 | + |
| 2-3 | + |
| 2-4 | ++ |
| 2-5 | + |
| 2-6 | ++ |
| 2-7 | + |
| 2-8 | ++++ |
| 2-9 | ++ |
| 2-10 | +++ |
| 2-11 | +++ |

TABLE 36-continued

CXCR3 ACTIVITY

| Compound Number | Activity |
|---|---|
| 2-12 | +++ |
| 2-13 | ++++ |
| 2-14 | + |
| 2-15 | + |
| 2-16 | + |
| 2-17 | ++ |
| 2-18 | + |
| 2-19 | + |
| 2-20 | ++ |
| 2-21 | + |
| 2-22 | + |
| 2-23 | + |
| 2-24 | + |
| 2-25 | + |
| 2-26 | + |
| 2-27 | ++ |
| 2-28 | + |
| 2-29 | +++ |
| 2-30 | ++ |
| 2-31 | ++ |
| 2-32 | + |
| 2-33 | + |
| 2-34 | + |
| 2-35 | ++ |
| 2-36 | +++ |
| 2-37 | ++ |
| 2-38 | + |
| 2-39 | + |
| 2-40 | + |
| 2-41 | ++ |
| 2-42 | ++++ |
| 2-43 | ++ |
| 2-44 | + |
| 2-45 | +++ |
| 2-46 | + |
| 2-47 | + |
| 2-48 | ++ |
| 2-49 | + |
| 2-50 | +++ |
| 2-51 | ++ |
| 2-52 | ++ |
| 2-53 | ++ |
| 2-54 | ++++ |
| 2-55 | + |
| 2-56 | +++ |
| 2-57 | + |
| 2-58 | ++ |
| 2-59 | +++ |
| 2-60 | ++ |
| 2-61 | ++++ |
| 2-62 | ++ |
| 2-63 | ++ |
| 2-64 | +++ |
| 2-65 | ++ |
| 2-66 | + |
| 2-67 | + |
| 2-68 | ++ |
| 2-69 | ++++ |
| 2-70 | +++ |
| 2-71 | ++ |
| 2-72 | + |
| 2-73 | + |
| 2-74 | ++ |
| 2-75 | ++ |
| 2-76 | ++ |
| 2-77 | ++ |
| 2-78 | + |
| 2-79 | + |
| 2-80 | +++ |
| 2-81 | ++ |
| 2-82 | + |
| 3-1 | ++ |
| 3-2 | + |
| 3-3 | +++ |
| 3-4 | ++ |

TABLE 36-continued

CXCR3 ACTIVITY

| Compound Number | Activity |
|---|---|
| 3-5 | ++ |
| 3-6 | +++ |
| 3-7 | + |
| 3-8 | + |
| 3-9 | + |
| 3-10 | ++ |
| 3-11 | +++ |
| 3-12 | ++ |
| 3-13 | ++ |
| 3-14 | +++ |
| 4-2 | +++ |
| 4-3 | + |
| 4-4 | + |
| 4-5 | ++++ |
| 4-6 | + |
| 4-7 | ++++ |
| 4-8 | + |
| 4-9 | ++ |
| 4-10 | ++ |
| 4-11 | ++ |
| 4-12 | ++ |
| 4-13 | ++ |
| 4-14 | + |
| 4-15 | +++ |
| 4-16 | + |
| 4-17 | ++++ |
| 4-18 | ++ |
| 4-19 | + |
| 4-20 | + |
| 5-1 | + |
| 5-2 | ++ |
| 5-3 | ++ |
| 5-4 | ++ |
| 6-1 | ++ |
| 6-2 | ++ |
| 6-3 | ++ |
| 6-4 | ++ |
| 6-5 | ++ |
| 6-6 | + |
| 6-7 | ++ |
| 7-1 | ++ |
| 7-2 | ++ |
| 7-3 | ++ |
| 7-4 | +++ |
| 7-5 | ++++ |
| 7-6 | ++ |
| 7-7 | ++ |
| 7-8 | + |
| 7-9 | ++++ |
| 8-1 | + |
| 8-2 | + |
| 8-3 | + |
| 8-4 | + |
| 8-5 | + |
| 8-6 | ++ |
| 8-7 | + |
| 9-1 | + |
| 10-1 | + |
| 10-2 | ++ |
| 10-3 | + |
| 10-4 | + |
| 10-5 | + |
| 10-6 | + |
| 10-7 | + |
| 10-8 | + |
| 10-9 | + |
| 10-10 | + |
| 10-11 | + |
| 10-12 | + |
| 11-1 | ++++ |
| 11-2 | +++ |
| 11-3 | + |
| 11-4 | ++ |
| 11-5 | ++++ |
| 11-6 | + |

TABLE 36-continued

CXCR3 ACTIVITY

| Compound Number | Activity |
|---|---|
| 12-1 | ++ |
| 12-2 | + |
| 12-3 | ++ |
| 12-4 | + |
| 12-5 | + |
| 12-6 | ++ |
| 12-7 | + |
| 12-8 | ++ |
| 12-9 | ++++ |
| 12-10 | ++ |
| 12-11 | + |
| 12-12 | ++++ |
| 12-13 | + |
| 12-14 | ++ |
| 12-15 | ++ |
| 12-16 | ++++ |
| 12-17 | ++ |
| 12-18 | ++++ |
| 12-19 | +++ |
| 12-20 | + |
| 12-21 | + |
| 12-22 | + |
| 12-23 | + |
| 12-24 | +++ |
| 12-25 | + |
| 12-26 | + |
| 12-27 | ++ |
| 12-28 | + |
| 12-29 | + |
| 12-30 | ++ |
| 12-31 | + |
| 12-32 | + |
| 12-33 | ++ |
| 12-34 | ++ |
| 12-35 | + |
| 12-36 | + |
| 12-37 | ++ |
| 12-38 | +++ |
| 12-39 | + |
| 12-40 | + |
| 12-41 | + |
| 12-42 | + |
| 12-43 | + |
| 12-44 | + |
| 12-45 | + |
| 12-46 | + |
| 12-47 | + |
| 12-48 | ++ |
| 12-49 | + |
| 12-50 | + |
| 12-51 | + |
| 12-52 | + |
| 12-53 | + |
| 12-54 | ++ |
| 12-55 | + |
| 12-56 | + |
| 12-57 | + |
| 12-58 | + |
| 12-59 | + |
| 12-60 | + |
| 12-61 | + |
| 12-62 | + |
| 12-63 | + |
| 12-64 | + |
| 12-65 | + |
| 12-66 | + |
| 12-67 | + |
| 12-68 | + |
| 12-69 | + |
| 12-70 | ++ |
| 12-71 | + |
| 12-72 | + |
| 12-73 | + |
| 12-74 | + |
| 12-75 | + |

TABLE 36-continued

CXCR3 ACTIVITY

| Compound Number | Activity |
|---|---|
| 12-76 | + |
| 12-77 | + |
| 12-78 | + |
| 12-79 | + |
| 12-80 | + |
| 12-81 | + |
| 12-82 | +++ |
| 12-83 | ++ |
| 12-84 | + |
| 12-85 | ++++ |
| 12-86 | +++ |
| 12-87 | + |
| 12-88 | + |
| 12-89 | ++++ |
| 12-90 | ++ |
| 12-91 | + |
| 12-92 | ++ |
| 12-93 | + |
| 12-94 | + |
| 12-95 | + |
| 12-96 | + |
| 12-97 | + |
| 12-98 | + |
| 12-99 | ++ |
| 12-100 | + |
| 12-101 | ++++ |
| 12-102 | ++ |
| 12-103 | + |
| 12-104 | + |
| 12-105 | ++++ |
| 12-106 | +++ |
| 12-107 | ++ |
| 12-108 | ++ |
| 12-109 | +++ |
| 12-110 | + |
| 12-111 | + |
| 12-112 | + |
| 12-113 | +++ |
| 12-114 | + |
| 12-115 | ++++ |
| 12-116 | ++ |
| 12-117 | ++ |
| 12-118 | + |
| 12-119 | +++ |
| 12-120 | + |
| 12-121 | + |
| 12-122 | + |
| 12-123 | + |
| 12-124 | +++ |
| 12-125 | ++ |
| 12-126 | ++ |
| 12-127 | ++ |
| 12-128 | + |
| 12-129 | +++ |
| 12-130 | + |
| 12-131 | + |
| 12-132 | ++ |
| 12-133 | ++ |
| 12-134 | ++ |
| 12-135 | + |
| 12-136 | + |
| 12-137 | ++ |
| 12-138 | + |
| 12-139 | + |
| 12-140 | + |
| 12-141 | + |
| 12-142 | + |
| 12-143 | + |
| 12-144 | + |
| 12-145 | + |
| 12-146 | ++++ |
| 12-147 | + |
| 12-148 | +++ |
| 12-149 | + |
| 12-150 | + |

TABLE 36-continued

CXCR3 ACTIVITY

| Compound Number | Activity |
|---|---|
| 12-151 | + |
| 12-152 | + |
| 12-153 | + |
| 12-154 | + |
| 12-155 | + |
| 12-156 | + |
| 12-157 | + |
| 12-158 | + |
| 12-159 | + |
| 13-1 | + |
| 13-2 | ++ |
| 13-3 | ++ |
| 13-4 | ++ |
| 13-5 | ++ |
| 13-6 | ++++ |
| 13-7 | ++ |
| 14-1 | +++ |
| 14-2 | + |
| 14-3 | + |
| 14-4 | + |
| 14-5 | +++ |
| 14-6 | + |
| 14-7 | ++++ |
| 14-8 | + |
| 14-9 | +++ |
| 14-10 | ++++ |
| 14-11 | ++ |
| 14-12 | ++ |
| 14-13 | +++ |
| 14-14 | ++ |
| 14-15 | +++ |
| 14-16 | +++ |
| 14-17 | + |
| 14-18 | + |
| 14-19 | ++ |
| 14-20 | +++ |
| 14-21 | ++ |
| 14-22 | +++ |
| 14-23 | ++ |
| 14-24 | + |
| 14-25 | + |
| 14-26 | ++ |
| 14-27 | ++++ |
| 14-28 | + |
| 14-29 | +++ |
| 15-1 | + |
| 15-2 | + |
| 15-3 | + |
| 15-4 | + |
| 15-5 | + |
| 15-6 | + |
| 15-7 | + |
| 15-8 | + |
| 15-9 | + |
| 15-10 | + |
| 15-11 | + |
| 15-12 | +++ |
| 15-13 | ++++ |
| 15-14 | ++ |
| 15-15 | + |
| 15-16 | + |
| 15-17 | ++++ |
| 15-18 | + |
| 15-19 | ++ |
| 15-20 | + |
| 15-21 | ++ |
| 15-22 | + |
| 15-23 | ++ |
| 15-24 | +++ |
| 15-25 | + |
| 15-26 | + |
| 15-27 | + |
| 15-28 | ++++ |
| 15-29 | + |
| 15-30 | ++ |

TABLE 36-continued

CXCR3 ACTIVITY

| Compound Number | Activity |
|---|---|
| 15-31 | + |
| 15-32 | +++ |
| 15-33 | + |
| 15-34 | + |
| 15-35 | + |
| 15-36 | + |
| 15-37 | ++ |
| 15-38 | + |
| 15-39 | +++ |
| 15-40 | ++ |
| 15-41 | ++++ |
| 15-42 | +++ |
| 15-43 | + |
| 15-44 | + |
| 15-45 | +++ |
| 15-46 | + |
| 15-47 | + |
| 15-48 | + |
| 15-49 | + |
| 15-50 | + |
| 15-51 | + |
| 15-52 | + |
| 15-53 | ++ |
| 15-54 | + |
| 15-55 | + |
| 15-56 | + |
| 15-57 | + |
| 15-58 | + |
| 15-59 | + |
| 15-60 | + |
| 15-61 | + |
| 15-62 | + |
| 15-63 | + |
| 15-64 | ++ |
| 16-1 | + |
| 17-1 | + |
| 17-2 | +++ |
| 17-3 | ++ |
| 17-4 | ++ |
| 18-1 | + |
| 19-1 | +++ |
| 20-1 | ++ |
| 21-1 | ++ |
| 22-1 | + |
| 22-2 | +++ |
| 22-3 | + |
| 23-1 | ++++ |
| 23-2 | ++ |
| 23-3 | + |
| 23-4 | ++ |
| 23-5 | +++ |
| 23-6 | ++ |
| 23-7 | +++ |
| 23-8 | +++ |
| 23-9 | ++ |
| 24-1 | ++ |
| 24-2 | ++ |
| 25-1 | ++ |
| 25-2 | ++ |
| 25-3 | +++ |
| 26-1 | + |
| 26-2 | + |
| 26-3 | + |
| 27-1 | + |
| 27-2 | +++ |
| 27-3 | + |
| 27-4 | + |
| 27-5 | + |
| 27-6 | ++ |
| 27-7 | + |
| 28-1 | + |
| 28-2 | + |
| 28-3 | +++ |
| 29-1 | ++ |
| 30-1 | ++ |
| 31-1 | + |
| 32-1 | ++ |
| 32-2 | + |
| 33-1 | + |
| 34-1 | + |
| 35-1 | + |
| 35-2 | + |

Example 49

DMPK Assays

Formulation and Dosing

Compounds were formulated in 5% DMSO/5% Tween20 in $H_2O$, sonicated, vortexed, and put on stir plate overnight at a dose volume of 10 mL/kg. Balb/C (Jackson laboratories) or C57bl/6 (Taconic Biosciences) mice (8-9 weeks old) were acclimated to the colony for 3 days prior to dosing. Water and food were provided ab libitum. Compounds were administered by oral gavage. Groups of six animals received 3 to 4 bleeds per day with one terminal bleed. The time points were 30 min, 1 h, 2 h, 4 h, 6 h, 8 h, 24 h. Plasma was collected via centrifugation and analyzed for drug concentrations.

Preparation of Study Samples and Standards for Analysis by LC-MS/MS

50 µl of plasma was aliquoted into a 96 well deep-well polypropylene plate (2 mL) to which 5 µL of DMSO was added. For standards, 5 µl of test compound in DMSO at 10λ the standard concentration was added to 50 µl of blank matrix in a 96 well deep-well polypropylene plate. For example, for a 300 nM standard, the 10× DMSO concentration was 3 µM. Study samples that require dilution are diluted with the appropriate blank matrix. For example, for a 10× dilution, 5 µL of study sample is added to 45 µl of blank matrix. Protein was precipitated from study samples and standards with the addition of 150 µl of acetonitrile. After a clean plate map was placed firmly over the top of the 96-well plate, a bench top shaker was used for 1 min to ensure complete precipitation of protein. The precipitated protein was pelleted by centrifuging for 3,000 rpm for 10 min at 20° C. and then the clear supernatant was transferred to a clean 96-well plate and spun again under the same conditions in order to pellet any solid material that may have been transferred.

Analysis of Study Samples and Standards with LCMS with MRM Detection

An Agilent 1200 HPLC with binary pump and a Leap CTC with fast wash autosampler were used to introduce samples to the mass spectrometer. The reversed phase chromatography method was as shown in the following Table 37.

TABLE 37

| Time (min) | % A: 0.1% Formic Acid in water | % B: 0.1% Formic Acid in Acetonitrile | Flow (uL/min) |
|---|---|---|---|
| 0 | 95 | 5 | 1000 |
| 0.5 | 95 | 5 | 1000 |
| 1.25 | 0 | 100 | 1000 |

TABLE 37-continued

| Time (min) | % A: 0.1% Formic Acid in water | % B: 0.1% Formic Acid in Acetonitrile | Flow (uL/min) |
|---|---|---|---|
| 2.5 | 0 | 100 | 1000 |
| 3 | 95 | 5 | 1000 |
| 4 | 95 | 5 | 1000 |

The column used was a Phenomenex Luna C8 30×2 mm 5 μm with a security guard. Mass detection was performed by an Applied Biosystems 4000 Qtrap in MRM mode and ionization was achieved by positive electrospray with a source temperature of 500° C. The ion transitions, depolarizing potential and collision energies were dependent on the specific analyte.

Prepared samples were usually analyzed in reverse chronological order with bracketing standard curves. Typically at least 6 standards were used for quantification with a percent accuracy of +/−15% for all standards except at the LLOQ where a percent accuracy of +/−20% was allowed. The concentration time profile was fit using a one compartment model for the applicable mode of dosing using Phoenix WinNonLin 6.4.

The results of these assays are presented in the following Tables 38, 39 and 40.

TABLE 38

PHARMACOKINETIC PROPERTIES
BALB/c, 10 MG/KG, PO, MALE MICE

| Compound Number | Clearance (mL/min/kg) | $C_{max}$ (mM) | $AUC_{0-24}$ (mM*hr) |
|---|---|---|---|
| A | BQL | 0.004 | BLQ |
| B | BQL | 0.007 | BLQ |
| 1-20 | 527 | 0.23 | 0.53 |
| 1-25 | 782 | 0.07 | 0.34 |
| 1-26 | 41000 | 0.003 | 0.006 |
| 2-1 | 66 | 1.8 | 4.3 |
| 2-2 | — | 3.5 | — |
| 2-3 | 403 | 0.4 | 0.8 |
| 2-5 | 389 | 0.5 | 0.8 |
| 2-7 | 86 | 1.9 | 3.3 |
| 2-18 | 47 | 2.9 | 6.2 |
| 2-19 | 59 | 1.3 | 4.9 |
| 2-21 | 65 | 0.9 | 4.3 |
| 2-22 | 10 | 4.2 | 27 |
| 2-24 | 23 | 3.3 | 12.3 |
| 2-26 | 76 | 0.9 | 3.8 |
| 4-3 | 4627 | 0.03 | 0.06 |
| 4-4 | 10709 | 0.02 | 0.03 |
| 4-6 | 158 | 1.2 | 1.7 |
| 8-3 | 56 | 0.8 | 4.9 |

BQ: Below limit of quantification (limit amount)

TABLE 39

Pharmacokinetic Properties
C57BL/6, 10 mg/kg, PO, Male Mice

| Compound Number | Clearance (mL/min/kg) | $C_{max}$ (mM) | $AUC_{0-24}$ (mM * hr) |
|---|---|---|---|
| A | BQL | 0.002 | BQL |
| B | 9000 | 0.03 | 0.029 |
| 1-14 | 27000 | 0.006 | 0.011 |
| 2-2 | 176 | 0.9 | 1.7 |
| 2-15 | 37 | 0.97 | 7.5 |
| 2-22 | 19 | 2.9 | 15.1 |
| 2-24 | 38 | 1 | 7 |
| 4-6 | 2346 | 0.07 | 0.11 |
| 4-12 | 32 | 3.3 | 9 |
| 6-4 | 33 | 0.81 | 8.3 |
| 8-2 | 112 | 0.71 | 2.3 |
| 8-3 | 246 | 0.33 | 1.2 |

BQL: Below limit of quantification (limit amount)
ND: Not determined

TABLE 40

Pharmacokinetic Properties
C57BL/6, 60 mg/kg, PO

| Compound Number | Mice Gender | Clearance (mL/min/kg) | $C_{max}$ (mM) | $AUC_{0-24}$ (mM * hr) |
|---|---|---|---|---|
| 2-2 | Male | 266 | 2.7 | 6.7 |
| 2-23 | Male | 88 | 3.9 | 19 |
| 2-24 | Male | 58 | 3 | 29 |
| 2-47 | Female | 66 | 7.6 | 27.5 |
| 2-49 | Female | 131 | 7.1 | 14.1 |
| 2-55 | Female | 176 | 3 | 9.9 |
| 2-57 | Female | 393 | 1.5 | 4.4 |
| 4-14 | Female | 16 | 5.2 | 99 |
| 10-8 | Female | 431 | 1.5 | 3.9 |
| 10-9 | Female | 132 | 4.3 | 12.4 |
| 12-88 | Female | 280 | 3.1 | 6 |
| 12-100 | Female | ND | 0.37 | BQL |
| 12-114 | Female | 823 | 0.6 | 2.1 |
| 12-138 | Female | 851 | 0.5 | 1.8 |
| 12-152 | Female | 190 | 2.8 | 8.3 |
| 14-17 | Female | 22 | 22 | 78 |
| 14-18 | Female | 222 | 3.2 | 7.7 |
| 14-28 | Female | 47 | 5.2 | 33.8 |
| 15-2 | Female | 347 | 1.8 | 4.6 |
| 15-3 | Female | 666 | 0.6 | 2.4 |
| 15-6 | Female | 90 | 5.7 | 17.6 |
| 15-48 | Female | 98 | 6.7 | 16.3 |
| 15-62 | Female | 1100 | 0.6 | 1.4 |
| 18-1 | Female | 565 | 1.2 | 2.9 |
| 22-1 | Female | 34 | 7.3 | 48 |
| 27-3 | Female | 143 | 5.1 | 11.7 |
| 27-7 | Female | 92 | 4.3 | 17.6 |

BQL: Below limit of quantification (limit amount)
ND: Not determined

All of the U.S. patents, U.S. patent application publications, U.S. patent applications, foreign patents, foreign patent applications, and non-patent publications referred to in this specification, and/or listed in the Application Data Sheet, including U.S. Provisional Patent Application Nos. 62/383,202 filed on Sep. 2, 2016, and 62/478,496 filed on Mar. 29, 2017 are incorporated herein by reference, in their entirety. Aspects of the embodiments can be modified, if necessary to employ concepts of the various patents, applications, and publications to provide yet further embodiments.

While specific embodiments of the invention have been illustrated and described, it will be readily appreciated that the various embodiments described above can be combined to provide further embodiments, and that various changes can be made therein without departing from the spirit and scope of the invention. These and other changes can be made to the embodiments in light of the above-detailed description.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A compound having the structure of Formula I:

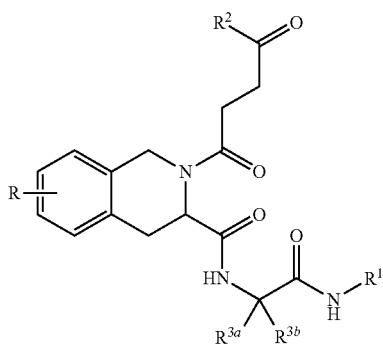

or a stereoisomer, isotope or pharmaceutically acceptable salt thereof, wherein:

R is hydrogen, hydroxy, cyano, halo or —OS(=O)$_2$R$^6$;

R$^1$ is aryl or heteroaryl and substituted with 0-4 R$^4$ groups;

R$^2$ is aryl or heteroaryl and substituted with 0-3 R$^5$ groups, or R$^2$ is —NR$^8$R$^9$;

R$^{3a}$ is hydrogen or alkyl and R$^{3b}$ is a nitrogen- or amine-containing moiety of carbon, at least one nitrogen atom and hydrogen, or R$^{3a}$ and R$^{3b}$ taken together with the carbon to which they are attached form a cyclic nitrogen- or amine-containing moiety of carbon, at least one nitrogen atom and hydrogen;

R$^4$ and R$^5$ are, at each occurrence, cyano, halo, alkyl, haloalkyl, aminoalkyl, hydroxyalkyl, hydroxy, alkoxy, phenyl, heterocyclyl, —S(=O)$_2$R$^6$, —C(=O)R$^6$, —C(=O)OR$^6$, —C(=O)NR$^6$N$^7$ or —NR$^6$R$^7$;

R$^6$ and R$^7$ are, at each occurrence, hydrogen or alkyl; and

R$^8$ is hydrogen or alkyl and R$^9$ is alkyl or aryl substituted with 0-4 R$^4$ groups, or R$^8$ and R$^9$ taken together with the nitrogen atom to which they are attached form a heterocyclyl substituted with 0-4 R$^4$ groups and optionally substituted with oxo (=O) or thioxo (=S).

2. The compound of claim 1, wherein R$^1$ is aryl substituted with 0-4 R$^4$ groups.

3. The compound of claim 1, wherein R$^1$ is heteroaryl substituted with 0-4 R$^4$ groups.

4. The compound of claim 1, wherein R$^2$ is aryl substituted with 0-3 R$^5$ groups.

5. The compound of claim 1, wherein R$^2$ is heteroaryl substituted with 0-3 R$^5$ groups.

6. The compound of claim 1, wherein R$^1$ and R$^2$ are phenyl, and the compound has the structure of Formula II, or a stereoisomer, isotope or pharmaceutically acceptable salt thereof:

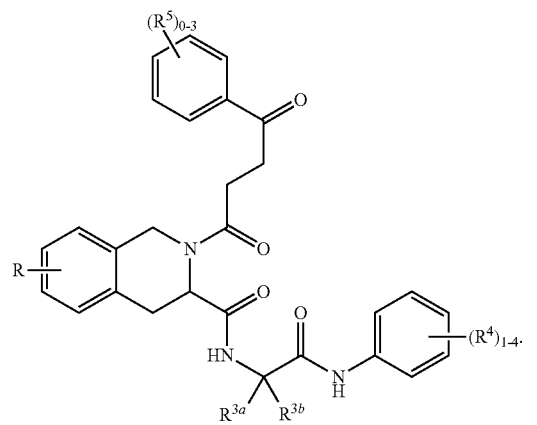

7. The compound of claim 1, wherein R$^1$ is substituted with at least two R$^4$ groups.

8. The compound of claim 1, wherein R$^1$ is substituted with at least three R$^4$ groups.

9. The compound of claim 1, wherein R$^1$ is substituted with at least three R$^4$ groups individually selected from halo and alkyl.

10. The compound of claim 1, wherein R$^2$ is substituted with zero R$^5$ groups.

11. The compound of claim 1, wherein R$^1$ and R$^2$ are phenyl, R$^{3a}$ is hydrogen, and the compound has the structure of Formula III, or a stereoisomer, isotope or pharmaceutically acceptable salt thereof:

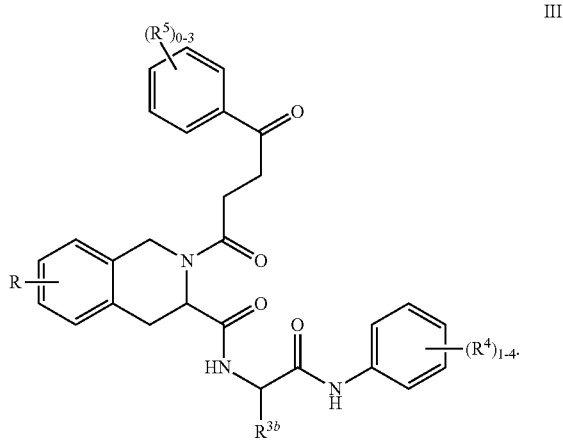

12. The compound of claim 1, wherein R$^1$ and R$^2$ are phenyl, R$^{3a}$ is hydrogen, and the compound has the structure of Formula IV, or a stereoisomer, isotope or pharmaceutically acceptable salt thereof:

IV

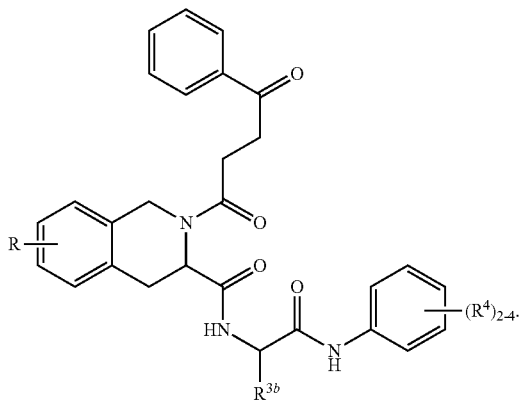

13. The compound of claim 1, wherein $R^2$ is $-NR^8R^9$ and the compound has the structure of Formula V, or a stereoisomer, isotope or pharmaceutically acceptable salt thereof:

V

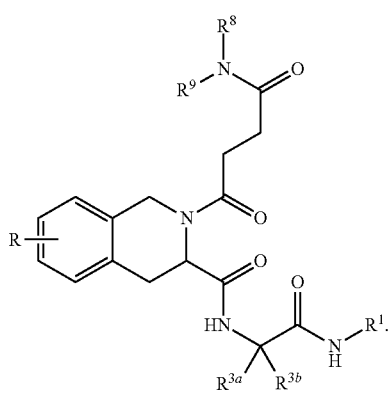

14. The compound of claim 13, wherein $R^8$ is hydrogen or alkyl and $R^9$ is alkyl or aryl substituted with 0-4 $R^4$ groups.

15. The compound of claim 13, wherein $R^8$ and $R^9$ taken together with the nitrogen atom to which they are attached form a heterocyclyl substituted with 0-4 $R^4$ groups and optionally substituted with oxo (=O) or thioxo (=S).

16. The compound of claim 1, wherein $R^2$ is $-NR^8R^9$ and $R^8$ and $R^9$ taken together with the nitrogen atom to which they are attached form a heterocyclyl, and the compound has the structure of Formula VI, or a stereoisomer, isotope or pharmaceutically acceptable salt thereof:

VI

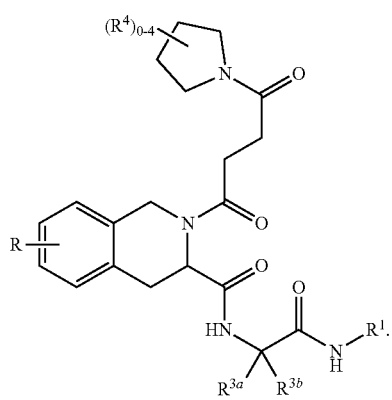

17. The compound of claim 1, wherein $R^2$ is $-NR^8R^9$ and $R^8$ and $R^9$ taken together with the nitrogen atom to which they are attached form a heterocyclyl, and the compound has the structure of Formula VII, or a stereoisomer, isotope or pharmaceutically acceptable salt thereof:

VII

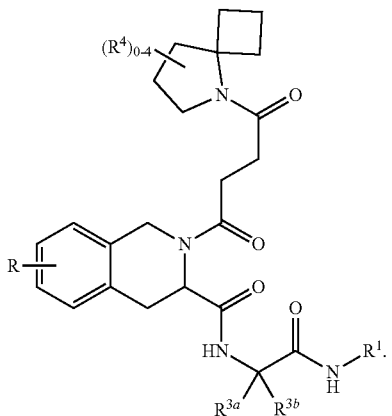

18. The compound of claim 1, wherein $R^2$ is $-NR^8R^9$ and $R^8$ and $R^9$ taken together with the nitrogen atom to which they are attached form a heterocyclyl, and the compound has the structure of Formula VIII, or a stereoisomer, isotope or pharmaceutically acceptable salt thereof:

VIII

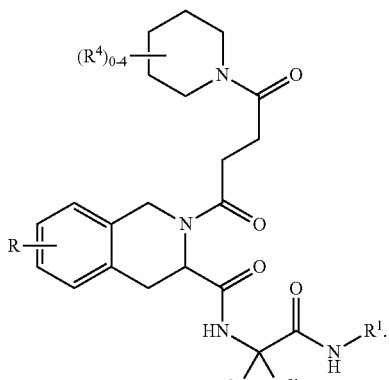

19. The compound of claim 1, wherein $R^2$ is —$NR^8R^9$ and $R^8$ and $R^9$ taken together with the nitrogen atom to which they are attached form a heterocyclyl, and the compound has the structure of Formula IX, or a stereoisomer, isotope or pharmaceutically acceptable salt thereof:

IX

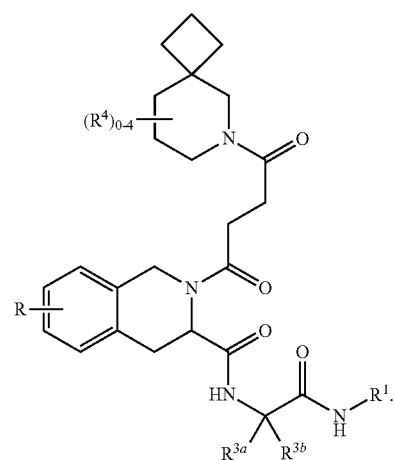

20. The compound of claim 1, wherein $R^2$ is —$NR^8R^9$ and $R^8$ and $R^9$ taken together with the nitrogen atom to which they are attached form a heterocyclyl, and the compound has the structure of Formula X, or a stereoisomer, isotope or pharmaceutically acceptable salt thereof:

X

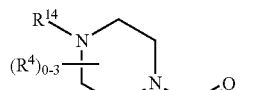
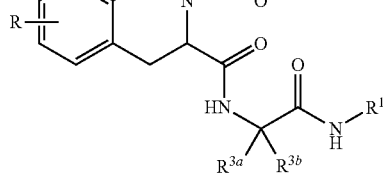

wherein $R^{14}$ is H or $R^4$.

21. The compound of claim 1, wherein $R^{3a}$ is hydrogen and $R^{3b}$ is a nitrogen- or amine-containing moiety of carbon, at least one nitrogen atom and hydrogen.

22. The compound of claim 21, wherein $R^{3b}$ is a nitrogen-containing heterocyclyl substituted with 0-4 $R^4$ groups, or wherein $R^{3b}$ is alkyl substituted with —$NR^{10}R^{11}$, —$N^+R^{10}R^{11}R^{12}$, —$NR^{12}C(=O)NR^{10}R^{11}$, —$C(=O)NR^{10}R^{11}$, —$NR^{12}C(=O)CH_2NR^{10}R^{11}$, —$NR^{12}N(=NR^{13})NR^{10}R^{11}$, —$NR^{10}SO_2R^{11}$, or a nitrogen-containing heterocyclyl substituted with 0-4 $R^4$ groups, and wherein $R^{10}$, $R^{11}$, $R^{12}$ and $R^{13}$ are independently hydrogen, alkyl or haloalkyl.

23. The compound of claim 22, wherein $R^{3b}$ is alkyl substituted with —$NR^{10}R^{11}$ or $N^+R^{10}R^{11}R^{12}$.

24. The compound of claim 23, wherein $R^{3b}$ is —$(CH_2)_{2-4}NH_2$.

25. The compound of claim 22, wherein $R^{3b}$ is alkyl substituted with —$NR^{12}N(=NR^{13})NR^{10}R^{11}$.

26. The compound of claim 22, wherein $R^{3b}$ is alkyl substituted with —$C(=O)NR^{10}R^{11}$, —$NR^{12}C(=O)NR^{10}R^{11}$ or —$NR^{12}C(=O)CH_2NR^{10}R^{11}$.

27. The compound of claim 22, wherein $R^{3b}$ is alkyl substituted with a nitrogen-containing heterocyclyl substituted with 0-4 $R^4$ groups.

28. The compound of claim 1, wherein $R^{3a}$ and $R^{3b}$ taken together with the carbon to which they are attached form a cyclic nitrogen- or amine-containing moiety of carbon, at least one nitrogen atom and hydrogen.

29. The compound of claim 28, wherein $R^{3a}$ and $R^{3b}$ taken together with the carbon to which they are attached form a nitrogen-containing heterocyclyl substituted with 0-4 $R^4$ groups.

30. The compound of claim 1, wherein the compound is a compound of Table A:

TABLE A
| Structure | Cpd. No. |
| --- | --- |
| 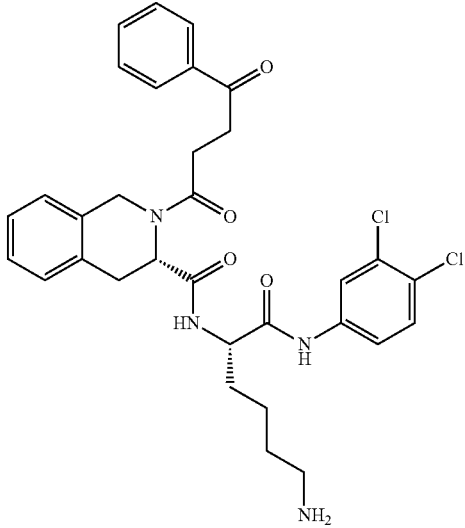 | 1-1 |
| 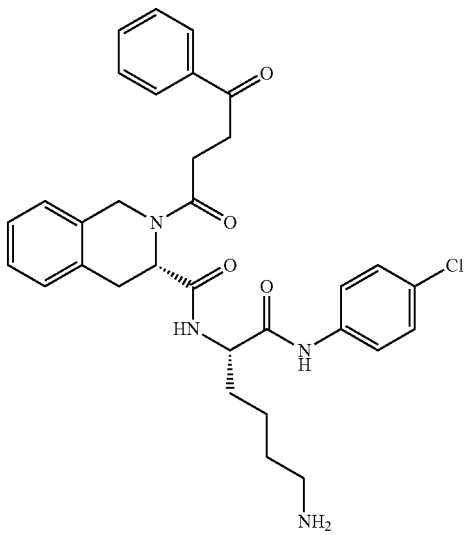 [SMILES: NCCCC[C@H](NC(=O)[C@@H]1Cc2ccccc2CN1C(=O)CCC(=O)c1ccccc1)C(=O)Nc1ccc(Cl)cc1] | 1-2 |
| 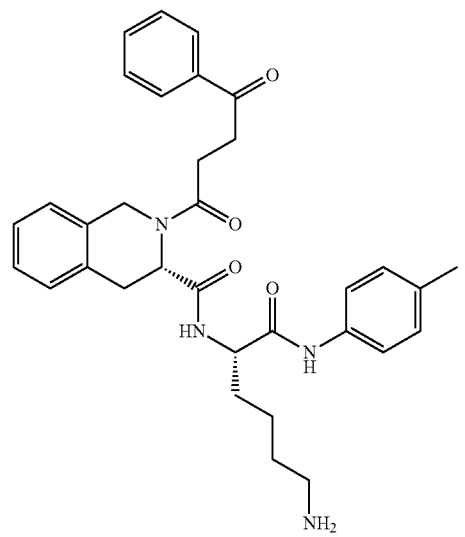 [SMILES: Cc1ccc(NC(=O)[C@H](CCCCN)NC(=O)[C@@H]2Cc3ccccc3CN2C(=O)CCC(=O)c2ccccc2)cc1] | 1-3 |

TABLE A-continued

| Structure | Cpd. No. |
|---|---|
| 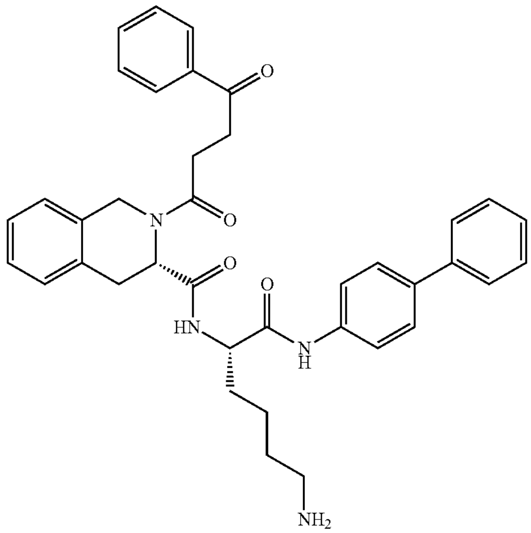 [SMILES: NCCCC[C@H](NC(=O)[C@@H]1Cc2ccccc2CN1C(=O)CCC(=O)c1ccccc1)C(=O)Nc1ccc(-c2ccccc2)cc1] | 1-5 |
| 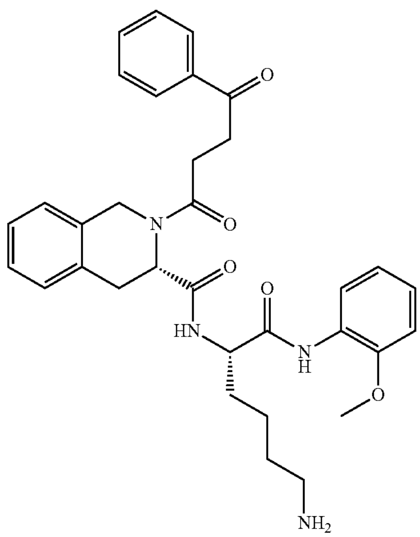 [SMILES: COc1ccccc1NC(=O)[C@H](CCCCN)NC(=O)[C@@H]1Cc2ccccc2CN1C(=O)CCC(=O)c1ccccc1] | 1-6 |
| 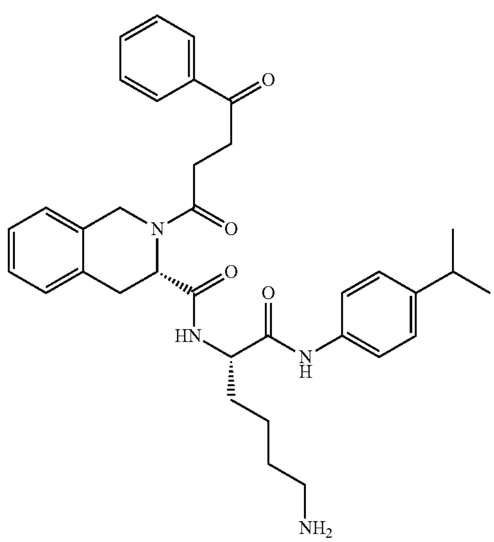 [SMILES: CC(C)c1ccc(NC(=O)[C@H](CCCCN)NC(=O)[C@@H]2Cc3ccccc3CN2C(=O)CCC(=O)c2ccccc2)cc1] | 1-7 |

TABLE A-continued
| Structure | Cpd. No. |
|---|---|
| 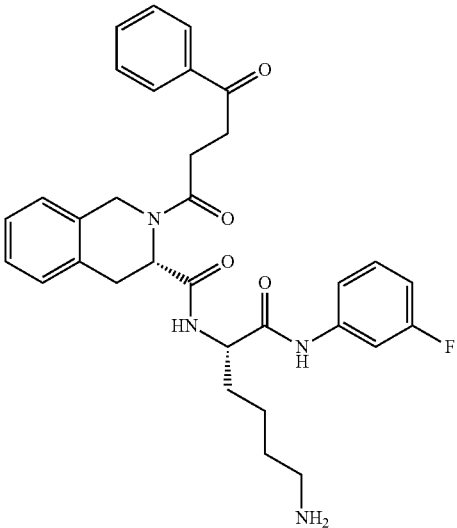 [SMILES: NCCCC[C@H](NC(=O)[C@@H]1Cc2ccccc2CN1C(=O)CCC(=O)c1ccccc1)C(=O)Nc1cccc(F)c1] | 1-8 |
| 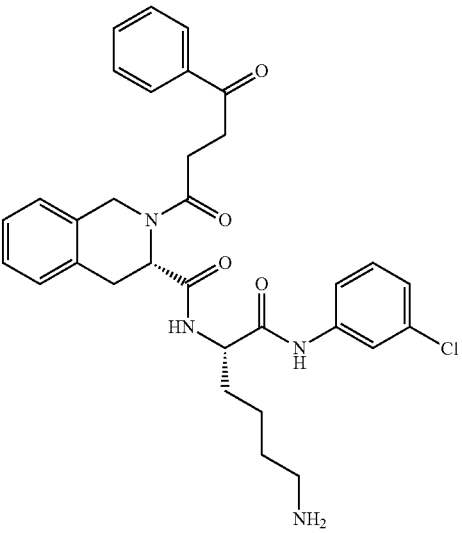 [SMILES: NCCCC[C@H](NC(=O)[C@@H]1Cc2ccccc2CN1C(=O)CCC(=O)c1ccccc1)C(=O)Nc1cccc(Cl)c1] | 1-9 |
| 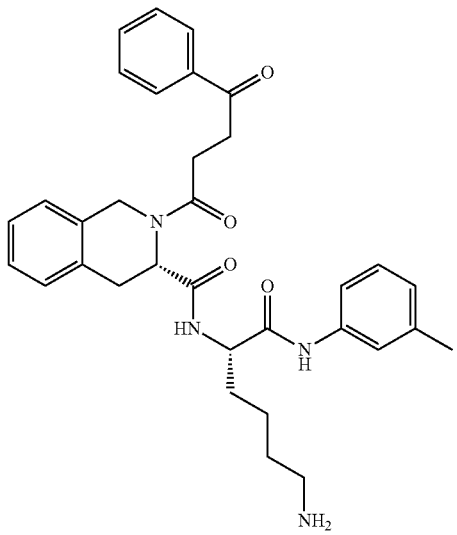 [SMILES: Cc1cccc(NC(=O)[C@H](CCCCN)NC(=O)[C@@H]2Cc3ccccc3CN2C(=O)CCC(=O)c2ccccc2)c1] | 1-10 |

TABLE A-continued
| Structure | Cpd. No. |
|---|---|
| 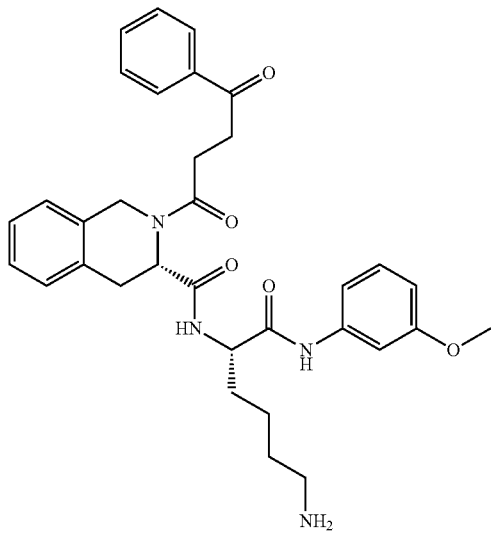 [SMILES: COc1cccc(NC(=O)[C@H](CCCCN)NC(=O)[C@@H]2Cc3ccccc3CN2C(=O)CCC(=O)c2ccccc2)c1] | 1-11 |
| 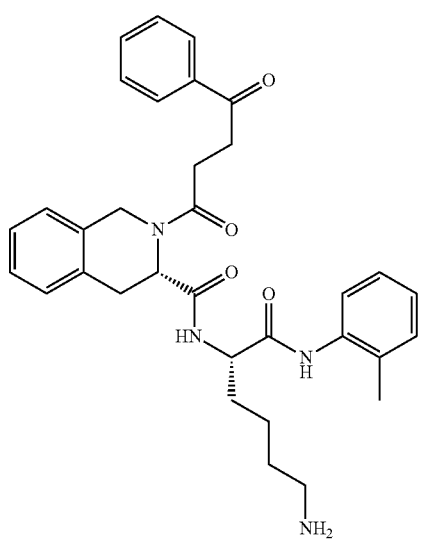 | 1-12 |
| 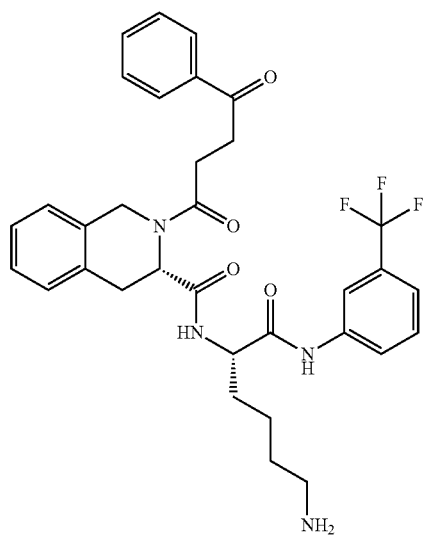 [SMILES: NCCCC[C@H](NC(=O)[C@@H]1Cc2ccccc2CN1C(=O)CCC(=O)c1ccccc1)C(=O)Nc1cccc(C(F)(F)F)c1] | 1-13 |

TABLE A-continued

| Structure | Cpd. No. |
|---|---|
| 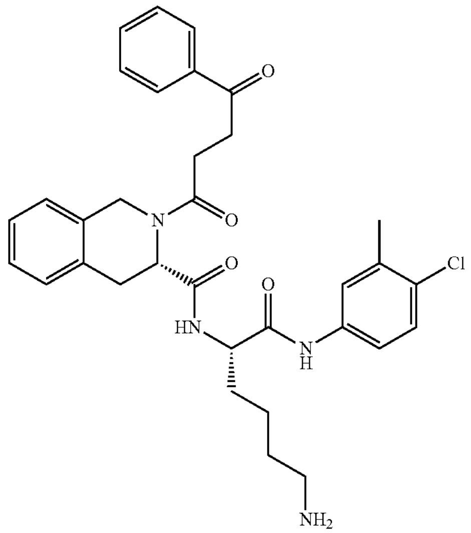 [SMILES: Cc1cc(NC(=O)[C@H](CCCCN)NC(=O)[C@@H]2Cc3ccccc3CN2C(=O)CCC(=O)c2ccccc2)ccc1Cl] | 1-14 |
| 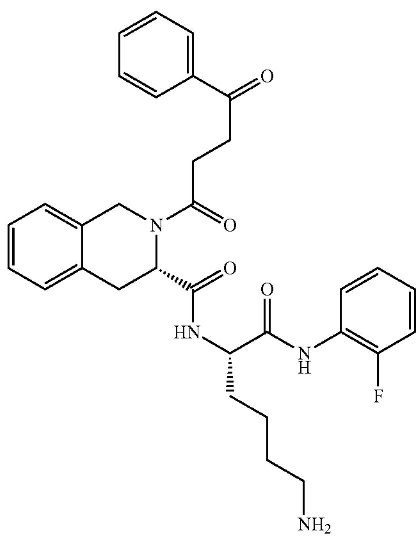 | 1-15 |
| 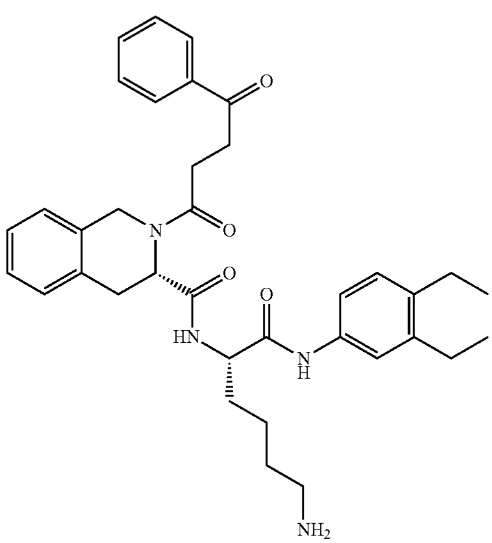 [SMILES: CCc1ccc(NC(=O)[C@H](CCCCN)NC(=O)[C@@H]2Cc3ccccc3CN2C(=O)CCC(=O)c2ccccc2)cc1CC] | 1-16 |

TABLE A-continued

| Structure | Cpd. No. |
|---|---|
| 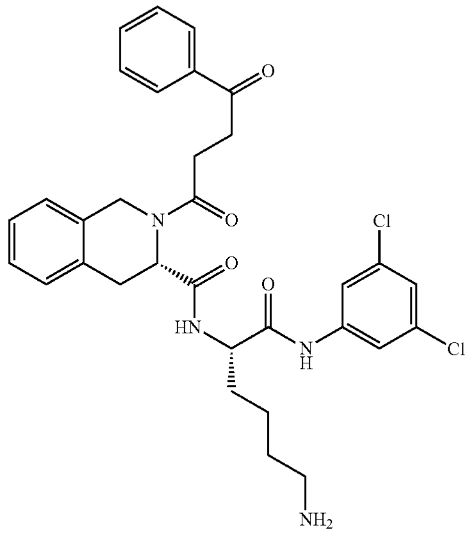 [SMILES: NCCCC[C@H](NC(=O)[C@@H]1Cc2ccccc2CN1C(=O)CCC(=O)c1ccccc1)C(=O)Nc1cc(Cl)cc(Cl)c1] | 1-17 |
| 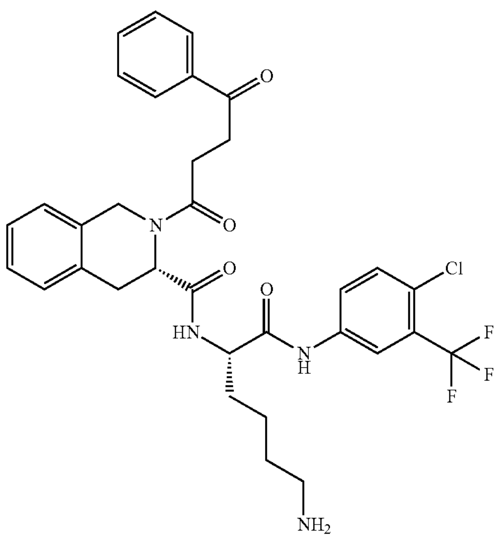 [SMILES: NCCCC[C@H](NC(=O)[C@@H]1Cc2ccccc2CN1C(=O)CCC(=O)c1ccccc1)C(=O)Nc1ccc(Cl)c(C(F)(F)F)c1] | 1-18 |
| 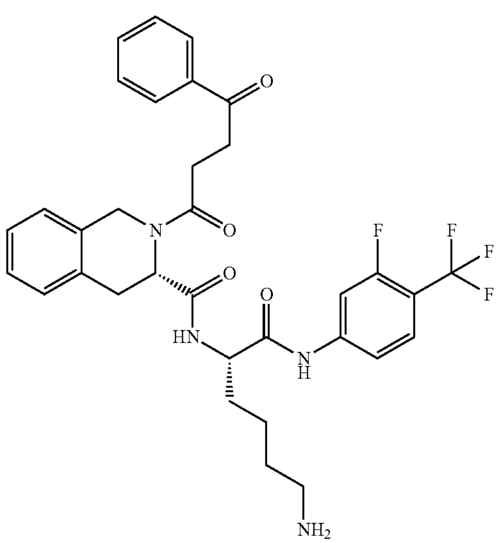 [SMILES: NCCCC[C@H](NC(=O)[C@@H]1Cc2ccccc2CN1C(=O)CCC(=O)c1ccccc1)C(=O)Nc1ccc(C(F)(F)F)c(F)c1] | 1-19 |

TABLE A-continued
| Structure | Cpd. No. |
|---|---|
| 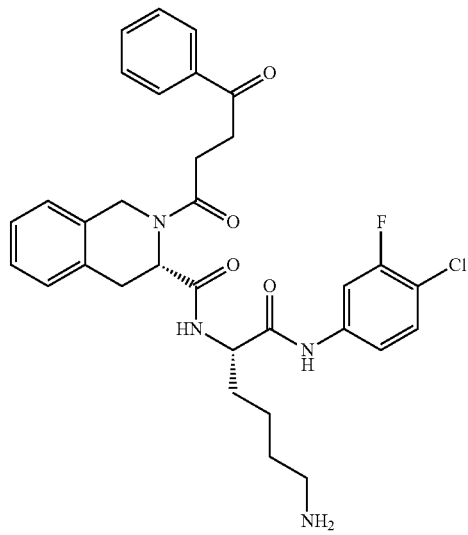 [SMILES: NCCCC[C@H](NC(=O)[C@@H]1Cc2ccccc2CN1C(=O)CCC(=O)c1ccccc1)C(=O)Nc1ccc(Cl)c(F)c1] | 1-20 |
| 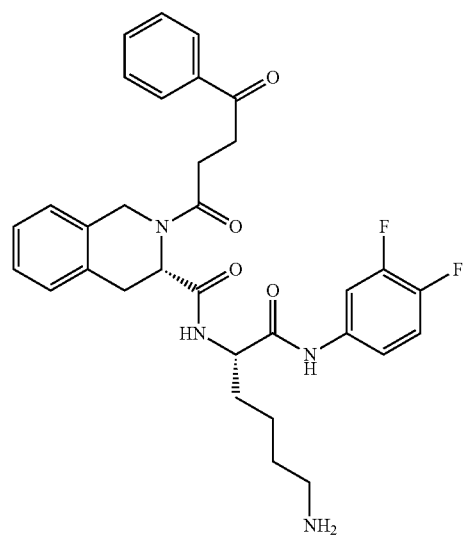 [SMILES: NCCCC[C@H](NC(=O)[C@@H]1Cc2ccccc2CN1C(=O)CCC(=O)c1ccccc1)C(=O)Nc1ccc(F)c(F)c1] | 1-21 |
| 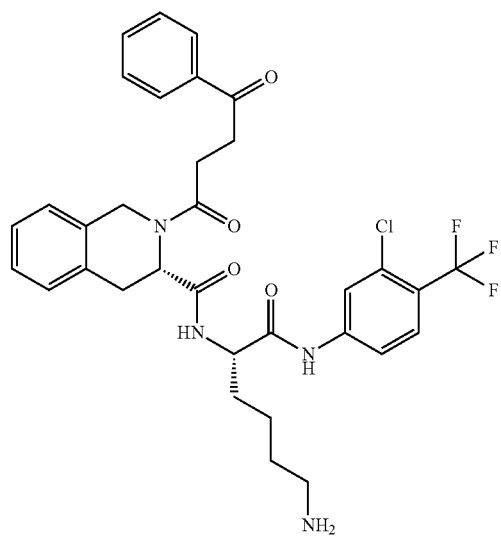 | 1-22 |

TABLE A-continued
| Structure | Cpd. No. |
|---|---|
| 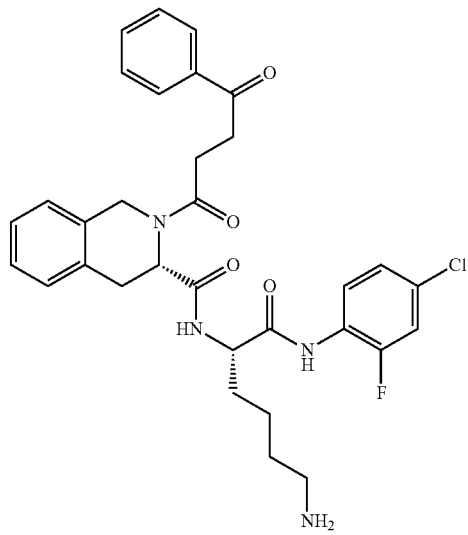 | 1-23 |
| 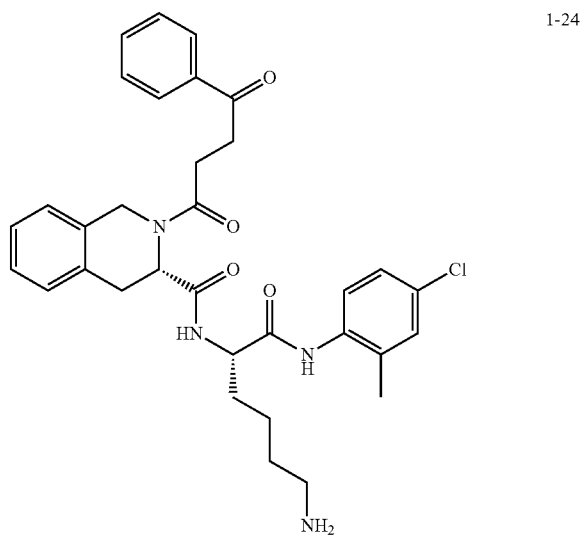 | 1-24 |
| 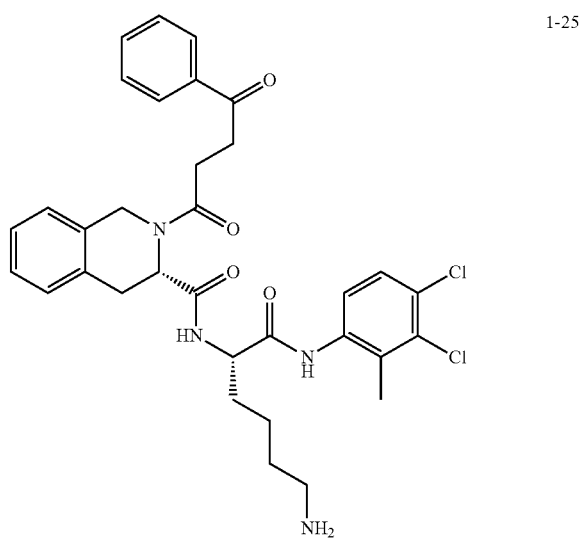 | 1-25 |

TABLE A-continued
| Structure | Cpd. No. |
|---|---|
| 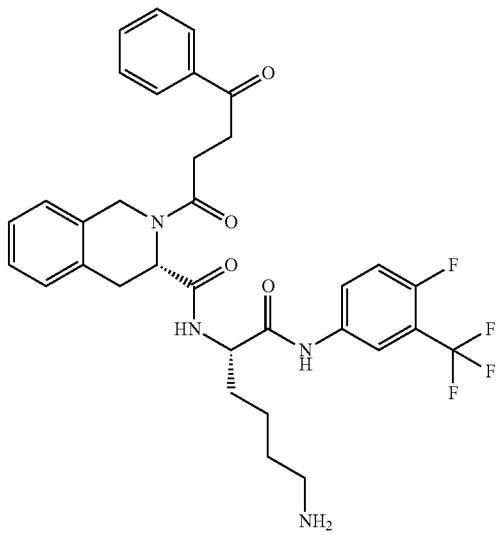 [SMILES: NCCCC[C@H](NC(=O)[C@@H]1Cc2ccccc2CN1C(=O)CCC(=O)c1ccccc1)C(=O)Nc1ccc(F)c(C(F)(F)F)c1] | 1-26 |
| 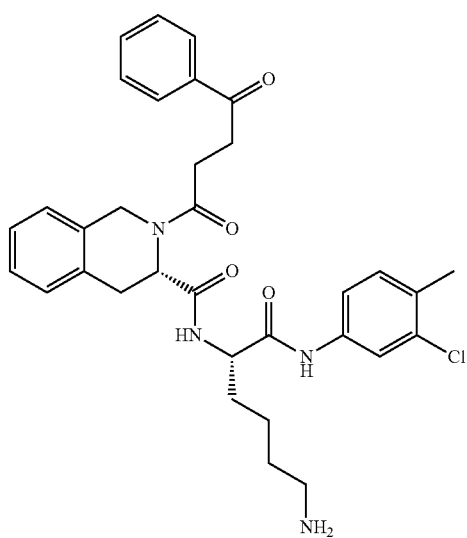 [SMILES: Cc1ccc(NC(=O)[C@H](CCCCN)NC(=O)[C@@H]2Cc3ccccc3CN2C(=O)CCC(=O)c2ccccc2)cc1Cl] | 1-27 |
| 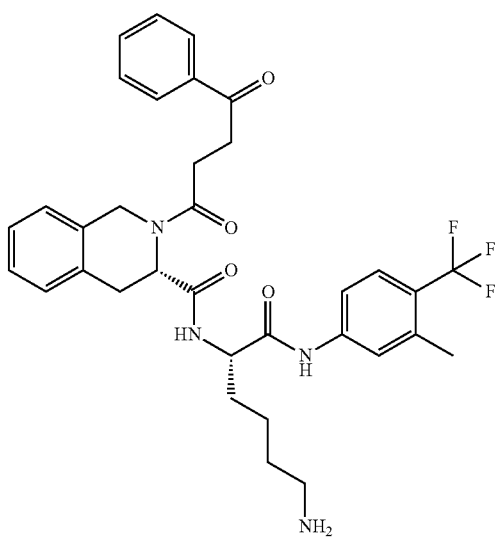 [SMILES: Cc1cc(NC(=O)[C@H](CCCCN)NC(=O)[C@@H]2Cc3ccccc3CN2C(=O)CCC(=O)c2ccccc2)ccc1C(F)(F)F] | 1-28 |

TABLE A-continued
| Structure | Cpd. No. |
|---|---|
| 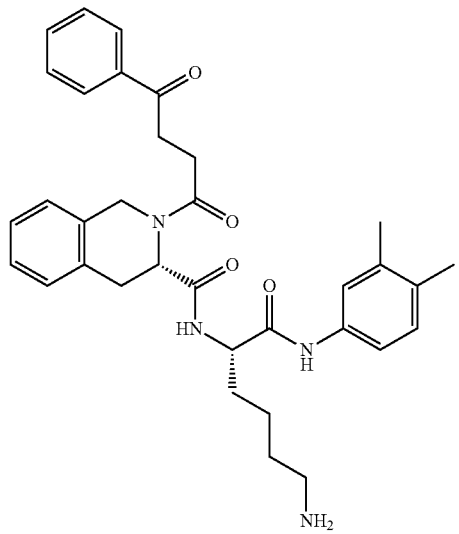 [SMILES: Cc1ccc(NC(=O)[C@H](CCCCN)NC(=O)[C@@H]2Cc3ccccc3CN2C(=O)CCC(=O)c2ccccc2)cc1C] | 1-29 |
| 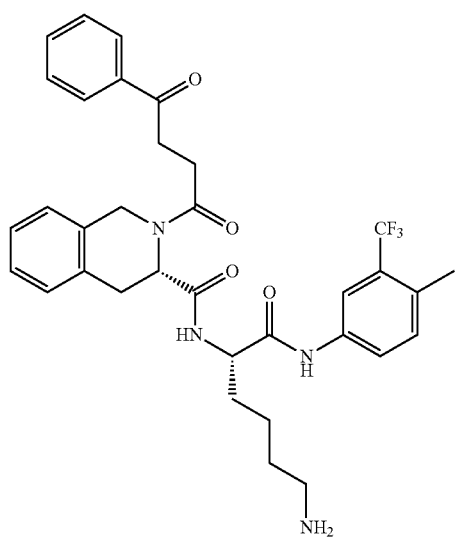 | 1-30 |
| 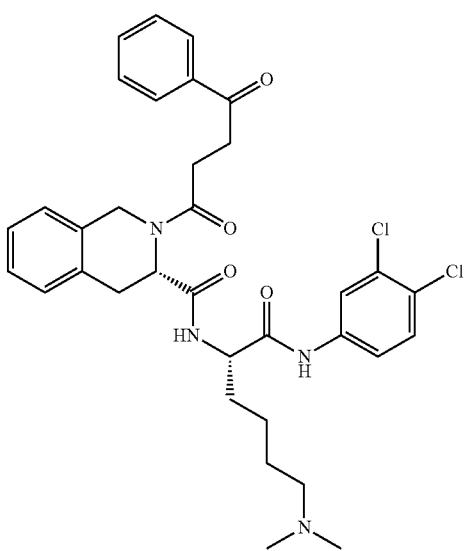 [SMILES: CN(C)CCCC[C@H](NC(=O)[C@@H]1Cc2ccccc2CN1C(=O)CCC(=O)c1ccccc1)C(=O)Nc1ccc(Cl)c(Cl)c1] | 1-31 |

TABLE A-continued
| Structure | Cpd. No. |
|---|---|
| 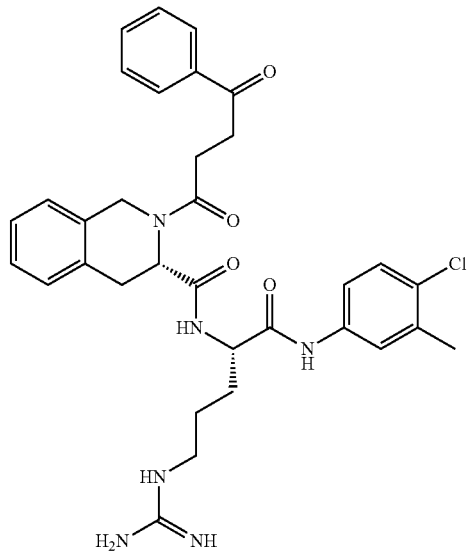 [SMILES: Cc1cc(NC(=O)[C@H](CCCNC(=N)N)NC(=O)[C@@H]2Cc3ccccc3CN2C(=O)CCC(=O)c2ccccc2)ccc1Cl] | 1-32 |
| 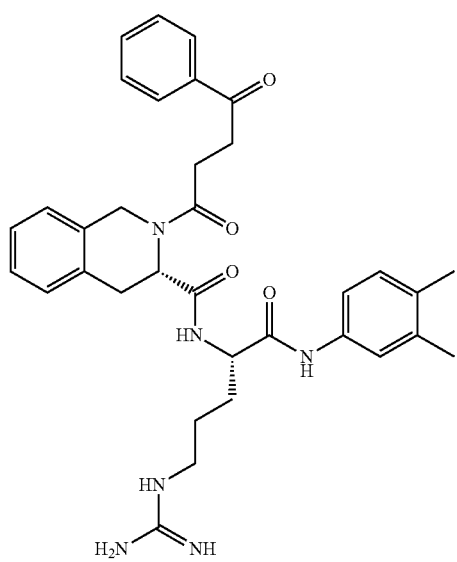 [SMILES: Cc1ccc(NC(=O)[C@H](CCCNC(=N)N)NC(=O)[C@@H]2Cc3ccccc3CN2C(=O)CCC(=O)c2ccccc2)cc1C] | 1-33 |

TABLE A-continued
| Structure | Cpd. No. |
|---|---|
| 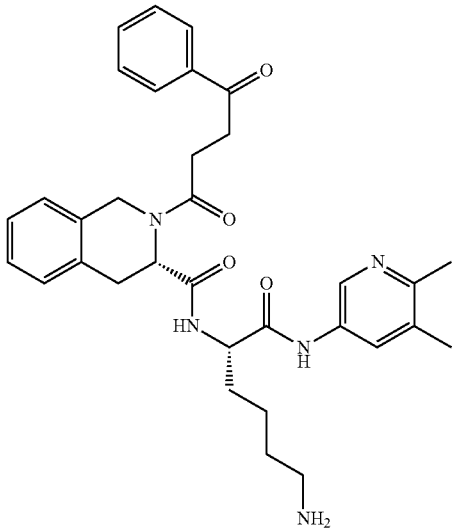 [SMILES: Cc1cc(NC(=O)[C@H](CCCCN)NC(=O)[C@@H]2Cc3ccccc3CN2C(=O)CCC(=O)c2ccccc2)cnc1C] | 1-34 |
| 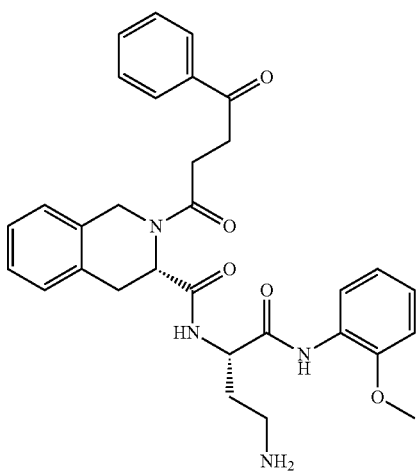 [SMILES: COc1ccccc1NC(=O)[C@H](CCN)NC(=O)[C@@H]1Cc2ccccc2CN1C(=O)CCC(=O)c1ccccc1] | 1-35 |
| 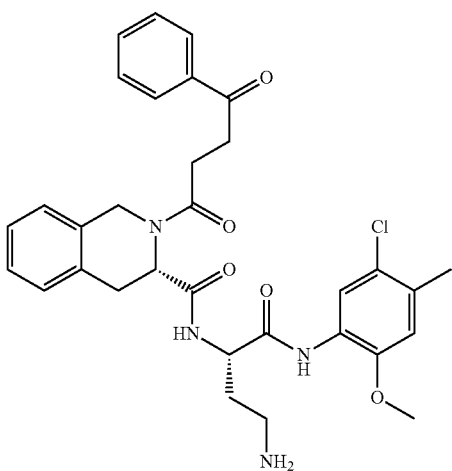 [SMILES: COc1cc(C)c(Cl)cc1NC(=O)[C@H](CCN)NC(=O)[C@@H]1Cc2ccccc2CN1C(=O)CCC(=O)c1ccccc1] | 1-36 |

TABLE A-continued
| Structure | Cpd. No. |
|---|---|
| 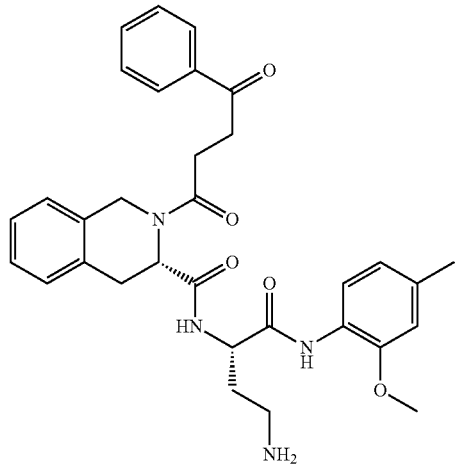 [SMILES: COc1cc(C)ccc1NC(=O)[C@H](CCN)NC(=O)[C@@H]1Cc2ccccc2CN1C(=O)CCC(=O)c1ccccc1] | 1-37 |
| 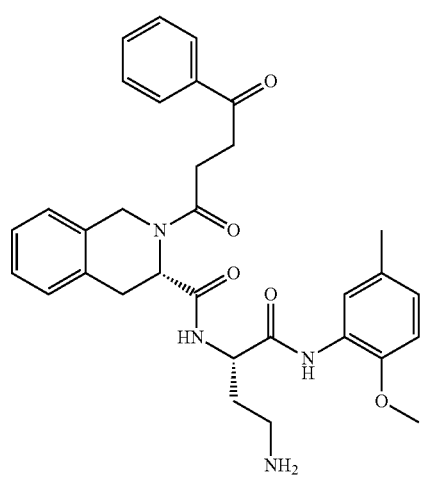 [SMILES: COc1ccc(C)cc1NC(=O)[C@H](CCN)NC(=O)[C@@H]1Cc2ccccc2CN1C(=O)CCC(=O)c1ccccc1] | 1-38 |
| 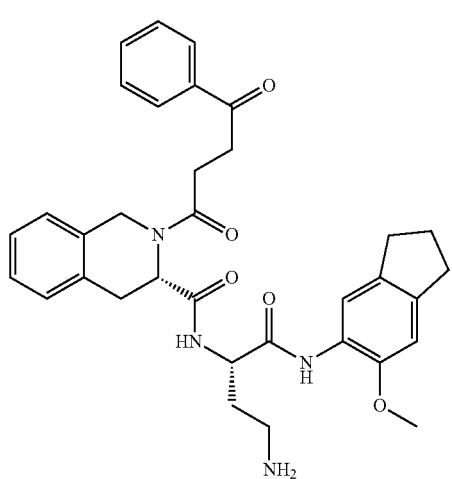 [SMILES: COc1cc2c(cc1NC(=O)[C@H](CCN)NC(=O)[C@@H]1Cc3ccccc3CN1C(=O)CCC(=O)c1ccccc1)CCC2] | 1-39 |

TABLE A-continued
| Structure | Cpd. No. |
|---|---|
| 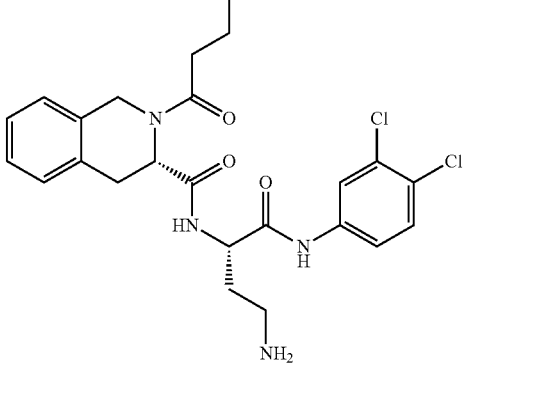 | 2-1 |
| 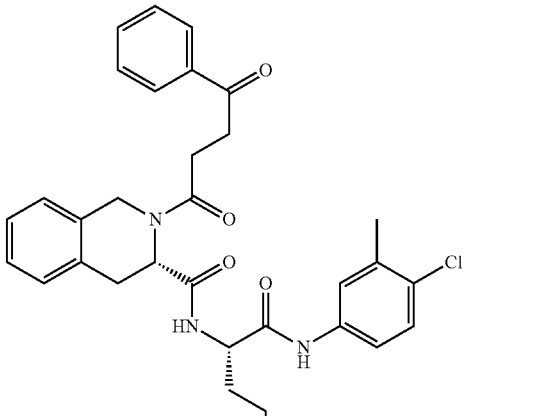 | 2-2 |
| 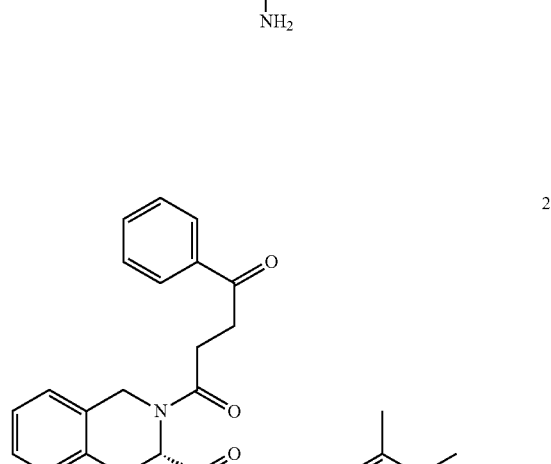 | 2-3 |

TABLE A-continued

| Structure | Cpd. No. |
|---|---|
| 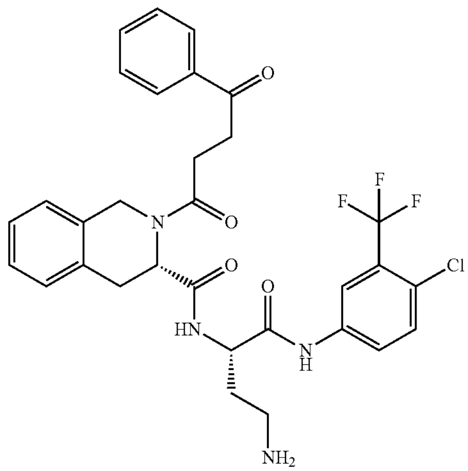 [SMILES: NCC[C@H](NC(=O)[C@@H]1Cc2ccccc2CN1C(=O)CCC(=O)c1ccccc1)C(=O)Nc1ccc(Cl)c(C(F)(F)F)c1] | 2-4 |
| 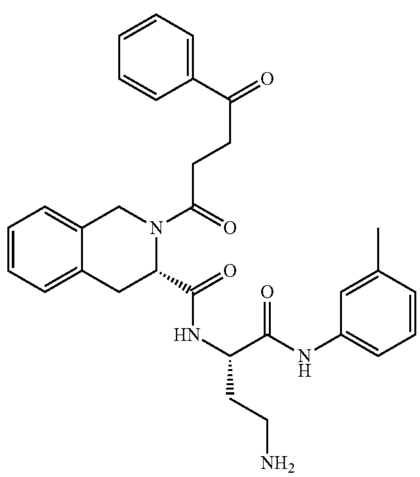 [SMILES: Cc1cccc(NC(=O)[C@H](CCN)NC(=O)[C@@H]2Cc3ccccc3CN2C(=O)CCC(=O)c2ccccc2)c1] | 2-5 |
| 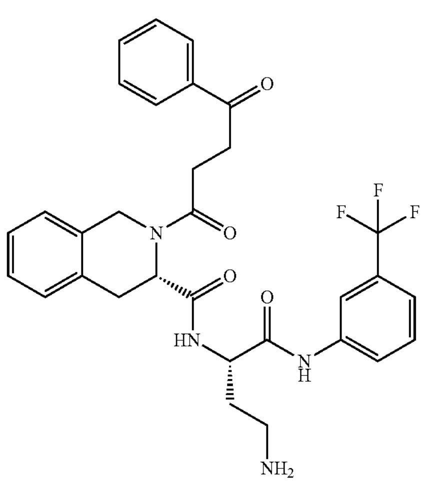 [SMILES: NCC[C@H](NC(=O)[C@@H]1Cc2ccccc2CN1C(=O)CCC(=O)c1ccccc1)C(=O)Nc1cccc(C(F)(F)F)c1] | 2-6 |

TABLE A-continued
| Structure | Cpd. No. |
|---|---|
| 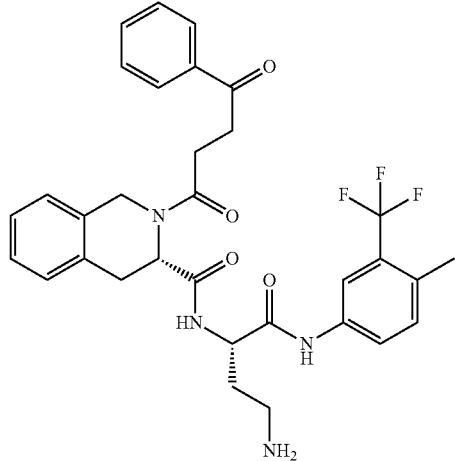 [SMILES: Cc1ccc(NC(=O)[C@H](CCN)NC(=O)[C@@H]2Cc3ccccc3CN2C(=O)CCC(=O)c2ccccc2)cc1C(F)(F)F] | 2-7 |
| 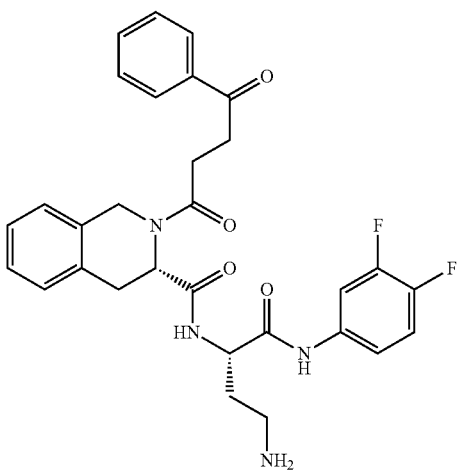 [SMILES: NCC[C@H](NC(=O)[C@@H]1Cc2ccccc2CN1C(=O)CCC(=O)c1ccccc1)C(=O)Nc1ccc(F)c(F)c1] | 2-8 |
| 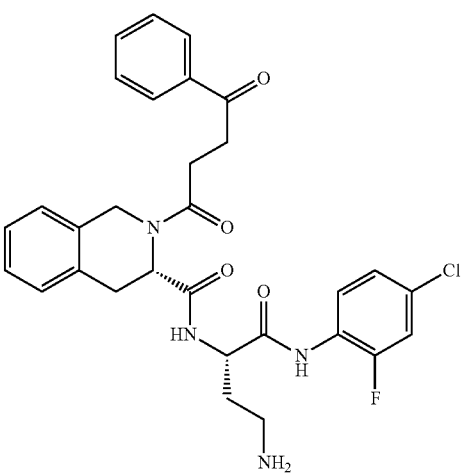 | 2-9 |

TABLE A-continued
| Structure | Cpd. No. |
|---|---|
| 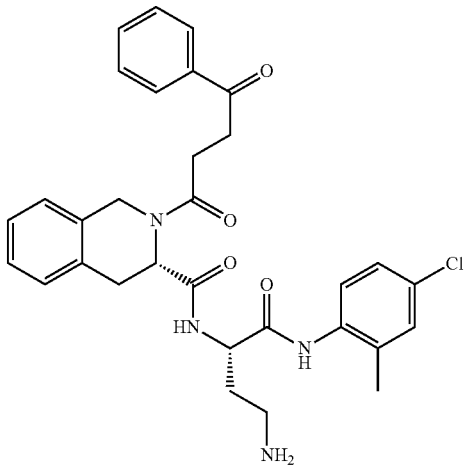 [SMILES: NCC[C@H](NC(=O)[C@@H]1Cc2ccccc2CN1C(=O)CCC(=O)c1ccccc1)C(=O)Nc1ccc(Cl)cc1F] | 2-10 |
| 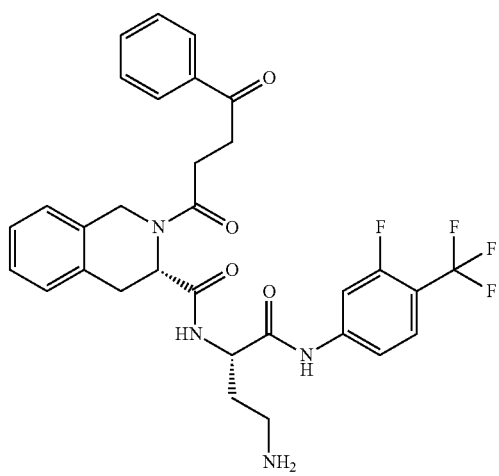 [SMILES: NCC[C@H](NC(=O)[C@@H]1Cc2ccccc2CN1C(=O)CCC(=O)c1ccccc1)C(=O)Nc1ccc(C(F)(F)F)c(F)c1] | 2-11 |
| 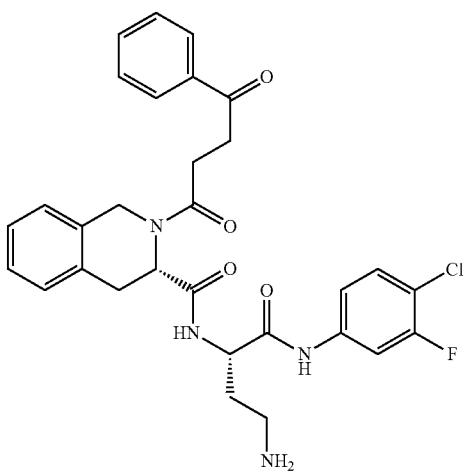 [SMILES: NCC[C@H](NC(=O)[C@@H]1Cc2ccccc2CN1C(=O)CCC(=O)c1ccccc1)C(=O)Nc1ccc(Cl)c(F)c1] | 2-12 |

TABLE A-continued
| Structure | Cpd. No. |
|---|---|
| 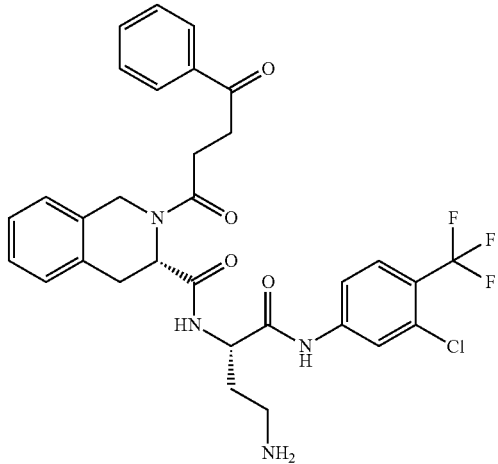 [SMILES: NCC[C@H](NC(=O)[C@@H]1Cc2ccccc2CN1C(=O)CCC(=O)c1ccccc1)C(=O)Nc1ccc(C(F)(F)F)c(Cl)c1] | 2-13 |
| 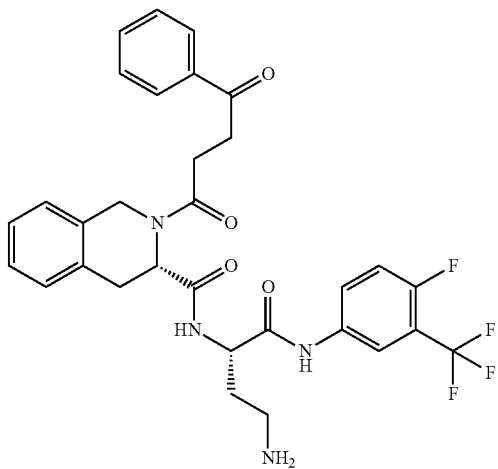 [SMILES: NCC[C@H](NC(=O)[C@@H]1Cc2ccccc2CN1C(=O)CCC(=O)c1ccccc1)C(=O)Nc1ccc(F)c(C(F)(F)F)c1] | 2-14 |
| 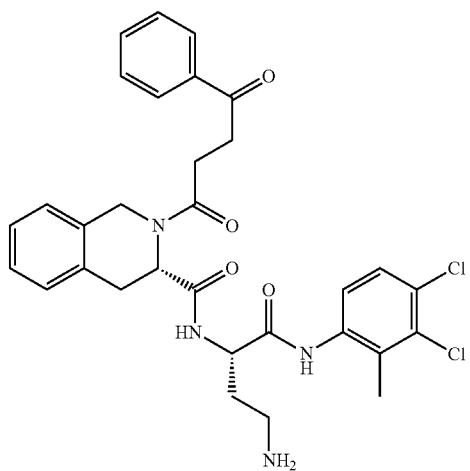 [SMILES: Cc1c(NC(=O)[C@H](CCN)NC(=O)[C@@H]2Cc3ccccc3CN2C(=O)CCC(=O)c2ccccc2)ccc(Cl)c1Cl] | 2-15 |

TABLE A-continued
| Structure | Cpd. No. |
|---|---|
| 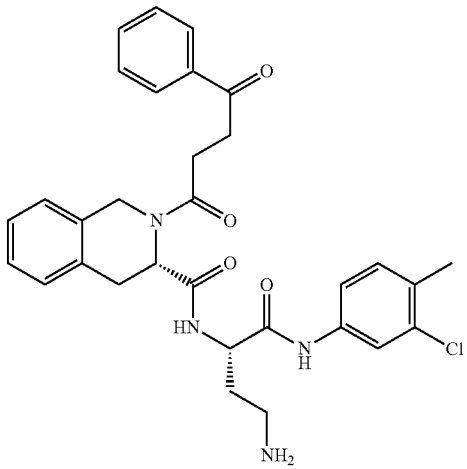 [SMILES: Cc1ccc(NC(=O)[C@H](CCN)NC(=O)[C@@H]2Cc3ccccc3CN2C(=O)CCC(=O)c2ccccc2)cc1Cl] | 2-16 |
| 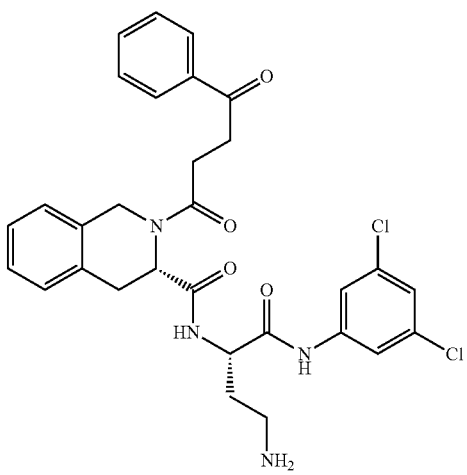 [SMILES: NCC[C@H](NC(=O)[C@@H]1Cc2ccccc2CN1C(=O)CCC(=O)c1ccccc1)C(=O)Nc1cc(Cl)cc(Cl)c1] | 2-17 |
| 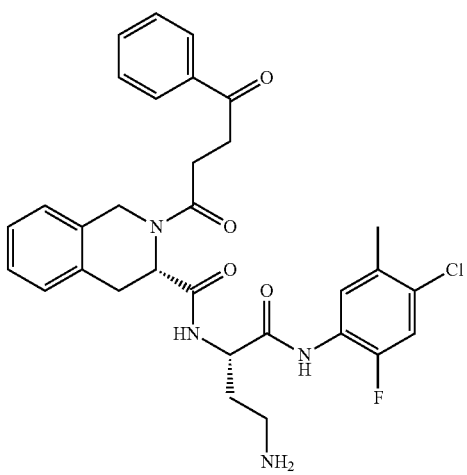 [SMILES: Cc1cc(NC(=O)[C@H](CCN)NC(=O)[C@@H]2Cc3ccccc3CN2C(=O)CCC(=O)c2ccccc2)c(F)cc1Cl] | 2-18 |

TABLE A-continued
| Structure | Cpd. No. |
|---|---|
| 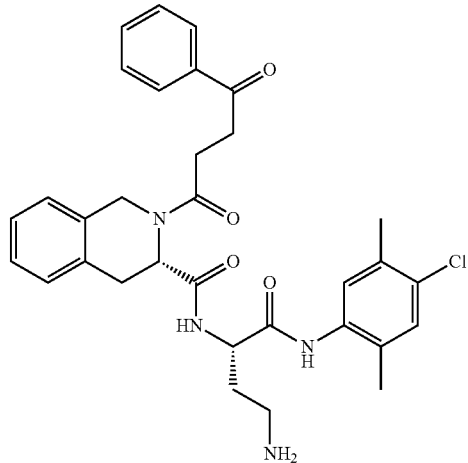 [SMILES: Cc1cc(NC(=O)[C@H](CCN)NC(=O)[C@@H]2Cc3ccccc3CN2C(=O)CCC(=O)c2ccccc2)c(C)cc1Cl] | 2-19 |
| 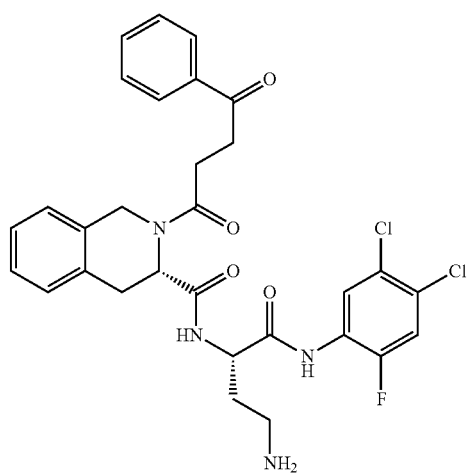 [SMILES: NCC[C@H](NC(=O)[C@@H]1Cc2ccccc2CN1C(=O)CCC(=O)c1ccccc1)C(=O)Nc1cc(Cl)c(Cl)cc1F] | 2-20 |
| 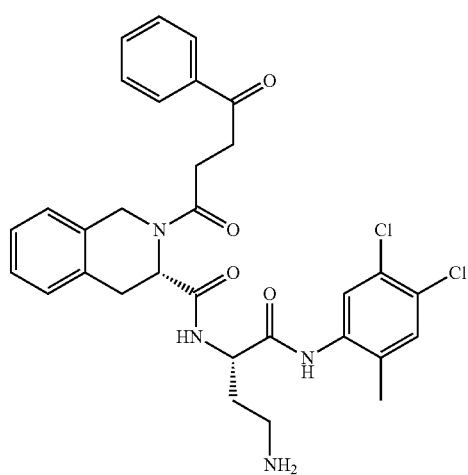 [SMILES: Cc1cc(Cl)c(Cl)cc1NC(=O)[C@H](CCN)NC(=O)[C@@H]1Cc2ccccc2CN1C(=O)CCC(=O)c1ccccc1] | 2-21 |

TABLE A-continued
| Structure | Cpd. No. |
|---|---|
| 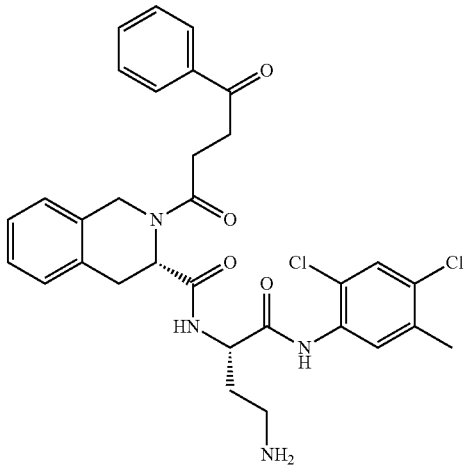 [SMILES: Cc1cc(NC(=O)[C@H](CCN)NC(=O)[C@@H]2Cc3ccccc3CN2C(=O)CCC(=O)c2ccccc2)c(Cl)cc1Cl] | 2-22 |
| 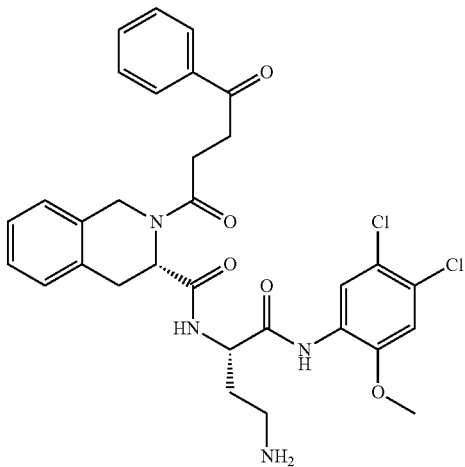 [SMILES: COc1cc(Cl)c(Cl)cc1NC(=O)[C@H](CCN)NC(=O)[C@@H]1Cc2ccccc2CN1C(=O)CCC(=O)c1ccccc1] | 2-23 |
| 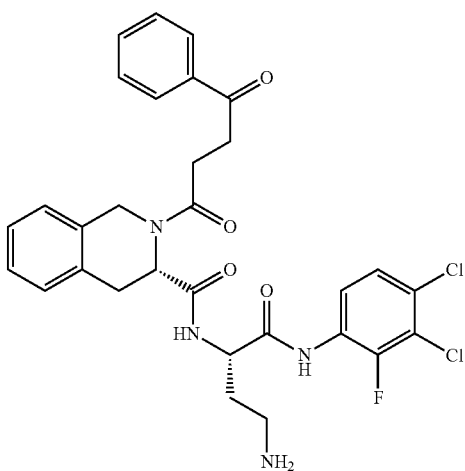 [SMILES: NCC[C@H](NC(=O)[C@@H]1Cc2ccccc2CN1C(=O)CCC(=O)c1ccccc1)C(=O)Nc1ccc(Cl)c(Cl)c1F] | 2-24 |

TABLE A-continued
| Structure | Cpd. No. |
|---|---|
| 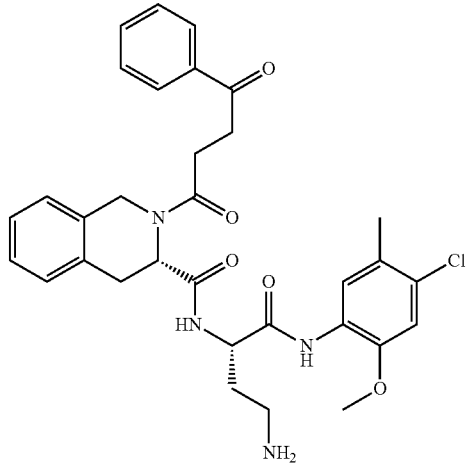 | 2-25 |
| 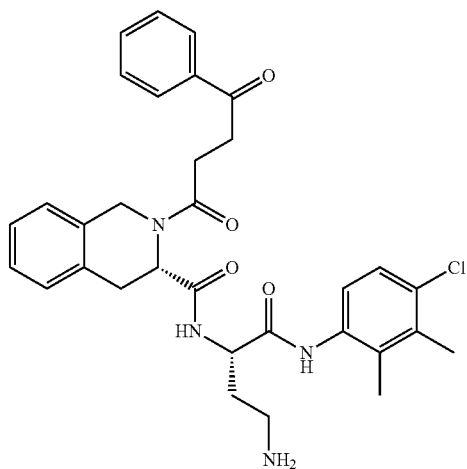 [SMILES: Cc1c(Cl)ccc(NC(=O)[C@H](CCN)NC(=O)[C@@H]2Cc3ccccc3CN2C(=O)CCC(=O)c2ccccc2)c1C] | 2-26 |
| 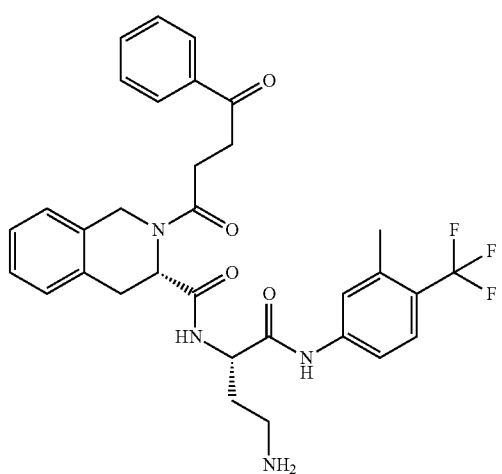 [SMILES: Cc1cc(NC(=O)[C@H](CCN)NC(=O)[C@@H]2Cc3ccccc3CN2C(=O)CCC(=O)c2ccccc2)ccc1C(F)(F)F] | 2-27 |

| Structure | Cpd. No. |
|---|---|
| 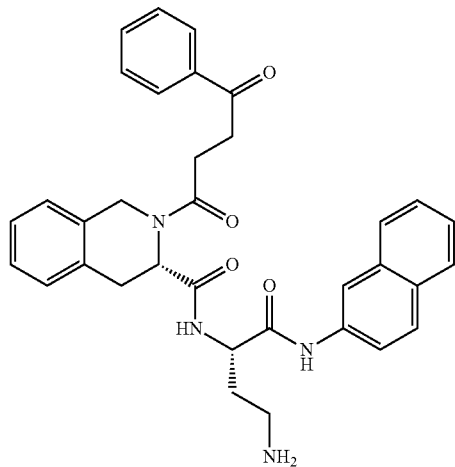 [SMILES: NCC[C@H](NC(=O)[C@@H]1Cc2ccccc2CN1C(=O)CCC(=O)c1ccccc1)C(=O)Nc1ccc2ccccc2c1] | 2-28 |
| 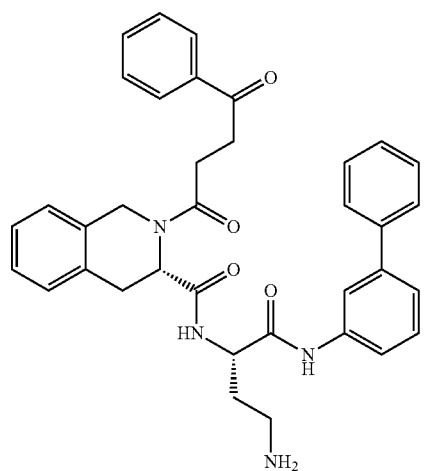 [SMILES: NCC[C@H](NC(=O)[C@@H]1Cc2ccccc2CN1C(=O)CCC(=O)c1ccccc1)C(=O)Nc1cccc(-c2ccccc2)c1] | 2-29 |
| 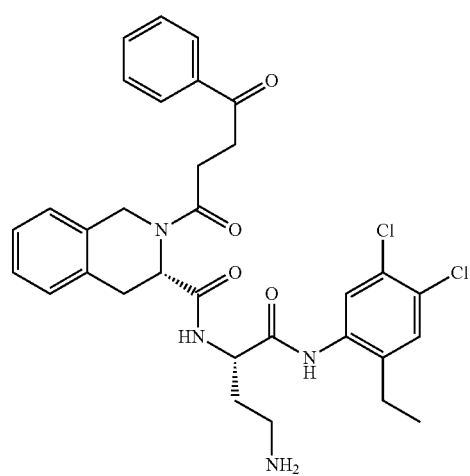 [SMILES: CCc1cc(Cl)c(Cl)cc1NC(=O)[C@H](CCN)NC(=O)[C@@H]1Cc2ccccc2CN1C(=O)CCC(=O)c1ccccc1] | 2-30 |

TABLE A-continued
| Structure | Cpd. No. |
|---|---|
| 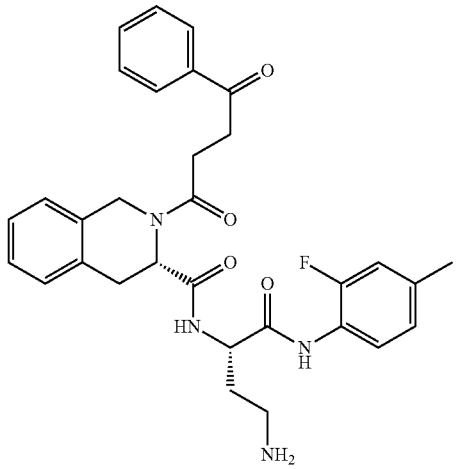 | 2-31 |
| 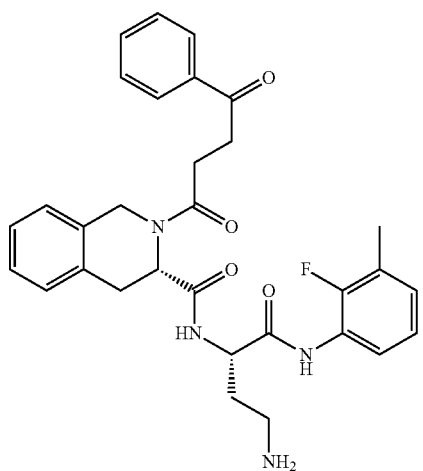 | 2-32 |
| 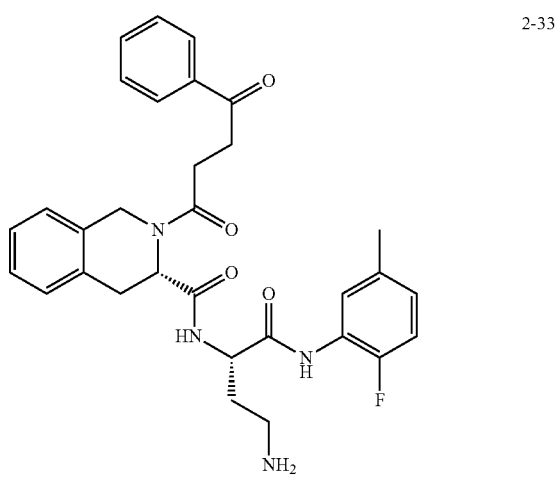 | 2-33 |

TABLE A-continued
| Structure | Cpd. No. |
|---|---|
| 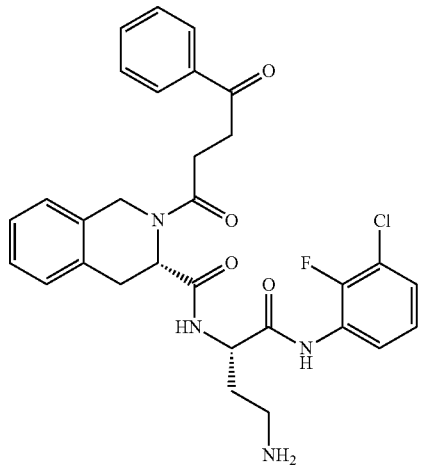 [SMILES: NCC[C@H](NC(=O)[C@@H]1Cc2ccccc2CN1C(=O)CCC(=O)c1ccccc1)C(=O)Nc1cccc(Cl)c1F] | 2-34 |
| 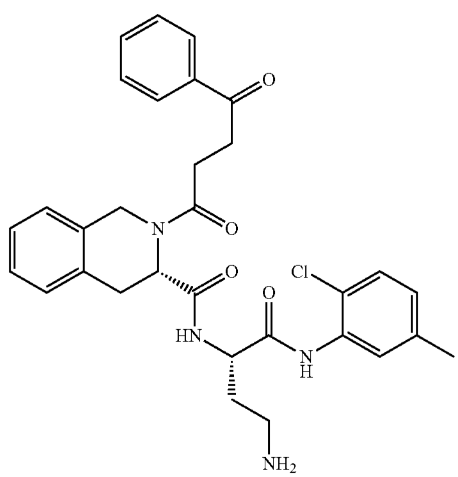 [SMILES: Cc1ccc(Cl)c(NC(=O)[C@H](CCN)NC(=O)[C@@H]2Cc3ccccc3CN2C(=O)CCC(=O)c2ccccc2)c1] | 2-35 |
| 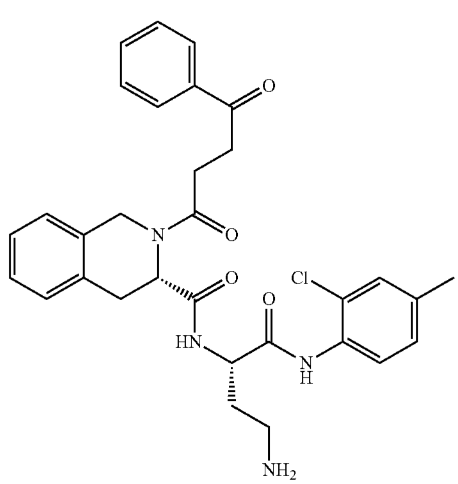 [SMILES: Cc1ccc(NC(=O)[C@H](CCN)NC(=O)[C@@H]2Cc3ccccc3CN2C(=O)CCC(=O)c2ccccc2)c(Cl)c1] | 2-36 |

TABLE A-continued
| Structure | Cpd. No. |
|---|---|
| 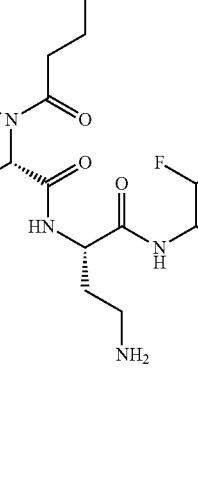 | 2-37 |
| 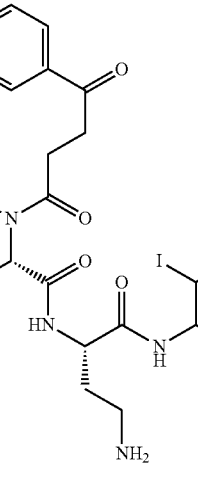 | 2-38 |
| 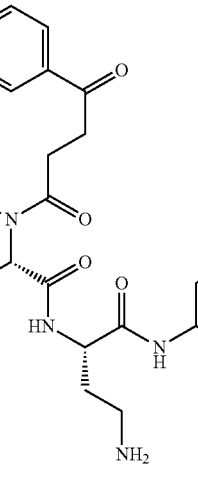 | 2-39 |

TABLE A-continued
| Structure | Cpd. No. |
|---|---|
| 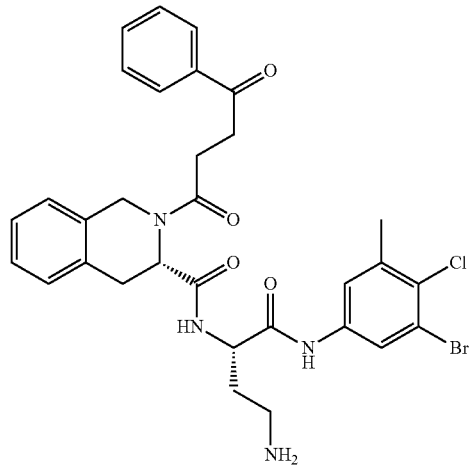 [SMILES: Cc1cc(NC(=O)[C@H](CCN)NC(=O)[C@@H]2Cc3ccccc3CN2C(=O)CCC(=O)c2ccccc2)cc(Br)c1Cl] | 2-40 |
| 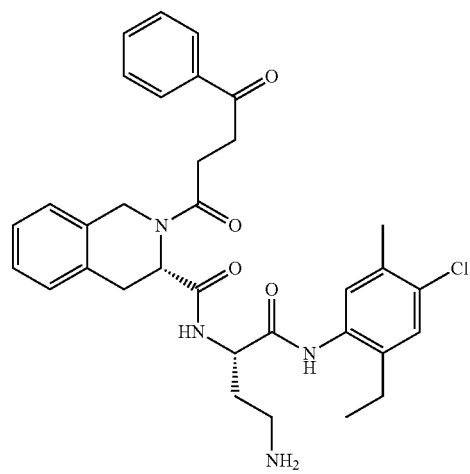 [SMILES: CCc1cc(Cl)c(C)cc1NC(=O)[C@H](CCN)NC(=O)[C@@H]1Cc2ccccc2CN1C(=O)CCC(=O)c1ccccc1] | 2-41 |
| 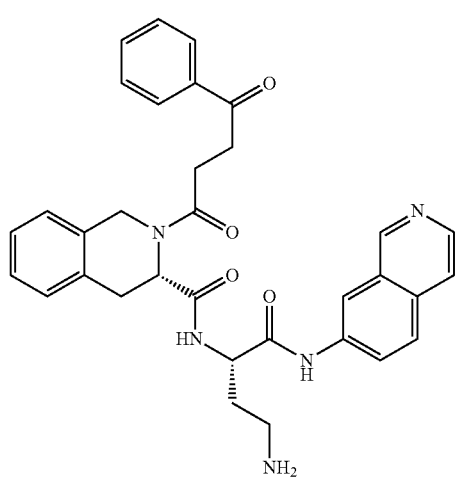 [SMILES: NCC[C@H](NC(=O)[C@@H]1Cc2ccccc2CN1C(=O)CCC(=O)c1ccccc1)C(=O)Nc1ccc2ccncc2c1] | 2-42 |

TABLE A-continued
| Structure | Cpd. No. |
|---|---|
| 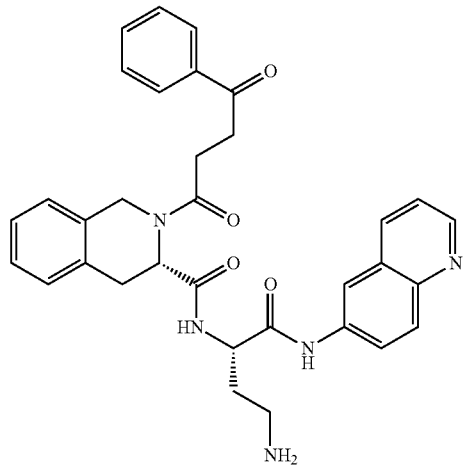 [SMILES: NCC[C@H](NC(=O)[C@@H]1Cc2ccccc2CN1C(=O)CCC(=O)c1ccccc1)C(=O)Nc1ccc2ncccc2c1] | 2-43 |
| 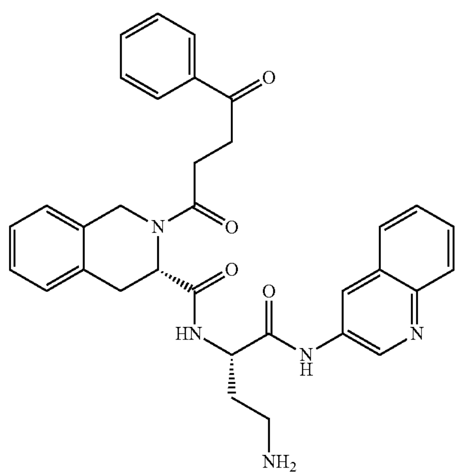 [SMILES: NCC[C@H](NC(=O)[C@@H]1Cc2ccccc2CN1C(=O)CCC(=O)c1ccccc1)C(=O)Nc1cnc2ccccc2c1] | 2-44 |
| 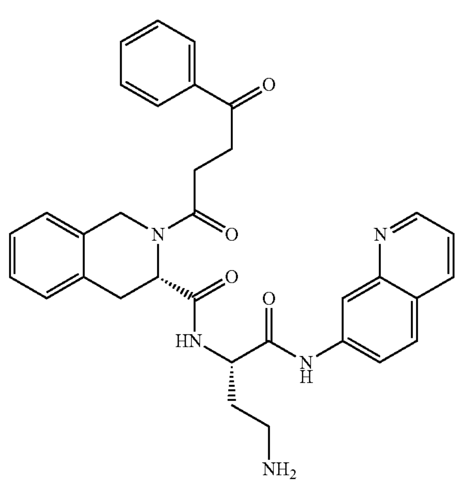 [SMILES: NCC[C@H](NC(=O)[C@@H]1Cc2ccccc2CN1C(=O)CCC(=O)c1ccccc1)C(=O)Nc1ccc2cccnc2c1] | 2-45 |

TABLE A-continued

| Structure | Cpd. No. |
|---|---|
| 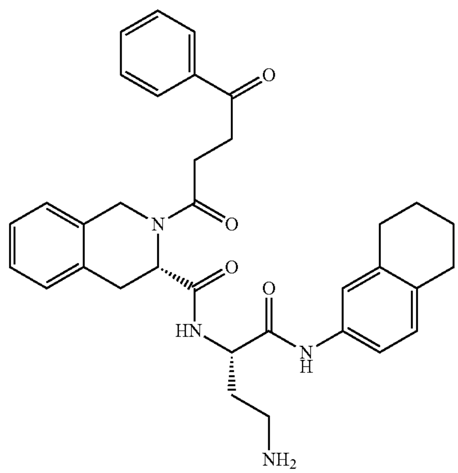 [SMILES: NCC[C@H](NC(=O)[C@@H]1Cc2ccccc2CN1C(=O)CCC(=O)c1ccccc1)C(=O)Nc1ccc2c(c1)CCCC2] | 2-46 |
| 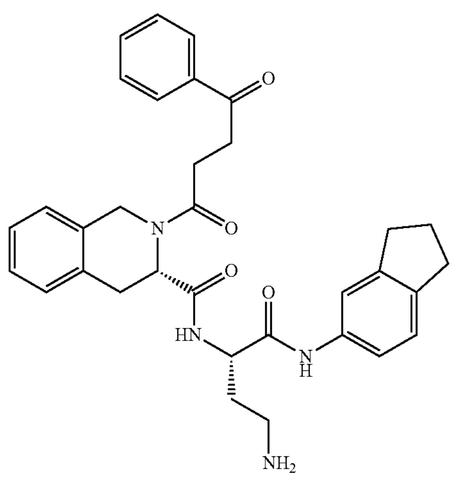 [SMILES: NCC[C@H](NC(=O)[C@@H]1Cc2ccccc2CN1C(=O)CCC(=O)c1ccccc1)C(=O)Nc1ccc2c(c1)CCC2] | 2-47 |
| 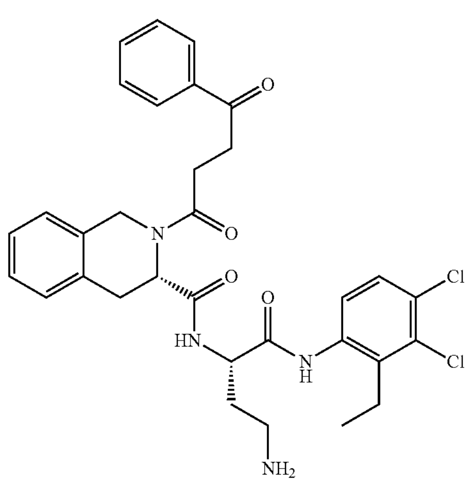 [SMILES: CCc1c(NC(=O)[C@H](CCN)NC(=O)[C@@H]2Cc3ccccc3CN2C(=O)CCC(=O)c2ccccc2)ccc(Cl)c1Cl] | 2-48 |

TABLE A-continued
| Structure | Cpd. No. |
|---|---|
| 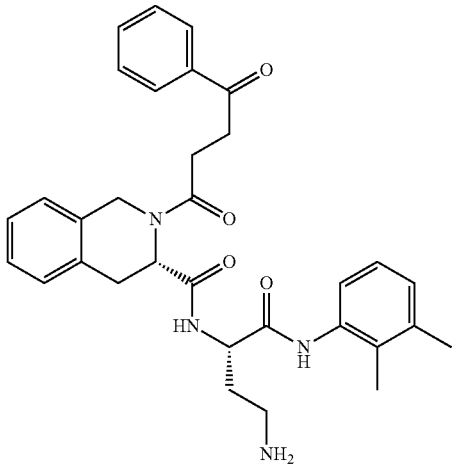 [SMILES: Cc1cccc(NC(=O)[C@H](CCN)NC(=O)[C@@H]2Cc3ccccc3CN2C(=O)CCC(=O)c2ccccc2)c1C] | 2-49 |
| 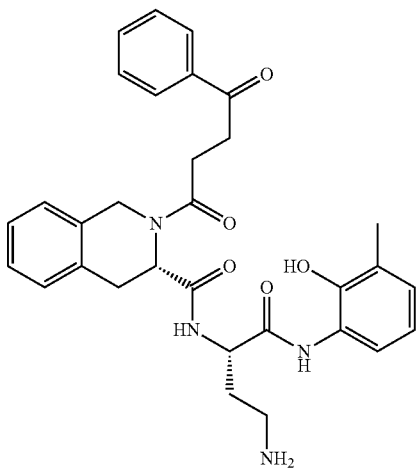 | 2-50 |
| 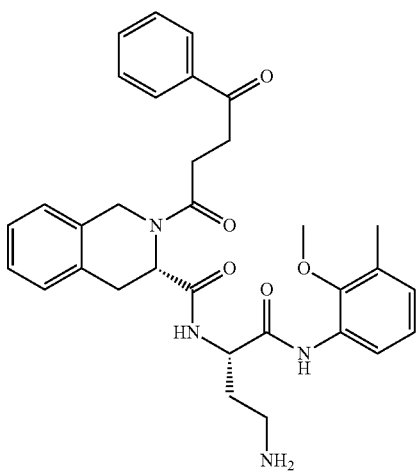 [SMILES: COc1c(C)cccc1NC(=O)[C@H](CCN)NC(=O)[C@@H]1Cc2ccccc2CN1C(=O)CCC(=O)c1ccccc1] | 2-51 |

TABLE A-continued
| Structure | Cpd. No. |
|---|---|
| 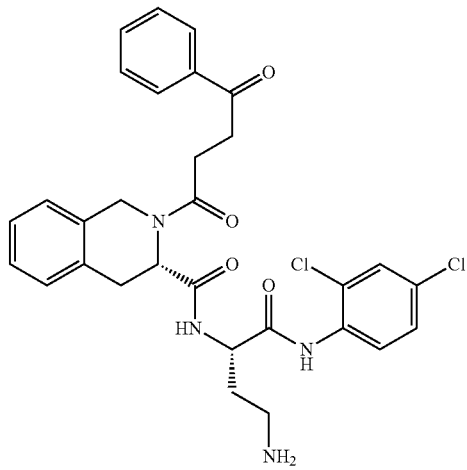 [SMILES: NCC[C@H](NC(=O)[C@@H]1Cc2ccccc2CN1C(=O)CCC(=O)c1ccccc1)C(=O)Nc1ccc(Cl)cc1Cl] | 2-52 |
| 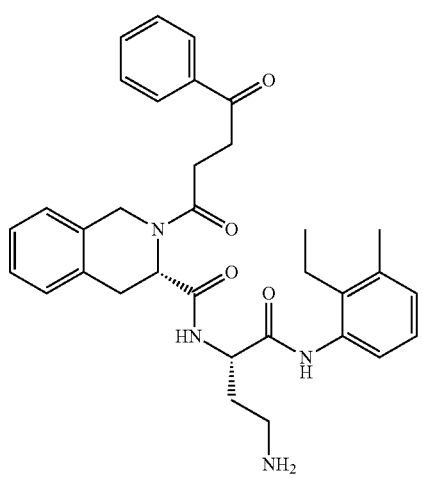 [SMILES: CCc1c(C)cccc1NC(=O)[C@H](CCN)NC(=O)[C@@H]1Cc2ccccc2CN1C(=O)CCC(=O)c1ccccc1] | 2-53 |
| 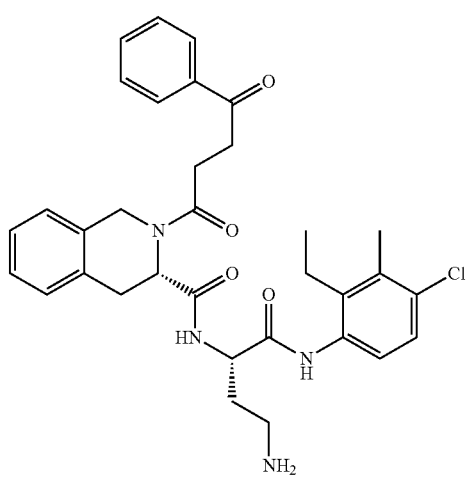 [SMILES: CCc1c(NC(=O)[C@H](CCN)NC(=O)[C@@H]2Cc3ccccc3CN2C(=O)CCC(=O)c2ccccc2)ccc(Cl)c1C] | 2-54 |

TABLE A-continued
| Structure | Cpd. No. |
|---|---|
| 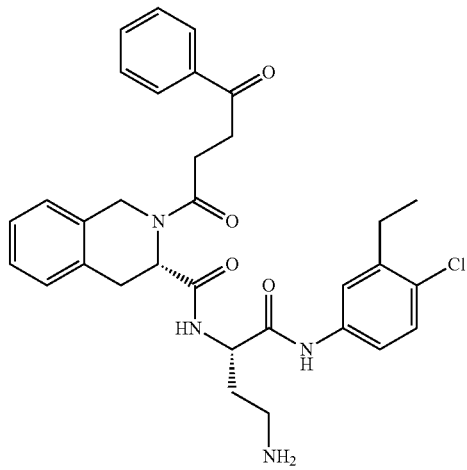 [SMILES: CCc1cc(NC(=O)[C@H](CCN)NC(=O)[C@@H]2Cc3ccccc3CN2C(=O)CCC(=O)c2ccccc2)ccc1Cl] | 2-55 |
| 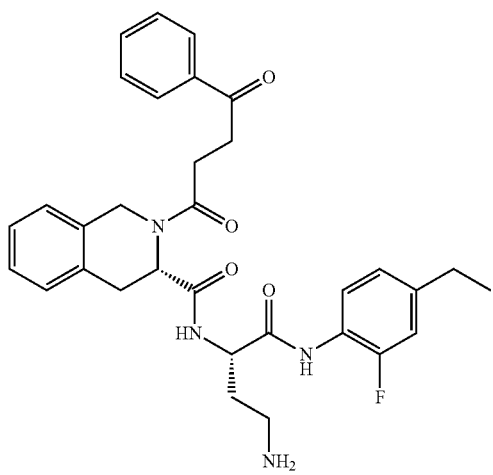 [SMILES: CCc1ccc(NC(=O)[C@H](CCN)NC(=O)[C@@H]2Cc3ccccc3CN2C(=O)CCC(=O)c2ccccc2)c(F)c1] | 2-56 |
| 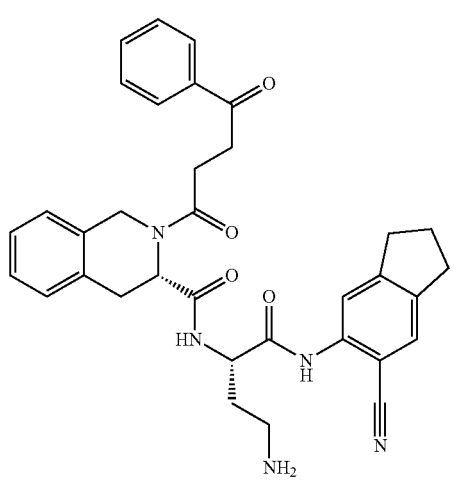 [SMILES: N#Cc1cc2c(cc1NC(=O)[C@H](CCN)NC(=O)[C@@H]1Cc3ccccc3CN1C(=O)CCC(=O)c1ccccc1)CCC2] | 2-57 |

TABLE A-continued
| Structure | Cpd. No. |
|---|---|
| 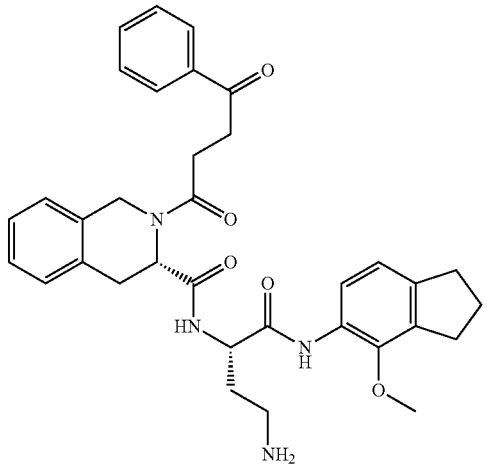 [SMILES: COc1c(NC(=O)[C@H](CCN)NC(=O)[C@@H]2Cc3ccccc3CN2C(=O)CCC(=O)c2ccccc2)ccc2c1CCC2] | 2-58 |
| 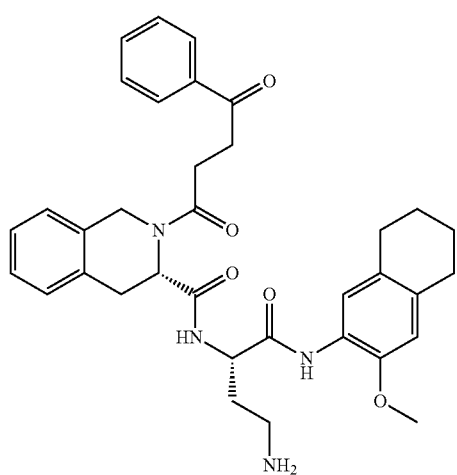 [SMILES: COc1cc2c(cc1NC(=O)[C@H](CCN)NC(=O)[C@@H]1Cc3ccccc3CN1C(=O)CCC(=O)c1ccccc1)CCCC2] | 2-59 |
| 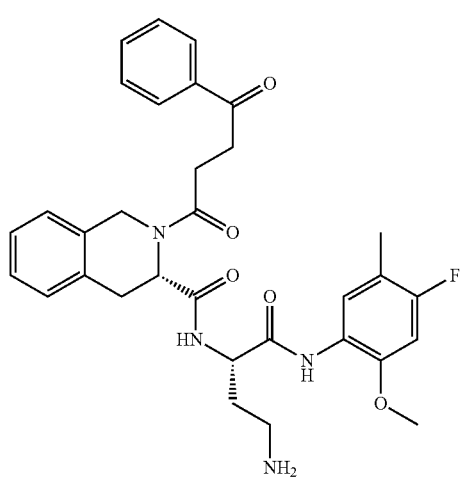 [SMILES: COc1cc(F)c(C)cc1NC(=O)[C@H](CCN)NC(=O)[C@@H]1Cc2ccccc2CN1C(=O)CCC(=O)c1ccccc1] | 2-60 |

TABLE A-continued
| Structure | Cpd. No. |
|---|---|
| 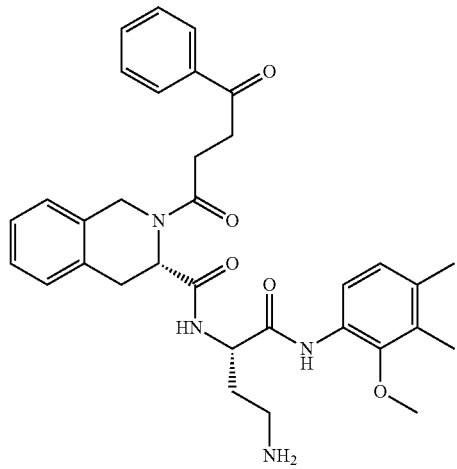 [SMILES: COc1c(NC(=O)[C@H](CCN)NC(=O)[C@@H]2Cc3ccccc3CN2C(=O)CCC(=O)c2ccccc2)ccc(C)c1C] | 2-61 |
| 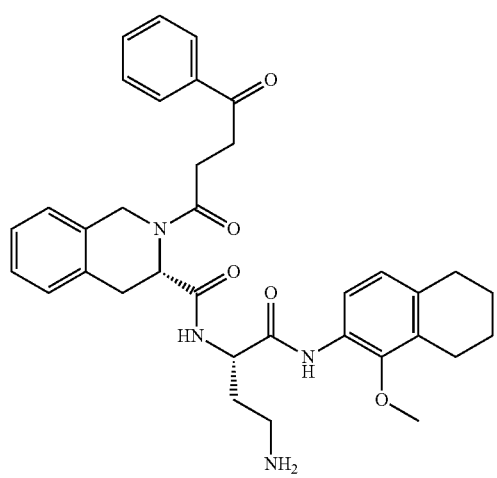 [SMILES: COc1c(NC(=O)[C@H](CCN)NC(=O)[C@@H]2Cc3ccccc3CN2C(=O)CCC(=O)c2ccccc2)ccc2c1CCCC2] | 2-62 |
| 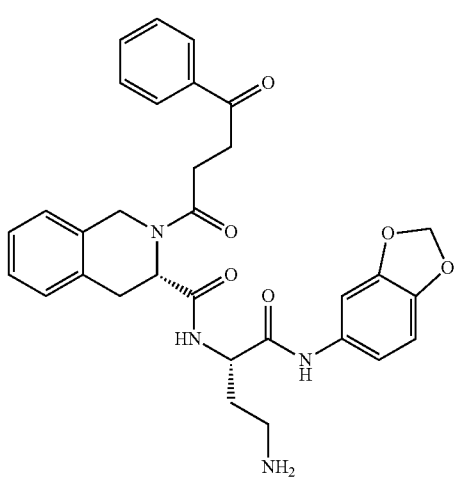 | 2-63 |

TABLE A-continued
| Structure | Cpd. No. |
|---|---|
| 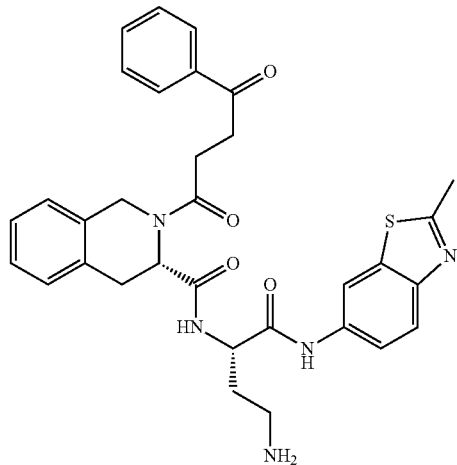 [SMILES: Cc1nc2ccc(NC(=O)[C@H](CCN)NC(=O)[C@@H]3Cc4ccccc4CN3C(=O)CCC(=O)c3ccccc3)cc2s1] | 2-64 |
| 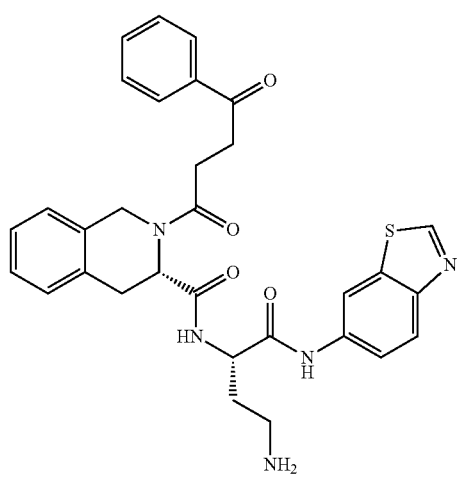 [SMILES: NCC[C@H](NC(=O)[C@@H]1Cc2ccccc2CN1C(=O)CCC(=O)c1ccccc1)C(=O)Nc1ccc2ncsc2c1] | 2-65 |
| 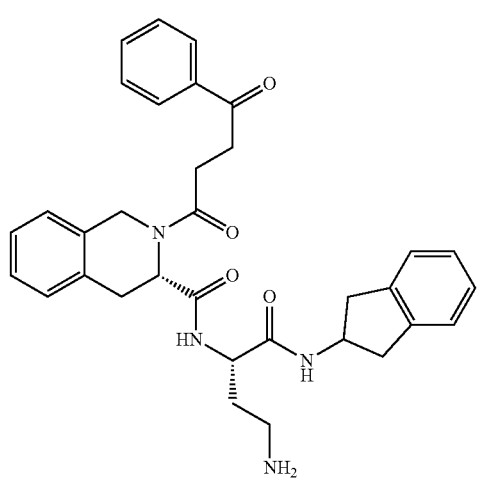 [SMILES: NCC[C@H](NC(=O)[C@@H]1Cc2ccccc2CN1C(=O)CCC(=O)c1ccccc1)C(=O)NC1Cc2ccccc2C1] | 2-66 |

TABLE A-continued
| Structure | Cpd. No. |
|---|---|
| 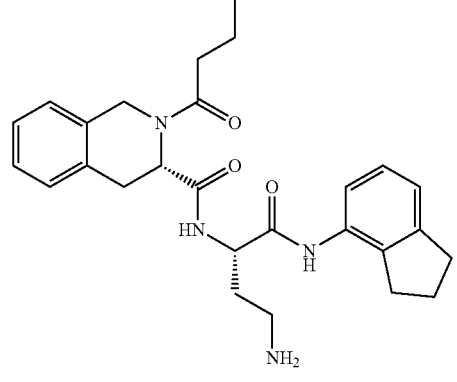 | 2-67 |
| 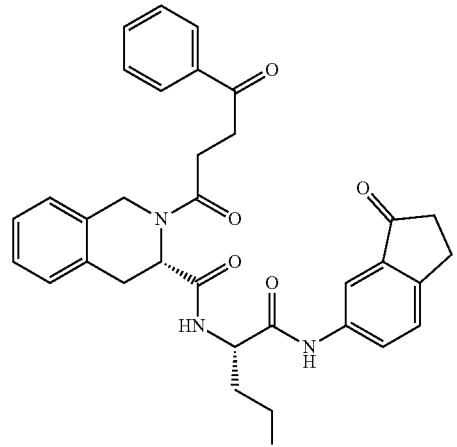 | 2-68 |
| 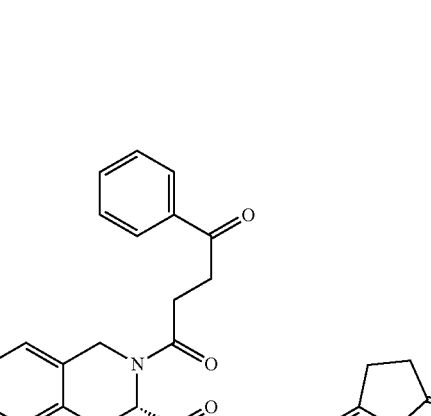 | 2-69 |

TABLE A-continued

| Structure | Cpd. No. |
|---|---|
| 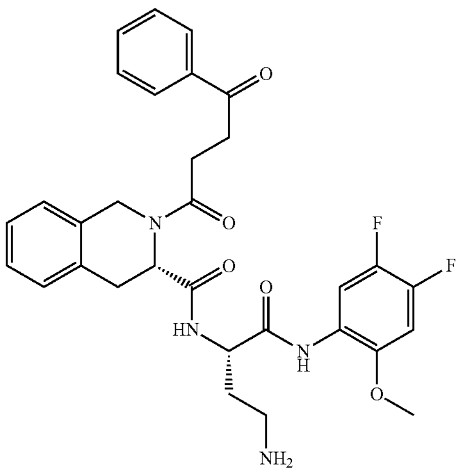 | 2-70 |
| 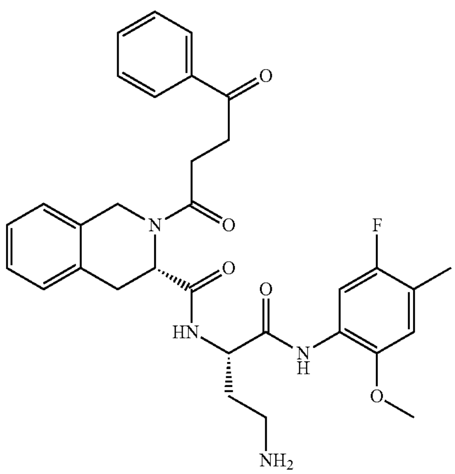 | 2-71 |
| 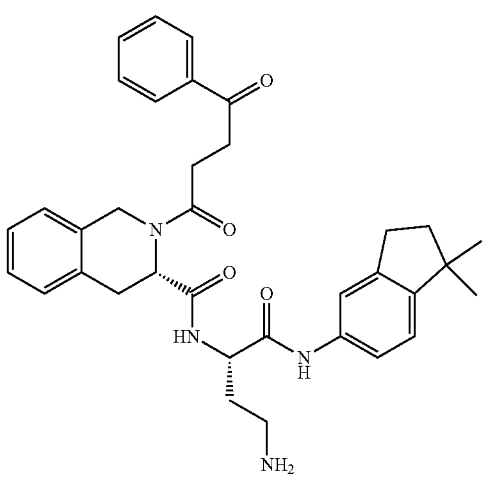 [SMILES: CC1(C)CCc2cc(NC(=O)[C@H](CCN)NC(=O)[C@@H]3Cc4ccccc4CN3C(=O)CCC(=O)c3ccccc3)ccc21] | 2-72 |

TABLE A-continued
| Structure | Cpd. No. |
|---|---|
| 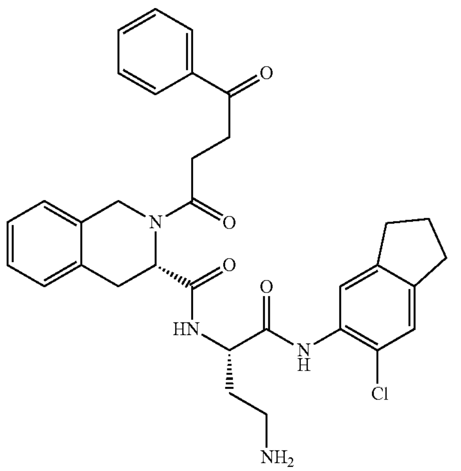 [SMILES: NCC[C@H](NC(=O)[C@@H]1Cc2ccccc2CN1C(=O)CCC(=O)c1ccccc1)C(=O)Nc1cc2c(cc1Cl)CCC2] | 2-73 |
| 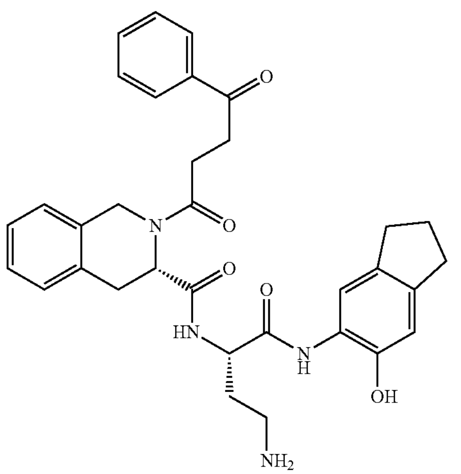 [SMILES: NCC[C@H](NC(=O)[C@@H]1Cc2ccccc2CN1C(=O)CCC(=O)c1ccccc1)C(=O)Nc1cc2c(cc1O)CCC2] | 2-74 |
| 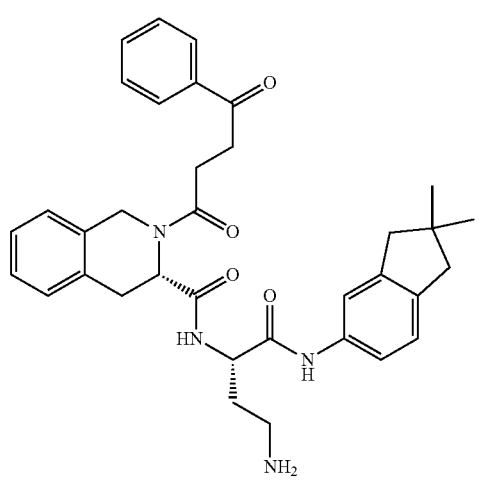 [SMILES: CC1(C)Cc2ccc(NC(=O)[C@H](CCN)NC(=O)[C@@H]3Cc4ccccc4CN3C(=O)CCC(=O)c3ccccc3)cc2C1] | 2-75 |

TABLE A-continued
| Structure | Cpd. No. |
|---|---|
| 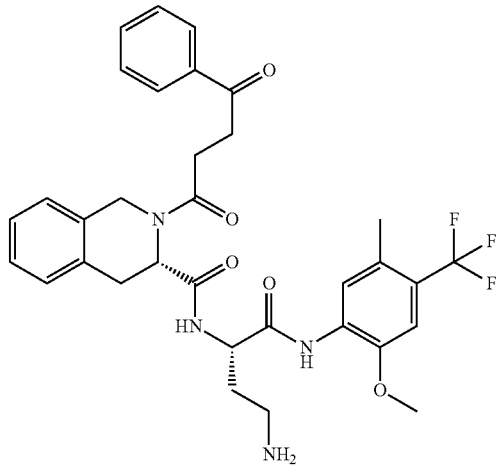 [SMILES: COc1cc(C(F)(F)F)c(C)cc1NC(=O)[C@H](CCN)NC(=O)[C@@H]1Cc2ccccc2CN1C(=O)CCC(=O)c1ccccc1] | 2-76 |
| 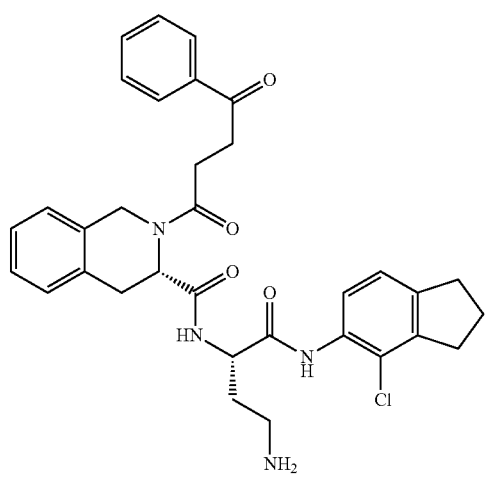 [SMILES: NCC[C@H](NC(=O)[C@@H]1Cc2ccccc2CN1C(=O)CCC(=O)c1ccccc1)C(=O)Nc1ccc2c(c1Cl)CCC2] | 2-77 |
| 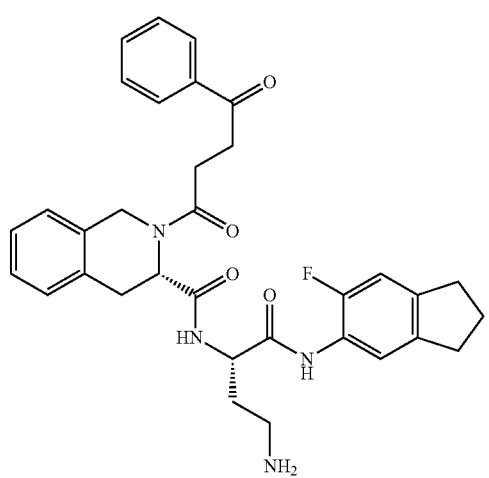 [SMILES: NCC[C@H](NC(=O)[C@@H]1Cc2ccccc2CN1C(=O)CCC(=O)c1ccccc1)C(=O)Nc1cc2c(cc1F)CCC2] | 2-78 |

TABLE A-continued

| Structure | Cpd. No. |
|---|---|
| 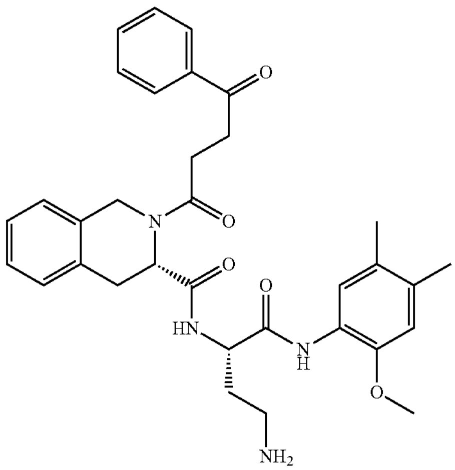 | 2-79 |
| 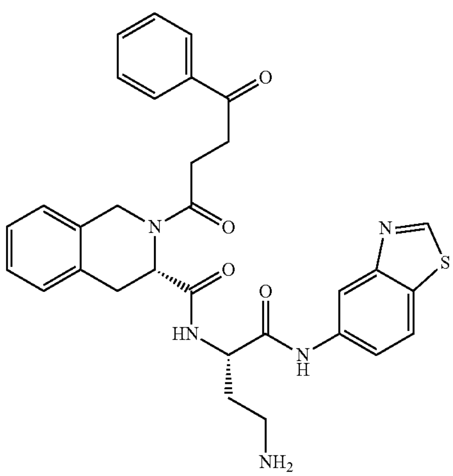 [SMILES: NCC[C@H](NC(=O)[C@@H]1Cc2ccccc2CN1C(=O)CCC(=O)c1ccccc1)C(=O)Nc1ccc2scnc2c1] | 2-80 |
| 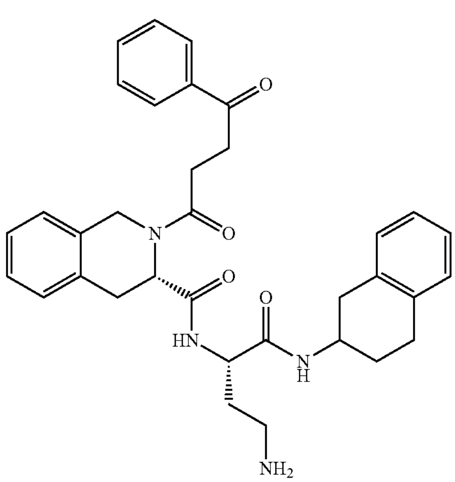 [SMILES: NCC[C@H](NC(=O)[C@@H]1Cc2ccccc2CN1C(=O)CCC(=O)c1ccccc1)C(=O)NC1CCc2ccccc2C1] | 2-81 |

TABLE A-continued
| Structure | Cpd. No. |
|---|---|
| 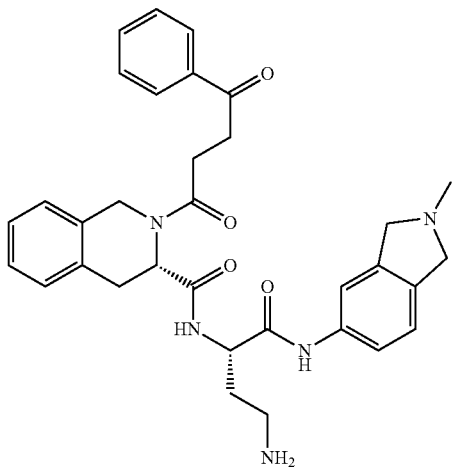 | 2-82 |
| 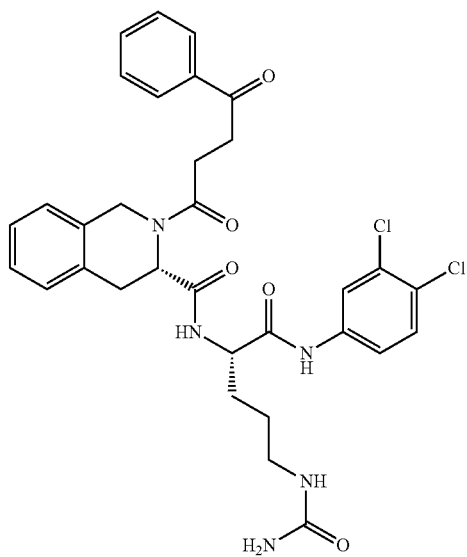 [SMILES: NC(=O)NCCC[C@H](NC(=O)[C@@H]1Cc2ccccc2CN1C(=O)CCC(=O)c1ccccc1)C(=O)Nc1ccc(Cl)c(Cl)c1] | 3-1 |
| 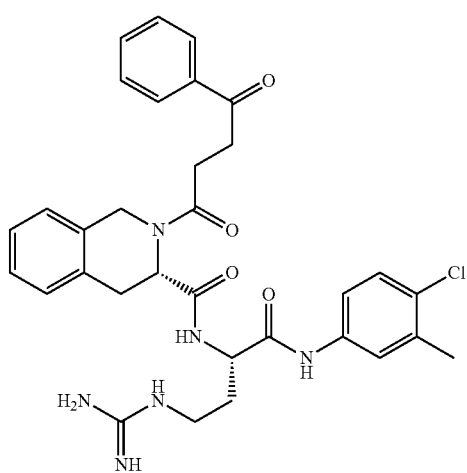 [SMILES: Cc1cc(NC(=O)[C@H](CCNC(=N)N)NC(=O)[C@@H]2Cc3ccccc3CN2C(=O)CCC(=O)c2ccccc2)ccc1Cl] | 3-2 |

TABLE A-continued
| Structure | Cpd. No. |
|---|---|
| 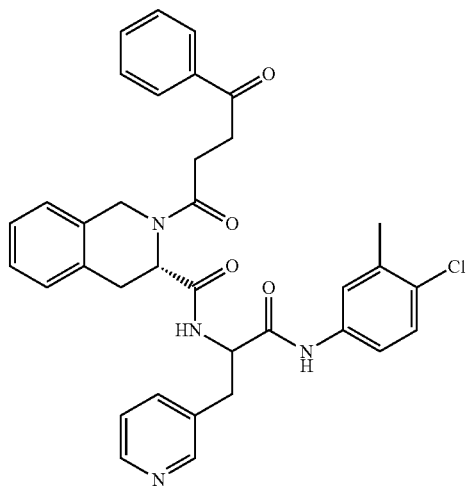 [SMILES: Cc1cc(NC(=O)C(Cc2cccnc2)NC(=O)[C@@H]2Cc3ccccc3CN2C(=O)CCC(=O)c2ccccc2)ccc1Cl] | 3-3 |
| 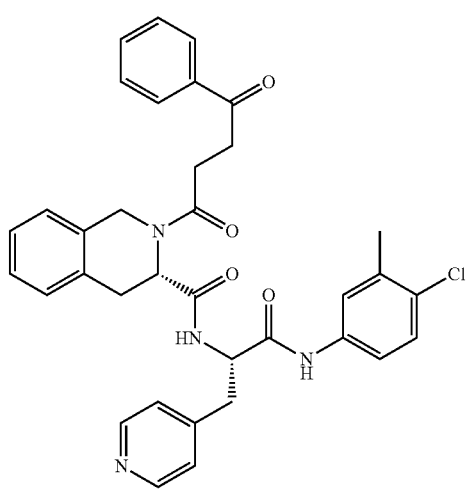 [SMILES: Cc1cc(NC(=O)[C@H](Cc2ccncc2)NC(=O)[C@@H]2Cc3ccccc3CN2C(=O)CCC(=O)c2ccccc2)ccc1Cl] | 3-4 |
| 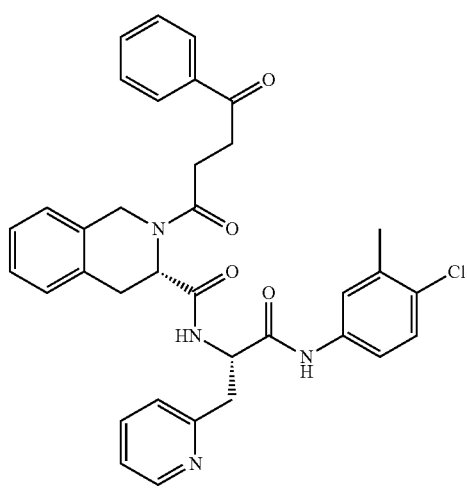 [SMILES: Cc1cc(NC(=O)[C@H](Cc2ccccn2)NC(=O)[C@@H]2Cc3ccccc3CN2C(=O)CCC(=O)c2ccccc2)ccc1Cl] | 3-5 |

TABLE A-continued

| Structure | Cpd. No. |
|---|---|
| 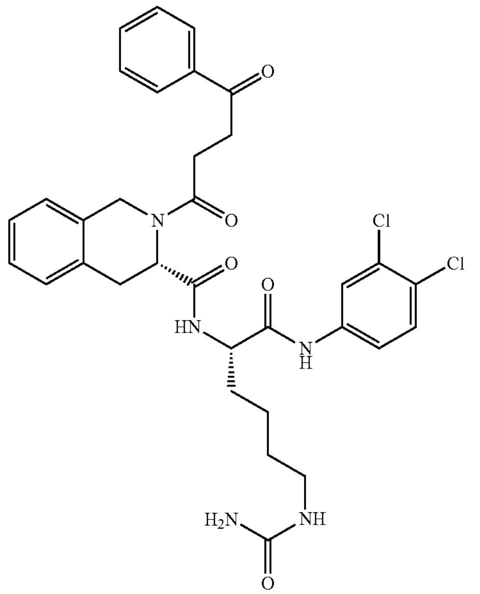 [SMILES: NC(=O)NCCCC[C@H](NC(=O)[C@@H]1Cc2ccccc2CN1C(=O)CCC(=O)c1ccccc1)C(=O)Nc1ccc(Cl)c(Cl)c1] | 3-6 |
| 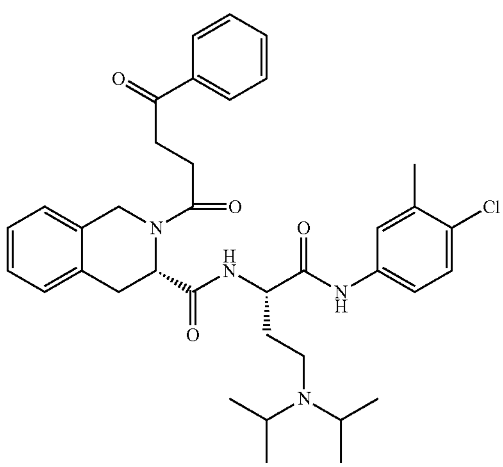 [SMILES: Cc1cc(NC(=O)[C@H](CCN(C(C)C)C(C)C)NC(=O)[C@@H]2Cc3ccccc3CN2C(=O)CCC(=O)c2ccccc2)ccc1Cl] | 3-7 |
| 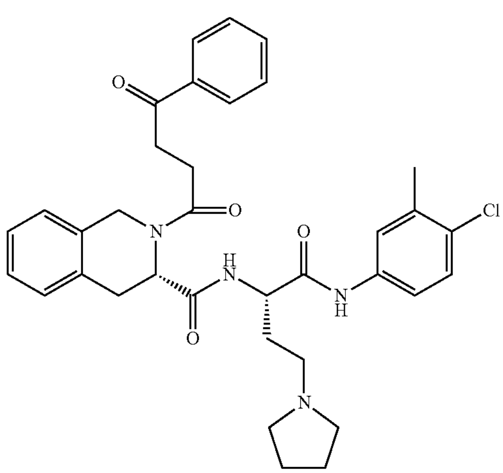 [SMILES: Cc1cc(NC(=O)[C@H](CCN2CCCC2)NC(=O)[C@@H]2Cc3ccccc3CN2C(=O)CCC(=O)c2ccccc2)ccc1Cl] | 3-8 |

TABLE A-continued
| Structure | Cpd. No. |
|---|---|
| 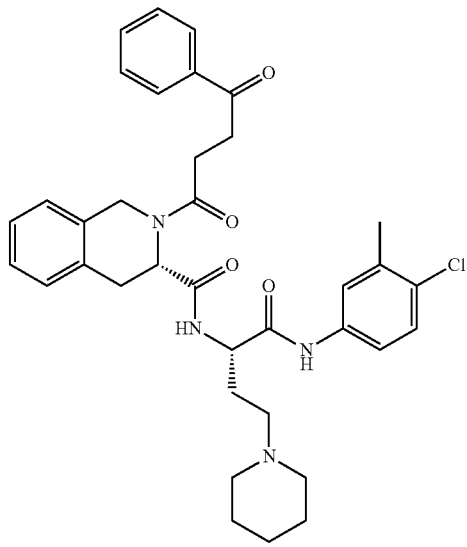 [SMILES: Cc1cc(NC(=O)[C@H](CCN2CCCCC2)NC(=O)[C@@H]2Cc3ccccc3CN2C(=O)CCC(=O)c2ccccc2)ccc1Cl] | 3-9 |
| 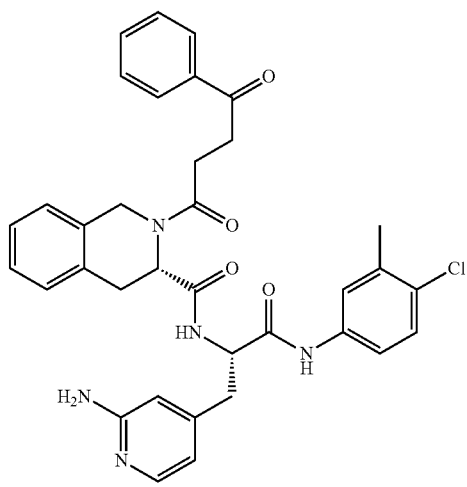 [SMILES: Cc1cc(NC(=O)[C@H](Cc2ccnc(N)c2)NC(=O)[C@@H]2Cc3ccccc3CN2C(=O)CCC(=O)c2ccccc2)ccc1Cl] | 3-10 |
| 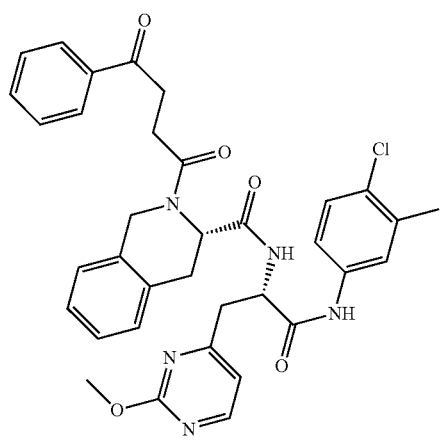 [SMILES: COc1nccc(C[C@H](NC(=O)[C@@H]2Cc3ccccc3CN2C(=O)CCC(=O)c2ccccc2)C(=O)Nc2ccc(Cl)c(C)c2)n1] | 3-11 |

TABLE A-continued
| Structure | Cpd. No. |
|---|---|
| 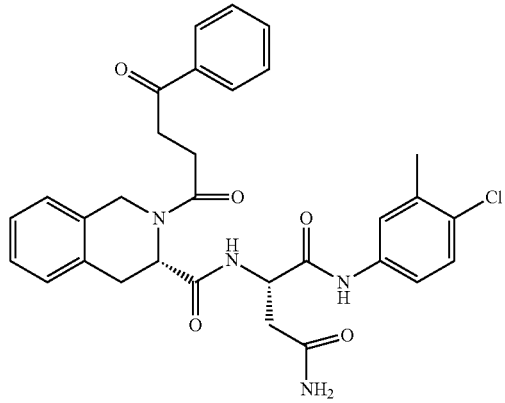 [SMILES: Cc1cc(NC(=O)[C@H](CC(N)=O)NC(=O)[C@@H]2Cc3ccccc3CN2C(=O)CCC(=O)c2ccccc2)ccc1Cl] | 3-12 |
| 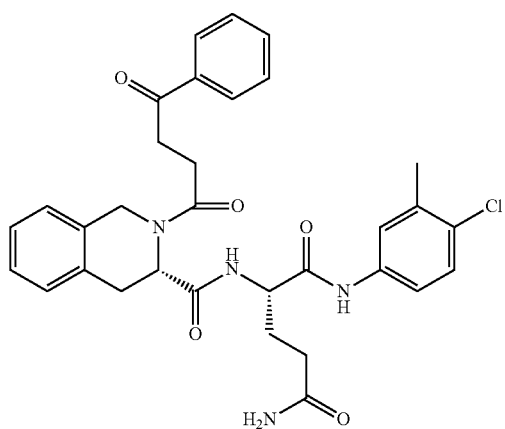 [SMILES: Cc1cc(NC(=O)[C@H](CCC(N)=O)NC(=O)[C@@H]2Cc3ccccc3CN2C(=O)CCC(=O)c2ccccc2)ccc1Cl] | 3-13 |
| 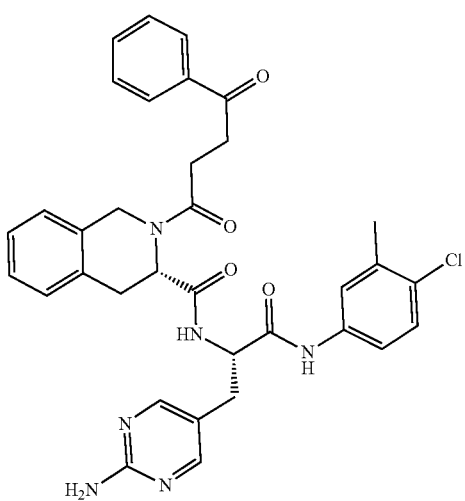 [SMILES: Cc1cc(NC(=O)[C@H](Cc2cnc(N)nc2)NC(=O)[C@@H]2Cc3ccccc3CN2C(=O)CCC(=O)c2ccccc2)ccc1Cl] | 3-14 |

TABLE A-continued
| Structure | Cpd. No. |
|---|---|
| 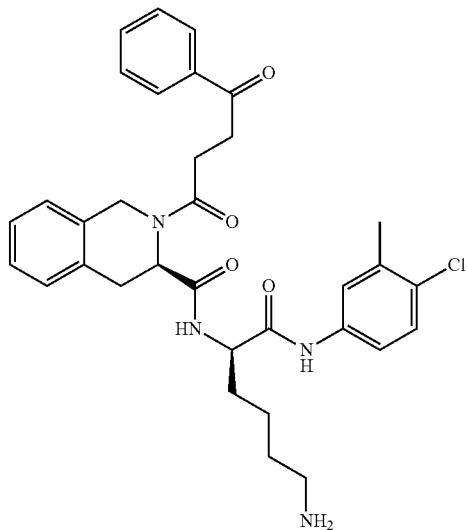 [SMILES: Cc1cc(NC(=O)[C@@H](CCCCN)NC(=O)[C@H]2Cc3ccccc3CN2C(=O)CCC(=O)c2ccccc2)ccc1Cl] | 4-2 |
| 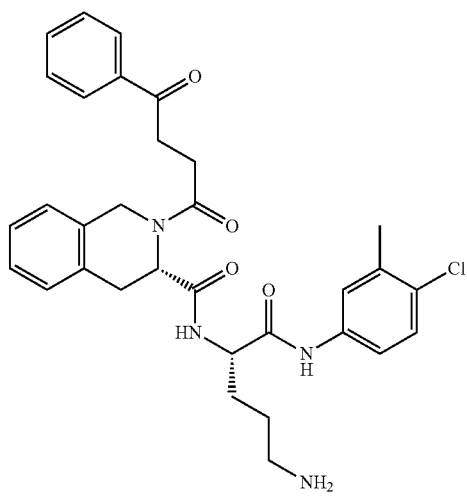 [SMILES: Cc1cc(NC(=O)[C@H](CCCN)NC(=O)[C@@H]2Cc3ccccc3CN2C(=O)CCC(=O)c2ccccc2)ccc1Cl] | 4-3 |
| 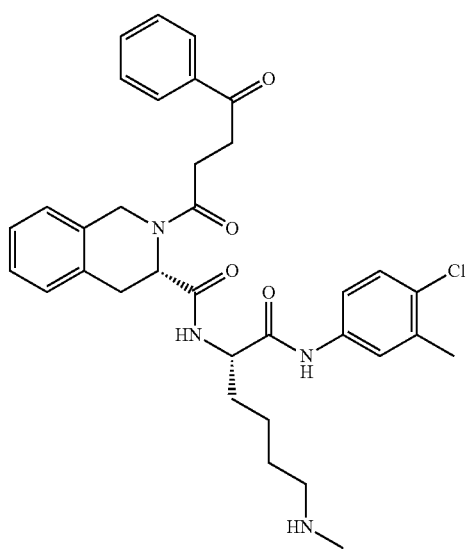 [SMILES: CNCCCC[C@H](NC(=O)[C@@H]1Cc2ccccc2CN1C(=O)CCC(=O)c1ccccc1)C(=O)Nc1ccc(Cl)c(C)c1] | 4-4 |

TABLE A-continued

| Structure | Cpd. No. |
|-----------|----------|
| 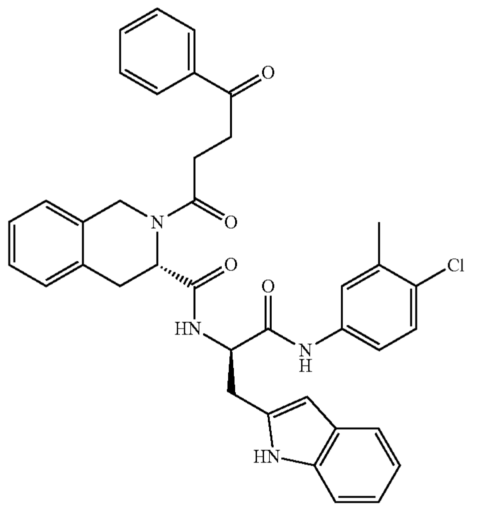 [SMILES: Cc1cc(NC(=O)[C@@H](Cc2cc3ccccc3[nH]2)NC(=O)[C@@H]2Cc3ccccc3CN2C(=O)CCC(=O)c2ccccc2)ccc1Cl] | 4-5 |
| 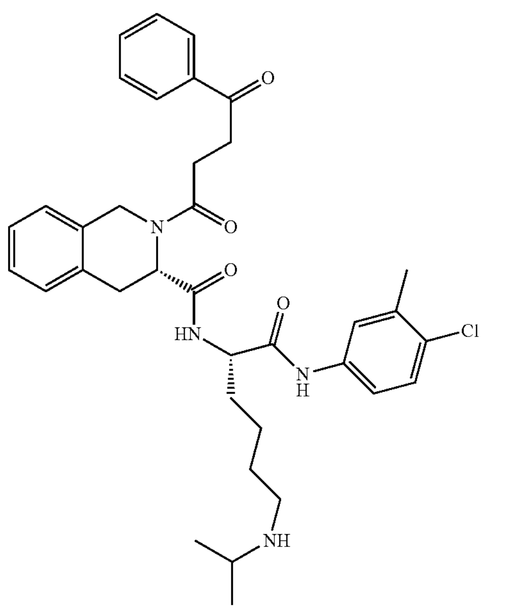 [SMILES: Cc1cc(NC(=O)[C@H](CCCCNC(C)C)NC(=O)[C@@H]2Cc3ccccc3CN2C(=O)CCC(=O)c2ccccc2)ccc1Cl] | 4-6 |
| 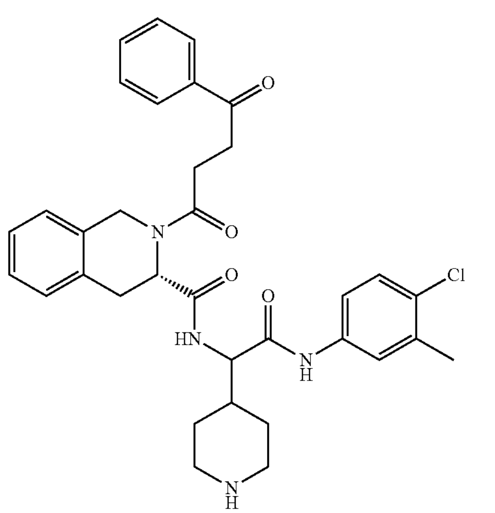 [SMILES: Cc1cc(NC(=O)C(NC(=O)[C@@H]2Cc3ccccc3CN2C(=O)CCC(=O)c2ccccc2)C2CCNCC2)ccc1Cl] | 4-7 |

TABLE A-continued
| Structure | Cpd. No. |
|---|---|
| 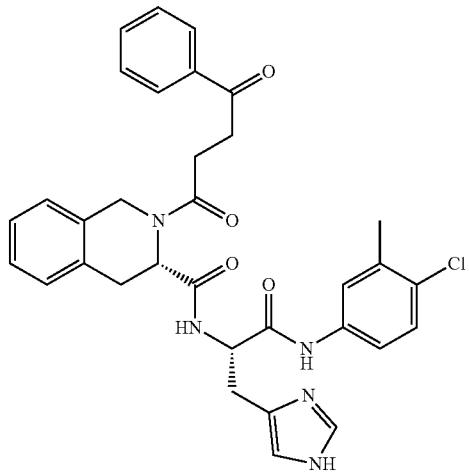 [SMILES: Cc1cc(NC(=O)[C@H](Cc2c[nH]cn2)NC(=O)[C@@H]2Cc3ccccc3CN2C(=O)CCC(=O)c2ccccc2)ccc1Cl] | 4-8 |
| 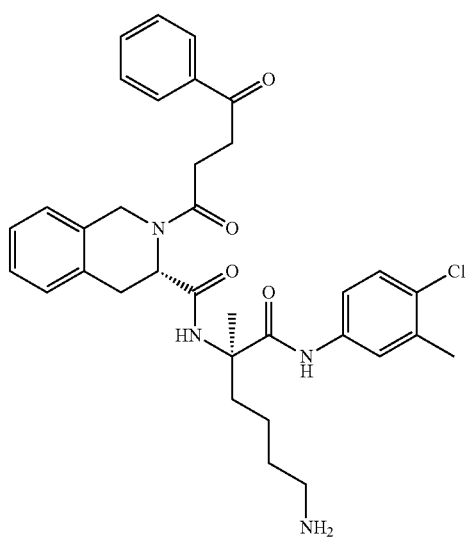 [SMILES: Cc1cc(NC(=O)[C@@](C)(CCCCN)NC(=O)[C@@H]2Cc3ccccc3CN2C(=O)CCC(=O)c2ccccc2)ccc1Cl] | 4-9 |
| 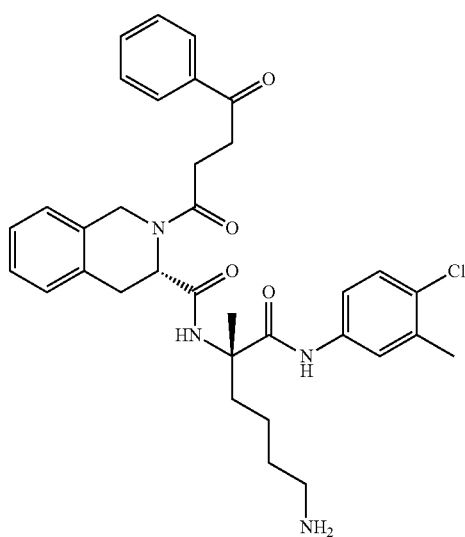 [SMILES: Cc1cc(NC(=O)[C@](C)(CCCCN)NC(=O)[C@@H]2Cc3ccccc3CN2C(=O)CCC(=O)c2ccccc2)ccc1Cl] | 4-10 |

TABLE A-continued
| Structure | Cpd. No. |
|---|---|
| 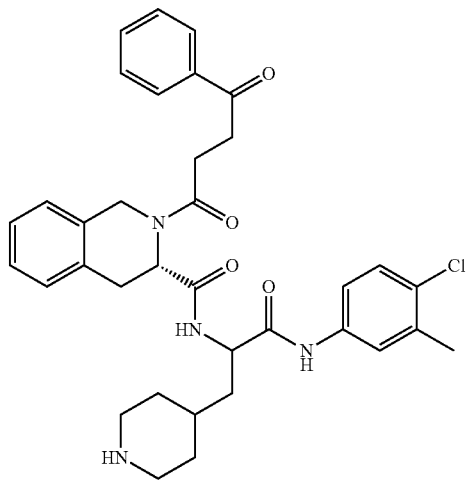 [SMILES: Cc1cc(NC(=O)C(CC2CCNCC2)NC(=O)[C@@H]2Cc3ccccc3CN2C(=O)CCC(=O)c2ccccc2)ccc1Cl] | 4-11 |
| 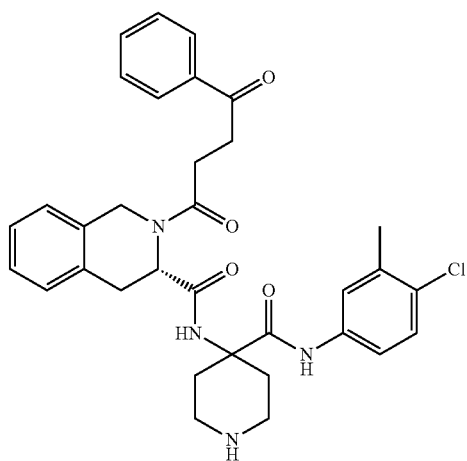 [SMILES: Cc1cc(NC(=O)C2(NC(=O)[C@@H]3Cc4ccccc4CN3C(=O)CCC(=O)c3ccccc3)CCNCC2)ccc1Cl] | 4-12 |
| 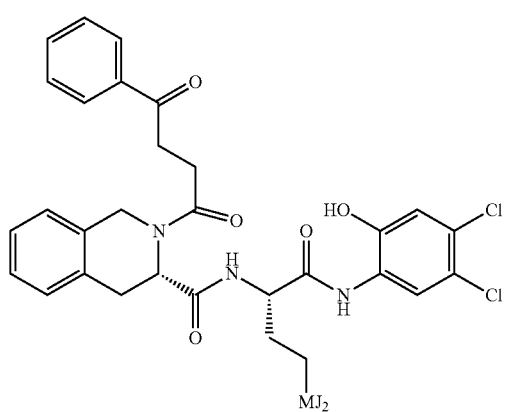 | 4-13 |

TABLE A-continued
| Structure | Cpd. No. |
|---|---|
| 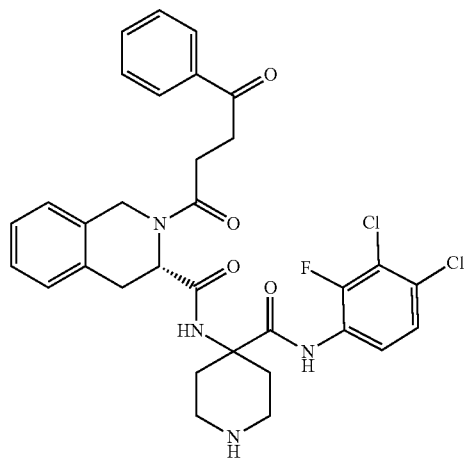 [SMILES: O=C(CCC(=O)N1Cc2ccccc2C[C@H]1C(=O)NC1(C(=O)Nc2ccc(Cl)c(Cl)c2F)CCNCC1)c1ccccc1] | 4-14 |
| 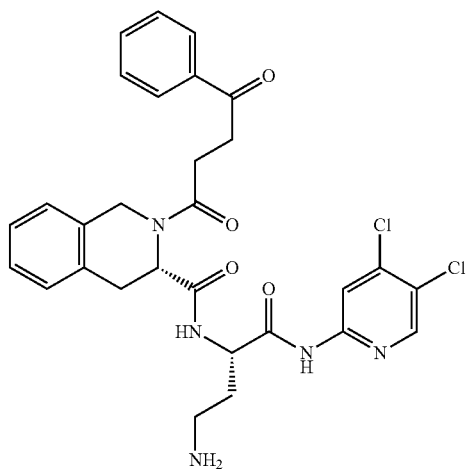 [SMILES: NCC[C@H](NC(=O)[C@@H]1Cc2ccccc2CN1C(=O)CCC(=O)c1ccccc1)C(=O)Nc1cc(Cl)c(Cl)cn1] | 4-15 |
| 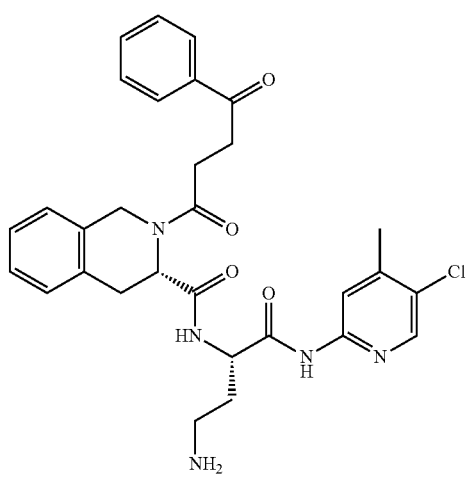 [SMILES: Cc1cc(NC(=O)[C@H](CCN)NC(=O)[C@@H]2Cc3ccccc3CN2C(=O)CCC(=O)c2ccccc2)ncc1Cl] | 4-16 |

TABLE A-continued
| Structure | Cpd. No. |
|---|---|
| 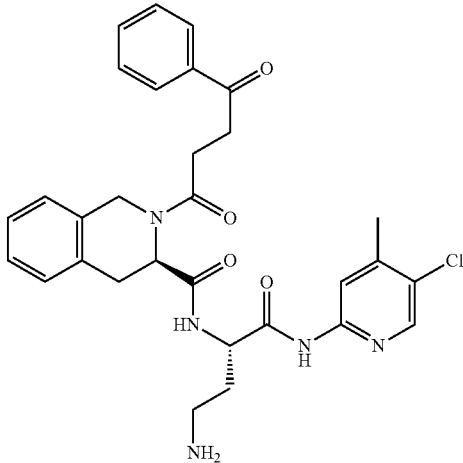 [SMILES: Cc1cc(NC(=O)[C@H](CCN)NC(=O)[C@H]2Cc3ccccc3CN2C(=O)CCC(=O)c2ccccc2)ncc1Cl] | 4-17 |
| 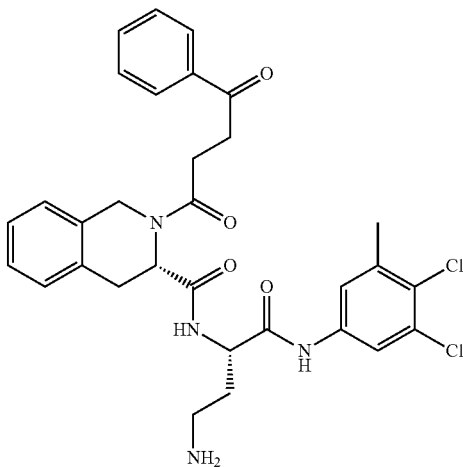 [SMILES: Cc1cc(NC(=O)[C@H](CCN)NC(=O)[C@@H]2Cc3ccccc3CN2C(=O)CCC(=O)c2ccccc2)cc(Cl)c1Cl] | 4-18 |
| 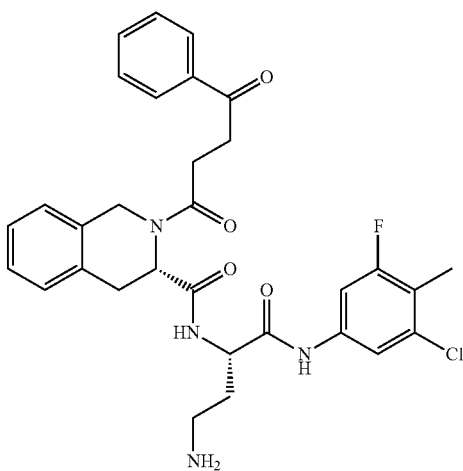 [SMILES: Cc1c(F)cc(NC(=O)[C@H](CCN)NC(=O)[C@@H]2Cc3ccccc3CN2C(=O)CCC(=O)c2ccccc2)cc1Cl] | 4-19 |

TABLE A-continued
| Structure | Cpd. No. |
|---|---|
| 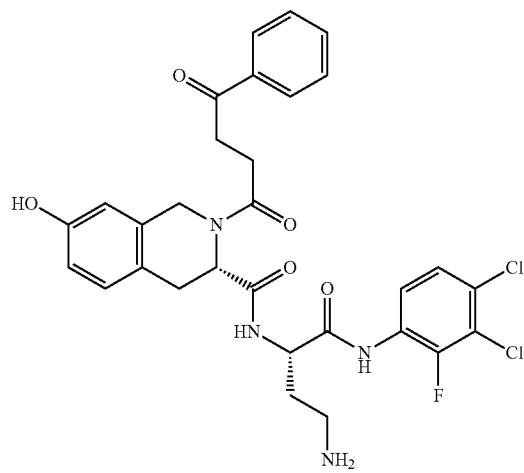 [SMILES: NCC[C@H](NC(=O)[C@@H]1Cc2ccc(O)cc2CN1C(=O)CCC(=O)c1ccccc1)C(=O)Nc1ccc(Cl)c(Cl)c1F] | 4-20 |
| 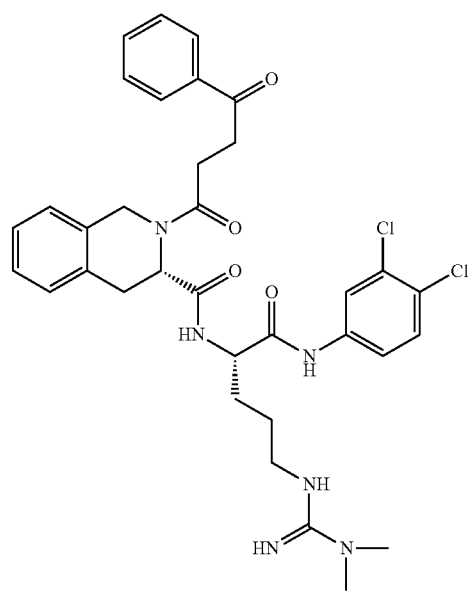 [SMILES: CN(C)C(=N)NCCC[C@H](NC(=O)[C@@H]1Cc2ccccc2CN1C(=O)CCC(=O)c1ccccc1)C(=O)Nc1ccc(Cl)c(Cl)c1] | 5-1 |
| 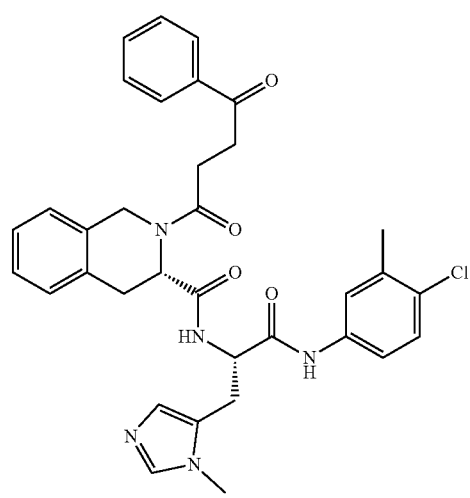 [SMILES: Cc1cc(NC(=O)[C@H](Cc2cncn2C)NC(=O)[C@@H]2Cc3ccccc3CN2C(=O)CCC(=O)c2ccccc2)ccc1Cl] | 5-2 |

TABLE A-continued
| Structure | Cpd. No. |
|---|---|
| 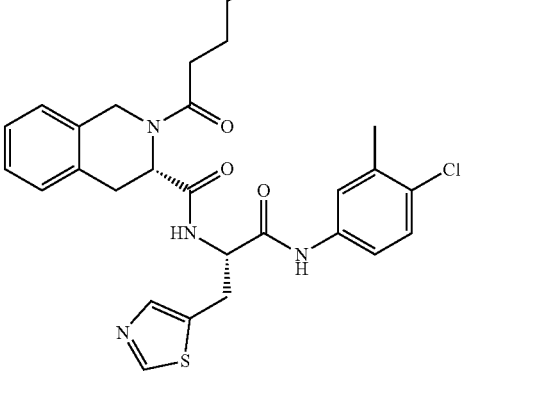 | 5-3 |
| 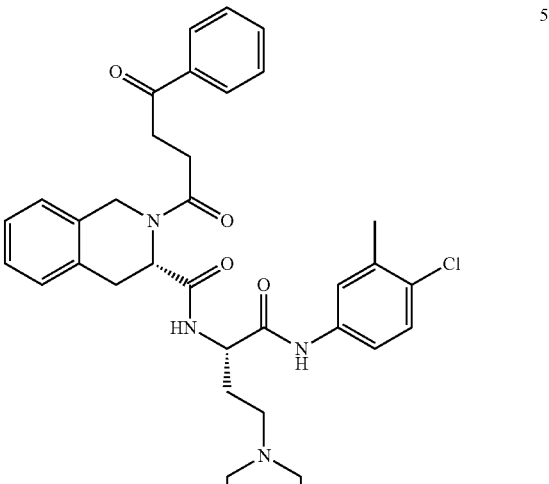 | 5-4 |
| 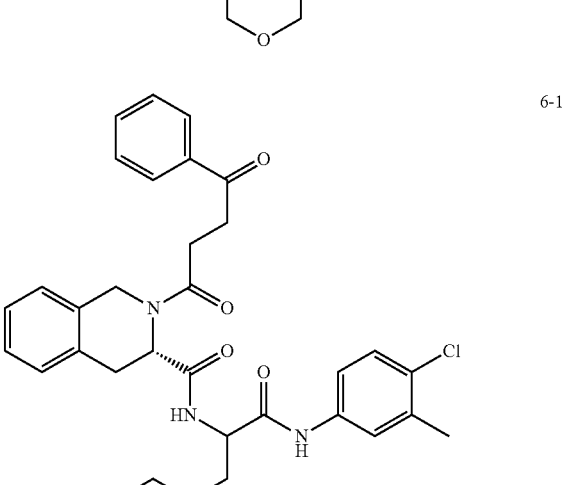 | 6-1 |

TABLE A-continued
| Structure | Cpd. No. |
|---|---|
| 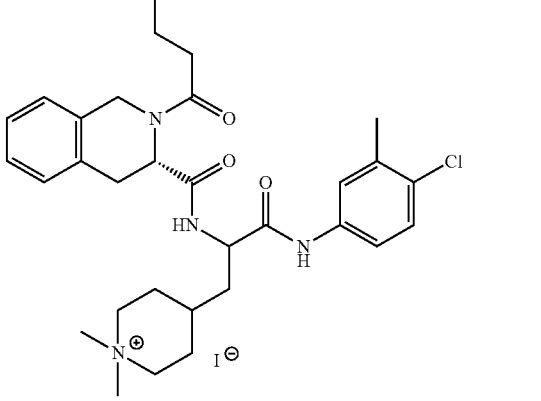 | 6-2 |
| 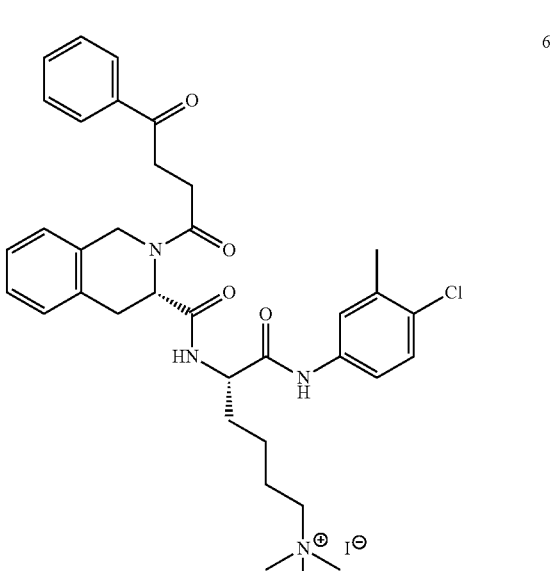 | 6-3 |
| 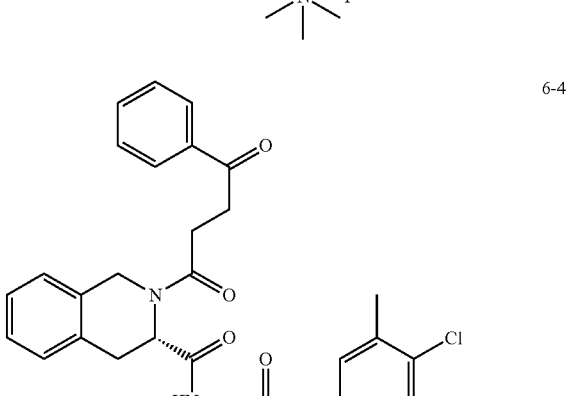 | 6-4 |

TABLE A-continued
| Structure | Cpd. No. |
|---|---|
| 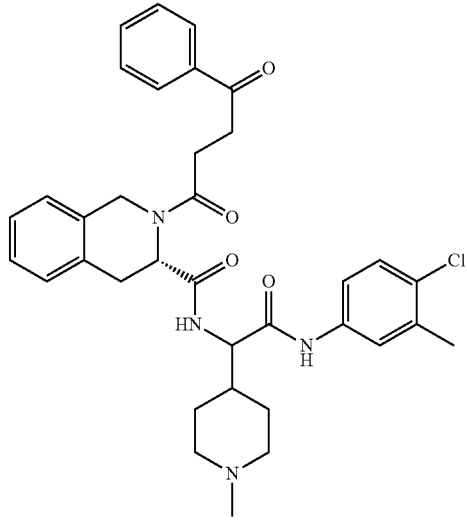 [SMILES: Cc1cc(NC(=O)C(NC(=O)[C@@H]2Cc3ccccc3CN2C(=O)CCC(=O)c2ccccc2)C2CCN(C)CC2)ccc1Cl] | 6-5 |
| 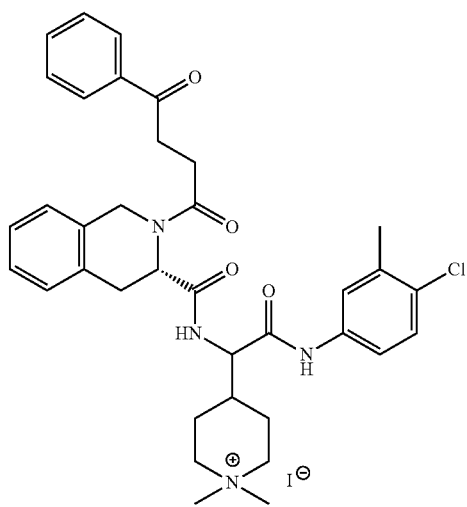 [SMILES: Cc1cc(NC(=O)C(NC(=O)[C@@H]2Cc3ccccc3CN2C(=O)CCC(=O)c2ccccc2)C2CC[N+](C)(C)CC2)ccc1Cl ; [I-]] | 6-6 |
| 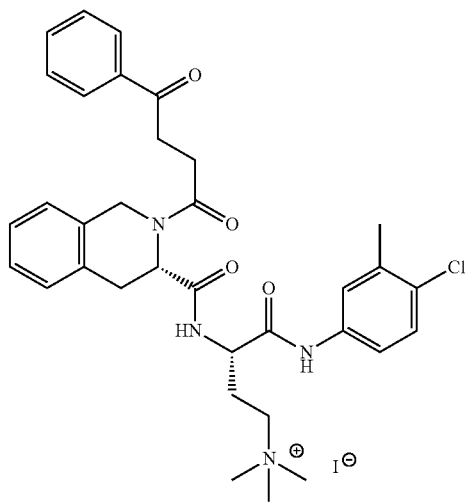 [SMILES: Cc1cc(NC(=O)[C@H](CC[N+](C)(C)C)NC(=O)[C@@H]2Cc3ccccc3CN2C(=O)CCC(=O)c2ccccc2)ccc1Cl ; [I-]] | 6-7 |

TABLE A-continued
| Structure | Cpd. No. |
|---|---|
| 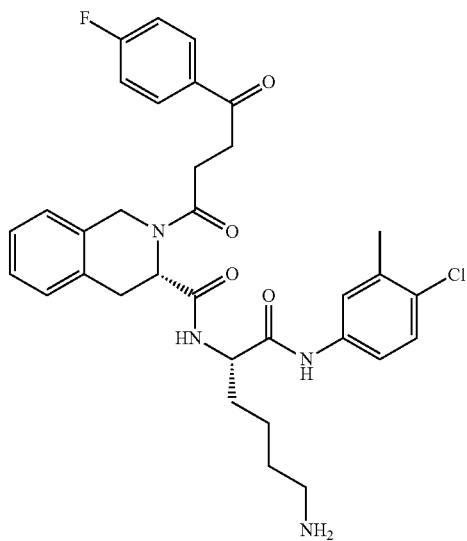 [SMILES: Cc1cc(NC(=O)[C@H](CCCCN)NC(=O)[C@@H]2Cc3ccccc3CN2C(=O)CCC(=O)c2ccc(F)cc2)ccc1Cl] | 7-1 |
| 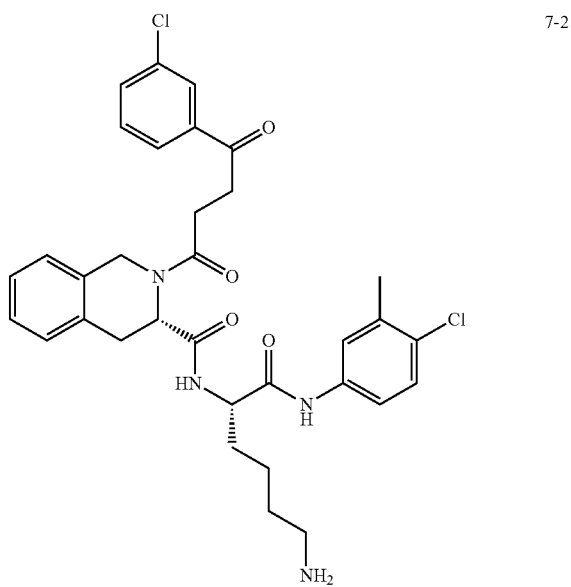 | 7-2 |

TABLE A-continued
| Structure | Cpd. No. |
|---|---|
| 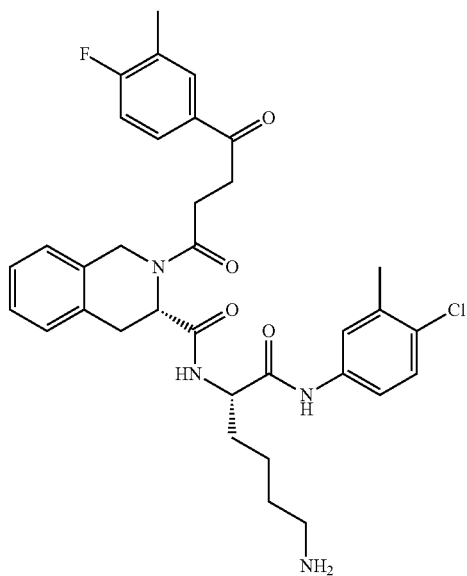 [SMILES: Cc1cc(C(=O)CCC(=O)N2Cc3ccccc3C[C@H]2C(=O)N[C@@H](CCCCN)C(=O)Nc2ccc(Cl)c(C)c2)ccc1F] | 7-3 |
| 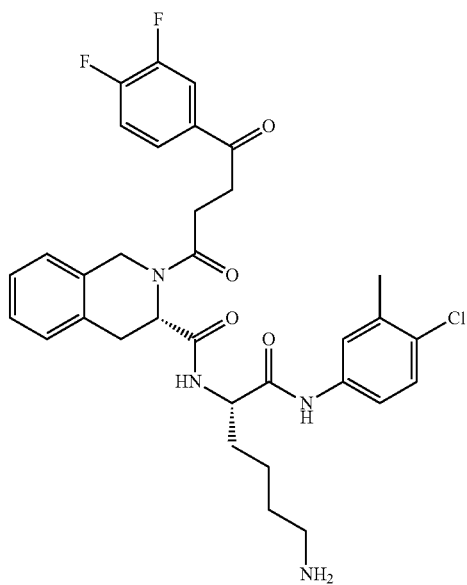 [SMILES: Cc1cc(NC(=O)[C@H](CCCCN)NC(=O)[C@@H]2Cc3ccccc3CN2C(=O)CCC(=O)c2ccc(F)c(F)c2)ccc1Cl] | 7-4 |

TABLE A-continued
| Structure | Cpd. No. |
|---|---|
| 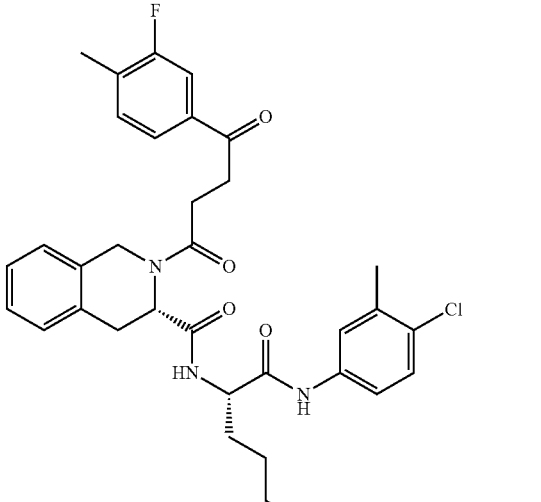 | 7-5 |
| 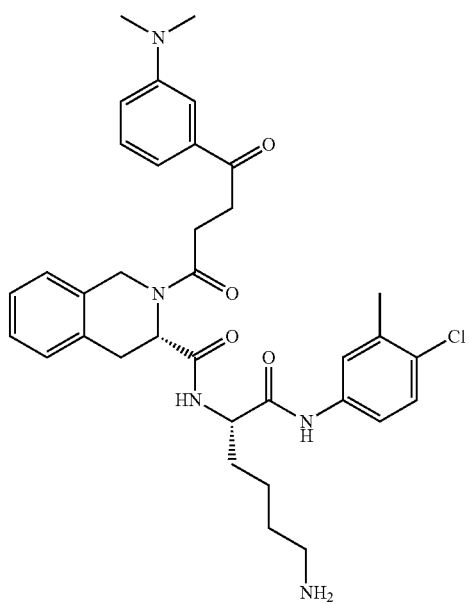 [SMILES: Cc1cc(NC(=O)[C@H](CCCCN)NC(=O)[C@@H]2Cc3ccccc3CN2C(=O)CCC(=O)c2cccc(N(C)C)c2)ccc1Cl] | 7-6 |

TABLE A-continued
| Structure | Cpd. No. |
|---|---|
| 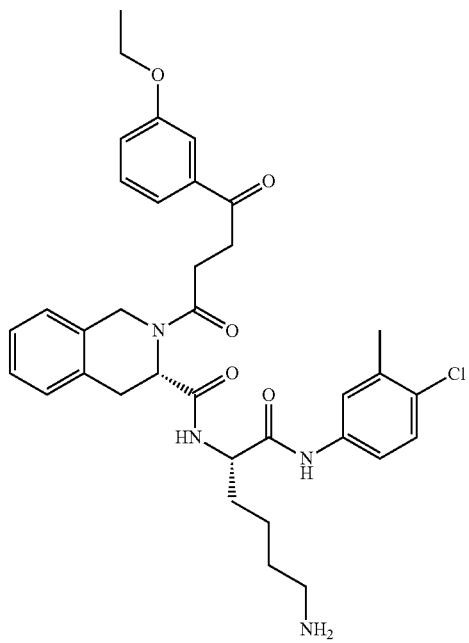 [SMILES: CCOc1cccc(C(=O)CCC(=O)N2Cc3ccccc3C[C@H]2C(=O)N[C@@H](CCCCN)C(=O)Nc2ccc(Cl)c(C)c2)c1] | 7-7 |
| 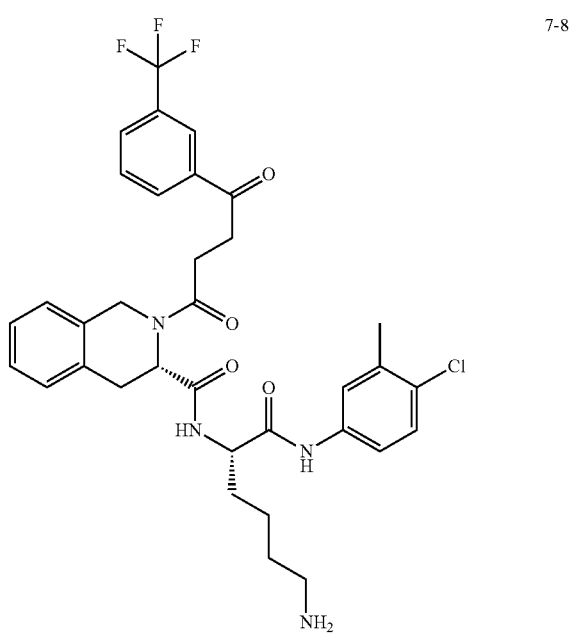 | 7-8 |

TABLE A-continued
| Structure | Cpd. No. |
|---|---|
| 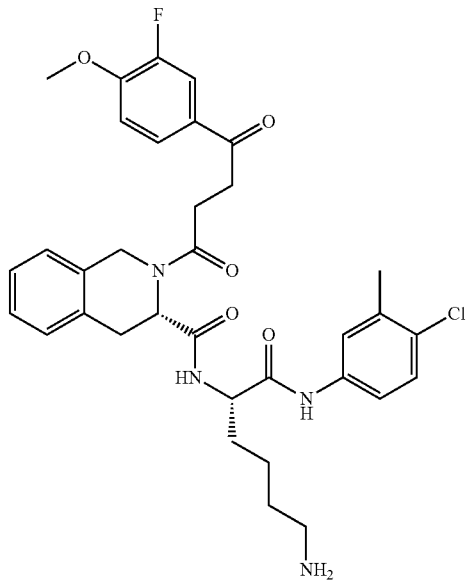 [SMILES: COc1ccc(C(=O)CCC(=O)N2Cc3ccccc3C[C@H]2C(=O)N[C@@H](CCCCN)C(=O)Nc2ccc(Cl)c(C)c2)cc1F] | 7-9 |
| 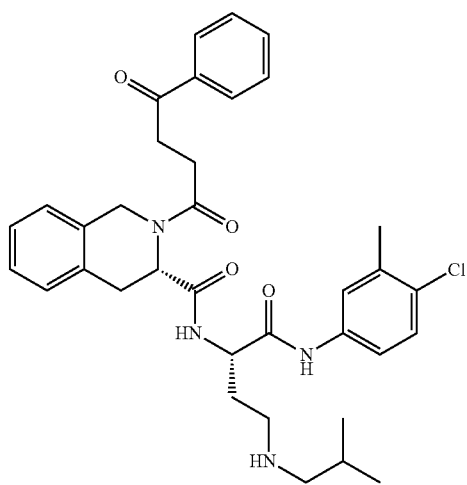 [SMILES: Cc1cc(NC(=O)[C@H](CCNCC(C)C)NC(=O)[C@@H]2Cc3ccccc3CN2C(=O)CCC(=O)c2ccccc2)ccc1Cl] | 8-1 |
| 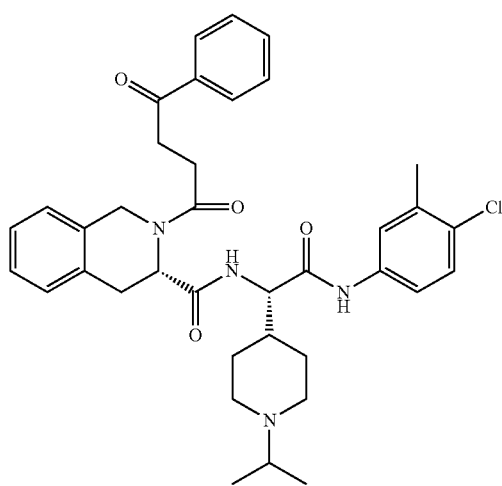 [SMILES: Cc1cc(NC(=O)[C@@H](NC(=O)[C@@H]2Cc3ccccc3CN2C(=O)CCC(=O)c2ccccc2)C2CCN(C(C)C)CC2)ccc1Cl] | 8-2 |

TABLE A-continued

| Structure | Cpd. No. |
|---|---|
| 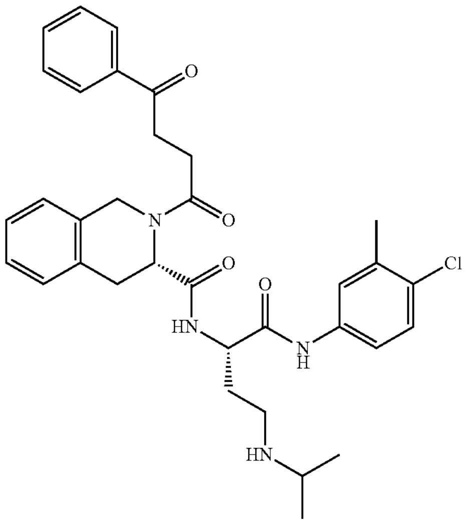 [SMILES: Cc1cc(NC(=O)[C@H](CCNC(C)C)NC(=O)[C@@H]2Cc3ccccc3CN2C(=O)CCC(=O)c2ccccc2)ccc1Cl] | 8-3 |
| 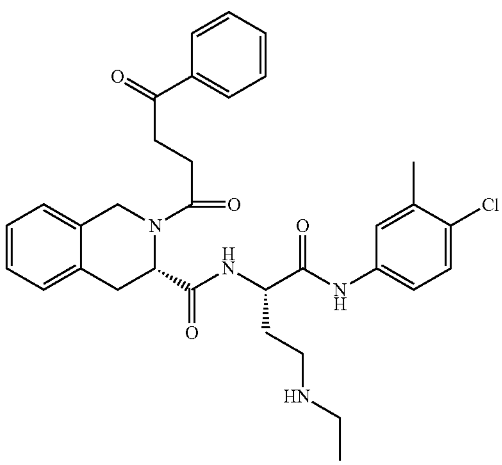 [SMILES: CCNCC[C@H](NC(=O)[C@@H]1Cc2ccccc2CN1C(=O)CCC(=O)c1ccccc1)C(=O)Nc1ccc(Cl)c(C)c1] | 8-4 |
| 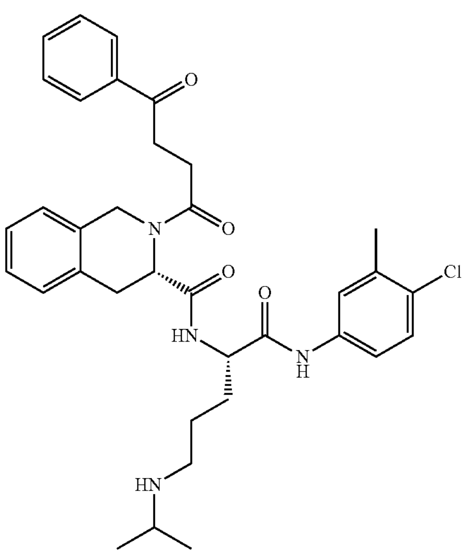 [SMILES: Cc1cc(NC(=O)[C@H](CCCNC(C)C)NC(=O)[C@@H]2Cc3ccccc3CN2C(=O)CCC(=O)c2ccccc2)ccc1Cl] | 8-5 |

TABLE A-continued
| Structure | Cpd. No. |
|---|---|
| 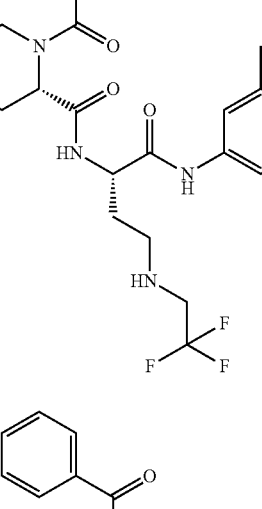 | 8-6 |
| 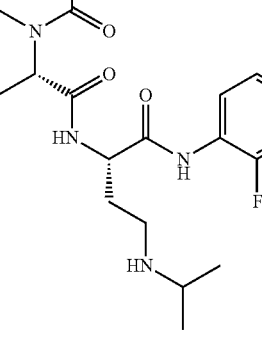 | 8-7 |
| 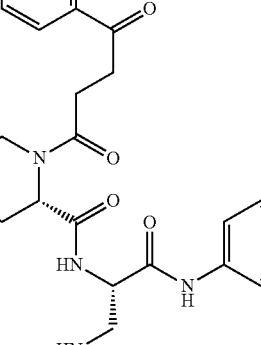 | 9-1 |

TABLE A-continued
| Structure | Cpd. No. |
|---|---|
| 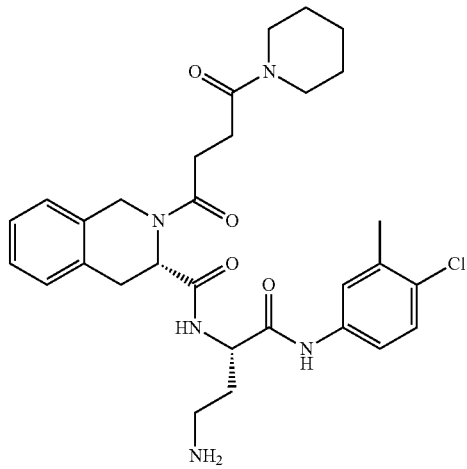 [SMILES: Cc1cc(NC(=O)[C@H](CCN)NC(=O)[C@@H]2Cc3ccccc3CN2C(=O)CCC(=O)N2CCCCC2)ccc1Cl] | 10-1 |
| 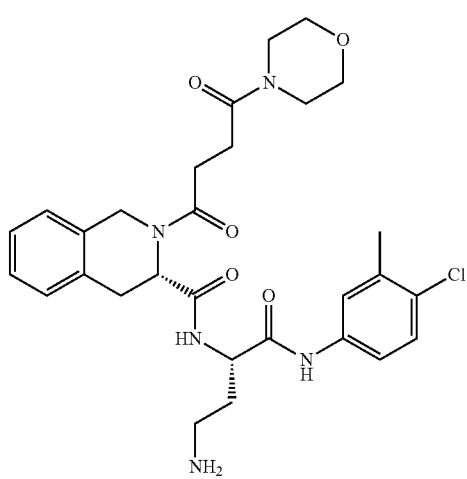 [SMILES: Cc1cc(NC(=O)[C@H](CCN)NC(=O)[C@@H]2Cc3ccccc3CN2C(=O)CCC(=O)N2CCOCC2)ccc1Cl] | 10-2 |
| 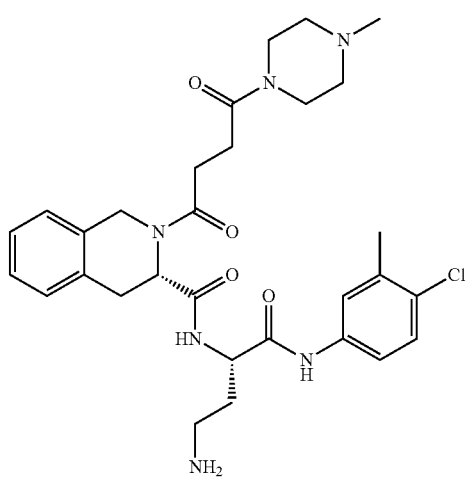 [SMILES: Cc1cc(NC(=O)[C@H](CCN)NC(=O)[C@@H]2Cc3ccccc3CN2C(=O)CCC(=O)N2CCN(C)CC2)ccc1Cl] | 10-3 |

TABLE A-continued
| Structure | Cpd. No. |
|---|---|
| 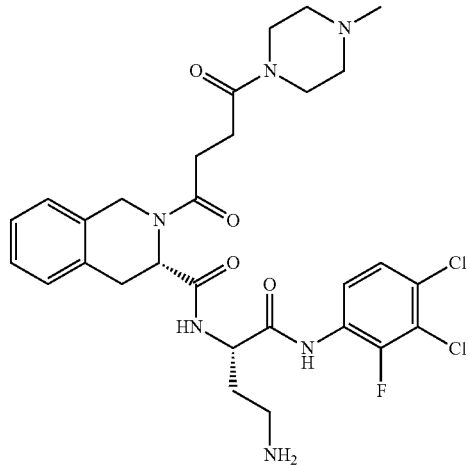 [SMILES: CN1CCN(C(=O)CCC(=O)N2Cc3ccccc3C[C@H]2C(=O)N[C@@H](CCN)C(=O)Nc2ccc(Cl)c(Cl)c2F)CC1] | 10-4 |
| 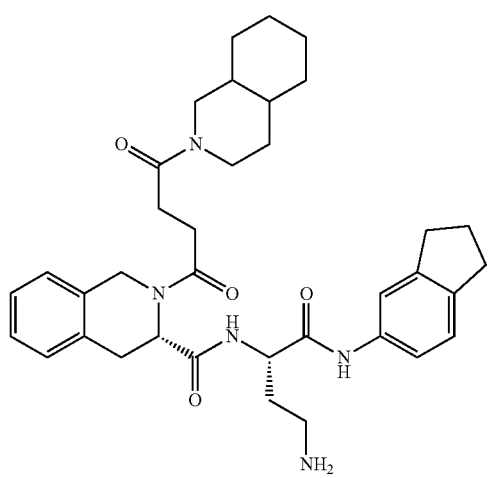 [SMILES: NCC[C@H](NC(=O)[C@@H]1Cc2ccccc2CN1C(=O)CCC(=O)N1CCC2CCCCC2C1)C(=O)Nc1ccc2c(c1)CCC2] | 10-5 |
| 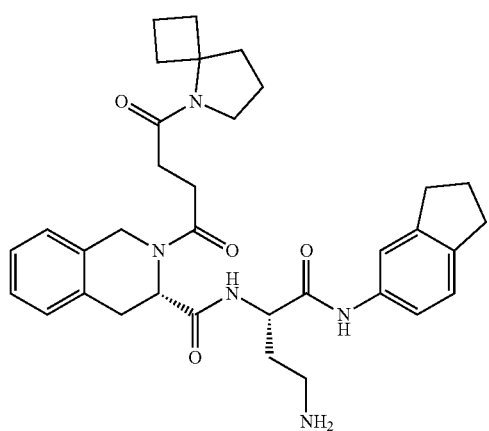 [SMILES: NCC[C@H](NC(=O)[C@@H]1Cc2ccccc2CN1C(=O)CCC(=O)N1CCCC12CCC2)C(=O)Nc1ccc2c(c1)CCC2] | 10-6 |

TABLE A-continued
| Structure | Cpd. No. |
|---|---|
| 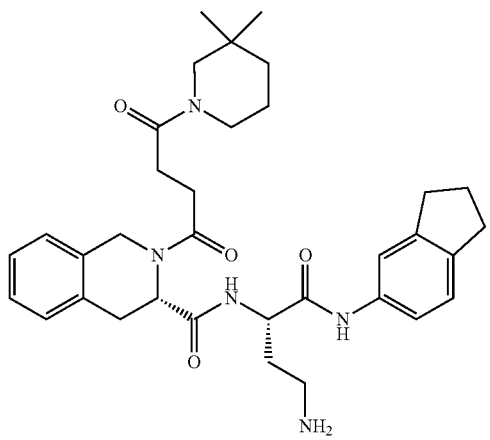 [SMILES: CC1(C)CCCN(C(=O)CCC(=O)N2Cc3ccccc3C[C@H]2C(=O)N[C@@H](CCN)C(=O)Nc2ccc3c(c2)CCC3)C1] | 10-7 |
| 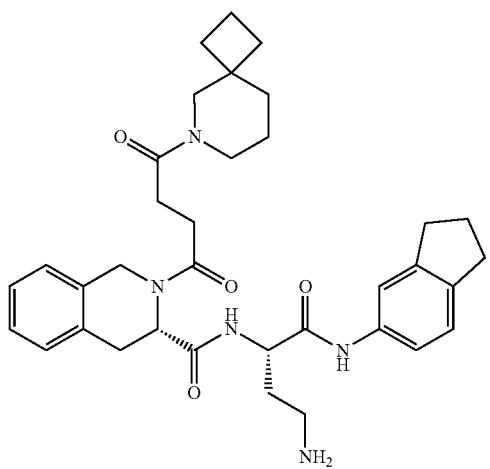 [SMILES: NCC[C@H](NC(=O)[C@@H]1Cc2ccccc2CN1C(=O)CCC(=O)N1CCCC2(CCC2)C1)C(=O)Nc1ccc2c(c1)CCC2] | 10-8 |
| 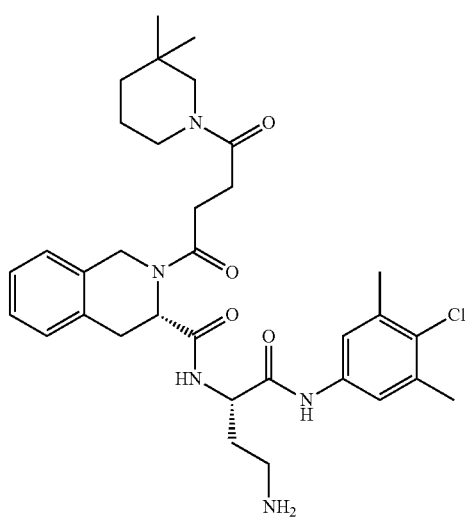 [SMILES: Cc1cc(NC(=O)[C@H](CCN)NC(=O)[C@@H]2Cc3ccccc3CN2C(=O)CCC(=O)N2CCCC(C)(C)C2)cc(C)c1Cl] | 10-9 |

TABLE A-continued

| Structure | Cpd. No. |
|---|---|
| 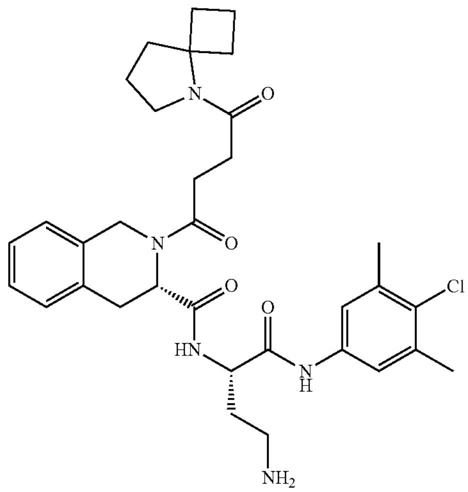 [SMILES: Cc1cc(NC(=O)[C@H](CCN)NC(=O)[C@@H]2Cc3ccccc3CN2C(=O)CCC(=O)N2CCCC23CCC3)cc(C)c1Cl] | 10-10 |
| 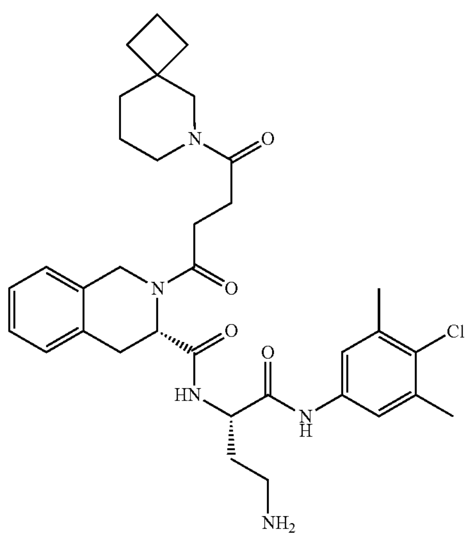 [SMILES: Cc1cc(NC(=O)[C@H](CCN)NC(=O)[C@@H]2Cc3ccccc3CN2C(=O)CCC(=O)N2CCCC3(CCC3)C2)cc(C)c1Cl] | 10-11 |
| 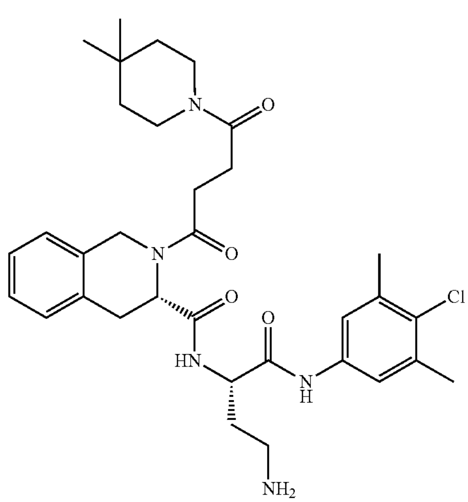 [SMILES: Cc1cc(NC(=O)[C@H](CCN)NC(=O)[C@@H]2Cc3ccccc3CN2C(=O)CCC(=O)N2CCC(C)(C)CC2)cc(C)c1Cl] | 10-12 |

TABLE A-continued
| Structure | Cpd. No. |
|---|---|
| 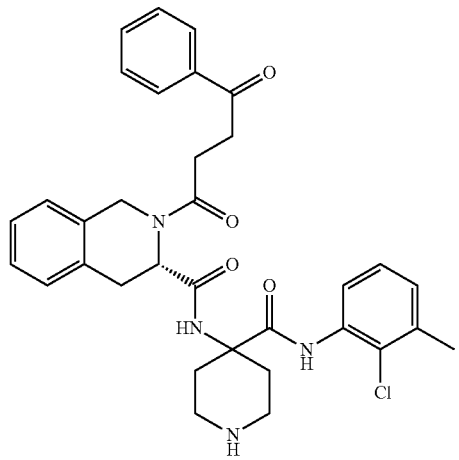 [SMILES: Cc1cccc(NC(=O)C2(NC(=O)[C@@H]3Cc4ccccc4CN3C(=O)CCC(=O)c3ccccc3)CCNCC2)c1Cl] | 11-1 |
| 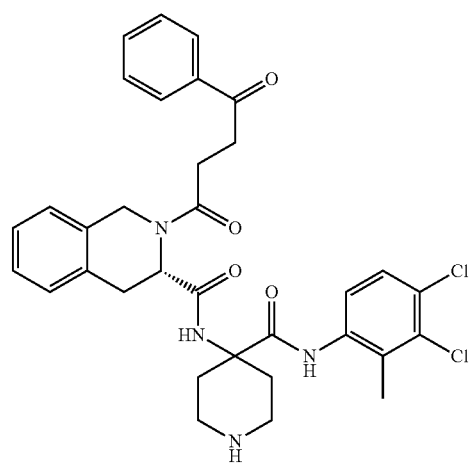 | 11-2 |
| 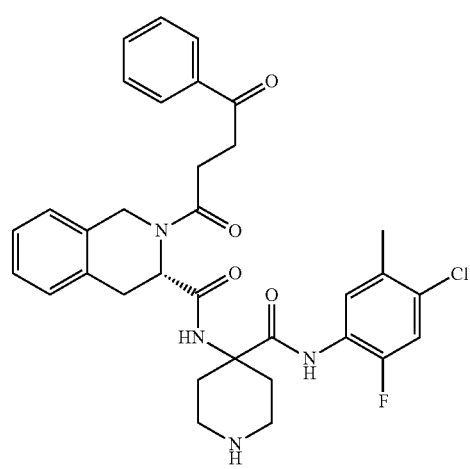 [SMILES: Cc1cc(NC(=O)C2(NC(=O)[C@@H]3Cc4ccccc4CN3C(=O)CCC(=O)c3ccccc3)CCNCC2)c(F)cc1Cl] | 11-3 |

TABLE A-continued
| Structure | Cpd. No. |
|---|---|
| 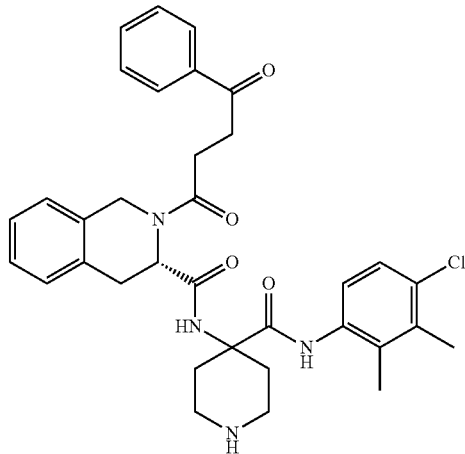 [SMILES: Cc1c(Cl)ccc(NC(=O)C2(NC(=O)[C@@H]3Cc4ccccc4CN3C(=O)CCC(=O)c3ccccc3)CCNCC2)c1C] | 11-4 |
| 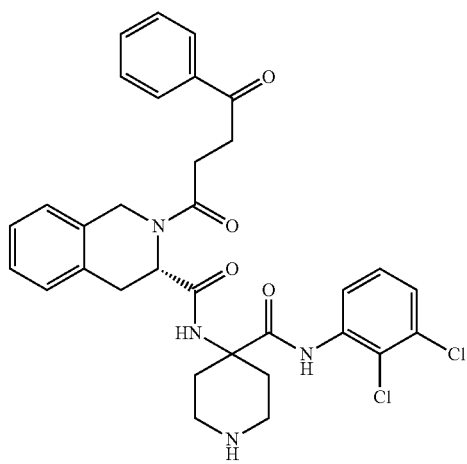 [SMILES: O=C(CCC(=O)N1Cc2ccccc2C[C@H]1C(=O)NC1(C(=O)Nc2cccc(Cl)c2Cl)CCNCC1)c1ccccc1] | 11-5 |
| 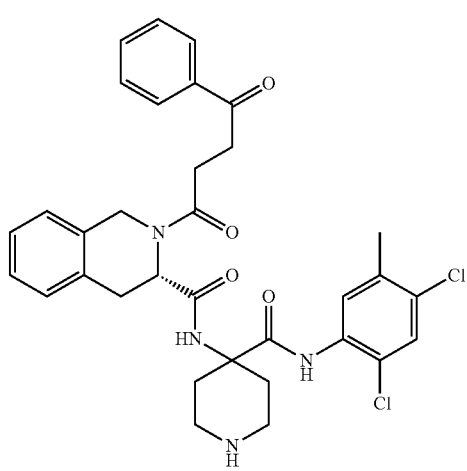 | 11-6 |

TABLE A-continued
| Structure | Cpd. No. |
|---|---|
| 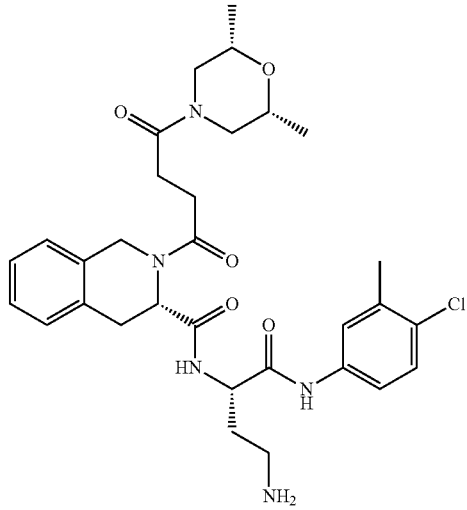 | 12-1 |
| 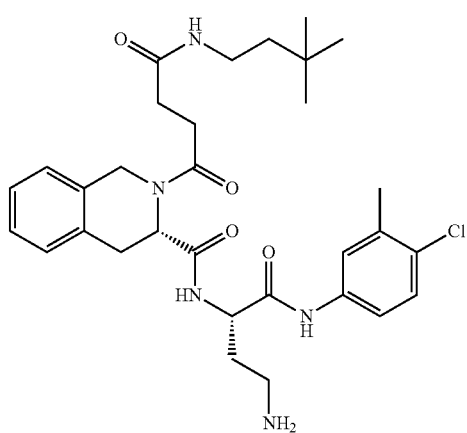 [SMILES: Cc1cc(NC(=O)[C@H](CCN)NC(=O)[C@@H]2Cc3ccccc3CN2C(=O)CCC(=O)NCCC(C)(C)C)ccc1Cl] | 12-2 |
| 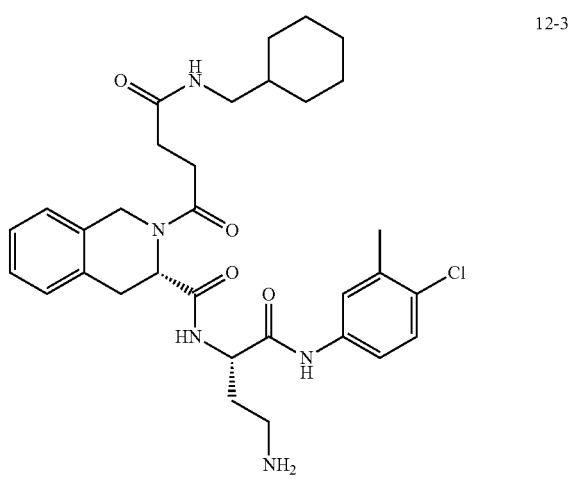 | 12-3 |

TABLE A-continued
| Structure | Cpd. No. |
|---|---|
| 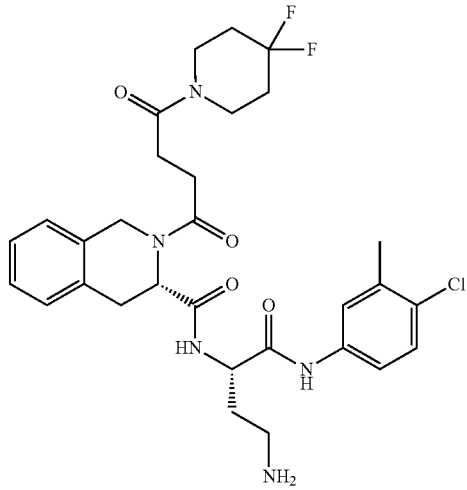 [SMILES: Cc1cc(NC(=O)[C@H](CCN)NC(=O)[C@@H]2Cc3ccccc3CN2C(=O)CCC(=O)N2CCC(F)(F)CC2)ccc1Cl] | 12-4 |
| 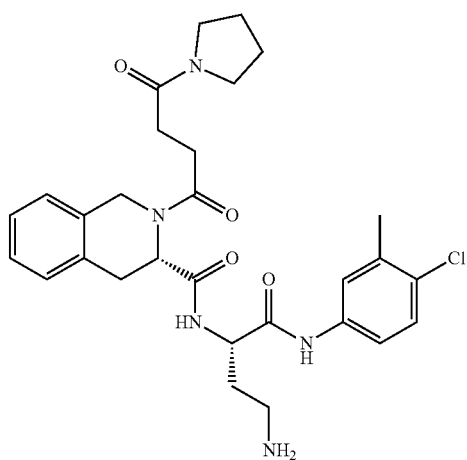 [SMILES: Cc1cc(NC(=O)[C@H](CCN)NC(=O)[C@@H]2Cc3ccccc3CN2C(=O)CCC(=O)N2CCCC2)ccc1Cl] | 12-5 |
| 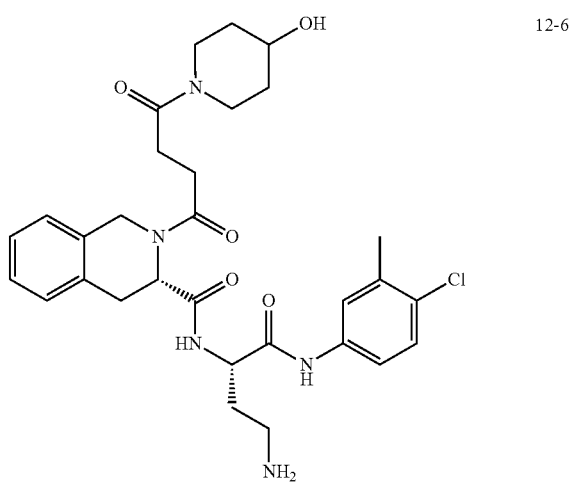 | 12-6 |

TABLE A-continued
| Structure | Cpd. No. |
|---|---|
| 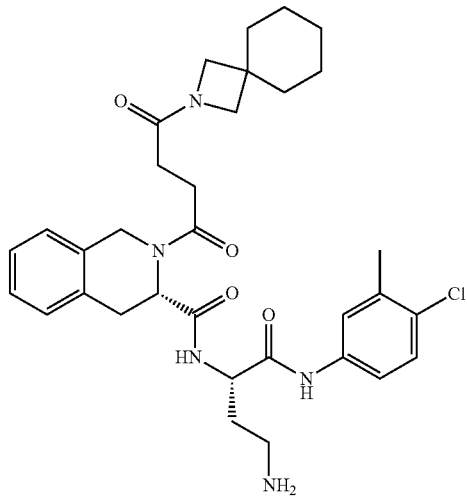 [SMILES: Cc1cc(NC(=O)[C@H](CCN)NC(=O)[C@@H]2Cc3ccccc3CN2C(=O)CCC(=O)N2CC3(CCCCC3)C2)ccc1Cl] | 12-7 |
| 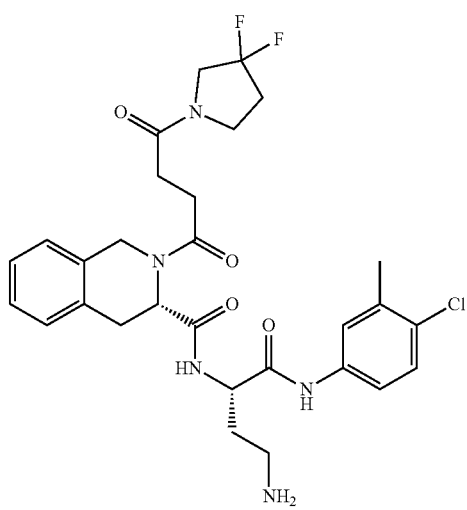 [SMILES: Cc1cc(NC(=O)[C@H](CCN)NC(=O)[C@@H]2Cc3ccccc3CN2C(=O)CCC(=O)N2CCC(F)(F)C2)ccc1Cl] | 12-8 |
| 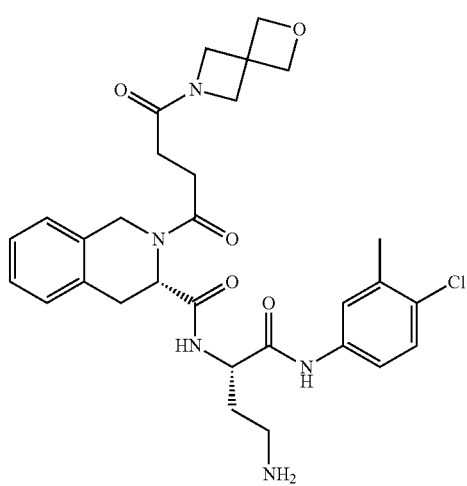 [SMILES: Cc1cc(NC(=O)[C@H](CCN)NC(=O)[C@@H]2Cc3ccccc3CN2C(=O)CCC(=O)N2CC3(COC3)C2)ccc1Cl] | 12-9 |

TABLE A-continued
| Structure | Cpd. No. |
|---|---|
| 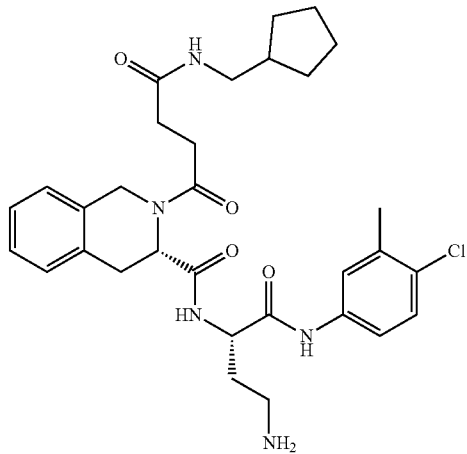 [SMILES: Cc1cc(NC(=O)[C@H](CCN)NC(=O)[C@@H]2Cc3ccccc3CN2C(=O)CCC(=O)NCC2CCCC2)ccc1Cl] | 12-10 |
| 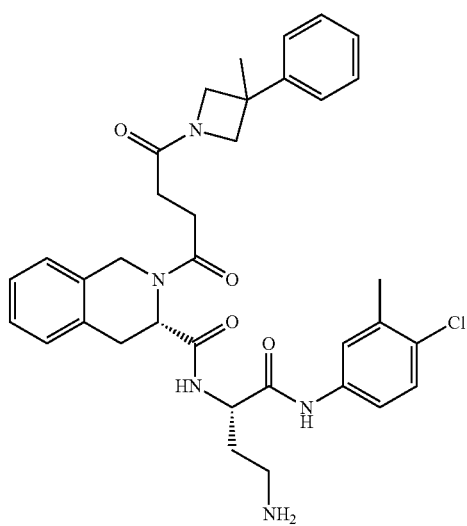 [SMILES: Cc1cc(NC(=O)[C@H](CCN)NC(=O)[C@@H]2Cc3ccccc3CN2C(=O)CCC(=O)N2CC(C)(c3ccccc3)C2)ccc1Cl] | 12-11 |
| 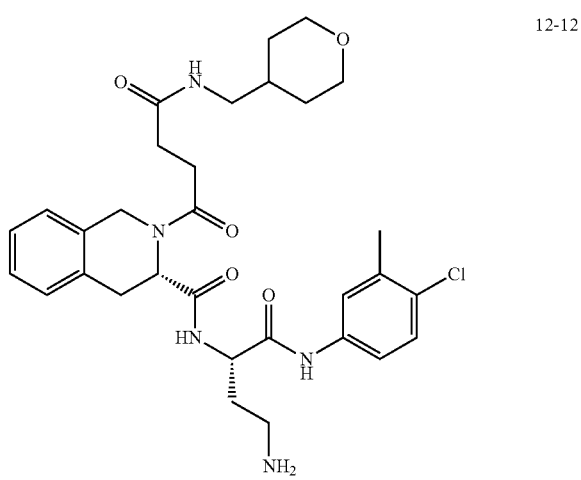 | 12-12 |

TABLE A-continued

| Structure | Cpd. No. |
|---|---|
| 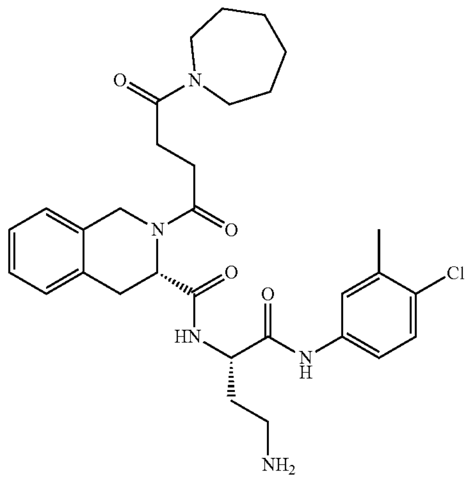 | 12-13 |
| 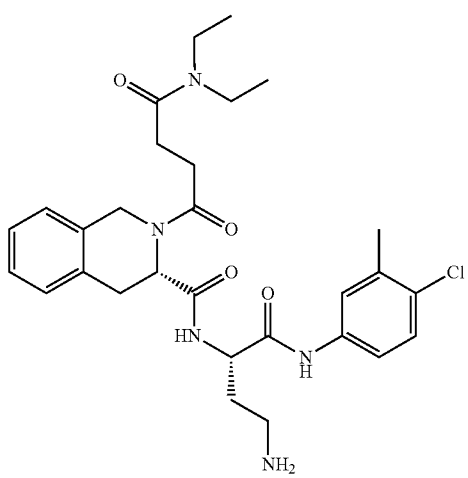 [SMILES: CCN(CC)C(=O)CCC(=O)N1Cc2ccccc2C[C@H]1C(=O)N[C@@H](CCN)C(=O)Nc1ccc(Cl)c(C)c1] | 12-14 |
| 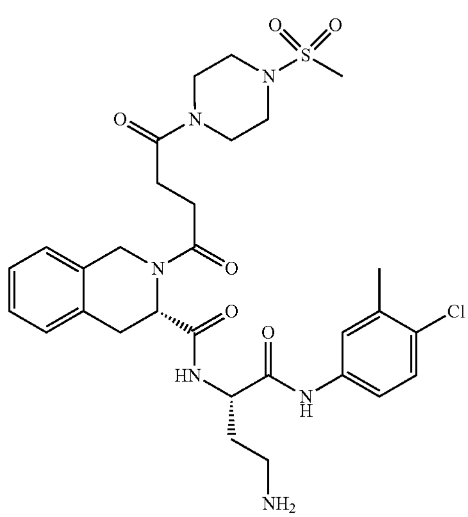 [SMILES: Cc1cc(NC(=O)[C@H](CCN)NC(=O)[C@@H]2Cc3ccccc3CN2C(=O)CCC(=O)N2CCN(S(C)(=O)=O)CC2)ccc1Cl] | 12-15 |

TABLE A-continued
| Structure | Cpd. No. |
|---|---|
| 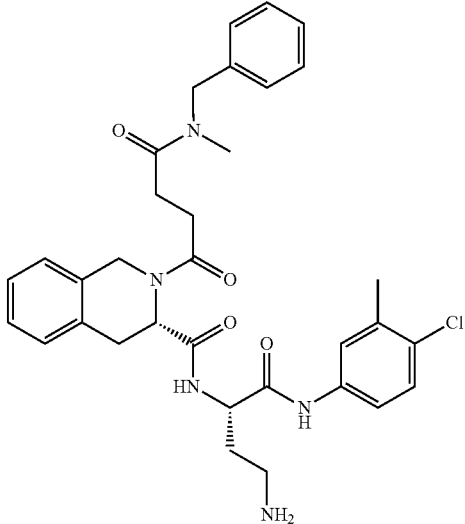 [SMILES: Cc1cc(NC(=O)[C@H](CCN)NC(=O)[C@@H]2Cc3ccccc3CN2C(=O)CCC(=O)N(C)Cc2ccccc2)ccc1Cl] | 12-16 |
| 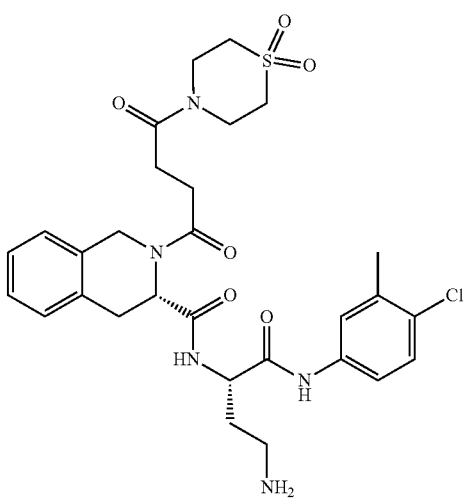 [SMILES: Cc1cc(NC(=O)[C@H](CCN)NC(=O)[C@@H]2Cc3ccccc3CN2C(=O)CCC(=O)N2CCS(=O)(=O)CC2)ccc1Cl] | 12-17 |
| 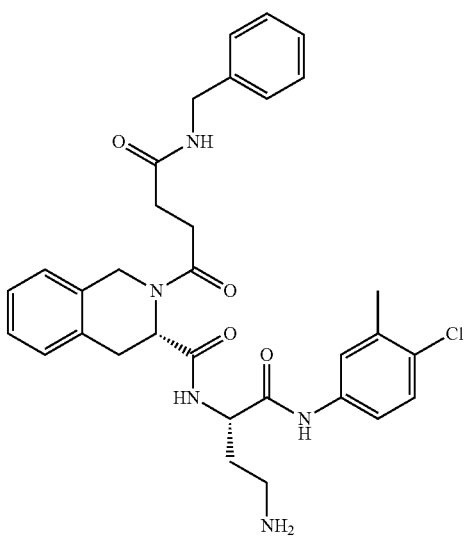 [SMILES: Cc1cc(NC(=O)[C@H](CCN)NC(=O)[C@@H]2Cc3ccccc3CN2C(=O)CCC(=O)NCc2ccccc2)ccc1Cl] | 12-18 |

TABLE A-continued
| Structure | Cpd. No. |
|---|---|
| 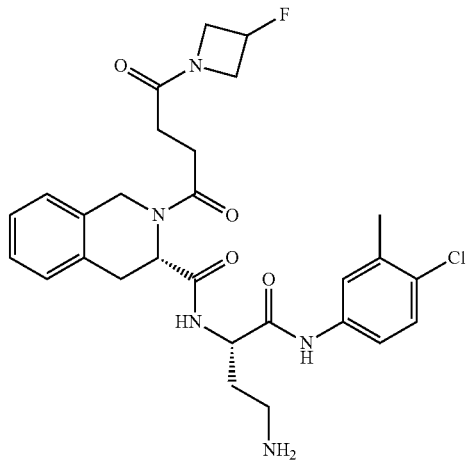 [SMILES: Cc1cc(NC(=O)[C@H](CCN)NC(=O)[C@@H]2Cc3ccccc3CN2C(=O)CCC(=O)N2CC(F)C2)ccc1Cl] | 12-19 |
| 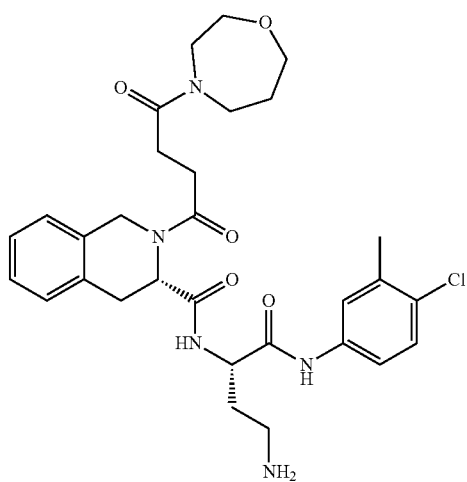 [SMILES: Cc1cc(NC(=O)[C@H](CCN)NC(=O)[C@@H]2Cc3ccccc3CN2C(=O)CCC(=O)N2CCCOCC2)ccc1Cl] | 12-20 |
| 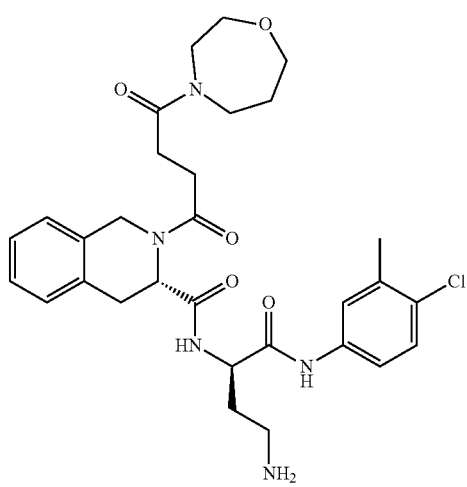 [SMILES: Cc1cc(NC(=O)[C@@H](CCN)NC(=O)[C@@H]2Cc3ccccc3CN2C(=O)CCC(=O)N2CCCOCC2)ccc1Cl] | 12-21 |

TABLE A-continued
| Structure | Cpd. No. |
|---|---|
| 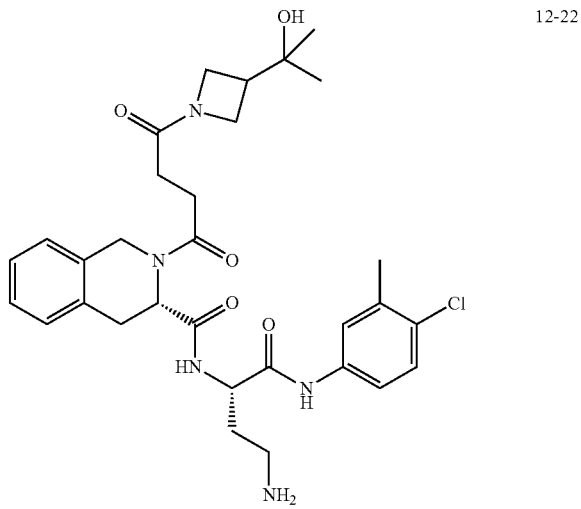 | 12-22 |
| 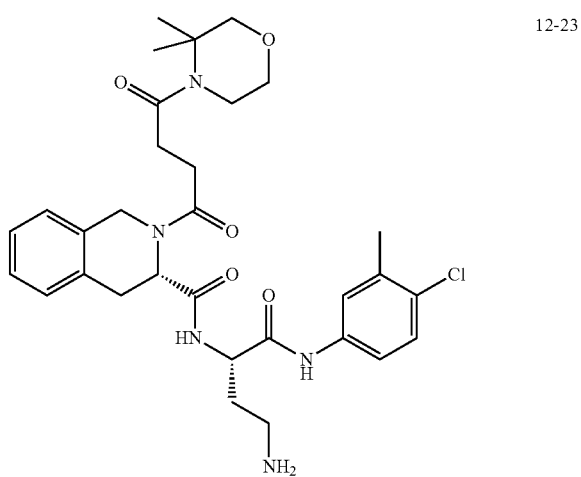 | 12-23 |
| 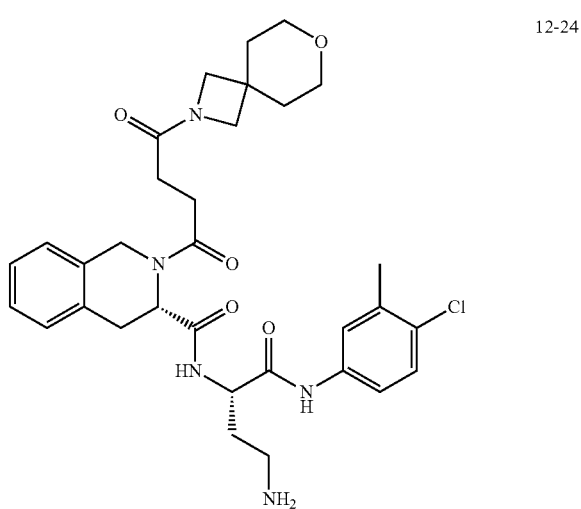 | 12-24 |

TABLE A-continued
| Structure | Cpd. No. |
|---|---|
| 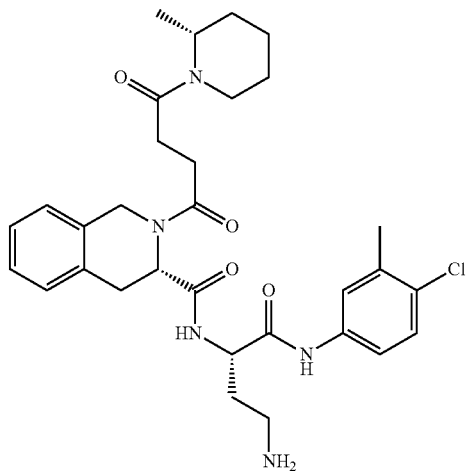 [SMILES: Cc1cc(NC(=O)[C@H](CCN)NC(=O)[C@@H]2Cc3ccccc3CN2C(=O)CCC(=O)N2CCCC[C@H]2C)ccc1Cl] | 12-25 |
| 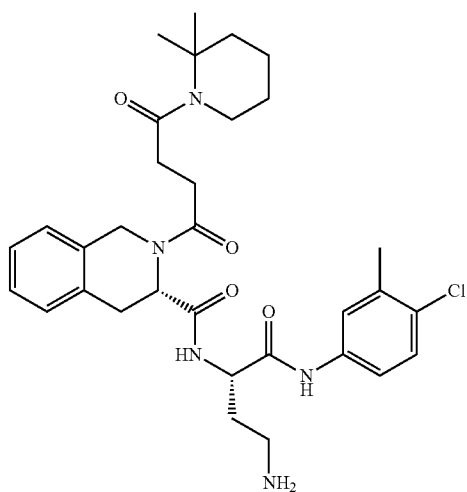 [SMILES: Cc1cc(NC(=O)[C@H](CCN)NC(=O)[C@@H]2Cc3ccccc3CN2C(=O)CCC(=O)N2CCCCC2(C)C)ccc1Cl] | 12-26 |
| 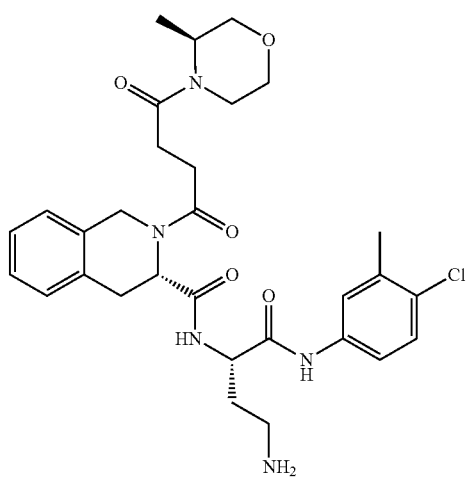 | 12-27 |

TABLE A-continued
| Structure | Cpd. No. |
|---|---|
| 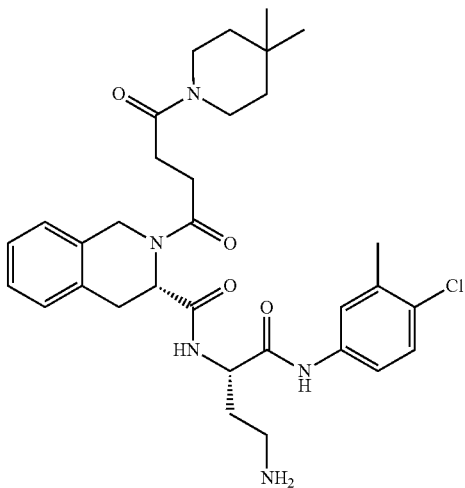 [SMILES: Cc1cc(NC(=O)[C@H](CCN)NC(=O)[C@@H]2Cc3ccccc3CN2C(=O)CCC(=O)N2CCC(C)(C)CC2)ccc1Cl] | 12-28 |
| 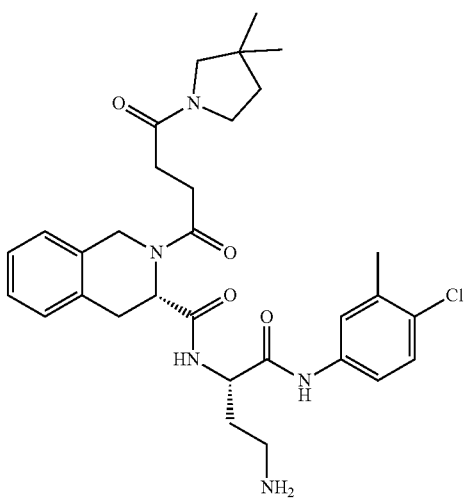 [SMILES: Cc1cc(NC(=O)[C@H](CCN)NC(=O)[C@@H]2Cc3ccccc3CN2C(=O)CCC(=O)N2CCC(C)(C)C2)ccc1Cl] | 12-29 |
| 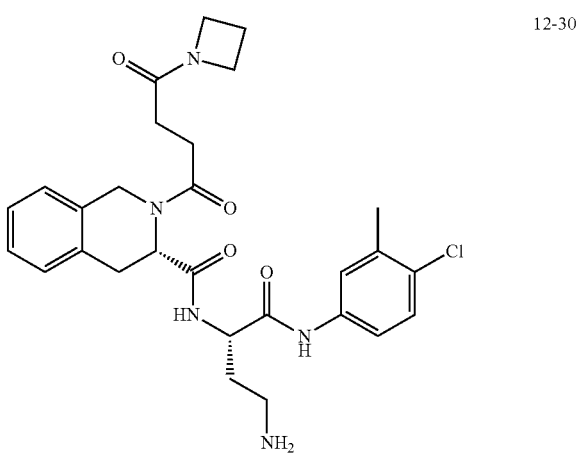 | 12-30 |

TABLE A-continued
| Structure | Cpd. No. |
|---|---|
| 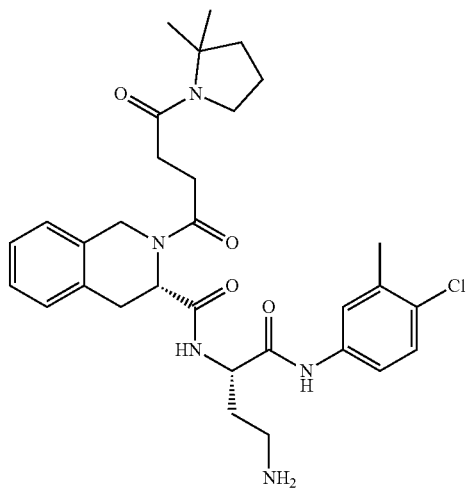 [SMILES: Cc1cc(NC(=O)[C@H](CCN)NC(=O)[C@@H]2Cc3ccccc3CN2C(=O)CCC(=O)N2CCCC2(C)C)ccc1Cl] | 12-31 |
| 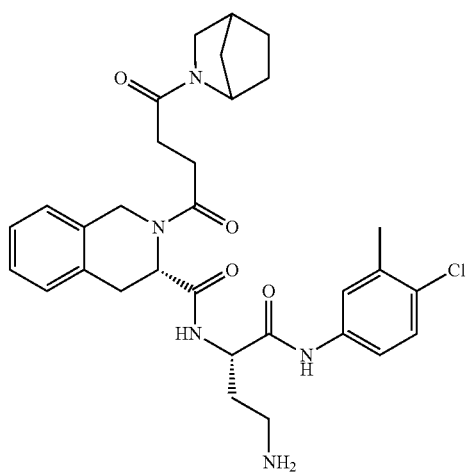 [SMILES: Cc1cc(NC(=O)[C@H](CCN)NC(=O)[C@@H]2Cc3ccccc3CN2C(=O)CCC(=O)N2CC3CCC2C3)ccc1Cl] | 12-32 |
| 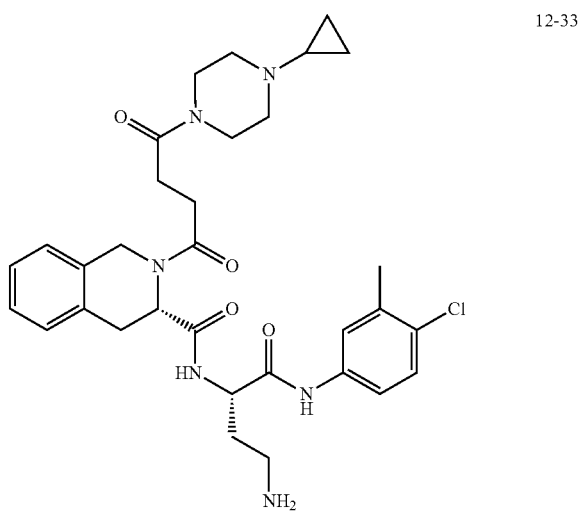 | 12-33 |

TABLE A-continued

| Structure | Cpd. No. |
|---|---|
| 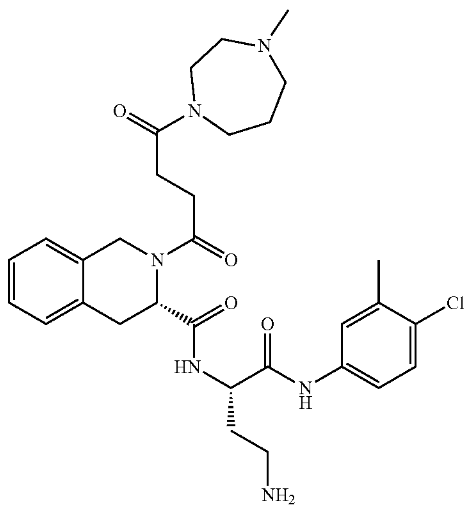 [SMILES: Cc1cc(NC(=O)[C@H](CCN)NC(=O)[C@@H]2Cc3ccccc3CN2C(=O)CCC(=O)N2CCCN(C)CC2)ccc1Cl] | 12-34 |
| 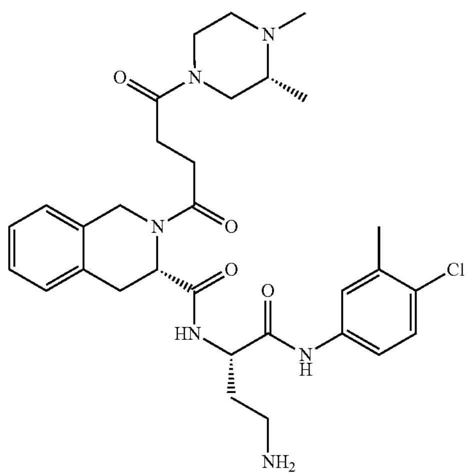 [SMILES: Cc1cc(NC(=O)[C@H](CCN)NC(=O)[C@@H]2Cc3ccccc3CN2C(=O)CCC(=O)N2CCN(C)[C@H](C)C2)ccc1Cl] | 12-35 |
| 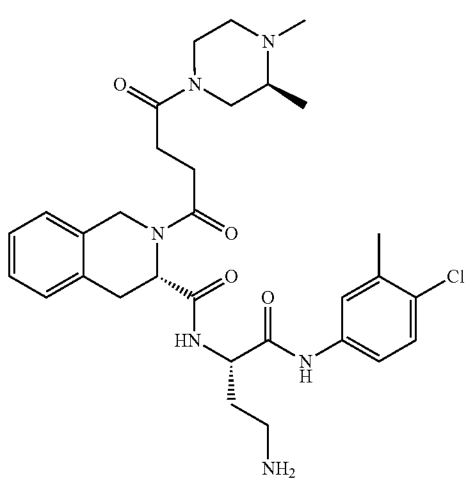 [SMILES: Cc1cc(NC(=O)[C@H](CCN)NC(=O)[C@@H]2Cc3ccccc3CN2C(=O)CCC(=O)N2CCN(C)[C@@H](C)C2)ccc1Cl] | 12-36 |

TABLE A-continued

| Structure | Cpd. No. |
|---|---|
| 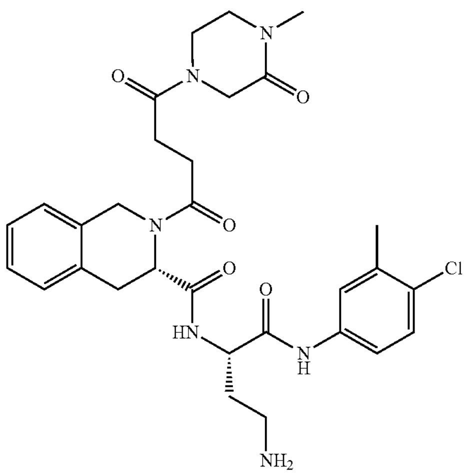 [SMILES: Cc1cc(NC(=O)[C@H](CCN)NC(=O)[C@@H]2Cc3ccccc3CN2C(=O)CCC(=O)N2CCN(C)C(=O)C2)ccc1Cl] | 12-37 |
| 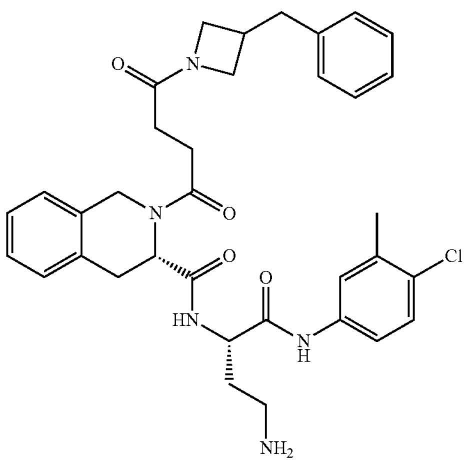 [SMILES: Cc1cc(NC(=O)[C@H](CCN)NC(=O)[C@@H]2Cc3ccccc3CN2C(=O)CCC(=O)N2CC(Cc3ccccc3)C2)ccc1Cl] | 12-38 |
| 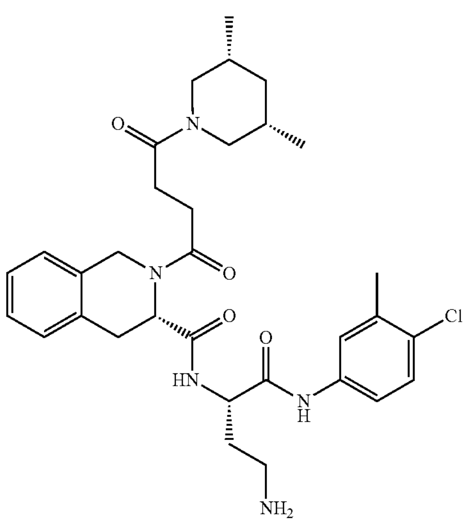 | 12-39 |

TABLE A-continued
| Structure | Cpd. No. |
|---|---|
| 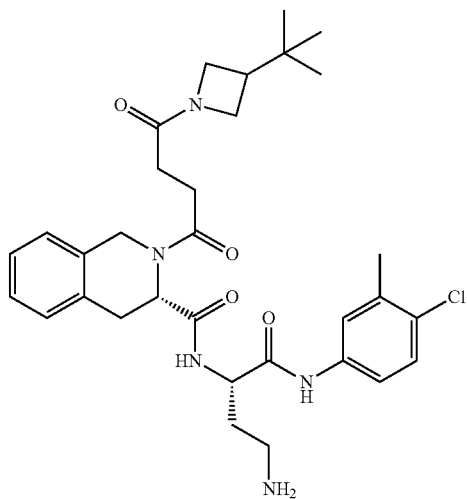 [SMILES: Cc1cc(NC(=O)[C@H](CCN)NC(=O)[C@@H]2Cc3ccccc3CN2C(=O)CCC(=O)N2CC(C(C)(C)C)C2)ccc1Cl] | 12-40 |
| 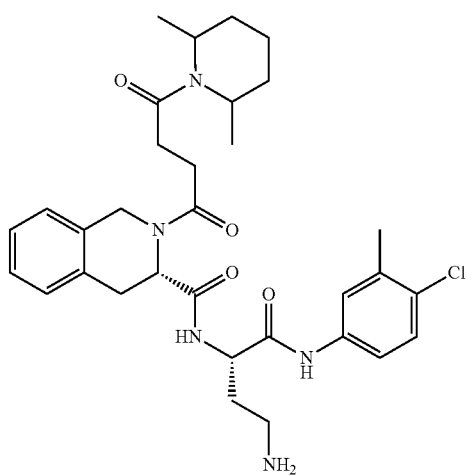 [SMILES: Cc1cc(NC(=O)[C@H](CCN)NC(=O)[C@@H]2Cc3ccccc3CN2C(=O)CCC(=O)N2C(C)CCCC2C)ccc1Cl] | 12-41 |
| 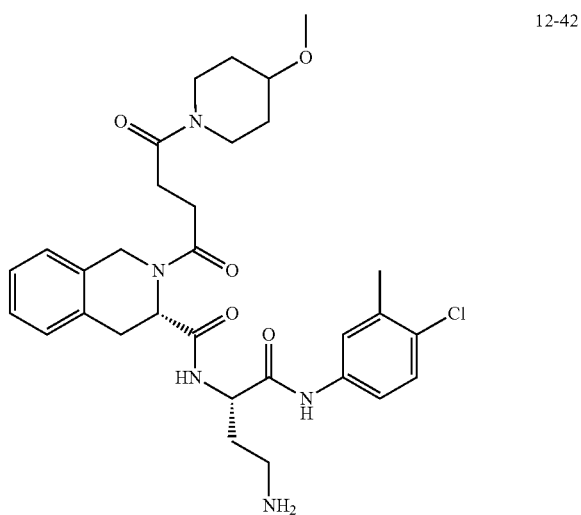 | 12-42 |

TABLE A-continued
| Structure | Cpd. No. |
|---|---|
| 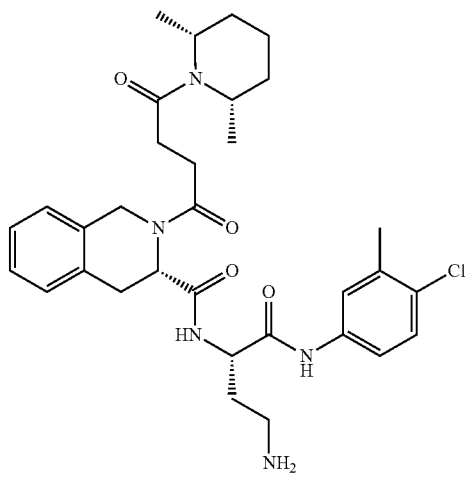 [SMILES: Cc1cc(NC(=O)[C@H](CCN)NC(=O)[C@@H]2Cc3ccccc3CN2C(=O)CCC(=O)N2[C@H](C)CCC[C@@H]2C)ccc1Cl] | 12-43 |
| 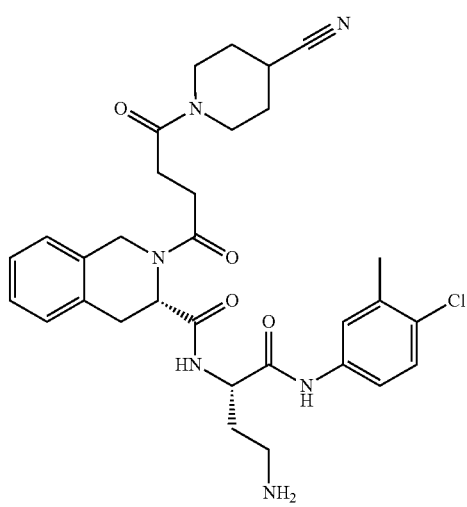 [SMILES: Cc1cc(NC(=O)[C@H](CCN)NC(=O)[C@@H]2Cc3ccccc3CN2C(=O)CCC(=O)N2CCC(C#N)CC2)ccc1Cl] | 12-44 |
| 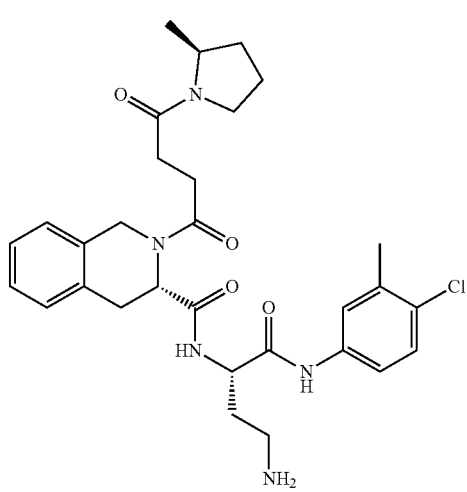 [SMILES: Cc1cc(NC(=O)[C@H](CCN)NC(=O)[C@@H]2Cc3ccccc3CN2C(=O)CCC(=O)N2CCC[C@@H]2C)ccc1Cl] | 12-45 |

TABLE A-continued
| Structure | Cpd. No. |
|---|---|
| 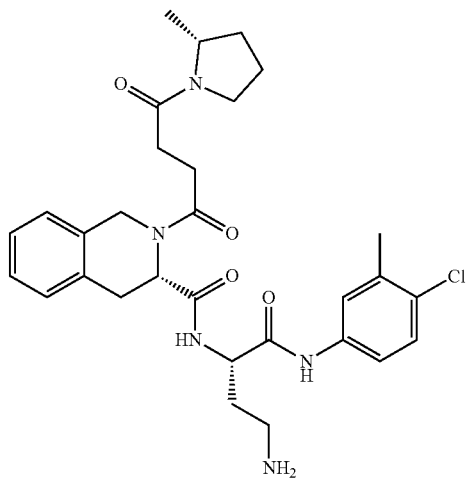 [SMILES: Cc1cc(NC(=O)[C@H](CCN)NC(=O)[C@@H]2Cc3ccccc3CN2C(=O)CCC(=O)N2CCC[C@H]2C)ccc1Cl] | 12-46 |
| 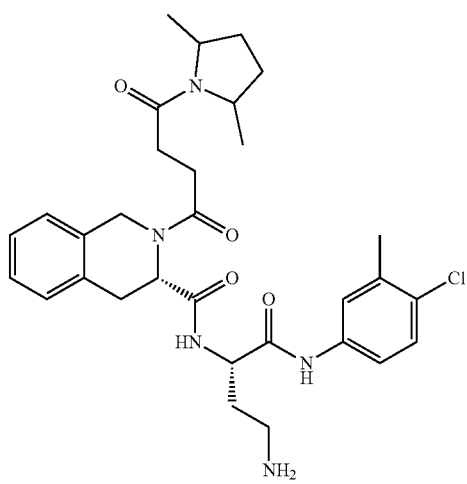 [SMILES: Cc1cc(NC(=O)[C@H](CCN)NC(=O)[C@@H]2Cc3ccccc3CN2C(=O)CCC(=O)N2C(C)CCC2C)ccc1Cl] | 12-47 |
| 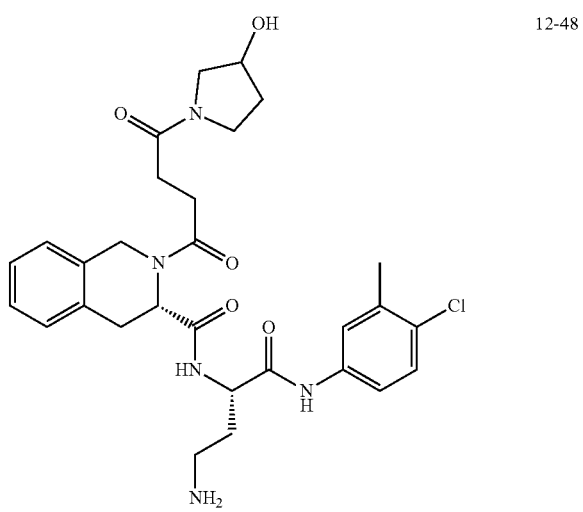 | 12-48 |

TABLE A-continued

| Structure | Cpd. No. |
|---|---|
| 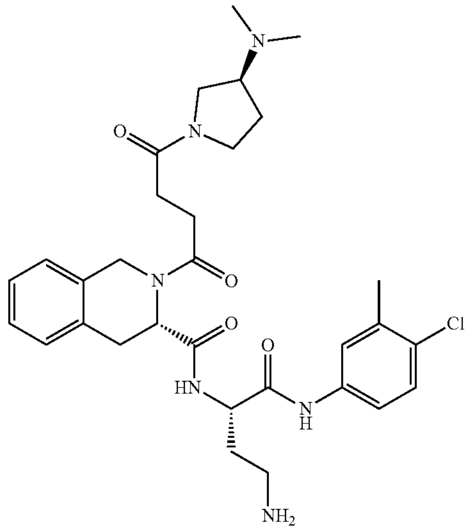 [SMILES: Cc1cc(NC(=O)[C@H](CCN)NC(=O)[C@@H]2Cc3ccccc3CN2C(=O)CCC(=O)N2CC[C@H](N(C)C)C2)ccc1Cl] | 12-49 |
| 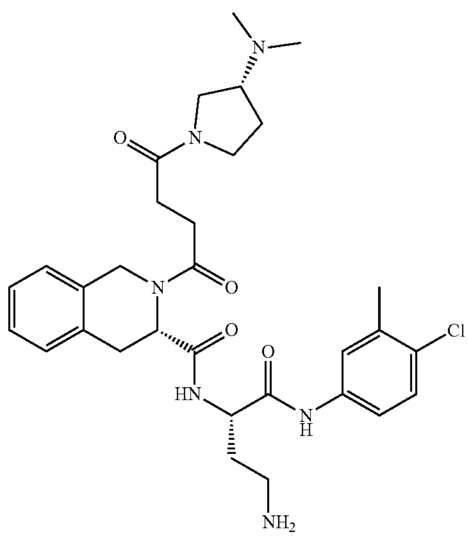 | 12-50 |
| 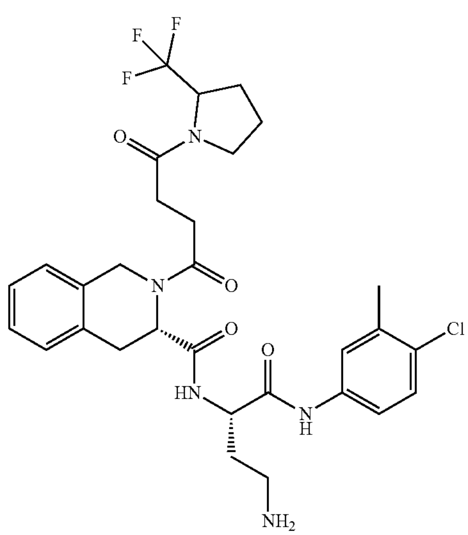 [SMILES: Cc1cc(NC(=O)[C@H](CCN)NC(=O)[C@@H]2Cc3ccccc3CN2C(=O)CCC(=O)N2CCCC2C(F)(F)F)ccc1Cl] | 12-51 |

TABLE A-continued
| Structure | Cpd. No. |
|---|---|
| 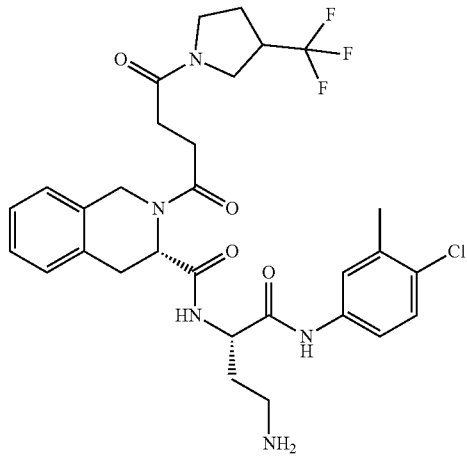 [SMILES: Cc1cc(NC(=O)[C@H](CCN)NC(=O)[C@@H]2Cc3ccccc3CN2C(=O)CCC(=O)N2CCC(C(F)(F)F)C2)ccc1Cl] | 12-52 |
| 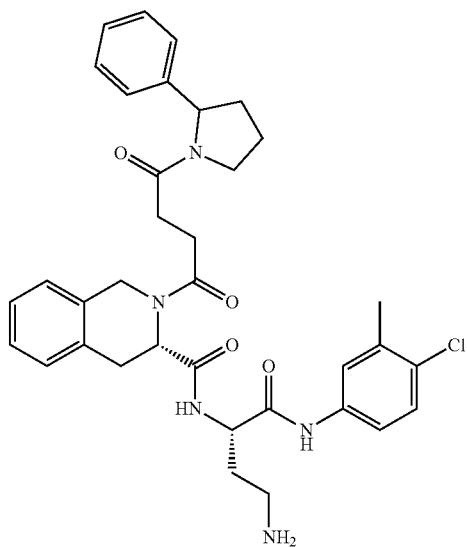 [SMILES: Cc1cc(NC(=O)[C@H](CCN)NC(=O)[C@@H]2Cc3ccccc3CN2C(=O)CCC(=O)N2CCCC2c2ccccc2)ccc1Cl] | 12-53 |
| 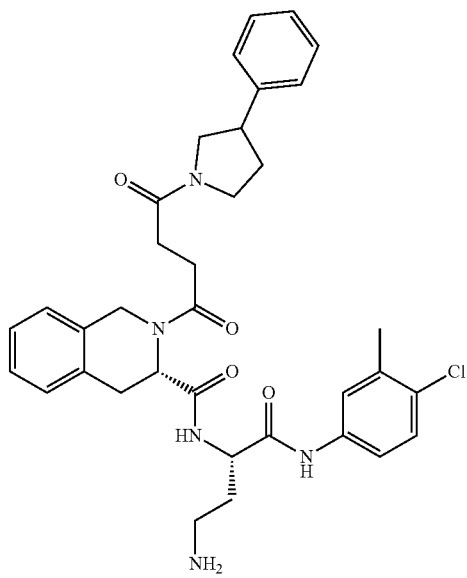 [SMILES: Cc1cc(NC(=O)[C@H](CCN)NC(=O)[C@@H]2Cc3ccccc3CN2C(=O)CCC(=O)N2CCC(c3ccccc3)C2)ccc1Cl] | 12-54 |

TABLE A-continued
| Structure | Cpd. No. |
|---|---|
| 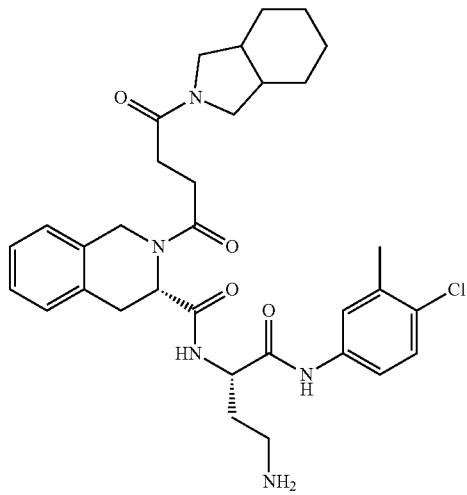 [SMILES: Cc1cc(NC(=O)[C@H](CCN)NC(=O)[C@@H]2Cc3ccccc3CN2C(=O)CCC(=O)N2CC3CCCCC3C2)ccc1Cl] | 12-55 |
| 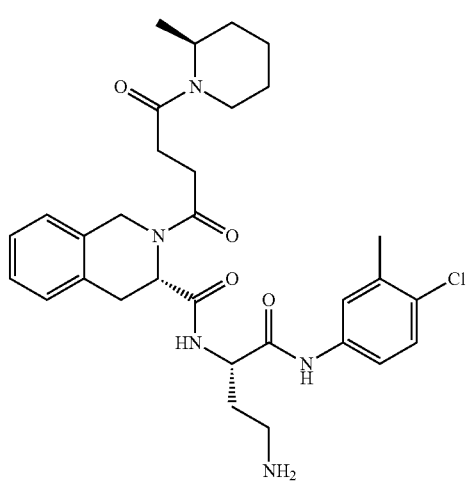 [SMILES: Cc1cc(NC(=O)[C@H](CCN)NC(=O)[C@@H]2Cc3ccccc3CN2C(=O)CCC(=O)N2CCCC[C@@H]2C)ccc1Cl] | 12-56 |
| 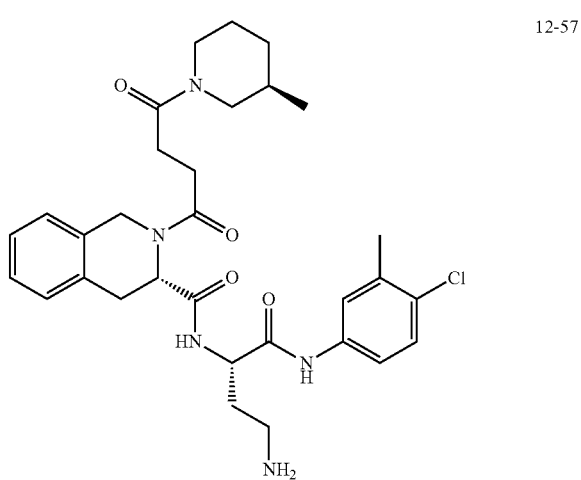 | 12-57 |

TABLE A-continued
| Structure | Cpd. No. |
|---|---|
| 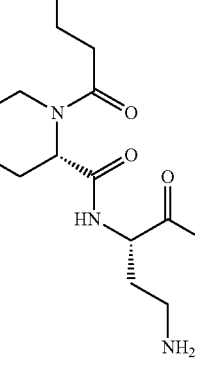 | 12-58 |
| 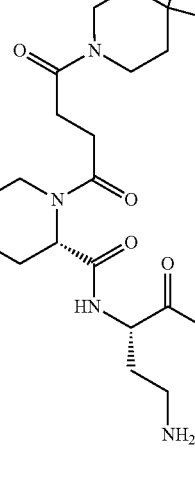 | 12-59 |
| 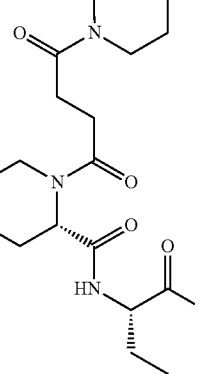 | 12-60 |

TABLE A-continued

| Structure | Cpd. No. |
|---|---|
| 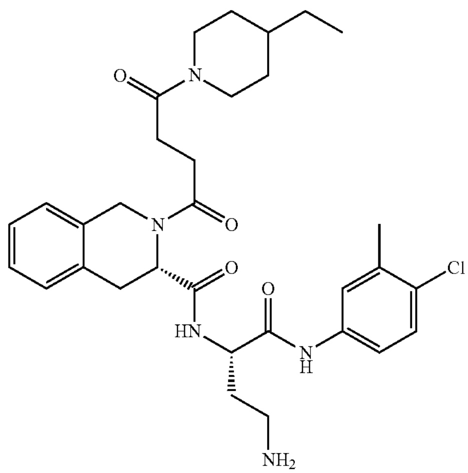 | 12-61 |
| 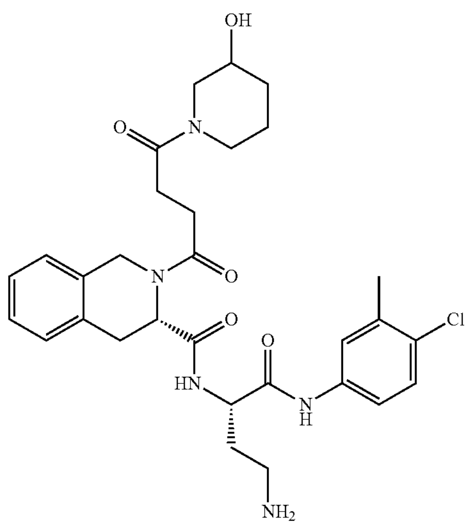 | 12-62 |
| 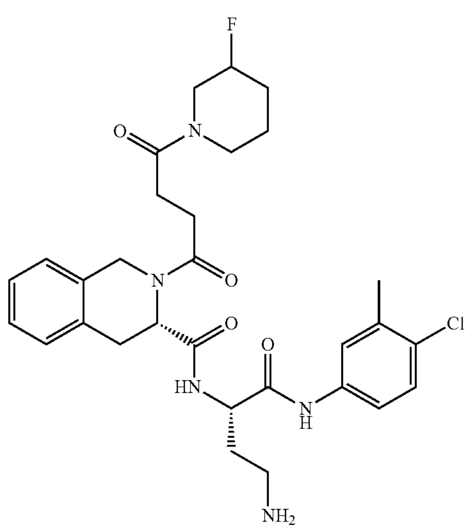 [SMILES: Cc1cc(NC(=O)[C@H](CCN)NC(=O)[C@@H]2Cc3ccccc3CN2C(=O)CCC(=O)N2CCCC(F)C2)ccc1Cl] | 12-63 |

TABLE A-continued
| Structure | Cpd. No. |
|---|---|
| 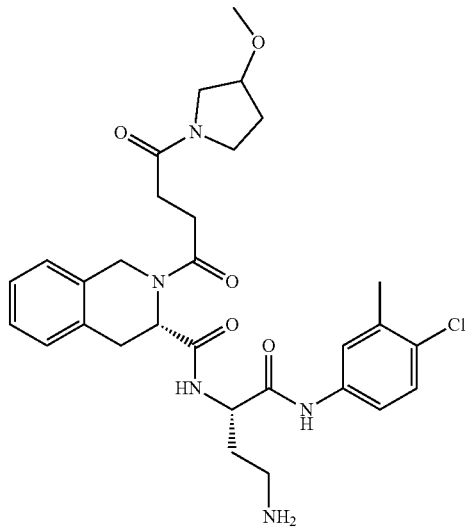 [SMILES: COC1CCN(C(=O)CCC(=O)N2Cc3ccccc3C[C@H]2C(=O)N[C@@H](CCN)C(=O)Nc2ccc(Cl)c(C)c2)C1] | 12-64 |
| 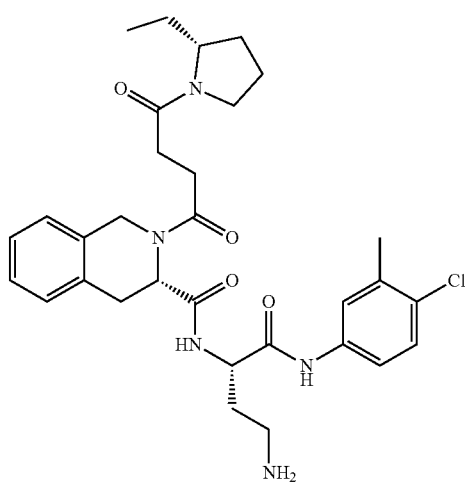 [SMILES: CC[C@@H]1CCCN1C(=O)CCC(=O)N1Cc2ccccc2C[C@H]1C(=O)N[C@@H](CCN)C(=O)Nc1ccc(Cl)c(C)c1] | 12-65 |
| 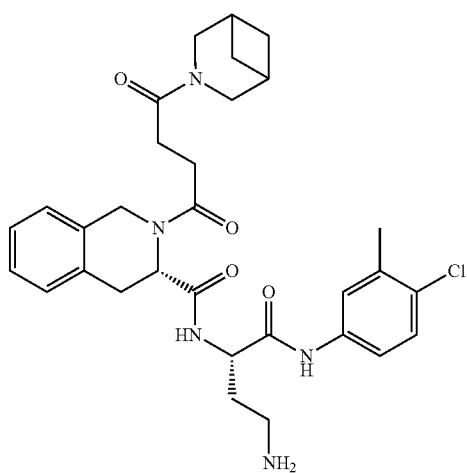 [SMILES: Cc1cc(NC(=O)[C@H](CCN)NC(=O)[C@@H]2Cc3ccccc3CN2C(=O)CCC(=O)N2CC3CC(C3)C2)ccc1Cl] | 12-66 |

TABLE A-continued
| Structure | Cpd. No. |
|---|---|
| 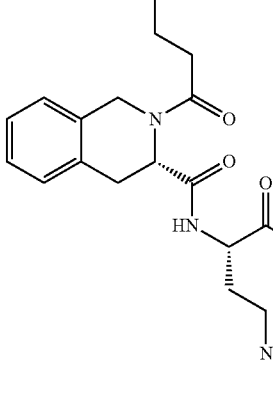 | 12-67 |
| 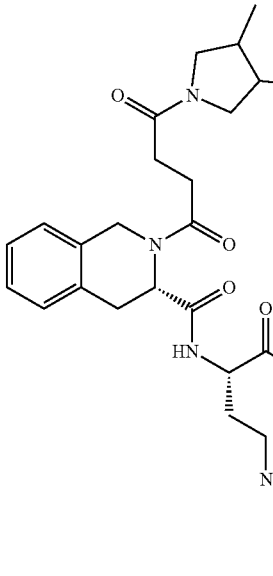 | 12-68 |
| 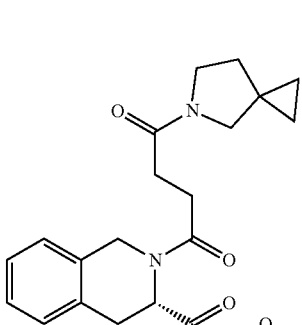 | 12-69 |

TABLE A-continued

| Structure | Cpd. No. |
|---|---|
| 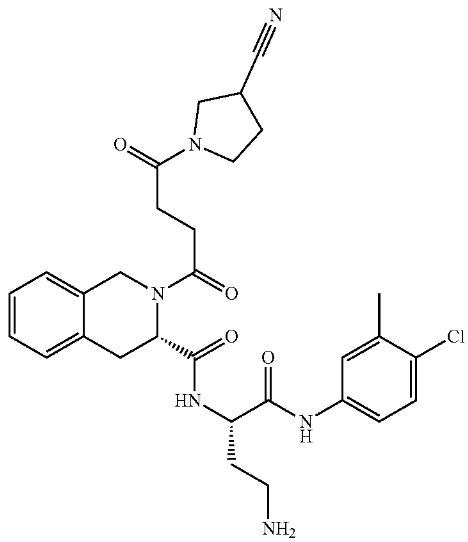 [SMILES: Cc1cc(NC(=O)[C@H](CCN)NC(=O)[C@@H]2Cc3ccccc3CN2C(=O)CCC(=O)N2CCC(C#N)C2)ccc1Cl] | 12-70 |
| 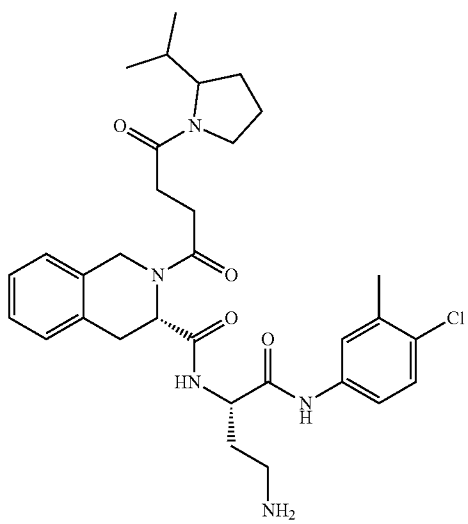 [SMILES: Cc1cc(NC(=O)[C@H](CCN)NC(=O)[C@@H]2Cc3ccccc3CN2C(=O)CCC(=O)N2CCCC2C(C)C)ccc1Cl] | 12-71 |
| 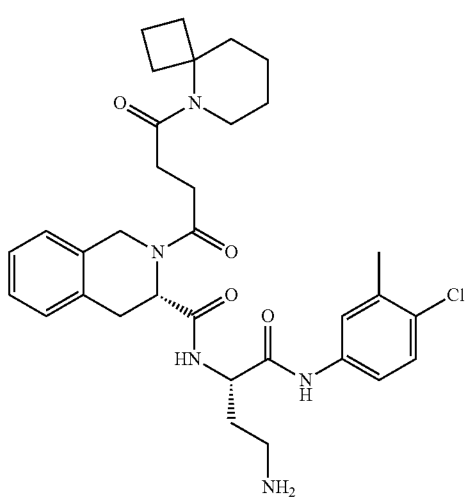 [SMILES: Cc1cc(NC(=O)[C@H](CCN)NC(=O)[C@@H]2Cc3ccccc3CN2C(=O)CCC(=O)N2CCCCC23CCC3)ccc1Cl] | 12-72 |

TABLE A-continued
| Structure | Cpd. No. |
|---|---|
| 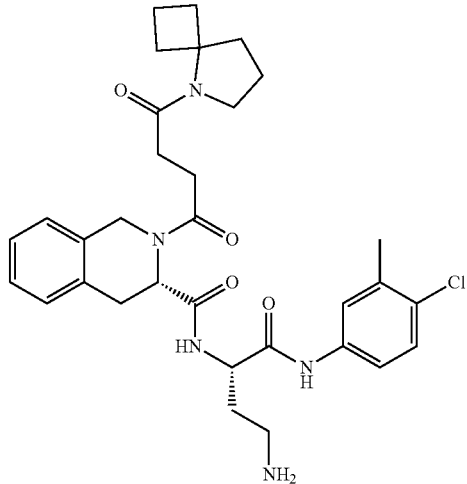 [SMILES: Cc1cc(NC(=O)[C@H](CCN)NC(=O)[C@@H]2Cc3ccccc3CN2C(=O)CCC(=O)N2CCCC23CCC3)ccc1Cl] | 12-73 |
| 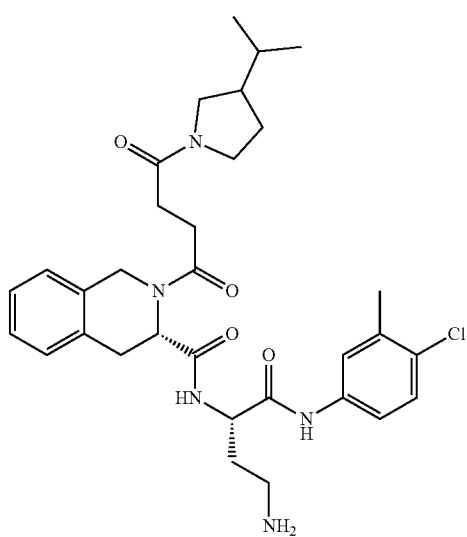 [SMILES: Cc1cc(NC(=O)[C@H](CCN)NC(=O)[C@@H]2Cc3ccccc3CN2C(=O)CCC(=O)N2CCC(C(C)C)C2)ccc1Cl] | 12-74 |
| 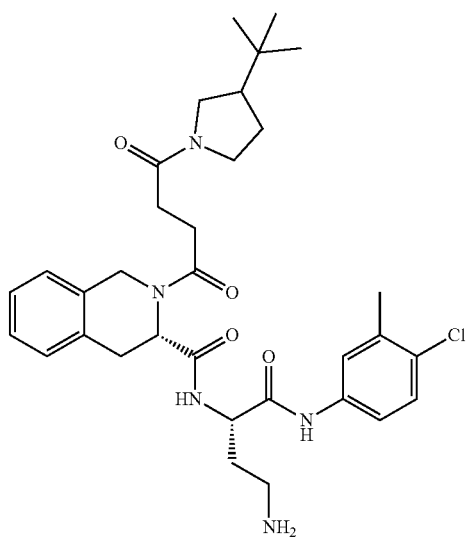 [SMILES: Cc1cc(NC(=O)[C@H](CCN)NC(=O)[C@@H]2Cc3ccccc3CN2C(=O)CCC(=O)N2CCC(C(C)(C)C)C2)ccc1Cl] | 12-75 |

TABLE A-continued
| Structure | Cpd. No. |
|---|---|
| 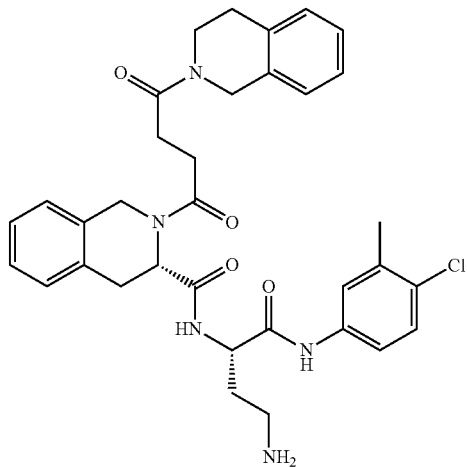 [SMILES: Cc1cc(NC(=O)[C@H](CCN)NC(=O)[C@@H]2Cc3ccccc3CN2C(=O)CCC(=O)N2CCc3ccccc3C2)ccc1Cl] | 12-76 |
| 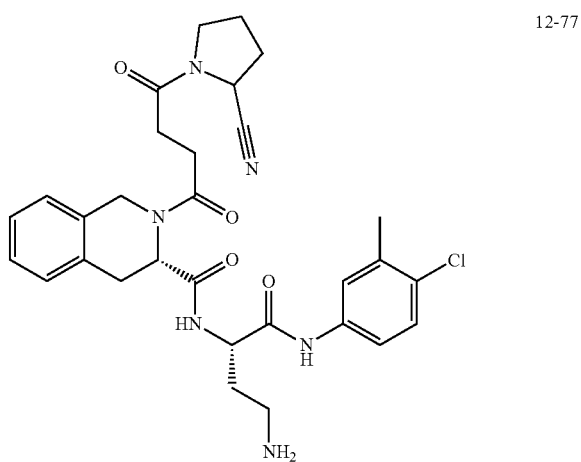 | 12-77 |
| 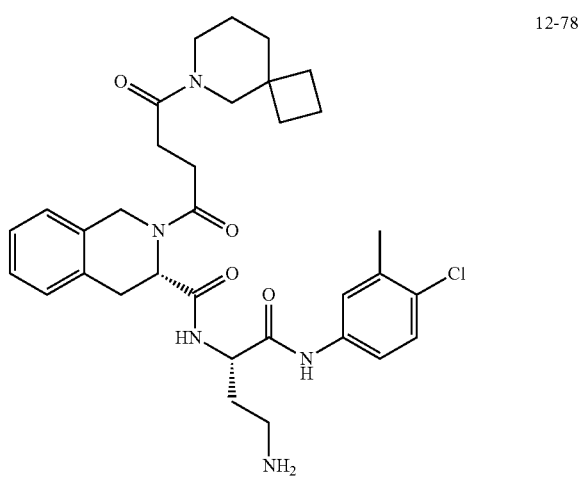 | 12-78 |

TABLE A-continued
| Structure | Cpd. No. |
|---|---|
| 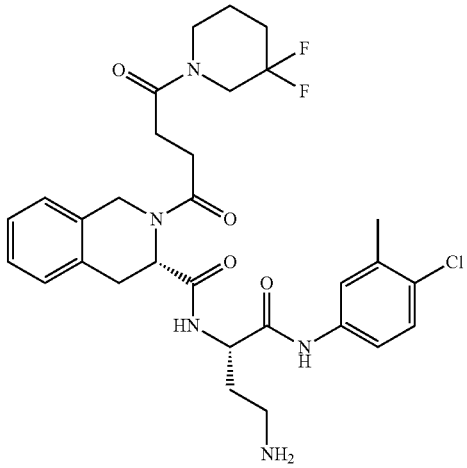 [SMILES: Cc1cc(NC(=O)[C@H](CCN)NC(=O)[C@@H]2Cc3ccccc3CN2C(=O)CCC(=O)N2CCCC(F)(F)C2)ccc1Cl] | 12-79 |
| 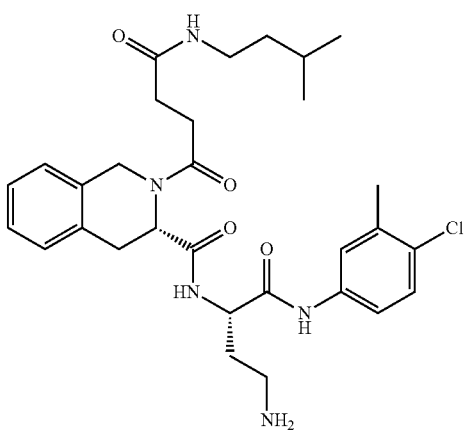 | 12-80 |
| 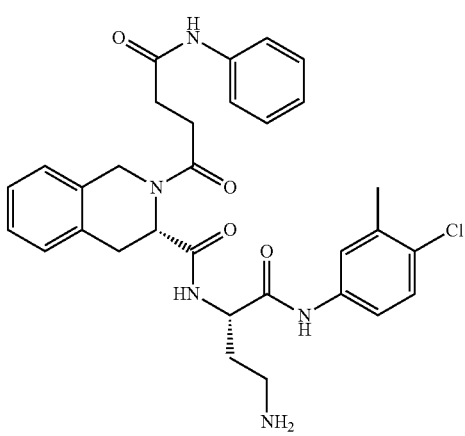 [SMILES: Cc1cc(NC(=O)[C@H](CCN)NC(=O)[C@@H]2Cc3ccccc3CN2C(=O)CCC(=O)Nc2ccccc2)ccc1Cl] | 12-81 |

TABLE A-continued
| Structure | Cpd. No. |
|---|---|
| 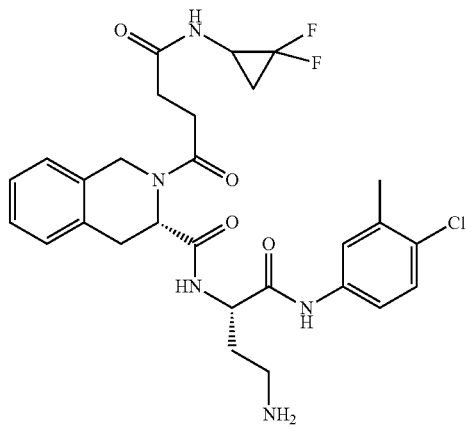 [SMILES: Cc1cc(NC(=O)[C@H](CCN)NC(=O)[C@@H]2Cc3ccccc3CN2C(=O)CCC(=O)NC2CC2(F)F)ccc1Cl] | 12-82 |
| 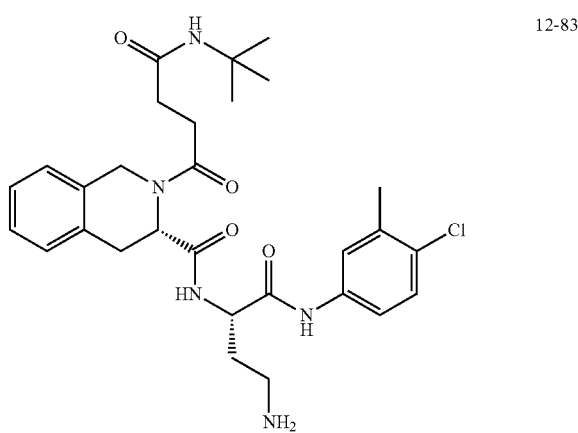 | 12-83 |
| 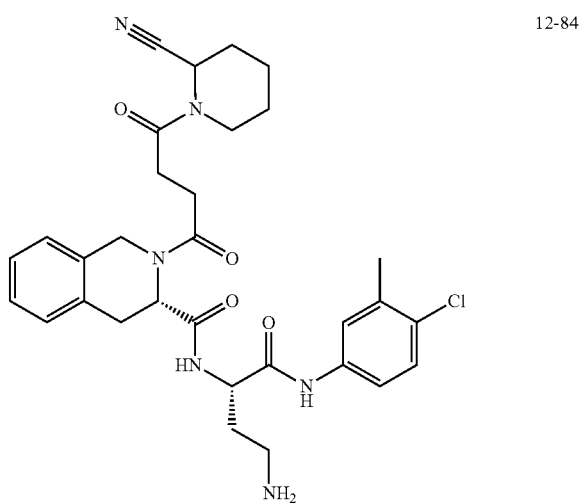 | 12-84 |

TABLE A-continued

| Structure | Cpd. No. |
|-----------|----------|
| 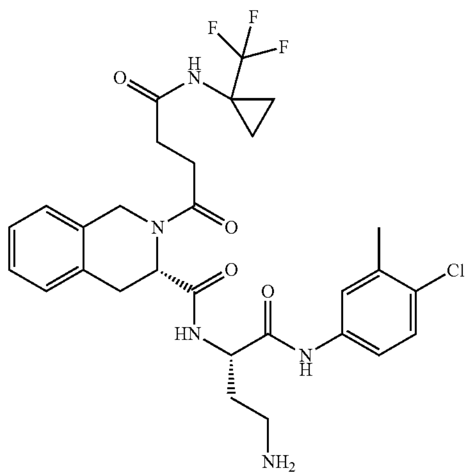 [SMILES: Cc1cc(NC(=O)[C@H](CCN)NC(=O)[C@@H]2Cc3ccccc3CN2C(=O)CCC(=O)NC2(C(F)(F)F)CC2)ccc1Cl]          | 12-85    |
| 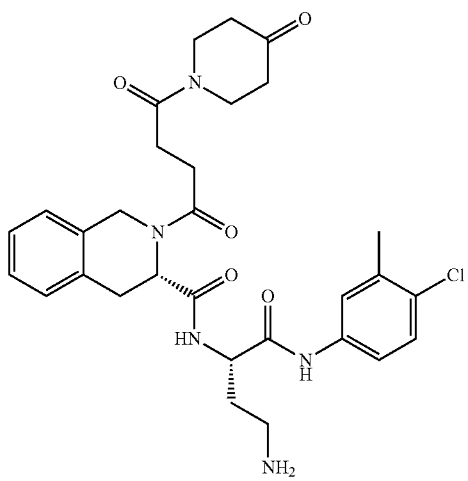 [SMILES: Cc1cc(NC(=O)[C@H](CCN)NC(=O)[C@@H]2Cc3ccccc3CN2C(=O)CCC(=O)N2CCC(=O)CC2)ccc1Cl]          | 12-86    |
| 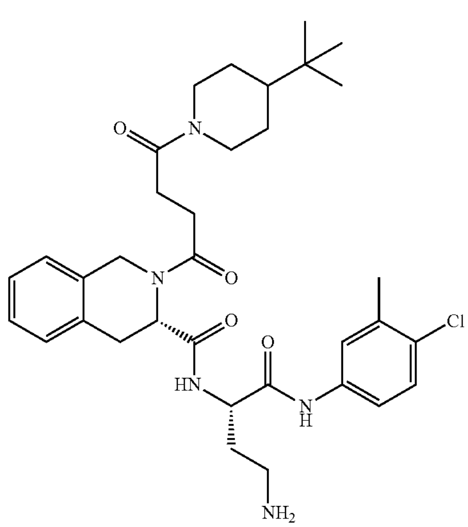 [SMILES: Cc1cc(NC(=O)[C@H](CCN)NC(=O)[C@@H]2Cc3ccccc3CN2C(=O)CCC(=O)N2CCC(C(C)(C)C)CC2)ccc1Cl]          | 12-87    |

TABLE A-continued

| Structure | Cpd. No. |
|---|---|
| 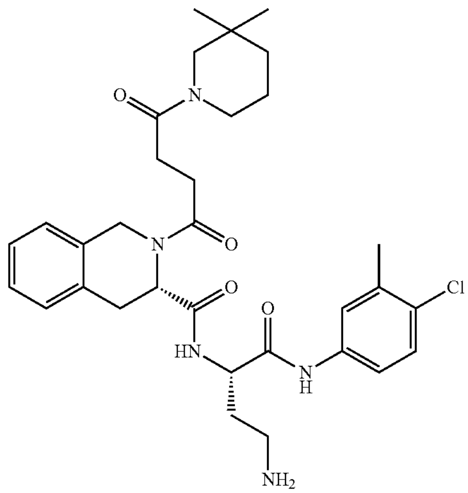 [SMILES: Cc1cc(NC(=O)[C@H](CCN)NC(=O)[C@@H]2Cc3ccccc3CN2C(=O)CCC(=O)N2CCCC(C)(C)C2)ccc1Cl] | 12-88 |
| 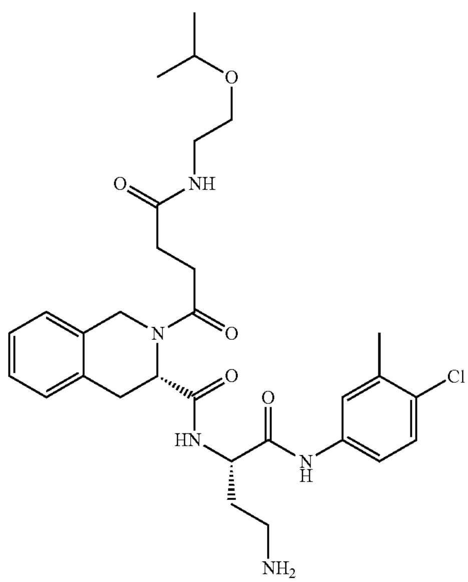 [SMILES: Cc1cc(NC(=O)[C@H](CCN)NC(=O)[C@@H]2Cc3ccccc3CN2C(=O)CCC(=O)NCCOC(C)C)ccc1Cl] | 12-89 |
| 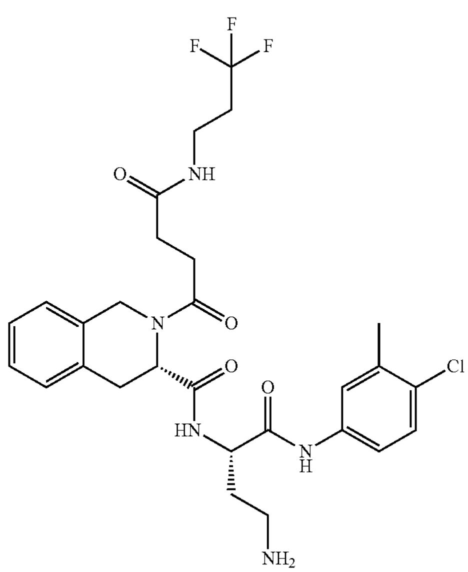 [SMILES: Cc1cc(NC(=O)[C@H](CCN)NC(=O)[C@@H]2Cc3ccccc3CN2C(=O)CCC(=O)NCCC(F)(F)F)ccc1Cl] | 12-90 |

TABLE A-continued
| Structure | Cpd. No. |
|---|---|
| 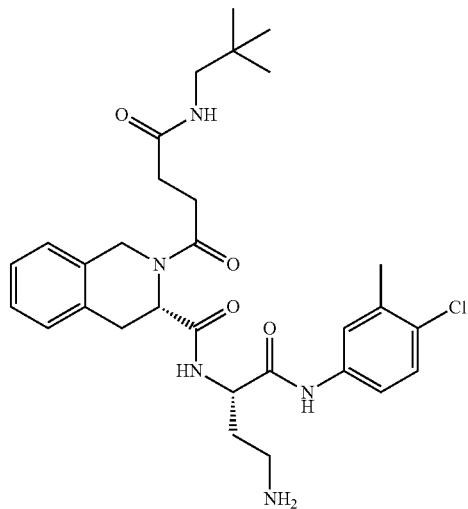 [SMILES: Cc1cc(NC(=O)[C@H](CCN)NC(=O)[C@@H]2Cc3ccccc3CN2C(=O)CCC(=O)NCC(C)(C)C)ccc1Cl] | 12-91 |
| 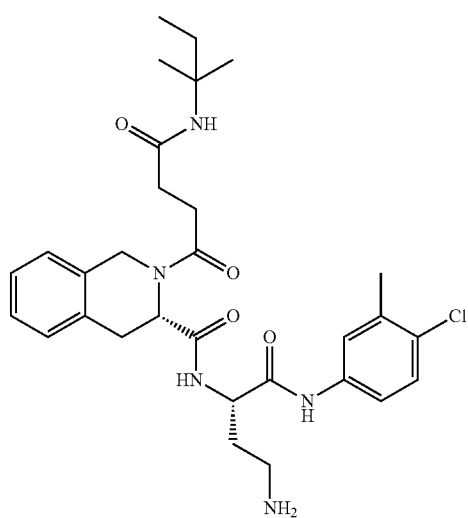 [SMILES: CCC(C)(C)NC(=O)CCC(=O)N1Cc2ccccc2C[C@H]1C(=O)N[C@@H](CCN)C(=O)Nc1ccc(Cl)c(C)c1] | 12-92 |
| 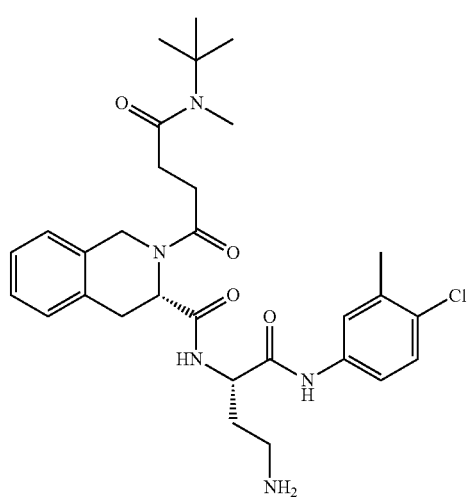 [SMILES: Cc1cc(NC(=O)[C@H](CCN)NC(=O)[C@@H]2Cc3ccccc3CN2C(=O)CCC(=O)N(C)C(C)(C)C)ccc1Cl] | 12-93 |

TABLE A-continued
| Structure | Cpd. No. |
|---|---|
| 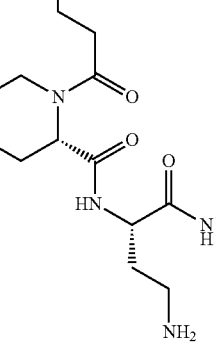 | 12-94 |
| 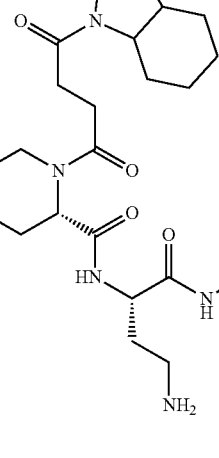 | 12-95 |
| 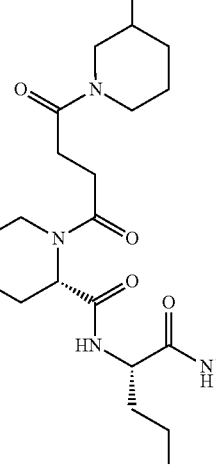 | 12-96 |

TABLE A-continued
| Structure | Cpd. No. |
|---|---|
| 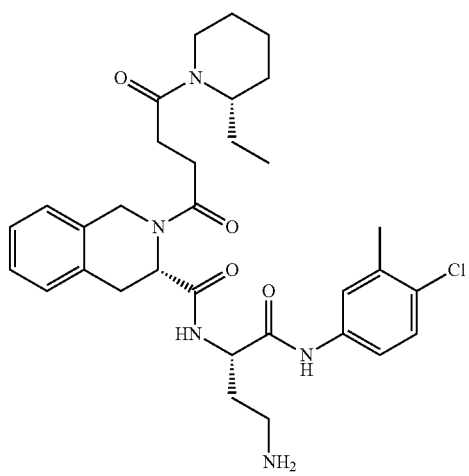 [SMILES: CC[C@H]1CCCCN1C(=O)CCC(=O)N1Cc2ccccc2C[C@H]1C(=O)N[C@@H](CCN)C(=O)Nc1ccc(Cl)c(C)c1] | 12-97 |
| 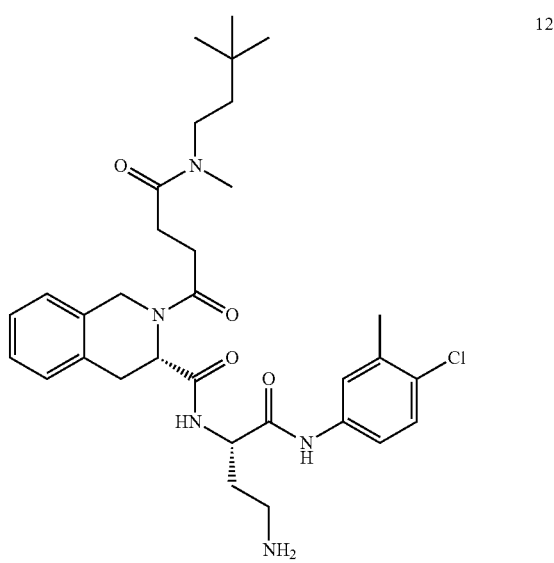 | 12-98 |
| 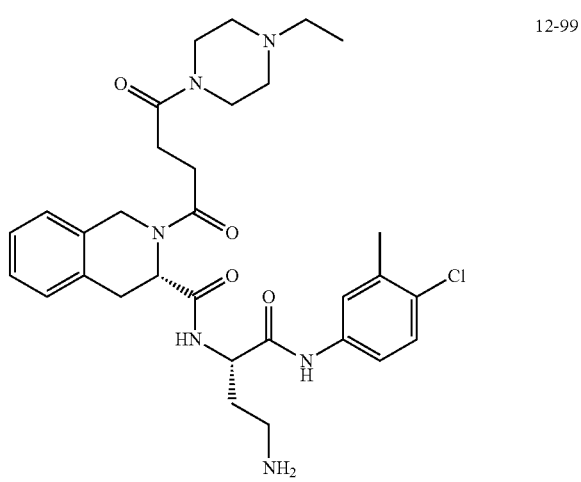 | 12-99 |

TABLE A-continued

| Structure | Cpd. No. |
|---|---|
| 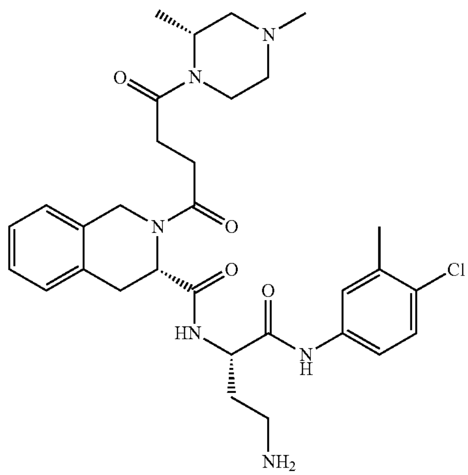 [SMILES: Cc1cc(NC(=O)[C@H](CCN)NC(=O)[C@@H]2Cc3ccccc3CN2C(=O)CCC(=O)N2CCN(C)C[C@H]2C)ccc1Cl] | 12-100 |
| 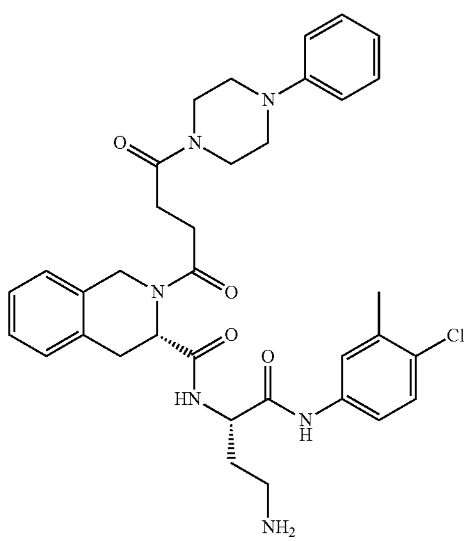 [SMILES: Cc1cc(NC(=O)[C@H](CCN)NC(=O)[C@@H]2Cc3ccccc3CN2C(=O)CCC(=O)N2CCN(c3ccccc3)CC2)ccc1Cl] | 12-101 |
| 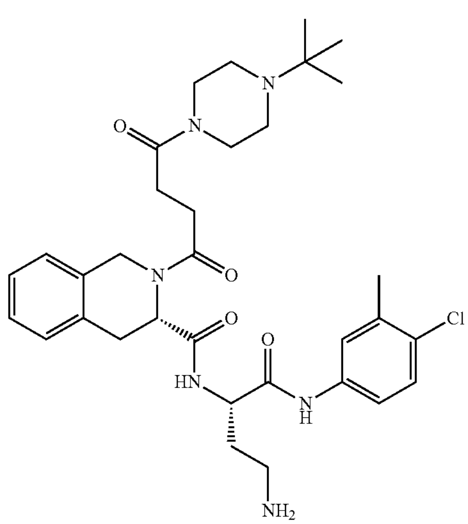 | 12-102 |

TABLE A-continued
| Structure | Cpd. No. |
|---|---|
| 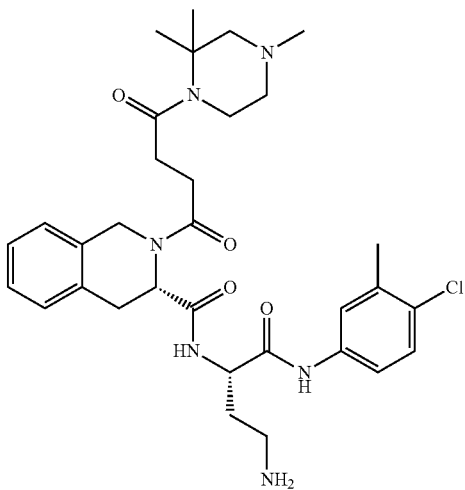 [SMILES: Cc1cc(NC(=O)[C@H](CCN)NC(=O)[C@@H]2Cc3ccccc3CN2C(=O)CCC(=O)N2CCN(C)CC2(C)C)ccc1Cl] | 12-103 |
| 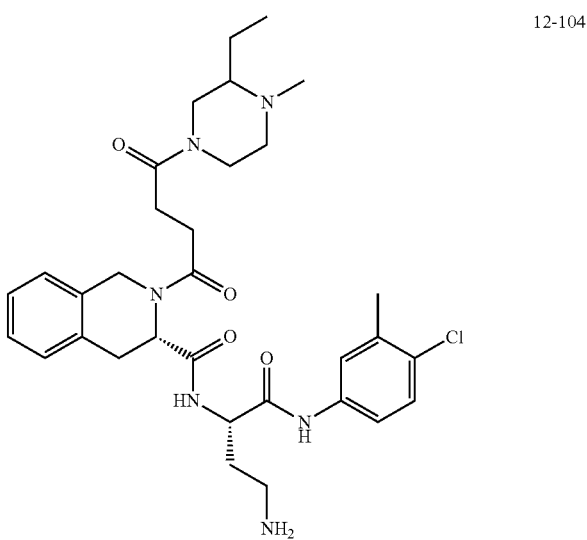 | 12-104 |
| 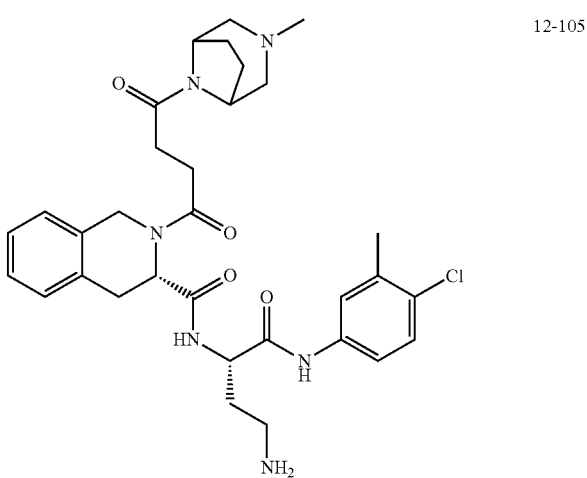 | 12-105 |

TABLE A-continued
| Structure | Cpd. No. |
|---|---|
| 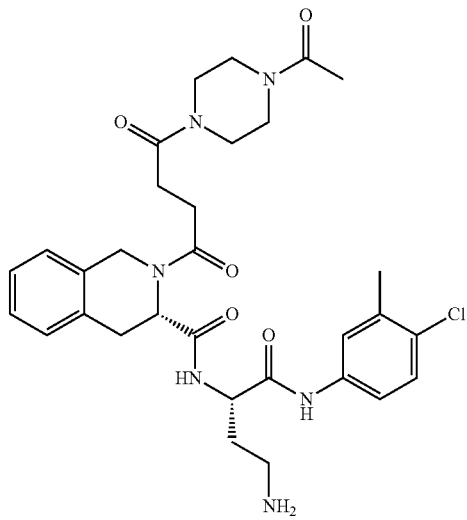 [SMILES: CC(=O)N1CCN(C(=O)CCC(=O)N2Cc3ccccc3C[C@H]2C(=O)N[C@@H](CCN)C(=O)Nc2ccc(Cl)c(C)c2)CC1] | 12-106 |
| 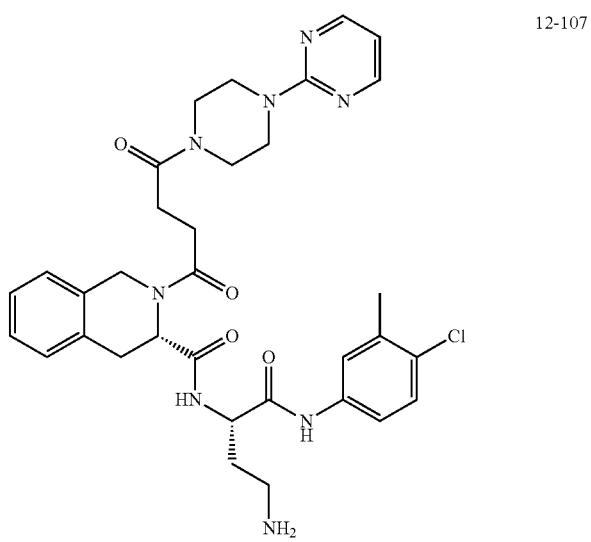 | 12-107 |
| 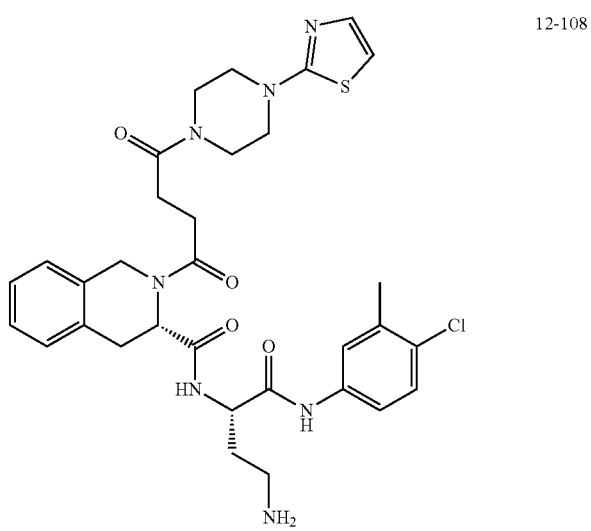 | 12-108 |

TABLE A-continued
| Structure | Cpd. No. |
|---|---|
| 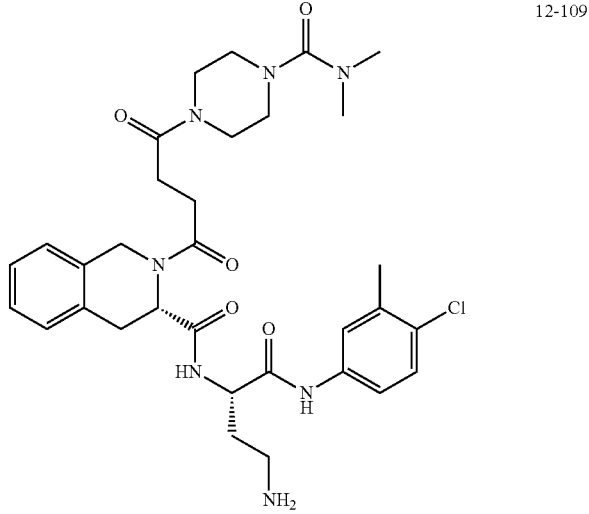 | 12-109 |
| 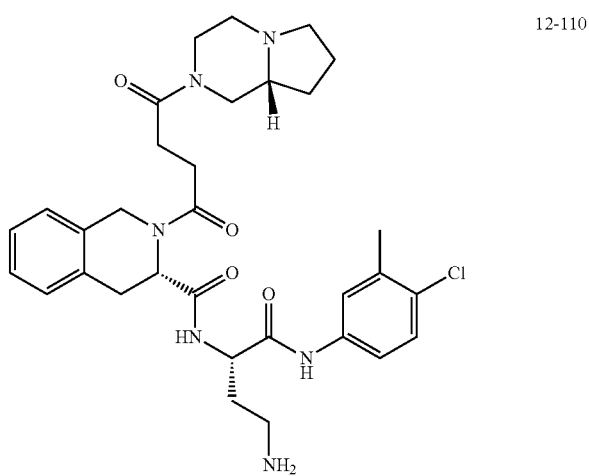 | 12-110 |
| 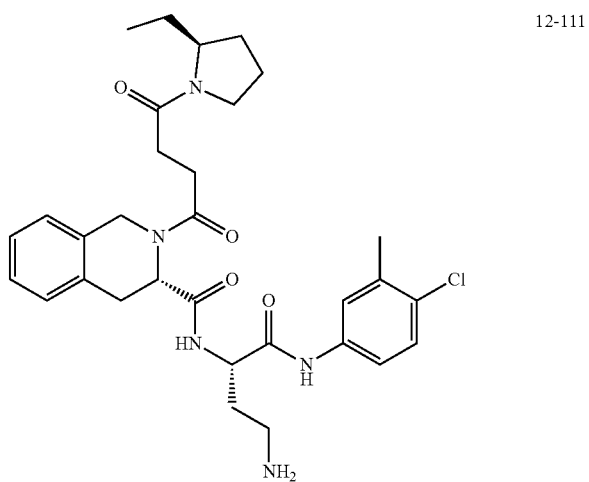 | 12-111 |

TABLE A-continued

| Structure | Cpd. No. |
|---|---|
| 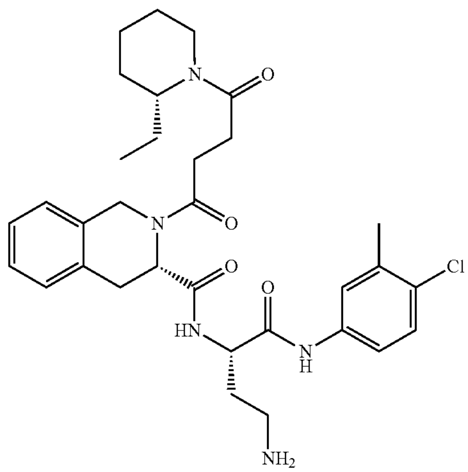 [SMILES: CC[C@@H]1CCCCN1C(=O)CCC(=O)N1Cc2ccccc2C[C@H]1C(=O)N[C@@H](CCN)C(=O)Nc1ccc(Cl)c(C)c1] | 12-112 |
| 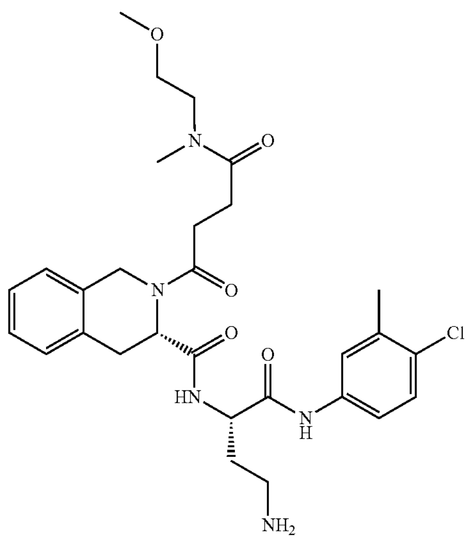 [SMILES: COCCN(C)C(=O)CCC(=O)N1Cc2ccccc2C[C@H]1C(=O)N[C@@H](CCN)C(=O)Nc1ccc(Cl)c(C)c1] | 12-113 |
| 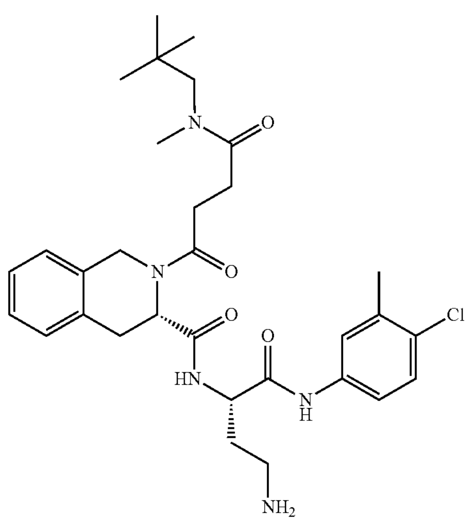 [SMILES: Cc1cc(NC(=O)[C@H](CCN)NC(=O)[C@@H]2Cc3ccccc3CN2C(=O)CCC(=O)N(C)CC(C)(C)C)ccc1Cl] | 12-114 |

TABLE A-continued

| Structure | Cpd. No. |
|---|---|
| 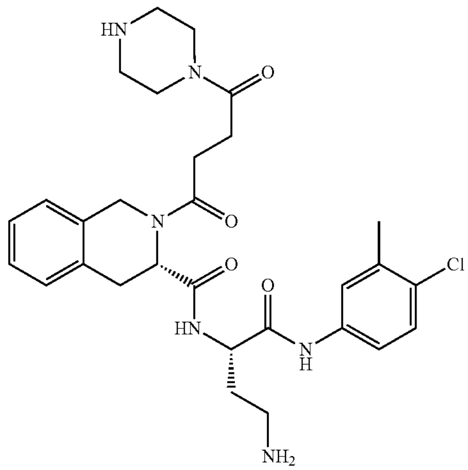 [SMILES: Cc1cc(NC(=O)[C@H](CCN)NC(=O)[C@@H]2Cc3ccccc3CN2C(=O)CCC(=O)N2CCNCC2)ccc1Cl] | 12-115 |
| 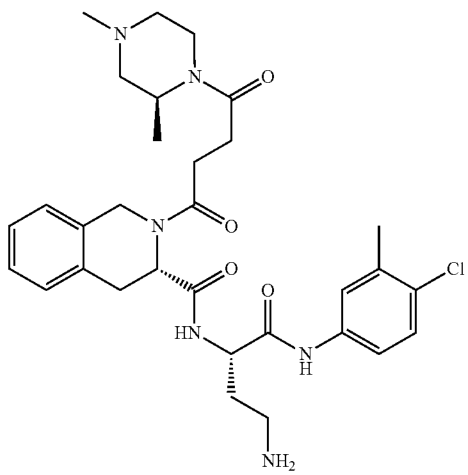 [SMILES: Cc1cc(NC(=O)[C@H](CCN)NC(=O)[C@@H]2Cc3ccccc3CN2C(=O)CCC(=O)N2CCN(C)C[C@@H]2C)ccc1Cl] | 12-116 |
| 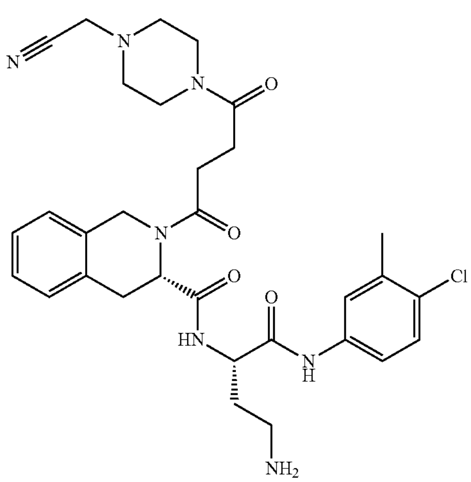 [SMILES: Cc1cc(NC(=O)[C@H](CCN)NC(=O)[C@@H]2Cc3ccccc3CN2C(=O)CCC(=O)N2CCN(CC#N)CC2)ccc1Cl] | 12-117 |

TABLE A-continued

| Structure | Cpd. No. |
|---|---|
| 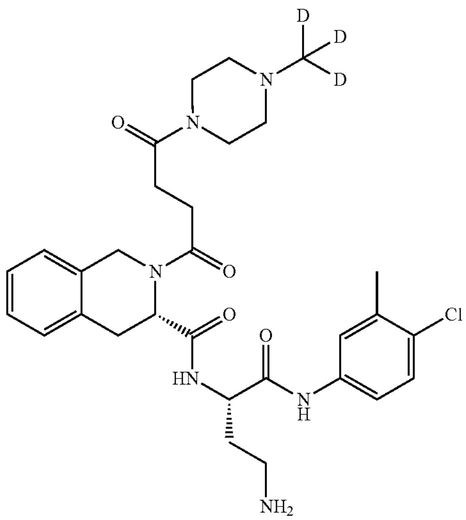 [SMILES: [2H]C([2H])([2H])N1CCN(C(=O)CCC(=O)N2Cc3ccccc3C[C@H]2C(=O)N[C@@H](CCN)C(=O)Nc2ccc(Cl)c(C)c2)CC1] | 12-118 |
| 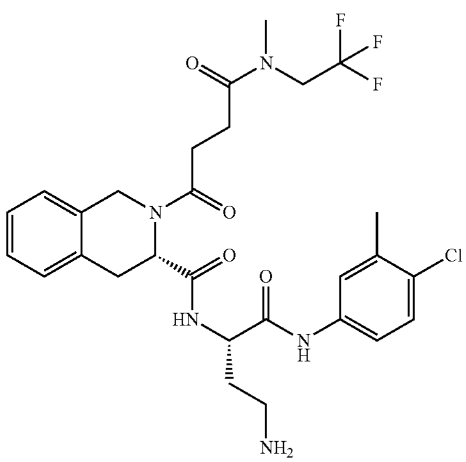 [SMILES: Cc1cc(NC(=O)[C@H](CCN)NC(=O)[C@@H]2Cc3ccccc3CN2C(=O)CCC(=O)N(C)CC(F)(F)F)ccc1Cl] | 12-119 |
| 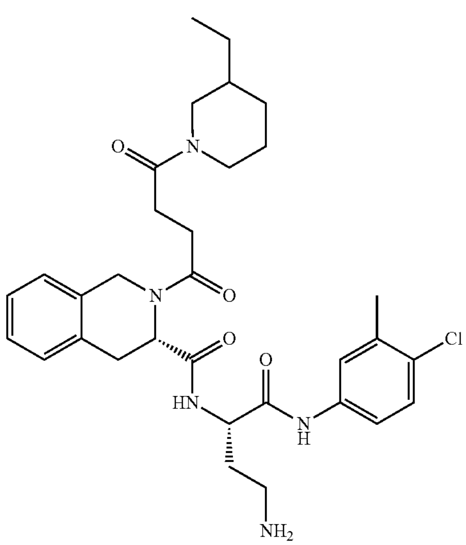 [SMILES: CCC1CCCN(C(=O)CCC(=O)N2Cc3ccccc3C[C@H]2C(=O)N[C@@H](CCN)C(=O)Nc2ccc(Cl)c(C)c2)C1] | 12-120 |

TABLE A-continued
| Structure | Cpd. No. |
|---|---|
| 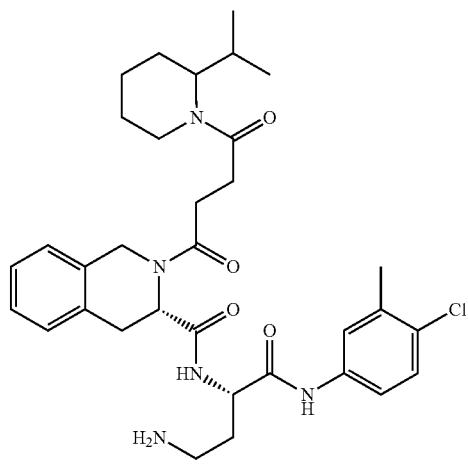 [SMILES: Cc1cc(NC(=O)[C@H](CCN)NC(=O)[C@@H]2Cc3ccccc3CN2C(=O)CCC(=O)N2CCCCC2C(C)C)ccc1Cl] | 12-121 |
| 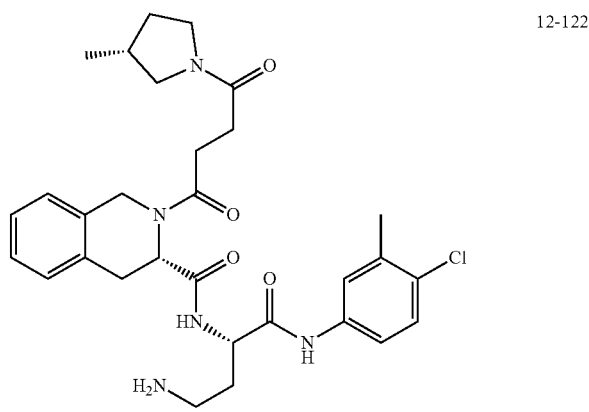 | 12-122 |
| 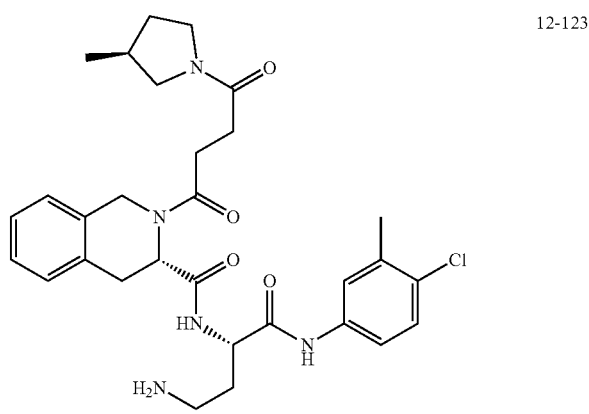 | 12-123 |

TABLE A-continued

| Structure | Cpd. No. |
|---|---|
| 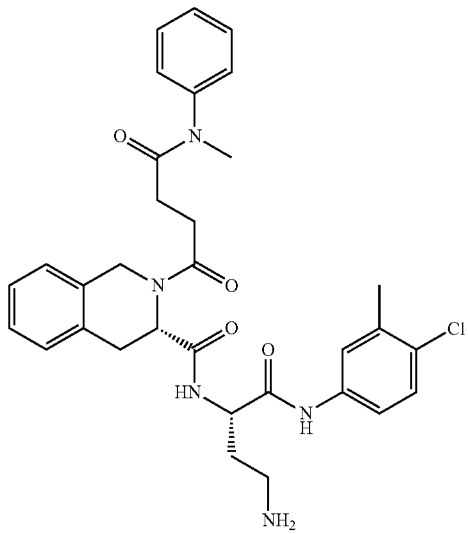 [SMILES: Cc1cc(NC(=O)[C@H](CCN)NC(=O)[C@@H]2Cc3ccccc3CN2C(=O)CCC(=O)N(C)c2ccccc2)ccc1Cl] | 12-124 |
| 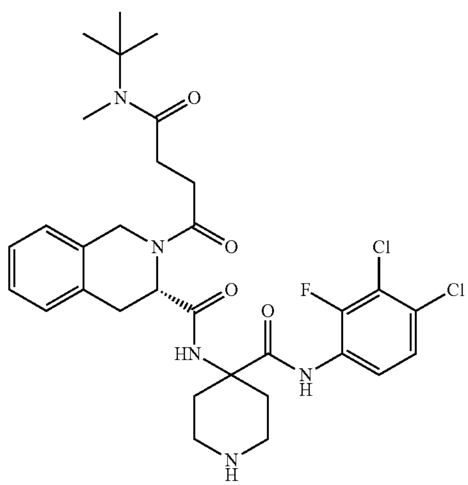 [SMILES: CN(C(=O)CCC(=O)N1Cc2ccccc2C[C@H]1C(=O)NC1(C(=O)Nc2ccc(Cl)c(Cl)c2F)CCNCC1)C(C)(C)C] | 12-125 |
| 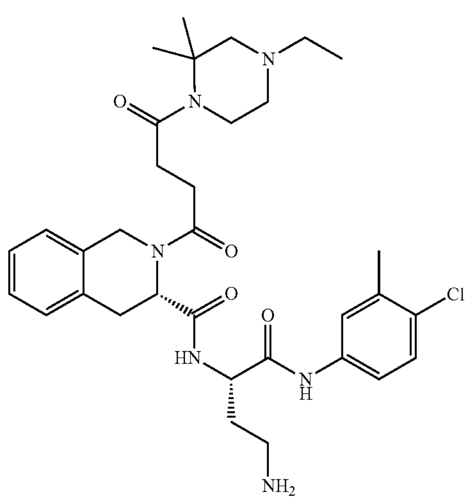 [SMILES: CCN1CCN(C(=O)CCC(=O)N2Cc3ccccc3C[C@H]2C(=O)N[C@@H](CCN)C(=O)Nc2ccc(Cl)c(C)c2)C(C)(C)C1] | 12-126 |

TABLE A-continued
| Structure | Cpd. No. |
|---|---|
| 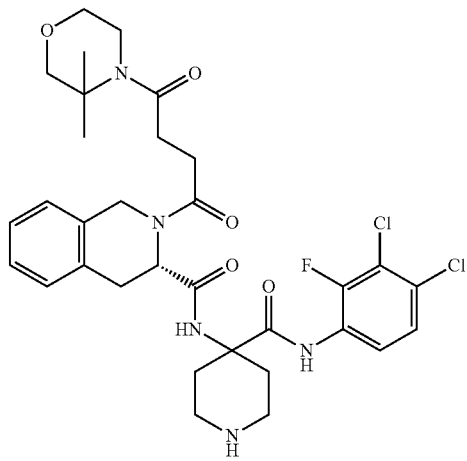 | 12-127 |
| 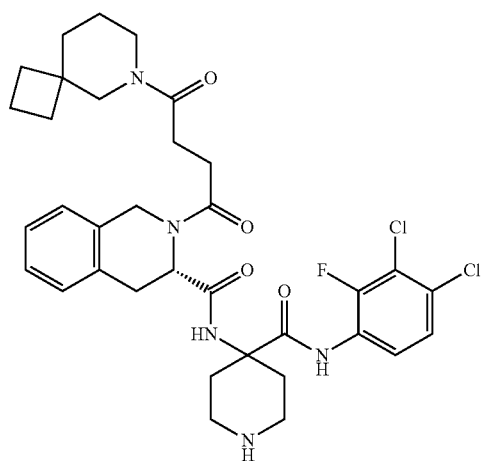 [SMILES: O=C(NC1(C(=O)Nc2ccc(Cl)c(Cl)c2F)CCNCC1)[C@@H]1Cc2ccccc2CN1C(=O)CCC(=O)N1CCCC2(CCC2)C1] | 12-128 |
| 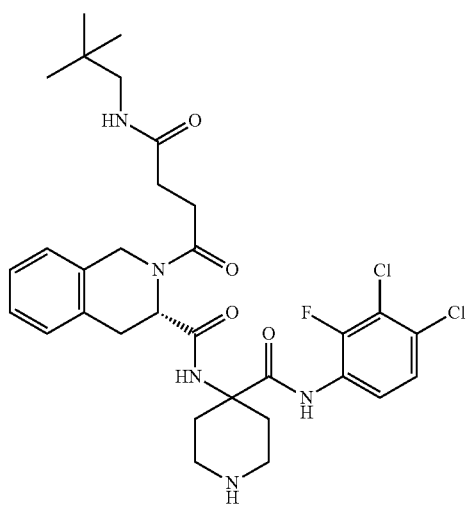 [SMILES: CC(C)(C)CNC(=O)CCC(=O)N1Cc2ccccc2C[C@H]1C(=O)NC1(C(=O)Nc2ccc(Cl)c(Cl)c2F)CCNCC1] | 12-129 |

TABLE A-continued

| Structure | Cpd. No. |
|---|---|
| 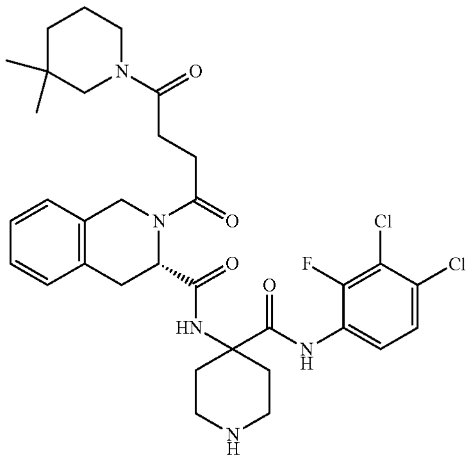 [SMILES: CC1(C)CCCN(C(=O)CCC(=O)N2Cc3ccccc3C[C@H]2C(=O)NC2(C(=O)Nc3ccc(Cl)c(Cl)c3F)CCNCC2)C1] | 12-130 |
| 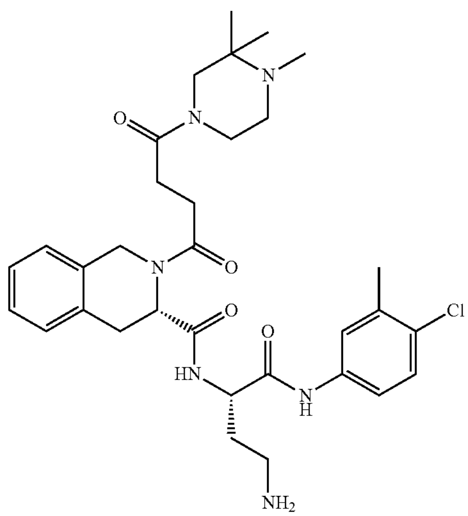 [SMILES: Cc1cc(NC(=O)[C@H](CCN)NC(=O)[C@@H]2Cc3ccccc3CN2C(=O)CCC(=O)N2CCN(C)C(C)(C)C2)ccc1Cl] | 12-131 |
| 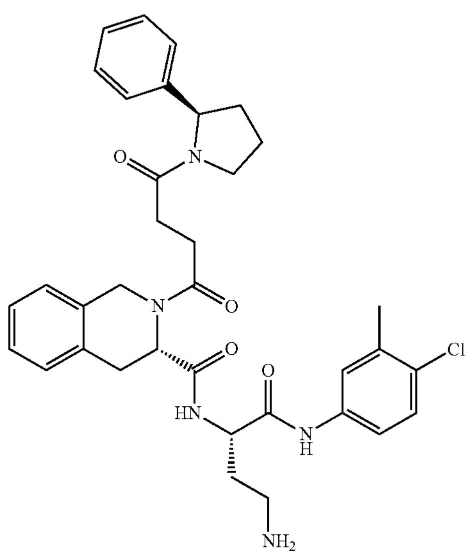 [SMILES: Cc1cc(NC(=O)[C@H](CCN)NC(=O)[C@@H]2Cc3ccccc3CN2C(=O)CCC(=O)N2CCC[C@@H]2c2ccccc2)ccc1Cl] | 12-132 |

TABLE A-continued

| Structure | Cpd. No. |
|---|---|
| 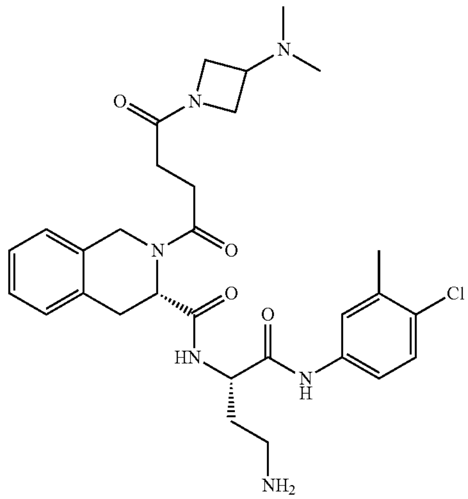 [SMILES: Cc1cc(NC(=O)[C@H](CCN)NC(=O)[C@@H]2Cc3ccccc3CN2C(=O)CCC(=O)N2CC(N(C)C)C2)ccc1Cl] | 12-133 |
| 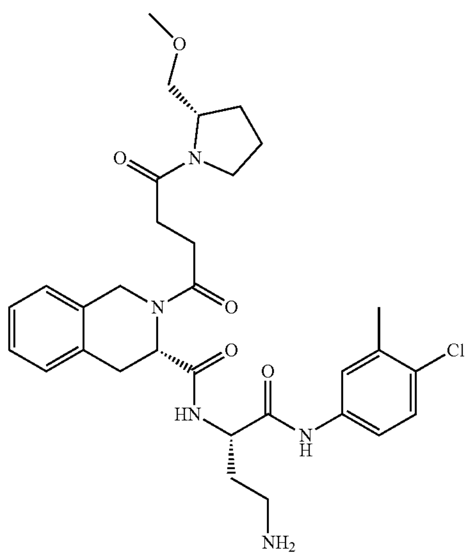 [SMILES: COC[C@@H]1CCCN1C(=O)CCC(=O)N1Cc2ccccc2C[C@H]1C(=O)N[C@@H](CCN)C(=O)Nc1ccc(Cl)c(C)c1] | 12-134 |
| 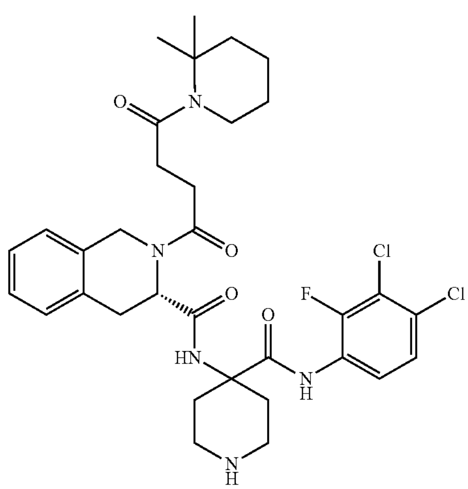 [SMILES: CC1(C)CCCCN1C(=O)CCC(=O)N1Cc2ccccc2C[C@H]1C(=O)NC1(C(=O)Nc2ccc(Cl)c(Cl)c2F)CCNCC1] | 12-135 |

TABLE A-continued
| Structure | Cpd. No. |
|---|---|
| 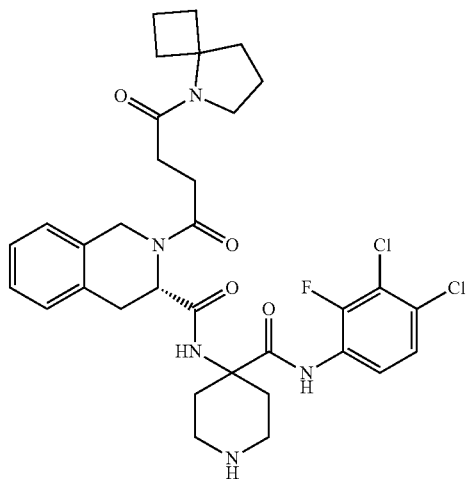 [SMILES: O=C(NC1(C(=O)Nc2ccc(Cl)c(Cl)c2F)CCNCC1)[C@@H]1Cc2ccccc2CN1C(=O)CCC(=O)N1CCCC12CCC2] | 12-136 |
| 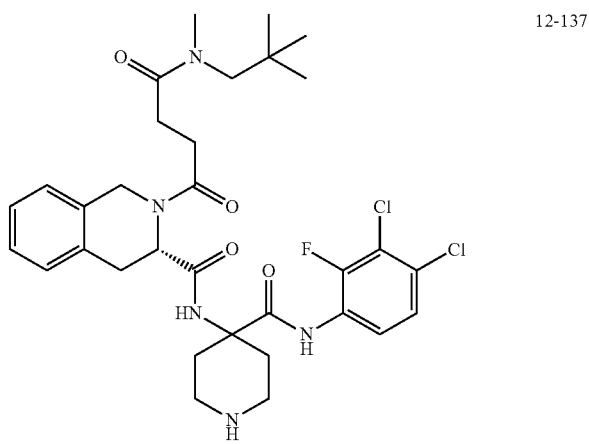 | 12-137 |
| 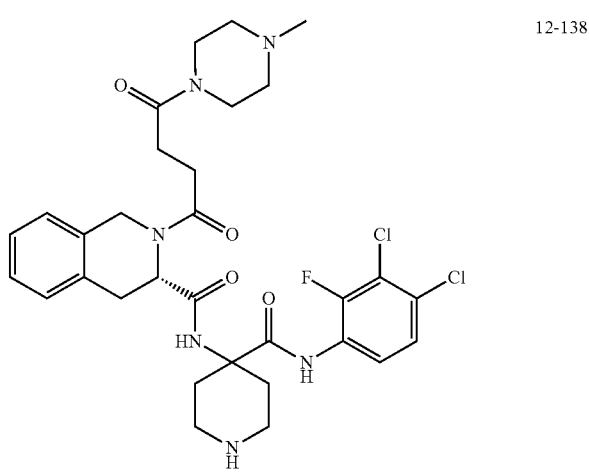 | 12-138 |

TABLE A-continued

| Structure | Cpd. No. |
|---|---|
| 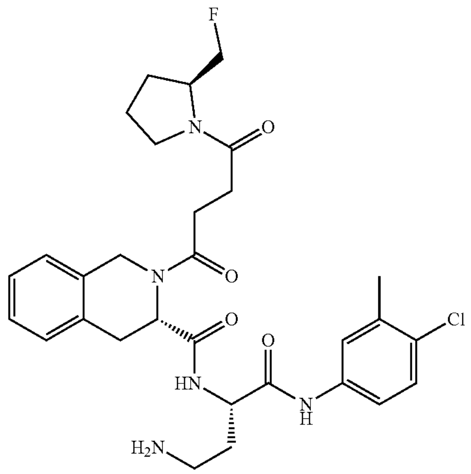 [SMILES: Cc1cc(NC(=O)[C@H](CCN)NC(=O)[C@@H]2Cc3ccccc3CN2C(=O)CCC(=O)N2CCC[C@H]2CF)ccc1Cl] | 12-139 |
| 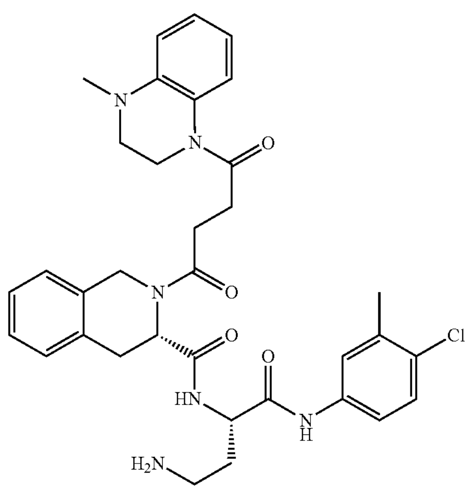 [SMILES: Cc1cc(NC(=O)[C@H](CCN)NC(=O)[C@@H]2Cc3ccccc3CN2C(=O)CCC(=O)N2CCN(C)c3ccccc32)ccc1Cl] | 12-140 |
| 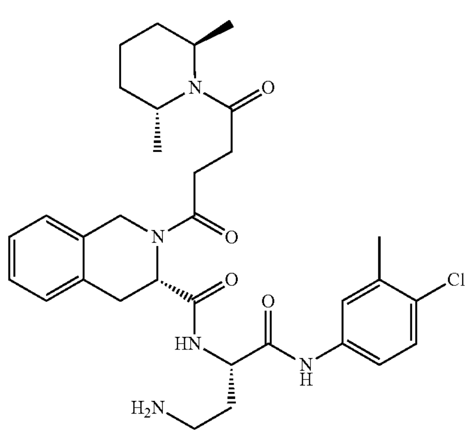 [SMILES: Cc1cc(NC(=O)[C@H](CCN)NC(=O)[C@@H]2Cc3ccccc3CN2C(=O)CCC(=O)N2[C@H](C)CCC[C@H]2C)ccc1Cl] | 12-141 |

TABLE A-continued
| Structure | Cpd. No. |
|---|---|
| 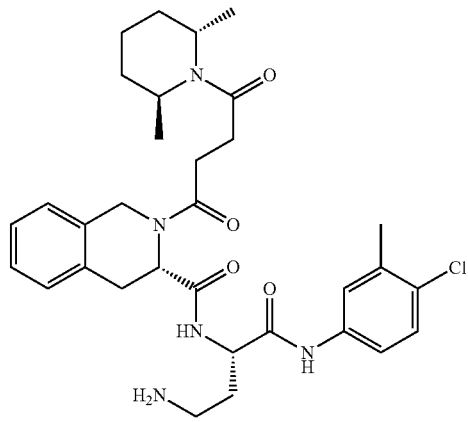 [SMILES: Cc1cc(NC(=O)[C@H](CCN)NC(=O)[C@@H]2Cc3ccccc3CN2C(=O)CCC(=O)N2[C@@H](C)CCC[C@@H]2C)ccc1Cl] | 12-142 |
| 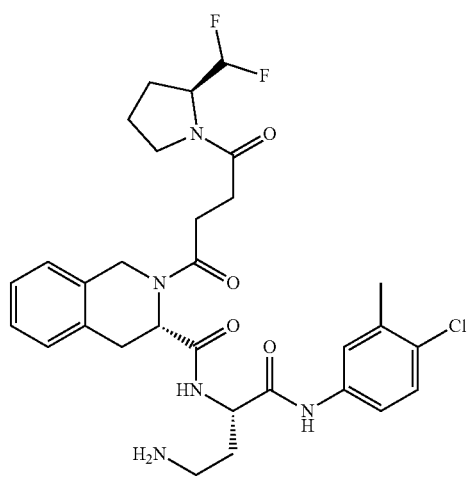 [SMILES: Cc1cc(NC(=O)[C@H](CCN)NC(=O)[C@@H]2Cc3ccccc3CN2C(=O)CCC(=O)N2CCC[C@H]2C(F)F)ccc1Cl] | 12-143 |
| 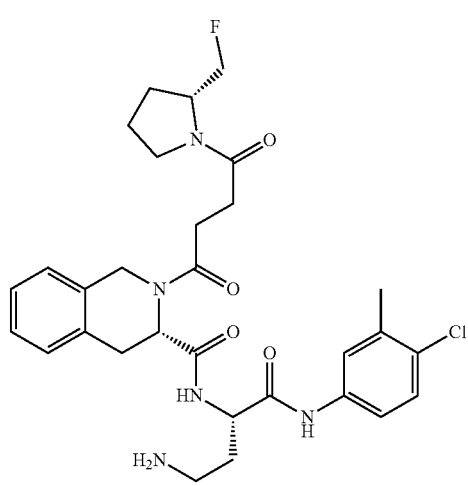 [SMILES: Cc1cc(NC(=O)[C@H](CCN)NC(=O)[C@@H]2Cc3ccccc3CN2C(=O)CCC(=O)N2CCC[C@@H]2CF)ccc1Cl] | 12-144 |

TABLE A-continued

| Structure | Cpd. No. |
|---|---|
| 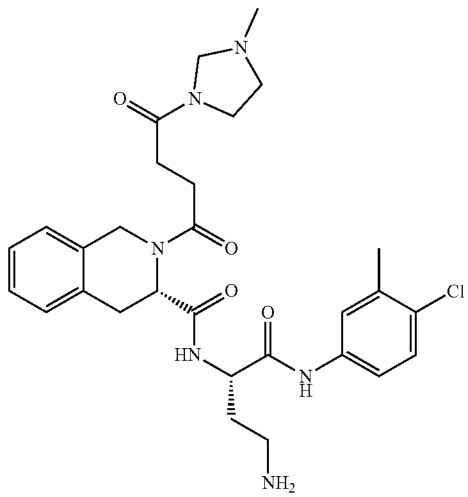 [SMILES: Cc1cc(NC(=O)[C@H](CCN)NC(=O)[C@@H]2Cc3ccccc3CN2C(=O)CCC(=O)N2CCN(C)C2)ccc1Cl] | 12-145 |
| 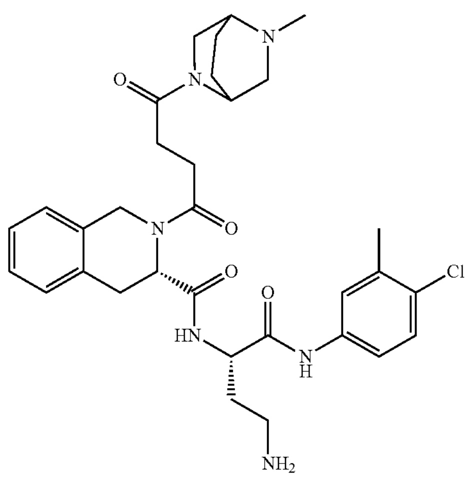 [SMILES: Cc1cc(NC(=O)[C@H](CCN)NC(=O)[C@@H]2Cc3ccccc3CN2C(=O)CCC(=O)N2CC3CCC2CN3C)ccc1Cl] | 12-146 |
| 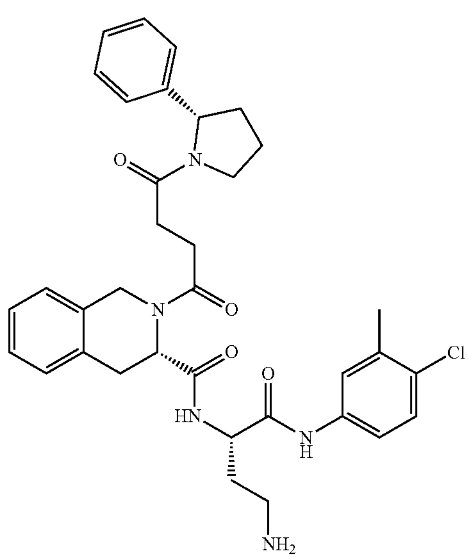 | 12-147 |

TABLE A-continued
| Structure | Cpd. No. |
|---|---|
| 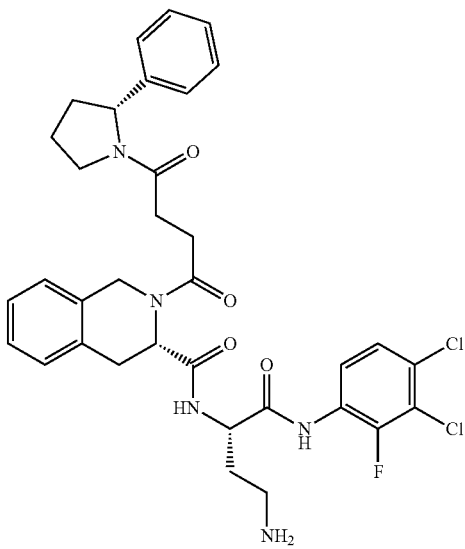 [SMILES: NCC[C@H](NC(=O)[C@@H]1Cc2ccccc2CN1C(=O)CCC(=O)N1CCC[C@@H]1c1ccccc1)C(=O)Nc1ccc(Cl)c(Cl)c1F] | 12-148 |
| 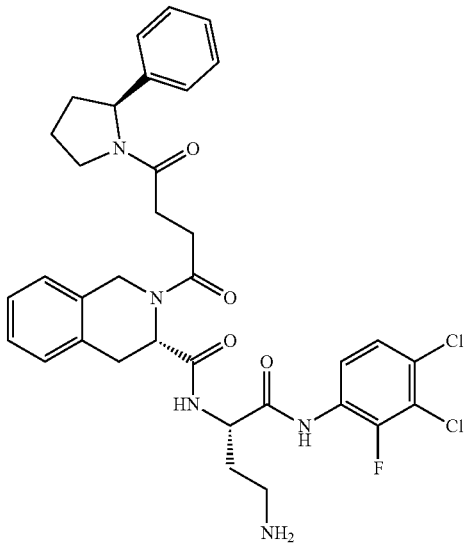 [SMILES: NCC[C@H](NC(=O)[C@@H]1Cc2ccccc2CN1C(=O)CCC(=O)N1CCC[C@H]1c1ccccc1)C(=O)Nc1ccc(Cl)c(Cl)c1F] | 12-149 |
| 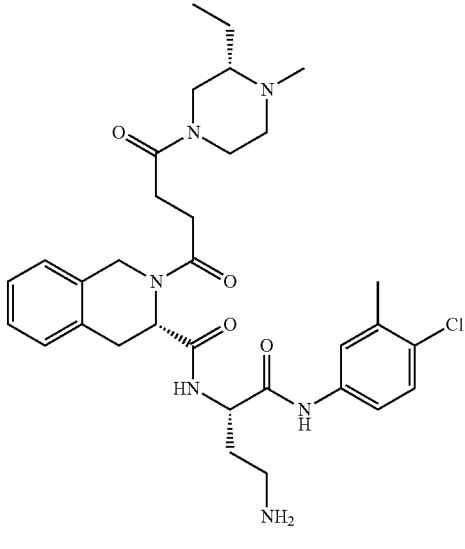 [SMILES: CC[C@H]1CN(C(=O)CCC(=O)N2Cc3ccccc3C[C@H]2C(=O)N[C@@H](CCN)C(=O)Nc2ccc(Cl)c(C)c2)CCN1C] | 12-150 |

TABLE A-continued
| Structure | Cpd. No. |
|---|---|
| 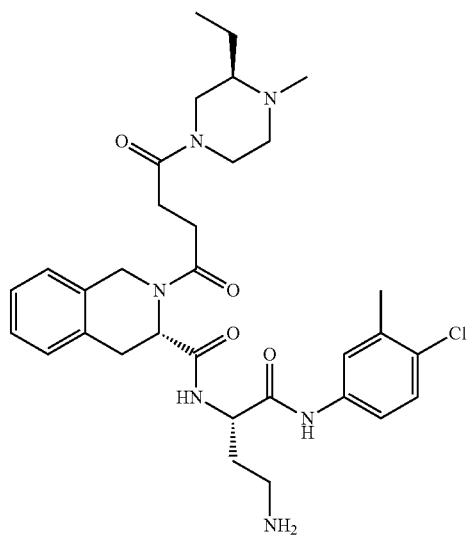 [SMILES: CC[C@@H]1CN(C(=O)CCC(=O)N2Cc3ccccc3C[C@H]2C(=O)N[C@@H](CCN)C(=O)Nc2ccc(Cl)c(C)c2)CCN1C] | 12-151 |
| 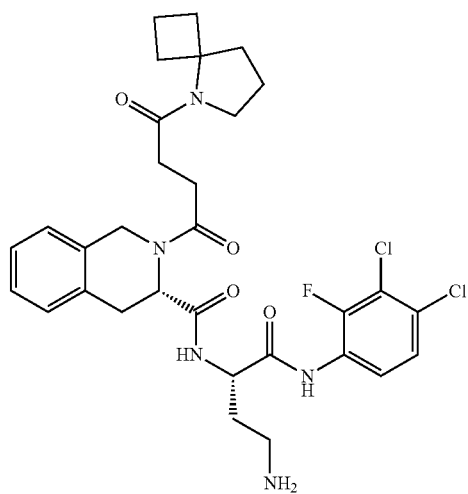 | 12-152 |
| 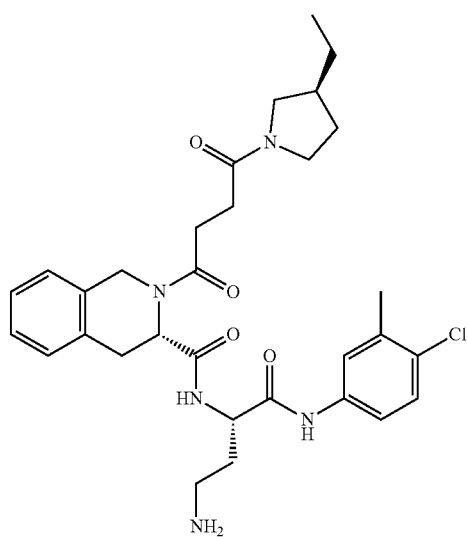 [SMILES: CC[C@H]1CCN(C(=O)CCC(=O)N2Cc3ccccc3C[C@H]2C(=O)N[C@@H](CCN)C(=O)Nc2ccc(Cl)c(C)c2)C1] | 12-153 |

TABLE A-continued
| Structure | Cpd. No. |
|---|---|
| 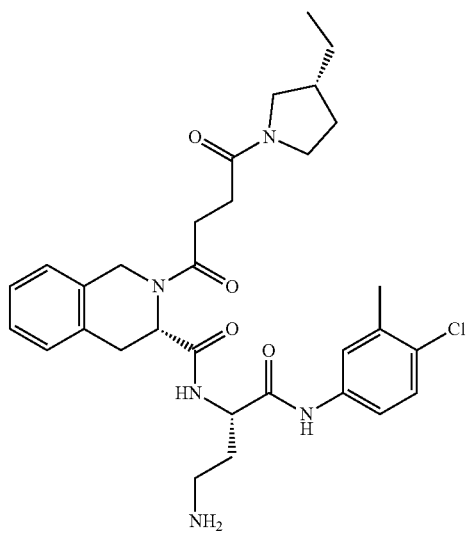 [SMILES: CC[C@@H]1CCN(C(=O)CCC(=O)N2Cc3ccccc3C[C@H]2C(=O)N[C@@H](CCN)C(=O)Nc2ccc(Cl)c(C)c2)C1] | 12-154 |
| 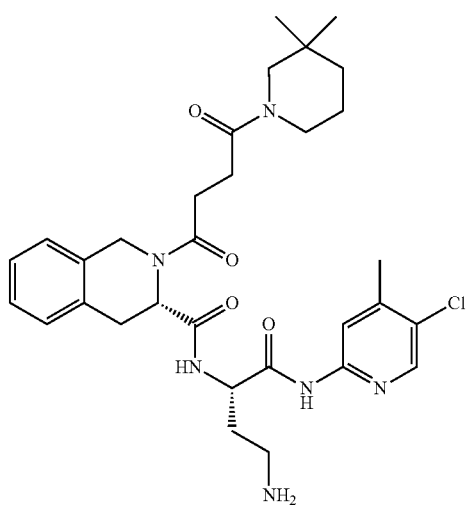 [SMILES: Cc1cc(NC(=O)[C@H](CCN)NC(=O)[C@@H]2Cc3ccccc3CN2C(=O)CCC(=O)N2CCCC(C)(C)C2)ncc1Cl] | 12-155 |
| 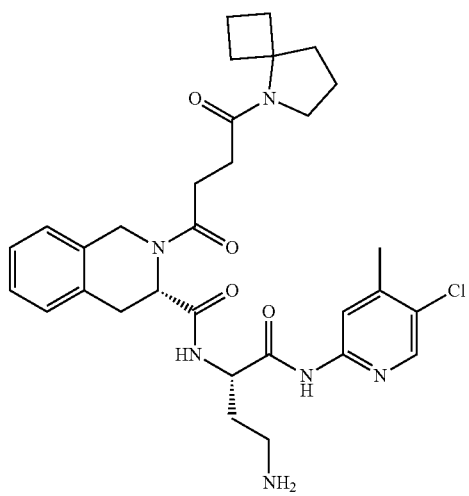 [SMILES: Cc1cc(NC(=O)[C@H](CCN)NC(=O)[C@@H]2Cc3ccccc3CN2C(=O)CCC(=O)N2CCCC23CCC3)ncc1Cl] | 12-156 |

TABLE A-continued
| Structure | Cpd. No. |
|---|---|
| 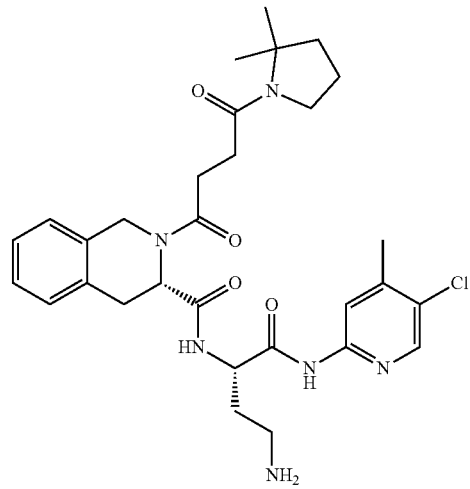 [SMILES: Cc1cc(NC(=O)[C@H](CCN)NC(=O)[C@@H]2Cc3ccccc3CN2C(=O)CCC(=O)N2CCCC2(C)C)ncc1Cl] | 12-157 |
| 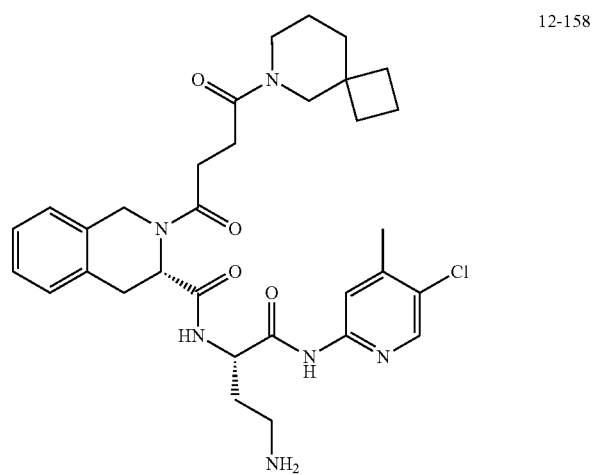 | 12-158 |
| 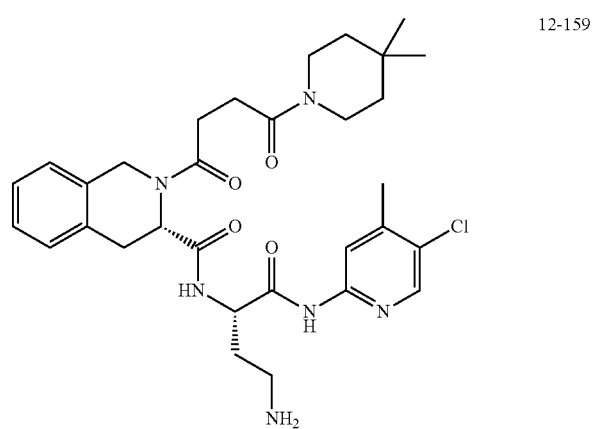 | 12-159 |

TABLE A-continued
| Structure | Cpd. No. |
|---|---|
| 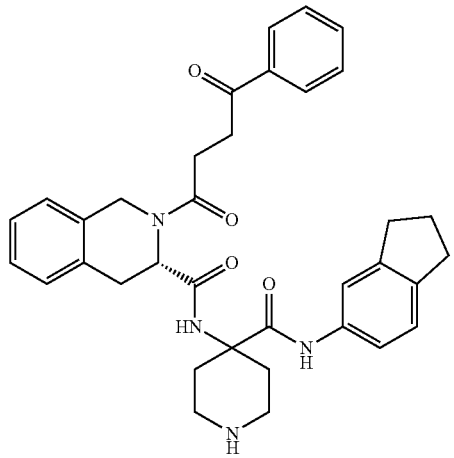 [SMILES: O=C(CCC(=O)N1Cc2ccccc2C[C@H]1C(=O)NC1(C(=O)Nc2ccc3c(c2)CCC3)CCNCC1)c1ccccc1] | 13-1 |
| 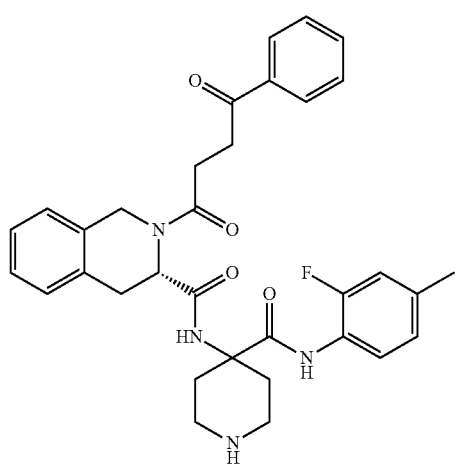 [SMILES: Cc1ccc(NC(=O)C2(NC(=O)[C@@H]3Cc4ccccc4CN3C(=O)CCC(=O)c3ccccc3)CCNCC2)c(F)c1] | 13-2 |
| 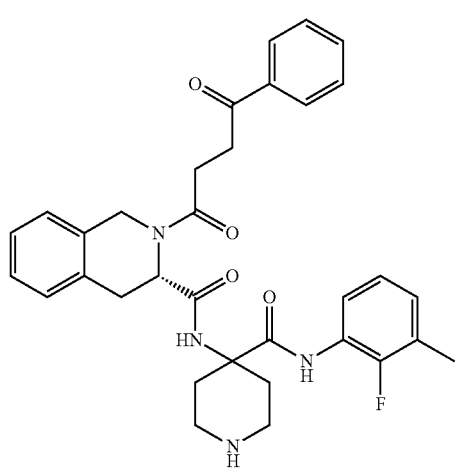 [SMILES: Cc1cccc(NC(=O)C2(NC(=O)[C@@H]3Cc4ccccc4CN3C(=O)CCC(=O)c3ccccc3)CCNCC2)c1F] | 13-3 |

TABLE A-continued
| Structure | Cpd. No. |
|---|---|
| 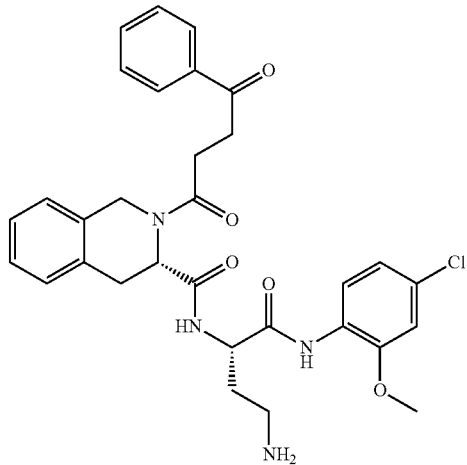 [SMILES: COc1cc(Cl)ccc1NC(=O)[C@H](CCN)NC(=O)[C@@H]1Cc2ccccc2CN1C(=O)CCC(=O)c1ccccc1] | 13-4 |
| 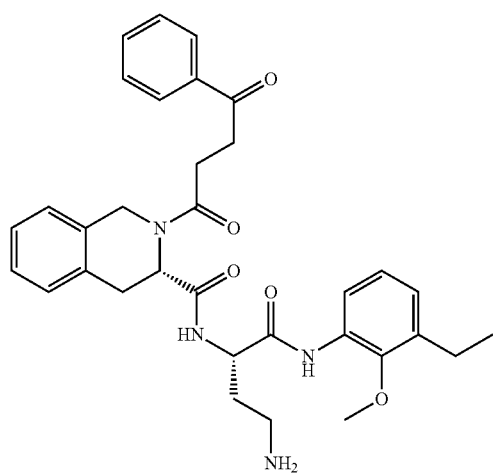 [SMILES: CCc1cccc(NC(=O)[C@H](CCN)NC(=O)[C@@H]2Cc3ccccc3CN2C(=O)CCC(=O)c2ccccc2)c1OC] | 13-5 |
| 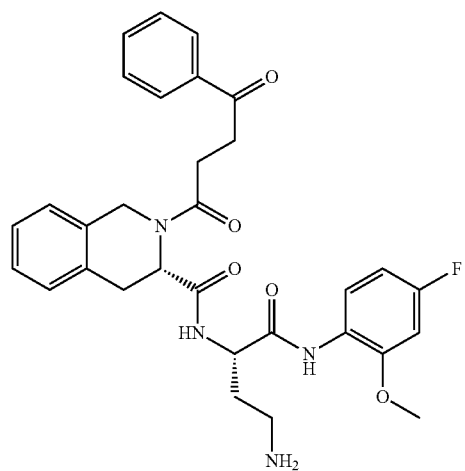 [SMILES: COc1cc(F)ccc1NC(=O)[C@H](CCN)NC(=O)[C@@H]1Cc2ccccc2CN1C(=O)CCC(=O)c1ccccc1] | 13-6 |

TABLE A-continued
| Structure | Cpd. No. |
|---|---|
| 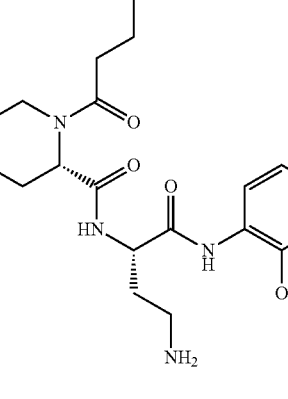 | 13-7 |
| 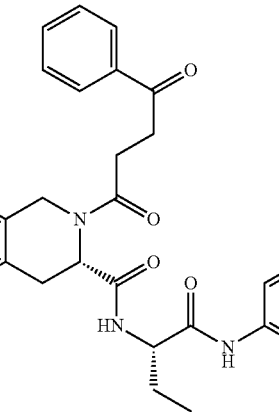 | 14-1 |
| 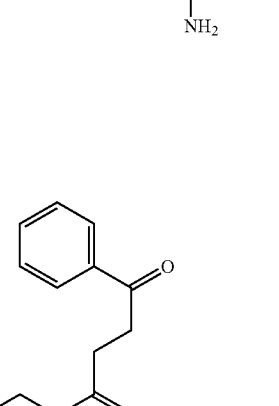 | 14-2 |

TABLE A-continued
| Structure | Cpd. No. |
|---|---|
| 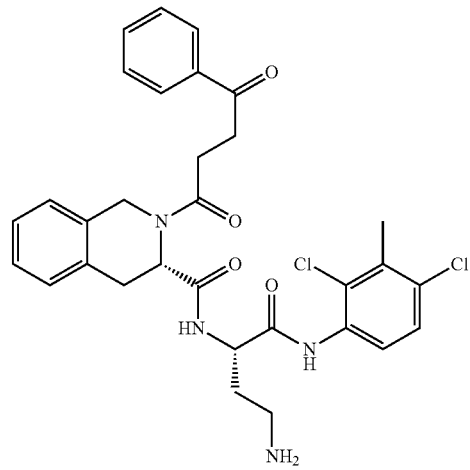 [SMILES: Cc1c(Cl)ccc(NC(=O)[C@H](CCN)NC(=O)[C@@H]2Cc3ccccc3CN2C(=O)CCC(=O)c2ccccc2)c1Cl] | 14-3 |
| 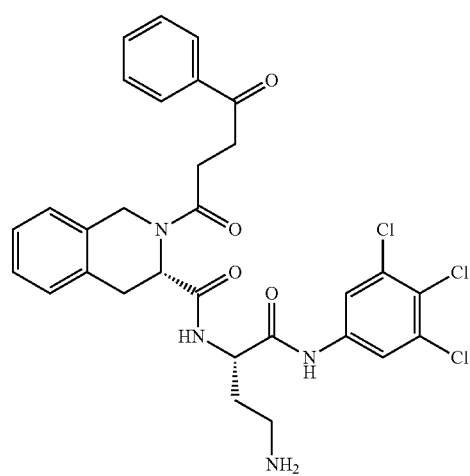 [SMILES: NCC[C@H](NC(=O)[C@@H]1Cc2ccccc2CN1C(=O)CCC(=O)c1ccccc1)C(=O)Nc1cc(Cl)c(Cl)c(Cl)c1] | 14-4 |
| 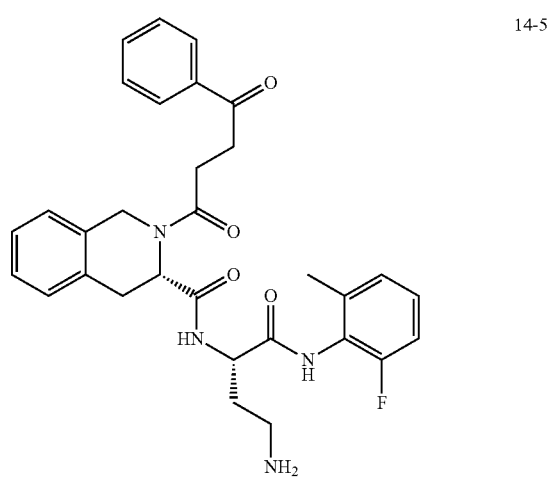 | 14-5 |

TABLE A-continued

| Structure | Cpd. No. |
|---|---|
| 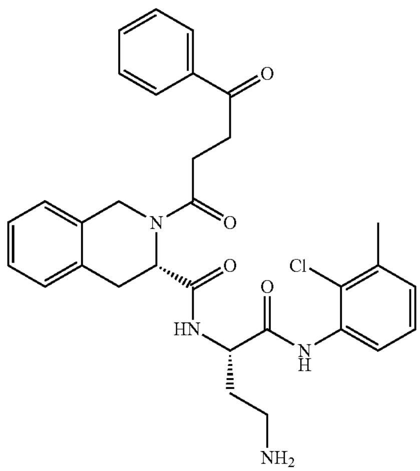 [SMILES: Cc1cccc(NC(=O)[C@H](CCN)NC(=O)[C@@H]2Cc3ccccc3CN2C(=O)CCC(=O)c2ccccc2)c1Cl] | 14-6 |
| 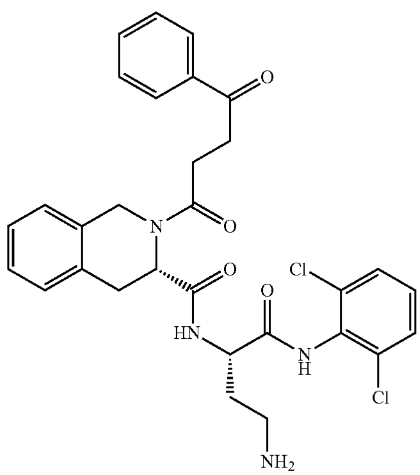 [SMILES: NCC[C@H](NC(=O)[C@@H]1Cc2ccccc2CN1C(=O)CCC(=O)c1ccccc1)C(=O)Nc1c(Cl)cccc1Cl] | 14-7 |
| 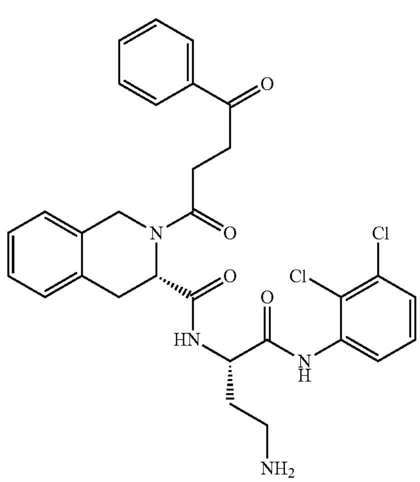 | 14-8 |

TABLE A-continued

| Structure | Cpd. No. |
|---|---|
| 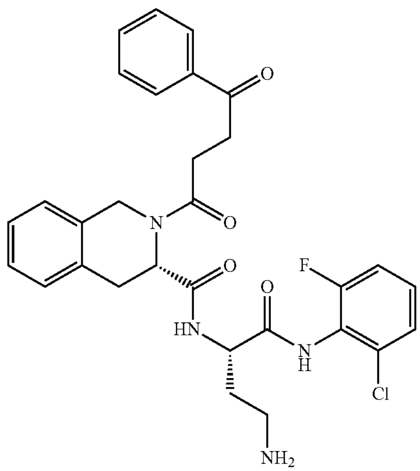 | 14-9 |
| 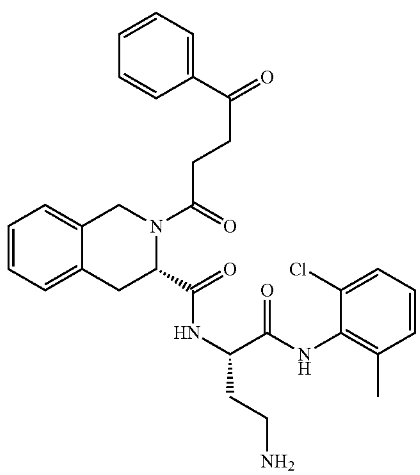 [SMILES: Cc1cccc(Cl)c1NC(=O)[C@H](CCN)NC(=O)[C@@H]1Cc2ccccc2CN1C(=O)CCC(=O)c1ccccc1] | 14-10 |
| 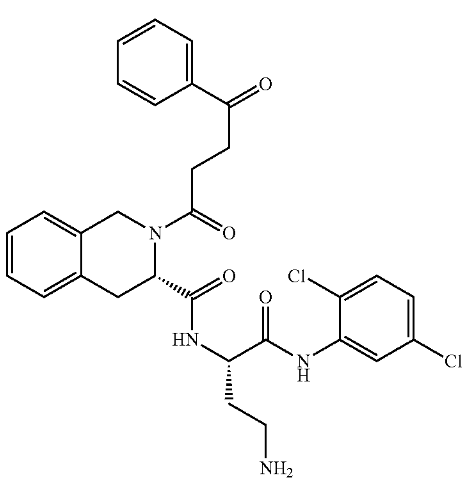 [SMILES: NCC[C@H](NC(=O)[C@@H]1Cc2ccccc2CN1C(=O)CCC(=O)c1ccccc1)C(=O)Nc1cc(Cl)ccc1Cl] | 14-11 |

TABLE A-continued
| Structure | Cpd. No. |
|---|---|
| 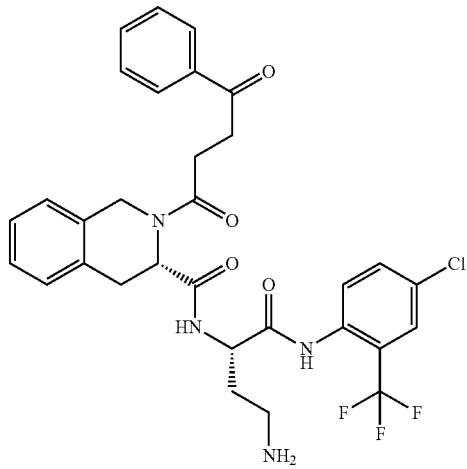 [SMILES: NCC[C@H](NC(=O)[C@@H]1Cc2ccccc2CN1C(=O)CCC(=O)c1ccccc1)C(=O)Nc1ccc(Cl)cc1C(F)(F)F] | 14-12 |
| 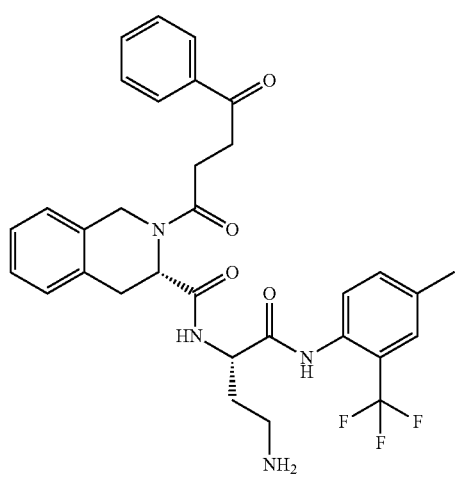 | 14-13 |
| 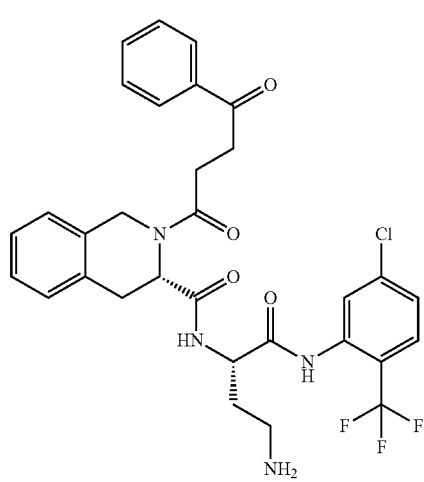 [SMILES: NCC[C@H](NC(=O)[C@@H]1Cc2ccccc2CN1C(=O)CCC(=O)c1ccccc1)C(=O)Nc1cc(Cl)ccc1C(F)(F)F] | 14-14 |

TABLE A-continued
| Structure | Cpd. No. |
|---|---|
| 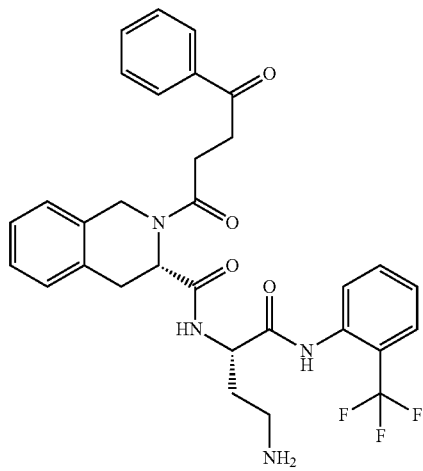 [SMILES: NCC[C@H](NC(=O)[C@@H]1Cc2ccccc2CN1C(=O)CCC(=O)c1ccccc1)C(=O)Nc1ccccc1C(F)(F)F] | 14-15 |
| 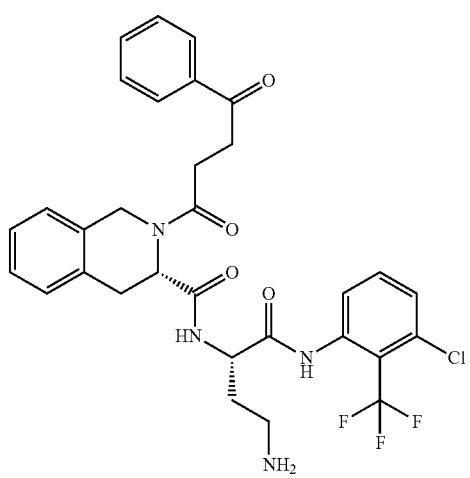 [SMILES: NCC[C@H](NC(=O)[C@@H]1Cc2ccccc2CN1C(=O)CCC(=O)c1ccccc1)C(=O)Nc1cccc(Cl)c1C(F)(F)F] | 14-16 |
| 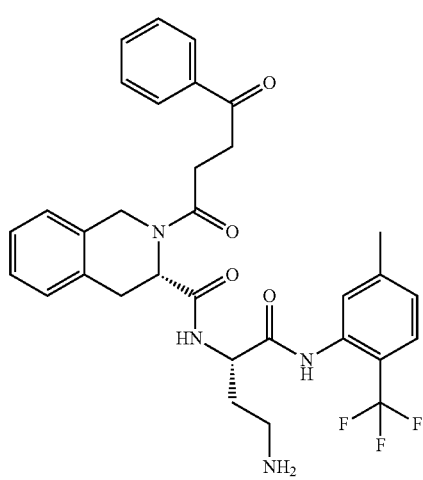 [SMILES: Cc1ccc(C(F)(F)F)c(NC(=O)[C@H](CCN)NC(=O)[C@@H]2Cc3ccccc3CN2C(=O)CCC(=O)c2ccccc2)c1] | 14-17 |

TABLE A-continued
| Structure | Cpd. No. |
|---|---|
| 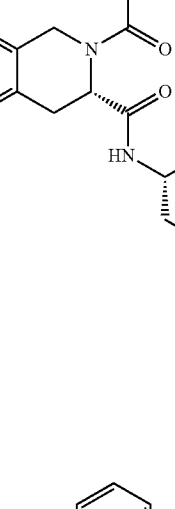 | 14-18 |
| 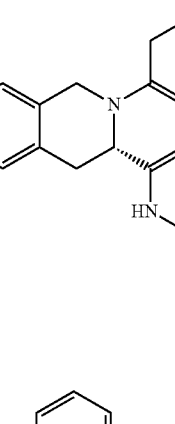 | 14-19 |
| 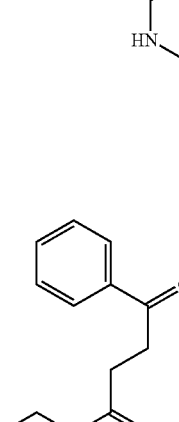 | 14-20 |

TABLE A-continued
| Structure | Cpd. No. |
|---|---|
| 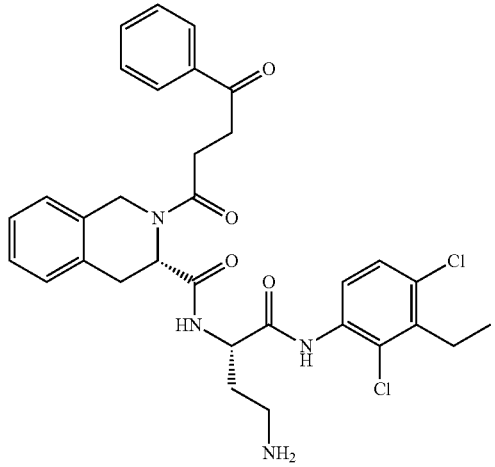 [SMILES: CCc1c(Cl)ccc(NC(=O)[C@H](CCN)NC(=O)[C@@H]2Cc3ccccc3CN2C(=O)CCC(=O)c2ccccc2)c1Cl] | 14-21 |
| 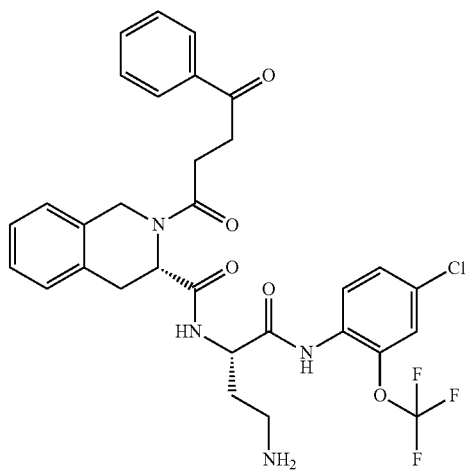 [SMILES: NCC[C@H](NC(=O)[C@@H]1Cc2ccccc2CN1C(=O)CCC(=O)c1ccccc1)C(=O)Nc1ccc(Cl)cc1OC(F)(F)F] | 14-23 |
| 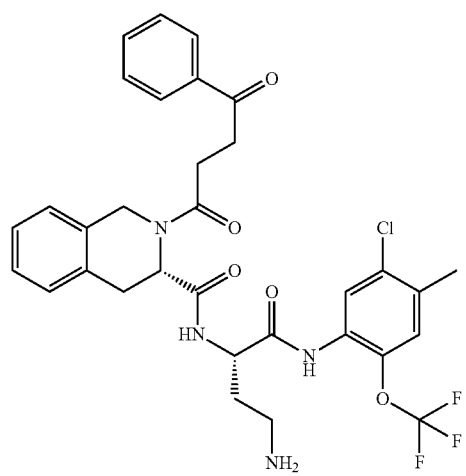 | 14-24 |

TABLE A-continued
| Structure | Cpd. No. |
|---|---|
| 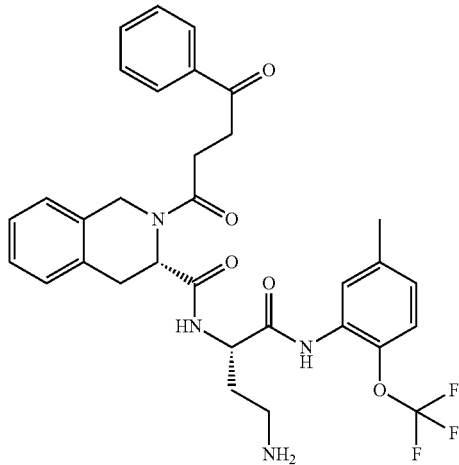 [SMILES: Cc1ccc(OC(F)(F)F)c(NC(=O)[C@H](CCN)NC(=O)[C@@H]2Cc3ccccc3CN2C(=O)CCC(=O)c2ccccc2)c1] | 14-25 |
| 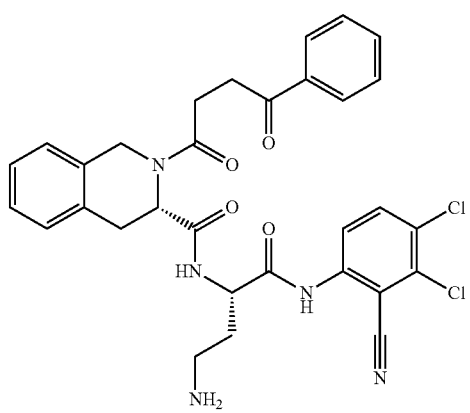 [SMILES: N#Cc1c(NC(=O)[C@H](CCN)NC(=O)[C@@H]2Cc3ccccc3CN2C(=O)CCC(=O)c2ccccc2)ccc(Cl)c1Cl] | 14-26 |
| 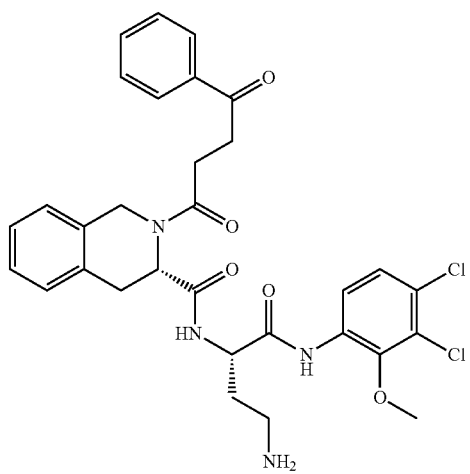 [SMILES: COc1c(NC(=O)[C@H](CCN)NC(=O)[C@@H]2Cc3ccccc3CN2C(=O)CCC(=O)c2ccccc2)ccc(Cl)c1Cl] | 14-27 |

TABLE A-continued
| Structure | Cpd. No. |
|---|---|
| 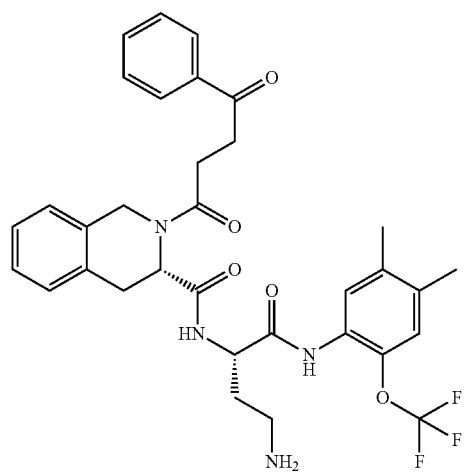 [SMILES: Cc1cc(NC(=O)[C@H](CCN)NC(=O)[C@@H]2Cc3ccccc3CN2C(=O)CCC(=O)c2ccccc2)c(OC(F)(F)F)cc1C] | 14-28 |
| 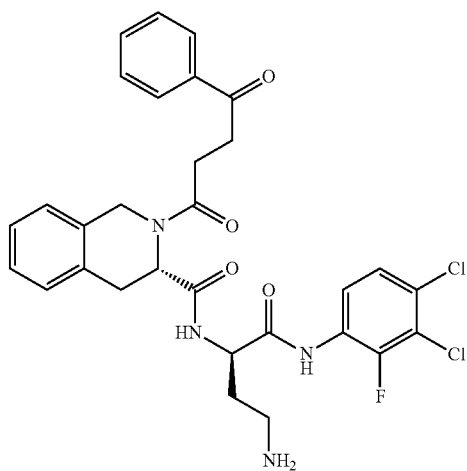 [SMILES: NCC[C@@H](NC(=O)[C@@H]1Cc2ccccc2CN1C(=O)CCC(=O)c1ccccc1)C(=O)Nc1ccc(Cl)c(Cl)c1F] | 14-29 |
| 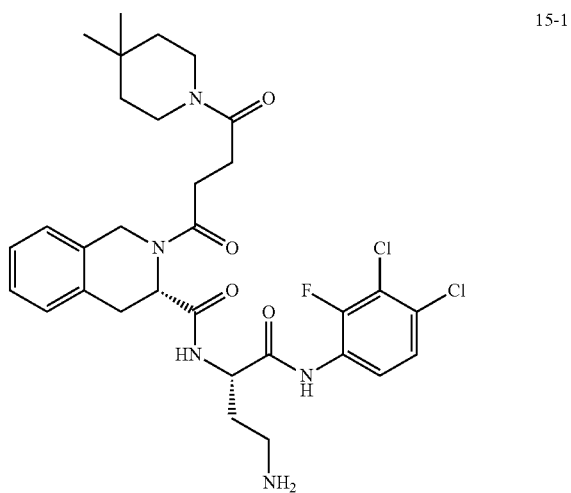 | 15-1 |

TABLE A-continued
| Structure | Cpd. No. |
|---|---|
| 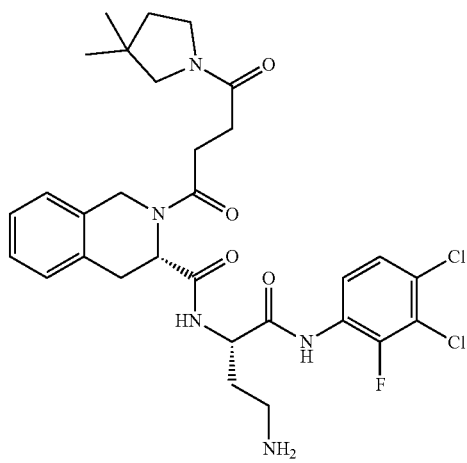 [SMILES: CC1(C)CCN(C(=O)CCC(=O)N2Cc3ccccc3C[C@H]2C(=O)N[C@@H](CCN)C(=O)Nc2ccc(Cl)c(Cl)c2F)C1] | 15-2 |
| 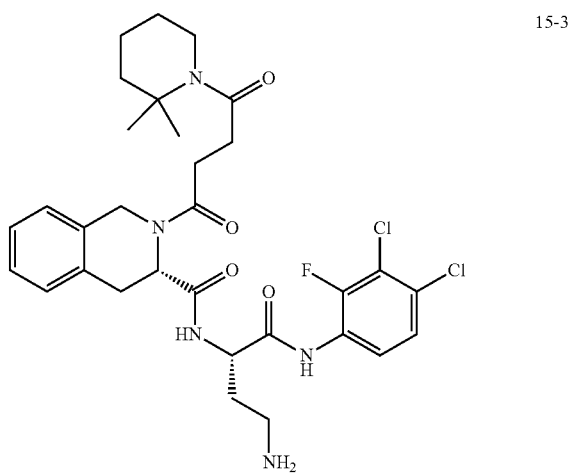 | 15-3 |
| 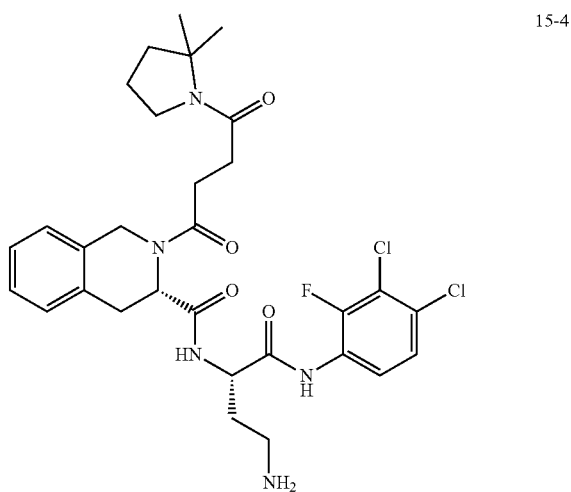 | 15-4 |

TABLE A-continued
| Structure | Cpd. No. |
|---|---|
| 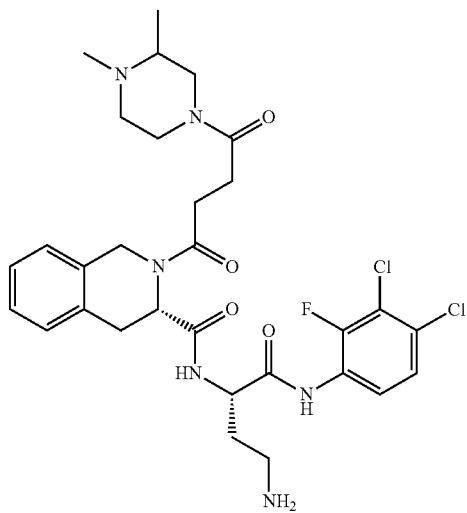 [SMILES: CC1CN(C(=O)CCC(=O)N2Cc3ccccc3C[C@H]2C(=O)N[C@@H](CCN)C(=O)Nc2ccc(Cl)c(Cl)c2F)CCN1C] | 15-5 |
| 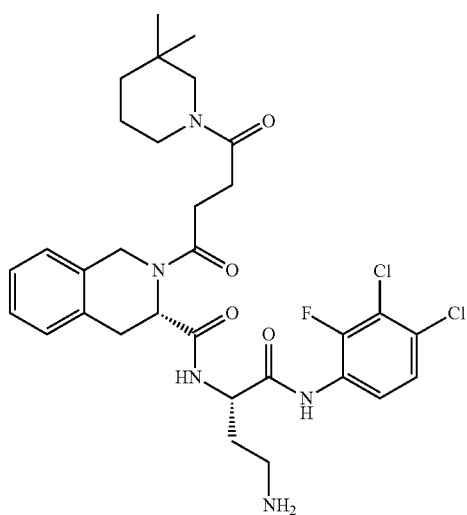 [SMILES: CC1(C)CCCN(C(=O)CCC(=O)N2Cc3ccccc3C[C@H]2C(=O)N[C@@H](CCN)C(=O)Nc2ccc(Cl)c(Cl)c2F)C1] | 15-6 |
| 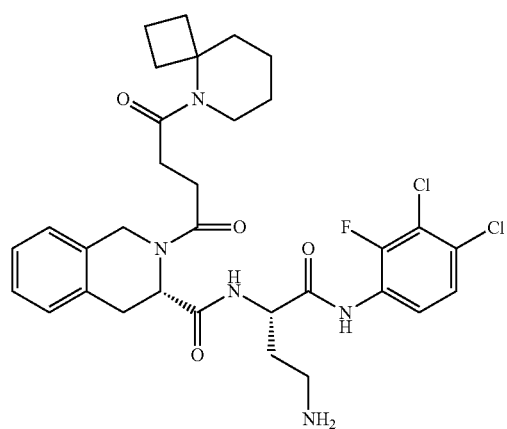 [SMILES: NCC[C@H](NC(=O)[C@@H]1Cc2ccccc2CN1C(=O)CCC(=O)N1CCCCC12CCC2)C(=O)Nc1ccc(Cl)c(Cl)c1F] | 15-7 |

TABLE A-continued
| Structure | Cpd. No. |
|---|---|
| 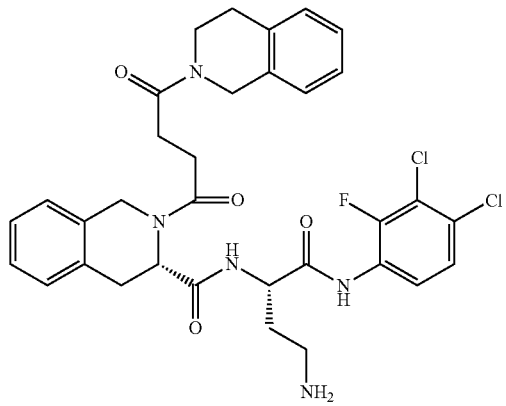 [SMILES: NCC[C@H](NC(=O)[C@@H]1Cc2ccccc2CN1C(=O)CCC(=O)N1CCc2ccccc2C1)C(=O)Nc1ccc(Cl)c(Cl)c1F] | 15-8 |
| 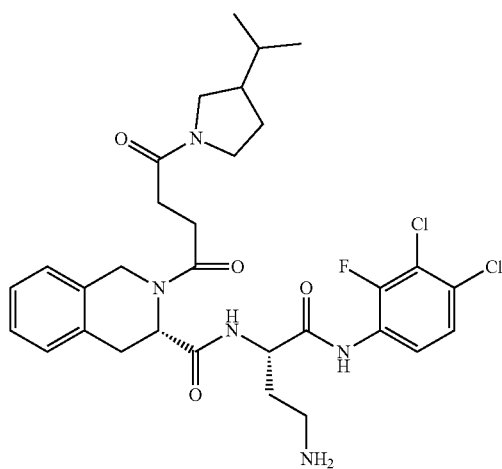 [SMILES: CC(C)C1CCN(C(=O)CCC(=O)N2Cc3ccccc3C[C@H]2C(=O)N[C@@H](CCN)C(=O)Nc2ccc(Cl)c(Cl)c2F)C1] | 15-9 |
| 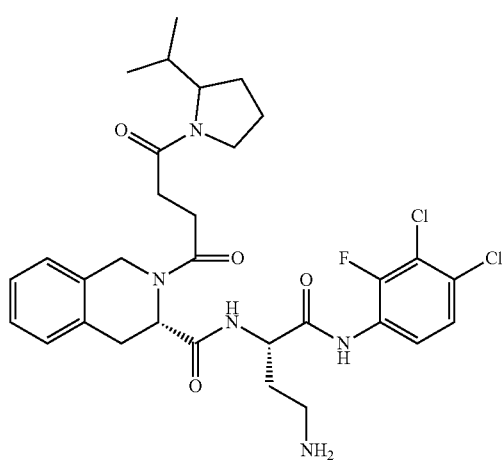 [SMILES: CC(C)C1CCCN1C(=O)CCC(=O)N1Cc2ccccc2C[C@H]1C(=O)N[C@@H](CCN)C(=O)Nc1ccc(Cl)c(Cl)c1F] | 15-10 |

TABLE A-continued
| Structure | Cpd. No. |
|---|---|
| 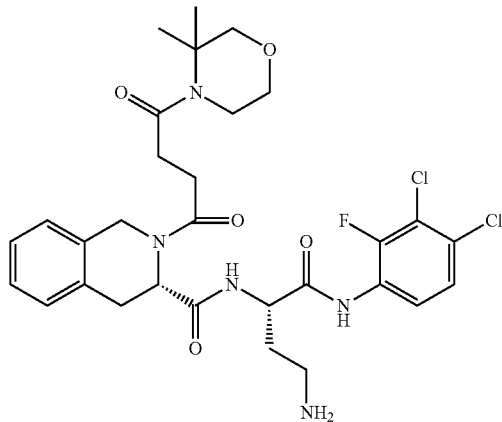 [SMILES: CC1(C)COCCN1C(=O)CCC(=O)N1Cc2ccccc2C[C@H]1C(=O)N[C@@H](CCN)C(=O)Nc1ccc(Cl)c(Cl)c1F] | 15-11 |
| 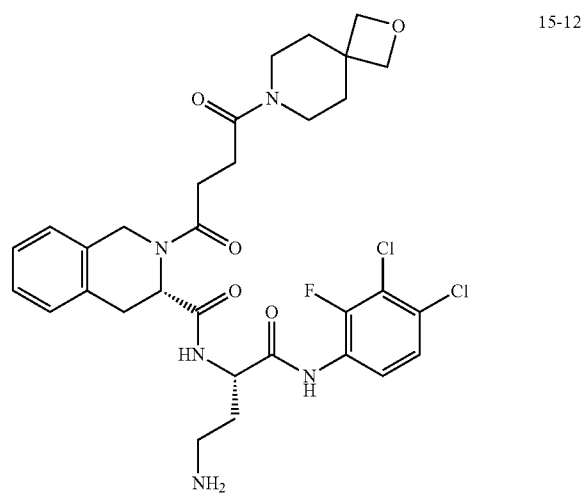 | 15-12 |
| 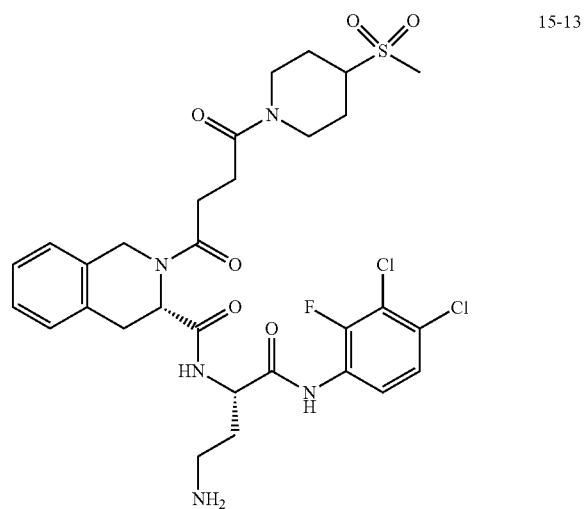 | 15-13 |

TABLE A-continued
| Structure | Cpd. No. |
|---|---|
| 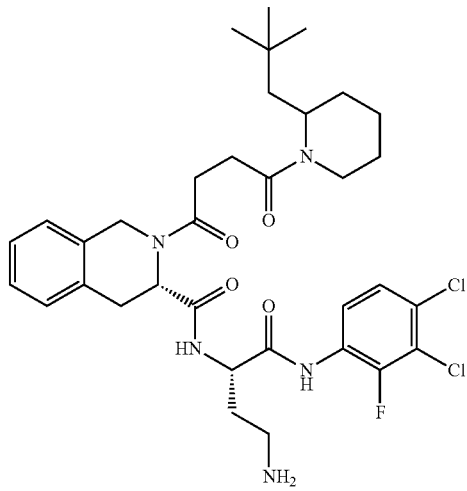 [SMILES: CC(C)(C)CC1CCCCN1C(=O)CCC(=O)N1Cc2ccccc2C[C@H]1C(=O)N[C@@H](CCN)C(=O)Nc1ccc(Cl)c(Cl)c1F] | 15-14 |
| 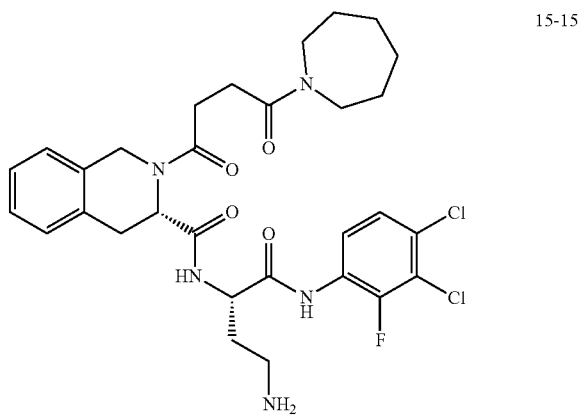 | 15-15 |
| 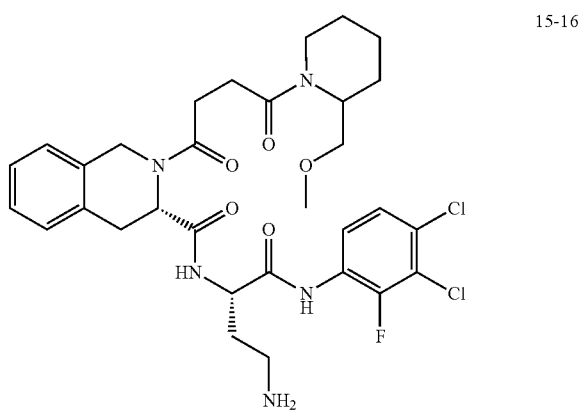 | 15-16 |

TABLE A-continued

| Structure | Cpd. No. |
|---|---|
| 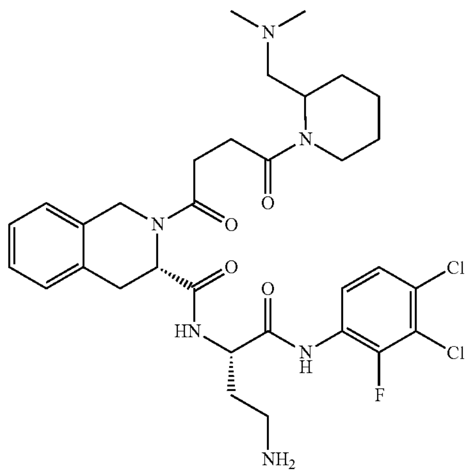 [SMILES: CN(C)CC1CCCCN1C(=O)CCC(=O)N1Cc2ccccc2C[C@H]1C(=O)N[C@@H](CCN)C(=O)Nc1ccc(Cl)c(Cl)c1F] | 15-17 |
| 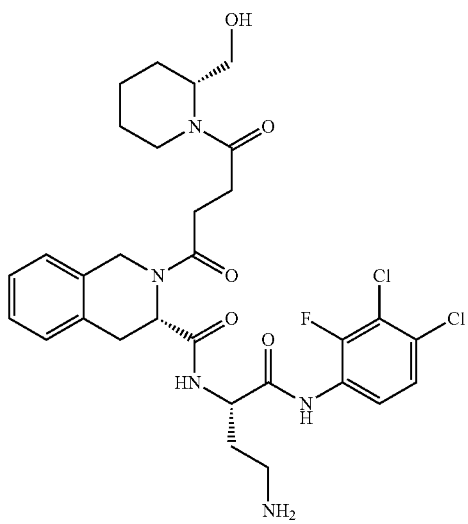 [SMILES: NCC[C@H](NC(=O)[C@@H]1Cc2ccccc2CN1C(=O)CCC(=O)N1CCCC[C@@H]1CO)C(=O)Nc1ccc(Cl)c(Cl)c1F] | 15-18 |
| 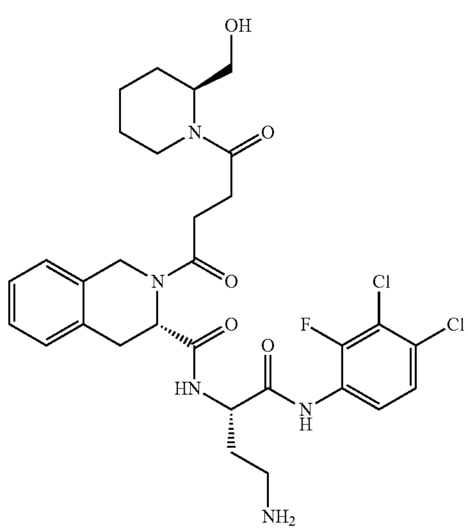 [SMILES: NCC[C@H](NC(=O)[C@@H]1Cc2ccccc2CN1C(=O)CCC(=O)N1CCCC[C@H]1CO)C(=O)Nc1ccc(Cl)c(Cl)c1F] | 15-19 |

TABLE A-continued

| Structure | Cpd. No. |
|---|---|
| 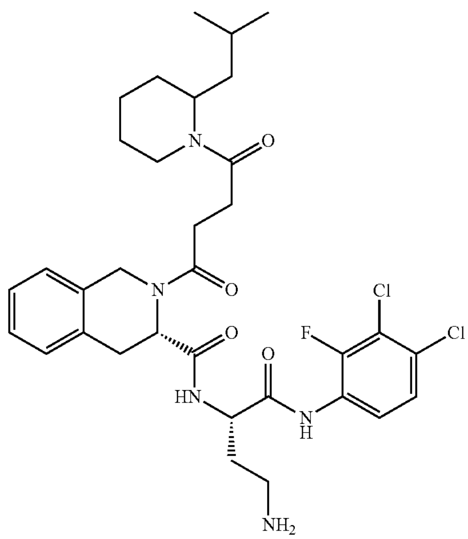 [SMILES: CC(C)CC1CCCCN1C(=O)CCC(=O)N1Cc2ccccc2C[C@H]1C(=O)N[C@@H](CCN)C(=O)Nc1ccc(Cl)c(Cl)c1F] | 15-20 |
| 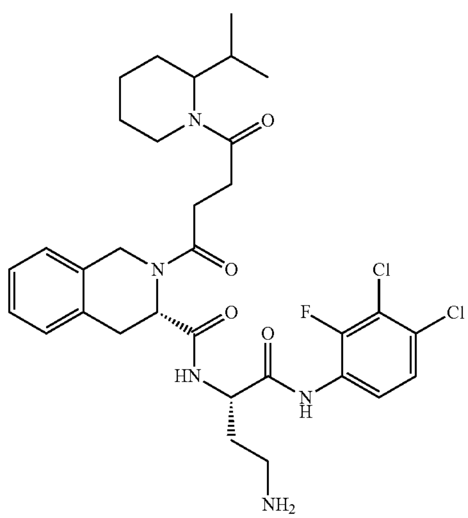 [SMILES: CC(C)C1CCCCN1C(=O)CCC(=O)N1Cc2ccccc2C[C@H]1C(=O)N[C@@H](CCN)C(=O)Nc1ccc(Cl)c(Cl)c1F] | 15-21 |
| 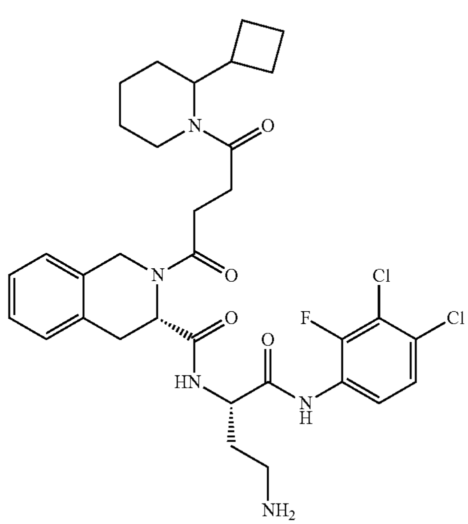 [SMILES: NCC[C@H](NC(=O)[C@@H]1Cc2ccccc2CN1C(=O)CCC(=O)N1CCCCC1C1CCC1)C(=O)Nc1ccc(Cl)c(Cl)c1F] | 15-22 |

TABLE A-continued
| Structure | Cpd. No. |
|---|---|
| 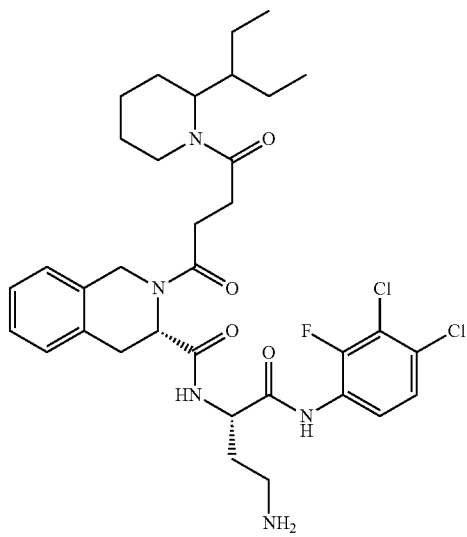 [SMILES: CCC(CC)C1CCCCN1C(=O)CCC(=O)N1Cc2ccccc2C[C@H]1C(=O)N[C@@H](CCN)C(=O)Nc1ccc(Cl)c(Cl)c1F] | 15-23 |
| 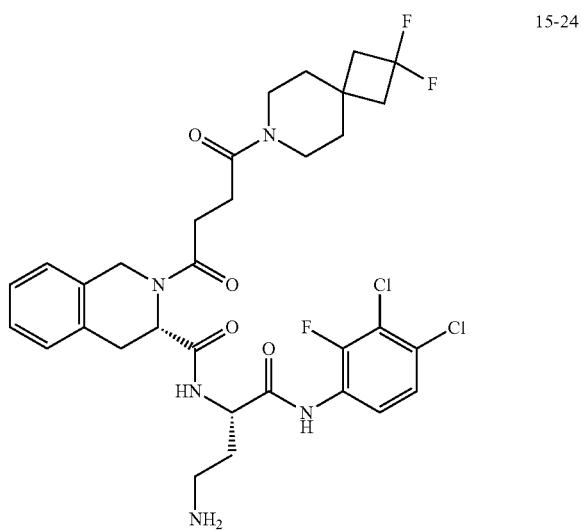 | 15-24 |
| 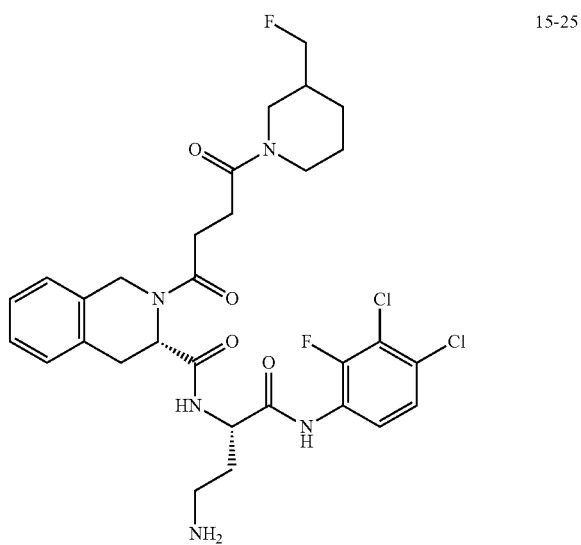 | 15-25 |

TABLE A-continued

| Structure | Cpd. No. |
|---|---|
| 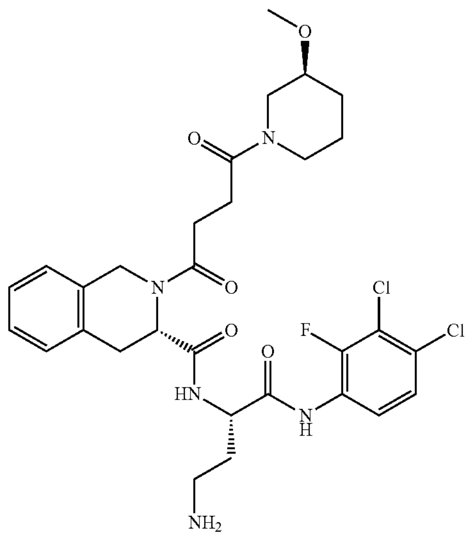 [SMILES: CO[C@H]1CCCN(C(=O)CCC(=O)N2Cc3ccccc3C[C@H]2C(=O)N[C@@H](CCN)C(=O)Nc2ccc(Cl)c(Cl)c2F)C1] | 15-26 |
| 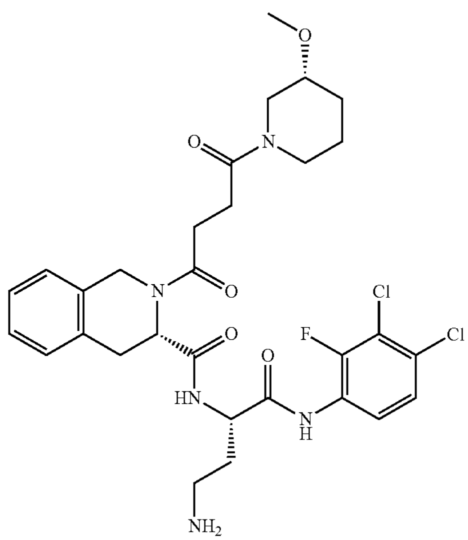 [SMILES: CO[C@@H]1CCCN(C(=O)CCC(=O)N2Cc3ccccc3C[C@H]2C(=O)N[C@@H](CCN)C(=O)Nc2ccc(Cl)c(Cl)c2F)C1] | 15-27 |
| 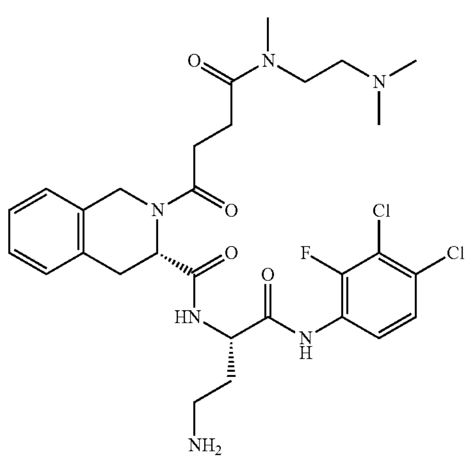 [SMILES: CN(C)CCN(C)C(=O)CCC(=O)N1Cc2ccccc2C[C@H]1C(=O)N[C@@H](CCN)C(=O)Nc1ccc(Cl)c(Cl)c1F] | 15-28 |

TABLE A-continued
| Structure | Cpd. No. |
|---|---|
| 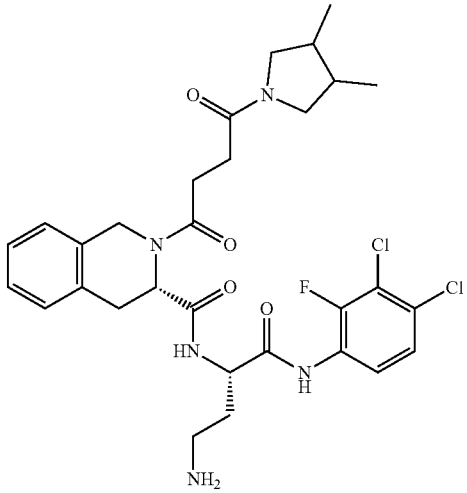 [SMILES: CC1CN(C(=O)CCC(=O)N2Cc3ccccc3C[C@H]2C(=O)N[C@@H](CCN)C(=O)Nc2ccc(Cl)c(Cl)c2F)CC1C] | 15-29 |
| 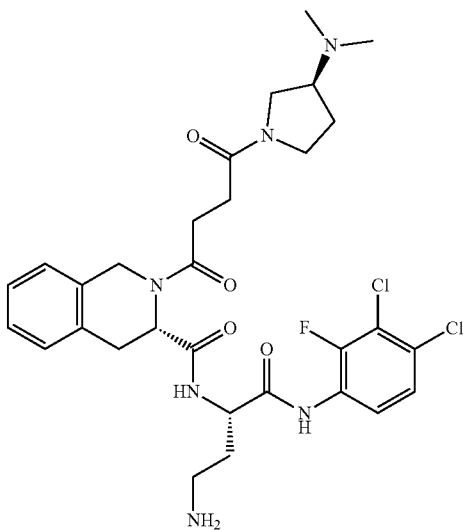 [SMILES: CN(C)[C@H]1CCN(C(=O)CCC(=O)N2Cc3ccccc3C[C@H]2C(=O)N[C@@H](CCN)C(=O)Nc2ccc(Cl)c(Cl)c2F)C1] | 15-30 |
| 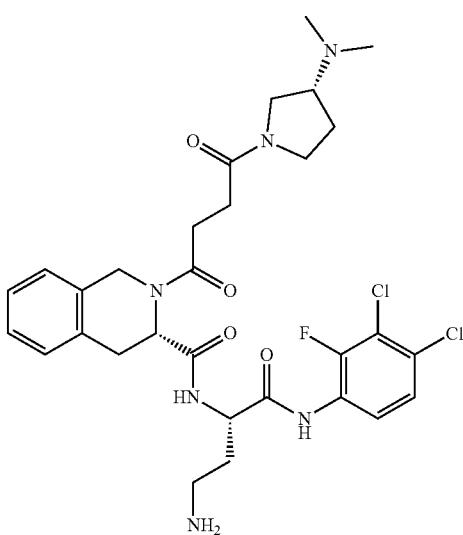 [SMILES: CN(C)[C@@H]1CCN(C(=O)CCC(=O)N2Cc3ccccc3C[C@H]2C(=O)N[C@@H](CCN)C(=O)Nc2ccc(Cl)c(Cl)c2F)C1] | 15-31 |

TABLE A-continued
| Structure | Cpd. No. |
|---|---|
| 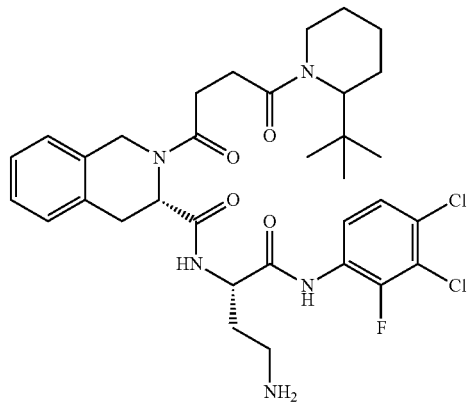 [SMILES: CC(C)(C)C1CCCCN1C(=O)CCC(=O)N1Cc2ccccc2C[C@H]1C(=O)N[C@@H](CCN)C(=O)Nc1ccc(Cl)c(Cl)c1F] | 15-32 |
| 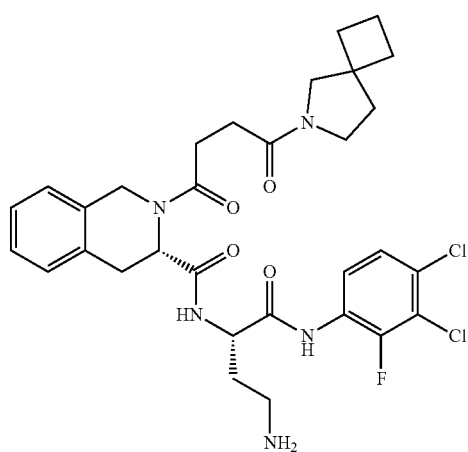 [SMILES: NCC[C@H](NC(=O)[C@@H]1Cc2ccccc2CN1C(=O)CCC(=O)N1CCC2(CCC2)C1)C(=O)Nc1ccc(Cl)c(Cl)c1F] | 15-33 |
| 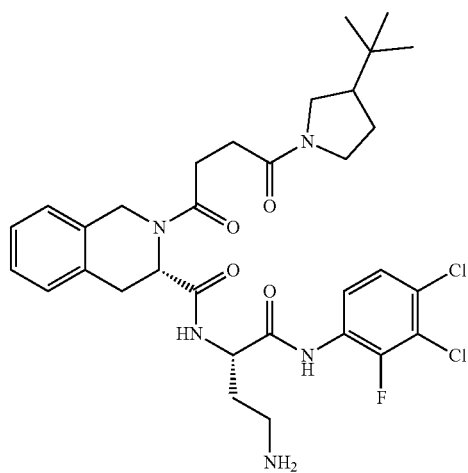 [SMILES: CC(C)(C)C1CCN(C(=O)CCC(=O)N2Cc3ccccc3C[C@H]2C(=O)N[C@@H](CCN)C(=O)Nc2ccc(Cl)c(Cl)c2F)C1] | 15-34 |

TABLE A-continued
| Structure | Cpd. No. |
|---|---|
| 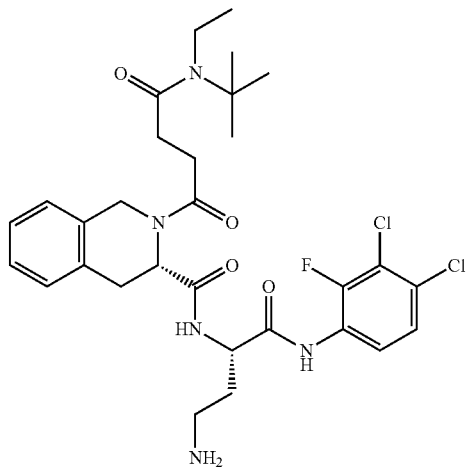 [SMILES: CCN(C(=O)CCC(=O)N1Cc2ccccc2C[C@H]1C(=O)N[C@@H](CCN)C(=O)Nc1ccc(Cl)c(Cl)c1F)C(C)(C)C] | 15-35 |
| 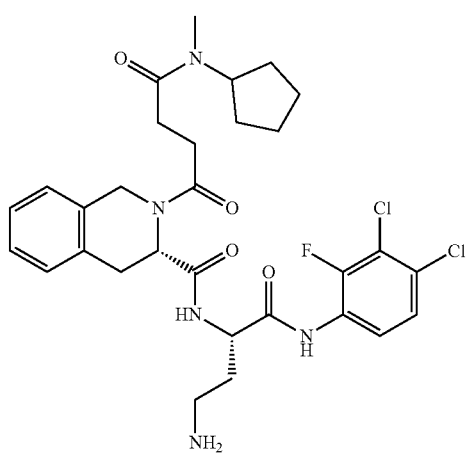 [SMILES: CN(C(=O)CCC(=O)N1Cc2ccccc2C[C@H]1C(=O)N[C@@H](CCN)C(=O)Nc1ccc(Cl)c(Cl)c1F)C1CCCC1] | 15-36 |
| 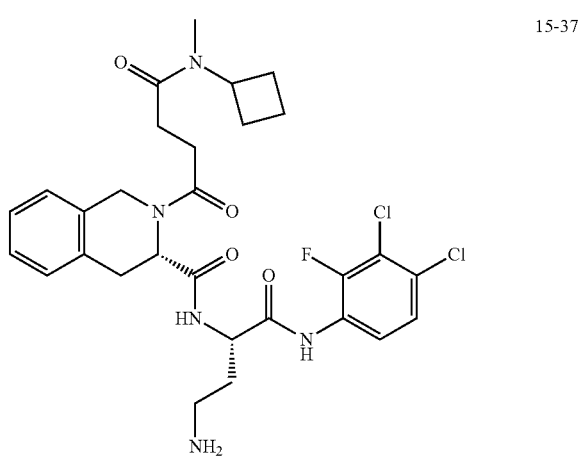 | 15-37 |

TABLE A-continued
| Structure | Cpd. No. |
|---|---|
| 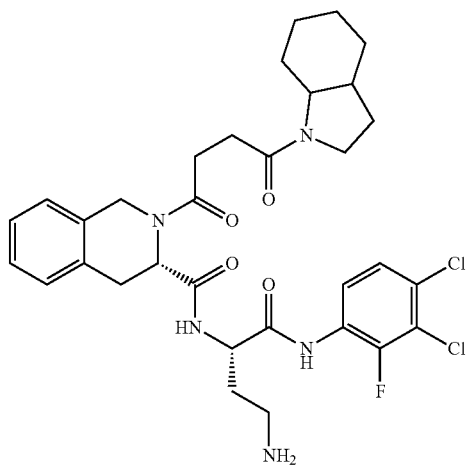 [SMILES: NCC[C@H](NC(=O)[C@@H]1Cc2ccccc2CN1C(=O)CCC(=O)N1CCC2CCCCC21)C(=O)Nc1ccc(Cl)c(Cl)c1F] | 15-38 |
| 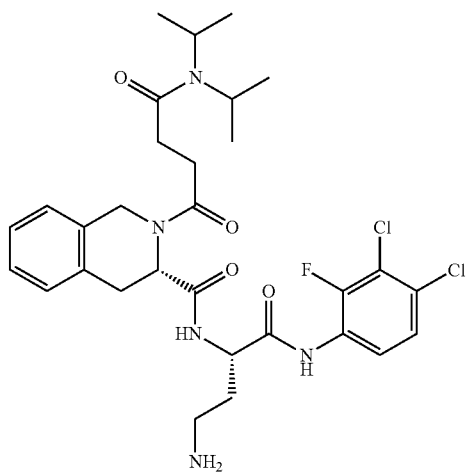 [SMILES: CC(C)N(C(=O)CCC(=O)N1Cc2ccccc2C[C@H]1C(=O)N[C@@H](CCN)C(=O)Nc1ccc(Cl)c(Cl)c1F)C(C)C] | 15-39 |
| 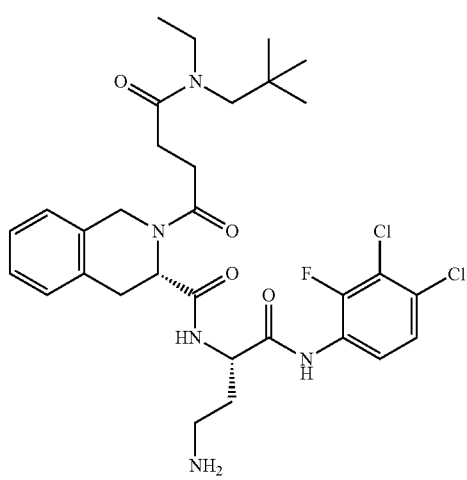 [SMILES: CCN(CC(C)(C)C)C(=O)CCC(=O)N1Cc2ccccc2C[C@H]1C(=O)N[C@@H](CCN)C(=O)Nc1ccc(Cl)c(Cl)c1F] | 15-40 |

TABLE A-continued
| Structure | Cpd. No. |
|---|---|
| 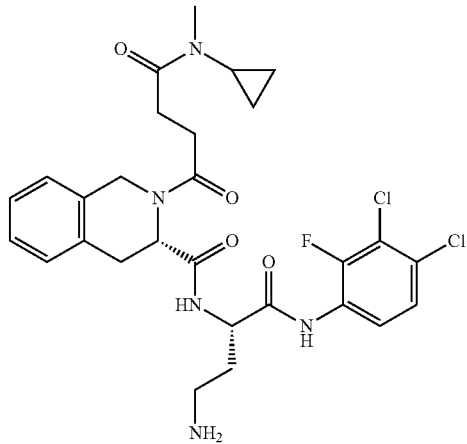 [SMILES: CN(C(=O)CCC(=O)N1Cc2ccccc2C[C@H]1C(=O)N[C@@H](CCN)C(=O)Nc1ccc(Cl)c(Cl)c1F)C1CC1] | 15-41 |
| 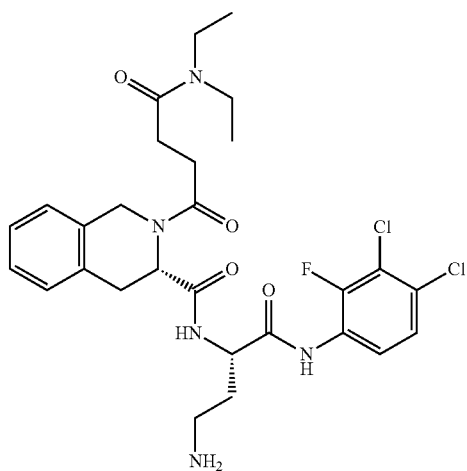 [SMILES: CCN(CC)C(=O)CCC(=O)N1Cc2ccccc2C[C@H]1C(=O)N[C@@H](CCN)C(=O)Nc1ccc(Cl)c(Cl)c1F] | 15-42 |
| 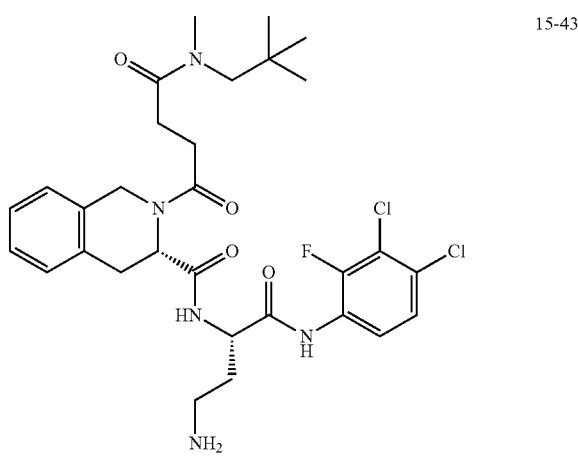 | 15-43 |

TABLE A-continued
| Structure | Cpd. No. |
|---|---|
| 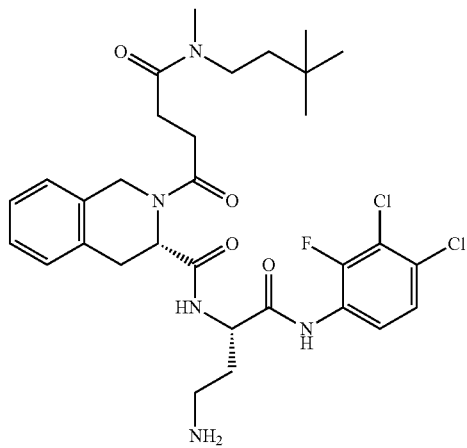 [SMILES: CN(CCC(C)(C)C)C(=O)CCC(=O)N1Cc2ccccc2C[C@H]1C(=O)N[C@@H](CCN)C(=O)Nc1ccc(Cl)c(Cl)c1F] | 15-44 |
| 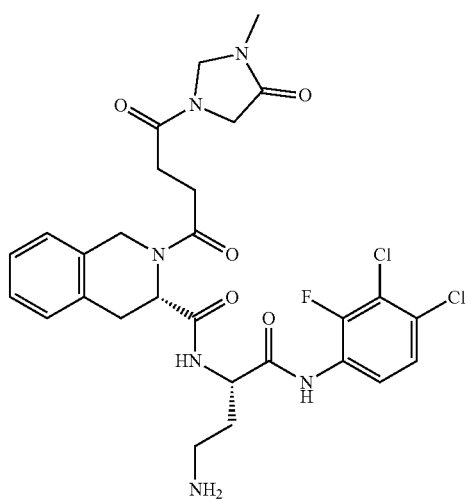 [SMILES: CN1CN(C(=O)CCC(=O)N2Cc3ccccc3C[C@H]2C(=O)N[C@@H](CCN)C(=O)Nc2ccc(Cl)c(Cl)c2F)CC1=O] | 15-45 |
| 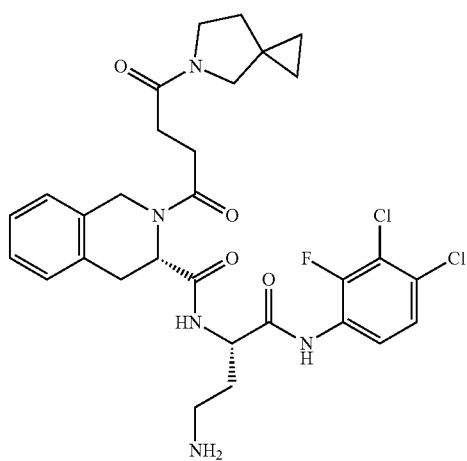 [SMILES: NCC[C@H](NC(=O)[C@@H]1Cc2ccccc2CN1C(=O)CCC(=O)N1CCC2(CC2)C1)C(=O)Nc1ccc(Cl)c(Cl)c1F] | 15-46 |

TABLE A-continued
| Structure | Cpd. No. |
|---|---|
| 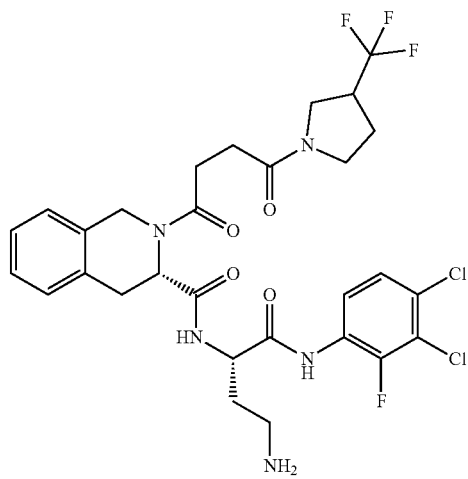 [SMILES: NCC[C@H](NC(=O)[C@@H]1Cc2ccccc2CN1C(=O)CCC(=O)N1CCC(C(F)(F)F)C1)C(=O)Nc1ccc(Cl)c(Cl)c1F] | 15-47 |
| 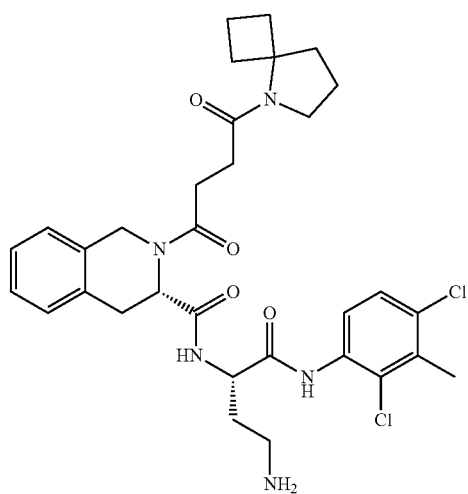 [SMILES: Cc1c(Cl)ccc(NC(=O)[C@H](CCN)NC(=O)[C@@H]2Cc3ccccc3CN2C(=O)CCC(=O)N2CCCC23CCC3)c1Cl] | 15-48 |
| 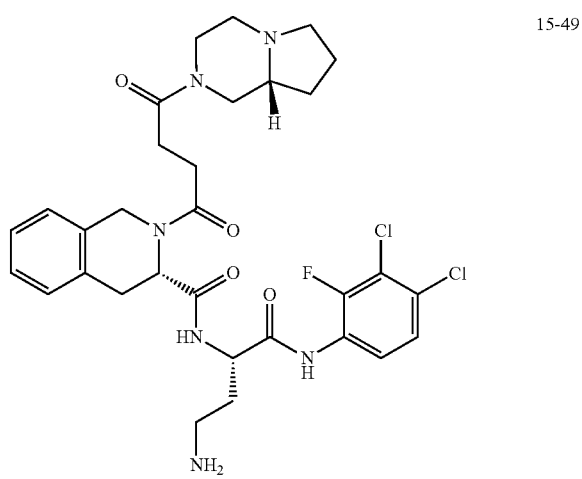 | 15-49 |

TABLE A-continued

| Structure | Cpd. No. |
|---|---|
| 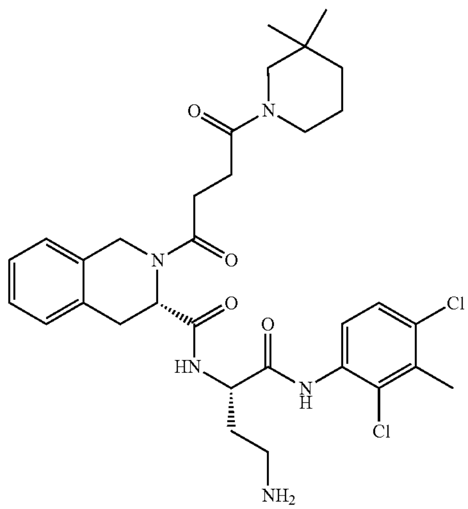 [SMILES: Cc1c(Cl)ccc(NC(=O)[C@H](CCN)NC(=O)[C@@H]2Cc3ccccc3CN2C(=O)CCC(=O)N2CCCC(C)(C)C2)c1Cl] | 15-50 |
| 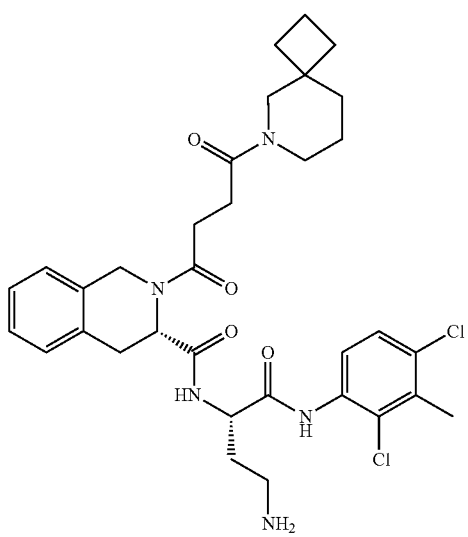 [SMILES: Cc1c(Cl)ccc(NC(=O)[C@H](CCN)NC(=O)[C@@H]2Cc3ccccc3CN2C(=O)CCC(=O)N2CCCC3(CCC3)C2)c1Cl] | 15-51 |
| 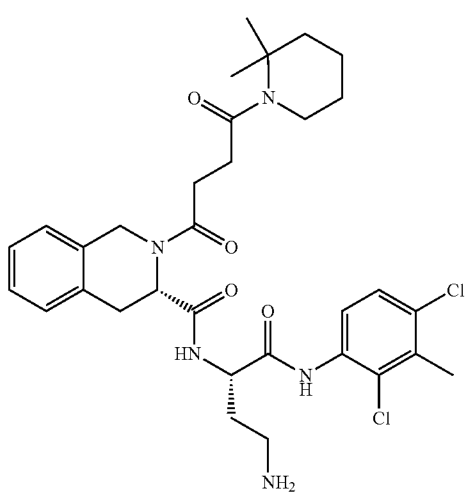 [SMILES: Cc1c(Cl)ccc(NC(=O)[C@H](CCN)NC(=O)[C@@H]2Cc3ccccc3CN2C(=O)CCC(=O)N2CCCCC2(C)C)c1Cl] | 15-52 |

TABLE A-continued
| Structure | Cpd. No. |
|---|---|
| 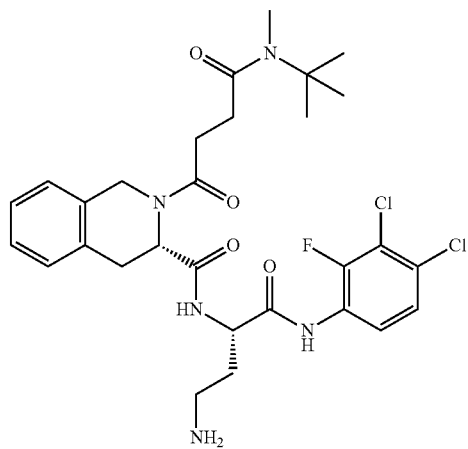 [SMILES: CN(C(=O)CCC(=O)N1Cc2ccccc2C[C@H]1C(=O)N[C@@H](CCN)C(=O)Nc1ccc(Cl)c(Cl)c1F)C(C)(C)C] | 15-53 |
| 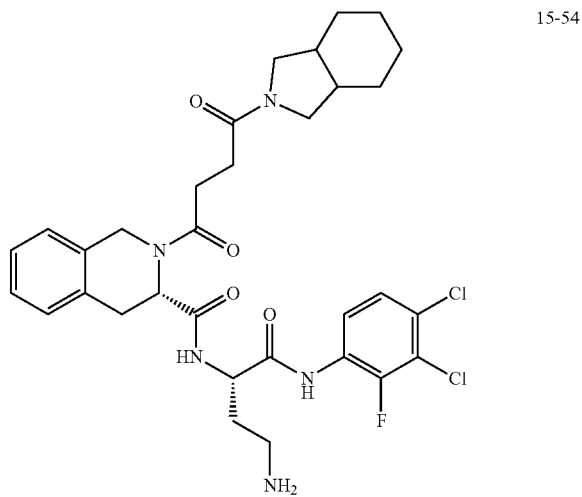 | 15-54 |
| 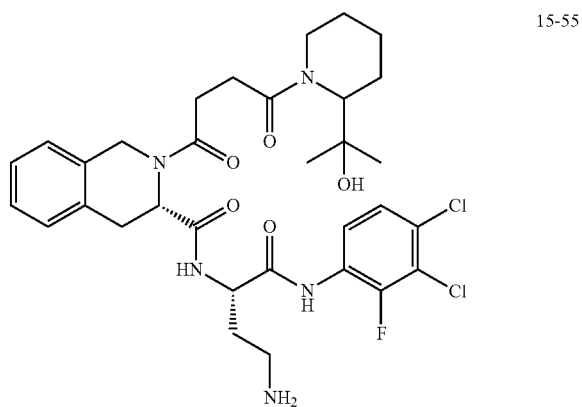 | 15-55 |

TABLE A-continued
| Structure | Cpd. No. |
|---|---|
| 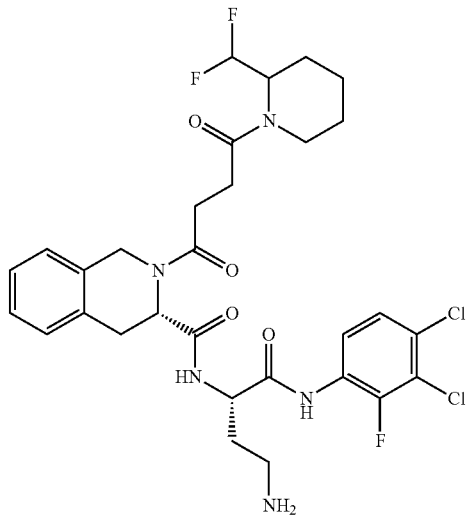 [SMILES: NCC[C@H](NC(=O)[C@@H]1Cc2ccccc2CN1C(=O)CCC(=O)N1CCCCC1C(F)F)C(=O)Nc1ccc(Cl)c(Cl)c1F] | 15-56 |
| 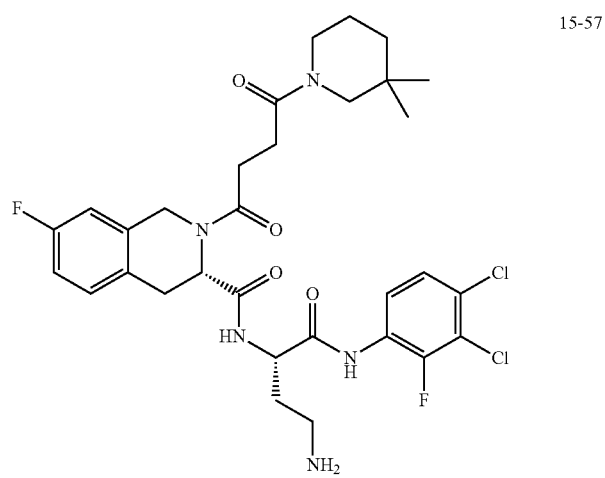 | 15-57 |
| 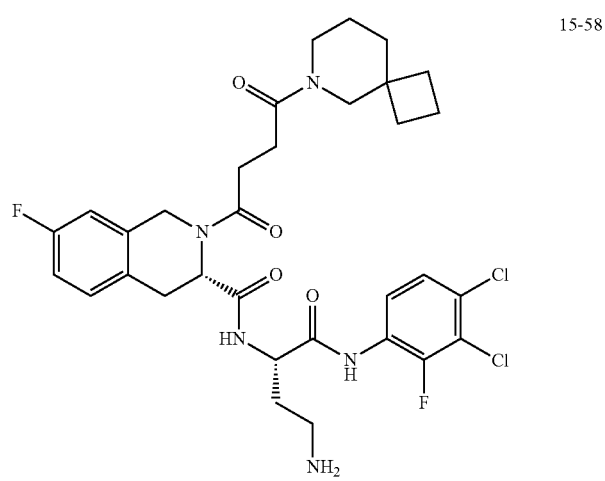 | 15-58 |

TABLE A-continued
| Structure | Cpd. No. |
|---|---|
| 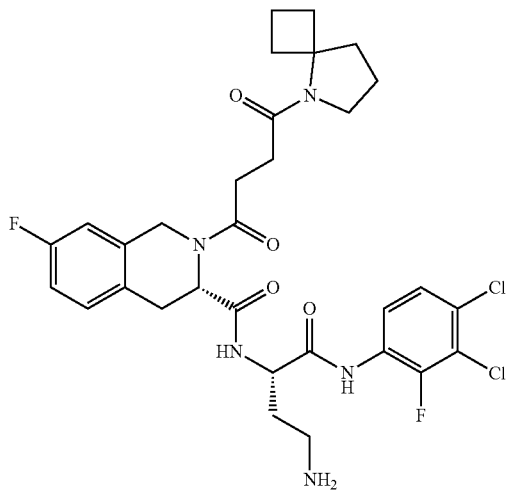 [SMILES: NCC[C@H](NC(=O)[C@@H]1Cc2ccc(F)cc2CN1C(=O)CCC(=O)N1CCCC12CCC2)C(=O)Nc1ccc(Cl)c(Cl)c1F] | 15-59 |
| 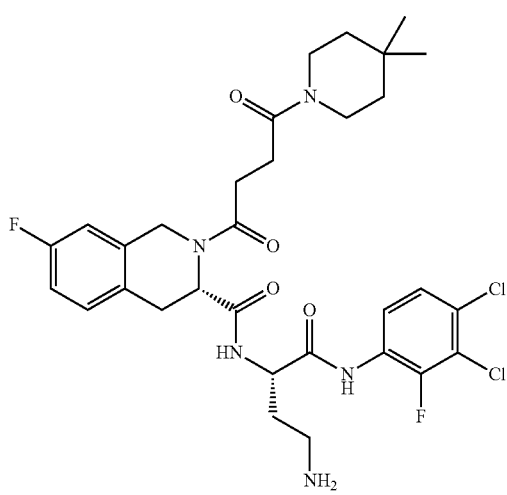 [SMILES: CC1(C)CCN(C(=O)CCC(=O)N2Cc3cc(F)ccc3C[C@H]2C(=O)N[C@@H](CCN)C(=O)Nc2ccc(Cl)c(Cl)c2F)CC1] | 15-60 |
| 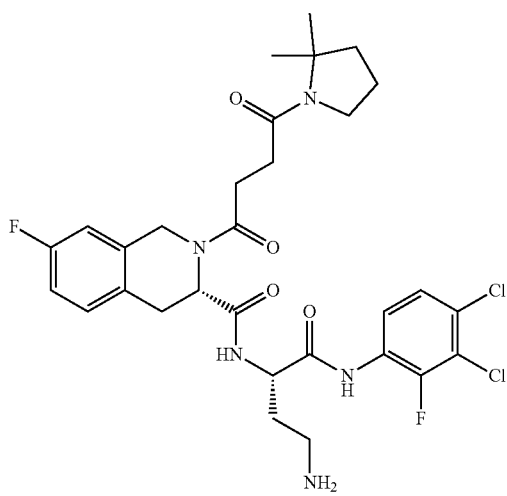 [SMILES: CC1(C)CCCN1C(=O)CCC(=O)N1Cc2cc(F)ccc2C[C@H]1C(=O)N[C@@H](CCN)C(=O)Nc1ccc(Cl)c(Cl)c1F] | 15-61 |

TABLE A-continued
| Structure | Cpd. No. |
|---|---|
| 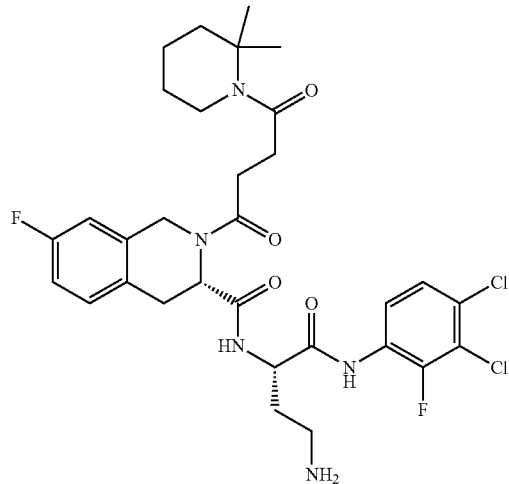 [SMILES: CC1(C)CCCCN1C(=O)CCC(=O)N1Cc2cc(F)ccc2C[C@H]1C(=O)N[C@@H](CCN)C(=O)Nc1ccc(Cl)c(Cl)c1F] | 15-62 |
| 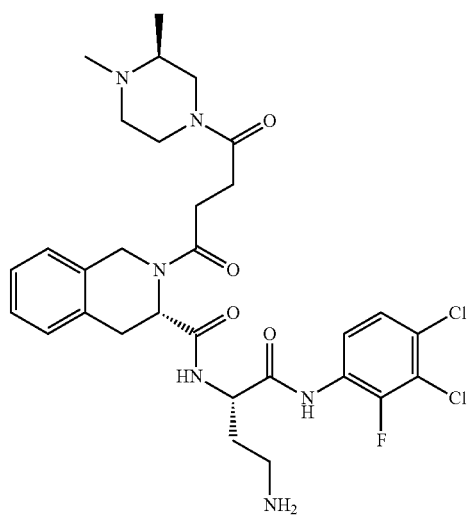 [SMILES: C[C@H]1CN(C(=O)CCC(=O)N2Cc3ccccc3C[C@H]2C(=O)N[C@@H](CCN)C(=O)Nc2ccc(Cl)c(Cl)c2F)CCN1C] | 15-63 |
| 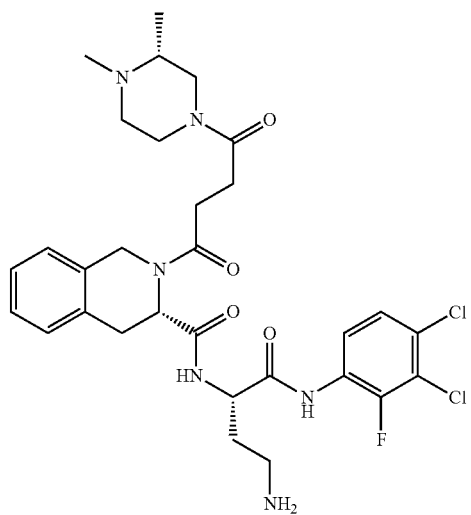 [SMILES: C[C@@H]1CN(C(=O)CCC(=O)N2Cc3ccccc3C[C@H]2C(=O)N[C@@H](CCN)C(=O)Nc2ccc(Cl)c(Cl)c2F)CCN1C] | 15-64 |

TABLE A-continued
| Structure | Cpd. No. |
|---|---|
| 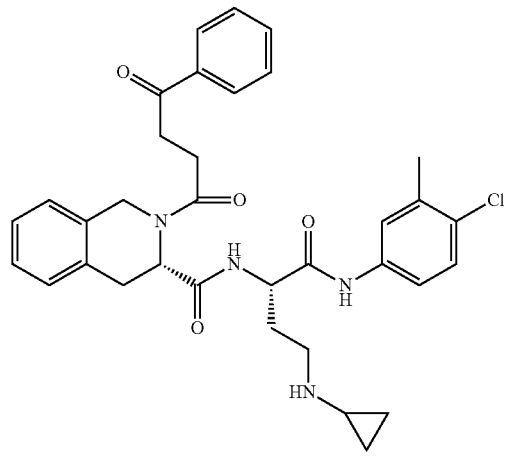 [SMILES: Cc1cc(NC(=O)[C@H](CCNC2CC2)NC(=O)[C@@H]2Cc3ccccc3CN2C(=O)CCC(=O)c2ccccc2)ccc1Cl] | 16-1 |
| 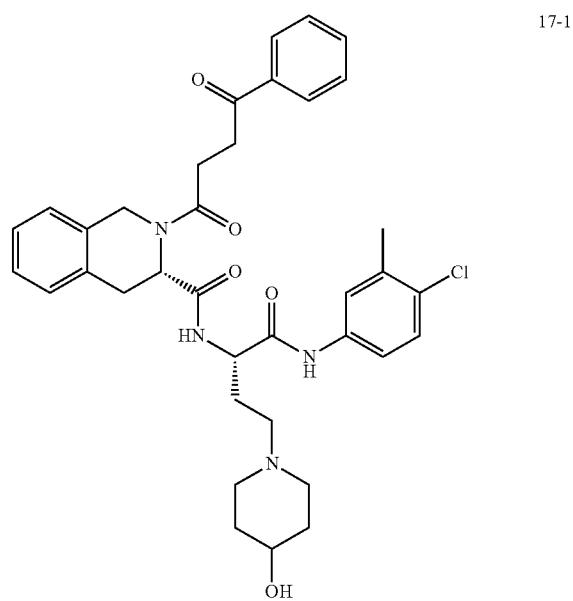 | 17-1 |

TABLE A-continued
| Structure | Cpd. No. |
|---|---|
| 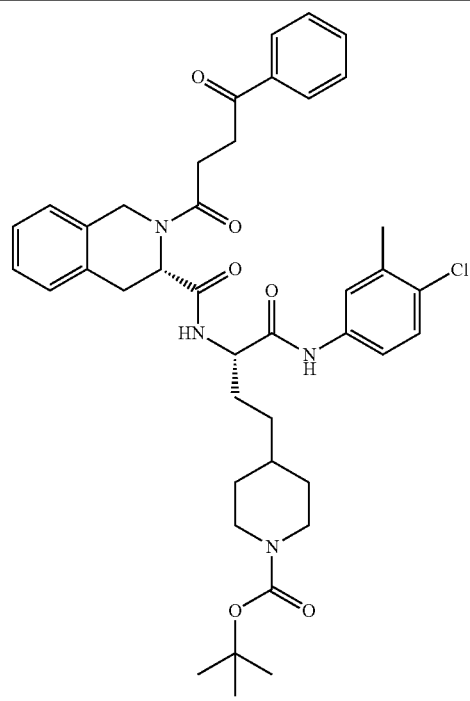 | 17-2 |
| 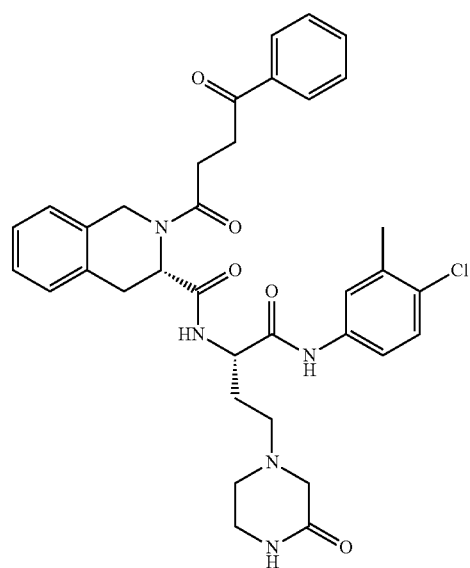 [SMILES: Cc1cc(NC(=O)[C@H](CCN2CCNC(=O)C2)NC(=O)[C@@H]2Cc3ccccc3CN2C(=O)CCC(=O)c2ccccc2)ccc1Cl] | 17-3 |

TABLE A-continued
| Structure | Cpd. No. |
|---|---|
| 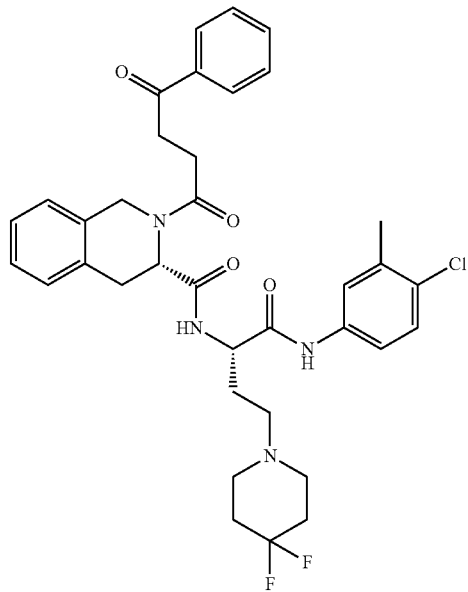 [SMILES: Cc1cc(NC(=O)[C@H](CCN2CCC(F)(F)CC2)NC(=O)[C@@H]2Cc3ccccc3CN2C(=O)CCC(=O)c2ccccc2)ccc1Cl] | 17-4 |
| 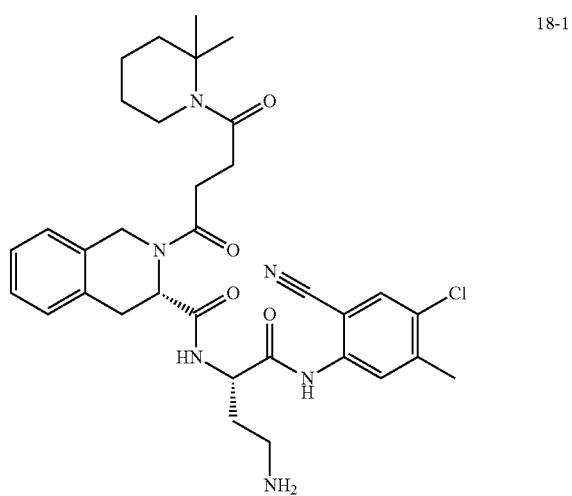 | 18-1 |

TABLE A-continued
| Structure | Cpd. No. |
|---|---|
| 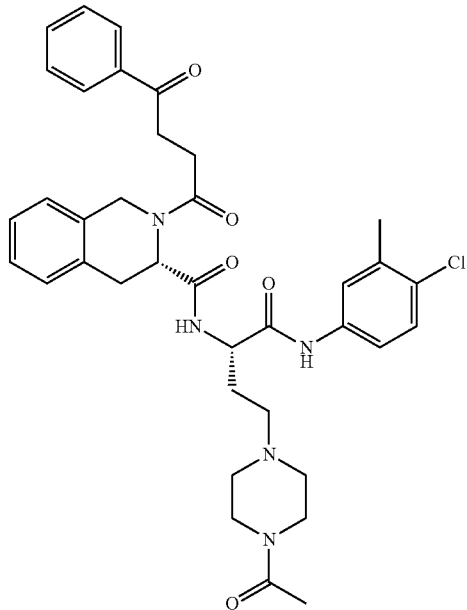 [SMILES: CC(=O)N1CCN(CC[C@H](NC(=O)[C@@H]2Cc3ccccc3CN2C(=O)CCC(=O)c2ccccc2)C(=O)Nc2ccc(Cl)c(C)c2)CC1] | 19-1 |
| 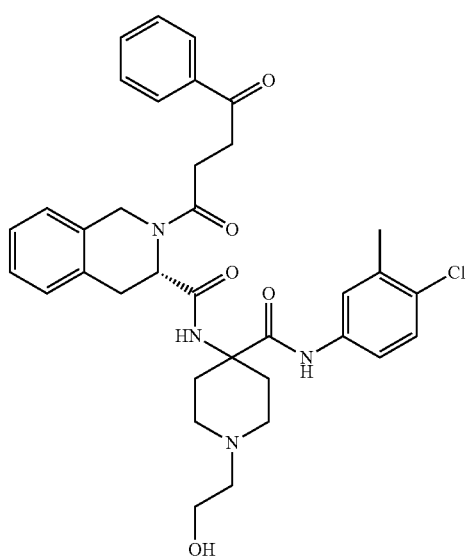 [SMILES: Cc1cc(NC(=O)C2(NC(=O)[C@@H]3Cc4ccccc4CN3C(=O)CCC(=O)c3ccccc3)CCN(CCO)CC2)ccc1Cl] | 20-1 |

TABLE A-continued

| Structure | Cpd. No. |
|---|---|
| 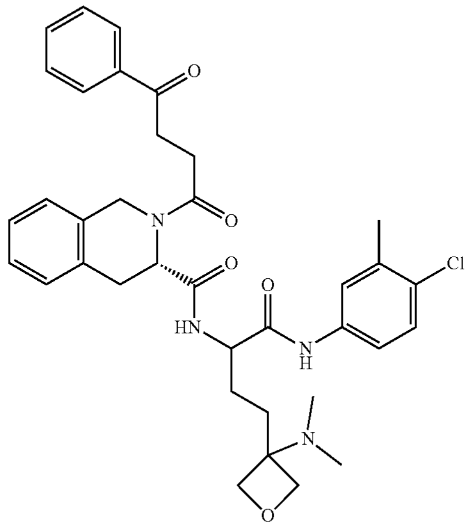 [SMILES: Cc1cc(NC(=O)C(CCC2(N(C)C)COC2)NC(=O)[C@@H]2Cc3ccccc3CN2C(=O)CCC(=O)c2ccccc2)ccc1Cl] | 21-1 |
| 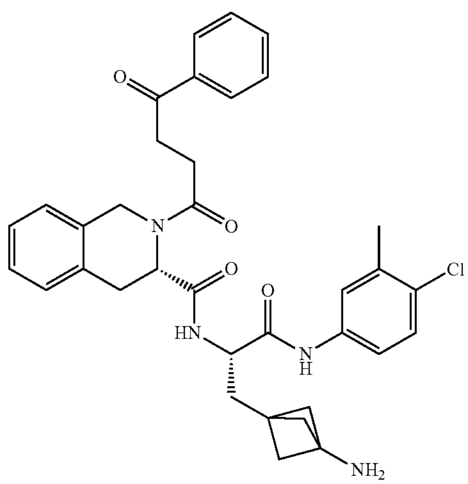 [SMILES: Cc1cc(NC(=O)[C@H](CC23CC(N)(C2)C3)NC(=O)[C@@H]2Cc3ccccc3CN2C(=O)CCC(=O)c2ccccc2)ccc1Cl] | 22-1 |
| 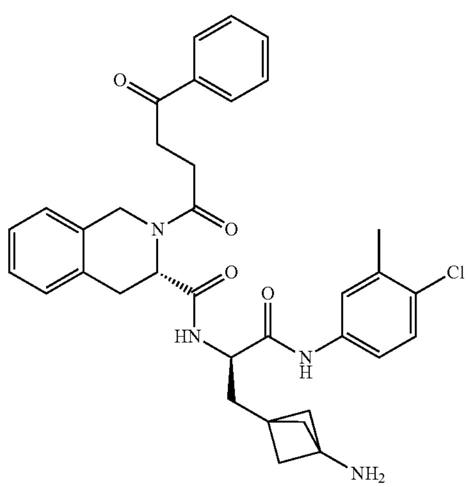 [SMILES: Cc1cc(NC(=O)[C@@H](CC23CC(N)(C2)C3)NC(=O)[C@@H]2Cc3ccccc3CN2C(=O)CCC(=O)c2ccccc2)ccc1Cl] | 22-2 |

TABLE A-continued
| Structure | Cpd. No. |
|---|---|
| 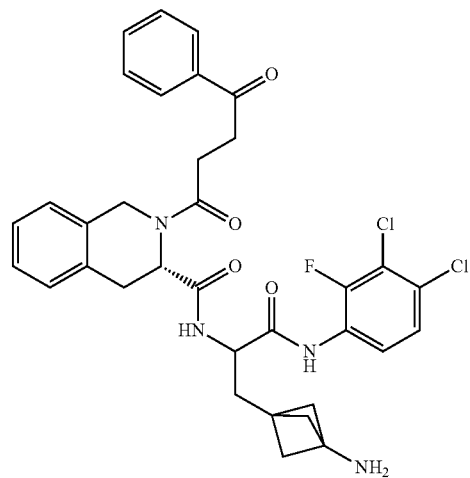 [SMILES: NC12CC(CC(NC(=O)[C@@H]3Cc4ccccc4CN3C(=O)CCC(=O)c3ccccc3)C(=O)Nc3ccc(Cl)c(Cl)c3F)(C1)C2] | 22-3 |
| 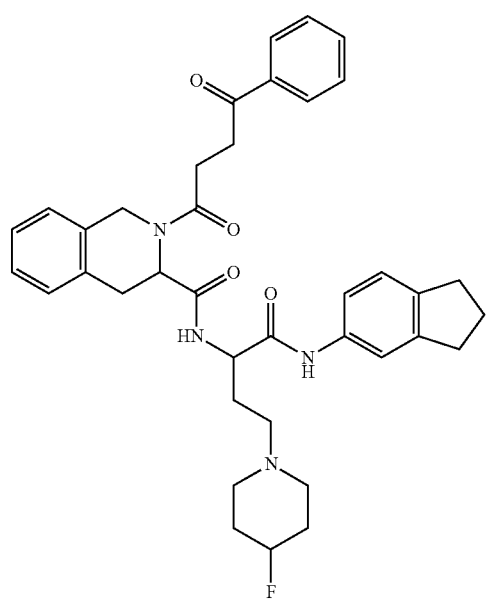 [SMILES: O=C(CCC(=O)N1Cc2ccccc2CC1C(=O)NC(CCN1CCC(F)CC1)C(=O)Nc1ccc2c(c1)CCC2)c1ccccc1] | 23-1 |

TABLE A-continued
| Structure | Cpd. No. |
|---|---|
| 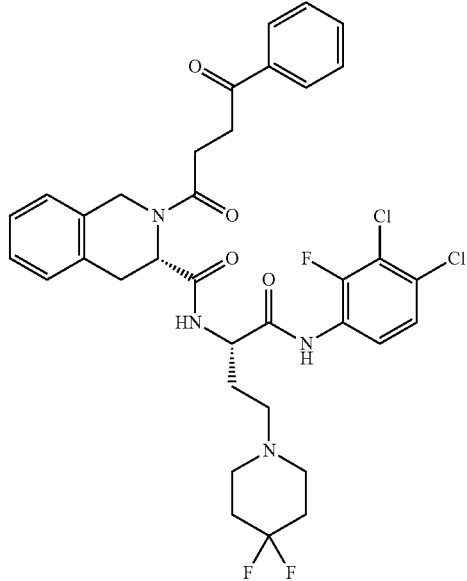 [SMILES: O=C(CCC(=O)N1Cc2ccccc2C[C@H]1C(=O)N[C@@H](CCN1CCC(F)(F)CC1)C(=O)Nc1ccc(Cl)c(Cl)c1F)c1ccccc1] | 23-2 |
| 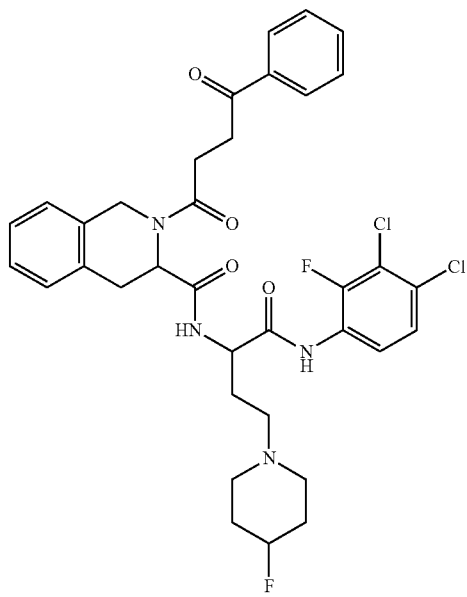 [SMILES: O=C(CCC(=O)N1Cc2ccccc2CC1C(=O)NC(CCN1CCC(F)CC1)C(=O)Nc1ccc(Cl)c(Cl)c1F)c1ccccc1] | 23-3 |

TABLE A-continued
| Structure | Cpd. No. |
|---|---|
| 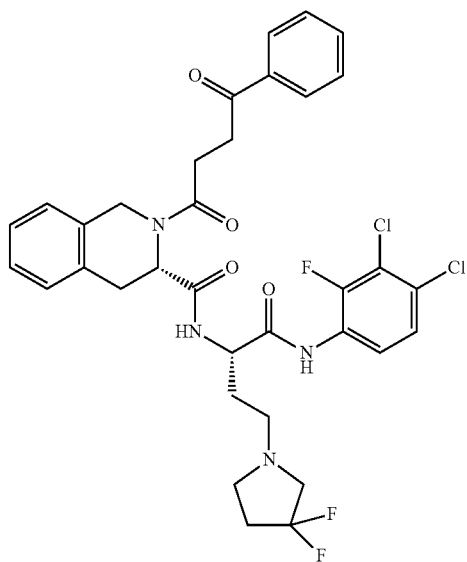 [SMILES: O=C(CCC(=O)N1Cc2ccccc2C[C@H]1C(=O)N[C@@H](CCN1CCC(F)(F)C1)C(=O)Nc1ccc(Cl)c(Cl)c1F)c1ccccc1] | 23-4 |
| 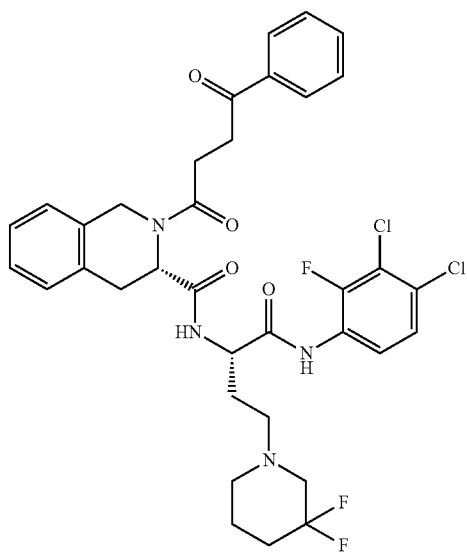 [SMILES: O=C(CCC(=O)N1Cc2ccccc2C[C@H]1C(=O)N[C@@H](CCN1CCCC(F)(F)C1)C(=O)Nc1ccc(Cl)c(Cl)c1F)c1ccccc1] | 23-5 |
| 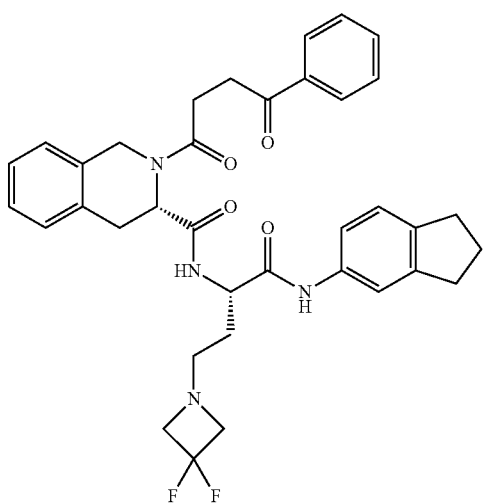 [SMILES: O=C(CCC(=O)N1Cc2ccccc2C[C@H]1C(=O)N[C@@H](CCN1CC(F)(F)C1)C(=O)Nc1ccc2c(c1)CCC2)c1ccccc1] | 23-6 |

TABLE A-continued
| Structure | Cpd. No. |
|---|---|
| 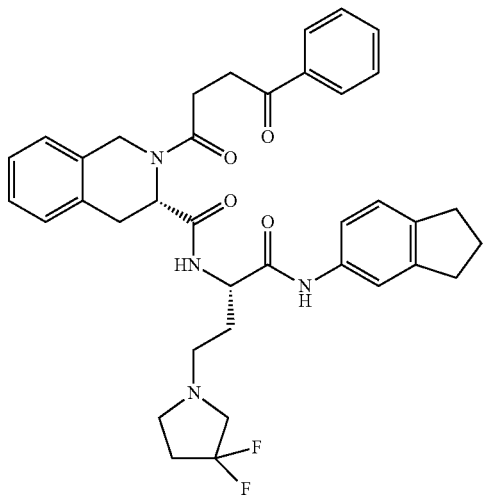 [SMILES: O=C(CCC(=O)N1Cc2ccccc2C[C@H]1C(=O)N[C@@H](CCN1CCC(F)(F)C1)C(=O)Nc1ccc2c(c1)CCC2)c1ccccc1] | 23-7 |
| 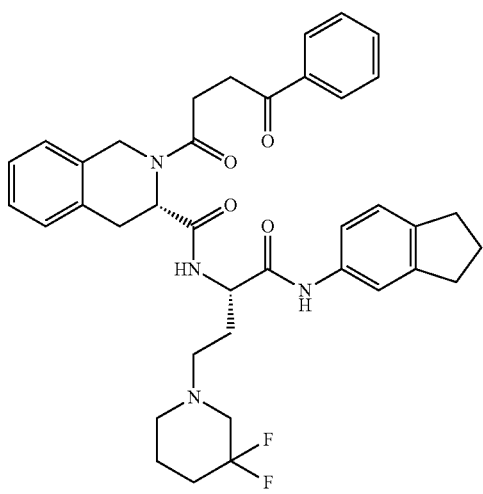 [SMILES: O=C(CCC(=O)N1Cc2ccccc2C[C@H]1C(=O)N[C@@H](CCN1CCCC(F)(F)C1)C(=O)Nc1ccc2c(c1)CCC2)c1ccccc1] | 23-8 |
| 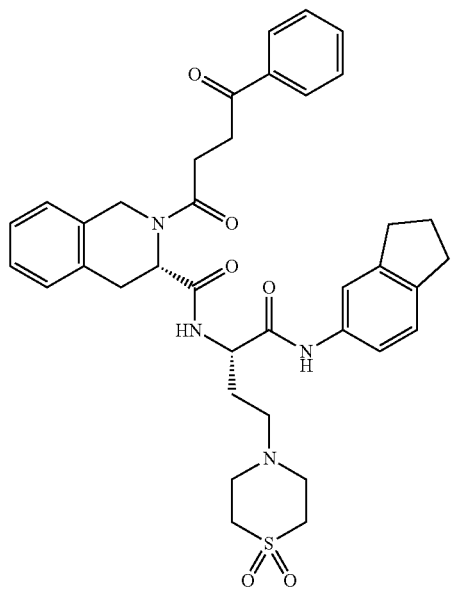 [SMILES: O=C(CCC(=O)N1Cc2ccccc2C[C@H]1C(=O)N[C@@H](CCN1CCS(=O)(=O)CC1)C(=O)Nc1ccc2c(c1)CCC2)c1ccccc1] | 23-9 |

TABLE A-continued
| Structure | Cpd. No. |
|---|---|
| 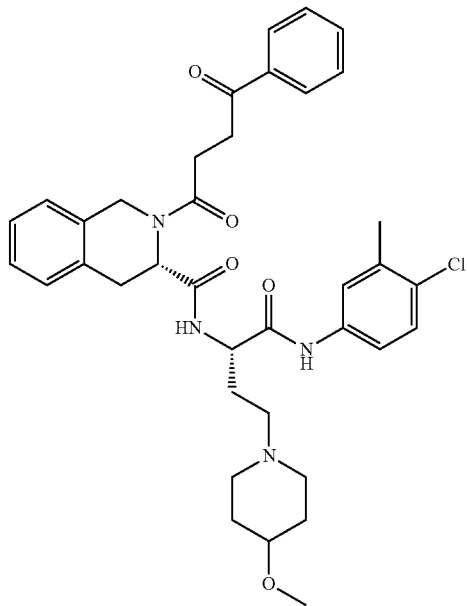 [SMILES: COC1CCN(CC[C@H](NC(=O)[C@@H]2Cc3ccccc3CN2C(=O)CCC(=O)c2ccccc2)C(=O)Nc2ccc(Cl)c(C)c2)CC1] | 24-1 |
| 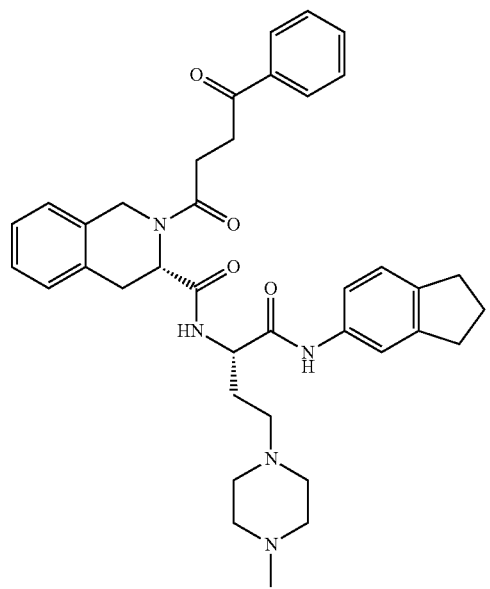 [SMILES: CN1CCN(CC[C@H](NC(=O)[C@@H]2Cc3ccccc3CN2C(=O)CCC(=O)c2ccccc2)C(=O)Nc2ccc3c(c2)CCC3)CC1] | 24-2 |

TABLE A-continued
| Structure | Cpd. No. |
|---|---|
| 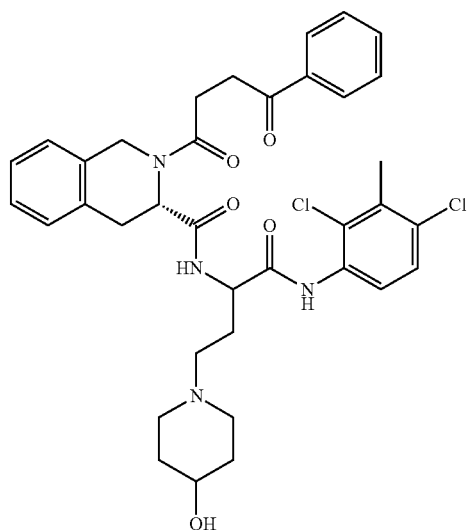 [SMILES: Cc1c(Cl)ccc(NC(=O)C(CCN2CCC(O)CC2)NC(=O)[C@@H]2Cc3ccccc3CN2C(=O)CCC(=O)c2ccccc2)c1Cl] | 25-1 |
| 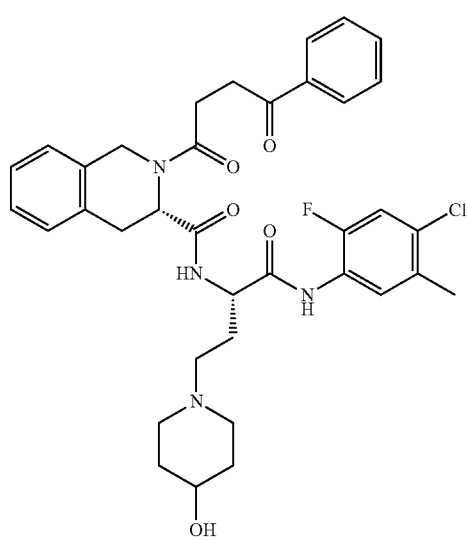 [SMILES: Cc1cc(NC(=O)[C@H](CCN2CCC(O)CC2)NC(=O)[C@@H]2Cc3ccccc3CN2C(=O)CCC(=O)c2ccccc2)c(F)cc1Cl] | 25-2 |
| 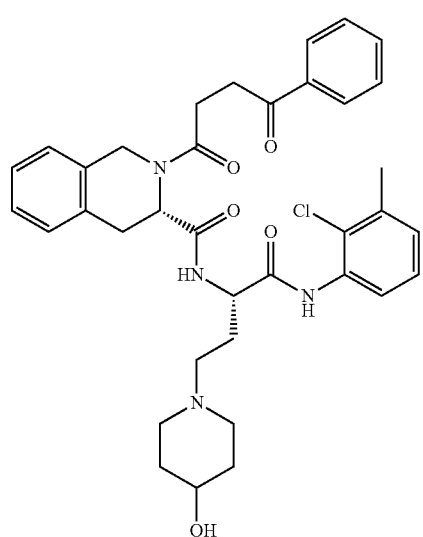 [SMILES: Cc1cccc(NC(=O)[C@H](CCN2CCC(O)CC2)NC(=O)[C@@H]2Cc3ccccc3CN2C(=O)CCC(=O)c2ccccc2)c1Cl] | 25-3 |

TABLE A-continued
| Structure | Cpd. No. |
|---|---|
| 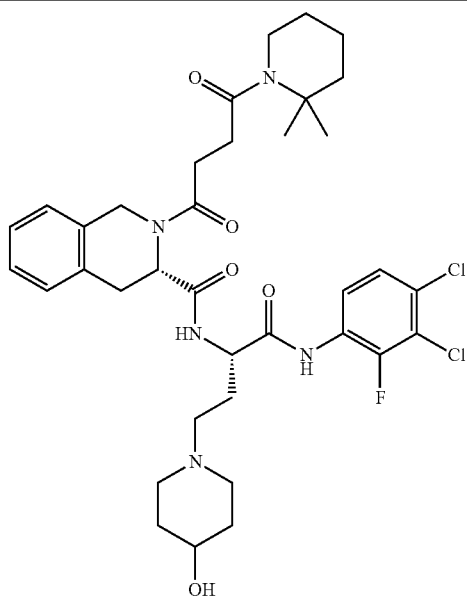 | 26-1 |
| 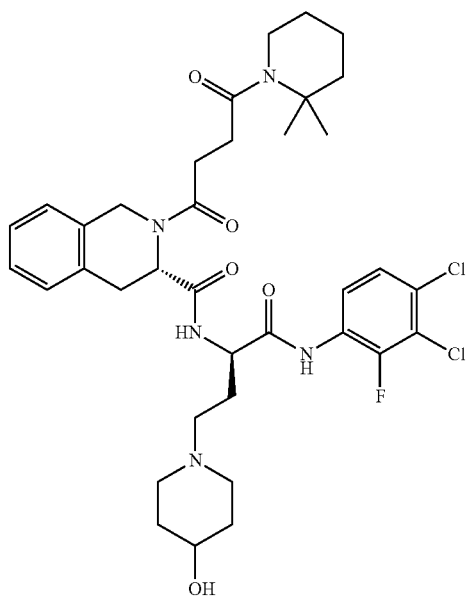 [SMILES: CC1(C)CCCCN1C(=O)CCC(=O)N1Cc2ccccc2C[C@H]1C(=O)N[C@H](CCN1CCC(O)CC1)C(=O)Nc1ccc(Cl)c(Cl)c1F] | 26-2 |

TABLE A-continued
| Structure | Cpd. No. |
|---|---|
| 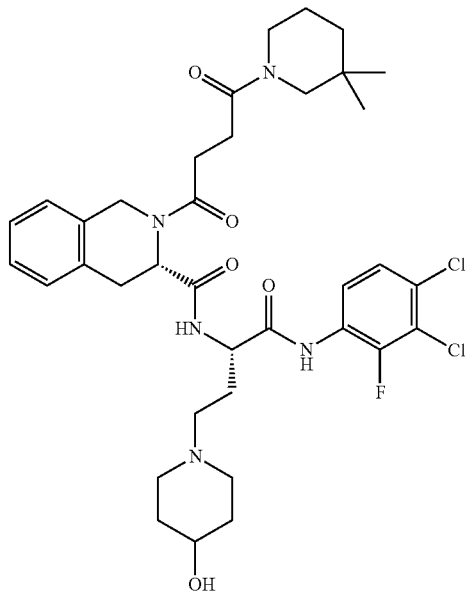 [SMILES: CC1(C)CCCN(C(=O)CCC(=O)N2Cc3ccccc3C[C@H]2C(=O)N[C@@H](CCN2CCC(O)CC2)C(=O)Nc2ccc(Cl)c(Cl)c2F)C1] | 26-3 |
| 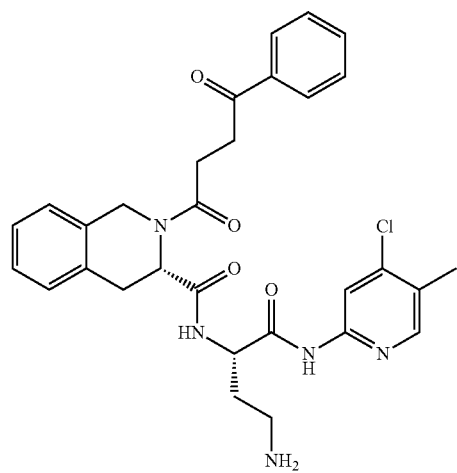 [SMILES: Cc1cnc(NC(=O)[C@H](CCN)NC(=O)[C@@H]2Cc3ccccc3CN2C(=O)CCC(=O)c2ccccc2)cc1Cl] | 27-1 |
| 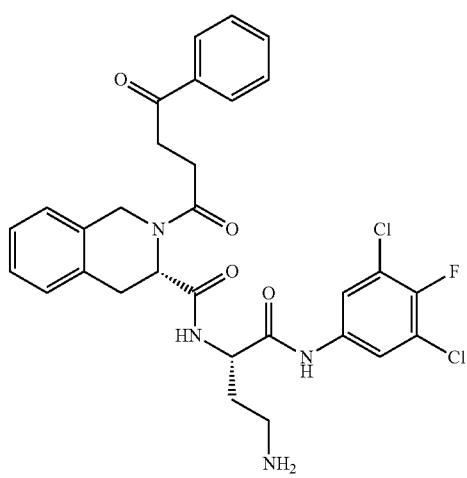 | 27-2 |

TABLE A-continued
| Structure | Cpd. No. |
|---|---|
| 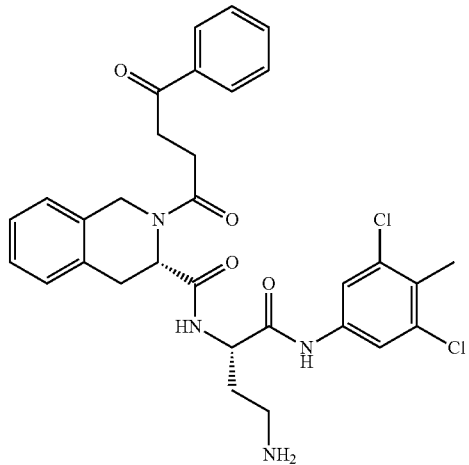 [SMILES: Cc1c(Cl)cc(NC(=O)[C@H](CCN)NC(=O)[C@@H]2Cc3ccccc3CN2C(=O)CCC(=O)c2ccccc2)cc1Cl] | 27-3 |
| 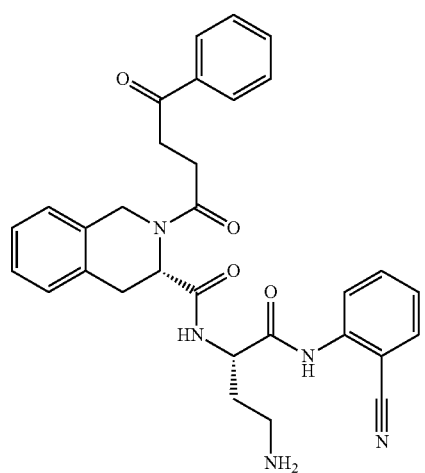 [SMILES: N#Cc1ccccc1NC(=O)[C@H](CCN)NC(=O)[C@@H]1Cc2ccccc2CN1C(=O)CCC(=O)c1ccccc1] | 27-4 |
| 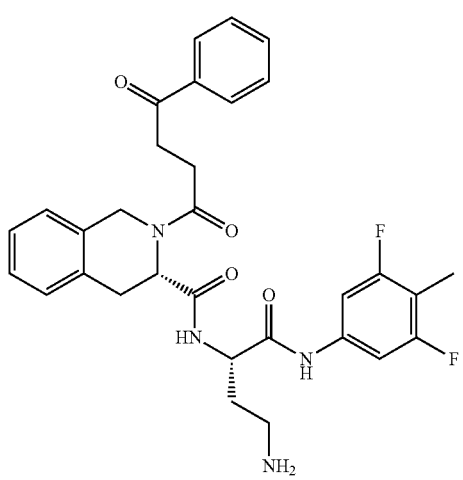 [SMILES: Cc1c(F)cc(NC(=O)[C@H](CCN)NC(=O)[C@@H]2Cc3ccccc3CN2C(=O)CCC(=O)c2ccccc2)cc1F] | 27-5 |

TABLE A-continued
| Structure | Cpd. No. |
|---|---|
| 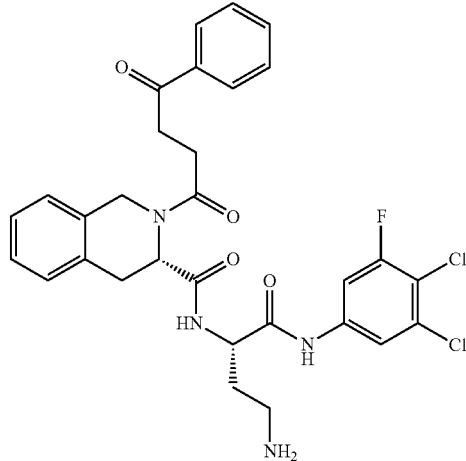 | 27-6 |
| 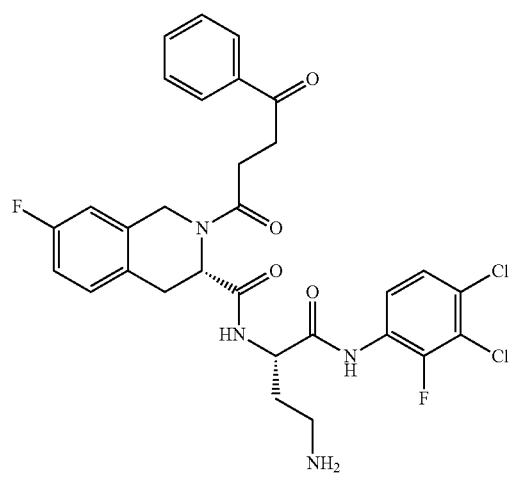 [SMILES: NCC[C@H](NC(=O)[C@@H]1Cc2ccc(F)cc2CN1C(=O)CCC(=O)c1ccccc1)C(=O)Nc1ccc(Cl)c(Cl)c1F] | 27-7 |
| 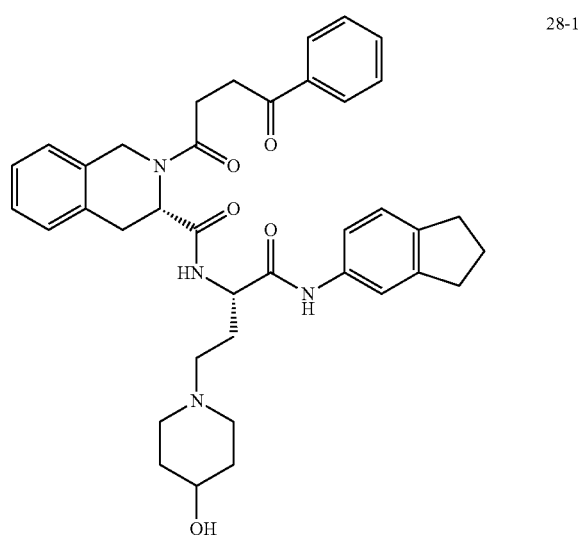 | 28-1 |

TABLE A-continued

| Structure | Cpd. No. |
|---|---|
| 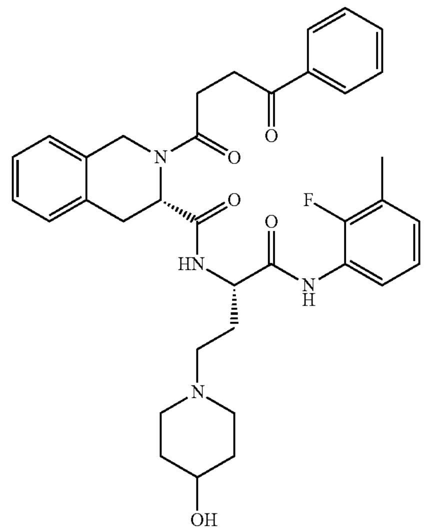 [SMILES: Cc1cccc(NC(=O)[C@H](CCN2CCC(O)CC2)NC(=O)[C@@H]2Cc3ccccc3CN2C(=O)CCC(=O)c2ccccc2)c1F] | 28-2 |
| 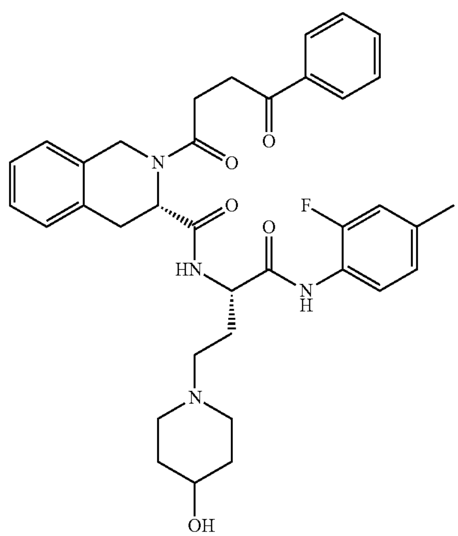 [SMILES: Cc1ccc(NC(=O)[C@H](CCN2CCC(O)CC2)NC(=O)[C@@H]2Cc3ccccc3CN2C(=O)CCC(=O)c2ccccc2)c(F)c1] | 28-3 |
| 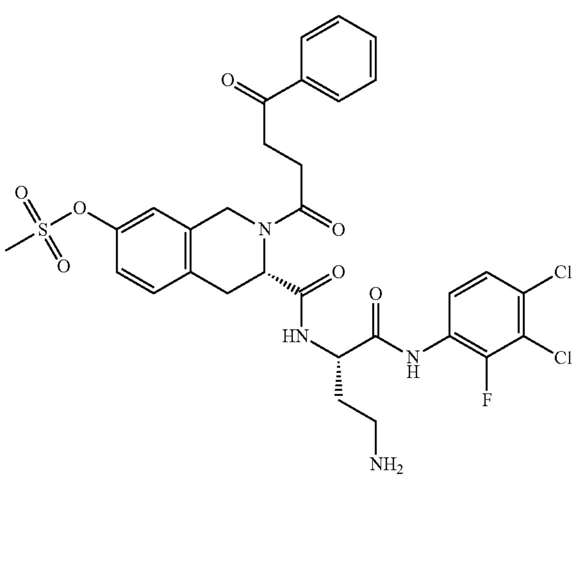 [SMILES: CS(=O)(=O)Oc1ccc2c(c1)CN(C(=O)CCC(=O)c1ccccc1)[C@H](C(=O)N[C@@H](CCN)C(=O)Nc1ccc(Cl)c(Cl)c1F)C2] | 29-1 |

TABLE A-continued
| Structure | Cpd. No. |
|---|---|
| 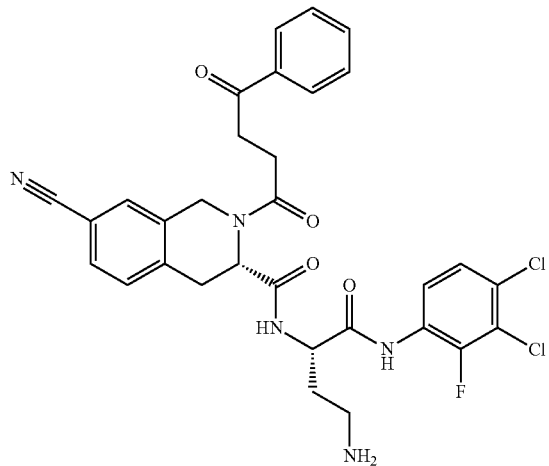 [SMILES: N#Cc1ccc2c(c1)CN(C(=O)CCC(=O)c1ccccc1)[C@H](C(=O)N[C@@H](CCN)C(=O)Nc1ccc(Cl)c(Cl)c1F)C2] | 30-1 |
| 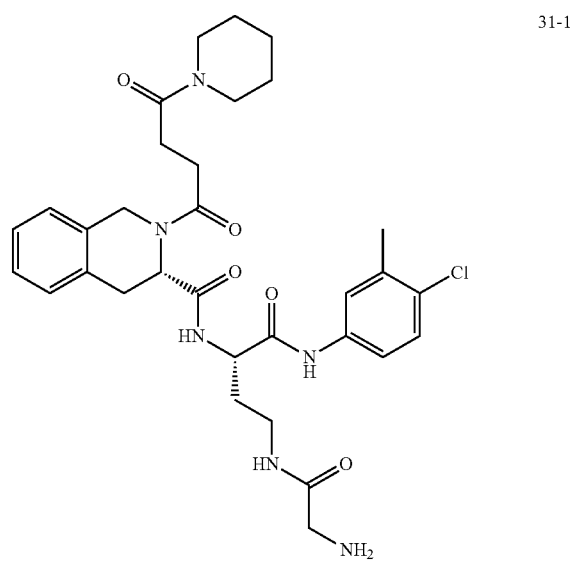 | 31-1 |
| 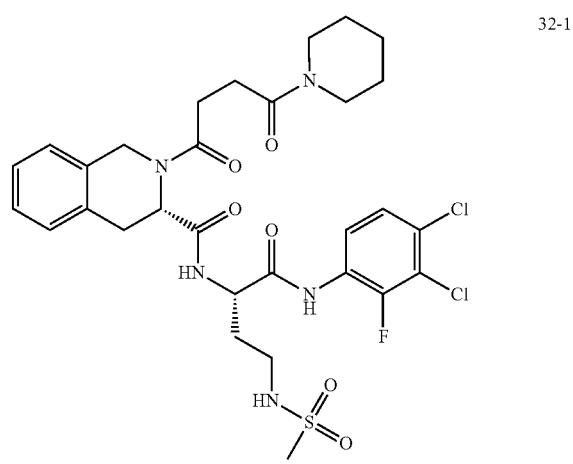 | 32-1 |

TABLE A-continued
| Structure | Cpd. No. |
|---|---|
| 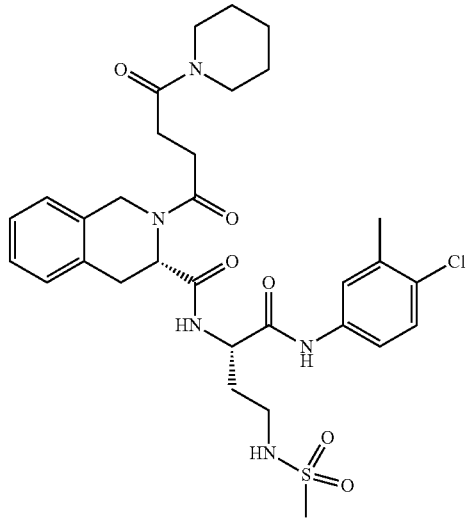 [SMILES: Cc1cc(NC(=O)[C@H](CCNS(C)(=O)=O)NC(=O)[C@@H]2Cc3ccccc3CN2C(=O)CCC(=O)N2CCCCC2)ccc1Cl] | 32-2 |
| 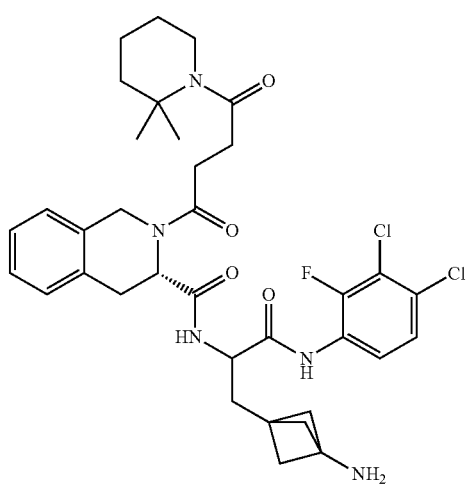 [SMILES: CC1(C)CCCCN1C(=O)CCC(=O)N1Cc2ccccc2C[C@H]1C(=O)NC(CC12CC(N)(C1)C2)C(=O)Nc1ccc(Cl)c(Cl)c1F] | 33-1 |
| 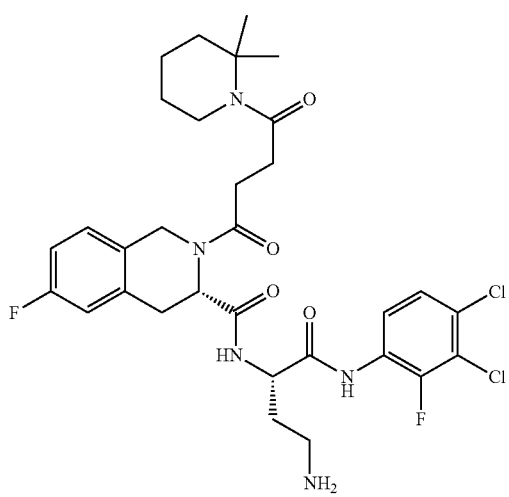 [SMILES: CC1(C)CCCCN1C(=O)CCC(=O)N1Cc2ccc(F)cc2C[C@H]1C(=O)N[C@@H](CCN)C(=O)Nc1ccc(Cl)c(Cl)c1F] | 34-1 |

TABLE A-continued

| Structure | Cpd. No. |
|---|---|
| 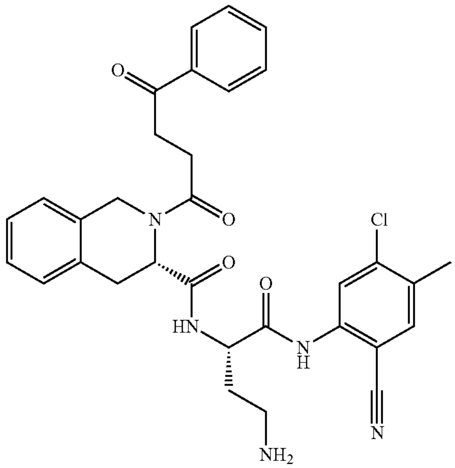 [SMILES: Cc1cc(C#N)c(NC(=O)[C@H](CCN)NC(=O)[C@@H]2Cc3ccccc3CN2C(=O)CCC(=O)c2ccccc2)cc1Cl] | 35-2 |
| 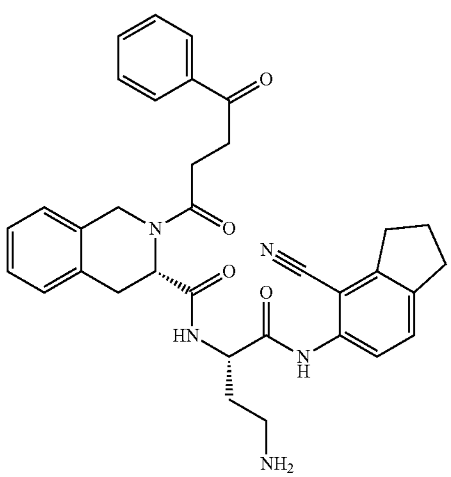 [SMILES: N#Cc1c(NC(=O)[C@H](CCN)NC(=O)[C@@H]2Cc3ccccc3CN2C(=O)CCC(=O)c2ccccc2)ccc2c1CCC2] | 35-1. |

31. The compound of claim 1, wherein the compound is a compound of Table B:

TABLE B

| Structure | Cpd. No. |
|---|---|
| | 1-14 |
| | 1-18 |
| 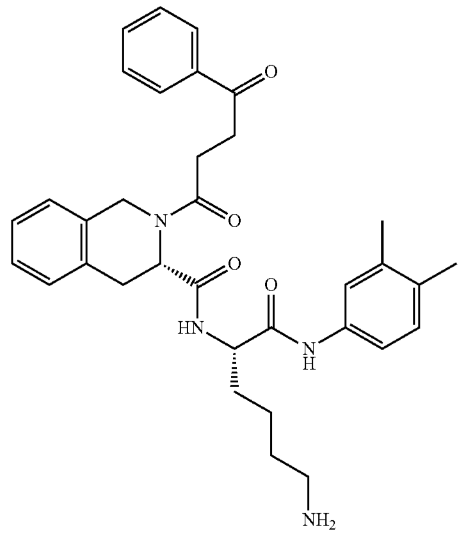 [SMILES: Cc1ccc(NC(=O)[C@H](CCCCN)NC(=O)[C@@H]2Cc3ccccc3CN2C(=O)CCC(=O)c2ccccc2)cc1C] | 1-29 |
| 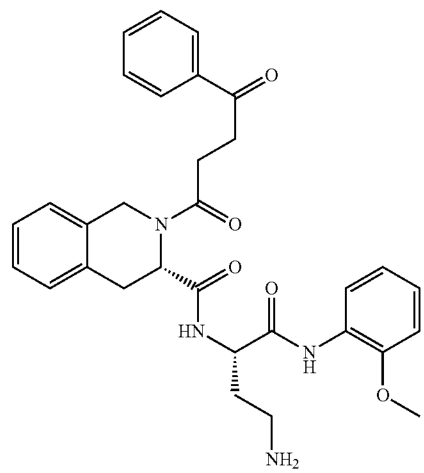 [SMILES: COc1ccccc1NC(=O)[C@H](CCN)NC(=O)[C@@H]1Cc2ccccc2CN1C(=O)CCC(=O)c1ccccc1] | 1-35 |
| 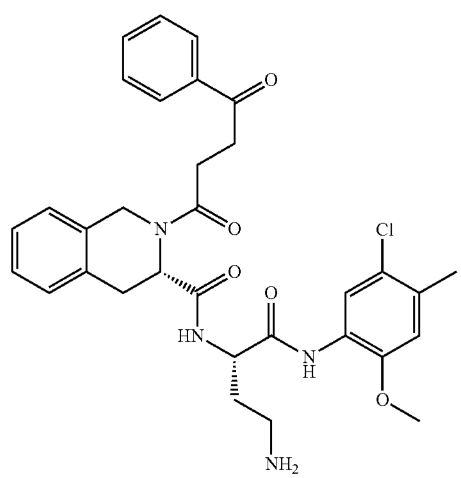 | 1-36 |

TABLE B-continued
| Structure | Cpd. No. |
|---|---|
| 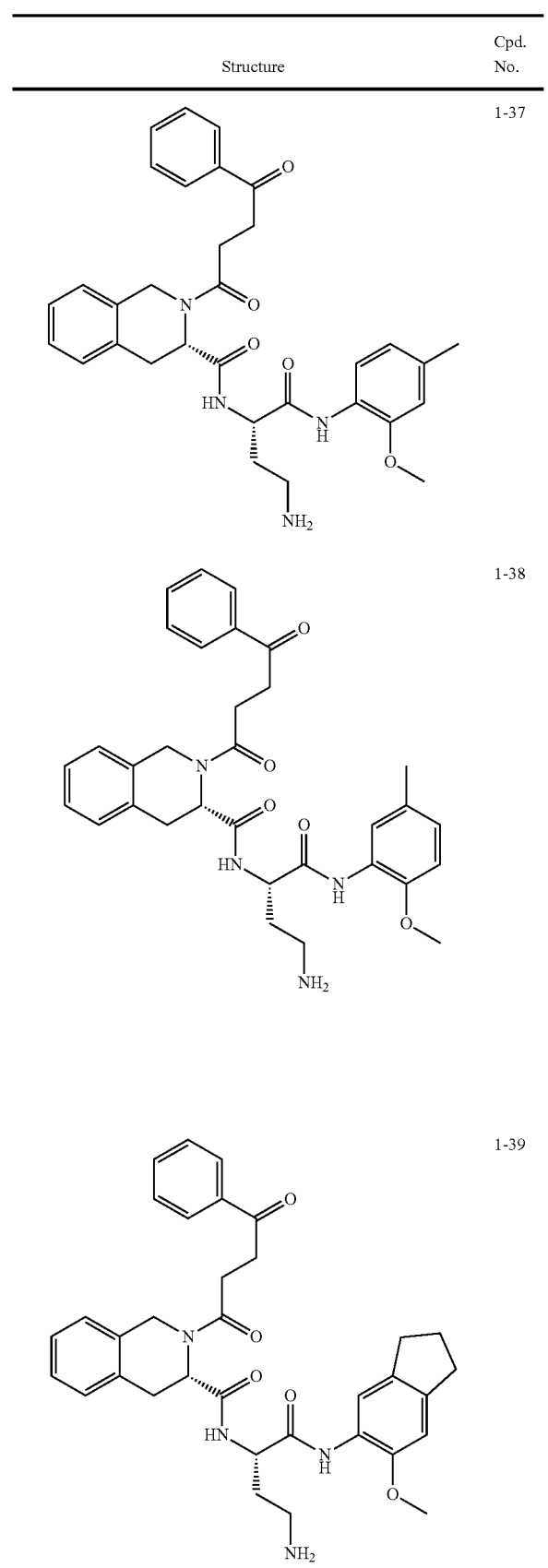 | 1-37 |
| 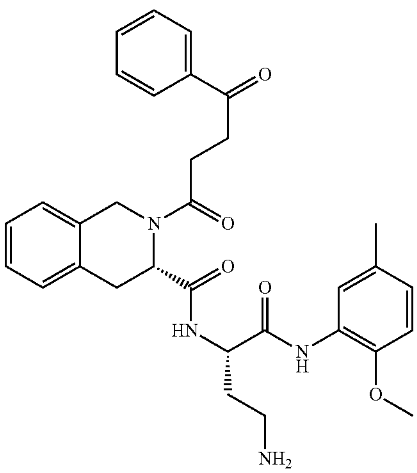 [SMILES: COc1ccc(C)cc1NC(=O)[C@H](CCN)NC(=O)[C@@H]1Cc2ccccc2CN1C(=O)CCC(=O)c1ccccc1] | 1-38 |
| 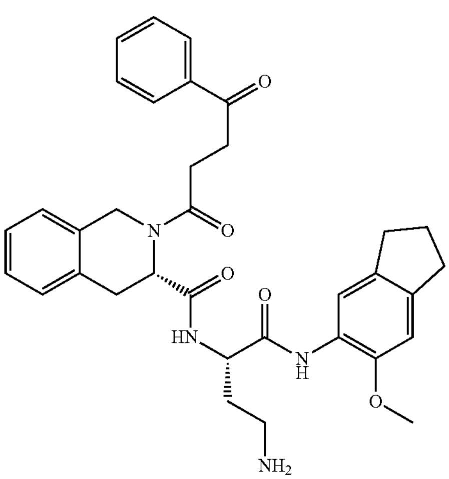 [SMILES: COc1cc2c(cc1NC(=O)[C@H](CCN)NC(=O)[C@@H]1Cc3ccccc3CN1C(=O)CCC(=O)c1ccccc1)CCC2] | 1-39 |
TABLE B-continued
| Structure | Cpd. No. |
|---|---|
| 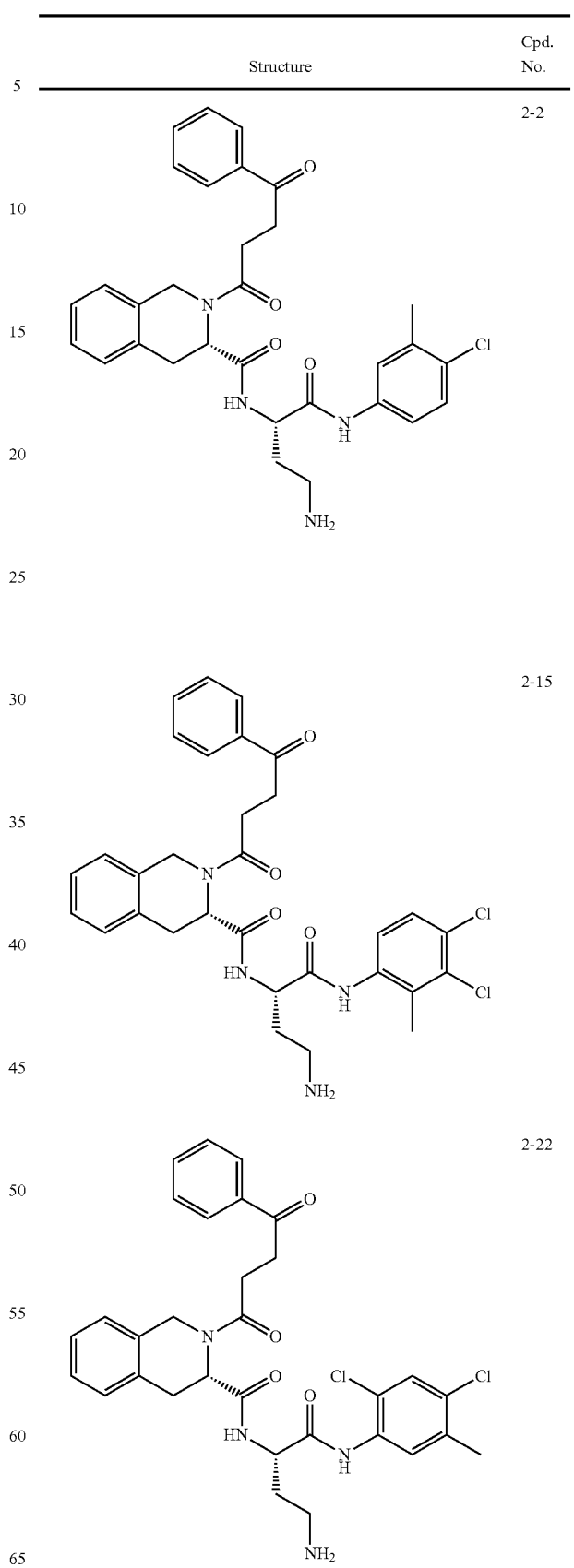 | 2-2 |
| 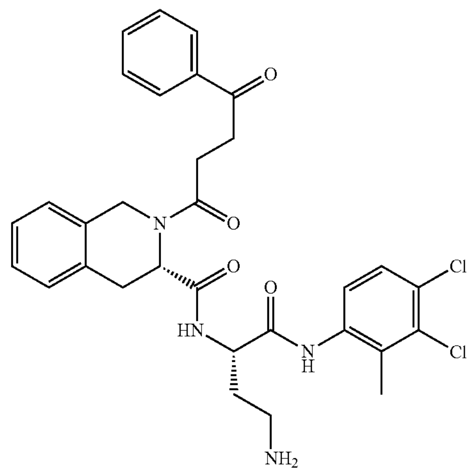 [SMILES: Cc1c(NC(=O)[C@H](CCN)NC(=O)[C@@H]2Cc3ccccc3CN2C(=O)CCC(=O)c2ccccc2)ccc(Cl)c1Cl] | 2-15 |
| 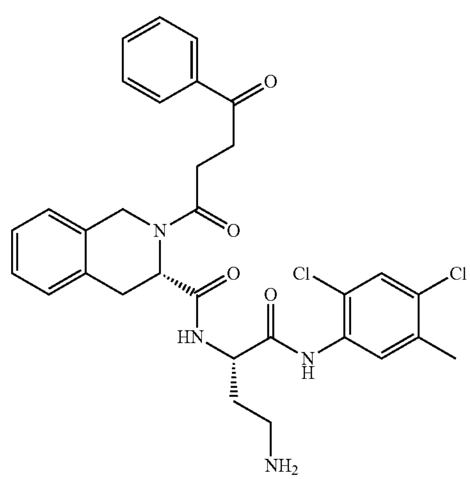 [SMILES: Cc1cc(NC(=O)[C@H](CCN)NC(=O)[C@@H]2Cc3ccccc3CN2C(=O)CCC(=O)c2ccccc2)c(Cl)cc1Cl] | 2-22 |

TABLE B-continued

| Structure | Cpd. No. |
|---|---|
| (structure) | 2-24 |
| (structure) | 2-25 |
| (structure) | 2-39 |
| (structure) | 2-57 |
| (structure) | 4-12 |
| (structure) | 4-14 |

TABLE B-continued

| Structure | Cpd. No. |
|---|---|
| (structure) | 8-4 |
| (structure) | 10-3 |
| (structure) | 12-73 |
| (structure) | 12-88 |
| (structure) | 12-104 |
| (structure) | 12-131 |

US 11,040,954 B1
TABLE B-continued
| Structure | Cpd. No. |
|---|---|
| 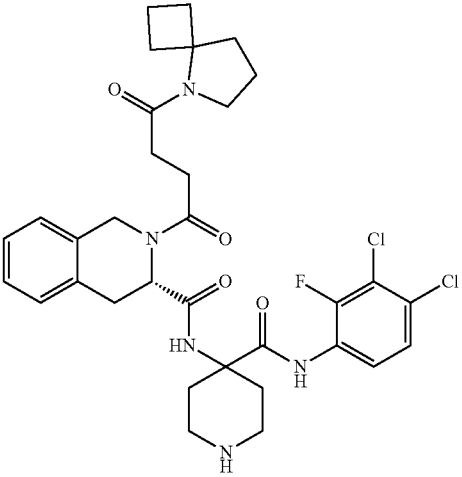 [SMILES: O=C(NC1(C(=O)Nc2ccc(Cl)c(Cl)c2F)CCNCC1)[C@@H]1Cc2ccccc2CN1C(=O)CCC(=O)N1CCCC12CCC2] | 12-136 |
| 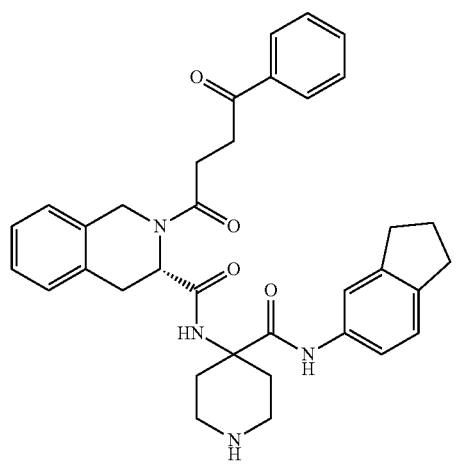 [SMILES: O=C(CCC(=O)N1Cc2ccccc2C[C@H]1C(=O)NC1(C(=O)Nc2ccc3c(c2)CCC3)CCNCC1)c1ccccc1] | 13-1 |
| 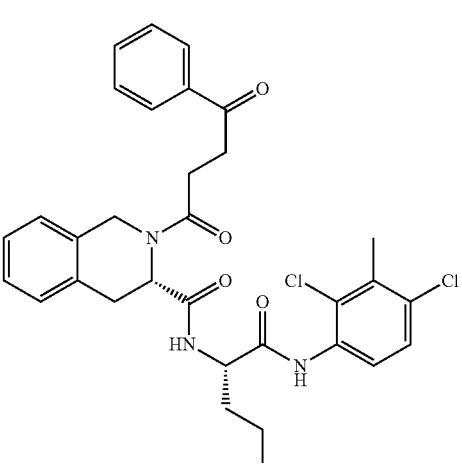 | 14-3 |
TABLE B-continued
| Structure | Cpd. No. |
|---|---|
| 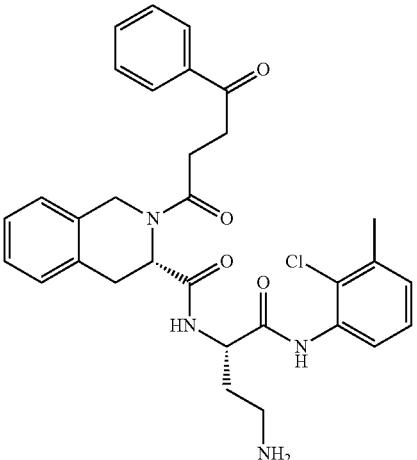 | 14-6 |
| 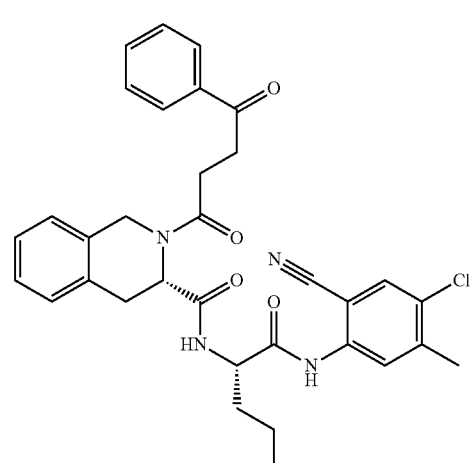 | 14-18 |
| 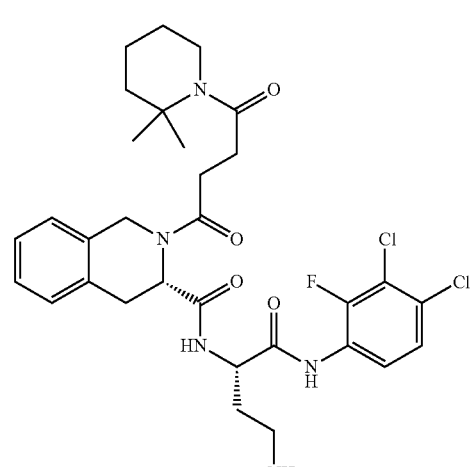 | 15-3 |

TABLE B-continued

| Structure | Cpd. No. |
|---|---|
| 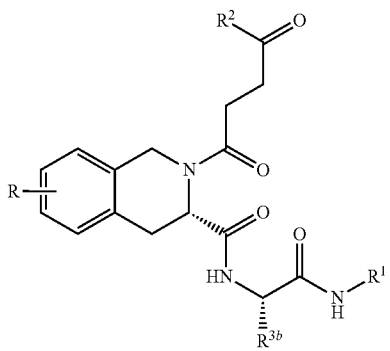 | 15-6 |
| 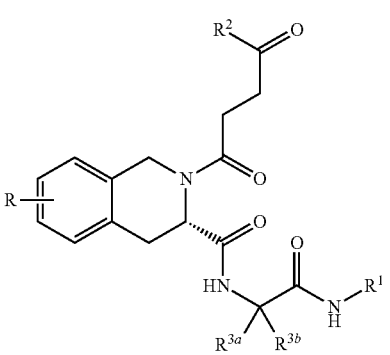 | 18-1. |

32. The compound of claim 1, wherein $R^{3a}$ is H and the compound of claim 1 is a stereoisomer having the structure of Formula XI:

![Formula XI]

or an isotope or pharmaceutically acceptable salt thereof.

33. The compound of claim 1, wherein $R^{3a}$ and $R^{3b}$ taken together with the carbon to which they are attached form a cyclic nitrogen- or amine-containing moiety of carbon, at least one nitrogen atom and hydrogen, and the compound of claim 1 is a stereoisomer having the structure of Formula XII:

![Formula XII]

or an isotope or pharmaceutically acceptable salt thereof.

34. The compound of claim 1 wherein R is hydrogen.

35. A pharmaceutical composition comprising a compound of claim 1 and at least one pharmaceutically acceptable excipient.

36. A method for agonizing a chemokine receptor of a cell comprising contacting the cell with a compound of claim 1, wherein the chemokine receptor is CXCR3.

* * * * *